(12) United States Patent
Suzuki et al.

(10) Patent No.: US 7,244,730 B2
(45) Date of Patent: Jul. 17, 2007

(54) 2-IMINOPYRROLIDINE DERIVATIVES

(75) Inventors: Shuichi Suzuki, Ushiku (JP); Makoto Kotake, Abiko (JP); Mitsuaki Miyamoto, Tsuchiura (JP); Tetsuya Kawahara, Ibaraki (JP); Akiharu Kajiwara, Tsukuba (JP); Ieharu Hishinuma, Moriya (JP); Kazuo Okano, Ibaraki (JP); Syuhei Miyazawa, Moriya (JP); Richard Clark, Tsuchiura (JP); Fumihiro Ozaki, Ushiku (JP); Nobuaki Sato, Tsuchiura (JP); Masanobu Shinoda, Ibaraki (JP); Atsushi Kamada, Ushiku (JP); Itaru Tsukada, Ushiku (JP); Fumiyoshi Matsuura, Tsukuba (JP); Yoshimitsu Naoe, Tsukuba (JP); Taro Terauchi, Tsukuba (JP); Yoshiaki Oohashi, Tsukuba (JP); Osamu Ito, Tsukuba (JP); Hiroshi Tanaka, Tsukuba (JP); Takashi Musya, Ushiku (JP); Motoji Kogushi, Moriya (JP); Tsutomu Kawada, Tsuchiura (JP); Toshiyuki Matsuoka, Tsukuba (JP); Hiroko Kobayashi, Tsuchiura (JP); Ken-ichi Chiba, Tsuchiura (JP); Akifumi Kimura, Tsukuba (JP); Naoto Ono, Tsukuba (JP)

(73) Assignee: Eisai Co., Ltd, Bunkyo-ku, Tokyo (JP)

( * ) Notice: Subject to any disclaimer, the term of this patent is extended or adjusted under 35 U.S.C. 154(b) by 92 days.

(21) Appl. No.: 10/475,188

(22) PCT Filed: Apr. 19, 2002

(86) PCT No.: PCT/JP02/03961

§ 371 (c)(1),
(2), (4) Date: Jun. 9, 2004

(87) PCT Pub. No.: WO02/085855

PCT Pub. Date: Oct. 31, 2002

(65) Prior Publication Data

US 2005/0004204 A1 Jan. 6, 2005

(30) Foreign Application Priority Data

Apr. 19, 2001 (JP) .............................. 2001-121829
Sep. 5, 2001 (JP) .............................. 2001-269422

(51) Int. Cl.
*A61K 31/535* (2006.01)
*A61K 31/40* (2006.01)
*C07D 265/30* (2006.01)
*C07D 241/04* (2006.01)
*C07D 209/44* (2006.01)

(52) U.S. Cl. .......................... 514/235.2; 514/254.09; 514/415; 544/106; 544/153; 544/358; 544/378; 548/471

(58) Field of Classification Search ............ 546/279.1; 514/416, 235.2, 254.09; 544/106, 153, 358, 544/373; 548/471

See application file for complete search history.

(56) References Cited

U.S. PATENT DOCUMENTS 3,717,648 A 2/1973 Diana .................... 260/293.78

(Continued)

FOREIGN PATENT DOCUMENTS

DE 2003825 12/1970

(Continued)

OTHER PUBLICATIONS

Kovtunenko et al; 5H-Imidazo[2,1-a]isoindole derivatives; 1985; Ukrainskii Khimicheskii Zhurnal; vol. 51; Issue 6; pp. 644-649.*

(Continued)

*Primary Examiner*—Kamal A. Saeed
*Assistant Examiner*—Susannah L. Chung
(74) *Attorney, Agent, or Firm*—Andrea L.C. Robidoux; Choate, Hall & Stewart LLP

(57) ABSTRACT

A 2-iminopyrrolidine derivative represented by the formula:

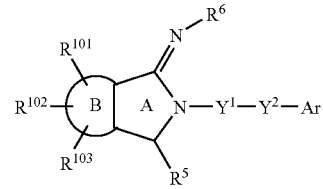

(I)

{wherein ring B represents a benzene ring, pyridine ring, etc.; $R^{101}$–$R^{103}$ represent hydrogen, halogen, $C_{1-6}$ alkyl, etc.; $R^5$ represents hydrogen, $C_{1-6}$ alkyl, $C_{1-6}$ alkoxy-$C_{1-6}$ alkyl, etc.; $R^6$ represents hydrogen, $C_{1-6}$ alkyl, $C_{1-6}$ alkyloxycarbonyl, etc.; $Y^1$ represents a single bond, —$CH_2$—, etc.; $Y^2$ represents a single bond, —CO—, etc.; and Ar represents hydrogen, a group represented by the formula:

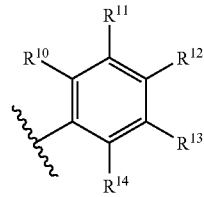

(II)

[wherein $R^{10}$–$R^{14}$ represent hydrogen, $C_{1-6}$ alkyl, hydroxyl, $C_{1-6}$ alkoxy, etc.; and $R^{11}$ and $R^{12}$ or $R^{12}$ and $R^{13}$ may bond together to form a 5- to 8-membered heterocyclic ring], etc.},
or a salt thereof.

16 Claims, No Drawings

U.S. PATENT DOCUMENTS

| | | | |
|---|---|---|---|
| 3,773,788 A | 11/1973 | Vis | 260/326.85 |
| 3,859,302 A | 1/1975 | Dixon | 260/309.6 |
| 3,887,577 A | 6/1975 | Dixon | 260/309.6 |
| 3,904,395 A | 9/1975 | Eilrich et al. | 71/92 |
| 3,920,688 A | 11/1975 | Eilrich et al. | 260/309.6 |
| 3,989,709 A | 11/1976 | White et al. | 260/294.8 |
| 4,004,016 A | 1/1977 | Yale et al. | 424/273 |
| 4,075,342 A | 2/1978 | Sale et al. | |
| 4,118,504 A | 10/1978 | Giraldi et al. | |
| 4,126,613 A | 11/1978 | Grisar et al. | 260/239 |
| 4,521,793 A | 6/1985 | Kabashima et al. | 346/201 |
| 5,143,912 A | 9/1992 | Burner et al. | 514/210 |
| 5,258,387 A | 11/1993 | Burner et al. | 514/291 |
| 5,362,738 A | 11/1994 | Burner et al. | 514/294 |
| 5,677,322 A | 10/1997 | Yasumura et al. | 514/369 |
| 5,935,952 A | 8/1999 | Todo et al. | 514/230.2 |
| 5,977,134 A | 11/1999 | Ciccarone et al. | 514/307 |
| 6,051,718 A | 4/2000 | Freyne et al. | 548/316.1 |
| 6,077,320 A | 6/2000 | Andrean | |
| 6,087,380 A | 7/2000 | Hauel | |
| 6,114,532 A | 9/2000 | Ries | |
| 6,187,799 B1 | 2/2001 | Wood et al. | 514/363 |
| 6,194,447 B1 | 2/2001 | Jensen et al. | 514/388 |
| 6,376,530 B1* | 4/2002 | Claiborne et al. | 514/416 |
| 2004/0004197 A1 | 1/2004 | Sano | |
| 2004/0004204 A1 | 1/2004 | Wang | |
| 2004/0242627 A1 | 12/2004 | Suzuki et al. | |
| 2004/0254376 A1 | 12/2004 | Suzuki et al. | |
| 2005/0004197 A1 | 1/2005 | Suzuki et al. | |
| 2005/0245592 A1 | 11/2005 | Suzuki et al. | |

FOREIGN PATENT DOCUMENTS

| | | |
|---|---|---|
| DE | 2154525 | 6/1972 |
| DE | 2551868 | 8/1976 |
| EP | 364204 | 10/1989 |
| EP | 638075 | 2/1994 |
| EP | 842161 | 7/1996 |
| EP | 934280 | 9/1997 |
| EP | 847749 | 6/1998 |
| EP | 1091942 | 7/1999 |
| EP | 1176141 | 3/2000 |
| GB | 1295478 | 11/1972 |
| GB | 1344663 | 1/1974 |
| JP | 48-42875 | 6/1973 |
| JP | S51-22720 | 2/1976 |
| JP | S51-125071 | 11/1976 |
| JP | 53-71063 | 6/1978 |
| JP | 62-22760 | 1/1987 |
| JP | 12-503678 | 10/1989 |
| JP | 4-244083 | 8/1990 |
| JP | 3-50555 | 3/1991 |
| JP | 4-504709 | 8/1992 |
| JP | H07-32103 | 2/1995 |
| JP | H08-225753 | 9/1996 |
| JP | 9-40643 | 2/1997 |
| JP | 10-167965 | 6/1998 |
| JP | 10-509150 | 9/1998 |
| JP | 11-509191 | 8/1999 |
| JP | 2002-155060 | 6/2002 |
| WO | WO 83/02920 | 9/1983 |
| WO | WO 96/05192 | 2/1996 |
| WO | WO 96/14844 | 5/1996 |
| WO | WO 98/00408 | 1/1998 |
| WO | WO 98/37075 | 8/1998 |
| WO | WO 99/26943 | 6/1999 |
| WO | WO 99/40072 | 8/1999 |
| WO | WO 00/01676 | 1/2000 |
| WO | WO 00/53582 | 9/2000 |
| WO | WO 00/67755 | 11/2000 |

OTHER PUBLICATIONS

Kovtunenko et al; 1-imino-2-alkylacylisoindoles; 1984; Ukrainskii Khimicheskii Zhurnal; vol. 50; Issue 10; pp. 1105-1110.*
Settimo et al., II Farmaco, 49(12), 829-834 (1994).*
Settimo et al., II Farmaco, 47(10), 1293-1313, 1992.*
Kigasawa et al., J. Het. Chem., 15, 369 (1978).*
Rehse et al., Arch. Pharm. (Weinheim) 328, 77-80 (1995);
Chackalamannil et al., Bio. Med. Chem. Let. 11 (2001) 2851-2853.*
Kovtunenko, et al (5H-Imidazo[2,1-a]isoindole derivatives; 1985; Ukrainskii Khimicheskii Zhurnal; vol. 51; Issue 6; pp. 644-649) and (1-imino-2-alkylacylisoindolines; 1984; Ukrainskii Zhurnal; vol. 50; Issue 10; pp. 1105-1110.*
Chemical Abstracts, vol. 127, abs.No. 81319.
Z.Naturforsch., B:Chemical Sci., (1996), 51(12), p. 1791-810.
Bulletin Soc.Chim.Belg., (1992), 101(6), p. 509-12.
Khim.Geterotsikl.Soedin., (1987), (9), p. 1264-9.
Vest.Kiev.Un-ta.Khimiya, (1985), (26), p. 21-5.
Ukr.Khim.Zh., (1985), 51(6), p. 644-9.
Arch Pharm., (1985), 318(8), p. 735-43.
Chemical Abstracts, vol. 103, abs.No. 104932.
Ukr.Khim.Zh., (1984), 50(11), p. 1198-203.
Chemical Abstracts, vol. 102, abs.No. 220805.
Ukr.Khim.Zh., (1984), 50(10), p. 1105-10.
Ukr.Khim.Zh., (1984), 50(5), p. 530-4.
Ukr.Khim.Zh., (1981), 47(7), p. 735-8.
Ukr.Khim.Zh., (1981), 47(3), p. 291-5.
J.Heterocycl.Chem., (1978), 15(3), p. 369-75.
Arch.Pharm., (1976), 309(5), p. 356-66.
Z.Naturforsch., Teil B, (1973), 28(11-12), p. 801-4.
Arzneim.-Forsch., (1973), 23(8), p. 1090-100.
Chemical Abstracts, vol. 76, abs.No. 153482.
Chemical Abstracts, vol. 72, abs.No. 132428.
Chemical Abstracts, vol. 53, abs.No. 16106c-16107d.
Chemical Abstracts, vol. 53, abs.No. 15082h-15085d.
Babichev, F.S., et al., "Structure Of Reaction Products Of 1-Amino-3H-Isoindole With Benzyl Chloride And .Alpha.-Bromoketones," *Ukrainskii Khimicheskii Zhurnal*, 50(6): 623-626, 1984. (Abstract).
Lessel, J., "Benzodiazepine Und Isoindole Durch Acylierung Von Amidinen Benzodiazepines And Isoindoles By Acylation Of Amidines," *Pharmazie*, 48(11): 812-816, 1993.
May, et al., "Chemie Und Biologische Eigenschaften Substituierter 3-Amino-1H-Isoindole," *Arzneim.-Forsch*, 30(11): 1487-1493, 1980.
O'Sullivan, R.D. and Parkins, A.W., "The Synthesis Of N-Heterocycles Using Ortho-Metallated Primary Benzylamine Complexes Of Palladium And Platinum," *J. Chem. Soc., Chem. Commun.*, 17: 1165-1166, 1984.
"Oxazines And Thiazines," *Chemical Abstracts*, 78: 478, 1973. (Abstract No. 111229).
Toja, E., et al., Synthesis And Pregnancy Terminating Activity Of 2-Arylimidazo '2, 1-a! Isoquinolines And Isoindoles, *Arzneim.-Forsch*, 33(11): 1222-6, 1983.
Sawanishi, H., et al., "Studies On Diazepines. XXI. Photochemical Synthesis Of 1H-2,4-Benzodiazepines From 4-Azidoisoquinolines," *Chem. Pharm. Bull.*, 33(10): 4564-4571, 1985.
Sawanish, H. and Tsuchiya, T., "Synthesis And Characterization Of 1H-2, 4-Benzodiazepines," *Heterocycles*, 22(12): 2725-2728, 1984.
Ahn, et al., "Structure-Activity Relationships of Pyrroloquinazolines as Thrombin Receptor Antagonists", *Bioorganic & Medicinal Chemistry Letters*, 9: 2073-2078, 1999.
Ahn, et al., "Inhibition of Cellular Action of Thrombin by N3-Cyclopropyl-7-{[4-(1-methylethyl)phenyl]methyl}-7H-pyrrolo[3,2-f]quinazoline-1,3-diamine (SCH 79797), a Nonpeptide Thrombin Receptor Antagonist," *Biochem. Pharm.*, 60: 1425-1434, 2000.

Alfaia, et al., "Quaternization Reaction of Heterocyclic Imines in Methanol—A Case of Strong Anti-Reactivity Selectivity Principle with Isoselective Temperature", *European Journal of Organic Chemistry*, 3627-3631, 2000.

Andrade-Gordon, et al., "Design, Synthesis, and Biological Characterization of a Peptide-mimetic Antagonist for a Tethered-ligand Receptor," *PNAS*, 96: 12257-12262, 1999.

Anisimova, et al., "Imidazo [1, 2-a] Benzimidazole Derivatives. X. Nitration of 2, 9-Disubstituted Imidazo [1, 2-a] Benzimidazole," *Khim. Geterotsikl. Soedin*, 2: 258-262, 1975.

Anisimova, et al., "Imidazo [1, 2-a] Benzimidazole Derivatives. 22. Synthesis of 2, 3-dihydroimidazo [1, 2-a]benzimidazoles from 3-(2-hydroxyethyl)-2-iminobenzimidazolines," *Khim. Geterotsikl. Soedin*, 7: 918-925, 1986.

Anisimova, et al., "Imidazo [1, 2-a] Benzimidazole Derivatives. 25. Reaction of 2, 9-disubstituted Imidazo [1, 2-a]benzimidazoles With Acrylic Acids and Their Derivatives," *Khim. Geterotsikl. Soedin*, 11: 1496-1502, 1987.

Babchiev, et al., "The Structure of the Salts of 2-amino.DELTA.1-pyrroline with Benzyl Chloride and .alpha-halo Ketones," *Ukr. Khim. Zh.*, 52: 398-401, 1986.

Bernatowicz, et al., "Development of Potent Thrombin Receptor Antagonist Peptides", *J. Med. Chem.* 39: 4879-4887, 1996.

Caroti, et al., "A Facile Synthesis of 5,7-Dihydro-5-Oxopyrido [3',2':5,6] Pyrimido-[1,2-a] Benzimidazoles. A New Heterocyclic Ring System", *J. Heterocycl. Chem.*, 23(6): 1833-1836, 1986.

Chackalamannil, et al., "Potent, Low Molecular Weight Thrombin Receptor Antagonists," *Bioorg. Med. Chem. Lett.*, 11: 2851-2853, 2001.

Cohen, et al., "Enantiospecific Synthesis of Leukotrienes $C_4$, $D_4$, and $E_4$ and [14,15-$^3$H2] Leukotriene $E_4$ Dimethyl Ester", *J. Am. Chem. Soc.* 105: 3661-3672, 1983.

Compernolle, et al., "Synthesis and Preliminary in vitro Metabolic Studies on N,N-Dimethyl-N'-2-Imidazolyl-N'-Benzyl-1,2-Ethanediamine, an Analog of the Carcinogenic Antihistamine Methapyrilene", *J. Heterocyclic Chem.*, 19: 1403-1408, 1982.

Da Settimo, et al., "Synthesis of 2-Methylbenzimidazole Derivatives Tested for Antiinflammatory Activity", *Farmaco*, 49(12): 829-834, 1994.

Da Settimo, et al., "Synthesis and Anti-Inflammatory Properties of 2-Amino-Benximidazole Derivatives", *Farmaco*, 47(10): 1293-1313, 1992.

Da Settimo, et al., "Synthesis and Antihypertensive Activity of Some 2-Aminobenzimidazole and Indole Derivatives", *Farmaco*, 46(2): 357-367, 1991.

Da Settimo, et al., "Synthesis and Evaluation of Aminoadamantane Derivatives for In Vitro Anti-HIV and Antitumor Activities", *Farmaco*, 50(5): 321-326, 1995.

Dixon, et al., "Bioactive Diversity and Screening Library Selection via Affinity Fingerprinting", *J.Chemical Information and Computer Sciences*, 38(6): 1192-1203, 1998.

Hoekstra, "Thrombin Receptor (PAR-1) Antagonists. Heterocycle-Based Peptidomimetics of the SFLLR Agonist Motif", *Bioorganic & Medicinal Chemistry Letters*, 8: 1649-1654, 1998.

Hung, et al., "Thrombin-Induced Events in Non-Platelet Cells are Mediated by the Unique Proteolytic Mechanisms Established for the Cloned Platelet Thrombin Receptor", *The Journal of Cell Biology*, 116(3): 827-832, 1992.

Hung, et al., "Cloned Platelet Thrombin Receptor is Necessary for Thrombin-Induced Platelet Activation", *J. Clin. Invest.*, 89: 1350-1353, 1992.

Janusz, et al., "New Cyclooxygenase-⅖-Lipoxygenase Inhibitors. 1. 7-tert-Butyl1-2,3-Dihydro-3,3-Dimethylbenzofuran Derivatives as Gastrointestinal Safe Antiinflammatory and Analgesic Agents: Discovery and Variation of the 5-Keto Substituent", *J. Med. Chem.* 41: 1112-1123, 1998.

Kato, et al., "In Vitro Antiplatelet Profile of FR171113, a Novel Non-peptide Thrombin Receptor Antagonist," *Europ. J. Pharm.*, 384: 197-202, 1999.

Klötzer et al., "Acylderivate von 2-Amino-1-pyrrolinen", *Monatshefte Fur Chemie*, 102(2): 627-634, 1971.

Korbonits, et al., "4-Aminobutanoic Amidoxime Derivatives. Synthesis of 1-Substituted 2-Hydroximinopyrrolidines, a Novel Type of Lactames," *Acta. Chim. Hung.*, 117: 239-245, 1984.

Koshchienko, et al., "Synthesis and Antibacterial Activity of 3-(alkoxymethyl)-2-amino-1-methylbenzimidazolium Chlorides," *Khim. Farm. Zh.*, 11: 14-14, 1977.

Koshchienko, et al., "New Synthesis of Imidazo [1,2-a] Benzimidazole Derivatives," *Khim. Geterotsikl. Soedin*, 1: 140-141, 1975.

Kovalev, et al., "Synthesis and Pharmacological Properties of Some Disubstituted Imidazo[1, 2-a] Benzimidazole Derivatives," *Khim. Farm. Zh.*, 13: 57-62, 1979.

Kovtunenko, et al., "Preparation and Reactions of 1R-2-iminopyrrolidines," *Ukr. Khim. Zh.*, 52: 63-70, 1986.

Kovtunenko, et al., "6,7-Dihydro-5H-pyrrolo[1,2-a]imidazole Derivatives," *Ukr. Khim. Zh.*, 52: 647-651, 1986.

Kuz'menk, et al., "Synthesis of 9-aminoimidazo [1,2-a]benzimidazoles and Their Deamination," *Khim. Geterotsikl. Soedin*, 11: 1517-1523, 1990.

Langlois, et al., "Synthesis of New Bicyclic Amidines. 1. Derivatives of Imidazole, 1,3,4-Triazole and Tetrazole," *J. Heterocycl. Chem*, 19: 193-200, 1982.

Latli, et al., "Novel and Potent 6-Chloro-3-pyridinyl Ligands for the α4β2 Neuronal Nicotinic Acetylcholine Receptor," *J. Med. Chem.*, 42: 2227-2234, 1999.

Lipinski, et al., "Bioisosteric Prototype Design of Biaryl Imidazolyl and Triazolyl Competitive Histamine $H_2$—Receptor Antagonists", *J. Med. Chem.* 29: 2154-2163, 1986.

Liu, et al., "The Mechanisms of Titanium Complex-Catalyzed Reduction of Aryl Halides by Sodium Borohydride is Strongly Solvent Dependent", *J. Org. Chem.* 59: 940-942, 1994.

Mancuso and Swern, "Activated Dimethyl Sulfoxide: Useful Reagents for Synthesis", *Reviews*, 165-185, 1981.

McComsey, et al., "Macrocyclic Hexapeptide Analogues of the Thrombin Receptor (PAR-1) Activation Motif Sfllrn" *Bioorganic & Medicinal Chemistry Letters*, 9: 255-260, 1999.

Ngaiza, et al., "A 14 Amino Acid Peptide Derived from the Amino Terminus of the Cleaved Thrombin Receptor Elevates Intracellular Calcium and Stimulates Prostacyclin Production in Human Endothelial Cells", *Biochem. & Biophys. Res. Comm.*, 179(3): 1656-1661, 1991.

North, et al., "A Study of Some 1-Alkyl-2,3-Dihydroimidazo [1,2-a] Benzimidazoles", *Journal of Heterocyclic Chemistry*, 6(5): 655-662, 1969.

Ogura, et al., "Studies on Heterocyclic Compounds, 10. Synthesis of Some Imidazo [1,2-a] Benzimidazoles with Potent Analgetic Activities", *J. Med. Chem.*, 15(9): 923-926, 1972.

Rehse, et al., "New NO-Donors with Antithrombotic and Vasodilating Activities", XI. 2-Nitrosiminobenzimidazoles, *Arch. Pharm.* 328:(1) 77-80, 1995.

Sarembock, et al., "Effectiveness of Recombinant Desulphatohirudin in Reducing Restenosis After Balloon Angioplasty of Atherosclerotic Femoral Arteries in Rabbits", *Circulation*, 84: 232-243, 1991.

Sato, et al., "Organic Solvent—and Halide Free Oxidation of Alcohols with Aqueous Hydrogen Peroxide", *J. Am. Chem. Soc.* 119: 12386-12387, 1997.

Tawada, et al., "Studies on Antidiabetic Agents. IX. A New Aldose Reductase Inhibitor, AD-5467, and Related 1,4-Benzoxazine and 1,4-Benzothiazine Derivatives: Synthesis and Biological Activity", *Chem. Pharm. Bull.* 38(5): 1238-1245, 1990.

Vassallo, et al.. "Structure-Function Relationships in the Activation of Platelet Thrombin Receptors by Receptor-Derived Peptides", *J. Bio. Chem.*, 267(9): 6081-6085, 1992.

Vu, et al., "Molecular Cloning of a Functional Thrombin Receptor Reveals a Novel Proteolytic Mechanism of Receptor Activation", *Cell*, 64: 1057-1068, 1991.

Vu. et al., "Domains Specifying Thrombin-Receptor Interaction", *Nature*, 353: 674-677, 1991.

Yale and Bristol, "1-Aralkyl-2(1H)-Pyridinimines and Their Derivatives," *J. Heterocycl. Chem*, 12: 1027-1029, 1975.

Yale, et al., "Quaternary Derivatives for 2-Aminobenzimidazole and 2-Phenylethyl-and Phenyloxymethyl Halides", *I.J. Heterocycl. Chem.*, 15(3): 505-507, 1978.

Zhao, et al., "A Novel Chromium Trioxide Catalyzed Oxidation of Primary Alcohols to the Carboxylic Acids", *Tetrahedron Letters*, 39: 5323-5326, 1998.

Study Report, Eisai Co., Ltd. "E5555:Protease-activated Receptor-1 Binding of E5555 in Human Platelet Membrane" Tsukuba Research Laboratories, Japan; Study No. M01035 (2002).

Study Report, Eisai Co., Ltd. "E5555: Inhibitory Effect of E55555 on Human Platelet Aggregation in vitro" Tsukuba Research Laboratories, Japan; Study No. M01027 (2002).

Study Report, Eisai Co., Ltd. "E5555: Inhibitory Effect on Rat Smooth Muscle Cell Proliferation" Tsukuba Research Laboratories, Japan; Study No. M01038 (2002).

Ahn et al., "Development of Proteinase-Activated Receptor 1 Antagonist as Therapeutic Agents for Thrombosis, Restensosi and Inflammatory Diseases", Current Pharmaceutical Design, 2349-65, 2003.

Supplementary Partial European Search Report in a corresponding EP application No.: EP 02720534, Dec. 16, 2005.

Babichev, et al., "The Structure of Products of the Reaction of 1-Amino-3H-Isoindole with Benzyle Chloride and α-Bromoketones," *Ukr. Khim. Zh.*, 50: 623-626, 1984 (original and abstract).

Cunningham et al:, "Protease-activated receptor 1 mediates Thrombin-dependent, cell-mediated renal inflammation in crescentic glomerulonephritis", *J. Exp. Med.*, 191(3):455-61, 2000.

Even-Ram et al., "Thrombin receptor overexpression in malignant and physiological invasion processes", *Nature Medicine*, 4(8):909-14, 1998.

Gabazza et al., "Thrombin in the airways of asthmatic patients", *Lung*, 177(4):253-621999,. (Abstract only).

Hauck et al., "□-Thrombin stimulates contraction of human bronchial rings by activation of protease-activated receptors", *Am. J. Physiol.*, 277: L22-L29, 1999.

Junge et al., "The contribution of protease-activated receptor 1 to neuronal damage caused by transient focal cerebral ischemia", *PNAS*, 100(22):13019-024, 2003.

Marty et al., "Amelioration of collagen-induced arthritis by thrombin inhibition", *J. Clin. Invest.*, 107(5):631-40, 2001.

Nantermet, et al., "Nonpeptidic small-molecule antagonists of the human platelet thrombin receptor (PAR-1)", 221$^{st}$ *ACS National Meeting (San Diego)*/MEDI/Protease-Activated Receptor Antagonists, Paper 341: (Oral), Wed Apr. 4, 2001. (Abstract only).

Vergnolle et al., A role for proteinase-activated receptor-1 in inflammatory bowel disease:, *J. Clin. Invest.*, 114(10):1444-56, 2004.

Yang et al., "Reduction of arthristis severity in protease-activated receptor-deficient mice", *Arthritis & Rheumatism*, 52(4):1325-32, 2005.

\* cited by examiner

2-IMINOPYRROLIDINE DERIVATIVES

PRIORITY INFORMATION

This application is the U.S. National Stage of International Application Number PCT/JP02/03961, filed Apr. 19, 2002, published in Japanese. This application claims priority under 35 U.S.C. 119 or 365 to Japan, Application Nos. P2001-121829, filed Apr. 19, 2001 and P2001-269422, filed Sep. 5, 2001. The entire teachings of the above applications are incorporated herein by reference.

TECHNICAL FIELD

The present invention relates to novel 2-iminopyrrolidine derivatives, salts thereof, and pharmaceutical compositions containing the same and the like.

BACKGROUND ART

A recent approach for thrombosis have involved inhibiting thrombin enzyme activity, and compounds used for this purpose have included heparin, low molecular weight heparin, hirudin, argatroban, hirulog and the like. All such compounds inhibit the enzyme activity of thrombin, and work by inhibiting fibrin blood clot formation without specifically inhibiting the effect of thrombin on cells. Bleeding tendency is therefore a common side effect encountered in the clinic. The role of thrombin in thrombosis is not limited to its blood clotting activity, as it is believed to also participate in platelet aggregation at sites of vascular injury occurring as a result of the activation of platelet thrombin receptor.

Another approach for thrombosis has been the use of intravenous injection agents such as Abciximab, Eptifibatide and Tirofiban, as GPIIb/IIIa receptor antagonists. These compounds, while exhibiting powerful anti-thrombotic effects by suppressing platelet aggregation induced by various stimulation such as thrombin, ADP, collagen, PAF or the like, also produce a bleeding tendency as a side effect similarly to thrombin enzyme activity inhibitors. For this reason, no such compounds have yet been marketed, although their development as oral agents continues to progress.

Restenosis is a vascular hypertrophic response to vascular wall injury induced by invasive treatment such as coronary angioplasty, and this phenomenon may be provoked by the direct or indirect effect of thrombin on cells. Platelets adhere to injured blood vessels, leading to release of growth factors and eliciting proliferation of smooth muscle cells. Smooth muscle cells may also be affected indirectly by the action of thrombin on endothelial cells. Also, platelet adhesion occurs and procoagulant activity increases at sites of vascular injury. Smooth muscle cells can undergo further direct stimulation due to the high local thrombin concentration which is produced at such sites. While recent studies using the powerful thrombin inhibitor hirudin have suggested that thrombin induces cell proliferation during the process of restenosis, it has not yet been determined whether the thrombin effect is direct or indirect (Sarembock et al., Circulation 1992, 84:232–243). Despite the implication of the cellular effects of thrombin in a variety of pathological symptoms, no therapeutically active substance is known which specifically blocks such effects.

The thrombin receptor (PAR1) has recently been cloned (Vu et al., Cell, 1991, 64:1057–1068), opening an important door to development of substances which target cellular thrombin receptors. Detailed examination of the amino acid sequence of this thrombin receptor has revealed a thrombin binding site and hydrolysis site located in the 100 residue amino terminal domain of the receptor. Later research by amino acid mutation in the receptor has established that limited hydrolysis of this portion of the thrombin receptor by thrombin is necessary for receptor activation (Vu et al., Nature, 1991, 353:674–677). A synthetic peptide corresponding to the amino acid sequence newly generated by hydrolysis of the thrombin receptor (the synthetic peptide is known as "thrombin receptor activating peptide", or TRAP) can activate receptors which have not been hydrolyzed by thrombin. This suggests that upon the cleavage of the receptor, the new amino acid sequence generated at the amino terminal (known as the "tethered ligand peptide") functions as the ligand and interacts with the distal binding site. Further studies of TRAP have confirmed homology of the thrombin receptors present in platelet, endothelial cell, fibroblast and smooth muscle cell (Hung et al., J. Cell. Biol. 1992, 116:827–832, Ngaiza, Jaffe, Biochem. Biophys. Res. Commun. 1991, 179:1656–1661).

Research on the structure activity relationship of TRAP suggests that the pentapeptide Phe-Leu-Leu-Arg-Asn is a weak antagonist for platelet thrombin receptors activated by either thrombin or TRAP (Vassallo. et al., J. Biol. Chem., 1992, 267:6081–6085(1992)). Different approaches to receptor antagonism have also been examined by other groups. One of these approaches has been an attempt to prepare antibodies for the thrombin binding domain of the thrombin receptor. Such antibodies specifically and effectively suppress activation of platelets by thrombin, and act as thrombin receptor antagonists (Hung et al., J. Clin. Invest. 1992, 89:1350–1353). Another approach has been development of peptide derivatives from TRAP (Steven M. S., J. Med. Chem. 1996, 39:4879–4887; William J. H., Bioorg. Med. Chem. Lett. 1998, 8:1649–1654; David F. M., Bioorg. Med. Chem. Lett. 1999, 9:255–260). Yet another has been development of low molecular weight compounds discovered by high throughput screening using various assay systems such as receptor binding (Andrew W. S. et al., Bioorg. Med Chem. Lett. 1999, 9:2073–2078; Scherig Plough WO99/26943; Halord S. et al., ACS meeting in October 2001).

DISCLOSURE OF THE INVENTION

Compounds having antagonistic action on thrombin receptors are expected to exhibit excellent effects for therapy or prevention of diseases associated with thrombin, and therefore offer promise for effective therapy or prevention of, for example, thrombosis, vascular restenosis, deep venous thrombosis, pulmonary embolism, cerebral infarction, heart disease, disseminated intravascular coagulation, hypertension, inflammatory diseases, rheumatism, asthma, glomerulonephritis, osteoporosis, neurological disorders, malignant tumors, and the like. It has been ardently desired to provide thrombin receptor antagonists which are satisfactory in numerous aspects including pharmacological activity, thrombin receptor specificity, safety, dosage and oral efficacy.

However, the conventional thrombin receptor antagonists have been inadequate in terms of receptor specificity and oral efficacy.

It is therefore an object of the present invention to search for and discover compounds having excellent thrombin receptor inhibiting activity and being therefore useful as thrombin receptor antagonists.

As a result of much vigorous research conducted under the circumstances described above, the present inventors have completed this invention upon successfully synthesizing novel 2-iminopyrrolidine derivatives represented by the following general formula (I), and also upon unexpectedly finding that these compounds or their salts have excellent thrombin receptor inhibiting activity and are useful as thrombin receptor antagonists.

The present invention resides in the following:

<1> a compound represented by the formula:

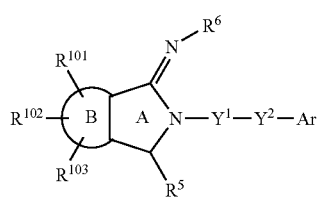

(I)

{wherein ring B represents an optionally substituted (1) aromatic hydrocarbon ring or (2) aromatic heterocycle optionally having 1 or 2 nitrogen; $R^{101}$, $R^{102}$ and $R^{103}$ are the same or different and each represents (1) hydrogen or (2) a group selected from Substituent Group C below; $R^5$ represents (1) hydrogen, (2) cyano, (3) halogen or (4) a group selected from Substituent Group A below; $R^6$ represents (1) hydrogen, (2) $C_{1-6}$ alkyl, (3) acyl, (4) carbamoyl, (5) hydroxyl, (6) $C_{1-6}$ alkoxy, (7) $C_{1-6}$ alkyloxycarbonyloxy, (8) $C_{3-8}$ cycloalkyl, (9) $C_{1-6}$ alkyloxycarbonyl optionally substituted with acyloxy or (10) a $C_{6-14}$ aromatic hydrocarbon ring group or 5- to 14-membered aromatic heterocyclic group (each of the foregoing members being optionally substituted with at least one group selected from Substituent Group E); $Y^1$ represents a single bond, —(CH$_2$)$_m$—, —CR$^8$—, —CR$^8$R$^9$—, —CH$_2$CO—, —NR$^8$—, —SO—, —SO$_2$—, —CO—, —CONR$^8$— or —SO$_2$NR$^8$— [wherein m represents an integer of 1 to 3, and $R^8$ and $R^9$ are the same or different and each represents hydrogen, halogen, $C_{1-6}$ alkyl, carboxyl or $C_{1-6}$ alkoxycarbonyl]; $Y^2$ represents a single bond, O, N, —(CH$_2$)$_m$—, —CR$^8$—, CR$^8$R$^9$—, —CO—, —SO—, —SO$_2$— or —C(=N—OR$^8$)— [wherein m, $R^8$ and $R^9$ are as defined above]; Ar represents (1) hydrogen, (2) a group represented by the formula:

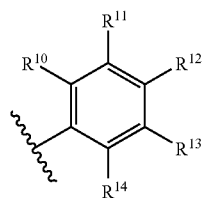

(II)

[wherein $R^{10}$, $R^{11}$, $R^{12}$, $R^{13}$ and $R^{14}$ are the same or different and each represents (1) hydrogen, (2) cyano, (3) halogen, (4) nitro or (5) a group selected from Substituent Group B below, and $R^{11}$ and $R^{12}$ or $R^{12}$ and $R^{13}$ may bond together to form a 5- to 8-membered heterocycle optionally having 1 to 4 hetero atoms selected from N, S and O and also optionally substituted with at least one group selected from Substituent Group F] or (3) a 5- to 14-membered aromatic heterocyclic group optionally substituted with at least one group selected from Substituent Group G below.

<Substituent Group A> The group consisting of $C_{1-6}$ alkyl, alkylidene, $C_{2-6}$ alkenyl, $C_{2-6}$ alkynyl, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, sulfonylamino, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group A' below;

<Substituent Group A'> The group consisting of $C_{1-6}$ alkyl, $C_{2-6}$ alkenyl, $C_{2-6}$ alkynyl, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, ureido, ureylene, sulfonylamino, sulfonyl, sulfamoyl, halogen, $C_{3-8}$ cycloalkyl, a heterocyclic alkyl group, a 5- to 14-membered non-aromatic heterocyclic group, a $C_{6-14}$ aromatic hydrocarbon ring group and a 5- to 14-membered aromatic heterocyclic group, wherein the $C_{6-14}$ aromatic hydrocarbon ring group and the 5- to 14-membered aromatic heterocyclic group may be substituted with at least one group selected from the group consisting of $C_{1-6}$ alkyl, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, nitro, amino, $C_{1-6}$ alkylamino, $C_{3-8}$ cycloalkylamino, acylamino, ureido, ureylene, sulfonylamino, sulfonyl, sulfamoyl, halogen and $C_{3-8}$ cycloalkyl;

<Substituent Group B> The group consisting of $C_{1-6}$ alkyl, $C_{2-6}$ alkenyl, $C_{2-6}$ alkynyl, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ aminoalkyl, $C_{1-6}$ alkylamino, $C_{3-8}$ cycloalkylamino, acylamino, ureido, sulfonylamino, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group B' below;

<Substituent Group B'> The group consisting of $C_{1-6}$ alkyl, $C_{2-6}$ alkenyl, $C_{2-6}$ alkynyl, oxo, cyano, $C_{1-6}$ cyanoacyl, $C_{2-7}$ acyl, $C_{1-6}$ alkanoyl, benzoyl, aralkanoyl, $C_{1-6}$ alkoxyalkylcarbonyl, $C_{1-6}$ hydroxyalkylcarbonyl, carboxyl, $C_{1-6}$ carboxyalkyl, $C_{1-6}$ carboxyalkyloxy, carbamoyl, carbamoylalkyloxy, $C_{1-6}$ alkoxycarbonyl, $C_{1-10}$ alkoxycarbonyl-$C_{1-6}$ alkyl, $C_{1-10}$ alkoxycarbonyl-$C_{1-6}$ alkyloxy, $C_{1-6}$ monoalkylaminocarbonyl, $C_{2-6}$ dialkylaminocarbonyl, hydroxyl, $C_{1-6}$ alkoxy, $C_{1-10}$ alkoxyalkyl, $C_{1-10}$ aralkyloxyalkyl, $C_{1-6}$ hydroxyalkyl, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, phenylsulfonylamino, $C_{1-6}$ alkylsulfonyl, phenylsulfonyl, $C_{1-6}$ monoalkylaminosulfonyl, $C_{2-6}$ dialkylaminosulfonyl, sulfamoyl, halogeno, $C_{3-8}$ cycloalkyl, a 5- to 14-membered non-aromatic heterocyclic group, a $C_{6-14}$ aromatic hydrocarbon ring group, a 5- to 14-membered aromatic heterocyclic group, a heterocyclic aminocarbonyl group, a heterocyclic aminosulfonyl group and isoxazolinyl, wherein the 5- to 14-membered non-aromatic heterocyclic group, the $C_{6-14}$ aromatic hydrocarbon ring group, the 5- to 14-membered aromatic heterocyclic group and isoxazolinyl may be independently substituted with at least one group selected from the group consisting of $C_{1-6}$ alkyl, oxo, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, nitro, amino, $C_{1-6}$ aminoalkyl, $C_{1-6}$ alkylamino, $C_{1-6}$ dialkylamino, $C_{3-8}$ cycloalkylamino, acylamino, ureido, ureylene, alkylsulfonylamino, alkylsulfonyl, sulfamoyl, halogeno and $C_{3-8}$ cycloalkyl;

<Substituent Group C> The group consisting of (1) cyano, (2) halogen and (3) $C_{1-6}$ alkyl, $C_{2-8}$ alkenyl, $C_{2-8}$ alkynyl, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, ureido, sulfonylamino, sulfonyl, sulfamoyl, $C_{3-8}$ cycloalkyl, a 5- to 14-membered non-aromatic heterocyclic group, a $C_{6-14}$ aromatic hydrocarbon ring group and 5- to 14-membered aromatic heterocyclic group (each of the foregoing members being optionally substituted with at least one group selected from Substituent Group C' below);

<Substituent Group C'> The group consisting of $C_{1-6}$ alkyl, $C_{2-8}$ alkenyl, $C_{2-8}$ alkynyl, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, ureido, ureylene, sulfonylamino, sulfonyl, sulfamoyl, halogeno, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group;

<Substituent Group E> The group consisting of $C_{1-6}$ alkyl, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, ureido, ureylene, sulfonylamino, sulfonyl, sulfamoyl, halogen and $C_{3-8}$ cycloalkyl;

<Substituent Group F> The group consisting of (1) hydrogen, (2) cyano, (3) halogen, (4) oxo and (5) $C_{1-6}$ alkyl, alkenyl, alkynyl, acyl, $C_{1-6}$ alkanoyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, imino, $C_{1-6}$ aminoalkyl, $C_{1-6}$ alkylamino, $C_{3-8}$ cycloalkylamino, acylamino, ureido, sulfonylamino, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group (each of the foregoing members being optionally substituted with at least one group selected from Substituent Group F' below);

<Substituent Group F'> The group consisting of $C_{1-6}$ alkyl, oxo, cyano, acyl, carboxyl, carbamoyl, $C_{1-6}$ alkoxycarbonyl, benzyloxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, $C_{1-6}$ alkylsulfonyl, sulfamoyl, halogeno, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group;

<Substituent Group G> The group consisting of $C_{1-6}$ alkyl, cyano, acyl, carboxyl, carbamoyl, $C_{1-6}$ alkoxycarbonyl, $C_{1-6}$ alkylaminocarbonyl, sulfonyl, sulfamoyl, halogeno and $C_{3-8}$ cycloalkyl.} or a salt thereof;

<2> a compound according to <1> or a salt thereof, wherein ring B represents a further optionally substituted benzene ring or pyridine ring; $R^{101}$, $R^{102}$ and $R^{103}$ are the same or different and each represents a group selected from the group consisting of hydrogen, halogen, $C_{1-6}$ alkyl, $C_{1-6}$ alkylaminocarbonyl, $C_{1-6}$ alkoxy, $C_{1-6}$ alkylamino and $C_{3-8}$ cycloalkyl; $R^5$ represents a group selected from the group consisting of hydrogen, $C_{1-6}$ alkyl and $C_{1-6}$ alkoxy-$C_{1-6}$ alkyl; $R^6$ represents a group selected from the group consisting of hydrogen, $C_{1-6}$ alkyl and $C_{1-6}$ alkyloxycarbonyl optionally substituted with acyloxy; $Y^1$ represents a single bond or $-(CH_2)_m-$ [wherein m represents an integer of 1 to 3]; $Y^2$ represents a single bond or $-CO-$; and Ar represents hydrogen or a group represented by the formula:

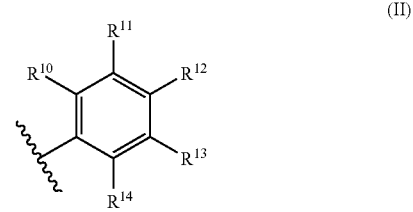

(II)

[wherein $R^{10}$, $R^{11}$, $R^{12}$, $R^{13}$ and $R^{14}$ are the same or different and each represents a group selected from the group consisting of hydrogen, $C_{1-6}$ alkyl, hydroxyl, $C_{1-6}$ alkoxy, $C_{1-6}$ alkylamino, $C_{3-8}$ cycloalkylamino, acylamino, a 5- to 14-membered non-aromatic heterocyclic group and $C_{1-6}$ alkyloxycarbonyloxy, and $R^{11}$ and $R^{12}$ or $R^{12}$ and $R^{13}$ may bond together to form a 5- to 8-membered heterocyclic ring (i) optionally having 1 to 4 hetero atoms selected from N, S and O and (ii) optionally substituted with at least one group selected from the group consisting of cyano, oxo, and $C_{1-6}$ alkyl, acyl, $C_{1-6}$ alkanoyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, sulfonyl and a 5- to 14-membered non-aromatic heterocyclic group (each of the foregoing member being optionally substituted with at least one group selected from Substituent Group F''' below)

<Substituent Group F'''> The group consisting of $C_{1-6}$ alkyl, oxo, cyano, acyl, carboxyl and $C_{1-6}$ alkoxy];

<3> a compound according to <1> or a salt thereof, wherein ring B is an optionally substituted benzene ring;

<4> a compound according to <1> or a salt thereof, wherein $Y^1$ is $-CH_2-$;

<5> a compound according to <1> or a salt thereof, wherein $Y^2$ is $-CO-$;

<6> a compound according to <1> or a salt thereof, wherein $Y^1$ is $-CH_2-$ and $Y^2$ is $-CO-$;

<7> a compound according to <1> or a salt thereof, wherein $Y^1$ is a single bond, $Y^2$ is a single bond and Ar is hydrogen;

<8> a compound according to <1> or a salt thereof, Ar is a group represented by the formula:

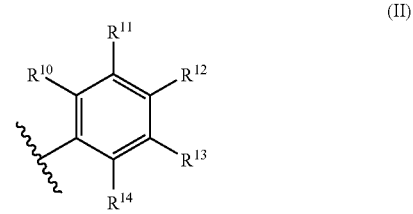

(II)

[wherein $R^{10}$, $R^{11}$, $R^{12}$, $R^{13}$ and $R^{14}$ are as defined above];

<9> a compound according to <8> or a salt thereof, wherein $R^{10}$ and $R^{14}$ are hydrogen;

<10> a compound according to <1> or a salt thereof, wherein Ar is (1) a group represented by the formula:

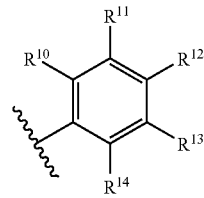

(II)

[wherein $R^{10}$, $R^{11}$, $R^{12}$, $R^{13}$ and $R^{14}$ are as defined above] or (2) a 5- to 14-membered aromatic heterocyclic group optionally substituted with at least one group selected from Substituent Group G above;

<11> a compound according to <10> or a salt thereof, wherein $R^{10}$ and $R^{14}$ are hydrogen;

<12> a compound according to <1> or a salt thereof, wherein Ar is a group represented by the formula:

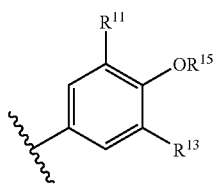

(IV)

[wherein $R^{11}$ and $R^{13}$ are as defined above, $R^{15}$ represents (1) hydrogen or (2) a group selected from Substituent Group H below, and $R^{11}$ and $R^{15}$ may bond together to form a 5- to 8-membered heterocycle optionally substituted with at least one group selected from Substituent Group F above and optionally having 1 or 2 hetero atoms selected from N, S and O.

<Substituent Group H> The group consisting of $C_{1-6}$ alkyl, $C_{2-6}$ alkenyl, $C_{2-6}$ alkynyl, acyl, $C_{1-6}$ alkoxycarbonyl, aminocarbonyl, $C_{1-6}$ alkylaminocarbonyl, $C_{3-8}$ cycloalkyl, $C_{1-6}$ aminoalkyl, sulfonyl, $C_{3-8}$ cycloalkylamino, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group H' below;

<Substituent Group H'> The group consisting of $C_{1-6}$ alkyl, $C_{2-6}$ alkenyl, $C_{2-6}$ alkynyl, oxo, cyano, $C_{1-6}$ cyanoalkyl, $C_{2-7}$ acyl, $C_{1-6}$ alkanoyl, benzoyl, aralkanoyl, $C_{1-6}$ alkoxyalkylcarbonyl, $C_{1-6}$ hydroxyalkylcarbonyl, carboxyl, $C_{1-6}$ carboxyalkyl, $C_{1-6}$ carboxyalkyloxy, carbamoyl, carbamoylalkyloxy, $C_{1-6}$ alkoxycarbonyl, $C_1$-$C_{10}$ alkoxycarbonyl-$C_{1-6}$ alkyl, $C_{1-10}$ alkoxycarbonyl-$C_{1-6}$ alkyloxy, $C_{1-6}$ monoalkylaminocarbonyl, $C_{2-6}$ dialkylaminocarbonyl, hydroxyl, $C_{1-6}$ alkoxy, $C_{1-10}$ alkoxyalkyl, $C_{1-10}$ aralkyloxyalkyl, $C_{1-6}$ hydroxyalkyl, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, phenylsulfonylamino, $C_{1-6}$ alkylsulfonyl, phenylsulfonyl, $C_{1-6}$ monoalkylaminosulfonyl, $C_{2-6}$ dialkylaminosulfonyl, sulfamoyl, halogeno, $C_{3-8}$ cycloalkyl, a 5- to 14-membered non-aromatic heterocyclic group, a $C_{6-14}$ aromatic hydrocarbon ring group, a 5- to 14-membered aromatic heterocyclic group, a heterocyclic aminocarbonyl group, a heterocyclic aminosulfonyl group and isoxazolinyl, wherein the 5- to 14-membered non-aromatic heterocyclic group, the $C_{6-14}$ aromatic hydrocarbon ring group, the 5- to 14-membered aromatic heterocyclic group and isoxazolinyl may be independently substituted with at least one group selected from the group consisting of $C_{1-6}$ alkyl, oxo, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, nitro, amino, $C_{1-6}$ aminoalkyl, $C_{1-6}$ alkylamino, $C_{1-6}$ dialkylamino, $C_{3-8}$ cycloalkylamino, acylamino, ureido, ureylene, alkylsulfonylamino, alkylsulfonyl, sulfamoyl, halogeno and $C_{3-8}$ cycloalkyl];

<13> a compound according to <1> or a salt thereof, wherein Ar is a group represented by the formula:

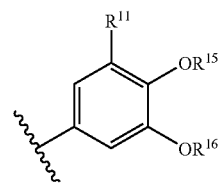

(V)

[wherein $R^{11}$ and $R^{15}$ are as defined above, and $R^{16}$ represents (1) hydrogen or (2) a group selected from Substituent Group H above, and $R^{11}$ and $R^{15}$ or $R^{15}$ and $R^{16}$ may bond together to form a 5- to 6-membered heterocycle optionally substituted with at least one group selected from Substituent Group F above and also optionally having 1 or 2 hetero atoms selected from N, S and O];

<14> a compound according to <1> or a salt thereof, wherein Ar is a group represented by the formula:

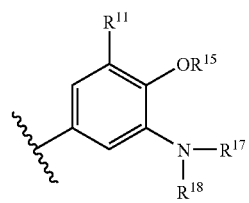

(VI)

[wherein $R^{11}$ and $R^{15}$ are as defined above, and $R^{17}$ and $R^{18}$ are the same or different and each represents (1) hydrogen or (2) a group selected from Substituent Group I below, and $R^{11}$ and $R^{15}$, $R^{15}$ and $R^{17}$, $R^{15}$ and $R^{18}$ or $R^{17}$ and $R^{18}$ may bond together to form a 5- to 8-membered heterocycle optionally substituted with at least one group selected from Substituent Group F above and also optionally having 1 or 2 hetero atoms selected from N, S and O.

<Substituent Group I> The group consisting of $C_{1-6}$ alkyl, $C_{2-6}$ alkenyl, $C_{2-6}$ alkynyl, acyl, carbamoyl, $C_{1-6}$ alkoxycarbonyl, $C_{1-6}$ alkylaminocarbonyl, $C_{1-6}$ aminoalkyl, sulfonyl, sulfamoyl, $C_{3-8}$ cycloalkyl, a 5- to 14-membered non-aromatic heterocyclic group, a $C_{6-14}$ aromatic hydrocarbon ring group and a 5- to 14-membered aromatic heterocyclic group, each of the foregoing members being optionally substituted with at least one group selected from Substituent Group I' below;

<Substituent Group I'> The group consisting of $C_{1-6}$ alkyl, $C_{2-6}$ alkenyl, $C_{2-6}$ alkynyl, oxo, cyano, $C_{1-6}$ cyanoalkyl, $C_{2-7}$ acyl, $C_{1-6}$ alkanoyl, benzoyl, aralkanoyl, $C_{1-6}$ alkoxyalkylcarbonyl, $C_{1-6}$ hydroxyalkylcarbonyl, carboxyl, $C_{1-6}$ carboxyalkyl, $C_{1-6}$ carboxyalkyloxy, carbamoyl, carbamoylalkyloxy, $C_{1-6}$ alkoxycarbonyl, $C_{1-10}$ alkoxycarbonyl-$C_{1-6}$ alkyl, $C_{1-10}$ alkoxycarbonyl-$C_{1-6}$ alkyloxy, $C_{1-6}$ monoalkylaminocarbonyl, $C_{2-6}$ dialkylaminocarbonyl, hydroxyl, $C_{1-6}$ alkoxy, $C_{1-10}$ alkoxyalkyl, $C_{1-10}$ aralkyloxyalkyl, $C_{1-6}$ hydroxyalkyl, $C_{3-8}$ cycloalkyloxy, amino, $C_{1-6}$ alkylamino, $C_{3-8}$ cycloalkylamino, acylamino, ureido, ureylene, $C_{1-6}$ alkylsulfonylamino, phenylsulfonylamino, $C_{1-6}$ alkylsulfonyl, phenylsulfonyl, $C_{1-6}$ monoalkylaminosulfonyl, $C_{2-6}$ dialkylaminosulfonyl, sulfamoyl, halogeno, $C_{3-8}$ cycloalkyl, a 5- to 14-membered non-aromatic heterocyclic group, a $C_{6-14}$ aromatic hydrocarbon ring group, a 5- to 14-membered aromatic heterocyclic group, a heterocyclic aminocarbonyl group, a heterocyclic aminosulfonyl group and isoxazolinyl, wherein the 5- to 14-membered non-aromatic heterocyclic group, the $C_{6-14}$ aromatic hydrocarbon ring group, the 5- to 14-membered aromatic heterocyclic group and isoxazolinyl may be independently substituted with at least one group selected from the group consisting of $C_{1-6}$ alkyl, oxo, cyano, acyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, nitro, amino, $C_{1-6}$ aminoalkyl, $C_{1-6}$ alkylamino, $C_{1-6}$ dialkylamino, $C_{3-8}$ cycloalkylamino, acylamino, ureido, ureylene, alkylsulfonylamino, alkylsulfonyl, sulfamoyl, halogeno and $C_{3-8}$ cycloalkyl];

<15> a compound according to <1> or a salt thereof, wherein the compound is represented by the formula:

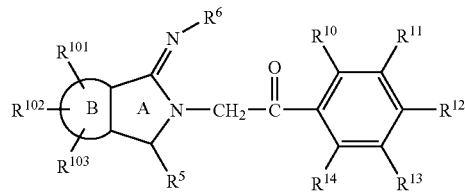

[wherein the definitions of the symbols are the same as given above];

<16> a compound according to <1> or a salt thereof, wherein the compound is represented by the formula:

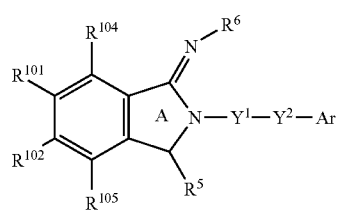

[wherein $R^{104}$ and $R^{105}$ are the same or different and each represents hydrogen, $C_{1-6}$ alkoxy, $C_{1-6}$ alkyl or halogen, and $R^{101}$, $R^{102}$, $R^5$, $R^6$, $Y^1$, $Y^2$ and Ar are as defined above];

<17> a compound according to <1> or a salt thereof, wherein the compound is represented by the formula:

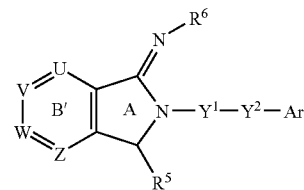

[wherein U represents N or CH, V represents N or $CR^{101}$, W represents N or $CR^{102}$, Z represents N or $CR^{105}$, one or two from U, V, W and Z are N, and $R^{101}$, $R^{102}$, $R^{105}$, $R^5$, $R^6$, $Y^1$, $Y^2$ and Ar are as defined above];

<18> a compound according to <16> or <17> or a salt thereof, wherein $Y^1$ is —$CH_2$—;

<19> a compound according to <16> or <17> or a salt thereof, wherein $Y^2$ is —CO—;

<20> a compound according to <17> or a salt thereof, wherein U is N and V is $CR^{101}$ [where $R^{101}$ are as defined above];

<21> a pharmaceutical composition comprising a compound according to <1> or a salt thereof;

<22> a composition according to <21>, wherein the composition is a thrombin receptor antagonist;

<23> a composition according to <21>, wherein the composition is a thrombin receptor PAR1 antagonist;

<24> a composition according to <21>, wherein the composition is a platelet aggregation inhibitor;

<25> a composition according to <21>, wherein the composition is a proliferation inhibitor for smooth muscle cells;

<26> a composition according to <21>, wherein the composition is a proliferation inhibitor for endothelial cells, fibroblasts, nephrocytes, osteosarcoma cells, muscle cells, cancer cells and/or glia cells;

<27> a composition according to <21>, wherein the composition is a therapeutic or preventive agent for thrombosis, vascular restenosis, deep venous thrombosis, pulmonary embolism, cerebral infarction, heart disease, disseminated intravascular coagulation, hypertension, inflammatory disease, rheumatism, asthma, glomerulonephritis, osteoporosis, neurological disease and/or malignant tumor;

<28> use of a compound according to <1> or a salt thereof for the manufacture of a thrombin receptor antagonist;

<29> use according to <28>, wherein the thrombin receptor antagonist is a PAR1 receptor antagonist;

<30> use of a compound according to <1> or a salt thereof for the manufacture of a platelet aggregation inhibitor;

<31> a method of treating a thrombin receptor mediated disease in a patient suffering from the disease, comprising administering to the patient, a therapeutically effective amount of a compound according to <1> or a salt thereof; and <32> a method for treating a proliferative disease of endothelial cells, fibroblasts, nephrocytes, osteosarcoma cells, muscle cells, cancer cells and/or glia cells, in a patient suffering from the disease, comprising administering to the patient, a therapeutically effective amount of a compound according to <1> or a salt thereof.

BEST MODE FOR CARRYING OUT THE INVENTION

The present invention will now be explained in greater detail.

Several of the structural formulas given for the compounds of the invention throughout the present specification will represent only a specific isomer for convenience, but the invention is not limited to such specific isomers and encompasses all isomers and isomer mixtures, including geometric isomers, asymmetric carbon-derived optical isomers, stereoisomers and tautomers which are implied by the structures of the compounds, and any isomer or mixture thereof may be used. The compounds of the invention therefore include those having asymmetric carbons in their molecules and existing as optically active forms or racemic forms, and all such compounds are encompassed by the invention without restrictions. There are also no restrictions on any crystalline polymorphism of the compounds, and any crystal forms may be used alone or in mixtures. The compounds of the invention and their salts may also be in the form of anhydrides or solvates such as hydrates, and all such forms are included within the scope of the claims of the present specification. Metabolites of the compounds of the invention produced by degradation in the body, as well as prodrugs of the compounds of the invention and their salts, are also encompassed within the scope of the claims of the present specification.

The symbols and terms used throughout the present specification will now be defined, with a more detailed description of the invention.

The term "and/or" as used throughout the present specification carries the meaning of both "and" and "or".

The term "halogen" used throughout the present specification refers to an atom such as fluorine, chlorine, bromine or iodine, and preferably fluorine, chlorine or bromine.

The term "$C_{1-6}$ alkyl" used throughout the present specification refers to an alkyl group of 1 to 6 carbons, and as examples of such groups there may be mentioned preferably linear or branched alkyl groups such as methyl, ethyl, n-propyl, iso-propyl, n-butyl, iso-butyl, sec-butyl, tert-butyl, n-pentyl, 1,1-dimethylpropyl, 1,2-dimethylpropyl, 2,2-dimethylpropyl, 1-ethylpropyl, 2-ethylpropyl, n-hexyl, 1-methyl-2-ethylpropyl, 1-ethyl-2-methylpropyl, 1,1,2-trimethylpropyl, 1-propylpropyl, 1-methylbutyl, 2-methylbutyl, 1,1-dimethylbutyl, 1,2-dimethylbutyl, 2,2-dimethylbutyl, 1,3-dimethylbutyl, 2,3-dimethylbutyl, 2-ethylbutyl, 2-methylpentyl and 3-methylpentyl, and more preferably methyl, ethyl, n-propyl, iso-propyl, n-butyl, iso-butyl, sec-butyl, tert-butyl and n-pentyl.

The term "$C_{2-6}$ alkenyl" used throughout the present specification refers to an alkenyl group of 2 to 6 carbons, and as preferred examples of such groups there may be mentioned vinyl, allyl, 1-propenyl, 2-propenyl, isopropenyl, 2-methyl-1-propenyl, 3-methyl-1-propenyl, 2-methyl-2-propenyl, 3-methyl-2-propenyl, 1-butenyl, 2-butenyl, 3-butenyl, 1-pentenyl, 1-hexenyl, 1,3-hexanedienyl and 1,6-hexanedienyl.

The term "$C_{2-6}$ alkynyl" used throughout the present specification refers to an alkynyl group of 2 to 6 carbons, and as preferred examples of such groups there may be mentioned ethynyl, 1-propynyl, 2-propynyl, 1-butynyl, 2-butynyl, 3-butynyl, 3-methyl-1-propynyl, 1-ethynyl-2-propynyl, 2-methyl-3-propynyl, 1-pentynyl, 1-hexynyl, 1,3-hexanediynyl and 1,6-hexanediynyl.

The term "$C_{3-8}$ cycloalkyl" used throughout the present specification refers to a cycloalkyl group composed of 3 to 8 carbons, and as examples there may be mentioned cyclopropyl, cyclobutyl, cyclopentyl, cyclohexyl, cycloheptyl and cyclooctyl.

The term "$C_{3-8}$ cycloalkenyl" used throughout the present specification refers to a $C_{3-8}$ cycloalkenyl group composed of 3 to 8 carbons, and as examples there may be mentioned cyclopropen-1-yl, cyclopropen-3-yl, cyclobuten-1-yl, cyclobuten-3-yl, 1,3-cyclobutadien-1-yl, cyclopenten-1-yl, cyclopenten-3-yl, cyclopenten-4-yl, 1,3-cyclopentadien-1-yl, 1,3-cyclopentadien-2-yl, 1,3-cyclopentadien-5-yl, cyclohexen-1-yl, cyclohexen-3-yl, cyclohexen-4-yl, 1,3-cyclohexadien-1-yl, 1,3-cyclohexadien-2-yl, 1,3-cyclohexadien-5-yl, 1,4-cyclohexadien-3-yl, 1,4-cyclohexadien-1-yl, cyclohepten-1-yl, cyclohepten-3-yl, cyclohepten-4-yl, cyclohepten-5-yl, 1,3-cycloheptadiene-2-yl, 1,3-cycloheptadiene-1-yl, 1,3-cycloheptadien-5-yl, 1,3-cycloheptadien-6-yl, 1,4-cycloheptadien-3-yl, 1,4-cycloheptadien-2-yl, 1,4-cycloheptadien-1-yl, 1,4-cycloheptadien-6-yl, 1,3,5-cycloheptatrien-3-yl, 1,3,5-cycloheptatrien-2-yl, 1,3,5-cycloheptatrien-1-yl, 1,3,5-cycloheptatrien-7-yl, cycloocten-1-yl, cycloocten-3-yl, cycloocten-4-yl, cycloocten-5-yl, 1,3-cyclooctadien-2-yl, 1,3-cyclooctadien-1-yl, 1,3-cyclooctadien-5-yl, 1,3-cyclooctadien-6-yl, 1,4-cyclooctadien-3-yl, 1,4-cyclooctadien-2-yl, 1,4-cyclooctadien-1-yl, 1,4-cyclooctadien-6-yl, 1,4-cyclooctadien-7-yl, 1,5-cyclooctadien-3-yl, 1,5-cyclooctadien-2-yl, 1,3,5-cyclooctatrien-3-yl, 1,3,5-cyclooctatrien-2-yl, 1,3,5-cyclooctatrien-1-yl, 1,3,5-cyclooctatrien-7-yl, 1,3,6-cyclooctatrien-2-yl, 1,3,6-cyclooctatrien-1-yl, 1,3,6-cyclooctatrien-5-yl and 1,3,6-cyclooctatrien-6-yl.

The term "$C_{1-6}$ alkoxy" used throughout the present specification refers to an alkoxy group of 1 to 6 carbons, and as preferred examples there may be mentioned methoxy, ethoxy, n-propoxy, iso-propoxy, sec-propoxy, n-butoxy, iso-butoxy, sec-butoxy, tert-butoxy, n-pentyloxy, iso-pentyloxy, sec-pentyloxy, n-hexlyoxy, iso-hexlyoxy, 1,1-dimethylpropyloxy, 1,2-dimethylpropoxy, 2,2-dimethylpropyloxy, 2-ethylpropoxy, 1-methyl-2-ethylpropoxy, 1-ethyl-2-methylpropoxy, 1,1,2-trimethylpropoxy, 1,2,2-trimethylpropoxy, 1,1-dimethylbutoxy, 1,2-dimethylbutoxy, 2,2-dimethylbutoxy, 2,3-dimethylbutoxy, 1,3-dimethylbutoxy, 2-ethylbutoxy, 1,3-dimethylbutoxy, 2-methylpentoxy, 3-methylpentoxy and hexyloxy.

The term "$C_{2-6}$ alkenyloxy" used throughout the present specification refers to an alkenyloxy group of 2 to 6 carbons, and as preferred examples there may be mentioned vinyloxy, allyloxy, 1-propenyloxy, 2-propenyloxy, isopropenyloxy, 2-methyl-1-propenyloxy, 3-methyl-1-propenyloxy, 2-methyl-2-propenyloxy, 3-methyl-2-propenyloxy, 1-butenyloxy, 2-butenyloxy, 3-butenyloxy, 1-pentenyloxy, 1-hexenyloxy, 1,3-hexanedienyloxy and 1,6-hexanedienyloxy.

The term "acyl" used throughout the present specification refers to an atomic group derived by removing the OH group from a carboxyl group of a carboxylic acid, and it is preferably a $C^{2-7}$ acyl group (an atomic group derived by removing the OH group from a carboxyl group of a $C^{2-7}$ carboxylic acid (more preferably fatty acid)), of which preferred examples include acetyl, propionyl, butyryl and benzoyl.

The term "$C_{6-14}$ aromatic hydrocarbon ring group" used throughout the present specification refers to an aromatic hydrocarbon ring group composed of 6 to 14 carbons, and includes monocyclic groups as well as fused rings such as bicyclic and tricyclic groups. As specific examples of such groups there may be mentioned phenyl, indenyl, 1-naphthyl, 2-naphthyl, azulenyl, heptalenyl, biphenyl, indacenyl, acenaphthyl, fluorenyl, phenalenyl, phenanthrenyl, anthracenyl, cyclopentacyclooctenyl and benzocyclooctenyl.

The term "5- to 14-membered aromatic heterocyclic group" used throughout the present specification refers to a monocyclic, bicyclic or tricyclic 5- to 14-membered aromatic heterocyclic group comprising one or more hetero atoms selected from the group consisting of nitrogen, sulfur and oxygen. As specific examples of such groups there may be mentioned (i) nitrogen-containing aromatic heterocyclic groups such as pyrrolyl, pyridyl, pyridazinyl, pyrimidinyl, pyrazinyl, triazolyl, tetrazolyl, benzotriazolyl, pyrazolyl, imidazolyl, benzimidazolyl, indolyl, isoindolyl, indolidinyl, purinyl, indazolyl, quinolyl, isoquinolyl, quinolidyl, phthalazyl, naphthylidinyl, quinoxalyl, quinazolinyl, cinnolinyl, pteridinyl, imidazotriazinyl, pyrazinopyridazinyl, acridinyl, phenanthridinyl, carbazolyl, carbazolinyl, perimidinyl, phenanthrolinyl, phenacenyl, imidazopyridinyl, imidazopyrimidinyl, pyrazolopyridinyl, pyrazolopyridinyl, etc.; (ii) sulfur-containing aromatic heterocyclic groups such as thienyl, benzothienyl, etc.; (iii) oxygen-containing aromatic heterocyclic groups such as furyl, pyranyl, cyclopentapyranyl, benzofuryl, isobenzofuryl, etc.; and (iv) aromatic heterocyclic groups containing 2 or more different hetero atoms, such as thiazolyl, isothiazolyl, benzothiazolyl, benzothiadiazolyl, phenothiazinyl, isoxazolyl, furazanyl, phenoxazinyl, oxazolyl, isoxazolyl, benzoxazolyl, oxadiazolyl, pyrazoloxazolyl, imidazothiazolyl, thienofuranyl, furopyrrolyl, pyridoxazinyl, etc.

The term "5- to 14-membered non-aromatic heterocyclic group" used throughout the present specification refers to a monocyclic, bicyclic or tricyclic 5- to 14-membered non-aromatic heterocyclic group comprising one or more hetero atoms selected from the group consisting of nitrogen, sulfur and oxygen. As specific examples of such groups there may be mentioned pyrrolidyl, pyrrolyl, piperidyl, piperazyl, imidazolyl, pyrazolidyl, imidazolidyl, morpholyl, tetrahydrofuryl, tetrahydropyranyl, aziridinyl, oxiranyl and oxathiolanyl. Non-aromatic heterocyclic groups also include a pyridone ring-derived group, and a non-aromatic fused ring (for example, a phthalimide ring-derived group and a succinimide ring-derived group).

The term "5- to 8-membered heterocycle" used throughout the present specification refers to a 5- to 8-membered aromatic or non-aromatic heterocycle.

The term "aryl" used throughout the present specification refers to an atomic group remaining after elimination of one hydrogen atom bonded to the ring of the aromatic hydrocarbon, and there may be mentioned phenyl, tolyl, xylyl, biphenyl, naphthyl, anthoryl and phenanthoryl.

The term "alkylidene" used throughout the present specification refers to a divalent group derived by the loss of two hydrogen atoms from the same carbon of an aliphatic hydrocarbon (preferably a $C_{1-6}$ alkane), and there may be mentioned ethylidene and the like.

The expression "optionally substituted" appearing throughout the present specification has the same meaning as "having one or multiple substituents in any desired combination at substitutable positions".

The term "hetero atom" used throughout the present specification refers specifically to oxygen, sulfur, nitrogen, phosphorus, arsenic, antimony, silicon, germanium, tin, lead, boron, mercury and the like, and preferably oxygen, sulfur and nitrogen.

Throughout the present specification, the prefix "n-" signifies a normal type or primary substituent, "sec-" signifies a secondary substituent, "t-" signifies a tertiary substituent and "i-" signifies an iso type substituent.

The definitions of ring B, $R^{101}$, $R^{102}$, $R^{103}$, $R^5$, $R^6$, $Y^1$, $Y^2$, and Ar in the compounds of the invention represented by the general formula (I) above are as explained above, but ring B is preferably a benzene ring or a 6-membered aromatic heterocycle containing 1 or 2 nitrogen atoms, with benzene ring and pyridine ring being more preferred. Thus, as more preferred examples among compounds with a benzene ring as ring B there may be mentioned a compound represented by the formula:

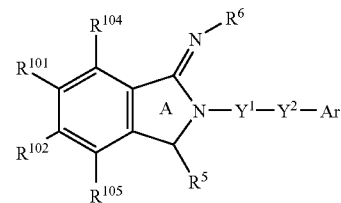

[wherein $R^{104}$ and $R^{105}$ are the same or different and each represents hydrogen, $C_{1-6}$ alkoxy, $C_{1-6}$ alkyl or halogen; and $R^{101}$, $R^{102}$, $R^5$, $R^6$, $Y^1$, $Y^2$ and Ar have the same definitions given above].

As more preferred examples among compounds with a 6-membered aromatic heterocycle containing 1 or 2 nitrogen atoms as ring B there may be mentioned a compound represented by the formula:

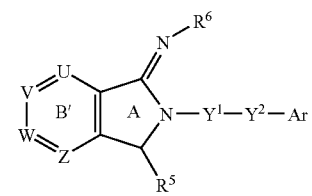

[wherein U represents N or CH (preferably N); V represents N or $CR^{101}$ (preferably $CR^{101}$); W represents N or $CR^{102}$; Z represents N or $CR^{105}$; one or two atoms selected from U, V, W and Z are N; and $R^{101}$, $R^{102}$, $R^{105}$, $R^5$, $R^6$, $Y^1$, $Y^2$ and Ar have the same definitions given above].

Also, $R^{101}$, $R^{102}$ and $R^{103}$ are each preferably a group selected from the group consisting of hydrogen, halogen, $C_{1-6}$ alkyl, $C_{1-6}$ alkylaminocarbonyl, $C_{1-6}$ alkoxy, $C_{1-6}$ alkylamino and $C_{3-8}$ cycloalkyl.

$R^5$ is preferably a group selected from the group consisting of hydrogen, $C_{1-6}$ alkyl and $C_{1-6}$ alkoxy-$C_{1-6}$ alkyl, and $R^6$ is preferably a group selected from the group consisting of hydrogen, $C_{1-6}$ alkyl and $C_{1-6}$ alkyloxycarbonyl optionally substituted with acyloxy.

$Y^1$ preferably represents a single bond or —$(CH_2)_m$— [wherein m represents an integer of 1 to 3] and $Y^2$ preferably represents a single bond or —CO—, there being more preferred (i) a combination that $Y^1$ is —$CH_2$— and $Y^2$ is —CO—, and (ii) a combination that $Y^1$ and $Y^2$ are both single bonds.

Ar preferably represents hydrogen or a group represented by the formula:

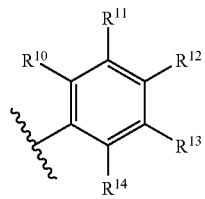

(II)

[wherein $R^{10}$, $R^{11}$, $R^{12}$, $R^{13}$ and $R^{14}$ have the same definitions given above].

(i) When $Y^1$ is —$CH_2$— and $Y^2$ is —CO—, Ar is preferably a group represented by the general formula (II) above, and (ii) when $Y^1$ and $Y^2$ are both single bonds, Ar is preferably hydrogen.

$R^{10}$, $R^{11}$, $R^{12}$, $R^{13}$ and $R^{14}$ are the same or different and are each preferably a group selected from the group consisting of hydrogen, $C_{1-6}$ alkyl, hydroxyl, $C_{1-6}$ alkoxy, $C_{1-6}$ alkylamino, $C_{3-8}$ cycloalkylamino, acylamino, a 5- to 14-membered non-aromatic heterocyclic group and $C_{1-6}$ alkyloxycarbonyloxy, and especially $R^{10}$ and $R^{14}$ are more preferably hydrogen. Also, $R^{11}$ and $R^{12}$ or $R^{12}$ and $R^{13}$ may bond together to form a 5- to 8-membered heterocyclic ring (i) optionally having 1 to 4 hetero atoms selected from N, S and O and (ii) optionally substituted with at least one group selected from the group consisting of cyano, oxo, and $C_{1-6}$ alkyl, acyl, $C_{1-6}$ alkanoyl, carboxyl, carbamoyl, $C_{1-6}$ alkoxycarbonyl, $C_{1-6}$ alkylaminocarbonyl, hydroxyl, $C_{1-6}$ alkoxy, $C_{3-8}$ cycloalkyloxy, amino, $C_{1-6}$ alkylamino, sulfonyl and a 5- to 14-membered non-aromatic heterocyclic group, each optionally substituted with at least one group selected from Substituent Group F" below:

<Substituent Group F"> The group consisting of $C_{1-6}$ alkyl, oxo, cyano, acyl, carboxyl and $C_{1-6}$ alkoxy.

The preferred group for (ii) above is the group consisting of cyano, oxo, $C_{1-6}$ alkyl, cyano-$C_{1-6}$ alkyl, $C_{1-6}$ acyl, carboxyl, $C_{1-6}$ alkoxycarbonyl, $C_{1-6}$ alkylaminocarbonyl, hydroxyl and $C_{1-6}$ alkoxy.

Thus, as more preferred examples for Ar when $R^{10}$ and $R^{14}$ are hydrogen there may be mentioned a group represented by the formula:

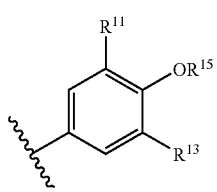

(IV)

[wherein $R^{11}$ and $R^{13}$ have the same definitions given above, $R^{15}$ represents (1) hydrogen or (2) a group selected from Substituent Group H above, and $R^{11}$ and $R^{15}$ may bond together to form a 5- to 8-membered heterocycle optionally substituted with at least one group selected from Substituent Group F above and optionally having 1 or 2 hetero atoms selected from N, S and O];

a group represented by the formula:

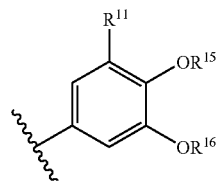

(V)

[wherein $R^{11}$ and $R^{15}$ have the same definitions given above, $R^{16}$ represents (1) hydrogen or (2) a group selected from Substituent Group H above, and $R^{11}$ and $R^{15}$ or $R^{15}$ and $R^{16}$ may bond together to form a 5- to 6-membered heterocycle optionally substituted with at least one group selected from Substituent Group F above and optionally having 1 or 2 hetero atoms selected from N, S and O];

and a group represented by the formula:

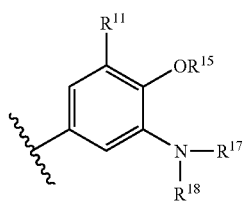

(VI)

[wherein $R^{11}$ and $R^{15}$ have the same definitions given above, $R^{17}$ and $R^{18}$ are the same or different and each represents (1) hydrogen or (2) a group selected from Substituent Group I, and $R^{11}$ and $R^{15}$, $R^{15}$ and $R^{17}$, $R^{15}$ and $R^{18}$ or $R^{17}$ and $R^{18}$ may bond together to form a 5- to 8-membered heterocycle optionally substituted with at least one group selected from Substituent Group F above and optionally having 1 or 2 hetero atoms selected from N, S and O].

The term "salt" used throughout the present specification is not particularly restrictive so long as the salt is formed with a compound of the invention and is pharmacologically acceptable, but preferably there may be mentioned hydrogen halide acid salts (for example, hydrofluoride, hydrochloride, hydrobromide and hydroiodide), inorganic acid salts (for example, sulfate, nitrate, perchlorate, phosphate, carbonate and bicarbonate), organic carboxylate (for example, acetate, trifluoroacetate, oxalate, maleate, tartarate, fumarate and citrate), organosulfonate (for example, methanesulfonate, trifluoromethanesulfonate, ethanesulfonate, benzenesulfonate, toluenesulfonate and camphorsulfonate), amino acid salts (for example, aspartate and glutamate), quaternary amine salts, alkali metal salts (for example, sodium salts and potassium salts) or alkaline earth metal salts (for example, magnesium salts and calcium salts), and more preferred as "pharmacologically acceptable salts" are hydrochloride, oxalate, trifluoroacetate and the like.

The following may be mentioned as specific preferred examples of the compounds of the invention represented by the general formula (I) and their salts explained above.

2-[2-(3,5-di-tert-butyl-4-hydroxy-phenyl)-2-oxo-ethyl]-6-ethoxy-3-imino-2,3-dihydro-1H-isoindole-5-carboxylic acid methylamide trifluoroacetate; 2-[2-(3,5-di-tert-butyl-4-hydroxy-phenyl)-2-oxo-ethyl]-6-dimethylamino-3-imino-2,3-dihydro-1H-isoindole-5-carboxylic acid methylamide hydrobromide; 1-(3,5-di-tert-butyl-4-hydroxy-phenyl)-2-(7- fluoro-1-imino-5,6-dimethoxy-1,3-dihydro-isoindol-2-yl)-ethanone hydrobromide; 1-(8-tert-butyl-4-methyl-3,4-dihydro-2H-benzo[1,4]oxazin-6-yl)-2-(5,6-diethoxy-7-fluoro-1-imino-1,3-dihydro-isoindol-2-yl)-ethanone hydrobromide; 2-[2-(3-tert-butyl-4,5-dimethoxy-phenyl)-2-oxo-ethyl]-6-ethoxy-3-imino-2,3-dihydro-1H-isoindole-5-carboxylic acid methylamide hydrobromide; 1-(3,5-di-tert-butyl-4-hydroxy-phenyl)-2-(5-ethoxy-7-fluoro-1-imino-6-methoxy-1,3-dihydro-isoindol-2-yl)-ethanone hydrobromide; 2-[2-(3-tert-butyl-4-hydroxy-5-isopropoxy-phenyl)-2-oxo-ethyl]-6-ethoxy-3-imino-2,3-dihydro-1H-isoindole-5-carboxylic acid methylamide hydrobromide; 6-[2-(8-tert-butyl-4-methyl-3,4-dihydro-2H-benzo[1,4]oxazin-6-yl)-2-oxo-ethyl]-3-ethoxy-7-imino-6,7-dihydro-5H-pyrrolo[3,4-b]pyridine-2-carboxylic acid methylamide hydrochloride; 2-[2-(7-tert-butyl-3-methyl-3H-benzimidazol-5-yl)-2-oxo-ethyl]-6-ethoxy-3-imino-2,3-dihydro-1H-isoindole-5-carboxylic acid methylamide hydrobromide; 2-[2-(3-tert-butyl-5-dimethylamino-4-hydroxy-phenyl)-2-oxo-ethyl]-6-ethoxy-3-imino-2,3-dihydro-1H-isoindole-5-carboxylic acid methylamide hydrobromide; 5-{2-tert-butyl-4-[2-(2-cyclopropyl-7-imino-5,7-dihydro-pyrrolo[3,4-b]pyridin-6-yl)-acetyl]-6-(pyrrolidin-1-yl)-phenoxy}-pentanoic acid trifluoroacetate; 5-{2-tert-butyl-4-[2-(7-fluoro-1-imino-5,6-dimethoxy-1,3-dihydro-isoindol-2-yl)-acetyl]-6-(pyrrolidin-1-yl)-phenoxy}-pentanoic acid trifluoroacetate; 2-[2-(3-tert-butyl-5-dimethylamino-4-methoxy-phenyl)-2-oxo-ethyl]-6-ethoxy-3-imino-2,3-dihydro-1H-isoindole-5-carboxylic acid methylamide hydrobromide; 2-(1-(3-tert-butyl-5-[2-(7-fluoro-1-imino-5,6-dimethoxy-1,3-dihydro-isoindol-2-yl)-acetyl]-2-methoxy-phenyl)-pyrrolidin-3-yloxy)-butyric acid trifluoroacetate; 2-(1-{3-tert-butyl-5-[2-(7-fluoro-1-imino-5,6-dimethoxy-1,3-dihydro-isoindol-2-yl)-acetyl]-2-methoxy-phenyl)-pyrrolidin-3-yloxy)-butyric acid trifluoroacetate; 1-(3-tert-butyl-5-dimethylamino-4-methoxy-phenyl)-2-(7-fluoro-1-imino-5,6-dimethoxy-1,3-dihydro-isoindol-2-yl)-ethanone hydrobromide; 2-[2-(3-tert-butyl-5-dimethylamino-4-methoxy-phenyl)-2-oxo-ethyl]-6-dimethylamino-3-imino-2,3-dihydro-1H-isoindole-5-carboxylic acid methylamide hydrobromide; 6-[2-(3-tert-butyl-5-dimethylamino-4-methoxy-phenyl)-2-oxo-ethyl]-3-ethoxy-7-imino-6,7-dihydro-5H-pyrrolo[3,4-b]pyridine-2-carboxylic acid methylamide hydrochloride; 2-[2-(3-tert-butyl-5-ethoxy-4-methoxy-phenyl)-2-oxo-ethyl]-6-dimethylamino-3-imino-2,3-dihydro-1H-isoindole-5-carboxylic acid methylamide hydrobromide; 2-[2-(3-tert-butyl-5-ethoxy-4-methoxy-phenyl)-2-oxo-ethyl]-6-ethoxy-3-imino-2,3-dihydro-1H-isoindole-5-carboxylic acid methylamide hydrobromide; 1-(3-tert-butyl-5-ethoxy-4-methoxy-phenyl)-2-(5,6-diethoxy-7-fluoro-1-imino-1,3-dihydro-isoindol-2-yl)-ethanone hydrobromide; 6-[2-(3-tert-butyl-5-ethoxy-4-methoxy-phenyl)-2-oxo-ethyl]-3-ethoxy-7-imino-6,7-dihydro-5H-pyrrolo[3,4-b]pyridine-2-carboxylic acid methylamide trifluoroacetate; {3-tert-butyl-5-[2-(7-fluoro-1-imino-5,6-dimethoxy-1,3-dihydro-isoindol-2-yl)-acetyl]-2-methoxy-phenoxy}-acetonitrile hydrobromide; 4-(3-tert-butyl-5-[2-(7-fluoro-1-imino-5,6-dimethoxy-1,3-dihydro-isoindol-2-yl)-acetyl]-2-methoxy-phenoxy)-butyronitrile hydrobromide; 2-[2-(3-tert-butyl-5-cyanomethoxy-4-methoxy-phenyl)-2-oxo-ethyl]-6-dimethylamino-3-imino-2,3-dihydro-1H-isoindole-5-carboxylic acid methylamide hydrobromide; 2-{2-[3-tert-butyl-5-(3-cyano-propoxy)-4-methoxy-phenyl]-2-oxo-ethyl}-6-dimethylamino-3-imino-2,3-dihydro-1H-isoindole-5-carboxylic acid methylamide hydrobromide; 2-[2-(8-tert-butyl-4-cyanomethyl-3,4-dihydro-2H-benzo[1,4]oxazin-6-yl)-2-oxo-ethyl]-6-ethoxy-3-imino-2,3-dihydro-1H-isoindole-5-carboxylic acid methylamide trifluoroacetate; 6-[2-(8-tert-butyl-4-cyanomethyl-3,4-dihydro-2H-benzo[1,4]oxazin-6-yl)-2-oxo-ethyl]-3-ethoxy-7-imino-6,7-dihydro-5H-pyrrolo[3,4-b]pyridine-2-carboxylic acid methylamide trifluoroacetate; (8-tert-butyl-6-[2-(7-fluoro-1-imino-5,6-dimethoxy-1,3-dihydro-isoindol-2-yl)-acetyl]-2,3-dihydro-benzo[1,4]oxazin-4-yl)-acetonitrile trifluoroacetate; {8-tert-butyl-6-[2-(5,6-diethoxy-7-fluoro-1-imino-1,3-dihydro-isoindol-2-yl)-acetyl]-2,3-dihydro-benzo[1,4]oxazin-4-yl}-acetonitrile trifluoroacetate; (8-tert-butyl-6-[2-(2-cyclopropyl-7-imino-5,7-dihydro-pyrrolo[3,4-b]pyridin-6-yl)-acetyl]-2,3-dihydro-benzo[1,4]oxazin-4-yl)-acetonitrile trifluoroacetate; 2-[2-(8-tert-butyl-4-cyanomethyl-3,4-dihydro-2H-benzo[1,4]oxazin-6-yl)-2-oxo-ethyl]-6-dimethylamino-3-imino-2,3-dihydro-1H-isoindole-5-carboxylic acid methylamide trifluoroacetate; 2-[2-(3-tert-butyl-5-cyanomethoxy-4-methoxy-phenyl)-2-oxo-ethyl]-6-ethoxy-3-imino-2,3-dihydro-1H-isoindole-5-carboxylic acid methylamide hydrobromide; 2-(2-[3-tert-butyl-5-(3-cyano-propoxy)-4-methoxy-phenyl]-2-oxo-ethyl}-6-ethoxy-3-imino-2,3-dihydro-1H-isoindole-5-carboxylic acid methylamide hydrobromide; 1-(3-tert-butyl-S-ethoxy-4-methoxy-phenyl)-2-(7-fluoro-1-imino-5,6-dimethoxy-1,3-dihydro-isoindol-2-yl)-ethanone hydrobromide; 2-[2-(3-tert-butyl-4-methoxy-5-morpholino-phenyl)-2-oxo-ethyl]-6-ethoxy-3-imino-2,3-dihydro-1H-isoindole-5-carboxylic acid methylamide hydrobromide; 1-(3-tert-butyl-4-methoxy-5-morpholino-phenyl)-2-(7-fluoro-1-imino-5,6-dimethoxy-1,3-dihydro-isoindol-2-yl)-ethanone hydrobromide; 1-(3-tert-butyl-4-methoxy-5-morpholino-phenyl)-2-(2-cyclopropyl-7-imino-5,7-dihydro-pyrrolo[3,4-b]pyridin-6-yl)-ethanone hydrobromide; (3-tert-butyl-5-[2-(5,6-diethoxy-7-fluoro-1-imino-1,3-dihydro-isoindol-2-yl)-acetyl]-2-methoxy-phenoxy)-acetonitrile hydrobromide; 4-{3-tert-butyl-5-[2-(5,6-diethoxy-7-fluoro-1-imino-1,3-dihydro-isoindol-2-yl)-acetyl]-2-methoxy-phenoxy)-butyronitrile hydrobromide; 4-{3-tert-butyl-5-[2-(2-cyclopropyl-7-imino-5,7-dihydro-pyrrolo[3,4-b]pyridin-6-yl)-acetyl]-2-methoxy-phenoxy}-butyronitrile hydrobromide; 1-(3-tert-butyl-5-dimethylamino-4-methoxy-phenyl)-2-(5,6-diethoxy-7-fluoro-1-imino-1,3-dihydro-isoindol-2-yl)-ethanone hydrobromide; 1-(3-tert-butyl-4-methoxy-5-morpholino-phenyl)-2-(5,6-diethoxy-7-fluoro-1-imino-1,3-dihydro-isoindol-2-yl)-ethanone hydrobromide; 6-[2-(3-tert-butyl-4-methoxy-5-morpholino-phenyl)-2-oxo-ethyl]-3-ethoxy-7-imino-6,7-dihydro-5H-pyrrolo[3,4-b]pyridine-2-carboxylic acid methylamide hydrobromide; 2-tert-butyl-4-[2-(5-ethoxy-1-imino-6-methylcarbamoyl-1,3-dihydro-isoindol-2-yl)-acetyl]-phenyl methanesulfonate hydrobromide; 2-tert-butyl-4-[2-(5-dimethylamino-1-imino-6-methylcarbamoyl-1,3-dihydro-isoindol-2-yl)-acetyl]-phenyl methanesulfonate hydrobromide; 2-tert-butyl-4-[2-(3-ethoxy-7-imino-2-methylcarbamoyl-5,7-dihydro-pyrrolo[3,4-b]pyridin-6-yl)-acetyl]-phenyl methanesulfonate hydrobromide; 2-[2-(3-tert-butyl-4-cyanomethoxy-5-dimethylamino-phenyl)-2-oxo-ethyl]-6-dimethylamino-3-imino-2,3-dihydro-1H-isoindole-5-carboxylic acid methylamide hydrobromide; 2-[2-(3-tert-butyl-4-methoxy-5-(pyrrolidin-1-yl)-phenyl)-2-oxo-ethyl]-6-ethoxy-3-imino-2,3-dihydro-1H-isoindole-5-carboxylic acid methylamide hydrobromide; 1-(3-tert-butyl-4-methoxy-5-(pyrrolidin-1-yl)-phenyl)-2-(5,6-diethoxy-7-fluoro-1-imino-1,3-dihydro-isoindol-2-yl)-ethanone hydrobromide; 2-[2-(3-tert-butyl-4-methoxy-5-(pyrrolidin-1-yl)-phenyl)-2-oxo-ethyl]-6-dimethylamino-3-imino-2,3-dihydro-1H-isoindole-5-carboxylic acid methylamide hydrobromide; 1-(3-tert-butyl-4-methoxy-5-(pyrrolidin-1-yl)-phenyl)-2-(2- cyclopropyl-7-imino-5,7-dihydro-pyrrolo[3,4-b]pyridine-6-yl)-ethanone hydrobromide; 1-(3-tert-butyl-4-methoxy-5-(pyrrolidin-1-yl)-phenyl)-2-(7-fluoro-1-imino-5,6-dimethoxy-1,3-dihydro-isoindol-2-yl)-ethanone hydrobromide; 2-[2-(3-tert-butyl-5-isopropoxy-4-methoxy-phenyl)-2-oxo-ethyl]-6-ethoxy-3-imino-2,3-dihydro-1H-isoindole-5-carboxylic acid methylamide hydrobromide; 1-(3-tert-butyl-5-isopropoxy-4-methoxy-phenyl)-2-(5,6-diethoxy-7-fluoro-1-imino-1,3-dihydro-isoindol-2-yl)-ethanone hydrobromide; 1-(3-tert-butyl-5-isopropoxy-4-methoxy-phenyl)-2-(7-fluoro-1-imino-5,6-dimethoxy-1,3-dihydro-isoindol-2-yl)-ethanone hydrobromide; ethyl 2-{8-tert-butyl-6-[2-(5-ethoxy-1-imino-6-methylcarbamoyl-1,3-dihydro-isoindol-2-yl)-acetyl}-2,3-dihydro-benzo[1,4]oxazin-4-yl)-propionate hydrochloride; ethyl 2-{8-tert-butyl-6-[2-(3-ethoxy-7-imino-2-methylcarbamoyl-5,7-dihydro-pyrrolo[3,4-b]pyridin-6-yl)-acetyl]-2,3-dihydro-benzo[1,4]oxazin-4-yl}-propionate hydrochloride; 2-[2-(3-dimethylamino-5-isopropyl-4-methoxy-phenyl)-2-oxo-ethyl]-6-ethoxy-3-imino-2,3-dihydro-1H-isoindole-5-carboxylic acid methylamide hydrobromide; 2-(5,6-diethoxy-7-fluoro-1-imino-1,3-dihydro-isoindol-2-yl)-1-(3-dimethylamino-5-isopropyl-4-methoxy-phenyl)-ethanone hydrobromide; 2-[2-(3-tert-butyl-4-methoxy-5-methylamino-phenyl)-2-oxo-ethyl]-6-ethoxy-3-imino-2,3-dihydro-1H-isoindole-5-carboxylic acid methylamide hydrobromide; 6-[2-(3-tert-butyl-5-isopropoxy-4-methoxy-phenyl)-2-oxo-ethyl]-3-ethoxy-7-imino-6,7-dihydro-5H-pyrrolo[3,4-b]pyridine-2-carboxylic acid methylamide trifluoroacetate; 2-[2-(3-tert-butyl-5-isopropoxy-4-methoxy-phenyl)-2-oxo-ethyl]-6-dimethylamino-3-imino-2,3-dihydro-1H-isoindole-5-carboxylic acid methylamide trifluoroacetate; 2-{2-[3-tert-butyl-5-(4-cyano-piperidin-1-yl)-4-methoxy-phenyl]-2-oxo-ethyl}-6-ethoxy-3-imino-2,3-dihydro-1H-isoindole-5-carboxylic acid methylamide hydrobromide; 1-(3-tert-butyl-4-hydroxy-phenyl)-2-(5,6-diethoxy-7-fluoro-1-imino-1,3-dihydro-isoindol-2-yl)-ethanone hydrobromide; 2-{8-tert-butyl-6-[2-(5-ethoxy-1-imino-6-methylcarbamoyl-1,3-dihydro-isoindol-2-yl)-acetyl]-2,3-dihydro-benzo[1,4]oxazin-4-yl}-2-methyl-propanoic acid hydrochloride; 2-{8-tert-butyl-6-[2-(3-ethoxy-7-imino-2-methylcarbamoyl-5,7-dihydro-pyrrolo[3,4-b]pyridin-6-yl)-acetyl]-2,3-dihydro-benzo[1,4]oxazin-4-yl}-2-methyl-propanoic acid hydrochloride; 2-tert-butyl-6-dimethylamino-4-[2-(5-ethoxy-1-imino-6-methylcarbamoyl-1,3-dihydro-isoindol-2-yl)-acetyl]-phenyl acetate hydrobromide; 2-{2-[3-tert-butyl-4-methoxy-5-(2-oxo-oxazolidin-3-yl)-phenyl]-2-oxo-ethyl}-6-ethoxy-3-imino-2,3-dihydro-1H-isoindole-5-carboxylic acid methylamide hydrobromide; 2-tert-butyl-4-[2-(5,6-diethoxy-7-fluoro-1-imino-1,3-dihydro-isoindol-2-yl)-acetyl]-phenyl acetate hydrobromide; 2-tert-butyl-4-[2-(5-ethoxy-1-imino-6-methylcarbamoyl-1,3-dihydro-isoindol-2-yl)-acetyl]-phenyl acetate hydrobromide; 1-{3-tert-butyl-5-[2-(5,6-diethoxy-7-fluoro-1-imino-1,3-dihydro-isoindol-2-yl)-acetyl]-2-methoxy-phenyl}-piperidin-4-one hydrobromide; 1-(3-tert-butyl-5-dimethylamino-4-methoxy-phenyl)-2-(5-ethoxy-7-fluoro-1-imino-6-methoxy-1,3-dihydro-isoindol-2-yl)-ethanone hydrobromide; 2-{2-[3-tert-butyl-5-(ethyl-methyl-amino)-4-methoxy-phenyl]-2-oxo-ethyl}-6-ethoxy-3-imino-2,3-dihydro-1H-isoindole-5-carboxylic acid methylamide hydrobromide; 6-{2-[3-tert-butyl-5-(ethyl-methyl-amino)-4-methoxy-phenyl]-2-oxo-ethyl}-3-ethoxy-7-imino-6,7-dihydro-5H-pyrrolo[3,4-b]pyridine-2-carboxylic acid methylamide trifluoroacetate; 2-tert-butyl-4-[2-(5,6-diethoxy-7-fluoro-1-imino-1,3-dihydro-isoindol-2-yl)-acetyl]-6-dimethylamino-phenyl methanesulfonate hydrobromide; 1-[3-tert-butyl-5-(4-hydroxy-piperidin-1-yl)-4-methoxy-phenyl]-2-(5,6-diethoxy-7-fluoro-1-imino-1,3-dihydro-isoindol-2-yl)-ethanone hydrobromide; 6-{2-[3-tert-butyl-5-(4-hydroxy-piperidin-1-yl)-4-methoxy-phenyl]-2-oxo-ethyl}-3-ethoxy-7-imino-6,7-dihydro-5H-pyrrolo[3,4-b]pyridine-2-carboxylic acid methylamide trifluoroacetate; 1-[3-tert-butyl-5-(4-hydroxy-piperidin-1-yl)-4-methoxy-phenyl]-2-(7-fluoro-1-imino-5,6-dimethoxy-1,3-dihydro-isoindol-2-yl)-ethanone hydrobromide; 1-(3-tert-butyl-5-dimethylamino-4-hydroxy-phenyl)-2-(5,6-diethoxy-7-fluoro-1-imino-1,3-dihydro-isoindol-2-yl)-ethanone hydrobromide; 6-[2-(3-tert-butyl-5-dimethylamino-4-ethoxy-phenyl)-2-oxo-ethyl]-3-ethoxy-7-imino-6,7-dihydro-5H-pyrrolo[3,4-b]pyridine-2-carboxylic acid methylamide trifluoroacetate; 2-[2-(3-tert-butyl-5-dimethylamino-4-methoxy-phenyl)-2-oxo-ethyl]-6-dimethylamino-3-imino-2,3-dihydro-1H-isoindole-5-carboxylic acid methylamide hydrobromide; 1-(3-tert-butyl-4-methoxy-5-methylamino-phenyl)-2-(5,6-diethoxy-7-fluoro-1-imino-1,3-dihydro-isoindol-2-yl)-ethanone hydrobromide; 1-[3-tert-butyl-5-(4-hydroxy-piperidin-1-yl)-4-methoxy-phenyl]-2-(5-ethoxy-7-fluoro-1-imino-6-methoxy-1,3-dihydro-isoindol-2-yl hydrobromide; 2-(5,6-diethoxy-7-fluoro-1-imino-1,3-dihydro-isoindol-2-yl)-1-[3-dimethylamino-5-(1-fluoro-1-methyl-ethyl)-4-methoxy-phenyl]-ethanone hydrobromide; 1-[3-tert-butyl-5-(3-hydroxy-pyrrolidin-1-yl)-4-methoxy-phenyl]-2-(5,6-diethoxy-7-fluoro-1-imino-1,3-dihydro-isoindol-2-yl)-ethanone trifluoroacetate; 2-[2-(3-tert-butyl-5-ethylamino-4-methoxy-phenyl)-2-oxo-ethyl]-6-ethoxy-3-imino-2,3-dihydro-1H-isoindole-5-carboxylic acid methylamide hydrobromide; 2-[2-(3-tert-butyl-5-ethylamino-4-methoxy-phenyl)-2-oxo-ethyl]-6-ethoxy-3-imino-2,3-dihydro-1H-isoindole-5-carboxylic acid methylamide hydrobromide; 1-(3-tert-butyl-5-ethoxy-4-hydroxy-phenyl)-2-(5,6-diethoxy-7-fluoro-1-imino-1,3-dihydro-isoindol-2-yl)-ethanone hydrobromide; 2-[2-(3-tert-butyl-5-ethoxy-4-hydroxy-phenyl)-2-oxo-ethyl]-6-ethoxy-3-imino-2,3-dihydro-1H-isoindole-5-carboxylic acid methylamide hydrobromide; 2-tert-butyl-4-[2-(5,6-diethoxy-7-fluoro-1-imino-1,3-dihydro-isoindol-2-yl)-acetyl]-6-ethoxy-phenyl ethyl-carbamate hydrobromide; 2-tert-butyl-6-ethoxy-4-[2-(5-ethoxy-1-imino-6-methylcarbamoyl-1,3-dihydro-isoindol-2-yl)-acetyl]-phenyl ethyl-carbamate hydrobromide; 2-tert-butyl-6-(3-cyano-propoxy)-4-[2-(5,6-diethoxy-7-fluoro-1-imino-1,3-dihydro-isoindol-2-yl)-acetyl]-phenyl methanesulfonate hydrobromide; 1-(3-tert-butyl-4-methoxy-5-piperazin-1-yl-phenyl)-2-(5,6-diethoxy-7-fluoro-1-imino-1,3-dihydro-isoindol-2-yl)-ethanone dihydrochloride; 2-(2-{3-tert-butyl-4-methoxy-5-[(2-methoxyethyl)-methylamino]-phenyl}-2-oxo-ethyl)-6-dimethylamino-3-imino-2,3-dihydro-1H-isoindole-5-carboxylic acid methylamide hydrobromide; 1-[3-tert-butyl-5-(2-hydroxyethylamino)-4-methoxy-phenyl]-2-(5,6-diethoxy-7-fluoro-1-imino-1,3-dihydro-isoindol-2-yl)-ethanone hydrochloride; 1-{3-tert-butyl-5-[(2-hydroxyethyl)-methylamino]-4-methoxy-phenyl}-2-(5,6-diethoxy-7-fluoro-1-imino-1,3-dihydro-isoindol-2-yl)-ethanone dihydrochloride; 2-{2-[3-tert-butyl-5-(3,4-dihydroxy-pyrrolidin-1-yl)-4-methoxy-phenyl]-2-oxo-ethyl}-6-ethoxy-3-imino-2,3-dihydro-1H-isoindole-5-carboxylic acid methylamide trifluoroacetate; 1-[3-tert-butyl-5-(3-hydroxy-4-methoxy-pyrrolidin-1-yl)-4-methoxy-phenyl]-2-(5,6-diethoxy-7-fluoro-1-imino-1,3-dihydro-isoindol-2-yl)-ethanone trifluoroacetate; (3-tert-butyl-5-[2-(5,6-diethoxy-7-fluoro-1-imino-1,3-dihydro-isoindol-2-yl)-acetyl]-2-methoxy-phenylamino)-acetonitrile hydrobromide; 1-(3-tert-butyl-4-hydroxy-5-morpholino-phenyl)-2-(5,6-diethoxy-7-fluoro-1-imino-1,3-dihydroisoindol-2-yl)-ethanone hydrochloride; 1-{3-tert-butyl-5-[ethyl-(2-hydroxyethyl)-amino]-4-methoxy-phenyl}-2-(5,6-diethoxy-7-fluoro-1-imino-1,3-dihydro-isoindol-2-yl)-acetyl hydrochloride; (4-{3-tert-butyl-5-[2-(5,6-diethoxy-7-fluoro-1-imino-1,3-dihydro-isoindol-2-yl)-acetyl]-2-methoxy-phenyl}-piperazin-1-yl)-acetonitrile hydrobromide; 2-(2-{3-tert-butyl-5-[(2-hydroxyethyl)-methylamino]-4-methoxy-phenyl}-2-oxo-ethyl)-6-dimethylamino-3-imino-2,3-dihydro-1H-isoindole-5-carboxylic acid methylamide dihydrochloride; 1-{3-tert-butyl-5-[(3-hydroxypropyl)-methylamino]-4-methoxy-phenyl}-2-(5,6-diethoxy-7-fluoro-1-imino-1,3-dihydro-isoindol-2-yl)-ethanone dihydrochloride; 1-{3-tert-butyl-5-[(2-hydroxyethyl)-(2-methoxyethyl)-amino]-4-methoxy-phenyl}-2-(5,6-diethoxy-7-fluoro-1-imino-1,3-dihydro-isoindol-2-yl)-ethanone dihydrochloride; 1-[3-tert-butyl-5-(3-hydroxy-4-methoxy-pyrrolidin-1-yl)-4-methoxy-phenyl]-2-(5,6-diethoxy-7-fluoro-1-imino-1,3-dihydro-isoindol-2-yl)-ethanone trifluoroacetate; 1-(3-amino-5-tert-butyl-4-methoxy-phenyl)-2-(5,6-diethoxy-7-fluoro-1-imino-1,3-dihydro-isoindol-2-yl)-ethanone hydrobromide; 2-[2-(3-tert-butyl-5-isopropylamino-4-methoxy-phenyl)-2-oxo-ethyl]-6-ethoxy-3-imino-2,3-dihydro-1H-isoindole-5-carboxylic acid methylamide hydrobromide; 1-[3-(4-acetyl-piperazin-1-yl)-5-tert-butyl-4-methoxy-phenyl]-2-(5,6-diethoxy-7-fluoro-1-imino-1,3-dihydro-isoindol-2-yl)-ethanone hydrobromide; 1-[3-tert-butyl-5-(3-hydroxy-4-methoxy-pyrrolidin-1-yl)-4-methoxy-phenyl]-2-(5,6-diethoxy-7-fluoro-1-imino-1,3-dihydro-isoindol-2-yl)-ethanone trifluoroacetate; 1-[3-tert-butyl-5-(3,4-dimethoxy-pyrrolidin-1-yl)-4-methoxy-phenyl]-2-(5,6-diethoxy-7-fluoro-1-imino-1,3-dihydro-isoindol-2-yl)-ethanone hydrobromide; (4-{3-tert-butyl-5-[2-(5,6-diethoxy-7-fluoro-1-imino-1,3-dihydro-isoindol-2-yl)-acetyl]-2-methoxy-phenyl}-piperazin-1-yl)-acetic acid dihydrochloride; 1-{3-tert-butyl-5-[4-(2-hydroxy-acetyl)-piperazin-1-yl]-4-methoxy-phenyl}-2-(5,6-diethoxy-7-fluoro-1-imino-1,3-dihydro-isoindol-2-yl)-ethanone hydrobromide; 4-{3-tert-butyl-5-[2-(5,6-diethoxy-7-fluoro-1-imino-1,3-dihydro-isoindol-2-yl)-acetyl]-2-methoxy-phenyl}-piperazine-1-carboxylic acid ethylamide hydrobromide; ethyl (4-{3-tert-butyl-5-[2-(5,6-diethoxy-7-fluoro-1-imino-1,3-dihydro-isoindol-2-yl)-acetyl]-2-methoxy-phenyl)-piperazin-1-yl)-acetate dihydrochloride; 1-(3-tert-butyl-4-methoxy-5-[4-(2-methoxy-acetyl)-piperazin-1-yl]-phenyl}-2-(5,6-diethoxy-7-fluoro-1-imino-1,3-dihydro-isoindol-2-yl)-ethanone hydrobromide; 1-(4-{3-tert-butyl-5-[2-(5,6-diethoxy-7-fluoro-1-imino-1,3-dihydro-isoindol-2-yl)-acetyl]-2-methoxy-phenyl}-piperazin-1-yl)-propan-1-one hydrobromide; 1-[3-tert-butyl-5-(3-ethoxy-4-hydroxy-pyrrolidin-1-yl)-4-methoxy-phenyl]-2-(5,6-diethoxy-7-fluoro-1-imino-1,3-dihydro-isoindol-2-yl)-ethanone trifluoroacetate; 1-(3,5-di-tert-butyl-4-hydroxy-phenyl)-2-(7-imino-2-methyl-5,7-dihydro-pyrrolo[3,4-b]pyridin-6-yl)-ethanone hydrochloride; 1-(3,5-di-tert-butyl-4-hydroxy-phenyl)-2-(3-ethoxy-7-imino-2,4-dimethyl-5,7-dihydro-pyrrolo[3,4-b]pyridin-6-yl)-ethanone hydrobromide; 2-[2-(3,5-di-tert-butyl-4-hydroxy-phenyl)-2-oxo-ethyl]-6-ethoxy-3-imino-2,3-dihydro-1H-isoindole-5-carboxamide hydrobromide; 2-[2-(8-tert-butyl-4-methyl-3,4-dihydro-2H-benzo[1,4]oxazin-6-yl)-2-oxo-ethyl]-6-ethoxy-3-imino-2,3-dihydro-1H-isoindole-5-carboxylic acid methylamide hydrobromide; 6-[2-(3,5-di-tert-butyl-4-hydroxy-phenyl)-2-oxo-ethyl]-3-ethoxy-7-imino-6,7-dihydro-5H-pyrrolo[3,4-b]pyridine-2-carboxylic acid methylamide hydrochloride; 1-(3,5-di-tert-butyl-4-hydroxy-phenyl)-2-(2-ethyl-7-imino-5,7-dihydro-pyrrolo[3,4-b]pyridin-6-yl)-ethanone hydrobromide; 2-(2-cyclopropyl-7-imino-5,7-dihydro-pyrrolo[3,4-b]pyridin-6-yl)-ethanone)-1-(3,5-di-tert-butyl-4-hydroxy-phenyl)-ethanone hydrobromide; 2-[2-(8-tert-butyl-3-oxo-3,4-dihydro-2H-benzo[1,4]oxazin-6-yl)-2-oxo-ethyl]-6-ethoxy-3-imino-2,3-dihydro-1H-isoindole-5-carboxylic acid methylamide hydrobromide; and 1-(3-tert-butyl-5-isopropylamino-4-methoxy-phenyl)-2-(5,6-diethoxy-7-fluoro-1-imino-1,3-dihydro-isoindol-2-yl)-ethanone hydrobromide.

Production processes for compounds of the invention and salts thereof will now be described. Various processes are possible for production of the compounds of the invention represented by the general formula (I) above and their salts, and the synthesis may be carried out by ordinary organic synthesis methods. The following representative production processes will now be presented.

[Representative Production Processes]

Compounds represented by the general formulas (A1-c) and (A1-c'), which are aromatic or heteroaromatic ring-fused cyclic amidines, may be synthesized from (A1-a) and (A1-b) by the methods described later.

<Production Process A>

A process of synthesizing the aromatic or heteroaromatic ring-fused cyclic amidine compounds (A1-c) and (A1-c'), and compound (A3-b), imino-protected compound (A1-c).

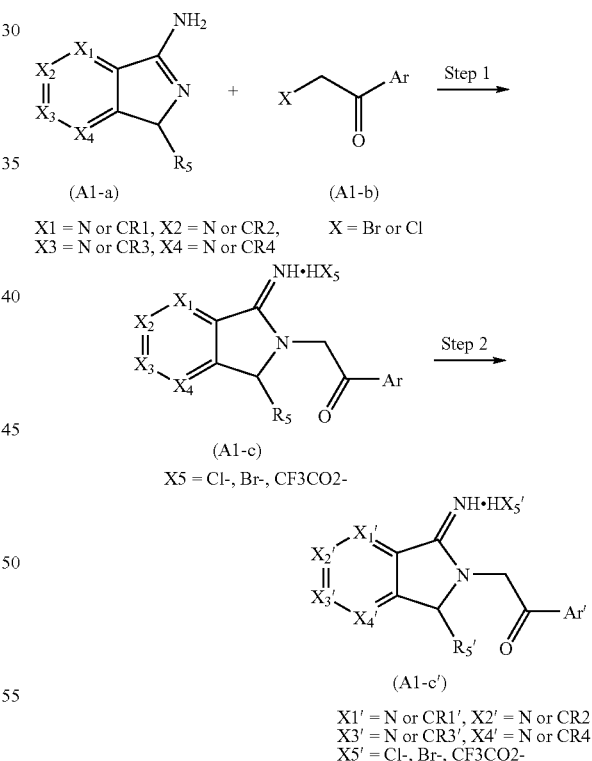

This scheme is a method of synthesizing (A1-c) from (A1-a) and (A1-b) by the methods described later.

In the formulas, Ar and Ar' have the same definition as Ar in the compounds represented by formula (I) in claim 1. R1, R2, R3, R4 and R5, and R1', R2', R3', R4' and R5' are defined in Production Process B onward.

Step 1 is a coupling reaction between compounds (A1-a) and (A1-b). Compound (A1-c) may be obtained from these compounds by dissolving both compounds in dimethylformamide, acetonitrile, an alcohol or the like, and selecting the temperature conditions from room temperature to reflux temperature. As an alternative method, (A1-a) may be reacted with sodium hydride in a solvent such as tetrahydrofuran or dimethylformamide and then reacted with (A1-b) at room temperature or while cooling on ice to obtain a salt free form of (A1-c), which may then be treated with any of various acids. Preferably, it is reacted with a 5 N hydrogen chloride or 5 N hydrogenbromide acetic acid solution in an organic solvent to yield (A1-c) as an ammonium salt.

Step 2 is a step of partial structural modification after Step 1 to yield compound (A1-c'). In this step, in cases where (A1-c) contains a tert-butyl group as the protecting group of carboxyl or a tert-butyloxycarbonyl group as the protecting group of amino or amide hydrogen, deprotection is accomplished by reaction with 5 N hydrogen chloride in an organic solvent such as ethyl acetate or dioxane, using trifluoroacetic acid, if necessary diluting with dichloromethane, to yield (A1-c'). When (A1-c) contains an alkyl ester, heating to reflux may be accomplished in concentrated hydrochloric acid for hydrolysis to yield (A1-c') as a carboxylic acid. When (A1-c) contains tetrahydropyranyl, methoxymethyl or trialkylsilyl as a hydroxyl-protecting group, it may be deprotected by using 5 N hydrogen chloride in a water-containing organic solvent such as ethyl acetate and dioxane, trifluoroacetic acid or dilute hydrogen chloride in a solvent such as tetrahydrofuran and an alcohol, to yield (A1-c'). When (A1-c) contains benzyl as the protecting group for hydroxyl or carboxyl, or when it contains a double bond, the deprotecting reaction or conversion to a saturated compound may be accomplished by hydrogenation in a solvent such as ethyl acetate or an alcohol, in the presence of a metal catalyst such as palladium hydroxide, to yield (A1-c'). When (A1-c) has carboxyl, it may be converted to an ester under acidic alcohol conditions or to an amide derivative under condensing conditions to yield (A1-c'). When (A1-c) has cyano, it may be converted to a carboxylic acid or carboxamide under hydrolyzing conditions to yield (A1-c').

The term "5- to 14-membered aromatic heterocyclic group" used throughout the present specification refers to a monocyclic, bicyclic or tricyclic 5- to 14-membered aromatic heterocyclic group comprising one or more hetero atoms selected from the group consisting of nitrogen, sulfur and oxygen. As specific examples of such groups there may be mentioned (i) nitrogen-containing aromatic heterocyclic groups such as pyrrolyl, pyridyl, pyridazinyl, pyrimidinyl, pyrazinyl, triazolyl, tetrazolyl, benzotriazolyl, pyrazolyl, imidazolyl, benzimidazolyl, indolyl, isoindolyl, indolidinyl, purinyl, indazolyl, quinolyl, isoquinolyl, quinolidyl, phthalazyl, naphthylidinyl, quinoxalyl, quinazolinyl, cinnolinyl, pteridinyl, imidazotriazinyl, pyrazinopyridazinyl, acridinyl, phenanthridinyl, carbazolyl, carbazolinyl, perimidinyl, phenanthrolinyl, phenacenyl, imidazopyridinyl, imidazopyrimidinyl, pyrazolopyridinyl, etc.; (ii) sulfur-containing aromatic heterocyclic groups such as thienyl, benzothienyl, etc.; (iii) oxygen-containing aromatic heterocyclic groups such as furyl, pyranyl, cyclopentapyranyl, benzofuryl, isobenzofuryl, etc.; and (iv) aromatic heterocyclic groups containing 2 or more different hetero atoms, such as thiazolyl, isothiazolyl, benzothiazolyl, benzothiadiazolyl, phenothiazinyl, isoxazolyl, furazanyl, phenoxazinyl, oxazolyl, isoxazolyl, benzoxazolyl, oxadiazolyl, pyrazoloxazolyl, imidazothiazolyl, thienofuranyl, furopyrrolyl, pyridoxazinyl, etc.

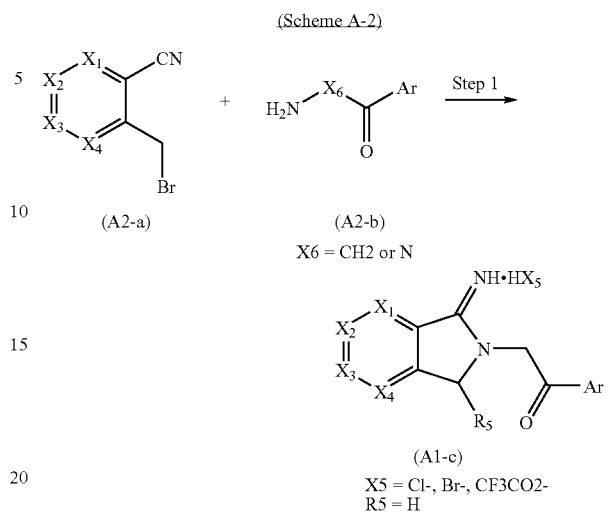

This scheme is a method synthesizing compound (A1-c) from compounds (A2-a) and (A2-b). The compound represented by (A2-a) is one of the intermediates shown in Production Processes B to H, or a compound which can be easily converted from one of the intermediates.

In the formulas, Ar has the same definition as Ar in the compound represented by formula (I) in claim 1. X1, X2, X3 and X4 have the same definitions as X1, X2, X3 and X4 in Scheme A-1.

Step 1 is a reaction for alkylation of the amino group and subsequent ring closure of the secondary amine produced thereby, in an one-pot synthesis. The both compounds are reacted in a dimethylformamide solvent from room temperature to 100° C. However, when the compound represented by (A2-b) is an amine salt, the reaction is conducted in the presence of 1,8-diazabicyclo[5.4.0]undec-7-ene.

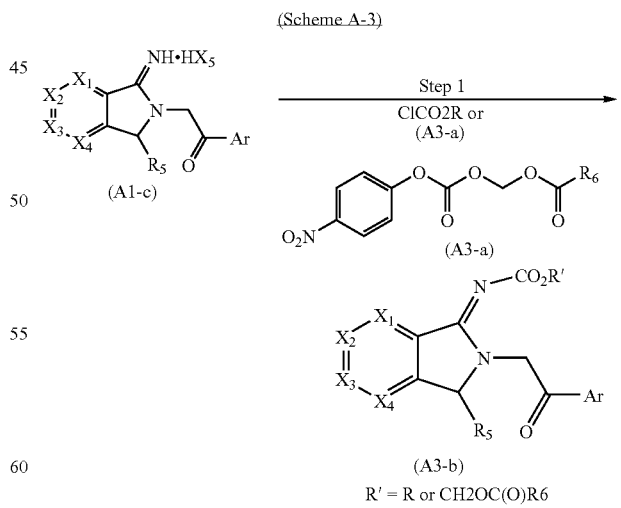

This scheme is a method of protecting the imino group of compound (A1-c). In the formulas, Ar has the same definition as Ar in the compound represented by formula (I) in claim 1. X1, X2, X3, X4 and R5 have the same definitions as X1, X2, X3, X4 and R5 in Scheme A-1. R represents optionally substituted alkyl or alkenyl, and R6 represents alkyl.

Step 1 is a reaction for introduction of a substituent at the imino group. An alkyl chlorocarbonate or a carbonate having nitrophenol as a leaving group (A3-a), is reacted therewith by reaction in a two-layer system using a base such as a 1 N aqueous sodium hydroxide solution or saturated bicarbonate water, in a solvent such as tetrahydrofuran, to yield (A3-b).

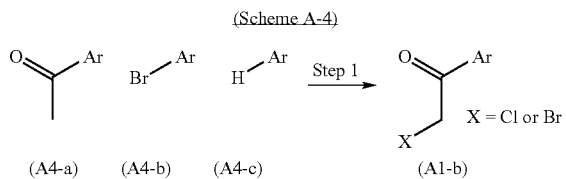

This scheme is a method of synthesizing a 2-halogeno-1-ethanone derivative represented by (A1-b) in Scheme A-1 from (A4-a), (A4-b) or (A4-c). In the formulas, Ar has the same definition as Ar in the compound represented by formula (I) in claim 1.

Step 1 is carried out by the following 3 methods corresponding to the starting compounds (A4-a), (A4-b) and (A4-c), respectively.

(1) Compound (A4-a) may be treated with a halogenating reagent in the presence of an appropriate solvent to yield (A1-b). Preferably, (A4-a) is continuously treated with tert-butyldimethylsilyl trifluoromethanesulfonate, N-bromosuccinimide or N-chlorosuccinimide in tetrahydrofuran in the presence of triethylamine, to yield (A1-b). More preferably, (A4-a) is treated with tetrabutylammonium tribromide in a solvent mixture of dichloromethane and methanol or in acetic acid to yield (A1-b).

(2) After introducing ethanolether as a methyl ketone equivalent at the bromide position of (A4-b) by Stille coupling in an appropriate solvent, the resulting compound may be treated with a halogenating reagent to yield (A1-b). Preferably, (A4-b) is treated with tributyl(1-ethoxyvinyl)tin, tetrakis(triphenylphosphine)palladium and cesium fluoride in toluene or 1,4-dioxane while heating and ethyl vinyl ether is introduced, and then halogenation is carried out with N-bromosuccinimide or N-chlorosuccinimide to yield (A1-b). Alternatively, introduction of ethyl vinyl ether at the bromide position of (A4-b) may be followed by treatment with preferably 5 N hydrochloric acid-acetone under appropriate acidic conditions to yield (A4-a).

(3) Compound (A4-c) may be treated with a Lewis acid catalyst and Friedel-Crafts acylating reagent in an appropriate solvent to directly yield (A1-b). Preferably, (A4-c) is treated with bromoacetyl chloride or chloroacetyl chloride in dichloromethane in the presence of aluminum chloride to yield (A1-b).

An aromatic or heteroaromatic ring-fused amidine represented by (A1-a) may be synthesized by either Production Process B or C below. Production Process B is a process utilizing a regioselective reduction reaction on a phthalonitrile derivative.

<Production Process B>

A process for synthesis of an aromatic or heteroaromatic ring-fused amidine represented by (A1-a) as the starting material for Scheme A-1 of Production Process A, utilizing a regioselective reduction reaction on a phthalonitrile derivative.

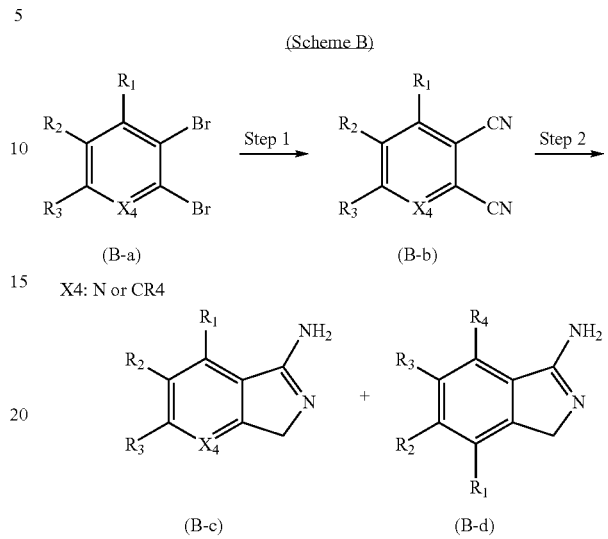

This scheme is a method of synthesizing benzamidine derivatives (B-c) and (B-d) from compound (B-a). The definition of X4 in the formulas is the same as X4 in Scheme A-1 of Production Process A. R1 and R4 represent hydrogen, halogeno, optionally substituted alkyl or optionally substituted alkoxy. R2 and R3 represent hydrogen, halogeno, optionally substituted alkyl, optionally substituted alkenyl, optionally substituted alkoxy, optionally substituted amino, optionally substituted carboxyl, optionally substituted aminocarbonyl, optionally substituted aminosulfonyl, optionally substituted sulfonylamino or optionally substituted alkanoylamino.

Step 1 is a reaction for introduction of a cyano group. Compound (B-b) may be obtained by heating compound (B-a) and copper (I) cyanide at 140–160° C. in a solvent such as dimethylformamide, dimethylsulfoxide, N-methylpiperidone or hexamethylphosphoramide or a mixture thereof.

Step 2 is a reaction of regioselective reduction of (B-b) and subsequent ring closure of the resulting amine in the system. The reaction conditions may be selected from the following 4 types: 1) hydrogenation reaction using a metal catalyst such as platinum oxide, platinum-carbon or palladium-carbon in a solvent such as ethyl acetate or an alcohol or a mixture thereof, at room temperature and normal pressure, 2) hydride reduction by reaction with diisobutyl aluminum hydride, lithium aluminum hydride or the like on ice or at room temperature in a solvent such as tetrahydrofuran or diethyl ether, 3) reaction with sodium borohydride in the presence of trifluoroacetic acid, 4) reaction with sodium borohydride in the presence of cobalt chloride or the like. Compound (B-d) is also obtained as a result of the substitution on (B-b), but it may be separated and purified by silica gel column chromatography, and both isomers may be used for the reaction represented by Scheme A-1. When a benzylamine derivative is obtained which does not undergo ring closure under reducing reaction conditions, it may be adsorbed onto silica gel and allowed to stand at room temperature from 3 hours to 1 day to yield a cyclic amidine (A1-a).

Compound (B-a) and (B-b) above may also be purchased, or optionally synthesized by any of the methods from Scheme B-1 to Scheme B-15 described below.

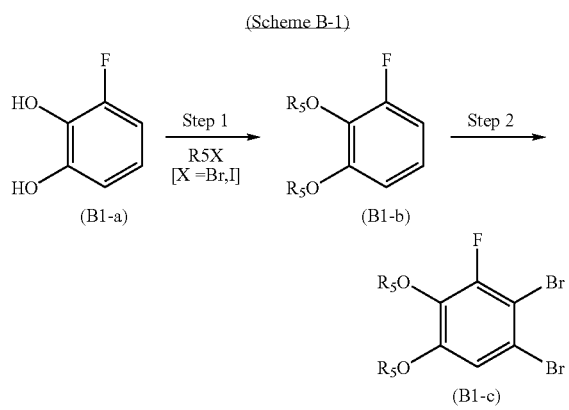

This scheme is a general synthesis method for a fluorocatechol derivative. In the formulas, R5 represents an optionally substituted alkyl or cycloalkyl.

Step 1 is a method for alkylation of the two hydroxyl groups of (B1-a). Compound (B1-b) may be obtained by reaction with an alkyl halide in a solvent such as dimethylformamide, acetonitrile or acetone in the presence of an inorganic base such as potassium carbonate or cesium carbonate, at a temperature from room temperature to reflux temperature.

Step 2 is a step of regioselective dibromination. Compound (B1-c) may be obtained by a method of reaction with bromine or N-bromosuccinimide in a solvent such as an alcohol or acetonitrile, either while cooling on ice or at room temperature, or by a method of reaction with bromine in an acetic acid solvent in the presence of sodium acetate, from room temperature to 80° C.

Conversion of an alkyl group of compound (B1-c) may be accomplished by the following method.

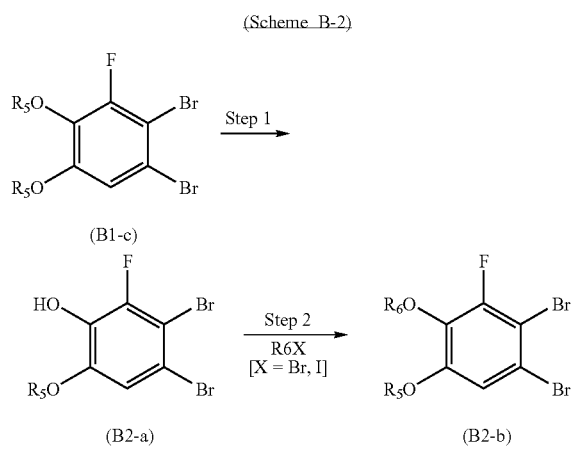

This scheme is a method for synthesis of a fluorocatechol derivative (B2-b) with different substituents. In the formulas, R5 and R6 each represent an optionally substituted alkyl or cycloalkyl.

Step 1 is a step of selective removal of an alkyl group. Compound (B2-a) may be obtained by reaction with two equivalents of aluminum chloride in dichloromethane, from freezing to room temperature.

Step 2 is a step of alkylation, where compound (B2-b) may be obtained similarly to Step 1 of Scheme B-1.

Hydroxyl may then be reductively removed from compound (B2-a).

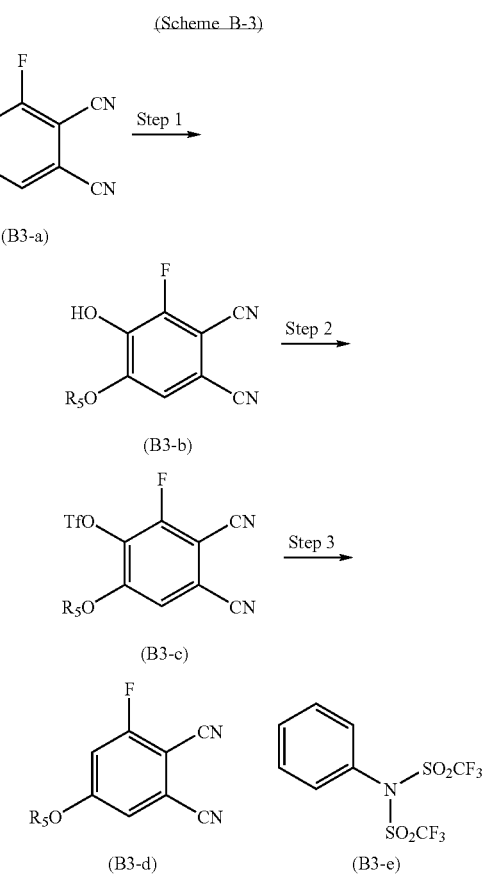

This scheme is a method for synthesis of compound (B3-d) from compound (B3-a). In the formulas, R5 represents an optionally substituted alkyl or cycloalkyl.

Step 1 is a step of removal of alkyl of the compound represented by (B3-a), which may be synthesized by the method of Scheme B-1. Compound (B3-b) may then be obtained similarly to Step 1 of Scheme B-2.

Step 2 is a step of conversion of hydroxyl to a trifluoromethanesulfonate (triflate). Compound (B3-c) may be obtained by reaction with trifluoromethanesulfonic anhydride in a solvent such as dichloromethane in the presence of a base such as triethylamine or pyridine, or by reaction with compound (B3-e) in the presence of triethylamine or dimethylaminopyridine.

Step 3 is a reaction for reductive removal of the triflate. It may be carried out by heated reaction with a palladium catalyst in dimethylformamide in the presence of formic acid and tributylamine. The palladium catalyst used may be bis(triphenylphosphine)palladium dichloride, and the method is preferably ligand substitution with a bidentate ligand such as diphenylphosphinopropane or the like.

(Scheme B-4)

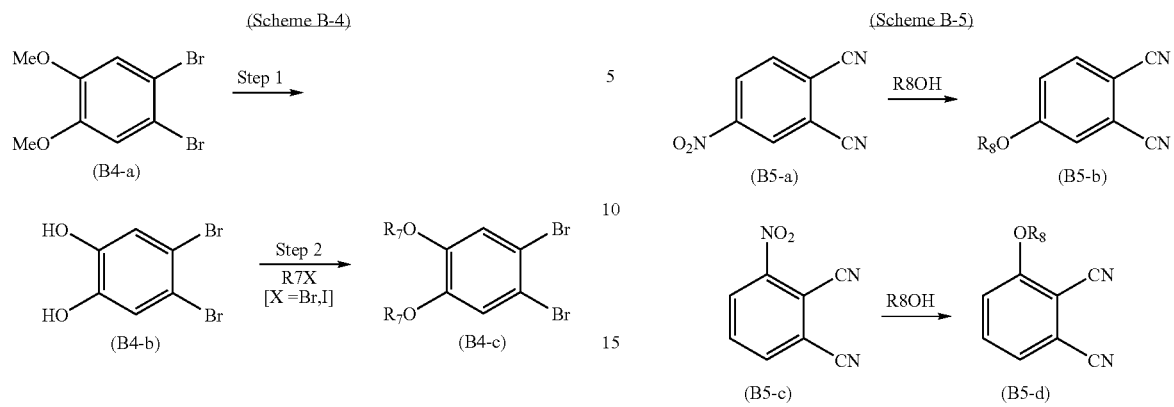

This scheme is a method for synthesis of a catechol derivative from a commercially available compound (B4-a). In the formulas, R7 represents an optionally substituted alkyl or cycloalkyl group.

Step 1 is a dealkylation step. Compound (B4-a) may be reacted with boron tribromide in a solvent such as dichloromethane to yield (B4-b).

Step 2 is an alkylation step. Compound (B4-c) may be obtained similarly to Step 1 of Scheme B-1.

(Scheme B-4')

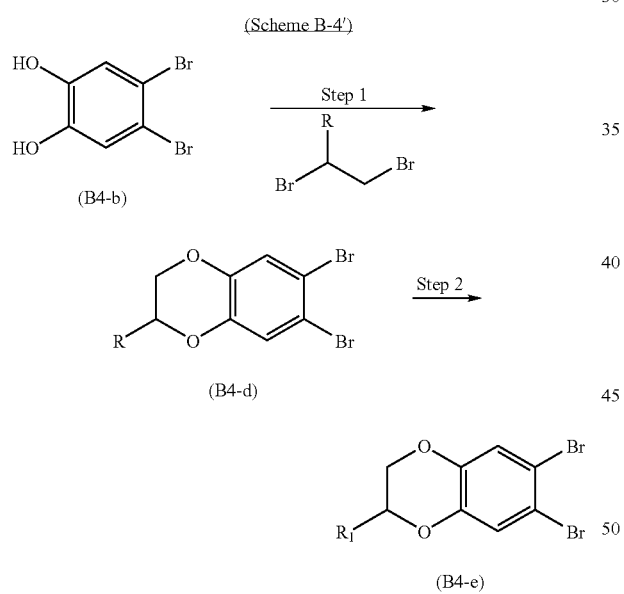

This scheme is a method for synthesis of cyclic catechol derivatives (B4-d) and (B4-e). In the formulas, R represents hydrogen, alkyl or alkyloxycarbonyl. R' represents alkyl optionally substituted with hydroxyl or alkoxy.

Step 1 is a step of alkylation followed by cyclization, and the reaction conditions may be according to the method of alkylation in Step 1 of Scheme B-1.

Step 2 is a substitution reaction wherein R of (B4-d) is alkyloxycarbonyl. Compound (B4-e) may be obtained by reduction of the ester group with lithium borohydride or etherification with sodium hydride and an alkylating agent.

(Scheme B-5)

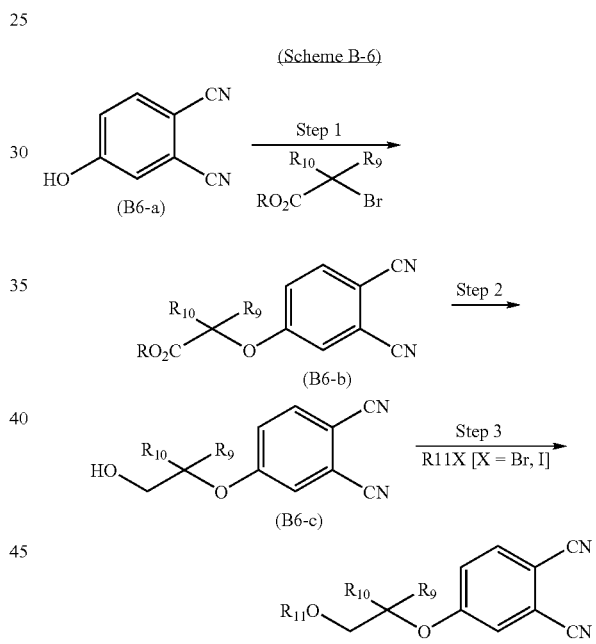

This scheme is a method for synthesis of a monosubstituted alkoxy derivative using a 3- or 4-nitrophthalonitrile substitution reaction, as described in C. C. Leznoff et al., Can. J. Chem., 72, 1990(1994). In the formulas, R8 represents optionally substituted alkyl or cycloalkyl.

(Scheme B-6)

This scheme is a method for synthesis of monosubstituted alkoxy derivatives (B6-b), (B6-c) and (B6-d). In the formulas, R represents alkyl, R9 and R10 represent hydrogen or optionally substituted alkyl, and R11 represents optionally substituted alkyl.

Step 1 is a reaction for alkylation of compound (B6-a). Compound (B6-b) may be obtained similarly to Step 1 of Scheme B-1, using an α-bromoester as the alkylating agent.

Step 2 is a reaction for reduction of an ester. Compound (B6-c) may be obtained by reaction with lithium borohydride in a tetrahydrofuran solution of (B6-b) [R=Et or Me] while cooling on ice.

Step 3 is a step of ether synthesis by alkylation. Compound (B6-d) may be obtained by reaction with sodium hydride in a solvent such as tetrahydrofuran or dimethylformamide, followed by reaction with an alkyl halide.

(Scheme B-7)

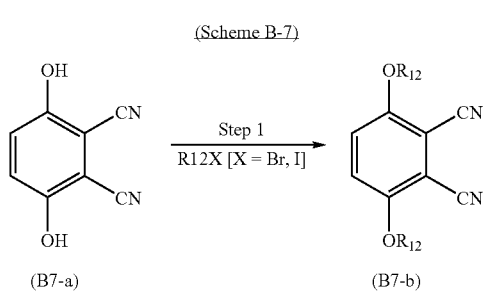

This scheme is a method for synthesis of a para-substituted dialkoxy derivative (B7-b) by alkylation similarly to Step 1 of Scheme B-1. In the formulas, R12 represents optionally substituted alkyl or cycloalkyl.

(Scheme B-8)

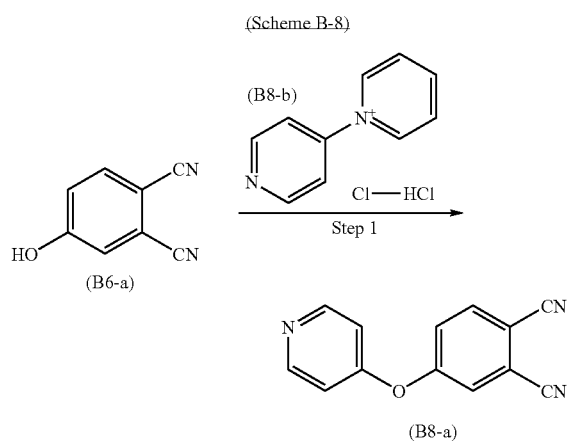

This scheme is a method for synthesis of a 4-pyridinol derivative (B8-a).

Step 1 accomplishes etherification at the 4 position of the pyridine. Compound (B8-a) may be obtained by reaction with compound (B8-b) while heating to reflux in an alcohol solvent, in the presence of aqueous sodium hydroxide.

(Scheme B-9)

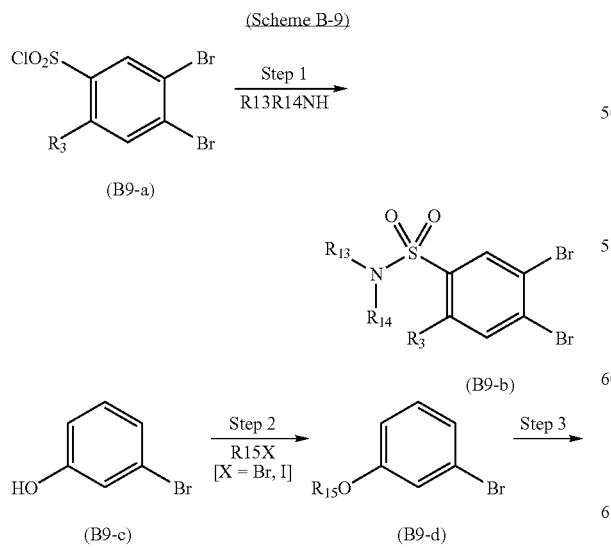

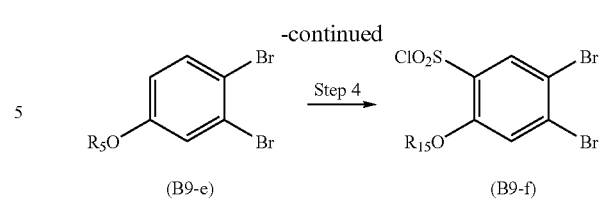

This scheme is a method for synthesis of a substituted sulfonamide derivative (B9-b). In the formulas, R3 represents hydrogen or optionally substituted alkoxy, and R13 and R14 represent hydrogen or optionally substituted alkyl. R13 and R14 may also form a ring with the N. R15 represents optionally substituted alkyl.

Step 1 is a step of amidation. Compound (B9-b) may be obtained by reaction with aqueous ammonia or an aqueous alkylamine solution, or an organic solvent solution, in a solvent such as tetrahydrofuran or dimethylformamide.

Synthesis of compound (B9-f), corresponding to compound (B9-a) wherein R3 is alkoxy, may be carried out in the following manner.

Step 2 is a step of alkylation, which may be carried out similarly to Step 1 of Scheme B-1.

Step 3 is a step of regioselective bromination, which may be carried out similarly to Step 2 of Scheme B-1.

Step 4 is a reaction for introduction of a chlorosulfonyl group. Compound (B9-f) may be obtained by reaction with chlorosulfonic acid in a solvent such as dichloromethane.

(Scheme B-10)

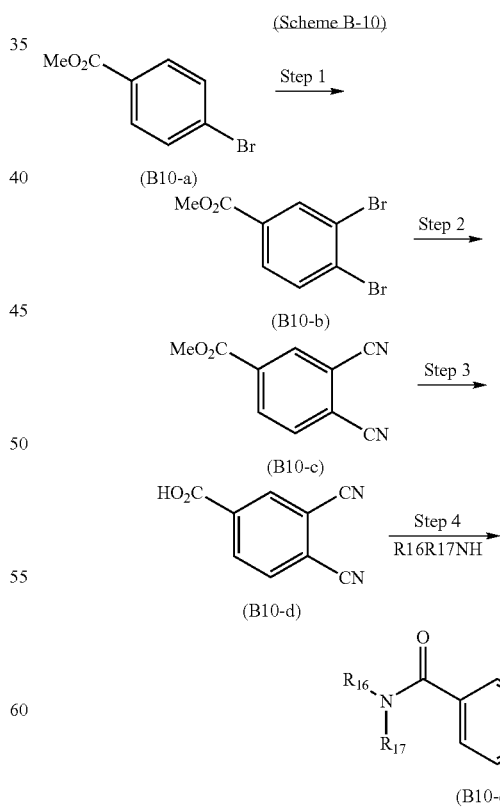

This scheme is a production method for a monosubstituted carboxamide derivative (B10-e) or ester (B10-c). In the formulas, R16 and R17 represent hydrogen or optionally substituted alkyl. R16 and R17 may also form a ring with the N.

Step 1 is a regioselective bromination reaction. Compound (B10-b) may be obtained by reaction with N-bromosuccinimide in concentrated sulfuric acid at room temperature.

Step 2 is a step of dinitrilation similarly to Step 1 of Scheme B.

Step 3 is a step of synthesizing a carboxylic acid from an ester with cyano. Compound (B10-d) may be obtained by reaction with lithium iodide in a dimethylformamide solvent.

Step 4 is a step of amidation. Compound (B10-e) may be obtained by any of the following 3 methods. 1) A method of reaction with an alkyl chlorocarbonate in a solvent such as tetrahydrofuran, ethyl acetate or dichloromethane, in the presence of a base such as triethylamine, to produce a mixed acid anhydride in the reaction system, followed by reaction with an organic solvent solution or aqueous solution of an amine. 2) A method of reaction with an amine together with a condensation agent such as dicyclohexylcarbodiimide or a water-soluble carbodiimide, in a solvent such as tetrahydrofuran, acetonitrile or dichloromethane, in the presence of hydroxybenzotriazole. 3) A method of activation of the carboxyl group with triethylamine and diethyl cyanophosphonate and reaction with an amine.

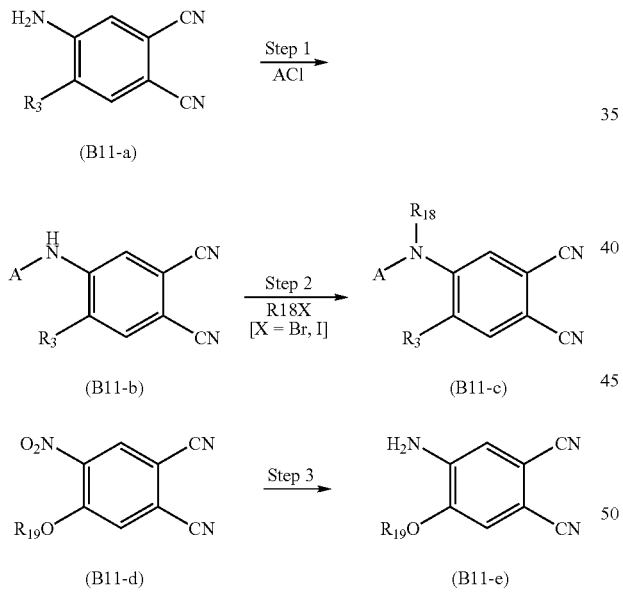

This scheme is a synthesis method for aniline derivatives (B11-b) and (B11-c). In the formulas, A represents alkanoyl, alkylsulfonyl, optionally substituted aminocarbonyl or alkoxycarbonyl. R3 represents hydrogen or optionally substituted alkoxy, and R18 and R19 represent optionally substituted alkyl or cycloalkyl.

Step 1 is a step of introducing a substituent at the amino group. Compound (B11-b) may be obtained by reaction with an acid chloride, alkyl chlorocarbonate or alkylsulfonyl chloride in a solvent such as tetrahydrofuran, ethyl acetate or dichloromethane or in the absence of a solvent, and in the presence of a base such as pyridine, or alternatively for synthesis of a urea derivative, by reaction with triphosgene in the presence of a base such as triethylamine or dimethylaminopyridine followed by reaction with an organic solvent solution or aqueous solution of an amine.

Step 2 is a step of N-alkylation reaction. This may be accomplished by reaction with an alkyl halide in a dimethylsulfoxide solvent, in the presence of sodium hydroxide powder. Alternatively, compound (B11-c) may be obtained by reaction with sodium hydride in a solvent such as tetrahydrofuran or dimethylformamide, followed by reaction with an alkyl halide.

Compound (B11-a) wherein R3 is an alkoxy group may be synthesized in the following manner using compound (B11-d) which can be synthesized by the method described in C. C. Leznoff et al., Can. J. Chem., 73, 435(1995).

Step 3 is a step of reduction of the nitro group to yield an aniline. Compound (B11-e) may be obtained by adding iron powder in an alcohol solvent in the presence of ammonium chloride powder, and heating to reflux.

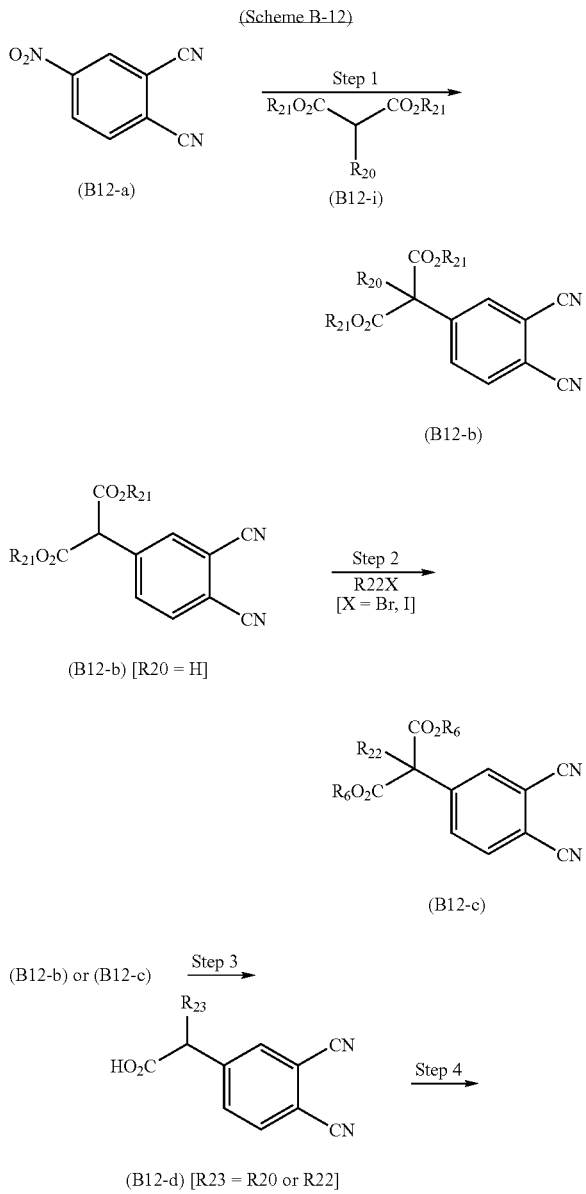

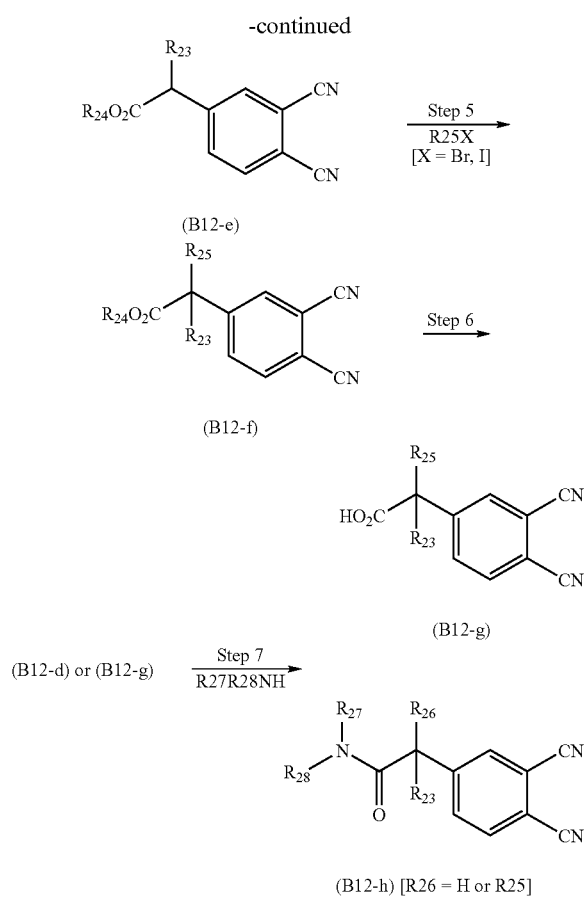

Step 1 is a step of substitution reaction at the nitro group of compound (B12-a) with a malonate derivative. When R20 in compound (B12-i) is hydrogen, compound (B12-b) may be obtained under the conditions described in M. P. Roze et al., Zh. Org. Khim, 28, 827(1992), or when R20 is a group other than hydrogen, it may be obtained by a method of using sodium hydride in dimethylformamide on the corresponding malonate to generate an anion, followed by reaction with compound (B12-a). When R20 is H, an alkyl group may also be introduced in other way.

Step 2 is a step of alkylation on the malonate a-carbon. Compound (B12-c) may be obtained by using sodium hydride in dimethylformamide to generate an anion, followed by reaction with an alkyl halide.

Step 3 is a step of decarboxylation of compound (B12-b) or (B12-c). When $R^{21}$ is ethyl or methyl, compound (B12-d) may be obtained by reaction with aqueous lithium hydroxide in a solvent mixture of tetrahydrofuran and alcohol for hydrolysis, followed by heating to reflux for decarboxylation. When $R^{21}$ is tert-butyl, the dicarboxylic acid obtained by treatment with trifluoroacetic acid may be heated to reflux in xylene for decarboxylation.

Step 4 is a step of esterification. When R24 is methyl, this may be accomplished by reaction with trimethylsilyldiazomethane in an acetonitrile and alcohol solvent. When R24 is tert-butyl, it may be accomplished by reaction with di-tert-butyl dicarbonate in tert-butyl alcohol in the presence of dimethylaminopyridine, or by reaction with dimethylformamide di-tert-butylacetal.

Compounds (B12-f) and (B12-h) having quaternary carbons may also be synthesized.

Step 5 is a step of alkylation of compound (B12-e) [R24=tBu], wherein compound (B12-f) may be obtained similarly to Step 2 above.

Step 6 is a step of conversion to a carboxyl group. Compound (B12-g) may be obtained by dissolution at room temperature in trifluoroacetic acid diluted with an organic solvent such as dichloromethane.

Step 7 is a step of obtaining compound (B12-h) according to the method of Scheme B-10, Step 4, under conditions for amidation of compound (B12-d) or (B12-g).

This scheme is a method for synthesis of phenylacetic acid derivatives (B12-e, f, h). In the formulas, R20 represents hydrogen, optionally substituted alkyl or alkoxy. R21 and R24 represent alkyl, and R22 and R25 represent optionally substituted alkyl. R23 represents R20 or R22, and R26 represents hydrogen or R25. R27 and R28 represent hydrogen or optionally substituted alkyl.

(Scheme B-13)

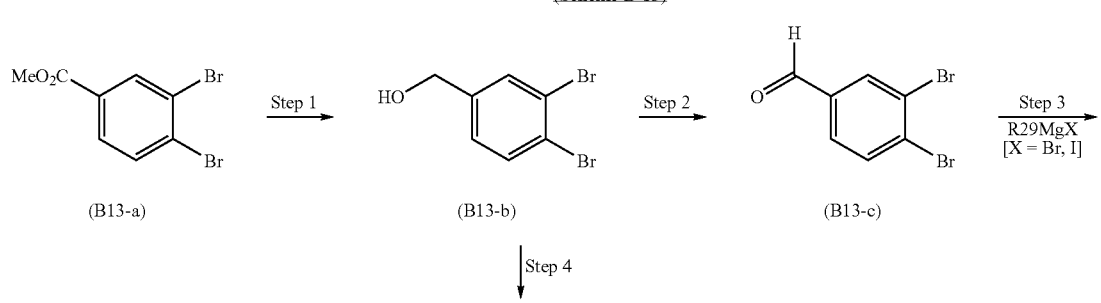

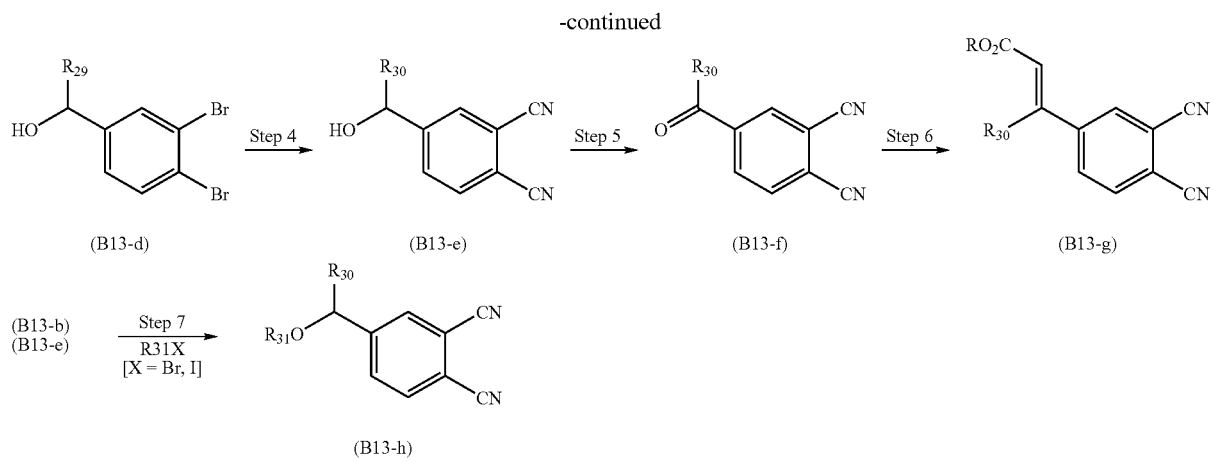

This scheme is a method for synthesis of compounds (B13-e), (B13-g) and (B13-h) from compound (B13-a). In the formulas, R29 and R31 represent optionally substituted alkyl, R30 represents hydrogen or R29, and R represents lower alkyl.

Step 1 is a step of reduction of ester. Compound (B13-b) may be obtained by reaction with lithium borohydride in tetrahydrofuran while cooling on ice.

Step 2 is a step of obtaining compound (B13-c) by Swern oxidation.

Step 3 is a step of introducing an alkyl group. Compound (B13-d) may be obtained by using a Grignard reagent in a solvent such as tetrahydrofuran. The obtained compound (B13-b) or (B13-d) may be converted to a dinitrile (B13-e) by conducting Step 4 using the conditions for Scheme B, Step 1. Conversion to a styrene derivative is also possible.

Step 5 is a step of obtaining compound (B13-f) through oxidation of the hydroxyl group by Swern oxidation.

Step 6 is a step of conversion to a conjugated ester. Compound (B13-g) may be obtained by Horner-Emmons reaction or Wittig reaction. Conversion from (B13-e) to an alkoxy derivative is also possible.

Step 7 is a step of alkylation of the hydroxyl group, wherein compound (B13-h) may be obtained similarly to Scheme B-6, Step 3.

A compound represented by (B-b) in Scheme B may also be synthesized from readily available phthalic anhydride by the method described in D. Wohrle et al., Synthesis, 194 (1993), R. D. George et al., J. Heterocyclic. Chem., 32, 495(1995) or by the method shown in the following Scheme B-14.

(Scheme B-14)

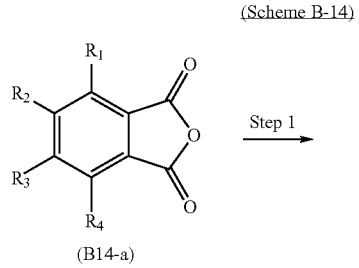

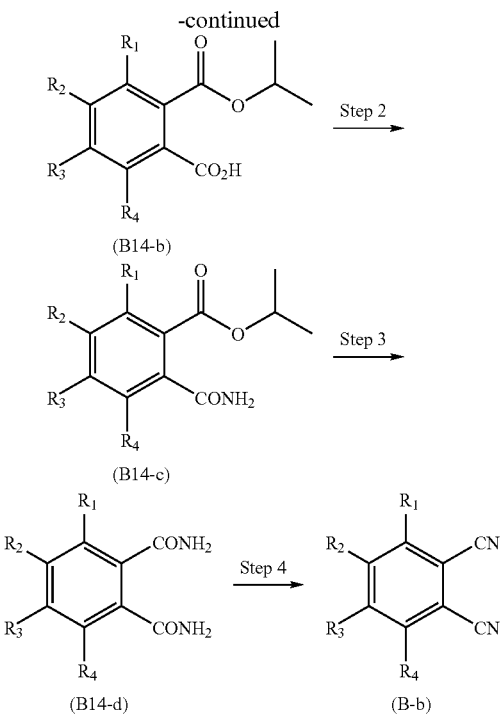

This scheme is a method for synthesis of compound (B-b) using phthalic anhydride as the starting material. R1, R2, R3 and R4 have the same definitions as in Scheme B.

Step 1 is a step of synthesizing a phthalic acid monoester. Compound (B14-b) may be obtained by heating to reflux in isopropanol.

Step 2 is a step of conversion to a carboxamide, wherein compound (B14-c) may be obtained by the method described in Scheme B-10, Step 4.

Step 3 is a step of obtaining a carboxamide from the ester. Compound (B14-d) may be obtained by heating to reflux in an ammonia-saturated alcohol solvent.

Step 4 is a step of synthesizing a nitrile by dehydration of the carboxamide. A compound represented by (B-b) may be obtained by reaction with trifluoroacetic anhydride in a solvent such as tetrahydrofuran in the presence of pyridine, while cooling on ice.

(Scheme B-15)

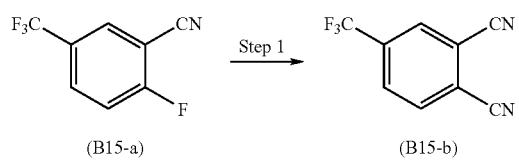

This scheme is a method for converting compound (B15-a) to a dinitrile in a single step to synthesize a trifluoromethyl-substituted derivative (B15-b).

Step 1 is a step of introducing a cyano group. Compound (B15-b) may be obtained by heating a dimethylformamide solution of compound (B15-a) at 110° C. in the presence of sodium cyanide.

The compounds represented by (A1-a) in Production Process A, Scheme A-1 may also be synthesized by the following Production Process C via reduction of an azide group.

<Production Process C>

(Scheme C)

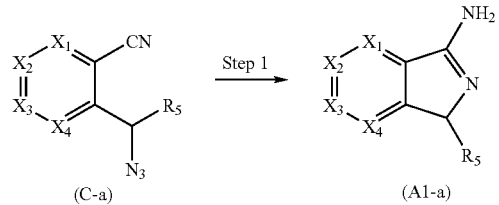

X1 = N or CR1, X2 = N or CR2,
X3 = N or CR3, X4 = N or CR4

This is a process for synthesizing a compound represented by (A1-a) in Production Process A, Scheme A-1 by reduction of the azide group.

In the formulas, R5 represents hydrogen or optionally substituted alkyl.

Step 1 is a step of reducing the azide group of compound (C-a) and synthesizing a cyclic amidine by ring closure of the resulting amine, and compound (A1-a) may be obtained by either of the following two methods. 1) A reaction using an organophosphorus reagent such as triphenylphosphine or triethylphosphine in a hydrous tetrahydrofuran solvent, or 2) a hydrogenation reaction-using a metal catalyst such as palladium-carbon in ethyl acetate, alcohol or a mixture thereof.

A benzylamine derivative may be obtained under reducing reaction conditions without promoting ring closure, by adsorption on silica gel and standing at room temperature from 3 hours to 1 day, to yield a cyclic amidine (A1-a).

A compound represented by (C-a) may be synthesized by selecting any of Production Processes D to H below, which differ mainly in the method of introducing the cyano group and azide group.

<Production Process D>

(Scheme D)

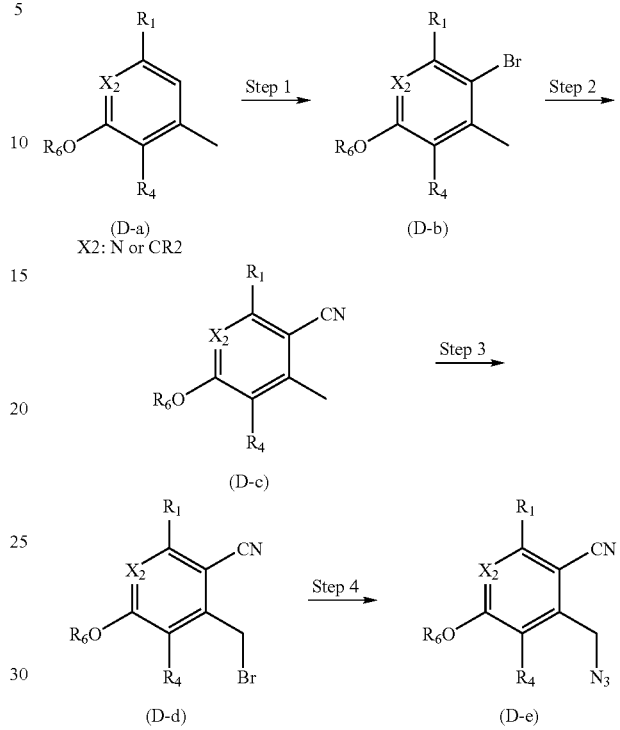

X2: N or CR2

This scheme is a method for synthesis of compound (D-e) from compound (D-a). In the formulas, R1 represents hydrogen, halogeno, optionally substituted alkyl or alkoxy. R2 represents hydrogen, optionally substituted alkyl, optionally substituted alkoxy or optionally substituted amino. R4 represents hydrogen, halogeno or optionally substituted alkoxy. R6 represents optionally substituted alkyl.

Step 1 is a step of regioselective bromination, wherein compound (D-b) may be obtained by the same method as in Scheme B-1, Step 2.

Step 2 is a step of cyanation and may be selected from either of the following two methods. 1) A method of heating together with sodium cyanide, potassium cyanide, zinc cyanide or the like in a solvent such as acetonitrile, propionitrile, valeronitrile or dimethylformamide, in the presence of a palladium catalyst and copper (I) iodide. The palladium catalyst used may be tetrakis(triphenylphosphine)palladium, bis(triphenylphosphine)palladium dichloride, or the like. 2) A method of using copper (I) cyanide as explained in Scheme B, Step 1. Compound (D-c) is preferably obtained by method 1).

Step 3 is a step of introducing a bromo group by radical reaction. Compound (D-d) may be obtained by heating to reflux together with N-bromosuccinimide in a solvent such as carbon tetrachloride or chlorobenzene, in the presence of azoisobutyronitrile or benzoyl peroxide.

Step 4 is a step of introducing an azide group. Compound (D-e) may be obtained by reaction with sodium azide in a dimethylformamide solvent at room temperature while cooling on ice. In Scheme D, the compounds represented by (D-a) to (D-c) may be synthesized by the methods of the following Schemes D-1 to D-4, for example.

(Scheme D-1)

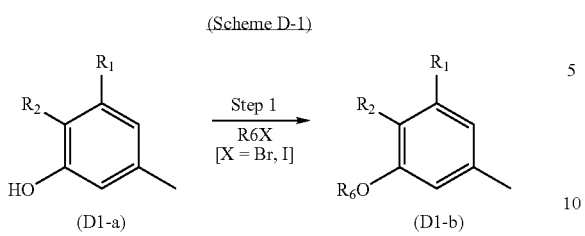

This scheme is a synthesis method employed when the phenol derivative represented by (D1-a) is available. In the formulas, R1, R2 and R6 have same definitions as in Scheme D.

Step 1 is a step of alkylating compound (D1-a), wherein compound (D1-b) may be obtained by the same method as in Scheme B-1, Step 1.

(Scheme D-2)

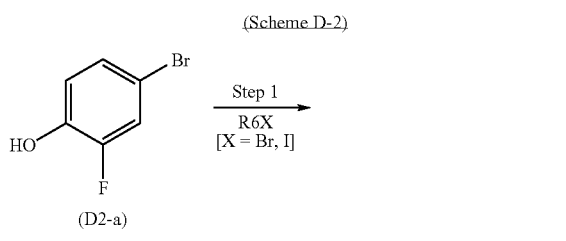

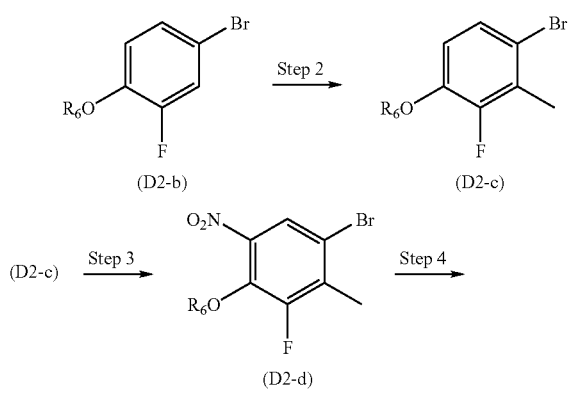

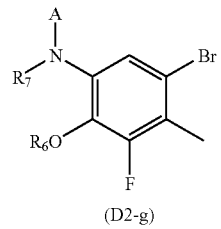

(D2-g)

This scheme is a synthesis method employed when R4 is fluorine in a compound represented by (D-a) or (D-b). In the formulas, A represents optionally substituted alkanoyl, alkylsulfonyl, aminocarbonyl or alkoxycarbonyl. R7 represents hydrogen, optionally substituted alkyl or tert-butyloxycarbonyl. R6 has the same definition as in Scheme D.

Step 1 is a step of alkylating the phenol, wherein compound (D2-b) may be obtained by the same method as in Scheme B-1, Step 1.

Step 2 is a step of introducing a methyl group. Compound (D2-c) may be synthesized by reaction with a strong base such as lithium diisopropylamide in a solvent such as tetrahydrofuran or diethyl ether for lithiation, followed by reaction with methyl iodide. An aniline derivative may also be synthesized from compound (D2-c).

Step 3 is a step of nitration, wherein compound (D2-d) may be obtained by the method described in C. C. Leznoff et al., Can. J. Chem., 73, 435(1995).

The synthesis method for compounds (D2-f) and (D2-g) shown in Steps 4 to 6 may be carried out by the same method as in Scheme B-11. When a tert-butoxycarbonyl group is to be introduced as a protecting group for R7 in compound (D2-f), this may be accomplished by reaction with di-tert-butyl dicarbonate in a solvent such as acetonitrile, in the presence of dimethylaminopyridine.

When R1 is alkoxy in a compound represented by (D-c), the synthesis may be conducted, for example, by the following Scheme D-3 via lithiation at the ortho position relative to the nitrile group.

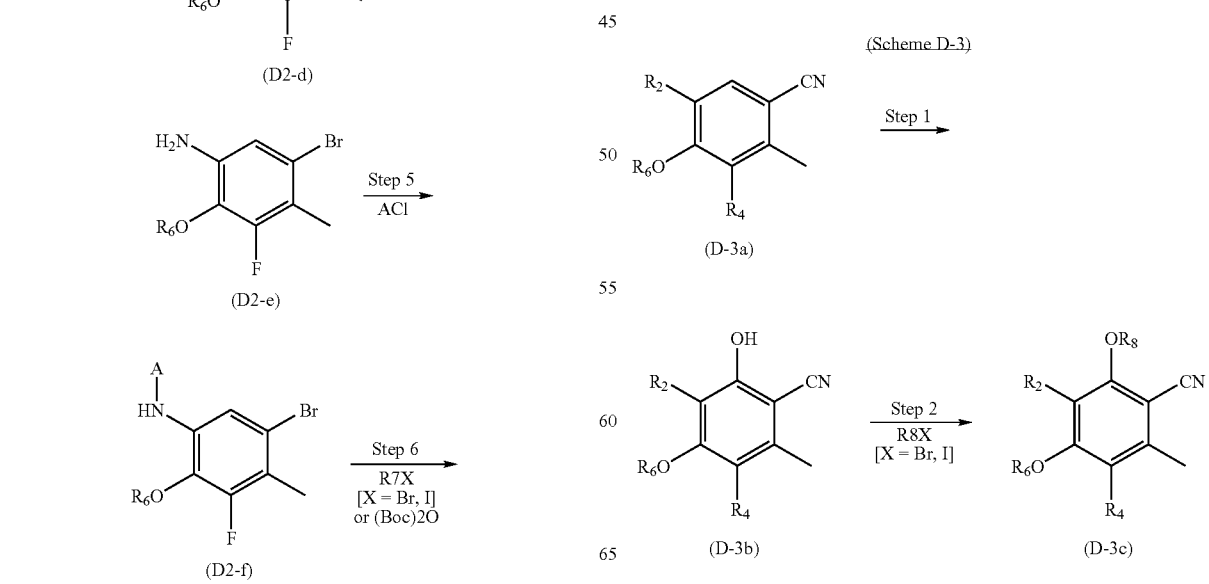

Compound (D3-a) is a compound represented by (D-c) [R1=H] which may be synthesized by the method of Scheme D. In the formulas, R8 represents optionally substituted alkyl.

Step 1 is a step of introducing a phenolic hydroxyl group. Compound (D3-a) may be reacted with a strong base such as lithium diisopropylamide in a solvent such as tetrahydrofuran or diethyl ether for lithiation, and then reacted with a trialkyl borate for introduction of borane. Compound (D3-b) may also be obtained by oxidation using alkaline hydrogen peroxide.

Step 2 is a step of alkylation of the phenol, wherein compound (D3-c) may be obtained by the same method as in Scheme B-1, Step 1.

(Scheme D-4)

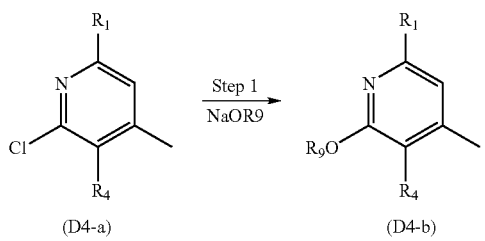

This scheme is a synthesis method for a compound represented by (D-a) wherein X2 is nitrogen, using a 2-chloropyridine derivative as a pyridine derivative for the starting material. In the formulas, R1 and R4 have the same definitions as in Scheme D. R9 represents optionally substituted alkyl.

Step 1 is a step of introducing an alkoxy group at the 2-position of the pyridine. Compound (D4-b) may be obtained using a sodium alkoxide prepared using sodium hydride in the corresponding alcohol solvent, employing conditions from reflux to 120° C. with a sealed tube.

Synthesis of a compound represented by (C-a) in Production Process C, Scheme C, wherein X1 is nitrogen, such as a pyridine, pyrazine or pyrimidine derivative, may be carried out by the methods shown in Production Process E to E-2 below.

<Production Process E>

(Scheme E)

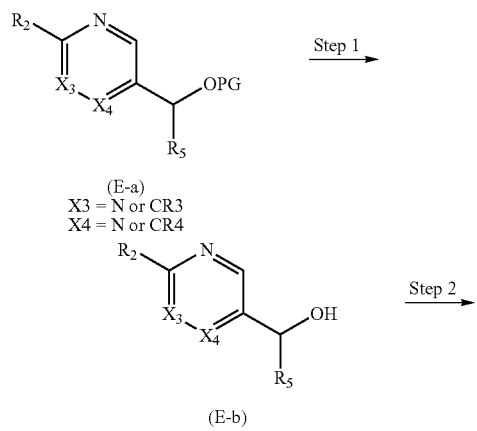

PG: Protecting Group

This scheme is a synthesis method for a pyridine derivative (E-e). In the formulas, R2 represents hydrogen, halogeno, optionally substituted alkyl, cycloalkyl, optionally substituted alkylaminocarbonyl, carboxyl, alkoxycarbonyl, optionally substituted carbamoyl, an optionally substituted aromatic heterocyclic group or an optionally substituted non-aromatic heterocyclic group. R3 represents hydrogen, carboxyl, alkoxycarbonyl, optionally substituted alkyl, optionally substituted alkoxy, optionally substituted alkylaminocarbonyl or carbamoyl. R4 and R5 represent hydrogen or optionally substituted alkyl.

Step 1 is a step of removing the silyl group serving as the hydroxyl-protecting group in a compound represented by (E-a). This may be accomplished by reaction with tetrabutylammonium fluoride or tris(dimethylamino)sulfonium difluorotrimethylsilicate in a tetrahydrofuran solvent either at room temperature or while cooling on ice. The tetrabutylammonium fluoride may also be used in the copresence of acetic acid in order to trap the generated anions.

Step 2 is a step of azidation, wherein compound (E-c) may be obtained by selecting either the method described in A. S. Thompson et al., J. Org. Chem., 58, 5886(1993), or by a two-step process involving reaction with mesyl chloride in a solvent such as dichloromethane in the presence of a base such as triethylamine to synthesize a mesylate or chloride, followed by reaction with sodium azide in a solvent such as dimethylformamide.

Step 3 is a step of oxidation of the pyridine nitrogen atom. Compound (E-d) may be obtained by oxidation using a peracid such as m-chloroperbenzoic acid in a solvent such as dichloromethane.

Step 4 is a step of introducing a cyano group. Compound (E-e) may be obtained by applying the conditions described in W. K. Fife, J. Org. Chem., 48, 1375(1983).

(Scheme E-1)

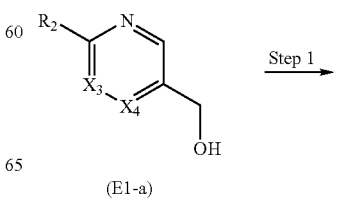

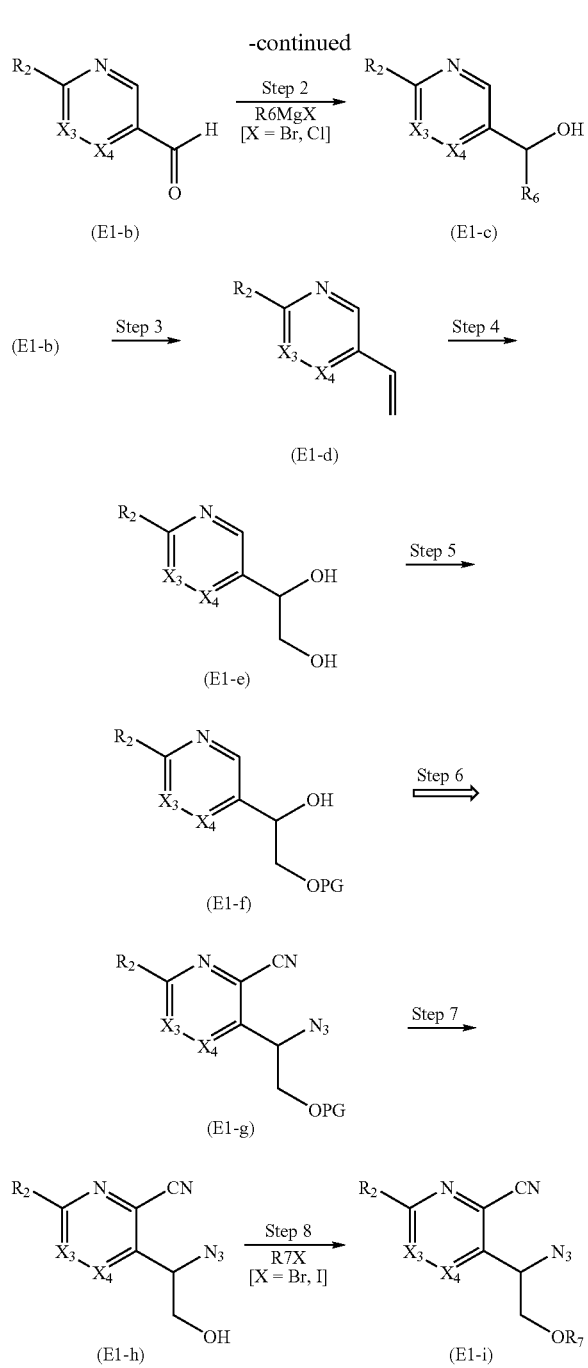

room temperature. A hydroxymethyl group (E1-f) or alkoxymethyl group (E1-i) may also be introduced.

Step 3 is a step of introducing methylene into compound (E1-b), wherein compound (E1-d) may be obtained by Wittig reaction using an ylide prepared from methyltriphenylphosphonium bromide and butyllithium.

Step 4 is a step of dihydroxylation of compound (E1-d). Compound (E1-e) may be obtained by reaction with a catalytic amount of osmium tetraoxide in an acetone/water mixed solvent, in the presence of N-methylmorpholine N-oxide.

Step 5 is a step of protecting the hydroxyl group with a silyl group. For a tert-butyldimethylsilyl group, reaction may be conducted with tert-butyldimethylsilyl chloride in a solvent such as dichloromethane, in the presence of triethylamine and dimethylaminopyridine, or for introduction of a tert-butyldiphenylsilyl group, reaction may be conducted with tert-butyldiphenylsilyl chloride in dimethylformamide, in the presence of imidazole, to yield compound (E1-f). Compound (E1-f) may be converted to compound (E1-g) by the conversion method of Steps 2 to 4 of Scheme E.

Step 7 is a step of removing the silyl group serving as the hydroxyl-protecting group, wherein compound (E1-h) may be obtained by similarly to Scheme E, Step 1. An alkyl group or alkoxycarbonylmethyl group may also be introduced into compound (E1-h).

Step 8 is a step of alkylation. Compound (E1-i) may be obtained by reaction with sodium hydride in a solvent such as dimethylformamide or tetrahydrofuran, followed by reaction with an alkyl halide.

<Production Process E-2>

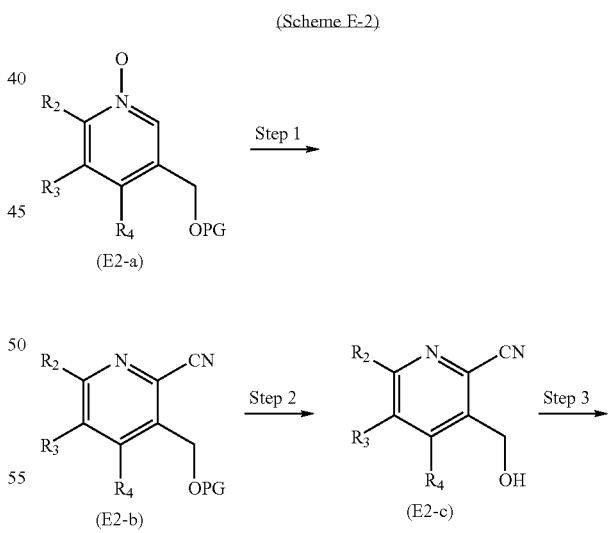

This scheme is a synthesis method for introduction of the substituent R5 in a compound represented by (E-b). In the formulas, R2 has the same definition as in Scheme E. R6 represents lower alkyl and R7 represents hydrogen or optionally substituted alkyl.

Step 1 is a step of oxidation of the hydroxyl group of compound (E1-a). Compound (E1-b) may be obtained by heating to reflux together with manganese dioxide, using chloroform as the solvent.

Step 2 is a step of introducing an alkyl group, wherein a compound represented by (E1-c) may be obtained by reaction with a Grignard reagent in a solvent such as tetrahydrofuran or diethyl ether under conditions from freezing to

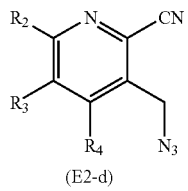

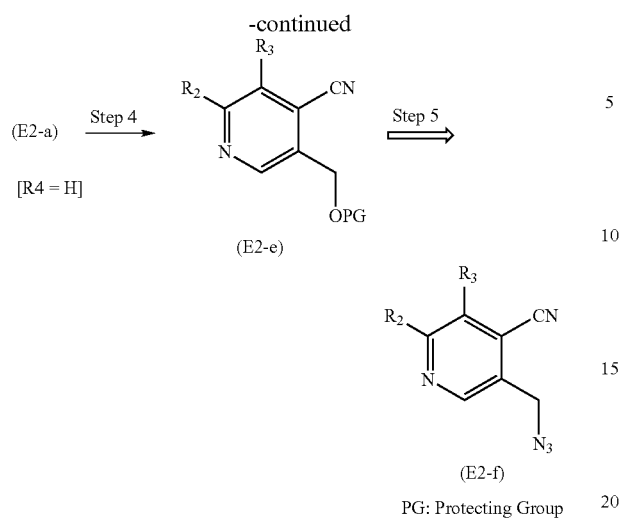

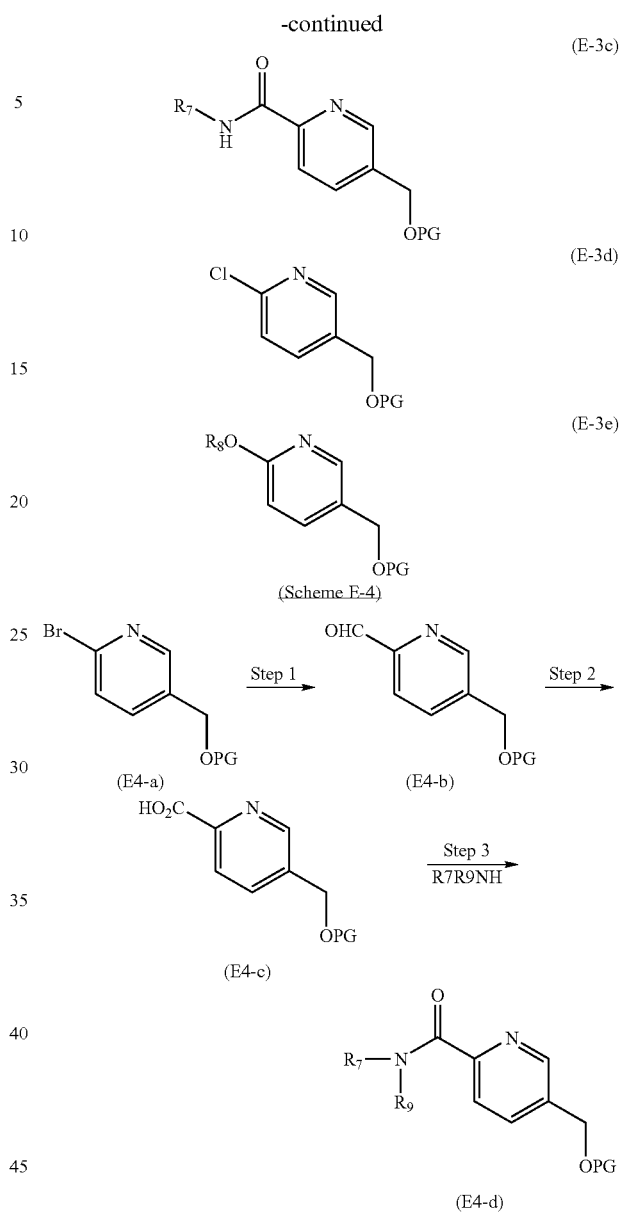

This scheme is a synthesis method for the pyridine derivatives (E2-d) and (E2-f). In the formulas, R2, R3 and R4 have the same definitions as in Scheme E.

Step 1 is a step of introducing a nitrile group, wherein compound (E2-b) may be obtained by the method shown in Scheme E, Step 4.

Step 2 is a step of removing the silyl protecting group, wherein compound (E2-c) may be obtained by the method shown in Scheme E, Step 1. Particularly preferred is a method of reacting tris(dimethylamino)sulfonium difluorotrimethylsilicate in the presence of acetic acid.

Step 3 is a step of azidation, wherein compound (E2-d) may be obtained by the method of Scheme E, Step 2. A compound (E2-a) wherein R4=H may be utilized to synthesize a pyridine derivative wherein X3 is nitrogen in a compound represented by (C-a) of Scheme C.

Step 4 is a step of nitrilation at the 4-position of the pyridine N-oxide, wherein compound (E2-e) may be synthesized by O-methylation with dimethylsulfuric acid without a solvent, followed by reaction with potassium cyanide in an ethanol/water mixed solvent. Compound (E2-e) may also be converted to compound (E2-f) by the method of Scheme E-2, Steps 2 and 3.

Each of the intermediates represented by the general formulas in Schemes E to E-2 may also be synthesized by the methods shown in the following Schemes E-3 to E-21. Synthesis of an R2 or R3 disubstituted derivative may be accomplished by introduction of a functional group by ortho metalation of compound (E3-a). Here, any of compounds (E3-c) to (E3-e) may be used as compounds represented by (E3-a), and they may be synthesized by the methods of Schemes E-4 to E-6 below.

(Scheme E-3)

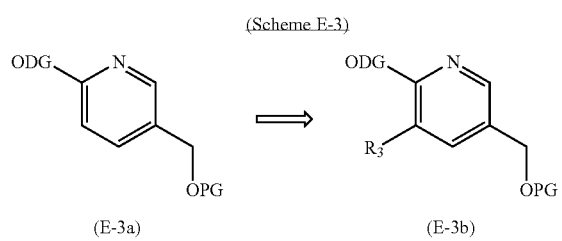

ODG: ortho-Directing Group
PG: Protecting Group

These schemes are synthesis methods for 2-substituted pyridine derivatives (E3-c), (E3-d), (E3-e) and (E4-d). In the formulas, R7, R8 and R9 represent hydrogen or optionally substituted alkyl.

Step 1 is a step of converting the bromo group to a formyl group in compound (E4-a) synthesized by the method described in J. W. Ellingboe et al., J. Med. Chem., 37, 542(1994). Compound (E4-b) may be obtained by halogen-metal exchange lithiation using butyllithium at −78° C. in a solvent such as tetrahydrofuran or diethyl ether, followed by reaction with N-formylmorpholine or dimethylformamide.

Step 2 is a step of converting compound (E4-b) to a carboxylic acid by oxidation. Compound (E4-c) may be obtained by reaction with sodium hypochlorite as an oxidizing agent at room temperature in a tert-butanol/water mixed solvent in the presence of sodium dihydrogenphosphate and 2-methyl-2-butene as a peroxide scavenger.

Step 3 is a step of amidation, wherein compound (E4-d) may be obtained similarly to Scheme B-10, Step 4. Compound (E3-c) is compound (E4-d) where R9=H, and compound (E4-d) itself is converted to the final target compound as a monosubstituted derivative of compound (E-a) in Scheme E, by Production Process A.

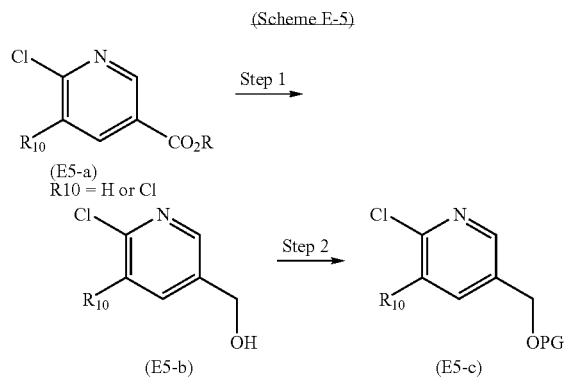

This scheme is a synthesis method for a 2-chloropyridine derivative (E5-c). In the formulas, R represents lower alkyl.

Step 1 is a step of synthesizing an alcohol by reduction of a commercially available ester (E5-a). The reduction may be accomplished using sodium borohydride in an alcohol solvent under conditions from room temperature to reflux.

Step 2 is a step of protecting the hydroxyl group with a silyl group, wherein compound (E5-c) may be obtained similarly to Scheme E-1, Step 5. Compound (E3-d) is compound (E5-c) where R10=H, and compound (E5-c) itself is converted to the final target compound as a monosubstituted derivative of compound (E-a) in Scheme E, by Production Process A.

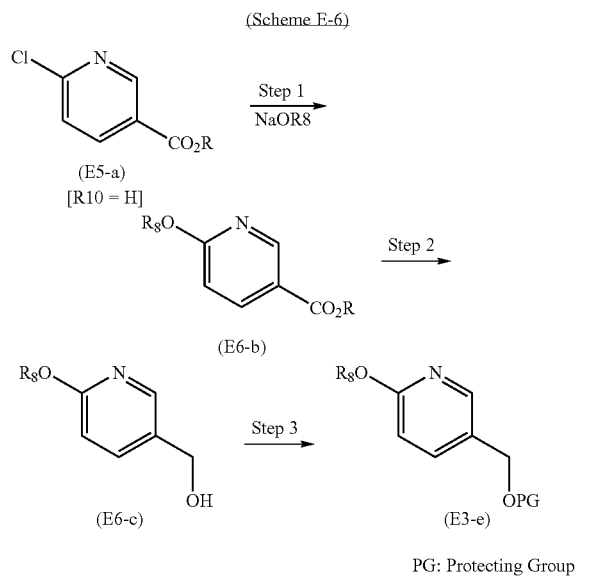

PG: Protecting Group

This scheme is a synthesis method for a 2-alkoxypyridine derivative (E3-e). In the formulas, R and R8 represent optionally substituted alkyl.

Step 1 is a step of introducing an alkoxy group, wherein compound (E6-b) may be obtained similarly to Scheme D-4, Step 1.

Step 2 is a step of reduction of the ester. Compound (E6-c) may be obtained by reaction with lithium aluminum hydride in a solvent such as tetrahydrofuran while cooling on ice.

Step 3 is a step of protecting the hydroxyl group with a silyl group, wherein compound (E3-e) may be obtained similarly to Scheme E-1, Step 5. Compound (E3-e) itself may be utilized as a monosubstituted derivative of compound (E-a) in Scheme E.

The following is a method of introducing substituent R3 in compound (E3-a).

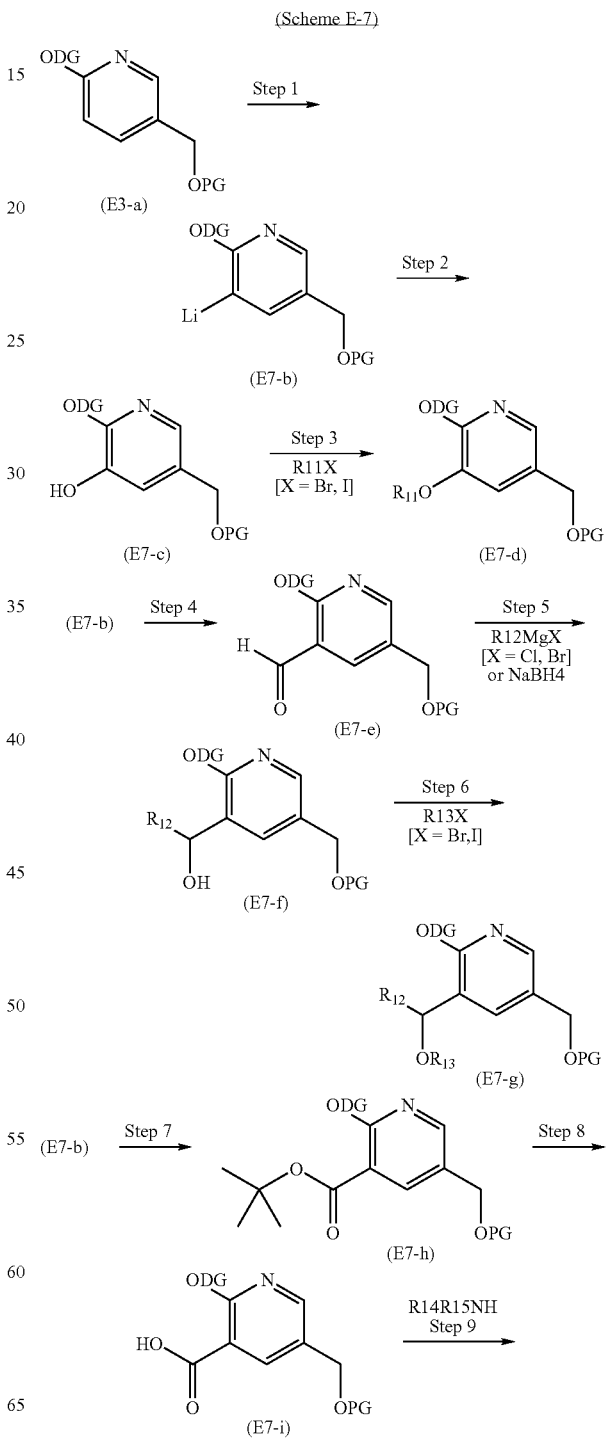

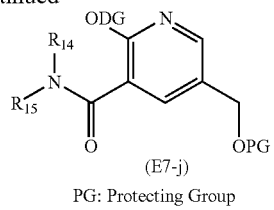

(E7-j)

PG: Protecting Group

This scheme is a synthesis method for substituent introduction to compound (E3-a) via ortho-lithiation. In the formulas, R11 and R13 represent optionally substituted alkyl, R12 represents hydrogen or lower alkyl, and R14 and R15 represent hydrogen or optionally substituted alkyl.

Step 1 is a step of ortho-lithiation utilizing an ODG. Intermediate (E7-b) may be obtained in situ by using phenyllithium in a tetrahydrofuran solvent, in the presence of 1) butyllithium as a base and 2) a catalytic amount of diisopropylamine. Compound (E7-b) may then be reacted with any of various electrophilic reagents for introduction of substituents.

Step 2 is a step of introducing a hydroxyl group. Compound (E7-c) may be obtained by reaction of compound (E7-b) with trimethylborate, followed by oxidation using alkaline aqueous hydrogen peroxide.

Step 3 is a step of alkylation of the phenolic hydroxyl group, wherein compound (E7-d) may be obtained by the method of Scheme B-1, Step 1.

Step 4 is a step of introducing a formyl group. Compound (E7-e) may be obtained by reaction of compound (E7-b) with dimethylformamide or N-formylmorpholine at −70° C.

Step 5 is a step of alkylation and reduction to synthesize an alcohol (E7-f). A compound wherein R12 is alkyl may be synthesized by reaction with a Grignard reagent in tetrahydrofuran, and reduction when R12 is hydrogen may be accomplished using sodium borohydride in an alcohol solvent.

Step 6 is a step of alkylation of the hydroxyl group, wherein compound (E7-g) may be obtained by the method of Scheme B-6, Step 3. When R13 is a tetrahydropyranyl (THP) group introduced as a protecting group, compound (E7-g) [R13=THP] may be obtained by reaction with dihydropyran in a solvent such as dichloromethane using a catalytic amount of p-toluenesulfonic acid or camphorsulfonic acid as the acid. A carboxyl ester or carboxamide group may also be introduced.

Step 7 is a step of introducing a tert-butoxycarbonyl group. Compound (E7-h) may be obtained by reaction of compound (E7-b) with di-tert-butyl dicarbonate at −70° C.

Step 8 is a step of removing the tert-butyl group. Compound (E7-i) may be obtained by dissolution in trifluoroacetic acid diluted with an organic solvent such as dichloromethane, and reaction at room temperature.

Step 9 is a step of amidation, wherein compound (E7-j) may be obtained by the method described in Scheme B-10, Step 4.

Compound (E8-a), a compound represented by (E3-b) wherein the ODG is chloride, may be converted in the manner shown in Scheme E-8 below.

(Scheme E-8)

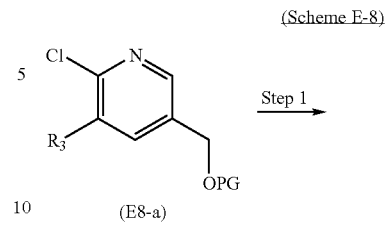

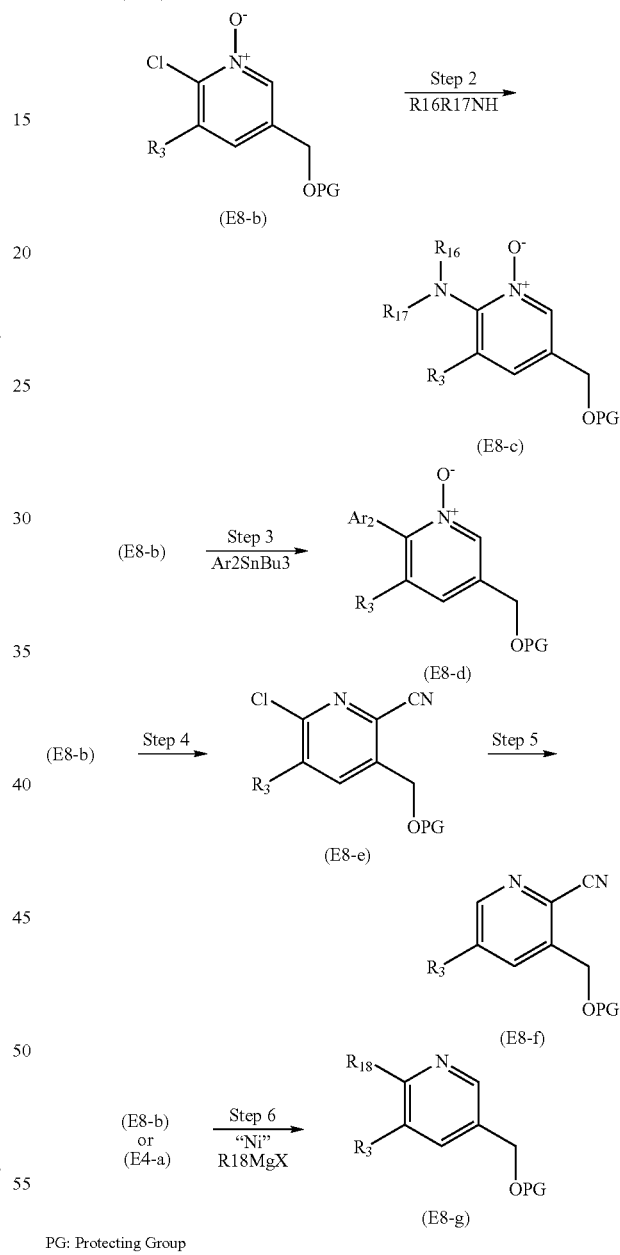

PG: Protecting Group

This scheme is a synthesis method for compounds (E8-c), (E8-d), (E8-f) and (E8-g). In the formulas, R3 has the same definition as in Scheme (E-3). R16, R17 and R18 represent optionally substituted alkyl or optionally substituted cycloalkyl, and R16 and R17 may optionally form a ring together with the N. Ar2 represents an aromatic heterocyclic group.

Step 1 is a step of oxidation of the pyridine nitrogen atom, wherein compound (E8-b) may be obtained by the method of Scheme E, Step 3.

Step 2 is a step of introducing an amino group by substitution. Compound (E8-c) may be obtained by reaction in an alcohol solvent in the presence of an amine, under conditions from room temperature to reflux.

Step 3 is a step of introducing a heteroaromatic ring by Stille reaction. Compound (E8-d) may be obtained by heating to reflux together with a tin reagent in a solvent such as toluene or xylene, in the presence of a palladium catalyst. The palladium catalyst is preferably tetrakis(triphenylphosphine)palladium.

A pyridine 6-unsubstituted derivative may also be synthesized by the following method.

Step 4 is a step of nitrilation in the same manner as Scheme E, Step 4, to yield compound (E8-e).

Step 5 is a step of reductive removal of the chloro group. Compound (E8-f) may be obtained by heating to reflux in an acetonitrile solvent in the presence of a palladium catalyst and ammonium formate. The palladium catalyst is preferably tetrakis(triphenylphosphine)palladium. An alkyl group may also be introduced at the pyridine 6-position.

Step 6 is a step of alkylation. Compound (E8-g) may be obtained by reaction of (E8-a) or (E4-a: R3=H) with a Grignard reagent in a solvent such as tetrahydrofuran or diethyl ether, in the presence of a nickel catalyst under conditions from freezing to room temperature. The nickel catalyst is preferably [1,2-bis(diphenylphosphino)ferrocenyl]nickel(II) chloride, but another bidentate phosphine ligand such as 1,3-bis(diphenylphosphino)propane may also be used.

The side chain of a compound represented by (E9-a) may also be converted. Here, compounds represented by (E9-a) include compounds represented by (E7-g) wherein R13 is a THP group, and compounds represented by (E7-g) [R13=THP] which have been subjected to a conversion shown in Scheme E-8.

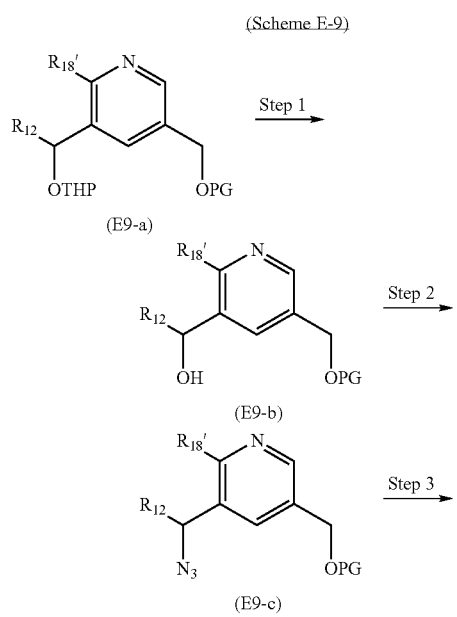

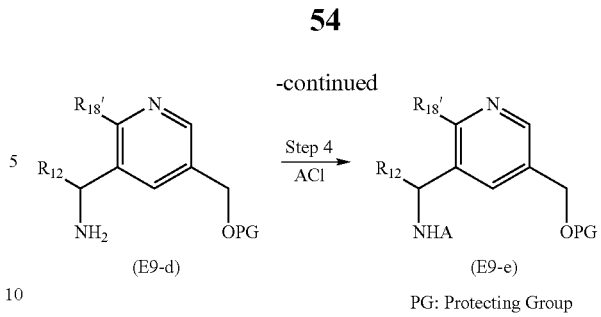

PG: Protecting Group

This scheme is a synthesis method for compound (E9-e) having a substituted amino group. In the formulas, A has the same definition as in Scheme B-11 and R12 has the same definition as in Scheme E-7. R18' represents R18, Ar2, hydrogen, optionally substituted alkoxy or optionally substituted amino (wherein R18 and Ar2 have the same definitions as in Scheme E-8).

Step 1 is a step of removing the THP group serving as the hydroxyl-protecting group. Compound (E9-b) may be obtained by reaction in an alcohol solvent in the presence of a catalytic amount of p-toluenesulfonic acid as an acid.

Step 2 is a step of azidation of the hydroxyl group, wherein compound (E9-c) may be obtained similarly to Scheme E, Step 2.

Step 3 is a step of reduction of the azide group, wherein compound (E9-d) may be obtained under the same conditions as in Scheme C, Step 1.

Step 4 is a step of introducing a substituent at the amino group, wherein compound (E9-e) may be obtained similarly to Scheme B-11, Step 1.

In the case of a compound represented by (E3-b), wherein the ODG is a carboxamide derivative, the reaction is preferably followed by protection of the amide hydrogen with a Boc group in the manner shown below.

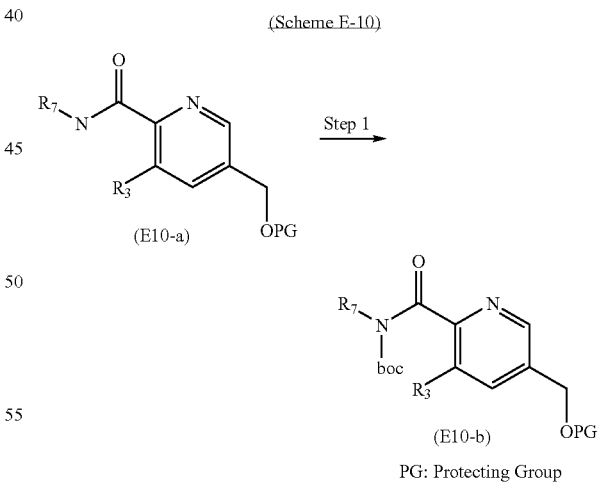

PG: Protecting Group

This scheme is a synthesis method for compound (E10-b). In the formulas, R3 and R7 have the same definitions as in Scheme E-3.

Step 1 is a step of introducing a Boc group at the amide nitrogen atom as a protecting group. Compound (E10-b) may be obtained by reaction with di-tert-butyl dicarbonate in a solvent such as acetonitrile in the presence of dimethylaminopyridine.

A compound represented by (E-a) in Scheme E, wherein R2 is substituted methyl or alkyl, may be synthesized by the following method.

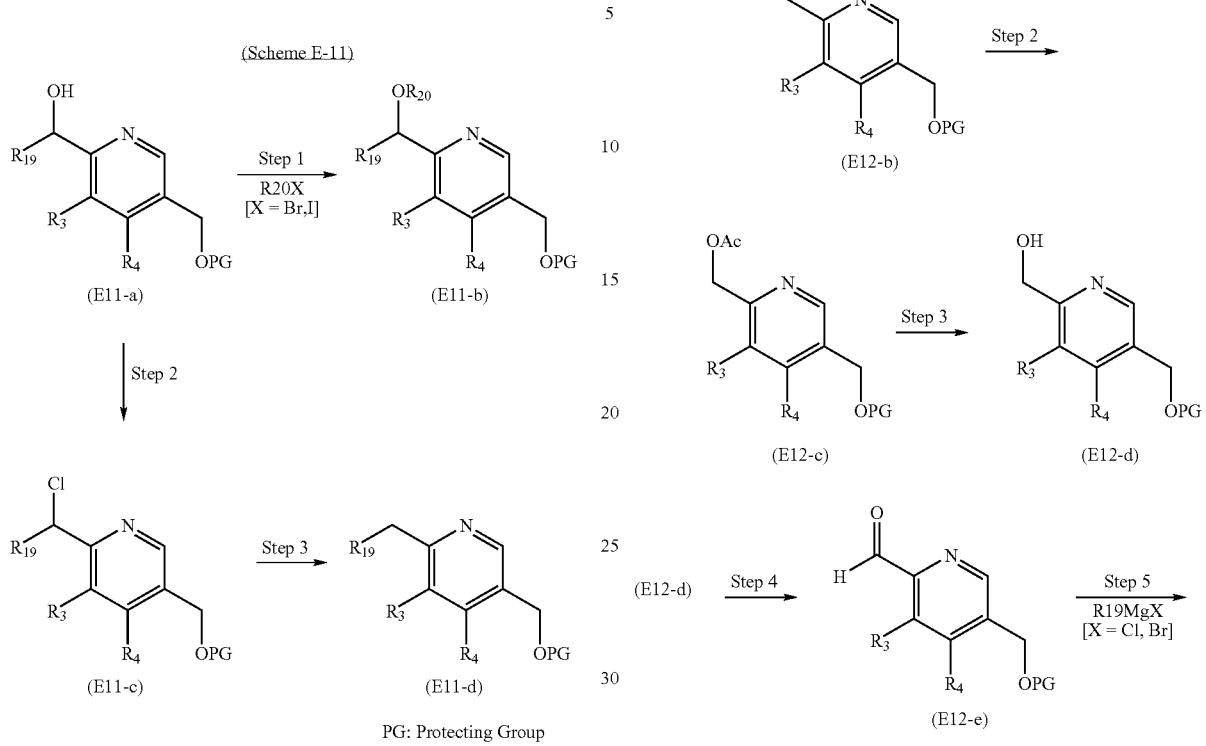

PG: Protecting Group

This scheme is a synthesis method for (E11-b) and (E11-d). In the formulas, R19 represents optionally substituted alkyl or cycloalkyl. R20 represents optionally substituted alkyl. R3 and R4 have the same definitions as in Scheme E.

Step 1 is a step of alkylation of the hydroxyl group of compound (E11-a), which may be synthesized by the method shown in Scheme E-12 below, to yield compound (E11-b) by the method of Scheme B-6, Step 3.

Step 2 is a step of converting the hydroxyl group to a chloro group. Compound (E11-c) may be obtained by reaction with thionyl chloride in a solvent such as dichloromethane at room temperature, followed by treatment under basic conditions.

Step 3 is a step of removing the chloro group by reduction. Compound (E11-d) may be obtained by hydrogenation in an alcohol solvent at room temperature and normal pressure in the presence of a metal catalyst such as palladium-carbon.

(Scheme E-12)

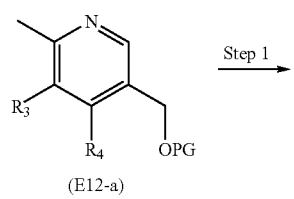

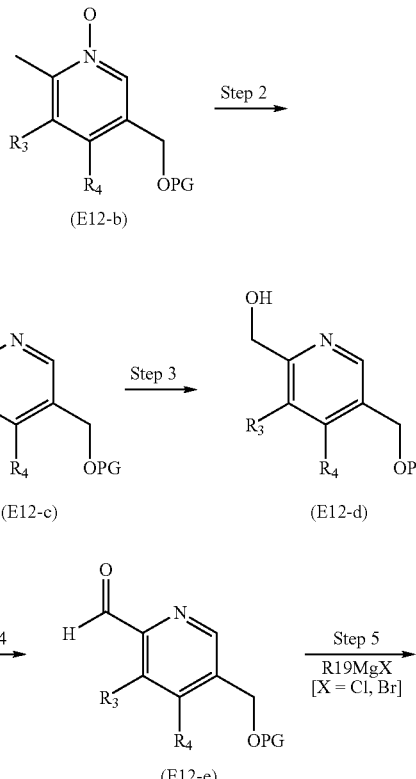

PG: Protecting Group

This scheme is a synthesis method for compound (E11-a). In the formulas, R3 and R4 have the same definitions as in Scheme E. R19 has the same definition as in Scheme E-11.

Step 1 is a step of oxidation of the pyridine nitrogen atom of compound (E12-a), wherein compound (E12-b) may be obtained similarly to Scheme E, Step 3.

Steps 2 and 3 accomplish introduction of a hydroxyl group at the methyl group by rearrangement. An acetate (E12-c) may be obtained by heating compound (E12-b) from 120° C. to 140° C. in acetic anhydride. This may then be reacted with sodium methoxide or potassium carbonate in an alcohol solvent to yield compound (E12-d).

An alkyl group may also be introduced into compound (E12-d).

Step 4 is a step of obtaining an aldehyde by oxidation of the hydroxyl group. Compound (E12-e) may be obtained by heating to reflux together with manganese dioxide in a chloroform solvent.

Step 5 is a step of alkylation. Compound (E12-f) may be obtained by reaction with a Grignard reagent in a solvent such as tetrahydrofuran or diethyl ether.

(Scheme E-13)

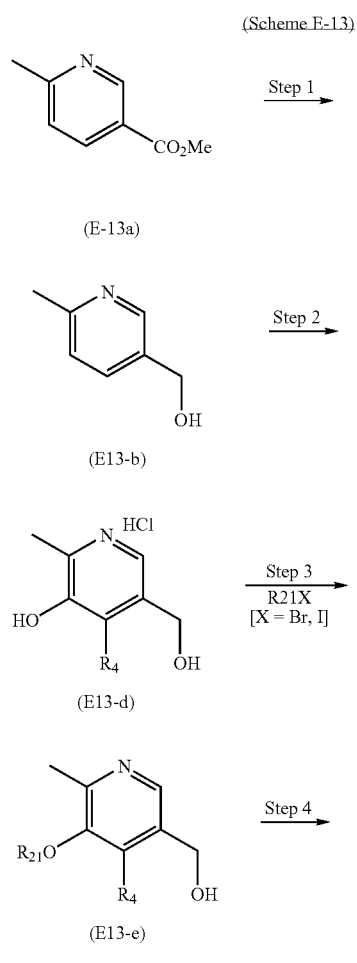

(E-13a)
(E13-b)
(E13-c)
(E13-d)
(E13-e)
(E13-f)
PG: Protecting Group (Scheme E-14)

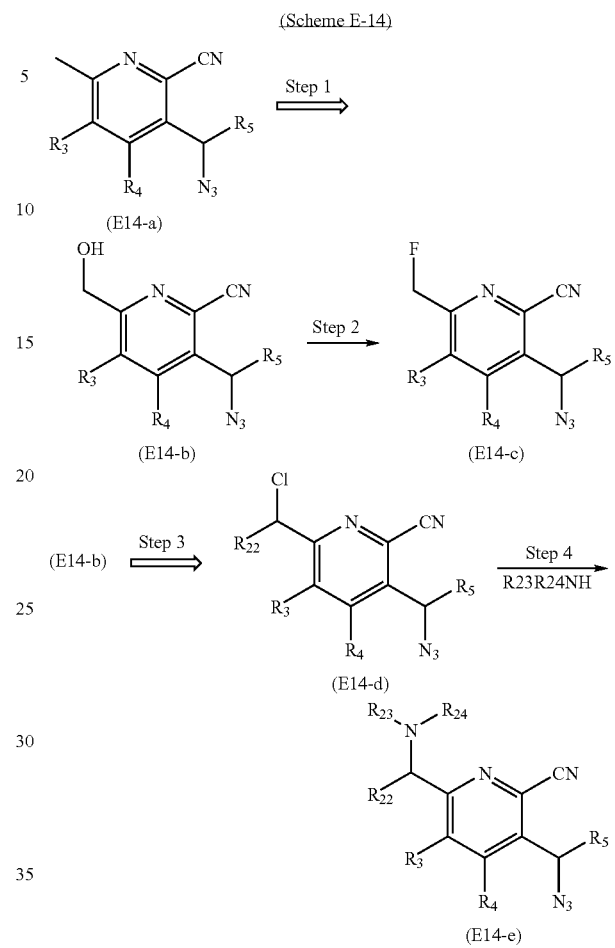

(E14-a)
(E14-b)
(E14-c)
(E14-d)
(E14-e)

This scheme is a synthesis method for a compound represented by (E12-a). In the formulas, R4 has the same definition as in Scheme E. R21 represents optionally substituted alkyl or cycloalkyl.

Step 1 is a step of reducing the commercially available compound (E13-a), wherein compound (E13-b) may be obtained similarly to Scheme E-5, Step 1.

Step 2 is a step of protecting the hydroxyl group with a silyl group, wherein compound (E13-c) may be obtained similarly to Scheme E-1, Step 5. Also, a compound represented by (E12-a) wherein R3 is alkoxy may be synthesized in the following manner.

Step 3 is a step of selectively alkylating the phenolic hydroxyl group of compound (E13-d) either obtained commercially or synthesized by the method described in Y. Morisawa et al., J. Med. Chem., 17, 1235(1974). Compound (E13-e) may be obtained by stirring in dimethylformamide together with 2 equivalents of sodium hydride at room temperature for 3 hours to 1 day to produce a sufficient amount of phenoxy anion, followed by reaction with an alkyl halide.

Step 4 is a step of protecting the hydroxyl group with a silyl group, and it may be carried out according to the method in Scheme E-1, Step 5.

This scheme is a synthesis method for compounds (E14-b), (E14-c) and (E14-e) utilizing a compound represented by (E-e) in Scheme E wherein R2 is methyl. In the formulas, R3 and R4 have the same definitions as in Scheme E. R22 has the same definition as R19 in Scheme E-13, or represents hydrogen. R23 and R24 represent hydrogen or optionally substituted alkyl.

Step 1 is a step of introducing a hydroxyl group at the methyl group, wherein compound (E14-b) may be obtained utilizing the same conversion as the method shown in Scheme E-12.

Step 2 is a step of fluorination. Compound (E14-c) may be obtained by reaction with diethylaminosulfur trifluoride in dichloromethane or 1,2-dichloroethane, under conditions from −70° C. to room temperature.

Steps 3 and 4 accomplish introduction of an amino group.

Step 3 is a step of introduction of an alkyl group and conversion to a halogeno group, wherein compound (E14-d) may be obtained similarly to the series of steps shown in Scheme E-12 and E-11 for obtaining compound (E11-c).

Step 4 is a step of introducing an amino group. Compound (E14-e) may be obtained by reaction with an alkylamine hydrochloride in a solvent such as acetonitrile in the presence of sodium carbonate.

Of the compounds represented by (E-a) in Scheme E or (E2-b) in Scheme E-2, those wherein R2 is a substituent via a double bond may be synthesized by the methods of Scheme E-15 and E-16.

(Scheme E-15)

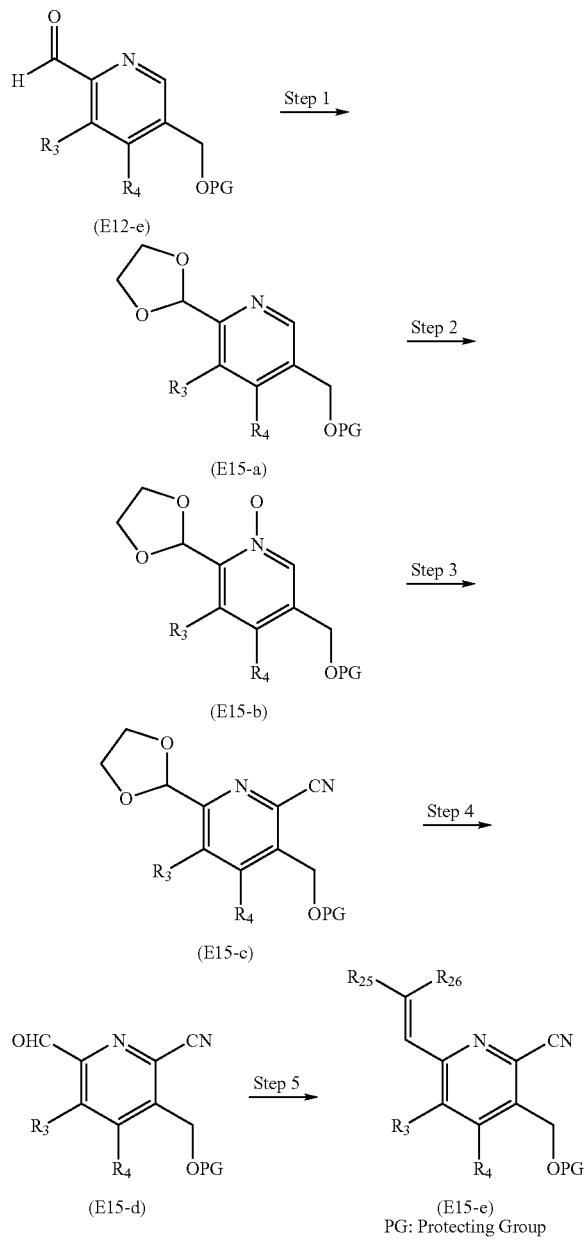

(Scheme E-16)

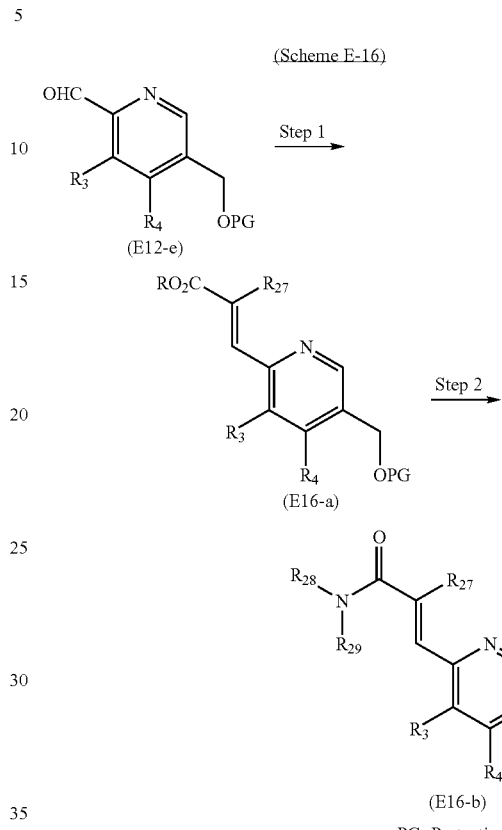

PG: Protecting Group

Step 5 is a step of carbon-carbon bond formation, wherein compound (E15-e) may be obtained by Wittig reaction or Horner-Emmons reaction.

This scheme is a method for synthesis of an unsaturated ester and unsaturated amide. In the formulas, R3 and R4 have the same definitions as in Scheme E. R27 represents hydrogen or lower alkyl, and R28 and R29 represent hydrogen or optionally substituted alkyl.

Step 1 is a step of carbon-carbon bond formation, wherein compound (16-a) may be obtained by Wittig reaction or Horner-Emmons reaction.

Step 2 is a step of amidation of the ester. Compound (E16-b) may be obtained by reaction with an amine hydrochloride in the presence of trimethylaluminum.

This scheme is a synthesis method for compound (E15-e). In the formulas, R3 and R4 have the same definitions as in Scheme E. R25 and R26 represent hydrogen or optionally substituted alkyl.

Step 1 is a step of protecting the formyl group of compound (E12-a). Compound (E15-a) may be obtained by heating to reflux in a toluene/ethylene glycol mixed solvent in the presence of a p-toluenesulfonic acid catalyst while removing the water using a Dean-Stark trap.

Steps 2 and 3 accomplish conversion in the same manner as Scheme E, Steps 3 and 4 to yield compound (E15-c).

Step 4 is a step of removing the formyl-protecting group. Compound (E15-d) may be obtained by heating at 80° C. in 80% aqueous acetic acid.

(Scheme E-17)

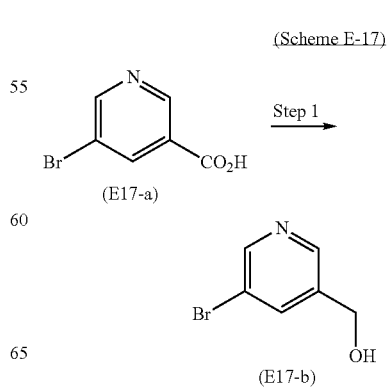

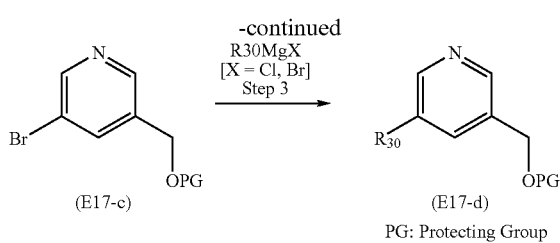

This scheme is a synthesis method for a substituted pyridine (E17-d) which is a compound represented by (E-a) wherein R3 is alkyl. In the formulas, R30 represents optionally substituted alkyl or cycloalkyl.

Step 1 is a step of reducing the carboxyl group. Compound (E17-b) may be obtained by using an alkylchlorocarbonate in a solvent such as tetrahydrofuran in the presence of triethylamine to produce a mixed acid anhydride in the system, and then reducing it with sodium borohydride to yield compound (E17-b).

Step 2 is a step of protecting the hydroxyl group with a silyl group, wherein compound (E17-c) may be obtained similarly to Scheme E-1, Step 5.

Step 3 is a step of alkylation using a nickel catalyst, wherein compound (E17-d) may be obtained by the same method for alkyl group introduction at the pyridine α-carbon as shown in Scheme E-8, Step 6.

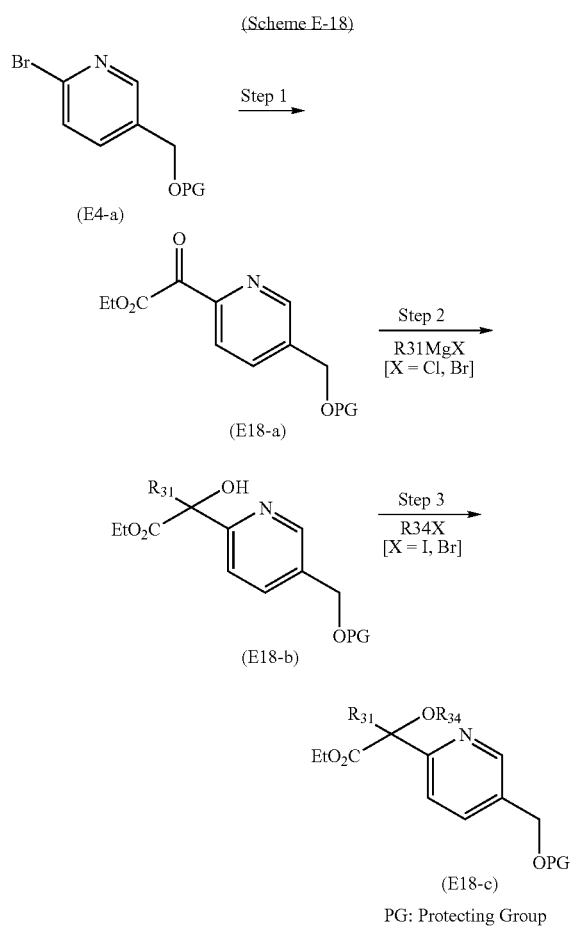

This scheme is a method for synthesis of a pyridinium methylcarboxylate derivative from compound (E4-a) mentioned above. In the formulas, R31 and R34 represent optionally substituted alkyl.

Step 1 is a step of carbon-carbon bond formation of compound (E4-a) using a halogen-metal exchange method. Compound (E18-a) may be obtained by lithiation with butyllithium followed by treatment with diethyl oxalate.

Step 2 is a step of introducing an alkyl group using a Grignard reagent.

Step 3 is a step of alkylating the hydroxyl group, wherein compound (E18-c) may be obtained by the method of Scheme B-6, Step 3.

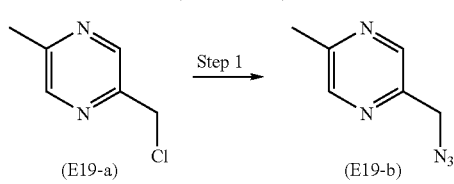

This scheme is a synthesis method for a pyrazine derivative (E19-b).

Step 1 is a step of azidating compound (E19-a) synthesized by the method described in I. Iovel et al., Oppi Briefs, 23, 188(1991), wherein compound (E19-b) may be obtained by the method of Scheme D, Step 4.

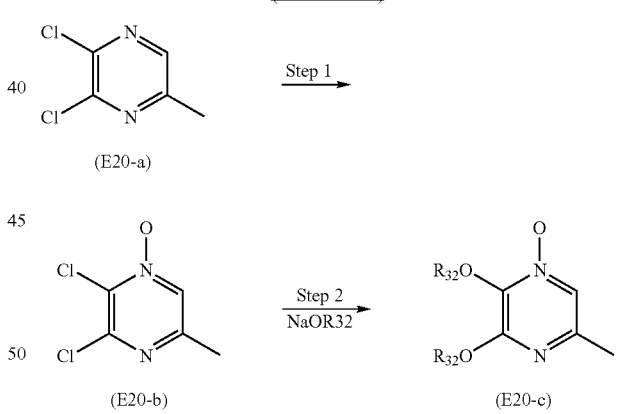

This scheme is a synthesis method for a dialkoxy-substituted pyrazine derivative (E20-c). In the formulas, R32 represents optionally substituted alkyl.

Step 1 is a step of regioselective oxidation of the nitrogen atom of compound (E20-a) synthesized by the method described in J. Adachi et al., J. Org. Chem., 37, 221(1972). Compound (E20-b) may be obtained by oxidation with potassium peroxodisulfate in sulfuric acid.

Step 2 is a step of substitution of the halogeno groups with alkoxy groups. Compound (E20-c) may be obtained by reaction with a sodium alkoxide prepared with sodium hydride in the corresponding alcohol solvent.

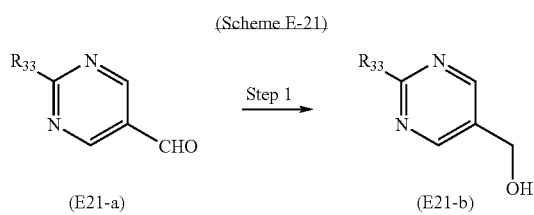

This scheme is a synthesis method for a pyrimidine derivative (E21-b). In the formulas, R33 represents one of the substituents (alkyl, alkoxy, alkylamino) mentioned in the following publications.

Step 1 is a step of synthesizing an alcohol by reduction of an aldehyde (E21-a) synthesized by the method described in J. T. Gupton, J. Heterocyclic Chem., 28, 1281(1991). Compound (E21-b) may be obtained by reaction with sodium borohydride in an alcohol solvent.

<Production Process F>

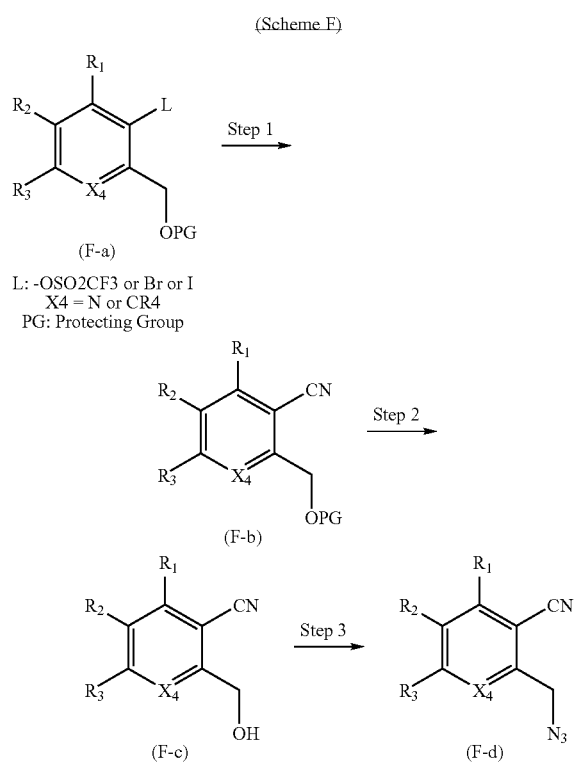

This scheme is a synthesis method for compound (F-d). In the formulas, R1 represents hydrogen, halogeno or optionally substituted alkoxy. R2 represents hydrogen, optionally substituted alkyl, alkoxycarbonyl, carbamoyl or optionally substituted alkylaminocarbonyl. R3 represents hydrogen, halogeno, optionally substituted alkoxy or alkylamino. R4 represents hydrogen, halogeno or optionally substituted alkoxy.

Step 1 is a step of introduction of a nitrile group. Compound (F-b) may be obtained according to the method of Scheme D, Step 2.

Step 2 is a step of removing the silyl group serving as a protecting group, wherein compound (F-c) may be obtained according to the method of Scheme E, Step 1.

Step 3 is a step of azidation, wherein compound (F-d) may be obtained according to the method of Scheme E, Step 2.

Compounds represented by (F-a) to (F-c) in Scheme F may also be synthesized, for example, using the methods of Schemes F-1 to F-8 below.

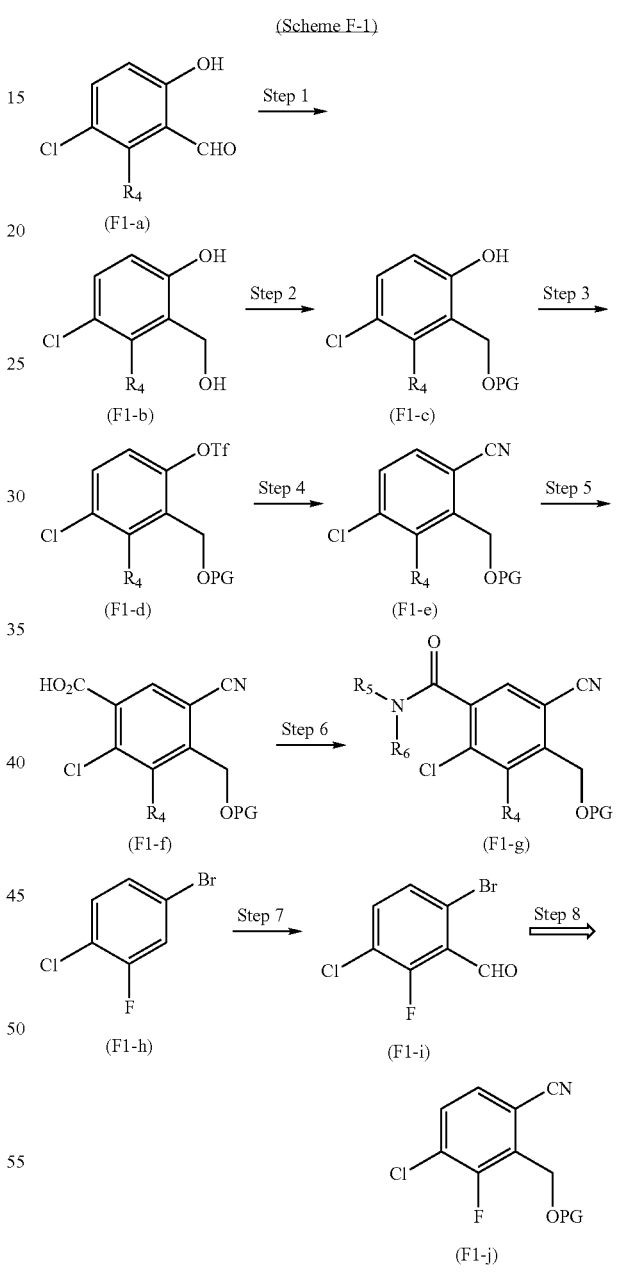

This scheme is a synthesis method for (F1-e), (F1-g) and (F1-j) in which are compounds represented by (F-b) wherein R3=Cl. In the formulas, R4 has the same definition as in Scheme F. R5 and R6 represent hydrogen or optionally substituted alkyl.

Step 1 is a step of synthesizing an alcohol by reduction of the aldehyde (F1-a). Compound (F1-b) may be obtained by reaction with sodium borohydride in an alcohol or dichloromethane solvent.

Step 2 is a step of protecting the hydroxyl group with a silyl group, wherein compound (F1-c) may be obtained similarly to Scheme E-1, Step 5.

Step 3 is conversion of the phenolic hydroxyl group to a triflate. Compound (F1-d) may be obtained similarly to Scheme B-3, Step 2. Compound (F1-d) may also be converted to a carboxamide derivative.

Step 4 is a step of nitrilation based on the route shown in Scheme F.

Step 5 is a step of introducing a carboxyl group via ortho-lithiation. Compound (F1-f) may be obtained by lithiation using lithium diisopropylamide in a solvent such as tetrahydrofuran at −78° C., followed by reaction with carbon dioxide.

Step 6 is a step of amidation, wherein compound (F1-g) may be obtained similarly to Scheme B-10, Step 4.

A compound represented by compound (F1-e) wherein R4=F may be synthesized from a commercially available compound (F1-h) in the following manner.

Step 7 is a step of introducing a formyl group, wherein compound (F1-i) may be obtained by lithiation using lithium diisopropylamide in a solvent such as tetrahydrofuran at −78° C., followed by reaction with N-formylmorpholine.

Step 8 is a step of conversion in the same manner as Scheme F-1 (excluding Step 3) to obtain compound (F1-j).

A compound represented by (F-a) wherein R3=F may be synthesized by a method similar to the one described above.

-continued

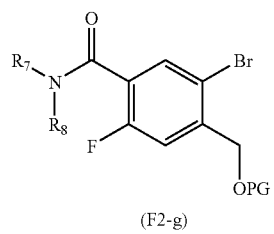

(F2-g)

PG: Protecting Group

This scheme is a synthesis method for compounds (F2-e) and (F2-g) as compounds represented by (F-a). In the formulas, R7 and R8 represent hydrogen or optionally substituted alkyl, or R7 and R8 may optionally form a ring together with N.

Step 1 is a step of introducing a bromo group by radical reaction, wherein compound (F2-b) may be obtained similarly to Scheme D, Step 3.

Steps 2 and 3 accomplish conversion of the bromo group to a hydroxyl group. The acetate (F2-c) may be synthesized by reaction with potassium acetate in a solvent such as dimethylformamide. Compound (F2-d) may then be obtained by methanolysis using potassium carbonate in methanol.

Step 4 is a step of protecting the hydroxyl group with a silyl group. Compound (F2-e) may be obtained similarly to Scheme E-1, Step 5.

Steps 5 and 6 accomplish introduction and amidation of a carboxyl group, wherein compound (F2-g) may be obtained similarly to Scheme F-1, Steps 5 and 6 above.

(Scheme F-2)

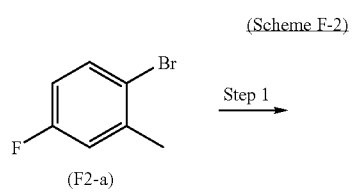

(F2-a)

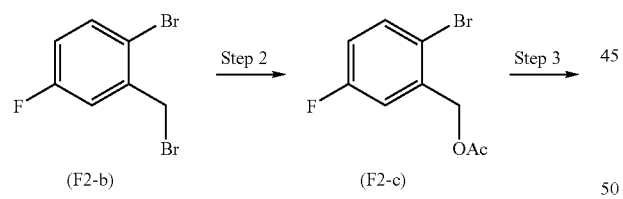

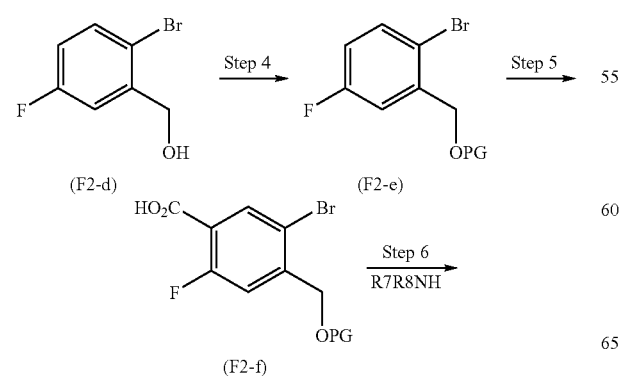

(Scheme F-3)

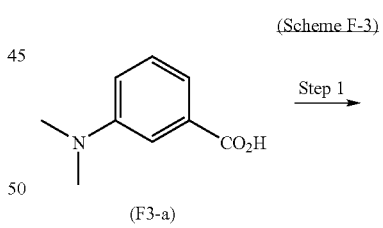

This scheme is a synthesis method for compound (F3-c).

Step 1 is a step of reducing the carboxyl group, wherein compound (F3-b) may be obtained similarly to Scheme E-17, Step 1.

Step 2 is a step of regioselective bromination. Compound (F3-c) may be obtained by reaction with benzyltrimethylammonium tribromide in a dichloromethane/alcohol mixed solvent at room temperature in the presence of potassium carbonate.

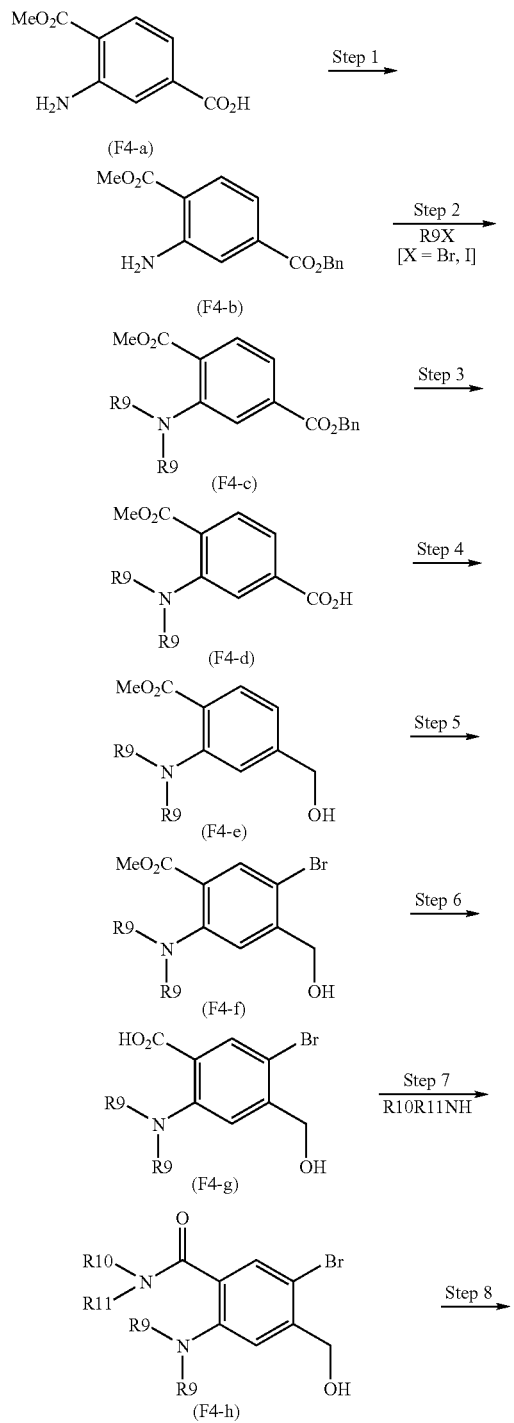

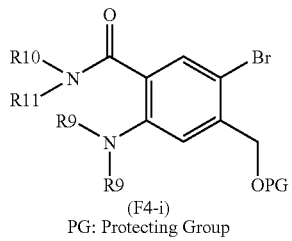

PG: Protecting Group

This scheme is a synthesis method for compound (F4-h). In the formulas, R9, R10 and R11 represent hydrogen or optionally substituted alkyl.

Step 1 is a step of benzylesterification of compound (F4-a). Compound (F4-b) may be obtained by reaction with benzyl bromide in dimethylformamide at room temperature, in the presence of potassium carbonate.

Step 2 is a step of dialkylation of the amino group. Compound (F4-c) may be obtained by a method of reaction with an alkyl halide in dimethylformamide in the presence of potassium carbonate, or when R9 is methyl, by a method of reaction with formalin while heating to reflux in a formic acid solvent.

Step 3 is a step of debenzylation. Compound (F4-d) may be obtained by hydrogenation in tetrahydrofuran in the presence of palladium hydroxide-carbon.

Steps 4 and 5 can yield compound (F4-f) by the same method as in Scheme F-3. However, Step 4 is conducted at a temperature of −40° C. to −20° C.

Step 6 is a step of hydrolysis of the ester. Compound (F4-g) may be obtained by reaction with a 1 N aqueous sodium hydroxide solution while heating to reflux in a tetrahydrofuran/alcohol mixed solvent.

Step 7 is a step of amidation wherein compound (F4-h) may be obtained similarly to Scheme B-10, Step 4, but a condensing agent such as dicyclohexyl carbodiimide is preferably used.

Step 8 is a step of protecting the hydroxyl group with a silyl group, wherein compound (F4-i) may be obtained by the same method as in Scheme E-1, Step 5.

A pyridine derivative represented by (F-a) wherein X4 is nitrogen may be synthesized by the method shown in the following Scheme F-5.

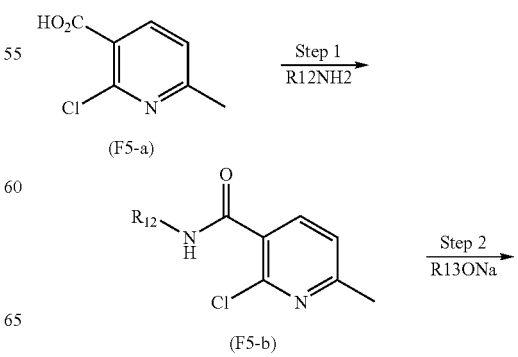

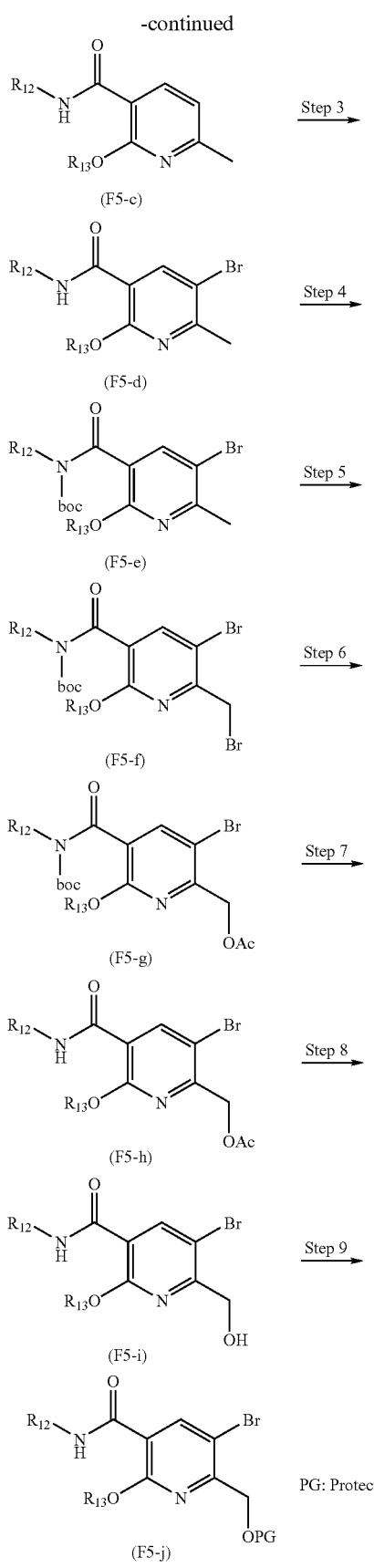

This scheme is a synthesis method for a pyridine derivative (F5-j). In the formulas, R12 represents optionally substituted alkyl, and R13 represents lower alkyl.

Step 1 is a step of amidation, wherein compound (F5-b) may be obtained similarly to Scheme B-10, Step 4.

Step 2 is a step of substitution of the halogeno group at the pyridine 2-position. Compound (F5-c) may be obtained by generating a sodium alkoxide from sodium hydride in the corresponding alcohol solvent.

Step 3 is a step of bromination, wherein compound (F5-d) may be obtained similarly to Scheme B-1, Step 2.

Step 4 is a step of protecting the amide with a tert-butyloxycarbonyl group, wherein compound (F5-e) may be obtained similarly to Scheme E-10.

Steps 5 to 9 may be carried out by conversion in the same manner as for synthesis of compounds (F2-a) to (F2-f) in Scheme F-2 above, but Step 7 is also included for removal of the tert-butyloxycarbonyl group serving as the amide-protecting group. The reaction is conducted at room temperature together with trifluoroacetic acid diluted with dichloromethane.

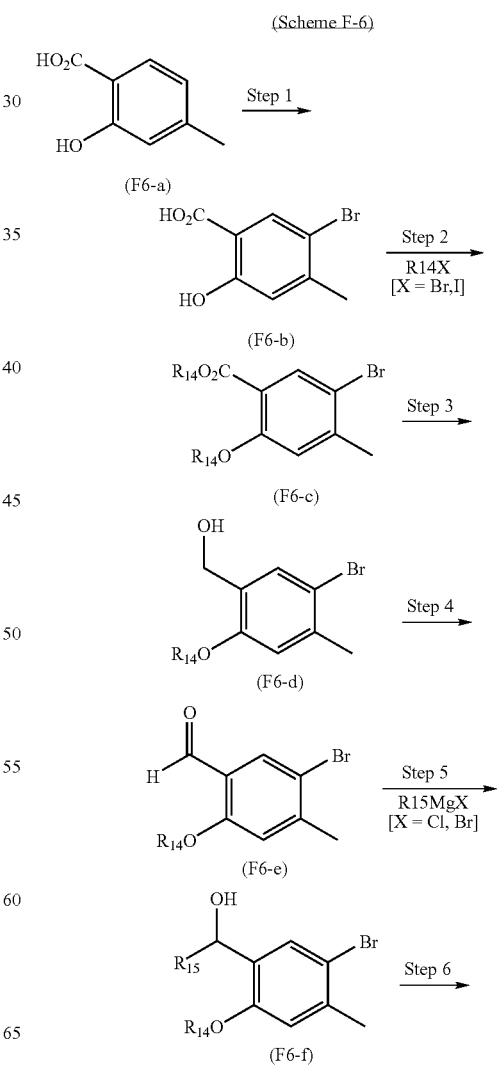

(Scheme F-6)

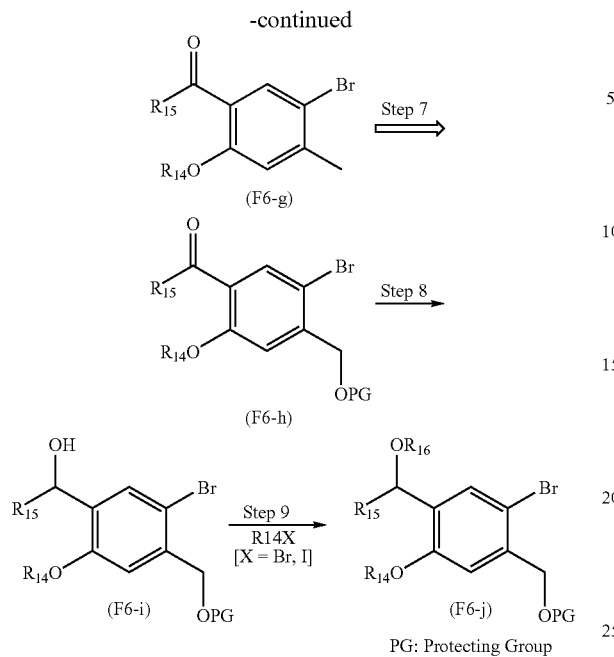

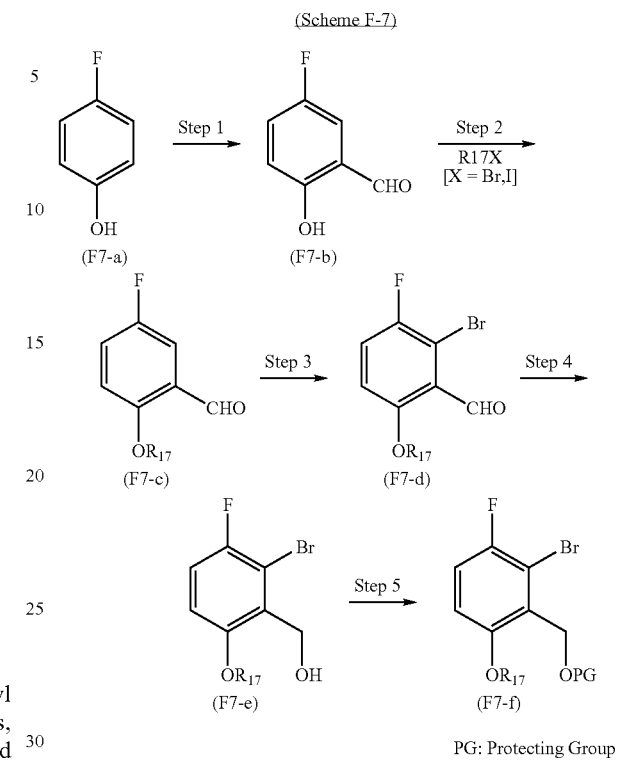

This scheme is a synthesis method for an alkoxyalkyl (F6-j) or alkylketone (F6-h) derivative. In the formulas, R14, R15 and R16 each represent optionally substituted alkyl.

Step 1 is a step of regioselective bromination, wherein compound (F6-b) may be synthesized by reaction with bromine in an alcohol or acetonitrile solvent.

Step 2 is a single step of esterification and etherification. Compound (F6-c) may be obtained by reaction with an alkyl halide in a solvent such as dimethylformamide in the presence of potassium carbonate.

Step 3 is a step of synthesizing an alcohol by reduction of the ester, wherein compound (F6-d) may be obtained similarly to Scheme B-13, Step 1.

Step 4 is a step of synthesizing an aldehyde by oxidation, wherein compound (F6-e) may be obtained by Swern oxidation.

Step 5 is a step of introducing an alkyl group. Compound (F6-f) may be obtained by reaction with a Grignard reagent in a solvent such as tetrahydrofuran or diethyl ether.

Step 6 is a step of synthesizing a ketone by oxidation, wherein compound (F6-g) may be obtained by Swern oxidation.

Step 7 is a step of obtaining compound (F6-h) by the same conversion method as Steps (F2-a) to (F2-e) in Scheme F-2 above. Compound (F6-h) may also be converted to (F6-j) having an alkoxyalkyl group.

Step 8 is a step of reduction, wherein compound (F6-i) may be obtained similarly to Scheme B-13, Step 1.

Step 9 is a step of alkylating the hydroxyl group, wherein compound (F6-j) may be obtained according to the method of Scheme B-6, Step 3.

Compounds (F7-f) and (F8-b) which are compounds represented by (F-a) wherein R4 or R1 is an alkoxy group may be synthesized by the methods shown in the following Schemes F-7 and F-8, respectively.

This scheme is a synthesis method for compound (F7-f). In the formulas, R17 represents optionally substituted alkyl.

Step 1 is a step of introducing a formyl group at the ortho position relative to the hydroxyl group. Compound (F7-b) may be obtained by reaction with tetramethylenetetramine in trifluoroacetic acid, followed by acid hydrolysis using aqueous sulfuric acid.

Step 2 is a step of alkylating the hydroxyl group, wherein compound (F7-c) may be obtained similarly to Scheme B-1, Step 1.

Step 3 is a step of bromination, wherein compound (F7-d) may be obtained by lithiation using butyllithium in the presence of N,N',N'-trimethylethylenediamine, followed by reaction with 1,2-dibromotetrafluoroethane.

Step 4 is a step of reducing the formyl group, and it may be accomplished using sodium borohydride in the same manner as above.

Step 5 is a step of protecting the hydroxyl group, wherein compound (F7-f) may be obtained by the same method as in Scheme E-1, Step 5.

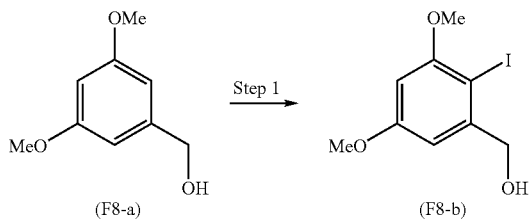

This scheme is a synthesis method for compound (F8-b). Step 1 is a step of regioselective iodination. Compound (F8-b) may be obtained by reaction with iodine in chloroform at room temperature in the presence of mercury trifluoroacetate. A compound represented by (F-d) may be synthesized from compound (F8-b) by conducting the reactions shown in Scheme F, Step 1 and Step 3 without protection of the hydroxyl group.

Synthesis of carboxamide derivatives may be carried out by the methods shown in Production Process G and Production Process H below.

<Production Process G>

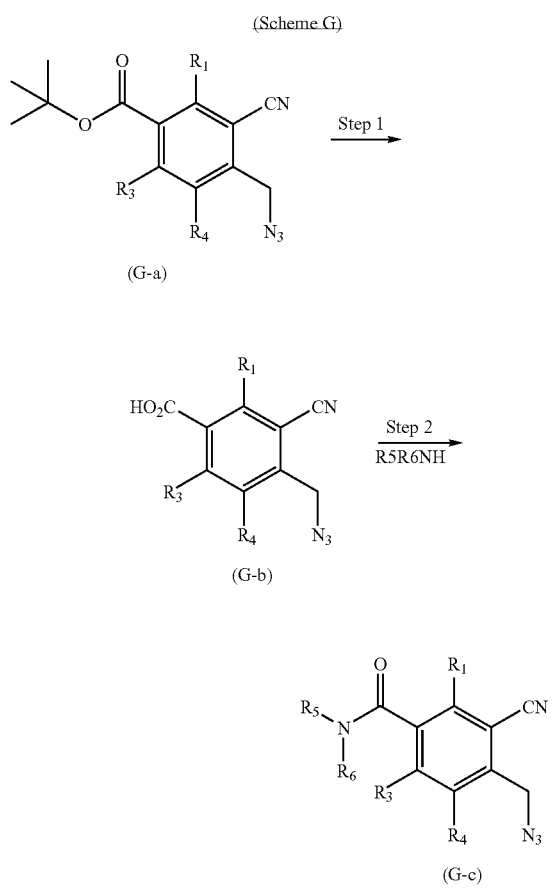

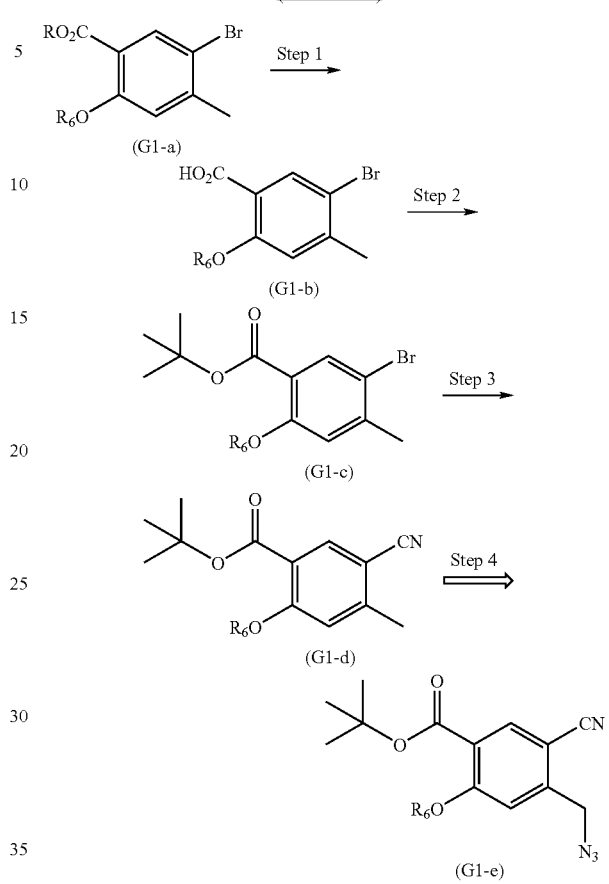

This scheme is synthesis method for a carboxamide (G-c). In the formulas, R1 represents hydrogen or optionally substituted alkoxy, and R3 represents optionally substituted alkoxy. R4 represents hydrogen or halogeno, and R5 and R6 represent hydrogen or optionally substituted alkyl.

Step 1 is a step of removing the tert-butyl group. Compound (G-b) may be obtained by dissolution in trifluoroacetic acid diluted with an organic solvent such as dichloromethane and reaction at room temperature.

Step 2 is a step of amidation, wherein compound (G-c) may be obtained similarly to Scheme B-10, Step 4.

A compound represented by (G-a) may be synthesized by the method shown in Schemes G-1 to G-3.

The compound represented by (G-a) may itself be converted to a compound represented by (A1-c) by the method shown in Scheme C.

This is a synthesis method for compound (G1-e). In the formulas, R6 represents optionally substituted alkyl.

Step 1 is a step of hydrolysis of the ester of compound (G1-a) which may be synthesized by the method shown in Scheme F-6. Compound (G1-b) may be obtained by reaction with lithium hydroxide and aqueous sodium hydroxide in an alcohol solvent.

Step 2 is a step of tert-butylesterification. Di-tert-butyl dicarbonate is reacted therewith in tert-butyl alcohol, in the presence of dimethylaminopyridine. Alternatively, compound (G1-c) may be obtained by heating together with dimethylformamide tert-butylacetal in a solvent such as benzene or toluene.

Step 3 is a step of nitrilation, wherein compound (G1-d) may be obtained similarly to Scheme D, Step 2.

Step 4 may be carried out by conversion in the same manner as Steps 3 and 4 in Scheme D to yield compound (G1-e).

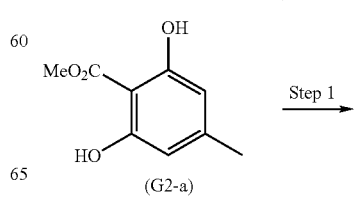

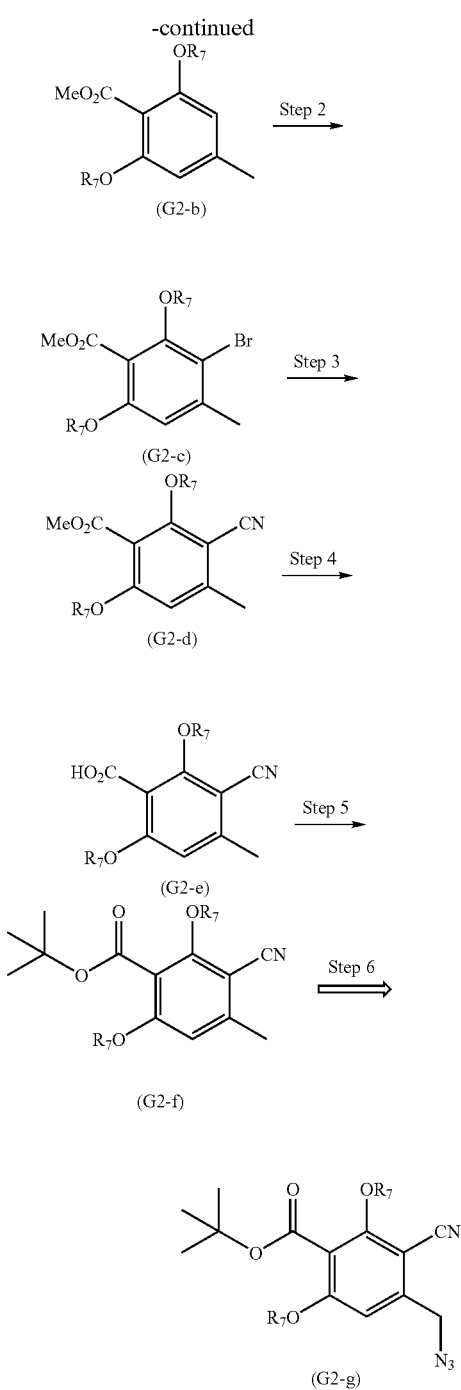

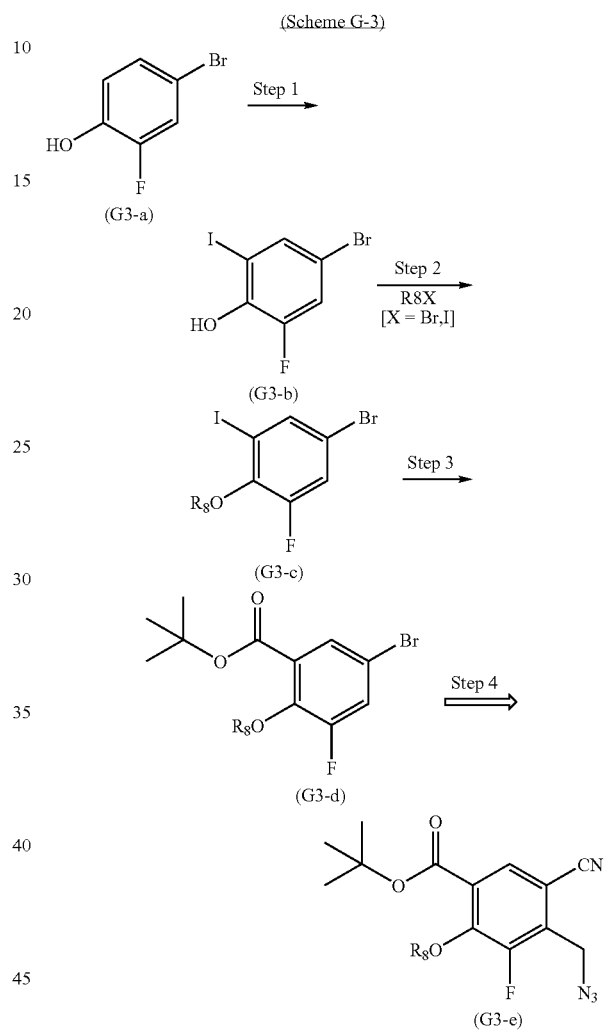

Step 5 is a step of tert-butylesterification, wherein compound (G2-f) may be obtained similarly to Scheme G-1, Step 2.

Step 6 may be carried out by conversion in the same manner as Steps 3 and 4 in Scheme D to yield compound (G2-g).

This scheme is a synthesis method for a dialkoxy derivative (G2-g). In the formulas, R7 represents optionally substituted alkyl.

Step 1 is a step of alkylating the hydroxyl group, wherein compound (G2-b) may be obtained similarly to Scheme B-1, Step 1.

Steps 2 and 3 may be carried out by the same conversion method as in Steps 2 and 3 of Scheme D to yield compound (G2-d).

Step 4 is a step of hydrolyzing the ester, wherein compound (G2-e) may be obtained by reaction with aqueous lithium hydroxide in an alcohol solvent.

This scheme is a synthesis method for a fluorine-containing compound (G3-e). In the formulas, R8 represents optionally substituted alkyl.

Step 1 is a step of regioselective iodination. Compound (G3-b) may be obtained by reaction with N-iodosuccinimide in dimethylformamide at room temperature.

Step 2 is a method of alkylating the hydroxyl group, wherein compound (G3-c) may be obtained similarly to Scheme B-1, Step 1.

Step 3 is a step of introducing a tert-butoxycarbonyl group by iodine-metal exchange. Compound (G3-d) may be obtained by conversion to a magnesium reagent according to the method described in Knochel et al., Angew. Chem., Int. Ed. Engl., 37, 1701(1998), followed by reaction with di-tert-butyl dicarbonate.

The conversion shown in Step 4 may be carried out by the series of steps for conversion shown in Scheme F-1 to obtain (G3-e).

<Production Process H>

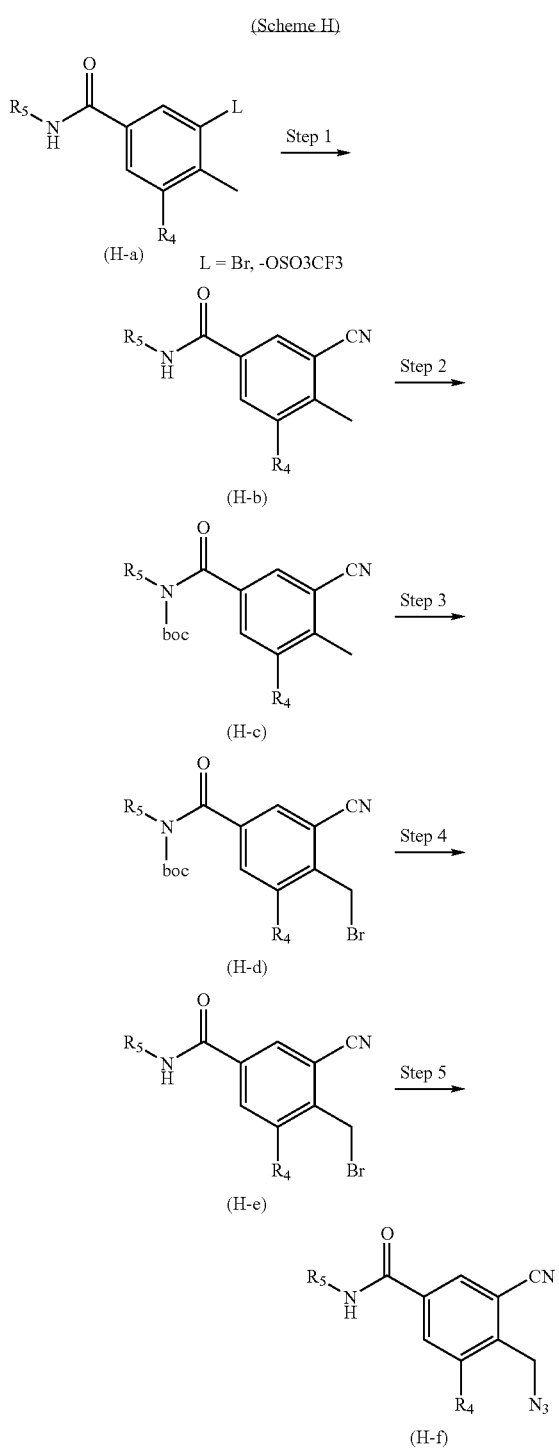

This scheme is a synthesis method for a carboxamide derivative (H-f). In the formulas, R4 represents halogeno or optionally substituted alkoxy, and R5 represents optionally substituted alkyl.

In this scheme, Steps 1, 3 and 5 may be carried out in the same manner as Steps 2, 3 and 4 shown in D, and compound (H-f) may be obtained by adding steps of protecting (Step 2) and deprotecting (Step 4) the amide. The protection and deprotection of the amide may be carried out by the method shown in Scheme F-5.

The compounds shown in Scheme H may be synthesized by the methods shown in the following Schemes H-1 and H-2.

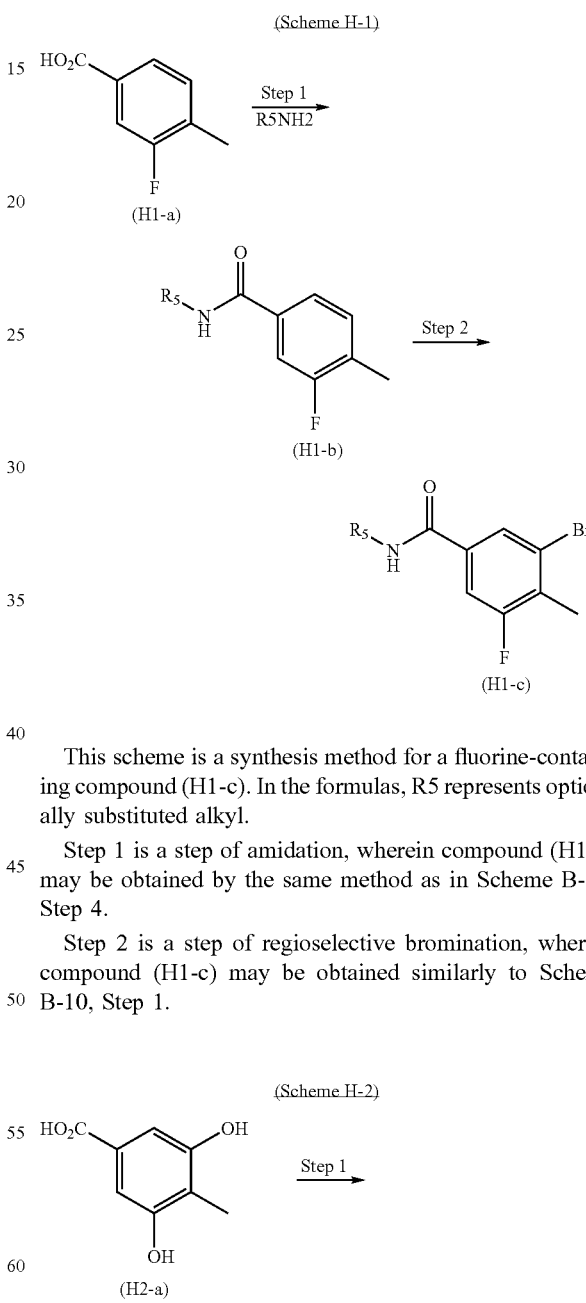

This scheme is a synthesis method for a fluorine-containing compound (H1-c). In the formulas, R5 represents optionally substituted alkyl.

Step 1 is a step of amidation, wherein compound (H1-b) may be obtained by the same method as in Scheme B-10, Step 4.

Step 2 is a step of regioselective bromination, wherein compound (H1-c) may be obtained similarly to Scheme B-10, Step 1.

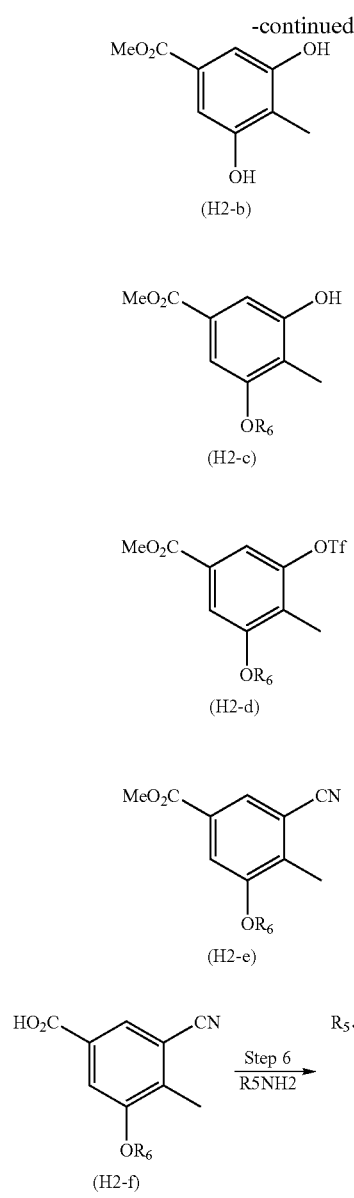

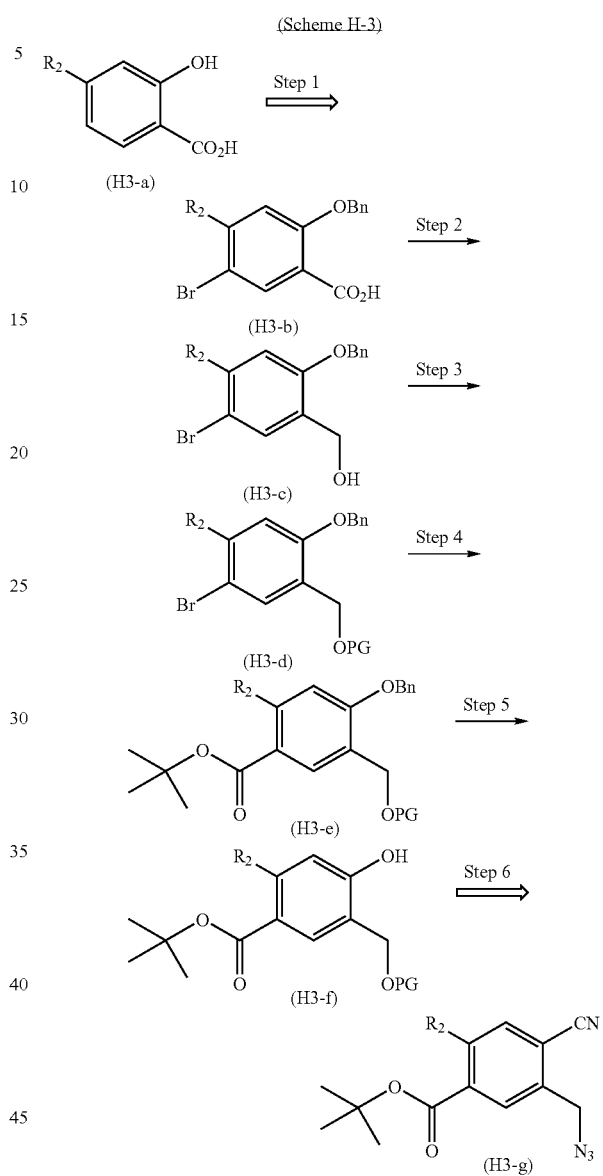

<Production Process H-3>

This scheme is a synthesis method for an alkoxy-containing compound (H2-g). In the formulas, R6 represents optionally substituted alkyl.

Step 1 is a step of esterification. Compound (H2-b) may be obtained by heating to reflux in methanol in the presence of a catalytic amount of concentrated sulfuric acid.

Step 2 is a step of monoalkylation. Compound (H2-c) may be obtained by reaction with an alkyl halide in dimethylformamide in the presence of 5 N aqueous sodium hydroxide.

Steps 3 and 4 accomplish nitrilation via a triflate, wherein compound (H2-e) may be obtained by the method shown in Scheme F-1.

Step 5 is a step of hydrolyzing the ester, wherein compound (H2-f) may be obtained by reaction with aqueous sodium hydroxide in an alcohol solvent or a tetrahydrofuran/alcohol mixed solvent.

Step 6 is a step of amidation, wherein compound (H2-g) may be obtained similarly to Scheme B-10, Step 4.

This scheme is a synthesis method for a derivative of a compound represented by (C-a) wherein R3 is carboxamide. In the formulas, R2 represents hydrogen, optionally substituted alkyl or alkoxy.

Step 1 is a step of conversion from a readily available salicylic acid derivative (H3-a) to compound (H3-b), and it may be conducted by the same method used for synthesis of compound (G1-b) [R6=benzyl] in Scheme G-1.

Step 2 is a step of synthesizing an alcohol by reduction of the carboxyl group, wherein compound (H3-c) may be obtained similarly to Scheme E-4, Step 2.

Step 3 is a step of protecting the hydroxyl group, wherein compound (E3-d) may be obtained similarly to Scheme E-1, Step 5.

Step 4 is a step of introducing a tert-butoxycarbonyl group by halogen-metal exchange. Compound (H3-e) may be obtained by lithiation with butyllithium followed by reaction with di-tert-butyl dicarbonate.

Step 5 is a step of removing the benzyl-protecting group. Compound (H3-f) may be obtained by hydrogenation in the presence of palladium-carbon.

The conversion of Step 6 may be carried out by the same series of reactions as shown in Production Process F to yield compound (H3-g).

Conversion to an amide derivative of compound (H3-g) may be accomplished by the same method shown in Production Process G. Here, the compound represented by (H3-g) as an intermediate may itself be converted to a compound represented by (A1-a) shown in Scheme C.

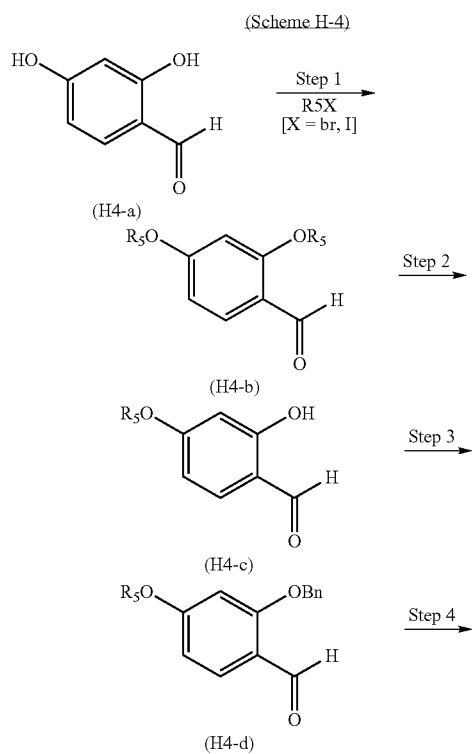

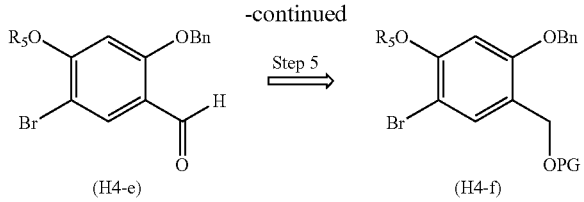

This scheme is a synthesis method for compound (H4-f) which is a compound represented by (H3-d) wherein R2 is alkoxy. In the formulas, R5 represents optionally substituted alkyl.

Step 1 is a step of alkylation of the two hydroxyl groups (R5 represents lower alkyl except benzyl), wherein compound (H4-b) may be obtained similarly to Scheme B-1, Step 1.

Step 2 is a step of regioselective dealkylation. Compound (H4-c) may be obtained by reaction with two equivalents of aluminum chloride in a solvent such as dichloromethane from freezing to room temperature.

Step 3 is a step of introducing benzyl as a protecting group for the hydroxyl group. Compound (H4-d) may be obtained by reaction with benzyl bromide in dimethylformamide in the presence of potassium carbonate.

Step 4 is a step of regioselective bromination, wherein compound (H4-e) may be synthesized by reaction with bromine in an alcohol or acetonitrile solvent.

The conversion of Step 5 may be conducted in the same manner as Steps 1 and 2 of Scheme F-1 to obtain compound (H4-f).

General synthesis methods for the starting materials used in Scheme A-4 of Production Process A will now be described.

<Production Process AP>

This is a process for synthesis of intermediates (AP1-c), (AP1-d), (AP1-e), (AP2-b), (AP2-c) and (AP2-d) as common starting materials for synthesis of aminophenol derivatives.

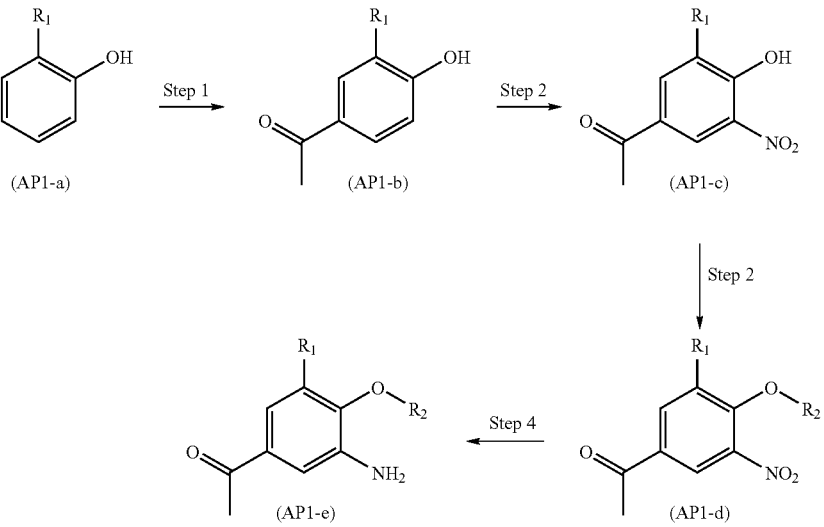

This scheme is a method for synthesis of compound (AP1-e) from compound (AP1-a). In the formulas, R1 represents hydrogen, optionally substituted alkyl, optionally substituted cycloalkyl or optionally substituted alkoxy. R2 has the same definition as R6 and R7 in Production Process MO.

Step 1 is a step of Friedel-Crafts acylation. Compound (AP1-b) may be obtained by reacting compound (AP1-a) with acetyl chloride in a solvent such as dichloromethane or toluene, in the presence of a Lewis acid such as aluminum chloride, zinc chloride or tin (IV) chloride, at −70° C. to room temperature.

Step 2 is a step of nitration. Compound (AP1-c) may be obtained by reaction with fuming nitric acid or concentrated nitric acid in a solvent such as toluene, hexane, ether or acetic anhydride. Alternatively, the reaction may be conducted by generating nitric acid from sodium nitrate and hydrochloric acid.

Step 3 is a step of introducing a substituent R2 having any of various structures at the hydroxyl group of compound (AP1-c). Compound (AP1-d) may be obtained by reaction with a halide, mesylate or tosylate in a solvent such as dimethylformamide, acetonitrile, tetrahydrofuran, dichloromethane or acetone, in the presence of a base such as potassium carbonate, cesium carbonate, sodium hydrogencarbonate, trialkylamine, a pyridine derivative or sodium hydride. In the formulas, R2 has the same definition as R6 in Step 1 of Production Process MO.

Step 4 is a step of reducing the nitro group. Compound (AP1-e) may be obtained by reaction in a solvent such as tetrahydrofuran, ethyl acetate, methanol or ethanol under a hydrogen atmosphere, in the presence of a catalyst such as palladium-carbon. Alternatively, compound (AP1-e) may be obtained by conducting the reaction in a solvent such as hydrous methanol or hydrous ethanol in the presence of ammonium chloride, with addition of iron at the reflux temperature of the solvent.

This scheme is a method for synthesis of (AP2-d) from (AP1-a). In the formulas, R1 represents hydrogen, optionally substituted alkyl, optionally substituted cycloalkyl or optionally substituted alkoxy.

Step 1 is a step of brominating the para-position relative to the phenolic hydroxyl group. Reaction with bromine is conducted in a solvent such as methanol, ethanol or chloroform. Alternatively, compound (AP2-a) may be obtained by reaction with N-bromosuccinimide in a solvent such as acetonitrile or dimethylformamide.

Step 2 is a step of nitration. Compound (AP2-b) may be obtained by reaction with fuming nitric acid or concentrated nitric acid in a solvent such as toluene, hexane, ether or acetic anhydride. Alternatively, the reaction may be conducted by generating nitric acid from sodium nitrate and hydrochloric acid.

Step 3 is a step of introducing a substituent R2 with any of various structures at the hydroxyl group of compound (AP2-b). Compound (AP2-c) may be obtained by reaction with a halide, mesylate or tosylate in a solvent such as dimethylformamide, acetonitrile, tetrahydrofuran, dichloromethane or acetone, in the presence of a base such as potassium carbonate, cesium carbonate, sodium hydrogencarbonate, trialkylamine, a pyridine derivative or sodium hydride. In the formulas, R2 has the same definition as R6 in Step 1 of Production Process MO.

Step 4 is a step of reducing the nitro group. Compound (AP2-d) may also be obtained by conducting the reaction in a solvent such as hydrous methanol or hydrous ethanol in the presence of ammonium chloride, with addition of iron at the reflux temperature of the solvent.

The following Production Processes PP to BOL are general production processes for aminophenol derivatives using compounds synthesized by Production Process AP as the starting materials.

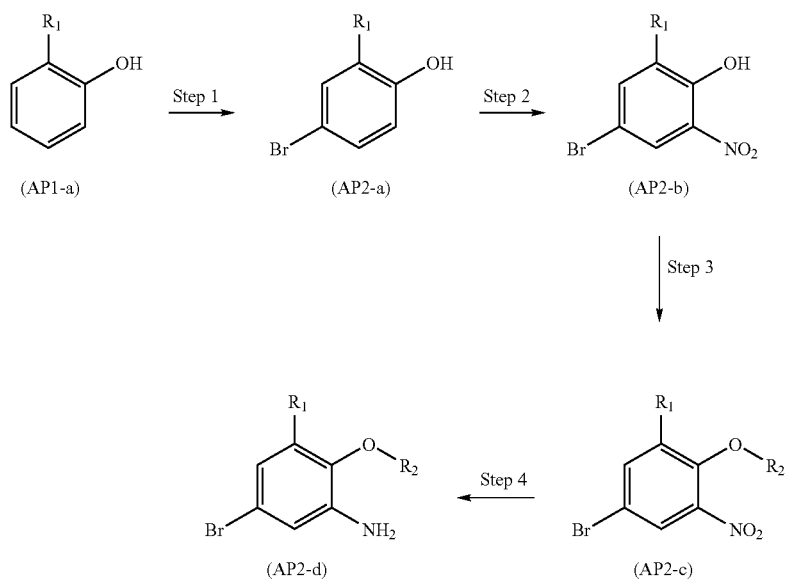

(Scheme AP-2)

<Production Process PP>

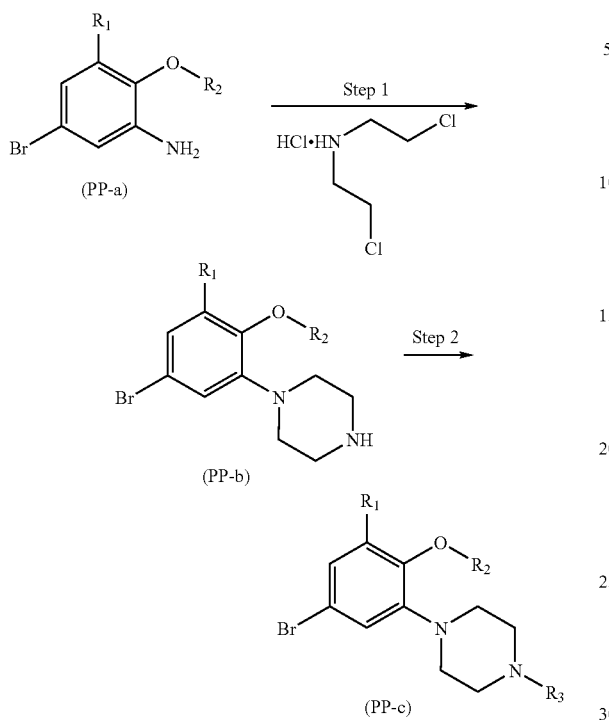

Production Process PP is a general synthesis method for a piperazine derivative.

Step I is a step of treating the amino group of compound (PP-a) with bischloroethylamine hydrochloride to form a piperazine ring. Preferably, compound (PP-a) is reacted with bischloroethylamine hydrochloride in 1,2-dichlorobenzene while heating to reflux, and the reaction is conducted while removing the generated hydrogen chloride gas to yield compound (PP-b).

In the formulas, R1 represents hydrogen, optionally substituted alkyl, optionally substituted cycloalkyl, optionally substituted alkoxy or optionally substituted alkylamino. R2 represents hydrogen or optionally substituted alkyl.

The formulas in Production Process PP show only a piperazine group, but any 5- to 8-membered ring containing more than one nitrogen atom may be formed, without any restriction to piperazine.

Step 2 is a step of introducing substituent R3 at the secondary amine position of the piperazine of compound (PP-b). Compound (PP-b) may be reacted with reagent R3-X1 (X1=halogen) in an appropriate solvent such as dichloromethane or tetrahydrofuran, in the presence of an inorganic base such as potassium carbonate or sodium hydrogencarbonate or in the presence of an organic base such as trialkylamine or a pyridine derivative to yield compound (PP-c) having R3 introduced therein. R3 of reagent R3-X1 represents optionally substituted alkyl, optionally substituted alkyl having cyano on the end or a branch, alkyl having protected or substituted carboxylic acid on the end or a branch, alkyl having protected or substituted hydroxyl on the end or a branch, alkyl having protected or substituted amino on the end or a branch, optionally substituted sulfonyl, optionally substituted acyl, or optionally substituted carbamoyl. The reagent used to introduce substituent R3 into compound (PP-b) may be, instead of R3-X1 mentioned above, di-t-butyl dicarbonate or optionally substituted isocyanate. Compound (PP-b) may be subjected to reductive amination using an optionally substituted aldehyde or ketone and sodium triacetoxyborohydride or sodium cyanoborohydride for introduction of substituent R3.

Compound (PP-c) obtained by this Production Process is converted to the final target compound by Production Process A.

<Production Process MO>

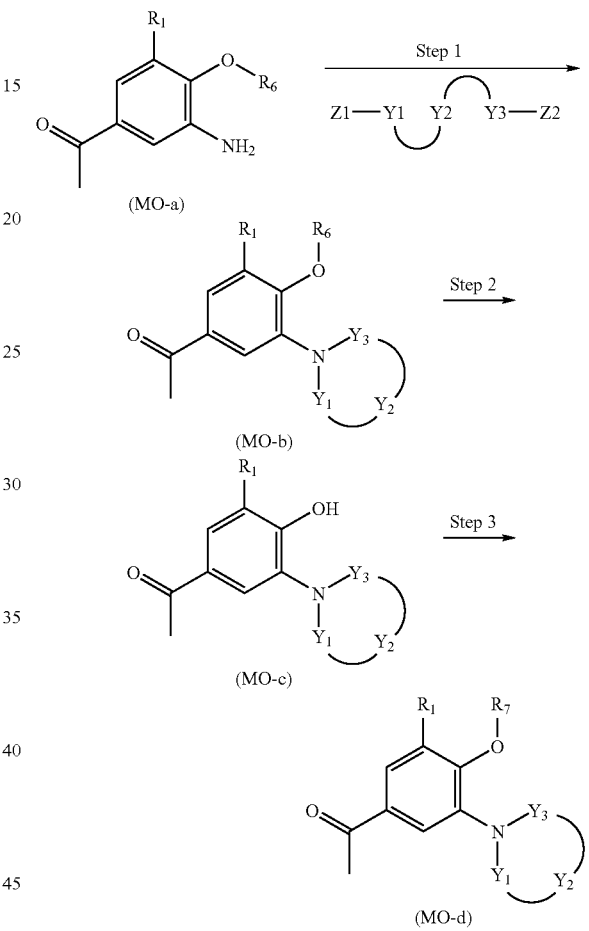

Production Process MO is a general production process for a heterocyclic amino derivative.

Step 1 is a step of treating the amino group of compound (MO-a) with a reagent represented by Z1-Y1-Y2-Y3-Z2 to form a nitrogen-containing ring.

Compound (MO-b) may be obtained by reacting compound (MO-a) with reagent Z1-Y1-Y2-Y3-Z2 in an appropriate solvent such as dimethylformamide, tetrahydrofuran or dichloromethane, in the presence of an inorganic base such as potassium carbonate, sodium hydrogencarbonate or cesium carbonate or in the presence of an organic base such as trialkylamine or a pyridine derivative.

Z1 and Z2 in the reagent Z1-Y1-Y2-Y3-Z2 represent leaving groups such as halogen or sulfonate. Y1 and Y3 represent methylene optionally substituted with alkyl, alkoxy or the like, carbonyl, carboxyl, sulfonyl or amide. Elements to form the main chain at the portion represented by —Y2- include carbon, oxygen, nitrogen and sulfur. There are no particular restrictions on the length of the chain. Where possible, the element forming the —Y2- main chain may also have as a substituent an optionally substituted alkyl, optionally substituted alkoxy, optionally substituted alkoxyalkyl, optionally substituted hydroxyalkyl, hydroxy, carbonyl, optionally protected or substituted carboxyl, optionally protected or substituted carboxyalkyl, optionally protected or substituted amine or optionally protected or substituted aminoalkyl. An oxo group may also be present on the —Y2- main chain and form a carbonyl, sulfonyl or sulfinyl group together with carbon or sulfur on the main chain.

In the formulas, R1 has the same definition as R1 in Step 1 of Production Process PP. R6 represents an optionally substituted alkyl, a protecting group for hydroxyl, such as methoxymethyl, tetrahydropyranyl or trialkylsilyl, or alternatively alkyl having cyano at the end or a branch, alkyl having protected or substituted carboxylic acid on the end or a branch, arylalkyl having protected or substituted carboxylic acid on the end or a branch, alkyl having a protected or substituted hydroxyl group on the end or a branch, arylalkyl having protected or substituted hydroxyl on the end or a branch, alkyl having protected or substituted amino on the end or a branch, arylalkyl having protected or substituted amino on the end or a branch, optionally substituted sulfonyl, optionally substituted acyl or optionally substituted carbamoyl.

Step 2 is a step of deprotection when R6 of compound (MO-b) is a protecting group for the phenolic hydroxyl group. For example, compound (MO-c) wherein R6 is methoxymethyl may be obtained by treating compound (MO-b) with an acidic mixed solvent such as 5 N hydrochloric acid/acetone or 10% aqueous perchloric acid/tetrahydrofuran.

Step 3 is a step of introducing a new substituent R7 at the phenolic hydroxyl group of compound (MO-c).

R7 has the same definition as R6 in Step 1 of Production Process MO.

Compound (MO-d) wherein X2 of reagent R7-X2 described below is a leaving group such as halogen or sulfonate may be synthesized in the following manner.

The compound (MO-d) may be obtained by reacting compound (MO-c) with reagent R7-X2 in an appropriate solvent such as dimethylformamide, acetonitrile, diethyl ether, tetrahydrofuran or dichloromethane, in the presence of an inorganic base such as potassium carbonate, sodium hydrogencarbonate or cesium carbonate or in the presence of an organic base such as trialkylamine or a pyridine derivative, or in the presence of sodium hydride.

Compound (MO-d) wherein R7 is methyl may be obtained at a high yield by reacting compound (MO-c) with diazomethane in diethyl ether or with trimethylsilyldiazomethane in acetonitrile-diisopropylethylamine-methanol.

Compound (MO-d) wherein X2 in reagent R7-X2 is hydroxyl may be obtained by reacting compound (MO-c) with reagent R7-X2 by the publicly known Mitsunobu reaction in an appropriate solvent such as tetrahydrofuran or toluene.

In Production Process MO, R6 and R7 may sometimes undergo conversion to a structure which is not defined herein by a method easily predictable by a person skilled in the art at an appropriate stage after introduction. Likewise, the —N—Y1-Y2-Y3(—N) portion obtained by cyclization in Step 1 may also undergo conversion to a structure which is not defined herein. (Conversion of the —N—Y1-Y2-Y3(—N) portion is described in some of the following Production Process examples).

Compounds (MO-b), (MO-c) and (MO-d) obtained in this Production Process are converted to the final target compounds by Production Process A.

<Production Process PR>

Production Process PR is a general synthesis method for pyrrolidine derivatives.

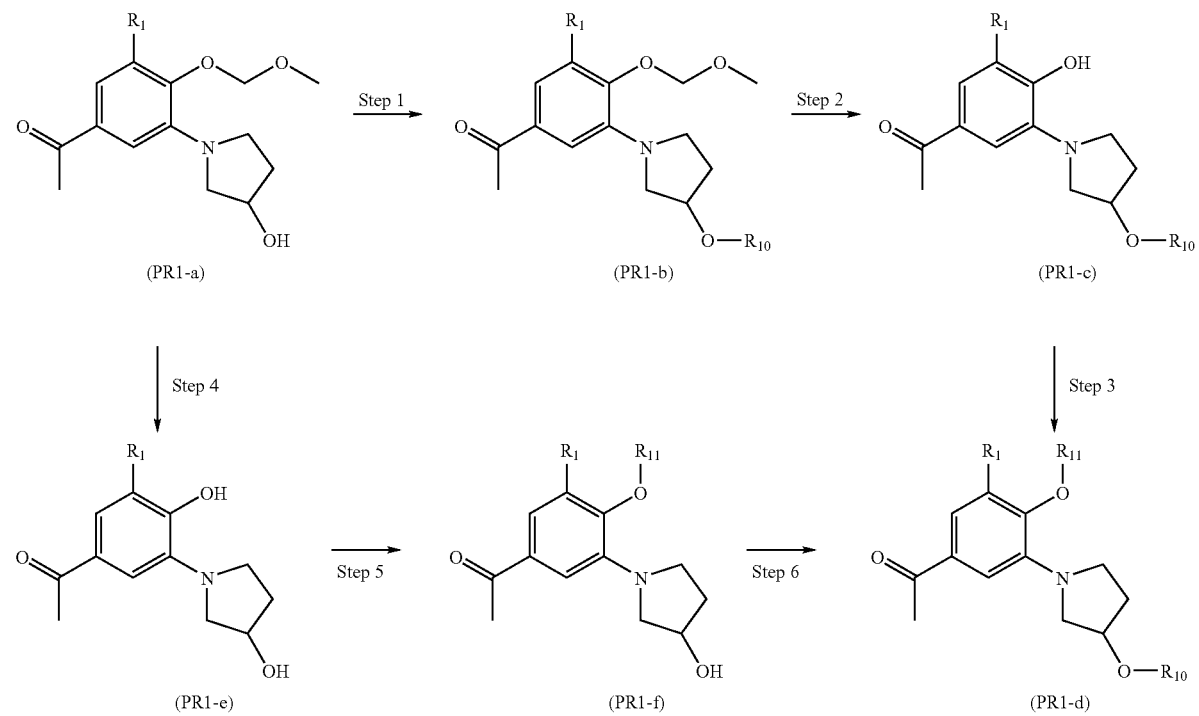

(Scheme PR-1)

Scheme PR-1 is one production process whereby the —N—Y1-Y2-Y3(—N) portion obtained by cyclization in Step 1 of Production Process MO may undergo additional structural conversion. In the formulas, R1 has the same definition as R1 in Step 1 of Production Process PP. R10 and R11 have the same definitions as R6 and R7 in Production Process MO. Although only methoxymethyl is mentioned as a protecting group for the phenolic hydroxyl groups of compounds (PR1-a) and (PR1-b), there is no limitation to methoxymethyl.

Step 1 is a step of introducing a substituent R10 at the hydroxyl group of compound (PR1-a). The reaction is conducted using reagent R10-X3 in an appropriate alkaline hydrous organic solvent, in the presence of a phase transfer catalyst. Preferably, compound (PR1-b) is obtained by reaction of reagent R10-X3 with compound (PR1-a) in a mixture of 50% aqueous sodium hydroxide and toluene in the presence of tetrabutylammonium bromide. Here, X3 is a leaving group such as a halogen or sulfonate.

Step 2 is a step of treating compound (PR1-b) in the same manner as Step 2 of Production Process MO to yield compound (PR1-c).

Step 3 is a step of introducing a new substituent R11 at the phenolic hydroxyl group of compound (PR1-c). Compound (PR1-c) may be treated in the same manner as for introduction of R7 in Step 3 of Production Process MO to yield compound (PR1-d) having R11 introduced therein.

Step 4 is a step of treating compound (PR1-a) in the same manner as Step 2 of Production Process MO to yield compound (PR1-e).

Step 5 is a step of selectively introducing substituent R11 only at the phenolic hydroxyl group of compound (PR1-e). Utilizing the difference in reactivity between the two hydroxyl groups of compound (PR1-e), treatment may be carried out in the same manner as for introduction of R7 in Step 3 of Production Process MO to yield compound (PR1-f) having R11 introduced therein.

Step 6 is a step of treating compound (PR1-f) in the same manner as Step 1 of this Scheme PR-1 to yield compound (PR1-d).

Compounds (PR1-b) and (PR1-d) obtained in this Scheme PR-1 are converted to the final target compounds by Production Process A.

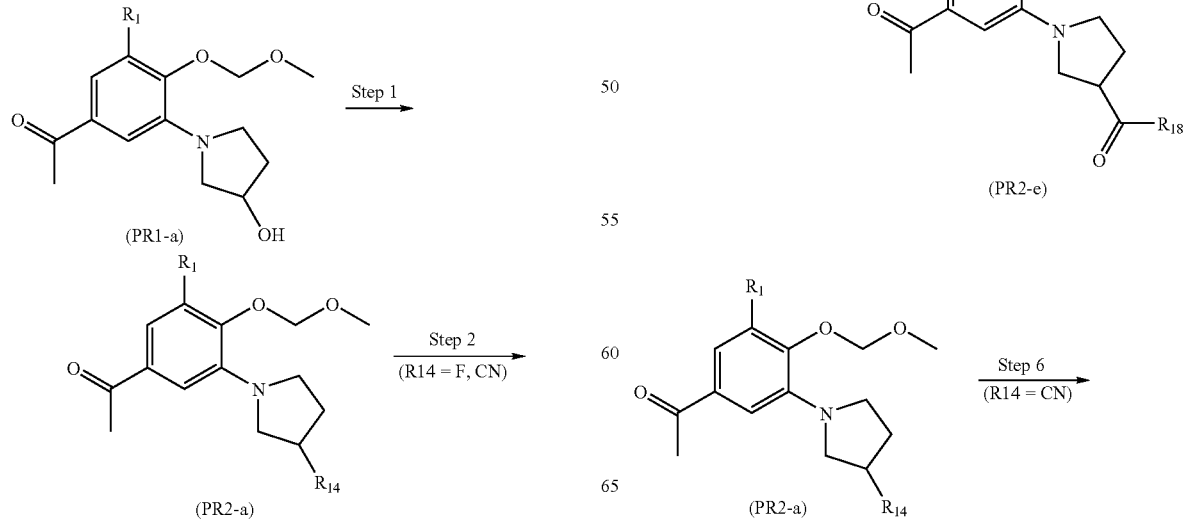

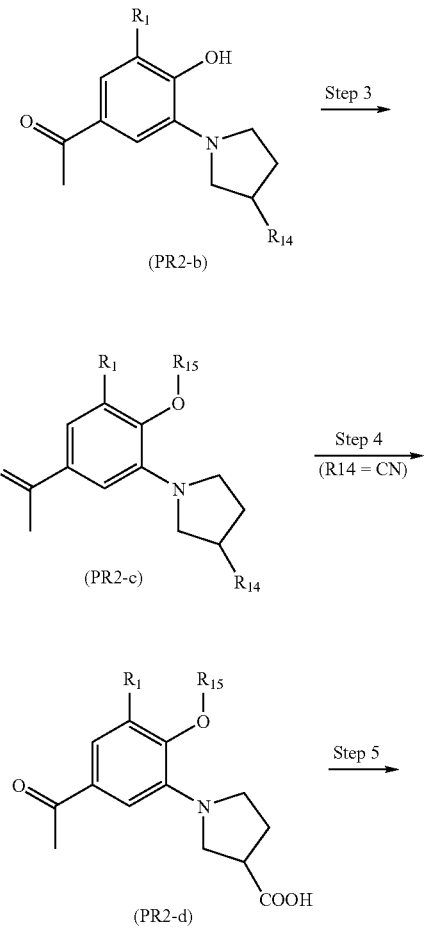

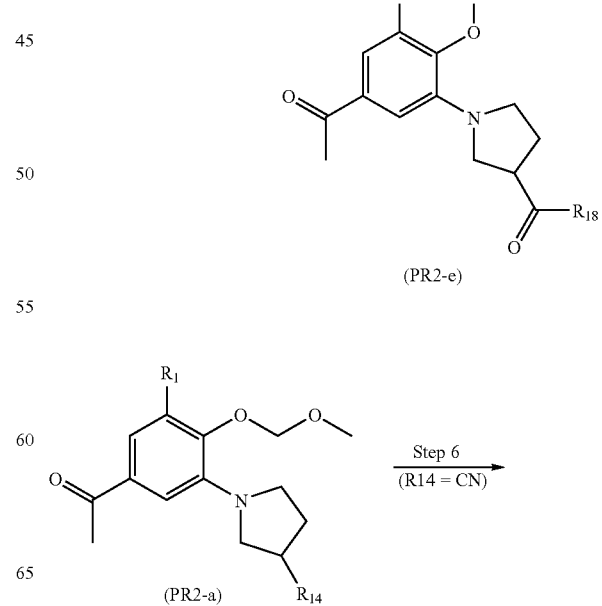

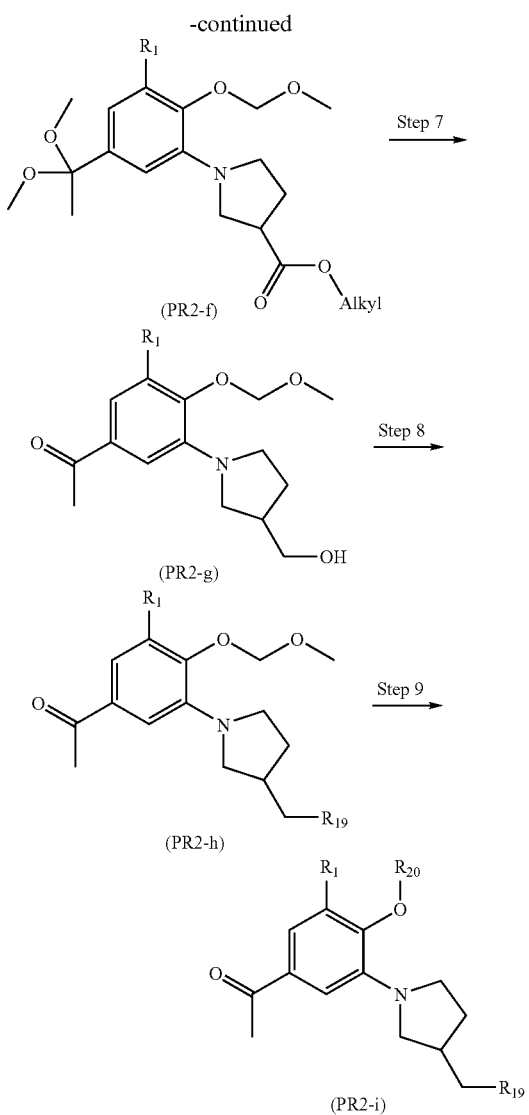

Step 2 is a step of treating compound (PR2-a) (R14=F or CN) in the same manner as Step 2 of Production Process MO to yield compound (PR2-b) (R14=F or CN).

Step 3 is a step of introducing substituent R15 at the phenolic hydroxyl group of compound (PR2-b) (R14=F or CN). Compound (PR2-b) may be treated in the same manner as for introduction of R7 in Step 3 of Production Process MO to yield compound (PR2-c) (R14=F or CN) having R15 introduced therein.

Step 4 is a step of converting compound (PR2-c) wherein R14=CN to compound (PR2-d) wherein the cyano group is converted to a carboxyl group by alkali hydrolysis. Preferably, compound (PR2-c) wherein R14=CN may be reacted by heating to reflux in a mixed solvent of aqueous sodium hydroxide and ethanol to yield compound (PR2-d).

Step 5 is a step of esterifying or amidating the carboxylic acid group of compound (PR2-d) for introduction of a substituent R18 by common methods. The carboxylic acid group of compound (PR2-d) may be converted to an active species by a common method such as an acid mixing method using a chloroformic acid ester or an acid chloride method using oxalyl chloride, and then reacted with an alcohol or amine for conversion to (PR2-e). Alternatively, (PR2-d) may be esterified by reaction with the corresponding alkyl halide reagent in the presence of an appropriate base or by reaction with di-tert-butyl dicarbonate in tert-butyl alcohol in the presence of dimethylaminopyridine. Compound (PR2-d) may also be subjected to dehydration reaction using an alcohol or amine and a peptide-forming condensing agent, for conversion to compound (PR2-e). The synthesis may also be carried out by other suitable known reactions. R18 represents amino or alkoxy.

Step 6 is a step of subjecting compound (PR2-a: R14=CN) to alkali hydrolysis in the same manner as Step 4 followed by treatment in the same manner as the esterification in Step 5, and then ketal protection of the carbonyl group of the acetophenone. After converting compound (PR2-a: R14=CN) to a carboxylic acid ester, it may be reacted with a ketalizing reagent such as methyl orthoformate under acidic conditions to yield compound (PR2-f). Preferably, the methyl orthoformate is reacted with the carbonyl group in methanol in the presence of an acid catalyst such as camphorsulfonic acid or p-toluenesulfonic acid and Molecular Sieve 3A, to yield compound (PR2-f).

Step 7 is a step of reducing the ester group of compound (PR2-f) for conversion to a hydroxymethyl group, and then selectively deprotecting only the ketal protection of the acetophenone carbonyl group. First, compound (PR2-f) is reacted with an ester-reducing reagent such as lithium aluminum hydride in an appropriate solvent such as tetrahydrofuran or diethyl ether, for conversion to a hydroxymethyl group. Next, under mildly acidic conditions, preferably under conditions with an acetic acid-tetrahydrofuran-water (4:1:1) mixed acid solvent, the ketal protecting group for the carbonyl group is selectively deprotected while leaving the methoxymethyl group for the phenolic hydroxyl, to yield compound (PR2-g).

Step 8 is a step of converting the hydroxyl group of compound (PR2-g) to substituent R19 (cyano or various alkoxy).

When R19 is cyano, treatment is carried out in the same manner as for conversion in Step 1 when R14 is cyano, to yield compound (PR2-h) wherein the hydroxymethyl group of compound (PR2-g) is converted to cyanomethyl, in which case R19 represents cyano. When R19 is an alkoxy group, compound (PR2-g) is treated in the same manner as Step 1 of Scheme PR-1 to yield compound (PR2-h) for conversion Scheme PR-2 is one production process whereby the —N—Y1-Y2-Y3(—N) portion obtained by cyclization in Step 1 of Production Process MO may undergo additional structural conversion. In the formulas, R1 has the same definition as R1 in Step 1 of Production Process PP. R15 and R20 have the same definitions as R6 and R7 in Production Process MO.

Step 1 is a step of replacing the hydroxyl group of compound (PR1-a) with a substituent R14 (F or CN). When R14 is fluoro, compound (PR1-a) may be treated with diethylaminosulfur trifluoride (DAST) in dichloromethane to yield compound (PR2-a: R14=F). When R14 is cyano, the hydroxyl group of compound (PR1-a) may first be converted to a leaving group with an acyl chloride reagent such as methanesulfonyl chloride in an appropriate solvent such as dichloromethane, in the presence of a base such as triethylamine. A hydrogen cyanide salt may then be reacted with this intermediate to introduce a cyano group. Preferably, the intermediate is added to dimethylformamide and reacted with sodium cyanide in the presence of tetrabutylammonium iodide to yield compound (PR2-a: R14=CN).

to the alkoxy group, in which case R19 has the same definition as OR10 in Scheme PR-1.

Step 9 is a step of deprotecting the methoxymethyl group serving as the protecting group for the phenolic hydroxyl of compound (PR2-h), and then introducing a substituent R20. First, compound (PR2-h) is treated in the same manner as Step 2 of Production Process MO to remove the methoxymethyl group. It is then treated in the same manner as for introduction of R7 in Step 3 of Production Process MO to yield compound (PR2-i) having R20 introduced therein.

Compounds (PR2-c), (PR2-e) and (PR2-i) obtained in this Scheme PR-2 are converted to the final target compounds by Production Process A.

compound (PR3-c) having two substituents R24 introduced therein. Alternatively, when R24 is a methoxymethyl group or the like, an excess of methoxymethyl chloride may be reacted with compound (PR3-a) in the presence of diisopropylethylamine to yield compounds (PR3-b) and (PR3-c). Compounds (PR3-b) and (PR3-c) may be separated by silica gel column chromatography.

Step 2 is a step of treating compound (PR3-b) in the same manner as Step 1 to yield compound (PR3-d) having a newly introduced substituent R25.

Step 3 is a step of stereoinversion of the hydroxyl group of compound (PR3-b) to yield compound (PR3-e). Com-

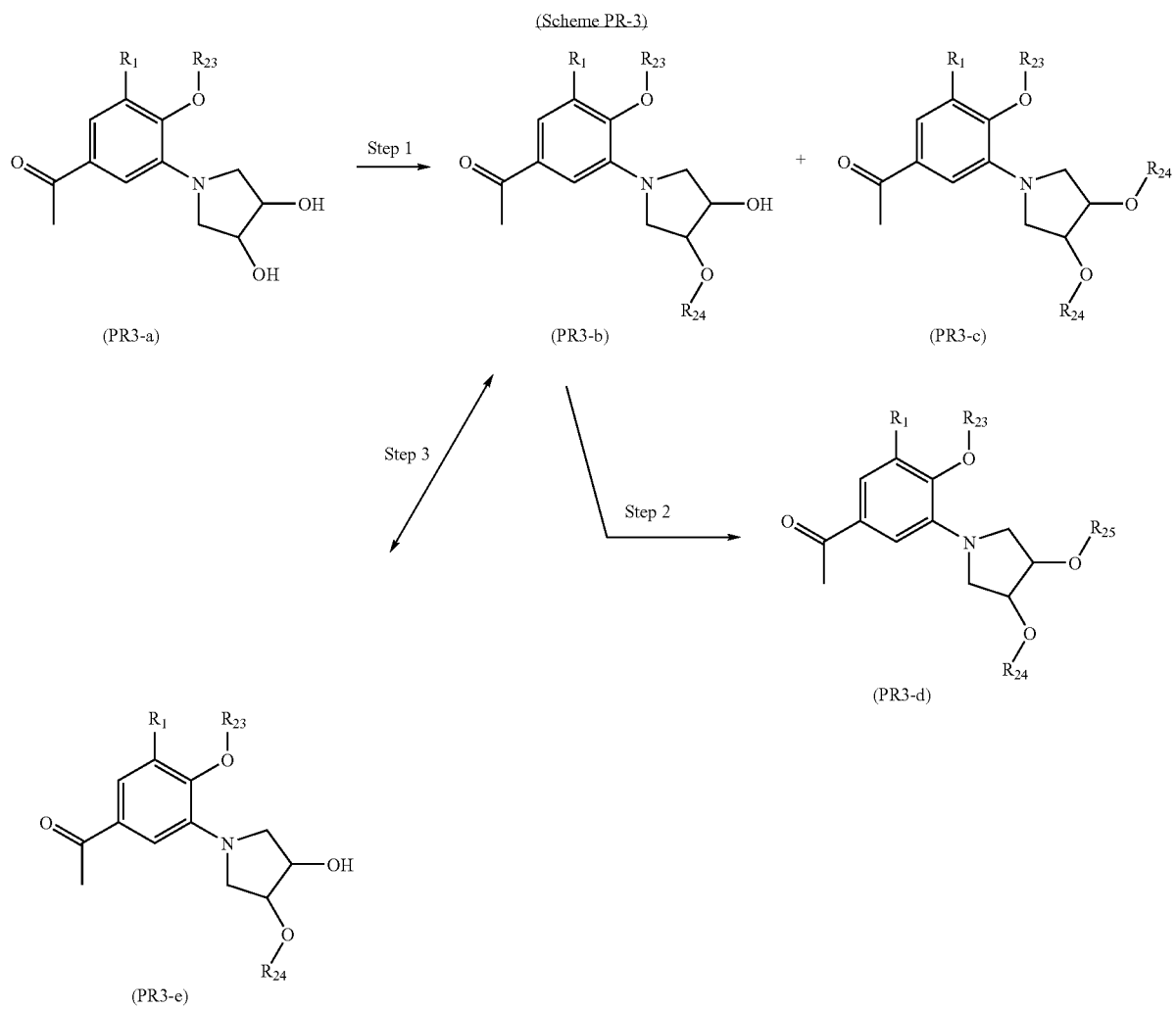

Scheme PR-3 is one production process whereby the —N—Y1-Y2-Y3(—N) portion obtained by cyclization in Step 1 of Production Process MO may undergo additional structural conversion. In the formulas, R1 has the same definition as R1 in Step 1 of Production Process PP. R23, R24 and R25 have the same definitions as R6 and R7 in Production Process MO.

Step 1 is a step of treating compound (PR3-a) in the same manner as Step 1 of Scheme PR-1 to yield compound (PR3-b) having one substituent R24 introduced therein and pound (PR3-b) is reacted with m-nitrobenzenesulfonyl chloride in dichloromethane in the presence of triethylamine and dimethylaminopyridine. It is then treated with cesium acetate while heating in dimethylsulfoxide to yield a hydroxyl-inverted acetate. This is treated with potassium carbonate in methanol to yield the hydroxyl-inverted compound (PR3-e).

Compounds (PR3-b), (PR3-c) and (PR3-d) obtained in Scheme PR-3 are converted to the final target compounds by Production Process A. Compound (PR3-e) may also be treated in the same manner as Step 2 of this Scheme and then converted to the final target compound by Production Process A.

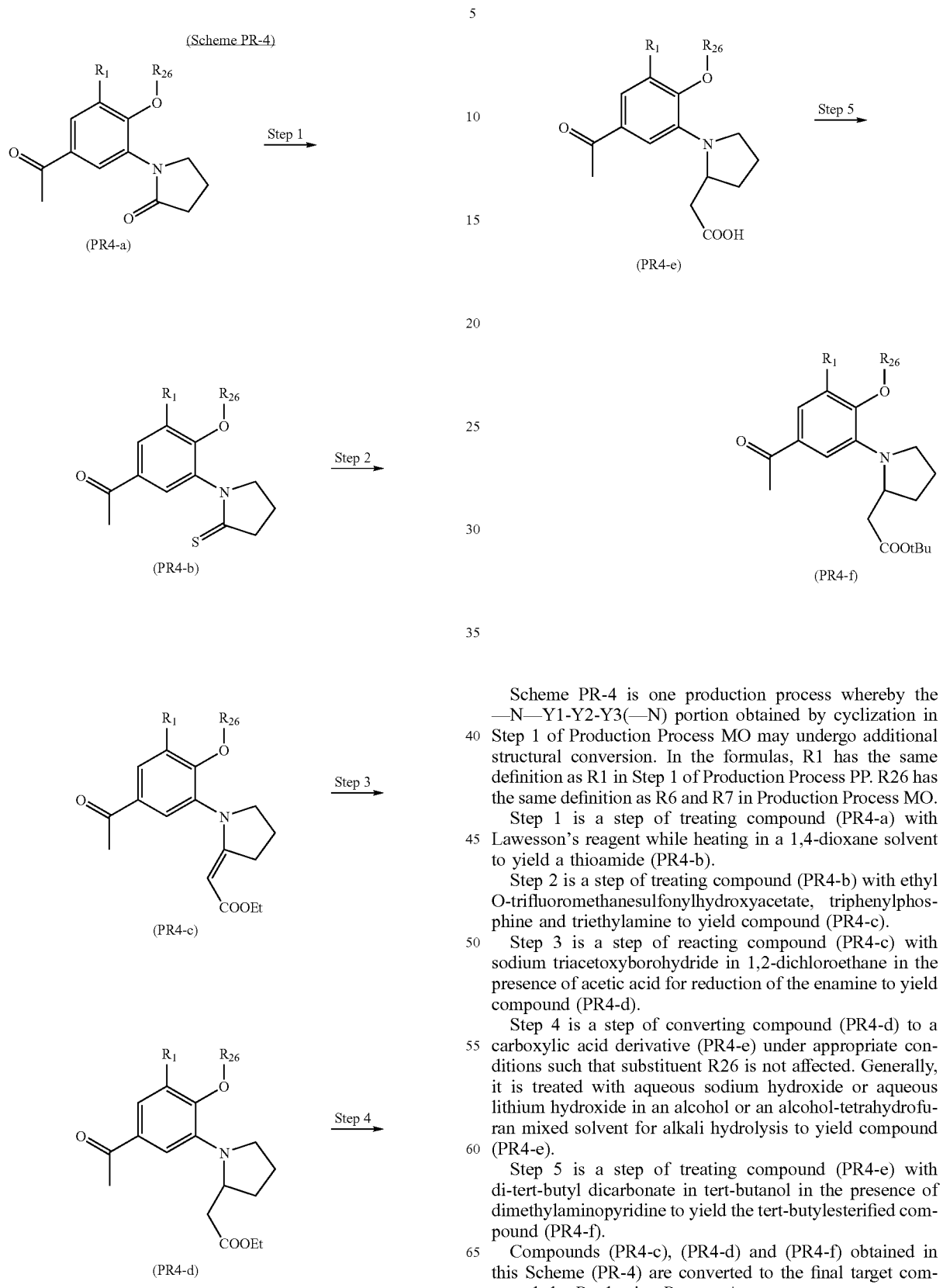

Scheme PR-4 is one production process whereby the —N—Y1-Y2-Y3(—N) portion obtained by cyclization in Step 1 of Production Process MO may undergo additional structural conversion. In the formulas, R1 has the same definition as R1 in Step 1 of Production Process PP. R26 has the same definition as R6 and R7 in Production Process MO.

Step 1 is a step of treating compound (PR4-a) with Lawesson's reagent while heating in a 1,4-dioxane solvent to yield a thioamide (PR4-b).

Step 2 is a step of treating compound (PR4-b) with ethyl O-trifluoromethanesulfonylhydroxyacetate, triphenylphosphine and triethylamine to yield compound (PR4-c).

Step 3 is a step of reacting compound (PR4-c) with sodium triacetoxyborohydride in 1,2-dichloroethane in the presence of acetic acid for reduction of the enamine to yield compound (PR4-d).

Step 4 is a step of converting compound (PR4-d) to a carboxylic acid derivative (PR4-e) under appropriate conditions such that substituent R26 is not affected. Generally, it is treated with aqueous sodium hydroxide or aqueous lithium hydroxide in an alcohol or an alcohol-tetrahydrofuran mixed solvent for alkali hydrolysis to yield compound (PR4-e).

Step 5 is a step of treating compound (PR4-e) with di-tert-butyl dicarbonate in tert-butanol in the presence of dimethylaminopyridine to yield the tert-butylesterified compound (PR4-f).

Compounds (PR4-c), (PR4-d) and (PR4-f) obtained in this Scheme (PR-4) are converted to the final target compounds by Production Process A.

(Scheme PR-5)

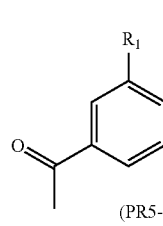
(PR5-a)

Step 1

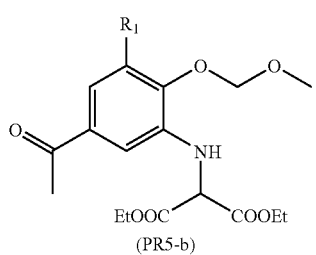
(PR5-b)

Step 2

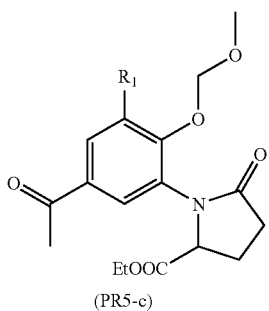
(PR5-c)

Step 3

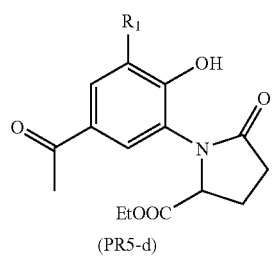
(PR5-d)

Step 4

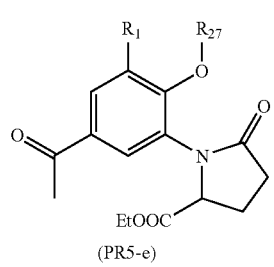
(PR5-e)

Step 5

-continued

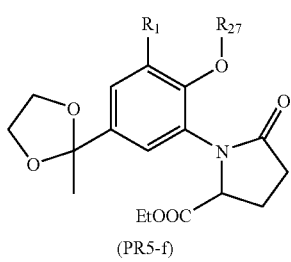
(PR5-f)

Step 6

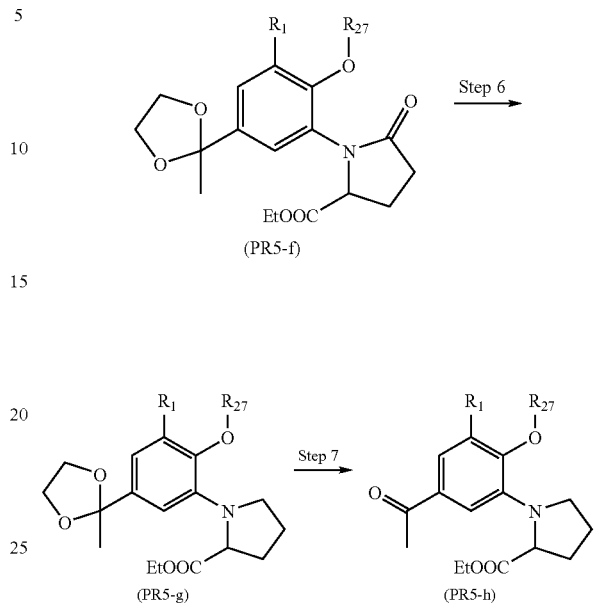
(PR5-g)   (PR5-h)

Step 7

Scheme PR-5 is one production process whereby the —N—Y1-Y2-Y3(—N) portion obtained by cyclization in Step 1 of Production Process MO may undergo additional structural conversion. In the formulas, R1 has the same definition as R1 in Step 1 of Production Process PP. R27 has the same definition as R6 and R7 in Production Process MO.

Step 1 is a step of treating compound (PR5-a) with a catalytic amount of rhodium (II) acetate dimer and the known reagent diethyl diazomalonate while heating in a toluene solvent, to yield compound (PR5-b).

Step 2 is a step of treating compound (PR5-b) with equivalents of sodium ethoxide and ethyl acrylate while heating in ethanol to yield the cyclized compound (PR5-c).

Step 3 is a step of treating compound (PR5-c) with 5 N hydrochloric acid while heating in ethanol to yield compound (PR5-d) having the methoxymethyl protecting group removed.

Step 4 is a step of converting compound (PR5-d) to compound (PR5-e) having a newly introduced substituent R27. Compound (PR5-e) may be obtained by treatment in the same manner as for introduction of R7 in Step 3 of Production Process MO.

Step 5 is a step of treating compound (PR5-e) with 1,2-bis(trimethylsiloxy)ethane and triethylsilyltriflate in dichloromethane to yield compound (PR5-f) wherein the acetyl carbonyl of compound (PR5-e) is ketal-protected.

Step 6 is a step of reducing the lactam carbonyl of compound (PR5-f) for conversion to methylene. Compound (PR5-f) may be reacted with tris(triphenylphosphine)rhodium(I) carbonyl hydride and diphenylsilane in an appropriate solvent such as tetrahydrofuran to yield compound (PR5-g).

Step 7 is a step of reacting compound (PR5-g) in 5% hydrochloric acid-tetrahydrofuran to yield the ketal-deprotected compound (PR5-h).

Compounds (PR5-d), (PR5-e) and (PR5-h) obtained in Scheme PR-5 are converted to the final target compound by Production Process A.

<Production Process PS>

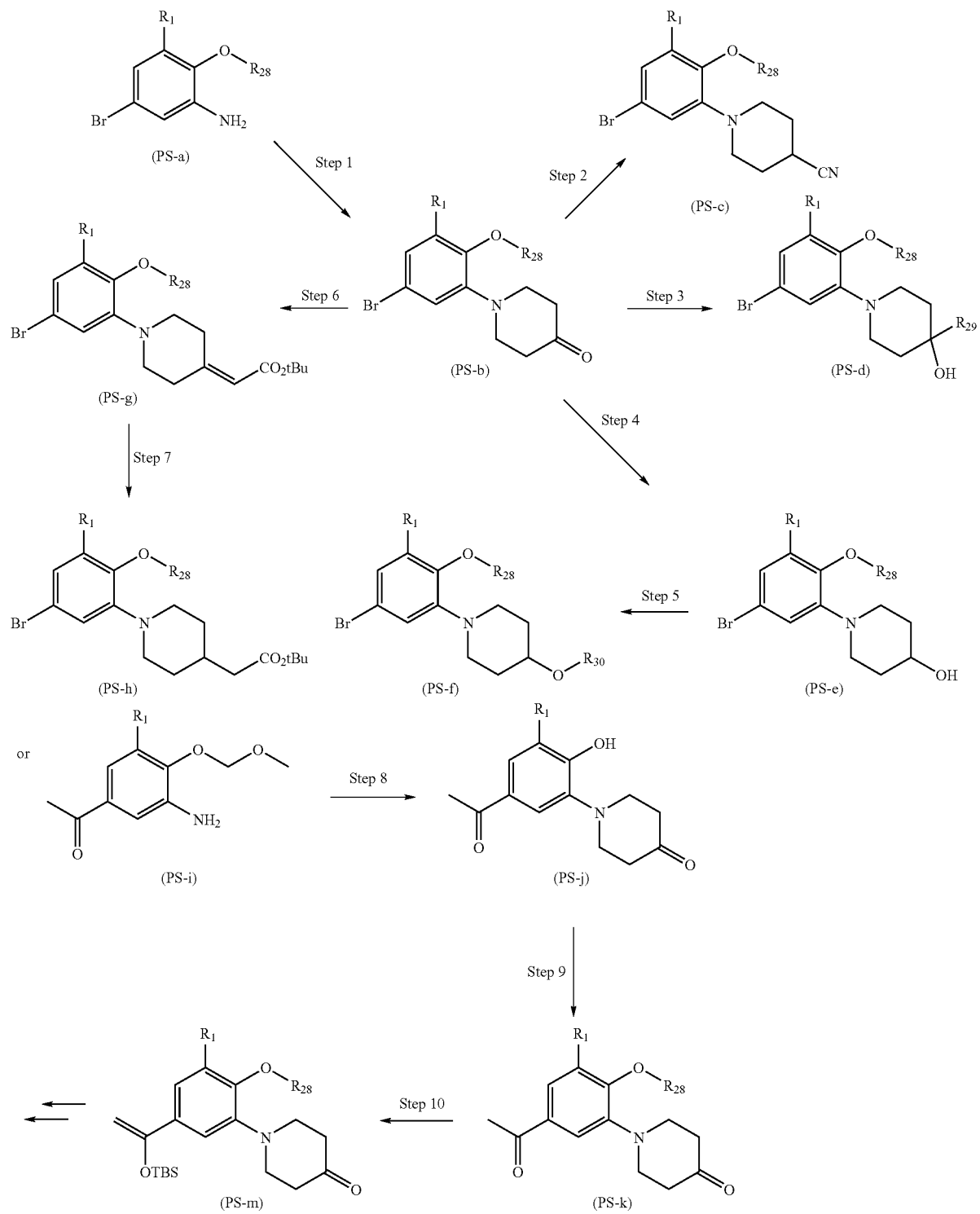

This Production Process PS is a general synthesis method for a piperidine derivative. In the formulas, R1 has the same definition as R1 in Step 1 of Production Process PP. R28 and R30 have the same definitions as R6 and R7 in Production Process MO.

Step 1 is a step of reacting compound (PS-a) with formaldehyde to produce an imine, and then subjecting it to hetero Diels-Alder reaction with a diene having an enol ether structure to form an oxopiperidine ring. Preferably, Compound (PS-a) is reacted with 37% formalin in dichloromethane in the presence of magnesium sulfate to produce an imine, and the reaction mixture is filtered with celite. After adding 2-trimethylsilyloxy-1,3-butadiene and toluene to the filtrate and cooling to −70° C., a 1 M hexane solution of diethylaluminum chloride is added dropwise and the temperature is raised. After completion of the reaction, it is exchanged with a tetrahydrofuran solution and treatment is carried out with 1 N hydrochloric acid to yield compound (PS-b) having the silylenol ether converted to a ketone.

Step 2 is a step of treating compound (PS-b) with p-toluenesulfonylmethyl isocyanide (TosMIC) in dimethoxyethane-tert-butanol in the presence of tert-butoxypotassium, to yield compound (PS-c) having the oxo group converted to cyano.

Step 3 is a step of reacting the carbonyl group of compound (PS-b) with any of various organometallic reagents to yield a tertiary alcohol (PS-d) having an added substituent R29. For example, compound (PS-b) may be reacted with methylmagnesium bromide in diethyl ether to yield compound (PS-d) having an added methyl group. R29 represents alkyl, alkenyl or alkynyl.

Step 4 is a step of treating compound (PS-b) with a reducing agent for conversion to an alcohol compound (PS-e). Any of various reducing agents may be used, but treatment with sodium borohydride in a methanol-dichloromethane mixed solvent is preferred to yield compound (PS-e).

Step 5 is a step of treating compound (PS-e) in the same manner as Step 1 of Scheme PR-1 of Production Process PR to yield compound (PS-f) having a newly introduced substituent R30 at the hydroxyl group. Substituent R30 has the same definition as R6 and R7 in Production Process MO.

Step 6 is a step of Horner-Emmons reaction at the carbonyl group of compound (PS-b) to yield the carbon-carbon bond formed unsaturated ester (PS-g). After treating a tert-butyl diethylphosphonoacetate with sodium hydride in 1,2-dimethoxyethane, compound (PS-b) dissolved in 1,2-dimethoxyethane is added to yield Compound (PS-g).

Step 7 is a step of 1,4-reduction of the unsaturated ester. Compound (PS-g) may be treated with sodium borohydride in a dichloromethane-methanol mixed solvent in the presence of a catalytic amount of nickel (II) chloride-6 hydrate, or reacted with magnesium in methanol for selective 1,4-reduction of the unsaturated ester to yield compound (PS-h).

A piperidine derivative may also be synthesized by the following Steps 8 to 10.

Step 8 is a step of treating compound (PS-i) in the same manner as Step 1 to yield compound (PS-j), with simultaneous formation of a oxopiperidine ring and deprotection of the methoxymethyl group serving as the phenolic hydroxyl-protecting group.

Step 9 is a step of treating compound (PS-j) in the same manner as for introduction of R7 in Step 3 of Production Process MO, to yield compound (PS-k) substituted with substituent R28.

Step 10 is a step of selectively protecting the carbonyl group of the acetophenone of compound (PS-k). After adding compound (PS-k) to tetrahydrofuran, adding triethylamine and cooling to −70° C., the mixture is treated with tert-butyldimethylsilyl trifluoromethanesulfonate. The state of the reaction is periodically examined by thin-layer column chromatography, and the temperature is gradually raised if necessary. Water may be added at low temperature to stop the reaction to yield compound (PS-m).

Finally, Compound (PS-m) may be treated in the same manner as in Steps 2, 3 and 4. Alternatively, it may be converted directly to an acyl bromide according to Production Process A for conversion to the final target compound.

Compounds (PS-b), (PS-c), (PS-d), (PS-e), (PS-f), (PS-g), (PS-h), (PS-j) and (PS-k) obtained in this Production Process are converted to the final target compounds by Production Process A.

<Production Process AN>

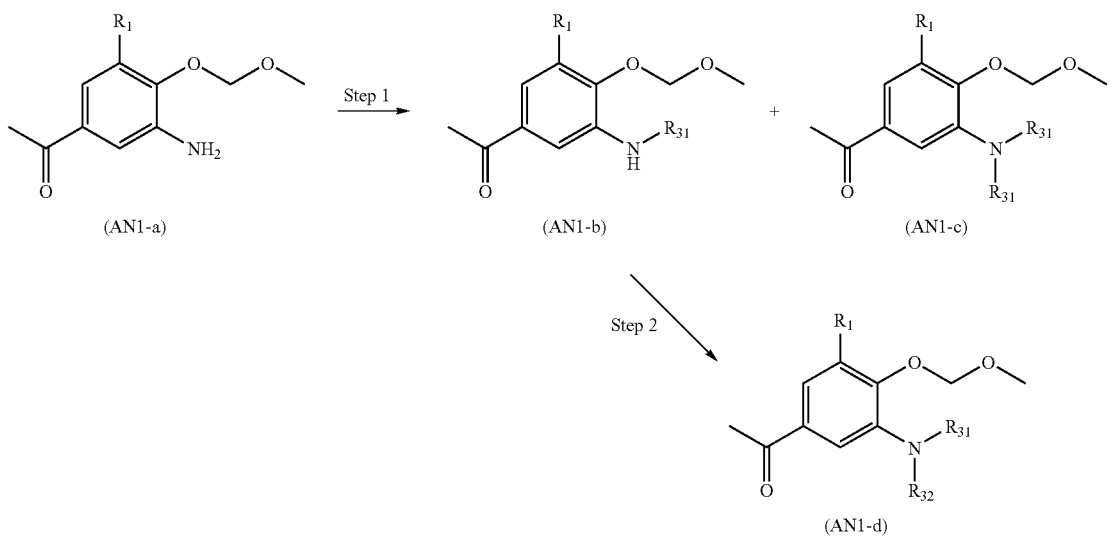

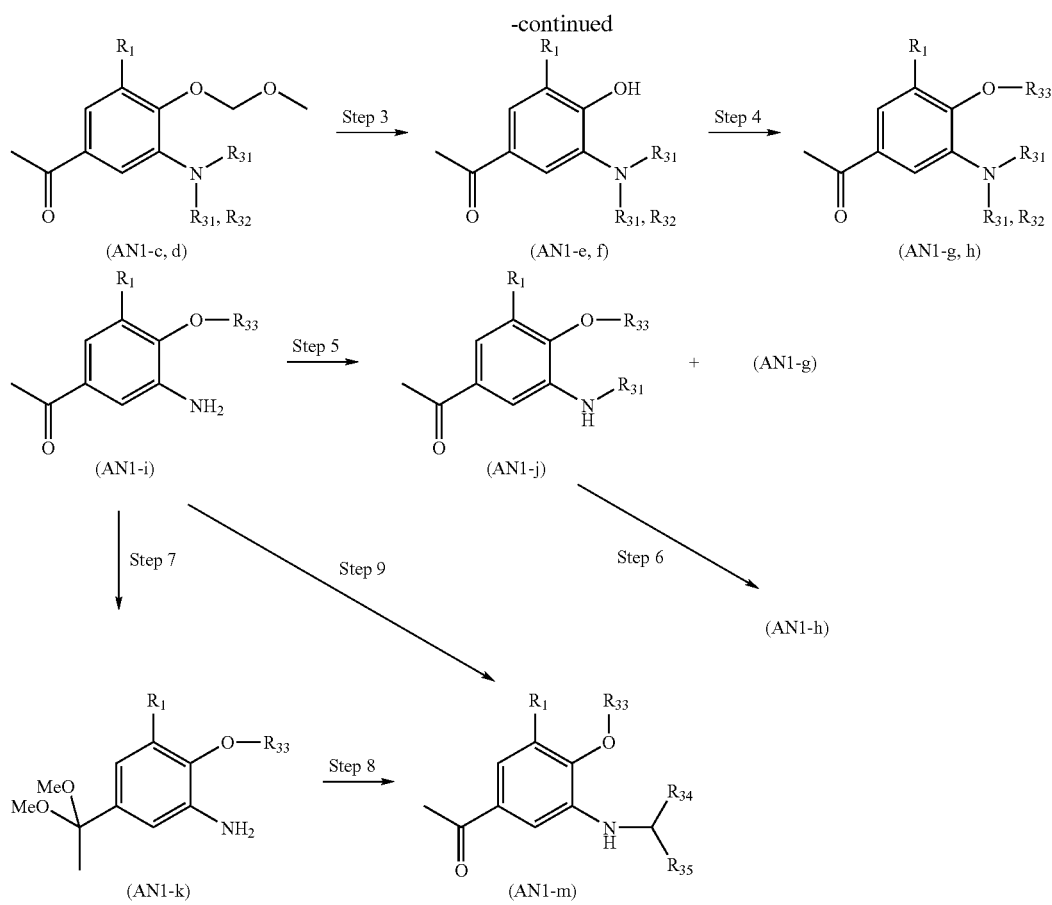

This scheme is a general synthesis for an aniline derivative. In the formulas, R1 has the same definition as in Step 1 of Production Process PP. R31, R32 and R33 have the same definitions as R6 and R7 in Production Process MO.

Step 1 is a step of introducing one or two substituents R31 at the amino group of compound (AN1-a). Compound (AN1-a) may be treated in approximately the same manner as for introduction of R7 at the hydroxyl group in Step 3 of Production Process MO to yield compounds (AN1-b) and (AN1-c). When R31 is bonded to the aniline amino group as simple alkyl and not via acyl or sulfonyl (for example, when R31-I or R31-Br is used as the reagent), a prolonged reaction with heating may be necessary to introduce the substituent R31. Incidentally, compounds (AN1-b) and (AN1-c) may be easily separated and purified by silica gel column chromatography.

Step 2 is a step of treating compound (AN1-b) in the same manner as Step 1 to yield compound (AN1-d) having a newly introduced substituent R32.

Step 3 is a step of treating compounds (AN1-c) and (AN1-d) in the same manner as Step 2 of Production Process MO to yield the respective compounds (AN1-e) and (AN1-f).

Step 4 is a step of treating compounds (AN1-e) and (AN1-f) in the same manner as for introduction of R7 in Step 3 of Production Process MO to yield the respective compounds (AN1-g) and (AN1-h).

Step 5 is a step of using compound (AN1-i) as the starting material for treatment in the same manner as Step 1 to yield compound (AN1-j) having substituents R31 and R33. Compound (AN1-g) can also be obtained by this method.

Step 6 is a step of treating compound (AN1-j) in the same manner as Step 2 to yield compound (AN1-h).

Step 7 is a step of treating compound (AN1-i) in the same manner as the ketalizing step of Step 6 in Scheme PR-2, to yield compound (AN1-k).

Step 8 is a step of using an aldehyde or ketone (represented by R34—(C=O)—R35) and a reducing agent for reductive amination to yield compound (AN1-m).

Compound (AN1-k) may be reacted with sodium cyanoborohydride in a methanol-acetic acid mixed solvent or reacted with sodium triacetoxyborohydride in a 1,2-dichloroethane-acetic acid mixed solvent, to directly yield compound (AN1-m) having the ketal protecting group also deprotected. Either or both R34 and R35 may be hydrogen, or R34 and R35 may together form a ring.

Step 9 is a step of using an aldehyde or ketone (represented by R34—(C=O)—R35) and a reducing agent for reductive amination to yield compound (AN1-m), without ketal protection of compound (AN1-i). In most cases, reaction is conducted with sodium triacetoxyborohydride in a 1,2-dichloroethane-acetic acid mixed solvent.

Compounds (AN1-b), (AN1-c), (AN1-d), (AN1-e), (AN1-f), (AN1-g), (AN1-h), (AN1-j) and (AN1-m) obtained in this Scheme AN-1 are converted to the final target compounds by Production Process A.

(Scheme AN-2)

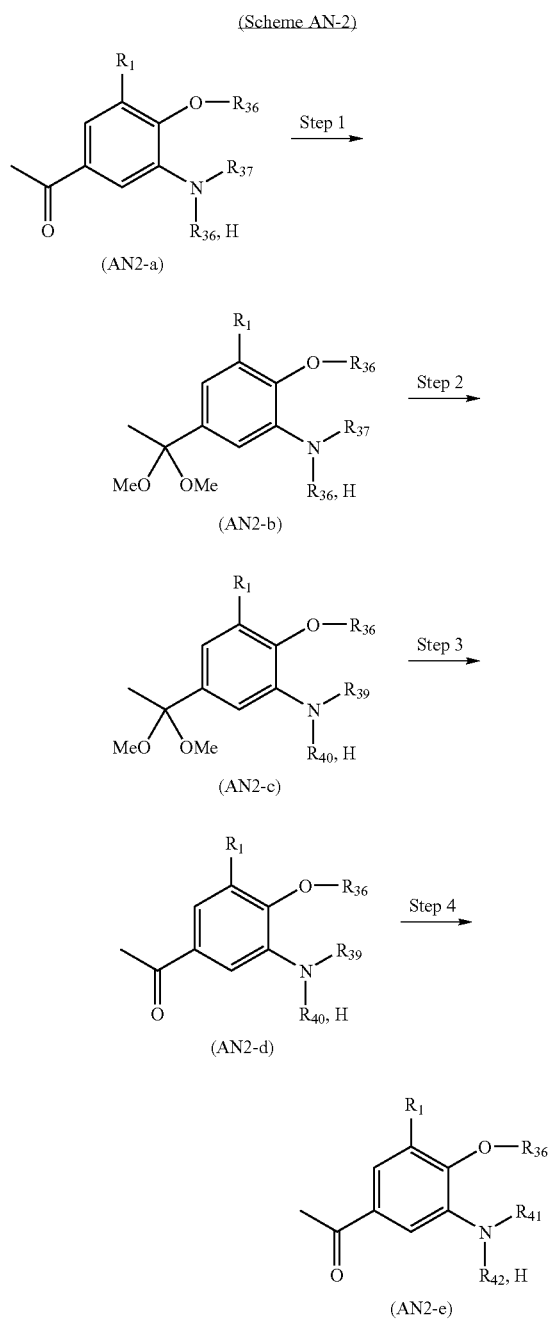

Scheme AN-2 is a general synthesis method for further structural conversion of the substituents on the aniline nitrogen of the intermediate synthesized in Scheme AN-1. In the formulas, R1 has the same definition as R1 in Step 1 of Production Process 1. R36 has the same definition as R6 and R7 in Production Process MO. Either or both R37 and R38 may form an amide bond with the aniline nitrogen, or the substituents may have ester structures. One of the substituents on the aniline nitrogen of the starting material (AN2-a) may be hydrogen.

Step 1 is a step of treating compound (AN2-a) in the same manner as the ketalizing reaction step of Step 6 in Scheme PR-2 of Production Process PR, to yield compound (AN2-b) having the carbonyl group protected.

Step 2 is a step of treating compound (AN2-b) with a reducing agent for conversion of an amide group to methyleneamino (from —N—CO— to —N—CH2-), or of an ester to an alcohol (from —CO—O— to —CH2-OH, from —O—CO— to —OH). Preferably, compound (AN2-b) may be treated with lithium aluminum hydride in diethyl ether to yield compound (AN2-c). Substituents R39 and R40 are defined as the structures after this conversion of R37 and R38.

Step 3 is a step of treating compound (AN2-c) in the same manner as the ketal deprotection step of Step 7 in Scheme PR-2, to yield compound (AN2-d).

Step 4 is a step carried out only when compound (AN2-d) has a hydroxyl group on substituent R39 or R40, and here a new substituent is introduced at the hydroxyl group to yield compound (AN2-e) by conversion to substituents R41 and R42.

The reaction of this step is conducted in the same manner as Step 1 in Scheme PR-1 of Production Process PR. Compounds (AN2-d) and (AN2-e) obtained in this Scheme (AN-2) are converted to the final target compounds by Production Process A.

<Production Process BO>

The following Schemes BO-1,2, 3 and 4 of Production Process. BO are general synthesis methods for benzoxazine derivatives.

(Scheme BO-1)

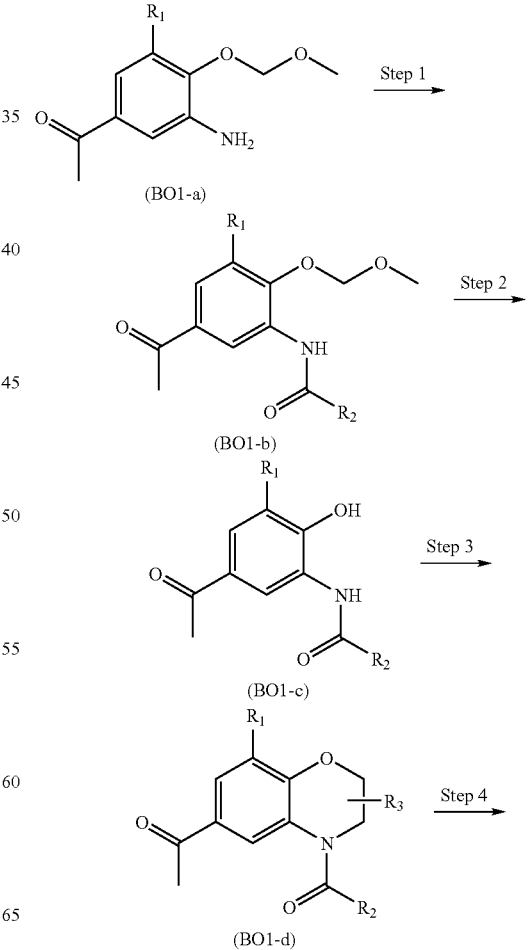

-continued

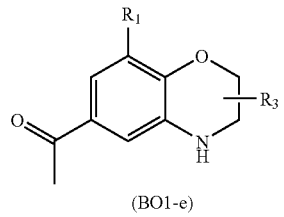

(BO1-e)

-continued

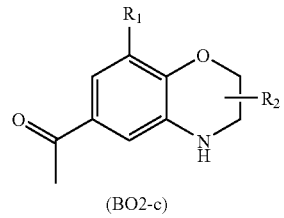

(BO2-c)

In the formulas, R1 has the same definition as R1 in Step 1 of Production Process PP. R2 represents hydrogen, optionally substituted alkyl or the like. R3 represents hydrogen, halogeno, oxo, optionally substituted alkyl, optionally substituted alkoxy, optionally substituted acyl, optionally substituted carboxyl or optionally substituted carbamoyl.

Step 1 is a step of acylating the amino group. Compound (BO1-b) may be obtained either by reaction with an acyl chloride at room temperature in a solvent such as tetrahydrofuran, methylene chloride or acetonitrile in the presence of a base such as pyridine or triethylamine, or by reaction with an acid anhydride in a pyridine solution.

Step 2 is a step of deprotecting the methoxymethyl group protecting the alcohol. Compound (BO1-c) may be obtained by reaction with dilute aqueous hydrochloric acid and 10% aqueous perchloric acid in a solvent such as tetrahydrofuran or acetone at room temperature.

Step 3 is a step of alkylating the hydroxyl and amino groups. Compound (BO1-d) may be obtained by reaction with a dihalide, dimesylate or ditosylate in a dimethylformamide solution in the presence of a base such as potassium carbonate, cesium carbonate or sodium hydride, while heating from room temperature to 150° C.

Step 4 is a step of deacylation. Compound (BO1-e) may be obtained either by reaction with an aqueous sodium hydroxide solution in a solvent such as methanol, ethanol or tetrahydrofuran, at room temperature to the reflux temperature of the solvent, or by reaction in an aqueous hydrochloric acid solution at room temperature to the reflux temperature of the solvent.

Compounds (BO1-d) and (BO1-e) obtained in this Scheme BO-1 are converted to the final target compounds by Production Process A.

(Scheme BO-2)

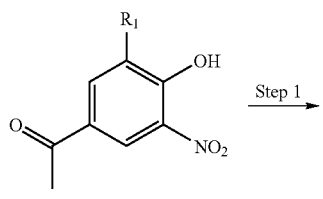

(BO2-a)

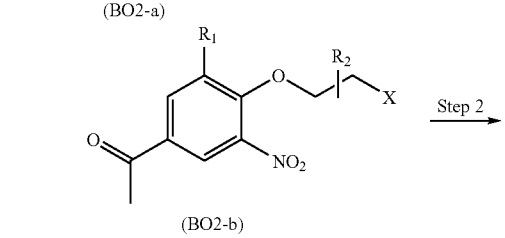

(BO2-b)

In the formulas, R1 has the same definition as R1 in Step 1 of Production Process PP. R2 has the same definition as R3 in Scheme BO-1.

Step 1 is a step of alkylating the hydroxyl group. Compound (BO2-b) may be obtained by reaction with a dihalide, dimesylate or ditosylate in a dimethylformamide solution while heating from room temperature to 150° C.

Step 2 is a step of forming an oxazine ring. Reaction is conducted with a dihalide, dimesylate or ditosylate in a dimethylformamide solution in the presence of a base such as potassium carbonate, cesium carbonate or sodium hydride, while heating from room temperature to 150° C. Reaction is then conducted at room temperature in an ethanol or methanol solution in the presence of a catalytic amount of palladium-carbon in a hydrogen atmosphere to yield compound (BO2-c).

Compound (BO2-c) obtained in this Scheme BO-2 is converted to the final target compound by Production Process A.

(Scheme BO-3)

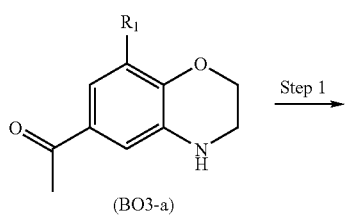

(BO3-a)

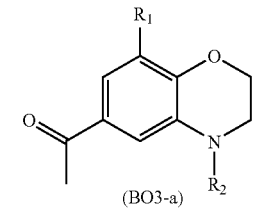

(BO3-a)

In the formulas, R1 represents hydrogen, optionally substituted alkyl, optionally substituted cycloalkyl or optionally substituted alkoxy. R2 represents hydrogen, optionally substituted alkyl, alkyl having cyano at the end or a branch, optionally substituted alkoxy, optionally substituted aryalkyl, optionally substituted acyl, optionally substituted sulfonyl, optionally substituted carbamoyl or optionally substituted carboxyl.

Step 1 is a step of alkylating, acylating, substituted carbamoylating or urethanating the amino group, by any of the following methods 1 to 4.

1. Compound (BO3-b) may be obtained by reaction with a halide, mesylate or tosylate in a dimethylformamide solution in the presence of a base such as potassium carbonate, cesium carbonate or sodium hydride, while heating from room temperature to 150° C.

2. Compound (BO3-b) may be obtained either by reaction with an acyl chloride, sulfonyl chloride or isocyanate at room temperature in a solvent such as tetrahydrofuran, methylene chloride or acetonitrile, in the presence of a base such as pyridine or triethylamine, or by reaction with an acid anhydride in a pyridine solution.

3. Compound (BO3-b) may be obtained by reaction with ethyl N-(1-cyano)iminoformate in a methanol or ethanol solvent in the presence of a catalytic amount of 4-dimethylaminopyridine, at room temperature to the reflux temperature of the solvent.

4. Compound (BO3-b) may be obtained by reaction with trimethyl orthoformate or triethyl orthoformate in a methanol or ethanol solvent in the presence of a catalytic amount of p-toluenesulfonic acid or camphorsulfonic acid, ketal protection of the acetyl group and introduction of different substituents by methods 1 to 3 above, followed by deprotection under acidic conditions.

Compound (BO3-b) obtained in this Scheme BO-3 is converted to the final target compound by Production Process A.

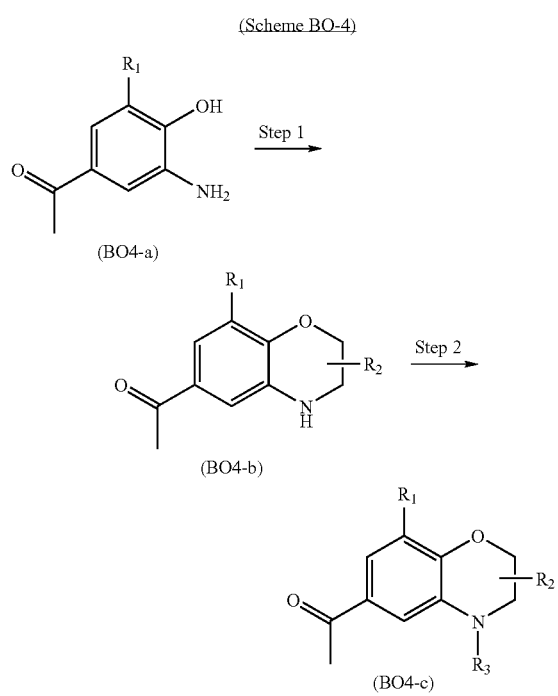

In the formulas, R1 has the same definition as R1 in Step 1 of Production Process PP. R2 has the same definition as R3 in Scheme BO-1. R3 has the same definition as R2 in Scheme BO-3.

Step 1 is a step of alkylation. Compound (BO4-b) may be obtained by the method described in Tawada, H., Sugiyama, Y., Ikeda, H., Yamamoto, Y., Meguro, K; Chem. Pharm. Bull., 38(5), 1238–1245(1990), or by reaction with allyl bromide, maleic anhydride or the like in a solvent such as methanol, ethanol or toluene in the presence of a base such as potassium carbonate, cesium carbonate or sodium hydrogencarbonate at room temperature to the reflux temperature of the solvent, followed by reaction in a methanol or ethanol solvent in the presence of a base such as potassium carbonate or triethylamine, at room temperature to the reflux temperature of the solvent.

Step 2 is a step of alkylating, acylating, substituted carbamoylating or urethanating the amino group. Compound (BO4-c) may be obtained by treatment in the same manner as Step 1 of Scheme BO-3.

Compounds (BO4-b) and (BO4-c) obtained in Scheme BO-4 are converted to the final target compound by Production Process A.

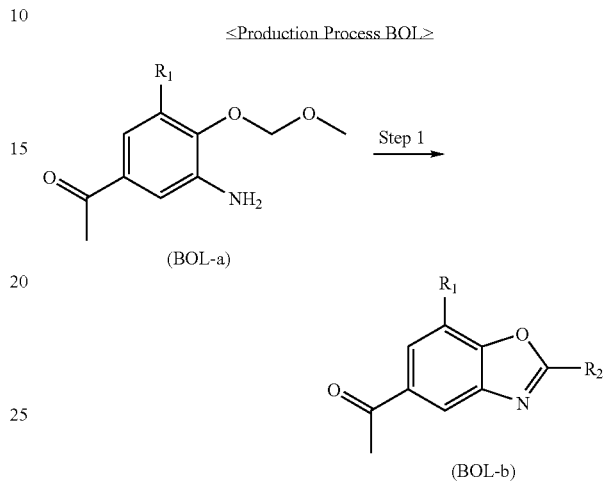

Production Process BOL is a general synthesis method for a benzoxazole derivative. In the formulas, R1 has the same definition as R1 in Step 1 of Production Process PP. R2 represents hydrogen, optionally substituted alkyl or optionally substituted alkoxy.

Step 1 is a step of forming an oxazole ring. Compound (BOL-b) may be obtained by reaction with an acid chloride in a solvent such as tetrahydrofuran, methylene chloride or acetonitrile in the presence of a base such as triethylamine, followed by reaction with dilute aqueous hydrochloric acid or p-toluenesulfonic acid in a solvent such as ethanol, methanol, tetrahydrofuran or methyl ethyl ketone.

The benzoxazoleethanone derivative (BOL-b) obtained in Production Process BOL is converted to the final compound by Production Process A.

<Production Process CA>

Schemes CA-1, 2 and 3 below in Production Process CA are general synthesis methods for catechol derivatives.

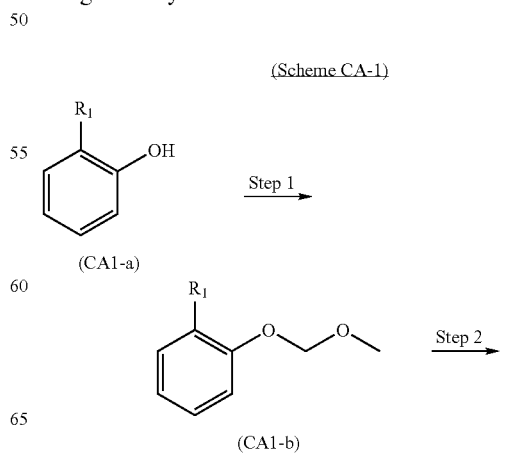

-continued

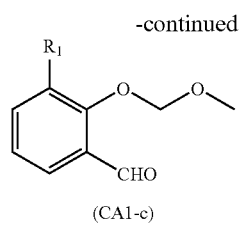
(CA1-c)

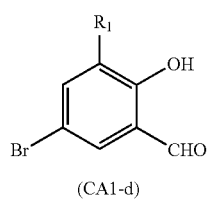
(CA1-d)

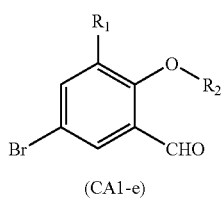
(CA1-e)

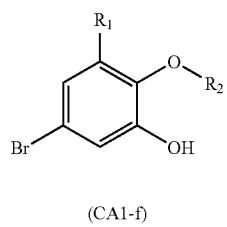
(CA1-f)

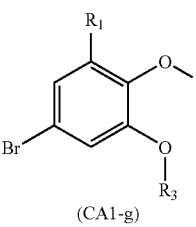
(CA1-g)

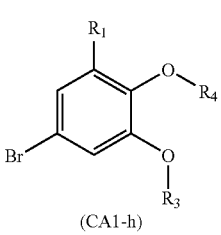
(CA1-h)

In the formulas, R1 has the same definition as R1 in Step 1 of Production Process PP. R2, R3 and R4 have the same definitions as R6 and R7 in Production Process MO.

Step 1 is a step of methoxymethylating the hydroxyl group of compound (CA1-a). Compound (CA1-b) is obtained by reaction of compound (CA1-a) and sodium hydride in dimethylformamide at room temperature, followed by reaction with methoxymethyl chloride(MOM-Cl).

Step 2 is a step of introducing a formyl group by ortholithiation utilizing the substituent effect of the methoxymethyl group of compound (CA1-b). The orthoformylated compound (CA1-c) is obtained by treatment of compound (CA1-b) with n-butyllithium in a diethyl ether solvent while cooling on ice in the presence of tetramethylethylenediamine, followed by treatment with a formylating agent such as dimethylformamide or N-formylmorpholine.

Step 3 is a step of brominating the para-position relative to the methoxymethyl group of compound (CA1-c). Compound (CA1-d) is obtained by reaction of compound (CA1-c) with bromine in methanol at room temperature, and removal of the methoxymethyl group by the hydrogen bromide generated in the system.

Step 4 is a step of introducing any of various substituents at the hydroxyl group of compound (CA1-d). Compound (CA1-e) is obtained by the same method as for introduction of R7 in Step 3 of Production Process MO.

Step 5 is a step of oxidative conversion of the formyl group to a hydroxyl group. Compound (CA1-f) is obtained by reacting compound (CA1-e) with m-chloroperbenzoic acid in dichloromethane at room temperature or with heating, and then hydrolyzing the purified ester using potassium carbonate in methanol.

Step 6 is a step of obtaining compound (CA1-g) having substituent R3 introduced therein by the same method as in Step 4 of Scheme CA-1.

Step 7 is a step of conversion to substituent R4 when R2 is a hydroxyl-protecting group. Compound (CA1-h) is obtained in the same manner as the continuous treatment in Steps 2 and 3 of Production Process MO.

Compounds (CA1-g) and (CA1-h) obtained in this Scheme CA-1 are converted to the final target compound by Production Process A.

(Scheme CA-2)

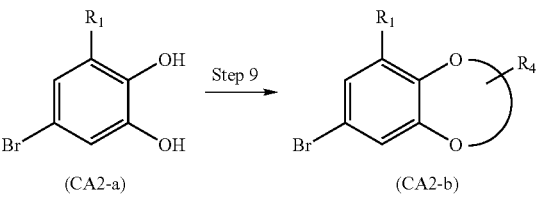

Scheme CA-2 is a general synthesis method for a cyclic catechol derivative. In the formulas, R1 has the same definition as R1 in Step 1 of Production Process PP. R2 and R4 have the same definitions as R6 and R7 in Production Process MO.

Step 8 is a step of conversion to a catechol when R2 is a removable hydroxyl-protecting group. When R2 is methoxymethyl, a diol (catechol) (CA2-a) is obtained by treating compound (CA1-f) with 6 N hydrochloric acid.

Step 9 is a step of cyclizing the catechol by alkylation. Compound (CA2-a) is reacted with a 1,2-dibromoethyl derivative in a solvent such as dimethylformamide, acetonitrile or acetone in the presence of a base such as potassium carbonate, cesium carbonate or sodium hydride, to yield a fused dioxane ring (CA2-b). Compound (CA2-a) may also be treated with acetone in the presence of phosphorus pentaoxide to yield a 5-membered cyclic product (CA2-b) as an acetonide.

Compound (CA2-b) obtained in this Scheme CA-2 is converted to the final target compound by Production Process A.

(Scheme CA-3)

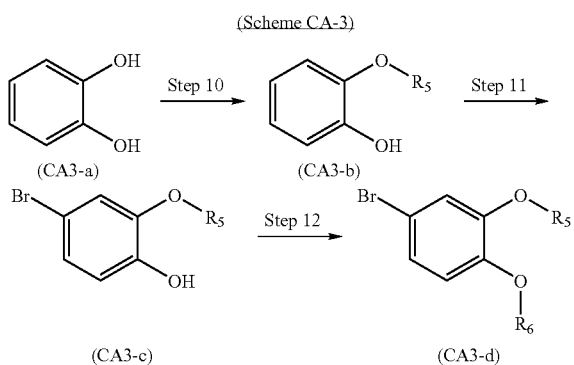

Scheme CA-3 is a general synthesis method for a disubstituted catechol derivative. In the formulas, R5 and R6 have the same definitions as R6 and R7 in Production Process MO.

Step 10 is a step of obtaining compound (CA3-b) by the same method as in Step 4 of Scheme CA-1 using the catechol (CA3-a) as the starting material.

Step 11 is a step of treating compound (CA3-b) by the same method as in Step 3 of Scheme CA-1 to yield compound (CA3-c) which is selectively brominated at the para-position relative to the non-substituted hydroxyl group.

Step 12 is a step of obtaining compound (CA3-d) having R6 introduced by the same method as in Step 4 of Scheme CA-1.

Compound (CA3-d) obtained by Scheme CA-3 is converted to the final target compound by Production Process A.

<Production Process CO>

Schemes CO-1, CO-2, CO-3, CO-4, CO-5, CO-6, CO-7, CO-8 and CO-9 in Production Process CO are general synthesis methods for phenol and phenoxy derivatives.

(Scheme CO-1)

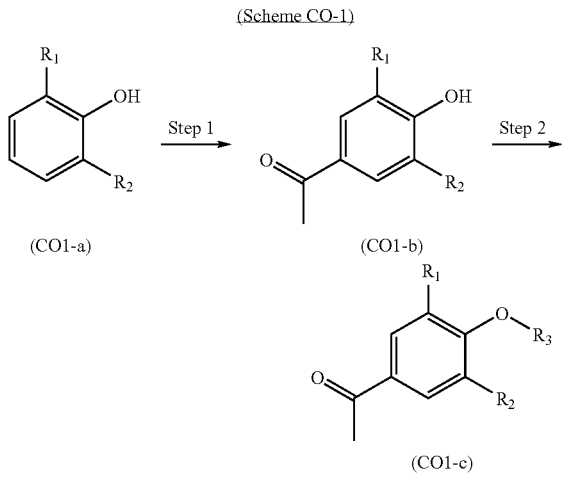

In the formulas of Scheme CO-1, R1 and R2 have the same definition as R1 in Step 1 of Production Process PP. R3 has the same definition as R6 and R7 in Production Process MO.

Step 1 is a step of Friedel-Crafts acylation. Compound (CO1-b) is obtained by reaction with acetyl chloride in a methylene chloride or toluene solvent in the presence of a Lewis acid such as aluminum chloride, zinc chloride or tin (IV) chloride, at −70° C. to room temperature.

Step 2 is a step of alkylation, carbonation, sulfonation or the like.

1. Compound (CO1-c) may be obtained by reaction with a halide, mesylate or tosylate in a dimethylformamide solution in the presence of a base such as potassium carbonate, cesium carbonate or sodium hydride, while heating from room temperature to 150° C.

2. Compound (CO1-c) may be obtained either by reaction with an acyl chloride, sulfonyl chloride or isocyanate in a solvent such as tetrahydrofuran, methylene chloride or acetonitrile in the presence of a base such as pyridine or triethylamine, at −15° C. to room temperature, or by reaction with an acid anhydride in a pyridine solution.

3. Compound (CO1-c) may also be obtained by reaction with phenyl chloroformate in a solvent such as tetrahydrofuran, methylene chloride or acetonitrile in the presence of a base such as pyridine or triethylamine, followed by reaction with an amine.

Compounds (CO1-b) and (CO1-c) obtained in this Scheme CO-1 are converted to the final target compounds by Production Process A. Compound (CO1-a) may also be used in the conversion of compound (A4-c) in Scheme A-4 of Production Process A.

(Scheme CO-2)

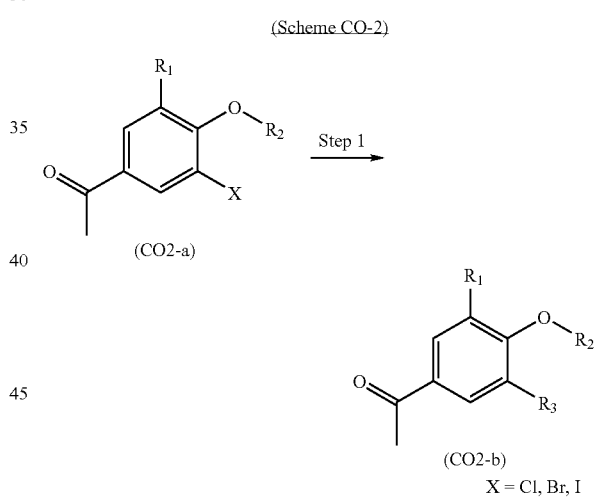

X = Cl, Br, I

Scheme CO-2 is a general synthesis method for an aromatic-substituted benzene derivative. In the formulas, R1 has the same definition as R1 in Step 1 of Production Process PP. R2 has the same definition as R6 and R7 in Production Process MO. R3 represents an aromatic ring.

Step 1 is a step of introducing an aromatic substituent using the Stille coupling method. Compound (CO2-b) is obtained by reaction with aromatic-substituted tributyltin in a solvent such as toluene or xylene under a nitrogen atmosphere in the presence of a catalytic amount of tetrakis (triphenylphosphine)palladium, at the reflux temperature of the solvent.

Compound (CO2-b) obtained in this Scheme CO-2 is converted to the final target compound by Production Process A.

(Scheme CO-3)

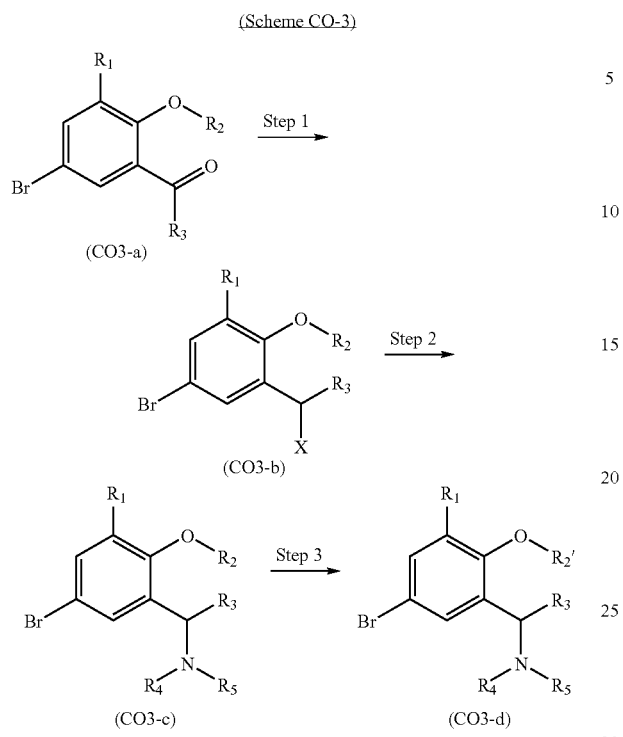

(Scheme CO-4)

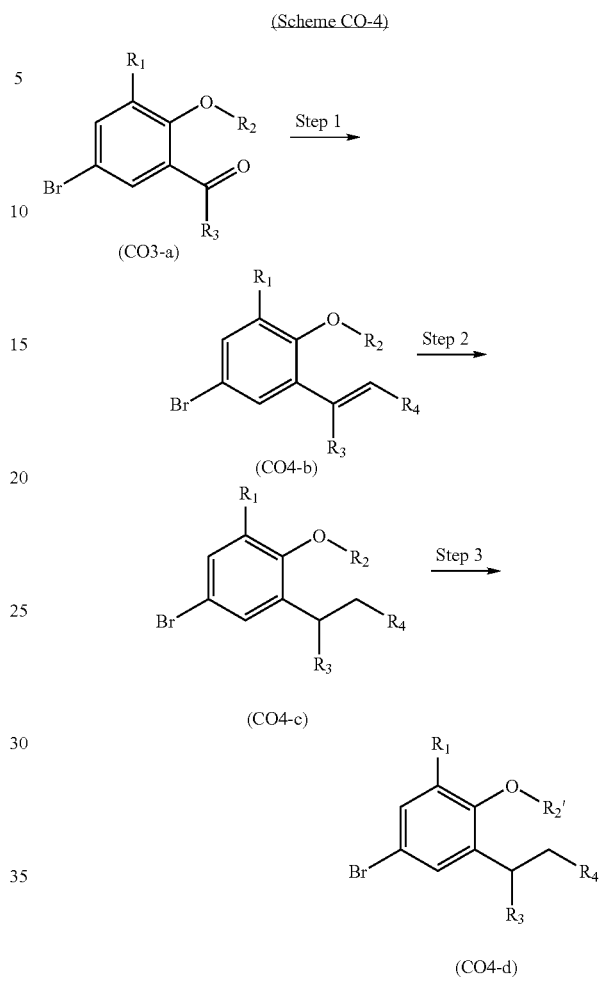

Scheme CO-3 is a general synthesis method for a benzylamine derivative. In the formulas, R1 and R3 have the same definition as R1 in Step 1 of Production Process PP. R2 and R2' have the same definitions as R6 and R7 in Production Process MO. R4 and R5 have the same definition as R2 in Scheme BO-3. R4 and R5 may also form a ring together. X represents hydroxyl or a sulfonate.

Step 1 is a step of introducing an alkyl halide. Compound (CO3-b) is obtained by reaction with sodium borohydride in a methanol or ethanol solvent, followed by reaction with methanesulfonyl chloride in dimethylformamide, in the presence of a base such as pyridine or triethylamine.

Step 2 is a step of amination.

1. Compound (CO$_3$-c) may be obtained by reaction with an amine in a methanol, ethanol, acetonitrile or tetrahydrofuran solvent.

2. Compound (CO$_3$-c) may be obtained by reaction with an amine in a dimethylformamide solvent in the presence of a base such as potassium carbonate or sodium hydride.

3. When X is hydroxyl, compound (CO$_3$-c) may be obtained by reaction with diphenylphosphoryl azide in a toluene solvent in the presence of a base such as 1,8-diazabicyclo[5.4.0]undec-7-ene to yield an azide, followed by reaction with a trialkylphosphine or triphenylphosphine in a tetrahydrofuran-water solvent.

Step 3 is a step of converting R2 to substituent R2' when R2 is a hydroxyl-protecting group. Compound (CO$_3$-d) is obtained in the same manner as the continuous treatment in Steps 2 and 3 of Production Process MO.

Compounds (CO$_3$-c) and (CO$_3$-d) obtained in this Scheme CO-3 are converted to the final target compounds by Production Process A.

Scheme CO-4 is a general synthesis method for phenol and phenoxy derivatives by Wittig reaction. In the formulas, R1 has the same definition as R1 in Production Process PP. R2 and R2' have the same definitions as R6 and R7 in Production Process MO. R3 represents hydrogen or lower alkyl. R4 represents optionally substituted alkyl, optionally substituted carboxyl, cyano or the like.

Step 1 is a step of alkylation utilizing a Wittig reaction. Reaction is conducted with a phosphorane derivative in a methylene chloride or tetrahydrofuran solvent. Alternatively, compound (CO$_4$-b) may be obtained by reaction with a phosphonium salt or phosphonate in a tetrahydrofuran or dimethylformamide solvent in the presence of a base such as potassium tert-butoxide or sodium hydride.

Step 2 is a step of reducing the olefin. Compound (CO$_4$-c) may be obtained by reaction in ethyl acetate, tetrahydrofuran or methanol under a hydrogen atmosphere in the presence of palladium-carbon, or by reaction with magnesium in methanol.

Step 3 is a step of conversion to substituent R2' when R2 is a hydroxyl-protecting group. Compound (CO$_4$-d) is obtained in the same manner as the continuous treatment in Steps 2 and 3 of Production Process MO.

Compounds (CO4-b), (CO4-c) and (CO$_4$-d) obtained in this Scheme CO-4 are converted to the final target compounds by Production Process A.

(Scheme CO-5)

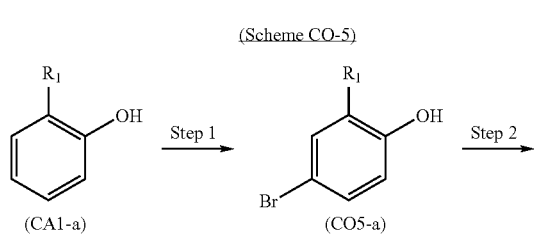

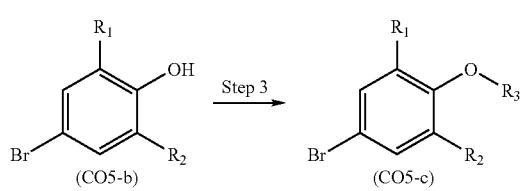

Scheme CO-5 is a general synthesis method for phenol and phenoxy derivatives utilizing a Friedel-Crafts reaction. In the formulas, R1 has the same definition as R1 in Step 1 of Production Process PP. R2 represents hydrogen, optionally substituted alkyl or optionally substituted cycloalkyl. R3 has the same definition as R6 and R7 in Production Process MO.

Step 1 is a step of bromination at the phenyl para-position. Reaction may be conducted with bromine in a methanol or ethanol solvent or with N-bromosuccinimide in an acetonitrile solvent to yield Compound (CO5-a).

Step 2 is a step of alkylation by Friedel-Crafts reaction. Compound (CO5-b) is obtained by reaction with an alkyl mesylate in a benzene or dichloroethane solvent in the presence of scandium triflate, by the method described in H. Katsuki et al., Synthesis 603(1999).

Step 3 is a step of introducing a substituent R3 at the hydroxyl group. Compound (CO5-c) is obtained by treatment in the same manner as for introduction of R7 in Step 3 of Production Process MO.

Compounds (CO5-b) and (CO5-c) obtained in Scheme CO-5 are converted to the final target compounds by Production Process A.

(Scheme CO-6)

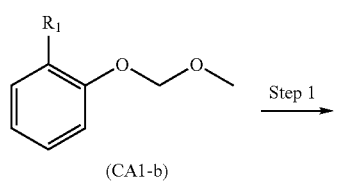

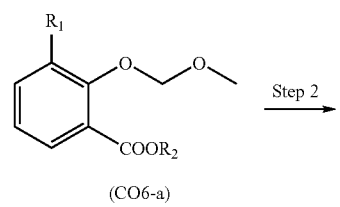

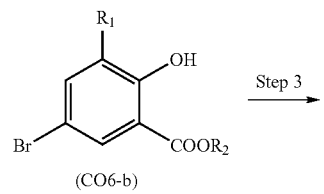

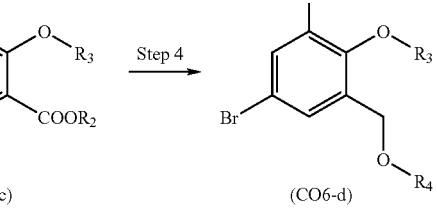

Scheme CO-6 is a general synthesis method for carboxylic acid derivatives and benzyl alcohol derivatives. In the formulas, R1 has the same definition as R1 in Step 1 of Production Process PP. R2 represents optionally substituted alkyl and R3 and R4 have the same definitions as R6 and R7 in Production Process MO.

Step 1 is a step of introducing a carboxyl group by ortholithiation utilizing the substituent effect of the methoxymethyl group of compound (CA1-b). Compound (CO6-a) is obtained by treating compound (CA1-b) with n-butyllithium in a diethyl ether solvent in the presence of tetramethylethylenediamine while cooling on ice, and then reacting it with an alkyl dicarbonate.

Step 2 is a step of deprotection of the methoxymethyl group serving as the alcohol-protecting group. Compound (CO6-b) is obtained by reaction with dilute aqueous hydrochloric acid and 10% aqueous perchloric acid in a tetrahydrofuran or acetone solvent at room temperature.

Step 3 is a step of introducing a substituent R3 at the hydroxyl group. Compound (CO6-c) is obtained by treatment in the same manner as for introduction of R7 in Step 3 of Production Process MO.

Step 4 is a step of reduction and alkylation of the carboxyl group. Compound (CO6-d) is obtained by reaction with lithium aluminum hydride in a diethyl ether or tetrahydrofuran solvent while cooling on ice, followed by the same method as in Step 3.

Compounds (CO6-b), (CO6-c) and (CO6-d) obtained in this Scheme CO-6 are converted to the final target compounds by Production Process A.

(Scheme CO-7)

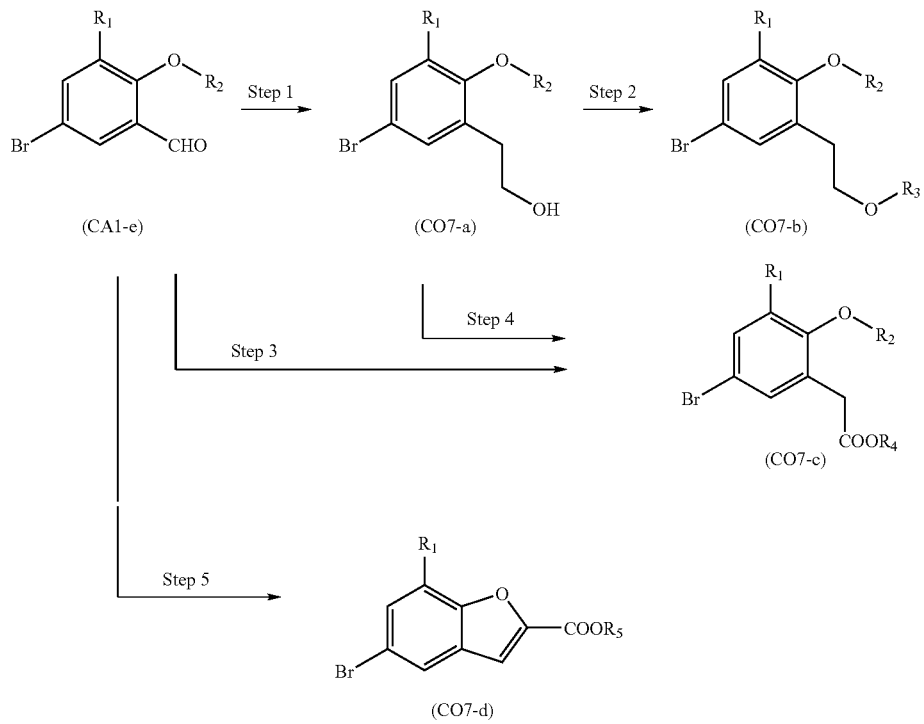

Scheme CO-7 is a general synthesis method for phenetyl alcohol derivatives, phenylacetic acid derivatives and benzofuran derivatives. In the formulas, R1 has the same definition as R1 in Step 1 of Production Process PP. R2 and R3 have the same definitions as R6 and R7 in Production Process MO. R4 and R5 represent optionally substituted alkyl.

Step 1 is a step of introducing a hydroxyl group by Wittig reaction followed by hydroboration reaction. The reaction is conducted with methyltriphenylphosphonium bromide in a tetrahydrofuran solvent in the presence of potassium tert-butoxide. Reaction is then conducted with borane-tetrahydrofuran in a tetrahydrofuran solvent and with 30% aqueous hydrogen peroxide to yield compound (CO7-a).

Step 2 is a step of introducing a substituent R3 at the hydroxyl group. Compound (CO7-b) is obtained by treatment in the same manner as for introduction of R7 in Step 3 of Production Process MO.

Step 3 is a step of carbon-carbon bond formation. Compound (CO7-c) is obtained by reaction with methylmethylthiomethyl sulfoxide in a tetrahydrofuran solvent in the presence of Triton B, at the reflux temperature of the solvent, followed by reaction with dilute aqueous hydrochloric acid in a methanol or ethanol solvent.

Step 4 is a step of oxidation. Compound (CO7-c) is obtained by the method described in Mangzho Zhao et al., Tetrahedron Lett. 39, 5323(1998) or the method described in Ryoji Noyori et al., J. Am. Chem. Soc., 119, 12386(1997).

Step 5 is a step of forming a furan ring when R2 is hydrogen. Compound (CO7-d) is obtained by reaction with a bromoacetic acid ester in a dimethylformamide solvent in the presence of potassium carbonate, at the reflux temperature of the solvent.

Compounds (CO7-a), (CO7-b), (CO7-c) and (CO7-d) obtained in this Scheme CO-7 are converted to the final target compounds by Production Process A.

(Scheme CO-8)

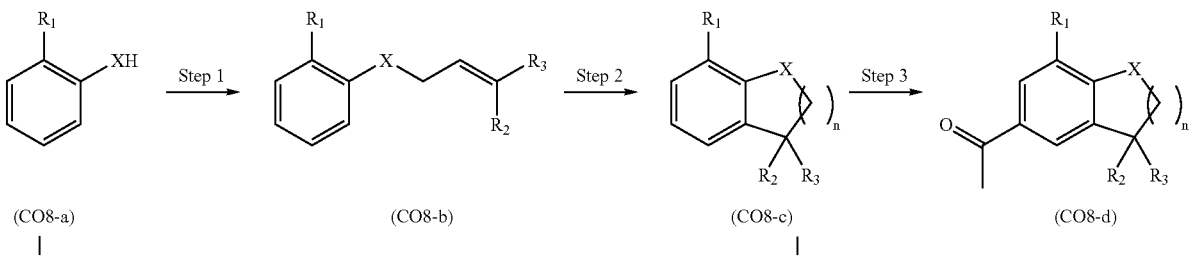

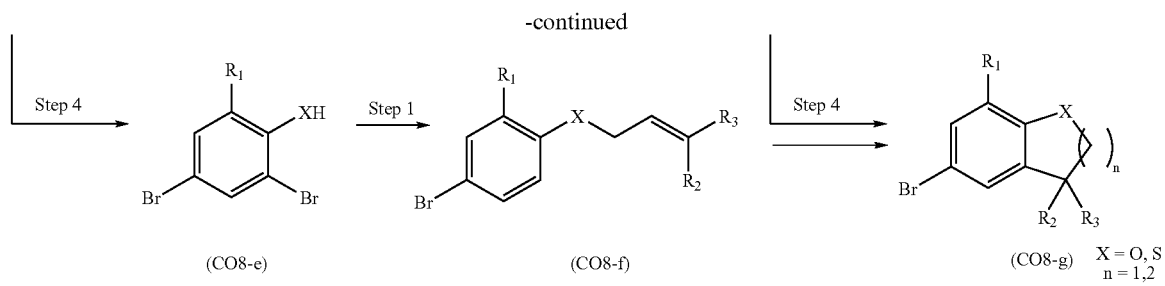

Scheme CO-8 is a general synthesis method for a 2,3-dihydrobenzofuran derivative or 2,3-dihydrobenzothiophene derivative. In the formulas, R1 has the same definition as R1 in Step 1 of Production Process PP. R2 and R3 represent hydrogen, optionally substituted alkyl or optionally substituted alkoxy.

Step 1 is a step of alkylation of the hydroxyl group. Compound (CO8-b) is obtained by reaction with an allyl halide, allyl mesylate or allyl tosylate in a solvent such as dimethylformamide, acetonitrile or acetone, in the presence of sodium iodide and in the presence of a base such as potassium carbonate, cesium carbonate or sodium hydride, according to the method described in J. M. Janusz et al., J. Med. Chem. 41, 1112(1998).

Step 2 is a step of forming a furan or thiophene ring. Compound (C08-c) is obtained by the method described in J. M. Janusz et al., J. Med. Chem. 41, 1112(1998), or by reaction at 210° C. in magnesium chloride.

Step 3 is a step of Friedel-Crafts acylation. Compound (CO8-d) is obtained by reaction with acetyl chloride in a methylene chloride or toluene solvent in the presence of a Lewis acid such as aluminum chloride, zinc chloride or tin (IV) chloride, at −70° C. to room temperature.

Step 4 is a step of bromination by reaction with bromine in a methanol or ethanol solvent. Alternatively, compounds (CO8-e) and (CO8-g) are obtained by reaction with N-bromosuccinimide in an acetonitrile or dimethylformamide solvent.

Step 5 is a step of forming a furan or thiophene ring. Compound (CO8-g) is obtained by reaction with sodium borohydride at 75° C. in a dimethylacetamide solvent in the presence of cyclopentadienyldichlorotitanium, by the method described in J. Schwaltz et al., J. Org. Chem. 59, 940(1994).

Compounds (CO8-d) and (CO8-g) obtained in this Scheme CO-8 are converted to the final target compounds by Production Process A.

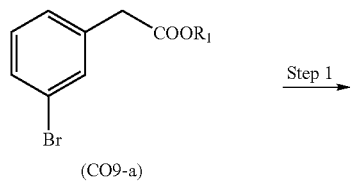

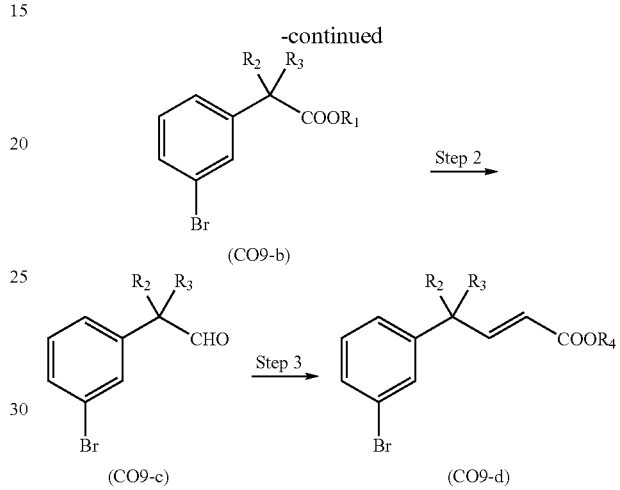

Scheme CO-9 is a general synthesis method for a carboxylic acid derivative. In the formulas, R1, R2, R3 and R4 represent hydrogen or optionally substituted alkyl.

Step 1 is a step of alkylation. Compound (CO9-b) is obtained by reaction with an alkyl halide, mesylate or tosylate in a tetrahydrofuran or dimethylformamide solvent, in the presence of potassium tert-butoxide or sodium hydride.

Step 2 is a step of reduction. Compound (CO9-c) is obtained by reaction with diisobutylaluminum hydride in a tetrahydrofuran solvent.

Step 3 is a step of carbon-carbon bond formation utilizing a Wittig reaction. The reaction is conducted with a phosphorane derivative in a methylene chloride or tetrahydrofuran solvent. Alternatively, compound (CO9-d) is obtained by reaction with either a phosphonium salt or phosphonate in a tetrahydrofuran or dimethylformamide solvent in the presence of a base such as potassium tert-butoxide or sodium hydride.

Compounds (CO9-b) and (CO9-d) obtained in this Scheme CO-9 are converted to the final target compounds by Production Process A.

Representative production processes for compounds according to the invention and salts thereof have been described above, but the starting compounds and reagents used for production of the compounds of the invention may also form salts or hydrates, and these are not particularly restricted so long as the reaction is not inhibited. When compound (I) of the invention is obtained as a free compound, a common method may be used to convert it to a salt which compound (I) may form. The different isomers (for example, geometric isomers, optical isomers based on asymmetric carbon, stereoisomers, tautomers or the like) obtained for compound (I) according to the invention may be purified and isolated using common separation means such as recrystallization, diastereomer salt methods, enzymatic resolution methods and chromatography methods (for example, thin-layer chromatography, column chromatography, gas chromatography, etc.).

The compounds of the invention represented by formula (I) and salts thereof exhibit excellent thrombin receptor antagonism and especially selective antagonism against PAR1 thrombin receptors. The compounds of the invention and their salts also exhibit excellent inhibition against platelet aggregation and smooth muscle cell proliferation, with high oral efficacy. The compounds of the invention and salts thereof can therefore inhibit the cellular response to thrombin which includes platelet aggregation, without inhibiting the catalytic activity of thrombin which converts fibrinogen to fibrin, and can also inhibit vascular smooth muscle proliferation occurring as a result of damage to vascular walls by coronary angioplasty and the like, through selective inhibition of PAR1.

Thus, the compounds of the invention and salts thereof may be used to obtain pharmaceutical compositions (formulations) as (i) thrombin receptor antagonists (especially PAR1 thrombin receptor antagonists), (ii) platelet aggregation inhibitors, (iii) smooth muscle cell proliferation inhibitors, (iv) endothelial cell, fibroblast, nephrocyte, osteosarcoma cell, muscle cell, cancer cell and/or glia cell proliferation inhibitors and (v) therapeutic or preventive agents for thrombosis, vascular restenosis, deep venous thrombosis, pulmonary embolism, cerebral infarction, heart disease, disseminated intravascular coagulation, hypertension, inflammatory diseases, rheumatism, asthma, glomerulonephritis, osteoporosis, neurological disease and/or malignant tumor.

The compounds of the invention and their salts may be administered for treatment of patients suffering from diseases associated with thrombin receptors, and for treatment of patients suffering from proliferative diseases of, for example, endothelial cell, fibroblast, nephrocyte, osteosarcoma cell, muscle cell, cancer cell and/or glia cell.

A compound of the invention represented by formula (I) above, a salt thereof or a hydrate of the foregoing may be formulated by a common method. As preferred dosage forms there may be mentioned tablets, powders, fine particles, granules, coated tablets, capsules, syrups, lozenges, inhalants, suppositories, injections, ointments, eye salves, eye drops, nasal drops, ear drops, paps, lotions and the like. For the formulation there may be employed any commonly used excipients, binders, disintegrators, lubricants, coloring agents, corrective coatings, and if necessary, stabilizers, emulsifiers, absorbefacients, surfactants, pH adjustors, preservatives, antioxidants, or the like, in combination with various components that are ordinarily used as materials for pharmaceutical formulations.

As such components there may be mentioned (1) animal and vegetable oils such as soybean oil, beef tallow and synthetic glycerides; (2) hydrocarbons such as liquid paraffin, squalane and solid paraffin; (3) ester oils such as octyldodecyl myristate and isopropyl myristate; (4) higher alcohols such as cetostearyl alcohol and behenyl alcohol; (5) silicone resins; (6) silicone oils; (7) surfactants such as polyoxyethylene fatty acid esters, sorbitan fatty acid esters, glycerin fatty acid esters, polyoxyethylene sorbitan fatty acid esters, polyoxyethylene hydrogenated castor oil and polyoxyethylene/polyoxypropylene block copolymer; (8) water-soluble polymers such as hydroxyethylcellulose, polyacrylic acid, carboxyvinyl polymer, polyethylene glycol, polyvinylpyrrolidone and methylcellulose; (9) lower alcohols such as ethanol and isopropanol; (10) polyhydric alcohols such as glycerin, propylene glycol, dipropylene glycol and sorbitol; (11) sugars such as glucose and sucrose; (12) inorganic powders such as silicic anhydride, magnesium aluminum silicate and aluminum silicate; (13) purified water, and the like.

Examples of (1) excipients which may be used include lactose, corn starch, white soft sugar, glucose, mannitol, sorbit, crystalline cellulose and silicon dioxide; examples of (2) binders which may be used include polyvinyl alcohol, polyvinyl ether, methylcellulose, ethylcellulose, gum arabic, tragacanth, gelatin, shellac, hydroxypropylcellulose, hydroxypropylmethylcellulose, polyvinylpyrrolidone, polypropylene glycol/polyoxyethylene block polymer, meglumine, calcium citrate, dextrin and pectin; examples of (3) disintegrators which may be used include starch, agar, gelatin powder, crystalline cellulose, calcium carbonate, sodium hydrogencarbonate, calcium citrate, dextrin, pectin and calcium carboxymethylcellulose; examples of (4) lubricants which may be used include magnesium stearate, talc, polyethylene glycol, silica and hydrogenated vegetable oils; examples of (5) coloring agents which may be used include any of those approved for addition to drugs; examples of (6) corrective coatings which may be used include cocoa powder, menthol, aromatic powders, mentha oil, borneol and powdered cinnamon; and examples of (7) antioxidants which may be used include those approved for addition to drugs, such as ascorbic acid, α-tocopherol and the like.

(i) An oral formulation may be prepared by combining a compound of the invention or its salt with an excipient, if necessary adding a binder, disintegrator, lubricant, coloring agent, corrective coating or the like, and forming a powder, fine particles, granules, tablets, coated tablets, capsules, etc. by a common method. (ii) Tablets or granules may, of course, also be coated with a sugar coating, gelatin coating or other type of suitable coating if necessary. (iii) In the case of a liquid formulation such as syrup, injection, eye drops or the like, a common method may be used for formulation with a pH adjustor, solubilizer, isotonizing agent or the like, as well as a solubilizing aid, stabilizer, buffering agent, suspending agent, antioxidant, etc. if necessary. In the case of a liquid formulation, it may also be lyophilized, and an injection may be administered intravenously, subcutaneously or intramuscularly. As preferred examples of suspending agents there may be mentioned methylcellulose, polysorbate 80, hydroxyethylcellulose, gum arabic, tragacanth powder, sodium carboxymethylcellulose, polyoxyethylene sorbitan monolaurate and the like; as preferred examples of solubilizing aids there may be mentioned polyoxyethylene hydrogenated castor oil, polysorbate 80, nicotinamide, polyoxyethylene sorbitan monolaurate and the like; as preferred examples of stabilizing agents there may be mentioned sodium sulfite, sodium metasulfite, ether and the like; and as preferred examples of preservatives there may be mentioned methyl p-oxybenzoate, ethyl p-oxybenzoate, sorbic acid, phenol, cresol, chlorocresol, and the like. (iv) There are no particular restrictions on the method of preparing an external application, and any common method may be employed. The base materials used may be any raw materials commonly employed in drugs, quasi drugs, cosmetics and the like, and as examples there may be mentioned raw materials such as animal and vegetable oils, mineral oils, ester oils, waxes, higher alcohols, fatty acids, silicone oils, surfactants, phospholipids, alcohols, polyhydric alcohols, water-soluble polymers, clay minerals, purified water and the like, with addition of pH adjustors, antioxidants, chelating agents, antiseptics and fungicides, coloring agents, aromas and the like if necessary. Also, there may be included differentiation-inducing components, or other components such as circulation promoters, microbicides, antiphlogistic agents, cell activators, vitamins, amino acids, humectants, keratolytic agents and the like, as necessary.

Although the dosage of a drug according to the invention will differ depending on the patient's severity of symptoms, age, gender and body weight, the dosage form and type of salt, drug sensitivity, the specific type of disease, etc., it will generally be from about 30 μg to 1000 mg, preferably from 100 μg to 500 mg and more preferably from 100 μg to 100 mg per day for adults in the case of oral administration or about 1–3000 μg/kg and preferably 3–1000 μg/kg per day for adults in the case of injection, administered once or divided over several times a day.

EXAMPLES

Preferred embodiments of the compounds of the invention represented by formula (I) above and salts thereof will now be explained, with the understanding that the following examples and test examples are only representative and are not intended to be restrictive on the compounds of the invention or salts thereof in any way. It will be apparent to those skilled in the art that the present invention can be carried out with various modifications added beyond these examples, and such modifications are also encompassed within the claims of the present specification.

Example 1

2-[2-(3,5-Di-tert-butyl-4-hydroxyphenyl)-2-oxo-ethyl]-6-ethoxy-3-imino-2,3-dihydro-1H-isoindole-5-carboxylic acid methylamide hydrobromide

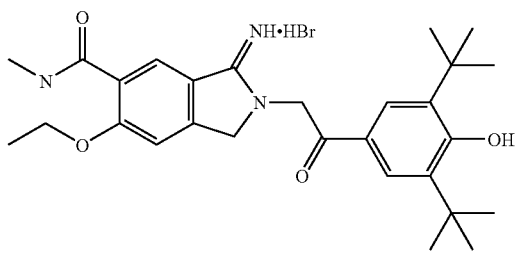

(Step 1) 5-Bromo-2-hydroxy-4-methylbenzoic acid

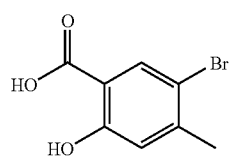

After dissolving 2-hydroxy-4-methylbenzoic acid (24.54 g, 161.29 mmol) in methanol (300 ml), the solution was cooled to −20° C. A solution of bromine (26.03 g) in methanol (50 ml) was added dropwise over 1 hour. The reaction mixture was stirred at room temperature for 1 hour and then concentrated. The residue was heated to dissolution in methanol (100 ml) and water (40 ml) was added. The precipitated crystals were filtered off and washed with 50% methanol-water. The precipitated crystals in the filtrate were also filtered off and washed with 50% methanol-water. The crystals were combined and dried to yield the title compound (24.8 g) as white crystals.

$^1$H-NMR(CDCl3) δ (ppm) 2.37(3H, s), 6.85(1H, s), 7.98 (1H, s).

(Step 2) 5-Bromo-2-ethoxy-4-methylbenzoic acid

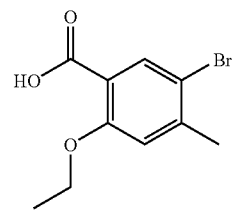

After dissolving 5-bromo-2-hydroxy-4-methylbenzoic acid (9.35 g) in dimethylformamide, potassium carbonate (14 g) and ethyl iodide (8 ml) were added in that order and the mixture was stirred at 50° C. for 3 hours. It was then diluted with ethyl acetate, washed with water and brine, dried over anhydrous magnesium sulfate, filtered and concentrated to yield ethyl 5-bromo-2-ethoxy-4-methylbenzoate. The product was dissolved in ethanol (100 ml), 5 N sodium hydroxide (20 ml) was added and the mixture was heated to reflux for 30 minutes. After adding 5 N hydrochloric acid (25 ml) for neutralization, extraction was performed with ethyl acetate. The extract was dried over anhydrous magnesium sulfate, filtered and concentrated to yield the title compound (10.4 g) as a white solid.

$^1$H-NMR(CDCl3) δ (ppm) 1.56(3H, t, J=6.8Hz), 2.45(3H, s), 4.31(2H, q, J=6.8 Hz), 6.91(1H, s), 8.31(1H, s).

(Step 3) N1,4-Dimethyl-5-bromo-2-ethoxybenzamide

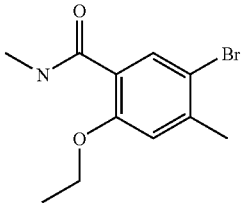

After dissolving 5-bromo-2-ethoxy-4-methylbenzoic acid in tetrahydrofuran (80 ml), triethylamine (3.5 ml) and ethyl chloroformate (2.4 ml) were added while cooling on ice, the mixture was stirred for 1 hour, and then a 40% methylamine aqueous solution (3.5 ml) was added. The reaction mixture was stirred for 1 hour, ethyl acetate was added and the mixture was washed with brine, after which the organic layer was dried over anhydrous magnesium sulfate and the solvent was distilled off under reduced pressure. The crystals of the residue were washed with hexane and filtered to yield the title compound (5.08 g) as white crystals.

(Step 4) N1,4-Dimethyl-5-cyano-2-ethoxybenzamide

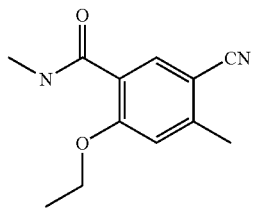

After dissolving N1,4-dimethyl-5-bromo-2-ethoxybenzamide (200 g) in propionitrile (1.5l), sodium cyanide (72 g), copper iodide (14 g) and tetrakis(triphenylphosphine)palladium (42 g) were added under a nitrogen atmosphere and the mixture was heated to reflux for 5 hours. Ethyl acetate and water were added and the reaction mixture was filtered through celite. The precipitated crystals in the filtrate were filtered off (15.4 g). This filtrate was then separated and washed with brine. The organic layer was dried over anhydrous magnesium sulfate and was concentrated after filtering off the insoluble portion. The obtained crystals were filtered off and washed with ethyl acetate (77.64 g). The crystals were combined to yield the title compound (93.04 g) as a white solid.

$^1$H-NMR(CDCl3) δ (ppm) 1.56(3H, t, J=7.2 Hz), 2.57 (3H, s), 4.28(2H, q, J=7.2 Hz), 6.86(1H, s), 7.93(1H, br), 8.04(1H, s).

(Step 5) tert-Butyl N-(5-cyano-2-ethoxy-4-methylbenzoyl)-N-methylcarbamate

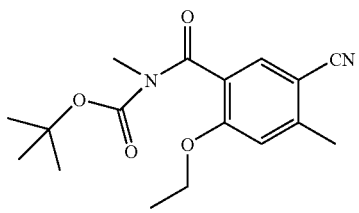

After suspending N1,4-dimethyl-5-cyano-2-ethoxybenzamide (92 g) in acetonitrile (1l), tert-butyl dicarbonate (110 g) and dimethylaminopyridine (2.6 g) were added and the mixture was stirred at room temperature overnight. The reaction mixture was heated to 90° C. and stirred for 3 hours. tert-Butyl dicarbonate (110 g) was further added and the mixture was stirred at 50° C. overnight. After cooling to room temperature, the precipitated crystals were filtered off (24.3 g). The filtrate was concentrated and the residue was purified by silica gel column chromatography (solvent: n-hexane-ethyl acetate) to yield the title compound (81.1 g) as a white solid.

$^1$H-NMR(CDCl3) δ (ppm) 1.23(9H, s), 1.39(3H, t, J=7.2 Hz), 2.55(3H, s), 3.29(3H, s), 4.04(2H, q, J=7.2 Hz), 6.72 (1H, s), 7.58(1H, s).

(Step 6) tert-Butyl N-[4-(bromomethyl)-5-cyano-2-ethoxybenzoyl]-N-methylcarbamate

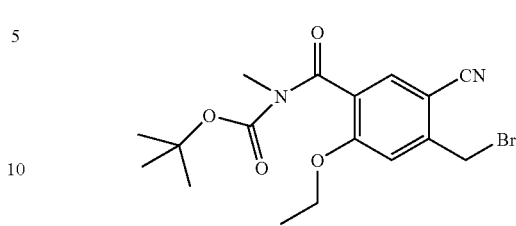

After dissolving tert-butyl N-(5-cyano-2-ethoxy-4-methylbenzoyl)-N-methylcarbamate (79.6 g) in carbon tetrachloride, azobisisobutyronitrile (4.1 g) was added and the mixture was heated to reflux. N-bromosuccinimide (50.3 g) was gradually added to the reaction mixture in small portions at a time. After heating to reflux for 2 hours, the mixture was filtered. The filtrate was concentrated and the residue was purified by silica gel column chromatography (solvent: n-hexane-ethyl acetate) to yield the title compound (29.81 g) as a white solid.

$^1$H-NMR(CDCl3) δ (ppm) 1.22(9H, s), 1.41(3H, t, J=7.2 Hz), 1.56(9H, s), 3.30(3H, s), 4.09(2H, q, J=7.2 Hz), 4.60 (2H, s), 6.96(1H, s), 7.60(1H, s).

(Step 7) N1-Methyl-4-(bromomethyl)-5-cyano-2-ethoxybenzamide

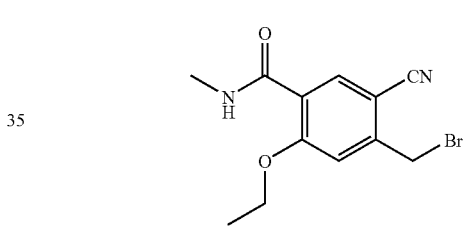

After dissolving tert-butyl N-[4-(bromomethyl)-5-cyano-2-ethoxybenzoyl]-N-methylcarbamate (39.9 g) in dichloromethane (300 ml), trifluoroacetic acid (50 ml) was added and the mixture was stirred at room temperature for 30 minutes. The reaction mixture was concentrated and the residue was purified by silica gel column chromatography (solvent: n-hexane-ethyl acetate) to yield the title compound (19.77 g) as a white solid.

$^1$H-NMR(CDCl3) δ (ppm) 1.54(3H, t, J=7.2 Hz), 3.02 (3H, d, J=4.8 Hz), 4.26(2H, q, J=7.2 Hz), 4.59(2H, s), 7.19(1H, s), 8.53(1H, s).

(Step 8) tert-Butyl 5-cyano-2-ethoxy-4-methylbenzoate

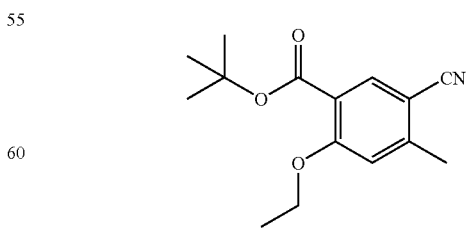

After dissolving 5-bromo-2-ethoxy-4-methylbenzoic acid (10.4 g) in toluene (100 ml) and ethyl acetate (20 ml), dimethylformamide di-tert-butylacetal (75 ml) was added and the mixture was heated to reflux for 8 hours. Ethyl acetate was then added, the mixture was washed with 1 N hydrochloric acid and brine in that order, dried over anhydrous magnesium sulfate, filtered and concentrated, and the residue was purified by silica gel column chromatography (solvent: n-hexane-ethyl acetate) to yield a tert-butyl ester (12.27 g) as a colorless oil. This was dissolved in propionitrile, and then sodium cyanide (3.82 g), copper iodide (740 mg) and tetrakis(triphenylphosphine)palladium (2.25 g) were added under a nitrogen atmosphere and the mixture was heated to reflux for 8 hours. Ethyl acetate and water were added, the reaction mixture was filtered through celite and the filtrate was washed with brine. The organic layer was dried over anhydrous magnesium sulfate and was concentrated after filtering off the insoluble portion, and the residue was purified by silica gel column chromatography (solvent: n-hexane-ethyl acetate) to yield the title compound (9.57 g) as a white solid.

$^1$H-NMR(CDCl3) δ (ppm) 1.47(3H, t, J=6.8 Hz), 1.57 (9H, s), 2.53(3H, s), 4.12(2H, q, J=6.8 Hz), 6.79(1H, s), 7.95(1H, s)

(Step 9) tert-Butyl 4-(bromomethyl)-5-cyano-2-ethoxybenzoate

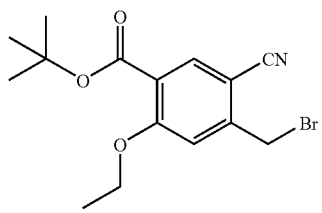

After dissolving tert-butyl 5-cyano-2-ethoxy-4-methylbenzoate (8.91 g) in carbon tetrachloride, N-bromosuccinimide (6.6 g) and benzoyl peroxide (400 mg) were added and the mixture was heated to reflux for 3 hours. The reaction mixture was filtered and concentrated. The residue was purified by silica gel column chromatography (solvent: n-hexane-ethyl acetate) to yield a mixture of the title compound and tert-butyl 5-cyano-2-ethoxy-4-methylbenzoate (starting material) (8.80 g) as a white solid.

$^1$H-NMR(CDCl3) δ (ppm) 1.50(3H, t, J=7.2 Hz), 1.58 (9H, s), 4.18(2H, q, J=7.2 Hz), 4.58(2H, s), 7.05(1H, s), 7.98(1H, s).

(Step 10) tert-Butyl 4-(azidomethyl)-5-cyano-2-ethoxybenzoate

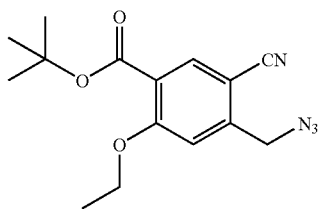

After dissolving tert-butyl 4-(bromomethyl)-5-cyano-2-ethoxybenzoate (2.20 g, 70% purity) in dimethylformamide (25 ml), sodium azide (2.1 g) was added and the mixture was stirred at 50° C. for 30 minutes. It was then diluted with ethyl acetate, washed with water, dried over anhydrous magnesium sulfate, filtered and concentrated to yield the title compound (1.913 g).

$^1$H-NMR(CDCl3) δ (ppm) 1.49(3H, t, J=6.8 Hz), 1.56 (9H, s), 4.18(2H, q, J=6.8 Hz), 4.62(2H, s), 7.04(1H, s), 8.01(1H, s).

(Step 11) 4-(Azidomethyl)-5-cyano-2-ethoxybenzoic acid

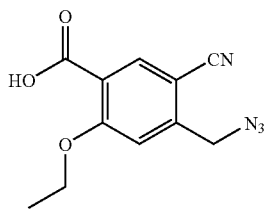

After dissolving tert-butyl 4-(azidomethyl)-5-cyano-2-ethoxybenzoate (1.923 g) in dichloromethane (12 ml), trifluoroacetic acid (3 ml) was added while cooling on ice. The mixture was stirred at room temperature for 20 minutes and concentrated. The title compound was obtained as light red crystals.

$^1$H-NMR(CDCl3) δ (ppm) 1.64(3H, t, J=6.8 Hz), 4.47 (2H, q, J=6.8 Hz), 4.74(2H, s), 7.23(1H, s), 8.46(1H, s).

(Step 12) N1-Methyl-4-(azidomethyl)-5-cyano-2-ethoxybenzamide

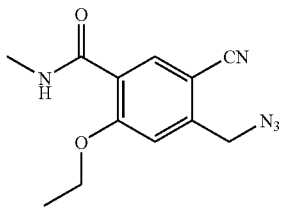

After dissolving 4-(azidomethyl)-5-cyano-2-ethoxybenzoic acid in dimethylformamide (20 ml), a 2M tetrahydrofuran solution of methylamine (4.2 ml), diethyl phosphonocyanidate (1.28 ml) and triethylamine (1.27 ml) were added while cooling on ice. The mixture was stirred at room temperature overnight, diluted with ethyl acetate and washed with water and brine. The organic layer was dried over anhydrous magnesium sulfate, filtered and concentrated to yield the title compound (931 mg).

After next dissolving N1-methyl-4-(bromomethyl)-5-cyano-2-ethoxybenzamide in dimethylformamide (100 ml), sodium azide (6 g) was added and the mixture was stirred at room temperature overnight. The reaction mixture was diluted with ethyl acetate and washed with water and brine, and then the organic layer was dried over anhydrous magnesium sulfate, filtered and concentrated to yield the title compound (15.5 g).

$^1$H-NMR(CDCl3) δ (ppm) 1.58(3H, t, J=6.8 Hz), 3.02 (3H, d, J=4.8 Hz), 4.32(2H, q, J=7.2 Hz), 4.67(2H, s), 7.10(1H, s), 7.74(1H, br), 8.55(1H, s).-

(Step 13) N5-Methyl-3-amino-6-ethoxy-1H-5-isoindolecarboxamide

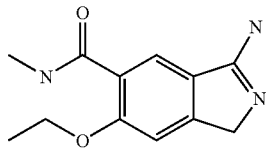

After dissolving N1-methyl-4-(azidomethyl)-5-cyano-2-ethoxybenzamide (931 mg) in tetrahydrofuran (10 ml), 28% aqueous ammonia (2 ml) and triethylphosphine (0.4 ml) were added in that order. The mixture was stirred at 50° C. for 15 minutes. The precipitated crystals were filtered off, washed with tetrahydrofuran, water and ethyl acetate in that order and dried to yield the title compound (365 mg).

$^1$H-NMR(DSMO-d6)δ (ppm) 1.38(3H, t, J=6.8 Hz), 2.79 (3H, d, J=4.8 Hz), 4.18(2H, q, J=6.8 Hz), 4.41(2H, s), 7.27(1H, s), 8.07(1H, br), 8.12(1H, s).

Example 1

Final Step

Method A

After dissolving tert-butyl 4,5-dicyano-2-ethoxybenzoate (440 mg) in dichloromethane (3 ml) and trifluoroacetic acid (3 ml), the solution was stirred at room temperature for 6 hours. The reaction mixture was concentrated to yield a carboxylic acid (350 mg) as a white solid. This was dissolved in dimethylformamide (3 ml), and then triethylamine (0.1 ml), diethyl phosphonocyanidate (0.11 ml) and a 2 N tetrahydrofuran solution of methylamine were added in that order and the mixture was stirred at room temperature overnight. Ethyl acetate was added and the reaction mixture was washed with water. The organic layer was dried over anhydrous magnesium sulfate. After filtering off the insoluble portion, the filtrate was concentrated and the residue was purified by silica gel column chromatography (solvent: n-hexane-ethyl acetate) to yield an amide (64 mg, 38% yield). This was dissolved in ethanol (3 ml), platinum oxide (20 mg) was added and the mixture was stirred at room temperature overnight. After filtering off the insoluble portion, the filtrate was concentrated and the residue was purified by silica gel column chromatography (solvent: ethyl acetate-methanol-aqueous ammonia) to yield a mixture of amidine regioisomers (17 mg). This was dissolved in ethanol (3 ml), and then 3,5-di-tert-butyl 4-hydroxyphenacylbromide (30 mg) was added and the mixture was heated to reflux for 30 minutes. The reaction mixture was concentrated and the residue was purified by silica gel column chromatography (solvent: dichloromethane-methanol) to yield the target compound (12 mg, 7% yield).

Method B

After dissolving N5-methyl-3-amino-6-ethoxy-1H-5-isoindolecarboxamide (389 mg) and 3,5-di-tert-butyl 4-hydroxyphenacylbromide in ethanol, the mixture was heated to reflux for 30 minutes. The reaction mixture was concentrated and the residue was purified by silica gel column chromatography (solvent: ethyl acetate-methanol) to yield the target compound (614 mg, 65.7% yield).

$^1$H-NMR(DSMO-d6) δ (ppm) 1.39(3H, t, J=6.8 Hz), 1.42(18H, s), 2.83(3H, d, J=4.8 Hz), 4.28(2H, q, J=6.8 Hz), 4.84(2H, s), 5.48(2H, s), 7.54(1H, s), 7.77(2H, s), 8.20(1H, q, J=4.8 Hz), 8.55(1H, s), 9.13(1H, br), 9.82(1H, br).

MS: m/e (ESI) 480.3 (MH+)

Example 2

2-[2-(3,5-Di-tert-butyl-4-hydroxy-phenyl)-2-oxo-ethyl]-6-dimethylamino-3-imino-2,3-dihydro-1H-isoindole-5-carboxylic acid methylamide hydrobromide

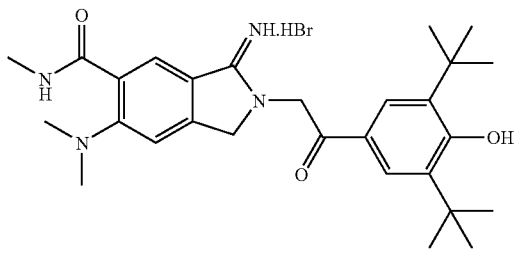

(Step 1) 4-Benzyl 1-methyl 2-aminoterephthalate

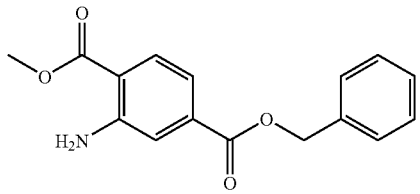

After dissolving 1-methyl 2-aminoterephthalate (8.00 g, 41.1 mmol) in dimethylformamide (80 ml), anhydrous potassium carbonate (6.25 g, 45.1 mmol) and benzyl bromide (4.12 ml, 43.1 mmol) were added and the mixture was stirred at room temperature for 15.5 hours. An excess of triethylamine was added, and after stirring for an additional 10 minutes at room temperature, ice water was added and extraction was performed with ethyl acetate. The ethyl acetate layer was washed with water and brine and then dried over anhydrous magnesium sulfate. Filtration was performed with silica gel-alumina and the solvent was distilled off under reduced pressure. IPE was added to the obtained oil for crystallization, and the crystals were filtered off. The filtrate was concentrated and then the same procedure was repeated twice to yield the title compound (8.21 g) as a light yellow powder.

(70% yield) $^1$H-NMR(CDCl3) δ (ppm) 3.89(3H, s), 5.34 (2H, s), 5.81(2H, s), 7.28(1H, dd, J=1.6, 8.4 Hz), 7.32–7.46 (6H, m), 7.90(1H, d, J=8.4 Hz).

(Step 2) 4-Benzyl 1-methyl 2-(dimethylamino)terephthalate

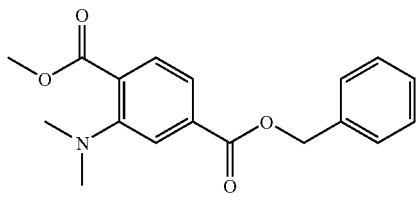

After dissolving 4-benzyl 1-methyl 2-aminoterephthalate (500 mg, 1.75 mmol) in formic acid (2 ml), 37% formalin (0.44 ml, 5.26 mmol) was added and the mixture was heated to reflux for 15 minutes. Ice water was added and extraction was performed with ethyl acetate. The ethyl acetate layer was washed with water, saturated aqueous sodium hydrogencarbonate and brine, and then dried over anhydrous magnesium sulfate. The solvent was distilled off under reduced pressure and the residue was purified by silica gel column chromatography (solvent: n-hexane-ethyl acetate) to yield the title compound (137 mg) as a yellow oil. (25% yield)

¹H-NMR(CDCl3) δ (ppm) 2.95(6H, s), 3.94(3H, s), 5.38 (2H, s), 7.32–7.48(5H, m), 7.57(1H, d, J=8.0 Hz), 7.70(1H, d, J=8.0 Hz), 7.75(1H, s).

(Step 3) Methyl 2-(dimethylamino)-4-(hydroxymethyl)benzoate

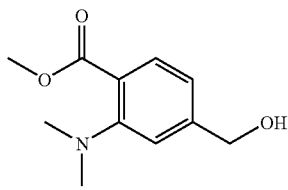

After dissolving 4-benzyl 1-methyl 2-(dimethylamino) terephthalate (1.66 g, 5.3 mmol) in tetrahydrofuran (30 ml), 20% palladium hydroxide-carbon (0.20 g) was added prior to catalytic reduction for 15 minutes at room temperature and normal pressure. The catalyst was separated off, and the solvent was distilled off under reduced pressure to yield a light yellow amorphous substance. This was dissolved in tetrahydrofuran (15 ml), triethylamine (0.81 ml, 5.8 mmol) was added and ethyl chloroformate (0.55 ml, 5.8 mmol) was added dropwise while stirring on ice. After stirring for 30 minutes, the precipitate was filtered off and the filtrate was cooled to −40° C. and stirred. A solution of sodium borohydride (0.44 g, 11.6 mmol) in 5 ml of water was added dropwise, and the temperature of the mixture was gradually increased to −20° C. over a period of 30 minutes. Acetone was added to the reaction mixture, the insoluble portion was filtered off and the solvent was distilled off under reduced pressure. Water was added to the residue and extraction was performed with ethyl acetate. The ethyl acetate layer was washed with water and brine and then dried over anhydrous magnesium sulfate. The solvent was distilled off under reduced pressure and the residue was purified by silica gel column chromatography (solvent: n-hexane-ethyl acetate). The title compound (1.02 g) was obtained as a light yellow oil. (92% yield)

¹H-NMR(CDCl3) δ (ppm) 2.93(6H, s), 3.91(3H, s), 4.70 (2H, s), 6.89(1H, m), 7.11(1H, m), 7.70(1H, d, J=8.0 Hz).

(Step 4) Methyl 5-bromo-2-(dimethylamino)-4-(hydroxymethyl)benzoate

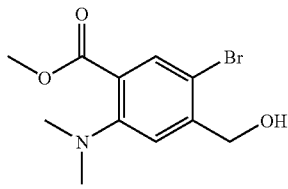

After dissolving methyl 2-(dimethylamino)-4-(hydroxymethyl)benzoate (1.023 g, 4.9 mmol) in a methylene chloride (15 ml) and methanol (6 ml) mixed solvent, calcium carbonate (2 g) was added, the mixture was stirred, and then benzyltrimethylammonium tribromide (2.100 g, 5.4 mmol) was gradually added and the mixture was stirred at room temperature for 50 minutes. The reaction mixture was filtered and the solvent was distilled off under reduced pressure. Water was added to the residue, extraction was performed with ethyl acetate and the ethyl acetate layer was washed with water and brine. The aqueous layer was then extracted with a methylene chloride and methanol mixed solvent, combined with the ethyl acetate layer, and dried over anhydrous magnesium sulfate. The solvent was distilled off under reduced pressure and the residue was purified by silica gel column chromatography (solvent: n-hexane-ethyl acetate) to yield the title compound (1.179 g) as a white solid. (84% yield)

¹H-NMR(CDCl3) δ (ppm) 2.92(6H, s), 3.91(3H, s), 4.71 (2H, s), 7.22(1H, m), 7.86(1H, s).

(Step 5) N1-Methyl-5-bromo-2-(dimethylamino)-4-(hydroxymethyl)benzamide

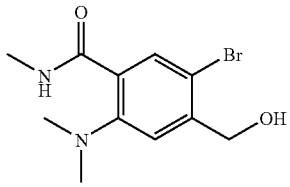

After dissolving the methyl 5-bromo-2-(dimethylamino)-4-(hydroxymethyl)benzoate (1.179 g, 4.1 mmol) in a tetrahydrofuran (10 ml)-methanol (10 ml) mixed solvent, a 1 N sodium hydroxide aqueous solution (9.8 ml, 9.8 mmol) was added and the mixture was heated to reflux for 4 hours. Next, 5 N hydrochloric acid (9.8 ml, 9.8 mmol) was added and the reaction mixture was concentrated under reduced pressure. Acetonitrile was added to the residue and the mixture was concentrated under reduced pressure, and then the same procedure was repeated twice. Acetonitrile (20 ml), a 2.0 M dimethylamine-tetrahydrofuran solution (4.1 ml, 8.2 mmol), 1-hydroxybenztriazole (1.11 g, 8.2 mmol) and dicyclohexylcarbodiimide (1.69 g, 8.2 mmol) were added to the residue in that order and the mixture was stirred at room temperature for 20 hours. The insoluble portion was filtered off, the reaction mixture was concentrated under reduced pressure, ethyl acetate was added and the mixture was filtered through alumina. The filtrate was concentrated under reduced pressure and the residue was purified by silica gel column chromatography (solvent: n-hexane-ethyl acetate) to yield the title compound (1.222 g) as a white solid. (100% yield)

¹H-NMR(CDCl3) δ (ppm) 2.76(6H, s), 3.02(3H, d, J=4.4 Hz), 4.71(2H, s), 7.41(1H, s), 8.29(1H, s).-

(Step 6) N1-Methyl-5-bromo-4-({(1-(tert-butyl)-1,1-diphenylsilyl]oxy}methyl)-2-(dimethylamino)benzamide

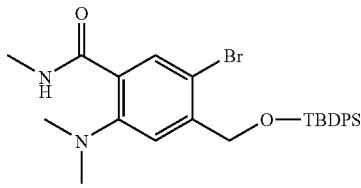

After dissolving N1-methyl-5-bromo-2-(dimethylamino)-4-(hydroxymethyl)benzamide (1.64 g, 5.71 mmol) in dimethylformamide (20 ml), imidazole (0.47 g, 6.9 mmol) and tert-butylchlorodiphenylsilane (1.78 ml, 6.9 mmol) were added while cooling on ice and the mixture was stirred at room temperature for 19 hours. The reaction mixture was poured into ice water and extraction was performed with ethyl acetate. The ethyl acetate layer was washed with water and brine and then dried over anhydrous magnesium sulfate. The solvent was distilled off under reduced pressure and then the residue was purified by silica gel column chromatography (solvent: n-hexane-ethyl acetate) to yield the title compound (2.60 g) as a colorless oil. (87% yield)

$^1$H-NMR(CDCl3) δ (ppm) 1.14(9H, s), 2.82(6H, s), 3.02 (3H, s), 4.79(2H, s), 7.35–7.48(7H, m), 7.64–7.75(5H, m), 8.37(1H, s).

(Step 7) N1-Methyl-4-({[1-(tert-butyl)-1,1-diphenylsilyl]oxy}methyl)-5-cyano-2-(dimethylamino)benzamide

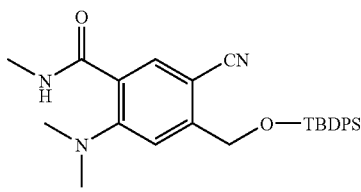

After dissolving N1-methyl-5-bromo-4-({[1-(tert-butyl)-1,1-diphenylsilyl]oxy}methyl)-2-(dimethylamino)benzamide (2.60 g, 5.0 mmol) in dimethylformamide (10 ml), copper (I) cyanide (0.58 g, 6.5 mmol) was added and the mixture was stirred at 180° C. for 5 hours. A 5% sodium cyanide aqueous solution (20 ml) was added to the reaction mixture and extraction was performed with ethyl acetate. The ethyl acetate layer was washed with water and brine and then dried over anhydrous magnesium sulfate. The solvent was distilled off under reduced pressure and then the residue was purified by silica gel column chromatography (solvent: n-hexane-ethyl acetate) to yield the title compound (1.91 g) as a faint yellow oil. (81% yield)

$^1$H-NMR(CDCl3) δ (ppm) 1.14(9H, s), 2.87(6H, s), 3.02 (3H, s), 4.95(2H, s), 7.34–7.51(7H, m), 7.60–7.74(4H, m), 7.88(1H, m), 8.11(1H, s).

(Step 8) N1-Methyl-5-cyano-2-(dimethylamino)-4-(hydroxymethyl)benzamide

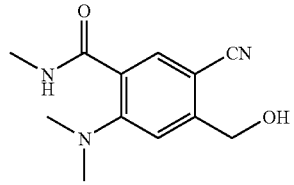

After dissolving N1-methyl-4-({[1-(tert-butyl)-1,1-diphenylsilyl]oxy)methyl)-5-cyano-2-(dimethylamino)benzamide (1.91 g, 4.1 mmol) in tetrahydrofuran (10 ml), acetic acid (0.64 ml, 11.2 mmol) and 1.0 M tetra-n-butylammonium fluoride (5.4 ml, 5.4 mmol) were added and the mixture was stirred at room temperature for 2 hours. The reaction mixture was concentrated under reduced pressure, saturated aqueous sodium hydrogencarbonate was added and extraction was performed with ethyl acetate. The ethyl acetate layer was washed with water and brine and then dried over anhydrous magnesium sulfate. The solvent was distilled off under reduced pressure and then n-hexane was added and the mixture was filtered. The title compound (0.84 g) was obtained as a faint yellow solid. (89% yield)

$^1$H-NMR(CDCl3) δ (ppm) 2.87(6H, s), 3.02(3H, d, J=5.2 Hz), 4.89(2H, s), 7.28(1H, s), 7.66(1H, m), 8.09(1H, s)

(Step 9) N1-Methyl-4-(azidomethyl)-5-cyano-2-(dimethylamino)benzamide

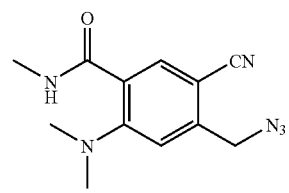

After dissolving N1-methyl-5-cyano-2-(dimethylamino)-4-(hydroxymethyl)benzamide (849 mg, 3.6 mmol) in tetrahydrofuran (20 ml), 1,8-diazabicyclo[5.4.0]undec-7-ene (0.77 ml, 5.1 mmol) and diphenylphosphoryl azide (1.1 ml, 5.1 mmol) were added and the mixture was stirred at room temperature for 15 hours. The reaction mixture was concentrated under reduced pressure and the residue was purified by silica gel column chromatography (solvent: n-hexane-ethyl acetate) to yield the title compound (755 mg) as a faint yellow powder. (80% yield)

$^1$H-NMR(CDCl3) δ (ppm) 2.94(6H, s), 3.03(3H, s), 4.61 (2H, s), 7.18(1H, s), 7.53(1H, m), 8.12(1H, s).

(Step 10) N5-Methyl-6-(dimethylamino)-3-imino-5-isoindolinecarboxamide

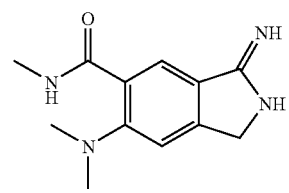

After dissolving N1-methyl-4-(azidomethyl)-5-cyano-2-(dimethylamino)benzamide (755 mg, 2.9 mmol) in methanol (50 ml), 10% palladium-carbon (50% wet) (0.2 g) was added prior to catalytic reduction for 30 minutes at room temperature and normal pressure. The catalyst was separated off, the solvent was distilled off under reduced pressure and ethyl acetate was added to the residue for crystallization. This was filtered off to yield the title compound (283 mg) as a faint yellow powder. (42% yield)

$^1$H-NMR(DSMO-$d_6$) δ (ppm) 2.77(6H, s), 2.80(3H, d, J=4.8 Hz), 4.42(2H, s), 7.20(1H, s), 7.94(1H, s), 8.58(1H, m).

Example 2

Final Step

After dissolving N5-methyl-6-(dimethylamino)-3-imino-5-isoindolinecarboxamide (150 mg) and 3,5-di-tert-butyl 4-hydroxyphenacylbromide (212 mg) in dimethylformamide (6 ml), the mixture was stirred at room temperature for 14 hours. The solvent was distilled off under reduced pressure and the residue was purified by silica gel column chromatography (solvent: n-hexane-ethyl acetate) to yield the target compound (114 mg) as light yellow crystals. (31% yield)

$^1$H-NMR(DSMO-$d_6$) δ (ppm) 1.44(18H, s), 2.80(3H, d, J=4.4 Hz), 2.94(6H, s), 4.75(2H, s), 5.46(2H, s), 7.17(1H, s), 7.79(2H, s), 8.05(1H, s), 8.10(1H, s), 8.37(1H, m), 8.94(1H, s), 9.54(1H, s).

Example 3

1-(3,5-Di-tert-butyl-4-hydroxy-phenyl)-2-(7-fluoro-1-imino-5,6-dimethoxy-1,3-dihydro-isoindol-2-yl)-ethanone hydrobromide

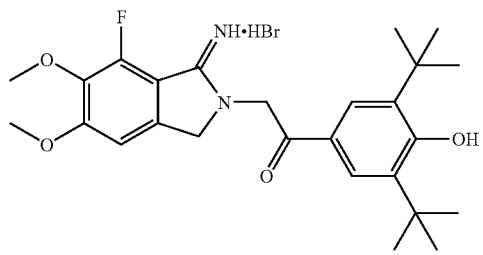

(Step 1) 1-Fluoro-2,3-dimethoxybenzene

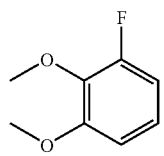

After dissolving the 3-fluorocatechol (30 g, 0.234 mol) in dimethylformamide (400 ml), methyl iodide (32 ml, 0.515 mol) and potassium carbonate (80.7 g, 0.515 mol) were added while stirring on ice, and the stirring was continued at room temperature for 18 hours. Water (500 ml) was added and extraction was performed with diethyl ether (400 ml×2), and then after washing the combined organic layers with brine (400 ml) and drying over anhydrous magnesium sulfate, the solvent was distilled off under reduced pressure to yield the title compound as a light yellow liquid (34 g, 93%).

$^1$H-NMR(CDCl3) δ (ppm) 3.86(3H, s), 3.92(3H, s), 6.65–6.98(3H, m).

(Step 2) 1,2-Dibromo-3-fluoro-4,5-dimethoxybenzene

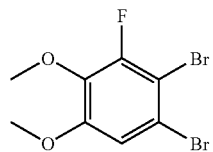

After dissolving 1-fluoro-2,3-dimethoxybenzene (34 g, 0.218 mol) in acetic acid (100 ml), sodium acetate (35.8 g, 0.437 mol) was added and a solution of bromine (22.6 ml, 0.458 mol) in acetic acid (100 ml) solution was added dropwise over 45 minutes while stirring on ice. After the dropwise addition, the mixture was stirred at 75° C. for 10 hours. It was then cooled to room temperature, the solvent was distilled off under reduced pressure, the obtained crude product was dissolved in diethyl ether (400 ml), washed with a saturated aqueous sodium hydrosulfite (200 ml), saturated aqueous sodium hydrogencarbonate (200 ml) and brine (200 ml) in that order and dried over anhydrous magnesium sulfate, and the solvent was distilled off under reduced pressure to yield a crude product as light yellow crystals (65.4 g, 95.6%). These were used without further purification for the following reaction.

$^1$H-NMR(CDCl3) δ (ppm) 3.85(3H, s), 3.90(3H, s), 6.99 (1H, s).

(Step 3) 3-Fluoro-4,5-dimethoxyphthalonitrile

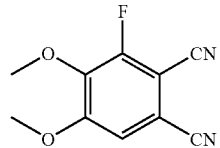

After dissolving the 1,2-dibromo-3-fluoro-4,5-dimethoxybenzene (40 g, 0.127 mol) in dimethylformamide (300 ml), CuCN (34.1 g, 0.381 mol) was added at room temperature while stirring and the mixture was stirred at 150° C. for 4 hours. After cooling on ice, a solution of sodium cyanide (44 g) in water (600 ml) was added and the mixture was stirred at room temperature for 10 minutes, after which extraction was performed with ethyl acetate (500 ml×3) and then after washing the combined organic layers with brine (500 ml) and drying over anhydrous magnesium sulfate, the solvent was distilled off under reduced pressure. The residue was purified by silica gel column chromatography (solvent: n-hexane-ethyl acetate) to yield the title compound (white crystals 12.0 g, 46%).

$^1$H-NMR(CDCl3) δ (ppm) 3.99(3H, s), 4.06(3H, s), 7.05 (1H, s).

(Step 4) 4-Fluoro-5,6-dimethoxy-1H-3-isoindoleamine

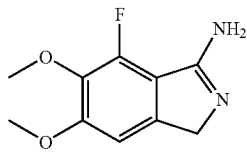

After dissolving 3-fluoro-4,5-dimethoxyphthalonitrile (450 mg, 2.18 mmol) in ethanol (50 ml), platinum oxide (0.1 g) was added. Catalytic hydrogenating reduction was carried out for 3 days at normal temperature and pressure. The catalyst was removed by celite filtration, washing was performed with methanol, and the filtrate was concentrated under reduced pressure. The obtained crude product was purified by silica gel column chromatography (solvent: ethyl acetate:methanol:27% aqueous ammonia=3:1:0.1) to yield the title compound as a brown solid (200 mg, 43%).

$^1$H-NMR(DSMO-$d_6$) δ (ppm) 3.76(3H, s), 3.83(3H, s), 4.38(2H, s), 7.08(1H, s).

Example 3

Final Step

After dissolving 4-fluoro-5,6-dimethoxy-1H-3-isoindoleamine (50 mg) and 3,5-di-tert-butyl 4-hydroxyphenacylbromide (93 mg) in dimethylformamide (7 ml), the mixture was stirred at room temperature for 15 hours. The solvent was distilled off under reduced pressure and the residue was purified by NAM silica gel column chromatography (solvent: methylene chloride-methanol) to yield the target compound (76 mg) as light yellow crystals.

$^1$H-NMR(DSMO-$d_6$) δ (ppm) 1.41(18H, s), 3.86(3H, s), 3.95(3H, s), 4.79(2H, s), 5.47(2H, s), 7.36(1H, s), 7.75(2H, s).

Example 4

1-(3,5-Di-tert-butyl-4-hydroxy-phenyl)-2-(5-ethoxy-7-fluoro-1-imino-6-methoxy-1,3-dihydro-isoindol-2-yl)-ethanone hydrobromide

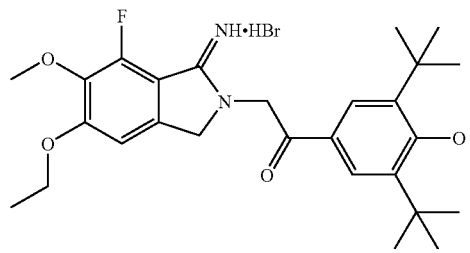

(Step 1) 3,4-Dibromo-6-ethoxy-2-fluorophenol

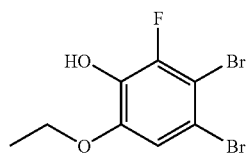

After dissolving 1,2-dibromo-3-fluoro-4,5-diethoxybenzene (5 g, 14.5 ml) in dichloromethane (70 ml), aluminum chloride (3.9 g, 29.3 mmol) was added while stirring on ice. The mixture was stirred at room temperature for 2 hours 30 minutes, 1 N hydrochloric acid (70 ml) was added and extraction was performed with ethyl acetate (70 ml×2) and then after washing the combined organic layers with brine (50 ml) and drying over anhydrous magnesium sulfate, the solvent was distilled off under reduced pressure. The residue was purified by silica gel column chromatography (solvent: n-hexane-ethyl acetate) to obtain the title compound (4.31 g, 94%).

$^1$H-NMR(CDCl3) δ (ppm) 1.45(3H, t, J=7.0 Hz), 4.10 (2H, q, J=7.0 Hz), 5.49(1H, s), 6.95(1H, s).

(Step 2) 1,2-Dibromo-5-ethoxy-3-fluoro-4-methoxybenzene

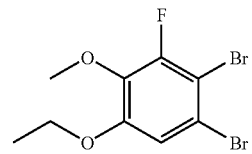

After dissolving 3,4-dibromo-6-ethoxy-2-fluorophenol (3.8 g, 12 mmol) in dimethylformamide (30 ml), methyl iodide (1.5 ml, 24 mmol) and potassium carbonate (3.3 g, 24 mmol) were added and the mixture was stirred at room temperature for 18 hours. Water (80 ml) was added, extraction was performed with diethyl ether (60 ml×2), and then after washing the combined organic layers with brine (80 ml) and drying over anhydrous magnesium sulfate, the solvent was distilled off under reduced pressure. The residue was purified by silica gel column chromatography (solvent: n-hexane-ethyl acetate) to yield the title compound (1.83 g, 46.7%).

$^1$H-NMR(CDCl3) δ (ppm) 1.45(3H, t, J=7.0 Hz), 3.90 (3H, s), 4.05(2H, q, J=7.0 Hz), 6.99(1H, s).

(Step 3) 5-Ethoxy-3-fluoro-4-methoxyphthalonitrile

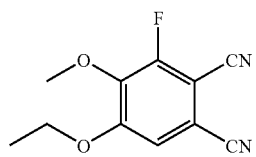

Synthesis was performed in the same manner as Step 3 of Example 3 to yield the title compound.

$^1$H-NMR(CDCl3) δ (ppm) 1.51(3H, t, J=6.7 Hz), 4.05 (3H, s), 4.16(2H, q, J=6.7 Hz), 7.05(1H, s).

(Step 4) 6-Ethoxy-4-fluoro-5-methoxy-1H-3-isoindoleamine

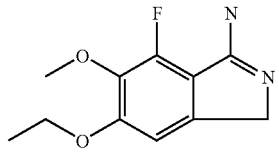

Synthesis was performed in the same manner as Step 4 of Example 3 to yield the title compound.

$^1$H-NMR(CDCl3) δ (ppm) 1.34(3H, t, J=6.7 Hz), 3.76 (3H, s), 4.08(2H, q, J=6.7 Hz), 4.37(2H, s), 7.04(1H, s).

Example 4 Final Step

Synthesis was performed in the same manner as the final step of Example 3 to yield the target compound as a yellow solid.

$^1$H-NMR(DSMO-d6) δ (ppm) 1.34–146(21H, m), 3.87 (3H, s), 4.22(2H, q, J=7.0 Hz), 4.77(2H, s), 5.47(2H, s), 7.34(1H, s), 7.75(2H, s), 9.03(1H, brs).

Example 5

{8-tert-Butyl-6-[2-(5,6-diethoxy-7-fluoro-1-imino-1,3-dihydro-isoindol-2-yl)acetyl]-2,3-dihydrobenzo[1,4]oxazin-4-yl}acetonitrile hydrobromide

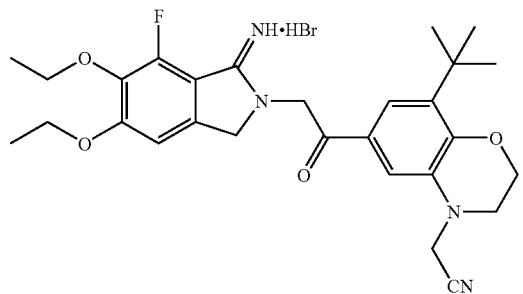

(Step 1) 1-[8-(tert-Butyl)-3,4-dihydro-2H-1,4-benzoxazin-6-yl]-1-ethanone

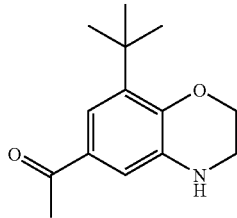

Potassium carbonate (4.65 g, 33.7 mmol) and 1,2-dibromoethane (31.7 g, 166.6 mmol) were added to a solution of 1-[3-(tert-butyl)-4-hydroxy-5-nitrophenyl]-1-ethanone (8.0 g, 33.7 mmol) in dimethylformamide (200 ml) and the mixture was stirred at room temperature for 12 hours. Ethyl acetate was added, the reaction mixture was washed with water and brine in that order and the organic layer was dried over anhydrous magnesium sulfate. The solvent was distilled off under reduced pressure and the residue was purified by silica gel column chromatography (solvent: n-hexane-ethyl acetate) to yield 1-[4-(2-bromoethoxy)-3-(tert-butyl)-5-nitrophenyl]-1-ethanone (8.1 g).

After adding 10% palladium-carbon (200 mg) to a solution of this compound (8.1 g, 23.5 mmol) in toluene (300 ml), the mixture was stirred at room temperature for 24 hours under a hydrogen stream. The reaction mixture was filtered through celite, and the filtrate was concentrated under reduced pressure to yield the title compound (5.1 g) as a yellow oil.

1H-NMR(CDCl3) δ (ppm) 1.38(9H, s), 2.52(3H, s), 3.46 (2H, t, J=6.8 Hz), 4.31(2H, t, J=6.8 Hz), 7.12(1H, d, J=2.0 Hz), 7.34(1H, d, J=2.0 Hz)

(Step 2) [6-Acetyl-8-(tert-butyl)-3,4-dihydro-2H-1,4-benzoxazin-4-yl]methyl cyanide

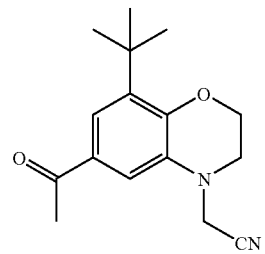

Potassium carbonate (3.6 g, 26 mmol) and bromoacetonitrile (15.4 g, 128.6 mmol) were added to a solution of 1-[8-(tert-butyl)-3,4-dihydro-2H-1,4-benzoxazin-6-yl]-1-ethanone (6.0 g, 25.5 mmol) in dimethylformamide (100 ml) and the mixture was stirred at 90° C. for 6 hours. Ethyl acetate was added, the reaction mixture was washed with water and brine in that order and the organic layer was dried over anhydrous magnesium sulfate. The solvent was distilled off under reduced pressure and then the residue was purified by silica gel column chromatography (solvent: n-hexane-ethyl acetate) to yield the title compound (6.9 g) as a light yellow oil.

1H-NMR(CDCl3) δ (ppm) 1.39(9H, s), 2.56(3H, s), 3.42 (2H, t, J=6.8 Hz), 4.24(2H, s), 4.41(2H, d, J=7.8 Hz), 7.29(1H, d, J=2.0 Hz), 7.48(1H, d, J=2.0 Hz).

(Step 3) [6-(2-Bromoacetyl)-8-(tert-butyl)-3,4-dihydro-2H-1,4-benzoxazin-4-yl]methyl cyanide

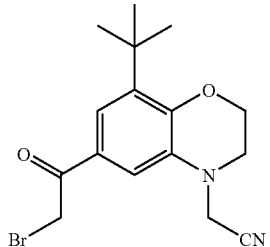

Triethylamine (0.76 ml, 5.5 mmol) and tert-butyl dimethylsilyltrifluoromethanesulfonate (0.73 g, 5.5 mmol) were added to a solution of [6-acetyl-8-(tert-butyl)-3,4-dihydro-2H-1,4-benzoxazin-4-yl]methyl cyanide (0.5 g, 1.8 mmol) in tetrahydrofuran (50 ml) while cooling on ice and the mixture was stirred at the same temperature for 30 minutes, after which N-bromosuccinimide (0.49 g, 2.7 mmol) was added and stirring was continued for 30 minutes. Ethyl acetate was added, the reaction mixture was washed with brine and the organic layer was dried over anhydrous magnesium sulfate. The solvent was distilled off under reduced pressure and then the residue was purified by silica gel column chromatography (solvent: n-hexane-ethyl acetate) to yield the title compound (310 mg) as a light yellow solid.

1H-NMR(CDCl3) δ (ppm) 1.39(9H, s), 3.42(2H, t, J=6.8 Hz), 4.24(2H, s), 4.40(2H, s), 4.43(2H, t, J=6.8 Hz), 7.32 (1H, d, J=2.0 Hz), 7.53(1H, d, J=2.0 Hz).

Example 5

Final Step

Synthesis was performed in the same manner as the final step of Example 3 to yield the target compound as a yellow solid.

1H-NMR(DSMO-d6) δ (ppm) 1.29(3H, t, J=7 Hz), 1.33–1.42(12H, m), 3.30–3.40(2H, m), 4.11(2H, q, J=7 Hz), 4.21(2H, q, J=7 Hz), 4.40(2H, m), 4.66(2H, s), 4.80(2H, s), 5.45(2H, s), 7.33(1H, s), 7.40–7.42(2H, m), 9.03(1H, br.s), 9.34(1H, br.s).

MS: m/e (ESI) 509.3 (MH+)

Example 6

1-(3-tert-Butyl-5-dimethylamino-4-methoxy-phenyl)-2-(5,6-diethoxy-7-fluoro-1-imino-1,3-dihydro-isoindol-2-yl)-ethanone hydrobromide

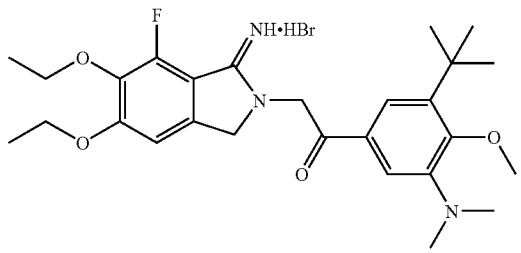

(Step 1) 1-[3-(tert-Butyl)-5-(dimethylamino)-4-methoxyphenyl]-1-ethanone

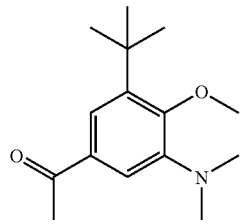

Potassium carbonate (8.5 g, 62 mmol) and methyl iodide (8.8 g, 62 mmol) were added to a solution of 1-[3-amino-5-(tert-butyl)-4-methoxyphenyl]-1-ethanone (6 g, 21 mmol) in dimethylformamide (50 ml) and the mixture was stirred at room temperature for 13 hours. Ethyl acetate was added, the reaction mixture was washed with water and brine in that order and the organic layer was dried over anhydrous magnesium sulfate. The solvent was distilled off under reduced pressure and then the residue was purified by silica gel column chromatography (solvent: n-hexane-ethyl acetate) to yield the title compound (1.9 g) as a light yellow oil.

1H-NMR(CDCl3) δ (ppm) 1.40(9H, s), 2.58(3H, s), 2.83(6H, s), 3.88(3H, s), 7.47(1H, s), 7.59(1H, s).

(Step 2) 2-Bromo-1-[3-(tert-butyl)-5-(dimethylamino)-4-methoxyphenyl]-1-ethanone

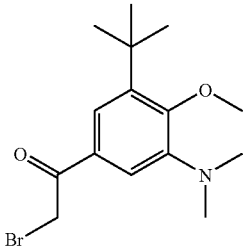

Triethylamine (3.2 ml, 22.9 mmol) and tert-butyl dimethylsilyltrifluoromethanesulfonate (3.02 g, 11.4 mmol) were added to a solution of 1-[3-(tert-butyl)-5-(dimethylamino)-4-methoxyphenyl]-1-ethanone (1.9 g, 7.63 mmol) in tetrahydrofuran (50 ml) while cooling on ice and the mixture was stirred at the same temperature for 30 minutes, after which N-bromosuccinimide (2.7 g, 15.2 mmol) was added and stirring was continued for 30 minutes. Ethyl acetate was added, the reaction mixture was washed with brine and the organic layer was dried over anhydrous magnesium sulfate. The solvent was distilled off under reduced pressure and then the residue was purified by silica gel column chromatography (solvent: n-hexane-ethyl acetate) to yield the title compound (2.2 g) as a white solid.

1H-NMR(CDCl3) δ (ppm) 1.40(9H, s), 2.80(6H, s), 3.89(3H, s), 4.42(2H, s), 7.49(1H, s), 7.60(1H, s).

Example 6

Final Step

Synthesis was performed in the same manner as the final step of Example 3 to yield the target compound as a yellow solid.

1H-NMR(DSMO-d6) δ (ppm) 1.29(3H, t, J=7.2 Hz), 1.37(9H, s), 1.39(3H, t, J=7.2 Hz), 2.74(6H, s), 3.82(3H, s), 4.14(2H, q, J=7.2 Hz), 4.21(2H, q, J=7.2 Hz), 4.77(2H, s), 5.46(2H, s), 7.32(1H, s), 7.45(1H, d, J=2.0 Hz), 7.53(1H, d, J=2.0 Hz).

MS: m/e (ESI) 486.2 (MH+)

Example 7

1-(3-tert-Butyl-4-methoxy-5-morpholino-phenyl)-2-(5,6-diethoxy-7-fluoro-1-imino-1,3-dihydro-isoindol-2-yl)-ethanone hydrobromide

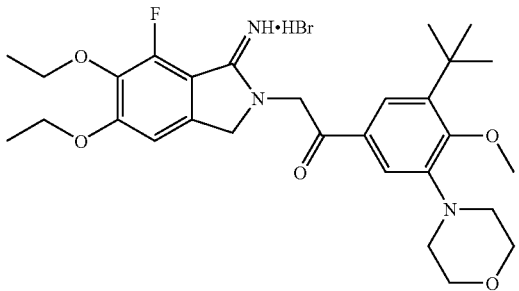

(Step 1) 1,2-Diethoxy-3-fluorobenzene

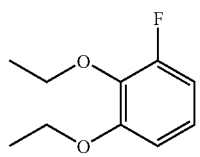

After dissolving 3-fluorocatechol (1200 g) in dimethylformamide (2500 ml) while cooling on ice, potassium carbonate (540 g) was added, after which ethyl iodide was gradually added. The reaction mixture was stirred at room temperature overnight, an ether-hexane solution was added, the mixture was washed with water and brine and the organic layer was dried over anhydrous magnesium sulfate. The solvent of the organic layer was distilled off under reduced pressure and then the residue was purified by silica gel column chromatography (solvent: n-hexane-ethyl acetate) to yield the title compound (269 g) as a yellow oil.

$^1$H-NMR(CDCl3) δ (ppm) 1.35(3H, t, J=7.0 Hz), 1.43 (3H, t, J=7.0 Hz), 4.07(2H, q, J=7.0 Hz), 4.12(2H, q, J=7.0 Hz), 6.65–6.95(3H, m).

(Step 2) 1,2-Dibromo-4,5-diethoxy-3-fluorobenzene

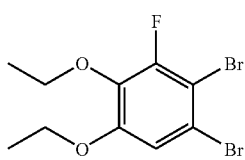

After dissolving the 1,2-diethoxy-3-fluorobenzene (269 g) in acetic acid (2000 ml), sodium acetate (294.5 g) was added. A solution of bromine (178 ml) in 150 ml of acetic acid was gradually added thereto dropwise while cooling on ice. After stirring overnight at room temperature, the mixture was stirred at 70° C. for 14 hours. The reaction mixture was poured into ice water, potassium carbonate was added to adjust the pH to 7, and extraction was performed with ether. The organic layer was dried over anhydrous magnesium sulfate to yield the title compound (480 g) as a brown oil.

$^1$H-NMR (CDCl3) δ (ppm) 1.35(3H, t, J=7.0 Hz), 1.43 (3H, t, J=7.0 Hz), 4.04(2H, q, J=7.0 Hz), 4.11(2H, q, J=7.0 Hz), 6.98(1H, s).

(Step 3) 4,5-Diethoxy-3-fluorophthalonitrile

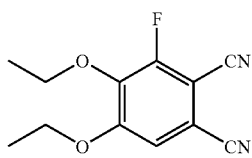

After dissolving the 1,2-dibromo-4,5-diethoxy-3-fluorobenzene (480 g) in dimethylformamide (1400 ml), copper cyanide (345 g) was added and the mixture was stirred at 150° C. for 3 hours. Saturated aqueous ammonia was added to the reaction mixture, and then the mixture was stirred overnight and extraction was performed with toluene. The organic layer was dried over anhydrous magnesium sulfate, the solvent was distilled off under reduced pressure and the residue was purified by silica gel column chromatography (solvent: n-hexane-ethyl acetate) to yield the title compound (513 g) as white crystals.

$^1$H-NMR(CDCl3) δ (ppm) 1.38(3H, t, J=7.0 Hz), 1.50 (3H, t, J=7.0 Hz), 4.16(2H, q, J=7.0 Hz), 4.27(2H, q, J=7.0 Hz), 7.04(1H, s).

(Step 4) 5,6-Diethoxy-4-fluoro-1H-3-isoindoleamine

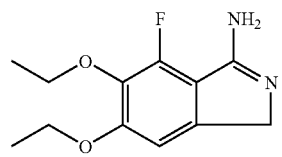

After dissolving 4,5-diethoxy-3-fluorophthalonitrile (103 g) in ethyl acetate-ethanol-methanol (600 ml-600 ml-300 ml), platinum oxide (8 g) was added and the mixture was stirred at room temperature for 4 days under a hydrogen stream. The reaction mixture was filtered through celite, the organic layer was distilled off under reduced pressure and the residue was purified by silica gel column chromatography (solvent: n-hexane-ethyl acetate) to yield the title compound (21 g) as yellow crystals.

$^1$H-NMR(DSMO-d6) δ (ppm) 1.23(3H, t, J=7.0 Hz), 1.33(3H, t, J=7.0 Hz), 4.01(2H, q, J=7.0 Hz), 4.08(2H, q, J=7.0 Hz), 4.37(2H, s), 6.0(2H, brs), 7.05(1H, s).

(Step 5) 1-[3-(tert-Butyl)-4-hydroxyphenyl]-1-ethanone

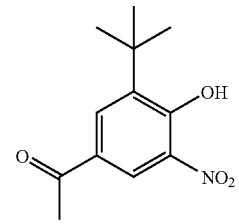

Acetyl chloride (287 g) was added to a mixture of aluminum chloride (488 g) and methylene chloride (1.8 l) at −60° C. while stirring. 2-tert-Butylphenol (500 g) was added at −70° C. to −50° C. over a period of 1.5 hours, and the temperature was then raised to 0° C. The reaction mixture was poured into ice and extraction was performed with ethyl acetate. The organic layer was washed with brine, the solvent was distilled off under reduced pressure, methanol (1 l) and potassium carbonate (300 g) were added to the residue and the mixture was stirred at room temperature for 2 hours. After adding water to the reaction mixture and neutralizing it with concentrated hydrochloric acid, extraction was performed with ethyl acetate and the organic layer was washed with brine. The organic layer was dried over anhydrous magnesium sulfate and concentrated under reduced pressure. Hexane was added to the residue and the resulting crystals were filtered off to yield the title compound (352 g) as white crystals.

$^1$H-NMR(CDCl3) δ (ppm) 1.41(3H, s), 2.55(3H, s), 6.73 (1H, d, J=8 Hz), 7.72(1H, dd, J=2, 8 Hz), 7.95(1H, d, J=2 Hz).-

(Step 6) 1-[3-(tert-Butyl)-4-hydroxy-5-nitrophenyl]-1-ethanone

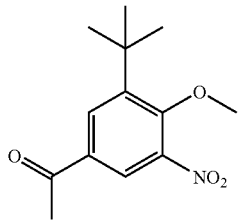

1-[3-(tert-Butyl)-4-hydroxyphenyl]-1-ethanone (739 g) was added to a mixture of 69% nitric acid (354 g), water (1 l) and methylene chloride (2 l) at 10° C. to 15° C. while stirring. After then adding diethyl ether (3 l) and acetic anhydride (28 ml), 5 N hydrochloric acid was further added at 10° C. to 15° C. The temperature of the reaction mixture was raised to room temperature over a period of 1.5 hours, and the mixture was then poured into ice water. The mixture was extracted with diethyl ether, and the organic layer was washed with brine and then dried over anhydrous magnesium sulfate. The solvent was distilled off under reduced pressure to yield the title compound (894 g) as a yellow oil.

$^1$H-NMR(CDCl3) δ (ppm) 1.44(3H, s), 2.60(3H, s), 8.23 (1H, d, J=2 Hz), 8.61(1H, d, J=2 Hz), 11.92(1H, s).

(Step 7) 1-[3-Amino-5-(tert-butyl)-4-methoxyphenyl]-1-ethanone

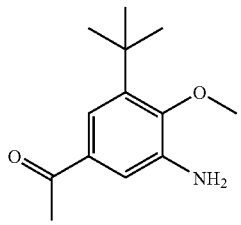

Iron powder (365 g) was added to a mixture of 1-[3-(tert-butyl)-4-methoxy-5-nitrophenyl]-1-ethanone (850 g), ammonium chloride (723 g), ethanol (4 l) and water (1 l) at 70° C. to 80° C. over a period of 1 hour. The reaction mixture was cooled to room temperature and then poured into a mixture of ice water and ethyl acetate and filtered through celite. The organic layer of the mother liquor was washed with brine and dried over anhydrous magnesium sulfate. The solvent was removed under reduced pressure and the resulting crystals were filtered off to yield the title compound (362 g) as white crystals.

$^1$H-NMR(CDCl3) δ (ppm) 1.40(3H, s), 2.54(3H, s), 3.76 (2H, br.s), 3.83(3H, s), 7.26(1H, d, J=2 Hz), 7.39(1H, d, J=2 Hz).

(Step 8) 1-[3-(tert-Butyl)-4-methoxy-5-morpholinophenyl]-1-ethanone

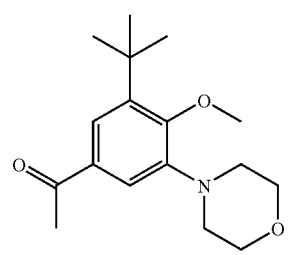

After dissolving 1-[3-amino-5-(tert-butyl)-4-methoxyphenyl]-1-ethanone (180 g) in dimethylformamide (800 ml), dibromoether (125 ml), potassium carbonate (225 g) and sodium iodide (12.2 g) were added and the mixture was stirred at 80° C. for 48 hours. The reaction mixture was cooled to room temperature, 3 l of ether was added and the mixture was washed 3 times with water. The organic layer was dried over anhydrous magnesium sulfate, and then the solvent was distilled off under reduced pressure and the residue was purified by silica gel column chromatography (solvent: n-hexane-ethyl acetate) to yield the title compound (76 g) as yellow crystals.

$^1$H-NMR(CDCl3) δ (ppm) 1.40(9H, s), 2.56(3H, s), 3.08 (4H, t, J=4.4 Hz), 3.89(4H, t, J=4.4 Hz), 3.98(3H, s), 7.48(1H, d, J=2.0 Hz), 7.65(1H, d, J=2.0 Hz).

(Step 9) 2-Bromo-1-[3-(tert-butyl)-4-methoxy-5-morpholinophenyl]-1-ethanone

After dissolving the 1-[3-(tert-butyl)-4-methoxy-5-morpholinophenyl]-1-ethanone (76 g) in tetrahydrofuran (600 ml), triethylamine (110 ml) and tert-butyl dimethylsilyltrifluoromethanesulfonate (75 ml) was added dropwise while cooling on ice. The reaction mixture was stirred for 30 minutes while cooling on ice and then N-bromosuccinimide (70 g) was gradually added. After stirring the reaction mixture for 30 minutes, 2 l of ether was added and the mixture was washed twice with water. The organic layer was dried over anhydrous magnesium sulfate, the solvent was distilled off under reduced pressure and the residue was purified by silica gel column chromatography (solvent: n-hexane-ethyl acetate) to yield the title compound (33.7 g) as light yellow crystals.

$^1$H-NMR(CDCl3) δ (ppm) 1.39(9H, s), 3.08(4H, t, J=4.8 Hz), 3.89(4H, t, J=4.8 Hz), 3.99(3H, s), 4.40(2H, s), 7.51 (1H, s), 7.68(1H, s).

Example 7

Final Step

After dissolving 5,6-diethoxy-4-fluoro-1H-3-isoindoleamine (20 g) and 2-bromo-1-[3-(tert-butyl)-4-methoxy-5-morpholinophenyl]-1-ethanone (34.2 g) in dimethylformamide (300 ml), the mixture was stirred at room temperature for 48 hours. The solvent was distilled off under reduced pressure, and ethyl acetate (500 ml) was added to the residue for crystallization. The obtained crystals were filtered and washed with ethyl acetate to yield the target compound (40 g) as white crystals.

$^1$H-NMR(DSMO-d$_6$) δ (ppm) 1.29(3H, t, J=6.8 Hz), 1.36(9H, s), 1.39(3H, t, J=6.8 Hz), 2.95–3.12(4H, m), 3.75–3.84(4H, m), 3.94(3H, s), 4.12(2H, q), 4.20(2H, q, J=6.8 Hz), 4.78(2H, s), 5.46(2H, s), 7.33(1H, s), 7.49(1H, s), 7.59(1H, s).

MS: m/e (ESI) 528.2 (MH+)

Example 7

Alternative Method (Step 1) 2-Chloro-1-[3-(tert-butyl)-4-methoxy-5-morpholinophenyl]-1-ethanone

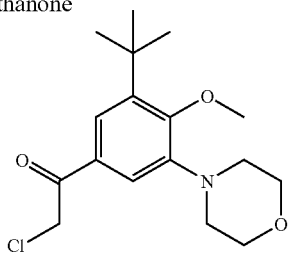

fter dissolving 1-[3-(tert-butyl)-4-methoxy-5-morpholinophenyl]-1-ethanone (9.5 g) in tetrahydrofuran (60 ml), triethylamine (13 ml) and tert-butyl dimethylsilyltrifluoromethanesulfonate (9.8 ml) were added dropwise while cooling on ice. The reaction mixture was stirred for 30 minutes while cooling on ice and then N-chlorosuccinimide (5.3 g) was gradually added. After continuing to stir the reaction mixture for 30 minutes, ether (2 l) was added thereto and the resulting mixture was washed twice with water. The organic layer was dried over anhydrous magnesium sulfate and then the residue was purified by silica gel column chromatography (solvent: n-hexane-ethyl acetate) to yield the title compound (4.87 g) as light yellow crystals.

$^1$H-NMR(CDCl3) δ (ppm) 1.39(9H, s), 3.06~3.14(4H, m), 3.86~3.94(4H, m), 3.99(3H, s), 4.66(2H, s), 7.26(1H, s), 7.49(1H, s), 7.64(1H, s).

Example 7

Alternative Method: Final Step 1-(3-tert-Butyl-4-methoxy-5-morpholino-phenyl)-2-(5,6-diethoxy-7-fluoro-1-imino-1,3-dihydro-isoindol-2-yl)-ethanone hydrochloride

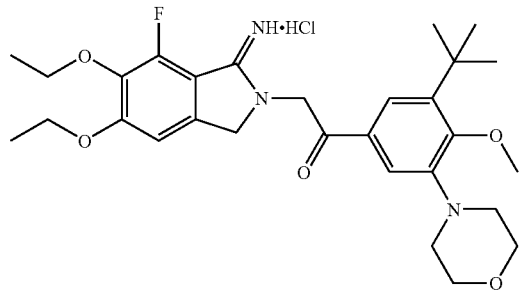

After dissolving 5,6-diethoxy-4-fluoro-1H-3-isoindoleamine (3.2 g) and 2-bromo-1-[3-(tert-butyl)-4-methoxy-5-morpholinophenyl]-1-ethanone (4.8 g) in dimethylformamide (15 ml), the mixture was stirred at room temperature for 48 hours. The solvent was distilled off under reduced pressure, and 50 ml of ethyl acetate was added to the residue for crystallization. The obtained crystals were filtered and then washed with ethyl acetate to yield the target compound (2.56 g) as white crystals.

$^1$H-NMR(DSMO-d$_6$) δ (ppm) 1.29(3H, t, J=6.8 Hz), 1.36(9H, s), 1.39(3H, t, J=6.8 Hz), 2.95~3.04(4H, m), 3.77~3.85(4H, m), 3.94(3H, s), 4.11(2H, q), 4.20(2H, q, J=6.8 Hz), 4.77(2H, s), 5.46(2H, s), 7.32(1H, s), 7.49(1H, s), 7.59(1H, s).

Example 8

1-[3-tert-Butyl-5-(4-hydroxy-piperidin-1-yl)-4-methoxyphenyl]-2-(5,6-diethoxy-7-fluoro-1-imino-1,3-dihydro-isoindol-2-yl)-ethanone hydrobromide

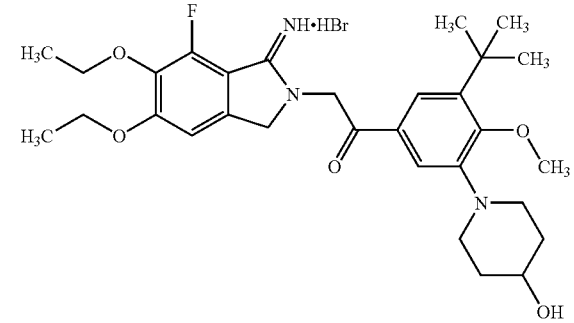

(Step 1) 4-Bromo-2-(tert-butyl)phenol

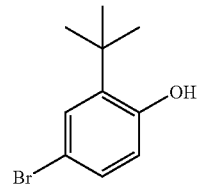

N-bromosuccinimide (580 g) was gradually added to a solution of 2-(tert-butyl)phenol (489 g) in acetonitrile (4000 ml) while cooling on ice. After stirring for 4 hours at below 20° C., ether (3000 ml) was added and the reaction mixture was washed twice with water. The organic layer was dried over anhydrous magnesium sulfate and the solvent was distilled off under reduced pressure to yield a crude product of the title compound (746 g) as a light yellow oil.

$^1$H-NMR(CDCl3) δ (ppm) 1.20(9H, s), 6.55(1H, d, J=8.4 Hz), 7.15(1H, dd, J=8.4 Hz, 2.0 Hz), 7.34(1H, d, J=2.0 Hz)

(Step 2) 4-Bromo-2-(tert-butyl)-6-nitrophenol

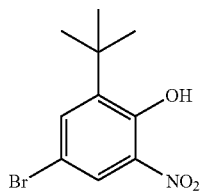

Concentrated nitric acid (112 ml) was gradually added dropwise to a solution of 4-bromo-2-(tert-butyl)phenol (485 g) in hexane (3000 ml) while cooling on ice. After stirring for 2 hours at below 20° C., ether (2000 ml) was added and the reaction mixture was washed with water. The organic layer was dried over anhydrous magnesium sulfate and the solvent was distilled off under reduced pressure. Hexane was added to the residue and the precipitated crystals were filtered to yield the title compound (418 g) as yellow crystals.

$^1$H-NMR(CDCl3) δ (ppm) 1.40(9H, s), 7.64(1H, d, J=2.4 Hz), 8.14(1H, d, J=2.4 Hz), 11.47(1H, s).

(Step 3) 4-Bromo-2-(tert-butyl)-6-nitrophenyl methyl ether

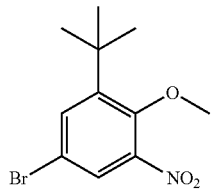

Potassium carbonate (453 g) and methyl iodide (164 ml) were added to a solution of 4-bromo-2-(tert-butyl)-6-nitrophenol (600 g) in dimethylformamide (6000 ml) and the mixture was stirred at 50° C. for 4 hours. Ether (6000 ml) was added and the reaction mixture was washed 3 times with water. The organic layer was dried over anhydrous magnesium sulfate and the solvent was distilled off under reduced pressure to yield a crude product of the title compound (569 g) as a yellow oil.

$^1$H-NMR(CDCl3) δ (ppm) 1.39(9H, s), 3.80(3H, s), 7.61 (1H, d, J=2.4 Hz), 7.76(1H, d, J=2.4 Hz).

(Step 4) 5-Bromo-3-(tert-butyl)-2-methoxyaniline

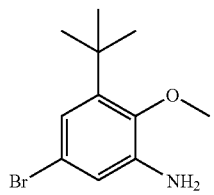

Ammonium chloride (38 g) was added to a solution of 4-bromo-2-(tert-butyl)-6-nitrophenyl methyl ether (20.6 g) in methanol-water (140 ml-140 ml) and iron (20 g) was gradually added while heating to reflux. The mixture was heated to reflux for 2 hours and then the reaction mixture was filtered through celite. The filtrate was concentrated under reduced pressure, ethyl acetate was added to the residue and the mixture was washed 3 times with brine. The organic layer was dried over anhydrous magnesium sulfate and the solvent was distilled off under reduced pressure to yield a crude product of the title compound (16.65 g) as a brown oil.

$^1$H-NMR(CDCl3) δ (ppm) 1.35(9H, s), 3.68(2H,bs), 3.76 (3H, s), 6.78(1H, d, J=2.0 Hz), 6.81(1H, d, J=2.0 Hz).

(Step 5) 1-[5-Bromo-3-(tert-butyl)-2-methoxyphenyl]-4-piperidinone

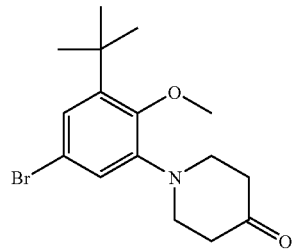

After adding a 37% formaldehyde aqueous solution (7.6 ml, 94 mmol) and anhydrous magnesium sulfate (43 g) in that order to a solution of 5-bromo-3-(tert-butyl)-2-methoxyaniline (22 g, 85 mmol) in methylene chloride (170 ml) at room temperature, the mixture was stirred at the same temperature for 4 hours. The reaction mixture was filtered through celite, and then washing was performed with methylene chloride (100 ml). The obtained filtrate was cooled to −70° C. and 2-(trimethylsilyloxy)-1,3-butadiene (16.2 ml, 92.3 mmol) was added. A 1.0 M Et2AlCl-Hex. solution (94 ml, 94 mmol) was also slowly added dropwise, and the mixture was stirred for 12 hours while gradually raising the temperature to room temperature. After completion of the reaction, dilution was carried out with Et$_2$O while cooling on ice, water (16 ml) was slowly added dropwise, and the mixture was stirred for an additional 2 hours at room temperature. After distilling off the solvent under reduced pressure, tetrahydrofuran (170 ml) was added, the pH was adjusted to 1 with a 1 N hydrochloric acid aqueous solution while cooling on ice, and the mixture was stirred for 1 hour. It was then diluted with water, and NaHCO$_3$ powder was added to render the solution basic, extraction was performed with ethyl acetate and the extract was washed with brine. After drying over anhydrous Na$_2$CO$_3$, the solvent was distilled off under reduced pressure and the residue was purified by silica gel column chromatography (solvent: n-hexane-ethyl acetate) to yield the title compound (9.0 g) as a brown oil.

$^1$H-NMR(CDCl3) δ (ppm) 1.35(9H, s), 2.54–2.70(4H, m), 3.25–3.42(4H, m), 3.97(3H, s), 6.99(1H, d, J=2.4 Hz), 7.14(1H, d, J=2.4 Hz).-

(Step 6) 1-[5-Bromo-3-(tert-butyl)-2-methoxyphenyl]-4-piperidinol

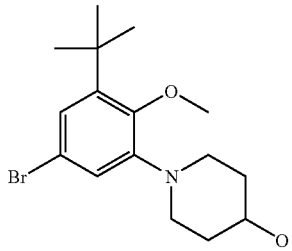

NaBH₄ (0.23 g, 6.1 mmol) was added to a mixed solution of. 1-[5-bromo-3-(tert-butyl)-2-methoxyphenyl]-4-piperidinone (2.0 g, 5.9 mmol) in methanol (12 ml)-methylene chloride (12 ml) while cooling on ice. After completion of the reaction, the mixture was diluted with water and extraction was performed with ethyl acetate. The extract was washed with brine and dried over anhydrous magnesium sulfate, and the solvent was distilled off under reduced pressure. The residue was purified by silica gel column chromatography (solvent: n-hexane-ethyl acetate) to yield the title compound (1.3 g).

¹H-NMR(CDCl3) δ (ppm) 1.34(9H, s), 1.66–1.82(2H, m), 1.96–2.13(2H, m), 2.62–2.79(2H, m), 3.25–3.43(2H, m), 3.74–3.87(1H, m), 3.89(3H, s), 6.97(1H, s), 7.07(1H, s).

(Step 7) 2-Bromo-1-[3-(tert-butyl)-5-(4-hydroxypiperidino)-4-methoxyphenyl]-1-ethanone

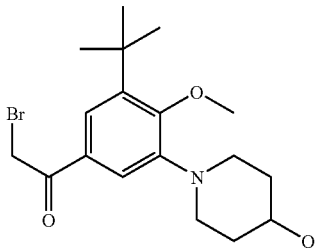

solution of the 1-[5-bromo-3-(tert-butyl)-2-methoxyphenyl]-4-piperidinol (1.3 g, 3.8 mmol), tributyl(1-ethoxyvinyl)tin (1.5 g, 4.2 mmol), tetrakis(triphenylphosphine)palladium (440 mg, 0.38 mmol) and CsF (1.27 g, 8.4 mmol) in 1,4-dioxane (8 ml) was stirred at 100° C. for 2.5 hours under a nitrogen stream. After completion of the reaction, the mixture was cooled to room temperature and diluted with Et₂O, and the insoluble portion was filtered through celite. The solvent was distilled off under reduced pressure, the obtained crude product was dissolved in tetrahydrofuran (8 ml)-water (0.8 ml), N-bromosuccinimide (0.75 g, 4.2 mmol) was added while cooling on ice and the mixture was stirred at the same temperature for 15 minutes. This was diluted with a saturated NaHCO₃ aqueous solution and ethyl acetate, and then the organic layer was separated and washed with brine. After drying with anhydrous magnesium sulfate, the solvent was distilled off under reduced pressure and the residue was purified by silica gel column chromatography (solvent: n-hexane-ethyl acetate) to yield the title compound (748 mg, 51%) as a light yellow oil.

¹H-NMR(CDCl3) δ (ppm) 1.39(9H, s), 1.68–1.85(2H, m), 1.98–2.12(2H, m), 2.68–2.84(2H, m), 3.29–3.47(2H, m), 3.77–3.90(1H, m), 3.99(3H, s), 4.40(2H, s), 7.54(1H, d, J=2.0 Hz), 7.66(1H, d, J=2.0 Hz).

Example 8

Final Step

A solution of 5,6-diethoxy-4-fluoro-1H-3-isoindoleamine (38 mg, 0.16 mmol) and 2-bromo-1-[3-(tert-butyl)-5-(4-hydroxypiperidino)-4-methoxyphenyl]-1-ethanone (68 mg, 0.18 mmol) in dimethylformamide (2 ml) was stirred at room temperature for 62 hours. After completion of the reaction, the solvent was distilled off and the residue was purified by NAM silica gel column chromatography (solvent: methylene chloride-methanol) to yield the target compound (57 mg) as a brown amorphous solid.

¹H-NMR(DSMO-d6) δ (ppm) 1.29(3H, t, J=6.8 Hz), 1.36(9H, s), 1.40(3H, t, J=6.8 Hz), 1.54–1.68(2H, m), 1.84–1.96(2H, m), 2.65–2.78(2H, m), 3.17–3.42(2H, m), 3.58–3.67(1H, m), 3.94(3H, s), 4.11(2H, q, J=6.8 Hz), 4.21(2H, q, J=6.8 Hz), 4.73(1H, d, J=3.2 Hz), 4.78(2H, s), 5.47(2H, s), 7.34(1H, s), 7.51(1H, s), 7.56(1H, s), 8.95–9.11 (1H, m), 9.18–9.36(1H, brs).

Example 9

2-(5,6-Diethoxy-7-fluoro-1-imino-1,3-dihydro-isoindol-2-yl)-1-[3-dimethylamino-5-(1-fluoro-1-methyl-ethyl)-4-methoxy-phenyl]-ethanone hydrobromide

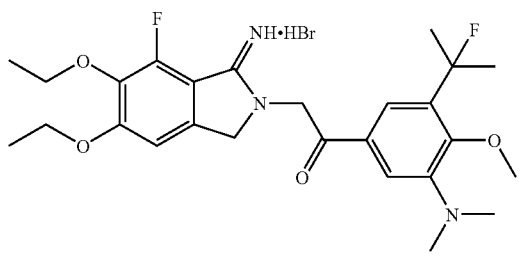

(Step 1) 4-Bromophenyl acetate

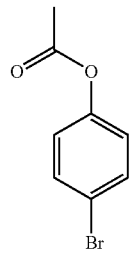

Anhydrous aluminum chloride (21 g) was suspended in methylene chloride (300 mL), and then acetyl chloride (12.3 g) was added while stirring and cooling on ice. The mixture was stirred for 10 minutes while cooling on ice and 4-bromophenol (24.5 g) was added. The reaction mixture was stirred at room temperature for 1 hour, and then ice water was added and extraction was performed with ethyl acetate. The organic layer was washed with brine and then dried over anhydrous magnesium sulfate. After distilling off the solvent under reduced pressure, the residue was purified by silica gel column chromatography (solvent: n-hexane-ethyl acetate) to yield the title compound (23.9 g) as an oil.

¹H-NMR (CDCl₃) δ: 2.28(3H, s), 6.98(2H, d, J=10 Hz), 7.49(2H, d, J=10 Hz).

(Step 2) 1-(5-Bromo-2-hydroxyphenyl)-1-ethanone

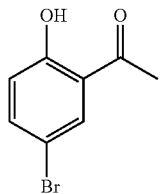

A mixture of 4-bromophenyl acetate (23.9 g) and anhydrous aluminum chloride (30 g) was stirred at 120–140° C. for 20 minutes. The reaction mixture was cooled to 60–80° C., ice water was added and extraction was performed with ethyl acetate. The organic layer was washed with brine and dried over anhydrous magnesium sulfate. After distilling off the solvent under reduced pressure, the residue was purified by silica gel column chromatography (solvent: n-hexane-ethyl acetate) to yield the title compound (21 g) as an oil.

¹H-NMR (CDCl₃) δ: 2.61(3H, s), 6.89(1H, d, J=8 Hz), 7.55(1H, dd, J=8, 2 Hz), 7.83(1H, d, J=2 Hz), 12.32(1H, s).

(Step 3) 1-(5-Bromo-2-hydroxy-3-nitrophenyl)-1-ethanone

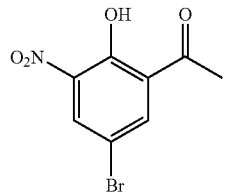

A mixture of 12 mL of concentrated nitric acid and 12 mL of concentrated sulfuric acid was added to a solution of the 1-(5-bromo-2-hydroxy-3-nitrophenyl)-1-ethanone in 80 mL of concentrated sulfuric acid while stirring at −5 to 0° C. over a period of 1 hour. Ice water was added to the mixture and extraction was performed with ethyl acetate. The organic layer was washed with brine and then dried over anhydrous magnesium sulfate. After distilling off the solvent under reduced pressure, the residue was purified by silica gel column chromatography (solvent: n-hexane-ethyl acetate) to yield the title compound (17.4 g) as yellow crystals.

¹H-NMR (CDCl₃) δ: 2.75(3H, s), 8.13(1H, d, J=2 Hz), 8.32(1H, d, J=2 Hz), 12.90(1H, s).

(Step 4) 1-(5-Bromo-2-methoxy-3-nitrophenyl)-1-ethanone

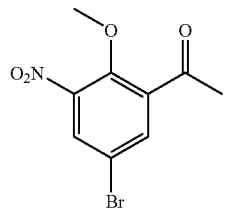

A mixture of the 1-(5-bromo-2-hydroxy-3-nitrophenyl)-1-ethanone (17.4 g), dimethylsulfuric acid (12.7 g), potassium carbonate (13.8 g) and acetone (200 mL) was heated to reflux for 15 hours, and then water was added to the mixture and extraction was performed with ethyl acetate. The organic layer was washed with brine and then dried over anhydrous magnesium sulfate. After distilling off the solvent under reduced pressure, the residue was purified by silica gel column chromatography (solvent: n-hexane-ethyl acetate) to yield the title compound (16.2 g) as a yellow oil.

¹H-NMR (CDCl₃) δ: 2.65(3H, s), 3.95(3H, s), 7.91(1H, d, J=2 Hz), 8.05(1H, d, J=2 Hz).

(Step 5) 1-(3-Amino-5-bromo-2-methoxyphenyl)-1-ethanone

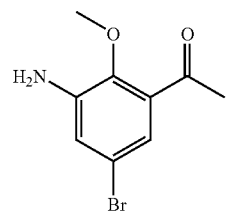

Iron (15 g) was added to a mixture of the 1-(5-bromo-2-methoxy-3-nitrophenyl)-1-ethanone (16.2 g), concentrated hydrochloric acid (20 mL) and methanol (60 mL) at room temperature. After stirring the mixture at 60° C. for 1 hour, it was neutralized with saturated aqueous sodium hydrogencarbonate and extraction was performed with ethyl acetate. The organic layer was washed with brine and then dried over anhydrous magnesium sulfate. After distilling off the solvent under reduced pressure and the residue was purified by silica gel column chromatography (solvent: n-hexane-ethyl acetate) to yield the title compound (12.8 g) as a yellow oil.

¹H-NMR (CDCl₃) δ: 2.60(3H, s), 3.78(3H, s), 4.00(2H, br.s), 6.99(1H, d, J=2 Hz), 7.07(1H, d, J=2 Hz).

(Step 6) 1-[5-Bromo-3-(dimethylamino)-2-methoxyphenyl]-1-ethanone

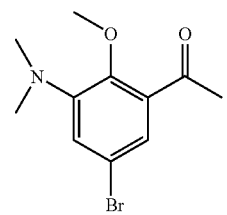

A mixture of 1-(3-amino-5-bromo-2-methoxyphenyl)-1-ethanone (12.8 g), iodomethane (60 mL), potassium carbonate (14.4 g) and N,N-dimethylformamide (200 mL) was stirred at 60 to 70° C. for 2 hours. Water was added to the mixture, extraction was performed with ethyl acetate, and the organic layer was washed with brine and then dried over anhydrous magnesium sulfate. After distilling off the solvent under reduced pressure, the residue was purified by silica gel column chromatography (solvent: n-hexane-ethyl acetate) to yield the title compound (9.6 g) as a yellow oil.

¹H-NMR (CDCl₃) δ: 2.60(3H, s), 2.82(6H, s), 3.80(3H, s), 7.08(1H, d, J=2 Hz), 7.25(1H, d, J=2 Hz).-

(Step 7) 2-[5-Bromo-3-(dimethylamino)-2-methoxyphenyl]-2-propanol

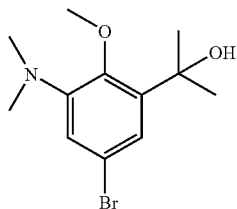

A solution of methylmagnesium bromide in ether was added to a solution of 1-[5-bromo-3-(dimethylamino)-2-methoxyphenyl]-1-ethanone (4 g) in diethyl ether while stirring at −70° C. After stirring at the same temperature for 30 minutes, saturated aqueous ammonium chloride was added, extraction was performed with ethyl acetate, and the organic layer was washed with brine and then dried over anhydrous magnesium sulfate. The solvent was distilled off under reduced pressure to yield the title compound (3.4 g) as an oil.

$^1$H-NMR (CDCl$_3$) δ: 1.56(3H, s), 1.58(3H, s), 2.76(6H, s), 3.91(3H, s), 6.95(1H, d, J=2 Hz), 7.04(1H, d, J=2 Hz).

(Step 8) N-[5-Bromo-3-(1-fluoro-1-methylethyl)-2-methoxyphenyl]-N,N-dime thylamine

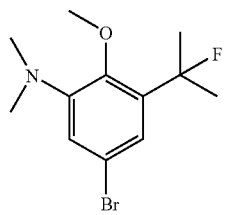

Diethylaminosulfur trifluoride (620 mg) was added to a solution of 2-[5-bromo-3-(dimethylamino)-2-methoxyphenyl]-2-propanol (1 g) in methylene chloride while stirring on ice. After stirring for an additional 30 minutes while cooling on ice, water was added, extraction was performed with ethyl acetate, and the organic layer was washed with brine and then dried over anhydrous magnesium sulfate. The solvent was distilled off under reduced pressure and the residue was purified by silica gel column chromatography (solvent: n-hexane-ethyl acetate) to yield the title compound (680 mg) as an oil.

$^1$H-NMR (CDCl$_3$) δ: 1.68(3H, s), 1.74(3H, s), 2.76(6H, s), 3.78(3H, s), 6.96(1H, d, J=2 Hz), 7.24(1H, d, J=2 Hz).

(Step 9) 2-Bromo-1-[3-(dimethylamino)-5-(1-fluoro-1-methylethyl)-4-methoxyphenyl]-1-ethanone

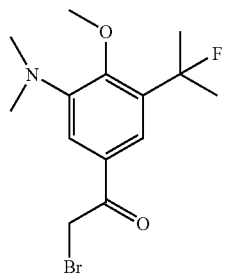

Synthesis was performed in the same manner as Step 7 of Example 8 to yield the title compound as a light yellow solid.

$^1$H-NMR (CDCl$_3$) δ: 1.70(3H, s), 1.79(3H, s), 2.81(6H, s), 3.79(3H, s), 4.48(2H, s), 7.56(1H, d, J=2 Hz), 7.74(1H, d, J=2 Hz).

Example 9

Final Step

Synthesis was performed in the same manner as the final step of Example 3 to yield the target compound as a yellow solid.

1H-NMR(DSMO-d6) δ (ppm) 1.29(3H, t, J=7 Hz), 1.40 (3H, t, J=7 Hz), 1.68(3H, s), 1.74(3H, s), 2.77(6H, s), 3.83(3H, s), 4.11(2H, q, J=7 Hz), 4.21(2H, q, J=7 Hz), 4.80(2H, s), 5.50(2H, s), 7.34(1H, brs), 7.50(1H, brs), 7.65 (1H, br.s).

MS: m/e (ESI) 490.4 (MH+)

Example 10

{3-tert-Butyl-5-[2-(5,6-diethoxy-7-fluoro-1-imino-1, 3-dihydro-isoindol-2-yl)-acetyl]-2-methoxy-phenylamino}-acetonitrile hydrobromide

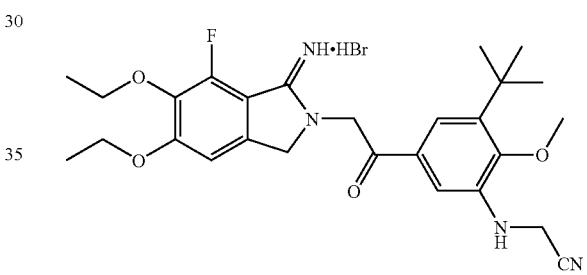

(Step 1) [5-Acetyl-3-(tert-butyl)-2-methoxyanilino]methyl cyanide

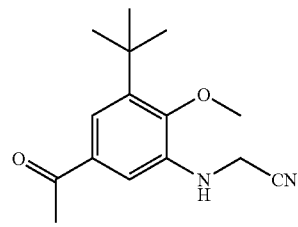

Bromoacetonitrile (6 ml) and potassium carbonate (1.4 g) were added to a solution of 1-[3-amino-5-(tert-butyl)-4-methoxyphenyl]-1-ethanone (2.0 g, 9.0 mmol) in dimethylformamide (50 ml) and the mixture was stirred at 70° C. for 3 hours. The reaction mixture was cooled to room temperature, ethyl acetate was added, washed was performed with water and brine in that order, the organic layer was dried over anhydrous magnesium sulfate and the solvent was distilled off under reduced pressure. The residue was purified by silica gel column chromatography (solvent: n-hexane-ethyl acetate) to yield the title compound (3.2 g) as a yellow oil.

$^1$H-NMR(CDCl3) δ (ppm) 1.39(9H, s), 2.59(3H, s), 3.77 (3H, s), 4.20(2H, d, J=4.0 Hz), 4.37–4.48(1H, m), 7.25(1H, d, J=2.0 Hz), 7.52(1H, d, J=2.0 Hz).

(Step 2) [5-(2-Bromoacetyl)-3-(tert-butyl)-2-methoxyanilinolmethyl cyanide

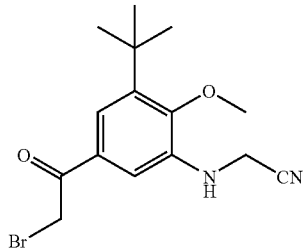

Triethylamine (3.7 g, 36.9 mmol) and tert-butyl dimethylsilyltrifluoromethanesulfonate (6.5 g, 24.6 mmol) were added to a solution of [5-acetyl-3-(tert-butyl)-2-methoxyanilino]methyl cyanide (3.2 g, 12.3 mmol) in tetrahydrofuran and the mixture was stirred for 30 minutes while cooling on ice, after which N-bromosuccinimide (2.6 g, 14.8 mmol) was added and the mixture was stirred for 2 hours while cooling on ice. Ethyl acetate was added, the reaction mixture was washed with water and brine in that order, the organic layer was dried over anhydrous magnesium sulfate and the solvent was distilled off under reduced pressure. The residue was purified by silica gel column chromatography (solvent: n-hexane-ethyl acetate) to yield the title compound (2.9 g) as a yellow oil.
$^1$H-NMR(CDCl3) δ (ppm) 1.41(9H, s), 3.79(3H, s), 4.19 (2H, d, J=4.0 Hz), 4.43(2H, s), 4.37–4.48(1H, m), 7.27(1H, d, J=2.0 Hz), 7.58(1H, d, J=2.0 Hz).

Example 10

Final Step

After dissolving [5-(2-bromoacetyl)-3-(tert-butyl)-2-methoxyanilino]methyl cyanide (500 mg, 1.4 mmol) and 5,6-diethoxy-4-fluoro-1H-3-isoindoleamine (340 mg, 1.4 mmol) in dimethylformamide (20 ml) and stirring the solution at room temperature for 14 hours, the organic layer was concentrated under reduced pressure and the residue was purified by NAM silica gel column chromatography (solvent: ethyl acetate-methanol). The obtained crude product was recrystallized from ethyl acetate to yield the target compound (320 mg) as light yellow crystals.
$^1$H-NMR(DSMO-d6) δ (ppm) 1.29(3H, t, J=7 Hz), 1.35–1.42(12H, m), 3.72(3H, s), 4.11(2H, q, J=7 Hz), 4.21 (2H, q, J=7 Hz), 4.36(2H, m), 4.81(2H, s), 5.49(2H, s), 6.15(1H, m), 7.32(1H, br.s), 7.34(1H, br.s), 7.39(1H, br.s)
MS: m/e (ESI) 497.2 (MH+).

Example 11

(4-{3-tert-Butyl-5-[2-(5,6-diethoxy-7-fluoro-1-imino-1,3-dihydro-isoindol-2-yl)-acetyl]-2-methoxyphenyl}piperazin-1-yl)-acetonitrile hydrobromide

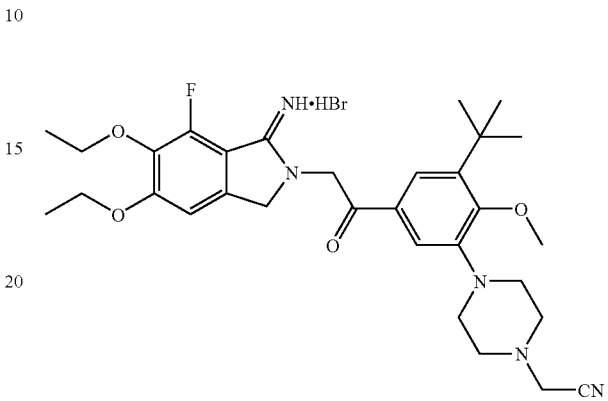

(Step 1) 1-(5-bromo-3-(tert-butyl)-2-methoxyphenyl]piperazine

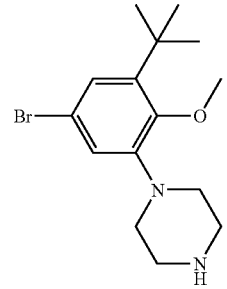

5-Bromo-3-(tert-butyl)-2-methoxyaniline (311 g) and bis (2-chloroethyl)amine hydrogenchloride (251 g) were suspended in 4 L of 1,2-dichlorobenzene, and the mixture was vigorously stirred for 22 hours at an external temperature of 200° C. The mixture was cooled to room temperature, and then potassium carbonate (620 g) and water were added and extraction was performed with methylene chloride (6 L). After drying over magnesium sulfate, the solvent was distilled off under reduced pressure to yield a black oil (460 g). Purification was performed by NH-silica gel column chromatography (solvent: n-hexane-ethyl acetate) to yield the title compound (161 g) as blackish purple solid (41%).
$^1$H-NMR(CDCl3) δ (ppm) 1.34(9H, s), 1.74(1H, brs), 2.99–3.09(8H, m), 3.90(3H, s), 6.95(1H, d, J=2.4 Hz), 7.08(1H, d, J=2.4 Hz).

(Step 2) 2-{4-[5-Bromo-3-(tert-butyl)-2-methoxyphenyl]piperazino}acetonitrile

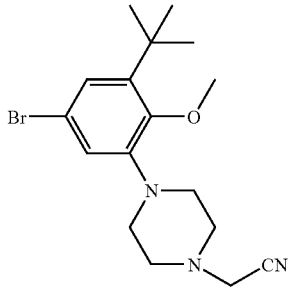

1-[5-bromo-3-(tert-butyl)-2-methoxyphenyl]piperazine (550 mg), potassium carbonate (302 mg), dimethylformamide (7 ml) and bromoacetonitrile (0.12 ml) were combined and the mixture was stirred at room temperature for 4 hours. The reaction mixture was diluted with ethyl acetate, the insoluble portion was filtered off, and the concentrated residue was purified by silica gel column chromatography (solvent: n-hexane-ethyl acetate) to yield the title compound (480 mg) as colorless crystals (78%).

$^1$H-NMR (CDCl3) δ (ppm) 1.35(9H, s), 2.89(4H, brs), 3.18(4H, brs), 3.69(2H, s), 3.88(3H, s), 6.95(1H, d, J=2.4 Hz), 7.12(1H, d, J=2.4 Hz).

Example 11

Final Step

After dissolving 2-{4-[5-(2-bromoacetyl)-3-(tert-butyl)-2-methoxyphenyl]piperazino}acetonitrile (361 mg) and 5,6-diethoxy-4-fluoro-1H-3-isoindoleamine (201 mg) in dimethylformamide (13 ml), the solution was stirred at room temperature overnight. The dimethylformamide was distilled off under reduced pressure and the residue was purified by NAM silica gel column chromatography (solvent: ethyl acetate-methanol) to yield a light brown oil, which was then crystallized from acetonitrile-ether to yield colorless crystals (372 mg)(68%).

$^1$H-NMR(DSMO-d6) δ (ppm) 1.29(3H, t, J=7.0 Hz), 1.37(9H, s), 1.40(3H, t, J=7.0 Hz), 2.71(4H, brs), 3.06(4H, brs), 3.83(2H, s), 3.94(3H, s), 4.11(2H, q, J=7.0 Hz), 4.21 (2H, q, J=7.0 Hz), 4.79(2H, s), 5.48(2H, s), 7.34(1H, s), 7.50(1H, d, J=2.0 Hz), 7.59(1H, d, J=2.0 Hz), 9.05(1H, brs), 9.27(1H, brs).

MS: m/e (ESI) 566.3 (MH+)

Example 12

1-[3-tert-Butyl-5-((3R,4R)-3-hydroxy-4-methoxy-pyrrolidin-1-yl)-4-methoxy-phenyl]-2-(5,6-diethoxy-7-fluoro-1-imino-1,3-dihydro-isoindol-2-yl)-ethanone trifluoroacetate

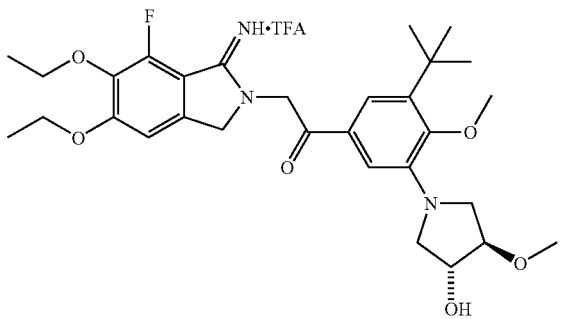

(Step 1) (2R,3R)-2,3-Dihydroxy-4-([(4-methylphenyl)sulfonyl]oxy)butyl 4-methyl-1-benzenesulfonate

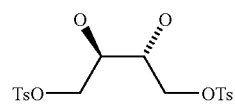

A solution of (4R,5S)-2,2-dimethyl-5-[(4-methylphenyl)sulfonyl]oxy-1,3-dioxolan-4-yl 4-methyl-1-benzenesulfonate (5.07 g, 10.8 mmol) in a tetrahydrofuran (50 ml) –10% perchloric acid water (50 ml) mixed solvent was stirred at 50° C. for 7 hours. The tetrahydrofuran was distilled off under reduced pressure, extraction was performed with ethyl acetate and the extract was washed with brine. After drying with anhydrous magnesium sulfate, the solvent was distilled off to yield a crude product which was then purified by silica gel column chromatography (solvent: n-hexane-ethyl acetate) to yield the title compound (5.14 g). This was used without further purification for the following reaction.

$^1$H-NMR(CDCl3) δ (ppm) 2.45(6H, s), 3.87–3.93(2H, m), 4.06(4H, d, J=6.0 Hz), 7.36(4H, d, J=8.0 Hz), 7.78(4H, d, J=8.0 Hz).

(Step 2) 1-(3-(tert-Butyl)-5-[(3R,4R)-3,4-dihydroxytetrahydro-1H-1-pyrrolyl]-4-methoxyphenyl]-1-ethanone

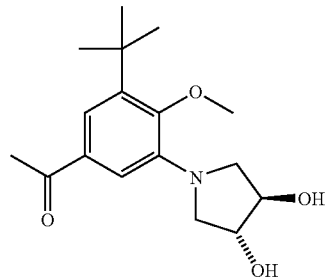

A suspension of 1-[3-amino-5-(tert-butyl)-4-methoxyphenyl]-1-ethanone (2.0 g, 9.0 mmol), (2R,3R)-2,3-dihydroxy-4-{([(4-methylphenyl)sulfonyl]oxy}butyl 4-methyl-1-benzenesulfonate (5.14 g), NaI (0.27 g, 1.8 mmol) and NaHCO3 (1.9 g) in EtOH (40 ml) was heated to reflux for 48 hours under a nitrogen stream. After distilling off the EtOH under reduced pressure and diluting with water, extraction was performed with ethyl acetate. The extract was washed with brine and dried over anhydrous magnesium sulfate, and the solvent was distilled off under reduced pressure. The residue was purified by silica gel column chromatography to yield the title compound (1.32 g, 48%) as a yellow viscous oil from the 1:2–1:3 hexane:ethyl acetate elution fractions containing 0.5% methanol.

$^1$H-NMR(CDCl3) δ (ppm) 1.41(9H, s), 2.56(3H, s), 3.04–3.22(2H, m), 3.59–3.78(5H, m), 4.23–4.37(2H, m), 7.35(1H, d, J=2.0 Hz), 7.51(1H, d, J=2.0 Hz).-

(Step 3) 1-{3-(tert-Butyl)-5-[(3R,4R)-3-hydroxy-4-(methoxymethoxy)tetrahydro-1H-1-pyrrolyl]-4-methoxyphenyl}-1-ethanone

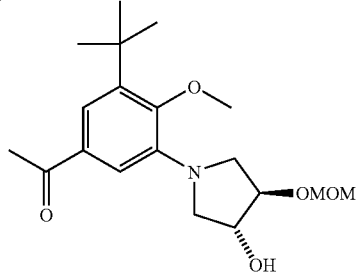

Diisopropylethylamine (2.3 ml, 13 mmol) was added to a solution of the 1-{3-(tert-butyl)-5-[(3R,4R)-3,4-dihydroxytetrahydro-1H-1-pyrrolyl]-4-methoxyphenyl}-1-ethanone (1.32 g, 4.29 mmol) in methylene chloride (10 ml) while cooling on ice, and then MOMCl (0.49 ml, 6.5 mmol) was added dropwise and the mixture was stirred at the same temperature for 10 minutes and then at room temperature for 2.5 hours. After completion of the reaction, it was diluted with water and extraction was performed with ethyl acetate. After washing with brine and drying over anhydrous magnesium sulfate, the solvent was distilled off under reduced pressure and the residue was purified by silica gel column chromatography (solvent: n-hexane-ethyl acetate) to yield the title compound (496 mg, 33%) as a light yellow oil.

$^1$H-NMR (CDCl3) δ (ppm) 1.39(9H, s), 2.56(3H, s), 3.24–3.36(2H, m), 3.46(3H, s), 3.49–3.62(2H, m), 3.70(3H, s), 3.99–4.08(1H, m), 4.26–4.36(1H, m), 4.68–4.80(2H, m), 7.34(1H, d, J=2.0 Hz), 7.52(1H, d, J=2.0 Hz).

(Step 4) 1-{3-(tert-Butyl)-4-methoxy-5-[(3R,4R)-3-methoxy-4-(methoxymethoxy)tetrahydro-1H-1-pyrrolyl]phenyl}-1-ethanone

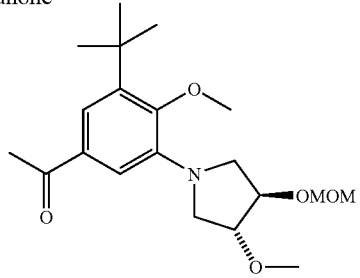

Tetra-n-butylammonium bromide (227 mg, 0.704 mmol) and methyl iodide (0.18 ml, 2.9 mmol) were added to a mixed solvent of 1-{3-(tert-butyl)-5-[(3R,4R)-3-hydroxy-4-(methoxymethoxy)tetrahydro-1H-1-pyrrolyl]-4-methoxyphenyl}-1-ethanone (496 mg, 1.41 mmol) in a toluene (3 ml) –50% aqueous NaOH (3 ml) mixed solvent in that order at room temperature and the mixture was stirred for 64 hours. It was then diluted with water, extraction was performed with ethyl acetate and the extract was washed with brine. After drying with anhydrous magnesium sulfate, the solvent was distilled off under reduced pressure and the residue was purified by silica gel column chromatography (solvent: n-hexane-ethyl acetate) to yield the title compound (397 mg, 77%) as a light yellow oil.

$^1$H-NMR(CDCl3) δ (ppm) 1.40(9H, s), 2.56(3H, s), 3.17–3.26(2H, m), 3.40(3H, s), 3.42(3H, s), 3.48–3.60(2H, m), 3.71(3H, s), 3.90–3.98(1H, m), 4.22–4.28(1H, m), 4.67–4.77(2H, m), 7.34(1H, d, J=2.0 Hz), 7.52(1H, d, J=2.0 Hz).

(Step 5) 2-Bromo-1-{3-(tert-butyl)-4-methoxy-5-[(3R,4R)-3-methoxy-4-(methoxymethoxy)tetrahydro-1H-1-pyrrolyl]phenyl}-1-ethanone

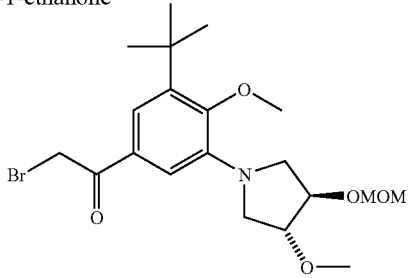

Triethylamine (0.46 ml, 3.3 mmol) and tert-butyl dimethylsilyltrifluoromethanesulfonate (0.37 ml, 1.6 mmol) were added dropwise in that order to a solution of 1-{3-(tert-butyl)-4-methoxy-5-[(3R,4R)-3-methoxy-4-(methoxymethoxy)tetrahydro-1H-1-pyrrolyl]phenyl}-1-ethanone (397 mg, 1.09 mmol) in tetrahydrofuran (4 ml) while cooling on ice, and the mixture was stirred at the same temperature for 20 minutes. N-Bromosuccinimide (290 mg, 1.63 mmol) was then added and stirring was continued at the same temperature for 15 minutes. After completion of the reaction, the mixture was diluted with saturated aqueous sodium hydrogencarbonate and ethyl acetate and the organic layer was separated. The organic layer was washed with brine and then dried over anhydrous magnesium sulfate. The solvent was distilled off under reduced pressure and the residue was purified by silica gel column chromatography (solvent: n-hexane-ethyl acetate) to yield the title compound (434 mg, 90%) as a light yellow oil.

$^1$H-NMR(CDCl3) δ (ppm) 1.41(9H, s), 3.16–3.27(2H, m), 3.41(3H, s), 3.43(3H, s), 3.48–3.60(2H, m), 3.72(3H, s), 3.90–3.97(1H, m), 4.22–4.30(1H, m), 4.42(2H, s), 4.69–4.78(2H, m), 7.37(1H, d, J=2.0 Hz), 7.54(1H, d, J=2.0 Hz).

Example 12

Final Step

A solution of 5,6-diethoxy-4-fluoro-1H-3-isoindoleamine (211 mg, 0.887 mmol) and 2-bromo-1-{3-(tert-butyl)-4-methoxy-5-[(3R,4R)-3-methoxy-4-(methoxymethoxy)tetrahydro-1H-1-pyrrolyl]phenyl}-1-ethanone (434 mg, 0.977 mmol) in dimethylformamide (4 ml) was stirred at room temperature for 17 hours. After completion of the reaction, the solvent was distilled off under reduced pressure and the residue was purified by NAM silica gel column chromatography (solvent: ethyl acetate-methanol) to yield the MOM-protected title compound (543 mg). This was then dissolved in trifluoroacetic acid (3 ml) —H$_2$O (3 drops) and the mixture was stirred at room temperature for 4.5 hours. The solvent was distilled off under reduced pressure and the resultant product was filtered through a small amount of NAM silica gel. After distilling off the methylene chloride-methanol (20:1–10:1) elution fractions under reduced pressure, the residue was triturated in diethyl ether. The obtained crystals were dried to yield the target compound (340 mg, 57%) as a brown amorphous solid.

$^1$H-NMR(DSMO-d6) δ (ppm) 1.29(3H, t, J=7.2 Hz), 1.37(9H, s), 1.39(3H, t, J=7.2 Hz), 2.91–2.99(1H, m), 3.03–3.12(1H, m), 3.30(3H, s), 3.40–3.58(2H, m), 3.63(3H, s), 3.71–3.79(1H, m), 4.10(2H, q, J=7.2 Hz), 4.10–4.30(3H, m), 4.78(2H, s), 5.25(1H, brs), 5.38–5.60(2H, m), 7.30(1H, s), 7.33(1H, s), 7.41(1H, s), 8.99–9.12(1H, m), 9.20–9.40 (1H, m).

MS: m/e (ESI) 558.3 (MH+)

Example 13

1-[3-(4-Acetyl-piperazin-1-yl)-5-tert-butyl-4-methoxy-phenyl]-2-(5,6-diethoxy-7-fluoro-1-imino-1,3-dihydro-isoindol-2-yl)ethanone hydrobromide

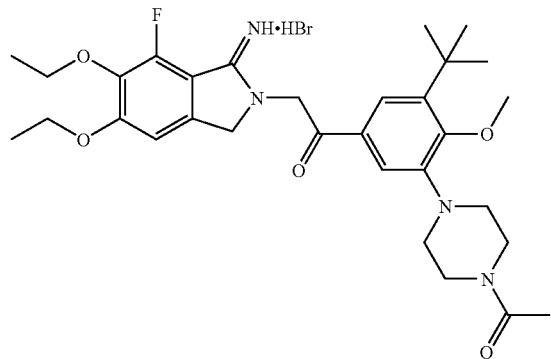

(Step 1) 1-{4-[5-Bromo-3-(tert-butyl)-2-methoxyphenyl]piperazino}-1-ethanone

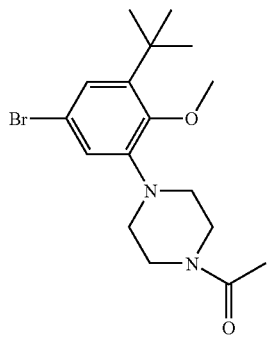

Acetyl chloride (0.10 ml) was mixed with a solution of 1-[5-bromo-3-(tert-butyl)-2-methoxyphenyl]piperazine (370 mg) and triethylamine (0.32 mL) in methylene chloride (8 ml), and the mixture was stirred at room temperature for 3 hours. The reaction mixture was diluted with ethyl acetate and, after filtering off the insoluble portion, was concentrated. The residue was purified by silica gel column chromatography (solvent: n-hexane-ethyl acetate) to yield the title compound (338 mg) as colorless crystals (81%).

$^1$H-NMR(CDCl3) δ (ppm) 1.35(9H, s), 2.14(3H, s), 2.96–3.06(4H, m), 3.62(2H, t, J=5.0 Hz), 3.78(2H, brs), 3.91(3H, s), 6.93(1H, d, J=2.4 Hz), 7.13(1H, d, J=2.4 Hz).

(Step 2) 1-[3-(4-Acetylpiperazino)-5-(tert-butyl)-4-methoxyphenyl]-2-bromo-1-ethanone

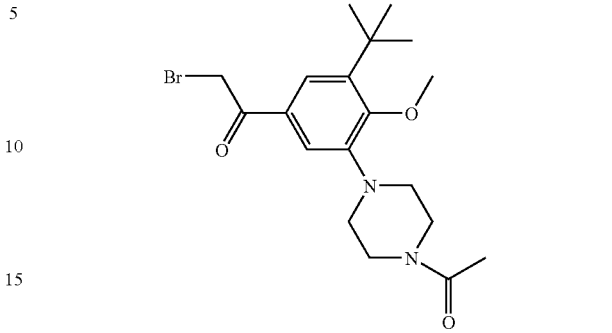

After adding the 1-{4-[5-bromo-3-(tert-butyl)-2-methoxyphenyl]piperazino}-1-ethanone (338 mg), tetrakis(triphenylphosphine)palladium (159 mg), tributyl(1-ethoxyvinyl)stannane (324 mg) and cesium fluoride (306 mg) to degassed dioxane (9 ml), the mixture was stirred at 95° C. for 3 hours under a nitrogen stream. The mixture was then cooled to room temperature, diluted with ethyl acetate and filtered through celite, and the filtrate was concentrated under reduced pressure. The residue was dissolved in tetrahydrofuran (7 ml) and H$_2$O (0.7 ml) and cooled to 0° C., and then N-bromosuccinimide (179 mg) was added. After 5 minutes, Na$_2$SO$_3$(aq) was added, extraction was performed with ethyl acetate, and the extract washed with brine and then concentrated under reduced pressure. The residue was purified by silica gel column chromatography (solvent: n-hexane-ethyl acetate) to yield the title compound (313 mg) as a light brown oil. (NMR revealed the presence of by-products that could not be easily separated). This was used directly for the following reaction.

Example 13

Final Step

After dissolving 1-[3-(4-acetylpiperazino)-5-(tert-butyl)-4-methoxyphenyl]-2-bromo-1-ethanone containing impurities (209 mg (a portion of the 313 mg from the previous reaction)) and 5,6-diethoxy-4-fluoro-1H-3-isoindoleamine (73 mg) in dimethylformamide (5 ml), the mixture was stirred at room temperature overnight. The dimethylformamide was distilled off under reduced pressure and the residue was purified by NAM silica gel column chromatography (solvent: ethyl acetate-methanol) to yield a light brown solid which was recrystallized from acetonitrile-ether to yield colorless crystals (83 mg) (21% from 1-{4-[5-bromo-3-(tert-butyl)-2-methoxyphenyl]piperazino}-1-ethanone).

$^1$H-NMR(DSMO-d6) δ (ppm) 1.29(3H, t, J=7.0 Hz), 1.37(9H, s), 1.40(3H, t, J=7.0 Hz), 2.04(3H, s), 2.93(2H, brs), 2.99(2H, brs), 3.65(4H, brs), 3.96(3H, s), 4.11(2H, q, J=7.0 Hz), 4.21(2H, q, J=7.0 Hz), 4.79(2H, s), 5.47(2H, s), 7.34(1H, s), 7.49(1H, sz), 7.61(1H, s), 9.05(1H, brs), 9.27 (1H, brs).

MS: m/e (ESI) 569.4 (MH+)

Example 14

1-{3-tert-Butyl-5-[4-(2-hydroxy-acetyl)piperazin-1-yl]-4-methoxy-phenyl}-2-(5,6-diethoxy-7-fluoro-1-imino-1,3-dihydro-isoindol-2-yl)-ethanone hydrobromide

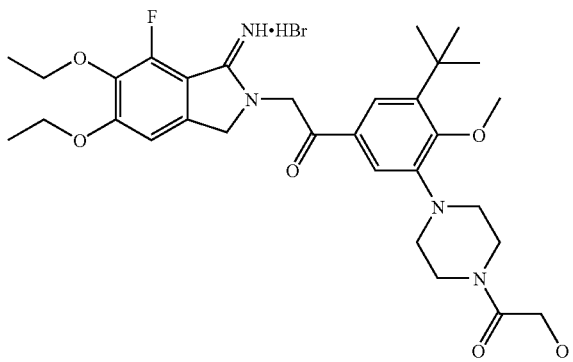

(Step 1) 1-{4-[5-Bromo-3-(tert-butyl)-2-methoxyphenyl]piperazino}-2-hydroxy-1-ethanone

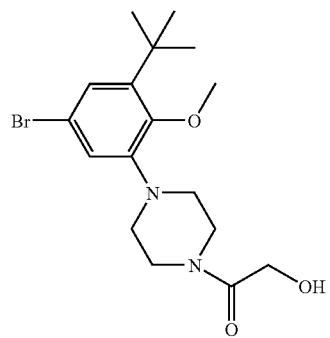

Acetoxyacetyl chloride (0.14 ml) was added to a solution of 1-[5-bromo-3-(tert-butyl)-2-methoxyphenyl]piperazine (360 mg) and triethylamine (0.31 ml) in $CH_2Cl_2$ (5 ml) while cooling on ice and the mixture was brought to room temperature and stirred for 1 hour. After quenching the reaction with brine, extraction was performed with ethyl acetate to yield a crude product of 2-{4-[5-bromo-3-(tert-butyl)-2-methoxyphenyl]piperazino}-2-oxoethyl acetate as a red oil. This crude product was dissolved in methanol (2.5 ml) and potassium carbonate (167 mg) was added. After 15 minutes, brine was added, extraction was performed with ethyl acetate, the extract was concentrated under reduced pressure and the residue was purified by silica gel column chromatography (solvent: n-hexane-ethyl acetate) to yield the title compound (285 mg) as light orange crystals (67%).

$^1$H-NMR(CDCl3) δ (ppm) 1.35(9H, s), 3.05(4H, t, J=4.4 Hz), 3.44(2H, t, J=5.2 Hz), 3.84(2H, brs), 3.90(3H, s), 4.21(2H, s), 6.93(1H, d, J=2.4 Hz), 7.14(1H, d, J=2.4 Hz).

(Step 2) 2-Bromo-1-[3-(tert-butyl)-5-(4-glycoloylpiperazino)-4-methoxyphenyl]-1-ethanone

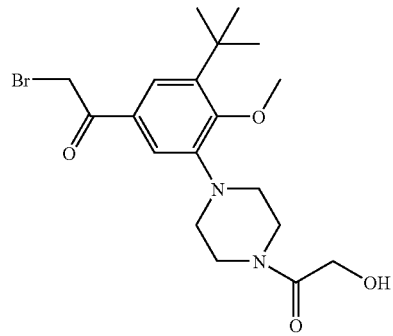

After adding the 1-{4-[5-bromo-3-(tert-butyl)-2-methoxyphenyl]piperazino}-2-hydroxy-1-ethanone (285 mg), tetrakis(triphenylphosphine)palladium (128 mg), tributyl(1-ethoxyvinyl)stannane (267 mg) and cesium fluoride (247 mg) to degassed dioxane (8 ml), the mixture was stirred at 90° C. for 3.5 hours under a $N_2$ atmosphere. The mixture was then cooled to room temperature, diluted with ethyl acetate and filtered through celite, and the filtrate was concentrated under reduced pressure. The residue was dissolved in THF (6 ml) and $H_2O$ (0.6 ml) and cooled to 0° C., and then N-bromosuccinimide (151 mg) was added. After 5 minutes, $Na_2SO_3$ (aq) was added, extraction was performed with ethyl acetate, and the extract was washed with brine and concentrated under reduced pressure. The residue was purified by silica gel column chromatography (solvent: n-hexane-ethyl acetate) to yield the title compound (186 mg) as colorless crystals (59%).

$^1$H-NMR(CDCl3) δ (ppm) 1.40(9H, s), 3.10(4H, brs), 3.48(2H, t, J=4.8 Hz), 3.88(2H, brs), 4.00(3H, s), 4.23(2H, s), 4.39(2H, s), 7.50(1H, d, J=2.2 Hz), 7.72(1H, d, J=2.2 Hz).

Example 14

Final Step

Synthesis was performed in the same manner as the final step of Example 3 to yield the target compound as a yellow solid.

$^1$H-NMR(DMSO-D6) δ (ppm) 1.29(3H, t, J=7.0 Hz), 1.37(9H, s), 1.40(3H, t, J=7.0 Hz), 2.98(4H, brs), 3.57(2H, brs), 3.70(2H, brs), 3.96(3H, s), 4.11(2H, q, J=7.0 Hz), 4.12(2H, s), 4.21(2H, q, J=7.0 Hz), 4.79(2H, s), 5.47(2H, s), 7.34(1H, s), 7.49(1H, d, J=2.0 Hz), 7.61(1H, d, J=2.0 Hz), 9.05(1H, brs), 9.27(1H, brs).

MS: m/e (ESI) 585.3 (MH+)

Example 15

Ethyl (4-{3-tert-butyl-5-[2-(5,6-diethoxy-7-fluoro-1-imino-1,3-dihydro-isoindol-2-yl)-acetyl]-2-methoxy-phenyl}piperazin-1-yl)-acetate dihydrochloride

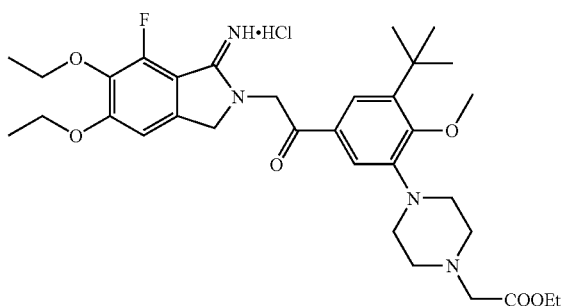

(Step 1) Ethyl 2-{4-[5-bromo-3-(tert-butyl)-2-methoxyphenyl]piperazino}acetate

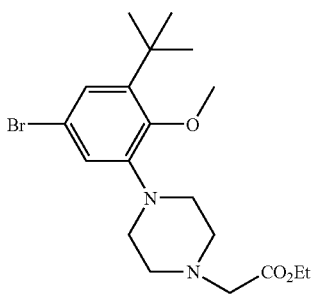

1-[5-Bromo-3-(tert-butyl)-2-methoxyphenyl]piperazine (750 mg), potassium carbonate (411 mg) and ethyl bromoacetate (0.27 ml) were stirred in dimethylformamide (4 ml) at room temperature for one day. The reaction mixture was diluted with ethyl acetate, the insoluble portion was filtered off and then the concentrated residue was purified by silica gel column chromatography (solvent: n-hexane-ethyl acetate) to yield the title compound (715 mg) as a light red oil (75%).

(Step 2) Ethyl 2-{4-[5-(2-bromoacetyl)-3-(tert-butyl)-2-methoxyphenyl]piperazino}acetate

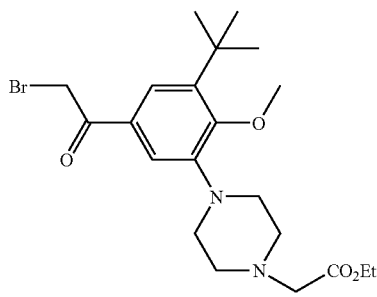

After adding the ethyl 2-{4-[5-bromo-3-(tert-butyl)-2-methoxyphenyl]piperazino}acetate (715 mg), tetrakis(triphenylphosphine)palladium (300 mg), tributyl(1-ethoxyvinyl) stannane (625 mg) and cesium fluoride (578 mg) to degassed dioxane (12 ml) under a nitrogen stream, the mixture was stirred at 90° C. for 3.5 hours. The mixture was then cooled to room temperature, diluted with ethyl acetate and filtered through celite, and the filtrate was concentrated under reduced pressure. The residue was dissolved in tetrahydrofuran (8 ml) and $H_2O$ (0.8 ml) and cooled to 0° C., and then N-bromosuccinimide (339 mg) was added. After 5 minutes, $Na_2SO_3$(aq) was added, extraction was performed with ethyl acetate, and the extract was washed with brine and concentrated under reduced pressure. The residue was purified by silica gel column chromatography (solvent: n-hexane-ethyl acetate) to yield the title compound (512 mg) as a light brown oil (65%).

$^1$H-NMR(CDCl3) δ (ppm) 1.30(3H, t, J=7.2 Hz), 1.39 (9H, s), 2.82(4H, brs), 3.16(4H, brs), 3.32(2H, s), 3.97(3H, s), 4.22(2H, q, J=7.2 Hz), 4.40(2H, s), 7.53(1H, d, J=2.4 Hz), 7.68(1H, d, J=2.4 Hz).

Example 15

Final Step (Method 1)

After dissolving ethyl 2-{4-[5-(2-bromoacetyl)-3-(tert-butyl)-2-methoxyphenyl]piperazino}acetate (480 mg) and 5,6-diethoxy-4-fluoro-1H-3-isoindoleamine (251 mg) in dimethylformamide (10 ml), the mixture was stirred at room temperature overnight. Dimethylformamide was distilled off under reduced pressure and the residue was purified by NAM silica gel column chromatography (solvent: ethyl acetate-methanol) to yield a light brown solid (530 mg), which was triturated with ethyl acetate-ether-n-hexane to obtain a colorless solid (513 mg). After dissolving this in a small amount of ethanol, 4 N hydrochloric acid-ethyl acetate (6 ml) was added and the solvent was distilled off after 5 minutes. The residue was crystallized from ethanol-ether to yield the target compound (511 mg) as almost colorless crystals (71%).

(Method 2)

Ethanol (2.5 ml) and 4 N hydrochloric acid-dioxane (2.5 ml) were added to tert-butyl 2-(4-{3-(tert-butyl)-5-[2-(5,6-diethoxy-7-fluoro-1-imino-2,3-dihydro-1H-2-isoindolyl) acetyl]-2-methoxyphenyl}piperazino)acetate hydrobromide (49 mg) and the mixture was stirred at room temperature for 3 days. After concentrating the reaction mixture under reduced pressure, ethanol was added and the mixture was reconcentrated. The residue was triturated with ether and filtered, and then dried to yield the target compound as a colorless solid (40 mg, 86%).

$^1$H-NMR(DSMO-d6) δ (ppm) 1.25(3H, t, J=7.0 Hz), 1.29(3H, t, J=7.0 Hz), 1.37(9H, s), 1.40(3H, t, J=7.0 Hz), 3.02–3.70(10H, m), 3.93(3H, s), 4.11(2H, q, J=7.0 Hz), 4.18–4.25(4H, m), 4.28(1H, brs), 4.80(2H, s), 5.54(2H, s), 7.34(1H, s), 7.50(1H, s), 7.64(1H, s), 9.08(1H, brs), 9.37 (1H, brs).

MS: m/e (ESI) 613.4 (MH+)

Example 16

1-{3-tert-Butyl-4-methoxy-5-[4-(2-methoxy-acetyl)piperazin-1-yl]phenyl}-2-(5,6-diethoxy-7-fluoro-1-imino-1,3-dihydro-isoindol-2-yl)-ethanone hydrobromide

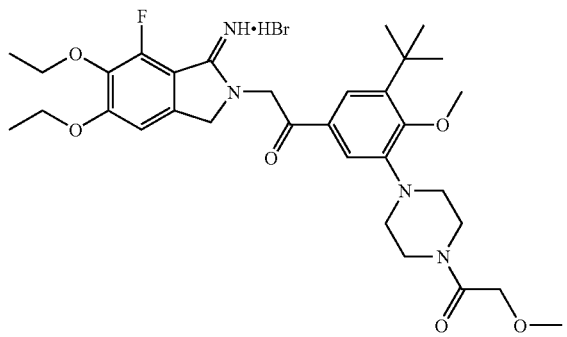

(Step 1) 1-{4-[5-Bromo-3-(tert-butyl)-2-methoxyphenyl]piperazino}-2-methoxy-1-ethanone

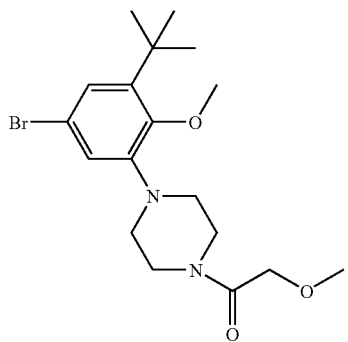

Methoxyacetyl chloride (0.28 ml) was added to a solution of 1-[5-bromo-3-(tert-butyl)-2-methoxyphenyl]piperazine (850 mg) and triethylamine (0.73 ml) in methylene chloride (12 ml) while cooling on ice, the mixture was brought to room temperature and stirred for 1 hour. The reaction mixture was diluted with ethyl acetate, the insoluble portion was filtered off, and the concentrated residue was purified by silica gel column chromatography (solvent: n-hexane-ethyl acetate) to yield the title compound (730 mg) as light red crystals (70%).

$^1$H-NMR(CDCl3) δ (ppm) 1.35(9H, s), 3.03(4H, brs), 3.45(3H, s), 3.67(2H, brs), 3.79(2H, brs), 3.91(3H, s), 4.15 (2H, s), 6.93(1H, d, J=2.4 Hz), 7.13(1H, d, J=2.4 Hz).

(Step 2) 2-Bromo-1-{3-(tert-butyl)-4-methoxy-5-[4-(2-methoxyacetyl)piperazino]phenyl}-1-ethanone

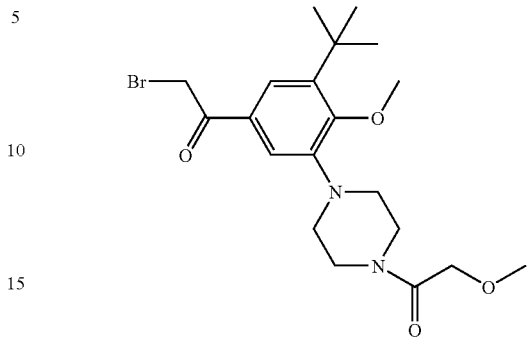

After adding the 1-{4-[5-bromo-3-(tert-butyl)-2-methoxyphenyl]piperazino}-2-methoxy-1-ethanone (730 mg), tetrakis(triphenylphosphine)palladium (317 mg), tributyl(1-ethoxyvinyl)stannane (660 mg) and cesium fluoride (611 mg) to degassed dioxane (16 ml), the mixture was stirred at 90° C. for 4 hours under a nitrogen stream. The mixture was then cooled to room temperature, diluted with ethyl acetate and filtered through celite, and the filtrate was concentrated under reduced pressure. The residue was dissolved in tetrahydrofuran (12 ml) and H$_2$O (1 ml) and cooled to 0° C., and then N-bromosuccinimide (390 mg) was added. After 5 minutes, Na$_2$SO$_3$(aq) was added, extraction was performed with ethyl acetate, the extract was washed with brine and the solvent was distilled off under reduced pressure. The residue was purified by silica gel column chromatography (solvent: n-hexane-ethyl acetate) to yield the title compound (597 mg) as a light green oil. (NMR revealed the presence of by-products that could not be easily separated). This was used directly for the following reaction.

$^1$H-NMR(CDCl3) δ (ppm) 1.40(9H, s), 3.08(4H, brs), 3.45(3H, s), 3.70(2H, brs), 3.82(2H, brs), 4.00(3H, s), 4.16 (2H, s), 4.40(2H, s), 7.50(1H, d, J=2.0 Hz), 7.71(1H, d, J=2.0 Hz).

Example 16

Final Step

After dissolving 2-bromo-1-{3-(tert-butyl)-4-methoxy-5-[4-(2-methoxyacetyl)piperazino]phenyl}-1-ethanone (597 mg (COntaining impurities)) and 5,6-diethoxy-4-fluoro-1H-3-isoindoleamine (224 mg) in dimethylformamide (12 ml), the mixture was stirred at room temperature overnight. The reaction mixture was concentrated under reduced pressure and the residue was purified by NAM silica gel column chromatography (solvent: ethyl acetate-methanol) to yield the title compound as a light brown solid. This was recrystallized from acetonitrile-ethyl acetate-ether to yield the target compound as light brown crystals (430 mg) (35% from 1-{4-[5-bromo-3-(tert-butyl)-2-methoxyphenyl]piperazino}-2-methoxy-1-ethanone).

$^1$H-NMR(DSMO-d6) δ (ppm) 1.29(3H, t, J=7.0 Hz), 1.37(9H, s), 1.40(3H, t, J=7.0 Hz), 2.98(4H, brs), 3.29(3H, s), 3.61(2H, brs), 3.67(2H, brs), 3.96(3H, s), 4.11(2H, q, J=7.0 Hz), 4.12(2H, s), 4.21(2H, q, J=7.0 Hz), 4.79(2H, s), 5.47(2H, s), 7.34(1H, s), 7.50(1H, d, J=2.0 Hz), 7.61(1H, d, J=2.0 Hz), 9.03(1H, brs), 9.28(1H, brs).

MS: m/e (ESI) 599.4 (MH+)

Example 17

1-[3-tert-Butyl-5-((3S,4S)-3-ethoxy-4-hydroxy-pyrrolidin-1-yl)-4-methoxy-phenyl]-2-(5,6-diethoxy-7-fluoro-1-imino-1,3-dihydro-isoindol-2-yl)ethanone trifluoroacetate

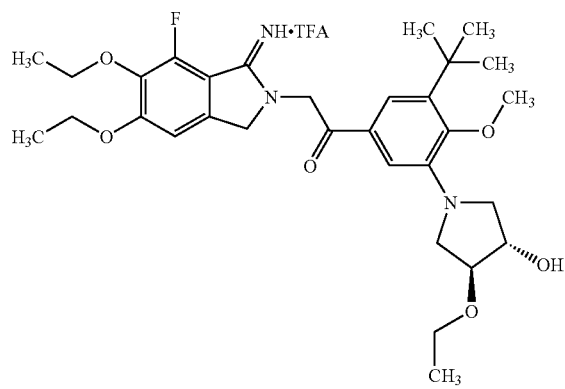

(Step 1) 1-{3-(tert-Butyl)-5-[(3S,4S)-3-ethoxy-4-(methoxymethoxy)tetrahydro-1H-1-pyrrolyl]-4-methoxyphenyl}-1-ethanone

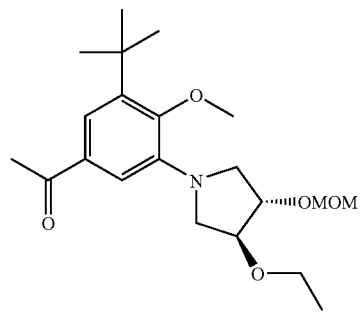

Tetra-n-butylammonium bromide (380 mg, 1.18 mmol) and ethyl iodide (0.4 ml, 5.0 mmol) were added to a solution of 1-{3-(tert-butyl)-5-[(3S,4S)-3-hydroxy-4-(methoxymethoxy)tetrahydro-1H-1-pyrrolyl]-4-methoxyphenyl}-1-ethanone (830 mg, 2.36 mmol) in a toluene (5 ml) −50% aqueous NaOH (5 ml) mixed solvent at room temperature in that order and the mixture was stirred for 19 hours. After further adding ethyl iodide (0.2 ml) and stirring for 9 hours, more ethyl iodide (0.2 ml) was added and stirring was continued for 60 hours. The mixture was diluted with water, extraction was performed with ethyl acetate and the extract was washed with brine. After drying with anhydrous magnesium sulfate, the solvent was distilled off under reduced pressure and the residue was purified by silica gel column chromatography (solvent: n-hexane-ethyl acetate) to yield the title compound (650 mg, 73%) as a light yellow oil.

$^1$H-NMR(CDCl3) δ (ppm) 1.22(3H, t, J=7.2 Hz), 1.41 (9H, s), 2.56(3H, s), 3.15–3.28(2H, m), 3.40(3H, s), 3.48–3.65(4H, m), 3.72(3H, s), 3.99–4.08(1H, m), 4.21–4.31(1H, m), 4.68–4.80(2H, m), 7.34(1H, d, J=2.0 Hz), 7.52(1H, d, J=2.0 Hz).

(Step 2) 2-Bromo-1-{3-(tert-butyl)-5-[(3S,4S)-3-ethoxy-4-(methoxymethoxy)tetrahydro-1H-1-pyrrolyl]-4-methoxyphenyl}-1-ethanone

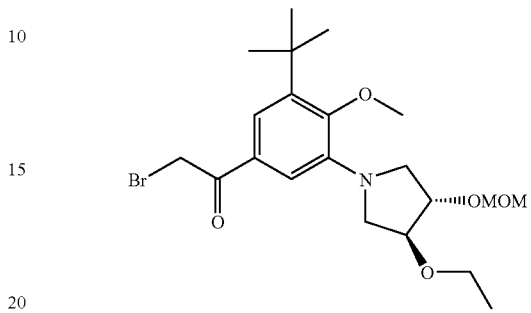

Triethylamine (0.52 ml, 3.7 mmol) and tert-butyl dimethylsilyltrifluoromethanesulfonate (0.51 ml, 2.2 mmol) were added dropwise in that order to a solution of 1-{3-(tert-butyl)-5-[(3S,4S)-3-ethoxy-4-(methoxymethoxy)tetrahydro-1H-1-pyrrolyl]-4-methoxyphenyl}-1-ethanone (650 mg, 1.71 mmol) in tetrahydrofuran (7 ml) while cooling on ice, and the mixture was stirred at the same temperature for 25 minutes. N-bromosuccinimide (427 mg, 2.40 mmol) was then added and stirring was continued at the same temperature for 25 minutes. After completion of the reaction, the reaction mixture was diluted with saturated aqueous sodium hydrogencarbonate and ethyl acetate and the organic layer was separated. The organic layer was washed with brine and then dried over anhydrous magnesium sulfate. The residue was purified by silica gel column chromatography (solvent: n-hexane-ethyl acetate) to yield the title compound (795 mg, 100%) as a light yellow oil.

$^1$H-NMR(CDCl3) δ (ppm) 1.22(3H, t, J=7.2 Hz), 1.41 (9H, s), 3.12–3.30(2H, m), 3.40(3H, s), 3.48–3.65(4H, m), 3.73(3H, s), 3.99–4.08(1H, m), 4.18–4.32(1H, m), 4.42(2H, s), 4.63–4.81(2H, m), 7.37(1H, d, J=2.0 Hz), 7.54(1H, d, J=2.0 Hz).

Example 17

Final Step

A solution of 5,6-diethoxy-4-fluoro-1H-3-isoindoleamine (95 mg, 0.40 mmol) and 2-bromo-1-{3-(tert-butyl)-5-[(3S,4S)-3-ethoxy-4-(methoxymethoxy)tetrahydro-1H-1-pyrrolyl]-4-methoxyphenyl}-1-ethanone (200 mg, 0.436 mmol) in dimethylformamide (3 ml) was stirred at room temperature for 68 hours. After completion of the reaction, the solvent was distilled off and the residue was purified by NAM silica gel column chromatography (solvent: ethyl acetate-methanol) to yield the MOM-protected title compound (235 mg). The product was then dissolved in trifluoroacetic acid (1 ml) —H$_2$O (1 drop), and the mixture was stirred at room temperature for 1.5 hours. The solvent was distilled off under reduced pressure, the obtained product was dissolved in ethyl acetate (2 ml) and the resultant solution was slowly added dropwise to stirred Et$_2$O (20 ml). The obtained crystals were filtered off and dried to yield the target compound (80 mg, 29%) as a brown amorphous solid.

$^1$H-NMR(DSMO-d6) δ (ppm) 1.10(3H, t, J=6.8 Hz), 1.29(3H, t, J=6.8 Hz), 1.37(9H, s), 1.39(3H, t, J=6.8 Hz), 2.90–3.12(2H, m), 3.28–3.58(4H, m), 3.63(3H, s), 3.80–3.89(1H, m), 4.11(2H, q, J=6.8 Hz), 4.12–4.31(3H, m), 4.79(2H, s), 5.38–5.57(2H, m), 7.30(1H, s), 7.34(1H, s), 7.41(1H, s), 8.98–9.10(1H, m), 9.20–9.35(1H, m).

MS: m/e (ESI) 572.4 (MH+)

Example 18

1-(3,5-Di-tert-butyl-4-hydroxy-phenyl)-2-(7-imino-2-methyl-5,7-dihydro-pyrrolo[3,4-b]pyridin-6-yl)-ethanone hydrochloride

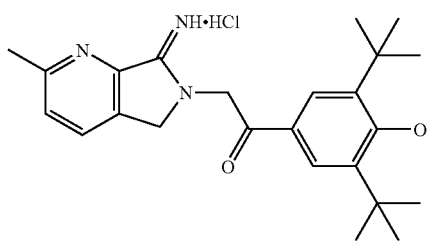

(Step 1) (6-Methyl-3-pyridyl)methanol

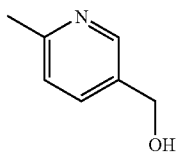

A solution of methyl 6-methylnicotinate (50 g, 0.33 mol) in anhydrous tetrahydrofuran (100 ml) was slowly added dropwise to a suspension of LAH (12.6 g, 0.33 mol) in anhydrous tetrahydrofuran (500 ml) over a period of 30 minutes while cooling on ice, and the mixture was stirred at the same temperature for 1 hour and 20 minutes. After confirming completion of the reaction by thin layer chromatography, H₂O (25 ml) was slowly added dropwise over a period of 30 minutes while cooling on ice, and the stirring was continued at room temperature for 30 minutes. Magnesium sulfate was added for drying, and the precipitate was filtered through celite and washed three times with ethyl acetate. The solvent was distilled off under reduced pressure to yield the title compound (33.6 g, 82%) as a yellow oil.

¹H-NMR(CDCl3) δ (ppm) 2.55(3H, s), 4.69(2H, brs), 7.16(1H, d, J=8.4 Hz), 7.61(1H, dd, J=8.4 and2.4 Hz), 8.46(1H, d, J=2.4 Hz).

(Step 2) 5-(Chloromethyl)-2-methylpyridine

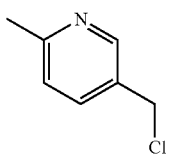

Triethylamine (96 ml, 0.69 mol) was added to a solution of (6-methyl-3-pyridyl)methanol (28.4 g, 0.23 mol) in methylene chloride (230 ml) while cooling on ice. Mesyl chloride (26.8 ml, 0.35 mol) was then slowly added dropwise over a period of 20 minutes at the same temperature and the mixture was stirred for 10 hours while gradually raising the temperature to room temperature. After confirming completion of the reaction by thin layer chromatography, the mixture was diluted with ethyl acetate and poured into saturated aqueous NaHCO₃. After separating the aqueous layer, extraction was performed with ethyl acetate, and the collected organic layer was washed with saturated aqueous NaCl and dried over anhydrous magnesium sulfate. The solvent was distilled off under reduced pressure to yield the title compound (12.2 g). This was used without further purification for the following reaction.

¹H-NMR(CDCl3) δ (ppm) 2.56(3H, s), 4.56(2H, s), 7.16(1H, d, J=8.0 Hz), 7.62(1H, dd, J=8.0 and2.4 Hz), 8.49(1H, d, J=2.4 Hz).

(Step 3) (6-Methyl-3-pyridyl)methyl azide

NaN₃ (11.2 g, 172 mmol) was added to a solution of the 5-(chloromethyl)-2-methylpyridine (12.2 g, 86.2 mmol) in dimethylformamide (120 ml) while cooling on ice and the mixture was stirred at the same temperature for 1 hour and then at room temperature for 2 hours. The reaction mixture was poured into semi-saturated aqueous sodium hydrogencarbonate, extraction was performed with ethyl acetate and the extract was washed with water and saturated aqueous NaCl. After drying with anhydrous magnesium sulfate, the solvent was distilled off under reduced pressure and the residue was purified by silica gel column chromatography (solvent: n-hexane-ethyl acetate) to yield the title compound (8.9 g, 26%, two steps) as a colorless oil.

¹H-NMR(CDCl3) δ (ppm) 2.57(3H, s), 4.34(2H, s), 7.19(1H, d, J=8.0 Hz), 7.55(1H, dd, J=8.0 and2.4 Hz), 8.45(1H, d, J=2.4 Hz).

(Step 4) 3-(Azidomethyl)-6-methyl-2-pyridinecarbonitrile

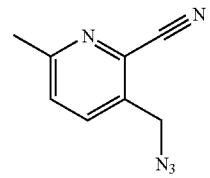

After adding 30% aqueous hydrogen peroxide (7.5 ml, 6.6 mmol) dropwise to a solution of (6-methyl-3-pyridyl)methyl azide (8.9 g, 6.0 mmol) and maleic anhydride (6.5 g, 6.6 mmol) in methylene chloride (90 ml) over a period of 5 minutes while cooling on ice, the mixture was stirred at room temperature for 16 hours. Maleic anhydride (3.25 g) and 30% aqueous hydrogen peroxide (3.75 ml) were added in a similar manner while cooling on ice, and the mixture was stirred at room temperature for 4 hours. Saturated aqueous sodium hydrogencarbonate (100 ml) was added to the reaction mixture, NaHCO₃ was further added to be basic, and extraction was performed with methylene chloride. The extract was washed with a brine and dried over anhydrous magnesium sulfate, and the solvent was distilled off to yield crude 5-(azidomethyl)-2-methyl-1-pyridiniumolate (7.45 g). This was used without further purification for the following reaction.

Trimethylsilyl cyanide (6.4 ml, 48 mmol) and dimethylcarbamyl chloride (4.2 ml, 46 mmol) were added in that order to a solution of the 5-(azidomethyl)-2-methyl-1-pyridiniumolate (7.08 g, 43.2 mmol) in methylene chloride (80 ml) at room temperature and the mixture was stirred at the same temperature for 23 hours. After confirming completion of the reaction by thin layer chromatography, saturated aqueous sodium hydrogencarbonate (80 ml) was added and the mixture was stirred for 10 minutes. The reaction mixture was diluted with ethyl acetate, the aqueous layer was separated and extraction was performed with ethyl acetate. The collected organic layer was washed with water and brine and dried over anhydrous magnesium sulfate. The solvent was distilled off under reduced pressure and the residue was purified by silica gel column chromatography (solvent: n-hexane-ethyl acetate) to yield the title compound (5.79 g, 56%, two steps) as a colorless oil.

$^1$H-NMR(CDCl3) δ (ppm) 2.62(3H, s), 4.63(2H, s), 7.41 (1H, d, J=8.0 Hz), 7.76(1H, d, J=8.0 Hz).

(Step 5) 2-Methyl-5H-pyrrolo[3,4-b]pyridine-7-amine

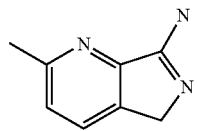

Triphenylphosphine (11 g, 42 mmol) was added to a mixed solution of 3-(azidomethyl)-6-methyl-2-pyridinecarbonitrile (5.79 g, 33.4 mmol) in a tetrahydrofuran (120 ml) —H$_2$O (6 ml) mixed solvent while cooling on ice and the mixture was stirred at room temperature for 22 hours. The solvent was distilled off under reduced pressure and the residue was purified by silica gel column chromatography. The solvent was distilled off from the ethyl acetate-methanol-29% aqueous ammonia (40:10:1) elution fraction, and washing was performed with ether-n-hexane to yield the title compound (1.65 g, 34%) as a brown solid. The solvent was also distilled off from the washed mother liquor to yield the title compound (0.49 g). The NMR data for both compounds matched exactly.

$^1$H-NMR(DSMO-d6) δ (ppm) 2.55(3H, s), 4.39(2H, s), 6.27(brs), 7.23(1H, d, J=8.0 Hz), 7.84(1H, d, J=8.0 Hz).

Example 18

Final Step

After slowly adding 60% sodium hydride (0.45 g, 11 mmol) to a solution of 2-methyl-5H-pyrrolo[3,4-b]pyridine-7-amine (1.5 g, 10 mmol) in tetrahydrofuran (30 ml) while cooling on ice, the mixture was stirred for 30 minutes. 2-Bromo-1-[3,5-di(tert-butyl)-4-hydroxyphenyl]-1-ethanone (4.0 g, 12 mmol) was then added and stirring was continued at room temperature for 2 hours. The solvent was distilled off and then the residue was dissolved in methanol (20 ml) and 4 N hydrochloric acid-ethyl acetate (20 ml) added dropwise while cooling on ice. After stirring at the same temperature for 30 minutes, the solvent was distilled off under reduced pressure and the residue was purified by silica gel column chromatography. The solvent was distilled off from the methylene chloride-methanol (5:1)-3% acetic acid elution fraction under reduced pressure to yield a crude product. The product was dissolved in EtOH and then treated with 4 N hydrochloric acid-ethyl acetate (20 ml). After distilling off the solvent under reduced pressure, the residue was recrystallized from ethanol-ethyl acetate, and the obtained crystals were washed with ethyl acetate and ether in that order and dried to yield the target compound (2.45 g, 56%) as a colorless amorphous solid.

$^1$H-NMR(DSMO-d6) δ (ppm) 1.41(18H, s), 2.67(3H, s), 4.84(2H, s), 5.63(2H, s), 7.70(1H, d, J=8.0 Hz), 7.78(2H, s), 8.08(1H, brs), 8.16(1H, d, J=8.0 Hz), 9.63(1H, brs), 9.94 (1H, brs).

MS: m/e (ESI) 394.1 (MH+)

Example 19

1-(3,5-Di-tert-butyl-4-hydroxy-phenyl)-2-(3-ethoxy-7-imino-2,4-dimethyl-5,7-dihydro-pyrrolo[3,4-b]pyridin-6-yl)-ethanone hydrochloride

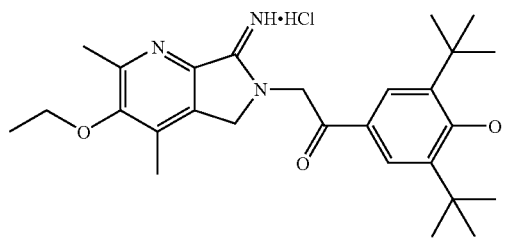

(Step 1) (5-Ethoxy-4,6-dimethyl-3-pyridyl)methanol

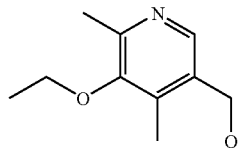

A suspension of 4-deoxypyridoxine hydrochloride (0.99 g, 5.2 mmol) in dimethylformamide (10 ml) was added dropwise to a suspension of 60% NaH (0.42 g, 10.5 mmol) in dimethylformamide (10 ml) while cooling on ice, and the mixture was stirred at room temperature for 1 day. Ethyl iodide (0.44 ml, 5.5 mmol) was then added dropwise at room temperature and stirring was continued for 17 hours. After confirming completion of the reaction by thin layer chromatography, the mixture was poured into semi-saturated aqueous sodium hydrogencarbonate and extraction was performed with ethyl acetate-tetrahydrofuran (1:1). The extract was washed with brine and dried over anhydrous magnesium sulfate, the solvent was distilled off under reduced pressure and the residue was purified by silica gel column chromatography (solvent: methylene chloride-methanol) to yield the title compound (0.415 g, 44%).

$^1$H-NMR(CDCl3) δ (ppm) 1.46(3H, t, J=7.2 Hz), 2.35 (3H, s), 2.63(3H, s), 3.89(2H, q, J=7.2 Hz), 4.75(2H, s), 8.36(1H, s).

(Step 2) (5-Ethoxy-4,6-dimethyl-3-pyridyl)methyl azide

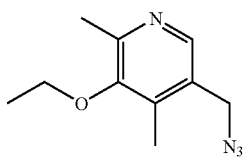

Diphenylphosphoryl azide (0.59 ml, 2.7 mmol) and 1,8-diazabicyclo[5.4.0]undec-7-ene (0.41 ml, 2.7 mmol) were added dropwise in that order to a solution of (5-ethoxy-4,6-dimethyl-3-pyridyl)methanol (0.415 g, 2.29 mmol) in toluene (5 ml) at room temperature, and the mixture was stirred for 16 hours. After confirming completion of the reaction by thin layer chromatography, the mixture was poured into water and extraction was performed with ethyl acetate. The extract was washed with saturated aqueous NaCl and dried over anhydrous magnesium sulfate, the solvent was distilled off under reduced pressure and the residue was purified by silica gel column chromatography (solvent: n-hexane-ethyl acetate) to yield the title compound (447 mg, 95%) as a colorless oil.

$^1$H-NMR(CDCl3) δ (ppm) 1.45(3H, t, J=7.2 Hz), 2.31 (3H, s), 2.54(3H, s), 3.87(3H, q, J=7.2 Hz), 8.14(1H, s).

(Step 3) 3-(Azidomethyl)-5-ethoxy-4,6-dimethyl-2-pyridinecarbonitrile

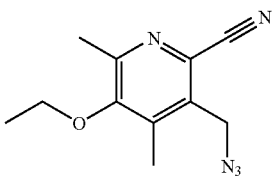

After adding 75% m-chloroperbenzoic acid (600 mg, 2.60 mmol) to a solution of (5-ethoxy-4,6-dimethyl-3-pyridyl) methyl (447 mg, 2.17 mmol) in methylene chloride (5 ml) while cooling on ice, the mixture was stirred for 5 hours while gradually raising the temperature to room temperature. After confirming completion of the reaction by thin layer chromatography, the mixture was poured into saturated aqueous sodium hydrogencarbonate and saturated with sodium chloride, after which extraction was performed with ethyl acetate-tetrahydrofuran (1:1). The extract was washed with brine and dried over anhydrous magnesium sulfate, and the solvent was distilled off under reduced pressure to yield crude N-oxide (637 mg). This compound was used without further purification for the following reaction.

Trimethylsilyl cyanide (0.30 ml, 2.2 mmol) and dimethylcarbamyl chloride (0.21 ml, 2.3 mmol) were added in that order to a solution of the N-oxide (333 mg, 1.5 mmol) in acetonitrile (6 ml) at room temperature and the mixture was stirred at the same temperature for 115 hours. After confirming completion of the reaction by thin layer chromatography, saturated aqueous sodium hydrogencarbonate was added and the mixture was stirred for 10 minutes. The reaction mixture was diluted with ethyl acetate, the aqueous layer was separated and extraction was performed with ethyl acetate. The collected organic layer was washed with water and brine and then dried over anhydrous magnesium sulfate. The solvent was distilled off under reduced pressure and the residue was purified by silica gel column chromatography (solvent: n-hexane-ethyl acetate) to yield the title compound (64 mg, 18%).

$^1$H-NMR(CDCl3) δ (ppm) 1.47(3H, t, J=7.2 Hz), 2.36 (3H, s), 2.54(3H, s), 3.92(2H, q, J=7.2 Hz), 4.59(2H, s).

(Step 4) 3-Ethoxy-2,4-dimethyl-5H-pyrrolo[3,4-b]pyridine-7-amine

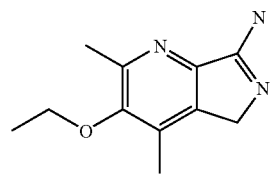

Triphenylphosphine (170 mg, 0.648 mmol) was added to a solution of the 3-(azidomethyl)-5-ethoxy-4,6-dimethyl-2-pyridinecarbonitrile (113 mg, 0.489 mmol) in a tetrahydrofuran (3 ml) —H$_2$O (0.15 ml) mixed solvent while cooling on ice, and the mixture was stirred at room temperature for 2.5 hours. The solvent was distilled off under reduced pressure and the residue was purified by silica gel column chromatography (solvent: ethyl acetate-methanol-29% NH$_3$ (aq)) to yield the title compound (69 mg, 69%) as a yellow solid.

$^1$H-NMR(DSMO-d6) δ (ppm) 1.35(3H, t, J=7.2 Hz), 2.26(3H, s), 2.46(3H, s), 3.85(2H, q, J=7.2 Hz), 4.33(2H, s).

Example 19

Final Step

After adding 60% sodium hydride (15 mg, 0.38 mmol) to a solution of the 3-ethoxy-2,4-dimethyl-5H-pyrrolo[3,4-b] pyridine-7-amine (69 mg, 0.34 mmol) in tetrahydrofuran (3 ml) while cooling on ice, the mixture was stirred at the same temperature for 10 minutes. 2-Bromo-1-[3,5-di(tert-butyl)-4-hydroxyphenyl]-1-ethanone (135 mg, 0.41 mmol) was then added while stirring on ice and stirred at room temperature for 2 hours. The solvent was distilled off under reduced pressure and the residue was purified by silica gel column chromatography (solvent=methylene chloride: methanol (30:1)-3% acetic acid). The product was dissolved in EtOH and treated with 4 N hydrochloric acid-ethyl acetate (1 ml), and the solvent was distilled off under reduced pressure. The residue was crystallized from ethanol to yield the target compound (52 mg, 32%).

$^1$H-NMR(DSMO-d6) δ (ppm) 1.40(3H, t, J=7.2 Hz), 1.42(18H, s), 2.32(3H, s), 2.58(3H, s), 3.99(2H, t, J=7.2 Hz), 4.81(2H, s), 5.52(2H, s), 7.76(2H, s), 8.07(1H, s), 9.37(1H, brs), 9.84(1H, brs).

MS: m/e (ESI) 452.2 (MH+)

Example 20

2-[2-(3,5-Di-tert-butyl-4-hydroxy-phenyl)-2-oxo-ethyl]-6-ethoxy-3-imino-2,3-dihydro-1H-isoindole-5-carboxamide hydrobromide

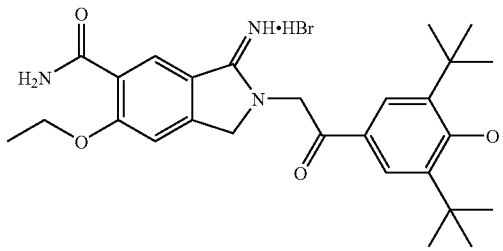

(Step 1) 4-(Azidomethyl)-2-ethoxy-5-(1-ethynyl)benzamide

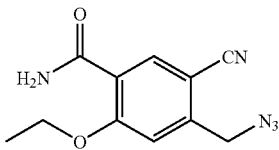

After dissolving 4-(azidomethyl)-5-cyano-2-ethoxybenzoic acid (0.7 g, 2.85 mmol) in tetrahydrofuran (15 ml), triethylamine (0.48 ml, 3.42 mmol) and ethyl chloroformate (0.3 ml, 3.14 mmol) were added while cooling on ice. The mixture was stirred for 10 minutes while cooling on ice, and then 27% aqueous ammonia (10 ml) was added and the mixture was stirred at room temperature for 10 minutes. Water (30 ml) was added to the reaction mixture, extraction was performed with ethyl acetate (20 ml×3), and then after washing the combined organic layers with brine (30 ml) and drying over anhydrous magnesium sulfate, the solvent was distilled off under reduced pressure. The obtained crude product (0.68 g) was used directly for the following reaction.

$^1$H-NMR(CDCl3) δ (ppm) 1.56(3H, t, J=7.3 Hz), 4.34 (2H, q, J=7.3 Hz), 4.68(2H, s), 7.14(1H, s), 8.55(1H, s).

(Step 2) 3-Amino-6-ethoxy-1H-5-isoindolecarboxamide

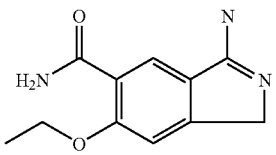

After dissolving crude 4-(azidomethyl)-2-ethoxy-5-(1-ethynyl)benzamide (0.68 g, 2.8 mmol) in tetrahydrofuran (20 ml)-water (1 ml), triphenylphosphine (1.12 g, 4.3 mmol) was added while stirring at room temperature. The mixture was stirred at room temperature for 23 hours, the solvent was distilled off under reduced pressure and the residue was purified by NAM silica gel column chromatography (solvent: ethyl acetate:methanol:27% aqueous ammonia) to yield the title compound (faint brown crystals, 460 mg, 74.9%).

Example 20

Final Step

Synthesis was performed in the same manner as the final step of Example 3 to yield the target compound as a yellow solid.

$^1$H-NMR(DSMO-d6) δ (ppm) 1.40(18H, s), 1.41(3H, t, J=7.5 Hz), 4.84(2H, s), 5.48(2H, s), 7.54(1H, s), 7.69(1H, brs), 7.77(2H, s), 8.07(1H, s), 8.63(1H, s), 9.15(1H, brs), 9.82(1H, brs).

MS: m/e (ESI) 466.1 (MH+)

Example 21

2-[2-(8-tert-Butyl-4-methyl-3,4-dihydro-2H-benzo[1,4]oxazin-6-yl)-2-oxo-ethyl]-6-ethoxy-3-imino-2,3-dihydro-1H-isoindole-5-carboxylic acid methylamide hydrobromide

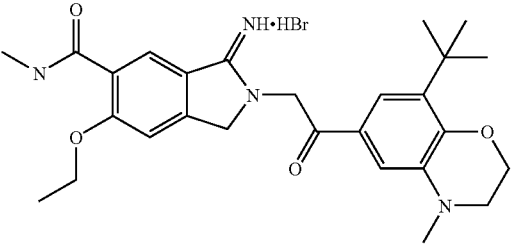

(Step 1) 1-[3-(tert-Butyl)-4-(methoxymethoxy)-5-nitrophenyl]-1-ethanone

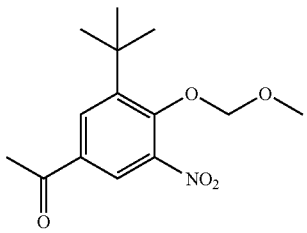

Diisopropylethylamine (65 ml, 373 mmol) was added to a solution of 1-[3-(tert-butyl)-4-hydroxy-5-nitrophenyl]-1-ethanone (58.6 g, 247 mmol) in tetrahydrofuran (350 ml) under a nitrogen atmosphere while cooling on ice, and then chloromethyl methyl ether (24.5 ml, 322 mmol) was added dropwise. After stirring at the same temperature for 30 minutes, ice water (250 ml) was added and extraction was performed twice with ethyl acetate. The organic layer was washed with 1 N hydrochloric acid water, water, saturated aqueous sodium hydrogencarbonate and brine in that order. The organic layer was dried over anhydrous magnesium sulfate and then the solvent was distilled off under reduced pressure to yield the title compound (69.4 g, 99.9% yield) as a light brown oil. This was used without purification for the following reaction.

$^1$H-NMR(CDCl3) δ (ppm) 1.42(9H, s), 2.59(3H, s), 8.08 (1H, d, J=2.0 Hz), 8.45(1H, d, J=2.0 Hz), 11.25(1H, s).

(Step 2) 1-[3-Amino-5-(tert-butyl)-4-(methoxymethoxy)phenyl]-1-ethanone

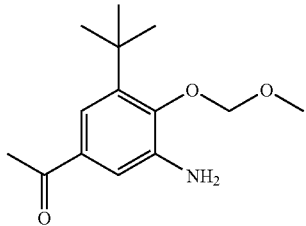

After adding 10% palladium-carbon (50% wet) (14 g) to a solution of the 1-[3-(tert-butyl)-4-(methoxymethoxy)-5-nitrophenyl]-1-ethanone (69.4 g, 247 mmol) in toluene (280 ml) at room temperature, the mixture was hydrogenated for 7 hours under normal pressure. The 10% palladium-carbon was removed by celite filtration and the solvent was distilled off under reduced pressure. The residue was recrystallized from hexane to yield the title compound (54.0 g, 87.1% yield) as light green granular crystals.

$^1$H-NMR(CDCl3) δ (ppm) 1.35(9H, s), 2.46(3H, s), 3.57 (3H, s), 5.01(2H, s), 5.13(2H, s), 7.14(1h, d, J=2.0 Hz), 7.27(1H, d, J=2.0 Hz).

(Step 3) N1-[5-Acetyl-3-(tert-butyl)-2-(methoxymethoxy)phenyl]acetamide

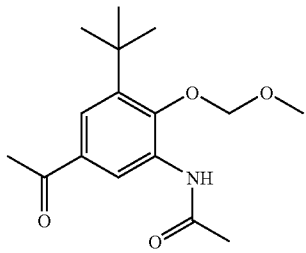

Triethylamine (60 ml, 430 mmol) was added to a solution of the 1-[3-amino-5-(tert-butyl)-4-(methoxymethoxy)phenyl]-1-ethanone (53.9 g, 215 mmol) in tetrahydrofuran (270 ml) while cooling on ice under a nitrogen atmosphere and then acetyl chloride (23 ml, 323 mmol) was added dropwise. After stirring at the same temperature for 10 minutes, the mixture was stirred at room temperature for 30 minutes. The solvent was distilled off under reduced pressure, water was added to the residue and then extraction was performed with ethyl acetate. The organic layer was washed with 1 N hydrochloric acid water, water, saturated aqueous sodium hydrogencarbonate and brine in that order. After drying with anhydrous magnesium sulfate, the solvent was distilled off under reduced pressure. The residue was recrystallized from ethyl acetate-hexane to yield the title compound (56.2 g, 89.3% yield) as light brown needle-like crystals.

(Step 4) N1-[5-Acetyl-3-(tert-butyl)-2-hydroxyphenyl]acetamide

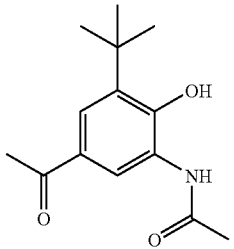

Chlorotrimethylsilane (36.5 ml, 288 mmol) was added dropwise to a solution of the N1-[5-acetyl-3-(tert-butyl)-2-(methoxymethoxy)phenyl]acetamide (56.2 g, 192 mmol) and sodium iodide (43.1 g, 288 mmol) in tetrahydrofuran (300 ml) under a nitrogen atmosphere while cooling on ice, and then the mixture was stirred at the same temperature for 10 minutes and at room temperature for 1 hour. The reaction mixture was poured into a saturated aqueous sodium hydrogencarbonate (400 ml)-ice (300 ml) mixed solvent while stirring. Following extraction twice with ethyl acetate, the organic layer was washed with saturated aqueous sodium hydrogencarbonate and brine in that order. After drying over anhydrous magnesium sulfate, the solvent was distilled off under reduced pressure. The residue was recrystallized from ethyl acetate-n-hexane to yield the title compound (first crystallization=30.5 g, second crystallization=3.55 g, 71.3% yield) as white needle-like crystals.

$^1$H-NMR(CDCl3) δ (ppm) 1.39(9H, s), 2.13(3H, s), 2.49 (3H, s), 7.66(1H, d, J=2.0 Hz), 7.68(1H, d, J=2.0 Hz), 10.04(1H, s), 10.24(1H, s).

(Step 5) 1-[4-Acetyl-8-(tert-butyl)-3,4-dihydro-2H-1,4-benzoxazin-6-yl]-1-ethanone

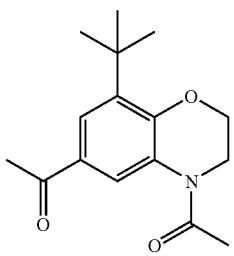

Potassium carbonate (113 g, 818 mmol) and 1,2-dibromoethane (64.1 g, 341 mmol) were added to a solution of the N1-[5-acetyl-3-(tert-butyl)-2-hydroxyphenyl]acetamide (34.0 g, 137 mmol) in dimethylformamide (280 ml) under a nitrogen atmosphere, and then the mixture was stirred at 70° C. for 17 hours. The solvent was distilled off under reduced pressure, ethyl acetate was added to the residue and the mixture was washed with water (3 times) and brine in that order. After drying over anhydrous magnesium sulfate, the solvent was distilled off under reduced pressure to yield the title compound (36.9 g, 98.1% yield) as light red crystals. These were used without purification for the following reaction.

$^1$H-NMR(CDCl3) δ (ppm) 1.36(9H, s), 2.26(3H, s), 2.50 (3H, s), 3.88(2H, t, J=4.8 Hz), 4.42(2H, t, J=4.8 Hz), 7.63(1H, s), 8.05(1H, s).

(Step 6) 1-[8-(tert-Butyl)-3,4-dihydro-2H-1,4-benzoxazin-6-yl]-1-ethanone

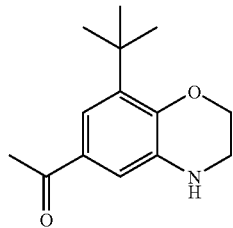

After adding 6 N aqueous sodium hydroxide (180 ml, 900 mmol) to a solution of the 1-[4-acetyl-8-(tert-butyl)-3,4-dihydro-2H-1,4-benzoxazin-6-yl]-1-ethanone (36.8 g, 134 mmol) in methanol (360 ml) under a nitrogen atmosphere, the mixture was stirred at 70° C. for 40 minutes. The methanol was distilled off under reduced pressure, and the precipitated crystals were filtered out and dried under reduced pressure to yield the title compound (30.6 g, 98.1% yield) as bright golden yellow crystals.

$^1$H-NMR(CDCl3) δ (ppm) 1.33(9H, s), 2.43(3H, s), 3.32 (2H, t, J=4.4 Hz), 4.19(2H, t, J=4.4 Hz), 5.94(1H, s), 7.08(1H, d, J=2.0 Hz), 7.10(1H, d, J=2.0 Hz).

(Step 7) 1-[8-(tert-Butyl)-4-methyl-3,4-dihydro-2H-1,4-benzoxazin-6-yl]-1-ethanone

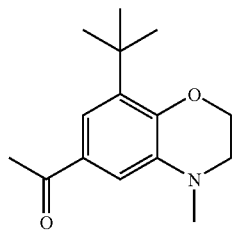

Potassium carbonate (2.43 g, 17.6 mmol) and methyl iodide (1.3 ml, 20.9 mmol) were added to a solution of the 1-[8-(tert-butyl)-3,4-dihydro-2H-1,4-benzoxazin-6-yl]-1-ethanone (3.73 g, 16.0 mmol) in dimethylformamide (35 ml) under a nitrogen atmosphere, and the mixture was stirred at room temperature for 1 day. The solvent was distilled off under reduced pressure, ethyl acetate was added to the residue and the mixture was washed with water (twice) and brine in that order. After drying over anhydrous magnesium sulfate, the solvent was distilled off under reduced pressure. The residue was subjected to silica gel chromatography (Wakogel-C200,60 g) and then fractionated with 2% ethyl acetate-toluene to yield the title compound (2.61 g, 66.0% yield) as bright golden yellow crystals.

$^1$H-NMR(CDCl3) δ (ppm) 1.33(9H, s), 2.49(3H, s), 2.89 (3H, s), 3.29(2H, t, J=4.4 Hz), 4.31(2H, t, J=4.4 Hz), 7.13(1H, d, J=2.0 Hz), 7.24(1H, d, J=2.0 Hz).

(Step 8) 2-Bromo-1-[8-(tert-butyl)-4-methyl-3,4-dihydro-2H-1,4-benzoxazin-6-yl]-1-ethanone

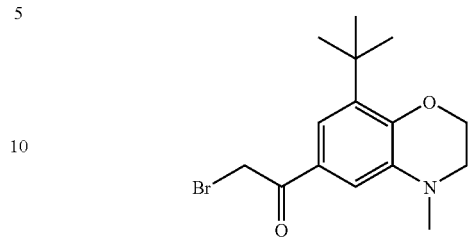

A solution of the 1-[8-(tert-butyl)-4-methyl-3,4-dihydro-2H-1,4-benzoxazin-6-yl]-1-ethanone (2.61 g, 10.6 mmol) and tetra-n-butylammonium tribromide (6.62 g, 13.7 mmol) in acetic acid was stirred at room temperature for 3.5 hours under a nitrogen atmosphere, and then n-butylammonium tribromide (1.02 g, 2.12 mmol) was added and stirring was continued for 45 minutes. After distilling off the solvent under reduced pressure, ethyl acetate was added to the residue and the mixture was washed with saturated aqueous sodium hydrogencarbonate (twice) and brine in that order. It was then dried over anhydrous magnesium sulfate, and the solvent was distilled off under reduced pressure. The residue was subjected to silica gel chromatography (Wakogel-C200, 80 g) and fractionated with hexane-toluene (1:3) to yield the title compound (977 mg, 28.4% yield) as bright golden yellow crystals.

$^1$H-NMR(CDCl3) δ (ppm) 1.33(9H, s), 2.90(3H, s), 3.30 (2H, t, J=4.4 Hz), 4.33(2H, t, J=4.4 Hz), 4.83(2H, s), 7.18(1H, d, J=2.0 Hz), 7.28(1H, d, J=2.0 Hz).

Example 21

Final Step

A solution of 3-amino-6-ethoxy-1H-5-isoindolecarboxamide (13 mg, 0.056 mmol) and the 2-bromo-1-[8-(tert-butyl)-4-methyl-3,4-dihydro-2H-1,4-benzoxazin-6-yl]-1-ethanone (22 mg, 0.067 mmol) in dimethylformamide (1 ml) was stirred at 50° C. for 19 hours under a nitrogen atmosphere. The solvent was distilled off under reduced pressure, and the residue was crystallized from acetonitrile to yield the target compound (19 mg, 61% yield) as bright golden yellow crystals.

$^1$H-NMR(DSMO-d6) δ (ppm) 1.37(9H, s), 1.43(3H, t, J=7.2 Hz), 2.84(3H, d, J=4.4 Hz), 2.92(3H, s), 3.33(2H, t, J=4.4 Hz), 4.31(2H, q, J=7.2 Hz), 4.36(2H, t, J=4.4 Hz), 4.85(2H, s), 5.47(2H, s), 7.18(1H, d, J=2.0 Hz), 7.30(1H, d, J=2.0 Hz), 7.55(1H, s), 8.21(1H, q, J=4,4 Hz), 8.57(1H, s), 9.18(1H, s), 9.83(1H, s).

Example 22

6-[2-(3,5-Di-tert-butyl-4-hydroxy-phenyl)-2-oxo-ethyl]-3-ethoxy-7-imino-6,7-dihydro-5H-pyrrolo[3,4-b]pyridine-2-carboxylic acid methylamide hydrochloride

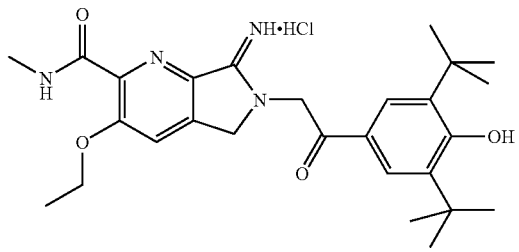

(Step 1) 6-Bromonicotinic acid

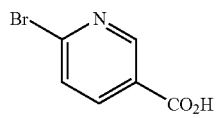

After dissolving 2-bromo-5-picoline (100 g, 0.291 mol) in 1000 ml of water, Aliquat336 (2 ml) was added, and then potassium permanganate (251 g, 0.797 mol) was gradually added over a period of 1 hour and 30 minutes while stirring at 110° C. This mixture was further stirred for an hour, the reaction mixture was filtered through celite without cooling and washed with water, and the filtrate was concentrated to approximately half volume under reduced pressure. After adding 48% hydrobromic acid (~300 ml), the precipitated crystals were filtered, washed with water and dried to yield the title compound (white crystals 52 g, 44%).

$^1$H-NMR(CDCl3) δ (ppm) 7.64(1H, d, J=8.0 Hz), 8.08 (1H, d, J=8.0 Hz), 9.03(1H, s).

(Step 2) (6-Bromo-3-pyridyl)methanol

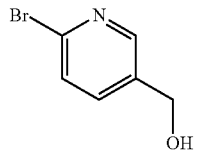

After dissolving 6-bromonicotinic acid (65.7 g, 0.325 mol) in tetrahydrofuran (1600 ml), triethylamine (54 ml, 0.39 mol) and ethyl chloroformate (32.6 ml, 0.341 mol) were added while stirring on ice. The mixture was stirred for 20 minutes while cooling on ice, and the white crystals which precipitated upon filtration were removed and washed with tetrahydrofuran. The filtrate was stirred while cooling on ice, and an aqueous solution (211 ml) of sodium borohydride (18.4 g, 0.488 mol) was gradually added dropwise over a period of 30 minutes. After continued stirring for 1 hour and 20 minutes while cooling on ice, 800 ml of water was added and extraction was performed with ethyl acetate (600 ml×2), and then after washing the combined organic layers with brine (300 ml) and drying over anhydrous magnesium sulfate, the solvent was distilled off under reduced pressure to yield the title compound (45.5 g, 74.5%). This was used without further purification for the following reaction.

$^1$H-NMR(CDCl3) δ (ppm) 4.70(2H, s), 7.46(1H, d, J=8.0 Hz), 7.59(1H, d, J=8.0 Hz), 8.34(1H, brs).

(Step 3) (6-Bromo-3-pyridyl)methyl [1-(tert-butyl)-1,1-diphenylsilyl]ether

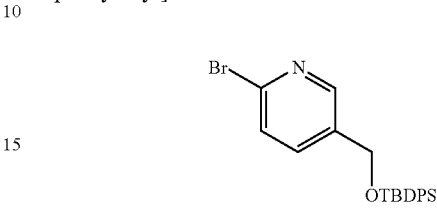

After dissolving the (6-bromo-3-pyridyl)methanol (45.5 g, 0.242 mol) in dimethylformamide (500 ml), tert-butyl diphenylsilyl chloride (69 ml, 0.266 mol) and imidazole (18 g, 0.264 mol) were added while stirring at room temperature. The mixture was stirred at room temperature for an additional 17 hours, 500 ml of water was added and extraction was performed with diethyl ether (500 ml×2), and then after washing the combined organic layers with brine (500 ml) and drying over anhydrous magnesium sulfate, the solvent was distilled off under reduced pressure. The residue was purified by silica gel column chromatography (solvent: n-hexane-ethyl acetate) to yield the title compound (light yellow syrup, 76.9 g, 74.3%).

$^1$H-NMR(CDCl3) δ (ppm) 1.08(9H, s), 4.71(2H, s), 7.34–7.47(6H, m), 7.52(1H, d, J=8.0 Hz), 7.65(4H, d, J=8.0 Hz), 7.71(1H, d, J=8.0 Hz), 8.29(1H, s).

(Step 4) 5-({[1-(tert-Butyl)-1,1-diphenylsilyl]oxy}methyl)-2-pyridinecarbaldehyde

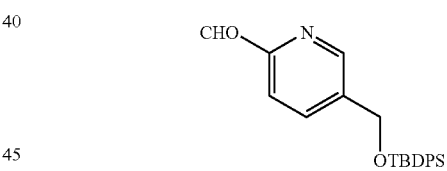

After dissolving (6-bromo-3-pyridyl)methyl [1-(tert-butyl)-1,1-diphenylsilyl]ether (119 g, 0.279 mol) in tetrahydrofuran (1400 ml), n-butyllithium (1.5 M n-hexane solution, 195 ml, 0.293 mol) was added dropwise at −70° C. while stirring for a period of 30 minutes. The mixture was stirred for an additional 40 minutes at −70° C., N-formylmorpholine (56.1 ml, 0.558 mol) was added all at once, stirring was continued for 90 minutes, and then saturated aqueous ammonium chloride (700 ml) was added and the temperature was raised to room temperature. Extraction was performed with ethyl acetate (600 ml×2), and then after washing the combined organic layers with brine (500 ml) and drying over anhydrous magnesium sulfate, the solvent was distilled off under reduced pressure. The residue was purified by silica gel column chromatography (solvent: n-hexane-ethyl acetate) to yield the title compound (59.5 g, 57%).

$^1$H-NMR(CDCl3) δ (ppm) 1.08(9H, s), 4.85(2H, s), 7.33–7.78(10H, m), 7.83(1H, d, J=8.0 Hz), 7.94(1H, d, J=8.0 Hz), 8.72(1H, s), 10.07(1H, s).

(Step 5) 5-({[1-(tert-Butyl)-1,1-diphenylsilyl]oxy}methyl)-2-pyridinecarboxylic acid

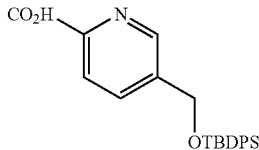

After dissolving the 5-({[1-(tert-butyl)-1,1-diphenylsilyl]oxy}methyl)-2-pyridinecarbaldehyde (59.5 g, 0.158 mol) in t-butanol (1050 ml) and water (210 ml), $NaH_2PO_4 \cdot 2H_2O$ (246 g, 1.58 mol), 2-methyl-2-butene (201 ml, 1.90 mol) and $NaClO_2$ (143 g, 1.58 mol) were added in that order while stirring on ice, and then the mixture was further stirred at room temperature for 80 minutes. Water (600 ml) was added to the reaction mixture, extraction was performed with a 1:1 ethyl acetate-tetrahydrofuran mixed solvent (500 ml×3), and then after washing the combined organic layers with brine (500 ml) and drying over anhydrous magnesium sulfate, the solvent was distilled off under reduced pressure to yield the title compound (53.5 g). This was used without further purification for the following reaction.

$^1$H-NMR(CDCl3) δ (ppm) 1.07(9H, s), 4.85(2H, s), 7.33–7.78(10H, m), 7.88(1H, d, J=8.0 Hz), 8.18(1H, d, J=8.0 Hz), 8.55(1H, s).

(Step 6) N2-Methyl-5-({[1-(tert-butyl)-1,1-diphenylsilyl]oxy}methyl)-2-pyridinecarboxamide

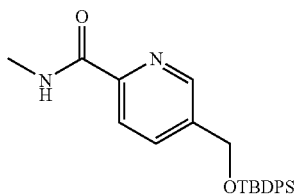

After dissolving 5-({[1-(tert-butyl)-1,1-diphenylsilyl]oxy}methyl)-2-pyridinecarboxylic acid (48.3 g, 0.123 mol) in tetrahydrofuran (615 ml), triethylamine (20.6 ml, 0.148 mol) and ethyl chloroformate (12.9 ml, 0.135 mol) were added while stirring on ice. The mixture was further stirred for 15 minutes while cooling on ice, a 10% aqueous methylamine solution (100 ml) was added, and stirring was continued for 15 minutes while cooling on ice. Brine (400 ml) was added, extraction was performed with a 1:1 ethyl acetate-tetrahydrofuran mixed solvent (400 ml×5), the extract was dried over anhydrous magnesium sulfate, and then the solvent was distilled off under reduced pressure. The residue was purified by silica gel column chromatography (solvent: dichloromethane-methanol) to yield the title compound (white crystals, 31.9 g, 64.2%).

$^1$H-NMR(CDCl3) δ (ppm) 1.08(9H, s), 3.03(3H, d, J=4.0 Hz), 4.80(2H, s), 7.33–7.49(6H, m), 7.65(4H, d, 8.0 Hz), 7.77(1H, d, J=8.0 Hz), 7.99(1H, brs), 8.15(1H, d, J=8.0 Hz), 8.27(1H, s).

(Step 7) N2-Methyl-5-({[1-(tert-butyl)-1,1-diphenylsilyl]oxy}methyl)-3-hydroxy-2-pyridinecarboxamide

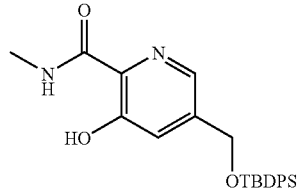

After dissolving the N2-methyl-5-({[1-(tert-butyl)-1,1-diphenylsilyl]oxy}methyl)-2-pyridinecarboxamide (31.9 g, 78.9 mmol) in tetrahydrofuran (526 ml), n-butyllithium (1.5 M n-hexane solution, 132 ml, 198 mmol) was added dropwise at −78° C. while stirring over a period of 20 minutes. The mixture was stirred at −78° C. for 50 minutes, B(OMe)$_3$ (35.4 ml, 316 mmol) was added, and then stirring was continued for 10 minutes, and at 0° C. for 20 minutes. A mixture of 30% aqueous hydrogen peroxide (70 ml), 27% aqueous ammonia and ammonium chloride (28.3 g) was added while stirring on ice, and stirring was continued at room temperature for 90 minutes. A 10% aqueous citric acid solution was added until the reaction mixture was acidic, extraction was performed with ethyl acetate (250 ml×2), and then after washing the combined organic layers with brine (300 ml) and drying over anhydrous magnesium sulfate, the solvent was distilled off under reduced pressure. The residue was purified by silica gel column chromatography (solvent: n-hexane-ethyl acetate) to yield the title compound (light yellow crystals 17.4 g, 52.5%).

$^1$H-NMR(CDCl3) δ (ppm) 1.09(9H, s), 3.02(3H, d, J=4.0 Hz), 4.75(2H, s), 7.31(1H, brs), 7.35–7.74(10H, m), 7.96(1H, brs), 7.97(1H, d, J=1.5 Hz), 12.17(1H, s).

(Step 8) N2-Methyl-5-({[1-(tert-butyl)-1,1-diphenylsilyl]oxy}methyl)-3-ethoxy-2-pyridinecarboxamide

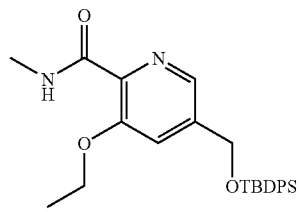

After dissolving N2-methyl-5-({[1-(tert-butyl)-1,1-diphenylsilyl]oxy}methyl)-3-hydroxy-2-pyridinecarboxamide (17.4 g, 41.4 mmol) in dimethylformamide (83 ml), ethyl iodide (3.6 ml, 45.5 mmol) and potassium carbonate (6.3 g, 45.5 mmol) were added while stirring at room temperature. The mixture was stirred at room temperature for an additional 9 hours, water (100 ml) was added and extraction was performed with ethyl acetate (80 ml×2), and then after washing the combined organic layers with brine (80 ml) and drying over anhydrous magnesium sulfate, the solvent was distilled off under reduced pressure to yield the title compound (22.5 g). This was used without further purification for the following reaction.

$^1$H-NMR(CDCl3) δ (ppm) 1.08(9H, s), 1.49(3H, t, J=7.3 Hz), 2.99(3H, d, J=4.0 Hz), 4.10(2H, q, J=7.3 Hz), 4.80(2H, s), 7.32–7.72(11H, m), 8.09(1H, s).

(Step 9) tert-Butyl N-{[5-({[1-(tert-butyl)-1,1-diphenylsilyl]oxy}methyl)-3-ethoxy-2-pyridyl]carbonyl}-N-methylcarbamate

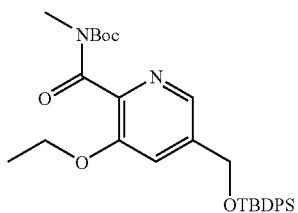

After dissolving the N2-methyl-5-({[1-(tert-butyl)-1,1-diphenylsilyl]oxy}methyl)-3-ethoxy-2-pyridinecarboxamide (crude, 41.4 mmol) in acetonitrile (140 ml), triethylamine (6.9 ml, 49.7 mmol), dimethylaminopyridine (0.51 g, 4.14 mmol) and tert-butyl dicarbonate (9.39 g, 43.5 mmol) were added at room temperature while stirring and the mixture was stirred at room temperature for 14 hours. The reaction mixture was concentrated to half volume under reduced pressure, water (100 ml) was added and extraction was performed with ethyl acetate (80 ml×2), and then after washing the combined organic layers with brine (80 ml) and drying over anhydrous magnesium sulfate, the solvent was distilled off under reduced pressure to yield a crude product (23.2 g). This was used without further purification for the following reaction.

$^1$H-NMR(CDCl3) δ (ppm) 1.08(9H, s), 1.15(9H, s), 1.39 (3H, t, J=7.0 Hz), 3.32(3H, s), 4.01(2H, q, J=7.0 Hz), 4.77(2H, s), 7.20(1H, s), 7.34–7.75(10H, m), 8.06(1H, s).

(Step 10) tert-Butyl N-{[3-ethoxy-5-(hydroxymethyl)-2-pyridyl]carbonyl}-N-methylcarbamate

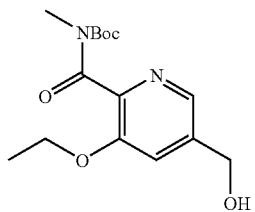

After dissolving tert-butyl N-{[5-({[1-(tert-butyl)-1,1-diphenylsilyl]oxy}methyl)-3-ethoxy-2-pyridyl]carbonyl}-N-methyl carbamate (crude, 41.4 mmol) in tetrahydrofuran (120 ml), tris(dimethylamino)sulfur (trimethylsilyl)difluoride (12.5 g, 45.5 mmol) was added while stirring on ice. The mixture was then stirred for an additional 20 minutes while cooling on ice, water (100 ml) was added and extraction was performed with ethyl acetate (80 ml×3), and then after washing the combined organic layers with brine (100 ml) and drying over anhydrous magnesium sulfate, the solvent was distilled off under reduced pressure. The residue was purified by silica gel column chromatography (solvent: n-hexane-ethyl acetate) to yield the title compound (7.9 g, 61.6% 3 step)

$^1$H-NMR(CDCl3) δ (ppm) 1.19(9H, s), 1.39(3H, t, J=7.0), 3.34(3H, s), 4.06(2H, q, J=7.0 Hz), 4.74(2H, brs), 7.26(1H, s), 8.07(1H, s).

(Step 11) 1-[(6-{[(tert-Butoxycarbonyl)(methyl)amino]carbonyl}-5-ethoxy-3-pyridyl)methyl]-1,2-triazadien-2-ium

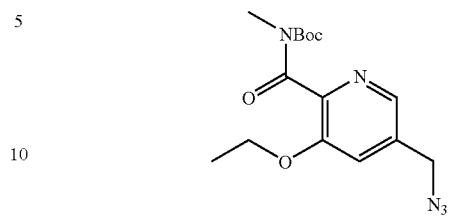

After dissolving the N-{[5-({[1-(tert-butyl)-1,1-diphenylsilyl]oxy}methyl)-3-ethoxy-2-pyridyl]carbonyl}-N-methyl carbamate (7.9 g, 25.5 mmol) in toluene (100 ml), diphenylphosphoryl azide (6.0 ml, 28.1 mmol) and 1,8-diazabicyclo[5.4.0]undec-7-ene (4.2 ml, 28.1 ml) were added while stirring on ice, and the mixture was further stirred at room temperature for 5 hours. Water (100 ml) was added and extraction was performed with ethyl acetate (80 ml×2), and then after washing the combined organic layers with brine (100 ml) and drying over anhydrous magnesium sulfate, the solvent was distilled off under reduced pressure to yield the title compound (7.85 g). This was used without further purification for the following reaction.

$^1$H-NMR(CDCl3) δ (ppm) 1.18(9H, s), 1.41(3H, t, J=7.0), 3.34(3H, s), 4.07(2H, q, J=7.0 Hz), 4.39(2H, s), 7.15(1H, s), 8.09(1H, s).

(Step 12) 5-(Azidomethyl)-2-{[(tert-butoxycarbonyl)(methyl)amino]carbonyl}-3-ethoxy-1-pyridiniumolate

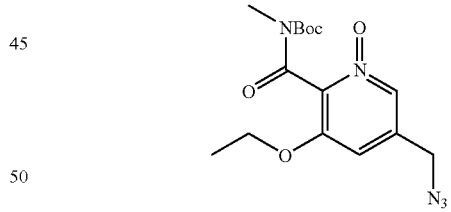

After dissolving the 1-[(6-{[(tert-butoxycarbonyl)(methyl)amino]carbonyl}-5-ethoxy-3-pyridyl)methyl]-1,2-triazadien-2-ium (crude product, 25.2 mmol) in dichloromethane (120 ml), m-chloroperbenzoic acid (6.92 g, 28.1 mmol) was added at room temperature while stirring and the mixture was stirred at room temperature for 4 hours. The reaction mixture was concentrated under reduced pressure and then the residue was purified by silica gel column chromatography (solvent: n-hexane-ethyl acetate) to yield the title compound (9.74 g, 100% up).

$^1$H-NMR(CDCl3) δ (ppm) 1.30(9H, s), 1.38(3H, t, J=7.0), 3.33(3H, s), 4.10(2H, q, J=7.0 Hz), 4.33(2H, s), 6.77(1H, s), 7.83(1H, s).-

(Step 13) 1-[(6-{[(tert-Butoxycarbonyl)(methyl)amino]carbonyl}-2-cyano-5-ethoxy-3-pyridyl)methyl]-1,2-triazadien-2-ium

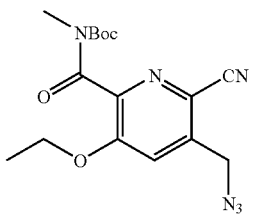

After dissolving 5-(azidomethyl)-2-{[(tert-butoxycarbonyl)(methyl)amino]carbonyl}-3-ethoxy-1-pyridiniumolate (9.74 g, 27.7 mmol) in acetonitrile (140 ml), trimethylsilyl cyanide (5.5 ml, 41.6 ml) and dimethylcarbamyl chloride (3.8 ml, 41.6 ml) were added at room temperature while stirring and the mixture was further stirred at 80° C. for 24 hours. It was then cooled to room temperature, water (100 ml) was added and extraction was performed with ethyl acetate (80 ml×2), and then after washing the combined organic layers with brine (100 ml) and drying over anhydrous magnesium sulfate, the solvent was distilled off under reduced pressure. The residue was purified by silica gel column chromatography (solvent: n-hexane-ethyl acetate) to yield the title compound (faint blue oil, 8.3 g, 83%).

¹H-NMR(CDCl3) δ (ppm) 1.28(9H, s), 1.44(3H, t, J=7.0), 3.32(3H, s), 4.17(2H, q, J=7.0 Hz), 4.69(2H, s), 7.27(1H, s).

(Step 14) tert-Butyl N-[(7-amino-3-ethoxy-5H-pyrrolo[3,4-b]pyridin-2-yl)carbonyl]-N-methylcarbamate

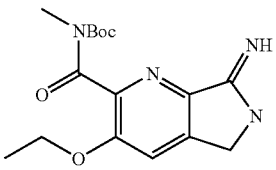

After dissolving the 1-[(6-{[(tert-butoxycarbonyl)(methyl)amino]carbonyl}-2-cyano-5-ethoxy-3-pyridyl)methyl]-1,2-triazadien-2-ium (8.3 g, 23 mmol) in tetrahydrofuran (100 ml) and water (5 ml), PPh₃ (10.3 g, 39.1 mmol) was added while stirring on ice and the mixture was further stirred at room temperature for 90 minutes. The reaction mixture was concentrated under reduced pressure, and the residue was purified by silica gel column chromatography (solvent: ethyl acetate:methanol:27% aqueous ammonia=3:1:0.1) to yield the title compound (brown solid, 5.63 g, 73.5%).

¹H-NMR(DSMO-d₆) δ (ppm) 1.02(9H, s), 1.27(3H, t, J=7.0 Hz), 3.18(3H, s), 4.11(2H, q, J=7.0 Hz), 4.46(2H, s), 7.72(1H, s).

Example 22

Final Step

Synthesis was performed in the same manner as the final step of Example 3 to yield the target compound as a yellow solid.

¹H-NMR(DSMO-d₆) δ (ppm) 1.35(3H, t, J=7.0 Hz), 1.41(18H, s), 2.77(3H, d, J=4.2 Hz), 4.25(2H, q, J=7.0 Hz), 87(2H, s), 5.52(2H, s), 7.76(2H, s), 7.99(1H, s), 8.07(1H, s), 8.53(1H, brq, J=4.2 Hz), 9.40(1H, brs), 9.95(1H, brs).

MS: m/e (ESI) 481.2 (MH+)

Example 23

1-(3,5-Di-tert-butyl-4-hydroxy-phenyl)-2-(2-ethyl-7-imino-5,7-dihydro-pyrrolo[3,4-b]pyridin-6-yl)-ethanone hydrobromide

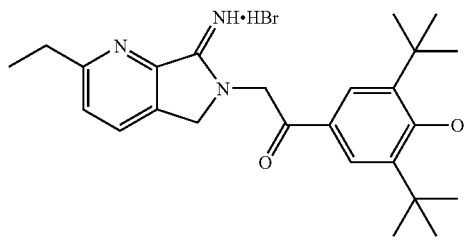

(Step 1) 1-(tert-Butyl)-1,1-diphenylsilyl [(6-vinyl-3-pyridyl)methyl]ether

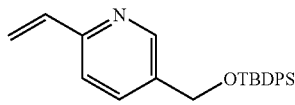

After dissolving 1-(tert-butyl)-1,1-diphenylsilyl [(6-chloro-3-pyridyl)methyl]ether (20 g, 52.3 mmol) in toluene (104 ml) and degassing the solution, tetrakis(triphenylphosphine)palladium (3.0 g, 2.6 mmol) and tributylvinyltin (16.5 ml, 56.5 mmol) were added under a nitrogen stream and the mixture was heated to reflux at 120° C. for 7 hours. The reaction mixture was then cooled to room temperature and concentrated under reduced pressure, and the residue was purified by silica gel column chromatography (solvent: n-hexane-ethyl acetate) to yield the title compound (17.46 g) as a colorless oil. (89.3% yield)

¹H-NMR(CDCl3) δ (ppm) 1.07(9H, s), 4.75(2H, s), 5.46 (1H, d, J=10 Hz), 6.18(1H, d, J=20 Hz), 6.82(1H, dd, J=10 Hz, J=20 Hz), 7.31(1H, d, J=8.0 Hz), 7.35–7.45(6H, m), 7.62(1H, d, J=8.0 Hz), 7.66(4H, d, J=7.0 Hz), 8.53(1H, s).

(Step 2) 1-(tert-Butyl)-1,1-diphenylsilyl [(6-ethyl-3-pyridyl)methyl]ether

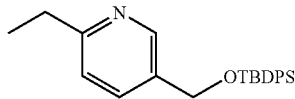

After dissolving 1-(tert-butyl)-1,1-diphenylsilyl [(6-vinyl-3-pyridyl)methyl]ether (8 g, 21.4 mmol) in ethyl acetate (80 ml), 10% palladium-carbon (3 g) was added and the mixture was stirred at room temperature for 0.5 hour under a hydrogen stream. The reaction mixture was filtered through celite and concentrated.

The title compound (7.81 g) was obtained as a light yellow oil. (97.1% yield)

$^1$H-NMR(CDCl3) δ (ppm) 1.07(9H, s), 1.31(3H, t, J=7.6 Hz), 2.82(2H, q, J=7.6 Hz), 4.74(2H, s), 7.12(1H, d, J=8.0 Hz), 7.34–7.48(6H, m), 7.55(1H, d, J=8.0 Hz), 7.67(4H, d, J=7.0 Hz), 8.45(1H, s).

(Step 3) (6-Ethyl-3-pyridyl)methanol

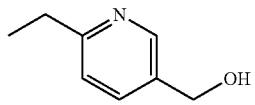

After dissolving the 1-(tert-butyl)-1,1-diphenylsilyl [(6-ethyl-3-pyridyl)methyl]ether (7.81 g, 20.8 mmol) in tetrahydrofuran (80 ml), TBAF (31.2 ml, 31.2 mmol) was added and the mixture was stirred at room temperature for 1 hour. The reaction mixture was quenched with water and was extracted with ethyl acetate. After washing the extract with brine, it was dried over anhydrous sodium sulfate and filtered, the filtrate was concentrated under reduced pressure and the residue was purified by silica gel column chromatography (solvent: n-hexane-ethyl acetate) to yield the title compound (2.25 g) as a colorless oil. (78.8% yield)

$^1$H-NMR(CDCl3) δ (ppm) 1.28(3H, t, J=7.6 Hz), 2.31 (1H, s), 2.81(2H, q, J=7.6 Hz), 4.67(2H, s), 5.15(1H, d, J=8.0 Hz), 7.63(1H, d, J=8.0 Hz), 8.46(1H, s).

(Step 4) (6-Ethyl-3-pyridyl)methyl azide

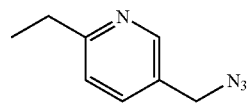

After dissolving (6-ethyl-3-pyridyl)methanol (2.25 g, 16.4 mmol) in toluene (25 ml), diphenylphosphoryl azide (4.2 ml, 19.6 mmol) and 1,8-diazabicyclo[5.4.0]undec-7-ene (2.9 ml, 19.6 mmol) were added while stirring on ice, and the mixture was further stirred at room temperature for 18 hours. Water was added for treatment and extraction was performed with ethyl acetate. The extract was washed with brine and then dried over sodium sulfate and filtered. The filtrate was concentrated under reduced pressure and the residue was purified by silica gel column chromatography (solvent: n-hexane-ethyl acetate) to yield the title compound (2.2 g) as a yellow oil. (84.5% yield)

$^1$H-NMR (CDCl3) δ (ppm) 1.31(3H, t, J=7.6 Hz), 2.84 (2H, q, J=7.6 Hz), 4.33(2H, s), 7.18(1H, d, J=8.0 Hz), 7.56(1H, d, J=8.0 Hz), 8.46(1H, s).

(Step 5) 5-(Azidomethyl)-2-ethyl-1-pyridiniumolate

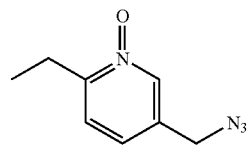

After dissolving the (6-ethyl-3-pyridyl)methyl azide (2.24 g, 13.8 mmol) in methylene chloride (25 ml), m-chloroperbenzoic acid (3.7 g, 15 mmol) was added while stirring on ice, and the mixture was stirred at room temperature for 18 hours. Saturated aqueous sodium hydrogencarbonate was added for treatment and extraction was performed with methylene chloride. The extract was dried over sodium sulfate and filtered, the filtrate was concentrated under reduced pressure and the residue was purified by silica gel column chromatography (solvent: n-hexane-ethyl acetate=1:2→ethyl acetate-methanol=4:1).

The title compound was obtained (2.16 g) as a light yellow oil. (87.6% yield)

$^1$H-NMR(CDCl3) δ (ppm) 1.28(3H, t, J=7.6 Hz), 2.92 (2H, q, J=7.6 Hz), 4.31(2H, s), 7.17(1H, d, J=8.0 Hz), 7.24(1H, d, J=8.0 Hz), 8.23(1H, s).

(Step 6) 3-(Azidomethyl)-6-ethyl-2-pyridinecarbonitrile

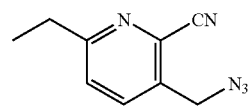

After dissolving 5-(azidomethyl)-2-ethyl-1-pyridiniumolate (2.16 g, 12.1 mmol) in acetonitrile (25 ml), 1.77 ml of trimethylsilylnitrile (13.3 mmol) and 1.23 ml of dimethylcarbamoyl chloride (13.3 mmol) were added under a nitrogen stream and the mixture was stirred at room temperature for 66 hours. Saturated aqueous sodium hydrogencarbonate was added for treatment and extraction was performed with ethyl acetate. The extract was dried over anhydrous sodium sulfate, the filtrate was concentrated under reduced pressure and the residue was purified by silica gel column chromatography (solvent: n-hexane-ethyl acetate) to yield the title compound (2.05 g) as a colorless oil. (90.4% yield)

$^1$H-NMR(CDCl3) δ (ppm) 1.31(3H, t, J=7.6 Hz), 2.87 (2H, q, J=7.6 Hz), 4.62(2H, s), 7.41(1H, d, J=8.0 Hz), 7.77(1H, d, J=8.0 Hz).

(Step 7) 2-Ethyl-5H-pyrrolo[3,4-b]pyridine-7-amine

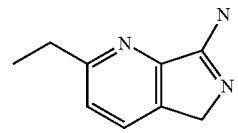

After dissolving 3-(azidomethyl)-6-ethyl-2-pyridinecarbonitrile (1.0 g, 5.34 mmol) in tetrahydrofuran (16 ml)-water (0.8 ml), triphenylphosphine (2.1 g, 8.01 mmol) was added while stirring on ice, and the mixture was further stirred at room temperature for 2.0 hours. The reaction mixture was concentrated under reduced pressure and the residue was purified by silica gel column chromatography (solvent: ethyl acetate, ethyl acetate:methanol=4:1, ethyl acetate:methanol:aqueous ammonia=2:1:0.1 in this order). The title compound (0.769 g) was obtained as a light green substance. (89.3% yield)

$^1$H-NMR(CDCl3) δ (ppm) 1.33(3H, t, J=7.6 Hz), 2.89 (2H, q, J=7.6 Hz), 4.47(2H, br), 4.56(2H, s), 5.16(1H, d, J=8.0 Hz), 7.73(1H, d, J=8.0 Hz).

Example 23

Final Step

Synthesis was performed in the same manner as the final step of Example 3 to yield the target compound as a yellow solid.

¹H-NMR(DSMO-d6) δ (ppm) 1.31(3H, t, J=7.6 Hz), 1.42(18H, s), 2.94(2H, q, J=7.6 Hz), 4.85(2H, s), 5.56(2H, s), 7.73(1H, d, J=8.0 Hz), 7.77(2H, s), 8.18(1H, d, J=8.0 Hz), 9.85(1H, s).

MS: m/e (ESI) 408.2 (MH+)

Example 24

2-(2-Cyclopropyl-7-imino-5,7-dihydro-pyrrolo[3,4-b]pyridin-6-yl)-ethanone)—1(3,5-di-tert-butyl-4-hydroxy-phenyl)-ethanone hydrobromide

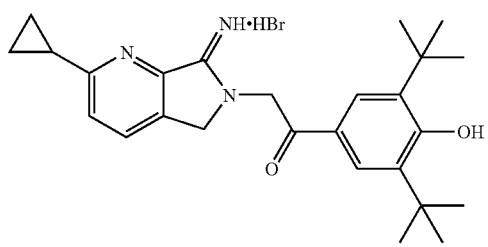

(Step 1) 1-(tert-Butyl)-1,1-diphenylsilyl [(6-cyclopropyl-3-pyridyl)methyl]ether

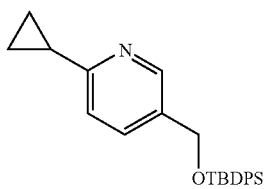

The following procedure was carried out to prepare 1.0 M cyclopropylmagnesium bromide. One third of a solution of cyclopropyl bromide (2.1 ml, 26 mmol) in anhydrous tetrahydrofuran (24 ml) was added all at once to magnesium (0.64 g, 26 mmol atom) prior to vigorous heating to reflux. The remaining two thirds of the solution was slowly added dropwise over a period of 15 minutes, and the reaction mixture was stirred for 30 minutes while heating to reflux. This was cooled to room temperature and used for the following reaction.

NiCl$_2$(dppf)$_2$ (0.45 g, 0.66 mmol) was added to a solution of 1-(tert-butyl)-1,1-diphenylsilyl [(6-chloro-3-pyridyl)methyl]ether (5.0 g, 13 mmol) in tetrahydrofuran (26 ml) at room temperature, after which 1.0 M cyclopropylmagnesium bromide (16 ml) was slowly added dropwise and stirring was continued at room temperature for 5.5 hours. Next, 1.0 M cyclopropylmagnesium bromide (10 ml) was slowly added dropwise over a period of 1.5 hours and stirring was continued for 15 hours. Saturated aqueous NH$_4$Cl was added, and then the mixture was stirred for 3 hours and filtered through celite and extraction was performed with ethyl acetate. After drying with anhydrous magnesium sulfate, the solvent was distilled off under reduced pressure and the residue was purified by silica gel column chromatography (solvent: n-hexane-ethyl acetate) to yield the title compound (1.3 g) as a mixture with impurities. This product was used without further purification for the following reaction.

(Step 2) (6-Cyclopropyl-3-pyridyl)methanol

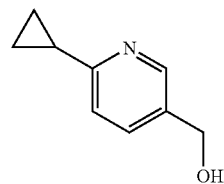

After adding 1.0 M tetra n-butylammonium fluoride-tetrahydrofuran (3.7 ml, 3.7 mmol) to a solution of 1-(tert-butyl)-1,1-diphenylsilyl [(6-cyclopropyl-3-pyridyl)methyl] ether (1.3 g) in tetrahydrofuran (7 ml) dropwise while cooling on ice, the mixture was stirred for 1 hour. After confirming completion of the reaction by thin layer chromatography, the solvent was distilled off under reduced pressure and the obtained residue was purified by silica gel column chromatography (solvent: n-hexane-ethyl acetate) to yield the title compound (283 mg, two steps, 14%) as a colorless oil.

¹H-NMR (CDCl3) δ (ppm) 0.88–1.07(4H, m), 1.80–1.95 (1H, m), 1.99–2.09(1H, m), 4.65(2H, s), 7.11(1H, d, J=8.0 Hz), 7.56(1H, brd, J=8.0 Hz), 8.39(1H, brs).

(Step 3) (6-Cyclopropyl-3-pyridyl)methyl azide

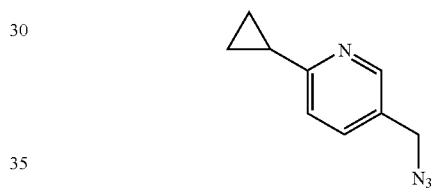

Diphenylphosphoryl azide (0.49 ml, 2.3 mmol) and 1,8-diazabicyclo[5.4.0]undec-7-ene (0.34 ml, 2.3 mmol) were added dropwise in that order at room temperature to a solution of (6-cyclopropyl-3-pyridyl)methanol (283 mg, 1.90 mmol) in toluene (4 ml) and the mixture was stirred for 3 hours. After confirming completion of the reaction by thin layer chromatography, it was diluted with ethyl acetate and washed with water and brine. Drying was performed with anhydrous magnesium sulfate, the solvent was distilled off under reduced pressure and the residue was purified by silica gel column chromatography (solvent: n-hexane-ethyl acetate) to yield the title compound (330 mg, quant.) as a colorless oil.

¹H-NMR(CDCl3) δ (ppm) 0.80–1.20(4H, s), 1.95–2.11 (1H, m), 4.30(2H, s), 7.15(1H, d, J=8.0 Hz), 7.50(1H, dd, J=8.0 and 2.4 Hz), 8.38(1H, d, J=2.4 Hz).

(Step 4) 5-(Azidomethyl)-2-cyclopropyl-1-pyridinium oxide

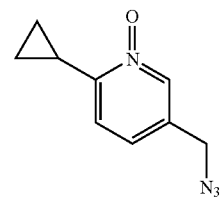

After adding 75% m-chloroperbenzoic acid (560 mg, 2.27 mmol) to a solution of (6-cyclopropyl-3-pyridyl)methyl azide (330 mg, 1.89 mmol) in methylene chloride (4 ml) while cooling on ice, the mixture was stirred for 17 hours while gradually raising the temperature to room temperature. After confirming completion of the reaction by thin layer chromatography, the reaction mixture was directly purified by silica gel column chromatography to yield the title compound (227 mg, 63%) as a colorless oil from the ethyl acetate-methanol (10:1) elution fraction.

$^1$H-NMR(CDCl3) δ (ppm) 0.71–0.89(2H, m), 1.11–1.31 (2H, m), 2.63–2.80(1H, m), 4.30(2H, s), 6.87(1H, d, J=8.0 Hz), 7.11(1H, brd, J=8.0 Hz), 8.26(1H, brs).

(Step 5) 3-(Azidomethyl)-6-cyclopropyl-2-pyridinecarbonitrile

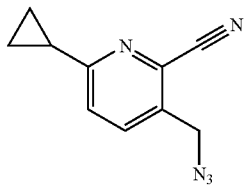

Trimethylsilyl cyanide (0.19 ml, 1.4 mmol) and dimethylcarbamyl chloride (0.13 ml, 1.4 mmol) were added in that order at room temperature to a solution of 5-(azidomethyl)-2-cyclopropyl-1-pyridinium oxide (227 mg, 1.19 mmol) in acetonitrile (4 ml), and the mixture was stirred at room temperature for 95 hours. After confirming completion of the reaction by thin layer chromatography, saturated aqueous sodium hydrogencarbonate was added and the mixture was stirred for 10 minutes. The reaction mixture was diluted with ethyl acetate, the aqueous layer was separated and extraction was performed with ethyl acetate. The collected organic layer was washed with water and brine and dried over anhydrous magnesium sulfate. The solvent was distilled off and the residue was purified by silica gel column chromatography (solvent: n-hexane-ethyl acetate) to yield the title compound (230 mg, 97%).

$^1$H-NMR(CDCl3) δ (ppm) 1.00–1.20(4H, m), 2.00–2.15 (1H, m), 4.58(2H, s), 7.38(1H, d, J=8.4 Hz), 7.67(1H, d, J=8.4 Hz).

(Step 6) Synthesis of 2-Cyclopropyl-5H-pyrrolo[3,4-b]pyridine-7-amine

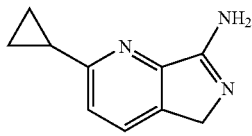

Triphenylphosphine (365 mg, 1.39 mmol) was added at room temperature to a solution of the 3-(azidomethyl)-6-cyclopropyl-2-pyridinecarbonitrile (230 mg, 1.15 mmol) in a tetrahydrofuran (4 ml) —H$_2$O (0.2 ml) mixed solvent and the mixture was stirred for 3 hours. The solvent was distilled off under reduced pressure and the residue was purified by silica gel column chromatography, to yield the title compound (180 mg, 90%) as a white amorphous solid from the ethyl acetate-methanol-29% NH$_3$(aq) (30:10:1) elution fraction.

$^1$H-NMR(CDCl3) δ (ppm) 0.85–1.12(4H, m), 2.10–2.27 (1H, m), 4.38(2H, s), 6.19(brs), 7.23(1H, d, J=8.0 Hz), 7.79(1H, d, J=8.0 Hz).

Example 24

Final Step

A solution of the 2-cyclopropyl-5H-pyrrolo[3,4-b]pyridine-7-amine (100 mg, 0.557 mmol) and 2-bromo-1-[[3,5-di(tert-butyl)-4-hydroxyphenyl]-1-ethanone (227 mg, 0.694 mmol) in dimethylformamide (5 ml) was stirred at room temperature for 17 hours. The solvent was distilled off under reduced pressure and the residue was crystallized from ethyl acetate to yield the target compound (210 mg, 73%) as a colorless amorphous solid.

$^1$H-NMR(DSMO-d$_6$) δ (ppm) 1.03–1.12(4H, m), 1.41 (18H, s), 2.26–2.36(1H, m), 4.81(2H, s), 5.53(2H, s), 7.71 (1H, d, J=8.0 Hz), 7.76(2H, s), 8.09(1H, d, J=8.0 Hz), 9.63(1H, brs).

MS: m/e (ESI) 420.2 (MH+)

Example 25

2-[2-(8-tert-Butyl-3-oxo-3,4-dihydro-2H-benzo[1,4] oxazin-6-yl)-2-oxo-ethyl]-6-ethoxy-3-imino-2,3-dihydro-1H-isoindole-5-carboxylic acid methylamide hydrobromide

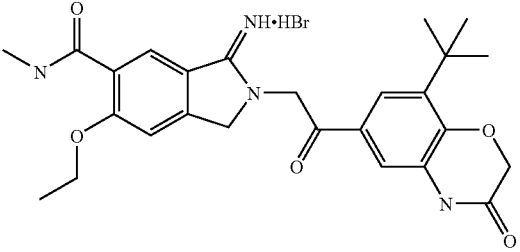

(Step 1) 1-[3-Amino-5-(tert-butyl)-4-hydroxyphenyl]-1-ethanone

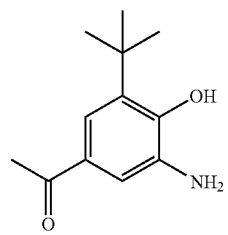

After adding 10% palladium-carbon (50% wet) (100 mg) to a solution of 1-[3-(tert-butyl)-4-hydroxy-5-nitrophenyl]-1-ethanone (1.00 g, 4.22 mmol) in ethyl acetate (10 ml) at room temperature, the mixture was hydrogenated for 3 hours under normal pressure. The 10% palladium-carbon was then filtered through celite and the solvent was distilled off under reduced pressure. The residue was subjected to silica gel chromatography (Wakogel-C200,10 g) to yield the title compound (627 mg, 71.8% yield) as a light red powder from the ethyl acetate-hexane (1:4~1:3) fraction.

¹H-NMR(CDCl3) δ (ppm) 1.36(9H, s), 2.42(3H, s), 6.10 (2H, s), 7.17(1H, d, J=2.4 Hz), 7.21(1H, d, J=2.4 Hz).

(Step 2) 6-Acetyl-8-(tert-butyl)-3,4-dihydro-2H-1,4-benzoxazin-3-one

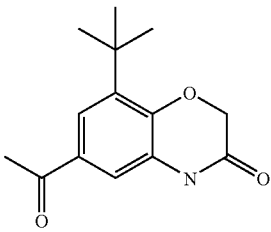

Chloroacetyl chloride (0.14 ml, 1.76 mmol) was added at room temperature to a solution of the 1-[3-amino-5-(tert-butyl)-4-hydroxyphenyl]-1-ethanone (300 mg, 1.45 mmol) in a methylene chloride (3 ml)-saturated aqueous sodium hydrogencarbonate (3 ml) mixed solvent, and the resultant mixture was stirred for 30 minutes. After adding ethyl acetate to the reaction mixture for separation, the organic layer was washed with brine. After drying over anhydrous magnesium sulfate, the solvent was distilled off under reduced pressure. The residue was dissolved in dimethylformamide (6 ml), potassium carbonate (401 mg, 2.90 mmol) was added and the mixture was stirred at 70° C. for 7 hours under a nitrogen atmosphere. The solvent was distilled off under reduced pressure, and then ethyl acetate was added to the residue and the mixture was washed with water and brine in that order. After drying over anhydrous magnesium sulfate, the solvent was distilled off under reduced pressure. The residue was subjected to silica gel chromatography (Wakogel-C200,7 g), and the fraction containing the target compound was obtained from the ethyl acetate-toluene (1:9~1:6) fractions and crystallized from diethyl ether-diisopropyl ether to yield the title compound (102 mg, 28.5% yield) as yellow ochre crystals.

¹H-NMR(CDCl3) δ (ppm) 1.36(9H, s), 2.51(3H, s), 4.65 (2H, s), 7.40(1H, d, J=2.0), 7.51(1H, d, J=2.0 Hz), 10.80(1H, s).

(Step 3) 6-(2-Bromoacetyl)-8-(tert-butyl)-3,4-dihydro-2H-1,4-benzoxazin-3-one

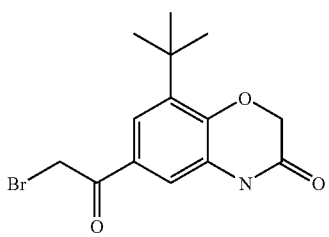

Tetra-n-butylammonium tribromide (64 mg, 0.13 mmol) was added to a solution of the 6-acetyl-8-(tert-butyl)-3,4-dihydro-2H-1,4-benzoxazin-3-one (30 mg, 0.12 mmol) in a methylene chloride (0.4 ml)-methanol (0.1 ml) mixed solvent under a nitrogen atmosphere, and the mixture was stirred at room temperature for 3 hours. After distilling off the solvent under reduced pressure, the residue was subjected to silica gel chromatography (Wakogel-C200,1 g) to yield the title compound (36 mg, 91% yield) as light yellow needle-like crystals from the chloroform fraction.

¹H-NMR(CDCl3) δ (ppm) 1.38(9H, s), 4.68(2H, s), 4.85 (2H, s), 7.43(1H, d, J=2.0 Hz), 7.56(1H, d, J=2.0 Hz), 10.85(1H, s).

Example 25

Final Step

A solution of 3-amino-6-ethoxy-1H-5-isoindolecarboxamide (72 mg, 0.31 mmol) and the 6-(2-bromoacetyl)-8-(tert-butyl)-3,4-dihydro-2H-1,4-benzoxazin-3-one (200 mg, 0.61 mmol) in dimethylformamide (1 ml) was stirred at 70° C. for 4 hours under a nitrogen atmosphere. The solvent was distilled off under reduced pressure, the residue was subjected to silica gel chromatography (NAM-200H, 5 g), and the fraction containing the target compound was obtained from the 5% methanol-chloroform~10% methanol-chloroform fractions and recrystallized from acetonitrile-methanol to yield the target compound (87 mg, 50% yield) as light red crystals.

¹H-NMR(DSMO-d6) δ (ppm) 1.39(9H, s), 1.43(3H, t, J=6.8 Hz), 2.84(3H, d, J=4,4 Hz), 4.30(2H, q, J=6.8Hz), 4.72(2H, s), 4.86(2H, s), 5.47(2H, s), 7.44(1H, d, J=2.0 Hz), 7.56(2H, s), 8.22(1H, q, J=4.4 Hz), 8.58(1H, s), 9.20(1H, s), 9.86(1H, s), 10.95(1H, s).

Example 26

1-(3-tert-Butyl-5-isopropylamino-4-methoxy-phenyl)-2-(5,6-diethoxy-7-fluoro-1-imino-1,3-dihydro-isoindol-2-yl)-ethanone hydrobromide

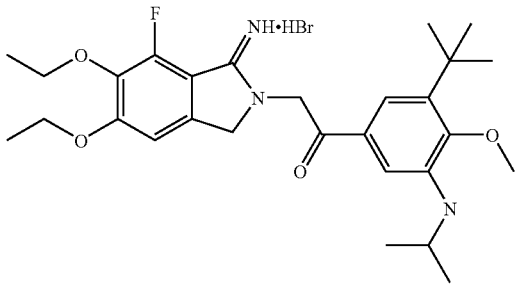

(Step 1) 1-[3-(tert-Butyl)-5-(isopropylamino)-4-methoxyphenyl]-1-ethanone

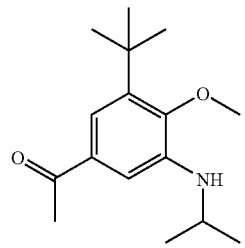

Trimethyl orthoformate (20 ml), p-toluenesulfonic acid (0.5 g, 1.9 mmol) and 3A-molecular sieves (4 g) were added to a solution of 1-[3-amino-5-(tert-butyl)-4-methoxyphenyl]-1-ethanone (4 g, 19 mmol) in methanol (20 ml) and the mixture was stirred at room temperature for 13 hours. The reaction mixture was filtered through celite and the solvent was distilled off under reduced pressure. Ethyl acetate was added to the residue, the mixture was washed with brine, and the organic layer was dried over anhydrous magnesium sulfate. The solvent was distilled off under reduced pressure to yield 5.2 g of 3-(tert-butyl)-5-(1,1-dimethoxyethyl)-2-methoxyaniline as a crude product. Acetone (1.7 ml, 22 mmol), acetic acid (3.2 ml, 56 mmol) and 3A-molecular sieves (2 g) were added to a solution of the compound (5.2 g, 19 mmol) in methanol (6 ml) and the mixture was stirred at room temperature for 3 hours. Sodium cyanoborohydride (1.1 g, 17 mmol) was added to the reaction mixture prior to stirring at room temperature for 2 hours. Ethyl acetate was added to the reaction mixture, washing was performed with saturated sodium hydrogencarbonate water and brine in that order, and the organic layer was dried over anhydrous magnesium sulfate. The solvent was distilled off under reduced pressure and then the residue was purified by silica gel column chromatography (solvent: n-hexane-ethyl acetate) to yield the title compound (1.0 g) as a light yellow oil.

$^1$H-NMR(CDCl3) δ (ppm) 1.25(6H, d, J=6.4 Hz), 1.40 (9H, s), 2.56(3H, s), 3.60–3.72(1H, m), 3.77(3H, s), 7.17 (1H, d, J=2.0 Hz), 7.31(1H, d, J=2.0 Hz).

(Step 2) 2-Bromo-1-[3-(tert-butyl)-5-(isopropylamino)-4-methoxyphenyl]-1-ethanone

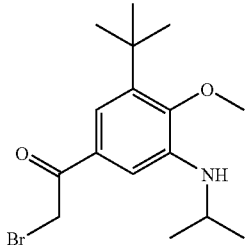

Triethylamine (0.63 ml, 4.5 mmol) and tert-butyl dimethylsilyltrifluoromethanesulfonate (0.6 g, 2.3 mmol) were added to a solution of the 1-[3-(tert-butyl)-5-(isopropylamino)-4-methoxyphenyl]-1-ethanone (0.4 g, 1.5 mmol) in tetrahydrofuran (50 ml) while cooling on ice and the mixture was stirred at the same temperature for 30 minutes, after which N-bromosuccinimide (0.53 g, 3.0 mmol) was added and stirring was continued for 30 minutes. Ethyl acetate was added to the reaction mixture, the mixture was washed with brine and the organic layer was dried over anhydrous magnesium sulfate. After distilling off the solvent under reduced pressure, the residue was purified by silica gel column chromatography (solvent: n-hexane-ethyl acetate) to yield the title compound (410 mg) as a light yellow oil.

$^1$H-NMR(CDCl3) δ (ppm) 1.26(6H, d, J=6.4 Hz), 1.40 (9H, s), 3.30–3.37(1H, m), 3.78(3H, s), 4.42(2H, s), 7.18 (1H, d, J=2.0 Hz), 7.34(1H, d, J=2.0 Hz).

Example 26

Final Step

Synthesis was performed in the same manner as the final step of Example 3 to yield the target compound as a yellow solid.

$^1$H-NMR(DSMO-d6) δ (ppm) 1.19(6H, d, J=6.4 Hz), 1.29(3H, t, J=7.2 Hz), 1.36(9H, s), 1.40(3H, t, J=7.2 Hz), 3.60~3.76(1H, m), 3.71(3H, s), 4.11(2H, q, J=7.2 Hz), 4.21(2H, q, J=7.2 Hz), 4.78(2H, s), 4.89(1H, d, J=8.4 Hz), 5.45(2H, s), 7.13(1H, s), 7.20(1H, s), 7.33(1H, s).

Example 27

1-(3-tert-Butyl-5-ethoxy-4-hydroxy-phenyl)-2-(5,6-diethoxy-7-fluoro-1-imino-1,3-dihydro-isoindol-2-yl)-ethanone hydrobromide

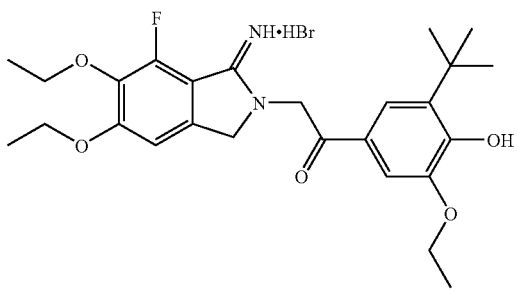

(Step 1) 1-(tert-Butyl)-2-(methoxymethoxy)benzene

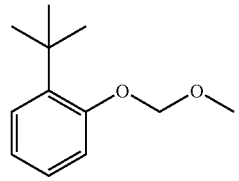

Sodium hydride (214 g, 4.90 mol) and chloromethyl methyl ether (394 g, 4.90) were gradually added to a solution of 2-tert-butylphenol (700 g, 4.67 mol) in dimethylformamide (3000 ml) while cooling on ice and the mixture was stirred at 0° C. for 2 hours. The reaction mixture was poured into ice water and extracted with ethyl acetate, and then the organic layer was washed with water and brine in that order and dried over anhydrous magnesium sulfate. The organic layer was concentrated under reduced pressure and the residue was purified by silica gel column chromatography (solvent: n-hexane-ethyl acetate) to yield the title compound (1013 g) as a light yellow oil.

$^1$H-NMR(CDCl3) δ (ppm) 1.42(9H, s), 3.52(3H, s), 5.24 (2H, s), 6.94(1H, t, J=8.2 Hz), 7.11(1H, d, J=8.2 Hz), 7.14(1H, t, J=8.2 Hz), 7.31(d, 1H, J=8.2 Hz).

(Step 2) 3-(tert-Butyl)-2-(methoxymethoxy)benzaldehyde

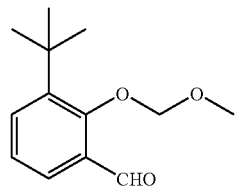

A 2.6 M hexane solution of n-BuLi was gradually added to a solution of the 1-(tert-butyl)-2-(methoxymethoxy)benzene (1013 g, 4.67 mol) and tetramethylethylenediamine (754 g, 6.5 ml) in dry ether while cooling on ice, and the mixture was stirred at room temperature for 3 hours. After recooling to 0° C., dimethylformamide (1000 ml, 14 mol) was gradually added and the mixture was stirred at room temperature for 1 hour. The reaction mixture was gradually added to ice water, extraction was performed with ethyl acetate, and the organic layer was washed with water and brine and then dried over anhydrous magnesium sulfate. The organic layer was concentrated under reduced pressure to yield a crude product of the title compound (1247 g) as a red oil.

$^1$H-NMR(CDCl3) δ (ppm) 1.43(9H, s), 3.64(3H, s), 5.03 (2H, s), 7.17(1H, t, J=8.2 Hz), 7.59(1H, d, J=8.2 Hz), 7.64(1H, d, J=8.2 Hz), 10.23(1H, s).

(Step 3) 5-Bromo-3-(tert-butyl)-2-hydroxybenzaldehyde

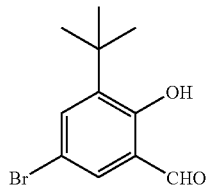

Bromine (747 g) was gradually added to a solution of the 3-(tert-butyl)-2-(methoxymethoxy)benzaldehyde (1247 g, 4.67 mol) in methanol (4000 ml) while cooling on ice. After stirring at 20° C. for 1 hour, the solvent was distilled off under reduced pressure, ethyl acetate was added to the residue, the mixture was washed with water, saturated sodium aqueous hydrogencarbonate and brine in that order and the organic layer was dried over anhydrous magnesium sulfate. The organic layer was concentrated under reduced pressure to yield a crude product of the title compound (1333 g) as a red oil.

$^1$H-NMR(CDCl3) δ (ppm) 1.42(9H, s), 3.62(3H, s), 5.03 (2H, s), 7.64(1H, s), 7.81(1H, s), 10.12(1H, s).

(Step 4) 5-Bromo-3-(tert-butyl)-2-(methoxymethoxy)benzaldehyde

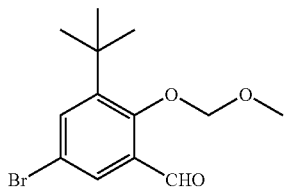

I-PrNEt$_2$ (834 g, 6.46 g) and chloromethyl methyl ether (451 g, 5.60 mol) were gradually added to a solution of the 5-bromo-3-(tert-butyl)-2-hydroxybenzaldehyde (1333 g, 4.67 mol) in methylene chloride (4000 ml) while cooling on ice, and the mixture was stirred at room temperature for 2 days. After first distilling off the solvent under reduced pressure, ethyl acetate was added to the residue, washing was performed twice with brine, the organic layer was dried over anhydrous magnesium sulfate and concentrated under reduced pressure, and the residue was purified by silica gel column chromatography (solvent: n-hexane-ethyl acetate) to yield the title compound (1338 g) as a light yellow oil.

$^1$H-NMR(CDCl3) δ (ppm) 1.40(9H, s), 3.61(3H, s), 5.02 (2H, s), 7.67(1H, s), 7.82(1H, s), 10.13(1H, s).

(Step 5) 5-Bromo-3-(tert-butyl)-2-(methoxymethoxy)phenol

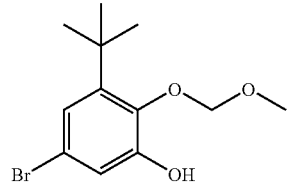

After adding 70% mCPBA (25 g) to a solution of 5-bromo-3-(tert-butyl)-2-(methoxymethoxy)benzaldehyde (30 g, 97 mmol) in methylene chloride (200 ml), the mixture was stirred at 50° C. for 2 hours. The organic layer was washed with a saturated sodium thiosulfate solution and saturated sodium hydrogencarbonate solution and then dried over anhydrous magnesium sulfate. After distilling off the solvent under reduced pressure, the residue was purified by silica gel column chromatography (solvent: n-hexane-ethyl acetate) to yield the title compound (17 g) as a light yellow oil.

$^1$H-NMR(CDCl3) δ (ppm) 1.30(9H, s), 3.68(3H, s), 4.96 (2H, s), 6.88(1H, s), 7.02(1H, s), 8.21(1H, s).

(Step 6) 5-Bromo-1-(tert-butyl)-3-ethoxy-2-(methoxymethoxy)benzene

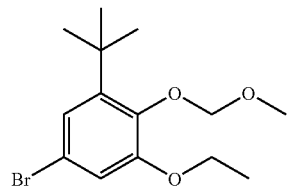

Cesium carbonate (10.05 g, 30.9 mmol) and EtI (2.58 ml, 32.2 mmol) were added to a solution of the 5-bromo-3-(tert-butyl)-2-(methoxymethoxy)phenol (7.76 g, 26.8 mmol) in acetonitrile and the mixture was stirred at room temperature for 3 hours. Ethyl acetate was added and the reaction mixture was washed with water and brine in that order. The organic layer was dried over anhydrous magnesium sulfate and then the residue was purified by silica gel column chromatography (solvent: n-hexane-ethyl acetate) to yield the title compound (6.5 g) as a yellow oil.

$^1$H-NMR(CDCl3) δ (ppm) 1.39(9H, s), 1.45(3H, t, J=7.2 Hz), 3.64(3H, s), 4.00(2H, q, J=7.2 Hz), 5.16(2H, s), 6.91 (1H, d, J=2.4 Hz), 7.04(1H, d, J=2.4 Hz).

(Step 7) 1-[3-(tert-Butyl)-5-ethoxy-4-hydroxyphenyl]-1-ethanone

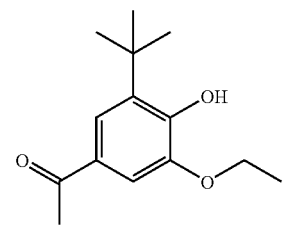

Aributyl(1-ethoxyvinyl)tin (7.77 g, 21.52 mmol) and Pd(PPh$_3$)$_4$ (1.18 g, 1.02 mmol) were added to a solution of the 5-bromo-1-(tert-butyl)-3-ethoxy-2-(methoxymethoxy)

benzene (6.5 g, 20.4 mmol) in toluene (68 ml) and the mixture was stirred at 100° C. for 18 hours. The reaction mixture was cooled to room temperature, ethyl acetate was added, the mixture was washed with 20% aqueous KF and filtered through celite, and the organic layer was dried over anhydrous magnesium sulfate and concentrated under reduced pressure. A 1 N HCl aqueous solution (15 ml) was added to a solution of the residue in methanol (80 ml), and the mixture was stirred at room temperature for 2 hours. Saturated sodium hydrogencarbonate solution was added to be basic and extraction was performed with ethyl acetate. The organic layer was dried over anhydrous magnesium sulfate and concentrated under reduced pressure, and the residue was purified by silica gel column chromatography (solvent: n-hexane-ethyl acetate) to yield the title compound (3.17 g) as colorless crystals.

$^1$H-NMR(CDCl3) δ (ppm) 1.43(9H, s), 1.48(3H, t, J=7.2 Hz), 2.56(3H, s), 4.18(2H, q, J=7.2 Hz), 6.54(s, 1H, ), 7.40(1H, s), 7.57(1H, s).

(Step 8) 2-Bromo-1-[3-(tert-butyl)-5-ethoxy-4-hydroxyphenyl]-1-ethanone

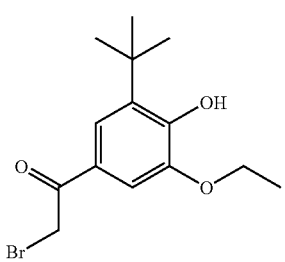

Tetra-n-butylammonium tribromide (321 mg, 0.666 mmol) was added to a solution of the 1-[3-(tert-butyl)-5-ethoxy-4-hydroxyphenyl]-1-ethanone (150 mg, 0.635 mmol) in methylene chloride-methanol (4 ml:1 ml) and the mixture was stirred at room temperature for 8 hours. After distilling off the solvent under reduced pressure, the residue was purified by silica gel column chromatography (solvent: n-hexane-ethyl acetate) to yield the title compound (60 mg) as colorless crystals.

$^1$H-NMR(CDCl3) δ (ppm) 1.43(9H, s), 1.49(3H, t, J=7.2 Hz), 4.19(2H, q, J=7.2 Hz), 4.41(2H, s), 6.63(1H, s), 7.42 (1H, d, J=2.0 Hz), 7.60(1H, d, J=2.0 Hz).

Example 27

Final Step

A solution of the 2-bromo-1-[3-(tert-butyl)-5-ethoxy-4-hydroxyphenyl]-1-ethanone (55 mg, 0.174 mmol) and 5,6-diethoxy-4-fluoro-1H-3-isoindoleamine (40 mg, 0.166 mmol) in dimethylformamide was stirred at room temperature for 7 hours. The solvent was distilled off under reduced pressure and the residue was purified by NAM silica gel (ethyl acetate:methanol) to yield the target compound (62 mg) as colorless crystals.

$^1$H-NMR(DSMO-d6) δ (ppm) 1.29(3H, t, J=7.0 Hz), 1.36–1.41(15H, m), 4.08–4.15(4H, m), 4.21(2H, q, J=7.0 Hz), 4.78(2H, s), 5.44(2H, s), 7.33(1H, s), 7.42(1H, s), 7.50(1H, s), 9.00(1H, brs), 9.30(1H, brs), 9.44(1H, brs).

MS: m/e (ESI) 473.2 (MH+)

Example 28

1-(3-tert-Butyl-5-ethoxy-4-methoxy-phenyl)-2-(5,6-diethoxy-7-fluoro-1-imino-1,3-dihydro-isoindol-2-yl)-ethanone hydrobromide

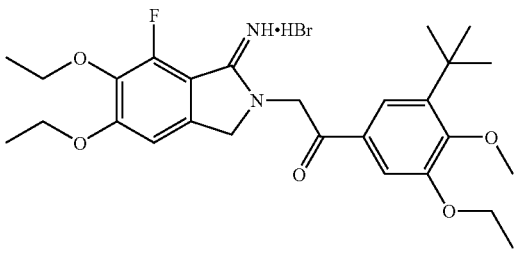

(Step 1) 2-Bromo-1-[3-(tert-butyl)-5-ethoxy-4-methoxyphenyl]-1-ethanone

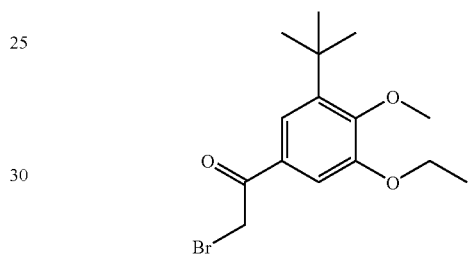

Cesium carbonate (662 mg, 2.03 mmol) and methyl iodide (0.14 ml, 2.20 mmol) were added to a solution of 1-[3-(tert-butyl)-5-ethoxy-4-hydroxyphenyl]-1-ethanone (400 mg, 1.69 mmol) in acetonitrile and the mixture was stirred at room temperature for 10 hours. Water was added to the reaction mixture, extraction was performed with ethyl acetate, the organic layer was washed with brine and dried over anhydrous magnesium sulfate, and the solvent was distilled off under reduced pressure. Tetra-n-butylammonium tribromide (841 mg, 1.74 mmol) was added to a solution of the residue in methylene chloride-methanol (8 ml:2 ml) and the mixture was stirred at room temperature for 8 hours. After distilling off the solvent under reduced pressure, the residue was purified by silica gel column chromatography (solvent: n-hexane-ethyl acetate) to yield the title compound (491 mg) as a colorless oil.

$^1$H-NMR(CDCl3) δ (ppm) 1.40(9H, s), 1.50(3H, t, J=7.2 Hz), 3.97(3H, s), 4.12(2H, q, J=7.2 Hz), 4.42(2H, s), 7.46 (1H, d, J=2.0 Hz), 7.59(1H, d, J=2.0 Hz).

Example 28

Final Step

A solution of 2-bromo-1-[3-(tert-butyl)-5-ethoxy-4-methoxyphenyl]-1-ethanone (52 mg, 0.159 mmol) and 5,6-diethoxy-4-fluoro-1H-3-isoindoleamine (33 mg, 0.139 mmol) in dimethylformamide was stirred at room temperature for 12 hours. After distilling off the solvent under reduced pressure, the residue was purified by NAM silica gel (methylene chloride-methanol) to yield the target compound (40.6 mg) as light orange crystals.

$^1$H-NMR(DSMO-d6) δ (ppm) 1.29(3H, t, J=7.2 Hz), 1.36(9H, s), 1.38–1.43(6H, m), 3.89(3H, s), 4.08–4.24(6H, m), 4.79(2H, s), 5.48(2H, s), 7.33(1H, s), 7.51(2H, d, J=5.2 Hz), 9.03(1H, brs), 9.26(1H, brs).

MS: m/e (ESI) 487.2 (MH+)

Example 29

2-tert-butyl-4-[2-(5,6-diethoxy-7-fluoro-1-imino-1,3-dihydro-isoindol-2-yl)-acetyl]-6-ethoxy-phenyl ethylcarbamate hydrobromide

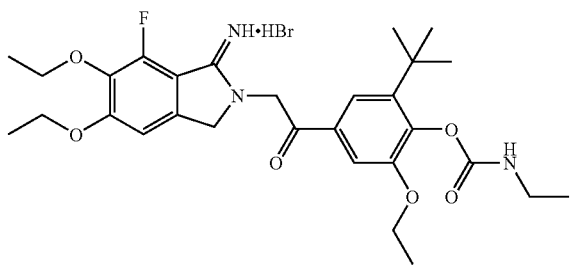

(Step 1) 4-(2-Bromoacetyl)-2-(tert-butyl)-6-ethoxyphenyl N-ethylcarbamate

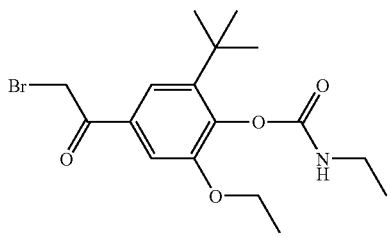

Triethylamine (0.02 ml, 0.130 mmol) and ethyl isocyanate (0.053 ml, 0.677 ml) were added to a solution of 1-[3-(tert-butyl)-5-ethoxy-4-hydroxyphenyl]-1-ethanone (100 mg, 0.423 mmol) in methylene chloride (4.2 ml) and the mixture was stirred at room temperature for 2 days. Ethyl acetate was added, and then the reaction mixture was washed with water, the organic layer was dried over anhydrous magnesium sulfate and the solvent was distilled off under reduced pressure. Tetra-n-butylammonium tribromide (214 mg, 444 mmol) was added to a solution of the residue in methylene chloride-methanol (5 ml:1.2 ml) and the mixture was stirred at room temperature for 8 hours. After distilling off the solvent under reduced pressure, the residue was purified by silica gel column chromatography (solvent: n-hexane-ethyl acetate) to yield the title compound (142 mg) as colorless crystals.

$^1$H-NMR(CDCl3) δ (ppm)

Example 29

Final Step

Synthesis was performed in the same manner as the final step of Example 3 to yield the target compound as a yellow solid.

$^1$H-NMR(DSMO-d6) δ (ppm) 1.08(3H, t, J=7.0 Hz), 1.27–1.33(15H, m), 1.40(3H, t, J=6.8 Hz), 3.06–3.14(2H, m), 4.03–4.14(4H, m), 4.21(2H, q, J=7.0 Hz), 4.80(2H, s), 5.50(2H, s), 7.34(1H, s), 7.51(1H, s), 7.55(1H, s), 7.86(1H, t, J=4.8 Hz), 9.02(1H, brs), 9.33(1H, brs).

MS: m/e (ESI) 544.3 (MH+)

Example 30

2-(5,6-Diethoxy-7-fluoro-1-imino-1,3-dihydro-isoindol-2-yl)-1-[3-dimethylamino-4-methoxy-5-(1-methoxy-1-methyl-ethyl)-phenyl]-ethanone hydrobromide

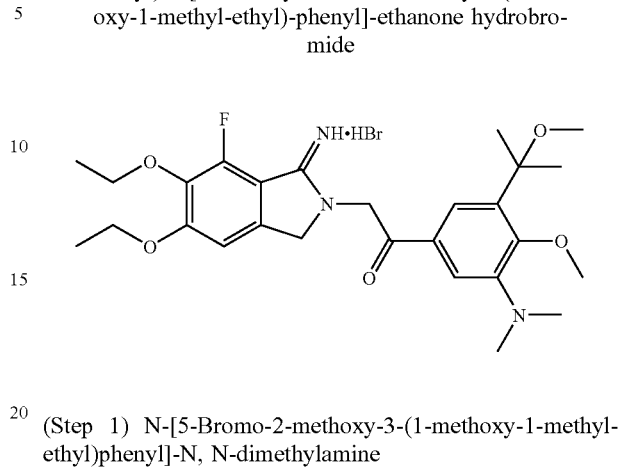

(Step 1) N-[5-Bromo-2-methoxy-3-(1-methoxy-1-methyl-ethyl)phenyl]-N, N-dimethylamine

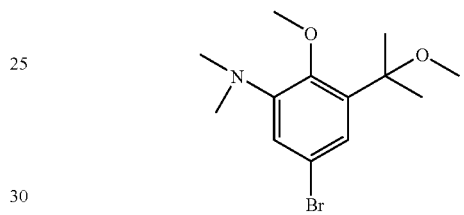

After dissolving 2-[5-bromo-3-(dimethylamino)-2-methoxyphenyl]-2-propanol (410 mg) in 100 mL of methanol-hydrochloric acid, the solution was heated to reflux for 14 hours. The reaction mixture was cooled to room temperature, saturated aqueous sodium hydrogencarbonate was added for neutralization, water was added and extraction was performed with ethyl acetate. The organic layer was washed with brine and then dried over anhydrous magnesium sulfate. After distilling off the solvent under reduced pressure, the residue was purified by silica gel column chromatography (solvent: n-hexane-ethyl acetate) to yield the title compound (370 mg) as an oil. $^1$H-NMR (CDCl3) δ: 1.57(3H, s), 1.60(3H, s), 2.77(6H, s), 3.40(3H, s), 3.77(3H, s), 6.95(1H, d, J=2 Hz), 7.16(1H, d, J=2 Hz).

(Step 2) 2-Bromo-1-[3-(dimethylamino)-4-methoxy-5-(1-methoxy-1-methylethyl)phenyl]-1-ethanone

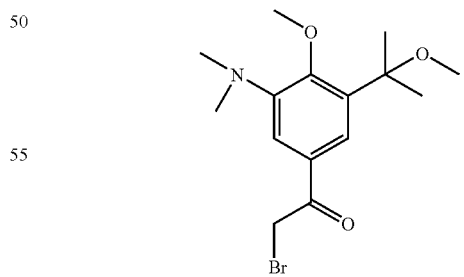

Synthesis was performed in the same manner as Step 7 of Example 8 to yield the title compound as a light yellow solid.

$^1$H-NMR (CDCl3) δ: 1.60(6H, s), 2.80(6H, s), 3.23(3H, s), 3.86(3H, s), 4.42(2H, s), 7.52(1H, d, J=2 Hz), 7.72(1H, d, J=2 Hz).

Example 30

Final Step $^1$H-NMR(DSMO-d6) δ (ppm) 1.29(3H, t, J=7 Hz), 1.40 (3H, t, J=7 Hz), 1.53(6H, s), 2.76(6H, s), 3.16(3H, s), 3.80(3H, s), 4.12(2H, q, J=7 Hz), 4.21(2H, q, J=7 Hz), 4.80(2H, s), 5.49(2H, s), 7.34(1H, br.s), 7.46(1H, br.s), 7.67(1H, br.s), 9.05(1H, br.s), 9.31(1H, br.s).

MS: m/e (ESI) 502.2 (MH+)

The compounds of the following examples were synthesized by the same method as the final step of Example 3 above, from various 2-imino-dihydropyrrolo[3,4-b]pyridine or 1-iminoisoindoline derivatives and various 2-bromo-1-ethanone derivatives, to obtain the respective target compounds as light yellow to yellow solids.

Example 31

1-(8-tert-Butyl-4-methyl-3,4-dihydro-2H-benzo[1,4]oxazin-6-yl)-2-(5,6-diethoxy-7-fluoro-1-imino-1,3-dihydro-isoindol-2-yl)-ethanone hydrobromide

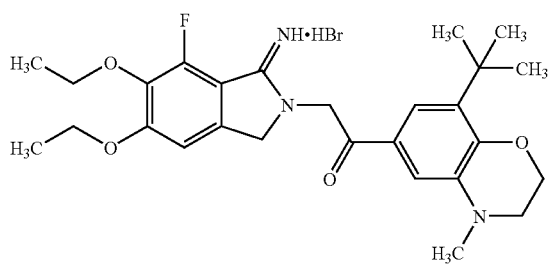

$^1$H-NMR(DSMO-d6) δ: 1.28(3H, t, J=7.1 Hz), 1.34(9H, s), 1.48(3H, t, J=7.1 Hz), 3.23–3.37(2H, m), 2.90(3H, s), 4.12(2H, q, J=7.1 Hz), 4.22(2H, q, J=7.1 Hz), 4.33(2H, brs), 4.79(2H, s), 5.46(2H, s), 7.16(1H, s), 7.27(1H, s), 7.33(1H, s), 9.04(1H, brs), 9.32(1H, brs).

MS: m/e (ESI) 484.3 (MH+)

Example 32

2-[2-(3-tert-Butyl-4,5-dimethoxy-phenyl)-2-oxo-ethyl]-6-ethoxy-3-imino-2,3-dihydro-1H-isoindole-5-carboxylic acid methylamide hydrobromide

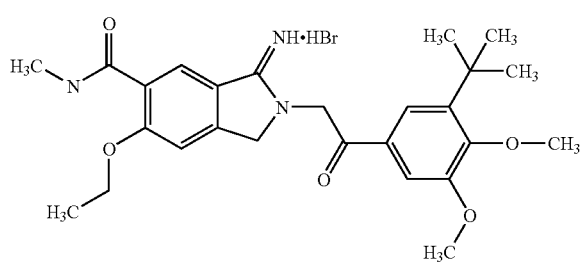

$^1$H-NMR(DSMO-d6) δ: 1.38(9H, s), 1.43(3H, t, J=7 Hz), 2.85(3H, d, J=5 Hz), 3.89(3H, s), 3.91(3H, s), 4.30(2H, q, J=7 Hz), 4.87(2H, s), 5.54(2H, s), 7.55(2H, s), 7.56(1H, s), 8.22(1H, q, J=8 Hz), 8.58(1H, s).

Example 33

2-[2-(3-tert-Butyl-4-hydroxy-5-isopropoxy-phenyl)-2-oxo-ethyl]-6-ethoxy-3-imino-2,3-dihydro-1H-isoindole-5-carboxylic acid methylamide hydrobromide

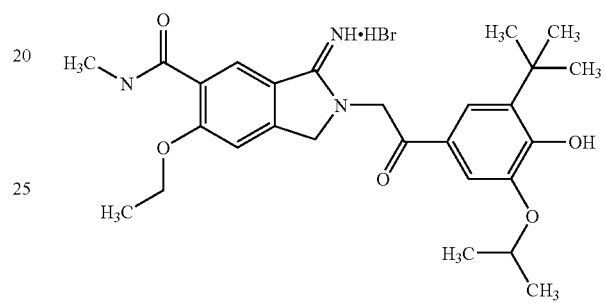

$^1$H-NMR(DSMO-d6) δ: 1.33(6H, d, J=6.0 Hz), 1.41(9H, s), 1.44(3H, t, J=7.2 Hz), 2.85(3H, d, J=4.4 Hz), 4.30(2H, q, J=7.2 Hz), 4.67(1H, m), 4.86(2H, s), 5.48(2H, s), 7.49(1H, s), 7.52(1H, s), 7.55(1H, s), 8.22(1H, m), 8.59(1H, s), 9.24(1H, s), 9.87(1H, s).

Example 34

6-[2-(8-tert-Butyl-4-methyl-3,4-dihydro-2H-benzo[1,4]oxazin-6-yl)-2-oxo-ethyl]-3-ethoxy-7-imino-6,7-dihydro-5H-pyrrolo[3,4-b]pyridine-2-carboxylic acid methylamide hydrochloride

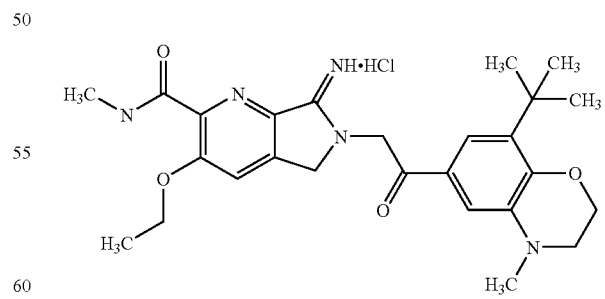

$^1$H-NMR(DSMO-d6) δ: 1.36(9H, s), 1.38(3H, t, J=6.8 Hz), 2.79(3H, d, J=4.0 Hz), 2.93(3H, s), 3.33(2H, s), 4.26(2H, q, J=6.8 Hz), 4.36(2H, s), 4.89(2H, s), 5.57(2H, s), 7.20(1H, s), 7.29(1H, s), 8.01(1H, s), 8.59(1H, q, J=4.0 Hz), 9.55(1H, s), 9.97(1H, s).

Example 35

2-[2-(7-tert-Butyl-3-methyl-3H-benzimidazol-5-yl)-2-oxo-ethyl]-6-ethoxy-3-imino-2,3-dihydro-1H-isoindole-5-carboxylic acid methylamide hydrobromide

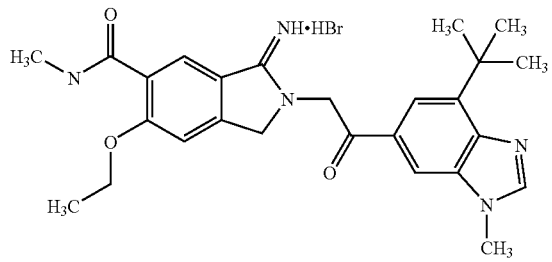

$^1$H-NMR(DSMO-d6) δ: 1.42(3H, t, J=7 Hz), 1.55(9H, s), 2.74(3H, d, J=4 Hz), 3.94(3H, s), 4.29(2H, q, J=7 Hz), 4.89(2H, s), 5.60(2H, s), 7.55(1H, s), 7.71(1H, s), 8.22(1H, q, J=4 Hz), 8.23(1H, s), 8.42(1H, s), 8.58(1H, s).
MS: m/e (ESI) 462.0 (MH+)

Example 36

2-[2-(3-tert-Butyl-5-dimethylamino-4-hydroxy-phenyl)-2-oxo-ethyl]-6-ethoxy-3-imino-2,3-dihydro-1H-isoindole-5-carboxylic acid methylamide hydrobromide

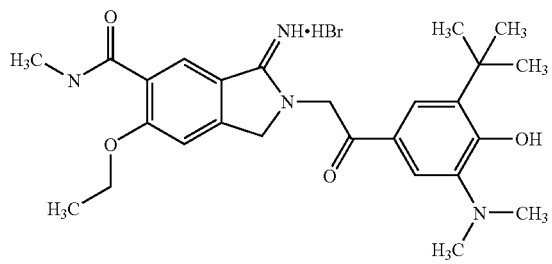

$^1$H-NMR(DSMO-d6) δ: 1.41(12H, m), 2.63(6H, s), 2.84 (2H, s), 4.30(2H, q, J=6.8 Hz), 4.86(2H, s), 5.47(2H, s), 7.56(1H, s), 7.66(1H, s), 7.71(1H, s), 8.22(1H, s), 8.57(1H, s), 9.17(1H, s), 9.84(1H, s).

Example 37

5-{2-tert-Butyl-4-[2-(2-cyclopropyl-7-imino-5,7-dihydro-pyrrolo[3,4-b]pyridin-6-yl)-acetyl]-6-(pyrrolidin-1-yl)-phenoxy}-pentanoic acid trifluoroacetate

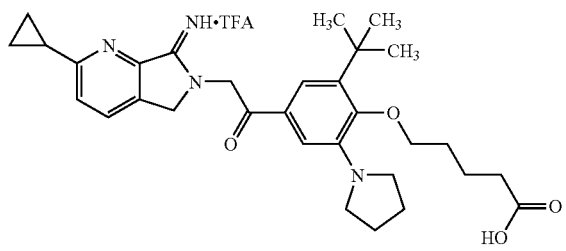

$^1$H-NMR(DSMO-d6) δ: 1.00–1.15(4H, m), 1.38(9H, s), 1.59–1.85(4H, m), 2.23–2.37(3H, m), 3.03–3.20(4H, m), 3.78–3.88(2H, m), 4.81(2H, s), 5.53(2H, s), 7.36(1H, s), 7.46(1H, s), 7.72(1H, d, J=8.0 Hz), 8.09(1H, d, J=8.0 Hz), 9.41–9.49(1H, m), 9.61–9.70(1H, m).
MS: m/e (ESI) 533.3 (MH+)

Example 38

5-(2-tert-Butyl-4-[2-(7-fluoro-1-imino-5,6-dimethoxy-1,3-dihydro-isoindol-2-yl)-acetyl]-6-(pyrrolidin-1-yl)-phenoxy)-pentanoic acid trifluoroacetate

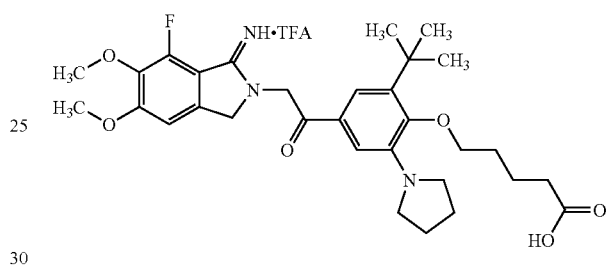

$^1$H-NMR(DSMO-d6) δ: 1.38(9H, s), 1.55–1.99(8H, m), 2.17–2.36(2H, m), 2.94–3.20(4H, m), 3.57–4.27(8H and H$_2$O, m), 4.79(2H, s), 5.47(2H, s), 7.36(2H, s), 7.45(1H, s), 9.01–9.11(1H, m), 9.22–9.35(1H, m).

Example 39

2-[2-(3-tert-Butyl-5-dimethylamino-4-methoxy-phenyl)-2-oxo-ethyl]-6-ethoxy-3-imino-2,3-dihydro-1H-isoindole-5-carboxylic acid methylamide hydrobromide

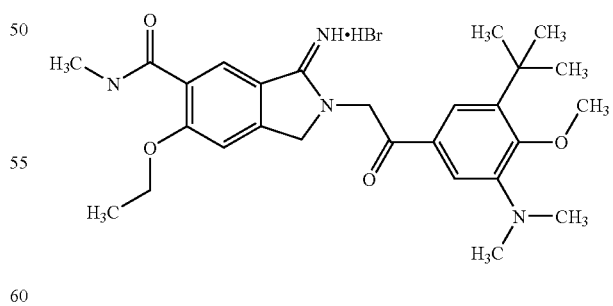

$^1$H-NMR(DSMO-d6) δ: 1.39(12H, m), 2.77(6H, s), 2.84 (3H, s), 3.85(3H, s), 4.30(2H, q, J=7.2 Hz), 4.86(2H, s), 5.52(2H, s), 7.48(1H, s), 7.56(2H, s), 8.22(1H, s), 8.57(1H, s), 9.18(1H, s), 9.85(1H, s).

Example 40

2-(1-{3-tert-Butyl-5-[2-(7-fluoro-1-imino-5,6-dimethoxy-1,3-dihydro-isoindol-2-yl)-acetyl]-2-methoxy-phenyl}-pyrrolidin-3-yloxy)-butyric acid trifluoroacetate

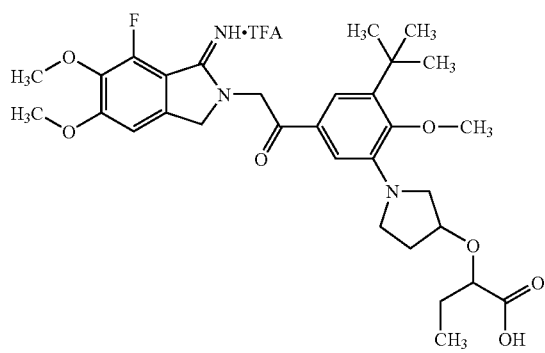

$^1$H-NMR(DSMO-d6) δ: 0.92(3H, t, J=7.6 Hz), 1.44(9H, s), 1.61–1.83(2H, m), 2.10–2.24(2H, m), 3.09–3.17(1H, m), 3.19–3.26(1H, m), 3.41–3.56(2H, m), 3.74(3H, s), 3.92(1H, dd, J=7.6 and4.8 Hz), 3.94(3H, s), 4.02(3H, s), 4.25–4.33 (1H, m), 4.85(2H, s), 5.45(2H, s), 7.24(1H, s), 7.46(1H, d, J=2.0 Hz), 7.60(1H, d, J=2.0 Hz).

Example 41

2-(1-{3-tert-Butyl-5-[2-(7-fluoro-1-imino-5,6-dimethoxy-1,3-dihydro-isoindol-2-yl)-acetyl]-2-methoxy-phenyl}-pyrrolidin-3-yloxy)-butyric acid trifluoroacetate

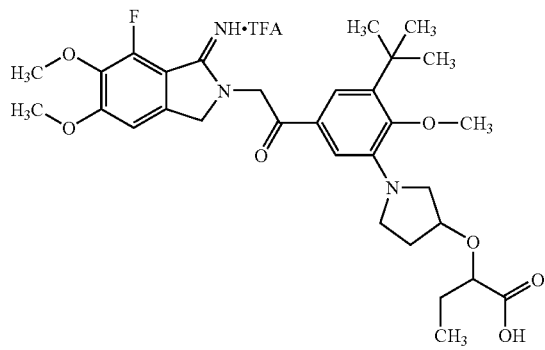

$^1$H-NMR(DSMO-d6) δ: 1.00(3H, t, J=7.6 Hz), 1.44(9H, s), 1.63–1.87(2H, m), 2.04–2.19(2H, m), 3.13–3.22(1H, m), 3.22–3.30(1H, m), 3.40–3.57(2H, m), 3.94(3H, s), 3.98(1H, dd, J=7.6 and4.4 Hz), 4.02(3H, s), 4.25–4.35 (1H, m), 4.86(2H, s), 5.45(2H, s), 7.24(1H, s), 7.46(1H, d, J=2.0 Hz), 7.60(1H, d, J=2.0 Hz).

Example 42

1-(3-tert-Butyl-5-dimethylamino-4-methoxy-phenyl)-2-(7-fluoro-1-imino-5,6-dimethoxy-1,3-dihydro-isoindol-2-yl)-ethanone hydrobromide

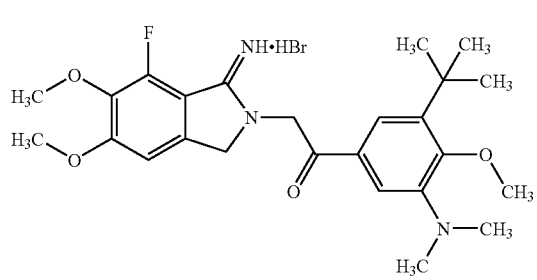

$^1$H-NMR(DSMO-d6) δ: 1.37(9H, s), 2.75(6H, s), 3.82 (3H, s), 3.87(3H, s), 3.95(3H, s), 4.80(2H, s), 5.49(2H, s), 7.37(1H, s), 7.45(1H, d, J=2.0 Hz), 7.53(1H, d, J=2.0 Hz), 9.06(1H, brs), 9.28(1H, brs).

Example 43

2-[2-(3-tert-Butyl-5-dimethylamino-4-methoxy-phenyl)-2-oxo-ethyl]-6-dimethylamino-3-imino-2,3-dihydro-1H-isoindole-5-carboxylic acid methylamide hydrobromide

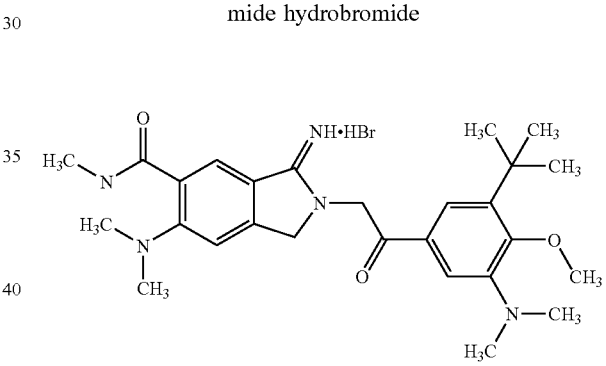

$^1$H-NMR(DSMO-d6) δ: 1.37(9H, s), 2.75(6H, s), 2.77 (3H, d, J=4.0 Hz), 2.92(6H, s), 3.82(3H, s), 4.73(2H, s), 5.44(2H, s), 7.15(1H, s), 7.45(1H, s), 7.53(1H, s), 8.06 (1H, ), 8.36(1H, q, J=4.0 Hz), 8.93(1H, brs), 9.49(1H, brs).

Example 44

6-[2-(3-tert-Butyl-5-dimethylamino-4-methoxy-phenyl)-2-oxo-ethyl]-3-ethoxy-7-imino-6,7-dihydro-5H-pyrrolo[3,4-b]pyridine-2-carboxylic acid methylamide hydrochloride

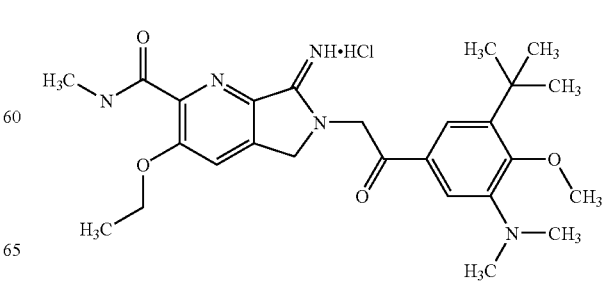

¹H-NMR(DSMO-d6) δ: 1.36(3H, t, J=6.8 Hz), 1.37(9H, s), 2.76(6H, s), 2.77(3H, d, J=4.0 Hz), 3.83(3H, s), 4.24(2H, q, J=6.8 Hz), 4.85(2H, s), 5.60(2H, s), 7.48(1H, s), 7.54(1H, s), 8.00(1H, s), 8.57(1H, q, J=4.0 Hz), 9.56(1H, brs), 9.97(1H, brs).

Example 45

2-[2-(3-tert-Butyl-5-ethoxy-4-methoxy-phenyl)-2-oxo-ethyl]-6-dimethylamino-3-imino-2,3-dihydro-1H-isoindole-5-carboxylic acid methylamide hydrobromide

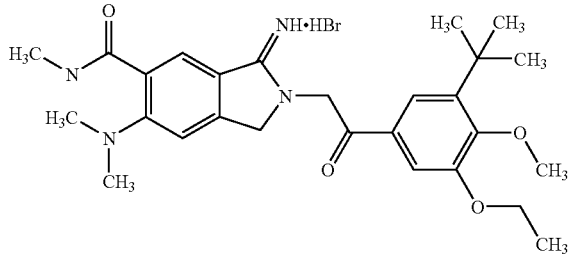

¹H-NMR(DSMO-d6) δ: 1.36(9H, S), 1.41(3H, t, J=6.8 Hz), 2.77(3H, d, J=4.4 Hz), 2.92(6H, s), 3.89(3H, s), 4.13(2H, q, J=6.8 Hz), 4.74(2H, s), 5.45(2H, s), 7.15(1H, s), 7.51(2H, d, J=7.6 Hz), 8.07(1H, s), 8.35–8.38(1H, m), 8.94(1H, brs), 9.54(1H, brs).
MS: m/e (ESI) 481.2 (MH+)

Example 46

2-[2-(3-tert-Butyl-5-ethoxy-4-methoxy-phenyl)-2-oxo-ethyl]-6-ethoxy-3-imino-2,3-dihydro-1H-isoindole-5-carboxylic acid methylamide hydrobromide

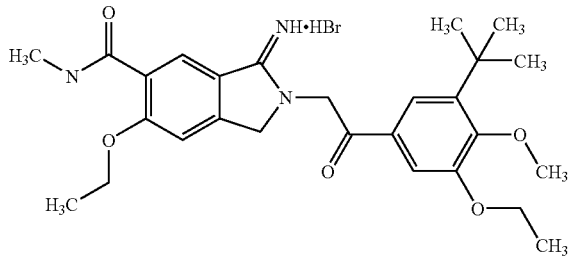

1H-NMR(DSMO-d6) δ: 1.36(9H, S), 1.39–1.43(6H, m), 2.82(3H, d, J=4.8 Hz), 3.89(3H, s), 4.13(2H, q, J=7.0 Hz), 4.28(2H, q, J=7.0 Hz), 4.85(2H, s), 5.50(2H, s), 7.51–7.54(3H, m), 8.21(1H, q, J=4.8 Hz), 8.56(1H, s), 9.20(1H, brs), 9.85(1H, brs).
MS: m/e (ESI) 482.2 (MH+)

Example 47

6-[2-(3-tert-Butyl-5-ethoxy-4-methoxy-phenyl)-2-oxo-ethyl]-3-ethoxy-7-imino-6,7-dihydro-5H-pyrrolo[3,4-b]pyridine-2-carboxylic acid methylamide trifluoroacetate

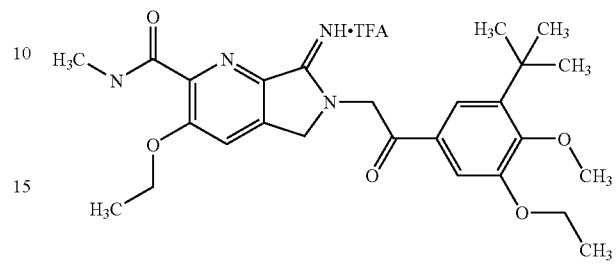

¹H-NMR(DSMO-d6) δ: 1.36(9H, S), 1.40–1.43(6H, m), 2.78(3H, d, J=4.8 Hz), 3.90(3H, s), 4.13(2H, q, J=7.0 Hz), 4.24(2H, q, J=7.0 Hz), 4.89(2H, s), 5.54(2H, s), 7.50–7.52(2H, m), 8.00(1H, s), 8.53(1H, m), 9.42(1H, brs), 9.96(1H, brs).
MS: m/e (ESI) 483.1 (MH+)

Example 48

{3-tert-Butyl-5-[2-(7-fluoro-1-imino-5,6-dimethoxy-1,3-dihydro-isoindol-2-yl)-acetyl]-2-methoxy-phenoxy}-acetonitrile hydrobromide

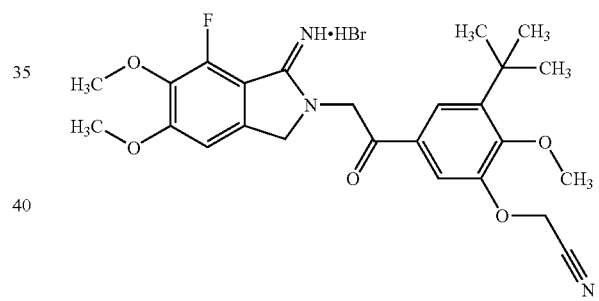

¹H-NMR(DSMO-d6) δ: 1.37(9H, s), 3.87(3H, s), 3.89(3H, s), 3.95(3H, s), 4.83(2H, s), 5.34(2H, s), 5.51(2H, s), 7.37(1H, s), 7.64(1H, s), 7.70(1H, s), 9.10(1H, brs), 9.37(1H, brs).

Example 49

4-{3-tert-Butyl-5-[2-(7-fluoro-1-imino-5,6-dimethoxy-1,3-dihydro-isoindol-2-yl)-acetyl]-2-methoxy-phenoxy}-butyronitrile hydrobromide

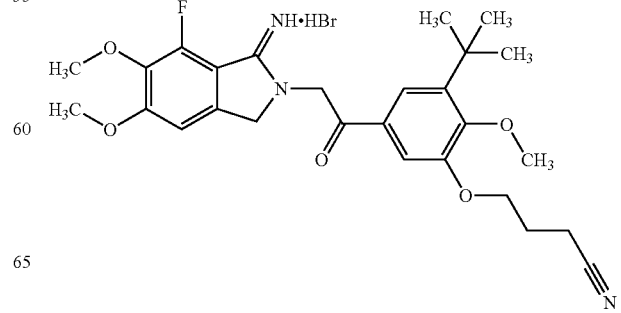

¹H-NMR(DSMO-d6) δ: 1.37(9H, s), 2.07–2.16(2H, m), 2.67–2.75(2H, m), 3.87(3H, s), 3.90(3H, s), 3.95(3H, s), 4.11–4.18(2H, m), 4.82(2H, s), 5.51(2H, s), 7.37(1H, s), 7.49–7.59(2H, m), 9.00–9.17(1H, brs), 9.27–9.40(1H, m).

Example 50

2-[2-(3-tert-Butyl-5-cyanomethoxy-4-methoxy-phenyl)-2-oxo-ethyl]-6-dimethylamino-3-imino-2,3-dihydro-1H-isoindole-5-carboxylic acid methylamide hydrobromide

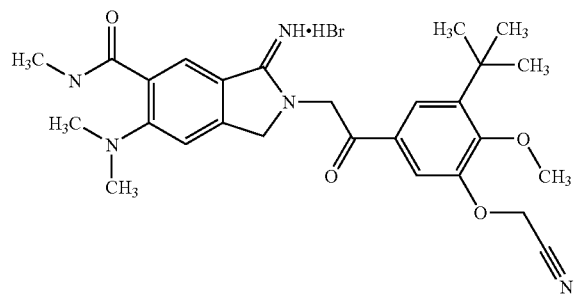

¹H-NMR(DSMO-d6) δ: 1.37(9H, s), 2.73–2.82(3H, m), 2.91(6H, s), 3.89(3H, s), 4.78(2H, s), 5.33(2H, s), 5.46(2H, s), 7.15(1H, s), 7.65(1H, s), 7.69(1H, s), 8.07(1H, s), 8.31–8.46(1H, m), 8.97(1H, brs), 9.55(1H, brs).

Example 51

2-{2-[3-tert-Butyl-5-(3-cyano-propoxy)-4-methoxy-phenyl]-2-oxo-ethyl}-6-dimethylamino-3-imino-2,3-dihydro-1H-isoindole-5-carboxylic acid methylamide hydrobromide

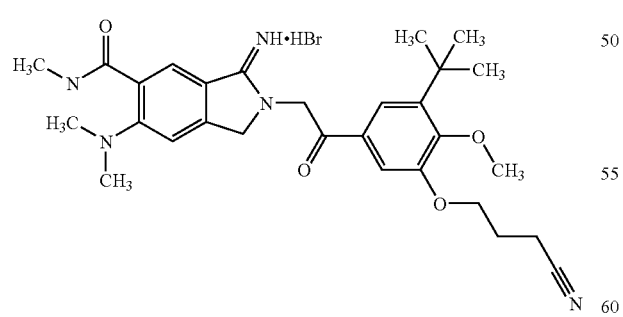

¹H-NMR(DSMO-d6) δ: 1.36(9H, s), 2.06–2.17(2H, m), 2.71(2H, t, J=7.6 Hz), 2.77(3H, d, J=4.8 Hz), 2.91(6H, s), 3.89(3H, s), 4.24(2H, t, J=6.0 Hz), 4.74(2H, s), 5.45(2H, s), 7.15(1H, s), 7.53(1H, s), 7.55(1H, s), 8.07(1H, s), 8.33–8.41(1H, m), 8.95(1H, brs), 9.55(1H, brs).

Example 52

2-[2-(8-tert-Butyl-4-cyanomethyl-3,4-dihydro-2H-benzo[1,4]oxazin-6-yl)-2-oxo-ethyl]-6-ethoxy-3-imino-2,3-dihydro-1H-isoindole-5-carboxylic acid methylamide trifluoroacetate

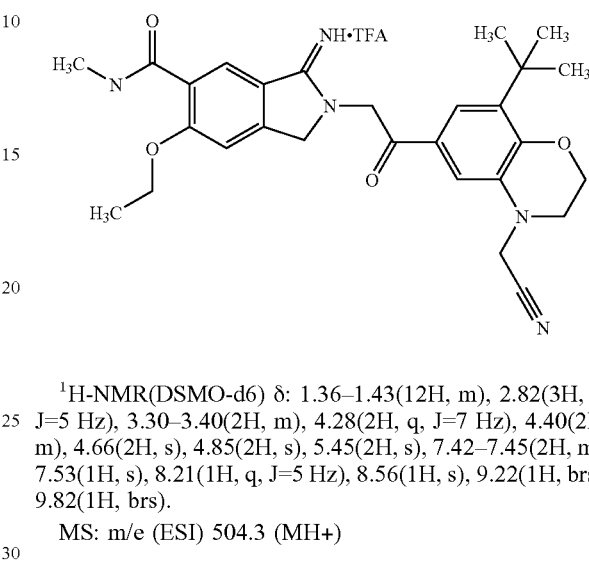

¹H-NMR(DSMO-d6) δ: 1.36–1.43(12H, m), 2.82(3H, d, J=5 Hz), 3.30–3.40(2H, m), 4.28(2H, q, J=7 Hz), 4.40(2H, m), 4.66(2H, s), 4.85(2H, s), 5.45(2H, s), 7.42–7.45(2H, m), 7.53(1H, s), 8.21(1H, q, J=5 Hz), 8.56(1H, s), 9.22(1H, brs), 9.82(1H, brs).
MS: m/e (ESI) 504.3 (MH+)

Example 53

6-[2-(8-tert-Butyl-4-cyanomethyl-3,4-dihydro-2H-benzo[1,4]oxazin-6-yl)-2-oxo-ethyl]-3-ethoxy-7-imino-6,7-dihydro-5H-pyrrolo[3,4-b]pyridine-2-carboxylic acid methylamide trifluoroacetate

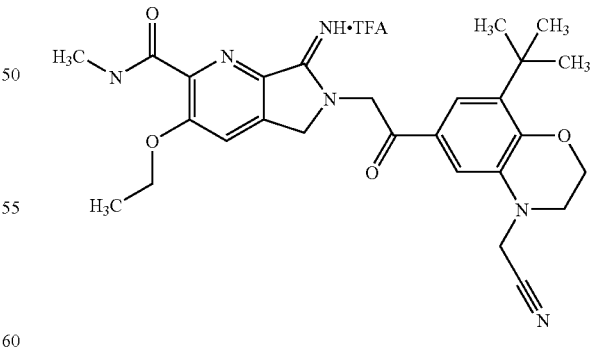

¹H-NMR(DSMO-d6) δ: 1.33–1.38(12H, s), 2.78(3H, d, J=5 Hz), 3.30–3.40(2H, m), 4.25(2H, q, J=7 Hz), 4.40(2H, m), 4.66(2H, s), 4.89(2H, s), 5.49(2H, s), 7.40–7.43(2H, m), 7.99(1H, s), 8.53(1H, q, J=5 Hz), 9.46(1H, brs), 9.93(1H, brs).
MS: m/e (ESI) 505.3 (MH+)

Example 54

{8-tert-Butyl-6-[2-(7-fluoro-1-imino-5,6-dimethoxy-1,3-dihydro-isoindol-2-yl)-acetyl]-2,3-dihydro-benzo[1,4]oxazin-4-yl}-acetonitrile trifluoroacetate

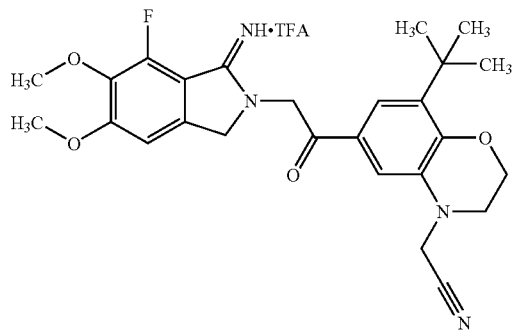

1H-NMR(DSMO-d6) δ: 1.36(9H, s), 3.30–3.40(2H, m), 3.87(3H, s), 3.95(3H, s), 4.40(2H, m), 4.66(2H, s), 4.82(2H, s), 5.45(2H, s), 7.36(1H, s), 7.40–7.42(2H, m), 9.06(1H, brs), 9.35(1H, brs).

MS: m/e (ESI) 481.3 (MH+)

Example 56

2-[2-(8-tert-Butyl-4-cyanomethyl-3,4-dihydro-2H-benzo[1,4]oxazin-6-yl)-2-oxo-ethyl]-6-dimethylamino-3-imino-2,3-dihydro-1H-isoindole-5-carboxylic acid methylamide trifluoroacetate

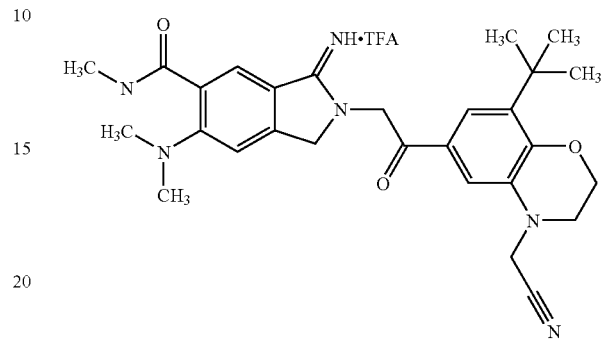

¹H-NMR(DSMO-d6) δ: 1.36(9H, s), 2.77(3H, d, J=4 Hz), 2.91(6H, s), 3.30–3.40(2H, m), 4.40(2H, m), 4.66(2H, s), 4.75(2H, s), 5.41(2H, s), 7.15(1H, s), 7.41–7.43(2H, m), 8.07(1H, s), 8.37(1H, q, J=4 Hz), 8.98(1H, brs), 9.53(1H, brs).

MS: m/e (ESI) 503.4 (MH+)

Example 55

{8-tert-Butyl-6-[2-(2-cyclopropyl-7-imino-5,7-dihydro-pyrrolo[3,4-b]pyridin-6-yl)-acetyl]-2,3-dihydro-benzo[1,4]oxazin-4-yl}-acetonitrile trifluoroacetate

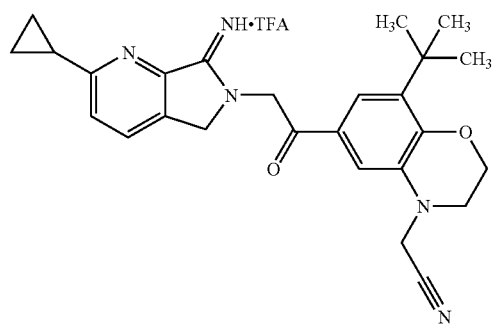

¹H-NMR(DSMO-d6) δ: 1.06–1.11(4H, m), 1.36(9H, s), 2.32(1H, m), 3.30–3.40(2H, m), 4.40(2H, m), 4.66(2H, s), 4.83(2H, s), 5.51(2H, s), 7.41–7.44(2H, m), 7.72(1H, d, J=8 Hz), 8.09(1H, d, J=8 Hz), 9.52, (1H, brs), 9.64(1H, brs).

MS: m/e (ESI) 444.3 (MH+)

Example 57

2-[2-(3-tert-Butyl-5-cyanomethoxy-4-methoxy-phenyl)-2-oxo-ethyl]-6-ethoxy-3-imino-2,3-dihydro-1H-isoindole-5-carboxylic acid methylamide hydrobromide

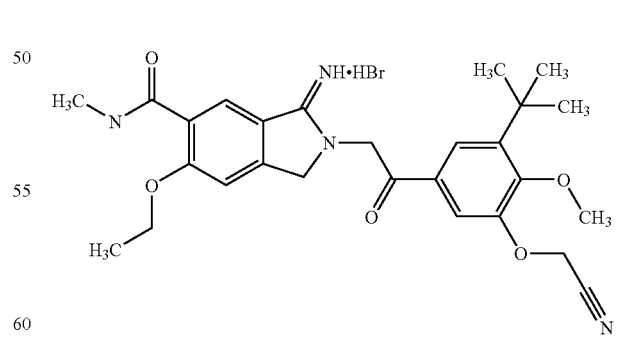

¹H-NMR(DSMO-d6) δ: 1.38(9H, s), 1.42(3H, t, J=6.8 Hz), 2.83(3H, d, J=4.8 Hz), 3.89(3H, s), 4.29(2H, q, J=6.8 Hz), 4.86(2H, s), 5.34(2H, s), 5.50(2H, s), 7.54(1H, s), 7.65(1H, s), 7.71(1H, s), 8.15–8.30(1H, m), 8.56(1H, s), 9.14–9.26(1H, m), 9.77–9.93(1H, m).

Example 58

2-{2-[3-tert-Butyl-5-(3-cyano-propoxy)-4-methoxy-phenyl]-2-oxo-ethyl}-6-ethoxy-3-imino-2,3-dihydro-1H-isoindole-5-carboxylic acid methylamide hydrobromide

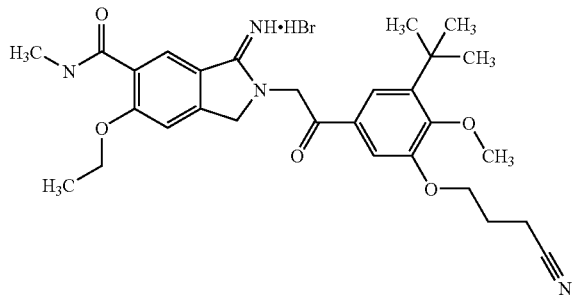

$^1$H-NMR(DSMO-d6) δ: 1.36(9H, s), 1.41(3H, t, J=6.8 Hz), 2.06–2.17(2H, m), 2.72(2H, t, J=7.2 Hz), 2.82(3H, d, J=4.8 Hz), 3.90(3H, s), 4.15(2H, t, J=6.0 Hz), 4.28(2H, q, J=6.8 Hz), 4.85(2H, s), 5.50(2H, s), 7.49–7.62(3H, m), 8.15–8.26(1H, m), 8.56(1H, s), 9.18(1H, brs), 9.85(1H, brs).

Example 59

1-(3-tert-Butyl-5-ethoxy-4-methoxy-phenyl)-2-(7-fluoro-1-imino-5,6-dimethoxy-1,3-dihydro-isoindol-2-yl)-ethanone hydrobromide

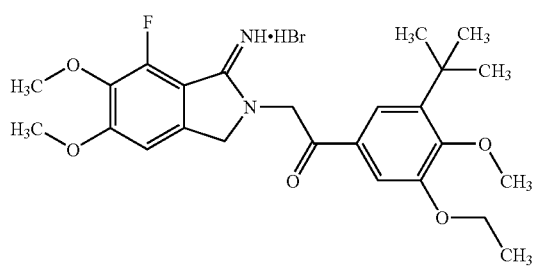

$^1$H-NMR(DSMO-d6) δ: 1.36(9H, S), 1.41(3H, t, J=7.0 Hz), 3.87(3H, s), 3.89(3H, s), 3.95(3H, s), 4.13(2H, q, J=7.0 Hz), 4.81(2H, s), 5.48(2H, s), 7.36(1H, s), 7.50(1H, s), 7.51(1H, s), 9.03(1H, brs), 9.30(1H, brs).
MS: m/e (ESI) 459.1 (MH+)

Example 60

2-[2-(3-tert-Butyl-4-methoxy-5-morpholino-phenyl)-2-oxo-ethyl]-6-ethoxy-3-imino-2,3-dihydro-1H-isoindole-5-carboxylic acid methylamide hydrobromide

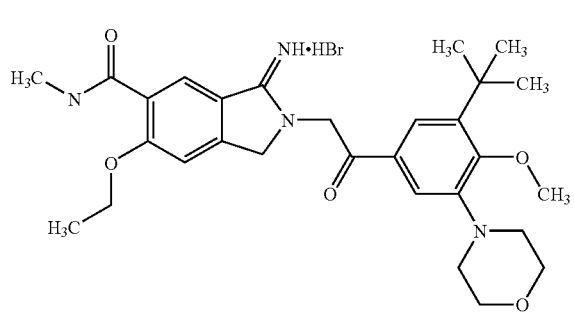

$^1$H-NMR(DSMO-d6) δ: 1.37(9H, s), 1.41(3H, t, J=6.8 Hz), 2.82(3H, d, J=4.0 Hz), 2.94–3.04(4H, m), 3.70–3.86 (4H, m), 3.95(3H, s), 4.28(2H, q, J=6.8 Hz), 4.85(2H, s), 5.51(2H, s), 7.50(1H, s), 7.54(1H, s), 7.61(1H, s), 8.20(1H, q, J=4.0 Hz), 8.56(1H, s), 9.16(1H, brs), 9.84(1H, brs).
MS: m/e (ESI) 524.2 (MH+)

Example 61

1-(3-tert-Butyl-4-methoxy-5-morpholino-phenyl)-2-(7-fluoro-1-imino-5,6-dimethoxy-1,3-dihydro-isoindol-2-yl)-ethanone hydrobromide

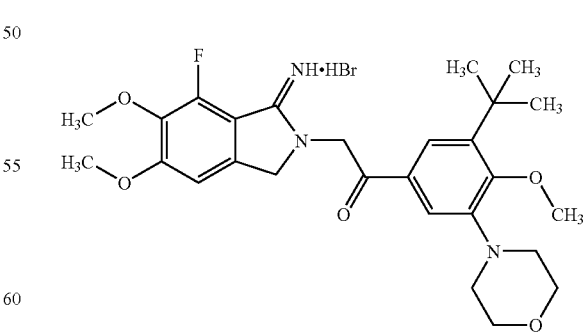

1H-NMR(DSMO-d6) δ: 1.37(9H, s), 2.95–3.05(4H, m), 3.74–3.85(4H, m), 3.87(3H, s), 3.95(3H, s), 3.96(3H, s), 4.81(2H, s), 5.51(2H, s), 7.37(1H, s), 7.49(1H, s), 7.60(1H, s).

Example 62

1-(3-tert-Butyl-4-methoxy-5-morpholino-phenyl)-2-(2-cyclopropyl-7-imino-5,7-dihydro-pyrrolo[3,4-b]pyridin-6-yl)-ethanone hydrobromide

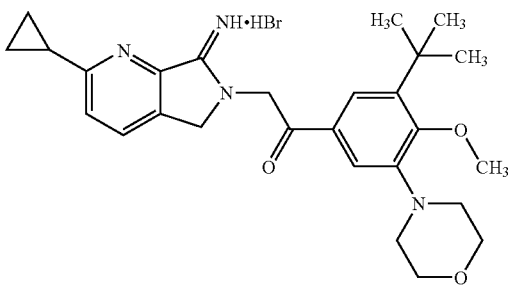

$^1$H-NMR(DSMO-d6) δ: 1.08–1.15(4H, m), 1.37(9H, s), 2.28–2.36(1H, m), 2.94–3.06(4H, m), 3.75–3.86(4H, m), 3.95(3H, s), 4.82(2H, s), 5.56(2H, s), 7.50(1H, s), 7.61(1H, s), 7.72(1H, d, J=8.0 Hz), 8.10(1H, d, J=8.0 Hz).

Example 64

4-{3-tert-Butyl-5-[2-(5,6-diethoxy-7-fluoro-1-imino-1,3-dihydro-isoindol-2-yl)-acetyl]-2-methoxy-phenoxy}-butyronitrile hydrobromide

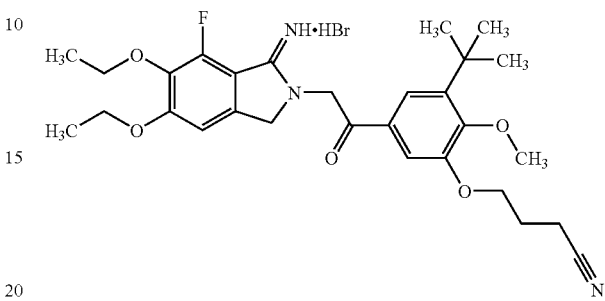

$^1$H-NMR(DSMO-d6) δ: 1.29(3H, t, J=6.8 Hz), 1.36(9H, s), 1.40(3H, t, J=6.8 Hz), 2.07–2.17(2H, m), 2.72(2H, t, J=7.2 Hz), 3.90(3H, s), 4.07–4.17(4H, m), 4.21(2H, q, J=6.8 Hz), 4.79(2H, s), 5.48(2H, s), 7.33(1H, s), 7.53(1H, s), 7.54(1H, s), 8.96–9.09(1H, m), 9.23–9.36(1H, m).

Example 63

{3-tert-Butyl-5-[2-(5,6-diethoxy-7-fluoro-1-imino-1,3-dihydro-isoindol-2-yl)-acetyl]-2-methoxy-phenoxy}-acetonitrile hydrobromide

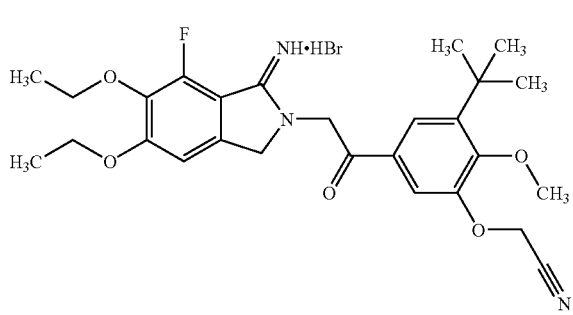

$^1$H-NMR(DSMO-d6) δ: 1.29(3H, t, J=6.8 Hz), 1.37(9H, s), 1.39(3H, t, J=6.8 Hz), 3.89(3H, s), 4.11(2H, q, J=6.8 Hz), 4.21(2H, q, J=6.8 Hz), 4.81(2H, s), 5.33(2H, s), 5.48(2H, s), 7.34(1H, s), 7.64(1H, s), 7.69(1H, s), 9.00–9.10(1H, m), 9.29–9.37(1H, m).

Example 65

4-{3-tert-Butyl-5-[2-(2-cyclopropyl-7-imino-5,7-dihydro-pyrrolo[3,4-b]pyridin-6-yl)-acetyl]-2-methoxy-phenoxy}-butyronitrile hydrobromide

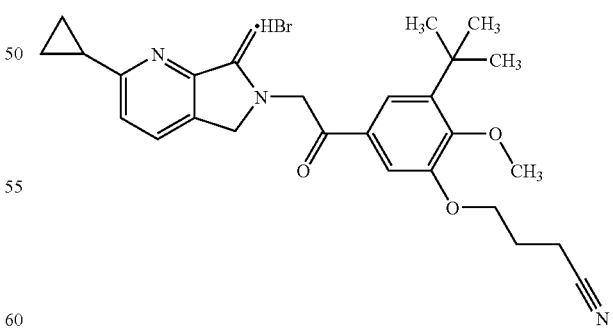

$^1$H-NMR(DSMO-d6) δ: 1.05–1.18(4H, m), 1.36(9H, s), 2.07–2.18(2H, m), 2.28–2.38(1H, m), 2.72(2H, t, J=7.2 Hz), 3.89(3H, s), 4.15(2H, t, J=6.0 Hz), 4.83(2H, s), 5.56(2H, s), 7.55(2H, brs), 7.72(1H, d, J=8.0 Hz), 8.10(1H, d, J=8.0 Hz), 9.04–9.55(2H, m).

Example 66

6-[2-(3-tert-Butyl-4-methoxy-5-morpholino-phenyl)-2-oxo-ethyl]-3-ethoxy-7-imino-6,7-dihydro-5H-pyrrolo[3,4-b]pyridine-2-carboxylic acid methylamide hydrobromide

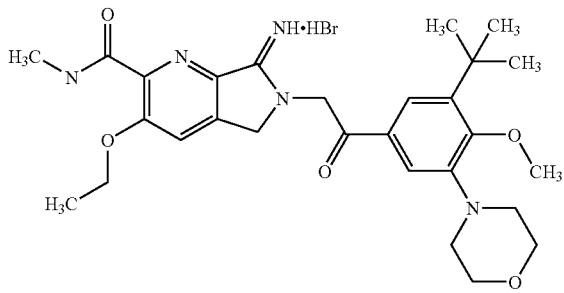

MS: m/e (ESI) 524.2 (MH+)

Example 67

2-tert-Butyl-4-[2-5-ethoxy-1-imino-6-methylcarbamoyl-1,3-dihydro-isoindol-2-yl]-acetyl]-phenyl methanesulfonate hydrobromide

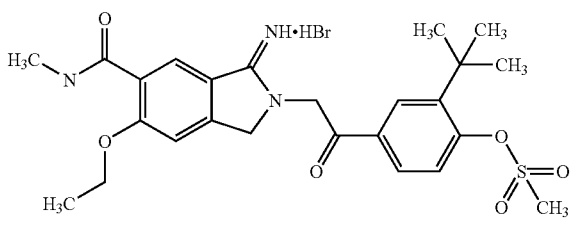

$^1$H-NMR(DSMO-d6) δ: 1.40–1.43(12H, m), 2.82(3H, d, J=4.8 Hz), 3.68(3H, s), 4.28(2H, q, J=6.8 Hz), 4.86(2H, s), 5.51(2H, s), 7.55(1H, s), 7.70(1H, d, J=8.4 Hz), 7.97–8.00 (2H, m), 8.19–8.22(1H, m), 8.56(1H, s), 9.20(1H, brs), 9.86(1H, brs).
MS: m/e (ESI) 502.1 (MH+)

Example 68

2-tert-Butyl-4-[2-(5-dimethylamino-1-imino-6-methylcarbamoyl-1,3-dihydro-isoindol-2-yl)-acetyl]-phenyl methanesulfonate hydrobromide

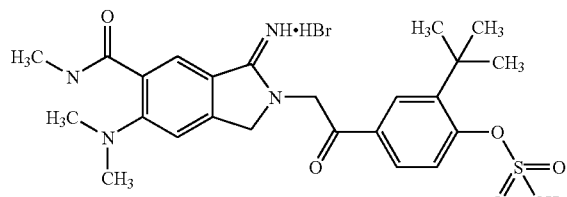

$^1$H-NMR(DSMO-d6) δ: 1.40(9H, S), 2.77(3H, d, J=4.8 Hz), 2.92(6H, s), 3.68(3H, s), 4.76(2H, s), 5.46(2H, s), 7.15(1H, s), 7.70(1H, d, J=8.4 Hz), 7.95–8.00(2H, m), 8.07(1H, s), 8.34–8.37(1H, m), 8.96(1H, brs), 9.57(1H, brs).
MS: m/e (ESI) 501.1 (MH+)

Example 69

2-tert-Butyl-4-[2-(3-ethoxy-7-imino-2-methylcarbamoyl-5,7-dihydro-pyrrolo[3,4-b]pyridin-6-yl)-acetyl]-phenyl methanesulfonate hydrobromide

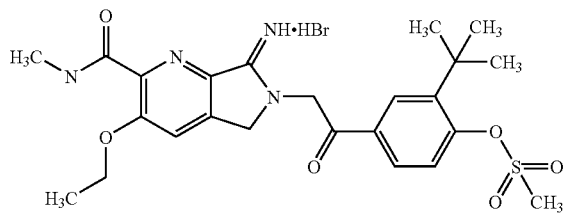

1H-NMR(DSMO-d6) δ: 1.36(3H, t, J=6.8 Hz), 1.41(9H, s), 2.77(3H, d, J=4.4 Hz), 3.68(3H, s), 4.24(2H, q, J=6.8 Hz), 4.90(2H, s), 5.54(2H, s), 7.70(1H, d, J=8.4 Hz), 7.95–8.00(3H, m), 8.52(1H, m), 9.44(1H, brs), 9.99(1H, brs).
MS: m/e (ESI) 503.1 (MH+)

Example 70

2-[2-(3-tert-Butyl-4-cyanomethoxy-5-dimethylamino-phenyl)-2-oxo-ethyl]-6-dimethylamino-3-imino-2,3-dihydro-1H-isoindole-5-carboxylic acid methylamide hydrobromide

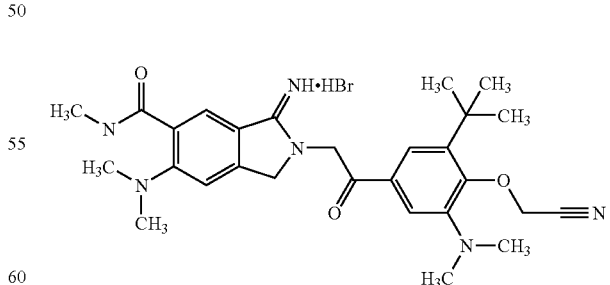

$^1$H-NMR(DSMO-d6) δ: 1.39(9H, S), 2.71(6H, s), 2.77 (3H, d, J=4.4 Hz), 2.91(6H, s), 4.74(2H, s), 5.25(2H, s), 5.46(2H, s), 7.15(1H, s), 7.57(1H, s), 7.60(1H, s), 8.06(1H, s), 8.35(1H, m), 8.92(1H, brs), 9.53(1H, brs).
MS: m/e (ESI) 505.2 (MH+)

Example 71

2-[2-(3-tert-Butyl-4-methoxy-5-(pyrrolidin-1-yl)-phenyl)-2-oxo-ethyl]-6-ethoxy-3-imino-2,3-dihydro-1H-isoindole-5-carboxylic acid methylamide hydrobromide

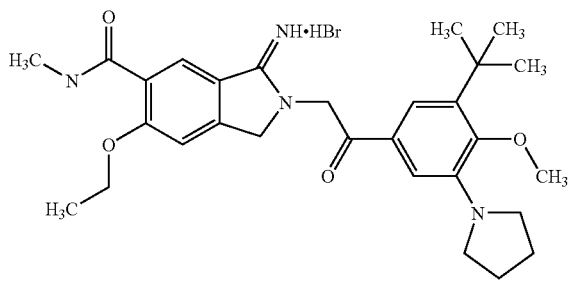

1H-NMR(DMSO-d6) δ: 1.38(9H, S), 1.41(3H, t, J=6.8 Hz), 1.91(4H, brs), 2.82(3H, d, J=4.0 Hz), 3.15(4H, brs), 3.64(3H, s), 4.27(2H, q, J=7.0 Hz), 4.83(2H, s), 5.47(2H, s), 7.35(1H, s), 7.43(1H, s), 7.53(1H, s), 8.18–8.21(1H, m), 8.55(1H, s).
MS: m/e (ESI) 507.2 (MH+)

Example 72

1-(3-tert-Butyl-4-methoxy-5-(pyrrolidin-1-yl)-phenyl)-2-(5,6-diethoxy-7-fluoro-1-imino-1,3-dihydro-isoindol-2-yl)-ethanone hydrobromide

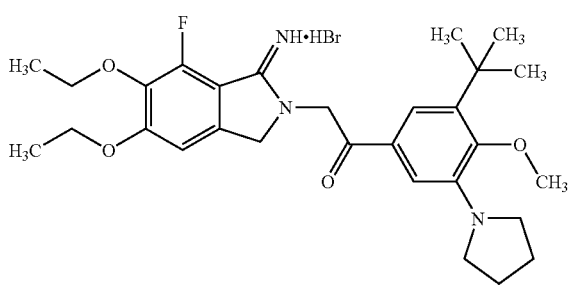

1H-NMR(DMSO-d6) δ: 1.29(3H, t, J=6.8 Hz), 1.37(9H, s), 1.39(3H, t, J=6.8 Hz), 1.91(4H, brs), 3.15(4H, brs), 3.64(3H, s), 4.11(2H, q, J=6.8 Hz), 4.21(2H, q, J=6.8 Hz), 4.78(2H, s), 5.46(2H, s), 7.33(1H, s), 7.34(1H, s), 7.42(1H, s), 9.01(1H, brs), 9.23(1H, brs).
MS: m/e (ESI)512.2 (MH+)

Example 73

2-[2-(3-tert-Butyl-4-methoxy-5-(pyrrolidin-1-yl)-phenyl)-2-oxo-ethyl]-6-dimethylamino-3-imino-2,3-dihydro-1H-isoindole-5-carboxylic acid methylamide hydrobromide

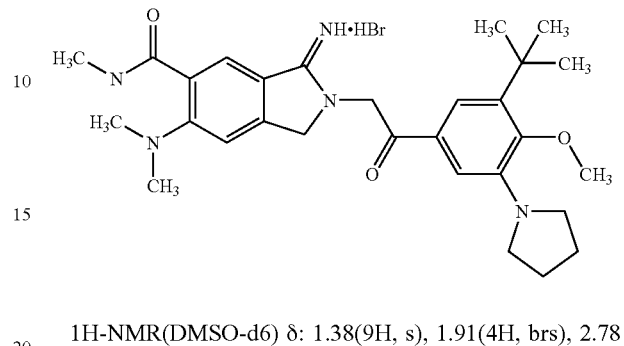

1H-NMR(DMSO-d6) δ: 1.38(9H, s), 1.91(4H, brs), 2.78 (3H, d, J=4.4 Hz), 2.91(6H, s), 3.15(4H, brs), 3.64(3H, s), 4.72(2H, s), 5.42(2H, s), 7.15(1H, s), 7.35(1H, s), 7.43(1H, s), 8.06(1H, s), 8.35–8.38(1H, m).
MS: m/e (ESI) 506.3 (MH+)

Example 74

1-(3-tert-Butyl-4-methoxy-5-(pyrrolidin-1-yl)-phenyl)-2-(2-cyclopropyl-7-imino-5,7-dihydro-pyrrolo[3,4-b]pyridin-6-yl)-ethanone hydrobromide

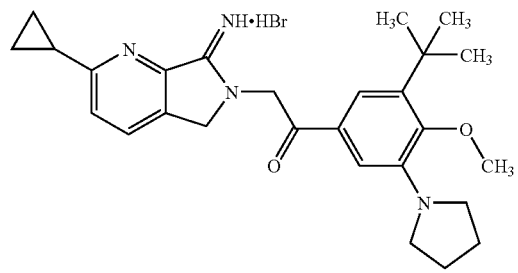

1H-NMR(DMSO-d6) δ: 1.08–1.11(4H, m), 1.38(9H, s), 1.91(4H, brs), 2.29–2.35(1H, m), 3.15(4H, brs), 3.65(3H, s), 4.81(2H, s), 5.56(2H, s), 7.36(1H, s), 7.44(1H, s), 7.72(1H, d, J=8.6 Hz), 8.09(1H, d, J=8.6 Hz), 9.50(1H, brs), 9.62(1H, brs).

Example 75

1-(3-tert-Butyl-4-methoxy-5-(pyrrolidin-1-yl)-phenyl)-2-(7-fluoro-1-imino-5,6-dimethoxy-1,3-dihydro-isoindol-2-yl)-ethanone hydrobromide

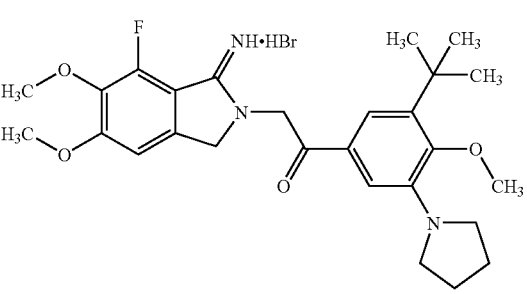

Example 73

2-[2-(3-tert-Butyl-4-methoxy-5-(pyrrolidin-1-yl)-phenyl)-2-oxo-ethyl]-6-dimethylamino-3-imino-2,3-dihydro-1H-isoindole-5-carboxylic acid methylamide hydrobromide 1H-NMR(DMSO-d6) δ: 1.38(9H, s), 1.91(4H, brs), 3.15 (4H, brs), 3.65(3H, s), 3.87(3H, s), 3.95(3H, s), 4.80(2H, s), 5.48(2H, s), 7.35(1H, s), 7.36(1H, s), 7.43(1H, s), 9.02(1H, brs), 9.23(1H, brs).

MS: m/e (ESI) 484.2 (MH+)

Example 76

2-[2-(3-tert-Butyl-5-isopropoxy-4-methoxy-phenyl)-2-oxo-ethyl]-6-ethoxy-3-imino-2,3-dihydro-1H-isoindole-5-carboxylic acid methylamide hydrobromide

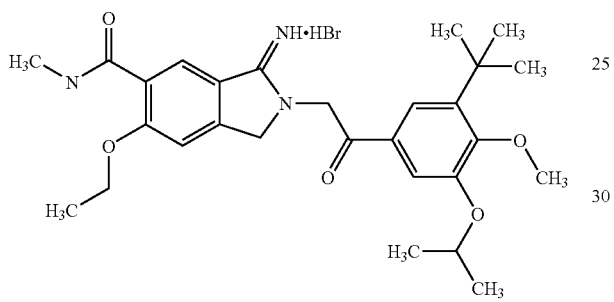

1H-NMR(DMSO-d6) δ: 1.33(6H, d, J=6.4 Hz), 1.36(9H, s), 1.41(3H, t, J=6.8 Hz), 2.82(3H, d, J=4.4 Hz), 3.88(3H, s), 4.28(2H, q, J=6.8 Hz), 4.64–4.77(1H, m), 4.85(2H, s), 5.49(2H, s), 7.51(2H, s), 7.54(1H, s), 8.14–8.26(1H, m), 8.56(1H, s), 9.12–9.21(1H, m), 9.79–9.89(1H, m).

Example 77

1-(3-tert-Butyl-5-isopropoxy-4-methoxy-phenyl)-2-(5,6-diethoxy-7-fluoro-1-imino-1,3-dihydro-isoindol-2-yl)-ethanone hydrobromide

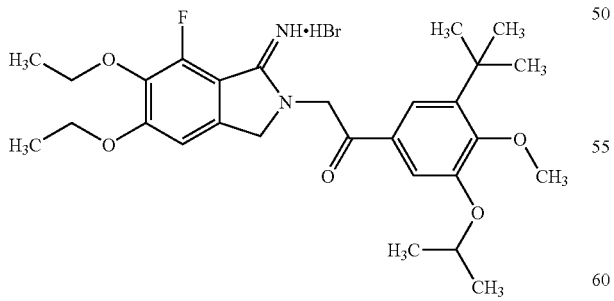

1H-NMR(DMSO-d6) δ: 1.29(3H, t, J=6.8 Hz), 1.33(6H, d, J=6.0 Hz), 1.35(9H, s), 1.39(3H, t, J=6.8 Hz), 3.88(3H, s), 4.11(2H, q, J=6.8 Hz), 4.21(2H, q, J=6.8 Hz), 4.64–4.77(1H, m), 4.80(2H, s), 5.47(2H, s), 7.33(1H, s), 7.50(2H, s), 9.05(1H, brs), 9.29(1H, brs).

Example 78

1-(3-tert-Butyl-5-isopropoxy-4-methoxy-phenyl)-2-(7-fluoro-1-imino-5,6-dimethoxy-1,3-dihydro-isoindol-2-yl)-ethanone hydrobromide

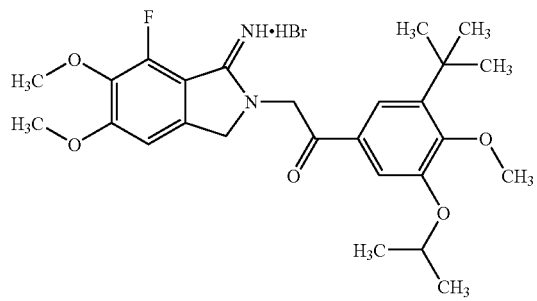

1H-NMR(DMSO-d6) δ: 1.33(6H, d, J=5.6 Hz), 1.35(9H, s), 3.87(3H, s), 3.88(3H, s), 3.95(3H, s), 4.64–4.76(1H, m), 4.81(2H, s), 5.48(2H, s), 7.36(1H, s), 7.50(2H, s), 8.99–9.16 (1H, m), 9.25–9.40(1H, m).

Example 79

Ethyl 2-{8-tert-butyl-6-{2-[5-ethoxy-1-imino-6-methylcarbamoyl-1,3-dihydro-isoindol-2-yl]-acetyl}-2,3-dihydro-benzo[1,4]oxazin-4-yl}-propanoate hydrochloride

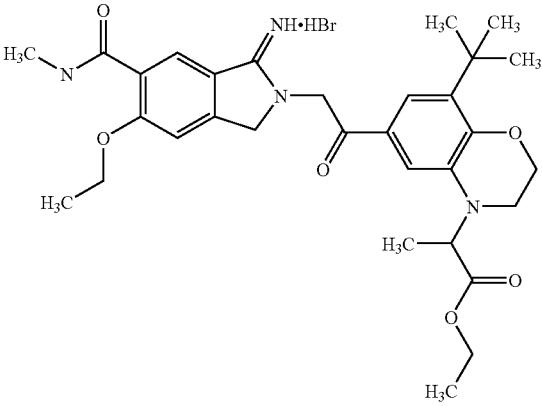

1H-NMR(DMSO-d6) δ: 1.15(3H, t, J=7 Hz), 1.30–1.50 (15H, m), 2.82(3H, d, J=5 Hz), 3.30–3.40(2H, m), 4.09(2H, m), 4.22–4.36(4H, m), 4.71(1H, q, J=6 Hz), 4.82(2H, s), 5.38(1H, d, J=18 Hz), 5.48(1H, d, J=18 Hz), 7.20(1H, brs), 7.28(1H, brs), 7.53(1H, s), 8.21(1H, q, J=5 Hz), 8.55(1H, s), 9.21(1H, brs), 9.82(1H, brs).

Example 80

Ethyl 2-{8-tert-butyl-6-[2-(3-ethoxy-7-imino-2-methylcarbamoyl-5,7-dihydro-pyrrolo[3,4-b]pyridin-6-yl)-acetyl]-2,3-dihydro-benzo[1,4]oxazin-4-yl}-propanoate hydrochloride

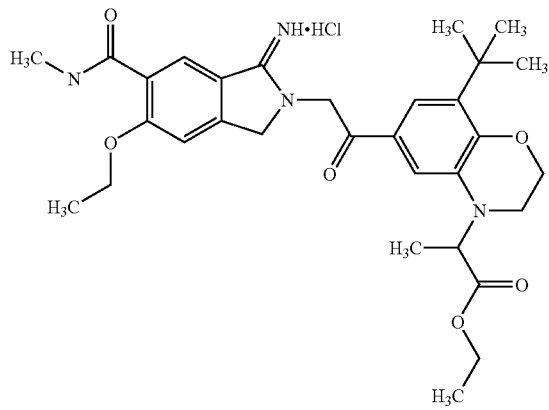

1H-NMR(DMSO-d6) δ: 1.15(3H, t, J=7 Hz), 1.32–1.39 (12H, m), 1.44(3H, d, J=7 Hz), 2.33(1H, m), 2.77(3H, d, J=5 Hz), 3.30–3.40(2H, m), 4.09(2H, m), 4.20–4.30(4H, m), 4.71(1H, q, J=7 Hz), 4.86(2H, s), 4.82(2H, s), 5.43(1H, d, J=18 Hz), 5.52(1H, d, J=18 Hz), 7.20(1H, d, J=2 Hz), 7.27(1H, d, J=2 Hz), 7.98(1H, s), 8.55(1H, q, J=5 Hz), 9.47(1H, brs), 9.92(1H, brs).
MS: m/e (ESI) 566.2 (MH+)

Example 81

2-[2-(3-Dimethylamino-5-isopropyl-4-methoxy-phenyl)-2-oxo-ethyl]-6-ethoxy-3-imino-2,3-dihydro-1H-isoindole-5-carboxylic acid methylamide hydrobromide

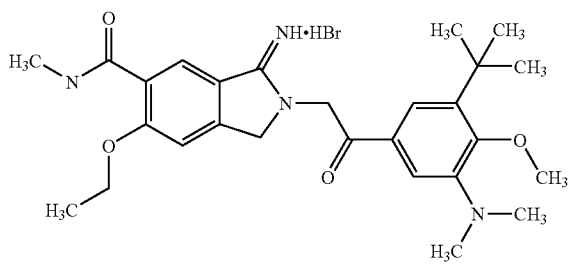

1H-NMR(DMSO-d6) δ: 1.20(6H, d, J=7.2 Hz), 1.41(3H, t, J=6.8 Hz), 2.78(6H, s), 2.81(3H, d, J=4.4 Hz), 3.77(3H, s), 4.28(2H, q, J=6.8 Hz), 4.84(2H, s), 5.49(2H, s), 7.36(1H, s), 7.51(1H, s), 7.54(1H, s), 8.20(1H, q, J=4.4 Hz), 8.56(1H, s), 9.17(1H, brs), 9.84(1H, brs).

Example 82

2-(5,6-Diethoxy-7-fluoro-1-imino-1,3-dihydro-isoindol-2-yl)-1-(3-dimethylamino-5-isopropyl-4-methoxy-phenyl)-ethanone hydrobromide

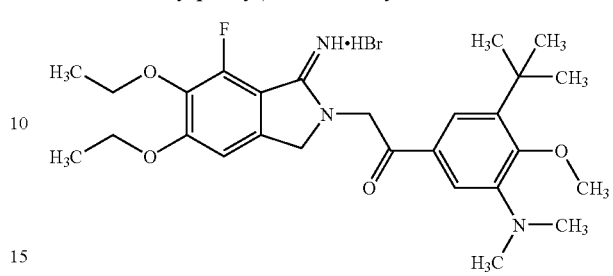

1H-NMR(DMSO-d6) δ: 1.20(6H, d, J=6.8 Hz), 1.29(3H, t, J=6.8 Hz), 1.39(3H, t, J=6.8 Hz), 2.78(6H, s), 3.76(3H, s), 4.11(2H, q, J=6.8 Hz), 4.22(2H, q, J=6.8 Hz), 4.79(2H, s), 5.47(2H, s), 7.34–7.36(2H, m), 7.52(1H, s).

Example 83

2-[2-(3-tert-Butyl-4-methoxy-5-methylamino-phenyl)-2-oxo-ethyl]-6-ethoxy-3-imino-2,3-dihydro-1H-isoindole-5-carboxylic acid methylamide hydrobromide

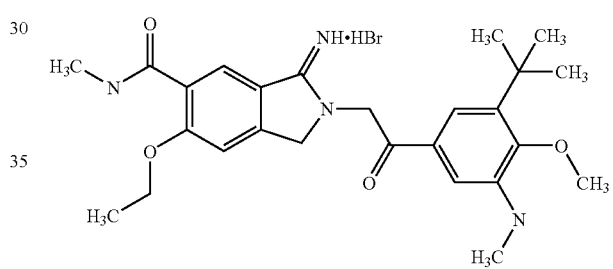

1H-NMR(DMSO-d6) δ: 1.37(9H, s), 1.41(3H, t, J=7.0 Hz), 2.76(3H, d, J=5.0 Hz), 2.82(3H, d, J=4.4 Hz), 3.72(3H, s), 4.28(2H, q, J=7.0 Hz), 4.84(2H, s), 5.47(2H, s), 5.51(1H, q, J=5.0 Hz), 7.05(1H, s), 7.24(1H, s), 7.54(1H, s), 8.21(1H, q, J=4.4 Hz), 8.55(1H, s), 9.17(1H, brs), 9.82(1H, brs).
MS: m/e (ESI) 467.3 (MH+)

Example 84

6-[2-(3-tert-Butyl-5-isopropoxy-4-methoxy-phenyl)-2-oxo-ethyl]-3-ethoxy-7-imino-6,7-dihydro-5H-pyrrolo[3,4-b]pyridine-2-carboxylic acid methylamide trifluoroacetate

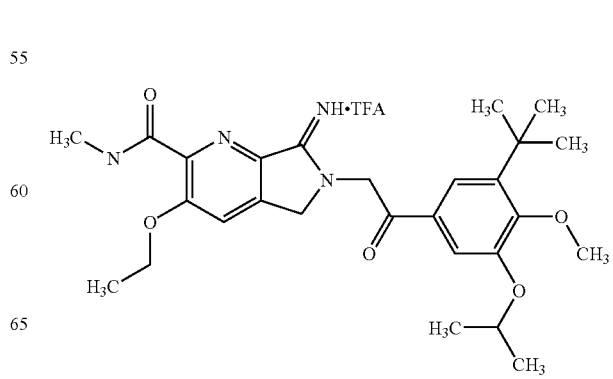

Example 82

2-(5,6-Diethoxy-7-fluoro-1-imino-1,3-dihydro-isoindol-2-yl)-1-(3-dimethylamino-5-isopropyl-4-methoxy-phenyl)-ethanone hydrobromide 1H-NMR(DMSO-d6) δ: 1.26–1.43(18H, m), 2.77(3H, d, J=4.8 Hz), 3.88(3H, s), 4.24(2H, q, J=6.8 Hz), 4.64–4.77 (1H, m), 4.88(2H, s), 5.52(2H, s), 7.50(2H, s), 7.99(1H, s), 8.47–8.58(1H, m), 9.34–9.46(1H, m), 9.90–10.03(1H, m).

Example 85

2-[2-(3-tert-Butyl-5-isopropoxy-4-methoxy-phenyl)-2-oxo-ethyl]-6-dimethylamino-3-imino-2,3-dihydro-1H-isoindole-5-carboxylic acid methylamide trifluoroacetate

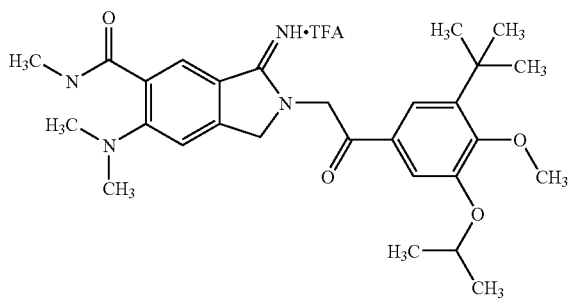

1H-NMR(DMSO-d6) δ: 1.33(6H, d, J=6.0 Hz), 1.35(9H, s), 2.77(3H, d, J=4.4 Hz), 2.91(6H, s), 3.88(3H, s), 4.63–4.80(3H, m), 5.44(2H, s), 7.15(1H, s), 7.50(2H, s), 8.07(1H, s), 8.31–8.43(1H, m), 8.88–8.99(1H, m), 9.46–9.60(1H, m).

Example 86

2-{2-[3-tert-Butyl-5-(4-cyano-piperidin-1-yl)-4-methoxy-phenyl]-2-oxo-ethyl}-6-ethoxy-3-imino-2,3-dihydro-1H-isoindole-5-carboxylic acid methylamide hydrobromide

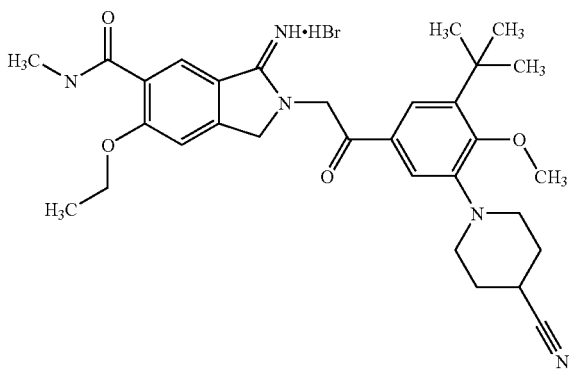

1H-NMR(DMSO-d6) δ: 1.36(9H, s), 1.41(3H, t, J=6.8 Hz), 1.88–2.13(4H, m), 2.82(3H, d, J=4.4 Hz), 2.86–2.98 (2H, m), 3.02–3.18(3H, m), 3.93(3H, s), 4.28(2H, q, J=6.8 Hz), 4.84(2H, s), 5.49(2H, s), 7.52(1H, d, J=1.6 Hz), 7.54 (1H, s), 7.61(1H, d, J=1.6 Hz), 8.14–8.26(1H, m), 8.56(1H, s), 9.10–9.18(1H, m), 9.81–9.88(1H, m).

MS: m/e (ESI) 546.2 (MH+)

Example 87

1-(3-tert-Butyl-4-hydroxy-phenyl)-2-(5,6-diethoxy-7-fluoro-1-imino-1,3-dihydro-isoindol-2-yl)-ethanone hydrobromide

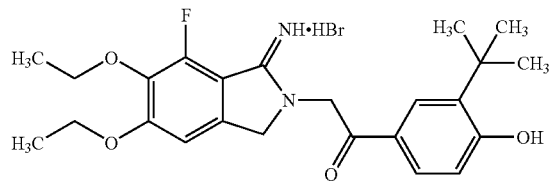

1H-NMR(DMSO-d6) δ: 1.29(3H, t, J=6.8 Hz), 1.37(9H, s), 1.40(3H, t, J=6.8 Hz), 4.11(2H, q, J=6.8 Hz), 4.21(2H, q, J=6.8 Hz), 4.78(2H, s), 5.40(2H, s), 6.95(1H, d, J=8.6 Hz), 7.32(1H, s), 7.75(1H, d, J=8.6 Hz), 7.80(1H, s), 9.00(1H, brs), 9.30(1H, brs).

MS: m/e (ESI) 429.1 (MH+)

Example 88

2-{8-tert-Butyl-6-[2-(5-ethoxy-1-imino-6-methylcarbamoyl-1,3-dihydro-isoindol-2-yl)-acetyl]-2,3-dihydro-benzo[1,4]oxazin-4-yl}-2-methyl-propanoic acid hydrochloride

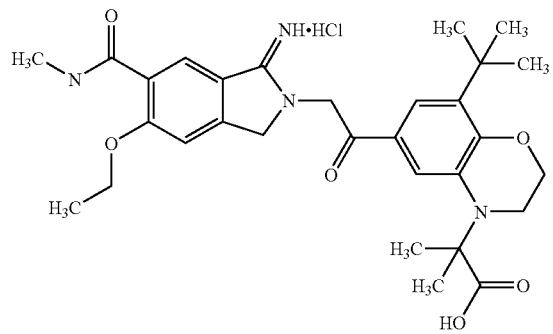

1H-NMR(DMSO-d6) δ: 1.36(9H, s), 1.38(3H, t, J=7 Hz), 1.48(6H, s), 2.82(3H, d, J=5 Hz), 3.30–3.40(2H, m), 4.22–4.40(4H, m), 4.82(2H, s), 5.40(2H, s), 7.08(1H, brs), 7.30(1H, brs), 7.52(1H, s), 8.21(1H, q, J=5 Hz), 8.55(1H, s), 9.22(1H, brs), 9.83(1H, brs).

MS: m/e (ESI) 551.2 (MH+)

Example 89

2-{8-tert-Butyl-6-[2-(3-ethoxy-7-imino-2-methylcarbamoyl-5,7-dihydro-pyrrolo[3,4-b]pyridin-6-yl)-acetyl]-2,3-dihydro-benzo[1,4]oxazin-4-yl}-2-methyl-propanoic acid hydrochloride

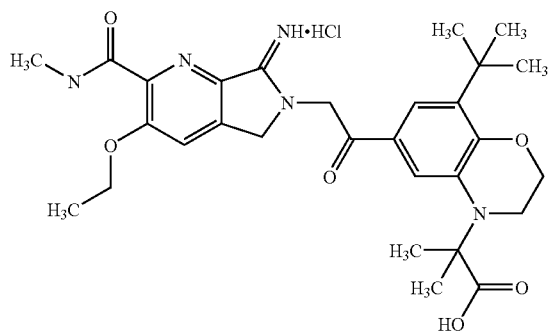

1H-NMR(DMSO-d6) δ: 1.30–1.40(12H, m), 1.48(6H, s), 2.77(3H, d, J=5 Hz), 3.30–3.40(2H, m), 4.22–4.33(4H, m), 4.85(2H, s), 5.43(2H, s), 7.08(1H, brs), 7.29(1H, brs), 7.98 (1H, s), 8.54(1H, q, J=5 Hz), 9.45(1H, brs), 9.91(1H, brs).

Example 90

2-tert-Butyl-6-dimethylamino-4-[2-(5-ethoxy-1-imino-6-methylcarbamoyl-1,3-dihydro-isoindol-2-yl)-acetyl]-phenyl acetate hydrobromide

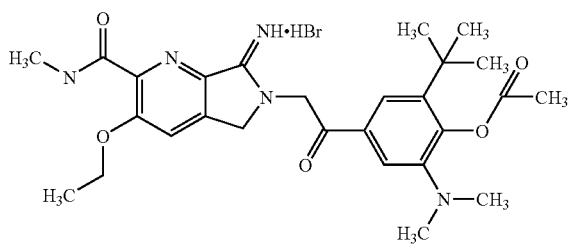

1H-NMR(DMSO-d6) δ: 1.33(9H, s), 1.41(3H, t, J=7.2 Hz), 2.33(3H, s), 2.65(6H, s), 2.82(3H, d, J=4.8 Hz), 4.27 (2H, q, J=7.2 Hz), 4.85(2H, s), 5.51(2H, s), 7.54(1H, s), 7.58(1H, s), 7.66(1H, s), 8.19–8.21(1H, m), 8.55(1H, s), 9.17(1H, brs), 9.84(1H, brs).

MS: m/e (ESI) 509.2 (MH+)

Example 91

2-{2-[3-tert-Butyl-4-methoxy-5-(2-oxo-oxazolidin-3-yl)-phenyl]-2-oxo-ethyl}-6-ethoxy-3-imino-2,3-dihydro-1H-isoindole-5-carboxylic acid methylamide hydrobromide

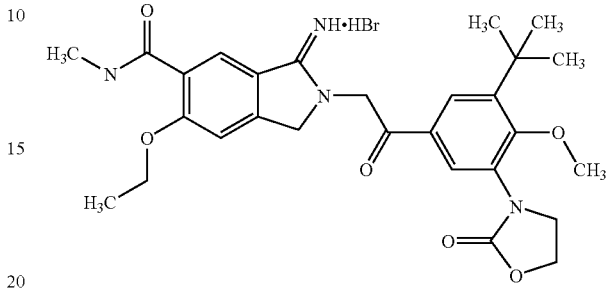

1H-NMR(DMSO-d6) δ: 1.38(9H, s), 1.41(3H, t, J=6.8 Hz), 2.82(3H, d, J=4.4 Hz), 3.82(3H, s), 3.93(2H, t, J=7.6 Hz), 4.28(2H, q, J=6.8 Hz), 4.54(2H, t, J=7.6 Hz), 4.85(2H, s), 5.46(2H, s), 7.54(1H, s), 7.83(1H, d, J=2.0 Hz), 7.99(1H, d, J=2.0 Hz), 8.20(1H, q, J=4.4 Hz), 8.56(1H, s).

Example 92

2-tert-Butyl-4-[2-(5,6-diethoxy-7-fluoro-1-imino-1,3-dihydro-isoindol-2-yl)-acetyl]-phenyl acetate hydrobromide

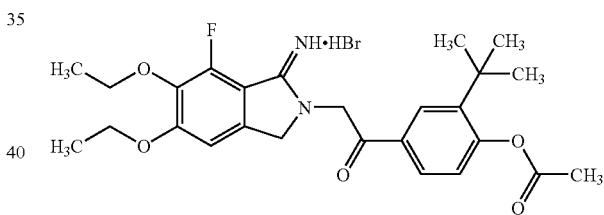

1H-NMR(DMSO-d6) δ: 1.29(3H, t, J=7.0 Hz), 1.34(9H, s), 1.40(3H, t, J=7.0 Hz), 2.37(3H, s), 4.12(2H, q, J=7.0 Hz), 4.21(2H, q, J=7.0 Hz), 4.81(2H, s), 5.49(2H, s), 7.31–7.34 (2H, m), 7.93(1H, d, J=8.4 Hz), 7.96(1H, s), 9.02(1H, brs), 9.30(1H, brs).

MS: m/e (ESI) 471.1 (MH+)

Example 93

2-tert-Butyl-4-[2-(5-ethoxy-1-imino-6-methylcarbamoyl-1,3-dihydro-isoindol-2-yl)-acetyl]-phenyl acetate hydrobromide

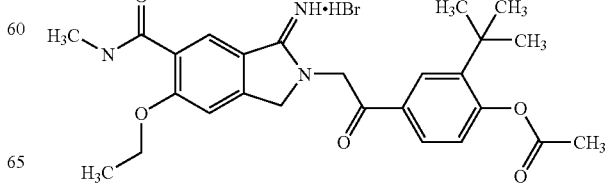

Example 89

2-{8-tert-Butyl-6-[2-(3-ethoxy-7-imino-2-methylcarbamoyl-5,7-dihydro-pyrrolo[3,4-b]pyridin-6-yl)-

1H-NMR(DMSO-d6) δ: 1.35(9H, s), 1.42(3H, t, J=7.0 Hz), 2.37(3H, s), 2.83(3H, d, J=4.4 Hz), 4.28(2H, q, J=7.0 Hz), 4.86(2H, s), 5.50(2H, s), 7.33(1H, d, J=8.4 Hz), 7.54 (1H, s), 7.94(1H, d, J=8.4 Hz), 7.97(1H, s), 8.19–8.21(1H, m), 8.56(1H, s), 9.20(1H, brs), 9.82(1H, brs).

MS: m/e (ESI) 466.2 (MH+)

Example 94

1-{3-tert-Butyl-5-[2-(5,6-diethoxy-7-fluoro-1-imino-1,3-dihydro-isoindol-2-yl)-acetyl]-2-methoxy-phenyl}-piperidin-4-one hydrobromide

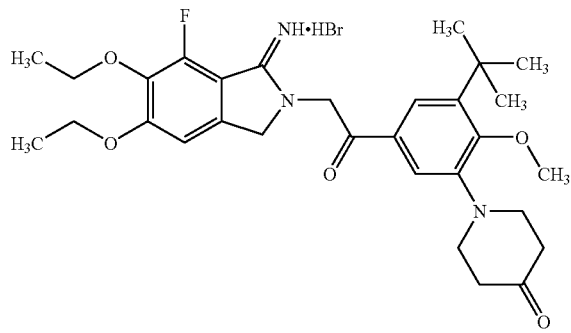

1H-NMR(DMSO-d6) δ: 1.29(3H, t, J=6.8 Hz), 1.38(9H, s), 1.39(3H, t, J=6.8 Hz), 2.48–2.62(4H, m), 3.28–3.45(4H, m), 4.02(3H, s), 4.11(2H, q, J=6.8 Hz), 4.20(2H, q, J=6.8 Hz), 4.79(2H, s), 5.48(2H, s), 7.33(2H, s), 7.56(2H, s), 7.62(2H, s).

Example 95

1-(3-tert-Butyl-5-dimethylamino-4-methoxy-phenyl)-2-(5-ethoxy-7-fluoro-1-imino-6-methoxy-1,3-dihydro-isoindol-2-yl)-ethanone hydrobromide

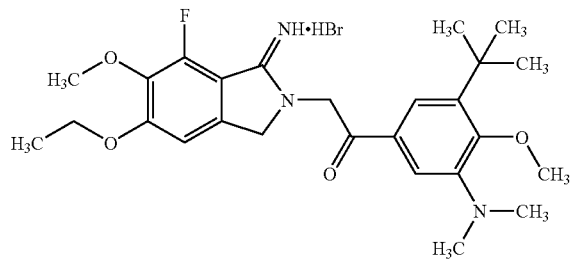

1H-NMR(DMSO-d6) δ: 1.37(9H, s), 1.40(3H, t, J=7.2 Hz), 2.75(6H, s), 3.82(3H, s), 3.87(3H, s), 4.20(2H, q, J=7.2 Hz), 4.78(2H, s), 5.48(2H, s), 7.34(1H, s), 7.45(1H, d, J=2.0 Hz), 7.53(1H, d, J=2.0 Hz).

MS: m/e (ESI) 472.2 (MH+)

Example 96

2-{2-[3-tert-Butyl-5-(ethyl-methyl-amino)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.01(3H, t, J=7.0 Hz), 1.37(9H, s), 1.41(3H, t, J=7.0 Hz), 2.74(3H, s), 2.82(3H, d, J=4.8 Hz), 3.13(2H, q, J=7.0 Hz), 3.83(3H, s), 4.28(2H, q, J=7.0 Hz), 4.84(2H, s), 5.49(2H, s), 7.48(1H, d, J=2.0 Hz), 7.54–7.55 (2H, m), 8.21(1H, q, J=4.8 Hz), 8.55(1H, s), 9.14(1H, brs), 9.81(1H, brs).

MS: m/e (ESI) 495.2 (MH+)

Example 97

6-{2-[3-tert-Butyl-5-(ethyl-methyl-amino)-4-methoxy-phenyl]-2-oxo-ethyl}-3-ethoxy-7-imino-6,7-dihydro-5H-pyrrolo[3,4-b]pyridine-2-carboxylic acid methylamide trifluoroacetate 1H-NMR(DMSO-d6) δ: 1.01(3H, t, J=7.0 Hz), 1.34–1.37 (12H, m), 2.74(3H, s), 2.78(3H, d, J=4.8 Hz), 3.13(2H, q, J=7.0 Hz), 3.83(3H, s), 4.24(2H, q, J=7.0 Hz), 4.87(2H, s), 5.52(2H, s), 7.47(1H, d, J=2.0 Hz), 7.54(1H, d, J=2.0 Hz), 7.99(1H, s), 8.53(1H, q, J=4.8 Hz), 9.40(1H, brs), 9.92(1H, brs).

MS: m/e (ESI) 496.2 (MH+)

Example 98

2-tert-Butyl-4-[2-(5,6-diethoxy-7-fluoro-1-imino-1,3-dihydro-isoindol-2-yl)-acetyl]-6-dimethylamino-phenyl methanesulfonate hydrobromide

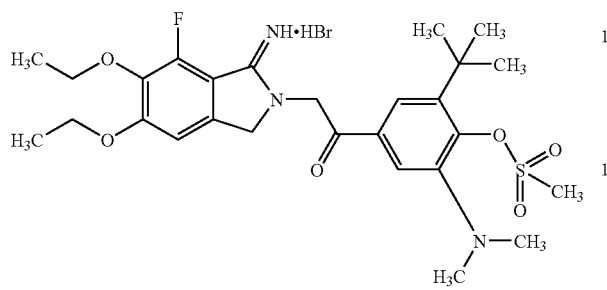

1H-NMR(DMSO-d6) δ: 1.29(3H, t, J=7.0 Hz), 1.40(3H, t, J=7.0 Hz), 1.44(9H, s), 2.67(6H, s), 3.73(3H, s), 4.12(2H, q, J=7.0 Hz), 4.21(2H, q, J=7.0 Hz), 4.80(2H, s), 5.51(2H, s), 7.34(1H, s), 7.67(1H, s), 7.75(1H, s).

MS: m/e (ESI) 550.1 (MH+)

Example 99

6-{2-[3-tert-Butyl-5-(4-hydroxy-piperidin-1-yl)-4-methoxy-phenyl]-2-oxo-ethyl}-3-ethoxy-7-imino-6,7-dihydro-5H-pyrrolo[3,4-b]pyridine-2-carboxylic acid methylamide trifluoroacetate

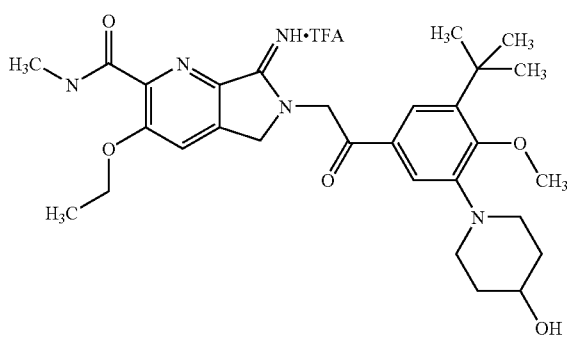

1H-NMR(DMSO-d6) δ: 1.26–1.50(12H, m), 1.50–1.68 (2H, m), 1.84–2.03(2H, m), 2.64–2.86(5H, m), 3.12–3.68 (3H, m), 3.94(3H, s), 4.23(2H, q, J=6.8 Hz), 4.87(2H, s), 5.52(2H, s), 7.44–7.70(2H, m), 7.99(1H, s), 8.41–8.63(1H, m), 9.37(1H, brs), 9.94(1H, brs).

MS: m/e (ESI) 538.3 (MH+)

Example 100

1-[3-tert-Butyl-5-(4-hydroxy-piperidin-1-yl)-4-methoxy-phenyl]-2-(7-fluoro-1-imino-5,6-dimethoxy-1,3-dihydro-isoindol-2-yl)-ethanone hydrobromide

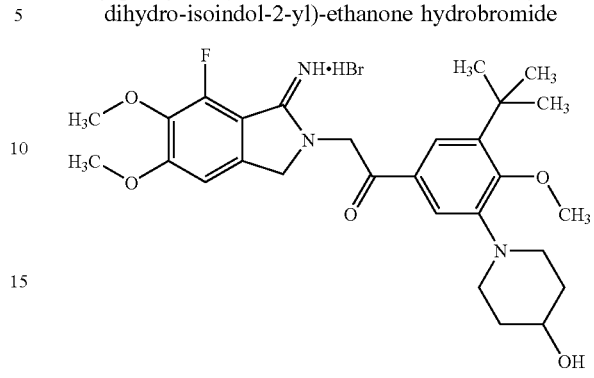

1H-NMR(DMSO-d6) δ: 1.36(9H, s), 1.54–1.70(2H, m), 1.84–2.00(2H, m), 2.65–2.80(2H, m), 3.19–3.50(2H, m), 3.55–3.70(1H, m), 3.86(3H, s), 3.93(3H, s), 3.95(3H, s), 4.73(1H, d, J=4.0 Hz), 4.80(2H, s), 5.48(2H, s), 7.36(1H, s), 7.51(1H, s), 7.56(1H, s), 8.99–9.40(2H, m).

Example 101

1-(3-tert-Butyl-5-dimethylamino-4-hydroxy-phenyl)-2-(5,6-diethoxy-7-fluoro-1-imino-1,3-dihydro-isoindol-2-yl)-ethanone hydrobromide

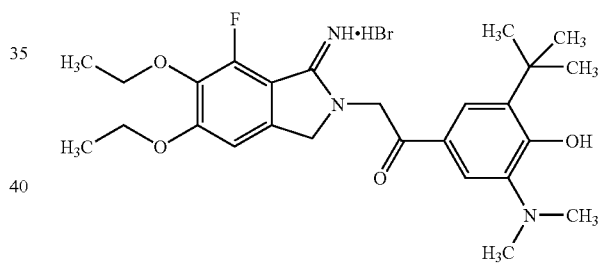

1H-NMR(DMSO-d6) δ: 1.29(3H, t, J=7.0 Hz), 1.38–1.41 (12H, m), 2.61(6H, s), 4.11(2H, q, J=7.0 Hz), 4.21(2H, q, J=7.0 Hz), 4.78(2H, s), 5.44(2H, s), 7.33(1H, s), 7.63(1H, s), 7.68(1H, s), 9.01(1H, brs), 9.26(1H, brs).

MS: m/e (ESI) 472.2 (MH+)

Example 102

6-[2-(3-tert-Butyl-5-dimethylamino-4-ethoxy-phenyl)-2-oxo-ethyl]-3-ethoxy-7-imino-6,7-dihydro-5H-pyrrolo[3,4-b]pyridine-2-carboxylic acid methylamide trifluoroacetate

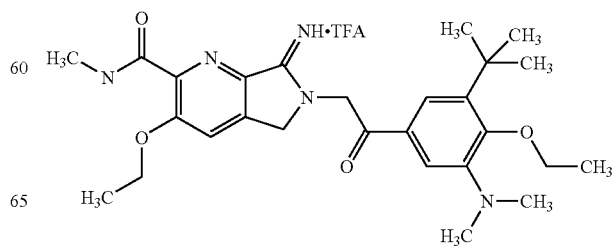

1H-NMR(DMSO-d6) δ: 1.34–1.39(15H, m), 2.75(6H, s), 2.78(3H, d, J=4.6 Hz), 4.13(2H, q, J=7.0 Hz), 4.24(2H, q, J=7.0 Hz), 4.87(2H, s), 5.52(2H, s), 7.45(1H, s), 7.55(1H, s), 7.99(1H, s), 8.53(1H, q, J=4.6 Hz), 8.55(1H, s), 9.39(1H, brs), 9.92(1H, brs).

MS: m/e (ESI) 496.2 (MH+)

Example 103

2-[2-(3-tert-Butyl-5-dimethylamino-4-methoxy-phenyl)-2-oxo-ethyl]-6-dimethylamino-3-imino-2,3-dihydro-1H-isoindole-5-carboxylic acid methylamide hydrobromide

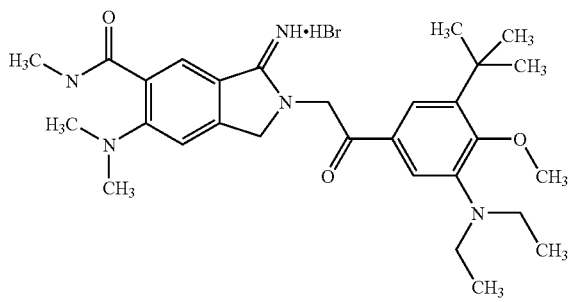

1H-NMR(DMSO-d6) δ: 0.98(6H, t, J=7.0 Hz), 1.37(9H, s), 2.78(3H, d, J=4.8 Hz), 2.92(6H, s), 3.16(4H, q, J=7.0 Hz), 3.85(3H, s), 4.74(2H, s), 5.44(2H, s), 7.15(1H, s), 7.49(1H, d, J=2.0 Hz), 7.55(1H, s), 7.55(1H, d, J=2.0 Hz), 8.07(1H, s), 8.37(1H, q, J=4.8 Hz), 8.92(1H, brs), 9.53(1H, brs).

MS: m/e (ESI) 508.2 (MH+)

Example 104

1-(3-tert-Butyl-4-methoxy-5-methylamino-phenyl)-2-(5,6-diethoxy-7-fluoro-1-imino-1,3-dihydro-isoindol-2-yl)-ethanone hydrobromide

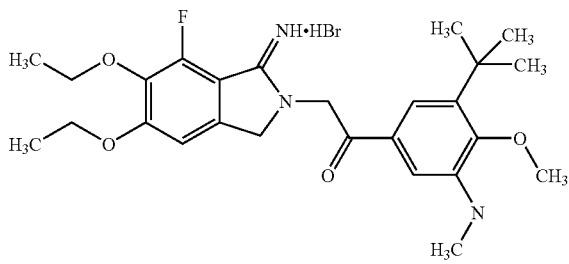

1H-NMR(DMSO-d6) δ: 1.29(3H, t, J=7.0 Hz), 1.37(9H, s), 1.40(3H, t, J=7.0 Hz), 2.76(3H, d, J=5.2 Hz), 3.72(3H, s), 4.11(2H, q, J=7.0 Hz), 4.21(2H, q, J=7.0 Hz), 4.79(2H, s), 5.46(2H, s), 5.50(1H, q, J=5.2 Hz), 7.04(1H, s), 7.23(1H, s), 7.33(1H, s).

MS: m/e (ESI) 472.1 (MH+)

Example 105

1-[3-tert-Butyl-5-(4-hydroxy-piperidin-1-yl)-4-methoxy-phenyl]-2-(5-ethoxy-7-fluoro-1-imino-6-methoxy-1,3-dihydro-isoindol-2-yl hydrobromide

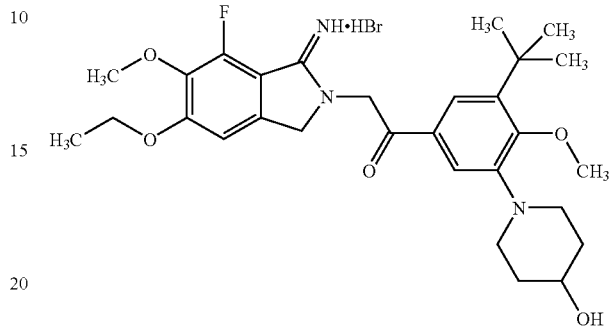

1H-NMR(DMSO-d6) δ: 1.36(9H, s), 1.40(3H, t, J=6.8 Hz), 1.54–1.68(2H, m), 1.83–1.96(2H, m), 2.64–2.78(2H, m), 3.21–3.48(2H, m), 3.58–3.69(1H, m), 3.87(3H, s), 3.94(3H, s), 4.22(2H, q, J=6.8 Hz), 4.73(1H, d, J=4.0 Hz), 4.79(2H, s), 5.48(2H, s), 7.34(1H, s), 7.51(1H, s), 7.56(1H, s), 9.00–9.12(1H, m), 9.20–9.34(1H, m).

MS: m/e (ESI) 528.2 (MH+)

Example 106

1-[3-tert-Butyl-5-(3-hydroxy-pyrrolidin-1-yl)-4-methoxy-phenyl]-2-(5,6-diethoxy-7-fluoro-1-imino-1,3-dihydro-isoindol-2-yl)-ethanone trifluoroacetate

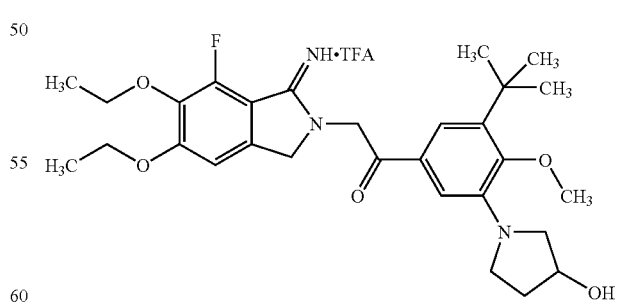

1H-NMR(DMSO-d6) δ: 1.40(9H, s), 1.79–1.92(1H, m), 1.98–2.12(1H, m), 2.90–2.99(1H, m), 3.08–3.18(1H, m), 3.20–3.60(2H, m), 3.65(3H, s), 3.89(3H, s), 3.97(3H, s), 4.30–4.43(1H, m), 4.81(2H, s), 5.50(2H, s), 7.34(1H, s), 7.39(1H, s), 7.43(1H, s), 9.08(1H, brs), 9.31(1H, brs).

Example 107

2-[2-(3-tert-Butyl-5-ethylamino-4-methoxy-phenyl)-2-oxo-ethyl]-6-ethoxy-3-imino-2,3-dihydro-1H-isoindole-5-carboxylic acid methylamide hydrobromide

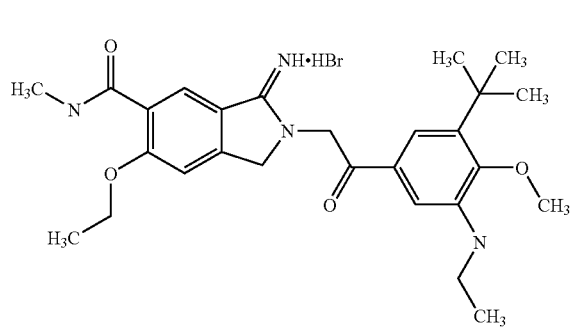

1H-NMR(DMSO-d6) δ: 1.20(3H, t, J=7.0 Hz), 1.37(9H, s), 1.41(3H, t, J=7.0 Hz), 2.82(3H, d, J=4.8 Hz), 3.12–3.17 (2H, m), 3.73(3H, s), 4.28(2H, q, J=7.0 Hz), 4.83(2H, s), 5.29(1H, t, J=6.0 Hz), 5.46(2H, s), 7.11(1H, s), 7.23(1H, s), 7.53(1H, s), 8.21(1H, q, J=4.8 Hz), 8.55(1H, s), 9.18(1H, brs), 9.80(1H, brs).

MS: m/e (ESI) 481.3 (MH+)

Example 108

2-[2-(3-tert-Butyl-5-ethylamino-4-methoxy-phenyl)-2-oxo-ethyl]-6-ethoxy-3-imino-2,3-dihydro-1H-isoindole-5-carboxylic acid methylamide hydrobromide

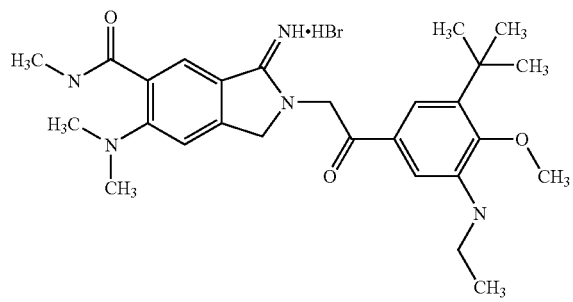

1H-NMR(DMSO-d6) δ: 1.20(3H, t, J=7.0 Hz), 1.37(9H, s), 2.78(3H, d, J=4.6 Hz), 2.92(6H, s), 3.12–3.19(2H, m), 3.72(3H, s), 4.73(2H, s), 5.28(1H, t, J=5.8 Hz), 5.42(2H, s), 7.10(1H, s), 7.15(1H, s), 7.23(1H, s), 8.06(1H, s), 8.37(1H, q, J=4.6 Hz), 8.92(1H, brs), 9.52(1H, brs).

MS: m/e (ESI) 480.3 (MH+)

Example 109

2-[2-(3-tert-Butyl-5-ethoxy-4-hydroxy-phenyl)-2-oxo-ethyl]-6-ethoxy-3-imino-2,3-dihydro-1H-isoindole-5-carboxylic acid methylamide hydrobromide

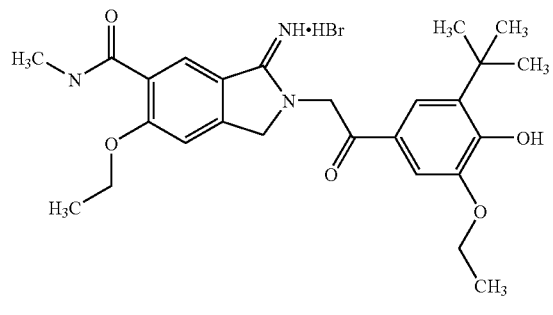

1H-NMR(DMSO-d6) δ: 1.36–1.43(15H, m), 2.82(3H, d, J=4.6 Hz), 4.12(2H, q, J=7.0 Hz), 4.28(2H, q, J=7.0 Hz), 4.83(2H, s), 5.45(2H, s), 7.43(1H, s), 7.51(1H, s), 7.53(1H, s), 8.20(1H, q, J=4.6 Hz), 8.55(1H, s).

MS: m/e (ESI) 468.2 (MH+)

Example 110

2-tert-Butyl-6-ethoxy-4-[2-(5-ethoxy-1-imino-6-methylcarbamoyl-1,3-dihydro-isoindol-2-yl)-acetyl]-phenyl ethylcarbamate hydrobromide

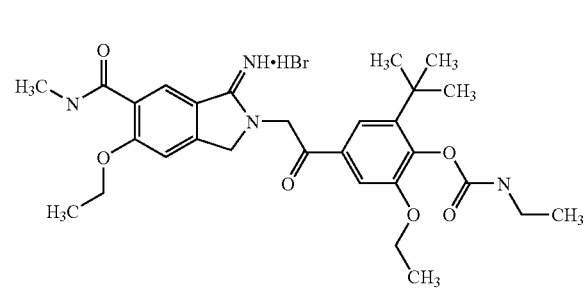

1H-NMR(DMSO-d6) δ: 1.09(3H, t, J=7.0 Hz), 1.31(3H, t, J=7.0 Hz), 1.34(9H, s), 1.42(3H, t, J=7.0 Hz), 2.82(3H, d, J=4.8 Hz), 3.05–3.11(2H, m), 4.07(2H, q, J=7.0 Hz), 4.28 (2H, q, J=7.0 Hz), 4.85(2H, s), 5.51(2H, s), 7.52(1H, s), 7.54(1H, s), 7.57(1H, s), 7.86(1H, t, J=6.0 Hz), 8.21(1H, q, J=4.8 Hz), 8.55(1H, s).

MS: m/e (ESI) 539.4 (MH+)

Example 111

2-tert-Butyl-6-(3-cyano-propoxy)-4-[2-(5,6-diethoxy-7-fluoro-1-imino-1,3-dihydro-isoindol-2-yl)-acetyl]-phenyl methanesulfonate hydrobromide

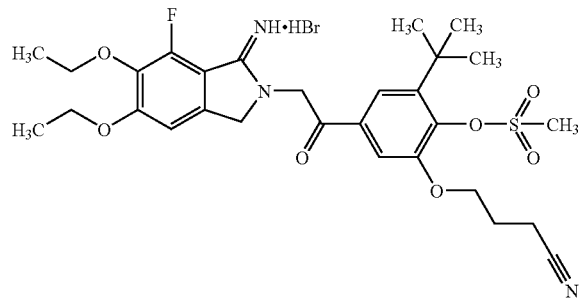

1H-NMR(DMSO-d6) δ: 1.29(3H, t, J=7.0 Hz), 1.40(3H, t, J=7.0 Hz), 1.44(9H, s), 2.10–2.17(2H, m), 2.69(2H, t, J=7.2 Hz), 3.67(3H, s), 4.12(2H, q, J=7.0 Hz), 4.21(2H, q, J=7.0 Hz), 4.82(2H, s), 5.53(2H, s), 7.35(1H, s), 7.63(1H, s), 7.66(1H, s), 9.08(1H, brs), 9.32(1H, brs).

MS: m/e (ESI) 590.2 (MH+)

Example 113

2-(2-{3-tert-Butyl-4-methoxy-5-[(2-methoxyethyl)-methylamino]-phenyl}-2-oxo-ethyl)-6-dimethylamino-3-imino-2,3-dihydro-1H-isoindole-5-carboxylic acid methylamide hydrobromide

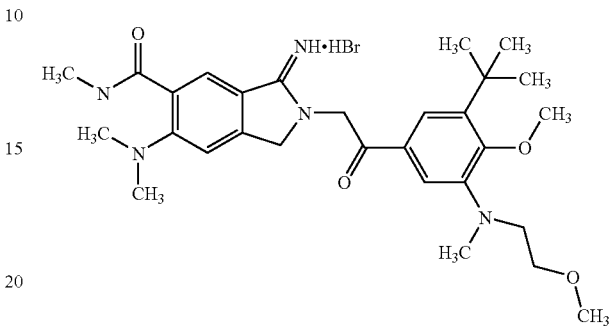

1H-NMR(DMSO-d6) δ: 1.36(9H, s), 2.77(3H, d, J=4.0 Hz), 2.80(3H, s), 2.91(6H, s), 3.18(3H, s), 3.20–3.48(4H, m), 3.81(3H, s), 4.73(2H, s), 5.43(2H, s), 7.15(1H, s), 7.50(1H, s), 7.53(1H, s), 8.06(1H, s), 8.36(1H, q, J=4.0 Hz).

MS: m/e (ESI) 524.3 (MH+)

Example 112

1-(3-tert-Butyl-4-methoxy-5-piperazin-1-yl-phenyl)-2-(5,6-diethoxy-7-fluoro-1-imino-1,3-dihydro-isoindol-2-yl)-ethanone dihydrochloride

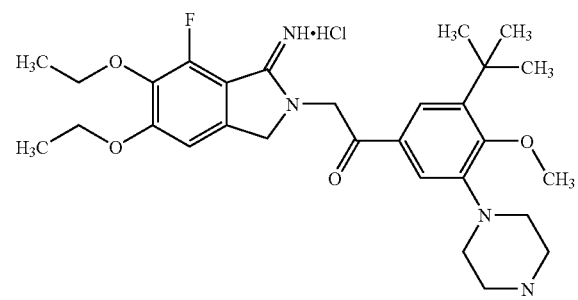

1H-NMR(DMSO-d6) δ: 1.29(3H, t, J=7.0 Hz), 1.37(9H, s), 1.40(3H, t, J=7.0 Hz), 3.21(4H, brs), 3.32(4H, brs), 3.94(3H, s), 4.11(2H, q, J=7.0 Hz), 4.21(2H, q, J=7.0 Hz), 4.79(2H, s), 5.55(2H, s), 7.34(1H, s), 7.50(1H, s), 7.64(1H, s), 9.04–9.16(3H, m), 9.40(1H, brs).

MS: m/e (ESI) 527.3 (MH+)

Example 114

1-[3-tert-Butyl-5-(2-hydroxyethylamino)-4-methoxy-phenyl]-2-(5,6-diethoxy-7-fluoro-1-imino-1,3-dihydro-isoindol-2-yl)-ethanone hydrochloride

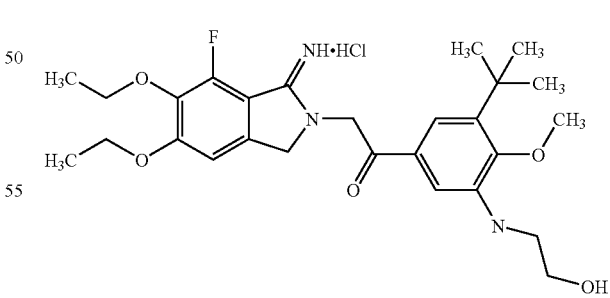

1H-NMR(DMSO-d6) δ: 1.38(3H, t, J=6.8 Hz), 1.45(9H, s), 1.50(3H, t, J=6.8 Hz), 3.44(2H, t, J=5.4 Hz), 3.83(2H, t, J=5.4 Hz), 3.89(3H, s), 4.18(2H, q, J=6.8 Hz), 4.24(2H, q, J=6.8 Hz), 4.91(2H, s), 5.49(2H, s), 7.21(1H, s), 7.55(1H, d, J=2.0 Hz), 7.66(1H, d, J=2.0 Hz).

MS: m/e (ESI) 502.3 (MH+)

Example 115

1-{3-tert-Butyl-5-[(2-hydroxyethyl)-methylamino]-4-methoxy-phenyl}-2-(5,6-diethoxy-7-fluoro-1-imino-1,3-dihydro-isoindol-2-yl)-ethanone dihydrochloride

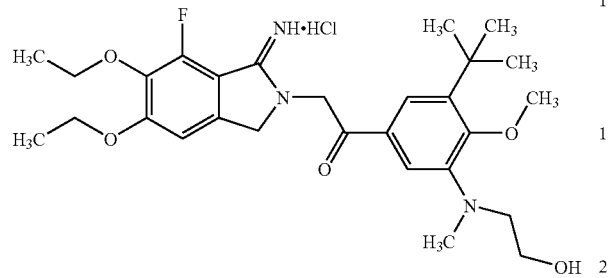

1H-NMR(DMSO-d6) δ: 1.36(3H, t, J=6.8 Hz), 1.44(9H, s), 1.49(3H, t, J=6.8 Hz), 3.04(3H, brs), 3.38–3.75(4H, m), 3.95(3H, s), 5.49(2H, s), 7.21(1H, s), 7.77–7.95(2H, m). MS: m/e (ESI) 516.4 (MH+)

Example 116

2-{2-[3-tert-Butyl-5-(3,4-dihydroxy-pyrrolidin-1-yl)-4-methoxy-phenyl]-2-oxo-ethyl}-6-ethoxy-3-imino-2,3-dihydro-1H-isoindole-5-carboxylic acid methylamide trifluoroacetate

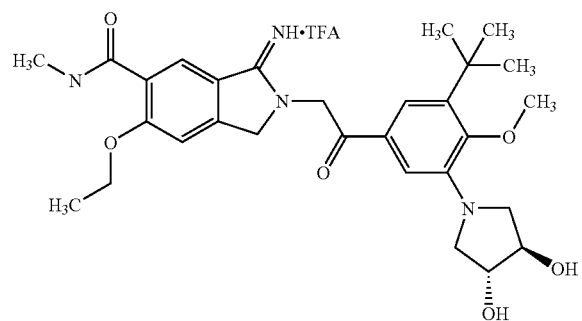

1H-NMR(DMSO-d6) δ: 1.37(9H, s), 1.41(3H, t, J=6.8 Hz), 2.82(3H, d, J=4.8 Hz), 2.88–2.95(2H, m), 3.50–3.59 (2H, m), 3.61(3H, s), 4.02(2H, brs), 4.28(2H, q, J=6.8 Hz), 4.83(2H, s), 5.37–5.60(2H, m), 7.29(1H, s), 7.38(1H, s), 7.54(1H, s), 8.12–8.28(1H, m), 8.55(1H, s), 9.14(1H, brs), 9.82(1H, brs).

Example 117

1-[3-tert-Butyl-5-((3R, 4R)-3-hydroxy-4-methoxy-pyrrolidin-1-yl)-4-methoxy-phenyl]-2-(5,6-diethoxy-7-fluoro-1-imino-1,3-dihydro-isoindol-2-yl)-ethanone trifluoroacetate

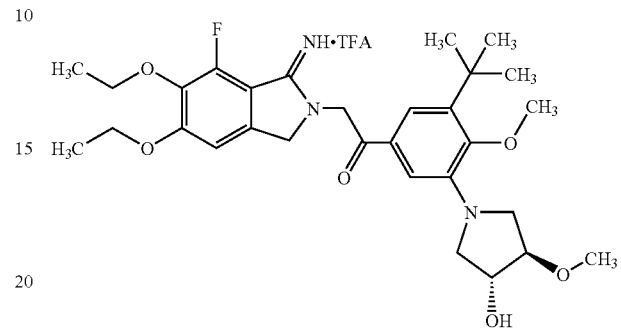

1H-NMR(DMSO-d6) δ: 1.29(3H, t, J=7.2 Hz), 1.37(9H, s), 1.39(3H, t, J=7.2 Hz), 2.91–2.99(1H, m), 3.03–3.12(1H, m), 3.30(3H, s), 3.40–3.58(2H, m), 3.63(3H, s), 3.71–3.79 (1H, m), 4.10(2H, q, J=7.2 Hz), 4.10–4.30(3H, m), 4.78(2H, s), 5.38–5.60(2H, m), 7.30(1H, s), 7.33(1H, s), 7.41(1H, s), 8.99–9.12(1H, m), 9.20–9.40(1H, m).

Example 118

1-(3-tert-Butyl-4-hydroxy-5-morpholino-phenyl)-2-(5,6-diethoxy-7-fluoro-1-imino-1,3-dihydro-isoindol-2-yl)-ethanone hydrochloride

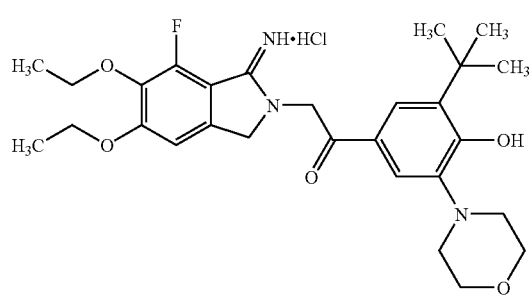

1H-NMR(DMSO-d6) δ: 1.29(3H, t, J=7.0 Hz), 1.38–1.41 (12H, m), 2.78–2.79(4H, m), 3.81–3.83(4H, m), 4.11(2H, q, J=7.0 Hz), 4.21(2H, q, J=7.0 Hz), 4.79(2H, s), 5.44(2H, s), 7.33(1H, s), 7.67(1H, s), 7.73(1H, s), 9.03(1H, brs), 9.20 (1H, brs), 9.28(1H, brs).
MS: m/e (ESI) 514.3 (MH+)

Example 119

1-{3-tert-Butyl-5-[ethyl-(2-hydroxyethyl)-amino]-4-methoxy-phenyl}-2-(5,6-diethoxy-7-fluoro-1-imino-1,3-dihydro-isoindol-2-yl)-acetyl hydrochloride

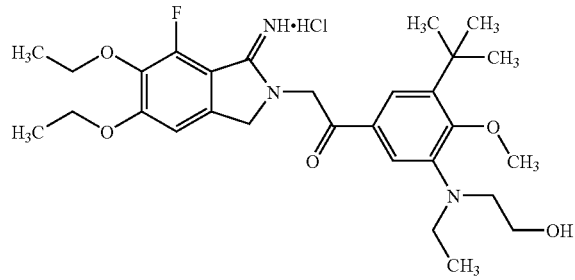

1H-NMR(DMSO-d6) δ: 0.96(3H, t, J=6.4 Hz), 1.28(3H, t, J=6.8 Hz), 1.37(9H, s), 1.39(3H, t, J=6.8 Hz), 3.14–3.26 (4H, m), 3.47(2H, t, J=6.0 Hz), 3.84(3H, s), 4.11(2H, q, J=6.8 Hz), 4.20(2H, q, J=6.8 Hz), 4.79(2H, s), 5.61(2H, s), 7.33(1H, s), 7.55(1H, s), 7.60(1H, s), 9.10(1H, brs), 9.57 (1H, brs).

Example 120

2-(2-{3-tert-Butyl-5-[(2-hydroxyethyl)-methylamino]-4-methoxy-phenyl}-2-oxo-ethyl)-6-dimethylamino-3-imino-2,3-dihydro-1H-isoindole-5-carboxylic acid methylamide dihydrochloride

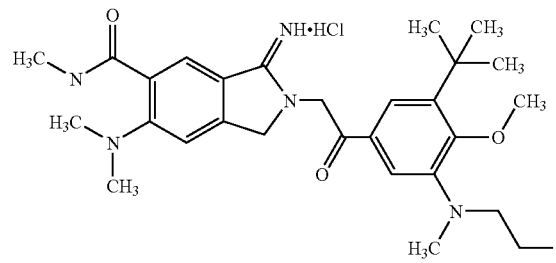

1H-NMR(DMSO-d6) δ: 1.36(9H, s), 2.75(3H, d, J=4.0 Hz), 2.81(3H, s), 2.91(6H, s), 3.17(2H, t, J=5.6 Hz), 3.52 (2H, t, J=5.4 Hz), 4.73(2H, s), 5.52(2H, s), 7.15(1H, s), 7.53(1H, s), 8.10(1H, s), 8.38(1H, q, J=4.0 Hz), 9.17(1H, brs), 9.65(1H, brs).

Example 121

1-{3-tert-Butyl-5-[(3hydroxypropyl)-methylamino]-4-methoxy-phenyl}-2-(5,6-diethoxy-7-fluoro-1-imino-1,3-dihydro-isoindol-2-yl)-ethanone dihydrochloride

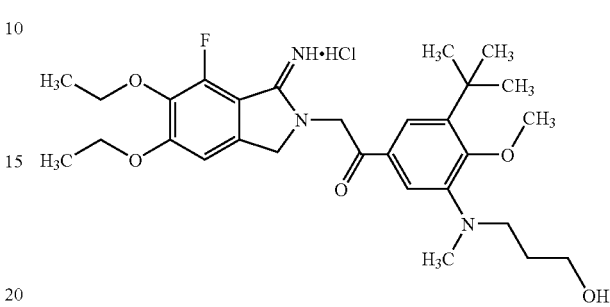

1H-NMR(DMSO-d6) δ: 1.28(3H, t, J=6.8 Hz), 1.36(9H, s), 1.39(3H, t, J=6.8 Hz), 1.61(2H, t, J=6.4 Hz), 2.75(3H, s), 3.14(2H, t, J=6.4 Hz), 3.38(2H, t, J=6.4 Hz), 3.82(3H, s), 4.11(2H, q, J=6.8 Hz), 4.20(2H, q, J=6.8 Hz), 4.79(2H, s), 5.55(2H, s), 7.33(1H, s), 7.51(1H, s), 7.54(1H, s), 9.08(1H, brs), 9.45(1H, brs).

Example 122

1-{3-tert-Butyl-5-[(2-hydroxyethyl)-(2-methoxyethyl)-amino]-4-methoxy-phenyl}-2-(5,6-diethoxy-7-fluoro-1-imino-1,3-dihydro-isoindol-2-yl)-ethanone dihydrochloride

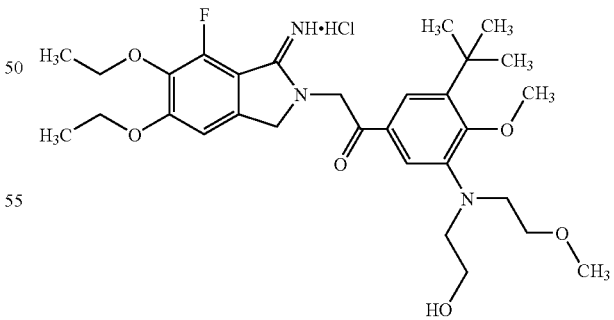

1H-NMR(DMSO-d6) δ: 1.29(3H, t, J=7.2 Hz), 1.36(9H, s), 1.39(3H, t, J=7.2 Hz), 3.15(3H, s), 3.28(2H, t, J=6.0 Hz), 3.20–3.78(4H, m), 3.46(2H, t, J=6.0 Hz), 3.82(3H, s), 4.12 (2H, q, J=7.2 Hz), 4.21(2H, q, J=7.2 Hz), 4.79(2H, s), 5.51(2H, s), 7.33(1H, s), 7.51(1H, s), 7.58(1H, s), 9.06(1H, brs), 9.39(1H, brs).

Example 123

1-(3-Amino-5-tert-butyl-4-methoxy-phenyl)-2-(5,6-diethoxy-7-fluoro-1-imino-1,3-dihydro-isoindol-2-yl)-ethanone hydrobromide

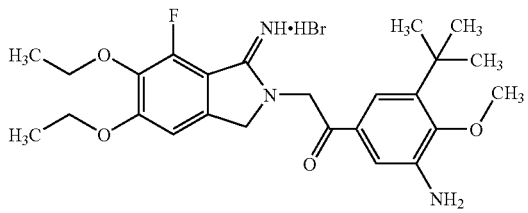

1H-NMR(DMSO-d6) δ: 1.38(3H, t, J=7.2 Hz), 1.43(9H, s), 1.50(3H, t, J=7.2 Hz), 3.85(3H, s), 4.17(2H, q, J=7.2 Hz), 4.24(2H, q, J=7.2 Hz), 4.82(2H, s), 5.39(2H, s), 7.19(1H, s), 7.44(1H, d, J=2.0 Hz), 7.48(1H, d, J=2.0 Hz).

MS: m/e (ESI) 458.2 (MH+)

Example 124

2-[2-(3-tert-Butyl-5-isopropylamino-4-methoxy-phenyl)-2-oxo-ethyl]-6-ethoxy-3-imino-2,3-dihydro-1H-isoindole-5-carboxylic acid methylamide hydrobromide

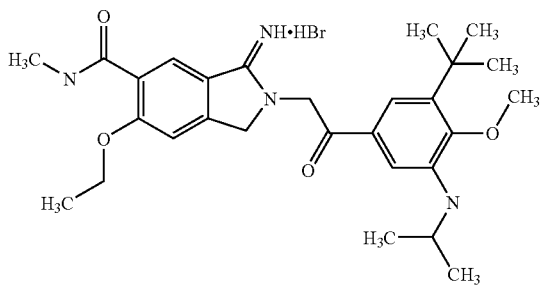

1H-NMR(DMSO-d6) δ: 1.19(6H, d, J=6.0 Hz), 1.36(9H, s), 1.41(3H, t, J=7.2 Hz), 2.82(3H, d, J=4.4 Hz), 3.60–3.78 (1H, m), 3.71(3H, s), 4.28(2H, q, J=7.2 Hz), 4.83(2H, s), 4.90(1H, d, J=6.0 Hz), 5.46(2H, s), 7.14(1H, s), 7.22(1H, s), 7.53(1H, s), 8.20(1H, d, J=4.4 Hz), 8.55(1H, s).

Example 125

1-[3-tert-Butyl-5-((3S, 4S)-3-hydroxy-4-methoxy-pyrrolidin-1-yl)-4-methoxy-phenyl]-2-(5,6-diethoxy-7-fluoro-1-imino-1,3-dihydro-isoindol-2-yl)-ethanone trifluoroacetate

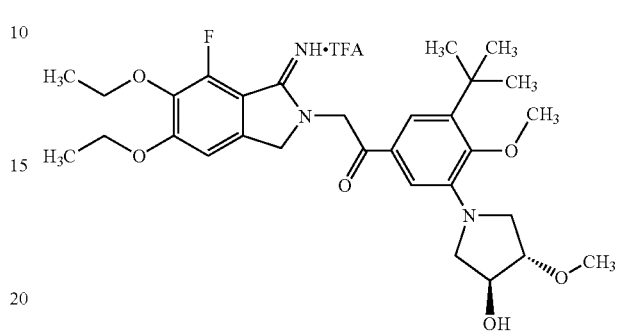

1H-NMR(DMSO-d6) δ: 1.29(3H, t, J=7.2 Hz), 1.37(9H, s), 1.39(3H, t, J=7.2 Hz), 2.91–2.99(1H, m), 3.03–3.12(1H, m), 3.30(3H, s), 3.40–3.58(2H, m), 3.63(3H, s), 3.71–3.79 (1H, m), 4.10(2H, q, J=7.2 Hz), 4.10–4.30(3H, m), 4.78(2H, s), 5.38–5.60(2H, m), 7.30(1H, s), 7.33(1H, s), 7.41(1H, s), 8.99–9.12(1H, m), 9.20–9.40(1H, m).

MS: m/e (ESI) 558.3 (MH+)

Example 126

1-[3-tert-Butyl-5-((3S, 4S)-3,4-dimethoxy-pyrrolidin-1-yl)-4-methoxy-phenyl]-2-(5,6-diethoxy-7-fluoro-1-imino-1,3-dihydro-isoindol-2-yl)-ethanone hydrobromide

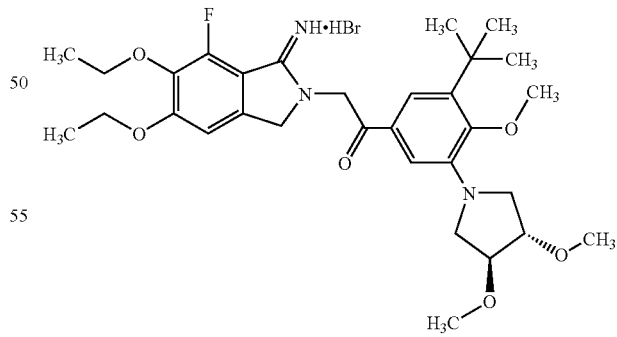

1H-NMR(DMSO-d6) δ: 1.28(3H, t, J=7.2 Hz), 1.37(9H, s), 1.39(3H, t, J=7.2 Hz), 3.03–3.16(2H, m), 3.29(6H, s), 3.36–3.52(2H, m), 3.64(3H, s), 3.91(2H, brs), 4.11(2H, q, J=7.2 Hz), 4.21(2H, q, J=7.2 Hz), 4.78(2H, s), 5.36–5.62 (2H, m), 7.33(2H, s), 7.44(1H, s), 8.95–9.35(2H, m).

MS: m/e (ESI) 572.4 (MH+)

Example 127

(4-{3-tert-Butyl-5-[2-(5,6-diethoxy-7-fluoro-1-imino-1,3-dihydro-isoindol-2-yl)-acetyl]-2-methoxy-phenyl}-piperazin-1-yl)-acetic acid dihydrochloride

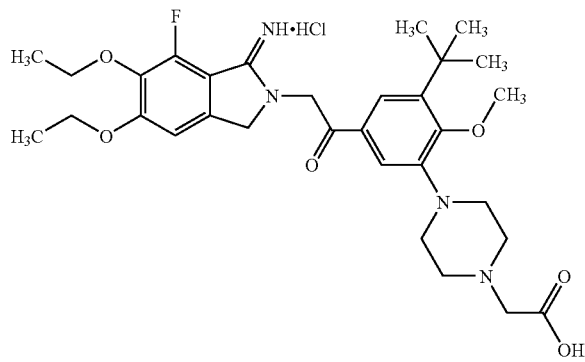

1H-NMR(DMSO-d6) δ: 1.29(3H, t, J=7.0 Hz), 1.38(9H, s), 1.40(3H, t, J=7.0 Hz), 3.10–3.69(10H, m), 3.93(3H, s), 4.12(2H, q, J=7.0 Hz), 4.21(2H, q, J=7.0 Hz), 4.22(2H, brs), 4.80(2H, s), 5.54(2H, s), 7.34(1H, s), 7.49(1H, s), 7.64(1H, s), 9.10(1H, brs), 9.40(1H, brs).
MS: m/e (ESI) 585.3 (MH+)

Example 128

4-{3-tert-Butyl-5-[2-(5,6-diethoxy-7-fluoro-1-imino-1,3-dihydro-isoindol-2-yl)-acetyl]-2-methoxy-phenyl}-piperazine-1-carboxylic acid ethylamide hydrobromide

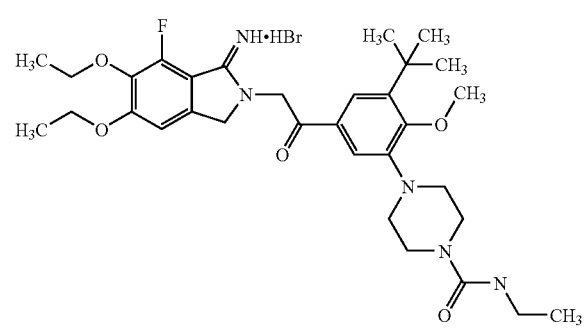

1H-NMR(DMSO-d6) δ: 1.01(3H, t, J=7.0 Hz), 1.30(3H, t, J=7.0 Hz), 1.37(9H, s), 1.40(3H, t, J=7.0 Hz), 2.93(4H, brs), 3.02–3.08(2H, m), 3.49(4H, brs), 3.95(3H, s), 4.12(2H, q, J=7.0 Hz), 4.22(2H, q, J=7.0 Hz), 4.79(2H, s), 5.48(2H, s), 7.34(1H, s), 7.50(1H, s), 7.60(1H, s).
MS: m/e (ESI) 598.3 (MH+)

Example 129

1-(4-{3-tert-Butyl-5-[2-(5,6-diethoxy-7-fluoro-1-imino-1,3-dihydro-isoindol-2-yl)-acetyl]-2-methoxy-phenyl}-piperazin-1-yl)-propan-1-one hydrobromide

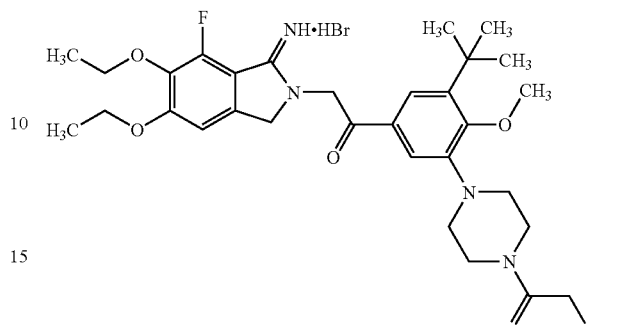

1H-NMR(DMSO-d6) δ: 1.00(3H, t, J=7.0 Hz), 1.29(3H, t, J=7.0 Hz), 1.37(9H, s), 1.40(3H, t, J=7.0 Hz), 2.36(2H, q, J=7.0 Hz), 2.94(2H, brs), 2.98(2H, brs), 3.66(4H, brs), 3.96(3H, s), 4.11(2H, q, J=7.0 Hz), 4.21(2H, q, J=7.0 Hz), 4.79(2H, s), 5.47(2H, s), 7.34(1H, s), 7.50(1H, d, J=2.0 Hz), 7.61(1H, d, J=2.0 Hz), 9.06(1H, brs), 9.28(1H, brs).
MS: m/e (ESI) 583.4 (MH+)

Example 130

1-(3,5-Di-tert-butyl-4-hydroxy-phenyl)-2-(1-imino-1,3-dihydro-isoindol-2-yl)-ethanone hydrobromide 1H-NMR(DMSO-d6) δ: 1.60(18H, s), 4.83(2H, s), 5.50(2H, s), 7.62–7.83(5H, m), 8.05(1H, s), 8.13–8.22(1H, m), 9.21(1H, brs), 9.90(1H, brs).

Example 131

1-(3,5-Di-tert-butyl-4-hydroxy-phenyl)-2-(1-imino-5-methoxy-1,3-dihydro-isoindol-2-yl)-ethanone hydrobromide 1H-NMR(DMSO-d6) δ: 1.41(18H, s), 3.88(3H, s), 4.78(2H, s), 5.46(2H, s), 7.24(1H, d, J=8.8 Hz), 7.35(1H, s), 7.77(2H, s), 8.10(1H, d, J=8.8 Hz), 9.04(1H, brs), 9.71(1H, brs).
MS: m/e (ESI) 409.1 (MH+)

Example 132

N-{2-[2-(3,5-Di-tert-butyl-4-hydroxy-phenyl)-2-oxo-ethyl]-3-imino-2,3-dihydro-1H-isoindol-5-yl}-acetamide hydrobromide 1H-NMR(DMSO-d6) δ: 1.41(18H, s), 2.10(3H, s), 4.77(2H, s), 5.49(2H, s), 7.59–7.71(2H, m), 7.76(2H, s), 8.01–8.12(1H, s), 8.68(1H, s), 9.19(1H, brs), 9.99(1H, brs), 10.37(1H, s).
MS: m/e (ESI) 436.1 (MH+)

Example 133

N-{2-[2-(3,5-Di-tert-butyl-4-hydroxy-phenyl)-2-oxo-ethyl]-1-imino-2,3-dihydro-1H-isoindol-5-yl}-acetamide hydrobromide 1H-NMR(DMSO-d6) δ: 1.42(18H, s), 2.12(3H, s), 4.81(2H, s), 5.47(2H, s), 7.69(1H, d, J=8.4 Hz), 7.77(2H, s), 8.00–8.20(3H, m), 9.07(1H, brs), 9.76(1H, brs), 10.51(1H, s).
MS: m/e (ESI) 436.1 (MH+)

Example 134

N-{2-[2-(3,5-Di-tert-butyl-4-hydroxy-phenyl)-2-oxo-ethyl]-3-imino-2,3-dihydro-1H-isoindol-5-yl}-methanesulfonamide hydrobromide 1H-NMR(DMSO-d6) δ: 1.42(18H, s), 3.11(3H, s), 4.80 (2H, s), 5.50(2H, s), 7.53(1H, d, J=8.8 Hz), 7.73(1H, d, J=8.8 Hz), 7.75(2H, s), 8.08(1H, s), 9.22(1H, brs), 10.02 (1H, brs).

MS: m/e (ESI) 472.1 (MH+)

Example 135

N-{2-[2-(3,5-Di-tert-butyl-4-hydroxy-phenyl)-2-oxo-ethyl]-1-imino-2,3-dihydro-1H-isoindol-5-yl}-methanesulfonamide hydrobromide 1H-NMR(DMSO-d6) δ: 1.40(18H, s), 3.16(3H, s), 4.81 (2H, s), 5.46(2H, s), 7.37(1H, d, J=8.8 Hz), 7.50(1H, s), 7.76(2H, s), 8.10(1H, d, J=8.8 Hz), 9.07(1H, brs), 9.97(1H, brs).

MS: m/e (ESI) 472.1 (MH+)

Example 136

1-(3,5-Di-tert-butyl-4-hydroxy-phenyl)-2-(1-imino-6-isopropoxy-1,3-dihydro-isoindol-2-yl)-ethanone hydrobromide 1H-NMR(DMSO-d6) δ: 1.32(6H, d, J=6.0 Hz), 1.42(18H, s), 4.52–4.70(1H, m), 4.76(2H, s), 5.49(2H, s), 7.33(1H, d, J=8.4 Hz), 7.64(1H, d, J=8.4 Hz), 7.77(2H, s), 7.82(1H, s), 9.21(1H, brs), 9.78(1H, brs).

MS: m/e (ESI) 437.1 (MH+)

Example 137

1-(3,5-Di-tert-butyl-4-hydroxy-phenyl)-2-(1-imino-5-isopropoxy-1,3-dihydro-isoindol-2-yl)-ethanone hydrobromide 1H-NMR(DMSO-d6) δ: 1.31(6H, d, J=6.0 Hz), 1.42(18H, s), 4.68–4.81(1H, m), 4.77(2H, s), 5.47(2H, s), 7.19(1H, d, J=9.6 Hz), 7.32(1H, s), 7.77(2H, s), 8.02–8.19(3H, m), 9.03(1H, brs), 9.70(1H, brs).

MS: m/e (ESI) 437.2 (MH+)

Example 138

1-(3,5-Di-tert-butyl-4-hydroxy-phenyl)-2-[1-imino-6-(2-methoxy-ethoxy)-1,3-dihydro-isoindol-2-yl]-ethanone hydrobromide 1H-NMR(DMSO-d6) δ: 1.42(18H, s), 3.32(3H, s), 3.71 (2H, t, J=4.4 Hz), 4.17(2H, t, J=4.4 Hz), 4.77(2H, s), 5.51(2H, s), 7.40(1H, d, J=8.4 Hz), 7.67(1H, d, J=8.4 Hz), 7.78(2H, s), 7.85(1H, m), 8.08(1H, brs), 9.24(1H, brs), 9.80(1H, s).

MS: m/e (ESI) 453.2 (MH+)

Example 139

1-(3,5-Di-tert-butyl-4-hydroxy-phenyl)-2-[1-imino-5-(2-methoxy-ethoxy)-1,3-dihydro-isoindol-2-yl]-ethanone hydrobromide 1H-NMR(DMSO-d6) δ: 1.42(18H, s), 3.30(3H, s), 3.66–3.75(2H, m.), 4.19–4.31(2H, m), 4.78(2H, s), 5.47(2H, s), 7.24(1H, d, J=8.8 Hz), 7.35(1H, s), 7.77(2H, s), 8.07(1H, brs), 8.10(1H, d, J=8.8 Hz), 9.06(1H, brs), 9.74(1H, s).

MS: m/e (ESI) 453.1 (MH+)

Example 140

N-{2-[2-(3,5-Di-tert-butyl-4-hydroxy-phenyl)-2-oxo-ethyl]-1-imino-2,3-dihydro-1H-isoindol-5-yl}-N-methyl-acetamide hydrobromide 1H-NMR(DMSO-d6) δ: 1.40(18H, s), 2.48(3H, s), 3.25 (3H, s), 4.85(2H, s), 5.51(2H, s), 7.66(1H, d, J=9.0 Hz), 7.76(3H, s), 8.10(1H, s), 8.21(1H, d, J=9.0 Hz), 9.26(1H, s), 9.94(1H, s).

MS: m/e (ESI) 450.2 (MH+)

Example 141

N-{2-[2-(3,5-Di-tert-butyl-4-hydroxy-phenyl)-2-oxo-ethyl]-3-imino-2,3-dihydro-1H-isoindol-5-yl}-N-methyl-acetamide hydrobromide 1H-NMR(DMSO-d6) δ: 1.40(18H, s), 2.48(3H, s), 3.25 (3H, brs), 4.86(2H, s), 5.53(2H, s), 7.75–7.83(2H, m), 8.10(1H, s), 8.16(1H, s), 9.29(1H, s), 9.94(1H, s).

MS: m/e (ESI) 450.2 (MH+)

Example 142

{2-[2-(3,5-Di-tert-butyl-4-hydroxy-phenyl)-2-oxo-ethyl]-3-imino-2,3-dihydro-1H-isoindol-5-yl}-urea hydrobromide 1H-NMR(DMSO-d6) δ: 1.40(18H, s), 4.74(2H, s), 5.49 (2H, s), 6.12(2H, s), 7.54–7.62(2H, m), 7.77(2H, s), 8.08 (1H, s), 8.43(1H, s), 9.07(1H, s), 9.21(1H, s), 9.94(1H, s).

Example 143

{2-[2-(3,5-Di-tert-butyl-4-hydroxy-phenyl)-2-oxo-ethyl]-1-imino-2,3-dihydro-1H-isoindol-5-yl}-urea hydrobromide 1H-NMR(DMSO-d6) δ: 1.41(18H, s), 4.76(2H, s), 5.43 (2H, s), 6.19(2H, s), 7.48(1H, d, J=7.7 Hz), 7.57(2H, s), 7.97(1H, s), 8.0(1H, d, J=7.7 Hz), 8.07(1H, s), 8.98(1H, s), 9.22(1H, s), 9.66(1H, s).

Example 144

1-(3,5-Di-tert-butyl-4-hydroxy-phenyl)-2-(1-imino-7-isopropoxy-1,3-dihydro-isoindol-2-yl)-ethanone hydrobromide 1H-NMR(DMSO-d6) δ: 1.40(6H, d, J=7.6 Hz), 1.42(18H, s), 4.78(2H, s), 4.87–5.02(1H, m), 5.49(2H, s), 7.26(1H, d, J=8.4 Hz), 7.30(1H, d, J=8.4 Hz), 7.82(1H, t, J=8.4 Hz), 7.77(2H, s), 8.04(1H, brs), 8.08(1H, s), 9.22(1H, brs).

MS: m/e (ESI) 437.2 (MH+)

Example 145

1-(3,5-Di-tert-butyl-4-hydroxy-phenyl)-2-(1-imino-6-methoxy-1,3-dihydro-isoindol-2-yl)-ethanone hydrobromide 1H-NMR(DMSO-d6) δ: 1.42(18H, s), 3.84(3H, s), 4.77 (2H, s), 5.52(2H, s), 7.38(1H, d, J=8.4 Hz), 7.67(1H, d, J=8.4 Hz), 7.78(2H, s), 7.86(1H, s), 8.08(1H, brs), 9.25(1H, brs), 9.85(1H, brs).
MS: m/e (ESI) 409.1 (MH+)

Example 146

1-(3,5-Di-tert-butyl-4-hydroxy-phenyl)-2-(6-fluoro-1-imino-1,3-dihydro-isoindol-2-yl)-ethanone hydrobromide 1H-NMR(DMSO-d6) δ: 1.41(18H, s), 4.85(2H, s), 5.52 (2H, s), 7.71(1H, dd, J=8.8 and 8.4 Hz), 7.77(2H, s), 7.80–7.88(1H, m), 8.06(1H, d, J=8.8 Hz).
MS: m/e (ESI) 397.2 (MH+)

Example 147

1-(3,5-Di-tert-butyl-4-hydroxy-phenyl)-2-(5-fluoro-1-imino-1,3-dihydro-isoindol-2-yl)-ethanone hydrobromide 1H-NMR(DMSO-d6) δ: 1.41(18H, s), 4.86(2H, s), 5.51 (2H, s), 7.52–7.61(1H, m), 7.69(1H, d, J=8.4 Hz), 7.77(2H, s), 8.22–8.31(1H, m), 9.24(1H, brs), 9.92(1H, brs).
MS: m/e (ESI) 397.1 (MH+)

Example 148

1-(3,5-Di-tert-butyl-4-hydroxy-phenyl)-2-(5-imino-5,7-dihydro-pyrrolo[3,4-b]pyridin-6-yl)-ethanone dihydrobromide 1H-NMR(DMSO-d6) δ: 1.40(18H, s), 4.91(2H, s), 5.58 (2H, s), 7.75(1H, dd, J=7.1,4.8 Hz), 7.78(2H, s), 8.08(2H, s), 8.67(1H, d, J=7.1), 8.94(1H, d, J=4.8 Hz), 9.56(1H, s), 10.27(1H, s).
MS: m/e (ESI) 380.1 (MH+)

Example 149

1-(3,5-Di-tert-butyl-4-hydroxy-phenyl)-2-[1-imino-6-(2-methoxy-1,1-dimethyl-ethoxy)-1,3-dihydro-isoindol-2-yl]-ethanone hydrobromide 1H-NMR(DMSO-d6) δ: 1.22(6H, s), 1.41(18H, s), 3.16 (3H, s), 3.91(2H, s), 4.77(2H, s), 5.49(2H, brs), 7.41(1H, d, J=8.0 Hz), 7.67(1H, d, J=8.0 Hz), 7.77(2H, s), 7.85(1H, s), 8.09(1H, brs), 9.22(1H, brs), 9.95(1H, brs).
MS: m/e (ESI) 481.3 (MH+)

Example 150

1-(3,5-Di-tert-butyl-4-hydroxy-phenyl)-2-[6-(2-hydroxy-1,1-dimethyl-ethoxy)-1-imino-1,3-dihydro-isoindol-2-yl]-ethanone hydrobromide 1H-NMR(DMSO-d6) δ: 1.23(6H, s), 1.41(18H, s), 3.79 (2H, s), 4.75(1H, s), 4.77(2H, s), 5.49(2H, s), 7.39(1H, dd, J=8.4 and 2.4 Hz), 7.66(1H, d, J=8.4 Hz), 7.77(2H, s), 7.83(1H, brs), 8.08(1H, brs), 9.21(1H, brs), 9.75(1H, brs).
MS: m/e (ESI) 467.2 (MH+)

Example 151

1-(3,5-Di-tert-butyl-4-hydroxy-phenyl)-2-(1-imino-6-isobutoxy-1,3-dihydro-isoindol-2-yl)-ethanone hydrobromide 1H-NMR(DMSO-d6) δ: 1.00(6H, d, J=6.8 Hz), 1.41(18H, s), 2.00–2.13(1H, m), 3.81(2H, d, J=6.8 Hz), 4.77(2H, s), 5.50(2H, s), 7.38(1H, d, J=8.8 Hz), 7.65(1H, d, J=8.0 Hz), 7.77(2H, s), 7.84(1H, s), 8.08(1H, brs), 9.22(1H, brs), 9.78 (1H, brs).
MS: m/e (ESI) 451.2 (MH+)

Example 152

Methyl 2-[2-(3,5-di-tert-butyl-4-hydroxy-phenyl)-2-oxo-ethyl]-3-imino-2,3-dihydro-1H-isoindole-5-carboxylate hydrobromide 1H-NMR(DMSO-d6) δ: 1.41(18H, s), 3.92(3H, s), 4.96 (2H, s), 5.53(2H, s), 7.77(2H, s), 7.92(1H, d, 8.0 Hz), 8.09(1H, s), 8.36(1H, d, 8.0 Hz), 8.91(1H, s), 9.39(1H, s), 10.09(1H, s).
MS: m/e (ESI) 437.1 (MH+)

Example 153

2-[2-(3,5-Di-tert-butyl-4-hydroxy-phenyl)-2-oxo-ethyl]-3-imino-2,3-dihydro-1H-isoindole-5-carboxamide hydrobromide 1H-NMR(DMSO-d6) δ: 1.41(18H, s), 4.92(2H, s), 5.54 (2H, s), 7.67(1H, s), 7.78(2H, s), 7.96(1H, d, J=8.0 Hz), 8.09(1H, s), 8.20(1H, s), 8.25(₁H, d, J=8.0 Hz), 8.77(1H, s), 9.34(1H, s), 10.01(1H, s).
MS: m/e (ESI) 422.1 (MH+)

Example 154

2-[2-(3,5-Di-tert-butyl-4-hydroxy-phenyl)-2-oxo-ethyl]-1-imino-2,3-dihydro-1H-isoindole-5-carboxamide hydrobromide 1H-NMR(DMSO-d6) δ: 1.41(18H, s), 4.92(2H, s), 5.54 (2H, s), 7.70(1H, s), 7.78(2H, s), 8.10(1H, s), 8.12(1H, d, 7.8 Hz), 8.21(1H, s), 8.22(1H, s), 8.27(1H, d, 7.8 Hz), 9.34(1H, s), 10.01(1H, s).
MS: m/e (ESI) 422.2 (MH+)

Example 155

2-(4 or 5-Cyano-2-imino-3-propyl-pyrrolidin-1-yl)-1-(3,5-di-tert-butyl-4-hydroxy-phenyl)-ethanone hydrobromide 1H-NMR(DMSO-d6) δ: 1.40(18H, s), 4.98(2H, s), 5.55 (2H, s), 7.78(2H, s), 8.02(1H, d, J=8.4 Hz), 8.10(1H, s), 8.28(1H, d, J=8.4 Hz), 8.67(1H, s), 9.48(1H, s), 10.06(1H, s), B:1.40(18H, s), 4.94(2H, s), 5.55(2H, s), 7.78(2H, s), 8.10, (1H, s), 8.18(1H, d, J=8.4 Hz), 8.32(1H, s), 8.38(1H, d, J=8.4 Hz), 9.48(1H, s), 10.17(1H, s).
MS: m/e (ESI) 404.1 (MH+)

Example 156

1-(3,5-Di-tert-butyl-4-hydroxy-phenyl)-2-(6-hydroxy-1-imino-1,3-dihydro-isoindol-2-yl)-ethanone hydrobromide 1H-NMR(DMSO-d6) δ: 1.41(18H, s), 4.71(2H, s), 5.48 (2H, s), 7.20(1H, d, J=8.4 Hz), 7.48–7.59(2H, m), 7.77(2H, s), 8.05(1H, brs), 9.12(1H, brs), 9.77(1H, brs), 10.22(1H, s).
MS: m/e (ESI) 395.1 (MH+)

Example 157

1-(3,5-Di-tert-butyl-4-hydroxy-phenyl)-2-(5-hydroxy-1-imino-1,3-dihydro-isoindol-2-yl)-ethanone hydrobromide 1H-NMR(DMSO-d6) δ: 1.41(18H, s), 4.72(2H, s), 5.42 (2H, s), 7.02(1H, d, J=8.4 Hz), 7.07(1H, s), 7.76(2H, s), 8.00(1H, d, J=8.4 Hz), 8.05(1H, brs), 8.93(1H, brs), 9.60 (1H, brs), 10.78(1H, brs).
MS: m/e (ESI) 395.1 (MH+)

Example 158

1-(3,5-Di-tert-butyl-4-hydroxy-phenyl)-2-[1-imino-6-(2-methoxy-1-methyl-ethoxy)-1,3-dihydro-isoindol-2-yl]-ethanone hydrobromide 1H-NMR(DMSO-d6) δ: 1.26(3H, d, J=6.0 Hz), 1.42(18H, s), 3.29(3H, s), 3.46–3.57(2H, m), 4.60–4.68(1H, m), 4.76 (2H, s), 5.51(2H, s), 7.37(1H, dd, J=8.4 and 2.4 Hz), 7.65(1H, d, J=8.4 Hz), 7.78(2H, s), 7.87(1H, brs), 8.05(1H, brs), 9.22(1H, brs), 9.79(1H, brs).
MS: m/e (ESI) 467.2 (MH+)

Example 159

2-[2-(3,5-Di-tert-butyl-4-hydroxy-phenyl)-2-oxo-ethyl]-3-imino-2,3-dihydro-1H-isoindole-5-carboxylic acid dimethylamide hydrobromide 1H-NMR(DMSO-d6) δ: 1.40(18H, s), 2.94(3H, s), 3.03 (3H, s), 4.91(2H, s), 5.53(2H, s), 7.77(2H, s), 7.84(1H, d, J=7.8 Hz), 7.86(1H, d, J=7.8 Hz), 8.10(1H, s), 8.32(1H, s), 9.31(1H, s), 9.93(1H, s).
MS: m/e (ESI) 450.2 (MH+)

Example 160

2-[2-(3,5-Di-tert-butyl-4-hydroxy-phenyl)-2-oxo-ethyl]-3-imino-2,3-dihydro-1H-isoindole-5-carboxylic acid hydrochloride 1H-NMR(DMSO-d6) δ: 1.40(18H, s), 4.94(2H, s), 5.57 (2H, s), 7.77(2H, s), 7.90(1H, d, J=7.1 Hz), 8.09(1H, s), 8.33(1H, d, J=7.1 Hz), 8.91(1H, s), 9.53(1H, s), 10.13(1H, s), 13.53(1H, s).
MS: m/e (ESI) 423.1 (MH+)

Example 161

3-{2-[2-(3,5-Di-tert-butyl-4-hydroxy-phenyl)-2-oxo-ethyl]-3-imino-2,3-dihydro-1H-isoindol-5-yl}-1,1-dimethyl-urea hydrobromide 1H-NMR(DMSO-d6) δ: 1.40(18H, s), 2.95(6H, s), 4.75 (2H, s), 5.49(1H, s), 7.61(1H, d, J=7.9 Hz), 7.64(1H, d, J=7.9 Hz), 7.77(2H, s), 8.06(1H, s), 8.48(1H, s), 8.72(1H, s), 9.15(1H, s), 9.88(1H, s).
MS: m/e (ESI) 465.2 (MH+)

Example 162

2-(6-tert-Butyl-1-imino-1,3-dihydro-isoindol-2-yl)-1-(3,5-di-tert-butyl-4-hydroxy-phenyl)-ethanone hydrobromide 1H-NMR(DMSO-d6) δ: 1.35(9H, s), 1.41(18H, s), 4.80 (2H, s), 5.49(2H, s), 7.69(1H, d, J=8.0 Hz), 7.76(2H, s), 7.87(1H, d, J=8.0 Hz), 8.30(1H, s), 9.19(1H, brs), 9.83(1H, brs).

Example 163

2-{2-[2-(3,5-Di-tert-butyl-4-hydroxy-phenyl)-2-oxo-ethyl]-3-imino-2,3-dihydro-1H-isoindol-5-yloxy}-propanoic acid hydrobromide 1H-NMR(DMSO-d6) δ: 1.41(18H, s), 1.55(3H, d, J=6.8 Hz), 4.75(2H, s), 4.90(1H, q, J=6.8 Hz), 5.49(2H, s), 7.34 (1H, dd, J=8.8 and 2.4 Hz), 7.65(1H, d, J=8.8 Hz), 7.73(1H, brs), 7.77(2H, s), 8.09(1H, brs), 9.22(1H, brs), 9.88(1H, brs).
MS: m/e (ESI) 467.2 (MH+)

Example 164

2-{2-[2-(3,5-Di-tert-butyl-4-hydroxy-phenyl)-2-oxo-ethyl]-3-imino-2,3-dihydro-1H-isoindol-5-yloxy}-2-methyl-propanoic acid hydrobromide 1H-NMR(DMSO-d6) δ: 1.41(18H, s), 1.59(6H, s), 4.75 (2H, s), 5.48(2H, s), 7.27(1H, dd, J=8.4 and 2.4 Hz), 7.65 (1H, d, J=8.4 Hz), 7.69(1H, d, J=2.4 Hz), 7.77(2H, s), 8.08(1H, brs), 9.17(1H, s), 9.93(1H, s).
MS: m/e (ESI) 481.2 (MH+)

Example 165

1-(3,5-Di-tert-butyl-4-hydroxy-phenyl)-2-(1-imino-6-methyl-1,3-dihydro-pyrrolo[3,4-c]pyridin-2-yl)-ethanone hydrochloride 1H-NMR(DMSO-d6) δ: 1.41(18H, s), 2.64(3H, s), 4.93 (2H, s), 5.58(2H, s), 7.78(2H, s), 8.06(1H, s), 8.09(1H, s), 8.94(1H, s), 9.61(1H, brs), 10.27(1H, brs).
MS: m/e (ESI) 394.2 (MH+)

Example 166

1-(3,5-Di-tert-butyl-4-hydroxy-phenyl)-2-(7-imino-2-methyl-5,7-dihydro-pyrrolo[3,4-b]pyridin-6-yl)-ethanone hydrochloride 1H-NMR(DMSO-d6) δ: 1.41(18H, s), 2.67(3H, s), 4.84 (2H, s), 5.63(2H, s), 7.70(1H, d, J=8.0 Hz), 7.78(2H, s), 8.08(1H, brs), 8.16(1H, d, J=8.0 Hz), 9.63(1H, s), 9.94 (1H, brs).
MS: m/e (ESI) 394.1 (MH+)

Example 167

1-(7-tert-Butyl-3,3-dimethyl-2,3-dihydro-benzofuran-5-yl)-2-(1-imino-6-isopropoxy-1,3-dihydro-isoindol-2-yl)-ethanone hydrobromide 1H-NMR(DMSO-d6) δ: 1.30–1.37(21H, m), 4.39(2H, s), 4.59–4.71(1H, m), 4.77(2H, s), 5.48(2H, s), 7.34(1H, d, J=8.8H), 7.65(1H, d, J=8.8 Hz), 7.72(1H, s), 7.80(1H, s), 7.82(1H, s), 9.25(1H, brs), 9.79(1H, brs).
MS: m/e (ESI) 435.1 (MH+)

Example 168

1-(3,5-Di-tert-butyl-4-hydroxy-phenyl)-2-(6-ethoxy-1-imino-1,3-dihydro-isoindol-2-yl)-ethanone hydrobromide 1H-NMR(DMSO-d6) δ: 1.38(3H, t, J=6.8 Hz), 1.42(18H, s), 4.11(2H, q, J=6.8 Hz), 4.77(2H, s), 5.51(2H, s), 7.36(1H, dd, J=8.4 and 2.4 Hz), 7.66(1H, d, J=8.4 Hz), 7.78(2H, s), 7.84(1H, brs), 8.08(1H, s), 9.22(1H, brs), 9.81(1H, s).
MS: m/e (ESI) 423.1 (MH+)

Example 169

1-(3,5-Di-tert-butyl-4-hydroxy-phenyl)-2-(5-ethoxy-1-imino-1,3-dihydro-isoindol-2-yl)-ethanone hydrobromide 1H-NMR(DMSO-d6) δ: 1.36(3H, t, J=6.8 Hz), 1.42(18H, s), 4.16(2H, q, J=6.8 Hz), 4.78(2H, s), 5.49(2H, s), 7.21(1H, d, J=8.8 Hz), 7.33(1H, s), 7.78(2H, s), 8.05(1H, s), 8.12(1H, d, J=8.8 Hz), 9.08(1H, brs), 9.75(1H, brs).
MS: m/e (ESI) 423.2 (MH+)

Example 170

1-(3,5-Di-tert-butyl-4-hydroxy-phenyl)-2-(1-imino-4,7-diisopropoxy-1,3-dihydro-isoindol-2-yl)-ethanone hydrobromide 1H-NMR(DMSO-d6) δ: 1.25(6H, d, J=6.0 Hz), 1.38(6H, d, J=6.0 Hz), 1.42(18H, s), 4.64(1H, qq, J=6.0 Hz, 6.0 Hz), 4.69(2H, s), 4.87(1H, qq, J=6.0 Hz, 6.0 Hz), 5.48(2H, s), 7.24(1H, d, J=9.2 Hz), 7.38(1H, d, J=9.2 Hz), 7.76(2H, s), 8.05(1H, brs).

Example 171

1-{2-[2-(3,5-Di-tert-butyl-4-hydroxy-phenyl)-2-oxo-ethyl]-3-imino-2,3-dihydro-1H-isoindol-5-yl}-3-methyl-urea hydrobromide 1H-NMR(DMSO-d6) δ: 1.40(18H, s), 2.67(3H, s), 4.74(2H, s), 5.48(2H, s), 7.55(1H, d, J=8.4 Hz), 7.59(1H, d, J=8.4 Hz), 7.77(2H, s), 8.06(1H, s), 8.44(1H, s), 8.97(1H, s), 9.15(1H, s), 10.40(1H, s).
MS: m/e (ESI) 451.2 (MH+)

Example 172

Methyl {2-[2-(3,5-di-tert-butyl-4-hydroxy-phenyl)-2-oxo-ethyl]-3-imino-2,3-dihydro-1H-isoindol-5-yl}-acetate hydrochloride 1H-NMR(DMSO-d6) δ: 1.40(18H, s), 3.64(3H, s), 3.88(2H, s), 4.83(2H, s), 5.54(2H, s), 7.70(1H, d, J=8.0 Hz), 7.73(1H, d, J=8.0 Hz), 7.78(2H, s), 8.02–8.10(1H, br), 8.13(1H, s), 9.94(1H, s).

Example 173

{2-[2-(3,5-Di-tert-butyl-4-hydroxy-phenyl)-2-oxo-ethyl]-3-imino-2,3-dihydro-1H-isoindol-5-yl}-acetic acid hydrobromide 1H-NMR(DMSO-d6) δ: 1.40(18H, s), 3.74(2H, s), 4.83(2H, s), 5.55(2H, s), 7.69(1H, d, J=8.0 Hz), 7.71(1H, d, J=8.0 Hz), 7.78(2H, s), 8.14(1H, s), 9.94(1H, s).

Example 174

1-(3,5-Di-tert-butyl-4-hydroxy-phenyl)-2-(1-imino-4-isopropoxy-1,3-dihydro-isoindol-2-yl)-ethanone hydrobromide 1H-NMR(DMSO-d6) δ: 1.36–1.50(24H, m), 4.79(2H, s), 4.87–4.98(1H, m), 5.50(2H, s), 7.26(1H, d, J=7.6 Hz), 7.30(1H, d, J=8.4 Hz), 7.73(1H, d, J=7.6 Hz), 7.77(2H, s), 8.03(1H, brs), 8.07(1H, brs), 9.23(1H, brs).

Example 175

1-(3,5-Di-tert-butyl-4-hydroxy-phenyl)-2-[1-imino-6-(1-methoxy-1-methyl-ethyl)-1,3-dihydro-isoindol-2-yl]-ethanone hydrobromide 1H-NMR(DMSO-d6) δ: 1.13(t, J=6.8 Hz), 1.41(18H, s), 3.25(3H, s), 3.66(s), 4.12(q, J=6.8 Hz), 5.12(2H, s), 5.54(2H, s), 7.78(2H, s), 7.79(1H, d, J=6.8 Hz), 7.86(1H, d, J=6.8 Hz), 8.39(1H, s).

Example 176

Ethyl {2-[2-(3,5-di-tert-butyl-4-hydroxy-phenyl)-2-oxo-ethyl]-3-imino-2,3-dihydro-1H-isoindol-5-yl}-methoxy-acetate hydrobromide 1H-NMR(DMSO-d6) δ: 1.13(3H, t, J=6.8 Hz), 1.41(18H, s), 3.38(3H, s), 4.12(2H, q, J=6.8 Hz), 4.86(2H, s), 5.12(1H, s), 5.53(2H, s), 7.78(2H, m), 7.79–7.84(2H, s), 8.31(1H, s).

Example 177

2-{2-[2-(3,5-Di-tert-butyl-4-hydroxy-phenyl)-2-oxo-ethyl]-3-imino-2,3-dihydro-1H-isoindol-5-yl}-3-methyl-butyric acid hydrobromide 1H-NMR(DMSO-d6) δ: 0.67(3H, d, J=6.5), 1.04(3H, d, J=6.5), 1.17(1H, t, J=6.5), 1.41(18H, s), 2.25–2.36(1H, m), 4.82(2H, s), 5.54(2H, s), 7.72(1H, d, J=7.0), 7.75(1H, d, J=7.0), 7.77(2H, s), 8.27(1H, s), 10.03(1H, s).
MS: m/e (ESI) 479.4 (MH+)

Example 178 tert-Butyl 2-[2-(3,5-di-tert-butyl-4-hydroxy-phenyl)-2-oxo-ethyl]-6-ethoxy-1-imino-2,3-dihydro-1H-isoindole-5-carboxylate hydrobromide 1H-NMR(DMSO-d6) δ: 1.39(3H, t, J=6.8 Hz), 1.41(18H, s), 1.53(9H, s), 4.14(2H, q, J=6.8 Hz), 4.80(2H, s), 5.53(2H, s), 7.78(2H, s), 7.83(1H, s), 8.02(1H, s).

Example 179

2-[2-(3,5-Di-tert-butyl-4-hydroxy-phenyl)-2-oxo-ethyl]-6-ethoxy-1-imino-2,3-dihydro-1H-isoindole-5-carboxylic acid trifluoroacetate 1H-NMR(DMSO-d6) δ: 1.39(3H, t, J=6.8 Hz), 1.41(18H, s), 4.15(2H, q, J=6.8 Hz), 4.80(2H, s), 5.53(2H, s), 7.78(2H, s), 7.87(1H, s), 8.05(1H, s), 9.06(1H, s), 10.05(1H, s).

Example 180

1-(3,5-Di-tert-butyl-4-hydroxy-phenyl)-2-(5,6-di-ethoxy-1-imino-1,3-dihydro-isoindol-2-yl)-ethanone hydrobromide 1H-NMR(DMSO-d6) δ: 1.25–1.41(24H, m), 4.08(2H, q, J=6.8 Hz), 4.14(2H, q, J=6.8 Hz), 4.71(2H, s), 5.44(2H, s), 7.35(1H, s), 7.75(2H, s), 7.81(1H, s), 9.05(1H, brs), 9.59(1H, brs).

Example 181

1-(3,5-Di-tert-butyl-4-hydroxy-phenyl)-2-(4,7-difluoro-1-imino-1,3-dihydro-isoindol-2-yl)-ethanone trifluoroacetate 1H-NMR(DMSO-d6) δ: 4.77(2H, s), 5.19(2H, s), 7.49(1H, M), 7.60(1H, m), 7.68(2H, s).

Example 182

1-(3,5-Di-tert-butyl-4-hydroxy-phenyl)-2-[6-(2-hydroxy-1-methyl-ethoxy)-1-imino-1,3-dihydro-isoindol-2-yl]-ethanone trifluoroacetate 1H-NMR(DMSO-d6) δ: 1.25(3H, d, J=6.4 Hz), 1.42(18H, s), 3.50–3.63(2H, m), 4.42–4.53(1H, m), 4.76(2H, s), 4.95(1H, t, J=5.6 Hz), 5.50(2H, s), 7.36(1H, brd, J=8.8 Hz), 7.64(1H, d, J=8.8 Hz), 7.78(2H, s), 7.84(1H, brs), 8.08(1H, brs), 9.21(1H, brs), 9.78(1H, s).
MS: m/e (ESI) 453.4 (MH+)

Example 183

2-{2-[2-(3,5-Di-tert-butyl-4-hydroxy-phenyl)-2-oxo-ethyl]-3-imino-2,3-dihydro-1H-isoindol-5-yloxy}-butyric acid trifluoroacetate 1H-NMR(DMSO-d6) δ: 1.02(3H, t, J=6.8 Hz), 1.42(18H, s), 1.86–2.10(2H, m), 4.68–4.83(3H, m), 5.50(2H, s), 7.36(1H, dd, J=8.4 and 0.8 Hz), 7.67(1H, d, J=8.4 Hz), 7.77(1H, s), 7.78(2H, s), 8.08(1H, brs), 9.25(1H, brs), 9.87(1H, brs).
MS: m/e (ESI) 481.3 (MH+)

Example 184

{2-[2-(3,5-Di-tert-butyl-4-hydroxy-phenyl)-2-oxo-ethyl]-3-imino-2,3-dihydro-1H-isoindol-5-yl}-methoxy-acetic acid trifluoroacetate 1H-NMR(DMSO-d6) δ: 1.41(18H, s), 3.38(3H, s), 4.83(2H, s), 4.99(1H, s), 5.52(2H, s), 7.77–7.83(2H, m), 7.78(2H, s), 8.07(1H, br), 8.32(1H, s), 9.29(1H, brs), 9.95(1H, brs).

Example 185

2-[2-(3,5-Di-tert-butyl-4-hydroxy-phenyl)-2-oxo-ethyl]-6-ethoxy-3-imino-2,3-dihydro-1H-isoindole-5-carboxylic acid trifluoroacetate 1H-NMR(DMSO-d6) δ: 1.37(3H, t, J=6.8 Hz), 1.41(18H, s), 4.21(2H, q, J=6.8 Hz), 4.83(2H, s), 5.46(2H, s), 7.53(1H, s), 7.75(2H, s), 8.49(1H, s), 9.16(1H, br), 9.78(1H, br).

Example 186

2-{2-[2-(3,5-Di-tert-butyl-4-hydroxy-phenyl)-2-oxo-ethyl]-3-imino-2,3-dihydro-1H-isoindol-5-yl}-2-methoxy-propanoic acid trifluoroacetate 1H-NMR(DMSO-d6) δ: 1.41(18H, s), 1.69(3H, s), 3.18(3H, s), 4.83(2H, s), 5.52(2H, s), 7.78(3H, s), 7.86(1H, d, J=8.0 Hz), 8.07(1H, br), 8.41(1H, s), 9.32(1H, s), 9.99(1H, s).

Example 187

N-{3-tert-Butyl-2-hydroxy-5-[2-(7-imino-2-methyl-5,7-dihydro-pyrrolo[3,4-b]pyridin-6-yl)-acetyl]-phenyl}-N-methyl-methanesulfonamide hydrochloride 1H-NMR(DMSO-d6) δ: 1.37(9H, s), 2.66(3H, s), 3.14(6H, s×2), 4.05(2H, s), 5.47–5.62(2H, m), 7.70(1H, d, J=8.0 Hz), 7.81(1H, s), 7.97(1H, s), 8.16(1H, d, J=8.0 Hz), 9.57(1H, brs), 9.95(1H, s), 10.01(1H, s).
MS: m/e (ESI) 445.2 (MH+)

Example 188

2-[2-(3,5-Di-tert-butyl-4-hydroxy-phenyl)-2-oxo-ethyl]-3-imino-2,3-dihydro-1H-isoindole-5-carboxylic acid methylamide hydrochloride 1H-NMR(DMSO-d6) δ: 1.40(18H, s), 2.82(3H, d, 5.3 Hz), 4.91(2H, s), 5.55(2H, s), 7.77(2H, s), 7.85(1H, d, J=8.1 Hz), 8.03–8.12(1H, br), 8.21(1H, d, J=8.1 Hz), 8.70(1H, q, J=5.3 Hz), 8.74(1H, s), 10.05(1H, s).

Example 189

2-[2-(3,5-Di-tert-butyl-4-hydroxy-phenyl)-2-oxo-ethyl]-1-imino-2,3-dihydro-1H-isoindole-5-carboxylic acid methylamide hydrochloride 1H-NMR(DMSO-d6) δ: 1.40(18H, s), 2.81(3H, d, J=5.3 Hz), 4.91(2H, s), 5.56(2H, s), 7.79(2H, s), 8.08(1H, s), 8.09(1H, d, =8.1 Hz), 8.17(1H, s), 8.31(1H, d, J=8.1 Hz), 8.74(1H, q, J=5.3), 9.44(1H, s), 8.74(1H, s), 10.05(1H, s), 10.12(1H, s).

Example 190

2-{2-[2-(3,5-Di-tert-butyl-4-hydroxy-phenyl)-2-oxo-ethyl]-3-imino-2,3-dihydro-1H-isoindol-5-yl}-2-methoxy-propionamide hydrobromide 1H-NMR(DMSO-d6) δ: 1.41(18H, s), 1.68(3H, s), 3.18(3H, s), 4.83(2H, s), 5.52(2H, s), 7.34(1H, brs), 7.43(1H, brs), 7.74–7.78(1H, m), 7.77(2H, s), 7.84(1H, d, J=8.0 Hz), 8.34(1H, s).

Example 191

2-{2-[2-(3,5-Di-tert-butyl-4-hydroxy-phenyl)-2-oxo-ethyl]-3-imino-2,3-dihydro-1H-isoindol-5-yl}-2-methoxy-N-methyl-propionamide hydrobromide 1H-NMR(DMSO-d6) δ: 1.41(18H, s), 1.69(3H, s), 2.58 (3H, d, J=4.4 Hz), 3.18(3H, s), 4.83(2H, s), 5.52(2H, s), 7.71–7.82(2H, m), 7.85(2H, s), 7.99(1H, brs), 8.31(1H, s).

Example 192

1-(3,5-Di-tert-butyl-4-hydroxy-phenyl)-2-(7-imino-2-propyl-5,7-dihydro-pyrrolo[3,4-b]pyridin-6-yl)-ethanone hydrochloride 1H-NMR(DMSO-d6) δ: 0.93(3H, t, J=7.2 Hz), 1.41(18H, s), 1.70–1.83(2H, m), 2.89(2H, t, J=7.6 Hz), 4.84(2H, s), 5.57(2H, s), 7.71(1H, d, J=8.0 Hz), 7.77(2H, s), 8.08(1H, s), 8.17(1H, d, J=8.0 Hz), 9.52(1H, brs), 9.85(1H, brs).
MS: m/e (ESI) 422.2 (MH+)

Example 193

2-[2-(3,5-Di-tert-butyl-4-hydroxy-phenyl)-2-oxo-ethyl]-3-imino-2,3-dihydro-1H-isoindole-5-sulfonic acid dimethylamide hydrochloride 1H-NMR(DMSO-d6) δ: 1.40(18H, s), 2.67(6H, s), 4.99 (2H, s), 5.55(2H, s), 7.77(2H, s), 8.06(1H, d, J=8.1 Hz), 8.16(1H, d, J=8.1 Hz), 8.73(1H, s).
MS: m/e (ESI) 486.2 (MH+)

Example 194

2-{2-[3-tert-Butyl-4-hydroxy-5-(methanesulfonyl-methyl-amino)-phenyl]-2-oxo-ethyl}-3-imino-2,3-dihydro-1H-isoindole-5-carboxylic acid dimethylamide hydrobromide 1H-NMR(DMSO-d6) δ: 1.39(18H, s), 2.95(3H, s), 3.03 (3H, s), 3.15(6H, s), 4.92(2H, s), 5.52(2H, s), 7.81–7.88(3H, m), 7.97(1H, s), 8.32(1H, s), 9.39(1H, s), 9.95(1H, s), 10.04(1H, s).
MS: m/e (ESI) 501.2 (MH+)

Example 195

({2-[2-(3,5-Di-tert-butyl-4-hydroxy-phenyl)-2-oxo-ethyl]-3-imino-2,3-dihydro-1H-isoindole-5-carbonyl}-methyl-amino)-acetic acid trifluoroacetate 1H-NMR(DMSO-d6) δ: 1.40(18H, s), 3.00(3H, s), 4.20 (2H, s), 4.92(2H, s), 5.55(2H, s), 7.77–7.88(2H, m), 7.78 (2H, s), 8.09(1H, s), 8.24–8.39(1H, 2s), 9.39(1H, br), 9.93–10.03(1H, br).
MS: m/e (ESI) 494.3 (MH+)

Example 196

1-(3,5-Di-tert-butyl-4-hydroxy-phenyl)-2-(4-ethoxy-1-imino-1,3-dihydro-isoindol-2-yl)-ethanone hydrobromide 1H-NMR(DMSO-d6) δ: 1.25–1.53(21H, m), 4.37(2H, q, J=6.8 Hz), 4.80(2H, s), 5.50(2H, s), 7.24–7.31(2H, m), 7.68–7.79(3H, m), 8.07(1H, brs), 8.32(1H, brs), 9.24(1H, brs).

Example 197

1-(3,5-Di-tert-butyl-4-hydroxy-phenyl)-2-(1-imino-4-methoxy-1,3-dihydro-isoindol-2-yl)-ethanone hydrobromide 1H-NMR(DMSO-d6) δ: 1.42(18H, s), 4.00(3H, s), 4.80 (2H, s), 5.49(2H, s), 7.25(1H, d, J=8.4 Hz), 7.29(1H, d, J=7.6 Hz), 7.51–7.78(3H, m), 8.06(1H, brs), 8.64(1H, brs), 9.23(1H, brs).

Example 198

2-[2-(3,5-Di-tert-butyl-4-hydroxy-phenyl)-2-oxo-ethyl]-6-ethoxy-1-imino-2,3-dihydro-1H-isoindole-5-carboxylic acid methylamide trifluoroacetate 1H-NMR(DMSO-d6) δ: 1.38(9H, s), 1.42(3H, t, J=6.8 Hz), 2.81(3H, d, J=4.8 Hz), 4.21(2H, q, J=6.8 Hz), 4.80(2H, s), 5.52(2H, s), 7.77(2H, s), 7.91(1H, s), 7.94(1H, s), 8.21–8.23(1H, m).
MS: m/e (ESI) 480.3 (MH+)

Example 199

2-[2-(3,5-Di-tert-butyl-4-hydroxy-phenyl)-2-oxo-ethyl]-6-ethoxy-3-imino-2,3-dihydro-1H-isoindole-5-carboxylic acid methylamide trifluoroacetate 1H-NMR(DMSO-d6) δ: 1.39(3H, t, J=6.8 Hz), 1.42(18H, s), 2.83(3H, d, J=4.8 Hz), 4.28(2H, q, J=6.8 Hz), 4.84(2H, s), 5.48(2H, s), 7.54(1H, s), 7.77(2H, s), 8.20(1H, q, J=4.8 Hz), 8.55(1H, s), 9.13(1H, br), 9.82(1H, br).
MS: m/e (ESI) 480.3 (MH+)

Example 200

N-{3-tert-Butyl-5-[2-(5,6-diethoxy-1-imino-1,3-dihydro-isoindol-2-yl)-acetyl]-2-hydroxy-phenyl}-N-methyl-methanesulfonamide hydrobromide 1H-NMR(DMSO-d6) δ: 1.38(18H, m), 3.14(6H, s), 4.07–4.15(4H, m), 4.72(2H, s), 5.43(2H, s), 7.36(1H, s), 7.81(2H, s), 7.93(1H, s), 9.08(1H, brs), 9.60(1H, brs).

Example 201

2-[2-(3,5-Di-tert-butyl-4-hydroxy-phenyl)-2-oxo-ethyl]-3-imino-2,3-dihydro-1H-isoindole-5-carboxylic acid ethylamide hydrobromide 1H-NMR(DMSO-d6) δ: 1.15(3H, t, J=7.0 Hz), 1.40(18H, s), 3.27–3.45(2H, m), 4.93(2H, s), 5.53(2H, s), 7.77(2H, s), 7.85(1H, d, J=8.0 Hz), 8.01–8.23(1H, m), 8.22(1H, d, J=8.0 Hz), 8.70(1H, s), 8.72(1H, s), 9.34(1H, s), 10.01(1H, s).
MS: m/e (ESI) 450.3 (MH+)

Example 202

Methyl {2-[2-(3,5-di-tert-butyl-4-hydroxy-phenyl)-2-oxo-ethyl]-3-imino-2,3-dihydro-1H-isoindol-5-yl}-carbamate hydrobromide 1H-NMR(DMSO-d6) δ: 1.40(18H, s), 3.70(3H, s), 4.76 (2H, s), 5.51(2H, s), 7.61(1H, dd, J=8.4,1.8 Hz), 7.67(1H, d, J=8.4 Hz), 7.77(2H, s), 8.07(1H, brs), 8.49(1H, brs), 9.20 (1H, s), 9.99(1H, brs), 10.12(1H, s)
MS: m/e (ESI) 452.3 (MH+).

Example 203

Methyl {2-[2-(3,5-di-tert-butyl-4-hydroxy-phenyl)-2-oxo-ethyl]-1-imino-2,3-dihydro-1H-isoindol-5-yl}-carbamate hydrobromide 1H-NMR(DMSO-d6) δ: 1.40(18H, s), 3.70(3H, s), 4.80 (2H, s), 5.48(2H, s), 7.63(1H, dd, J=8.4,1.8 Hz), 7.77(2H, s), 7.92(1H, s), 8.09(1H, d, J=8.4 Hz), 9.06(1H, brs), 9.74(1H, brs), 10.33(1H, s).

MS: m/e (ESI) 452.3 (MH+)

Example 204

Ethyl 3-{2-[2-(3,5-di-tert-butyl-4-hydroxy-phenyl)-2-oxo-ethyl]-3-imino-2,3-dihydro-1H-isoindol-5-yl}-2-methyl-acrylate 1H-NMR(DMSO-d6) δ: 1.37(3H, t, J=6.8 Hz), 1.41(18H, s), 2.08(3H, s), 4.23(2H, q, J=6.8 Hz), 4.88(2H, s), 5.22(2H, s), 7.68(1H, s), 7.77(2H, s), 7.83–7.91(2H, m), 8.32(1H, s).

Example 205

1-(3,5-Di-tert-butyl-4-hydroxy-phenyl)-2-(1-imino-6-trifluoromethyl-1,3-dihydro-isoindol-2-yl)-ethanone hydrobromide 1H-NMR(DMSO-d6) δ: 4.98(2H, s), 5.56(2H, s), 7.78 (2H, s), 8.04(1H, d, J=8.0 Hz), 8.20(1H, d, J=8.0 Hz), 8.69(s, 1H).

Example 206

3-{2-[2-(3,5-Di-tert-butyl-4-hydroxy-phenyl)-2-oxo-ethyl]-3-imino-2,3-dihydro-1H-isoindol-5-yl}-2,N-dimethyl-acrylamide hydrobromide 1H-NMR(DMSO-d6) δ: 1.41(18H, s), 2.05(3H, s), 2.71 (3H, d, J=4.4 Hz), 4.87(2H, s), 5.53(2H, s), 7.31(1H, s), 7.76–7.80(2H, m), 7.78(2H, s), 8.10(1H, br), 8.30(1H, s).

Example 207

3-{2-[2-(3,5-Di-tert-butyl-4-hydroxy-phenyl)-2-oxo-ethyl]-3-imino-2,3-dihydro-1H-isoindol-5-yl}-2-methyl-acrylamide hydrobromide 1H-NMR(DMSO-d6) δ: 1.41(18H, s), 2.05(3H, s), 4.87 (2H, s), 5.53(2H, s), 5.76(1H, s), 7.22(1H, br), 7.34(1H, s), 7.63(1H, brs), 7.77(3H, s), 7.79(1H, d, J=5.2 Hz), 8.24(1H, s).

Example 208

1-(3,5-Di-tert-butyl-4-hydroxy-phenyl)-2-(5,6-dichloro-1-imino-1,3-dihydro-isoindol-2-yl)-ethanone hydrobromide 1H-NMR(DMSO-d6) δ: 4.53(2H, s), 5.66(2H, s), 7.55 (1H, s), 7.80(1H, s), 7.90(2H, s).

Example 209

1-(7-tert-Butyl-3,3-dimethyl-2,3-dihydro-benzofuran-5-yl)-2-(7-imino-2-methyl-5,7-dihydro-pyrrolo[3,4-b]pyridin-6-yl)-ethanone hydrobromide 1H-NMR(DMSO-d6) δ: 1.33(6H, s), 1.34(9H, s), 2.67 (3H, s), 4.39(2H, s), 4.85(2H, s), 5.54(2H, brs), 7.711(1H, d, J=8.0 Hz), 7.712(1H, s), 7.79(1H, s), 8.16(1H, d, J=8.0 Hz), 9.51(1H, brs), 9.95(1H, brs).

MS: m/e (ESI) 392.2 (MH+)

Example 210

1-(3,5-Di-tert-butyl-4-hydroxy-phenyl)-2-(7-imino-2-methoxymethyl-5,7-dihydro-pyrrolo[3,4-b]pyridin-6-yl)-ethanone hydrochloride 1H-NMR(DMSO-d6) δ: 1.42(18H, s), 3.41(3H, s), 4.67 (2H, s), 4.89(2H, s), 5.50–5.52(2H, m), 7.78(2H, s), 7.85 (1H, d, J=8.0 Hz), 8.08(1H, brs), 8.29(1H, d, J=8.0 Hz), 9.50–9.52(1H, m), 9.99(1H, brs).

MS: m/e (ESI) 424.2 (MH+)

Example 211

1-(3,5-Di-tert-butyl-4-hydroxy-phenyl)-2-(3-ethoxy-7-imino-2-methyl-5,7-dihydro-pyrrolo[3,4-b]pyridin-6-yl)-ethanone hydrochloride 1H-NMR(DMSO-d6) δ: 1.30–1.50(21H, m), 2.50(3H, s), 4.21(2H, q, J=7.2 Hz), 4.79(2H, s), 5.49(2H, s), 7.76(3H, s×2), 8.06(1H, s), 9.24(1H, brs), 9.74(1H, brs).

MS: m/e (ESI) 438.2 (MH+)

Example 212

1-(3,5-Di-tert-butyl-4-hydroxy-phenyl)-2-[1-imino-6-(piperidine-1-carbonyl)-1,3-dihydro-isoindol-2-yl]-ethanone hydrobromide 1H-NMR(DMSO-d6) δ: 1.30–1.70(6H, m), 1.40(18H, s), 3.28(2H, m), 3.60(2H, m), 4.88(2H, s), 5.55(2H, s), 7.79 (2H, s), 7.81(1H, d, J=8.4 Hz), 7.85(1H, d, J=8.4 Hz), 8.09(1H, brs), 8.27(1H, s), 9.34(1H, brs), 9.94(1H, brs).

MS: m/e (ESI) 490.3 (MH+)

Example 213

1-(3,5-Di-tert-butyl-4-hydroxy-phenyl)-2-(7-imino-2-methyl-5,7-dihydro-pyrrolo[3,4-b]pyrazin-6-yl)-ethanone hydrobromide 1H-NMR(DMSO-d6) δ: 1.40(18H, s), 2.72(3H, s), 4.93 (2H, s), 5.56(2H, s), 7.77(2H, s), 8.97(1H, s).

MS: m/e (ESI) 395.2 (MH+)

Example 214

1-(3,5-Di-tert-butyl-4-hydroxy-phenyl)-2-(2-dimethylaminomethyl-7-imino-5,7-dihydro-pyrrolo[3,4-b]pyridin-6-yl)-ethanone hydrochloride 1H-NMR(DMSO-d6) δ: 1.42(18H, s), 2.88(6H, s), 4.64 (2H, brs), 4.96(2H, s), 5.58–5.72(2H, m), 7.79(2H, s), 7.95–8.05(1H, m), 8.10(1H, s), 8.37(1H, d, J=8.4 Hz), 9.79–9.91(1H, m), 10.03–10.10(1H, m), 10.80–10.96(1H, m).

MS: m/e (ESI) 437.2 (MH+)

Example 215

1-(3,5-Di-tert-butyl-4-hydroxy-phenyl)-2-(2-imino-4-methoxymethyl-3-phenyl-pyrrolidin-1-yl)-ethanone hydrobromide 1H-NMR(DMSO-d6) δ: 1.42(18H, s), 2.64(3H, s), 4.73 (2H, s), 5.54(2H, s), 7.37(1H, d, J=8.4 Hz), 7.54–7.67(2H, m), 7.79(2H, s).
MS: m/e (ESI) 393.2 (MH+)

Example 216

1-(3,5-Di-tert-butyl-4-hydroxy-phenyl)-2-(3-ethoxy-7-imino-2,4-dimethyl-5,7-dihydro-pyrrolo[3,4-b]pyridin-6-yl)-ethanone hydrobromide 1H-NMR(DMSO-d6) δ: 1.40(3H, t, J=7.2 Hz), 1.42(18H, s), 2.32(3H, s), 2.58(3H, s), 3.99(2H, t, J=7.2 Hz), 4.81(2H, s), 5.52(2H, s), 7.76(2H, s), 8.07(1H, s), 9.37(1H, brs), 9.84(1H, brs).
MS: m/e (ESI) 452.2 (MH+)

Example 217

2-[2-(3,5-Di-tert-butyl-4-hydroxy-phenyl)-2-oxo-ethyl]-3-imino-2,3-dihydro-1H-isoindole-5-carboxylic acid (2-methoxy-ethyl)-amide hydrobromide 1H-NMR(DMSO-d6) δ: 1.40(18H, s), 3.27(3H, s), 3.31 (2H, s), 3.48(2H, brs), 4.91(2H, s), 5.52(2H, s), 7.77(2H, s), 7.86(1H, d, J=8.0), 8.09(1H, brs), 8.23(1H, d, J=8.0), 8.72 (1H, s), 8.77(1H, brs), 9.24(1H, brs), 10.03(1H, brs).

Example 218

2-[2-(3,5-Di-tert-butyl-4-hydroxy-phenyl)-2-oxo-ethyl]-3-imino-2,3-dihydro-1H-isoindole-5-carboxylic acid isopropylamide hydrobromide 1H-NMR(DMSO-d6) δ: 1.18(6H, d, J=6.9), 1.40(18H, s), 4.05–4.16(1H, m), 4.91(2H, s), 5.52(2H, s), 7.77(2H, s), 7.85(1H, d, J=8.0), 8.08(1H, s), 8.23(1H, dd, J=8.0, 1.1 Hz), 8.48(1H, d, J=7.8 Hz), 8.68(1H, s), 9.32(1H, brs), 10.00(1H, brs).
MS: m/e (ESI) 464.3 (MH+)

Example 219

2-[2-(3,5-Di-tert-butyl-4-hydroxy-phenyl)-2-oxo-ethyl]-3-imino-2,3-dihydro-1H-isoindole-5-sulfonamide hydrobromide 1H-NMR(DMSO-d6) δ: 1.40(18H, s), 4.95(2H, s), 5.53 (2H, s), 7.64(2H, s), 7.77(2H, s), 7.99(1H, d, J=7.9), 8.09 (1H, brs), 8.23(1H, d, J=7.9), 8.75(1H, s), 10.14(1H, brs).

Example 220

2-[2-(3,5-Di-tert-butyl-4-hydroxy-phenyl)-2-oxo-ethyl]-3-imino-2,3-dihydro-1H-isoindole-5-sulfonic acid methylamide hydrobromide 1H-NMR(DMSO-d6) δ: 1.40(18H, s), 2.47(3H), 4.96(2H, s), 5.54(2H, s), 7.72(1H, q, J=4.6 Hz), 7.77(2H, s), 8.02(1H, d, J=7.9), 8.09(1H, brs), 8.17(1H, dd, J=7.9, 1.2 Hz), 8.75 (1H, s), 10.14(1H, brs).

Example 221

1-(3,5-Di-tert-butyl-4-hydroxy-phenyl)-2-(7-imino-2,5-dimethyl-5,7-dihydro-pyrrolo[3,4-b]pyridin-6-yl)-ethanone hydrochloride 1H-NMR(DMSO-d6) δ: 1.42(18H, s), 1.48(3H, d, J=7.0 Hz), 2.67(3H, s), 5.00(1H, q, J=7.0 Hz), 5.4(1H, d, J=18.4 Hz), 5.6(1H, d, J=18.4 Hz), 7.73(1H, d, J=8.0 Hz), 7.79(2H, s), 8.05(1H, s), 8.18(1H, d, J=8.0 Hz), 9.45(1H, s), 9.93(1H, s).
MS: m/e (ESI) 408.2 (MH+)

Example 222

2-{2-[2-(3,5-Di-tert-butyl-4-hydroxy-phenyl)-2-oxo-ethyl]-3-imino-2,3-dihydro-1H-isoindol-5-yl}-2-methoxy-acetamide hydrobromide 1H-NMR(DMSO-d6) δ: 1.41(18H, s), 3.33(3H, s), 4.77 (1H, br), 4.85(2H, s), 5.51(2H, s), 7.39(1H, brs), 7.61(1H, brs), 7.73–7.83(2H, m), 7.86(2H, s), 8.27(1H, s).

Example 223

{2-[2-(3,5-Di-tert-butyl-4-hydroxy-phenyl)-2-oxo-ethyl]-3-imino-2,3-dihydro-1H-isoindol-5-yl}-methoxy-acetic acid hydrazide hydrobromide 1H-NMR(DMSO-d6) δ: 1.41(18H, s), 4.35(1H, br), 4.84 (3H, s), 4.86(2H, s), 5.52(2H, s), 7.76(4H, s), 8.27(1H, s).

Example 224

1-[3-tert-Butyl-4-hydroxy-5-(2-methoxy-ethyl)-phenyl]-2-(7-imino-2-methyl-5,7-dihydro-pyrrolo[3,4-b]pyridin-6-yl)-ethanone hydrochloride 1H-NMR(DMSO-d6) δ: 1.39(9H, s), 2.67(3H, s), 2.94 (2H, t, J=6.8 Hz), 3.27(3H, s), 3.55(2H, t, J=6.8 Hz), 4.84(2H, s), 5.46–5.52(2H, m), 7.65–7.74(3H, m), 8.15(1H, d, J=8.0 Hz), 9.40(1H, s), 9.46–9.56(1H, m), 9.93(1H, s).
MS: m/e (ESI) 396.1 (MH+)

Example 225

Methyl 3-tert-butyl-2-hydroxy-5-[2-(7-imino-2-methyl-5,7-dihydro-pyrrolo[3,4-b]pyridin-6-yl)-acetyl]-benzoate hydrochloride 1H-NMR(DMSO-d6) δ: 1.42(9H, s), 2.67(3H, s), 3.98 (3H, s), 4.86(2H, s), 5.58–5.69(1H, m), 7.71(1H, d, J=8.0 Hz), 8.05(1H, s), 8.17(1H, d, J=8.0 Hz), 8.38(1H, s), 9.99 (1H, s), 12.07(1H, s).
MS: m/e (ESI) 396.0 (MH+)

Example 226

2-{2-[3-tert-Butyl-4-hydroxy-5-(methanesulfonyl-methyl-amino)-phenyl]-2-oxo-ethyl}-6-ethoxy-1-imino-2,3-dihydro-1H-isoindole-5-carboxylic acid methylamide hydrobromide 1H-NMR(DMSO-d6) δ: 1.37(9H, s), 1.41(3H, t, J=6.8 Hz), 2.81(3H, d, J=4.4 Hz), 3.13(6H, s), 4.19(2H, q, J=6.8 Hz), 4.80(2H, s), 5.48(2H, s), 7.79(1H, s), 7.94(2H, s), 8.04(1H, s), 8.25(1H, br).
MS: m/e (ESI) 531.2 (MH+)

Example 227

2-{2-[3-tert-Butyl-4-hydroxy-5-(methanesulfonyl-methyl-amino)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.37(9H, s), 1.41(3H, t, J=6.8 Hz), 2.81(3H, d, J=4.4 Hz), 3.13(6H, s), 4.17(2H, q, J=6.8 Hz), 4.83(2H, s), 5.43(2H, s), 7.53(1H, s), 7.80(1H, s), 7.92(1H, s), 8.19(1H, br), 8.56(1H, s).
MS: m/e (ESI) 531.2 (MH+)

Example 228

2-{2-[3-(Acetyl-methyl-amino)-5-tert-butyl-4-hydroxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.37(9H, s), 1.41(3H, t, J=6.8 Hz), 2.12(3H, s), 2.82(3H, d, J=4.4 Hz), 3.10(3H, s), 4.18 (2H, q, J=6.8 Hz), 4.47(2H, s), 4.82(2H, s), 5.42(2H, s), 7.53(1H, s), 7.82(1H, s), 7.91(1H, s), 8.21(1H, d, J=2.0 Hz), 8.54(1H, s), 9.21(1H, brs), 9.83(1H, brs).

Example 229

1-(3,5-Di-tert-butyl-4-hydroxy-phenyl)-2-[6-(1-hydroxy-propyl)-1-imino-1,3-dihydro-isoindol-2-yl]-ethanone hydrobromide 1H-NMR(DMSO-d6) δ: 0.94(3H, t, J=7.6 Hz), 1.77–1.84 (2H, m), 4.74(1H, t, J=6.8 Hz), 4.89(2H, s), 5.48(2H, s), 7.67–7.78(2H, m), 7.79(1H, d, J=7.6 Hz), 7.93(2H, s), 8.13(1H, s).
MS: m/e (ESI) 439.2 (MH+) 3

Example 230

2-{6-[2-(3,5-Di-tert-butyl-4-hydroxy-phenyl)-2-oxo-ethyl]-7-imino-6,7-dihydro-5H-pyrrolo[3,4-b]pyridin-2-yl}-2-methoxy-propionamide hydrochloride 1H-NMR(DMSO-d6) δ: 1.39(3H, t, J=6.8 Hz), 1.41(18H, s), 1.81(3H, s), 3.16(3H, s), 4.87(2H, s), 5.63(2H, s), 7.39 (1H, s), 7.54(1H, s), 7.78(2H, s), 7.83(1H, d, J=7.2 Hz), 8.08(1H, s), 8.27(1H, d, J=7.2 Hz), 9.72(1H, br), 9.78(1H, br).
MS: m/e (ESI) 481.1 (MH+)

Example 231

N-{3-tert-Butyl-2-hydroxy-5-[2-(7-imino-2-methyl-5,7-dihydro-pyrrolo[3,4-b]pyridin-6-yl)-acetyl]-benzyl}-N-methyl-acetamide hydrochloride 1H-NMR(DMSO-d6) δ: 1.37(9H, s), 2.11(3H, s), 2.67 (3H, s), 3.10(3H, s), 4.48(2H, s), 4.86(2H, s), 5.55(2H, s), 7.71(1H, d, J=8.0 Hz), 7.82(1H, s), 7.92(1H, s), 8.15(1H, d, J=8.0 Hz), 9.58(1H, s), 9.95(1H, s).

Example 232

1-(3,5-Di-tert-butyl-4-hydroxy-phenyl)-2-(5-ethoxy-4-fluoro-1-imino-1,3-dihydro-isoindol-2-yl)-ethanone hydrobromide 1H-NMR(DMSO-d6) δ: 1.39(3H, t, J=6.9 Hz), 1.40(18H, s), 4.26(2H, q, J=6.9 Hz), 4.91(2H, s), 5.46(2H, s), 7.55(1H, t, J=8.0 Hz), 7.77(2H, s), 8.03(1H, d, J=8.0 Hz), 8.08(1H, s), 9.22(1H, s), 9.90(1H, brs).
MS: m/e (ESI) 441.2 (MH+)

Example 233

Methyl {2-[2-(3,5-di-tert-butyl-4-hydroxy-phenyl)-2-oxo-ethyl]-3-imino-2,3-dihydro-1H-isoindol-5-yl}-ethyl-carbamate hydrobromide 1H-NMR(DMSO-d6) δ: 1.10(3H, t, J=6.8 Hz), 1.42(18H, s), 3.62(3H, s), 3.70(2H, q, J=6.8 Hz), 4.86(2H, s), 5.52(2H, s), 7.72(1H, d, J=8.4 Hz), 7.78(2H, s), 7.79(1H, d, J=8.4 Hz), 8.16(1H, s).

Example 234

1-(3,5-Di-tert-butyl-4-hydroxy-phenyl)-2-(6 or 7-hydroxymethyl-1-imino-1,3,6,7-tetrahydro-5,8-dioxa-2-aza-cyclopenta[b]naphthalen-2-yl)-ethanone hydrobromide 1H-NMR(DMSO-d6) δ: 3.66(2H, brs), 4.05–4.16(2H, m), 4.45(1H, m), 4.68(2H, s), 5.15(1H, t, J=5.0 Hz), 5.56 (2H, s), 5.46(2H, s), 7.26(1H, s), 7.75(2H, s), 7.77(1H, s).

Example 235

2-[2-(3,5-Di-tert-butyl-4-hydroxy-phenyl)-2-oxo-ethyl]-3-imino-6-methyl-2,3-dihydro-1H-isoindole-5-carboxylic acid methylamide hydrobromide 1H-NMR(DMSO-d6) δ: 2.29(3H, s), 2.86(3H, d, J=5.0 Hz), 4.78(2H, s), 5.80(2H, s), 7.41(1H, s), 7.81(2H, s), 7.86(1H, s).

Example 236

1-(3,5-Di-tert-butyl-4-hydroxy-phenyl)-2-[1-imino-6-(1-methoxy-propyl)-1,3-dihydro-isoindol-2-yl]-ethanone hydrobromide 1H-NMR(DMSO-d6) δ: 0.90(3H, t, J=7.6 Hz), 1.50(18H, s), 1.61–1.75(2H, m), 3.23(3H, s), 4.25(1H, t, J=7.6 Hz), 4.80(2H, s), 5.92(2H, s), 7.32(1H, s), 7.50(1H, d, J=8.8 Hz), 7.70(1H, d, J=8.0 Hz), 7.98(2H, s), 8.70(2H, brs).

Example 237

N-(2-{3-tert-Butyl-2-hydroxy-5-[2-(7-imino-2-methyl-5,7-dihydro-pyrrolo[3,4-b]pyridin-6-yl)-acetyl]-phenyl}-ethyl)-N-methyl-acetamide hydrochloride 1H-NMR(DMSO-d6) δ: 1.398(9H, s), 2.019(3H, s), 2.482 (3H, s), 2.84–2.92(1H, m), 2.96–3.02(1H, m), 3.014(3H, s), 3.34–3.42(2H, m), 4.852(2H, s), 5.529(2H, s), 7.64–7.78 (3H, m), 8.155(1H, d, J=8.0 Hz), 9.50–9.60(2H, m), 9;90–9.99(2H, m).

Example 238

1-(3,5-Di-tert-butyl-4-hydroxy-phenyl)-2-(2-ethoxy-7-imino-5,7-dihydro-pyrrolo[3,4-b]pyridin-6-yl)-ethanone hydrobromide 1H-NMR(DMSO-d6) δ: 1.37(3H, t, J=7.0 Hz), 1.42(18H, s), 4.48(2H, q, J=7.0 Hz), 4.79(2H, s), 5.54(2H, s), 7.24(1H, d, J=8.8 Hz), 7.77(2H, s), 8.13(1H, d, J=8.8 Hz), 9.63(1H, s).

MS: m/e (ESI) 424.1 (MH+)

Example 239

2-[2-(3,5-Di-tert-butyl-4-hydroxy-phenyl)-2-oxo-ethyl]-6-ethoxy-3-imino-2,3-dihydro-1H-isoindole-5-carboxylic acid dimethylamide hydrobromide 1H-NMR(DMSO-d6) δ: 1.15(3H, t, J=7.0 Hz), 1.40(18H, s), 2.78(3H, s), 3.00(3H, s), 4.22(2H, q, J=7.0 Hz), 4.82(2H, s), 5.47(2H, s), 7.50(1H, s), 7.77(2H, s), 8.02(1H, s), 8.08(1H, brs), 9.67(1H, brs).

MS: m/e (ESI) 494.2 (MH+)

Example 240

3-tert-Butyl-N-ethyl-2-hydroxy-5-[2-(7-imino-2-methyl-5,7-dihydro-pyrrolo[3,4-b]pyridin-6-yl)-acetyl]-N-methyl-benzenesulfonamide hydrochloride 1H-NMR(DMSO-d6) δ: 1.09(3H, t, J=6.8 Hz), 1.38(9H, s), 2.63(3H, s), 2.87(3H, s), 3.24(2H, q, J=6.8 Hz), 4.86(2H, s), 6.24(2H, s), 7.44(1H, d, J=8.2 Hz), 7.82(1H, d, J=8.2 Hz), 8.11(1H, s), 8.16(1H, s), 10.08(1H, s), 11.98(1H, brs).

MS: m/e (ESI) 459.1 (MH+)

Example 241

Ethyl 3-{6-[2-(3,5-di-tert-butyl-4-hydroxy-phenyl)-2-oxo-ethyl]-7-imino-6,7-dihydro-5H-pyrrolo[3,4-b]pyridin-2-yl}-2-methyl-acrylate hydrobromide 1H-NMR(DMSO-d6) δ: 1.27(3H, t, J=6.8 Hz), 1.41(18H, s), 2.34(3H, s), 4.23(2H, q, J=6.8 Hz), 4.88(2H, s), 5.52(2H, s), 7.69(1H, s), 7.73(2H, s), 7.99(1H, d, J=8.4 Hz), 8.28(1H, d, J=8.4 Hz).

MS: m/e (ESI) 492.3 (MH+)

Example 242

2-(2-{3-[(Acetyl-methyl-amino)-methyl]-5-tert-butyl-4-hydroxy-phenyl}-2-oxo-ethyl)-6-ethoxy-1-imino-2,3-dihydro-1H-isoindole-5-carboxylic acid methylamide hydrobromide 1H-NMR(DMSO-d6) δ: 1.38(9H, s), 1.42(3H, t, J=6.8 Hz), 2.12(3H, s), 2.81(3H, d, J=4.8 Hz), 3.09(3H, s), 4.21(2H, q, J=6.8 Hz), 4.47(2H, s), 4.81(2H, s), 5.52(2H, s), 7.81(1H, s), 7.91(1H, s), 7.94(1H, s), 8.07(1H, s), 8.21–8.25(1H, m).

Example 243

2-[2-(3,5-Di-tert-butyl-4-hydroxy-phenyl)-2-oxo-ethyl]-6-fluoro-3-imino-2,3-dihydro-1H-isoindole-5-carboxylic acid methylamide hydrobromide 1H-NMR(DMSO-d6) δ: 1.41(18H, s), 2.82(3H, d, J=4.4 Hz), 4.90(2H, s), 5.51(2H, s), 7.74(2H, s), 7.76(1H, d, J=8.8 Hz), 8.51(1H, br), 8.54(1H, d, J=5.2 Hz).

Example 244

2-[2-(3,5-Di-tert-butyl-4-hydroxy-phenyl)-2-oxo-ethyl]-6-ethoxy-3-imino-2,3-dihydro-1H-isoindole-5-carboxylic acid (2-hydroxy-ethyl)-amide hydrobromide 1H-NMR(DMSO-d6) δ: 1.40(18H, s), 1.41(3H, t, J=6.5 Hz), 3.38(2H, dt, J=6.2,6.1 Hz), 3.55(2H, dt, J=6.2,6.0 Hz), 4.28(2H, q, J=6.5 Hz), 4.83(1H, t, J=6.1 Hz), 4.85(2H, s), 5.45(2H, s), 7.55(1H, s), 7.76(2H, s), 8.35(1H, t, J=6.0 Hz), 8.67(1H, s), 9.84(1H, brs).

MS: m/e (ESI) 510.3 (MH+)

Example 245

6-[2-(3,5-Di-tert-butyl-4-hydroxy-phenyl)-2-oxo-ethyl]-7-imino-6,7-dihydro-5H-pyrrolo[3,4-b]pyridine-2-carboxylic acid dimethylamide hydrobromide 1H-NMR(DMSO-d6) δ: 2.94(3H, s), 3.05(3H, s), 4.94(2H, s), 5.55(2H, s), 7.75(2H, s), 7.96(1H, d, J=10 Hz), 8.38(1H, d, J=10 Hz).

Example 246

1-{3-tert-Butyl-2-hydroxy-5-[2-(7-imino-2-methyl-5,7-dihydro-pyrrolo[3,4-b]pyridin-6-yl)-acetyl]-benzyl}-pyrrolidin-2-one hydrobromide 1H-NMR(DMSO-d6) δ: 1.380(9H, s), 1.93–2.03(2H, m), 2.34–2.40(2H, m), 2.672(3H, s), 3.500(2H, t, J=7.2 Hz, 2H), 4.426(2H, s), 4.865(2H, s), 5.570(2H, s), 7.709(2H, d, J=8.0 Hz), 7.812(2H, s), 8.164(1H, d, J=7.2 Hz), 9.951(1H, s), 10.674(1H, s).

Example 247

N-(1-{3-tert-Butyl-2-hydroxy-5-[2-(7-imino-2-methyl-5,7-dihydro-pyrrolo[3,4-b]pyridin-6-yl)-acetyl]-phenyl}-ethyl)-acetamide hydrobromide 1H-NMR(DMSO-d6) δ: 1.388(9H, s), 1.473(3H, d, J=6.8 Hz, 3H), 1.880(2H, m), 2.673(3H, s), 4.863(2H, s), 5.08–5.17(1H, m), 5.46–5.65(2H, m), 7.712(1H, d, J=8.0 Hz), 7.760(1H, s), 7.813(1H, s), 8.169(1H, d, J=8.0 Hz), 8.948(1H, d, J=7.6 Hz).

Example 248

N-(1-{3-tert-Butyl-2-hydroxy-5-[2-(7-imino-2-methyl-5,7-dihydro-pyrrolo[3,4-b]pyridin-6-yl)-acetyl]-phenyl}-ethyl)-N-methyl-acetamide hydrochloride 1H-NMR(DMSO-d6) δ: 1.362(9H, s), 1.577(3H, d, J=7.2 Hz), 2.095(3H, s), 2.673(3H, s), 2.895(3H, s), 4.866(2H, s), 5.54–5.76(3H, m), 7.711(1H, d, J=8.0 Hz), 7.806(1H, s), 7.924(1H, s), 8.163(1H, d, J=8.0 Hz), 9.577(1H, s), 9.952(1H, s), 11.076(1H, s).

Example 249

N-{3-tert-Butyl-5-[2-(3-ethoxy-7-imino-2,4-dimethyl-5,7-dihydro-pyrrolo[3,4-b]pyridin-6-yl)-acetyl]-2-hydroxy-benzyl}-N-methyl-acetamide hydrochloride 1H-NMR(DMSO-d6) δ: 1.32–1.45(12H, m), 2.11(3H, s), 2.31(3H, s), 2.58(3H, s), 3.11(3H, s), 3.90–4.20(2H and H2O), 4.78(2H, s), 4.84(2H, s), 5.59(2H, s), 7.81(1H, s), 7.93(1H, s), 9.61(1H, s), 9.85(1H, s), 11.28(1H, s).

MS: m/e (ESI) 481.2 (MH+)

Example 250

N-{3-tert-Butyl-5-[2-(3-ethoxy-7-imino-2,4-dimethyl-5,7-dihydro-pyrrolo[3,4-b]pyridin-6-yl)-acetyl]-2-hydroxy-phenyl}-N-methyl-methanesulfonamide hydrochloride 1H-NMR(DMSO-d6) δ: 1.34–1.42(12H, m), 2.32(3H, s), 2.58(3H, s), 3.15(6H, sX2), 3.99(2H, q, J=6.8 Hz), 4.83(1H, s), 5.50(1H, s), 7.81(1H, s), 7.96(1H, s), 9.42(1H, brs), 9.85(1H, brs), 10.03(1H, s).

MS: m/e (ESI) 503.2 (MH+)

Example 251

1-{3-tert-Butyl-2-hydroxy-5-[2-(7-imino-2-methyl-5,7-dihydro-pyrrolo[3,4-b]pyridin-6-yl)-acetyl]-phenyl}-pyrrolidin-2-one hydrobromide 1H-NMR(DMSO-d6) δ: 1.42(9H, s), 2.11–2.21(2H, m), 2.41–2.46(2H, m), 2.69(3H, s), 3.65–3.71(2H, m), 4.85(2H, s), 5.48(2H, s), 7.72(1H, d, J=8 Hz), 7.74(1H, s), 7.78(1H, s), 8.17(1H, d, J=8 Hz).

Example 252

1-{3-tert-Butyl-2-hydroxy-5-[2-(7-imino-2-methyl-5,7-dihydro-pyrrolo[3,4-b]pyridin-6-yl)-acetyl]-benzyl}-piperidin-2-one hydrobromide 1H-NMR(DMSO-d6) δ: 1.373(9H, s), 1.64–1.78(4H, m), 2.34–2.38(2H, m), 2.674(3H, s), 3.43–3.50(2H, m), 4.483(2H, s), 4.863(2H, s), 5.541(2H, s), 7.712(1H, d, J=8.0 Hz), 7.822(1H, d, J=2.0 Hz), 7.887(1H, d, J=2.0 Hz), 8.164(1H, d, J=8.0 Hz), 9.940(1H, s).

Example 253

1-(3,5-Di-tert-butyl-4-hydroxy-phenyl)-2-(2-dimethylaminomethyl-3-ethoxy-7-imino-4-methyl-5,7-dihydro-pyrrolo[3,4-b]pyridin-6-yl)-ethanone hydrobromide 1H-NMR(DMSO-d6) δ: 1.25(18H, s), 1.37(3H, t, J=6.8 Hz), 2.19(6H, s), 2.26(3H, s), 3.58(2H, s), 4.00(2H, q, J=6.8 Hz), 4.55(2H, brs), 4.88–4.92(2H, m), 7.41(2H, s).

MS: m/e (ESI) 495.3 (MH+)

Example 254 tert-Butyl [2-({2-[2-(3,5-di-tert-butyl-4-hydroxy-phenyl)-2-oxo-ethyl]-6-ethoxy-3-imino-2,3-dihydro-1H-isoindole-5-carbonyl}-amino)-ethyl]-carbamate hydrobromide 1H-NMR(DMSO-d6) δ: 1.35(9H, s), 1.40(18H, s), 1.42(3H, t, J=7.2 Hz), 3.08–3.40(2H, m), 3.60–3.78(2H, m), 4.27(2H, q, J=7.2 Hz), 4.84(2H, s), 5.44(2H, s), 6.85–6.94(1H, m), 7.55(1H, s), 7.75(2H, s), 8.29(1H, t, J=5.2 Hz), 8.59(1H, s), 9.83(1H, brs).

MS: m/e (ESI) 609.3 (MH+)

Example 255

2-[2-(3,5-Di-tert-butyl-4-hydroxy-phenyl)-2-oxo-ethyl]-6-ethoxy-3-imino-2,3-dihydro-1H-isoindole-5-carboxylic acid (2-amino-ethyl)-amide dihydrochloride 1H-NMR(DMSO-d6) δ: 1.40(18H, s), 1.42(3H, t, J=7.2 Hz), 2.96(2H, brt, J=6.4 Hz), 3.56(2H, brq, J=6.4 Hz), 4.28(2H, q, J=7.2 Hz), 4.84(2H, s), 5.53(2H, s), 7.56(1H, s), 7.55(1H, s), 7.77(2H, s), 8.04(3H, brs), 8.47(1H, t, J=5.6 Hz), 8.65(1H, s).

Example 256

({2-[2-(3,5-Di-tert-butyl-4-hydroxy-phenyl)-2-oxo-ethyl]-6-ethoxy-3-imino-2,3-dihydro-1H-isoindole-5-carbonyl}-amino)-acetic acid trifluoroacetate 1H-NMR(DMSO-d6) δ: 1.40(18H, s), 1.45(3H, t, J=7.0 Hz), 4.05(2H, d, J=5.4 Hz), 4.33(2H, q, J=7.0 Hz), 4.85(2H, s), 5.47(2H, s), 7.59(1H, s), 7.77(2H, s), 8.07(2H, s), 8.61(1H, t, J=5.4 Hz), 8.73(1H, s), 9.15(1H, brs), 9.88(1H, brs).

MS: m/e (ESI) 524.2 (MH+)

Example 257

2-[2-(3,5-Di-tert-butyl-4-hydroxy-phenyl)-2-oxo-ethyl]-6-ethoxy-3-imino-2,3-dihydro-1H-isoindole-5-carboxylic acid (2-acetylamino-ethyl)-amide hydrobromide 1H-NMR(DMSO-d6) δ: 1.40(18H, s), 1.41(3H, t, J=6.8 Hz), 3.18–3.37(4H, m), 4.28(2H, q, J=6.8 Hz), 4.84(2H, s), 5.46(2H, s), 7.55(1H, s), 7.76(2H, s), 7.96(1H, t, J=5.5 Hz), 8.07(1H, brs), 8.31(1H, t, J=5.1 Hz), 8.60(1H, s), 9.13(1H, brs), 9.82(1H, brs).

MS: m/e (ESI) 551.3 (MH+)

Example 258

Ethyl 2-[2-(3,5-di-tert-butyl-4-hydroxy-phenyl)-2-oxo-ethyl]-3-imino-2,3, 6,7-tetrahydro-1H-5,8-dioxa-2-aza-cyclopenta[b]naphthalene-6-carboxylate hydrobromide 1H-NMR(DMSO-d6) δ: 1.27(3H, t, J=7.2 Hz), 1.42(18H, s), 4.25(2H, q, J=7.2 Hz), 4.36–5,15(3H, m), 7.30(1H, s), 7.71(1H, s), 7.91(2H, s).

MS: m/e (ESI) 509.2 (MH+)

Example 259

Methyl {3-tert-butyl-2-hydroxy-5-[2-(7-imino-2-methyl-5,7-dihydro-pyrrolo[3,4-b]pyridin-6-yl)-acetyl]-phenyl}-methylcarbamate hydrobromide 1H-NMR(DMSO-d6) δ: 1,42(9H, s), 2.67(3H, s), 3.40 (3H, s), 3.79(3H, s), 4.88(2H, s), 5.60(2H, s), 7.68(1H, s), 7.70(1H, d, J=8 Hz), 7.80(1H, s), 7.15(1H, d, J=8 Hz).

Example 260

2-[2-(3,5-Di-tert-butyl-4-hydroxy-phenyl)-2-oxo-ethyl]-1-imino-6-methyl-2,3-dihydro-1H-isoindole-5-carboxylic acid methylamide hydrobromide 1H-NMR(DMSO-d6) δ: 2.42(3H, s), 2.78(3H, s), 4.82 (2H, s), 5.50(2H, s), 7.68(1H, s), 7.76(2H, s), 8.06(1H, s), 8.40(1H, d, J=6.0 Hz).

Example 261

2-[2-(3,5-Di-tert-butyl-4-hydroxy-phenyl)-2-oxo-ethyl]-1-imino-6-methyl-2,3-dihydro-1H-isoindole-5-carboxylic acid (2-methoxy-ethyl)-amide hydrobromide 1H-NMR(DMSO-d6) δ: 2.42(3H, s), 3.26(3H, s), 3.43 (4H, m), 4.82(2H, s), 5.50(2H, s), 7.66(1H, s), 7.76(2H, s), 8.05(1H, s), 8.48(1H, t, J=6.0 Hz).

Example 262

2-{2-[3-(1-Acetylamino-ethyl)-5-tert-butyl-4-hydroxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.38(9H, s), 1.42(3H, t, J=6.8 Hz), 1.46(3H, d, J=6.4 Hz), 1.86(3H, s), 2.82(3H, d, J=4.8 Hz), 4.28(2H, q, J=6.8 Hz), 4.84(2H, s), 5.06–5.13(1H, m), 5.36–5.51(2H, m), 7.52(1H, s), 7.74(1H, s), 7.77(1H, s), 8.19(1H, br).
MS: m/e (ESI) 509.2 (MH+)

Example 263

N-[2-Hydroxy-5-[2-(7-imino-2-methyl-5,7-dihydro-pyrrolo[3,4-b]pyridin-6-yl)-acetyl]-3-(2-methoxy-ethyl)-benzyl]-N-methyl-acetamide hydrobromide 1H-NMR(DMSO-d6) δ: 2.11(3H, s), 2.68(3H, s), 2.87 (2H, t, J=6.8 Hz), 3.06(3H, s), 3.22(3H, s), 3.53(2H, t, J=6.8 Hz), 4.48(2H, s), 4.87(2H, s), 5.48(2H, s), 7.71(1H, d, J=8.2 Hz), 7.78(1H, s), 7.82(1H, s), 8.17(1H, d, J=8.2 Hz).
MS: m/e (ESI) 425.1 (MH+)

Example 264

Methyl {2-[2-(3,5-di-tert-butyl-4-hydroxy-phenyl)-2-oxo-ethyl]-6-ethoxy-3-imino-2,3-dihydro-1H-isoindol-5-yl}-carbamate hydrobromide 1H-NMR(DMSO-d6) δ: 1.38–1.42(21H, m), 3.70(3H, s), 4.19(2H, q, J=6.8 Hz), 4.75(2H, s), 5.48(2H, s), 7.42(1H, s), 7.77(2H, s), 8.50(1H, s), 8.81(1H, s), 9.07(1H, brs), 9.79 (1H, brs).
MS: m/e (ESI) 496.2 (MH+)

Example 265

Methyl {2-[2-(3,5-di-tert-butyl-4-hydroxy-phenyl)-2-oxo-ethyl]-6-ethoxy-3-imino-2,3-dihydro-1H-isoindol-5-yl}-ethyl-carbamate hydrobromide 1H-NMR(DMSO-d6) δ: 1.05(3H, t, J=7.2 Hz), 1.33(3H, t, J=7.2 Hz), 1.42(18H, s), 3.26(3H, s), 3.43–3.51(2H, m), 4.18(2H, q, J=7.2 Hz), 4.18(2H, s), 5.47(2H, s), 7.50(1H, s), 7.77(2H, s), 8.04(1H, s), 9.11(1H, brs), 9.64(1H, brs).
MS: m/e (ESI) 542.2 (MH+)

Example 266

6-[2-(3,5-Di-tert-butyl-4-hydroxy-phenyl)-2-oxo-ethyl]-7-imino-6,7-dihydro-5H-pyrrolo[3,4-b]pyridine-2-carboxylic acid ethylamide hydrobromide 1H-NMR(DMSO-d6) δ: 1.19(3H, t, J=10 Hz), 3.42(2H, q, J=10 Hz), 4.99(2H, s), 5.38(2H, s), 7.78(2H, s), 8.35(1H, d, J=10 Hz), 8.43(1H, J=10 Hz, 1H), 8.83(1H, t, J=10 Hz).

Example 267

3-{6-[2-(3,5-Di-tert-butyl-4-hydroxy-phenyl)-2-oxo-ethyl]-7-imino-6,7-dihydro-5H-pyrrolo[3,4-b]pyridin-2-yl}-2-methyl-acrylamide hydrobromide 1H-NMR(DMSO-d6) δ: 1.42(18H, s), 2.33(3H, s), 4.89 (2H, s), 5.61(2H, s), 7.27(1H, brs), 7.35(1H, br), 7.68(1H, brs), 7.78(2H, s), 7.86(1H, d, J=8.4 Hz), 8.27(1H, d, =8.4 Hz), 9.71(1H, br).
MS: m/e (ESI) 463.1 (MH+)

Example 268

3-{6-[2-(3,5-Di-tert-butyl-4-hydroxy-phenyl)-2-oxo-ethyl]-7-imino-6,7-dihydro-5H-pyrrolo[3,4-b]pyridin-2-yl}-2-methyl-propionamide hydrobromide 1H-NMR(DMSO-d6) δ: 1.09(3H, d, J=6.4 Hz), 1.42(18H, s), 2.83–2.89(2H, m), 3.14–3.20(1H, m), 4.86(2H, s), 5.56 (2H, s), 6.75(1H, s), 7.29(1H, s), 7.66(1H, d, J=8.0 Hz), 7.77(2H, s), 8.07(1H, br), 8.17(1H, d, J=8.0 Hz), 9.47(1H, br), 9.81(1H, br).
MS: m/e (ESI) 465.2 (MH+)

Example 269

N-{3-tert-Butyl-2-hydroxy-5-[2-(7-imino-2-methyl-5,7-dihydro-pyrrolo[3,4-b]pyridin-6-yl)-acetyl]-benzyl}-N-methyl-methanesulfonamide hydrobromide 1H-NMR(DMSO-d6) δ: 1.409(9H, s), 2.678(3H, s), 2.737 (3H, s), 3.027(3H, s), 4.382(2H, s), 4.866(2H, s), 5.552(2H, s), 7.710(1H, d, J=8.0 Hz), 7.804(1H, d, J=2.0 Hz), 7.814 (1H, d, J=2.0 Hz), 8.163(1H, d, J=8.0 Hz), 9.944(1H, s).

Example 270

Benzyl {3-tert-butyl-2-hydroxy-5-[2-(7-imino-2-methyl-5,7-dihydro-pyrrolo[3,4-b]pyridin-6-yl)-acetyl]-benzyl}-methylcarbamate hydrobromide 1H-NMR(DMSO-d6) δ: 1.400(9H, s), 2.681(3H, s), 2.949 (3H, s), 4.533(2H, s), 4.861(2H, s), 5.165(2H, s), 5.504(2H, s), 7.24–7.42(5H, m), 7.716(1H, d, J=8.0 Hz), 7.804(1H, s), 8.170(1H, d, J=8.0 Hz), 9.952(1H, s).

Example 271

1-(3-tert-Butyl-4-hydroxy-5-nitro-phenyl)-2-(7-imino-2-methyl-5,7-dihydro-pyrrolo[3,4-b]pyridin-6-yl)-ethanone hydrobromide 1H-NMR(DMSO-d6) δ: 1.45(9H, s), 2.64(3H, s), 4.89 (2H, s), 5.60(2H, s), 7.73(1H, d, J=8.0 Hz), 8.07(1H, d, J=2.0 Hz), 8.18(1H, d, J=8.0 Hz), 8.52(1H, d, J=2.0 Hz), 9.52(1H, s), 10.02(1H, s), 11.50(1H, s).

Example 272

1-(3,5-Di-tert-butyl-4-hydroxy-phenyl)-2-(3-ethoxy-7-imino-4-methyl-2-propyl-5,7-dihydro-pyrrolo[3,4-b]pyridin-6-yl)-ethanone hydrochloride 1H-NMR(DMSO-d6) δ: 0.95(3H, t, J=7.2 Hz), 1.37–1.44 (21H, m), 1.71–1.82(2H, m), 2.32(3H, s), 2.83–2.90(2H, s), 3.97(2H, q, J=7.2 Hz), 4.81(2H, s), 5.52(2H, s), 7.77(2H, s), 8.08(1H, s), 9.41(1H, brs), 9.71(1H, brs).
MS: m/e (ESI) 480.2 (MH+)

Example 273

N-{3-tert-Butyl-5-[2-(3-ethoxy-7-imino-4-methyl-2-propyl-5,7-dihydro-pyrrolo[3,4-b]pyridin-6-yl)-acetyl]-2-hydroxy-benzyl}-N-methyl-acetamide hydrochloride 1H-NMR(DMSO-d6) δ: 0.96(3H, t, J=7.2 Hz), 1.37(9H, s), 1.40(3H, t, J=6.8 Hz), 1.65–1.82(2H, m), 2.11(3H, s), 2.32(3H, s), 2.81–2.85(2H, m), 3.11(3H, s), 3.98(2H, q, J=6.8 Hz), 4.48(2H, s), 4.84(2H, s), 5.47–5.56(2H, m), 7.81(1H, s), 7.92(1H, s), 9.46–9.56(1H, m), 9.72(1H, brs), 11.29(1H, s).
MS: m/e (ESI) 509.2 (MH+)

Example 274

2-[2-(3,5-Di-tert-butyl-4-hydroxy-phenyl)-2-oxo-ethyl]-6-ethoxy-3-imino-2,3-dihydro-1H-isoindole-5-carboxylic acid (2-methoxy-ethyl)-amide hydrobromide 1H-NMR(DMSO-d6) δ: 1.40(18H, s), 1.42(3H, t, J=7.3 Hz), 3.30(3H, s), 3.49(4H, brs), 4.27(2H, q, J=7.3 Hz), 4.84(2H, s), 5.48(2H, s), 7.56(1H, s), 7.76(2H, s), 8.07(1H, s), 8.26(1H, brs), 8.65(1H, s), 9.06(1H, brs), 9.85(1H, brs).
MS: m/e (ESI) 524.2 (MH+)

Example 275

2-[2-(3,5-Di-tert-butyl-4-hydroxy-phenyl)-2-oxo-ethyl]-6-ethoxy-3-imino-2,3-dihydro-1H-isoindole-5-carboxylic acid (3-methoxy-propyl)-amide hydrobromide 1H-NMR(DMSO-d6) δ: 1.40(18H, s), 1.40(3H, t, J=7.0 Hz), 1.74(1H, tt, J=6.4,6.3 Hz), 3.25(3H, s), 3.33(2H, dd, J=6.3,5.7 Hz), 3.61(2H, t, J=6.4 Hz), 4.25(2H, q, J=7.0 Hz), 4.83(2H, s), 5.47(2H, s), 7.53(1H, s), 7.76(2H, s), 8.07(1H, brs), 8.25(1H, t, J=5.7 Hz), 8.51(1H, s), 9.12(1H, brs), 9.80(1H, brs).
MS: m/e (ESI) 538.3 (MH+)

Example 276

1-(3,5-Di-tert-butyl-4-hydroxy-phenyl)-2-(7-imino-2-methyl-5-propyl-5,7-dihydro-pyrrolo[3,4-b]pyridin-6-yl)-ethanone hydrobromide 1H-NMR(DMSO-d6) δ: 0.80(3H, t, J=6.4 Hz), 1.42(18H, s), 1.82–1.94(2H, m), 2.04–2.14(2H, m), 2.67(3H, s), 5.03 (1H, q, J=2.8), 5.35(1H, d, J=18.8 Hz), 5.61(1H, d, 18.8 Hz), 7.72(1H, d, J=8.0 Hz), 7.71(2H, s), 8.16(1H, d, J=8.0 Hz), 9.95(1H, s).
MS: m/e (ESI) 436.2 (MH+)

Example 277

2-(2-{3-[(Acetyl-methyl-amino)-methyl]-5-tert-butyl-4-hydroxy-phenyl}-2-oxo-ethyl)-6-ethoxy-3-imino-2,3-dihydro-1H-isoindole-5-carboxylic acid (2-hydroxy-ethyl)-amide hydrobromide 1H-NMR(DMSO-d6) δ: 1.38(9H, s), 1.43(3H, t, J=7.1 Hz), 2.12(3H, s), 3.10(3H, s), 3.38(2H, dt, J=5.4, 5.2 Hz), 3.54(2H, dt, J=5.4, 4.9 Hz), 4.28(2H, q, J=7.1 Hz), 4.48(2H, s), 4.83(1H, t, J=4.9 Hz), 4.86(2H, s), 5.47(2H, s), 7.56(1H, s), 7.82(1H, s), 7.90(1H, s), 8.46(1H, t, J=5.2 Hz), 8.68(1H, s), 9.87(1H, brs).
MS: m/e (ESI) 539.2 (MH+)

Example 278

2-{2-[3-(1-Acetylamino-ethyl)-5-tert-butyl-4-hydroxy-phenyl]-2-oxo-ethyl}-6-ethoxy-3-imino-2,3-dihydro-1H-isoindole-5-carboxylic acid (2-hydroxy-ethyl)-amide hydrobromide 1H-NMR(DMSO-d6) δ: 1.39(9H, s), 1.42–1.48(6H, m), 1.88(3H, s), 3.38(2H, dt, J=5.5,5.2 Hz), 3.54(2H, dt, J=5.4, 4.9 Hz), 4.27(2H, q, J=6.8 Hz), 4.83(1H, t, J=4.9 Hz), 4.85(2H, s), 5.13(1H, dq, J=7.0, 6.4 Hz), 5.40(1H, d, J=18.0 Hz), 5.50(1H, d, J=18.0 Hz), 7.56(1H, s), 7.75(1H, s), 7.79(1H, s), 8.37(1H, t, J=5.2 Hz), 8.67(1H, s), 8.90(1H, d, J=6.4 Hz), 9.85(1H, brs).
MS: m/e (ESI) 539.2 (MH+)

Example 279

N-{3-tert-Butyl-2-hydroxy-5-[2-(7-imino-2-methoxymethyl-5,7-dihydro-pyrrolo[3,4-b]pyridin-6-yl)-acetyl]-benzyl}-N-methyl-acetamide hydrochloride 1H-NMR(DMSO-d6) δ: 1.37(9H, s), 2.11(3H, s), 3.10 (3H, s), 3.41(3H, s), 4.48(2H, s), 4.68(2H, s), 4.91(2H, s), 5.54(2H, s), 7.82(1H, s), 7.85(1H, d, J=8.0 Hz), 7.91(1H, s), 8.29(1H, d, J=8.0 Hz), 9.58(1H, brs), 10.00(1H, brs), 11.29 (1H, s).
MS: m/e (ESI) 453.1 (MH+)

Example 280

N-{3-tert-Butyl-2-hydroxy-5-[2-(7-imino-2-propyl-5,7-dihydro-pyrrolo[3,4-b]pyridin-6-yl)-acetyl]-benzyl}-N-methyl-acetamide hydrochloride 1H-NMR(DMSO-d6) δ: 0.93(3H, t, J=7.2 Hz), 1.37(9H, s), 1.72–1.82(2H, m), 2.11(3H, s), 2.86–2.93(2H, m), 3.10 (3H, s), 4.48(2H, s), 4.86(2H, s), 5.55(2H, s), 7.72(1H, d, J=8.0 Hz), 7.82(1H, s), 7.91(1H, s), 8.17(1H, d, J=8.0 Hz), 9.60(1H, brs), 9.85(1H, s), 11.28(1H, s).

MS: m/e (ESI) 451.1 (MH+)

Example 281

2-{2-[2-(3,5-Di-tert-butyl-4-hydroxy-phenyl)-2-oxo-ethyl]-1-imino-2,3-dihydro-1H-isoindol-5-yloxy}-propanoic acid trifluoroacetate 1H-NMR(DMSO-d6) δ: 1.41(18H, s), 1.53(3H, d, J=6,4 Hz), 4.75(2H, s), 4.89–4.98(1H, m), 5.45(2H, s), 7.16(1H, d, J=8.8 Hz), 7.22(1H, s), 7.77(2H, s), 8.07(1H, d, J=8.8 Hz), 9.07(1H, brs), 9.76(1H, brs).

MS: m/e (ESI) 467.2 (MH+)

Example 282

6-[2-(3,5-Di-tert-butyl-4-hydroxy-phenyl)-2-oxo-ethyl]-7-imino-6,7-dihydro-5H-pyrrolo[3,4-b]pyridine-2-carboxylic acid diethylamide hydrobromide 1H-NMR(DMSO-d6) δ: 1.06(3H, t, J=10 Hz), 1.16(3H, t, J=10 Hz), 3.20(2H, q, J=10 Hz), 3.49(2H, q, J=10 Hz), 4.92(2H, s), 5.53(2H, s), 7.74(2H, s), 7.90(1H, d, J=10 Hz), 8.37(1H, d, J=10 Hz).

Example 283

2-[2-(3,5-Di-tert-butyl-4-hydroxy-phenyl)-2-oxo-ethyl]-3-imino-6-methoxy-2,3-dihydro-1H-isoindole-5-carboxylic acid methylamide hydrobromide 1H-NMR(DMSO-d6) δ: 2.81(3H, d, J=6.0 Hz), 3.98(3H, s), 4.84(2H, s), 5.49(2H, s), 7.55(1H, s), 7.76(2H, s), 8.31 (1H, brs), 8.59(1H, s).

Example 284

2-[2-(3,5-Di-tert-butyl-4-hydroxy-phenyl)-2-oxo-ethyl]-3-imino-6-propoxy-2,3-dihydro-1H-isoindole-5-carboxylic acid methylamide hydrobromide 1H-NMR(DMSO-d6) δ: 0.98(3H, t, J=10 Hz), 1.82(2H, m), 2.82(3H, d, J=6.0 Hz), 4.20(2H, t, J=10 Hz), 4.85(2H, s), 5.46(2H, s), 7.56(1H, s), 7.76(2H, s), 8.31(1H, d, J=6.0 Hz), 8.59(1H, s).

Example 285

1-(3,5-Di-tert-butyl-4-hydroxy-phenyl)-2-(1-imino-1,3,6,7-tetrahydro-5,8-dioxa-2-aza-cyclopenta[b] naphthalen-2-yl)-ethanone hydrobromide 1H-NMR(DMSO-d6) δ: 1.32(3H, d, J=7.2 Hz), 1.42(18H, s), 3.90–3.98(1H, m), 4.30–4.44(2H, m), 4.69(2H, s), 5.45 (2H, s), 7.19–7.27(1H, m), 7.68–7.74(1H, m), 7.77(2H, s), 9.04(1H, brs), 9.64(1H, brs).

MS: m/e (ESI) 451.1 (MH+)

Example 286

1-{3-tert-Butyl-2-hydroxy-5-[2-(7-imino-2-methyl-5,7-dihydro-pyrrolo[3,4-b]pyridin-6-yl)-acetyl]-benzyl}-azepan-2-one hydrobromide 1H-NMR (DMSO-d6) δ: 1.370(9H, s), 1.46–1.59(4H, m), 1.61–1.7(2H, m), 2.54–2.60(2H, m), 2.674(3H, s), 3.54–3.60(2H, m), 4.506(2H, s), 4.865(2H, s), 5.521(2H, s), 7.711(1H, d, J=8.0 Hz), 7.811(1H, s), 7.987(1H, s), 8.160 (1H, d, J=8.0 Hz), 9.920(1H, s).

Example 287

6-Chloro-2-[2-(3,5-di-tert-butyl-4-hydroxy-phenyl)-2-oxo-ethyl]-3-imino-2,3-dihydro-1H-isoindole-5-carboxylic acid methylamide hydrobromide 1H-NMR(DMSO-d6) δ: 1.42(18H, s), 2.80(3H, d, J=4.8 Hz), 4.90(2H, s), 5.54(2H, s), 7.78(2H, s), 7.99(1H, s), 8.04–8.12(1H, br), 8.29(1H, s), 8.59(1H, q, J=4.4 Hz), 9.38(1H, br), 9.95(1H, br).

MS: m/e (ESI) 470.1 (MH+)

Example 288

1-(3,5-Di-tert-butyl-4-hydroxy-phenyl)-2-(1-imino-5,7-dimethoxy-1,3-dihydro-isoindol-2-yl)-ethanone hydrobromide 1H-NMR(DMSO-d6) δ: 1.49(18H, s), 3.91(3H, s), 3.99 (3H, s), 4.74(2H, s), 5.87(1H, brs), 6.02(2H, s), 6.52(1H, d, J=2 Hz), 6.64(1H, d, J=2 Hz), 7.46(1H, brs), 8.00(2H, s), 10.75(1H, brs).

MS: m/e (ESI) 439.0 (MH+)

Example 289

2-[2-(3,5-Di-tert-butyl-4-hydroxy-phenyl)-2-oxo-ethyl]-6-ethoxy-3-imino-2,3-dihydro-1H-isoindole-5-carboxamide hydrobromide 1H-NMR(DMSO-d6) δ: 1.40(18H, s), 1.41(3H, t, J=7.5 Hz), 4.84(2H, s), 5.48(2H, s), 7.54(1H, s), 7.69(1H, brs), 7.77(2H, s), 8.07(1H, s), 8.63(1H, s), 9.15(1H, brs), 9.82 (1H, brs).

MS: m/e (ESI) 466.1 (MH+)

Example 290

1-(3-tert-Butyl-4-hydroxy-5-methylaminomethyl-phenyl)-2-(7-imino-2-methyl-5,7-dihydro-pyrrolo[3,4-b]pyridin-6-yl)-ethanone dihydrochloride 1H-NMR(DMSO-d6) δ: 1.401(9H, s), 2.582(3H, t, J=4.8 Hz), 2.667(3H, s), 4.289(3H, s), 4.869(2H, s), 5.627(2H, s), 5.739(1H, s), 7.705(1H, d, J=8.0 Hz), 7.870(1H, s), 8.15–8.17(2H, m), 9.188(1H, s), 9.959(1H, s), 10.207(1H, s).

Example 291

2-[2-(3,5-Di-tert-butyl-4-hydroxy-phenyl)-2-oxo-ethyl]-3-imino-6-(2-methoxy-ethoxy)-2,3-dihydro-1H-isoindole-5-carboxylic acid methylamide hydrobromide 1H-NMR(DMSO-d6) δ: 2.84(3H, d, J=6.0 Hz), 3.76(2H, t, J=10 Hz), 4.85(2H, s), 5.46(2H, s), 7.56(1H, s), 7.76(2H, s), 8.31(1H, d, J=6.0 Hz), 8.59(1H, s).

Example 292

2-{2-[3-tert-Butyl-4-hydroxy-5-(2-oxo-piperidin-1-ylmethyl)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.38(9H, s), 1.42(3H, t, J=7.2 Hz), 1.64–1.75(4H, m), 2.33–2.37(2H, m), 2.83(3H, d, J=4.8 Hz), 3.44–3.49(2H, m), 4.28(2H, q, J=7.2 Hz), 4.48(2H, s), 4.85(2H, s), 5.47(2H, s), 7.54(1H, s), 7.82(1H, d, J=2.0 Hz), 7.88(1H, d, J=2.0 Hz), 8.20(1H, q, J=4.8 Hz), 8.56(1H, s), 9.20(1H, br), 9.83(1H, br), 11.55(1H, br).

MS: m/e (ESI) 535.2 (MH+)

Example 293

2-[2-(3-tert-Butyl-5-ethyl-4-hydroxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.16(3H, t, J=7.6 Hz), 1.40(9H, s), 1.41(3H, t, J=7.2 Hz), 2.70(2H, q, J=7.2 Hz), 2.82(3H, d, J=4.8 Hz), 4.28(2H, q, J=4.8 Hz), 4.84(2H, s), 5.45(2H, s), 7.53(1H, s), 7.68(1H, s), 7.70(1H, s), 8.20(1H, q, J=4.8 Hz), 8.55(1H, s).

MS: m/e (ESI) 452.1 (MH+)

Example 294

1-(3-tert-Butyl-5-ethyl-4-hydroxy-phenyl)-2-(3-ethoxy-7-imino-2,4-dimethyl-5,7-dihydro-pyrrolo[3,4-b]pyridin-6-yl)-ethanone hydrochloride 1H-NMR(DMSO-d6) δ: 1.15(3H, t, J=7.6 Hz), 1.32–1.46 (12H, m), 2.31(3H, s), 2.58(3H, s), 2.69(2H, q, J=7.6 Hz), 3.99(2H, q, J=7.2 Hz), 4.82(2H, s), 5.52(2H, s), 7.68(1H, s), 7.70(1H, s), 9.32(1H, brs), 9.48(1H, s), 9.83(1H, s).

MS: m/e (ESI) 424.1 (MH+)

Example 295

1-{3-tert-Butyl-5-[2-(3-ethoxy-7-imino-2,4-dimethyl-5,7-dihydro-pyrrolo[3,4-b]pyridin-6-yl)-acetyl]-2-hydroxy-benzyl}-piperidin-2-one hydrobromide 1H-NMR(DMSO-d6) δ: 1.32–1.44(12H, m), 1.64–1.78 (4H, m), 2.32(3H, s), 2.32–2.40(2H, m), 2.58(3H, s), 3.41–3.50(2H, m), 3.95–4.02(2H and AcOEt), 4.48(2H, s), 4.83(2H, s), 5.49(2H, s), 7.82(1H, s), 7.88(1H, s), 9.41(1H, brs), 9.85(1H, brs), 11.56(1H, s).

MS: m/e (ESI) 507.2 (MH+)

Example 296

Methyl {2-[2-(3,5-di-tert-butyl-4-hydroxy-phenyl)-2-oxo-ethyl]-6-ethoxy-7-fluoro-3-imino-2,3-dihydro-1H-isoindol-5-yl}-carbamate hydrochloride 1H-NMR(DMSO-d6) δ: 1.34(3H, t, J=7.2 Hz), 1.40(18H, s), 3.72(3H, s), 4.25(2H, q, J=7.2 Hz), 4.89(2H, s), 5.50(2H, s), 7.76(2H, s), 8.06(1H, s), 8.47(1H, s), 9.28(1H, s), 9.36 (1H, brs), 10.07(1H, brs).

MS: m/e (ESI) 514.1 (MH+)

Example 297

1-(3,5-Di-tert-butyl-4-hydroxy-phenyl)-2-(4-imino-3a,4,6,6a-tetrahydro-1H-pyrrolo[3,4-d]imidazol-5-yl)-ethanone hydrobromide 1H-NMR(DMSO-d6) δ: 1.31(18H, s), 4.54(2H, s), 5.20 (2H, s), 6.34(1H, s), 7.66(2H, s), 7.97(1H, s), 9.42(1H, s), 9.65(1H, s).

MS: m/e (ESI) 369.0 (MH+)

Example 298

2-[2-(3,5-Di-tert-butyl-4-hydroxy-phenyl)-2-oxo-ethyl]-3-imino-6-isopropoxy-2,3-dihydro-1H-isoindole-5-carboxylic acid methylamide hydrobromide 1H-NMR(DMSO-d6) δ: 1.38(6H, d, J=6.0 Hz), 2.83(3H, d, J=5.0 Hz), 4.83(2H, s), 4.86(1H, m), 5.46(2H, s), 7.56 (1H, s), 7.76(2H, s), 8.09(1H, d, J=5.0 Hz), 8.55(1H, s), 9.79(1H, brs).

Example 299

6-Cyclopropylmethoxy-2-[2-(3,5-di-tert-butyl-4-hydroxy-phenyl)-2-oxo-ethyl]-3-imino-2,3-dihydro-1H-isoindole-5-carboxylic acid methylamide hydrobromide 1H-NMR(DMSO-d6) δ: 0.41(2H, bd, J=8.0 Hz), 0.60(2H, bd, J=8.0 Hz), 2.85(3H, d, J=5.0 Hz), 4.15(2H, d, J=8.0 Hz), 4.83(2H, s), 5.46(2H, s), 7.56(1H, s), 7.76(2H, s), 8.09(1H, d, J=5.0 Hz), 8.55(1H, s).

Example 300

1-(3,5-Di-tert-butyl-4-hydroxy-phenyl)-2-(7-imino-3-methoxymethyl-2-methyl-5,7-dihydro-pyrrolo[3,4-b]pyridin-6-yl)-ethanone hydrochloride 1H-NMR(DMSO-d6) δ: 1.42(18H, s), 2.61(3H, s), 3.43 (3H, s), 4.63(3H, s), 4.85(3H, s), 5.58(3H, s), 7.77(2H, s), 8.07(1H, brs), 8.15(1H, s), 9.49–9.53(1H, m), 9.89–9.93 (1H, m).

Example 301

2-[2-(3-tert-Butyl-4-hydroxy-5-methyl-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.39(9H, s), 1.41(3H, t, J=6.8 Hz), 2.28, (3H, s), 2.82(3H, d, J=4.8 Hz), 4.28(2H, q, J=6.8 Hz), 4.84(2H, s), 5.44(2H, s), 7.53(1H, s), 7.70(1H, s), 8.17–8.23(1H, m), 8.55(1H, s).

MS: m/e (ESI) 438.1 (MH+)

Example 302

3-{6-[2-(3,5-Di-tert-butyl-4-hydroxy-phenyl)-2-oxo-ethyl]-7-imino-6,7-dihydro-5H-pyrrolo[3,4-b]pyridin-2-yl}-2-methoxy-acrylamide hydrobromide 1H-NMR(DMSO-d6) δ: 1.41(18H, s), 3.76(3H, s), 4.89 (2H, s), 5.55(2H, s), 6.71(1H, s), 7.65(1H, br), 7.75(2H, s), 7.98(1H, br), 8.27(1H, d, J=8.8 Hz), 8.29(1H, d, J=8.0 Hz).

MS: m/e (ESI) 479.1 (MH+)

Example 303

Methyl {2-[2-(3-tert-butyl-4-hydroxy-5-methyl-phenyl)-2-oxo-ethyl]-6-ethoxy-3-imino-2,3-dihydro-1H-isoindol-5-yl}-carbamate hydrobromide 1H-NMR(DMSO-d6) δ: 1.25–1.42(12H, m), 2.28(3H, s), 3.70(3H, s), 4.18(2H, q, J=6.8), 4.74(2H, s), 5.40(2H, s), 7.41(1H, s), 7.69(2H, s), 8.50(1H, s), 9.07(1H, brs).
MS: m/e (ESI) 454.1 (MH+)

Example 304

1-(3,5-Di-tert-butyl-4-hydroxy-phenyl)-2-(5-dimethylamino-1-imino-1,3-dihydro-isoindol-2-yl)-ethanone hydrobromide 1H-NMR(DMSO-d6) δ: 1.44(18H, s), 3.08(6H, s), 4.70(2H, s), 5.42(2H, s), 6.92–6.97(2H, m), 7.79(2H, s), 7.95(1H, d, J=9.6 Hz), 8.05(1H, s), 8.77(1H, s), 9.42(1H, s).

Example 305

1-(3-tert-Butyl-4-hydroxy-5-methyl-phenyl)-2-(3-ethoxy-7-imino-2,4-dimethyl-5,7-dihydro-pyrrolo[3,4-b]pyridin-6-yl)-ethanone hydrobromide 1H-NMR(DMSO-d6) δ: 1.39(9H, s), 1.40(3H, t, J=7.2 Hz), 2.28(3H, s), 2.31(3H, s), 2.58(3H, s), 3.99(2H, q, J=7.2 Hz), 4.82(2H, s), 5.47(2H, s), 7.70(2H, s), 9.35(1H, s), 9.40(1H, brs), 9.83(1H, brs).
MS: m/e (ESI) 410.0 (MH+)

Example 306

1-(3,5-Di-tert-butyl-4-hydroxy-phenyl)-2-(5,6-diethoxy-7-fluoro-1-imino-1,3-dihydro-isoindol-2-yl)-ethanone hydrobromide 1H-NMR(DMSO-d6) δ: 1.28(3H, t, J=7.0 Hz), 1.40(3H, t, J=7.0 Hz), 4.11(2H, q, J=7.0 Hz), 4.22(2H, q, J=7.0 Hz), 4.77(2H, s), 5.47(2H, s), 7.33(1H, s), 7.76(2H, s), 9.03(1H, brs).
MS: m/e (ESI) 485.1 (MH+)

Example 307

3-{6-[2-(3,5-Di-tert-butyl-4-hydroxy-phenyl)-2-oxo-ethyl]-7-imino-6,7-dihydro-5H-pyrrolo[3,4-b]pyridin-2-yl}-2-methoxy-acrylamide hydrobromide 1H-NMR(DMSO-d6) δ: 1.41(18H, s), 3.74,3.76(3H, each s), 4.85,4.89(2H, s), 5.56(2H, s), 6.02,6.70(1H, each s), 7.25(1H, br), 7.43(1H, br), 7.56,7.72(1H, each d, J=8.0 Hz and J=8.4 Hz), 7.74,7.75(2H, each s).

Example 308

2-[2-(3-Bromo-5-tert-butyl-4-hydroxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.38(9H, s), 1.41(3H, t, J=6.8 Hz), 2.82(3H, d, J=4.4 Hz), 4.28(2H, q, J=6.8 Hz), 4.84(2H, s), 5.44(2H, s), 7.53(1H, s), 7.76(1H, d, J=2.4 Hz), 8.05(1H, 2, J=2.0 Hz), 8.20(1H, q, J=4.4 Hz), 8.55(1H, s), 9.18(1H, br), 9.84(1H, br).
MS: m/e (ESI) 504.1 (MH+)

Example 309

2-[2-(3-tert-Butyl-4-hydroxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.37(9H, s), 1.41(3H, t, J=7.2 Hz), 2.82(3H, d, J=4.8 Hz), 4.28(2H, q, J=7.2 Hz), 4.84(2H, s), 5.45(2H, s), 6.98(1H, d, J=8.0 Hz), 7.53(1H, s), 7.64–7.71(1H, m), 7.76(1H, dd, J=1.6,8.4 Hz), 7.81(1H, d, J=1.6 Hz), 8.18–8.22(1H, m), 8.55(1H, s).
MS: m/e (ESI) 424.0 (MH+)

Example 310

2-(2-{3-tert-Butyl-4-hydroxy-5-[(methanesulfonyl-methyl-amino)-methyl]-phenyl}-2-oxo-ethyl)-6-ethoxy-3-imino-2,3-dihydro-1H-isoindole-5-carboxylic acid methylamide hydrobromide 1H-NMR(DMSO-d6) δ: 1.44(9H, s), 1.45(3H, t, J=7 Hz), 2.75(3H, s), 2.85(3H, d, J=6 Hz), 3.04(3H, s), 4.30(2H, q, J=7 Hz), 3.39(2H, s), 4.87(2H, s), 5.48(2H, s), 7.55(1H, s), 7.81(1H, s), 7.82(1H, s), 8.22(1H, q, J=6 Hz), 8.59(1H, s), 9.22(1H, brs), 9.84(1H, brs).

Example 311

3-tert-Butyl-2-hydroxy-5-[2-(7-imino-2-methyl-5,7-dihydro-pyrrolo[3,4-b]pyridin-6-yl)-acetyl]-benzonitrile hydrobromide 1H-NMR(DMSO-d6) δ: 1.28(9H, s), 2.68(3H, s), 4.82(2H, s), 5.30(2H, s), 7.66(1H, d, J=1 Hz), 7.70(1H, d, J=8 Hz), 7.81(1H, d, J=1 Hz), 8.14(1H, d, J=1 Hz).

Example 312

2-[2-(3,5-Di-tert-butyl-4-hydroxy-phenyl)-2-oxo-ethyl]-4,6-diethoxy-3-imino-2,3-dihydro-1H-isoindole-5-carboxylic acid methylamide hydrobromide 1H-NMR(DMSO-d6) δ: 1.44(3H, t, J=7 Hz), 1.47(3H, t, J=7 Hz), 1.51(18H, s), 3.04(3H, d, J=5 Hz), 4.13(2H, q, J=7 Hz), 4.38(2H, q, J=7 Hz), 4.74(2H, s), 5.88(1H, brs), 5.96(1H, q, J=5 Hz), 6.08(2H, s), 6.72(1H, s), 7.52(2H, brs), 7.99(2H, s).
MS: m/e (ESI) 524.0 (MH+)

Example 313

1-(3,5-Di-tert-butyl-4-hydroxy-phenyl)-2-(4-imino-1-methyl-4,6-dihydro-1H-pyrrolo[3,4-d]imidazol-5-yl)-ethanone hydrobromide 1H-NMR(DMSO-d6) δ: 3.79(3H, s), 4.71(2H, s), 5.38(2H, s), 7.76(2H, s), 8.04(1H, s), 8.95(1H, brs), 9.84(1H, brs).
MS: m/e (ESI) 383.0 (MH+)

Example 314

1-(3,5-Di-tert-butyl-4-hydroxy-phenyl)-2-(6-imino-1-methyl-4,6-dihydro-1H-pyrrolo[3,4-d]imidazol-5-yl)-ethanone hydrobromide 1H-NMR(DMSO-d6) δ: 3.92(3H, s), 4.55(2H, s), 5.40 (2H, s), 7.76(2H, s), 8.05(1H, brs), 8.17(1H, s), 9.06(1H, brs), 9.35(1H, brs).
MS: m/e (ESI) 383.0 (MH+)

Example 315

1-(3,5-Di-tert-butyl-4-hydroxy-phenyl)-2-[7-imino-3-(1-methoxy-ethyl)-2-methyl-5,7-dihydro-pyrrolo[3,4-b]pyridin-6-yl]-ethanone hydrobromide 1H-NMR(DMSO-d6) δ: 1.38(3H, d, J=6.4 Hz), 1.42(18H, s), 2.68(3H, s), 3.22(3H, s), 4.74(1H, q, J=6.4 Hz), 4.86(2H, brs), 5.55(2H, s), 7.77(2H, s), 8.16(1H, s).

Example 316

6-Ethoxy-2-[2-(7-hydroxy-indan-4-yl)-2-oxo-ethyl]-3-imino-2,3-dihydro-1H-isoindole-5-carboxylic acid methylamide hydrobromide 1H-NMR(DMSO-d6) δ: 1.413(3H, t, J=6.8 Hz), 1.92–2.02(2H, m), 2.749(2H, t, J=7.6 Hz), 2.826(3H, d, J=4.8 Hz), 4.278(2H, t, 6.8 Hz), 4.823(2H, s), 5.334(2H, s), 6.786(1H, d, J=8.4 Hz), 7.516(1H, s), 7.751(1H, d, J=8.4 Hz), 8.556(1H, s).

Example 317

1-(8-tert-Butyl-4-methyl-3,4-dihydro-2H-benzo[1,4]oxazin-6-yl)-2-(7-imino-2-methyl-5,7-dihydro-pyrrolo[3,4-b]pyridin-6-yl)-ethanone hydrobromide 1H-NMR(DMSO-d6) δ: 1.36(9H, s), 2.69(3H, s), 2.92 (3H, s), 3.31(2H, t, J=4.4 Hz), 4.36(2H, t, J=4.4 Hz), 4.85(2H, s), 5.52(2H, s), 7.19(1H, d, J=2.0 Hz), 7.30(1H, d, J=2.0 Hz), 7.71(1H, d, J=8.0 Hz), 8.16(1H, d, J=8.0 Hz), 9.75(2H, s).

Example 318

2-[2-(8-tert-Butyl-4-methyl-3,4-dihydro-2H-benzo[1,4]oxazin-6-yl)-2-oxo-ethyl]-6-ethoxy-3-imino-2,3-dihydro-1H-isoindole-5-carboxylic acid methylamide hydrobromide 1H-NMR(DMSO-d6) δ: 1.37(9H, s), 1.43(3H, t, J=7.2 Hz), 2.84(3H, d, J=4.4 Hz), 2.92(3H, s), 3.33(2H, t, J=4.4 Hz), 4.31(2H, q, J=7.2 Hz), 4.36(2H, t, J=4.4 Hz), 4.85(2H, s), 5.47(2H, s), 7.18(1H, d, J=2.0 Hz), 7.30(1H, d, J=2.0 Hz), 7.55(1H, s), 8.21(1H, q, J=4,4 Hz), 8.57(1H, s), 9.18 (1H, s), 9.83(1H, s).

Example 319

1-{3-tert-Butyl-4-hydroxy-5-[(2-methoxy-ethyl)-methyl-amino]-phenyl}-2-(7-imino-2-methyl-5,7-dihydro-pyrrolo[3,4-b]pyridin-6-yl)-ethanone hydrobromide 1H-NMR(DMSO-d6) δ: 1.41(9H, s), 2.69(3H, s), 2.71 (3H, s), 2.97(2H, t, J=5.2 Hz), 3.31(3H, s), 3.43(2H, t, J=5.2 Hz), 4.86(2H, s), 5.53(2H, s), 7.68(1H, d, J=2.0 Hz), 7.72 (1H, d, J=8.0 Hz), 7.80(1H, d, J=2.0 Hz), 8.17(1H, d, J=8.0 Hz), 9.18(1H, s), 9.47(1H, s), 9.91(1H, s).

Example 320

1-(3,5-Di-tert-butyl-4-hydroxy-phenyl)-2-[3-ethoxy-7-imino-4-methyl-2-(2-methyl-propenyl)-5,7-dihydro-pyrrolo[3,4-b]pyridin-6-yl]-ethanone hydrobromide 1H-NMR(DMSO-d6) δ: 1.36(3H, t, J=6.8 Hz), 1.42(18H, s), 1.99(3H, s), 2.10(1H, d, J=0.8 Hz), 2.30(3H, s), 3.93(2H, q, J=6.8 Hz), 4.83(2H, s), 5.54(2H, s), 6.53(1H, brs), 7.78 (2H, s), 9.48(1H, s).
MS: m/e (ESI) 492.1 (MH+)

Example 321

1-(3-tert-Butyl-4-hydroxy-phenyl)-2-(3-ethoxy-7-imino-2,4-dimethyl-5,7-dihydro-pyrrolo[3,4-b]pyridin-6-yl)-ethanone hydrobromide 1H-NMR(DMSO-d6) δ: 1.34–1.43(12H, m), 2.31(3H, s), 2.58(3H, s), 3.99(2H, q, J=7.2 Hz), 4.82(2H, s), 5.47(2H, s), 6.96(1H, d, J=8.4 Hz), 7.76(1H, dd, J=8.4 and 2.0 Hz), 7.81(1H, d, J=2.0 Hz), 9.42(1H, brs), 9.83(1H, brs), 10.62 (1H, s).
MS: m/e (ESI) 396.0 (MH+)

Example 322

N-{3-tert-Butyl-5-[2-(3-ethoxy-7-imino-2,4-dimethyl-5,7-dihydro-pyrrolo[3,4-b]pyridin-6-yl)-acetyl]-2-hydroxy-benzyl}-N-methyl-methane-sulfonamide hydrobromide 1H-NMR(DMSO-d6) δ: 1.37–1.44(12H, m), 2.32(3H, s), 2.59(3H, s), 2.73(3H, s), 3.02(3H, s), 4.00(2H, q, J=6.8 Hz), 4.38(2H, s), 4.83(2H, s), 5.51(2H, s), 7.80(2H, s), 9.26–9.50 (2H, m), 9.84(1H, s).
MS: m/e (ESI) 517.1 (MH+)

Example 323

2-(6-Chloro-5-ethoxy-1-imino-1,3-dihydro-isoindol-2-yl)-1-(3,5-di-tert-butyl-4-hydroxy-phenyl)-ethanone hydrobromide 1H-NMR(DMSO-d6) δ: 1.40(18H, s), 1.40(3H, t, J=6.8 Hz), 4.25(2H, q, J=6.8 Hz), 4.82(2H, s), 5.48(2H, s), 7.58 (1H, s), 7.77(2H, s), 8.06(1H, brs), 8.33(1H, s), 9.17(1H, brs), 9.73(1H, brs).

Example 324 tert-Butyl {6-[2-(3,5-di-tert-butyl-4-hydroxy-phenyl)-2-oxo-ethyl]-7-imino-6,7-dihydro-5H-pyrrolo[3,4-b]pyridin-2-yl}-ethyl-carbamate hydrobromide 1H-NMR(DMSO-d6) δ: 1.19(3H, t, J=7.2 Hz), 1.42(18H, s), 1.48(9H, s), 4.02(2H, q, J=7.2 Hz), 4.86(2H, s), 5.56(2H, s), 7.78(2H, s), 8.01(1H, d, J=8.6 Hz), 8.19(1H, d, J=8.6 Hz), 9.68(1H, s).
MS: m/e (ESI) 523.2 (MH+)

Example 325

1-(3,5-Di-tert-butyl-4-hydroxy-phenyl)-2-(2-ethylamino-7-imino-5,7-dihydro-pyrrolo[3,4-b]pyridin-6-yl)-ethanone hydrochloride 1H-NMR(DMSO-d6) δ: 1.17(3H, t, J=7.2 Hz), 1.42(18H, s), 3.41(2H, q, J=7.2 Hz), 4.63(2H, s), 5.51(2H, s), 6.84(1H, d, J=8.8 Hz), 7.72(1H, d, J=8.8 Hz), 7.77(2H, s), 8.06(1H, s), 9.21(1H, s), 9.32(1H, s).
MS: m/e (ESI) 423.1 (MH+)

Example 326

6-Ethoxy-2-[2-(4-hydroxy-naphthalen-1-yl)-2-oxo-ethyl]-3-imino-2,3-dihydro-1H-isoindole-5-carboxylic acid methylamide hydrobromide 1H-NMR(DMSO-d6) δ: 1.41(3H, t, J=6.8 Hz), 2.83(3H, d, J=4.8 Hz), 4.28(2H, q, J=6.8 Hz), 4.84(2H, s), 5.53(2H, s), 6.98–7.03(1H, m), 7.12–7.18(1H, m), 7.51–7.56(3H, m), 7.59–7.63(1H, m), 8.18–8.27(1H, m), 8.36–8.45(1H, m), 8.57(1H, s).
MS: m/e (ESI) 417.9 (MH+)

Example 327

6-Ethoxy-3-imino-2-(2-oxo-2-phenyl-ethyl)-2,3-dihydro-1H-isoindole-5-carboxylic acid methylamide hydrobromide 1H-NMR(DMSO-d6) δ: 1.41(3H, t, J=6.8 Hz), 2.82(3H, d, J=4.8 Hz), 4.28(2H, q, J=6.8 Hz), 4.88(2H, s), 5.55(2H, s), 7.54(1H, s), 7.61(2H, t, J=7.6 Hz), 7.74(1H, t, J=6.8 Hz), 8.02(2H, d, J=6.8 Hz), 8.20(2H, q, J=6.8 Hz), 8.57(1H, s).
MS: m/e (ESI) 351.9 (MH+)

Example 328

6-Ethoxy-2-[2-(4-hydroxy-phenyl)-2-oxo-ethyl]-3-imino-2,3-dihydro-1H-isoindole-5-carboxylic acid methylamide hydrobromide 1H-NMR(DMSO-d6) δ: 1.41(3H, t, J=6.8 Hz), 2.82(3H, d, J=4.4 Hz), 4.28(2H, q, J=6.8 Hz), 4.84(2H, s), 5.40(2H, s), 6.93(2H, d, J=8.8 Hz), 7.52(1H, s), 7.89(2H, d, J=8.8 Hz), 8.19–8.21(1H, m), 8.56(1H, s).
MS: m/e (ESI) 368.0 (MH+)

Example 329

Ethyl 3-{3-tert-butyl-5-[2-(5-ethoxy-1-imino-6-methylcarbamoyl-1,3-dihydro-isoindol-2-yl)-acetyl]-2-hydroxy-phenyl}-propanoate hydrobromide 1H-NMR(DMSO-d6) δ: 1.17(3H, t, J=7.2 Hz), 1.39(9H, s), 1.41(3H, t, J=7.2 Hz), 2.58(2H, t, J=6.4 Hz), 2.82(3H, d, J=4.8 Hz), 2.96(2H, t, J=6.4 Hz), 4.06(2H, q, J=7.2 Hz), 4.28(2H, q, J=7.2 Hz), 4.82(2H, s), 7.52(1H, s), 7.70(1H, s), 7.72(1H, s), 8.18(1H, q, J=4.8 Hz), 8.54(1H, s).
MS: m/e (ESI) 524.1 (MH+)

Example 330

2-Acetylamino-3-{6-[2-(3,5-di-tert-butyl-4-hydroxy-phenyl)-2-oxo-ethyl]-7-imino-6,7-dihydro-5H-pyrrolo[3,4-b]pyridin-2-yl}-propionamide hydrobromide 1H-NMR(DMSO-d6) δ: 1.42(18H, s), 1.86(3H, s), 3.09–3.15(1H, m), 3.27–3.33(1H, m), 4.69–4.73(1H, m), 4.86(2H, s), 5.55(2H, s), 7.09(1H, brs), 7.38(1H, brs), 7.67(1H, d, J=8.0 Hz), 7.77(2H, s), 8.16–8.21(2H, m).
MS: m/e (ESI) 508.1 (MH+)

Example 331

Ethyl 3-{3-tert-butyl-2-hydroxy-5-[2-(7-imino-2-methyl-5,7-dihydro-pyrrolo[3,4-b]pyridin-6-yl)-acetyl]-phenyl}-propanoate hydrobromide 1H-NMR(DMSO-d6) δ: 1.17(3H, t, J=7.2 Hz), 1.38(9H, s), 2.58(2H, t, 6.4 Hz), 2.68(3H, s), 2.95(2H, t, J=6.4 Hz), 4.06(2H, q, J=7.2 Hz), 4.83(2H, s), 5.47(2H, s), 7.68–7.74 (3H, m), 8.13(1H, d, J=8.0 Hz).
MS: m/e (ESI) 438.1 (MH+)

Example 332

2-[2-(3-Cyclohexyl-4-hydroxy-5-methyl-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.20–1.46(5H, m), 1.409(3H, t, J=6.8 Hz), 1.66–1.83(5H, m), 2.252(3H, s), 2.822(3H, d, J=4.8 Hz), 2.91–3.01(1H, m), 4.276(2H, q, J=6.8 Hz), 4.836(2H, s), 5.425(2H, s), 7.526(1H, s), 7.639(2H, s), 8.18–8.21(1H, m), 8.551(1H, s).

Example 333

1-(3-Cyclohexyl-4-hydroxy-5-methyl-phenyl)-2-(7-imino-2-methyl-5,7-dihydro-pyrrolo[3,4-b]pyridin-6-yl)-ethanone hydrobromide 1H-NMR(DMSO-d6) δ: 1.22–1.48(5H, m), 1.68–1.85 (5H, m), 2.262(3H, s), 2.680(3H, s), 2.93–3.02(1H, m), 4.854(2H, s), 5.496(2H, s), 7.651(2H, s), 7.713(1H, d, J=8.0 Hz), 8.159(1H, d, J=8.0 Hz).

Example 334

2-[2-(3-Cyclopentyl-4-hydroxy-5-methyl-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.409(3H, t, J=6.8 Hz), 1.47–1.82(6H, m), 1.93–2.03(2H, m), 2.252(3H, s), 2.822 (3H, d, J=4.4 Hz), 4.276(2H, q, J=6.8 Hz), 4.834(2H, s), 5.424(2H, s), 7.524(1H, s), 7.644(1H, s), 7.659(1H, s), 8.17–8.23(1H, m), 8.549(1H, s).

Example 335

1-(3-Cyclopentyl-4-hydroxy-5-methyl-phenyl)-2-(7-imino-2-methyl-5,7-dihydro-pyrrolo[3,4-b]pyridin-6-yl)-ethanone hydrobromide 1H-NMR(DMSO-d6) δ: 1.46–1.1.82(6H, m), 1.93–2.03 (2H, m), 2.252(3H, s), 2.669(3H, s), 4.839(2H, s), 5.479(2H, s), 7.63–7.68(2H, m), 7.700(1H, d, J=8.4 Hz), 8.145(1H, d, J=8.4 Hz).

Example 336

1-(3-Cyclopentyl-4-hydroxy-5-methyl-phenyl)-2-(3-ethoxy-7-imino-2,4-dimethyl-5,7-dihydro-pyrrolo[3,4-b]pyridin-6-yl)-ethanone hydrobromide 1H-NMR(DMSO-d6) δ: 1.394(3H, t, J=6.8 Hz), 1.47–1.58(2H, m), 1.60–1.82(4H, m), 1.94–2.04(2H, m), 2.250(3H, s), 2.310(3H, s), 2.578(3H, s), 3.988(2H, q, J=6.8 Hz), 4.811(2H, s), 5.457(2H, s), 7.645(1H, s), 7.659(1H, s).

Example 337

2-(2-{3-[(2-Benzyloxy-ethyl)-methyl-amino]-5-tert-butyl-4-hydroxy-phenyl}-2-oxo-ethyl)-6-ethoxy-3-imino-2,3-dihydro-1H-isoindole-5-carboxylic acid methylamide hydrobromide 1H-NMR(DMSO-d6) δ: 1.40(9H, s), 1.43(3H, t, J=6.8 Hz), 2.71(3H, s), 2.84(3H, d, J=4.4 Hz), 3.04(2H, t, J=5.2 Hz), 3.55(2H, t, J=5.2 Hz), 4.30(2H, q, J=6,8 Hz), 4.53(2H, s), 4.85(2H, s), 5.46(2H, s), 7.20–7.40(5H, m), 7.55(1H, s), 7.68(1H, d, J=1.6 Hz), 7.80(1H, d, J=1.6 Hz), 8.21(1H, q, J=4.4 Hz), 8.57(1H, s), 9.16(1H, s), 9.24(1H, s), 9.83(1H, s).

Example 338

2-(2-{3-tert-Butyl-4-hydroxy-5-[(2-hydroxy-ethyl)-methyl-amino]-phenyl}-2-oxo-ethyl)-6-ethoxy-3-imino-2,3-dihydro-1H-isoindole-5-carboxylic acid methylamide hydrobromide 1H-NMR(DMSO-d6) δ: 1.41(9H, s), 1.43(3H, t, J=6.8 Hz), 2.69(3H, s), 2.84(3H, d, J=4.8 Hz), 2.86(2H, t, J=5.2 Hz), 3.58(2H, t, J=5,2 Hz), 4.29(2H, q, J=6.8 Hz), 4.85(2H, s), 5.48(2H, s), 7.55(1H, s), 7.65(1H, d, J=1.6 Hz), 7.71(1H, d, J=1.6 Hz), 8.21(1H, q, J=4.8 Hz), 8.57(1H, s), 9.00–10.00 (2H, brs).

Example 339 tert-Butyl 6-[2-(3,5-di-tert-butyl-4-hydroxy-phenyl)-2-oxo-ethyl]-3-ethoxy-7-imino-4-methyl-6,7-dihydro-5H-pyrrolo[3,4-b]pyridine-2-carboxylate hydrobromide 1H-NMR(DMSO-d6) δ: 1.37(3H, t, 6.8 Hz), 1.42(18H, s), 1.58(9H, s), 2.37(3H, s), 4.08(2H, q, J=6.8 Hz), 4.90(2H, s), 5.54(2H, s), 7.77(2H, s), 8.00–8.12(1H, m), 9.42–9.55(1H, m), 9.98(1H, brs).

MS: m/e (ESI) 538.3 (MH+)

Example 340

6-[2-(3,5-Di-tert-butyl-4-hydroxy-phenyl)-2-oxo-ethyl]-3-ethoxy-7-imino-4-methyl-6,7-dihydro-5H-pyrrolo[3,4-b]pyridine-2-carboxylic acid trifluoroacetate 1H-NMR(DMSO-d6) δ: 1.34(3H, t, J=7.2 Hz), 1.42(18H, s), 2.35(3H, s), 4.11(2H, q, J=7.2 Hz), 4.89(2H, s), 5.53(2H, s), 7.77(2H, s), 8.02–8.12(1H, m), 9.42–9.50(1H, m), 9.99 (1H, brs).

MS: m/e (ESI) 482.2 (MH+)

Example 341

1-(3,5-Di-tert-butyl-4-hydroxy-phenyl)-2-(7-imino-2-thiazol-2-yl-5,7-dihydro-pyrrolo[3,4-b]pyridin-6-yl)-ethanone hydrobromide 1H-NMR(DMSO-d6) δ: 1.43(18H, s), 4.96(2H, s), 5.62 (2H, s), 7.79(2H, s), 8.03(1H, d, J=3.1 Hz), 8.09(1H, d, J=3.1 Hz), 8.42(1H, d, J=8.1 Hz), 8.54(1H, d, J=8.1 Hz), 9.90(1H, brs).

MS: m/e (ESI) 463.0 (MH+)

Example 342

2-[2-(3,5-Di-tert-butyl-4-hydroxy-phenyl)-2-oxo-ethyl]-6-ethoxy-3-imino-2,3-dihydro-1H-isoindole-5-sulfonic acid methylamide hydrobromide 1H-NMR(DMSO-d6) δ: 1.40(18H, s), 1.40(3H, t, J=7.0 Hz), 2.47(3H, brs), 4.35(2H, q, J=7.0 Hz), 4.87(2H, s), 5.49(2H, s), 7.15(1H, q, J=4.5 Hz), 7.67(1H, s), 7.76(2H, s), 8.06(1H, brs), 8.73(1H, s), 9.23(1H, brs), 9.94(1H, brs).

MS: m/e (ESI) 516.2 (MH+)

Example 343

2-[2-(3-tert-Butyl-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.36(9H, s), 1.41(3H, t, J=6.8 Hz), 2.83(3H, d, J=4.8 Hz), 3.93(3H, s), 4.28(2H, q, J=6.8 Hz), 4.85(2H, s), 5.49(2H, s), 7.19(1H, d, J=8.8 Hz), 7.54 (1H, s), 7.84(1H, d, J=2.4 Hz), 7.93(1H, dd, J=2.4,8.8 Hz), 8.17–8.23(1H, m), 8.56(1H, s).

MS: m/e (ESI) 438.0 (MH+)

Example 344

2-[2-(3-tert-Butyl-5-chloro-4-hydroxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.39(9H, s), 1.41(3H, t, J=6.8 Hz), 2.82(3H, d, J=4.4 Hz), 4.28(2H, q, J=6.8 Hz), 4.84(2H, s), 5.44(2H, s), 7.53(1H, s), 7.74(1H, s), 7.93(1H, s), 8.18–8.22(1H, m), 8.55(1H, s).

MS: m/e (ESI) 458.1 (MH+)

Example 345

2-{2-[3-tert-Butyl-5-(2-dimethylcarbamoyl-ethyl)-4-hydroxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.38(9H, s), 1.42(3H, t, J=7.2 Hz), 2.77–2.90(4H, m), 2.82(3H, d, J=4.8 Hz), 2.86(3H, s), 2.97(3H, s), 4.28(2H, q, J=7.2 Hz), 4.84(2H, s), 5.42(2H, s), 7.52(1H, s), 7.69(1H, s), 7.73(1H, s), 8.18(1H, q, J=4.8 Hz), 8.55(1H, s), 9.16(1H, brs), 9.8(1H, brs), 10.94(1H, brs).

MS: m/e (ESI) 523.1 (MH+)

Example 346

2-{2-[3-(2-Dimethylcarbamoyl-ethyl)-4-hydroxy-5-methyl-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.41(3H, t, J=7.2 Hz), 2.23(3H, s), 2.68(2H, t, J=6.4 Hz), 2.80–2.86(2H, m), 2.82(3H, d, J=4.8 Hz), 2.85(3H, s), 2.96(3H, s), 4.28(2H, q, J=7.2 Hz), 4.82(2H, s), 5.39(2H, s), 7.51(1H, s), 7.67(1H, s), 7.69(1H, s), 8.19(1H, q, J=4.8 Hz), 8.54(1H, s).

Example 347

2-{2-[3-tert-Butyl-5-(2-ethylcarbamoyl-ethyl)-4-hydroxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 0.98(3H, t, J=7.2 Hz), 1.37(9H, s), 1.40(3H, t, J=7.2 Hz), 2.48–2.53(2H, m), 2.82(3H, d, J=4.8 Hz), 2.82–2.88(2H, m), 3.04–3.12(2H, m), 4.28(2H, q, J=7.2 Hz), 4.82(2H, s), 5.40(2H, s), 7.52(1H, s), 7.69(1H, s), 7.71(1H, s), 8.17–8.24(2H, m), 8.55(1H, s).
MS: m/e (ESI) 523.3 (MH+)

Example 348

2-[2-(3,5-Di-tert-butyl-4-hydroxy-phenyl)-2-oxo-ethyl]-3-imino-6-methoxy-5-propyl-1,2,3,5-tetrahydro-isoindol-4-one hydrochloride 1H-NMR(DMSO-d6) δ: 0.97(3H, t, J=7 Hz), 1.43(18H, s), 1.69(2H, m), 4.07(3H, s), 4.08(2H, t, J=6 Hz), 4.56(2H, s), 4.79(2H, s), 6.04(1H, s), 7.79(1H, s), 7.98(2H, s).
MS: m/e (ESI) 468.0 (MH+)

Example 349

8-tert-Butyl-6-[2–5-ethoxy-1-imino-6-methylcarbamoyl-1,3-dihydro-isoindol-2-yl)-acetyl]-2,3-dihydro-benz 1H-NMR(DMSO-d6) δ: 1.42(9H, s), 1.43(3H, t, J=7 Hz), 2.84(3H, d, J=4 Hz), 3.72(3H, s), 4.29(2H, q, J=7 Hz), 4.34–4.38(1H, m), 4.55–4.60(1H, m), 4.85(2H, s), 5.45(2H, s), 5.50(1H, m), 7.43–7.45(1H, m), 7.51–7.53(1H, m), 7.54 (1H, s), 8.21(1H, q, J=4 Hz), 8.57(1H, s).

Example 350

8-tert-Butyl-6-[2-(7-imino-2-methyl-5,7-dihydro-pyrrolo[3,4-b]pyridin-6-yl)-acetyl]-2,3-dihydro-benzo[1,4

1H-NMR(DMSO-d6) δ: 1.49(9H, s), 2.69(3H, s), 3.71 (3H, s), 4.33–4.38(1H, m), 4.54–4.60(1H, m), 4.86(2H, s), 5.48–5.53(1H, m), 5.51(2H, s), 7.45(2H, s), 7.53(1H, s), 7.72(1H, d, J=8 Hz), 8.17(1H, d, J=8 Hz).

Example 351

1-(3,5-Di-tert-butyl-4-hydroxy-phenyl)-2-[5-ethoxy-1-imino-6-(1-methoxy-propyl)-1,3-dihydro-isoindol-2-yl]-ethanone hydrobromide 1H-NMR(DMSO-d6) δ: 0.83(3H, t, J=7.2 Hz), 1.30–1.42 (21H, m), 1.58–1.75(2H, m), 3.20(2H, s), 4.18(2H, q, J=7.2 Hz), 4.56(1H, t, J=5.6 Hz), 4.78(2H, s), 5.47(2H, s), 7.40 (1H, s), 7.77(2H, s), 8.14(1H, s), 9.08(1H, brs), 9.72(1H, brs).
MS: m/e (ESI) 495.3 (MH+)

Example 352

1-(3,5-Di-tert-butyl-4-hydroxy-phenyl)-2-(3-ethoxy-7-imino-5,7-dihydro-pyrrolo[3,4-b]pyridin-6-yl)-ethanone hydrobromide 1H-NMR(DMSO-d6) δ: ]1.40(3H, t, J=7.2 Hz), 1.41 (18H, s), 4.25(2H, q, J=7.2 Hz), 4.83(2H, s), 5.50(2H, s), 7.77(2H, s), 7.84(1H, d, J=2.4 Hz), 8.55(1H, d, J=2.4 Hz), 9.83(1H, brs).
MS: m/e (ESI) 424.2 (MH+)

Example 353

6-Ethoxy-2-[2-(4-hydroxy-3-methyl-phenyl)-2-oxo-ethyl]-3-imino-2,3-dihydro-1H-isoindole-5-carboxylic acid methylamide hydrobromide 1H-NMR(DMSO-d6) δ: 1.408(3H, t, J=6.8 Hz), 2.184 (3H, s), 2.822(3H, d, J=4.8 Hz), 4.274(2H, q, J=6.8 Hz), 4.836(2H, s), 5.403(2H, s), 6.942(1H, d, J=8.4 Hz), 7.519 (1H, s), 7.729(1H, d, J=8.4 Hz), 7.779(1H, s), 8.17–8.21(1H, m), 8.52–8.56(1H, m).

Example 354

2-(3-Ethoxy-7-imino-2-methyl-5,7-dihydro-pyrrolo[3,4-b]pyridin-6-yl)-1-(4-hydroxy-3-methyl-phenyl)-ethanone hydrobromide 1H-NMR(DMSO-d6) δ: 1.393(3H, t, J=6.8 Hz), 2.184 (3H, s), 2.310(3H, s), 2.577(3H, s), 3.986(2H, q, J=6.8 Hz), 4.819(2H, s), 5.442(2H, s), 6.944(1H, d, J=8.4 Hz), 7.734 (1H, dd, J=2.0,8.4 Hz), 7.781(1H, s).

Example 355

Methyl {2-tert-butyl-4-[2-(5-ethoxy-1-imino-6-methylcarbamoyl-1,3-dihydro-isoindol-2-yl)-acetyl]-phenoxy}-acetate hydrobromide 1H-NMR(DMSO-d6) δ: 1.36–1.43(12H, m), 2.82(3H, d, J=4.8 Hz), 3.72(3H, s), 4.29(2H, q, J=7.2 Hz), 4.83(2H, s), 5.01(2H, s), 5.44(2H, s), 7.09(1H, d, J=8.0 Hz), 7.52(1H, s), 7.84–7.90(2H, m), 8.19(1H, q, J=4.8 Hz), 8.56(1H, s).

Example 356

2-(2-{3-[(Acetyl-methyl-amino)-methyl]-4-hydroxy-5-methyl-phenyl}-2-oxo-ethyl)-6-ethoxy-3-imino-2,3-dihydro-1H-isoindole-5-carboxylic acid methylamide hydrobromide 1H-NMR(DMSO-d6) δ: 1.411(3H, t, J=6.8 Hz), 2.094 (3H, s), 2.215(3H, s), 2.824(3H, d, J=4.8 Hz), 3.044(3H, s), 4.279(2H, q, J=6.8 Hz), 4.482(2H, s), 4.849(2H, s), 5.418 (2H, s), 6.942(1H, d, J=8.4 Hz), 7.525(1H, s), 7.784(1H, s), 8.16–8.22(1H, m), 8.558(1H, s).

Example 357

N-{5-[2-(3-Ethoxy-7-imino-2,4-dimethyl-5,7-dihydro-pyrrolo[3,4-b]pyridin-6-yl)-acetyl]-2-hydroxy-3-methyl-benzyl}-N-methyl-acetamide hydrobromide 1H-NMR(DMSO-d6) δ: 1.393(3H, t, J=6.8 Hz), 2.093 (3H, s), 2.212(3H, s), 2.314(3H, s), 2.579(3H, s), 3.048(3H, s), 3.989(2H, q, J=6.8 Hz), 4.483(2H, s), 4.840(2H, s), 5.491(2H, s), 7.801(1H, s), 7.790(1H, s), 9.836(1H, s), 10.792(1H, s).

Example 358

N-{2-Hydroxy-5-[2-(7-imino-2-methyl-5,7-dihydro-pyrrolo[3,4-b]pyridin-6-yl)-acetyl]-3-methyl-benzyl}-N-methyl-acetamide hydrobromide 1H-NMR(DMSO-d6) δ: 2.093(3H, s), 2.215(3H, s), 2.670 (3H, s), 3.044(3H, s), 4.483(2H, s), 4.858(2H, s), 5.488(2H, s), 7.704(1H, d, J=8.0 Hz), 7.790(1H, s), 8.150(1H, d, J=8.0 Hz).

Example 359

N-{2-Hydroxy-5-[2-(7-imino-2-methyl-5,7-dihydro-pyrrolo[3,4-b]pyridin-6-yl)-acetyl]-3-methyl-benzyl}-N-methyl-methanesulfonamide hydrobromide 1H-NMR(DMSO-d6) δ: 2.226(3H, s), 2.657(3H, s), 2.699 (3H, s), 2.968(3H, s), 4.264(2H, s), 4.803(2H, s), 5.402(2H, s), 7.664(1H, d, J=8.0 Hz), 7.717(2H, s), 8.114(1H, d, J=8.0 Hz).

Example 360

N-{6-[2-(3,5-Di-tert-butyl-4-hydroxy-phenyl)-2-oxo-ethyl]-7-imino-6,7-dihydro-5H-pyrrolo[3,4-b]pyridin-2-yl}-acetamide hydrobromide 1H-NMR(DMSO-d6) δ: 1.42(18H, s), 2.18(3H, s), 4.83 (2H, s), 5.55(2H, s), 7.77(2H, s), 8.22(1H, d, J=8.2 Hz), 8.37(1H, d, J=8.2 Hz), 10.65(1H, s).
MS: m/e (ESI) 437.2 (MH+)

Example 361

{2-tert-Butyl-4-[2–5-ethoxy-1-imino-6-methylcarbamoyl-1,3-dihydro-isoindol-2-yl)-acetyl]-phenoxy}-acetic acid hydrobromide 1H-NMR(DMSO-d6) δ: 1.37–1.43(12H, m), 2.82(3H, d, J=4.8 Hz), 4.25–4.30(4H, m), 4.81(2H, s), 5.58(2H, s), 7.46–7.52(1H, m), 7.72–7.80(2H, m), 8.17–8.22(1H, m), 8.52(1H, s), 12.07(1H, brs).
MS: m/e (ESI) 480.1 (MH+)

Example 362

2-{2-[3-tert-Butyl-4-hydroxy-5-(2-oxo-pyrrolidin-1-yl)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.43(9H, s), 1.44(3H, t, J=7 Hz), 2.13–2.23(2H, m), 2.42–2.48(2H, m), 2.85(3H, d, J=5 Hz), 3.65–3.71(2H, m), 4.30(2H, q, J=7 Hz), 4.86(2H, s), 5.45 (2H, s), 7.55(1H, s), 7.66(1H, d, J=1 Hz), 7.80(1H, d, J=1 Hz), 8.21(1H, q, J=5 Hz), 8.58(1H, s).

Example 363

2-{2-[3-tert-Butyl-4-(2,2-dimethyl-propoxy)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.11(9H, s), 1.43(9H, s), 1.44 (3H, t, J=7 Hz), 2.85(3H, d, J=5 Hz), 8.85(2H, s), 4.30(2H, q, J=7 Hz), 4.87(2H, s), 5.49(2H, s), 7.22(1H, d, J=9 Hz), 7.55(1H, s), 7.88(1H, d, J=2 Hz), 7.92(1H, dd, J=2 Hz, 9 Hz), 8.21(1H, q, J=5 Hz), 8.59(s, 1H).

Example 364

3-tert-Butyl-5-[2–5-ethoxy-1-imino-6-methylcarbamoyl-1,3-dihydro-isoindol-2-yl)-acetyl]-2-hydroxy-benzyl carbamate hydrobromide 1H-NMR(DMSO-d6) δ: 1.42(9H, s), 1.44(3H, t, J=7 Hz), 2.85(3H, d, J=5 Hz), 4.30(2H, q, J=7 Hz), 4.57(2H, s), 4.86(1H, s), 5.47(2H, s), 4.55(1H, s), 7.82(2H, s), 8.21(1H, q, J=5 Hz), 7.58(1H, s), 7.21(1H, brs), 9.46(1H, brs), 9.84 (1H, brs).

Example 365

N-{6-[2-(3,5-Di-tert-butyl-4-hydroxy-phenyl)-2-oxo-ethyl]-7-imino-2-methyl-6,7-dihydro-5H-pyrrolo[3,4-b]pyridin-3-ylmethyl}-acetamide hydrobromide 1H-NMR(DMSO-d6) δ: 1.39(18H, s), 1.92(3H, s), 2.65 (3H, s), 4.39(2H, d, J=6.0 Hz), 4.81(2H, s), 5.46(2H, s), 7.69(2H, s), 7.98(1H, s), 8.52(1H, t, J=6.0 Hz).

Example 366

Methyl {8-tert-butyl-6-[2-(5-ethoxy-1-imino-6-methylcarbamoyl-1,3-dihydro-isoindol-2-yl)-acetyl]-2,3-dihydro-benzo[1,4]oxazin-4-yl}-acetate hydrobromide 1H-NMR(DMSO-d6) δ: 1.38(9H, s), 1.43(3H, t, J=6.8 Hz), 2.84(3H, d, J=4.4 Hz), 3.51(2H, t, J=4.4 Hz), 3.66(3H, s), 4.30(6H, m), 4.84(2H, s), 5.43(2H, s), 7.06(1H, s), 7.29(1H, s), 7.54(1H, s), 8.21(1H, q, J=4.4 Hz), 8.57(1H, s), 9.19(1H, s), 9.81(1H, s).

Example 367

Benzyl {8-tert-butyl-6-[2-(5-ethoxy-1-imino-6-methylcarbamoyl-1,3-dihydro-isoindol-2-yl)-acetyl]-2,3-dihydro-benzo[1,4]oxazin-4-yl}-acetate hydrobromide 1H-NMR(DMSO-d6) δ: 1.38(9H, s), 1.44(3H, t, J=6.8 Hz), 2.85(3H, d, J=4.4 Hz), 3.53(2H, t, J=3.6 Hz), 4.30(2H, q, J=6.8 Hz), 4.32(2H, t, J=3.6 Hz), 4.38(2H, s), 4.84(2H, s), 5.16(2H, s), 5.39(2H, s), 7.10(1H, s), 7.20–7.35(6H, m), 7.56(1H, s), 8.21(1H, q, J=4.4 Hz), 8.58(1H, s), 9.20(1H, s), 9.83(1H, s).

Example 368

{8-tert-Butyl-6-[2-(5-ethoxy-1-imino-6-methylcarbamoyl-1,3-dihydro-isoindol-2-yl)-acetyl]-2,3-dihydro-benzo[1,4]oxazin-4-yl}-acetic acid hydrobromide 1H-NMR(DMSO-d6) δ: 1.38(9H, s), 1.43(3H, t, J=6.8 Hz), 2.84(3H, d, J=4.8 Hz), 3.50(2H, t, J=4.4 Hz), 4.14(2H, s), 4.30(4H, m), 4.84(2H, s), 5.44(2H, s), 7.07(1H, d, J=1.6 Hz), 7.27(1H, d, J=1.6 Hz), 7.53(1H, s), 8.21(1H, q, J=4.8 Hz), 8.57(1H, s), 9.22(1H, s), 9.82(1H, s), 12.50(1H, s).

Example 369

{8-tert-Butyl-6-[2-(7-imino-2-methyl-5,7-dihydro-pyrrolo[3,4-b]pyridin-6-yl)-acetyl]-2,3-dihydro-benzo[1,4]oxazin-4-yl}-acetic acid hydrobromide 1H-NMR(DMSO-d6) δ: 1.38(9H, s), 2.69(3H, s), 4.12 (2H, s), 4.30(2H, t, J=4.0 Hz), 4.85(2H, s), 5.51(2H, s), 7.07(1H, s), 7.27(2H, s), 7.71(1H, d, J=7.6 Hz), 8.15(1H, d, J=7.6 Hz), 9.85(1H, s).

Example 370

Methyl {4-[2-(5-ethoxy-1-imino-6-methylcarbamoyl-1,3-dihydro-isoindol-2-yl)-acetyl]-2-ethyl-phenoxy}-acetate hydrobromide 1H-NMR(DMSO-d6) δ: 1.18(t, 3H, J=7.2 Hz), 1.42(t, 3H, J=7.2 Hz), 2.70(q, 2H, J=7.2 Hz), 2.82(d, 3H, J=4.8 Hz), 3.71(s, 3H), 4.29(q, 2H, J=7.2 Hz), 4.86(s, 2H), 5.00(s, 2H), 5.43(s, 2H), 7.08(d, 1H, J=8.0 Hz), 7.52(s, 1H), 7.78~7.87 (m, 2H), 8.18(q, 1H, J=4.8 Hz), 8.57(s, 1H).

Example 371

6-Ethoxy-3-imino-2-[2-oxo-2-(3,4,5-trimethoxy-phenyl)-ethyl]-2,3-dihydro-1H-isoindole-5-carboxylic acid methylamide hydrobromide 1H-NMR(DMSO-d6) δ: 1.41(3H, t, J=6.8 Hz), 2.82(3H, d, J=4.8 Hz), 3.76(3H, s), 3.87(6H, s), 4.28(2H, q, J=7.2 Hz), 4.87(2H, s), 5.56(2H, s), 7.32(2H, s), 7.54(1H, s), 8.17–8.23(1H, m), 8.56(1H, s).
MS: m/e (ESI) 442.2 (MH+)

Example 372

1-(3,5-Di-tert-butyl-4-hydroxy-phenyl)-2-(7-imino-2-methyl-5,7-dihydro-pyrrolo[3,4-d]pyrimidin-6-yl)-ethanone hydrobromide 1H-NMR(DMSO-d6) δ: 1.40(18H, s), 2.84(3H, s), 4.96 (2H, s), 5.59(2H, s), 7.76(2H, s), 9.26(1H, s).
MS: m/e (ESI) 395.2 (MH+)

Example 373

6-Ethoxy-2-[2-(4-hydroxy-3-isopropyl-phenyl)-2-oxo-ethyl]-3-imino-2,3-dihydro-1H-isoindole-5-carboxylic acid methylamide hydrobromide 1H-NMR(DMSO-d6) δ: 1.193(6H, d, J=6.8 Hz), 1.410 (3H, t, J=6.8 Hz), 2.823(3H, d, J=4.8 Hz), 3.20–3.30(1H, m), 4.278(2H, q, J=6.8 Hz), 4.839(2H, s), 5.412(2H, s), 6.950 (1H, d, J=8.4 Hz), 7.523(1H, s), 7.735(1H, d, J=8.4 Hz), 7.779(1H, s), 8.198(1H, d, J=4.8 Hz), 8.552(1H, s).

Example 374

2-[2-(3-Cyclopentyl-4-hydroxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.409(3H, t, J=6.8 Hz), 1.49–1.84(6H, m), 1.92–2.03(2H, m), 2.821(3H, d, J=4.8 Hz), 4.276(2H, q, J=6.8 Hz), 4.835(2H, s), 5.413(2H, s), 6.944(1H, d, J=8.4 Hz), 7.522(1H, s), 7.727(1H, d, J=8.4 Hz), 7.785(1H, s), 8.18–8.21(1H, m), 8.552(1H, s).

Example 375

N-{3-tert-Butyl-5-[2-(5-ethoxy-1-imino-1,3-dihydro-isoindol-2-yl)-acetyl]-2-hydroxy-benzyl}-N-methyl-acetamide hydrobromide 1H-NMR(DMSO-d6) δ: 1.36(3H, t, J=6.8 Hz), 1.37(9H, s), 2.11(3H, s), 3.10(3H, s), 4.16(2H, q, J=6.8 Hz), 4.48(2H, s), 4.79(2H, s), 5.43(2H, s), 7.22(1H, d, J=8.8 Hz), 7.32(1H, s), 7.82(1H, s), 7.91(1H, s), 8.09(1H, d, J=8.8 Hz), 9.10(1H, s), 9.72(1H, s), 11.27(1H, s).

Example 376

6-Ethoxy-2-[2-(3-ethyl-4-hydroxy-phenyl)-2-oxo-ethyl]-3-imino-2,3-dihydro-1H-isoindole-5-carboxylic acid methylamide hydrobromide 1H-NMR(DMSO-d6) δ: 1.149(3H, t, J=7.6 Hz), 1.407 (3H, t, 6.8 Hz), 2.597(3H, q, J=7.6 Hz), 2.820(3H, d, J=4.8 Hz), 4.273(2H, q, J=6.8 Hz), 4.838(2H, s), 5.406(2H, s), 6.946(1H, d, J=8.4 Hz), 7.519(1H, s), 7.70–7.78(2H, m), 8.16–8.23(1H, m), 8.549(1H, s).

Example 377

2-[2-(3-Cyclopentyl-4-hydroxy-5-methyl-phenyl)-2-oxo-ethyl]-6-ethoxy-3-imino-2,3-dihydro-1H-isoindole-5-carboxamide hydrobromide 1H-NMR(DMSO-d6) δ: 1.415(3H, t, J=6.8 Hz), 1.41–1.83(6H, m), 1.92–2.03(2H, m), 2.249(3H, s), 4.273 (2H, q, J=6.8 Hz), 4.834(2H, s), 5.427(2H, s), 7.522(1H, s), 7.642(1H, s), 7.657(1H, s), 7.693(1H, s), 7.756(1H, s), 8.617(1H, s).

Example 378

N-{3-tert-Butyl-5-[2-(5-ethoxy-1-imino-1,3-dihydro-isoindol-2-yl)-acetyl]-2-hydroxy-benzyl}-N-methyl-methanesulfonamide hydrobromide 1H-NMR(DMSO-d6) δ: 1.37(3H, t, J=6.8 Hz), 1.41(9H, s), 2.73(3H, s), 3.02(3H, s), 4.16(2H, q, J=6.8 Hz), 4.37(2H, s), 4.79(2H, s), 5.46(2H, s), 7.21(1H, dd, J=2.0, 8.8 Hz), 7.32(1H, d, J=2.0 Hz), 7.80(1H, s), 7.81(1H, s), 8.09(1H, d, J=8.8 Hz), 9.10(1H, s), 9.72(1H, s), 12.06(1H, s).

Example 379

{2-tert-Butyl-4-[2-(5,6-diethoxy-1-imino-1,3-dihydro-isoindol-2-yl)-acetyl]-phenoxy}-acetic acid hydrobromide 1H-NMR(DMSO-d6) δ: 1.35–1.44(15H, m), 4.08(2H, q, J=7.2 Hz), 4.15(2H, q, J=7.2 Hz), 4.72(2H, s), 4.87(2H, s), 5.45(3H, s), 7.07(1H, d, J=8.8 Hz), 7.34(1H, s), 7.87(1H, d, J=8.8 Hz), 9.13(1H, s), 9.67(1H, s).
MS: m/e (ESI) 467.1 (MH+)

Example 380

2-[2-(3-tert-Butyl-4-carbamoylmethoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.35–1.44(12H, m), 2.82(3H, d, J=5.2 Hz), 4.27(2H, q, J=7.2 Hz), 4.66(2H, s), 4.85(2H, s), 5.45(2H, s), 7.03(1H, d, J=8.8 Hz), 7.33–7.45(2H, m), 7.53(1H, s), 7.85(1H, s), 7.89(1H, d, J=8.8 Hz), 8.19(1H, d, J=0.8 Hz), 8.55(1H, s).
MS: m/e (ESI) 481.2 (MH+)

Example 381

6-Ethoxy-2-[2-(4-ethoxy-3-methylcarbamoyl-phenyl)-2-oxo-ethyl]-3-imino-2,3-dihydro-1H-isoindole-5-carboxylic acid methylamide hydrobromide 1H-NMR(DMSO-d6) δ: 1.41(6H, t, J=7.2 Hz), 2.82(3H, s), 2.83(3H, s), 4.29(4H, qq, J=6.8 Hz, 7.2 Hz), 4.86(2H, s), 5.49(2H, s), 7.32(1H, d, J=8.4), 7.53(1H, s), 8.07(1H, d, J=8.4), 8.13(1H, s), 8.21(1H, s), 8.35(1H, s), 8.56(1H, s).
MS: m/e (ESI) 453.1 (MH+)

Example 382

2-Ethoxy-5-[2-(7-imino-2-methyl-5,7-dihydro-pyrrolo[3,4-b]pyridin-6-yl)-acetyl]-N-methyl-benzamide hydrobromide 1H-NMR(DMSO-d6) δ: 1.41(3H, t, J=6.8 Hz), 2.67(3H, s), 2.82(3H, d, J=4.4 Hz), 4.29(2H, q, J=6.8 Hz), 4.87(2H, s), 5.55(2H, s), 7.32(1H, d, J=8.4 Hz), 7.70(1H, d, J=8.4 Hz), 8.08(1H, d, J=8.4 Hz), 8.12–8.17(2H, m), 8.35(1H, s).

Example 383

2-Ethoxy-5-[2-(3-ethoxy-7-imino-2,4-dimethyl-5,7-dihydro-pyrrolo[3,4-b]pyridin-6-yl)-acetyl]-N-methyl-benzamide hydrobromide 1H-NMR(DMSO-d6) δ: 1.40(6H, t, J=6.8 Hz), 2.32(3H, s), 2.58(3H, s), 2.82(3H, d, J=4.4 Hz), 4.01(2H, q, J=6.8 Hz), 4.29(2H, q, J=6.8 Hz), 4.83(2H, s), 5.54(2H, s), 7.32(1H, d, J=8.4 Hz), 8.08(1H, d, J=8.4 Hz), 8.13(1H, d, J=4.4 Hz), 8.35(1H, s), 9.50(1H, brs), 9.87(1H, brs).

Example 384

2-Ethoxy-5-[2-(3-ethoxy-7-imino-2,4-dimethyl-5,7-dihydro-pyrrolo[3,4-b]pyridin-6-yl)-acetyl]-N-methyl-benzamide hydrobromide 1H-NMR(DMSO-d6) δ: 1.44(18H, s), 4.89(2H, s), 5.54(2H, s), 7.70(1H, dd, J=2.4,9.6 Hz), 7.77–7.86(3H, m), 7.89(1H, d, J=9.6 Hz), 7.95(1H, d, J=2.4 Hz), 7.99(1H, m), 8.08(1H, s), 8.49(2H, d, J=3.2 Hz), 9.31(1H, s), 9.82(1H, s).

Example 385

1-(3,5-Di-tert-butyl-4-hydroxy-phenyl)-2-[1-imino-5-(pyridin-3-yloxy)-1,3-dihydro-isoindol-2-yl]-ethanone hydrobromide 1H-NMR(DMSO-d6) δ: 1.44(18H, s), 4.85(2H, s), 5.52(2H, s), 7.51(1H, dd, J=2.4,8.8 Hz), 7.55(1H, d, J=2.4 Hz), 7.77–7.84(3H, m), 8.00(1H, m), 8.09(1H, m), 8.28(1H, d, J=8.8 Hz), 8.46–8.53(2H, m), 9.24(1H, s), 9.22(1H, s).

Example 386 tert-Butyl {2-tert-butyl-4-[2-(3-ethoxy-7-imino-2,4-dimethyl-5,7-dihydro-pyrrolo[3,4-b]pyridin-6-yl)-acetyl]-phenoxy}-acetate hydrobromide 1H-NMR(DMSO-d6) δ: 1.37–1.42(12H, m), 1.43(9H, s), 2.32(3H, s), 2.58(3H, s), 3.99(2H, q, J=6.8 Hz), 4.83(2H, s), 4.86(2H, s), 5.50(2H, s), 7.05(1H, d, J=8.8 Hz), 7.86(1H, d, J=2.0 Hz), 7.90(1H, dd, J=8.8 and 2.0 Hz), 9.40–9.47(1H, m), 9.82–9.89(1H, m).
MS: m/e (ESI) 510.3 (MH+)

Example 387

{2-tert-Butyl-4-[2-(3-ethoxy-7-imino-2,4-dimethyl-5,7-dihydro-pyrrolo[3,4-b]pyridin-6-yl)-acetyl]-phenoxy}-acetic acid trifluoroacetate 1H-NMR(DMSO-d6) δ: 1.34–1.67(12H, m), 2.31(3H, s), 2.58(3H, s), 3.99(2H, q, J=6.8 Hz), 4.83(2H, s), 4.89(2H, s), 5.50(2H, s), 7.07(1H, d, J=8.8 Hz), 7.85(1H, d, J=2.0 Hz), 7.89(1H, dd, J=8.8 and 2.0 Hz), 9.40–9.49(1H, m), 9.81–9.91(1H, m).
MS: m/e (ESI) 454.2 (MH+)

Example 388

{2-tert-Butyl-4-[2-(6-carbamoyl-5-ethoxy-1-imino-1,3-dihydro-isoindol-2-yl)-acetyl]-phenoxy}-acetic acid trifluoroacetate 1H-NMR(DMSO-d6) δ: 1.40(9H, s), 1.40(3H, t, J=7.0 Hz), 4.27(2H, q, J=7.0 Hz), 4.85(2H, s), 4.88(2H, s), 5.46(2H, s), 7.07(1H, d, J=8.4 Hz), 7.53(1H, s), 7.69(1H, brs), 7.76(1H, brs), 7.86(1H, s), 7.88(1H, d, J=8.4 Hz), 8.63(1H, s), 9.20–9.26(1H, m), 9.85(1H, brs).
MS: m/e (ESI) 468.1 (MH+)

Example 389

1-(3,5-Di-tert-butyl-4-hydroxy-phenyl)-2-[7-imino-2-(2-methyl-2H-pyrazol-3-yl)-5,7-dihydro-pyrrolo[3,4-b]pyridin-6-yl]-ethanone hydrobromide 1H-NMR(DMSO-d6) δ: 1.41(18H, s), 4.24(3H, s), 4.96(2H, s), 5.62(2H, s), 6.99(1H, s), 7.55(1H, s), 7.79(2H, s), 8.22(1H, d, J=8.0 Hz), 8.35(1H, d, J=8.0 Hz).
MS: m/e (ESI) 460.2 (MH+)

Example 390

2-[2-(3,5-Di-tert-butyl-4-hydroxy-phenyl)-2-oxo-ethyl]-6-ethoxy-7-fluoro-3-imino-2,3-dihydro-1H-isoindole-5-carboxylic acid methylamide hydrobromide 1H-NMR(DMSO-d6) δ: 1.33(3H, t, J=7.2 Hz), 1.42(18H, s), 2.82(3H, d, J=4.4 Hz), 4.29(2H, q, J=7.2 Hz), 4.99(2H, s), 5.51(2H, s), 7.77(2H, s), 8.29(1H, s), 8.36–8.41(1H, m).
MS: m/e (ESI) 498.2 (MH+)

Example 391

{2-tert-Butyl-4-[2-(7-imino-2-methyl-5,7-dihydro-pyrrolo[3,4-b]pyridin-6-yl)-acetyl]-phenoxy}-acetic acid hydrochloride 1H-NMR(DMSO-d6) δ: 1.40(9H, s), 2.68(3H, s), 4.86 (2H, s), 4.89(2H, s), 5.55(2H, s), 7.08(1H, d, J=9.2 Hz), 7.71(1H, d, J=7.2 Hz), 7.86(1H, s), 7.89(1H, d, J=9.2 Hz), 8.15(1H, d, J=7.2 Hz), 9.57(1H, s), 9.95(1H, s).
MS: m/e (ESI) 394.0 (MH+)

Example 392

{4-[2-(5-Ethoxy-1-imino-6-methylcarbamoyl-1,3-dihydro-isoindol-2-yl)-acetyl]-2-methoxy-phenoxy}-acetic acid hydrobromide 1H-NMR(DMSO-d6) δ: 1.41(3H, t, J=7.2 Hz), 2.82(3H, d, J=4.8 Hz), 3.85(3H, s), 4.28(2H, q, J=7.2 Hz), 4.84(2H, s), 4.85(2H, s), 5.46(2H, s), 7.06(1H, d, J=8.0 Hz), 7.50(1H, s), 7.53(1H, s), 7.64(1H, d, J=7.8 Hz), 8.19(1H, q, J=4.8 Hz), 8.56(1H, s), 9.27(1H, s), 9.85(1H, s).
MS: m/e (ESI) 456.1 (MH+)

Example 393

1-(3,5-Di-tert-butyl-4-hydroxy-phenyl)-2-(1-imino-5-methoxy-7-methyl-1,3-dihydro-isoindol-2-yl)-ethanone hydrobromide 1H-NMR(DMSO-d6) δ: 1.41(18H, s), 2.63(3H, s), 3.85 (3H, s), 4.54(2H, s), 5.48(2H, s), 7.01(1H, d, J=2 Hz), 7.17(1H, d, J=2 Hz), 7.76(2H, s).
MS: m/e (ESI) 423.0 (MH+)

Example 394

1-{3-tert-Butyl-4-hydroxy-5-[(2-hydroxy-ethyl)-methyl-amino]-phenyl}-2-(5-ethoxy-1-imino-1,3-dihydro-isoindol-2-yl)-ethanone hydrobromide 1H-NMR(DMSO-d6) δ: 1.38(3H, t, J=7.2 Hz), 1.40(9H, s), 2.69(3H, s), 2.86(2H, t, J=4.8 Hz), 3.58(2H, t, J=4,8 Hz), 4.18(2H, q, J=7.2 Hz), 4.78(2H, s), 5.44(2H, s), 7.22(1H, d, J=8.8 Hz), 7.33(1H, s), 7.65(1H, s), 7.69(1H, d, J=8,8 Hz).

Example 395

2-[2-(8-tert-Butyl-4,4-dimethyl-thiochroman-6-yl)-2-oxo-ethyl]-6-ethoxy-3-imino-2,3-dihydro-1H-isoindole-5-carboxylic acid methylamide hydrobromide 1H-NMR(DMSO-d6) δ: 1.38(6H, s), 1.44(3H, t, J=7 Hz), 1.53(9H, s), 1.91–1.97(2H, m), 2.85(3H, d, J=5 Hz), 3.08–3.14(2H, m), 4.31(2H, q, J=7 Hz), 4.87(2H, s), 5.53 (2H, s), 7.56(1H, s), 7.77(1H, s), 7.94(1H, s), 8.22(1H, q, J=5 Hz), 8.59(1H, s).

Example 396

2-[2-(8-tert-Butyl-4,4-dimethyl-1-oxo-thiochroman-6-yl)-2-oxo-ethyl]-6-ethoxy-3-imino-2,3-dihydro-1H-isoindole-5-carboxylic acid methylamide hydrobromide 1H-NMR(DMSO-d6) δ: 1.37(3H, s), 1.43(3H, t, J=7 Hz), 1.55(3H, s), 1.61(9H, s), 2.80–2.90(2H, m), 2.85(3H, d, J=5 Hz), 3.07–3.27(2H, m), 4.61(2H, q, J=7 Hz), 4.89(2H, s), 5.45–5.68(2H, m), 7.57(1H, s), 7.86(1H, s), 8.13(1H, s), 8.22(1H, q, J=5 Hz), 8.59(1H, s).

Example 397

Ethyl {2-[2-(3,5-di-tert-butyl-4-hydroxy-phenyl)-2-oxo-ethyl]-5-ethoxy-6-methylcarbamoyl-2,3-dihydro-isoindol-1-ylidene}-carbamate 1H-NMR(DMSO-d6) δ: 1.37(3H, t, J=7.2 Hz), 1.46(18H, s), 1.55(3H, t, J=6.8 Hz), 3.01(3H, t, J=4.8 Hz), 4.25(2H, q, J=7.2 Hz), 4.32(2H, q, J=7.2 Hz), 4.63(2H, s), 5.11(2H, s), 5.80(1H, s), 6.98(1H, s), 7.88(2H, s), 8.82(1H, s).
MS: m/e (ESI) 552.3 (MH+)

Example 398

2-[2-(3-tert-Butyl-4-hydroxy-phenyl)-2-oxo-ethyl]-6-ethoxy-1-imino-2,3-dihydro-1H-isoindole-5-carboxylic acid methylamide hydrobromide 1H-NMR(DMSO-d6) δ: 1.37(9H, s), 1.42(3H, t, J=6.8 Hz), 2.81(1H, d, J=4.4 Hz), 4.20(2H, q, J=6.8 Hz), 4.80(2H, s), 5.46(2H, s), 6.96(1H, d, J=8.4 Hz), 7.77(1H, d, J=8.0 Hz), 7.81(1H, s), 7.94(1H, s), 8.01(1H, s), 8.24(1H, d, J=4.4 Hz).
MS: m/e (ESI) 424.2 (MH+)

Example 399

2-[2-(2-tert-Butyl-pyridin-4-yl)-2-oxo-ethyl]-6-ethoxy-3-imino-2,3-dihydro-1H-isoindole-5-carboxylic acid methylamide hydrobromide 1H-NMR(DMSO-d6) δ: 1.37(9H, s), 1.42(3H, t, J=6.8 Hz), 2.83(3H, d, J=4.4 Hz), 4.28(2H, q, J=6.8 Hz), 4.89(2H, s), 5.53(2H, s), 7.55(1H, s), 7.71(1H, d, J=6.4 Hz), 7.85(1H, s), 8.20(1H, d, J=4.4 Hz), 8.57(1H, s), 8.82(1H, d, J=5.6 Hz), 9.24(1H, brs), 9.90(1H, brs).

Example 400

1-(3,5-Di-tert-butyl-4-hydroxy-phenyl)-2-[1-imino-6-(pyridin-4-yloxy)-1,3-dihydro-isoindol-2-yl]-ethanone hydrobromide 1H-NMR(DMSO-d6) δ: 1.44(18H, s), 4.93(2H, s), 5.55 (2H, s), 7.30(2H, d, J=6.8 Hz), 7.76–7.83(3H, m), 7.96(1H, d, J=8.4 Hz), 8.12(1H, d, J=2.0 Hz), 8.52(2H, d, J=6.8 Hz).

1H-NMR(DMSO-d6) δ: 1.44(18H, s), 4.90(2H, s), 5.54 (2H, s), 7.31(2H, d, J=7.2 Hz), 7.64(1H, dd, J=2.0, 8.4 Hz), 7.75(1H, d, J=2.0 Hz), 7.80(2H, s), 8.10(1H, s), 8.36(1H, d, J=8.4 Hz), 8.51(2H, d, J=7.2 Hz), 9.31(1H, s), 10.00(1H, s).

Example 402

2-{2-[8-tert-Butyl-4-(2-hydroxy-ethyl)-3,4-dihydro-2H-benzo[1,4]oxazin-6-yl]-2-oxo-ethyl}-6-ethoxy-3-imino-2,3-dihydro-1H-isoindole-5-carboxylic acid methylamide hydrobromide 1H-NMR(DMSO-d6) δ: 1.36(9H, s), 1.43(3H, t, J=6.8 Hz), 2.84(3H, d, J=4.8 Hz), 3.43(2H, t, J=6.0 Hz), 3.50(2H, t, J=4.0 Hz), 3.63(2H, t, J=6.0 Hz), 4.25(2H, t, J=4.0 Hz), 4.29(2H, q, J=6.8 Hz), 4.85(2H, s), 5.50(2H, s), 7.22(2H, s), 7.54(1H, s), 8.22(1H, q, J=4.8 Hz), 8.57(1H, s), 9.31(1H, s), 9.88(1H, s).

Example 403

N-{6-[2-(3,5-Di-tert-butyl-4-hydroxy-phenyl)-2-oxo-ethyl]-7-imino-6,7-dihydro-5H-pyrrolo[3,4-b]pyridin-2-yl}-methanesulfonamide hydrochloride 1H-NMR(DMSO-d6) δ: 1.42(18H, s), 3.56(3H, s), 4.80 (2H, s), 5.59(2H, s), 7.26(1H, d, J=8.8 Hz), 7.78(2H, s), 8.08(1H, s), 8.17(1H, d, J=8.8 Hz), 9.50(1H, s), 9.65(1H, s), 11.19(1H, s).
MS: m/e (ESI) 473.2 (MH+)

Example 404

2-[2-(3-Cyclopentyl-5-fluoro-4-hydroxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.41(3H, t, J=7.2 Hz), 1.21–1.33 (2H, m), 1.52–1.69(2H, m), 1.74–1.80(2H, m), 1.93–2.02 (2H, m), 2.82(3H, d, J=4.8 Hz), 4.11–4.13(1H, m), 4.28(2H, q, J=6.8 Hz), 4.84(2H, s), 5.45(2H, s), 7.53(1H, s), 7.65–7.71(2H, m), 8.19–8.22(1H, m), 8.56(1H, s).
MS: m/e (ESI) 454.2 (MH+)

Example 405

2-[2-(7-tert-Butyl-2-hydroxymethyl-benzofuran-5-yl)-2-oxo-ethyl]-6-ethoxy-3-imino-2,3-dihydro-1H-isoindole-5-carboxylic acid methylamide hydrobromide 1H-NMR(DMSO-d6) δ: 1.42(3H, t, J=6.8 Hz), 1.49(9H, s), 2.83(3H, d, J=4.8 Hz), 4.29(2H, q, J=7.2 Hz), 4.64(2H, d, J=6.0 Hz), 4.88(2H, s), 5.85(2H, d, J=6.0 Hz), 6.94(1H, s), 7.55(1H, s), 7.77(1H, s), 8.19–8.23(1H, m), 8.24(1H, s), 8.57(1H, s).
MS: m/e (ESI) 478.2 (MH+)

Example 406

1-(3,5-Di-tert-butyl-4-hydroxy-phenyl)-2-(1-imino-5-methoxy-7-methoxymethoxy-1,3-dihydro-isoindol-2-yl)-ethanone hydrobromide 1H-NMR(DMSO-d6) δ: 1.50(18H, s), 3.64(3H, s), 3.90 (3H, s), 4.75(2H, s), 5.34(1H, s), 6.04(2H, s), 6.68(1H, d, J=2 Hz), 6.80(1H, d, J=2 Hz), 7.47(1H, brs), 8.00(2H, s).
MS: m/e (ESI) 470.0 (MH+)

Example 407

1-(3,5-Di-tert-butyl-4-hydroxy-phenyl)-2-(7-hydroxy-1-imino-5-methoxy-1,3-dihydro-isoindol-2-yl)-ethanone hydrobromide 1H-NMR(DMSO-d6) δ: 1.42(18H, s), 3.84(3H, s), 4.69 (2H, s), 5.43(2H, s), 6.55(1H, s), 6.78(1H, s), 7.75(2H, s), 8.04(1H, s), 8.34(1H, s), 9.10(1H, s), 11.78(1H, s).
MS: m/e (ESI) 426.0 (MH+)

Example 408

2-{2-tert-Butyl-4-[2-(5,6-diethoxy-1-imino-1,3-dihydro-isoindol-2-yl)-acetyl]-phenoxy}-acetamide hydrobromide 1H-NMR(DMSO-d6) δ: 1.32–1.48(15H, m), 4.09(2H, q, J=7.2 Hz), 4.15(2H, q, J=7.2 Hz), 4.66(2H, s)4.73(2H, s), 5.43(2H, s), 7.03(1H, d, J=8.8 Hz), 7.35(1H, s), 7.36–7.44 (2H, m), 7.78(1H, s), 7.86(1H, s), 7.90(1H, d, J=8.8 Hz), 9.01–9.16(1H, brs), 9.50–9.65(1H, brs).
MS: m/e (ESI) 468.2 (MH+)

Example 409

2-[2-(3-tert-Butyl-4-hydroxy-5-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.41(9H, s), 1.44(3H, t, J=7 Hz), 2.85(3H, d, J=5 Hz), 3.90(3H, s), 4.30(2H, q, J=7 Hz), 4.87(2H, s), 5.51(2H, s), 7.47(1H, s), 7.55(2H, s), 8.21(1H, q, J=5 Hz), 8.58(1H, s).

Example 410

1-(3,5-Di-tert-butyl-4-hydroxy-phenyl)-2-(3-hydroxymethyl-7-imino-2-methyl-5,7-dihydro-pyrrolo[3,4-b]pyridin-6-yl)-ethanone hydrochloride 1H-NMR(DMSO-d6) δ: 1.42(18H, s), 2.58(3H, s), 4.69 (2H, s), 4.86(2H, s), 5.60(2H, s), 7.78(2H, s), 8.05–8.10(1H, m), 8.20(1H, s), 9.44–9.50(1H, m), 9.85–9.90(1H, m).

Example 411

1-(3,5-Di-tert-butyl-4-hydroxy-phenyl)-2-[7-imino-2-methyl-3-(tetrahydropyran-2-yloxymethyl)-5,7-dihydro-pyrrolo[3,4-b]pyridin-6-yl]-ethanone hydrobromide 1H-NMR(DMSO-d6) δ: 1.42(18H, s), 1.30–1,85(6H, m), 2.63(3H, s), 3.48–3.55(1H, m), 3.75–3.82(1H, m), 4.68(1H, d, J=14.4 Hz), 4.79(1H, brs), 4.86(2H, s), 4.88(1H, d, J=14.4 Hz), 5.54(2H, s), 7.76(2H, s), 8.20(1H, s), 9.85–9.95(1H, m).

Example 412

2-(3-Aminomethyl-7-imino-2-methyl-5,7-dihydro-pyrrolo[3,4-b]pyridin-6-yl)-1-(3,5-di-tert-butyl-4-hydroxy-phenyl)-ethanone hydrochloride 1H-NMR(DMSO-d6) δ: 1.42(18H, s), 2.74(3H, s), 4.23–4.30(2H, m), 4.90(2H, s), 5.59(2H, s), 7.78(2H, s),8.09 (1H, s), 8.25(1H, brs), 9.55–9.64(1H, m), 9.95–10.02(1H, m).

Example 413 tert-Butyl {6-[2-(3,5-di-tert-butyl-4-hydroxy-phenyl)-2-oxo-ethyl]-7-imino-2-methyl-6,7-dihydro-5H-pyrrolo[3,4-b]pyridin-3-ylmethyl}-carbamate hydrobromide 1H-NMR(DMSO-d6) δ: 1.40(27H, s), 2.64(3H, s), 4.28–4.32(2H, m), 4.84(2H, s), 5.49(2H, s), 7.55–7.60(1H, m), 7.72(2H, s), 7.97(1H, s).

Example 414

1-(3,5-Di-tert-butyl-4-hydroxy-phenyl)-2-(5-hydroxymethyl-7-imino-2-methyl-5,7-dihydro-pyrrolo[3,4-b]pyridin-6-yl)-ethanone hydrobromide 1H-NMR(DMSO-d6) δ: 1.40(18H, s), 2.67(3H, s), 3.89(1H, brs), 4.08(1H, d, J=12.0 Hz), 5.46(2H, dd, J=18.4 Hz, 18.4 Hz), 7.70(1H, d, J=8.0 Hz), 7.73(2H, s), 8.15(1H, d, J=8.0 Hz).

Example 415

2-[2-(3-tert-Butyl-4-carbamoylmethoxy-phenyl)-2-oxo-ethyl]-6-ethoxy-3-imino-2,3-dihydro-1H-isoindole-5-carboxamide hydrobromide 1H-NMR(DMSO-d6) δ: 1.26–1.30(12H, m), 4.15(2H, q, J=7.2 Hz), 4.54(2H, s), 4.73(2H, s), 5.33(2H, s), 6.91(1H, d, J=8.8 Hz), 7.24–7.31(2H, m), 7.41(1H, s), 7.57(1H, s), 7.65(1H, s), 7.78(1H, d, J=8.8 Hz), 8.51(1H, s).
MS: m/e (ESI) 467.1 (MH+)

Example 416

2-[2-(3-tert-Butyl-4-methanesulfonylamino-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.39–1.47(12H, m), 2.83(3H, d, J=5.2 Hz), 3.26(3H, s), 4.28(2H, q, J=7.2 Hz), 4.87(2H, s), 5.50(2H, s), 7.51–7.60(2H, m), 7.84–7.92(1H, m), 7.95–8.03(1H, m), 8.16–8.23(1H, m), 8.57(1H, s), 8.92(1H, brs), 9.21(1H, brs).
MS: m/e (ESI) 501.2 (MH+)

Example 417

2-[2-(3,5-Di-tert-butyl-4-hydroxy-phenyl)-2-oxo-ethyl]-6-dimethylamino-3-imino-2,3-dihydro-1H-isoindole-5-carboxylic acid methylamide hydrobromide 1H-NMR(DMSO-d6) δ: 1.44(18H, s), 2.80(3H, d, J=4.4 Hz), 2.94(6H, s), 4.75(2H, s), 5.46(2H, s), 7.17(1H, s), 7.79(2H, s), 8.05(1H, s), 8.10(1H, s), 8.37(1H, m), 8.94(1H, s), 9.54(1H, s).

Example 418

6-Chloro-2-[2-(3,5-di-tert-butyl-4-hydroxy-phenyl)-2-oxo-ethyl]-7-fluoro-3-imino-2,3-dihydro-1H-isoindole-5-carboxylic acid methylamide hydrobromide 1H-NMR(DMSO-d6) δ: 1.41(18H, s), 2.81(3H, d, J=4,4 Hz), 5.06(2H, s), 5.52(2H, s), 7.76(2H, s), 8.20(1H, s), 8.64–8.72(1H, m).
MS: m/e (ESI) 488.2 (MH+)

Example 419

1-(3,5-Di-tert-butyl-4-hydroxy-phenyl)-2-[1-imino-6-(1-methyl-piperidin-4-yloxy)-1,3-dihydro-isoindol-2-yl]-ethanone hydrobromide 1H-NMR(DMSO-d6) δ: 1.44(9H, s), 1.85–2.22(4H, m), 2.60(3H, s), 2.73–3.12(4H, m), 4.61(1H, m), 4.79(2H, s), 5.51(2H, s), 7.46(1H, ddd, J=2.4,5.2,8.8 Hz), 7.70(1H, dd, J=5.2,8.8 Hz), 7.80(2H, s), 7.87(1H, dd, J=2.4,5.2 Hz), 8.09(1H, s), 9.25(1H, s), 9.76(1H, s).

Example 420

1-(3,5-Di-tert-butyl-4-hydroxy-phenyl)-2-[1-imino-5-(1-methyl-piperidin-4-yloxy)-1,3-dihydro-isoindol-2-yl]-ethanone hydrobromide 1H-NMR(DMSO-d6) δ: 1.44(9H, s), 1.86(2H, m), 2.14(2H, m), 2.59(3H, s), 2.92(4H, m), 4.78(1H, m), 4.79(2H, s), 5.47(2H, s), 7.29(1H, dd, J=2.0, 8.8 Hz), 7.44(1H, d, J=2.0 Hz), 7.79(2H, s), 8.11(1H, d, J=8.8 Hz), 9.06(1H, s), 9.72(1H, s).

Example 421

6-Ethoxy-3-imino-2-[2-oxo-2-(5,6,7,8-tetrahydro-naphthalen-2-yl)-ethyl]-2,3-dihydro-1H-isoindole-5-carboxylic acid methylamide hydrobromide 1H-NMR(DMSO-d6) δ: 1.408(3H, t, J=6.8 Hz), 1.73–1.78(4H, m), 2.77–2.83(4H, m), 4.276(2H, q, J=6.8 Hz), 4.856(2H, s), 5.470(2H, s), 7.276(1H, d, J=7.6 Hz), 7.526(1H, s), 7.716(1H, s)., 8.17–8.24(1H, m), 8.553(1H, s).

Example 422

1-(3,5-Di-tert-butyl-4-hydroxy-phenyl)-2-(6-ethoxy-3-imino-1,3-dihydro-pyrrolo[3,4-c]pyridin-2-yl)-ethanone hydrobromide 1H-NMR(DMSO-d6) δ: 1.35(3H, t, J=7.0 Hz), 1.41(18H, s), 4.44(2H, q, J=7.0 Hz), 4.83(2H, s), 5.46(2H, s), 7.17(1H, s), 7.76(2H, s), 9.02(1H, s).
MS: m/e (ESI) 424.3 (MH+)

Example 423

N-{2-tert-Butyl-4-[2-(3-ethoxy-7-imino-2,4-dimethyl-5,7-dihydro-pyrrolo[3,4-b]pyridin-6-yl)-acetyl]-phenyl}-methanesulfonamide hydrobromide 1H-NMR(DMSO-d6) δ: 1.39(3H, t, J=7.2 Hz), 1.44(9H, s), 2.32(3H, s), 2.59(3H, s), 3.26(3H, s), 3.98(2H, q, J=7.2 Hz), 4.85(2H, s), 5.56(2H, s), 7.57(1H, d, J=8.0 Hz), 7.88(1H, brd, J=8.0 Hz), 8.00(1H, brs), 8.92(1H, brs), 9.40–9.51(1H, m), 9.85–9,94(1H, m).
MS: m/e (ESI) 473.2 (MH+)

Example 424

1-(3,5-Di-tert-butyl-4-hydroxy-phenyl)-2-(5-ethoxy-6-fluoro-1-imino-1,3-dihydro-isoindol-2-yl)-ethanone hydrobromide 1H-NMR(DMSO-d6) δ: 1.40(3H, t, J=7.0 Hz), 1.41(18H, s), 4.23(2H, q, J=7.0 Hz), 4.78(2H, s), 5.48(2H, s), 7.60(1H, d, J=7.0 Hz), 7.75(2H, s), 8.04(1H, d, J=11.0 Hz).

Example 425

2-[2-(3-Cyclopentyl-5-ethyl-4-hydroxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.150(3H, t, J=7.6 Hz), 1.408 (3H, t, J=6.8 Hz), 1.45–1.84(6H, m), 1.94–2.04(2H, m), 2.662(2H, q, J=7.6 Hz), 2.824(3H, d, J=4.4 Hz), 4.276(2H, q, J=6.8 Hz), 4.835(2H, s), 5.438(2H, s), 7.523(1H, s), 7.628(1H, s), 7.670(1H, s), 8.17–8.23(1H, m), 8.547(1H, d, J=0.8 Hz).

Example 426

N-{6-[2-(3,5-Di-tert-butyl-4-hydroxy-phenyl)-2-oxo-ethyl]-7-imino-6,7-dihydro-5H-pyrrolo[3,4-b]pyridin-2-yl}-N-ethyl-acetamide hydrobromide 1H-NMR(DMSO-d6) δ: 1.10(3H, t, J=7.0 Hz), 1.34(18H, s), 2.07(3H, s), 3.91(2H, q, J=7.0 Hz), 4.81(2H, s), 5.29(2H, s), 7.54(2H, s), 7.85(1H, d, J=8.2 Hz), 8.27(1H, d, J=8.2 Hz).
MS: m/e (ESI) 465.2 (MH+)

Example 427

N-{2-tert-Butyl-4-[2-(7-imino-2-methyl-5,7-dihydro-pyrrolo[3,4-b]pyridin-6-yl)-acetyl]-phenyl}-methanesulfonamide hydrobromide 1H-NMR(DMSO-d6) δ: 1.44(9H, s), 2.69(3H, s), 4.88 (2H, s), 5.57(2H, s), 7.53–7.58(1H, m), 7.72(1H, d, J=8.0 Hz), 7.82–8.00(2H, m), 8.18(1H, d, J=8.0 Hz).

Example 428

Methyl 7-tert-butyl-5-[2-(5-ethoxy-1-imino-6-methylcarbamoyl-1,3-dihydro-isoindol-2-yl)-acetyl]-benzofuran-2-carboxylate hydrobromide 1H-NMR(DMSO-d6) δ: 1.42(3H, t, J=6.8 Hz), 1.51(9H, s), 2.83(3H, d, J=4.8 Hz), 3.93(3H, s), 4.29(2H, q, J=6.8 Hz), 4.89(2H, s), 5.61(2H, s), 7.55(1H, d, J=1.2 Hz), 7.95 (1H, d, J=1.2 Hz), 7.97(1H, s), 8.18–8.22(1H, m), 8.44(1H, s), 8.58(1H, s).
MS: m/e (ESI) 506.2 (MH+)

Example 429 tert-Butyl 8-tert-butyl-6-[2-(5-ethoxy-1-imino-6-methylcarbamoyl-1,3-dihydro-isoindol-2-yl)-acetyl]-2,3-dihydro-benzo[1,4]dioxine-2 or 3-carboxylate hydrobromide 1H-NMR(DMSO-d6) δ: 1.41(9H, s), 1,43(9H, s), 1.44 (3H, t, J=7 Hz), 2.84(3H, d, J=5 Hz), 4.25–4.35(1H, m), 4.30(2H, q, J=7 Hz), 4.51–4.57(1H, m), 4.85(2H, s), 5.30–5.34(1H, m), 5.46(2H, s), 7.46(1H, d, J=3 Hz), 7.52 (1H, d, J=3 Hz), 7.55(1H, s), 8.21(1H, q, J=5 Hz), 8.58(s, 1H), 9.22(1H, brs), 9.85(1H, brs).

Example 430

2-[2-(3-tert-Butyl-4-hydroxy-5-methoxy-phenyl)-2-oxo-ethyl]-6-ethoxy-3-imino-2,3-dihydro-1H-isoindole-5-carboxamide hydrobromide 1H-NMR(DMSO-d6) δ: 1.40(9H, s), 1.45(3H, t, J=7 Hz), 3.89(3H, s), 4.30(2H, q, J=7 Hz), 4.86(2H, s), 5.50(2H, s), 7.47(1H, s), 7.55(2H, s), 7.71(1H, s), 7.78(1H, s), 8.64(1H, s).

Example 431

2-[2-(3-tert-Butyl-4-methanesulfonylamino-phenyl)-2-oxo-ethyl]-6-ethoxy-3-imino-2,3-dihydro-1H-isoindole-5-carboxamide hydrobromide 1H-NMR(DMSO-d6) δ: 1.38–1.46(12H, m), 3.27(3H, s), 4.29(2H, q, J=7.2 Hz), 4.87(2H, s), 5.51(2H, s), 7.53–7.60 (2H, m), 7.68–7.72(1H, m), 7.76–7.81(1H, m), 7.86–7.91 (1H, m), 8.00(1H, s), 8.64(1H, s), 8.93(1H, brs), 9.22(1H, brs).
MS: m/e (ESI) 487.2 (MH+)

Example 432

1-(3-Cyclopentyl-5-ethyl-4-hydroxy-phenyl)-2-(3-ethoxy-7-imino-2,4-dimethyl-5,7-dihydro-pyrrolo[3,4-b]pyridin-6-yl)-ethanone hydrochloride 1H-NMR(DMSO-d6) δ: 1.151(3H, t, J=7.6 Hz), 1.393 (3H, t, J=6.8 Hz), 1.46–1.82(6H, m), 1.94–2.03(2H, m), 2.311(3H, s), 2.579(3H, s), 2.662(2H, q, J=7.6 Hz), 3.054 (3H, s), 3.988(2H, q, J=6.8 Hz), 4.820(2H, s), 5.503(2H, s), 7.630(1H, d, J=2.0 Hz), 7.673(1H, d, J=2.0 Hz), 9.324(1H, s), 9.454(1H, s).

Example 433

2-[2-(3-tert-Butyl-5-cyclopentyl-4-hydroxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.392(9H, s), 1.37–1.43(3H, m), 1.40–1.84(6H, m), 1.96–2.06(2H, m), 2.822(3H, d, J=4.4 Hz), 4.276(2H, q, J=6.8 Hz), 4.835(2H, s), 5.473(2H, s), 7.530(1H, s), 7.709(1H, s), 7.690(1H, s), 8.18–8.24(1H, m9,8.545(1H, s).

Example 434

1-(3-tert-Butyl-5-cyclopentyl-4-hydroxy-phenyl)-2-(3-ethoxy-7-imino-2,4-dimethyl-5,7-dihydro-pyrrolo[3,4-b]pyridin-6-yl)-ethanone hydrobromide 1H-NMR(DMSO-d6) δ: 1.391(9H, s), 1.37–1.43(3H, m), 1.40–1.85(6H, m), 1.96–2.07(2H, m), 2.311(3H, s), 2.578 (3H, s), 3.987(2H, q, J=7.6 Hz), 4.807(2H, s), 5.495(2H, s), 7.683(1H, s), 7.707(1H, s).

Example 435

1-(3,5-Di-tert-butyl-4-hydroxy-phenyl)-2-(5-ethoxy-6-fluoro-1-imino-7-methoxy-1,3-dihydro-isoindol-2-yl)-ethanone hydrochloride 1H-NMR(DMSO-d6) δ: 1.40(3H, t, J=7.0 Hz), 1.41(18H, s), 4.05(3H, d, J=3.0 Hz), 4.22(2H, q, J=7.0 Hz), 4.71(2H, s), 5.45(2H, s), 7.24(1H, d, J=6.0 Hz), 7.75(2H, s), 7.60(1H, d, J=7.0 Hz), 7.75(2H, s), 8.04(1H, d, J=11.0 Hz).
MS: m/e (ESI) 471.2 (MH+)

Example 436

1-(3,5-Di-tert-butyl-4-hydroxy-phenyl)-2-(7-imino-3-propyl-5,7-dihydro-pyrrolo[3,4-b]pyridin-6-yl)-ethanone hydrobromide 1H-NMR(DMSO-d6) δ: 0.92(3H, t, J=5.0 Hz), 1.41(18H, s), 1.67(2H, dd, J=5.3,5.0 Hz), 2.77(2H, t, J=5.3 Hz), 4.88(2H, s), 5.54(2H, s), 7.78(2H, s), 8.08(1H, brs), 8.12(1H, brs), 8.77(1H, s), 9.40(1H, brs), 10.02(1H, brs).
MS: m/e (ESI) 422.2 (MH+)

Example 437

2-(2-Amino-7-imino-5,7-dihydro-pyrrolo[3,4-b]pyridin-6-yl)-1-(3,5-di-tert-butyl-4-hydroxy-phenyl)-ethanone hydrobromide 1H-NMR(DMSO-d6) δ: 1.41(18H, s), 4.64(2H, s), 5.49(2H, s), 6.53(2H, s), 6.86(1H, d, J=8.6 Hz), 7.76(2H, s), 7.78(1H, d, J=8.6 Hz), 9.40(1H, s).
MS: m/e (ESI) 395.1 (MH+)

Example 438

6-Ethoxy-3-imino-2-[2-(4-methoxy-3-trifluoromethyl-phenyl)-2-oxo-ethyl]-2,3-dihydro-1H-isoindole-5-carboxylic acid methylamide hydrobromide 1H-NMR(DMSO-d6) δ: 1.42(3H, t, J=7.2 Hz), 2.82(3H, d, J=4.8 Hz), 4.02(3H, s), 4.28(2H, q, J=7.2 Hz), 4.87(2H, s), 5.51(2H, s), 7.49(1H, d, J=8.0 Hz), 7.54(1H, s), 8.17(1H, s), 8.20–8.22(1H, m), 8.29(1H, d, J=8.0 Hz), 8.57(1H, s).
MS: m/e (ESI) 450.1 (MH+)

Example 439

2-(2-Biphenyl-3-yl-2-oxo-ethyl)-6-ethoxy-3-imino-2,3-dihydro-1H-isoindole-5-carboxylic acid methylamide; hydrobromide 1H-NMR(DMSO-d6) δ: 1.44(3H, t, J=7 Hz), 2.85(3H, d, J=5 Hz), 4.31(2H, q, J=7 Hz), 4.92(2H, s), 5.64(2H, s), 7.42–7.48(1H, m), 7.51–7.58(3H, m), 7.71–7.80(3H, m), 8.00–8.08(2H, m), 8.23(1H, q, J=5 Hz), 8.27–8.29(1H, m), 8.60(1H, s).

Example 440

6-Ethoxy-3-imino-2-[2-oxo-2-(3-trifluoromethyl-phenyl)-ethyl]-2,3-dihydro-1H-isoindole-5-carboxylic acid methylamide hydrobromide 1H-NMR(DMSO-d6) δ: 1.41(3H, t, J=6.8 Hz), 2.82(3H, d, J=4.8 Hz), 4.28(2H, q, J=7.2 Hz), 4.90(2H, s), 5.62(2H, s), 7.56(1H, s), 7.87(1H, t, J=8.4 Hz), 8.12(1H, d, J=8.0 Hz), 8.19–8.23(1H, m), 8.28(1H, s), 8.31(1H, d, J=8.0 Hz), 8.57(1H, s).
MS: m/e (ESI) 420.1 (MH+)

Example 441

({3-tert-Butyl-5-[2-(5-ethoxy-1-imino-6-methylcarbamoyl-1,3-dihydro-isoindol-2-yl)-acetyl]-2-hydroxy-phenyl}-methyl-amino)-acetic acid hydrobromide 1H-NMR(DMSO-d6) δ: 1.41(9H, s), 1.43(3H, t, J=7.2 Hz), 2.75(3H, s), 2.84(3H, d, J=4.4 Hz), 3.71(2H, s), 4.30(2H, q, J=7.2 Hz), 4.86(2H, s), 5.47(2H, s), 7.55(1H, s), 7.66(1H, d, J=1.2 Hz), 7.84(1H, d, J=1.2 Hz), 8.22(1H, q, J=4.4 Hz), 8.58(1H, s), 9.22(1H, s), 9.85(1H, s).

Example 442

2-[2-(3-tert-Butyl-4-hydroxy-5-methoxy-phenyl)-2-oxo-ethyl]-6-dimethylamino-3-imino-2,3-dihydro-1H-isoindole-5-carboxylic acid methylamide hydrobromide 1H-NMR(DMSO-d6) δ: 1.40(9H, s), 2.80(3H, d, J=4.4 Hz), 2.94(6H, s), 3.89(3H, s), 4.76(2H, s), 5.45(2H, s), 7.17(1H, s), 7.45(1H, d, J=2.0 Hz), 7.54(1H, J=2.0 Hz), 8.09(1H, s), 8.38(1H, m), 8.97(1H, s), 9.54(1H, s), 9.66(1H, s).

Example 443

1-(3-tert-Butyl-4-hydroxy-5-methoxy-phenyl)-2-(3-ethoxy-7-imino-2,4-dimethyl-5,7-dihydro-pyrrolo[3,4-b]pyridin-6-yl)-ethanone hydrobromide 1H-NMR(DMSO-d6) δ: 1.20–1.50(12H, m), 2.31(3H, s), 2.58(3H, s), 3.87(3H, s), 3.99(2H, q, J=6.8 Hz), 4.83(2H, s), 5.52(2H, s), 7.44(1H, s), 7.53(1H, s), 9.33–9.48(1H, m), 9.67(1H, s), 9.80–9.92(1H, m).
MS: m/e (ESI) 426.2 (MH+)

Example 444

1-(3,5-Di-tert-butyl-4-hydroxy-phenyl)-2-(5-imino-2-methyl-5,7-dihydro-1-oxa-4,6-diaza-s-indacen-6-yl)-ethanone hydrobromide 1H-NMR(DMSO-d6) δ: 1.42(18H, s), 2.61(3H, s), 4.90(2H, s), 5.55(2H, s), 7.03(1H, s), 7.77(2H, s), 8.40(1H, s), 10.04(1H, brs).
MS: m/e (ESI) 434.2 (MH+)

Example 445

{2-tert-Butyl-4-[2-(5,6-diethoxy-7-fluoro-1-imino-1,3-dihydro-isoindol-2-yl)-acetyl]-phenoxy}-acetic acid hydrochloride 1H-NMR(DMSO-d6) δ: 1.28(3H, t, J=7.0 Hz), 1.40(9H, s), 1.40(3H, t, J=7.0 Hz), 4.10(2H, q, J=7.0 Hz), 4.21(2H, q, J=7.0 Hz), 4.79(2H, s), 4.88(2H, s), 5.47(2H, s), 7.06(1H, d, J=8.5 Hz), 7.32(1H, s), 7.85(1H, s), 7.88(1H, d, J=8.5 Hz).

Example 446

{2-tert-Butyl-4-[2-(5-ethoxy-4-fluoro-1-imino-6-methoxycarbonylamino-1,3-dihydro-isoindol-2-yl)-acetyl]-phenoxy}-acetic acid hydrochloride 1H-NMR(DMSO-d6) δ: 1.33(3H, t, J=7.0 Hz), 1.40(9H, s), 3.72(3H, s), 4.25(2H, q, J=7.0 Hz), 4.89(2H, s), 4.91(2H, s), 5.47(2H, s), 7.07(1H, d, J=8.0 Hz), 7.85(1H, s), 7.89(1H, d, J=8.0 Hz), 8.46(1H, s), 9.30(1H, s).

Example 447

6-[2-(3,5-Di-tert-butyl-4-hydroxy-phenyl)-2-oxo-ethyl]-3-ethoxy-7-imino-6,7-dihydro-5H-pyrrolo[3,4-b]pyridine-2-carboxylic acid methylamide hydrochloride 1H-NMR(DMSO-d6) δ: 1.35(3H, t, J=7.0 Hz), 1.41(18H, s), 2.77(3H, d, J=4.2 Hz), 4.25(2H, q, J=7.0 Hz), 4.87(2H, s), 5.52(2H, s), 7.76(2H, s), 7.99(1H, s), 8.07(1H, s), 8.53 (1H, brq, J=4.2 Hz), 9.40(1H, brs), 9.95(1H, brs).
MS: m/e (ESI) 481.2 (MH+)

Example 448

1-(3,5-Di-tert-butyl-4-hydroxy-phenyl)-2-(2-diethylamino-7-imino-5,7-dihydro-pyrrolo[3,4-b]pyridin-6-yl)-ethanone hydrobromide 1H-NMR(DMSO-d6) δ: 1.13(6H, t, J=6.8 Hz), 1.42(18H, s), 3.60(4H, q, J=6.8 Hz), 4.65(2H, s), 5.50(2H, s), 7.01(1H, d, J=8.8 Hz), 7.77(2H, s), 7.84(1H, d, J=8.8 Hz), 9.28(1H, s).
MS: m/e (ESI) 451.3 (MH+)

Example 449

2-[2-(3-tert-Butyl-4-hydroxy-5-methoxy-phenyl)-2-oxo-ethyl]-6-ethoxy-7-fluoro-3-imino-2,3-dihydro-1H-isoindole-5-carboxylic acid methylamide hydrobromide 1H-NMR(DMSO-d6) δ: 1.32(3H, t, J=6.8 Hz), 1.38(9H, s), 2.82(3H, d, J=4.8 Hz), 3.88(2H, s), 4.29(2H, q, J=6.8 Hz), 4.99(2H, s), 5.51(2H, s), 7.46(1H, s), 7.53(1H, s), 8.29(1H, s), 8.36–8.43(1H, m).
MS: m/e (ESI) 472.2 (MH+)

Example 450

{2-tert-Butyl-4-[2-(5-ethoxy-4-fluoro-1-imino-6-methylcarbamoyl-1,3-dihydro-isoindol-2-yl)-acetyl]-phenoxy}-acetic acid hydrobromide 1H-NMR(DMSO-d6) δ: 1.33(3H, t, J=7.2 Hz), 2.82(3H, d, J=4.8 Hz), 4.29(2H, q, J=6.8 Hz), 4.89(2H, s), 5.00(2H, s), 5.48(2H, s), 7.08(1H, d, J=8.4 Hz), 7.86(1H, d, J=2.4 Hz), 7.89(1H, dd, J=2.4, 8.4 Hz), 8.29(1H, s), 8.36–8.41(1H, m), 9.47(1H, s), 10.04(1H, s).
MS: m/e (ESI) 500.2 (MH+)

Example 451

1-(8-tert-Butyl-2,3-dihydro-benzo[1,4]dioxin-6-yl)-2-(7-imino-2-methyl-5,7-dihydro-pyrrolo[3,4-b]pyridin-6-yl)-ethanone; compound with tert-butyl acetate 1H-NMR(DMSO-d6) δ: 1.41(9H, s), 1.44(9H, s), 2.68 (3H, s), 4.27–4.32(1H, m), 4.52–4.57(1H, m), 4.86(2H, s), 5.30–5.35(1H, m), 5.53(2H, s), 7.46(2H, d, J=2 Hz), 7.52 (1H, d, J=2 Hz), 7.72(1H, d, J=8 Hz), 8.33(1H, d, J=8 Hz).

Example 452

Methyl {3-tert-butyl-2-hydroxy-5-[2-(7-imino-2-methyl-5,7-dihydro-pyrrolo[3,4-b]pyridin-6-yl)-acetyl]-phenoxy}-acetate hydrobromide 1H-NMR(DMSO-d6) δ: 1.41(9H, s), 2.69(3H, s), 3.72 (3H, s), 4.86(2H, s), 4.93(2H, s), 5.53(2H, s), 7.41(1H, d, J=1 Hz), 7.57(1H, d, J=1 Hz, ), 7.72(1H, d, J=8 Hz), 8.17(1H, d, J=8 Hz).

Example 453

Methyl {3-tert-butyl-5-[2-(5-ethoxy-1-imino-6-methylcarbamoyl-1,3-dihydro-isoindol-2-yl)-acetyl]-2-hydroxy-phenoxy}-acetate hydrobromide 1H-NMR(DMSO-d6) δ: 1.41(9H, s), 1.43(3H, t, J=7 Hz), 2.85(3H, d, J=5 Hz), 3.73(3H, s), 4.30(2H, q, J=7 Hz), 4.86(2H, s), 4.93(2H, s), 5.47(2H, s), 7.42(1H, s), 7.55(1H, s), 7.57(1H, s), 8.21(1H, q, J=5 Hz), 8.58(1H, s).

Example 454

1-(3-tert-Butyl-4-hydroxy-5-methoxy-phenyl)-2-(7-imino-2-methyl-5,7-dihydro-pyrrolo[3,4-b]pyridin-6-yl)-ethanone hydrobromide 1H-NMR(DMSO-d6) δ: 1.41(9H, s), 2.69(3H, s), 3.90 (3H, s), 4.88(2H, s), 5.58(2H, s), 7.47(1H, d, J=2 Hz), 7.55(1H, d, J=2 Hz), 7.73(1H, d, J=8 Hz), 8.18(1H, d, J=8 Hz).

Example 455

Methyl 3-{3-tert-Butyl-5-[2-(5-ethoxy-1-imino-6-methylcarbamoyl-1,3-dihydro-isoindol-2-yl)-acetyl]-2-hydroxy-phenyl}-propanoate hydrobromide 1H-NMR(DMSO-d6) δ: 1.41(9H, s), 1.43(3H, t, J=7 Hz), 2.52(2H, t, J=8 Hz), 2.85(3H, d, J=5 Hz), 2.97(2H, t, J=8 Hz), 3.62(3H, s), 4.30(2H, q, J=7 Hz), 4.85(2H, s), 5.44(2H, s), 7.55(1H, s), 7.71(1H, s), 7.73(1H, s), 8.22(1H, q, J=5 Hz), 8.58(1H, s).

Example 456

8-tert-Butyl-6-[2-(7-imino-2-methyl-5,7-dihydro-pyrrolo[3,4-b]pyridin-6-yl)-acetyl]-2,3-dihydro-benzo[1,4]dioxine-2 or 3-carboxylic acid trifluoroacetate 1H-NMR(DMSO-d6) δ: 1.43(9H, s), 2.69(3H, s), 4.31–4.37(1H, m), 4.51–4.57(1H, m), 4.87(2H, s), 5.30–5.35(1H, m), 5.52(2H, s), 7.45(1H, s), 7.52(1H, s), 7.73(1H, d, J=8 Hz), 8.17(1H, d, J=8 Hz), 9.52(1H, s), 9.97(1H, s).

Example 457

1-(3,5-Di-tert-butyl-4-hydroxy-phenyl)-2-(3-imidazol-1-ylmethyl-7-imino-2-methyl-5,7-dihydro-pyrrolo[3,4-b]pyridin-6-yl)-ethanone hydrobromide 1H-NMR(DMSO-d6) δ: 1.33(18H, s), 2.64(3H, s), 4.73 (2H, s), 5.26(2H, s), 5.47(2H, s), 6.99(1H, s), 7.20(1H, s), 7.50(3H, brs), 7.77(1H, s).

Example 458

6-[2-(3-tert-Butyl-4-hydroxy-5-methoxy-phenyl)-2-oxo-ethyl]-3-ethoxy-7-imino-6,7-dihydro-5H-pyrrolo[3,4-b]pyridine-2-carboxylic acid methylamide hydrochloride 1H-NMR(DMSO-d6) δ: 1.35(3H, t, J=7.0 Hz), 1.37(9H, s), 2.77(3H, d, J=4.0 Hz), 3.87(3H, s), 4.24(2H, q, J=7.0 Hz), 4.88(2H, s), 5.54(2H, s), 7.44(1H, s), 7.52(1H, s), 8.00(1H, s), 8.52(1H, brq, J=4.0 Hz), 9.45(1H, brd, J=8.0 Hz), 9.67(1H, s), 9.94(1H, brd, J=8.0 Hz).

Example 459

{2-tert-Butyl-4-[2-(3-ethoxy-7-imino-2-methylcarbamoyl-5,7-dihydro-pyrrolo[3,4-b]pyridin-6-yl)-acetyl]-phenoxy}-acetic acid hydrochloride 1H-NMR(DMSO-d6) δ: 1.35(3H, t, J=6.9 Hz), 1.39(9H, s), 2.77(3H, d, J=4.0 Hz), 4.23(2H, q, J=6.9 Hz), 4.83(2H, s), 4.88(2H, s), 5.55(2H, s), 7.05(1H, d, J=7.7 Hz), 7.85(1H, s), 7.88(1H, d, J=7.7 Hz), 7.98(1H, s), 8.56(1H, brq, J=4.0 Hz), 9.95(1H, s).

Example 460

Methyl 2-tert-butyl-4-[2-(5-ethoxy-1-imino-6-methylcarbamoyl-1,3-dihydro-isoindol-2-yl)-acetyl]-benzoate hydrobromide 1H-NMR(DMSO-d6) δ: 1.37(9H, s), 1.42(3H, t, J=7.2 Hz), 2.83(3H, d, J=4.8 Hz), 3.86(3H, s), 4.28(2H, q, J=7.2 Hz), 4.87(2H, s), 5.51(2H, s), 7.54(1H, s), 7.55(1H, d, J=8.0 Hz), 7.91(1H, d, J=8.0 Hz), 8.06(1H, s), 8.20(1H, q, J=4.8 Hz), 8.57(1H, s).
MS: m/e (ESI) 466.2 (MH+)

Example 461

Isopropenyl {2-[2-(3,5-di-tert-butyl-4-hydroxy-phenyl)-2-oxo-ethyl]-5-ethoxy-4-fluoro-6-methylcarbamoyl-2,3-dihydro-isoindol-1-ylidene}-carbamate 1H-NMR(DMSO-d6) δ: 1.46(3H, t, J=7.2 Hz), 1.47(18H, s), 2.07(3H, d, J=0.4 Hz), 3.01(3H, d, J=4.4 Hz), 4.35(2H, dq, J=1.2,6.8 Hz), 4.73(3H, s), 4.90(1H, s), 5.13(2H, s), 5.83(1H, s), 7.88(2H, s), 8.63(1H, s).
MS: m/e (ESI) 582.3 (MH+)

Example 462

2-[2-(3-tert-Butyl-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.322(9H, s), 1.405(3H, t, J=6.8 Hz), 2.90(2H, 2H), 4.20–4.32(2H, m), 4.869(2H, s), 5.533(2H, s), 7.45–7.58(2H, m), 7.75–7.86(2H, m), 7.972(1H, s), 8.18–8.22(1H, m), 8.547(1H, d, J=1.2 Hz).

Example 463

2-[2-(3-tert-Butyl-5-ethyl-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.215(3H, t, J=7.6 Hz), 1.317 (9H, s), 1.408(3H, t, J=6.8 Hz), 2.700(2H, q, J=7.6 Hz), 2.821(3H, d, J=4.8 Hz), 4.276(2H, q, J=6.8 Hz), 4.863(2H, s), 5.517(2H, s), 7.470(1H, s), 7.531(1H, s), 7.612(1H, s), 7.679(1H, s), 7.799(1H, s), 8.19–8.22(1H, m).

Example 464

1-(3,5-Di-tert-butyl-4-hydroxy-phenyl)-2-(7-imino-2-morpholino-5,7-dihydro-pyrrolo[3,4-b]pyridin-6-yl)-ethanone hydrobromide 1H-NMR(DMSO-d6) δ: 1.41(18H, s), 3.64(4H, t, J=4.6 Hz), 3.72(4H, t, J=4.6 Hz), 4.70(2H, s), 5.51(2H, s), 7.26 (1H, d, J=8.8 Hz), 7.76(2H, s), 7.94(1H, d, J=8.8 Hz), 9.45(1H, s).
MS: m/e (ESI) 465.2 (MH+)

Example 465 tert-Butyl 4-{6-[2-(3,5-di-tert-butyl-4-hydroxy-phenyl)-2-oxo-ethyl]-7-imino-6,7-dihydro-5H-pyrrolo[3,4-b]pyridin-2-yl}-piperazine-1-carboxylate hydrobromide 1H-NMR(DMSO-d6) δ: 1.41(27H, s), 3.44(4H, t, J=4.8 Hz), 3.68(4H, br), 4.70(2H, s), 5.51(2H, s), 7.27(1H, d, J=8.8 Hz), 7.76(2H, s), 7.94(1H, d, J=8.8 Hz), 9.46(1H, s).
MS: m/e (ESI) 564.4 (MH+)

Example 466

6-[2-(3,5-Di-tert-butyl-4-hydroxy-phenyl)-2-oxo-ethyl]-2-ethoxy-5-imino-6,7-dihydro-5H-pyrrolo[3,4-b]pyridine-3-carboxylic acid methylamide hydrochloride 1H-NMR(DMSO-d6) δ: 1.32–1.48(12H, m), 2.80–2.87 (3H, m), 4.58(2H, q, J=6.8 Hz), 4.84(2H, s), 5.47(2H, s), 7.77(2H, s), 8.25–8.33(1H, m), 8.93(1H, s), 9.30–9.38(1H, m), 9.95–10.02(1H, m).
MS: m/e (ESI) 481.2 (MH+)

Example 467

1-(3,5-Di-tert-butyl-4-hydroxy-phenyl)-2-(7-imino-2-piperazin-1-yl-5,7-dihydro-pyrrolo[3,4-b]pyridin-6-yl)-ethanone dihydrochloride 1H-NMR(DMSO-d6) δ: 1.42(18H, s), 3.19(4H, br), 3.93 (4H, t, J=4.8 Hz), 4.72(2H, s), 5.58(2H, s), 7.35(1H, d, J=8.8 Hz), 7.78(2H, s), 8.00(1H, d, J=8.8 Hz), 8.07(1H, s), 9.36 (2H, br), 9.51(1H, s), 9.60(1H, s).
MS: m/e (ESI) 464.2 (MH+)

Example 468 tert-Butyl 2-{2-tert-butyl-4-[2-(5-ethoxy-1-imino-6-methylcarbamoyl-1,3-dihydro-isoindol-2-yl)-acetyl]-phenoxy}-2-methyl-propanoate hydrobromide 1H-NMR(DMSO-d6) δ: 1.35(9H, s), 1.39(9H, s), 1.41 (3H, t, J=7.2 Hz), 1.65(6H, s), 2.82(3H, d, J=4.8 Hz), 4.27(2H, q, J=7.2 Hz), 4.84(2H, s), 5.43(2H, s), 6.68(1H, d, J=8.8 Hz), 7.52(1H, s), 7.86(1H, d, J=8.8 Hz), 7.87(1H, s), 8.19(1H, q, J=4.8 Hz), 8.55(1H, s).
MS: m/e (ESI) 566.4 (MH+)

Example 469

2-{2-tert-Butyl-4-[2-(5-ethoxy-1-imino-6-methylcarbamoyl-1,3-dihydro-isoindol-2-yl)-acetyl]-phenoxy}-2-methyl-propanoic acid hydrobromide 1H-NMR(DMSO-d6) δ: 1.34–1.46(12H, m), 1.66(6H, s), 2.82(3H, d, J=4.8 Hz), 4.27(2H, q, J=7.2 Hz), 4.84(2H, s), 5.45(2H, s), 6.73(1H, d, J=8.8 Hz), 7.53(1H, s), 7.85(1H, d, J=8.8 Hz), 7.87(1H, s), 8.19(1H, q, J=4.8 Hz), 8.56(1H, s), 9.25(1H, brs), 9.86(1H, brs).
MS: m/e (ESI) 510.2 (MH+)

Example 470

2-[2-(3,5-Di-tert-butyl-4-hydroxy-phenyl)-2-oxo-ethyl]-5-ethoxy-4-fluoro-6-methylcarbamoyl-2,3-dihydro-isoindol-1-ylidenecarbamoyloxymethyl acetate 1H-NMR(DMSO-d6) δ: 1.47(3H, t, J=8.2 Hz), 1.48(18H, s), 2.18(3H, s), 3.02(3H, d, J=5.2 Hz), 4.22(2H, q, J=8.2 Hz), 5.13(2H, ABq, J=16.0 Hz), 5.86(1H, s), 5.89(2H, s), 7.87(2H, s), 8.46(1H, s).
MS: m/e (ESI) 614.3 (MH+)

Example 471

2-[2-(3,5-Di-tert-butyl-4-hydroxy-phenyl)-2-oxo-ethyl]-5-ethoxy-4-fluoro-6-methylcarbamoyl-2,3-dihydro-isoindol-1-ylidenecarbamoyloxymethyl 2,2-dimethyl-propionate 1H-NMR(DMSO-d6) δ: 1.20,1.23(9H, each s), 1.47(18H, s), 1.48(3H, t, J=6.8 Hz), 3.02(3H, d, J=4.8 Hz), 4.41(2H, q, J=6.8 Hz), 4.87(2H, s), 5.63(2H, s), 5.87(1H, s), 5.88(2H, s), 7.87,7.89(1H, each s).
MS: m/e (ESI) 656.4 (MH+)

Example 472

Methyl 3-{2-tert-butyl-4-[2-(5-ethoxy-1-imino-6-methylcarbamoyl-1,3-dihydro-isoindol-2-yl)-acetyl]-phenoxy}-acrylate hydrobromide 1H-NMR(DMSO-d6) δ: 1.34–1.43(12H, m), 2.82(3H, d, J=4.8 Hz), 3.67(3H, s), 4.28(2H, q, 7.2 Hz), 4.86(2H, s), 5.49(2H, s), 7.43(1H, d, J=8.8 Hz), 7.54(1H, s), 7.87(1H, d, J=12 Hz), 7.92–8.02(3H, m), 8.17–8.23(1H, m), 8.56(1H, s).
MS: m/e (ESI) 508.2 (MH+)

Example 473

Methyl 3-{2-tert-butyl-4-[2-(5-ethoxy-1-imino-6-methylcarbamoyl-1,3-dihydro-isoindol-2-yl)-acetyl]-phenoxy}-propanoate hydrobromide 1H-NMR(DMSO-d6) δ: 1.32(9H, s), 1.41(3H, t, J=7.2 Hz), 2.82(3H, d, J=4.8 Hz), 2.89(2H, t, J=6.4 Hz), 3.62(3H, s), 4.28(2H, q, J=7.2 Hz), 4.36(2H, t, J=6.4 Hz), 4.84(2H, s), 5.45(2H, s), 7.19(1H, d, J=8.8 Hz), 7.53(1H, s), 7.83(1H, s), 7.91(1H, d, J=8.8 Hz), 8.19(1H, q, J=4.8 Hz), 8.55(1H, s).

Example 474

Ethyl {4-[2-(5-ethoxy-1-imino-6-methylcarbamoyl-1,3-dihydro-isoindol-2-yl)-acetyl]-2,6-dimethoxy-phenoxy}-acetate hydrobromide 1H-NMR(DMSO-d6) δ: 1.19(3H, t, J=7.2 Hz), 1.41(3H, t, J=7.2 Hz), 2.82(3H, d, J=4.8 Hz), 3.85(6H, s), 4.14(2H, q, J=7.2 Hz), 4.27(2H, q, J=7.2 Hz), 4.69(2H, s), 4.86(2H, s), 5.55(2H, s), 7.31(2H, s), 7.53(1H, s), 8.16–8.23(1H, m), 8.56(1H, s), 9.39(1H, brs), 9.91(1H, brs).
MS: m/e (ESI) 514.3 (MH+)

Example 475

{2-tert-Butyl-4-[2-(1-imino-5,7-dimethoxy-1,3-dihydro-isoindol-2-yl)-acetyl]-phenoxy}-acetic acid trifluoroacetate 1H-NMR(DMSO-d6) δ: 1.40(9H, s), 3.89(3H, s), 3.97(3H, s), 4.71(2H, s), 4.87(2H, s), 5.40(2H, s), 6.75(1H, s), 6.91(1H, s), 7.07(1H, d, J=8.8 Hz), 7.85(1H, s), 7.87(1H, d, J=8.8 Hz), 8.45(1H, brs), 9.08(1H, brs).
MS: m/e (ESI) 441.1 (MH+)

Example 476

3-{6-[2-(3-tert-Butyl-4-hydroxy-5-methoxy-phenyl)-2-oxo-ethyl]-7-imino-6,7-dihydro-5H-pyrrolo[3,4-b]pyridin-2-yl}-2-methyl-acrylamide hydrobromide 1H-NMR(DMSO-d6) δ: 1.36(9H, s), 2.32(3H, d, J=1.2 Hz), 3.86(3H, s), 4.54(2H, s), 5.13(2H, s), 7.17–7.21(2H, br), 7.31(1H, s), 7.49(1H, s), 7.56(1H, s), 7.62(1H, d, J=8.0 Hz), 8.06(1H, d, J=8.0 Hz).

Example 477

1-(3-tert-Butyl-4-hydroxy-5-methoxy-phenyl)-2-[7-imino-2-methyl-3-(tetrahydropyran-2-yloxymethyl)-5,7-dihydro-pyrrolo[3,4-b]pyridin-6-yl]-ethanone hydrobromide 1H-NMR(DMSO-d6) δ: 1.39(9H, s), 1.40–1.90(6H, m), 2.62(3H, s), 3.45–3.55(1H, m), 3.74–3.82(1H, m), 3.88(3H, s), 4.67(1H, d, J=14.0 Hz), 4.76–4.81(1H, m), 4.85(2H, s), 4.87(1H, d, J=14.0 Hz), 5.50–5.53(2H, m), 7.45(1H, d, J=2.0 Hz), 7.53(1H, d, J=2.0 Hz), 8.19(1H, s).

Example 478

1-(3-tert-Butyl-4-hydroxy-5-methoxy-phenyl)-2-(3-hydroxymethyl-7-imino-2-methyl-5,7-dihydro-pyrrolo[3,4-b]pyridin-6-yl)-ethanone hydrobromide 1H-NMR(DMSO-d6) δ: 1.38(9H, s), 2.58(3H, s), 3.88(3H, s), 4.69(2H, s), 4.86(2H, s), 5.57(2H, s), 7.45(1H, d, J=2.0 Hz), 7.53(1H, d, J=2.0 Hz), 8.20(1H, s).

Example 479 tert-Butyl (2-tert-butyl-4-{2-[7-imino-2-methyl-3-(tetrahydropyran-2-yloxymethyl)-5,7-dihydro-pyrrolo[3,4-b]pyridin-6-yl]-acetyl}-phenoxy)-acetate hydrobromide 1H-NMR(DMSO-d6) δ: 1.41(9H, s), 1.44(9H, s), 1.30–1.89(6H, m), 2.63(3H, s), 3.48–3.55(1H, m), 3.75–3.82(1H, m), 4.68(1H, d, J=14.4 Hz), 4.79(1H, t, J=1.8 Hz), 4.86(2H, s), 4.87(1H, d, J=14.4 Hz), 4.88(2H, s), 5.53(2H, s), 7.05(1H, d, J=8.8 Hz), 7.86(1H, d, J=2.0 Hz), 7.90(1H, dd, J=8.98,2.2 Hz), 8.20(1H, s).

Example 480 tert-Butyl {2-tert-butyl-4-[2-(3-hydroxymethyl-7-imino-2-methyl-5,7-dihydro-pyrrolo[3,4-b]pyridin-6-yl)-acetyl]-phenoxy}-acetate hydrobromide 1H-NMR(DMSO-d6) δ: 1.40(9H, s), 1.44(9H, s), 2.58(3H, s), 4.68(2H, s), 4.84–4.91(2H, m), 4.86(2H, s), 5.55(2H, s), 7.05(1H, d, J=8.8 Hz), 7.86(1H, brs), 7.89(1H, d, J=8.8 Hz), 8.20(1H, s), 9.53(1H, d, J=7.2 Hz), 9.88(1H, d, J=7.2 Hz).

Example 481

{2-tert-Butyl-4-[2-(3-hydroxymethyl-7-imino-2-methyl-5,7-dihydro-pyrrolo[3,4-b]pyridin-6-yl)-acetyl]-phenoxy}-acetic acid hydrobromide 1H-NMR(DMSO-d6) δ: 1.40(9H, s), 2.58(3H, s), 4.69(2H, s), 4.85–4.93(2H, m), 4.90(2H, s), 5.54(2H, s), 7.08(1H, d, J=8.8 Hz), 7.86(1H, d, J=2.0 Hz), 7.89(1H, dd, J=8.8, 2.0 Hz), 8.20(1H, s), 9.51(1H, d, J=8.4 Hz), 9.89(1H, d, J=8.4 Hz).

Example 482

1-(3-tert-Butyl-2-hydroxy-5-{2-[7-imino-2-methyl-3-(tetrahydropyran-2-yloxymethyl)-5,7-dihydro-pyrrolo[3,4-b]pyridin-6-yl]-acetyl}-benzyl)-piperidin-2-one hydrobromide 1H-NMR(DMSO-d6) δ: 1.38(9H, s), 1.40–1.80(10H, m), 2.30–2.40(2H, m), 3.30–3.3.40(2H, m), 3.42–3.50(2H, m), 4.48(2H, s), 4.68(1H, d, J=14.4 Hz), 4.77–4.80(1H, m), 4.88(1H, d, J=14.4 Hz), 4.88(2H, s), 5.52(2H, s), 7.83(1H, d, J=1.6 Hz), 7.87(1H, d, J=1.6 Hz), 8.20(1H, s).

Example 483

1-{3-tert-Butyl-2-hydroxy-5-[2-(3-hydroxymethyl-7-imino-2-methyl-5,7-dihydro-pyrrolo[3,4-b]pyridin-6-yl)-acetyl]-benzyl}-piperidin-2-one hydrochloride 1H-NMR(DMSO-d6) δ: 1.37(9H, s), 1.65–1.78(4H, m), 2.30–2.40(2H, m), 2.58(3H, s), 3.40–3.50(2H, m), 4.48(2H, s), 4.61(2H, s), 4.87(2H, s), 5.55(2H, s), 7.82(1H, d, J=2.0 Hz), 7.88(1H, d, J=2.0 Hz), 8.20(1H, s), 9.52(1H, d, J=9.2 Hz), 9.88(1H, d, J=9.2 Hz), 11.55(1H, s).

Example 484

1-(3-tert-Butyl-4-hydroxy-5-methoxy-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=7.0 Hz), 1.37(9H, s), 1.40(3H, t, J=7.0 Hz), 3.86(3H, s), 4.11(2H, q, J=7.0 Hz), 4.20(2H, q, J=7.0 Hz), 4.79(2H, s), 5.45(2H, s), 7.32(1H, s), 7.43(1H, s), 7.52(1H, s).

Example 485

6-[2-(3-tert-Butyl-4-methanesulfonylamino-phenyl)-2-oxo-ethyl]-3-ethoxy-7-imino-6,7-dihydro-5H-pyrrolo[3,4-b]pyridine-2-carboxylic acid methylamide hydrochloride 1H-NMR(DMSO-d6) δ: 1.37(3H, t, J=6.9 Hz), 1.42(9H, s), 2.77(3H, d, J=4.0 Hz), 3.26(3H, s), 4.25(2H, q, J=6.9 Hz), 4.90(2H, s), 5.55(2H, s), 7.56(1H, d, J=8.0 Hz), 7.88(1H, d, J=8.0 Hz), 8.00(2H, s), 8.52(1H, brq, J=4.0 Hz), 8.94(1H, brs), 9.50(1H, brs), 9.98(1H, brs).

Example 486

{4-[2-(5-Ethoxy-1-imino-6-methylcarbamoyl-1,3-dihydro-isoindol-2-yl)-acetyl]-2-isopropoxy-phenoxy}-acetic acid hydrochloride 1H-NMR(DMSO-d6) δ: 1.28(6H, d, J=6.0 Hz), 1.41(3H, t, J=7.2 Hz), 2.82(3H, d, J=4.8 Hz), 4.28(2H, q, J=7.2 Hz), 4.60–4.69(1H, m), 4.85(4H, s), 5.44(2H, s), 7.05(1H, d, J=8.8 Hz), 7.51(1H, s), 7.53(1H, s), 7.62(1H, d, J=8.8 Hz), 8.17–8.23(1H, m), 8.56(1H, s), 9.24(1H, brs), 9.83(1H, brs).
MS: m/e (ESI) 483.9 (MH+)

Example 487

1-(3,5-Di-tert-butyl-4-hydroxy-phenyl)-2-(2-ethyl-7-imino-5,7-dihydro-pyrrolo[3,4-b]pyridin-6-yl)-ethanone hydrobromide 1H-NMR(DMSO-d6) δ: 1.31(3H, t, J=7.6 Hz), 1.42(18H, s), 2.94(2H, q, J=7.6 Hz), 4.85(2H, s), 5.56(2H, s), 7.73(1H, d, J=8.0 Hz), 7.77(2H, s), 8.18(1H, d, J=8.0 Hz), 9.85(1H, s).
MS: m/e (ESI) 408.2 (MH+)

Example 488

2-[2-(4-Acetyl-piperazin-1-yl)-7-imino-5,7-dihydro-pyrrolo[3,4-b]pyridin-6-yl]-1-(3,5-di-tert-butyl-4-hydroxy-phenyl)-ethanone hydrobromide 1H-NMR(DMSO-d6) δ: 1.46(18H, s), 2.17(3H, s), 3.69–3.83(8H, br), 4.74(2H, s), 4.85(2H, s), 7.23(1H, d, J=8.8 Hz), 7.88(1H, d, J=8.8 Hz), 7.89(2H, s).
MS: m/e (ESI) 506.3 (MH+)

Example 489

6-[2-(3-tert-Butyl-4-hydroxy-5-methoxy-phenyl)-2-oxo-ethyl]-2-ethoxy-5-imino-6,7-dihydro-5H-pyrrolo[3,4-b]pyridine-3-carboxylic acid methylamide hydrochloride 1H-NMR(DMSO-d6) δ: 1.33–1.44(12H, m), 2.80–2.87 (3H, m), 3.88(3H, s), 4.58(2H, q, J=6.8 Hz), 4.86(2H, s), 5.48(2H, s), 7.45(1H, s), 7.53(1H, s), 8.23–8.36(1H, m), 8.93(1H, s), 9.35–9.44(1H, m), 9.68(1H, s), 9.98–10.07(1H, m).
MS: m/e (ESI) 455.2 (MH+)

Example 490

6-[2-(3-Cyclopentyl-4-hydroxy-5-methyl-phenyl)-2-oxo-ethyl]-2-ethoxy-5-imino-6,7-dihydro-5H-pyrrolo[3,4-b]pyridine-3-carboxylic acid methylamide hydrochloride 1H-NMR(DMSO-d6) δ: 1.40(3H, t, J=7.2 Hz), 1.46–1.83 (6H, m), 1.91–2.03(2H, m), 2.25(3H, s), 2.78–2.89(4H, m), 4.58(2H, q, J=7.2 Hz), 4.85(2H, s), 5.42(2H, s), 7.655(1H, s), 7.664(1H, s), 8.20–8.40(1H, m), 8.93(1H, s), 9.35(1H, s), 9.37–9.49(1H, m), 9.95–10.08(1H, m).
MS: m/e (ESI) 451.1 (MH+)

Example 491

{2-tert-Butyl-4-[2-(2-ethoxy-5-imino-3-methylcarbamoyl-5,7-dihydro-pyrrolo[3,4-b]pyridin-6-yl)-acetyl]-phenoxy}-acetic acid trifluoroacetate 1H-NMR(DMSO-d6) δ: 1.28–1.49(12H, m), 2.84(3H, d, J=4.8 Hz), 4.58(2H, q, J=6.8 Hz), 4.86(2H, s), 4.89(2H, s), 5.45(2H, s), 7.08(1H, d, J=8.0 Hz), 7.86(1H, s), 7.90(1H, d, J=8.0 Hz), 8.25–8.39(1H, m), 8.93(1H, s), 9.34–9.45(1H, m), 9.95–10.05(1H, m).
MS: m/e (ESI) 483.1 (MH+)

Example 492

Methyl {2-tert-butyl-4-[2-(5-ethoxy-1-imino-6-methylcarbamoyl-1,3-dihydro-isoindol-2-yl)-acetyl]-6-methoxy-phenoxy}-acetate hydrobromide 1H-NMR(DMSO-d6) δ: 1.37(9H, s), 1.41(3H, t, J=6.8 Hz), 2.48(3H, s), 2.82(3H, d, J=4.8 Hz), 3.73(3H, s), 3.84 (3H, s), 4.28(2H, q, J=6.8 Hz), 4.74(2H, s), 4.85(2H, s), 5.52(2H, s), 7.53–7.55(3H, m), 8.20(1H, d, J=4.8 Hz), 8.55(1H, s), 9.20(1H, brs), 9.85(1H, brs).
MS: m/e (ESI) 526.2 (MH+) 6

Example 493

2-{2-[3-tert-Butyl-4-(2-carbamoyl-ethoxy)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.31(9H, s), 1.38–1.45(3H, m), 2.58–2.65(2H, m), 2.82(3H, d, J=4.8 Hz), 4.23–4.35(4H, m), 4.85(2H, s), 5.47(2H, s), 6.94–7.02(1H, m), 7.18(1H, d, J=8.4 Hz), 7.45–7.56(2H, m), 7.83(1H, s), 7.91(1H, d, J=8.4 Hz), 8.15–8.25(1H, m), 8.55(1H, s), 9.21(1H, brs), 9.82(1H, brs).
MS: m/e (ESI) 495.2 (MH+)

Example 494

3-{2-tert-Butyl-4-[2-(5-ethoxy-1-imino-6-methylcarbamoyl-1,3-dihydro-isoindol-2-yl)-acetyl]-phenoxy}-propanoic acid hydrobromide 1H-NMR(DMSO-d6) δ: 1.34(9H, s), 1.41(3H, t, J=7.2 Hz), 2.77(2H, t, J=6.0 Hz), 2.82(3H, d, J=4.8 Hz), 4.28(2H, q, J=7.2 Hz), 4.32(2H, t, J=6.0 Hz), 4.85(2H, s), 5.48(2H, s), 7.19(1H, d, J=8.8 Hz), 7.53(1H, s), 7.84(1H, s), 7.91(1H, d, J=8.8 Hz), 8.20(1H, q, J=4.8 Hz), 8.56(1H, s), 9.26(1H, brs, ), 9.85(1H, brs).
MS: m/e (ESI) 496.3 (MH+)

Example 495

{2-tert-Butyl-4-[2-(5-ethoxy-1-imino-6-methylcarbamoyl-1,3-dihydro-isoindol-2-yl)-acetyl]-6-methoxy-phenoxy}-acetic acid trifluoroacetate 1H-NMR(DMSO-d6) δ: 1.38(9H, s), 1.42(3H, t, J=6.8 Hz), 2.83(3H, d, J=4.4 Hz), 4.66(2H, s), 4.85(2H, s), 5.50 (2H, s), 7.52(1H, s), 7.54(1H, s), 7.56(1H, s), 8.20(1H, q, J=5.2 Hz), 8.56(1H, s), 9.18(1H, brs), 9.84(1H, brs).
MS: m/e (ESI) 512.2 (MH+)

Example 496

2-{2-tert-Butyl-4-[2-(5-ethoxy-1-imino-6-methylcarbamoyl-1,3-dihydro-isoindol-2-yl)-acetyl]-phenoxy}-propanoic acid trifluoroacetate 1H-NMR(DMSO-d6) δ: 1.36–1.48(12H, m), 1.59(3H, d, J=6.8 Hz), 2.82(3H, d, J=4.4 Hz), 4.28(2H, q, J=6.8 Hz), 4.84(2H, s), 5.08–5.18(1H, m), 5.44(2H, s), 6.95–7.00(1H, m), 7.53(1H, s), 7.80–7.94(2H, m), 8.14–8.26(1H, m), 8.55 (1H, s), 9.19(1H, brs), 9.83(1H, brs).
MS: m/e (ESI) 496.2 (MH+)

Example 497

2-{2-tert-Butyl-4-[2-(5-ethoxy-1-imino-6-methylcarbamoyl-1,3-dihydro-isoindol-2-yl)-acetyl]-phenoxy}-butyric acid trifluoroacetate 1H-NMR(DMSO-d6) δ: 1.06(3H, t, J=7.2 Hz), 1.33–1.57 (12H, m), 1.94–2.11(2H, m), 2.82(3H, d, J=4.8 Hz), 4.27 (2H, q, J=6.8 Hz), 4.84(2H, s), 5.05(1H, t, J=5.6 Hz), 5.44(2H, s), 6.97(1H, d, J=8.4 Hz), 7.53(1H, s), 7.78–7.97 (2H, m), 8.11–8.26(1H, m), 8.55(1H, s), 9.11–9.24(1H, m), 9.76–9.85(1H, m).

Example 498

1-(3,5-Di-tert-butyl-4-hydroxy-phenyl)-2-(7-fluoro-1-imino-5,6-dimethoxy-1,3-dihydro-isoindol-2-yl)-ethanone hydrobromide 1H-NMR(DMSO-d6) δ: 1.41(18H, s), 3.86(3H, s), 3.95 (3H, s), 4.79(2H, s), 5.47(2H, s), 7.36(1H, s), 7.75(2H, s).

Example 499

1-(8-tert-Butyl-4-methyl-3,4-dihydro-2H-benzo[1,4] oxazin-6-yl)-2-(5,6-diethoxy-7-fluoro-1-imino-1,3-dihydro-isoindol-2-yl)-ethanone hydrobromide 1H-NMR(DMSO-d6) δ: 1.28(3H, t, J=7.1 Hz), 1.34(9H, s), 1.48(3H, t, J=7.1 Hz), 3.23–3.37(2H, m), 2.90(3H, s), 4.12(2H, q, J=7.1 Hz), 4.22(2H, q, J=7.1 Hz), 4.33(2H, brs), 4.79(2H, s), 5.46(2H, s), 7.16(1H, s), 7.27(1H, s), 7.33(1H, s), 9.04(1H, brs), 9.32(1H, brs).

MS: m/e (ESI) 484.3 (MH+)

Example 500 tert-Butyl {2-tert-butyl-4-[2-(2-ethyl-7-imino-5,7-dihydro-pyrrolo[3,4-b]pyridin-6-yl)-acetyl]-phenoxy}-acetate hydrobromide 1H-NMR(DMSO-d6) δ: 1.31(3H, t, J=7.4 Hz), 1.40(9H, s), 1.43(9H, s), 2.94(2H, q, J=7.4 Hz), 4.85(4H, s), 5.54(2H, s), 7.05(1H, d, J=8.4 Hz), 7.73(1H, d, J=8.0 Hz), 7.86(1H, d, J=1.8 Hz), 7.90(1H, dd, J=8.4 Hz, J=1.8 Hz), 8.18(1H, d, J=8.0 Hz).

MS: m/e (ESI) 466.2 (MH+)

Example 501

{2-tert-Butyl-4-[2-(2-ethyl-7-imino-5,7-dihydro-pyrrolo[3,4-b]pyridin-6-yl)-acetyl]-phenoxy}-acetic acid trifluoroacetate 1H-NMR(DMSO-d6) δ: 1.31(3H, t, J=7.4 Hz), 1.40(9H, s), 2.94(2H, q, J=7.4 Hz), 4.86(2H, s), 4.88(2H, s), 5.54(2H, s), 7.08(1H, d, J=8.6 Hz), 7.73(1H, d, J=8.0 Hz), 7.86(1H, d, J=1.6 Hz), 7.90(1H, dd, J=8.6 Hz, J=1.6 Hz), 8.18(1H, d, J=8.0 Hz), 9.54(1H, s), 9.86(1H, s).

MS: m/e (ESI) 410.1 (MH+)

Example 502

1-(3,5-Di-tert-butyl-4-hydroxy-phenyl)-2-(7-imino-2-isopropyl-5,7-dihydro-pyrrolo[3,4-b]pyridin-6-yl)-ethanone hydrobromide 1H-NMR(DMSO-d6) δ: 1.32(6H, d, J=6.8 HZ), 1.42(18H, s), 3.18–3.28(1H, m), 4.84(2H, s), 5.55(2H, s), 7.75(1H, d, J=8.4 Hz), 7.77(2H, s), 8.18(1H, d, J=8.4 Hz), 9.72(1H, br).

MS: m/e (ESI) 422.2 (MH+)

Example 503

2-[2-(8-tert-Butyl-2,3-dihydro-benzo[1,4]dioxin-6-yl)-2-oxo-ethyl]-6-ethoxy-3-imino-2,3-dihydro-1H-isoindole-5-carboxylic acid methylamide hydrobromide 1H-NMR(DMSO-d6) δ: 1.38(9H, s), 1.43(3H, t, J=7 Hz), 2.85(3H, d, J=5 Hz), 4.31(2H, q, J=7 Hz), 4.32–4.43(4H, m), 4.86(2H, s), 5.46(2H, s, ), 7.44(1H, s), 7.47(1H, s), 7.54(1H, s), 8.22(1H, q, J=5 Hz), 8.58(1H, s).

Example 504

2-[2-(3-tert-Butyl-4,5-dimethoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.38(9H, s), 1.43(3H, t, J=7 Hz), 2.85(3H, d, J=5 Hz), 3.89(3H, s), 3.91(3H, s), 4.30(2H, q, J=7 Hz), 4.87(2H, s), 5.54(2H, s), 7.55(2H, s), 7.56(1H, s), 8.22(1H, q, J=8 Hz), 8.58(1H, s).

Example 505

1-(8-tert-Butyl-4-methyl-3,4-dihydro-2H-benzo[1,4]oxazin-6-yl)-2-(3-ethoxy-7-imino-2,4-dimethyl-5,7-dihydro-pyrrolo[3,4-b]pyridin-6-yl)-ethanone hydrobromide 1H-NMR(DMSO-d6) δ: 1.36(9H, s), 1.41(3H, t, J=7.2 Hz), 2.33(3H, s), 2.60(3H, s), 2.93(3H, s), 4.01(2H, q, J=7.2 Hz), 4.36(2H, t, J=4.4 Hz), 4.83(2H, s), 5.51(2H, s), 7.19(1H, d, J=1.6 Hz), 7.29(1H, d, J=1.6 Hz), 9.20–10.00(2H, brs).

Example 506

3-{2-tert-Butyl-4-[2-5-ethoxy-1-imino-6-methylcarbamoyl-1,3-dihydro-isoindol-2-yl)-acetyl]-phenyl}-acrylic acid hydrobromide 1H-NMR(DMSO-d6) δ: 1.39–1.46(12H, m), 2.82(3H, d, J=4.8 Hz), 4.28(2H, q, J=7.2 Hz), 4.87(2H, s), 5.53(2H, s), 6.35(1H, d, J=16 Hz), 7.54(1H, s), 7.79(1H, d, J=8.0 Hz), 7.90(1H, d, J=8.0 Hz), 7.99(1H, s), 8.17–8.23(1H, m), 8.27(1H, d, J=16 Hz), 8.57(1H, s), 9.26(1H, brs), 9.87(1H, brs).

MS: m/e (ESI) 478.2 (MH+)

Example 507

7-tert-Butyl-5-[2-(5-ethoxy-1-imino-6-methylcarbamoyl-1,3-dihydro-isoindol-2-yl)-acetyl]-2-methyl-benzofuran-3-carboxylic acid trifluoroacetate 1H-NMR(DMSO-d6) δ: 1.42(3H, t, J=6.8 Hz), 1.49(9H, s), 2.81(3H, s), 2.83(3H, d, J=4.4 Hz), 4.29(2H, q, J=6.8 Hz), 4.88(2H, s), 5.62(2H, s), 7.55(1H, s), 7.81(1H, s), 8.18–8.24(1H, m), 8.47(1H, s), 8.57(1H, s).

MS: m/e (ESI) 566.2 (MH+)

Example 508

3-tert-Butyl-5-[2-(5-ethoxy-1-imino-6-methylcarbamoyl-1,3-dihydro-isoindol-2-yl)-acetyl]-2-hydroxy-benzoic acid trifluoroacetate 1H-NMR(DMSO-d6) δ: 1.40(9H, s), 1.41(3H, t, J=6.8 Hz), 2.83(3H, d, J=4.8 Hz), 4.28(2H, q, J=6.8 Hz), 4.85(2H, s), 5.49(2H, s), 7.54(1H, s), 7.98(1H, d, J=2.0 Hz), 8.12–8.22(1H, m), 8.38(1H, d, J=2.4 Hz), 8.56(1H, s).

MS: m/e (ESI) 468.2 (MH+)

Example 509

3-{2-tert-Butyl-4-[2-(5-ethoxy-1-imino-6-methylcarbamoyl-1,3-dihydro-isoindol-2-yl)-acetyl]-phenyl}-propanoic acid trifluoroacetate 1H-NMR(DMSO-d6) δ: 1.41(9H, s), 2.55(2H, t, J=8.0 Hz), 2.82(3H, d, J=4.8 Hz), 3.17(2H, t, J=8.0 Hz), 4.28(2H, q, J=7.2 Hz), 4.85(2H, s), 5.49(2H, s), 7.48(1H, d, J=8.0 Hz), 7.53(1H, s), 7.81(1H, d, J=8.0 Hz), 7.93(1H, s), 8.16–8.24(1H, m), 8.56(1H, s), 9.23(1H, brs), 9.85(1H, brs).

MS: m/e (ESI) 480.2 (MH+)

Example 510

2-{2-tert-Butyl-4-[2-(3-ethoxy-7-imino-2,4-dimethyl-5,7-dihydro-pyrrolo[3,4-b]pyridin-6-yl)-acetyl]-phenoxy}-propanoic acid trifluoroacetate 1H-NMR(DMSO-d6) δ: 1.34–1.47(12H, m), 1.59(3H, d, J=6.4 Hz), 2.31(3H, s), 2.58(3H, s), 3.99(2H, q, J=6.8 Hz), 4.83(2H, s), 5.13(1H, q, J=6.4 Hz), 5.49(2H, s), 6.97(1H, d, J=8.4 Hz), 7.86(1H, s), 7.88(1H, d, J=8.4 Hz), 9.36–9.45 (1H, m), 9.81–9.90(1H, m).
MS: m/e (ESI) 468.2 (MH+)

Example 511

2-(2-Cyclopropyl-7-imino-5,7-dihydro-pyrrolo[3,4-b]pyridin-6-yl)-ethanone)-1-(3,5-di-tert-butyl-4-hydroxy-phenyl)-ethanone hydrobromide 1H-NMR(DMSO-d6) δ: 1.03–1.12(4H, m), 1.41(18H, s), 2.26–2.36(1H, m), 4.81(2H, s), 5.53(2H, s), 7.71(1H, d, J=8.0 Hz), 7.76(2H, s), 8.09(1H, d, J=8.0 Hz), 9.63(1H, brs).
MS: m/e (ESI) 420.2 (MH+)

Example 512

{2-tert-Butyl-4-[2-(7-fluoro-1-imino-5,6-dimethoxy-1,3-dihydro-isoindol-2-yl)-acetyl]-phenoxy}-acetic acid hydrochloride 1H-NMR(DMSO-d6) δ: 1.39(9H, s), 3.85(3H, s), 3.95 (3H, s), 4.81(2H, s), 4.88(2H, s), 5.47(2H, s), 7.07(1H, d, J=8.8 Hz), 7.35(1H, s), 7.82–7.90(2H, m).

Example 513

1-(8-tert-Butyl-4-methyl-3,4-dihydro-2H-benzo[1,4]oxazin-6-yl)-2-(7-fluoro-1-imino-5,6-dimethoxy-1,3-dihydro-isoindol-2-yl)-ethanone hydrochloride 1H-NMR(DMSO-d6) δ: 1.34(9H, s), 2.90(3H, s), 3.25–3.36(3H, m), 3.86(3H, s), 3.95(3H, s), 4.33(2H, dd, J=5.5, 4.1 Hz), 4.79(2H, s), 5.44(2H, s), 7.15(1H, s), 7.26 (1H, s), 7.35(1H, s).

Example 514

1-(3,5-Di-tert-butyl-4-hydroxy-phenyl)-2-(7-imino-2-(pyrrolidin-1-yl)-5,7-dihydro-pyrrolo[3,4-b]pyridin-6-yl)-ethanone hydrobromide 1H-NMR(DMSO-d6) δ: 1.41(18H, s), 1.94–2.00(4H, br), 3.45–3.52(4H, br), 4.67(2H, s), 5.50(2H, s), 6.87(1H, d, J=8.8 Hz), 7.76(2H, s), 7.86(1H, d, J=8.8 Hz), 9.25(2H, s).
MS: m/e (ESI) 449.2 (MH+)

Example 515

1-(3,5-Di-tert-butyl-4-hydroxy-phenyl)-2-[2-(ethyl-methyl-amino)-7-imino-5,7-dihydro-pyrrolo[3,4-b]pyridin-6-yl]-ethanone hydrobromide 1H-NMR(DMSO-d6) δ: 1.10(3H, t, J=7.0 Hz), 1.41(18H, s), 3.09(3H, s), 3.67(2H, q, J=7.0 Hz), 4.66(2H, s), 5.50(2H, s), 7.04(1H, d, J=8.8 Hz), 7.77(2H, s), 8.86(1H, d, J=8.8 Hz), 9.32(2H, s).
MS: m/e (ESI) 437.2 (MH+)

Example 516

2-tert-Butyl-4-[2-(5-ethoxy-1-imino-6-methylcarbamoyl-1,3-dihydro-isoindol-2-yl)-acetyl]-benzoic acid hydrochloride 1H-NMR(DMSO-d6) δ: 1.42(9H, s), 2.82(3H, d, J=4.8 Hz), 4.28(2H, q, J=7.2 Hz), 4.87(2H, s), 5.53(2H, s), 7.48–7.56(2H, m), 7.89(1H, d, J=8.0 Hz), 8.03(1H, s), 8.15–8.23(1H, m), 8.56(1H, s), 9.30(1H, brs), 9.88(1H, brs).
MS: m/e (ESI) 452.1 (MH+)

Example 517

2-[2-(4-tert-Butyl-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.32(9H, s), 1.42(3H, t, J=7.2 Hz), 2.82(3H, d, J=4.8 Hz), 4.28(2H, q, J=7.2 Hz), 4.87(2H, s), 5.48(2H, s), 7.54(1H, s), 7.63(2H, d, J=7.2 Hz), 7.95(2H, d, J=7.2 Hz), 8.18–8.24(1H, m), 8.56(1H, s).
MS: m/e (ESI) 408.1 (MH+)

Example 518

1-(8-tert-Butyl-4-methyl-3,4-dihydro-2H-benzo[1,4]oxazin-6-yl)-2-(2-cyclopropyl-7-imino-5,7-dihydro-pyrrolo[3,4-b]pyridin-6-yl)-ethanone hydrobromide 1H-NMR(DMSO-d6) δ: 1.03–1.16(4H, m), 1.35(9H, s), 2.26–2.37(1H, m), 2.91(3H, s), 4.34(2H, brs), 4.82(2H, s), 5.52(2H, brs), 7.17(1H, s), 7.28(1H, s), 7.72(1H, d, J=8.0 Hz), 8.09(1H, d, J=8.0 Hz), 9.42–9.53(1H, m), 9.60–9.71 (1H, m).
MS: m/e (ESI) 419.1 (MH+)

Example 519

2-[2-(3,3-Dimethyl-2,3-dihydro-benzofuran-5-yl)-2-oxo-ethyl]-6-ethoxy-3-imino-2,3-dihydro-1H-isoindole-5-carboxylic acid methylamide hydrobromide 1H-NMR(DMSO-d6) δ: 1.34(6H, s), 1.41(3H, t, J=7.2 Hz), 2.82(3H, d, J=4.4 Hz), 4.28(2H, q, J=7.2 Hz), 4.37(2H, s), 4.85(2H, s), 5.43(2H, s), 6.98(1H, d, J=8.0 Hz), 7.53(1H, s), 7.87(1H, d, J=8.0 Hz), 7.89(1H, s), 8.14–8.25(1H, m), 8.56(1H, s).
MS: m/e (ESI) 422.1 (MH+)

Example 520

2-(5,6-Diethoxy-7-fluoro-1-imino-1,3-dihydro-isoindol-2-yl)-1-(3,3-dimethyl-2,3-dihydro-benzofuran-5-yl)-ethanone hydrobromide 1H-NMR(DMSO-d6) δ: 1.29(3H, t, J=6.8 Hz), 1.34(9H, s), 1.40(3H, t, J=6.8 Hz), 4.11(2H, q, J=6.8 Hz), 4.21(2H, q, J=6.8 Hz), 4.37(2H, s), 4.79(2H, s), 5.41(2H, s), 6.97(1H, d, J=8.4 Hz), 7.33(1H, s), 7.85(1H, d, J=8.4 Hz), 7.88(1H, s).
MS: m/e (ESI) 427.1 (MH+)

Example 521

2-(3-Chloro-2-diethylamino-7-imino-5,7-dihydro-pyrrolo[3,4-b]pyridin-6-yl)-1-(3,5-di-tert-butyl-4-hydroxy-phenyl)-ethanone hydrobromide 1H-NMR(DMSO-d6) δ: 1.15(6H, t, J=7.2 Hz), 1.42(18H, s), 3.51(4H, q, J=7.2 Hz), 4.73(2H, s), 5.54(2H, s), 7.77(2H, s), 8.20(1H, s), 9.51(1H, s).
MS: m/e (ESI) 485.2 (MH+)

Example 522

{8-tert-Butyl-6-[2-(2-ethyl-7-imino-5,7-dihydro-pyrrolo[3,4-b]pyridin-6-yl)-acetyl]-2,3-dihydro-benzo[1,4]oxazin-4-yl}-acetic acid hydrobromide 1H-NMR(DMSO-d6) δ: 1.30(3H, t, J=7.6 Hz), 1.35(9H, s), 2.93(2H, q, J=7.6 Hz), 3.47(2H, br), 4.01(2H, s), 4.27(2H, br), 4.81(2H, s), 5.50(2H, s), 7.06(1H, s), 7.23(1H, s), 7.70(1H, d, J=8.0 Hz), 8.15(1H, d, J=8.0 Hz).
MS: m/e (ESI) 451.1 (MH+)

Example 523

7-Cyano-2-[2-(3,5-di-tert-butyl-4-hydroxy-phenyl)-2-oxo-ethyl]-3-imino-2,3-dihydro-1H-isoindole-5-carboxylic acid methylamide hydrobromide 1H-NMR(DMSO-d6) δ: 1.44(18H, s), 2.86(3H, d, J=4.4 Hz), 5.17(2H, s), 5.54(2H, s), 7.76(2H, s), 8.69(1H, d, J=1.2 Hz), 8.88(1H, m), 9.05(1H, d, J=1.2 Hz).

Example 524

1-(3,5-Di-tert-butyl-4-hydroxy-phenyl)-2-(5-ethoxy-7-fluoro-1-imino-6-methoxy-1,3-dihydro-isoindol-2-yl)-ethanone hydrobromide 1H-NMR(DMSO-d6) δ: 1.34–146(21H, m), 3.87(3H, s), 4.22(2H, q, J=7.0 Hz), 4.77(2H, s), 5.47(2H, s), 7.34(1H, s), 7.75(2H, s), 9.03(1H, brs).

Example 525

{2-tert-Butyl-4-[2-(5-ethoxy-7-fluoro-1-imino-6-methoxy-1,3-dihydro-isoindol-2-yl)-acetyl]-phenoxy}-acetic acid hydrochloride 1H-NMR(DMSO-d6) δ: 1.30–1.48(12H, m), 3.86(3H, s), 4.22(2H, q, J=7.0 Hz), 4.79(2H, s), 4.88(2H, s), 5.49(2H, s), 7.07(1H, d, J=8.7 Hz), 7.33(1H, s), 7.82–7.90(2H, m), 9.08(1H, brd), 9.45(brs).
MS: m/e (ESI) 473.1 (MH+)

Example 526

Methyl 2-{3-[2-(5-ethoxy-1-imino-6-methylcarbamoyl-1,3-dihydro-isoindol-2-yl)-acetyl]-phenyl}-2-methyl-propanoate hydrobromide 1H-NMR(DMSO-d6) δ: 1.388(3H, t, J=6.8 Hz), 1.529(6H, s), 2.810(3H, d, J=4.8 Hz), 3.570(3H, s), 4.257(2H, q, J=6.8 Hz), 4.852(2H, s), 5.475(2H, s), 7.487(1H, s), 7.54–7.68(2H, m), 7.857(1H, s), 7.91(1H, d, J=8.0 Hz), 8.239(1H, q, J=4.8 Hz), 8.498(1H, s).

Example 527

{2-tert-Butyl-6-[2-(5-ethoxy-1-imino-6-methylcarbamoyl-1,3-dihydro-isoindol-2-yl)-acetyl]-phenoxy}-acetic acid hydrochloride 1H-NMR(DMSO-d6) δ: 1.34(9H, s), 1.40(2H, t, J=7.1 Hz), 2.82(3H, d, J=4.7 Hz), 4.27(2H, q, J=7.1 Hz), 4.37(2H, s), 4.86(2H, s), 5.42(2H, s), 7.27(1H, t, J=8.0 Hz), 7.53(1H, s), 7.64(1H, d, J=8.0 Hz), 7.79(1H, d, J=8.0 Hz), 8.20(1H, brq, J=4.7 Hz), 8.57(1H, s), 9.40(1H, brd), 9.94(1H, brd).
MS: m/e (ESI) 482.2 (MH+)

Example 528

{2-tert-Butyl-6-[2-(5,6-diethoxy-7-fluoro-1-imino-1,3-dihydro-isoindol-2-yl)-acetyl]-phenoxy}-acetic acid hydrochloride 1H-NMR(DMSO-d6) δ: 1.28(3H, t, J=6.9 Hz), 1.32–1.46(12H, m), 4.11(2H, q, J=6.9 Hz), 4.22(2H, q, J=6.7 Hz), 4.38(2H, s), 4.82(2H, s), 5.43(2H, s), 7.27(1H, t, J=5.2 Hz), 7.32(1H, s), 7.63(1H, d, J=5.2 Hz), 7.80(1H, d, J=5.2 Hz), 9.11(1H, brs), 9.45(1H, brs).
MS: m/e (ESI) 487.2 (MH+)

Example 529

3-tert-Butyl-5-[2-(5-ethoxy-1-imino-6-methylcarbamoyl-1,3-dihydro-isoindol-2-yl)-acetyl]-2-methoxy-benzoic acid trifluoroacetate 1H-NMR(DMSO-d6) δ: 1.38(9H, s), 1.42(3H, t, J=7.2 Hz), 2.83(3H, d, J=4.8 Hz), 3.88(3H, s), 4.28(2H, q, J=7.2 Hz), 4.85(2H, s), 5.51(2H, s), 7.54(1H, s), 7.98(1H, d, J=2.0 Hz), 8.15(1H, d, J=2.4 Hz), 8.16–8.22(1H, m), 8.56(1H, s), 9.19(1H, brs), 9.87(1H, brs).
MS: m/e (ESI) 482.3 (MH+)

Example 530

Methyl 3-tert-butyl-2-carboxymethoxy-5-[2-(5-ethoxy-1-imino-6-methylcarbamoyl-1,3-dihydro-isoindol-2-yl)-acetyl]-benzoate trifluoroacetate 1H-NMR(DMSO-d6) δ: 1.39(3H, t, J=7.2 Hz), 1.41(9H, s), 2.82(3H, d, J=4.4 Hz), 3.88(3H, s), 4.28(2H, q, J=7.2 Hz), 4.55(2H, s), 4.85(2H, s), 5.53(2H, s), 7.54(1H, s), 8.04(1H, d, J=2.4 Hz), 8.16(1H, d, J=3.0 Hz), 8.18–8.23(1H, m), 8.55(1H, s), 9.26(1H, brs), 9.89(1H, brs).
MS: m/e (ESI) 540.3 (MH+)

Example 531

{3-tert-Butyl-5-[2-(5-ethoxy-1-imino-6-methylcarbamoyl-1,3-dihydro-isoindol-2-yl)-acetyl]-2-methoxy-benzoylamino}-acetic acid trifluoroacetate 1H-NMR(DMSO-d6) δ: 1.39(9H, s), 1.41(3H, t, J=7.2 Hz), 2.82(3H, d, J=4.8 Hz), 3.88(3H, s), 3.96(2H, d, J=5.6 Hz), 4.28(2H, q, J=7.2 Hz), 4.85(2H, brs), 5.50(2H, brs), 7.54(1H, s), 7.93(1H, s), 8.18–8.22(1H, m), 8.56(1H, s), 8.81(1H, t, J=5.6 Hz), 9.23(1H, s), 9.86(1H, s).
MS: m/e (ESI) 539.3 (MH+)

Example 532

({3-tert-Butyl-5-[2-(5-ethoxy-1-imino-6-methylcarbamoyl-1,3-dihydro-isoindol-2-yl)-acetyl]-2-methoxy-benzoyl}-methyl-amino)-acetic acid trifluoroacetate 1H-NMR(DMSO-d6) δ: 1.36,1.38(9H, each, s), 1.41(3H, t, J=7.2 Hz), 2.82(3H, d, J=4.8 Hz), 2.92,3.08(3H, each, s), 3.78,3.88(3H, each, s), 3.82,3.92(2H, each, s), 4.28(2H, q, J=7.2 Hz), 4.85(2H, brs), 5.51(2H, brs), 7.54(1H, brs), 7.74(1H, brs), 7.91(1H, brs), 8.55(1H, brs), 8.18–8.22(1H, m), 9.24(1H, brs), 9.88(1H, brs).

MS: m/e (ESI) 553.4 (MH+)

Example 533

5-{2-tert-Butyl-4-[2-(5-ethoxy-1-imino-6-methylcarbamoyl-1,3-dihydro-isoindol-2-yl)-acetyl]-phenoxy}-pentanoic acid hydrobromide 1H-NMR(DMSO-d6) δ: 1.37(9H, s), 1.41(3H, t, J=7.2 Hz), 1.67–1.88(4H, m), 2.31(2H, t, J=7.2 Hz), 2.82(3H, d, J=4.8 Hz), 4.13(2H, t, J=7.2 Hz), 4.27(2H, q, J=7.2 Hz), 4.85(2H, s), 5.46(2H, s), 7.17(1H, d, J=8.0 Hz), 7.53(1H, s), 7.84(1H, s), 7.90(1H, d, J=8.0 Hz), 8.20(1H, q, J=4.8 Hz), 8.56(1H, s), 9.24(1H, brs), 9.84(1H, brs), 12.05(1H, brs).

MS: m/e (ESI) 524.2 (MH+)

Example 534

1-(3,5-Di-tert-butyl-4-hydroxy-phenyl)-2-(5-ethoxy-7-fluoro-1-imino-1,3-dihydro-isoindol-2-yl)-ethanone hydrobromide 1H-NMR(DMSO-d6) δ: 1.20(21H, m), 4.18(2H, q, J=7.2 Hz), 4.78(2H, s), 5.36(2H, s), 7.12(1H, d, J=12.0 Hz), 7.18(1H, s), 7.64(2H, s).

MS: m/e (ESI) 441.2 (MH+)

Example 535

{2-tert-Butyl-4-[2-(5-ethoxy-1-imino-6-methylcarbamoyl-1,3-dihydro-isoindol-2-yl)-acetyl]-6-(pyrrolidin-1-yl)-phenoxy}-acetic acid trifluoroacetate 1H-NMR(DMSO-d6) δ: 1.38(9H, s), 1.41(3H, t, J=6.8 Hz), 1.82–1.93(4H, m), 2.83(3H, d, J=4.8 Hz), 3.04–3.18 (4H, m), 4.28(2H, q, J=6.8 Hz), 4.40(2H, s), 4.84(2H, s), 5.49(2H, s), 7.41(1H, s), 7.48(1H, s), 7.54(1H, s), 8.13–8.25 (1H, m), 8.56(1H, s), 9.15(1H, brs), 9.83(1H, brs).

MS: m/e (ESI) 551.4 (MH+)

Example 536

{2-tert-Butyl-4-[2-(5,6-diethoxy-7-fluoro-1-imino-1,3-dihydro-isoindol-2-yl)-acetyl]-6-(pyrrolidin-1-yl)-phenoxy}-acetic acid trifluoroacetate 1H-NMR(DMSO-d6) δ: 1.29(3H, t, J=6.8 Hz), 1.34–1.43 (12H, m), 1.83–1.92(4H, m), 3.07–3.16(4H, m), 4.11(2H, q, J=6.8 Hz), 4.21(2H, q, J=6.8 Hz), 4.78(2H, s), 5.47(2H, s), 7.33(1H, s), 7.39(1H, s), 7.46(1H, s).

MS: m/e (ESI) 556.2 (MH+)

Example 537

{2-tert-Butyl-4-[2-(2-cyclopropyl-7-imino-5,7-dihydro-pyrrolo[3,4-b]pyridin-6-yl)-acetyl]-6-(pyrrolidin-1-yl)-phenoxy}-acetic acid trifluoroacetate 1H-NMR(DMSO-d6) δ: 1.04–1.14(4H, m), 1.38(9H, s), 1.82–1.94(4H, m), 2.27–2.36(1H, m), 3.03–3.18(4H, m), 4.40(2H, s), 4.82(2H, s), 5.55(2H, s), 7.41(1H, s), 7.48(1H, s), 7.72(1H, d, J=8.0 Hz), 8.08(1H, d, J=8.0 Hz).

MS: m/e (ESI) 491.3 (MH+)

Example 538

{4-tert-Butyl-2-[2-(5-ethoxy-1-imino-6-methylcarbamoyl-1,3-dihydro-isoindol-2-yl)-acetyl]-phenoxy}-acetic acid hydrochloride 1H-NMR(DMSO-d6) δ: 1.25(9H, s), 1.41(3H, t, J=6.7 Hz), 2.82(3H, brs), 4.27(2H, q, J=6.7 Hz), 4.86(2H, s), 4.91(2H, s), 5.37(2H, s), 7.14(1H, d, J=9.0 Hz), 7.50(1H, s), 7.69(1H, brd, J=9.0 Hz), 7.83(1H, s), 8.20(1H, brq, J=4.0 Hz), 9.32(1H, brs), 9.87(1H, brs).

MS: m/e (ESI) 482.2 (MH+)

Example 539

{4-tert-Butyl-2-[2-(5,6-diethoxy-7-fluoro-1-imino-1,3-dihydro-isoindol-2-yl)-acetyl]-phenoxy}-acetic acid hydrochloride 1H-NMR(DMSO-d6) δ: 1.24–1.32(12H, m), 1.39(3H, t, J=6.7 Hz), 4.12(2H, q, J=6.7 Hz), 4.22(2H, q, J=6.7 Hz), 4.82(2H, s), 4.89(2H, s), 5.37(2H, s), 7.14(1H, d, J=8.3 Hz), 7.31(1H, s), 7.69(1H, dd, J=8.3,2.8 Hz), 7.83(1H, d, J=2.8 Hz), 9.02(1H, brs).

MS: m/e (ESI) 487.1 (MH+)

Example 540

1-(3,5-Di-tert-butyl-4-hydroxy-phenyl)-2-[2-ethyl-7-imino-3-(tetrahydropyran-2-yloxymethyl)-5,7-dihydro-pyrrolo[3,4-b]pyridin-6-yl]-ethanone hydrobromide 1H-NMR(DMSO-d6) δ: 1.30(3H, t, J=7.3 Hz), 1.30–1.80 (6H, m), 1.42(18H, s), 2.93(2H, q, J=7.3 Hz), 3.47–3.55(1H, m), 3.75–3.82(1H, m), 4.69(1H, d, J=13.6 Hz), 4.78–4.81 (1H, m), 4.86(2H, s), 4.90(1H, d, J=13.6 Hz), 5.55(2H, s), 7.77(2H, s), 8.21(1H, s), 9.75–9.82(1H, m).

Example 541

1-(3,5-Di-tert-butyl-4-hydroxy-phenyl)-2-(2-ethyl-3-hydroxymethyl-7-imino-5,7-dihydro-pyrrolo[3,4-b]pyridin-6-yl)-ethanone hydrobromide 1H-NMR(DMSO-d6) δ: 1.04(3H, t, J=6.8 Hz), 1.42(18H, s), 2.87(2H, q, J=6.8 Hz), 4.72(2H, s), 4.86(2H, s), 5.59(2H, s), 7.78(2H, s), 8.07(1H, brs), 8.21(1H, s), 9.53(1H, d, J=8.0 Hz), 9.75(1H, d, J=8.0 Hz).

Example 542

Ethyl 3-{3-tert-butyl-5-[2-(5-ethoxy-1-imino-6-methylcarbamoyl-1,3-dihydro-isoindol-2-yl)-acetyl]-2-methoxy-phenyl}-propanoate hydrobromide 1H-NMR(DMSO-d6) δ: 1.165(3H, t, J=7.2 Hz), 1.371 (9H, s), 1.411(3H, t, J=7.2 Hz), 2.67–2.73(2H, m), 2.822 (3H, d, J=4.8 Hz), 2.96–3.02(2H, m), 3.799(3H, s), 4.058 (2H, q, J=7.2 Hz), 4.278(2H, q, J=7.2 Hz), 4.147(2H, q, J=7.2 Hz), 4.851(2H, s), 5.505(2H, s), 7.542(1H, s), 7.779 (1H, d, J=2.0 Hz), 7.838(1H, d, J=2.0 Hz), 8.206(1H, q, J=4.8 Hz), 8.558(1H, s).

Example 543

3-{3-tert-Butyl-5-[2-(5-ethoxy-1-imino-6-methylcarbamoyl-1,3-dihydro-isoindol-2-yl)-acetyl]-2-methoxy-phenyl}-propanoic acid hydrobromide 1H-NMR(DMSO-d6) δ: 1.371(9H, s), 1.402(3H, t, J=7.2 Hz), 2.630(2H, t, J=7.6 Hz), 2.814(3H, d, J=3.2 Hz), 2.93–2.99(2H, m), 3.802(3H, s), 4.267(2H, q, J=7.2 Hz), 4.838(2H, s), 5.600(2H, s), 7.522(1H, s), 7.785(1H, s), 7.848(1H, s), 8.204(1H, s), 8.215(1H, s), 8.573(1H, s), 10.033(1H, d, J=8.4 Hz), 12.262(1H, s)

Example 544

2-[2-(8-tert-Butyl-4-carbamoylmethyl-3,4-dihydro-2H-benzo[1,4]oxazin-6-yl)-2-oxo-ethyl]-6-ethoxy-3-imino-2,3-dihydro-1H-isoindole-5-carboxylic acid methylamide hydrobromide 1H-NMR(DMSO-d6) δ: 1.38(9H, s), 1.43(3H, t, J=7.2 Hz), 2.84(3H, d, J=4.8 Hz), 3.51(2H, t, J=4.0 Hz), 3.90(2H, s), 4.31(2H, q, J=7.2 Hz), 4.34(2H, t, J=4.0 Hz), 4.84(2H, s), 5.43(2H, s), 7.02(1H, d, J=1.6 Hz), 7.12(1H, s), 7.27(1H, d, J=1.6 Hz), 7.50(1H, s), 7.54(1H, s), 8.22(1H, q, J=4.8 Hz), 8.56(1H, s), 9.22(1H, s), 9.81(1H, s).

Example 545

2-[2-(3-tert-Butyl-5-hydroxy-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.38(9H, s, ), 1.43(3H, t, J=7.0 Hz), 2.85(3H, d, J=5.0 Hz), 3.90(3H, s), 4.29(2H, q, J=7.0 Hz), 4.85(2H, s), 5.48(2H, s), 7.41(1H, d, J=2.0 Hz), 7.45 (1H, d, J=2.0 Hz), 7.55(1H, s), 8.22(1H, q, J=5.0 Hz), 8.58(1H, s), 9.32(1H, brs), 9.91(1H, brs), 10.03(1H, s).

Example 546

{3-tert-Butyl-5-[2-(5-ethoxy-1-imino-6-methylcarbamoyl-1,3-dihydro-isoindol-2-yl)-acetyl]-2-methoxy-phenoxy}-acetic acid trifluoroacetate 1H-NMR(DMSO-d6) δ: 1.39(9H, s), 1.43(3H, t, J=7 Hz), 1.47(9H, s), 2.85(3H, d, J=5 Hz), 3.98(3H, s), 4.30(2H, q, J=7 Hz), 4.82(2H, s), 4.87(2H, s), 5.51(2H, s), 7.44(1H, d, J=2 Hz), 7.56(1H, s), 7.58(1H, d, J=2 Hz), 8.22(1H, q, J=5 Hz), 8.59(1H, s), 9.25(1H, brs), 9.88(1H, brs).

Example 547

2-{2-[3-tert-Butyl-4-(2H-tetrazol-5-ylmethoxy)-phenyl]-2-oxo-ethyl}-6-ethoxy-3-imino-2,3-dihydro-1H-isoindole-5-carboxylic acid methylamide hydrochloride 1H-NMR(DMSO-d6) δ: 1.32(9H, s), 1.42(3H, t, J=7.2 Hz), 2.82(3H, d, J=4.8 Hz), 4.28(2H, q, J=7.2 Hz), 4.85(2H, s), 5.48(2H, s), 5.64(2H, s), 7.00(1H, d, J=8.0 Hz), 7.33–7.45(2H, m), 7.53(1H, s), 7.86(1H, s), 7.94(1H, d, J=8.0 Hz), 8.20(1H, q, J=4.8 Hz), 8.56(1H, s), 9.25(1H, brs), 9.85(1H, brs).

MS: m/e (ESI) 506.2 (MH+)

Example 548

Ethyl {2-tert-butyl-4-[2-(5-ethoxy-1-imino-6-methylcarbamoyl-1,3-dihydro-isoindol-2-yl)-acetyl]-6-(pyrrolidin-1-yl)-phenoxy}-acetate hydrobromide 1H-NMR(DMSO-d6) δ: 1.24(3H, t, J=6.4 Hz), 1.31–1.50 (12H, m), 1.78–1.99(4H, m), 2.82(3H, d, J=4.4 Hz), 3.02–3.17(4H, m), 4.22–4.40(4H, m), 4.49(2H, s), 4.84(2H, s), 5.48(2H, s), 7.42(1H, s), 7.49(1H, s), 7.53(1H, s), 8.13–8.28(1H, m), 8.55(1H, s), 9.14(1H, brs), 9.83(1H, brs).

MS: m/e (ESI) 579.3 (MH+)

Example 549

{Ethyl (2-tert-butyl-4-[2-(5,6-diethoxy-7-fluoro-1-imino-1,3-dihydro-isoindol-2-yl)-acetyl]-6-(pyrrolidin-1-yl)-phenoxy}-acetate hydrobromide 1H-NMR(DMSO-d6) δ: 1.23(3H, t, J=7.2 Hz), 1.29(3H, t, J=7.2 Hz), 1.33–1.48(12H, m), 1.82–1.94(4H, m), 3.04–3.16(4H, m), 4.11(2H, q, J=7.2 Hz), 4.15–4.30(4H, m), 4.49(2H, s), 4.78(2H, s), 5.48(2H, s), 7.33(1H, s), 7.42(1H, s), 7.48(1H, s).

MS: m/e (ESI) 584.3 (MH+)

Example 550

2-[2-(3,5-tert-Butyl-4-hydroxy-phenyl)-2-oxo-ethyl]-7-fluoro-3-imino-2,3-dihydro-1H-isoindole-5-carboxylic acid methylamide hydrobromide 1H-NMR(DMSO-d6) δ: 1.44(18H, s), 2.85(3H, d, J=4.4 Hz), 5.05(2H, s), 5.55(2H, s), 7.79(2H, s), 8.13(1H, dd, J=1.3, 9.5 Hz), 8.69(1H, d, J=1.3 Hz), 8.77(1H, m).

Example 551

{2-tert-Butyl-4-[2-(7-fluoro-1-imino-5,6-dimethoxy-1,3-dihydro-isoindol-2-yl)-acetyl]-6-(pyrrolidin-1-yl)-phenoxy}-acetic acid trifluoroacetate 1H-NMR(DMSO-d6) δ: 1.37(9H, s), 1.70–2.08(4H, m), 2.88–3.21(4H, m), 3.86(3H, s), 3.95(3H, s), 4.39(2H, s), 4.80(2H, s), 5.48(2H, s), 7.36(1H, s), 7.39(1H, s), 7.47(1H, s), 9.07(1H, brs), 9.29(1H, brs).

MS: m/e (ESI) 528.1 (MH+)

Example 552

{8-tert-Butyl-6-[2-(5,6-diethoxy-7-fluoro-1-imino-1,3-dihydro-isoindol-2-yl)-acetyl]-2,3-dihydro-benzo[1,4]oxazin-4-yl}-acetic acid hydrochloride 1H-NMR(DMSO-d6) δ: 1.31(3H, t, J=7.2 Hz), 1.38(9H, s), 1.41(3H, t, J=7.2 Hz), 3.50(2H, t, J=4.4 Hz), 4.13(2H, q, J=7.2 Hz), 4.16(2H, s), 4.22(2H, q, J=7.2 Hz), 4.31(2H, t, J=4.4 Hz), 4.79(2H, s), 5.44(2H, s), 7.06(1H, d, J=2.0 Hz), 7.26(1H, d, J=2.0 Hz), 7.33(1H, s), 9.02(1H, s), 9.35(1H, s), 12.71(1H, s).

Example 553

{8-tert-Butyl-6-[2-(3-ethoxy-7-imino-2,4-dimethyl-5,7-dihydro-pyrrolo[3,4-b]pyridin-6-yl)-acetyl]-2,3-dihydro-benzo[1,4]oxazin-4-yl}-acetic acid hydrochloride 1H-NMR(DMSO-d6) δ: 1.38(9H, s), 1.41(3H, t, J=7.2 Hz), 2.33(3H, s), 2.60(3H, s), 3.50(2H, t, J=4.4 Hz), 4.01(2H, q, J=7.2 Hz), 4.16(2H, s), 4.31(2H, t, J=4.4 Hz), 4.83(2H, s), 5.49(2H, s), 7.07(1H, d, J=1.6 Hz), 7.28(1H, d, J=1.6 Hz), 9.45(1H, s), 9.84(1H, s), 12.71(1H, s).

Example 554

2-[2-(8-tert-Butyl-3,4-dihydro-2H-benzo[1,4]oxazin-6-yl)-2-oxo-ethyl]-6-ethoxy-3-imino-2,3-dihydro-1H-isoindole-5-carboxylic acid methylamide hydrobromide 1H-NMR(DMSO-d6) δ: 1.36(9H, s), 1.43(3H, t, J=7.2 Hz), 2.84(3H, d, J=4.8 Hz), 3.36(2H, t, J=4.4 Hz), 4.23(2H, t, J=4.4 Hz), 4.29(2H, q, J=7.2 Hz), 4.84(2H, s), 5.43(2H, s), 7.14(1H, d, J=2.0 Hz), 7.18(1H, d, J=2.0 Hz), 7.54(1H, s), 8.22(1H, q, J=4.8 Hz), 8.57(1H, s), 9.28(1H, s), 9.88(1H, s).

Example 555

{8-tert-Butyl-6-[2-(7-fluoro-1-imino-5,6-dimethoxy-1,3-dihydro-isoindol-2-yl)-acetyl]-2,3-dihydro-benzo[1,4]oxazin-4-yl}-acetic acid trifluoroacetate 1H-NMR(DMSO-d6) δ: 1.35(9H, s), 3.48(2H, brs), 3.86(2H, s), 3.95(2H, s), 4.12(2H, s), 4.28(2H, brs), 4.78(2H, s), 5.42(2H, s), 7.04(1H, s), 7.24(1H, s), 7.34(1H, s).
MS: m/e (ESI) 500.1 (MH+)

Example 556

1-(3,5-Di-tert-butyl-4-hydroxy-phenyl)-2-(7-fluoro-1-imino-6-methoxy-5-propoxy-1,3-dihydro-isoindol-2-yl)-ethanone hydrochloride 1H-NMR(DMSO-d6) δ: 1.00(3H, t, J=7.1 Hz), 1.41(18H, s), 1.75–1.86(2H, m), 3.87(3H, s), 4.12(2H, t, J=6.4 Hz), 4.78(2H, s), 5.47(2H, s), 7.34(1H, s), 7.75(2H, s).

Example 557

{2-tert-Butyl-4-[2-(7-fluoro-1-imino-6-methoxy-5-propoxy-1,3-dihydro-isoindol-2-yl)-acetyl]-phenoxy}-acetic acid hydrochloride 1H-NMR(DMSO-d6) δ: 0.99(3H, t, J=7.5 Hz), 1.38(9H, s), 1.72–1.86(2H, m), 3.87(3H, s), 4.11(2H, t, J=6.4 Hz), 4.78(2H, s), 4.87(2H, s), 5.47(2H, s), 7.07(1H, d, J=8.1 Hz), 7.34(1H, s), 7.78–7.92(2H, m), 9.06(1H, brs).

Example 558

2-[2-(3,3-Dimethyl-2-oxo-2,3-dihydro-1H-indol-5-yl)-2-oxo-ethyl]-6-ethoxy-3-imino-2,3-dihydro-1H-isoindole-5-carboxylic acid methylamide hydrobromide 1H-NMR(DMSO-d6) δ: 1.30(6H, s), 1.40(3H, t, J=7.2 Hz), 2.82(3H, d, J=4.8 Hz), 4.27(2H, q, J=7.2 Hz), 4.85(2H, s), 5.44(2H, s), 7.03(1H, d, J=8.0 Hz), 7.52(1H, s), 7.90(1H, d, J=8.0 Hz), 7.97(1H, s), 8.16–8.24(1H, m), 8.55(1H, s), 10.90(1H, s).
MS: m/e (ESI) 435.0 (MH+)

Example 559

6-Ethoxy-3-imino-2-[2-oxo-2-(1,3,3-trimethyl-2-oxo-2,3-dihydro-1H-indol-5-yl)-ethyl]-2,3-dihydro-1H-isoindole-5-carboxylic acid methylamide hydrobromide 1H-NMR(DMSO-d6) δ: 1.30–1.43(9H, m), 2.82(3H, d, J=4.8 Hz), 3.19(3H, s), 4.27(2H, q, J=7.2 Hz), 4.85(2H, s), 5.45(2H, s), 7.20–7.24(1H, m), 7.52–7.54(1H, m), 7.98–8.02(2H, m), 8.17–8.21(1H, m), 8.56(1H, s).
MS: m/e (ESI) 449.1 (MH+)

Example 560

{5-[2-(5-Ethoxy-1-imino-6-methylcarbamoyl-1,3-dihydro-isoindol-2-yl)-acetyl]-3,3-dimethyl-2-oxo-2,3-dihydro-indol-1-yl}-acetic acid hydrochloride 1H-NMR(DMSO-d6) δ: 1.34(6H, s), 1.41(3H, t, J=7.2 Hz), 2.82(3H, d, J=4.8 Hz), 4.28(2H, q, J=7.2 Hz), 4.53(2H, s), 4.86(2H, s), 5.46(2H, s), 7.24(1H, d, J=8.0 Hz), 7.58(1H, s), 7.97(1H, d, J=8.0 Hz), 8.03(1H, s), 8.17–8.25(1H, m), 8.56(1H, s), 9.25(1H, brs), 9.85(1H, brs).
MS: m/e (ESI) 493.1 (MH+)

Example 561

2-{3-[2-(5-Ethoxy-1-imino-6-methylcarbamoyl-1,3-dihydro-isoindol-2-yl)-acetyl]-phenyl}-2-methyl-propanoic acid hydrobromide 1H-NMR(DMSO-d6) δ: 1.410(3H, t, J=6.8 Hz), 1.514(9H, s), 2.823(3H, d, J=4.8 Hz), 4.279(2H, q, J=6.8 Hz), 4.869(2H, s), 5.525(2H, s), 7.539(1H, s), 7.582(1H, t, J=7.6 Hz), 7.716(1H, d, J=8.4 Hz), 7.913(1H, d, J=8.4 Hz), 7.924(1H, s), 8.205(1H, q, J=4.8 Hz), 8.563(1H, s).

Example 562

Ethyl 4-{3-[2-(5-ethoxy-1-imino-6-methylcarbamoyl-1,3-dihydro-isoindol-2-yl)-acetyl]-phenyl}-4-methyl-2-pentenoate hydrobromide 1H-NMR(DMSO-d6) δ: 1.182(3H, 7.2 Hz), 1.405(3H, t, J=7.2 Hz), 1.482(6H, s), 2.817(3H, d, J=4.8 Hz), 4.098(2H, q, J=7.2 Hz), 4.274(2H, q, J=7.2 Hz), 4.868(2H, s), 5.529(2H, s), 5.821(1H, d, J=15.6 Hz), 7.026(1H, d, J=15.6 Hz), 7.539(1H, s), 7.592(1H, t, J=7.6 Hz), 7.713(1H, d, J=8.0 Hz), 7.900(1H, s), 7.931(1H, d, J=8.0 Hz), 8.206(1H, q, J=4.8 Hz), 8.55(1H, s).

Example 563

Ethyl 4-{3-[2-(5,6-diethoxy-7-fluoro-1-imino-1,3-dihydro-isoindol-2-yl)-acetyl]-phenyl}-4-methyl-2-pentenoate hydrobromide 1H-NMR(DMSO-d6) δ: 1.184(3H, t, J=7.2 Hz), 1.285 (3H, t, J=6.8 Hz), 1.390(3H, t, J=6.8 Hz), 1.482(6H, s), 4.06–4.14(4H, m), 4.208(2H, q, J=7.2 Hz), 4.817(2H, s), 5.511(2H, s), 5.821(1H, d, J=15.6 Hz), 7.028(1H, d, J=15.6 Hz), 7.335(1H, s), 7.56–7.61(1H, m), 7.705(1H, d, J=8.0 Hz), 7.87–7.91(2H, m).

Example 564

Methyl 2-{3-[2-(5,6-diethoxy-7-fluoro-1-imino-1,3-dihydro-isoindol-2-yl)-acetyl]-phenyl}-2-methyl-propanoate hydrobromide 1H-NMR(DMSO-d6) δ: 1.284(3H, t, J=7.2 Hz), 1.390 (3H, t, J=6.8 Hz), 1.548(6H, s), 3.590(3H, s), 4.110(2H, q, J=6.8 Hz), 4.208(2H, t, J=7.2 Hz), 4.820(2H, s), 5.517(2H, s), 7.341(1H, s), 7.55–7.70(2H, m), 7.85–7.94(2H, m).

Example 565

2-{3-[2-(5,6-Diethoxy-7-fluoro-1-imino-1,3-dihydro-isoindol-2-yl)-acetyl]-phenyl}-2-methyl-propanoic acid hydrobromide 1H-NMR(DMSO-d6) δ: 1.282(3H, t, J=6.8 Hz), 1.387 (3H, t, J=6.8 Hz), 1.514(6H, s), 4.106(2H, q, J=6.8 Hz), 4.205(2H, q, J=6.8 Hz), 4.818(2H, s), 5.521(2H, s), 7.23–7.42(2H, m), 7.579(1H, t, J=8.0 Hz), 7.705(1H, d, J=8.0 Hz), 7.86–7.93(2H, m).

Example 566

8-tert-Butyl-6-[2-(7-imino-2-methyl-5,7-dihydro-pyrrolo[3,4-b]pyridin-6-yl)-acetyl]-2,3-dihydro-benzo[1,4]oxazin-4-ylmethylene-cyanamide hydrobromide 1H-NMR(DMSO-d6) δ: 1.37(9H, s), 2.70(3H, s), 4.05 (2H, t, J=5 Hz), 4.39(2H, t, J=5 Hz), 5.04(2H, s), 6.33(2H, s), 7.49(1H, d, J=8 Hz), 7.86(1H, d, J=8 Hz), 7.87(1H, d, J=8 Hz), 8.43(1H, d, J=8 Hz), 9.70(1H, s).
MS: m/e (ESI) 431.0 (MH+)

Example 567

2-[2-(8-tert-Butyl-4-cyanoiminomethyl-3,4-dihydro-2H-benzo[1,4]oxazin-6-yl)-2-oxo-ethyl]-6-ethoxy-3-imino-2,3-dihydro-1H-isoindole-5-carboxylic acid methylamide hydrobromide 1H-NMR(DMSO-d6) δ: 1.36(9H, s), 1.40(3H, t, J=7 Hz), 2.83(3H, d, J=5 Hz), 4.00(2H, t, J=5 Hz), 4.28(2H, q, J=7 Hz), 4.44(2H, t, J=5 Hz), 4.82(2H, s), 5.40(2Hs), 7.51(1H, s), 7.70(1H, d, J=2 Hz), 8.19(1H, d, J=2 Hz), 8.20(1H, s), 8.52(1H, s), 9.44(1H, s).
MS: m/e (ESI) 517.0 (MH+)

Example 568

8-tert-Butyl-6-[2-(5,6-diethoxy-7-fluoro-1-imino-1,3-dihydro-isoindol-2-yl)-acetyl]-2,3-dihydro-benzo[1,4]oxazin-4-ylmethylene-cyanamide hydrobromide 1H-NMR(DMSO-d6) δ: 1.29(3H, t, J=7 Hz), 1.36(9H, s), 1.40(3H, t, J=7 Hz), 4.00(2H, t, J=5 Hz), 4.12(2H, q, J=7 Hz), 4.21(2H, q, J=7 Hz), 4.43(2H, t, J=5 Hz), 4.80(2H, s), 5.43(2H, s), 7.32(1H, s), 7.70(1H, d, J=2 Hz), 8.17(1H, d, J=2 Hz), 9.43(1H, s).
MS: m/e (ESI) 522.0 (MH+)

Example 569

4-{3-[2-(5-Ethoxy-1-imino-6-methylcarbamoyl-1,3-dihydro-isoindol-2-yl)-acetyl]-phenyl)-4-methyl-2-pentenoic acid hydrochloride 1H-NMR(DMSO-d6) δ: 1.401(3H, t, J=6.8 Hz), 1.472 (6H, s), 2.814(3H, d, J=4.8 Hz), 4.268(2H, q, J=6.8 Hz), 4.862(2H, s), 5.565(2H, s), 5.745(1H, d, J=16.0 Hz), 6.969 (1H, d, J=16.0 Hz), 7.528(1H, s), 7.586(1H, t, J=8.0 Hz), 7.69–7.73(1H, m), 7.89–7.92(1H, m), 8.209(1H, q, J=4.8 Hz), 8.559(1H, s), 9.388(1H, s).

Example 570

4-{3-[2-(5,6-Diethoxy-7-fluoro-1-imino-1,3-dihydro-isoindol-2-yl)-acetyl]-phenyl}-4-methyl-2-pentenoic acid hydrochloride 1H-NMR(DMSO-d6) δ: 1.284(3H, t, J=6.8 Hz), 1.389 (3H, t, J=6.8 Hz), 1.472(6H, s), k4.109(2H, q, J=6.8 Hz), 4.207(2H, q, J=6.8 Hz), 4.817(2H, s), 5.545(2H, s), 5.745(1 h, d, J=16.0 Hz), 6.970(1 h, d, J=16.0 Hz), 7.332(1H, s), 7.582(1H, t, J=8.0 Hz), 7.69–7.73(1H, m), 7.8707.92(2H, m), 9.081(1H, s), 9.466(1H, s).

Example 571

2-[2-(3-tert-Butyl-4-hydroxy-5-methylaminomethyl-phenyl)-2-oxo-ethyl]-6-ethoxy-3-imino-2,3-dihydro-1H-isoindole-5-carboxylic acid methylamide hydrochloride 1H-NMR(DMSO-d6) δ: 1.37–1.42(12H, m), 2.578(3H, d, J=2.8 Hz), 2.806(3H, d, J=4.4 Hz), 4.258(2H, q, J=6.8 Hz), 4.277(2H, s), 4.843(2H, s), 5.567(2H, s), 7.513(1H, s), 7.861(1H, d, J=2.4 Hz), 8.154(1H, s), 8.207(1H, q, J=4.4 Hz), 8.559(1H, s), 9.248(1H, s), 9.559(1H, s), 10.001(1H, s), 10.227(1H, s).

Example 572

1-(3-tert-Butyl-4-hydroxy-5-methylaminomethyl-phenyl)-2-(5,6-diethoxy-7-fluoro-1-imino-1,3-dihydro-isoindol-2-yl)-ethanone hydrochloride 1H-NMR(DMSO-d6) δ: 1.298(3H, t, J=6.8 Hz), 1.385 (3H, t, J=6.8 Hz), 1.396(9H, s), 2.575(3H, s), 4.101(2H, q, J=6.8 Hz), 4.201(2H, q, J=6.8 Hz), 4.269(2H, s), 4.798(2H, s), 5.519(2H, s), 7.321(1H, s), 7.852(1H, d, J=1.6 Hz), 8.092(1H, s), 9.080(1H, s), 9.494(1H, s), 10.179(1H, s).

Example 573

Ethyl N-{2-tert-butyl-4-[2-(5-ethoxy-1-imino-6-methylcarbamoyl-1,3-dihydro-isoindol-2-yl)-acetyl)-phenyl}-succinate hydrobromide 1H-NMR(DMSO-d6) δ: 1.16(3H, t, J=6.8 Hz), 1.33(9H, s), 1.40(3H, t, J=6.8 Hz), 2.56(2H, d, J=5.6 Hz), 2.58(3H, d, J=5.6 Hz), 2.80(3H, d, J=6.4 Hz), 4.04(2H, q, J=6.8 Hz), 4.25(2H, q, J=6.8 Hz), 4.85(2H, s), 5.56(2H, s), 7.29(1H, d, J=8.4 Hz), 7.53(1H, s), 7.84(1H, d, J=8.4 Hz), 7.98(1H, s), 8.19(1H, q, J=5.2 Hz), 8.56((1H, s), 9.44(1H, s), 9.98(1H, brs).

MS: m/e (ESI) 551.4 (MH+)

Example 574

Ethyl N-{2-tert-butyl-4-[2-(5-ethoxy-1-imino-6-methylcarbamoyl-1,3-dihydro-isoindol-2-yl)-acetyl]-phenyl}-N-methyl-succinate hydrobromide 1H-NMR(DMSO-d6) δ: 1.13(3H, t, J=7.2 Hz), 1.35(9H, s), 1.40(3H, t, J=7.2 Hz), 2.13–2.22(4H, m), 2.81(3H, d, J=4.4 Hz), 3.08(3H, s), 3.98(2H, q, J=7.2 Hz), 4.26(2H, q, J=7.2 Hz), 4.13(2H, s), 5.49(3H, s), 7.23(1H, d, J=8.8 Hz), 7.51(1H, s), 7.94(1H, d, J=8.8 Hz), 8.17–8.21(2H, m), 8.52(1H, brs).

Example 575

1-(3,5-Di-tert-butyl-4-hydroxy-phenyl)-2-(3-ethoxy-7-imino-2-methoxy-5,7-dihydro-pyrrolo[3,4-b]pyridin-6-yl)-ethanone hydrobromide 1H-NMR(DMSO-d6) δ: 1.40(3H, t, J=8.0 Hz), 1.41(18H, s), 4.03(3H, s), 4.18(2H, q, J=8.0 Hz), 4.73(2H, s), 5.45(2H, s), 7.68(1H, s), 7.73(2H, s).

Example 576

1-(3-tert-Butyl-4-(pyrrolidin-1-yl)-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=7.2 Hz), 1.38(3H, t, J=7.2 Hz), 1.42(9H, s), 1.88–1.95(4H, m), 2.90–2.98(4H, m), 4.11(2H, q, J=7.2 Hz), 4.20(2H, q, J=7.2 Hz), 4.79(2H, s), 5.45(2H, s), 7.32(1H, s), 7.65(1H, d, J=8.4 Hz), 7.88(dd, J=8.4, 2.0 Hz), 7.92(1H, d, J=2.0 Hz).

Example 577 tert-Butyl {2-tert-butyl-4-[2-(5,6-diethoxy-7-fluoro-1-imino-1,3-dihydro-isoindol-2-yl)-acetyl]-phenylamino}-acetate hydrobromide 1H-NMR(DMSO-d6) δ: 1.28(3H, t, J=7.2 Hz), 1.39(3H, t, J=7.2 Hz), 1.40(18H, s), 4.05(2H, d, J=6.0 Hz), 4.11(2H, q, J=7.2 Hz), 4.20(2H, q, J=7.2 Hz), 4.75(2H, s), 5.36(2H, s), 5.87(1H, t, J=6.0 Hz), 6.53(1H, d, J=8.4 Hz), 7.30(1H, s), 7.71(1H, dd, J=8.4, 2.0 Hz), 7.77(1H, d, J=2.0 Hz).

Example 578

{2-tert-Butyl-4-[2-(5,6-diethoxy-7-fluoro-1-imino-1,3-dihydro-isoindol-2-yl)-acetyl]-phenylamino}-acetic acid hydrochloride 1H-NMR(DMSO-d6) δ: 1.28(3H, t, J=7.2 Hz), 1.40(3H, t, J=7.2 Hz), 1.40(9H, s), 4.09(2H, brs), 4.11(2H, q, J=7.2 Hz), 4.20(2H, q, J=7.2 Hz), 4.78(2H, s), 5.38(2H, s), 6.57(1H, d, J=8.8 Hz), 7.32(1H, brs), 7.72(1H, dd, J=8.8, 2.0 Hz), 8.48–9.03(1H, m), 9.30–9.35(1H, m).

Example 579

1-(8-tert-Butyl-4-methyl-3,4-dihydro-2H-benzo[1,4]oxazin-6-yl)-2-(5-ethoxy-7-fluoro-1-imino-6-methoxy-1,3-dihydro-isoindol-2-yl)-ethanone hydrobromide 1H-NMR(DMSO-d6) δ: 1.36(9H, s), 1.42(3H, t, J=6.8 Hz), 2.92(3H, s), 3.89(3H, s), 4.24(2H, q, J=6.8 Hz), 4.36(2H, t, J=4.4 Hz), 4.80(2H, s), 5.46(2H, s), 7.17(1H, s), 7.28(1H, s), 7.35(1H, s), 9.08(1H, s), 9.26(1H, s).

Example 580

2-[2-(8-tert-Butyl-4-methyl-3,4-dihydro-2H-benzo[1,4]oxazin-6-yl)-2-oxo-ethyl]-6-ethoxy-7-fluoro-3-imino-2,3-dihydro-1H-isoindole-5-carboxylic acid methylamide hydrobromide 1H-NMR(DMSO-d6) δ: 1.34(3H, t, J=6.8 Hz), 1.37(9H, s), 2.84(3H, d, J=4.8 Hz), 2.93(3H, s), 4.32(2H, q, J=6, 8 Hz), 4.36(2H, t, 4.4 Hz), 5.01(2H, s), 5.49(2H, s), 7.19(1H, d, J=2.0 Hz), 7.29(1H, d, J=2.0 Hz), 8.30(1H, s), 8.41(1H, q, J=4.8 Hz), 9.47(1H, s), 10.02(1H, s).

Example 581

2-[2-(3-Dimethylamino-4-hydroxy-phenyl)-2-oxo-ethyl]-6-ethoxy-3-imino-2,3-dihydro-1H-isoindole-5-carboxylic acid methylamide hydrochloride 1H-NMR(DMSO-d6) δ: 1.43(3H, t, J=6.8 Hz), 2.84(3H, d, J=4.4 Hz), 3.10(6H, s), 4.29(2H, q, J=6.8 Hz), 4.87(2H, s), 5.54(2H, s), 7.25(1H, d, J=8.4 Hz), 7.55(1H, s), 7.93(1H, m), 8.23(2H, m), 8.58(1H, s), 9.46(1H, s), 9.95(1H, s).

Example 582

1-(3,5-Di-tert-butyl-4-hydroxy-phenyl)-2-(7-fluoro-1-imino-5-isopropoxy-6-methoxy-1,3-dihydro-isoindol-2-yl)-ethanone hydrobromide 1H-NMR(DMSO-d6) δ: 1.34(6H, d, J=6.0 Hz), 1.40(18H, s), 3.85(3H, s), 4.74–4.85(3H, m), 5.47(2H, s), 7.36(1H, s), 7.75(2H, s).

Example 583

{2-tert-Butyl-4-[2-(7-fluoro-1-imino-5-isopropoxy-6-methoxy-1,3-dihydro-isoindol-2-yl)-acetyl]-phenoxy}-acetic acid hydrochloride 1H-NMR(DMSO-d6) δ: 1.34(6H, d, J=6.0 Hz), 1.39(9H, s), 3.84(3H, s), 4.72–4.85(3H, m), 4.88(2H, s), 5.45(2H, s), 7.07(1H, d, J=7.9 Hz), 7.82–7.92(2H, m).

MS: m/e (ESI) 487.2 (MH+)

Example 584

{8-tert-Butyl-6-[2-(5-ethoxy-7-fluoro-1-imino-6-methoxy-1,3-dihydro-isoindol-2-yl)-acetyl]-2,3-dihydro-benzo[1,4]oxazin-4-yl}-acetic acid hydrochloride 1H-NMR(DMSO-d6) δ: 1.34(9H, s), 1.38(3H, t, J=7.0 Hz), 3.48(2H, brs), 3.86(3H, s), 4.14(2H, s), 4.20(2H, q, J=7.0 Hz), 4.28(2H, brs), 4.76(2H, s), 5.44(2H, s), 7.03(1H, s), 7.23(1H, s), 7.32(1H, s), 9.03(1H, brs).

Example 585

{8-tert-Butyl-6-[2-(7-fluoro-1-imino-6-methoxy-5-propoxy-1,3-dihydro-isoindol-2-yl)-acetyl]-2,3-dihydro-benzo[1,4]oxazin-4-yl}-acetic acid hydrochloride 1H-NMR(DMSO-d6) δ: 0.98(3H, t, J=7.6 Hz), 1.34(9H, s), 1.74–1.85(2H, m), 3.48(2H, brt, J=4.3 Hz), 3.86(3H, s), 4.08–4.18(4H, m), 4.28(2H, brt, J=4.3 Hz), 4.77(2H, s), 5.44(2H, s), 7.04(1H, s), 7.23(1H, s), 7.32(1H, s), 9.03(1H, brs).

Example 586

1-(8-tert-Butyl-4-ethyl-3,4-dihydro-2H-benzo[1,4]oxazin-6-yl)-2-(2-ethyl-7-imino-5,7-dihydro-pyrrolo[3,4-b]pyridin-6-yl)-ethanone hydrobromide 1H-NMR(DMSO-d6) δ: 1.09(3H, t, J=7.0 Hz), 1.30(3H, t, J=7.6 Hz), 1.34(9H, s), 2.94(2H, q, J=7.6 Hz), 3.35(2H, t, J=4.4 Hz), 3.40(2H, q, J=7.0 Hz), 4.27(2H, t, J=4.4 Hz), 4.84(2H, s), 5.52(2H, s), 7.19(1H, s), 7.21(1H, s), 7.72(1H, d, J=8.0 Hz), 8.17(1H, d, J=8.0 Hz).
MS: m/e (ESI) 421.2 (MH+)

Example 587

1-(8-tert-Butyl-4-propyl-3,4-dihydro-2H-benzo[1,4]oxazin-6-yl)-2-(2-ethyl-7-imino-5,7-dihydro-pyrrolo[3,4-b]pyridin-6-yl)-ethanone hydrobromide 1H-NMR(DMSO-d6) δ: 0.90(3H, t, J=7.2 Hz), 1.30(3H, t, J=7.6 Hz), 1.34(9H, s), 1.52–1.62(2H, m), 2.94(2H, q, J=7.6 Hz), 3.27(2H, t, J=7.4 Hz), 3.38(2H, t, J=4.4 Hz), 4.25(2H, t, J=4.4 Hz), 4.84(2H, s), 5.54(2H, s), 7.15(1H, d, J=2.0 Hz), 7.21(1H, d, J=2.0 Hz), 7.72(1H, d, J=8.0 Hz), 8.17(1H, d, J=8.0 Hz).
MS: m/e (ESI) 435.2 (MH+)

Example 588

1-{3-tert-Butyl-5-[2-(2-ethyl-7-imino-5,7-dihydro-pyrrolo[3,4-b]pyridin-6-yl)-acetyl]-2-hydroxy-benzyl)-piperidin-2-one hydrobromide 1H-NMR(DMSO-d6) δ: 1.26(3H, t, J=7.2 Hz), 1.34(9H, s), 1.68(4H, br), 2.32(2H, br), 2.86(2H, q, J=7.2 Hz), 3.25–3.40(2H, mr), 4.40(2H, s), 4.53(2H, s), 5.12(2H, s), 7.48(1H, d, J=8.0 Hz), 7.77(1H, br), 7.82(1H, br), 7.96(1H, d, J=8.0 Hz).
MS: m/e (ESI) 463.2 (MH+)

Example 589

N-{3-tert-Butyl-5-[2-(2-ethyl-7-imino-5,7-dihydro-pyrrolo[3,4-b]pyridin-6-yl)-acetyl]-2-hydroxy-benzyl}-N-methyl-acetamide trifluoroacetate 1H-NMR(DMSO-d6) δ: 1.30(3H, t, J=7.6 Hz), 1.37(9H, s), 2.11(3H, s), 2.94(2H, q, J=7.6 Hz), 3.10(3H, s), 4.48(2H, s), 4.86(2H, s), 5.51(2H, s), 7.73(1H, d, J=8.2 Hz), 7.81(1H, d, J=2.0 Hz), 7.90(1H, d, J=2.0 Hz), 8.17(1H, d, J=8.2 Hz), 9.52(1H, s), 9.85(1H, s), 11.28(1H, s).
MS: m/e (ESI) 437.2 (MH+)

Example 590

{2-[(Acetyl-methyl-amino)-methyl]-6-tert-butyl-4-[2-(2-ethyl-7-imino-5,7-dihydro-pyrrolo[3,4-b]pyridin-6-yl)-acetyl]-phenoxy}-acetic acid trifluoroacetate 1H-NMR(DMSO-d6) δ: 1.31(3H, t, J=7.6 Hz); 1.40,1.41 (9H, each s), 2.02,2.10(3H, each s), 2.80,2.94(3H, each s), 2.92–2.97(2H, m), 4.49,4.52(2H, each s), 4.62,4.70(2H, each s), 4.86,5.55(2H, each s), 7.49,7.53(1H, each s), 7.74 (1H, d, J=8.0 Hz), 7.84,7.89(1H, each s), 8.18(1H, d, J=8.0 Hz), 9.52(1H, brs), 9.89(1H, brs).

Example 591

{2-[(Acetyl-methyl-amino)-methyl]-6-tert-butyl-4-[2-(3-ethoxy-7-imino-2,4-dimethyl-5,7-dihydro-pyrrolo[3,4-b]pyridin-6-yl)-acetyl]-phenoxy}-acetic acid trifluoroacetate 1H-NMR(DMSO-d6) δ: 1.39(3H, t, J=6.8 Hz), 1.40(9H, s), 2.01,2.09(3H, each s), 2.31(3H, s), 2.58,2.79(3H, each s), 2.93,3.14(3H, each s), 3.98(2H, q, J=7.2 Hz), 4.48,4.52(2H, each s), 4.61,4.69(2H, each s), 4.82(2H, s), 5.52,5.54(2H, each s), 7.47,7.51(1H, each d, J=2.0 Hz), 7.83,7.88(1H, each d, J=2.0 Hz), 9.43(1H, s), 9.88(1H, s).

Example 592

{8-tert-Butyl-6-[2-(2-cyclopropyl-7-imino-5,7-dihydro-pyrrolo[3,4-b]pyridin-6-yl)-acetyl]-2,3-dihydro-benzo[1,4]oxazin-4-yl}-acetic acid hydrochloride 1H-NMR(DMSO-d6) δ: 1.00–1.19(4H, m), 1.35(9H, s), 2.23–2.36(1H, m), 4.14(2H, s), 4.20–4.37(2H, m), 4.80(2H, s), 5.49(2H, s), 7.04(1H, s), 7.25(1H, s), 7.70(1H, d, J=8.4 Hz), 8.07(1H, d, J=8.4 Hz), 9.52(1H, brs), 9.58–9.63(1H, m).
MS: m/e (ESI) 463.2 (MH+)

Example 593

6-Ethoxy-3-imino-2-[2-oxo-2-(1,2,3,3-tetramethyl-2,3-dihydro-1H-indol-5-yl)-ethyl]-2,3-dihydro-1H-isoindole-5-carboxylic acid methylamide hydrobromide 1H-NMR(DMSO-d6) δ: 1.02(3H, s), 1.15(3H, d, J=6.4 Hz), 1.27(3H, s), 1.41(3H, t, J=7.2 Hz), 2.80(3H, s), 2.82 (3H, d, J=4.8 Hz), 3.19(1H, q, J=3.4 Hz), 4.27(2H, q, J=7.2 Hz), 4.82(2H, s), 5.35(2H, s), 6.60(1H, d, J=8.4 Hz), 7.52 (1H, s), 7.60(1H, s), 7.77(1H, d, J=8.4 Hz), 8.20(1H, d, J=4.8 Hz), 8.55(1H, brs).
MS: m/e (ESI) 449.2 (MH+) 2

Example 594

2-[2-(5-tert-Butyl-furan-3-yl)-2-oxo-ethyl]-6-ethoxy-3-imino-2,3-dihydro-1H-isoindole-5-carboxylic acid methylamide hydrobromide 1H-NMR(DMSO-d6) δ: 1.28(9H, s), 1.43(3H, t, J=7.2 Hz), 2.84(3H, d, J=4.4 Hz), 4.29(2H, q, J=7.2 Hz), 4.86(2H, s), 5.24(2H, s), 6.48(1H, d, J=0.8 Hz), 7.54(1H, s), 8.22(1H, m), 8.58(1H, s), 8.63(1H, d, J=0.8 Hz).

Example 595

{2,6-Di-tert-butyl-4-[2-(5-ethoxy-1-imino-6-methylcarbamoyl-1,3-dihydro-isoindol-2-yl)-acetyl]-phenoxy}-acetic acid hydrochloride 1H-NMR(DMSO-d6) δ: 1.39–1.42(3H, m), 1.404(18H, s), 2.818(3H, d, J=4.4 Hz), 4.266(2H, s), 4.272(2H, q, J=6.8 Hz), 4.847(2H, s), 5.572(2H, s), 7.534(1H, s), 7.891(2H, s), 8.214(1H, q, J=4.4 Hz), 8.554(1H, s), 9.309(1H, s), 9.309(1H, s), 9.913(1H, s).

Example 596

{2,6-Di-tert-butyl-4-[2-(5,6-diethoxy-7-fluoro-1-imino-1,3-dihydro-isoindol-2-yl)-acetyl]-phenoxy}-acetic acid hydrochloride 1H-NMR(DMSO-d6) δ: 1.285(3H, t, J=6.8 Hz), 1.34–1.45(21H, s), 4.110(2H, q, J=6.8 Hz), 4.209(2H, q, J=6.8 Hz), 4.262(2H, s), 4.796(2H, s), 5.555(2H, s), 7.333(1H, s), 7.878(2H, s), 9.085(1H, s), 9.412(1H, s).

Example 597

1-{3-[2-(5-Ethoxy-1-imino-6-methylcarbamoyl-1,3-dihydro-isoindol-2-yl)-acetyl]-phenyl)-cyclopentanecarboxylic acid hydrochloride 1H-NMR(DMSO-d6) δ: 1.386(3H, t, J=6.8 Hz), 1.50–1.77(6H, m), 2.37–2.50(2H, m), 2.806(3H, d, J=4.4 Hz), 4.256(2H, q, J=6.8 Hz), 4.919(2H, s), 4.97–5.04(1H, m), 7.15–7.42(4H, m), 7.478(1H, s), 8.14–8.21(1H, m), 8.534(1H, s).

Example 598

1-{3-[2-(5,6-Diethoxy-7-fluoro-1-imino-1,3-dihydro-isoindol-2-yl)-acetyl]-phenyl}-cyclopentanecarboxylic acid hydrochloride 1H-NMR(DMSO-d6) δ: 1.264(3H, t, J=6.8 Hz), 1.379(3H, t, J=6.8 Hz), 1.55–1.77(6H, m), 2.43–2.50(2H, m), 4.075(2H, q, J=6.8 Hz), 4.188(2H, q, J=6.8 Hz), 4.879(2H, s), 4.95–5.02(1H, m), 7.23–7.40(5H, m).

Example 599

Ethyl 1-{3-[2-(5-ethoxy-1-imino-6-methylcarbamoyl-1,3-dihydro-isoindol-2-yl)-acetyl]-phenyl}-cyclopentanecarboxylate hydrobromide 1H-NMR(DMSO-d6) δ: 1.079(3H, t, J=7.2 Hz), 1.408(3H, t, J=6.8 Hz), 1.60–1.74(4H, m), 1.83–1.94(2H, m), 2.52–2.60(2H, m), 2.821(3H, d, J=4.4 Hz), 4.016(2H, q, J=7.2 Hz), 4.276(2H, q, J=6.8 Hz), 4.871(2H, s), 5.520(2H, s), 7.52–7.72(2H, m), 7.884(1H, s), 7.924(1H, d, J=7.6 Hz), 8.215(1H, q, J=4.4 Hz), 8.554(1H, s).

Example 600

Ethyl 1-{3-[2-(5,6-diethoxy-7-fluoro-1-imino-1,3-dihydro-isoindol-2-yl)-acetyl]-phenyl}-cyclopentanecarboxylate hydrobromide 1H-NMR(DMSO-d6) δ: 1.079(3H, t, J=7.2 Hz), 1.287(3H, t, J=6.8 Hz), 1.393(3H, t, J=6.8 Hz), 1.60–1.74(4H, m), 1.84–1.94(2H, m), 2.52–2.60(2H, m), 4.016(2H, q, J=6.8 Hz), 4.113(2H, q, J=7.2 Hz), 4.211(2H, q, J=6.8 Hz), 4.822(2H, s), 5.504(2 h, s), 7.339(1H, s), 7.582(1H, t, J=8.0 Hz), 7.691(1H, d, J=8.0 Hz), 7.877(1H, s), 7.911(1H, d, J=7.6 Hz).

Example 601

6-Ethoxy-3-imino-2-[2-oxo-2-(1,3,3-trimethyl-2,3-dihydro-1H-indol-5-yl)-ethyl]-2,3-dihydro-1H-isoindole-5-carboxylic acid methylamide hydrobromide 1H-NMR(DMSO-d6) δ: 1.27(6H, s), 1.41(3H, t, J=7.2 Hz), 2.82(3H, d, J=4.8 Hz), 2.86(3H, s), 3.28(2H, s), 4.28(2H, q, J=7.2 Hz), 4.81(2H, s), 5.32(2H, s), 6.57(1H, d, J=8.0 Hz), 7.51(1H, s), 7.59(1H, s), 7.76(1H, d, J=8.0 Hz), 8.17–8.23(1H, m), 8.54(1H, s), 9.16(1H, brs), 9.72(1H, brs).

Example 602

1-[3-tert-Butyl-4-(2H-tetrazol-5-ylmethoxy)-phenyl]-2-(5,6-diethoxy-7-fluoro-1-imino-1,3-dihydro-isoindol-2-yl)-ethanone hydrochloride 1H-NMR(DMSO-d6) δ: 1.26–1.43(15H, m), 4.11(2H, q, J=7.2 Hz), 4.21(2H, q, J=7.2 Hz), 4.80(2H, s), 5.46(2H, s), 5.63(2H, s), 6.94–7.06(1H, m), 7.31–7.45(3H, m), 9.04(1H, brs), 9.33(1H, brs).

MS: m/e (ESI) 511.2 (MH+)

Example 603

2-[2-(8-tert-Butyl-4-carbamoylmethyl-3,4-dihydro-2H-benzo[1,4]oxazin-6-yl)-2-oxo-ethyl]-6-ethoxy-7-fluoro-3-imino-2,3-dihydro-1H-isoindole-5-carboxylic acid methylamide hydrobromide 1H-NMR(DMSO-d6) δ: 1.34(3H, t, J=7.2 Hz), 1.38(9H, s), 2.84(3H, d, J=4.4 Hz), 3.51(2H, t, J=4.4 Hz), 3.90(2H, s), 4.31(2H, q, J=7.2 Hz), 4.34(2H, t, J=4.4 Hz), 5.00(2H, s), 5.46(2H, s), 7.01(1H, s), 7.13(1H, s), 7.27(1H, s), 7.52(1H, s), 8.30(1H, s), 8.41(1H, q, J=4.4 Hz), 9.47(1H, s), 10.02(1H, s).

Example 604

2-{8-tert-Butyl-6-[2-(5,6-diethoxy-7-fluoro-1-imino-1,3-dihydro-isoindol-2-yl)-acetyl]-2,3-dihydro-benzo[1,4]oxazin-4-yl}-acetamide hydrobromide 1H-NMR(DMSO-d6) δ: 1.31(3H, t, J=6.8 Hz), 1.38(9H, s), 1.41(3H, t, J=6.8 Hz), 3.51(2H, t, J=4.4 Hz), 3.90(2H, s), 4.13(2H, q, J=6.8 Hz), 4.22(2H, q, J=6.8 Hz), 4.34(2H, J=4.4 Hz), 4.79(2H, s), 5.43(2H, s), 7.00(1H, d, J=2.0 Hz), 7.13(1H, s), 7.26(1H, d, J=2.0 Hz), 7.34(1H, s), 7.51(1H, s), 9.02(1H, s), 9.35(1H, s).

Example 605

2-[2-(3,5-Di-tert-butyl-4-hydroxy-phenyl)-ethyl]-6-ethoxy-3-imino-2,3-dihydro-1H-isoindole-5-carboxylic acid methylamide hydrochloride 1H-NMR(DMSO-d6) δ: 1.29(18H, s), 1.41(3H, t, J=7.2 Hz), 2.83(3H, d, J=4.4 Hz), 2.90(2H, t, J=7.2 Hz), 3.93(2H, t, J=7.2 Hz), 4.27(2H, q, J=7.2 Hz), 4.75(2H, s), 6.81(1H, s), 6.92(2H, s), 7.47(1H, s), 8.18(1H, q, J=4.4 Hz), 8.56(1H, s), 9.17(1H, s), 9.71(1H, s).

Example 606

1-[8-tert-Butyl-4-(3-hydroxy-propyl)-3,4-dihydro-2H-benzo[1,4]oxazin-6-yl]-2-(2-ethyl-7-imino-5,7-dihydro-pyrrolo[3,4-b]pyridin-6-yl)-ethanone hydrochloride 1H-NMR(DMSO-d6) δ: 1.31(3H, t, J=7.4 Hz), 1.34(9H, s), 1.71(2H, m), 2.94(2H, q, J=7.4 Hz), 3.26–3.72(6H, m), 4.26(2H, t, J=4.8 Hz), 4.85(2H, s), 5.53(2H, s), 7.21(2H, s), 7.73(1H, d, J=8.0 Hz), 8.17(1H, d, J=8.0 Hz), 9.55(1H, s), 9.85(1H, s).
MS: m/e (ESI) 451

Example 607

2-{2-[8-tert-Butyl-4-(3-hydroxy-propyl)-3,4-dihydro-2H-benzo[1,4]oxazin-6-yl]-2-oxo-ethyl}-6-ethoxy-3-imino-2,3-dihydro-1H-isoindole-5-carboxylic acid methylamide hydrochloride 1H-NMR(DMSO-d6) δ: 0.90(3H, t, J=7.2 Hz), 1.30(3H, t, J=7.6 Hz), 1.34(9H, s), 1.52–1.62(2H, m), 2.94(2H, q, J=7.6 Hz), 3.27(2H, t, J=7.4 Hz), 3.38(2H, t, J=4.4 Hz), 4.25(2H, t, J=4.4 Hz), 4.84(2H, s), 5.54(2H, s), 7.15(1H, d, J=2.0 Hz), 7.21(1H, d, J=2.0 Hz), 7.72(1H, d, J=8.0 Hz), 8.17(1H, d, J=8.0 Hz).

Example 608

6-Ethoxy-3-imino-2-[2-oxo-2-(1,4,4-trimethyl-2-oxo-1,2,3,4-tetrahydro-quinolin-6-yl)-ethyl]-2,3-dihydro-1H-isoindole-5-carboxylic acid methylamide hydrobromide 1H-NMR(DMSO-d6) δ: 1.27(6H, s), 1.41(3H, t, J=7.2 Hz), 2.54(2H, s), 2.82(3H, d, J=4.8 Hz), 3.29(2H, s), 4.28(2H, q, J=7.2 Hz), 4.86(2H, s), 5.49(2H, s), 7.32(1H, d, J=8.0 Hz), 7.54(1H, s), 7.89(1H, s), 7.95(1H, d, J=8.0 Hz), 8.18–8.24(1H, m), 8.56(1H, s), 9.24(1H, brs), 9.86(1H, brs).

Example 609

{2-[(Acetyl-methyl-amino)-methyl]-6-tert-butyl-4-[2-(5,6-diethoxy-7-fluoro-1-imino-1,3-dihydro-isoindol-2-yl)-acetyl]-phenoxy}-acetic acid trifluoroacetate 1H-NMR(DMSO-d6) δ: 1.29(3H, t, J=6.8 Hz), 1.39(12H, s), 2.01,2.10(3H, each s), 2.80,2.94(3H, each s), 4.11,4.22 (2H, each brd, J=6.8 Hz), 4.48,4.52(2H, each s), 4.61,4.69 (2H, each s), 4.80(2H, s), 5.47(2H, s), 7.33(1H, s), 7.48, 7.51(1H, each s), 7.83,7.87(1H, each s), 9.06(1H, s), 9.32 (1H, s).
MS: m/e (ESI) 572.3 (MH+)

Example 610

Methyl {2-[(acetyl-methyl-amino)-methyl]-6-tert-butyl-4-[2-(5,6-diethoxy-7-fluoro-1-imino-1,3-dihydro-isoindol-2-yl)-acetyl]-phenoxy}-acetate trifluoroacetate 1H-NMR(DMSO-d6) δ: 1.29(3H, t, J=6.8 Hz), 1.39(12H, s), 2.01,2.09(3H, each s), 2.80,2.94(3H, each s), 3.75,3.77 (3H, each s), 4.11(2H, q, J=7.2 Hz), 4.21(2H, q, J=7.2 Hz), 4.06(2H, s), 4.64,4.68(2H, each s), 4.79(2H, s), 5.47(2H, s), 7.33(1H, s), 7.47,7.52(1H, each s), 7.83,7.87(1H, each d, J=2.0 Hz), 9.06(1H, each s).
MS: m/e (ESI) 586.4 (MH+)

Example 611

2-[2-(7-tert-Butyl-2-cyanoamino-benzoxazol-5-yl)-2-oxo-ethyl]-6-ethoxy-3-imino-2,3-dihydro-1H-isoindole-5-carboxylic acid methylamide trifluoroacetate 1H-NMR(DMSO-d6) δ: 1.08(3H, t, J=7 Hz), 1.44(9H, s), 2.84(3H, d, J=5 Hz), 4.28(2H, q, J=7 Hz), 4.84(2H, s), 5.52(2H, s), 5.55(1H, q, J=5 Hz), 7.54(1H, s), 7.64(1H, s), 8.21(1H, s), 8.56(1H, s).

Example 612

{8-tert-Butyl-6-[2-(3-ethoxy-7-imino-2-methylcarbamoyl-5,7-dihydro-pyrrolo[3,4-b]pyridin-6-yl)-acetyl]-2,3-dihydro-benzo[1,4]oxazin-4-yl}-acetic acid hydrochloride 1H-NMR(DMSO-d6) δ: 1.28–1.42(12H, m), 2.78(3H, d, J=4.5 Hz), 3.48(2H, brt, J=4.5 Hz), 4.15(2H, s), 4.24(2H, q, J=7.0 Hz), 4.30(2H, brt, J=4.5 Hz), 4.85(2H, s), 5.49(2H, s), 7.03(1H, s), 7.25(1H, s), 7.98(1H, s), 8.54(qH, brq, J=4.5 Hz), 9.48(1H, brd, J=7.0 Hz), 9.93(1H, brd, J=7.0 Hz).

Example 613

1-(3,5-Di-tert-butyl-4-hydroxy-phenyl)-2-(6-ethoxy-7-fluoro-1-imino-5-methoxy-1,3-dihydro-isoindol-2-yl)-ethanone hydrobromide 1H-NMR(DMSO-d6) δ: 1.28(3H, t, J=7.0 Hz), 1.41(18H, s), 3.95(3H, s), 4.10(2H, q, J=7.0 Hz), 4.79(2H, s), 5.48(2H, s), 7.36(1H, s), 7.77(2H, s), 8.07(1H, brs), 9.06(1H, brs), 9.28(1H, brs).

Example 614

Methyl (8-tert-butyl-6-[2-(7-fluoro-1-imino-5,6-dimethoxy-1,3-dihydro-isoindol-2-yl)-acetyl]-2,3-dihydro-benzo[1,4]oxazin-4-yl}-acetate hydrobromide 1H-NMR(DMSO-d6) δ: 1.35(9H, s), 3.49(2H, brs), 3.64 (3H, s), 3.86(3H, s), 3.95(3H, s), 4.25–4.34(3H, m), 4.78 (2H, s), 5.40(2H, s), 7.03(1H, s), 7.24(1H, s), 7.35(1H, s).
MS: m/e (ESI) 514.3 (MH+)

Example 615

2-{8-tert-Butyl-6-[2-(3-ethoxy-7-imino-2,4-dimethyl-5,7-dihydro-pyrrolo[3,4-b]pyridin-6-yl)-acetyl]-2,3-dihydro-benzo[1,4]oxazin-4-yl}-acetamide hydrobromide 1H-NMR(DMSO-d6) δ: 1.38(9H, s), 1.41(3H, t, J=6.4 Hz), 2.33(3H, s), 2.60(3H, s), 3.51(2H, s), 3.90(2H, s), 4.00(2H, q, J=6.4 Hz), 4.35(2H, s), 4.83(2H, s), 5.48(2H, s), 7.01(1H, s), 7.13(1H, s), 7.27(1H, s), 7.51(1H, s), 9.40(1H, s), 9.81(1H, s).

Example 616

{3-tert-Butyl-5-[2-(5,6-diethoxy-7-fluoro-1-imino-1,3-dihydro-isoindol-2-yl)-acetyl]-2-hydroxy-benzylamino}-acetic acid ditrifluoroacetate 1H-NMR(DMSO-d6) δ: 1.29(3H, t, J=7.2 Hz), 1.38(3H, t, J=7.2 Hz), 1.41(9H, s), 3.79(2H, brs), 4.12(2H, q, J=7.2 Hz), 4.23(2H, q, J=7.2 Hz), 4.25(2H, s), 4.80(2H, s), 5.43 (2H, s), 7.33(1H, s), 7.84(1H, s), 7.91(1H, s), 9.07(1H, s), 9.37(0.1H, s).

Example 617

{6-[2-(5-Ethoxy-1-imino-6-methylcarbamoyl-1,3-dihydro-isoindol-2-yl)-acetyl]-4,4-dimethyl-2-oxo-3,4-dihydro-2H-quinolin-1-yl}-acetic acid hydrochloride 1H-NMR(DMSO-d6) δ: 1.32(6H, s), 1.42(3H, t, J=7.2 Hz), 2.57(2H, s), 2.82(3H, d, J=4.8 Hz), 4.28(2H, q, J=7.2 Hz), 4.77(2H, s), 4.87(2H, s), 5.49(2H, s), 7.25(1H, d, J=8.0 Hz), 7.54(1H, s), 7.87–7.94(2H, m), 8.17–8.25(1H, m), 8.57(1H, s), 9.26(1H, brs), 9.87(1H, brs).
MS: m/e (ESI) 507.3 (MH+)

Example 618

1-(5-tert-Butyl-furan-3-yl)-2-(4-ethoxy-7-fluoro-1-imino-1,3-dihydro-isoindol-2-yl)-ethanone hydrobromide 1H-NMR(DMSO-d6) δ: 1.29(9H, s), 1.35(3H, t, J=7.2 Hz), 4.20(2H, q, J=7.2 Hz), 4.83(2H, s), 5.22(2H, s), 6.48 (1H, d, J=0.4 Hz), 7.41–7.54(2H, m), 8.61(1H, d, J=0.4 Hz).

Example 619

1-(5-tert-Butyl-furan-3-yl)-2-(5,6-diethoxy-7-fluoro-1-imino-1,3-dihydro-isoindol-2-yl)-ethanone hydrobromide 1H-NMR(DMSO-d6) δ: 1.29(9H, s), 1.31(3H, t, J=7.2 Hz), 1.42(3H, t, J=7.2 Hz), 4.13(2H, q, J=7.2 Hz), 4.23(2H, q, J=7.2 Hz), 4.82(2H, s), 5.22(2H, s), 6.48(1H, d, J=0.8 Hz), 7.34(1H, s), 8.60(1H, d, J=0.8 Hz), 9.10(1H, s), 9.41 (1H, s).

Example 620

2-[2-(3-tert-Butyl-4-hydroxy-5-isopropoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.33(6H, d, J=6.0 Hz), 1.41(9H, s), 1.44(3H, t, J=7.2 Hz), 2.85(3H, d, J=4.4 Hz), 4.30(2H, q, J=7.2 Hz), 4.67(1H, m), 4.86(2H, s), 5.48(2H, s), 7.49(1H, s), 7.52(1H, s), 7.55(1H, s), 8.22(1H, m), 8.59(1H, s), 9.24(1H, s), 9.87(1H, s).

Example 621

2-[2-(3-tert-Butyl-5-cyclopentyloxy-4-hydroxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.41(9H, s), 1.44(3H, t, J=7.2 Hz), 1.58(2H, m), 1.73–2.00(6H, m), 2.85(3H, d, J=4.4 Hz), 4.30(2H, q, J=7.2 Hz), 4.86(2H, s), 4.87(1H, m), 5.49(2H, s), 7.40(1H, s), 7.52(1H, s), 7.55(1H, s), 8.22(1H, m), 8.60(1H, s), 9.22(1H, s), 9.86(1H, s).

Example 622

Ethyl (3-tert-butyl-5-[2-(5-ethoxy-1-imino-6-methylcarbamoyl-1,3-dihydro-isoindol-2-yl)-acetyl]-2-hydroxy-phenyl}-acetate hydrobromide 1H-NMR(DMSO-d6) δ: 1.167(3H, t, J=6.8 Hz), 1.373 (9H, s), 1.409(3H, t, J=6.8 Hz), 2.822(3H, d, J=4.4 Hz), 3.757(3H, s), 3.819(2H, s), 4.102(2H, q, J=6.8 Hz), 4.277 (2H, q, J=6.8 Hz), 4.856(2H, s), 5.494(2H, s), 7.536(1H, s), 7.846(1H, s), 8.215(1H, s), 8.204(1H, s), 8.551(1H, s).

Example 623

Ethyl {3-tert-butyl-5-[2-(5,6-diethoxy-7-fluoro-1-imino-1,3-dihydro-isoindol-2-yl)-acetyl]-2-hydroxy-phenyl}-acetate hydrobromide 1H-NMR(DMSO-d6) δ: 1.164(3H, t, J=6.8 Hz), 1.285(3 h, t, J=6.8 Hz), 1.370(9H, s), 1.391(3H, t, J=7.2 Hz), 3.753(3H, s), 3.817(2H, s), 4.06–4.14(4H, m), 4.207(2H, q, J=7.2 Hz), 4.803(2H, s), 5.469(2H, s), 7.344(1H, s), 7.832 (2H, s).

Example 624

6-[2-(8-tert-Butyl-4-methyl-3,4-dihydro-2H-benzo[1,4]oxazin-6-yl)-2-oxo-ethyl]-3-ethoxy-7-imino-6,7-dihydro-5H-pyrrolo[3,4-b]pyridine-2-carboxylic acid methylamide hydrochloride 1H-NMR(DMSO-d6) δ: 1.36(9H, s), 1.38(3H, t, J=6.8 Hz), 2.79(3H, d, J=4.0 Hz), 2.93(3H, s), 3.33(2H, s), 4.26 (2H, q, J=6.8 Hz), 4.36(2H, s), 4.89(2H, s), 5.57(2H, s), 7.20(1H, s), 7.29(1H, s), 8.01(1H, s), 8.59(1H, q, J=4.0 Hz), 9.55(1H, s), 9.97(1H, s).

Example 625

6-[2-(8-tert-Butyl-4-carbamoylmethyl-3,4-dihydro-2H-benzo[1,4]oxazin-6-yl)-2-oxo-ethyl]-3-ethoxy-7-imino-6,7-dihydro-5H-pyrrolo[3,4-b]pyridine-2-carboxylic acid methylamide hydrochloride 1H-NMR(DMSO-d6) δ: 1.38(12H, s), 2.79(3H, d, J=4.8 Hz), 3.91(2H, s), 4.25(2H, q, J=6.8 Hz), 4.34(2H, t, J=4.4

Hz), 4.89(2H, s), 5.51(2H, s), 7.02(1H, s), 7.14(1H, s), 7.27(1H, s), 7.55(1H, s), 8.00(1H, s), 8.57(1H, q, J=4.8 Hz), 9.52(1H, s), 9.94(1H, s).

Example 626

=2-tert-Butyl-4-[2-(6-carbamoyl-5-ethoxy-1-imino-1,3-dihydro-isoindol-2-yl)-acetyl]-6-(pyrrolidin-1-yl)-phenoxy}-acetic acid trifluoroacetate 1H-NMR(DMSO-d6) δ: 1.38(9H, s), 1.42(3H, t, J=6.8 Hz), 1.83–1.93(4H, m), 3.06–3.16(4H, m), 4.27(2H, q, J=6.8 Hz), 4.40(2H, s), 4.84(2H, s), 5.49(2H, s), 7.41(1H, s), 7.48(1H, s), 7.54(1H, s), 7.70(1H, brs), 7.79(1H, brs), 8.62 (1H, s), 9.16(1H, brs), 9.84(1H, brs).

MS: m/e (ESI) 537.3 (MH+)

Example 627

{2-tert-Butyl-4-[2-(6-dimethylcarbamoyl-5-ethoxy-1-imino-1,3-dihydro-isoindol-2-yl)-acetyl]-6-(pyrrolidin-1-yl)-phenoxy}-acetic acid trifluoroacetate 1H-NMR(DMSO-d6) δ: 1.34(3H, t, J=6.8 Hz), 1.38(9H, s), 1.84–1.93(4H, m), 2.78(3H, s), 3.00(3H, s), 3.08–3.15 (4H, m), 4.22(2H, q, J=6.8 Hz), 4.40(2H, s), 4.83(2H, s), 5.49(2H, s), 7.42(1H, s), 7.48(1H, s), 7.50(1H, s), 8.03(1H, s), 9.13(1H, brs), 9.69(1H, brs).

MS: m/e (ESI) 565.4 (MH+)

Example 628

{2-tert-Butyl-4-[2-(6-ethoxy-7-fluoro-1-imino-5-methoxy-1,3-dihydro-isoindol-2-yl)-acetyl]-phenoxy}-acetic acid hydrochloride 1H-NMR(DMSO-d6) δ: 1.28(3H, t, J=6.7 Hz), 1.40(9H, s), 3.93(3H, s), 4.10(2H, q, J=6.7 Hz), 4.80(2H, s), 4.88(2H, s), 5.45(2H, s), 7.06(1H, d, J=8.0 Hz), 7.34(1H, s), 7.80–7.92(2H, m), 9.06(1H, brs), 9.37(1H, brs).

Example 629

Methyl {8-tert-butyl-6-[2-(3-ethoxy-7-imino-2-methylcarbamoyl-5,7-dihydro-pyrrolo[3,4-b]pyridin-6-yl)-acetyl]-2,3-dihydro-benzo[1,4]oxazin-4-yl}-acetate hydrobromide 1H-NMR(DMSO-d6) δ: 1.30–1.41(12H, m), 2.77(3H, d, J=4.8 Hz), 3.48(2H, brs), 3.64(3H, s), 4.20–4.33(6H, m), 4.86(2H, s), 5.44(2H, s), 7.04(1H, s), 7.26(1H, s), 7.98(1H, s), 8.52(1H, q, J=4.8 Hz).

Example 630

8-tert-Butyl-6-[2-(7-fluoro-1-imino-5,6-dimethoxy-1,3-dihydro-isoindol-2-yl)-acetyl]-4-methyl-3,4-dihydro-2H-benzo[1,4]oxazine-2-carboxylic acid trifluoroacetate 1H-NMR(DMSO-d6) δ: 1.38(9H, s), 2.88(3H, s), 3.23–3.42(2H, m), 3.87(3H, s), 3.95(3H, s), 4.79(2H, s), 5.15(1H, t, J=3.9 Hz), 5.45(2H, s), 7.17(1H, s), 7.32(1H, s), 7.35(1H, s).

Example 631 tert-Butyl (acetyl-{2-tert-butyl-4-[2-(5-ethoxy-1-imino-6-methylcarbamoyl-1,3-dihydro-isoindol-2-yl)-acetyl]-phenyl}-amino)-acetate hydrobromide 1H-NMR(DMSO-d6) δ: 1.32(9H, s), 1.42(9H, s), 1.43 (3H, t, J=6.8 Hz), 1.74(3H, s), 2.82(3H, d, J=4.4 Hz), 3.68(1H, d, J=16.8 Hz), 4.28(2H, q, J=6.8 Hz), 4.49(1H, d, J=16.8 Hz), 4.87(2H, s), 5.53(2H, s), 7.54(1H, s), 7.73(1H, d, J=8.0 Hz), 7.98(1H, dd, J=8.0, 2.0 Hz), 8.15(1H, d, J=2.0 Hz), 8.21(1H, q, J=4.4 Hz), 8.57(1H, s).

Example 632

(Acetyl-{2-tert-butyl-4-[2-(5-ethoxy-1-imino-6-methylcarbamoyl-1,3-dihydro-isoindol-2-yl)-acetyl]-phenyl}-amino)-acetic acid hydrochloride 1H-NMR(DMSO-d6) δ: 1.37(9H, s), 1.41(3H, t, J=6.8 Hz), 1.73(3H, s), 2.82(3H, d, J=4.4 Hz), 3.67(1H, d, J=16.8 Hz), 4.28(2H, q, J=6.8 Hz), 4.56(1H, d, J=16.8 Hz), 4.87 (2H, s), 5.58(2H, s), 7.54(1H, s), 7.75(1H, d, J=8.0 Hz), 7.97(1H, dd, J=8.0, 2.0 Hz), 8.17(1H, d, J=2.0 Hz), 8.21(1H, q, J=4.4 Hz), 8.57(1H, s), 9.34–9.40(1H, m), 9.90–9.98(1H, m).

Example 633 tert-Butyl ({2-tert-butyl-4-[2-(5-ethoxy-1-imino-6-methylcarbamoyl-1,3-dihydro-isoindol-2-yl)-acetyl]-phenyl}-methyl-amino)-acetate hydrobromide 1H-NMR(DMSO-d6) δ: 1.41(3H, t, J=5.2 Hz), 1.44(18H, s), 2.59(3H, s), 2.82(3H, d, J=4.8 Hz), 3.49(1H, brs), 4.27 (2H, q, J=5.2 Hz), 4.84(2H, s), 5.49(2H, s), 7.54(1H, s), 7.64(1H, d, J=8.4 Hz), 7.90(1H, dd, J=8.4, 2.4 Hz), 7.94(1H, d, J=2.4 Hz), 8.21(1H, q, J=4.8 Hz), 8.56(1H, s).

Example 634

{2-tert-Butyl-6-diethylamino-4-[2-(5-ethoxy-1-imino-6-methylcarbamoyl-1,3-dihydro-isoindol-2-yl)-acetyl]-phenoxy}-acetic acid trifluoroacetate 1H-NMR(DMSO-d6) δ: 0.95(6H, t, J=7.2 Hz), 1.38(9H, s), 1.41(3H, t, J=7.2 Hz), 2.82(3H, d, J=4.0 Hz), 3.11(4H, q, J=7.2 Hz), 4.28(2H, q, J=7.2 Hz), 4.73(2H, s), 4.84(2H, s), 5.48(2H, s), 7.54(2H, s), 7.59(1H, s), 8.20(1H, brs), 8.55 (1H, s), 9.17(1H, brs), 9.84(1H, brs).

MS: m/e (ESI) 553.3 (MH+)

Example 635

({2-tert-Butyl-4-[2-(5-ethoxy-1-imino-6-methylcarbamoyl-1,3-dihydro-isoindol-2-yl)-acetyl]-phenyl)-methyl-amino)-acetic acid hydrochloride 1H-NMR(DMSO-d6) δ: 1.41(3H, t, J=6.8 Hz), 1.44(9H, s), 2.62(3H, s), 2.82(3H, s), 3.83(1H, d, J=8.8 Hz), 4.17(1H, d, J=8.8 Hz), 4.27(2H, q, J=6.8 Hz), 4.84(2H, s), 5.54(2H, s), 6.34(1H, s), 7.66(1H, d, J=8.0 Hz), 7.91(1H, dd, J=8.0, 1.6 Hz), 7.94(1H, d, J=1.6 Hz), 8.56(1H, s), 9.29–9.33(1H, m), 9.48–9.92(1H, m).

Example 636

{2-tert-Butyl-4-[2-(5-dimethylamino-1-imino-6-methylcarbamoyl-1,3-dihydro-isoindol-2-yl)-acetyl]-6-(pyrrolidin-1-yl)-phenoxy}-acetic acid trifluoroacetate 1H-NMR(DMSO-d6) δ: 1.38(9H, s), 1.85–1.90(4H, m), 2.77(3H, d, J=4.4 Hz), 2.91(6H, s), 3.07–3.15(4H, m), 4.39(2H, s), 4.73(2H, s), 5.44(2H, s), 7.17(1H, s), 7.40(1H, s), 7.47(1H, s), 8.06(1H, s), 8.36(1H, brs), 8.90(1H, brs), 9.53(1H, brs).

MS: m/e (ESI) 550.4 (MH+)

Example 637

2-[2-(3-tert-Butyl-4-hydroxy-5-isopropoxy-phenyl)-2-oxo-ethyl]-6-dimethylamino-3-imino-2,3-dihydro-1H-isoindole-5-carboxylic acid methylamide hydrobromide 1H-NMR(DMSO-d6) δ: 1.33(6H, d, J=6.0 Hz), 1.41(9H, s), 2.80(3H, d, J=4.4 Hz), 2.94(6H, s), 4.68(1H, m), 4.76(2H, s), 5.45(2H, s), 7.17(1H, s), 7.48(1H, s), 7.52(1H, s), 8.10(1H, s), 8.39(1H, m).

Example 638

2-[2-(4-Acetyl-8-tert-butyl-3,4-dihydro-2H-benzo[1,4]oxazin-6-yl)-2-oxo-ethyl]-6-ethoxy-3-imino-2,3-dihydro-1H-isoindole-5-carboxylic acid methylamide hydrobromide 1H-NMR(DMSO-d6) δ: 1.39(9H, s), 1.43(3H, t, J=6.8 Hz), 2.30(3H, s), 2.84(3H, d, J=4.4 Hz), 3.91(2H, t, J=4.8 Hz), 4.29(2H, q, J=6.8 Hz), 4.48(2H, t, J=4.8 Hz), 4.86(2H, s), 5.45(2H, s), 7.55(1H, s), 7.67(1H, s), 8.00(1H, brs), 8.22(1H, q, J=4.4 Hz), 8.57(1H, s), 9.22(1H, s), 9.84(1H, s).

Example 639

Ethyl (2-tert-butyl-6-diethylamino-4-[2-(5-ethoxy-1-imino-6-methylcarbamoyl-1,3-dihydro-isoindol-2-yl)-acetyl]-phenoxy}-acetate hydrobromide 1H-NMR(DMSO-d6) δ: 0.94(6H, t, J=6.8 Hz), 1.23(3H, t, J=6.8 Hz), 1.37(9H, s), 1.41(3H, t, J=6.8 Hz), 2.83(3H, d, J=4.8 Hz), 3.05–3.10(4H, m), 4.17(2H, q, J=6.8 Hz), 4.27(2H, q, J=6.8 Hz), 4.80(2H, s), 4.84(2H, s), 5.53(2H, s), 7.54(1H, s), 7.55(1H, s), 7.61(1H, s), 8.21(1H, d, J=4.8 Hz), 8.56(1H, s), 9.29(1H, brs), 9.90(1H, brs).

MS: m/e (ESI) 581.4 (MH+)

Example 640

{3-tert-Butyl-5-[2-(5,6-diethoxy-7-fluoro-1-imino-1,3-dihydro-isoindol-2-yl)-acetyl]-2-hydroxy-benzylamino}-acetic acid hydrobromide 1H-NMR(DMSO-d6) δ: 1.29(3H, t, J=7.2 Hz), 1.38(3H, t, J=7.2 Hz), 1.41(9H, s), 3.79(2H, brs), 4.12(2H, q, J=7.2 Hz), 4.23(2H, q, J=7.2 Hz), 4.25(2H, s), 4.80(2H, s), 5.43(2H, s), 7.33(1H, s), 7.84(1H, s), 7.91(1H, s), 9.07(1H, s), 9.37(1H, s).

Example 641

{2-tert-Butyl-4-[2-(5-ethoxy-1-imino-6-methylcarbamoyl-1,3-dihydro-isoindol-2-yl)-acetyl]-6-(ethyl-methanesulfonyl-amino)-phenoxy}-acetic acid trifluoroacetate 1H-NMR(DMSO-d6) δ: 1.05(3H, t, J=6.8 Hz), 1.38(9H, s), 1.41(3H, t, J=6.8 Hz), 2.82(3H, d, J=4.8 Hz), 3.27(3H, s), 4.28(2H, q, J=6.8 Hz), 4.69–4.93(6H, m), 5.52(2H, s), 7.55(1H, s), 7.86(1H, s), 7.89(1H, s), 8.21(1H, d, J=4.4 Hz), 8.56(1H, s), 9.24(1H, brs), 9.88(1H, brs).

MS: m/e (ESI) 603.3 (MH+)

Example 642

{2-(Acetyl-ethyl-amino)-6-tert-butyl-4-[2-(5-ethoxy-1-imino-6-methylcarbamoyl-1,3-dihydro-isoindol-2-yl)-acetyl]-phenoxy}-acetic acid trifluoroacetate 1H-NMR(DMSO-d6) δ: 1.05(3H, t, J=6.8 Hz), 1.33–1.43(12H, m), 1.89(3H, s), 2.82(3H, d, J=4.8), 2.96–3.12(1H, m), 4.08–4.19(1H, m), 4.28(2H, q, J=6.8 Hz), 4.48(2H, dd, J=15.2 Hz, 15.6 Hz), 4.86(2H, s), 5.50(2H, s), 7.54(1H, s), 7.81(1H, s), 7.89(1H, s), 8.21(1H, d, J=4.4 Hz), 8.56(1H, s), 9.26(1H, brs), 9.88(1H, brs).

MS: m/e (ESI) 567.3 (MH+)

Example 643

{2-(Acetyl-methyl-amino)-6-tert-butyl-4-[2-(5-ethoxy-1-imino-6-methylcarbamoyl-1,3-dihydro-isoindol-2-yl)-acetyl]-phenoxy}-acetic acid trifluoroacetate 1H-NMR(DMSO-d6) δ: 1.36–1.43(12H, m), 1.83(3H, s), 2.82(3H, d, J=4.4 Hz), 3.15(3H, s), 4.28(2H, q, J=6.8 Hz), 4.44(2H, dd, J=15.6 Hz, 15.6 Hz), 4.85(2H, s), 5.48(2H, s), 7.54(1H, s), 7.87(1H, s), 7.95(1H, s), 8.21(1H, d, J=4.4 Hz), 8.55(1H, s), 9.23(1H, brs), 9.88(1H, brs).

MS: m/e (ESI) 553.3 (MH+)

Example 644

{2-tert-Butyl-4-[2-(1-imino-6-methylcarbamoyl-5-propoxy-1,3-dihydro-isoindol-2-yl)-acetyl]-6-(pyrrolidin-1-yl)-phenoxy}-acetic acid trifluoroacetate 1H-NMR(DMSO-d6) δ: 0.98(3H, t, J=7.6 Hz), 1.23(3H, t, J=7.2 Hz), 1.38(9H, s), 1.85–1.90(2H, m), 2.82(3H, d, J=4.8 Hz), 3.06–3.12(4H, m), 4.17(2H, q, J=6.4 Hz), 4.20(2H, q, J=7.2), 4.49(2H, s), 4.83(2H, s), 5.49(2H, s), 7.42(1H, br), 7.49(1H, br), 7.54(1H, s), 8.52(1H, s), 9.15(1H, brs), 9.83(1H, brs).

Example 645

{2-tert-Butyl-4-[2-(5-ethoxy-1-imino-6-methylcarbamoyl-1,3-dihydro-isoindol-2-yl)-acetyl]-6-isopropoxy-phenoxy}-acetic acid hydrobromide 1H-NMR(DMSO-d6) δ: 1.33(6H, d, J=6.0 Hz), 1.39(9H, s), 1.44(3H, t, J=7.2 Hz), 2.85(3H, d, J=4.8 Hz), 4.30(2H, q, J=7.2 Hz), 4.64(2H, s), 4.75(1H, m), 4.87(2H, s), 5.53(2H, s), 7.53(1H, d, J=2.0 Hz), 7.54(1H, d, J=2.0 Hz), 8.22(1H, m), 8.59(1H, s), 9.28(1H, m), 9.89(1H, s).

Example 646

{2-tert-Butyl-6-cyclopentyloxy-4-[2-(5-ethoxy-1-imino-6-methylcarbamoyl-1,3-dihydro-isoindol-2-yl)-acetyl]-phenoxy}-acetic acid hydrobromide 1H-NMR(DMSO-d6) δ: 1.38(9H, s), 1.44(3H, t, J=6.8 Hz), 1.63(2H, m), 1.69–1.83(4H, m), 1.95(2H, m), 2.85(3H, d, J=4.8 Hz), 4.30(2H, q, J=6.8 Hz), 4.59(2H, s), 4.87(2H, s), 4.93(1H, m), 5.55(2H, s), 7.48(1H, d, J=2.0 Hz), 7.54 (1H, d, J=2.0 Hz), 8.22(1H, m), 8.59(1H, s), 9.88(1H, s).

Example 647

7-tert-Butyl-5-[2-(5,6-diethoxy-7-fluoro-1-imino-1,3-dihydro-isoindol-2-yl)-acetyl]-benzoxazol-2-yl-cyanamide hydrobromide 1H-NMR(DMSO-d6) δ: 1.39(3H, t, J=7 Hz), 1.48(3H, t, J=7 Hz), 1.51(9H, s), 4.20(2H, q, J=7 Hz), 4.25(2H, J=7 Hz), 4.85(2H, s), 5.52(2H, s), 7.22(1H, s), 7.91(2H, d, J=2 Hz), 8.11(2H, J=2 Hz).

MS: m/e (ESI) 512.0 (MH+)

Example 648

Ethyl {2-tert-butyl-4-[2-(5-dimethylamino-1-imino-6-methylcarbamoyl-1,3-dihydro-isoindol-2-yl)-acetyl]-6-(pyrrolidin-1-yl)-phenoxy}-acetate trifluoroacetate 1H-NMR(DMSO-d6) δ: 1.23(3H, t, J=6.8 Hz), 1.37(9H, s), 1.82–1.91(4H, m), 2.77(3H, d, J=4.4 Hz), 2.91(6H, s), 3.04–3.14(4H, m), 4.21(2H, q, J=6.8 Hz), 4.49(2H, s), 4.73(2H, s), 5.44(2H, s), 7.15(1H, s), 7.42(1H, s), 7.48(1H, s), 8.06(1H, s), 8.33–8.41(1H, m), 8.93(1H, brs), 9.54(1H, brs).

MS: m/e (ESI) 578.3 (MH+)

Example 649

Methyl (acetyl-{3-tert-butyl-5-[2-(7-fluoro-1-imino-5,6-dimethoxy-1,3-dihydro-isoindol-2-yl)-acetyl]-2-hydroxy-phenyl}-amino)-acetate trifluoroacetate 1H-NMR(DMSO-d6) δ: 1.37(9H, s), 2.06(3H, s), 3.67 (3H, s), 3.87(3H, s), 3.96(3H, s), 4.40(2H, s), 4.52(2H, s), 4.81(2H, s), 5.41(2H, s), 7.36(1H, s), 7.79(1H, s), 7.94(1H, s), 9.06(1H, s), 9.34(1H, s), 10.90(1H, s).

Example 650

{2-tert-Butyl-4-[2-(5-ethoxy-1-imino-6-methylcarbamoyl-1,3-dihydro-isoindol-2-yl)-acetyl]-phenylamino}-acetic acid trifluoroacetate 1H-NMR(DMSO-d6) δ: 1.33(3H, t, J=7.0 Hz), 1.38(9H, s), 2.80(3H, d, J=7.2 Hz), 4.26(2H, s), 4.26(2H, q, J=7.0 Hz), 4.82(2H, s), 5.38(2H, s), 7.49(1H, d, J=6.0 Hz), 7.52 (1H, s), 7.73(1H, dd, J=6.0, 2.0 Hz), 7.77(1H, d, J=2.0 Hz), 8.15–8.24(1H, m), 8.55(1H, s), 9.18–9.23(1H, m), 9.78–9.82(1H, m).

Example 651

Ethyl (2-tert-butyl-4-[2-(5-ethoxy-1-imino-6-methylcarbamoyl-1,3-dihydro-isoindol-2-yl)-acetyl]-phenylamino)-acetate hydrobromide 1H-NMR(DMSO-d6) δ: 1.19(3H, t, J=7.2 Hz), 1.40(9H, s), 1.41(3H, t, J=6.8 Hz), 2.82(3H, d, J=4.8 Hz), 4.12(2H, q, J=7.2 Hz), 4.18(2H, d, J=6.4 Hz), 4.27(2H, q, J=6.8 Hz), 4.82(2H, s), 5.36(2H, s), 5.92(1H, t, J=6.8 Hz), 6.57(1H, d, J=8.8 Hz), 7.51(1H, s), 7.72(1H, dd, J=8.8, 2.0 Hz), 8.20 (1H, q, J=4.8 Hz), 8.54(1H, s).

Example 652

2-[2-(8-tert-Butyl-3-oxo-3,4-dihydro-2H-benzo[1,4]oxazin-6-yl)-2-oxo-ethyl]-6-ethoxy-3-imino-2,3-dihydro-1H-isoindole-5-carboxylic acid methylamide hydrobromide 1H-NMR(DMSO-d6) δ: 1.39(9H, s), 1.43(3H, t, J=6.8 Hz), 2.84(3H, d, J=4, 4 Hz), 4.30(2H, q, J=6.8 Hz), 4.72(2H, s), 4.86(2H, s), 5.47(2H, s), 7.44(1H, d, J=2.0 Hz), 7.56(2H, s), 8.22(1H, q, J=4.4 Hz), 8.58(1H, s), 9.20(1H, s), 9.86(1H, s), 10.95(1H, s).

Example 653

2-[2-(8-tert-Butyl-4-methyl-3-oxo-3,4-dihydro-2H-benzo[1,4]oxazin-6-yl)-2-oxo-ethyl]-6-ethoxy-3-imino-2,3-dihydro-1H-isoindole-5-carboxylic acid methylamide hydrobromide 1H-NMR(DMSO-d6) δ: 1.40(9H, s), 1.44(3H, t, J=6.8 Hz), 2.85(3H, d, J=4.8 Hz), 3.37(3H, s), 4.30(2H, q, J=6.8 Hz), 4.78(2H, s), 4.88(2H, s), 5.56(2H, s), 7.56(1H, s), 7.64(1H, d, J=1.6 Hz), 7.66(1H, d, J=1.6 Hz), 8.23(1H, q, J=4.8 Hz), 8.58(1H, s), 9.24(1H, s), 9.88(1H, s).

Example 654

2-[2-(8-tert-Butyl-4-methyl-3,4-dihydro-2H-benzo[1,4]oxazin-6-yl)-2-oxo-ethyl]-6-dimethylamino-3-imino-2,3-dihydro-1H-isoindole-5-carboxylic acid methylamide hydrobromide 1H-NMR(DMSO-d6) δ: 1.36(9H, s), 2.79(3H, d, J=4.8 Hz), 2.92(3H, s), 2.93(6H, s), 4.35(2H, t, J=4.4), 4.75(2H, s), 5.43(2H, s), 7.16(1H, s), 7.18(1H, d, J=2.0 Hz), 7.29(1H, d, J=2.0 Hz), 8.08(1H, s), 8.39(1H, q, J=4.8 Hz), 8.99(1H, s), 9.53(1H, s).

Example 655

4-{2-tert-Butyl-4-[2-(5-ethoxy-1-imino-6-methylcarbamoyl-1,3-dihydro-isoindol-2-yl)-acetyl]-6-(pyrrolidin-1-yl)-phenoxy}-butyric acid trifluoroacetate 1H-NMR(DMSO-d6) δ: 1.38(9H, s), 1.41(3H, t, J=7.2 Hz), 1.85–1.94(4H, m), 1.97–2.06(2H, m), 2.36–2.44(2H, m), 2.82(3H, d, J=4.8 Hz), 3.07–3.16(4H, m), 3.85(2H, t, J=6.8 Hz), 4.27(2H, q, J=7.2 Hz), 4.83(2H, s), 5.41–5.50 (2H, m), 7.36(1H, s), 7.46(1H, s), 7.53(1H, s), 8.16–8.24 (1H, m), 8.55(1H, m).

MS: m/e (ESI) 579.4 (MH+)

Example 656

4-{2-tert-Butyl-4-[2-(5,6-diethoxy-7-fluoro-1-imino-1,3-dihydro-isoindol-2-yl)-acetyl]-6-(pyrrolidin-1-yl)-phenoxy}-buric acid trifluoroacetate 1H-NMR(DMSO-d6) δ: 1.29(3H, t, J=6.8 Hz), 1.35–1.42 (12H, m), 1.82–1.92(4H, m), 1.94–2.08(2H, m), 2.41(2H, t, J=7.2 Hz), 3.06–3.16(4H, m), 3.60–3.80(2H, m), 4.11(2H, q, J=6.8 Hz), 4.20(2H, q, J=6.8 Hz), 4.78(2H, s), 5.46(2H, s), 7.33(1H, s), 7.35(1H, d, J=2.4 Hz), 7.45(1H, d, J=2.4 Hz).
MS: m/e (ESI) 584.4 (MH+)

Example 657

5-{2-tert-Butyl-4-[2-(5-ethoxy-1-imino-6-methylcarbamoyl-1,3-dihydro-isoindol-2-yl)-acetyl]-6-(pyrrolidin-1-yl}-phenoxy)-pentanoic acid trifluoroacetate 1H-NMR(DMSO-d6) δ: 1.38(9H, s), 1.41(3H, t, J=6.8 Hz), 1.60–1.70(2H, m), 1.75–1.84(2H, m), 1.86–1.94(4H, m), 2.29(2H, t, J=7.2 Hz), 2.82(3H, d, J=4.8 Hz), 3.08–3.17 (4H, m), 3.78–3.92(2H, m), 4.27(2H, q, J=6.8 Hz), 4.83(2H, s), 5.47(2H, s), 7.36(1H, s), 7.46(1H, s), 7.53(1H, s), 8.03–8.27(1H, m), 8.55(1H, s), 9.15(1H, brs), 9.84(1H, brs).
MS: m/e (ESI) 593.4 (MH+)

Example 658

5-{2-tert-Butyl-4-[2-(5,6-diethoxy-7-fluoro-1-imino-1,3-dihydro-isoindol-2-yl)-acetyl]-6-(pyrrolidin-1-yl)-phenoxy)-pentanoic acid trifluoroacetate 1H-NMR(DMSO-d6) δ: 1.28(3H, t, J=6.8 Hz), 1.33–1.46 (12H, m), 1.60–1.71(2H, m), 1.75–1.84(2H, m), 1.85–1.96 (4H, m), 2.29(2H, t, J=7.2 Hz), 3.07–3.18(4H, m), 3.76–3.93 (2H, m), 4.11(2H, q, J=6.8 Hz), 4.20(2H, q, J=6.8 Hz), 4.78(2H, s), 5.46(2H, s), 7.33(1H, s), 7.35(1H, s), 7.45(1H, s), 9.06(1H, brs), 9.28(1H, brs).
MS: m/e (ESI) 598.4 (MH+)

Example 659

Ethyl {2-tert-butyl-4-[2-(3-ethoxy-7-imino-2-methylcarbamoyl-5,7-dihydro-pyrrolo[3,4-b]pyridin-6-yl)-acetyl]-6-(pyrrolidin-1-yl)-phenoxy}-acetate hydrochloride 1H-NMR(DMSO-d6) δ: 1.23(3H, t, J=7.0 Hz), 1.26–1.44 (12H, m), 1.87(4H, brs), 2.77(3H, s), 3.11(4H, brs), 4.14–4.30(4H, m), 4.49(2H, s), 4.87(2H, s), 5.55(2H, s), 7.42(1H, s), 7.49(1H, s), 8.53(1H, brd), 9.46(1H, brs), 9.97(1H, brs).

Example 660

[2-tert-Butyl-4-[2-(5-ethoxy-1-imino-6-methylcarbamoyl-1,3-dihydro-isoindol-2-yl)-acetyl]-6-(2-oxo-pyrrolidin-1-yl)-phenoxy]-acetic acid trifluoroacetate 1H-NMR(DMSO-d6) δ: 1.27–1.46(12H, m), 2.02–2.16 (2H, m), 2.42(2H, d, J=8.1 Hz), 2.82(3H, d, J=4.5 Hz), 3.63(2H, t, J=7.0 Hz), 4.27(2H, q, J=6.8 Hz), 4.45(2H, s), 4.85(2H, s), 5.45(2H, s), 7.54(1H, s), 7.84(2H, s), 8.17–8.23 (1H, m), 8.55(1H, s).

Example 661

[2-tert-Butyl-4-[2-(5,6-diethoxy-7-fluoro-1-imino-1,3-dihydro-isoindol-2-yl)-acetyl]-6-(2-oxo-pyrrolidin-1-yl)-phenoxy]-acetic acid trifluoroacetate 1H-NMR(DMSO-d6) δ: 1.26(3H, t, J=7.1 Hz), 1.33–1.45 (12H, m), 2.04–2.17(2H, m), 2.42(2H, t, J=8.0 Hz), 3.63 (2H, brt, J=6.2 Hz), 4.11(2H, q, J=7.1 Hz), 4.21(2H, q, J=7.1 Hz), 4.43(2H, s), 4.80(2H, s), 5.45(2H, s), 7.34(1H, s), 7.82(1H, s), 7.83(1H, s).

Example 662

2-[2-(3,5-Di-tert-butyl-4-hydroxy-phenyl)-2-oxo-ethyl]-6-ethoxy-3-imino-2,3-dihydro-1H-isoindole-5-carbonitrile hydrobromide 1H-NMR(DMSO-d6) δ: 1.27(18H, s), 1.33(3H, t, J=7 Hz), 4.18(2H, q, J=7 Hz), 4.71(2H, s), 5.39(2H, s), 7.06(1H, s), 7.65(2H, s), 8.53(1H, s).
MS: m/e (ESI) 448.0 (MH+)

Example 663

7-tert-Butyl-5-[2-(5,6-diethoxy-7-fluoro-1-imino-1,3-dihydro-isoindol-2-yl)-acetyl]-1H-benzimidazol-2-yl-cyanamide hydrochloride 1H-NMR(DMSO-d6) δ: 1.38(3H, t, J=7 Hz), 1.45(3H, t, J=7 Hz), 1.54(9H, s), 4.18(2H, q, J=7 Hz), 4.26(2H, q, J=7 Hz), 4.92(2H, s), 5.59(2H, s), 7.23(2H, s), 8.06(1H, s), 8.22(1H, s).
MS: m/e (ESI) 511.0 (MH+)

Example 664

2-[2-(8-tert-Butyl-4-methyl-2-oxo-3,4-dihydro-2H-benzo[1,4]oxazin-6-yl)-2-oxo-ethyl]-6-ethoxy-3-imino-2,3-dihydro-1H-isoindole-5-carboxylic acid methylamide hydrobromide 1H-NMR(DMSO-d6) δ: 1.41(9H, s), 1.44(3H, t, J=6.8 Hz), 2.77(3H, s), 2.85(3H, d, J=4.8 Hz), 3.61(2H, s), 4.30 (2H, q, J=6.8 Hz), 4.86(2H, s), 5.47(2H, s), 7.56(1H, s), 7.67(1H, d, J=2.0 Hz), 7.86(1H, d, J=2.0 Hz), 8.22(1H, m), 8.59(1H, s).

Example 665

3-{2-tert-Butyl-4-[2-(5-ethoxy-1-imino-6-methylcarbamoyl-1,3-dihydro-isoindol-2-yl)-acetyl]-benzoylamino}-propanoic acid trifluoroacetate 1H-NMR(DMSO-d6) δ: 1.39(9H, s), 1.42(3H, t, J=6.8 Hz), 2.50(2H, t, J=6.8 Hz), 3.42(2H, t, J=6.8 Hz), 4.28(2H, t, J=6.8 Hz), 4.88(2H, s), 5.51(2H, s), 7.32(1H, d, J=8.0 Hz), 7.54(1H, s), 7.85(1H, t, J=7.6 Hz), 8.00(1H, s), 8.21(1H, d, J=4.8 Hz), 8.52(1H, t, J=5.2), 8.57(1H, s), 9.28(1H, brs), 9.87(1H, brs).
MS: m/e (ESI) 523.3 (MH+)

Example 666

2-{2-tert-Butyl-4-[2-(5-ethoxy-1-imino-6-methylcarbamoyl-1,3-dihydro-isoindol-2-yl)-acetyl]-benzoylamino)-propanoic acid trifluoroacetate 1H-NMR(DMSO-d6) δ: 1.17–1.44(15H, m), 2.83(3H, d, J=4.4 Hz), 4.28(2H, q, J=6.8 Hz), 4.39–4.42(1H, m), 4.88 (2H, s), 5.51(2H, s), 7.40(1H, d, J=7.6 Hz), 7.54(1H, s), 7.88(1H, d, J=9.6 Hz), 8.01(1H, s), 8.21(1H, d, J=4.4 Hz), 8.57(1H, s), 8.81(1H, d, J=7.6 Hz), 9.28(1H, brs), 9.86(1H, brs).
MS: m/e (ESI) 523.3 (MH+)

Example 667

{2-Cyclopentyl-4-[2-(5-ethoxy-1-imino-6-methylcarbamoyl-1,3-dihydro-isoindol-2-yl)-acetyl]-phenoxy}-acetic acid trifluoroacetate 1H-NMR(DMSO-d6) δ: 1.41(3H, t, J=7.2 Hz), 1.52–1.69 (4H, m), 1.70–1.80(2H, m), 1.93–2.05(2H, m), 2.82(3H, d, J=4.0 Hz), 4.28(2H, q, J=7.2 Hz), 4.85(2H, s), 4.87(2H, s), 5.44(2H, s), 7.05(1H, d, J=8.8 Hz), 7.53(1H, s), 7.83(1H, s), 7.85(1H, s), 8.21(1H, d, J=4.0 Hz), 8.55(1H, s), 9.21(1H, brs), 9.83(1H, brs).
MS: m/e (ESI) 494.4 (MH+)

Example 668

{2-tert-Butyl-4-[2-(5,6-diethoxy-7-fluoro-1-imino-1,3-dihydro-isoindol-2-yl)-acetyl]-6-dimethylaminophenoxy}-acetic acid trifluoroacetate 1H-NMR(DMSO-d6) δ: 1.28(3H, t, J=7.2 Hz), 1.38(9H, s), 1.40(3H, t, J=7.2 Hz), 2.70(6H, s), 4.12(2H, q, J=7.2 Hz), 4.21(2H, q, J=7.2 Hz), 4.66(2H, s), 4.79(2H, s), 5.49(2H, s), 7.34(1H, s), 7.51(1H, s), 7.57(1H, s), 9.06(1H, brs), 9.30 (1H, brs).
MS: m/e (ESI) 530.3 (MH+)

Example 669

{2-tert-Butyl-4-[2-(5,6-diethoxy-7-fluoro-1-imino-1,3-dihydro-isoindol-2-yl)-acetyl]-6-diethylaminophenoxy}-acetic acid trifluoroacetate 1H-NMR(DMSO-d6) δ: 0.95(6H, t, J=7.2 Hz), 1.29(3H, t, J=6.8 Hz), 1.37(9H, s), 1.39(3H, t, J=6.8 Hz), 3.10(4H, q, J=7.2 Hz), 4.13(2H, q, J=6.8 Hz), 4.21(2H, q, J=6.8 Hz), 4.72(2H, s), 4.79(2H, s), 5.47(2H, s), 7.34(1H, s), 7.52(1H, s), 7.59(1H, s), 9.05(1H, brs), 9.29(1H, brs).
MS: m/e (ESI) 558.4 (MH+)

Example 670

2-{2-[3-tert-Butyl-5-(3-carbamoyl-propoxy)-4-hydroxy-phenyl]-2-oxo-ethyl}-6-ethoxy-3-imino-2,3-dihydro-1H-isoindole-5-carboxylic acid methylamide trifluoroacetate 1H-NMR(DMSO-d6) δ: 1.39(9H, s), 1.42(3H, t, J=7 Hz), 1.95–2.03(2H, m), 2.25–2.31(2H, m), 2.83(3H, d, J=5 Hz), 4.03–4.08(2H, m), 4.28(2H, q, J=7 Hz), 4.83(2H, s), 5.45 (2H, s), 7.43(1H, s), 7.51(1H, s), 7.52(1H, s), 8.20(1H, q, J=5 Hz), 8.53(1H, s), 9.17(brs, 1H), 9.46(s, 1H).

Example 671

Ethyl {2-tert-butyl-4-[2-(5,6-diethoxy-7-fluoro-1-imino-1,3-dihydro-isoindol-2-yl)-acetyl]-6-dimethylamino-phenoxy}-acetate hydrochloride 1H-NMR(DMSO-d6) δ: 1.23(3H, t, J=6.8 Hz), 1.29(3H, t, J=7.2 Hz), 1.37–1.41(12H, m), 2.67(6H, s), 4.10(4H, q, J=6.8 Hz), 4.20(4H, q, J=7.2 Hz), 4.73(2H, s), 4.75(2H, s), 5.45(1H, s), 7.31(1H, s), 7.54(1H, s), 7.58(1H, s), 9.07(1H, brs), 9.39(1H, brs).
MS: m/e (ESI) 558.4 (MH+)

Example 672

Ethyl {2-tert-butyl-4-[2-(5,6-diethoxy-7-fluoro-1-imino-1,3-dihydro-isoindol-2-yl)-acetyl]-6-diethylamino-phenoxy}-acetate hydrochloride 1H-NMR(DMSO-d6) δ: 0.94(6H, t, J=7.2 Hz), 1.23(3H, t, J=7.2 Hz), 1.29(3H, t, J=7.2 Hz), 1.37(9H, s), 1.39(6H, t, J=7.2 Hz), 3.07(4H, q, J=7.2), 4.11(2H, q, J=7.2 Hz), 4.20(4H, q, J=7.2 Hz), 4.80(4H, s), 5.52(2H, s), 7.34(1H, s), 7.54(1H, s), 7.60(1H, s), 9.07(1H, brs), 9.39(1H, brs).
MS: m/e (ESI) 586.3 (MH+)

Example 673

{2-tert-Butyl-4-[2-(5-ethoxy-6-ethylcarbamoyl-1-imino-1,3-dihydro-isoindol-2-yl)-acetyl]-6-(pyrrolidin-1-yl)-phenoxy}-acetic acid hydrochloride 1H-NMR(DMSO-d6) δ: 1.13(3H, t, J=7.2 Hz), 1.38(9H, s), 1.42(3H, t, J=7.2 Hz), 1.85–1.93(4H, m), 3.06–3.15(4H, m), 4.25(2H, q, J=7.2 Hz), 4.40(2H, s), 4.84(2H, s), 5.51 (2H, s), 7.41(1H, s), 7.48(1H, s), 7.52(1H, s), 8.23(1H, tJ=4.8 Hz), 8.51(1H, s), 9.21(1H, brs), 9.85(1H, brs).
MS: m/e (ESI) 565.4 (MH+)

Example 674

{2-tert-Butyl-4-[2-(5-ethoxy-1-imino-6-propylcarbamoyl-1,3-dihydro-isoindol-2-yl)-acetyl]-6-(pyrrolidin-1-yl)-phenoxy}-acetic acid hydrochloride 1H-NMR(DMSO-d6) δ: 0.93(3H, t, J=7.2 Hz), 1.38(9H, s), 1.41(3H, t, J=7.2 Hz), 1.49–1.57(2H, m), 1.85–1.92(4H, m), 3.06–3.15(4H, m), 3.21–3.29(2H, m), 4.25(2H, q, J=7.2 Hz), 4.40(2H, s), 4.83(2H, s), 5.51(2H, s), 7.41(1H, s), 7.48(1H, s), 7.52(1H, s), 8.22(1H, t, J=4.8 Hz), 8.50(1H, s), 9.22(1H, brs), 9.86(1H, brs).
MS: m/e (ESI) 579.4 (MH+)

Example 675

Ethyl (2-tert-butyl-4-[2-(5-ethoxy-6-ethylcarbamoyl-1-imino-1,3-dihydro-isoindol-2-yl)-acetyl]-6-(pyrrolidin-1-yl)-phenoxy}-acetate hydrochloride 1H-NMR(DMSO-d6) δ: 1.13(3H, t, J=7.2 Hz), 1.23(3H, t, J=7.2 Hz), 1.38(9H, s), 1.41(3H, t, J=7.2 Hz), 1.84–1.91 (4H, m), 3.06–3.14(4H, m), 4.17–4.28(4H, m), 4.49(2H, s), 4.83(2H, s), 5.52(2H, s), 7.43(1H, s), 7.49(1H, s), 7.52(1H, s), 8.23(1H, t, J=4.8 Hz), 8.52(1H, s), 9.24(1H, brs), 9.86 (1H, brs).
MS: m/e (ESI) 593.4 (MH+)

Example 676

Ethyl (2-tert-butyl-4-[2-(5-ethoxy-1-imino-6-propyl-carbamoyl-1,3-dihydro-isoindol-2-yl)-acetyl]-6-pyrrolidin-1-yl-phenoxy}-acetate hydrochloride 1H-NMR(DMSO-d6) δ: 0.92(3H, t, J=7.2 Hz), 1.23(3H, t, J=7.2 Hz), 1.38(9H, s), 1.41(3H, t, J=7.2 Hz), 1.50–1.58 (2H, m), 1.84–1.92(4H, m), 3.07–3.14(4H, m), 3.21–3.28 (2H, m), 4.17–4.28(4H, m), 4.49(2H, s), 4.84(2H, s), 5.50 (2H, s), 7.43(1H, s), 7.49(1H, s), 7.52(1H, s), 8.22(1H, t, J=4.8 Hz), 8.50(1H, s), 9.19(1H, brs), 9.84(1H, brs).
MS: m/e (ESI) 607.4 (MH+)

Example 677

Ethyl 1-{3-tert-butyl-5-[2-(5-ethoxy-1-imino-6-methylcarbamoyl-1,3-dihydro-isoindol-2-yl)-acetyl]-2-hydroxy-phenyl}-5-oxo-pyrrolidine-2-carboxylate hydrobromide 1H-NMR(DMSO-d6) δ: 1.27(6H, t, J=7 Hz), 1.39(9H, s), 2.29–2.35(1H, m), 2.54–2.75(2H, m), 2.95(1H, dd, J=12, 9 Hz), 3.20(3H, d, J=5 Hz), 4.15–4.28(3H, m), 4.35(2H, q, J=7 Hz), 4.54(1H, d, J=19 Hz), 5.30(1H, d, J=11 Hz), 5.40(1H, d, J=19 Hz), 5.33(1H, d, J=11 Hz), 7.17(1H, s), 7.20(1H, s), 7.95(1H, d, J=2 Hz), 8.17(1H, q, J=5 Hz), 8.38(1H, s), 8.78(1H, d, J=2 Hz), 9.45(1H, brs), 10.02(1H, br, 2), 10.08 (1H, brs).
MS: m/e (ESI) 579.0 (MH+)

Example 678

Ethyl 1-{3-tert-butyl-5-[2-(5,6-diethoxy-7-fluoro-1-imino-1,3-dihydro-isoindol-2-yl)-acetyl]-2-hydroxy-phenyl}-5-oxo-pyrrolidine-2-carboxylate hydrobromide 1H-NMR(DMSO-d6) δ: 1.28(3H, t, J=7 Hz), 1.41(3H, t, J=7 Hz), 1.42(9H, s), 1.54(3H, t, J=7 Hz), 2.24–2.31(1H, m), 2.58(1H, ddd, J=14, 8, 3 Hz), 2.66(td, J=14, 5 Hz), 2.93(1H, ddd, J=14, 11, 8 Hz), 4.16–4.28(7H, m), 4.70(1H, d, J=19 Hz), 5.05(1H, d, J=19 Hz), 5.17(1H, d, J=19 Hz), 5.32(1H, d, J=19 Hz), 6.88(1H, s), 7.93(1H, d, J=2 Hz), 8.35(1H, d, J=2 Hz), 8.83(1H, s).
MS: m/e (ESI) 584.0 (MH+)

Example 679

Ethyl 1-{3-tert-butyl-5-[2-(5-ethoxy-1-imino-6-methylcarbamoyl-1,3-dihydro-isoindol-2-yl)-acetyl]-2-methoxy-phenyl}-5-oxo-pyrrolidine-2-carboxylate hydrobromide 1H-NMR(DMSO-d6) δ: 1.18(3H, t, J=7 Hz), 1.42(9H, s), 1.60(3H, t, J=7 Hz), 2.32–2.36(1H, m), 2.54–2.67(2H, m), 2.77–2.84(1H, m), 3.16(3H, d, J=5 Hz), 3.80(3H, s), 4.11–4.22(2H, m), 4.36(2H, q, J=7 Hz), 4.74(1H, d, J=19 Hz), 4.75(1H, m), 4.93(1H, d, J=19 Hz), 5.69(1H, d, J=18 Hz), 6.56(1H, d, J=18 Hz), 7.21(1H, s), 7.25(1H, s), 8.05 (1H, d, J=2 Hz), 8.13(1H, d, J=2 Hz), 8.19(1H, q, J=5 Hz), 9.48(1H, s).
MS: m/e (ESI) 593.0 (MH+)

Example 680

Ethyl 1-{3-tert-Butyl-5-[2-(5,6-diethoxy-7-fluoro-1-imino-1,3-dihydro-isoindol-2-yl)-acetyl]-2-methoxy-phenyl}-5-oxo-pyrrolidine-2-carboxylate hydrobromide 1H-NMR(DMSO-d6) δ: 1.18(3H, t, J=7 Hz), 1.42(3H, t, J=7 Hz), 1.43(9H, s), 1.54(3H, t, J=7 Hz), 2.31–2.36(1H, m), 2.54–2.65(2H, m), 2.76–2.84(1H, m), 3.81(3H, s), 4.15–4.23(6H, m), 4.65(1H, d, J=18 Hz), 4.74(1H, dt, J=2, 6 Hz), 4.86(1H, d, J=18 Hz), 5.61(1H, d, J=19 Hz), 6.87(1H, s), 6.98(1H, brs), 8.03(1H, d, J=2 Hz), 8.11(1H, d, J=2 Hz).
MS: m/e (ESI) 593.0 (MH+)

Example 681

2-[2-(3,5-Di-tert-butyl-4-hydroxy-phenyl)-2-oxo-ethyl]-7-ethoxy-3-imino-2,3-dihydro-1H-isoindole-5-carboxylic acid methylamide hydrobromide 1H-NMR(DMSO-d6) δ: 1.40(3H, t, J=6.8 Hz), 1.44(18H, s), 2.86(3H, d, J=4.4 Hz), 4.30(2H, q, J=6.8 Hz), 4.83(2H, s), 5.50(2H, s), 7.77(2H, s), 7.81(1H, s), 8.34(1H, s), 8.72 (1H, m).

Example 682

2-[2-(5-tert-Butyl-2-oxo-1,2,3,4-tetrahydro-quinolin-7-yl)-2-oxo-ethyl]-6-ethoxy-3-imino-2,3-dihydro-1H-isoindole-5-carboxylic acid methylamide hydrobromide 1H-NMR(DMSO-d6) δ: 1.43(12H, m), 2.45(2H, t, J=7.2 Hz), 2.84(3H, d, J=4.8 Hz), 3.18(2H, t, J=7.2 Hz), 4.30(2H, q, J=6.8 Hz), 4.87(2H, s), 5.47(2H, s), 7.41(1H, d, J=1.6 Hz), 7.56(1H, s), 7.61(1H, d, J=1.6 Hz), 8.23(1H, q, J=4.8 Hz), 8.58(1H, s), 9.22(1H, s), 9.86(1H, s), 10.33(1H, s).

Example 683

2-{2-[3-tert-Butyl-5-(3-carbamoyl-propoxy)-4-hydroxy-phenyl]-2-oxo-ethyl}-6-ethoxy-3-imino-2,3-dihydro-1H-isoindole-5-carboxamide trifluoroacetate 1H-NMR(DMSO-d6) δ: 1.39(9H, s), 1.42(3H, t, J=6.8 Hz), 1.93–2.04(2H, m), 2.28(2H, t, J=7.2 Hz), 4.05(2H, t, J=6.8 Hz), 4.28(2H, q, J=6.8 Hz), 4.84(2H, s), 5.45(2H, s), 6.83(1H, brs), 7.33(1H, brs), 7.44(1H, s), 7.52(1H, s), 7.53 (1H, s), 7.70(1H, brs), 7.78(1H, brs), 8.63(1H, s), 9.18(1H, brs), 9.46(1H, brs), 9.82(1H, brs).
MS: m/e (ESI) 511.3 (MH+)

Example 684

2-{2-[3-tert-Butyl-5-(3-carbamoyl-propoxy)-4-hydroxy-phenyl]-2-oxo-ethyl}-6-ethoxy-3-imino-2,3-dihydro-1H-isoindole-5-carboxylic acid dimethylamide trifluoroacetate 1H-NMR(DMSO-d6) δ: 1.29–1.46(12H, m), 1.93–2.06 (2H, m), 2.23–2.33(2H, m), 2.78(3H, s), 2.99(3H, s), 4.01–4.12(2H, m), 4.17–4.28(2H, m), 4.83(3H, s), 5.45(3H, s), 6.83(1H, brs), 7.33(1H, brs), 7.44(1H, s), 7.49(1H, s), 7.52(1H, s), 8.03(1H, s), 9.16(1H, brs), 9.46(1H, brs), 9.67 (1H, brs).
MS: m/e (ESI) 539.4 (MH+)

Example 685

2-{2-[3-tert-Butyl-5-(3-carbamoyl-propoxy)-4-hydroxy-phenyl]-2-oxo-ethyl}-6-dimethylamino-3-imino-2,3-dihydro-1H-isoindole-5-carboxylic acid methylamide trifluoroacetate 1H-NMR(DMSO-d6) δ: 1.39(9H, s), 1.93–2.04(2H, m), 2.23–2.33(2H, m), 2.77(3H, d, J=4.4 Hz), 2.93(6H, s), 4.01–4.09(2H, m), 4.73(2H, s), 5.40(2H, s), 7.14(1H, s), 7.43(1H, d, J=2.0 Hz), 7.51(1H, d, J=2.0 Hz), 8.06(1H, s), 8.34–8.39(1H, m), 8.86(1H, brs), 9.44(1H, brs), 9.52(1H, brs).

Example 686

4-{3-tert-Butyl-5-[2-(5,6-diethoxy-7-fluoro-1-imino-1,3-dihydro-isoindol-2-yl)-acetyl]-2-hydroxy-phenoxy}-butylamide trifluoroacetate 1H-NMR(DMSO-d6) δ: 1.28(3H, t, J=6.8 Hz), 1.34–1.46 (12H, m), 1.94–2.04(2H, m), 2.24–2.32(2H, m), 4.00–4.08 (2H, m), 4.11(2H, q, J=6.8 Hz), 4.21(2H, q, J=6.8 Hz), 4.78(2H, s), 5.45(2H, s), 6.82(1H, brs), 7.28–7.36(2H, m), 7.42(1H, s), 7.50(1H, s), 9.00–9.08(1H, m), 9.32(1H, brs), 9.46(1H, s).

Example 687

4-{3-tert-Butyl-5-[2-(7-fluoro-1-imino-5,6-dimethoxy-1,3-dihydro-isoindol-2-yl)-acetyl]-2-hydroxy-phenoxy}-butylamide trifluoroacetate 1H-NMR(DMSO-d6) δ: 1.40(9H, s), 1.92–2.05(2H, m), 2.23–2.34(2H, m), 3.86(3H, s), 3.95(3H, s), 4.01–4.09(2H, m), 4.81(2H, s), 5.46(2H, s), 6.83(1H, brs), 7.31–7.38(2H, m), 7.42(1H, s), 7.50(1H, s), 9.04–9.11(1H, m), 9.30–9.38 (1H, m), 9.46(1H, s).

Example 688

4-{3-tert-Butyl-5-[2-(2-ethyl-7-imino-5,7-dihydro-pyrrolo[3,4-b]pyridin-6-yl)-acetyl]-2-hydroxy-phenoxy}-butylamide trifluoroacetate 1H-NMR(DMSO-d6) δ: 1.30(3H, t, J=7.2 Hz), 1.40(9H, s), 1.94–2.05(2H, m), 2.24–2.34(2H, m), 2.95(2H, q, J=7.2 Hz), 4.01–4.11(2H, m), 4.85(2H, s), 5.53(2H, s), 6.82(1H, brs), 7.34(1H, brs), 7.44(1H, s), 7.51(1H, s), 7.73(1H, d, J=8.0 Hz), 8.18(1H, d, J=8.0 Hz), 9.46(1H, brs), 9.52–9.60 (1H, m), 9.82–9.90(1H, m).

Example 689

4-{3-tert-Butyl-5-[2-(2-cyclopropyl-7-imino-5,7-dihydro-pyrrolo[3,4-b]pyridin-6-yl)-acetyl]-2-hydroxy-phenoxy}-butylamide trifluoroacetate 1H-NMR(DMSO-d6) δ: 1.03–1.13(4H, m), 1.41(9H, s), 1.94–2.05(2H, m), 2.24–2.38(3H, m), 4.01–4.09(2H, m), 4.82(2H, s), 5.53(2H, s), 6.83(1H, brs), 7.35(1H, brs), 7.44 (1H, s), 7.52(1H, s), 7.72(1H, d, J=8.0 Hz), 8.10(1H, d, J=8.0 Hz), 9.47(1H, brs), 9.48–9.56(1H, m), 9.62–9.70(1H, m).

Example 690

2-{2-[3-tert-Butyl-5-(3-carbamoyl-propoxy)-4-hydroxy-phenyl]-2-oxo-ethyl}-3-imino-6-propoxy-2,3-dihydro-1H-isoindole-5-carboxylic acid methylamide trifluoroacetate 1H-NMR(DMSO-d6) δ: 0.99(3H, t, J=7.2 Hz), 1.41(9H, s), 1.75–1.87(2H, m), 1.93–2.02(2H, m), 2.24–2.32(2H, m), 2.82(3H, d, J=4.4 Hz), 4.02–4.08(2H, m), 4.13–4.20(2H, m), 4.83(2H, s), 5.46(2H, s), 6.83(1H, brs), 7.34(1H, brs), 7.42 (1H, s), 7.51(1H, s), 7.54(1H, s), 8.15–8.21(1H, m), 8.52 (1H, s), 9.18(1H, brs), 9.46(1H, brs), 9.82(1H, brs).

Example 691

{6-[2-(5-Ethoxy-1-imino-6-methylcarbamoyl-1,3-dihydro-isoindol-2-yl)-acetyl]-4,4-dimethyl-3,4-dihydro-2H-quinolin-1-yl}-acetic acid hydrochloride 1H-NMR(DMSO-d6) δ: 1.26(6H, s), 1.41(3H, t, J=7.2 Hz), 1.68–1.74(2H, m), 2.82(3H, d, J=4.8 Hz), 3.38–3.46 (2H, m), 4.21(2H, s), 4.27(2H, q, J=7.2 Hz), 4.83(2H, s), 5.35(2H, s), 6.57(1H, d, J=8.0 Hz), 7.52(1H, s), 7.63(1H, d, J=8.0 Hz), 7.75(1H, s), 8.20(1H, q, J=4.8 Hz), 8.55(1H, s), 9.18(1H, brs), 9.78(1H, brs).

MS: m/e (ESI) 493.3 (MH+)

Example 692

{6-[2-(5,6-Diethoxy-7-fluoro-1-imino-1,3-dihydro-isoindol-2-yl)-acetyl]-4,4-dimethyl-3,4-dihydro-2H-quinolin-1-yl}-acetic acid hydrochloride 1H-NMR(DMSO-d6) δ: 1.26(6H, s), 1.29(3H, t, J=7.2 Hz), 1.39(3H, t, J=7.2 Hz), 1.68–1.74(2H, m), 3.38–3.45 (2H, m), 4.07–4.22(4H, m), 4.20(2H, s), 4.77(2H, s), 5.35 (2H, s), 6.57(1H, d, J=8.4 Hz), 7.31(1H, s), 7.61(1H, d, J=8.4 Hz), 7.75(1H, s), 8.99(1H, brs), 9.33(1H, brs).

MS: m/e (ESI) 498.3 (MH+)

Example 693

{2-tert-Butyl-4-[2-(5-ethoxy-1-imino-6-methylcarbamoyl-1,3-dihydro-isoindol-2-yl)-acetyl]-6-piperidin-1-yl-phenoxy}-acetic acid trifluoroacetate 1H-NMR(DMSO-d6) δ: 1.39(9H, s), 1.43(3H, t, J=7 Hz), 1.49–1.57(2H, m), 1.63–1.70(4H, m), 2.85(3H, d, J=5 Hz), 2.88–2.98(4H, m), 4.30(2H, q, J=7 Hz), 4.85(2H, s), 4.87 (2H, s), 5.52(2H, s), 7.56(1H, s), 7.58(1H, s), 7.63(1H, s), 8.23(1H, q, J=5 Hz), 8.58(1H, s), 9.22(1H, brs), 9.87(1H, brs).

Example 694

{2-tert-Butyl-4-[2-(5-ethoxy-1-imino-6-methylcarbamoyl-1,3-dihydro-isoindol-2-yl)-acetyl]-6-morpholino-phenoxy}-acetic acid trifluoroacetate 1H-NMR(DMSO-d6) δ: 1.39(9H, s), 1.43(3H, t, J=7 Hz), 2.85(3H, d, J=5 Hz), 2.95–3.03(4H, m), 3.61–3.68(4H, m), 4.29(2H, q, J=7 Hz), 4.82(2H, s), 4.87(2H, s), 5.52(2H, s), 7.56(1H, s), 7.58(1H, s), 7.63(1H, s), 8.23(1H, q, J=5 Hz), 8.57(1H, s), 9.22(1H, brs), 9.87(1H, brs).

Example 695

{2-tert-Butyl-4-[2-(5,6-diethoxy-7-fluoro-1-imino-1,3-dihydro-isoindol-2-yl)-acetyl]-6-piperidin-1-yl-phenoxy}-acetic acid trifluoroacetate 1H-NMR(DMSO-d6) δ: 1.31(3H, t, J=7 Hz), 1.38(9H, s), 1.42(3H, t, J=7 Hz), 1.50–1.57(2H, m), 1.63–1.71(4H, m), 2.88–2.97(4H, m), 4.13(2H, q, J=7 Hz), 4.23(2H, q, J=7 Hz), 4.80(2H, s), 4.86(2H, s), 5.50(2H, s), 7.35(1H, s), 7.56(1H, s), 7.62(1H, s), 9.07(1H, brs), 9.32(1H, brs).

Example 696

{2-tert-Butyl-4-[2-(5,6-diethoxy-7-fluoro-1-imino-1,3-dihydro-isoindol-2-yl)-acetyl]-6-morpholino-phenoxy}-acetic acid trifluoroacetate 1H-NMR(DMSO-d6) δ: 1.31(3H, t, J=7 Hz), 1.39(9H, s), 1.42(3H, t, J=7 Hz), 2.95–3.03(4H, m), 3.71–3.78(4H, m), 4.13(2H, q, J=7 Hz), 4.23(2H, q, J=7 Hz), 4.80(2H, s), 4.82(2H, s), 5.52(2H, s), 7.35(1H, s), 7.56(1H, s), 7.65(1H, s), 9.07(1H, brs), 9.33(1H, brs).

Example 697

Ethyl 4-{3-tert-butyl-5-[2-(5-ethoxy-1-imino-6-methylcarbamoyl-1,3-dihydro-isoindol-2-yl}-acetyl]-2-hydroxy-phenoxy}-burate hydrobromide 1H-NMR(DMSO-d6) δ: 1.16(3H, t, J=6.5 Hz), 1.32–1.46 (12H, m), 1.95–2.08(2H, m), 2.57(2H, t, J=7.0 Hz), 2.83 (3H, d, J=5.0 Hz), 4.00–4.10(4H, m), 4.26(H, q, J=6.5 Hz), 4.83(2H, s), 5.45(2H, s), 7.40(1H, brs), 7.48–7.55(2H, m), 8.19(1H, 5.0 Hz), 8.54(1H, s).

Example 698

2-{2-[3-tert-Butyl-5-(3-carbamoyl-propoxy)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.34(9H, s), 1.40(3H, t, J=7.0 Hz), 1.94–2.08(2H, m), 2.28(2H, t, J=7.5 Hz), 2.82(3H, s), 3.89(3H, s), 4.06(2H, t, J=5.5 Hz), 4.26(2H, q, J=7.0 Hz), 4.84(2H, s), 5.50(2H, s), 6.80(1H, brs), 7.37(1H, brs), 7.48–7.55(3H, m), 8.17–8.25(1H, m), 8.55(1H, s), 9.25(1H, brs), 9.88(1H, brs).

Example 699

2-{2-[3-tert-Butyl-5-(3-carbamoyl-propoxy)-4-methoxy-phenyl]-2-oxo-ethyl}-6-ethoxy-3-imino-2,3-dihydro-1H-isoindole-5-carboxamide hydrobromide 1H-NMR(DMSO-d6) δ: 1.35(9H, s), 1.42(3H, t, J=7.0 Hz), 1.94–2.07(2H, m), 2.24–2.31(2H, m), 3.90(3H, s), 4.07(2H, t, J=6.5 Hz), 4.27(2H, q, J=7.0 Hz), 4.84(2H, s), 5.49(2H, s), 6.80(1H, brs), 7.37(1H, brs), 7.48–7.54(3H, m), 8.63(1H, s).

Example 700

2-{2-[3-tert-Butyl-5-(3-carbamoyl-propoxy)-4-methoxy-phenyl]-2-oxo-ethyl}-6-dimethylamino-3-imino-2,3-dihydro-1H-isoindole-5-carboxylic acid methylamide hydrobromide 1H-NMR(DMSO-d6) δ: 1.34(9H, s), 1.93–2.08(2H, m), 2.24–2.35(2H, m), 2.76(3H, brs), 2.82(6H, s), 3.89(3H, s), 4.03–4.12(2H, m), 4.74(2H, s), 5.47(2H, s), 6.80(1H, brs), 7.14(1H, s), 7.36(1H, brs), 7.48–7.56(2H, m), 8.07(1H, s), 8.31–8.42(1H, m), 9.01(1H, brs), 9.57(1H, brs).

Example 701

4-{3-tert-Butyl-5-[2-(5,6-diethoxy-7-fluoro-1-imino-1,3-dihydro-isoindol-2-yl)-acetyl]-2-methoxy-phenoxy}-butylamide hydrobromide 1H-NMR(DMSO-d6) δ: 1.26(3H, t, J=7.0 Hz), 1.34(9H, s), 1.40(3H, t, J=7.0 Hz), 1.94–2.07(2H, m), 2.27(2H, t, J=6.5 Hz), 3.88(3H, s), 4.02–4.15(4H, m), 4.21(2H, q, J=7.0 Hz), 4.79(2H, s), 5.48(2H, s), 7.32(1H, s), 7.50(1H, s), 7.51(1H, s).

Example 702

4-{3-tert-Butyl-5-[2-(7-fluoro-1-imino-5,6-dimethoxy-1,3-dihydro-isoindol-2-yl)-acetyl]-2-methoxy-phenoxy}-bulamide hydrobromide 1H-NMR(DMSO-d6) δ: 1.35(9H, s), 1.40(3H, t, J=7.0 Hz), 1.94–2.08(2H, m), 2.26(2H, t, J=6.5 Hz), 3.86(3H, s), 3.89(3H, s), 3.92(3H, s), 4.06(2H, t, J=5.5 Hz), 4.80(2H, s), 5.50(2H, s), 6.80(1H, brs), 7.34–7.39(2H, m), 7.50(1H, s), 7.51(1H, s), 9.10(1H, brs), 9.38(1H, brs).

Example 703

4-{3-tert-Butyl-5-[2-(2-ethyl-7-imino-5,7-dihydro-pyrrolo[3,4-b]pyridin-6-yl)-acetyl]-2-methoxy-phenoxy}-bulamide hydrobromide 1H-NMR(DMSO-d6) δ: 1.30(3H, t, J=7.5 Hz), 1.35(9H, s), 1.94–2.08(2H, m), 2.27(2H, t, J=7.0 Hz), 2.94(2H, q, J=7.5 Hz), 3.89(3H, s), 4.06(2H, t, J=5.5 Hz), 4.85(2H, s), 5.56(2H, s), 6.80(1H, brs), 7.37(1H, brs), 7.50(2H, brs), 7.72(1H, d, J=8.0 Hz), 8.18(1H, d, J=8.0 Hz), 9.56(1H, brs), 9.88(1H, brs).

Example 704

4-{3-tert-Butyl-5-[2-(2-cyclopropyl-7-imino-5,7-dihydro-pyrrolo[3,4-b]pyridin-6-yl)-acetyl]-2-methoxy-phenoxy}-butylamide hydrobromide 1H-NMR(DMSO-d6) δ: 1.05–1.12(4H, m), 1.35(9H, s), 1.94–2.07(2H, m), 2.23–2.36(3H, m), 3.89(3H, s), 4.06(2H, t, J=5.5 Hz), 4.82(2H, s), 5.55(2H, s), 6.80(1H, brs), 7.36(1H, brs), 7.51(2H, brs), 7.72(1H, d, J=8.0 Hz), 8.09(1H, d, J=8.0 Hz), 9.48–9.55(1H, m), 9.64–9.72(1H, m).

Example 705

2-{2-[3-tert-Butyl-5-(3-carbamoyl-propoxy)-4-methoxy-phenyl]-2-oxo-ethyl}-6-ethoxy-3-imino-2,3-dihydro-1H-isoindole-5-carboxylic acid ethylamide hydrobromide 1H-NMR(DMSO-d6) δ: 1.11(3H, t, J=6.0 Hz), 1.24–1.45 (12H, m), 1.96–2.07(2H, m), 2.22–2.33(2H, m), 3.23–3.39 (2H, m), 3.89(3H, s), 4.02–4.12(2H, m), 4.19–4.30(2H, m), 4.83(2H, s), 5.49(2H, s), 6.80(1H, brs), 7.35(1H, brs), 7.51 (3H, brs), 8.23(1H, brs), 8.52(1H, s), 9.21(1H, brs), 9.84 (1H, brs).

Example 706

Methyl 4-tert-butyl-6-[2-(5-ethoxy-1-imino-6-methylcarbamoyl-1,3-dihydro-isoindol-2-yl)-acetyl]-1-methyl-1H-benzimidazole-2-carboxylate hydrobromide 1H-NMR(DMSO-d6) δ: 1.54(9H, s), 1.62(3H, t, J=7 Hz), 3.21(3H, d, J=5 Hz), 4.06(3H, s), 4.37(2H, q, J=7 Hz), 4.38(3H, s), 5.04(2H, s), 6.32(2H, s), 7.21(1H, s), 7.25(1H, s), 7.84(1H, d, J=2 Hz), 8.22(1H, q, J=5 Hz), 8.93(1H, d, J=2 Hz), 9.56(1H, s), 10.44(1H, s).
MS: m/e (ESI) 520.0 (MH+)

Example 707

Ethyl 4-{2-tert-butyl-4-[2-(5-ethoxy-1-imino-6-methylcarbamoyl-1,3-dihydro-isoindol-2-yl)-acetyl]-6-methoxy-phenoxy}-burate hydrobromide 1H-NMR(DMSO-d6) δ: 1.21(3H, t, J=7 Hz), 1.38(9H, s), 1.44(3H, t, J=7 Hz), 2.01–2.09(2H, m), 2.48–2.57(2H, m), 2.85(3H, d, J=5 Hz), 3.88(3H, s), 4.07–4.13(2H, m), 4.09 (2H, q, J=7 Hz), 4.30(2H, q, J=7 Hz), 4.87(2H, s), 5.55(2H, s), 7.53(1H, s), 7.56(1H, s), 7.58(1H, s), 8.22(1H, q, J=5 Hz), 8.58(1H, s), 9.25(1H, brs), 9.87(1H, brs).

Example 708

Ethyl 4-{2-tert-butyl-4-[2-(5,6-diethoxy-7-fluoro-1-imino-1,3-dihydro-isoindol-2-yl)-acetyl]-6-methoxy-phenoxy}-burate hydrobromide 1H-NMR(DMSO-d6) δ: 1.20(3H, t, J=7 Hz), 1.32(3H, t, J=7 Hz), 1.38(9H, s), 1.42(3H, t, J=7 Hz), 2.00–2.09(2H, m), 2.50–2.56(2H, m), 3.88(3H, s), 4.09(2H, q, J=7 Hz), 4.13 (2H, q, J=7 Hz), 4.23(2H, q, J=7 Hz), 4.80(2H, s), 5.71(2H, s), 7.35(1H, s), 7.52(1H, s), 7.56(1H, s).

Example 709

{2-tert-Butyl-4-[2-(5-dimethylamino-1-imino-6-methylcarbamoyl-1,3-dihydro-isoindol-2-yl)-acetyl]-phenylamino}-acetic acid trifluoroacetate 1H-NMR(DMSO-d6) δ: 1.40(9H, s), 2.78(3H, d, J=4.8 Hz), 2.92(6H, s), 4.04–4.10(2H, m), 4.72(2H, s), 5.32(2H, s), 6.57(1H, d, J=8.4 Hz), 7.14(1H, s), 7.73(1H, dd, J=8.4, 2.0 Hz), 7.77(1H, d, J=2.0 Hz), 8.05(1H, s), 8.36(1H, t, J=4.8 Hz), 8.90–8.94(1H, m), 9.45–9.50(1H, m).

Example 710

Ethyl 5-tert-butyl-7-[2-(5-ethoxy-1-imino-6-methylcarbamoyl-1,3-dihydro-isoindol-2-yl)-acetyl]-2,3-dihydro-1H-benzo[d]pyrrolo[2,1-b]oxazole-3a-carboxylate hydrobromide 1H-NMR(DMSO-d6) δ: 1.27(3H, J=7 Hz), 1.40(9H, s), 1.61(3H, t, J=7 Hz), 1.91(1H, m), 2.05(1H, m), 2.27(1H, ddd, J=13, 7, 6 Hz), 2.72(1H, ddd, J=13, 7, 6 Hz), 3.12(3H, d, J=5 Hz), 3.44(1H, ddd, J=15, 7, 6 Hz), 3.58(1H, ddd, J=15, 7, 6 Hz), 4.23(1H, dq, J=10, 7 Hz), 4.25(1H, dq, J=10, 7 Hz), 4.45(2H, brs), 4.71(1H, d, J=18 Hz), 4.99(1H, d, J=18 Hz), 5.70(1H, d, J=19 Hz), 6.46(1H, d, J=19 Hz), 7.34(1 h, s), 7.56(1H, s), 7.72(1H, s), 8.30(1H, q, J=5 Hz), 9.50(1H, s), 10.19(1H, brs), 10.36(1H, brs).
MS: m/e (ESI) 563.0 (MH+)

Example 711

Ethyl 3-{4-tert-butyl-6-[2-(5-ethoxy-1-imino-6-methylcarbamoyl-1,3-dihydro-isoindol-2-yl)-acetyl]-1-methyl-1H-benzimidazol-2-yl}-propanoate hydrobromide 1H-NMR(DMSO-d6) δ: 1.20(3H, t, J=7 Hz), 1.28(3H, t, J=7 Hz), 1.57(9H, s), 3.03(2H, t, J=7 Hz), 3.18(2H, t, J=7 Hz), 3.19(3H, d, J=5 Hz), 3.92(3H, s), 4.17(2H, q, J=7 Hz), 4.37(2H, q, J=7 Hz), 5.04(2H, s), 6.24(2H, s), 7.20(1H, s), 7.76(1H, s), 8.04(1H, q, J=5 Hz), 8.67(1H, s), 9.56(1H, s), 10.21(1H, brs), 10.32(1H, brs).
MS: m/e (ESI) 562.0 (MH+)

Example 712

{2-tert-Butyl-6-dimethylamino-4-[2-(7-fluoro-1-imino-5,6-dimethoxy-1,3-dihydro-isoindol-2-yl)-acetyl]-phenoxy}-acetic acid trifluoroacetate 1H-NMR(DMSO-d6) δ: 1.38(9H, s), 2.70(6H, s), 3.87 (3H, s), 3.95(3H, s), 4.66(2H, s), 4.80(2H, s), 5.49(2H, s), 7.37(1H, s), 7.51(1H, s), 7.57(1H, s), 9.09(1H, brs), 9.31 (1H, brs).
MS: m/e (ESI) 502.2 (MH+)

Example 713

Ethyl {2-(1-amino-1-methyl-ethyl)-4-[2-(5-ethoxy-1-imino-6-methylcarbamoyl-1,3-dihydro-isoindol-2-yl)-acetyl]-phenoxy}-acetate hydrochloride 1H-NMR(DMSO-d6) δ: 1.224(3H, t, J=7.2 Hz), 1.401 (3H, t, J=6.8 Hz), 1.746(6H, s), 2.813(3H, d, J=4.4 Hz), 4.188(2H, q, J=7.2 Hz), 4.265(2H, q, J=6.8 Hz), 4.852(2H, s), 5.097(2H, s), 5.633(2H, s), 7.269(1H, d, J=8.8 Hz), 7.514(1H, s), 7.943(1H, s), 8.048(1H, d, J=8.8 Hz), 8.18–8.24(1H, m), 8.560(1H, s), 8.587(2H, s), 9.658(1H, s), 9.999(1H, s).

Example 714

Ethyl {2-(1-amino-1-methyl-ethyl)-4-[2-(5,6-diethoxy-7-fluoro-1-imino-1,3-dihydro-isoindol-2-yl)-acetyl]-phenoxy}-acetate hydrochloride 1H-NMR(DMSO-d6) δ: 1.223(3H, t, J=7.2 Hz), 1.283 (3H, t, J=6.8 Hz), 1.389(3H, t, J=6.8 Hz), 1.759(6H, s), 4.103(2H, q, J=7.2 Hz), 4.15–4.24(4H, m), 4.816(2H, s), 5.097(2H, s), 5.676(2H, s), 7.263(1H, d, J=8.8 Hz), 7.329

(1H, s), 7.954(1H, d, J=2.0 Hz), 8.034(1H, dd, J=2.0, 8.8 Hz), 8.668(2H, s), 9.141(1H, s), 9.765(1H, s).

Example 715

Ethyl {2-tert-butyl-4-[2-(5-dimethylamino-1-imino-6-methylcarbamoyl-1,3-dihydro-isoindol-2-yl)-acetyl]-phenylamino}-acetate hydrobromide 1H-NMR(DMSO-d6) δ: 1.31(3H, t, J=7.2 Hz), 1.38(9H, s), 2.77(3H, d, J=4.4 Hz), 2.92(6H, s), 3.70–3.82(2H, m), 3.87(2H, s), 4.76(2H, s), 5.36(1H, dd, J=5.6, 2.0 Hz), 5.46(2H, s), 7.15(1H, s), 7.56(1H, d, J=8.0 Hz), 7.92(1H, dd, J=8.0, 2.4 Hz), 8.01(1H, d, J=2.4 Hz), 8.07(1H, s), 8.38(1H, q, J=4.4 Hz), 11.69(1H, s).

Example 716

2-{2-[3-tert-Butyl-4-(3-carbamoyl-propoxy)-5-methoxy-phenyl]-2-oxo-ethyl}-6-ethoxy-3-imino-2,3-dihydro-1H-isoindole-5-carboxamide hydrobromide 1H-NMR(DMSO-d6) δ: 1.36(9H, s), 1.42(3H, t, J=7 Hz), 1.93–2.02(2H, m), 2.21–2.28(2H, m), 3.87(3H, s), 4.03–4.10(2H, m), 4.28(2H, q, J=7 Hz), 4.85(2H, s), 5.51 (2H, s), 6.78(1H, brs), 7.33(1H, brs), 7.51(1H, s), 7.54(1H, s), 7.56(1H, s), 7.70(1H, brs), 7.78(1H, brs), 8.62(1H, s).

Example 717

4-{2-tert-Butyl-4-[2-(5,6-diethoxy-7-fluoro-1-imino-1,3-dihydro-isoindol-2-yl)-acetyl]-6-methoxy-phenoxy}-bulamide hydrobromide 1H-NMR(DMSO-d6) δ: 1.28(3H, t, J=7 Hz), 1.37(9H, s), 1.39(3H, t, J=7 Hz), 1.93–2.02(2H, m), 2.22–2.28(2H, m), 3.87(3H, s), 4.03–4.09(2H, m), 4.11(2H, q, J=7 Hz), 4.21 (2H, q, J=7 Hz), 4.80(2H, s), 5.50(2H, s), 6.78(1H, brs), 7.32(1H, brs), 7.34(1H, s), 7.50(1H, s), 7.54(1H, s).

Example 718

2-{2-[3-tert-Butyl-4-(3-carbamoyl-propoxy)-5-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.38(9H, s), 1.42(3H, t, J=7 Hz), 1.93–2.02(2H, m), 2.21–2.28(2H, m), 2.82(3H, d, J=5 Hz), 3.87(3H, s), 4.03–4.10(2H, m), 4.28(2H, q, J=7 Hz), 4.85 (2H, s), 5.51(2H, s), 6.78(1H, brs), 7.32(1H, brs), 7.51(1H, s), 7.55(1H, s), 7.56(1H, s), 8.21(1H, q, J=5 Hz), 8.56(1H, s).

Example 719

[2-tert-Butyl-4-[2-(5,6-diethoxy-7-fluoro-1-imino-1,3-dihydro-isoindol-2-yl)-acetyl]-6-(3-hydroxy-pyrrolidin-1-yl)-phenoxy]-acetic acid trifluoroacetate 1H-NMR(DMSO-d6) δ: 1.29(3H, t, J=6.8 Hz), 1.38(9H, s), 1.40(3H, t, J=6.8 Hz), 1.78–1.84(1H, m), 1.97–2.05(1H, m), 2.91(1H, brd, J=10.4 Hz), 3.04–3.09(1H, m), 3.21–3.40 (2H, m), 4.11(2H, q, J=6.8 Hz), 4.20(2H, q, J=6.8 Hz), 4.32(2H, ABq, J=16.0 Hz), 4.34(1H, br), 4.78(2H, s), 5.49 (2H, s), 7.33(1H, s), 7.35(1H, s), 7.44(1H, s).

MS: m/e (ESI) 572.4 (MH+)

Example 720

[2-tert-Butyl-4-[2-(2-cyclopropyl-7-imino-5,7-dihydro-pyrrolo[3,4-b]pyridin-6-yl)-acetyl]-6-(3-hydroxy-pyrrolidin-1-yl)-phenoxy]-acetic acid trifluoroacetate 1H-NMR(DMSO-d6) δ: 1.08–1.10(4H, m), 1.38(9H, s), 1.77–1.84(1H, m), 1.99–2.06(1H, m), 2.08–2.16(1H, m), 2.90–2.96(1H, m), 3.03–3.09(1H, m), 3.29–3.40(2H, m), 4.35(1H, br), 4.39(2H, ABq, J=15.6 Hz), 4.82(2H, s), 5.57 (2H, s), 7.37(1H, d, J=2.0 Hz), 7.45(1H, d, J=2.4 Hz), 7.72(1H, d, J=8.0 Hz), 8.10(1H, d, J=8.0 Hz), 9.47(1H, brs), 9.66(1H, brs).

MS: m/e (ESI) 507.4 (MH+)

Example 721

(1-{3-tert-Butyl-5-[2-(5,6-diethoxy-7-fluoro-1-imino-1,3-dihydro-isoindol-2-yl)-acetyl]-2-hydroxy-phenyl)-pyrrolidin-3-yloxy)-acetic acid trifluoroacetate 1H-NMR(DMSO-d6) δ: 1.29(3H, t, J=6.8 Hz), 1.38(9H, s), 1.39(3H, t, J=6.8 Hz), 1.94–2.01(1H, m), 2.07–2.14(1H, m), 2.94(1H, brd, J=8.0 Hz), 3.01–3.17(2H, m), 3.37–3.42 (1H, m), 3.97(2H, s), 4.11(2H, q, J=6.8 Hz), 4.20(2H, q, J=6.8 Hz), 4.25(1H, br), 4.78(2H, s), 5.47(2H, d, J=8.0 Hz), 7.32(1H, s), 7.57(1H, s), 7.70(1H, s).

MS: m/e (ESI) 572.3 (MH+)

Example 722

(1-{3-tert-Butyl-5-[2-(2-cyclopropyl-7-imino-5,7-dihydro-pyrrolo[3,4-b]pyridin-6-yl)-acetyl]-2-hydroxy-phenyl}-pyrrolidin-3-yloxy)-acetic acid trifluoroacetate 1H-NMR(DMSO-d6) δ: 1.08–1.10(4H, m), 1.39(9H, s), 1.95–2.01(1H, m), 2.10–2.15(1H, m), 2.28–2.33(1H, m), 2.94(1H, brd, J=7.6 Hz), 3.01–3.06(1H, m), 3.09–3.14(1H, m), 3.41(1H, br), 4.00(2H, s), 4.27(1H, br), 4.81(2H, s), 4.53(2H, d, J=6.0 Hz), 7.58(1H, s), 7.69(1H, s), 7.71(1H, d, J=8.0 Hz), 8.09(1H, d, J=8.4 Hz).

MS: m/e (ESI) 507.3 (MH+)

Example 723

Ethyl 4-{2-tert-butyl-4-[2-(2-cyclopropyl-7-imino-5,7-dihydro-pyrrolo[3,4-b]pyridin-6-yl)-acetyl]-6-(pyrrolidin-1-yl)-phenoxy}-butyrate hydrobromide 1H-NMR(DMSO-d6) δ: 1.00–1.14(4H, m), 1.17(3H, d, J=6.8 Hz), 1.37(9H, s), 1.80–1.97(4H, m), 1.99–2.12(2H, m), 2.26–2.37(1H, m), 2.43–2.55(2H and DMSO, m), 3.05–3.18(4H, m), 3.75–3.93(2H, m), 4.05(2H, q, J=6.8 Hz), 4.81(2H, s), 5.54(2H, s), 7.36(1H, s), 7.46(1H, s), 7.71(1H, d, J=8.0 Hz), 8.09(1H, d, J=8.0 Hz), 9.46(1H, brs), 9.65(1H, brs).

MS: m/e (ESI) 547.4 (MH+)

Example 724

Ethyl 5-{2-tert-butyl-4-[2-(2-cyclopropyl-7-imino-5,7-dihydro-pyrrolo[3,4-b]pyridin-6-yl)-acetyl]-6-(pyrrolidin-1-yl)-phenoxy}-pentanoate hydrobromide 1H-NMR(DMSO-d6) δ: 1.05–1.14(4H, m), 1.16(3H, t, J=6.8 Hz), 1.38(9H, s), 1.63–2.00(8H, m), 2.27–2.42(3H, m), 3.06–3.19(4H, m), 3.75–3.93(2H, m), 4.04(2H, q, J=6.8 Hz), 4.81(2H, s), 5.54(2H, s), 7.36(1H, s), 7.46(1H, s), 7.71(1H, d, J=8.0 Hz), 8.09(1H, d, J=8.0 Hz), 9.45(1H, brs), 9.65(1H, brs).
MS: m/e (ESI) 561.4 (MH+)

Example 725

Ethyl 4-[2-tert-butyl-4-[2-(7-fluoro-1-imino-5,6-dimethoxy-1,3-dihydro-isoindol-2-yl)-acetyl]-6-(pyrrolidin-1-yl)-phenoxy}-butyrate hydrobromide 1H-NMR(DMSO-d6) δ: 1.17(3H, t, J=6.8 Hz), 1.37(9H, s), 1.82–1.96(4H, m), 1.99–2.11(2H, m), 2.44–2.55(2H and DMSO, m), 3.05–3.18(4H, m), 3.78–3.91(5H, m), 3.95(3H, s), 4.05(2H, q, J=6.8 Hz), 4.79(2H, s), 5.47(2H, s), 7.35(1H, s), 7.36(1H, s), 7.45(1H, s).
MS: m/e (ESI) 584.3 (MH+)

Example 726

Ethyl 5-{2-tert-butyl-4-[2-(7-fluoro-1-imino-5,6-dimethoxy-1,3-dihydro-isoindol-2-yl)-acetyl]-6-(pyrrolidin-1-yl)-phenoxy}-pentanoate hydrobromide 1H-NMR(DMSO-d6) δ: 1.16(3H, t, J=6.8 Hz), 1.37(9H, s), 1.62–1.99(8H, m), 2.32–2.43(2H, m), 3.03–3.20(4H, m), 3.77–3.92(5H, m), 3.95(3H, s), 4.04(2H, q, J=6.8 Hz), 4.79(2H, s), 5.47(2H, s), 7.36(2H, s), 7.45(1H, s), 9.08(1H, brs), 9.29(1H, brs).
MS: m/e (ESI) 598.4 (MH+)

Example 727

Ethyl 4-{3-tert-butyl-5-[2-(5-ethoxy-1-imino-6-methylcarbamoyl-1,3-dihydro-isoindol-2-yl)-acetyl]-2-methoxy-phenoxy}-burate hydrobromide 1H-NMR(DMSO-d6) δ: 1.17(3H, t, J=7.2 Hz), 1.36(9H, s), 1.41(3H, t, J=6.8 Hz), 2.04–2.08(2H, m), 2.48–2.53(2H, m), 2.82(3H, d, J=4.8 Hz), 3.89(3H, s), 4.04–4.12(4H, m), 4.28(2H, q, J=7.2 Hz), 4.85(2H, s), 5.51(2H, s), 7.50–7.56 (2H, m), 8.21(1H, d, J=5.2 Hz), 8.55(1H, s).
MS: m/e (ESI) 568.3 (MH+)

Example 728

Ethyl 4-{3-tert-butyl-5-[2-(5,6-diethoxy-7-fluoro-1-imino-1,3-dihydro-isoindol-2-yl)-acetyl]-2-methoxy-phenoxy}-butyrate hydrobromide 1H-NMR(DMSO-d6) δ: 1.17(3H, t, J=7.2 Hz), 1.29(3H, t, J=7.2 Hz), 1.36(9H, s), 1.40(3H, t, J=6.8 Hz), 2.03–2.08 (2H, m), 2.47–2.53(2H, m), 3.88(3H, s), 4.04–4.14(6H, m), 4.21(2H, q, J=6.8 Hz), 4.80(2H, s), 5.48(2H, s), 7.34(1H, s), 7.50(1H, d, J=2.0 Hz), 7.52(1H, d, J=2.0 Hz).
MS: m/e (ESI) 573.3 (MH+)

Example 729

Ethyl 4-{3-tert-butyl-5-[2-(7-fluoro-1-imino-5,6-dimethoxy-1,3-dihydro-isoindol-2-yl)-acetyl]-2-methoxy-phenoxy}-burate hydrobromide 1H-NMR(DMSO-d6) δ: 1.17(3H, t, J=7.2 Hz), 1.36(9H, s), 2.05–2.08(2H, m), 2.45–2.54(2H, m), 3.87(3H, s), 3.89 (3H, s), 3.96(3H, s), 4.04–4.12(4H, m), 4.81(2H, s), 5.51 (2H, s), 7.37(1H, s), 7.48–7.54(2H, m).
MS: m/e (ESI) 545.3 (MH+)

Example 730

Ethyl 4-{8-tert-butyl-6-[2-(5-dimethylamino-1-imino-6-methylcarbamoyl-1,3-dihydro-isoindol-2-yl)-acetyl]-2,3-dihydro-benzo[1,4]oxazin-4-yl}-butyrate hydrobromide 1H-NMR(DMSO-d6) δ: 1.41(3H, t, J=7.2 Hz), 1.34(9H, s), 1.78–1.85(2H, m), 2.38(2H, t, J=7.2 Hz), 2.77(3H, d, J=4.8 Hz), 2.91(6H, s), 3.32–3.38(4H, m), 4.04(2H, q, J=7.2 Hz), 4.23–4.28(2H, m), 4.74(1H, s), 5.44(1H, s), 7.15(1H, s), 7.22(2H, s), 8.08(1H, s), 8.38(1H, d, J=4.8 Hz).
MS: m/e (ESI) 578.4 (MH+)

Example 731

Ethyl 4-{8-tert-butyl-6-[2-(7-fluoro-1-imino-5,6-dimethoxy-1,3-dihydro-isoindol-2-yl)-acetyl]-2,3-dihydro-benzo[1,4]oxazin-4-yl}-butyrate hydrobromide 1H-NMR(DMSO-d6) δ: 1.15(3H, t, J=7.2 Hz), 1.34(9H, s), 1.78–1.84(2H, m), 2.38(2H, t, J=6.8 Hz), 3.30–3.38(4H, m), 3.87(3H, s), 3.98(3H, s), 4.04(2H, q, J=7.2 Hz), 4.23–4.28(2H, m), 4.80(1H, s), 5.47(1H, s), 7.21(2H, s), 7.36(1H, s).
MS: m/e (ESI) 556.3 (MH+)

Example 732

4-({3-tert-Butyl-5-[2-(5-ethoxy-1-imino-6-methylcarbamoyl-1,3-dihydro-isoindol-2-yl)-acetyl]-2-hydroxy-phenyl}-methyl-amino)-butyric acid hydrochloride 1H-NMR(DMSO-d6) δ: 1.16(3H, t, J=7.2 Hz), 1.41(9H, s), 1.43(3H, t, J=6.8 Hz), 1.65(2H, quint, J=7.2 Hz), 2.36 (2H, t, J=7.2 Hz), 2.56(3H, s), 2.84(3H, d, J=4.4 Hz), 2.91(1H, t, J=7.2 Hz), 4.03(2H, q, J=7.2 Hz), 4.29(2H, q, J=6.8 Hz), 4.85(2H, s), 5.48(2H, s), 7.55(1H, s), 7.69(1H, s), 7.77(1H, s), 8.22(1H, q, J=4.4 Hz), 8.57(1H, s), 9.22(1H, s), 9.86(1H, s).

Example 733

2-[2-(3-tert-Butyl-4-hydroxy-5-{[3-(hydroxymethyl-carbamoyl)-propyl]-methyl-amino}-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.41(9H, s), 1.43(3H, t, J=7.2 Hz), 1.62(2H, quint, J=7.2 Hz), 2.10(2H, t, J=7.2 Hz), 2.57(3H, s), 2.84(3H, d, J=4.8 Hz), 2.87(2H, t, J=7.2 Hz), 4.29(2H, q, J=7.2 Hz), 4.47(2H, t, J=6.0 Hz), 4.86(2H, s), 5.46(2H, d), 5.51(1H, t, J=6.0 Hz), 7.55(1H, s), 7.68(1H, s), 7.75(1H, s), 8.23(1H, q, J=4.8 Hz), 8.46(1H, t, J=6.0 Hz), 8.57(1H, s), 9.17(1H, s), 9.83(1H, s).

Example 734

2-[2-(7-tert-Butyl-2-methyl-benzoxazol-5-yl)-2-oxo-ethyl]-6-ethoxy-3-imino-2,3-dihydro-1H-isoindole-5-carboxylic acid methylamide hydrobromide 1H-NMR(DMSO-d6) δ: 1.43(3H, t, J=6.8 Hz), 1.49(9H, s), 2.72(3H, s), 2.85(3H, d, J=4.4 Hz), 4.30(2H, q, J=6.8 Hz), 4.90(2H, s), 5.61(2H, s), 7.57(1H, s), 7.85(1H, d, J=1.2 Hz), 8.23(1H, q, J=4.4 Hz), 8.28(1H, d, J=1.2 Hz), 8.59(1H, s), 9.26(1H, s), 9.89(1H, s).

Example 735

Ethyl {5-[2-(5-ethoxy-1-imino-6-methylcarbamoyl-1,3-dihydro-isoindol-2-yl)-acetyl]-1,3,3-trimethyl-2,3-dihydro-1H-indol-2-yl}-acetate hydrobromide 1H-NMR(DMSO-d6) δ: 1.072(6H, s), 1.202(3H, t, J=7.2 Hz), 1.401(3H, t, J=6.8 Hz), 2.57–2.74(2H, m), 2.815(3H, d, J=4.8 Hz), 3.608(1H, t, J=6.4 Hz), 4.116(2H, q, J=7.2 Hz), 4.265(2H, d, J=6.8 Hz), 4.830(2H, s), 5.381(2H, s), 6.608(1H, d, J=8.4 Hz), 7.516(1H, s), 7.612(1H, d, J=1.6 Hz), 7.785(1H, dd, J=1.6, 8.4 Hz), 8.213(1H, q, J=4.8 Hz), 8.537(1H, s), 9.224(1H, s), 9.814(1H, s).

Example 736

Ethyl {5-[2-(5,6-diethoxy-7-fluoro-1-imino-1,3-dihydro-isoindol-2-yl)-acetyl]-1,3,3-trimethyl-2,3-dihydro-1H-indol-2-yl}-acetate hydrobromide 1H-NMR(DMSO-d6) δ: 1.072(6H, s), 1.203(3H, t, J=7.2 Hz), 1.282(3H, t, J=6.8 Hz), 1.387(3H, t, J=6.8 Hz), 2.57–2.74(2H, m), 3.606(1H, t, J=6.4 Hz), 4.07–4.15(4H, m), 4.201(2H, d, J=7.2 Hz), 4.778(2H, s), 5.364(2H, s), 6.606(1H, d, J=8.0 Hz), 7.312(1H, s), 7.600(1H, d, J=1.6 Hz), 7.785(1H, dd, J=1.6, 8.0 Hz).

Example 737

({2-tert-Butyl-4-[2-(5,6-diethoxy-7-fluoro-1-imino-1,3-dihydro-isoindol-2-yl)-acetyl]-phenyl}-methyl-amino)-acetic acid trifluoroacetate 1H-NMR(DMSO-d6) δ: 1.29(3H, t, J=7.2 Hz), 1.39(3H, t, J=6.8 Hz), 1.44(9H, s), 2.62(3H, s), 3.50(2H, s), 4.10(2H, q, J=7.2 Hz), 4.20(2H, q, J=6.8 Hz), 4.80(2H, s), 5.47(2H, s), 7.33(1H, s), 7.65(1H, d, J=8.4 Hz), 7.891H, d, J=8.4 Hz), 7.93(1H, s), 9.02–9.10(1H, m), 9.23–9.34(1H, m).

Example 738

Ethyl [2-tert-butyl-4-[2-(5-ethoxy-1-imino-6-methylcarbamoyl-1,3-dihydro-isoindol-2-yl)-acetyl]-6-(3-hydroxy-pyrrolidin-1-yl)-phenoxy]-acetate hydrochloride 1H-NMR(DMSO-d6) δ: 1.23(3H, t, J=6.8 Hz), 1.37(9H, s), 1.41(3H, t, J=6.8 Hz), 1.78–1.84(1H, m), 1.98–2.09(1H, m), 2.73–2.77(1H, m), 2.82(3H, d, J=4.4 Hz), 2.78–2.84(1H, m), 2.90–2.97(1H, m), 3.03–3.09(1H, m), 4.21(2H, q, J=6.8 Hz), 4.27(2H, q, J=6.8 Hz), 4.35(1H, br,), 4.60(2H, s), 4.83(2H, s), 5.56(2H, s), 7.40(1H, s), 7.47(1H, s), 7.53(1H, s), 8.21(1H, brs), 8.56(1H, br), 9.36(1H, br).

MS: m/e (ESI) 595.5 (MH+)

Example 739

Ethyl [2-tert-butyl-4-[2-(2-cyclopropyl-7-imino-5,7-dihydro-pyrrolo[3,4-b]pyridin-6-yl)-acetyl]-6-(3-hydroxy-pyrrolidin-1-yl)-phenoxy]-acetate hydrochloride 1H-NMR(DMSO-d6) δ: 1.08–1.10(4H, m), 1.23(3H, t, J=6.8 Hz), 1.38(9H, s), 1.77–1.84(1H, m), 1.97–2.05(1H, m), 2.29–2.35(1H, m), 2.93(1H, brd, J=10.0 Hz), 3.02–3.09(1H, m), 3.26–3.42(2H, m), 4.21(2H, q, J=6.8 Hz), 4.33(1H, brs), 4.49(2H, ABq, J=15.6 Hz), 4.82(2H, s), 5.81(2H, s), 7.40(1H, s), 7.46(1H, s), 7.72(1H, d, J=8.4 Hz), 8.09(1H, d, J=8.4 Hz), 9.60(1H, br), 9.67(1H, br).

MS: m/e (ESI) 535.3 (MH+)

Example 740

Ethyl [2-tert-butyl-4-[2-(5,6-diethoxy-7-fluoro-1-imino-1,3-dihydro-isoindol-2-yl)-acetyl]-6-(3-hydroxy-pyrrolidin-1-yl)-phenoxy]-acetate hydrochloride 1H-NMR(DMSO-d6) δ: 1.19(3Ht, J=6.8 Hz), 1.29(3H, t, J=6.8 Hz), 1.38(9H, brs), 1.39(3H, t, J=6.8 Hz), 1.93–2.02(1H, m), 2.10–2.19(1H, m), 2.92(1H, dd, J=4.0, 10.0 Hz), 2.99–3.04(1H, m), 3.12(1H, dd, J=7.6, 15.6 Hz), 3.44(1H, dd, J=6.4, 10.0 Hz), 4.01(1H, q, J=6.8 Hz), 4.12(2H, q, J=6.8 Hz), 4.15(2H, s), 4.21(2H, q, J=6.8 Hz), 4.28(1H, br), 4.78(2H, s), 5.51(2H, s), 7.33(1H, s), 7.59(1H, s), 7.63(1H, s).

MS: m/e (ESI) 600.5 (MH+)

Example 741

Ethyl (1-{3-tert-butyl-5-[2-(5-ethoxy-1-imino-6-methylcarbamoyl-1,3-dihydro-isoindol-2-yl)-acetyl]-2-hydroxy-phenyl}-pyrrolidin-3-yloxy)-acetate hydrochloride 1H-NMR(DMSO-d6) δ: 1.18(3H, t, J=6.8 Hz), 1.39(9H, s), 1.41(3H, t, J=6.8 Hz), 1.94–2.02(1H, m), 2.11–2.18(1H, m), 2.82(3H, d, J=3.6 Hz), 2.94–2.98(1H, m), 3.03–3.09(1H, m), 3.12–3.19(1H, m), 3.45–3.49(1H, m), 4.11(2H, q, J=6.8 Hz), 4.16(2H, s), 4.25(2H, q, J=6.8 Hz), 4.83(2H, s), 5.52(2H, s), 7.52(1H, s), 7.62(1H, s), 7.66(1H, s), 8.21(1H, m), 8.56(1H, s), 9.38(1H, be), 9.93(1H, br).

MS: m/e (ESI) 595.4 (MH+)

Example 742

Ethyl (1-{3-tert-butyl-5-[2-(2-cyclopropyl-7-imino-5,7-dihydro-pyrrolo[3,4-b]pyridin-6-yl)-acetyl]-2-hydroxy-phenyl}-pyrrolidin-3-yloxy)-acetate hydrochloride 1H-NMR(DMSO-d6) δ: 1.08–1.10(4H, m), 1.18(3H, t, J=6.8 Hz), 1.38(9H, s), 1.96–2.03(1H, m), 2.12–2.17(1H, m), 2.28–2.34(1H, m), 2.98(1H, brd, J=9.2 Hz), 3.06–3.11 (1H, m), 3.13–3.19(1H, m), 3.49(1H, dd, J=5.2, 9.6 Hz), 4.11(2H, q, J=6.8 Hz), 4.16(2H, s), 4.30(1H, brs), 4.82(2H, s), 5.58(2H, s), 7.62(1H, s), 7.67(1H, s), 7.71(1H, d, J=8.0 Hz), 8.09(1H, d, J=8.0 Hz), 9.61(1H, brs), 9.66(1H, brs).
MS: m/e (ESI) 535.3 (MH+)

Example 743

2-{2-tert-Butyl-4-[2-(5-ethoxy-1-imino-6-methylcarbamoyl-1,3-dihydro-isoindol-2-yl)-acetyl]-6-(pyrrolidin-1-yl)-phenoxy}-acetoxymethyl 2,2-dimethyl-propionate hydrobromide 1H-NMR(DMSO-d6) δ: 1.15(9H, s), 1.37(9H, s), 1.41 (3H, t, J=7.2 Hz), 1.84–1.89(4H, m), 2.82(3H, d, J=4.8 Hz), 3.06–3.12(4H, m), 4.28(2H, q, J=7.2 Hz), 4.58(2H, s), 4.83(2H, s), 5.49(2H, s), 5.83(2H, s), 7.43(1H, s), 7.49(1H, s), 7.53(1H, s), 8.20(1H, q, J=4.8 Hz), 8.55(1H, s), 9.15(1H, brs), 9.82(1H, brs).
MS: m/e (ESI) 665.4 (MH+)

Example 744

2-(5,6-Diethoxy-7-fluoro-1-imino-1,3-dihydro-isoindol-2-yl)-1-(1,2,3,3-tetramethyl-2,3-dihydro-1H-indol-5-yl)-ethanone hydrobromide H-NMR(DMSO-d6) δ: 1.02(3H, s), 1.14(3H, d, J=6.4 Hz), 1.21–1.30(9H, m), 1.39(3H, t, J=6.8 Hz), 2.79(3H, s), 3.10–3.20(1H, m), 4.10(2H, q, J=6.8 Hz), 4.19(2H, q, J=6.8 Hz), 4.76(2H, s), 5.33(2H, s), 6.59(1H, d, J=8.4 Hz), 7.31 (1H, s), 7.60(1H, s), 7.75(1H, d, J=8, 4 Hz).
MS: m/e (ESI) 454.2 (MH+)

Example 745

Ethyl {2-tert-butyl-4-[2-(5,6-diethoxy-1-fluoro-1-imino-1,3-dihydro-isoindol-2-yl)-acetyl]-6-morpholino-phenoxy}-acetate hydrobromide 1H-NMR(DMSO-d6) δ: 1.27(3H, t, J=7 Hz), 1.31(3H, t, J=7 Hz), 1.39(9H, s), 1.42(3H, t, J=7.0 Hz), 2.95–3.01(4H, m), 3.69–3.77(4H, m), 4.13(2H, q, J=7 Hz), 4.23(2H, q, J=7 Hz), 4.25(2H, q, J=7 Hz), 4.81(2H, s), 4.92(2H, s), 5.53(2H, s), 7.35(1H, s), 7.57(1H, s), 7.66(1H, s), 9.08(1H, brs), 9.33(1H, brs).

Example 746

(1-{3-tert-Butyl-5-[2-(7-fluoro-1-imino-5,6-dimethoxy-1,3-dihydro-isoindol-2-yl)-acetyl]-2-hydroxy-phenyl}-pyrrolidin-3-yloxy)-acetic acid trifluoroacetate 1H-NMR(DMSO-d6) δ: 1.38(9H, s), 1.86–1.96(1H, m), 2.02–2.12(1H, m), 2.89–2.95(1H, m), 3.01–3.18(2H, m), 3.36–3.42(1H, m), 3.86(3H, s), 3.95(3H, s), 3.99(2H, brs), 4.23–4.27(1H, m), 4.80(1H, s), 5.47(2H, d, J=7.2 Hz), 7.35(1H, s), 7.58(1H, s), 7.70(1H, s).
MS: m/e (ESI) 544.4 (MH+)

Example 747

Ethyl (1-{3-tert-butyl-5-[2-(7-fluoro-1-imino-5,6-dimethoxy-1,3-dihydro-isoindol-2-yl)-acetyl]-2-hydroxy-phenyl}-pyrrolidin-3-yloxy)-acetate hydrochloride 1H-NMR(DMSO-d6) δ: 1.19(3H, t, J=6.8 Hz), 1.38(9H, s), 1.96–2.02(1H, m), 2.11–2.19(1H, m), 2.94–2.97(1H, m), 3.02–3.09(1H, m), 3.12–3.18(1H, m), 3.47(1H, dd, J=6.0, 10.4 Hz), 3.86(3H, s), 3.95(3H, s), 4.11(2H, q, J=6.8 Hz), 4.27–4.32(1H, m), 4.79(2H, s), 5.52(2H, s), 7.36(1H, s), 7.60(1H, s), 7.65(1H, s), 9.09(1H, s), 9.45(1H, s).
MS: m/e (ESI) 572.3 (MH+)

Example 748

Methyl 3-{3-tert-butyl-5-[2-(5,6-diethoxy-7-fluoro-1-imino-1,3-dihydro-isoindol-2-yl)-acetyl]-2-hydroxy-benzylamino}-propanoate hydrochloride 1H-NMR(DMSO-d6) δ: 1.29(3H, t, J=6.8 Hz), 1.40(3H, t, J=6.8 Hz), 1.41(9H, s), 2.84(2H, t, J=7.2 Hz), 3.19–3.27 (2H, m), 3.63(3H, s), 4.11(2H, q, J=7.2 Hz), 4.21(2H, q, J=7.2 Hz), 4.31(2H, brs), 4.80(2H, s), 5.51(2H, s), 7.34(1H, s), 7.86(1H, s), 8.10(1H, s), 9.08(1H, s), 9.13–9.17(1H, m), 9.45(1H, s), 10.20(1H, s).
MS: m/e (ESI) 544.3 (MH+)

Example 749

1-{3-tert-Butyl-5-[2-(5,6-diethoxy-7-fluoro-1-imino-1,3-dihydro-isoindol-2-yl)-acetyl]-2-hydroxy-benzyl}-5-oxo-pyrrolidine-2-carboxylic acid trifluoroacetate 1H-NMR(DMSO-d6) δ: 1.29(3H, t, J=6.8 Hz), 1.38(9H, s), 1.40(3H, t, J=6.8 Hz), 1.88–1.98(1H, m), 2.13–2.21(2H, m), 2.28–2.38(1H, m), 3.78–3.84(1H, m), 4.12(2H, q, J=6.8 Hz), 4.20(2H, q, J=6.8 Hz), 4.23(1H, brs), 4.71(1H, d, J=14.4 Hz), 4.78(2H, s), 5.40(2H, s), 7.32(1H, s), 7.69(1H, s), 7.73(1H, s).
MS: m/e (ESI) 570.4 (MH+)

Example 750

Methyl 1-{3-tert-butyl-5-[2-(5,6-diethoxy-7-fluoro-1-imino-1,3-dihydro-isoindol-2-yl)-acetyl]-2-hydroxy-benzyl}-5-oxo-pyrrolidine-2-carboxylate hydrochloride 1H-NMR(DMSO-d6) δ: 1.29(3H, t, J=6.8 Hz), 1.38(9H, s), 1.40(3H, t, J=6.8 Hz), 2.02–2.09(1H, m), 2.32–2.45(3H, m), 3.64(3H, s), 4.12(2H, q, J=6.8 Hz), 4.20(2H, q, J=6.8 Hz), 4.29(1H, d, J=17.6 Hz), 4.39–4.45(1H, m), 4.63(1H, d, J=14.4 Hz), 4.79(2H, s), 5.49(2H, d, J=8.4 Hz), 7.33(1H, s), 7.72(1H, s), 7.78(1H, s), 9.06(1H, s), 9.46(1H, s), 10.03(1H, s).
MS: m/e (ESI) 584.3 (MH+)

Example 751

(Acetyl-{3-tert-butyl-5-[2-(7-fluoro-1-imino-5,6-dimethoxy-1,3-dihydro-isoindol-2-yl)-acetyl]-2hydroxy-benzyl}-amino)-acetic acid trifluoroacetate 1H-NMR(DMSO-d6) δ: 1.35(9H, s), 1.96(3H, s), 2.49 (2H, s), 3.86(3H, s), 3.95(3H, s), 4.39(2H, s), 4.80(2H, s), -

5.47(2H, s), 7.34(1H, s), 7.76(1H, s), 7.88(1H, s), 8.31(1H, s).

MS: m/e (ESI) 530.2 (MH+)

Example 752

Ethyl (4-{3-tert-butyl-5-[2-(5-ethoxy-1-imino-6-methylcarbamoyl-1,3-dihydro-isoindol-2-yl)-acetyl]-benzyl}-piperazin-1-yl)-acetate hydrobromide 1H-NMR(DMSO-d6) δ: 1.16(3H, t, J=7.2 Hz), 1.32(9H, s), 1.41(3H, t, J=7.2 Hz), 2.35–2.55(8H, m), 2.82(3H, d, J=4.0 Hz), 3.18(2H, s), 3.56(2H, s), 4.05(2H, q, J=7.2 Hz), 4.28(2H, q, J=7.2 Hz), 4.86(2H, s), 5.52(2H, s), 7.54(1H, s), 7.67(1H, s), 7.75(1H, s), 7.87(1H, s), 8.21(1H, d, J=4.0), 8.56(1H, s), 9.28(1H, brs).

MS: m/e (ESI) 592.5 (MH+)

Example 753

Ethyl {2-tert-butyl-4-[2-(5-ethoxy-1-methoxycarbonylimino-6-methylcarbamoyl-1,3-dihydro-isoindol-2-yl)-acetyl]-6-(pyrrolidin-1-yl)-phenoxy}-acetate 1H-NMR(DMSO-d6) δ: 1.32(3H, t, J=6.8 Hz), 1.41(9H, s), 1.55(3H, t, J=6.8 Hz), 1.88–1.95(4H, m), 3.01(3H, d, J=4.8 Hz), 3.08–3.25(4H, m), 3.85(3H, s), 4.19–4.35(4H, m), 4.51(2H, s), 4.62(2H, s), 5.10(2H, s), 6.99(1H, s), 7.46(1H, s), 7.56(1H, s), 7.64–7.73(1H, m), 8.81(1H, s).

MS: m/e (ESI) 637.4 (MH+)

Example 754

2-[2-(7-tert-Butyl-2-methoxymethyl-benzoxazol-5-yl)-2-oxo-ethyl]-6-ethoxy-3-imino-2,3-dihydro-1H-isoindole-5-carboxylic acid methylamide hydrobromide 1H-NMR(DMSO-d6) δ: 1.45(3H, t, J=6.8 Hz), 1.50(9H, s), 2.86(3H, d, J=4.4 Hz), 3.47(3H, s), 4.31(2H, q, J=6.8 Hz), 4.82(2H, s), 4.92(2H, s), 5.63(2H, s), 7.51(1H, s), 7.91(1H, d, J=1.6 Hz), 8.23(1H, m), 8.39(1H, d, J=1.6 Hz), 8.61(1H, s), 9.30(1H, m), 9.92(1H, m).

Example 755

Ethyl 7-tert-butyl-5-(2-(5-ethoxy-1-imino-6-methylcarbamoyl-1,3-dihydro-isoindol-2-yl)-acetyl]-benzoxazole-2-carboxylate hydrobromide 1H-NMR(DMSO-d6) δ: 1.40(3H, t, J=6.8 Hz), 1.44(3H, t, J=7.2 Hz), 1.52(9H, s), 2.85(3H, d, J=4.4 Hz), 4.29(2H, q, J=6.8 Hz), 4.49(2H, q, J=7.2 Hz), 4.92(2H, s), 5.63(2H, s), 7.57(1H, s), 8.02(1H, s), 8.24(1H, q, J=4.4 Hz), 8.57(1H, s), 8.60(1H, s), 9.28(1H, s), 9.91(1H, s).

Example 756

{3-tert-Butyl-5-[2-(5-ethoxy-1-imino-6-methylcarbamoyl-1,3-dihydro-isoindol-2-yl)-acetyl]-benzyloxy}-acetic acid trifluoroacetate 1H-NMR(DMSO-d6) δ: 1.33(9H, s), 1.41(3H, t, J=7.2 Hz), 2.82(2H, d, J=4.8), 4.13(2H, s), 4.26(2H, q, J=7.2 Hz), 4.64(2H, s), 4.87(2H, s), 5.52(2H, s), 7.54(1H, s), 7.75(1H, s), 7.82(1H, s), 7.91(1H, s), 8.21(1H, d, J=4.8 Hz), 8.56(1H, s), 9.24(1H, brs), 9.86(1H, brs).

Example 757

2-{2-[3-tert-Butyl-5-(3-cyano-propoxy)-4-hydroxy-phenyl]-2-oxo-ethyl}-6-ethoxy-3-imino-2,3-dihydro-1H-isoindole-5-carboxylic acid methylamide trifluoroacetate 1H-NMR(DMSO-d6) δ: 1.42(9H, s), 1.44(3H, t, J=7.2 Hz), 2.11(2H, m), 2.85(3H, d, J=4.4 Hz), 4.12(2H, t, J=5.6 Hz), 4.30(2H, q, J=7.2 Hz), 4.86(2H, s), 5.49(2H, s), 7.46 (1H, s), 7.55(2H, s), 8.22(1H, m), 8.59(1H, s), 9.21(1H, m), 9.86(1H, m).

Example 758

2-(2-{3-tert-Butyl-4-hydroxy-5-[3-(2-methoxy-ethoxy)-propoxy]-phenyl}-2-oxo-ethyl)-6-ethoxy-3-imino-2,3-dihydro-1H-isoindole-5-carboxylic acid methylamide trifluoroacetate 1H-NMR(DMSO-d6) δ: 1.45(9H, s), 1.53(3H, t, J=7.2 Hz), 2.11(2H, m), 3.30(3H, s), 3.54(2H, m), 3.61(2H, m), 3.69(2H, t, J=7.2 Hz), 4.22(4H, m), 4.36(2H, q, J=7.2 Hz), 4.90(2H, s), 5.43(2H, s), 7.48(1H, sz), 7.52(1H, s), 7.67(1H, s), 8.54(1H, s).

Example 759

Ethyl {4-[2-(1-acetoxymethoxycarbonylimino-5-ethoxy-6-methylcarbamoyl-1,3-dihydro-isoindol-2-yl)-acetyl]-2-tert-butyl-6-(pyrrolidin-1-yl)-phenoxy}-acetate 1H-NMR(DMSO-d6) δ: 1.33(3H, t, J=7.2 Hz), 1.42(9H, s), 1.55(3H, t, J=7.2 Hz), 1.87–1.97(4H, m), 2.15(3H, s), 3.00(3H, d, J=4.8 Hz), 3.11–3.22(4H, m), 4.18–4.36(4H, m), 4.51(2H, s), 4.64(2H, s), 5.14(2H, s), 5.88(2H, s), 6.99(1H, s), 7.44(1H, s), 7.50–7.65(2H, m), 8.88(1H, s).

Example 760

Ethyl 1-{3-tert-butyl-5-[2-(5-ethoxy-1-imino-6-methylcarbamoyl-1,3-dihydro-isoindol-2-yl)-acetyl]-2-methoxy-phenyl}-pyrrolidine-2-carboxylate hydrobromide 1H-NMR(DMSO-d6) δ: 1.10(3H, t, J=7 Hz), 1.41(9H, s), 1.54(3H, t, J=7 Hz), 1.91–2.13(3H, m), 2.45(1H, q, J=7 Hz), 3.13(3H, d, J=5 Hz), 3.32(1H, br, t, J=7 Hz), 3.74(1H, br, t, J=7 Hz), 3.75(3H, s), 4.01(1H, qd, J=7, 2 Hz), 4.02(1H, qd, J=7, 2 Hz), 4.46(2H, brs), 4.58(1H, t, J=7 Hz), 4.86(2H, s), 6.12(2H, s), 7.35(1H, s), 7.61(1H, d, J=2 Hz), 7.66(1H, d, J=2 Hz), 8.30(1H, m), 9.50(1H, m).

MS: m/e (ESI) 579.0 (MH+)

Example 761

Ethyl 1-{3-tert-butyl-5-[2-(5,6-diethoxy-7-fluoro-1-imino-1,3-dihydro-isoindol-2-yl)-acetyl]-2-methoxy-phenyl}-pyrrolidine-2-carboxylate hydrobromide 1H-NMR(DMSO-d6) δ: 1.24(6H, t, J=7 Hz), 1.40(9H, s), 1.53(3H, t, J=7 Hz), 1.92–2.12(3H, m), 2.42–2.49(1H,), 3.35(1H, t, J=6 Hz), 3.71(1H, t, J=6 Hz), 3.73(3H, s), 4.01(2H, m), 4.18(4H, q, J=7 Hz), 4.60(1H, t, J=6 Hz), 4.77(2H, s), 6.09(2H, s), 6.85(1H, s), 7.62(2H, s).
MS: m/e (ESI) 584.0 (MH+)

Example 762

Ethyl 1-{3-tert-butyl-5-[2-(2-cyclopropyl-7-imino-5,7-dihydro-pyrrolo[3,4-b]pyridin-6-yl)-acetyl]-2-methoxy-phenyl}-pyrrolidine-2-carboxylate hydrobromide 1H-NMR(DMSO-d6) δ: 1.11(3H, t, J=7 Hz), 1.15–1.25 (4H, m), 1.40(9H, s), 1.92–2.11(4H, m), 2.15–2.21(1H, m), 2.41–2.49(1H, m), 3.35(1H, t, J=7 Hz), 3.71(1H, t, J=7 Hz), 3.73(3H, s), 4.01(1H, qd, J=7, 4 Hz), 4.02(1H, qd, qd, J=7, 4 Hz), 4.60(1H, t, J=7 Hz), 4.82(2H, s), 6.20(2H, s), 7.54 (1H, d, J=8 Hz), 7.63(1H, d, J=2 Hz), 7.64(1H, d, J=2 Hz), 7.79(1H, d, J=8 Hz).
MS: m/e (ESI) 519.0 (MH+)

Example 763

Ethyl {4-tert-butyl-6-[2-(5-ethoxy-1-imino-6-methylcarbamoyl-1,3-dihydro-isoindol-2-yl)-acetyl]-benzimidazol-1-yl}-acetate hydrobromide 1H-NMR(DMSO-d6) δ: 1.24(3H, t, 7 Hz), 1.41(3H, t, J=7 Hz), 1.57(9H, s), 2.84(3H, d, J=5 Hz), 4.19(2H, q, J=7H), 4.30(2H, q, J=7 Hz), 4.89(2H, s), 5.37(2H, s), 5.54(2H, s), 7.55(1H, s), 7.71(1H, d,=2 Hz), 8.21(1H, q, J=5 Hz), 8.26 (1H, d, J=2 Hz), 8.44(1H, s), 8.57(1H, s).
MS: m/e (ESI) 534.0 (MH+)

Example 764

Ethyl {4-tert-butyl-6-[2-(5,6-diethoxy-7-fluoro-1-imino-1,3-dihydro-isoindol-2-yl)-acetyl]-benzimidazol-1-yl}-acetate hydrobromide 1H-NMR(DMSO-d6) δ: 1.21(3H, t, J=7 Hz), 1.42(3H, t, J=7 Hz), 1.55(3H, t, J=7 Hz), 1.60(9H, s), 4.18–4.25(4H, m), 4.23(2H, q, J=7 Hz), 5.02(2H, s), 5.41(2H, s), 6.14(2H, s), 6.90(1H, s), 7.00(1H, s), 7.98(1H, s), 8.54(1H, brs), 8.99 (1H, brs), 10.78(1H, brs).
MS: m/e (ESI) 539.0 (MH+)

Example 765

Ethyl {4-tert-butyl-6-[2-(2-cyclopropyl-7-imino-5,7-dihydro-pyrrolo[3,4-b]pyridin-6-yl)-acetyl]-benzimidazol-1-yl}-acetate hydrobromide 1H-NMR(DMSO-d6) δ: 1.12–1.24(4H, m), 1.35(3H, t, J=7 Hz), 1.60(9H, s), 2.17–2.24(1H, m), 4.32(2H, q, J=7 Hz), 5.05(2H, s), 5.29(2H, s), 6.23(2H, s), 7.31(1H, brs), 7.37(1H, d, J=8 Hz), 7.82(1H, d, J=2 Hz), 7.84(1H, d, J=8 Hz), 8.08(1H, s), 8.85(1H, d, J=2 Hz).
MS: m/e (ESI) 474.0 (MH+)

Example 766

2-{2-[3-tert-Butyl-4-(3-carbamoyl-propoxy)-5-methoxy-phenyl]-2-oxo-ethyl}-6-dimethylamino-3-imino-2,3-dihydro-1H-isoindole-5-carboxylic acid methylamide hydrobromide 1H-NMR(DMSO-d6) δ: 1.39(9H, s), 1.95–2.04(2H, m), 2.23–2.30(2H, m), 2.79(3H, d, J=5 Hz), 2.93(6H, s), 3.89 (2H, s), 4.05–4.11(2H, m), 4.76(2H, s), 5.48(2H, s), 6.80 (1H, brs), 7.17(1H, s), 7.34(1H, brs), 7.52(1H, s), 7.57(1H, s), 8.09(1H, s), 8.38(1H, q, J=5 Hz).

Example 767

2-{2-[7-tert-Butyl-2-(2-cyano-ethyl)-benzoxazol-5-yl]-2-oxo-ethyl}-6-ethoxy-3-imino-2,3-dihydro-1H-isoindole-5-carboxylic acid methylamide hydrobromide 1H-NMR(DMSO-d6) δ: 1.44(3H, t, J=6.8 Hz), 1.50(9H, s), 2.85(3H, d, J=4.8 Hz), 3.12(2H, t, J=6.4 Hz), 3.45(2H, t, J=6.4 Hz), 4.31(2H, q, J=6.8 Hz), 4.91(2H, s), 5.61(2H, s), 7.56(1H, s), 7.88(1H, d, J=1.2 Hz), 8.23(1H, m), 8.37(1H, d, J=1.2 Hz), 8.60(1H, s), 9.28(1H, m), 9.90(1H, m).

Example 768

2-{2-[7-tert-Butyl-2-(2-carbamoyl-ethyl)-benzoxazol-5-yl]-2-oxo-ethyl}-6-ethoxy-3-imino-2,3-dihydro-1H-isoindole-5-carboxylic acid methylamide hydrobromide 1H-NMR(DMSO-d6) δ: 1.44(3H, t, J=6.8 Hz), 1.49(9H, s), 2.71(2H, t, J=7.2 Hz), 2.85(3H, d, J=4.8 Hz), 3.23(2H, t, J=7.2 Hz), 4.30(2H, q, J=6.8 Hz), 4.91(2H, s), 5.60(2H, s), 6.93(1H, s), 7.49(1H, s), 7.56(1H, s), 7.84(1H, d, J=1.6 Hz), 8.23(1H, m), 8.28(1H, d, J=1.6 Hz), 8.60(1H, s), 9.28(1H, m), 9.91(1H, m).

Example 769

3-{7-tert-Butyl-5-[2-(5-ethoxy-1-imino-6-methylcarbamoyl-1,3-dihydro-isoindol-2-yl)-acetyl]-benzoxazol-2-yl}-propanoic acid trifluoroacetate 1H-NMR(DMSO-d6) δ: 1.44(3H, t, J=7.2 Hz), 1.49(9H, s), 2.85(3H, d, J=4.8 Hz), 2.88(2H, t, J=7.6 Hz), 3.27(2H, t, J=7.6 Hz), 4.30(2H, q, J=7.2 Hz), 4.91(2H, s), 5.59(2H, s), 7.56(1H, s), 7.85(1H, d, J=1.2 Hz), 8.23(1H, m), 8.31(1H, d, J=1.2 Hz), 8.60(1H, s), 9.28(1H, m), 9.90(1H, m).

Example 770

2-{2-[3-tert-Butyl-4-hydroxy-5-(3-methylcarbamoyl-propoxy)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.41(9H, s), 1.44(3H, t, J=7 Hz), 1.97–2.06(2H, m), 2.26–2.35(2H, m), 2.58(3H, d, J=5 Hz), 2.84(3H, d, J=5 Hz), 4.03–4.10(2H, m), 4.29(2H, q, J=7 Hz), 4.85(2H, s), 5.48(2H, s), 7.44(1H, s), 7.53(1H, s), 7.55(1H, s), 7.72(1H, q, J=5 Hz), 8.22(1H, q, J=5 Hz), 8.57(1H, s).

Example 771

2-{2-[3-tert-Butyl-5-(3-dimethylcarbamoyl-propoxy)-4-hydroxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.41(9H, s), 1.43(3H, t, J=7 Hz), 1.96–2.06(2H, m), 2.52–2.59(2H, m), 2.83(3H, s), 2.85(3H, d, J=5 Hz), 2.98(3H, s), 4.06–4.14(2H, m), 4.30(2H, q, J=7 Hz), 4.85(2H, s), 5.48(2H, s), 7.46(1H, s), 7.53(1H, s), 7.55(1H, s), 8.22(1H, q, J=5 Hz), 8.58(1H, s).

Example 772

2-{2-[3-tert-Butyl-4-methoxy-5-(3-methylcarbamoyl-propoxy)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.38(9H, s), 1.43(3H, t, J=7 Hz), 1.98–2.08(2H, m), 2.26–2.33(2H, m), 2.57(3H, d, J=5 Hz), 2.84(3H, d, J=5 Hz), 3.92(3H, s), 4.05–4.12(2H, m), 4.29(2H, q, J=7 Hz), 4.86(2H, s), 5.53(2H, s), 7.53(1H, s), 7.56(2H, s), 7.78–7.88(1H, m), 8.22(1H, q, J=5 Hz), 8.58(1H, s).

Example 773

2-{2-[3-tert-Butyl-5-(3-dimethylcarbamoyl-propoxy)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.38(9H, s), 1.44(3H, t, J=7 Hz), 1.98–2.08(2H, m), 2.45–2.56(2H, m), 2.83(3H, s), 2.85(3H, d, J=5 Hz), 2.98(3H, s), 3.92(3H, s), 4.08–4.16(2H, m), 4.30(2H, q, J=7 Hz), 4.86(2H, s), 5.52(2H, s), 7.55(3H, s), 8.22(1H, q, J=5 Hz), 8.58(1H, s).

Example 774

2-(2-(7-tert-Butyl-benzoxazol-5-yl)-2-oxo-ethyl]-6-ethoxy-3-imino-2,3-dihydro-1H-isoindole-5-carboxylic acid methylamide hydrobromide 1H-NMR(DMSO-d6) δ: 1.43(3H, t, J=6.8 Hz), 1.50(9H, s), 2.85(3H, d, J=4.8 Hz), 4.31(2H, q, J=6.8 Hz), 4.91(2H, s), 5.62(2H, s), 7.57(1H, s), 7.93(1H, s), 8.23(1H, q, J=4.8 Hz), 8.45(1H, s), 8.59(1H, s), 8.98(1H, s), 9.26(1H, s), 9.90(1H, s).

Example 775

{5-[2-(5-Ethoxy-1-imino-6-methylcarbamoyl-1,3-dihydro-isoindol-2-yl)-acetyl]-7-methoxy-3,3-dimethyl-2,3-dihydro-indol-1-yl}-acetic acid trifluoroacetate 1H-NMR(DMSO-d6) δ: 1.39(6H, s), 1.44(3H, t, J=6.8 Hz), 3.76(3H, s), 4.27(2H, s), 4.30(2H, q, J=6.8 Hz), 4.85(2H, s), 5.39(2H, s), 7.32(1H, d, J=1.2 Hz), 7.42(1H, d, J=1.2 Hz), 7.55(1H, s), 8.22(1H, m), 8.58(1H, s), 9.21(1H, m), 9.83(1H, m).

Example 776

2-{2-[3-(3-Carbamoyl-propoxy)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.44(3H, t, J=7 Hz), 1.90–2.01(2H, m), 2.21–2.28(2H, m), 2.85(3H, d, J=5 Hz), 4.03–4.10(2H, m), 4.30(2H, q, J=7 Hz), 4.88(2H, s), 5.03(2H, s), 6.80(1H, brs), 7.29–7.37(2H, m), 7.48–7.57(3H, m), 7.49–7.54(1H, m), 8.23(1H, q, J=5 Hz), 8.59(1H, s).

Example 777

{2-tert-Butyl-4-[2-(5-ethoxy-1-imino-6-methylcarbamoyl-1,3-dihydro-isoindol-2-yl)-acetyl]-6-methoxy-phenylamino}-acetic acid hydrobromide 1H-NMR(DMSO-d6) δ: 1.40(9H, s), 1.44(3H, t, J=6.8 Hz), 2.88(3H, s), 3.77(3H, s), 3.99(2H, s), 4.27(2H, q, J=6.8 Hz), 4.81(2H, s), 5.32(2H, s), 7.38(1H, dd, J=7.2, 1.6 Hz), 7.60(1H, d, J=1.6 Hz), 8.45(1H, s).

Example 778

({2-tert-Butyl-4-[2-(5-ethoxy-1-imino-6-methylcarbamoyl-1,3-dihydro-isoindol-2-yl)-acetyl)-6-methoxy-phenyl}-methyl-amino)-acetic acid trifluoroacetate 1H-NMR(DMSO-d6) δ: 1.40(3H, t, J=6.4 Hz), 1.44(9H, s), 2.67(3H, s), 2.82(3H, d, J=4.8 Hz), 3.28(1H, d, J=20 Hz), 4.05(1H, d, J=20 Hz), 4.28(2H, q, J=6.4 Hz), 4.85(2H, s), 5.51(2H, s), 7.47(1H, d, J=2.0 Hz), 7.54(1H, s), 7.58(1H, d, J=2.0 Hz), 8.20(1H, q, J=4.8 Hz), 8.55(1H, s), 9.16–9.20(1H, m), 9.83–9.88(1H, m).

Example 779

2-[2-(7-tert-Butyl-3-cyanomethyl-3H-benzimidazol-5-yl)-2-oxo-ethyl]-6-ethoxy-3-imino-2,3-dihydro-1H-isoindole-5-carboxylic acid methylamide hydrobromide 1H-NMR(DMSO-d6) δ: 1.42(3H, t, J=7 Hz), 1.57(9H, s), 2.85(3H, d, J=4 Hz), 4.29(2H, q, J=7 Hz), 4.91(2H, s), 5.49(2H, s), 5.74(2H, s), 7.56(1H, s), 7.78(1H, d, J=1Hz), 8.22(1H, q, J=4 Hz), 8.39(1H, d, J=1Hz)., 8.56(1H, s), 8.59(1H, s), 9.28(1H, s), 9.48(1H, s).

MS: m/e (ESI) 487.0 (MH+)

Example 780

{4-tert-Butyl-6-[2-(5,6-diethoxy-7-fluoro-1-imino-1,3-dihydro-isoindol-2-yl)-acetyl]-benzimidazol-1-yl}-acetonitrile hydrobromide 1H-NMR(DMSO-d6) δ: 1.30(3H, t, J=7 Hz), 1.40(3H, t, J=7 Hz), 1.55(9H, s), 4.13(2H, q, J=7 Hz), 4.22(2H, q, J=7 Hz), 4.84(2H, s), 5.48(2H, s), 5.75(2H, s), 7.35(1H, s), 7.77(1H, d, J=2 Hz), 8.37(1H, d, J=2 Hz), 8.56(1H, s).

MS: m/e (ESI) 492.0 (MH+)

Example 781

{4-tert-Butyl-6-[2-(2-cyclopropyl-7-imino-5,7-dihydro-pyrrolo[3,4-b]pyridin-6-yl)-acetyl]-benzimidazol-1-yl}-acetonitrile hydrobromide 1H-NMR(DMSO-d6) δ: 1.05–1.16(4H, m), 1.56(9H, s), 2.30–2.37(1H, m), 4.89(2H, s), 5.65(2H, s), 5.74(2H, s), 7.74(1H, d, J=8 Hz), 7.78(1H, d, J=2 Hz), 8.12(1H, d, J=8 Hz), 8.39(1H, d, J=2 Hz), 8.57(1H, s).

MS: m/e (ESI) 427.0 (MH+)

Example 782

2-{2-[3-Acetylamino-5-tert-butyl-4-(3-carbamoyl-propoxy)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.36–1.43(12H, s), 2.01–2.07 (2H, m), 2.13(3H, s), 2.27(2H, t, J=7.2), 2.82(3H, d, J=4.4 Hz), 3.87(2H, t, J=6.8 Hz), 4.28(2H, t, J=6.8 Hz), 4.84(2H, s), 5.46(2H, s), 6.86(1H, s), 7.38(1H, s), 7.54(1H, s), 7.70 (1H, d, J=2.0), 8.17–8.23(2H, m), 8.55(1H, s), 9.65(1H, s), 9.83(1H, s).
MS: m/e (ESI) 566.3 (MH+)

Example 783

2-{2-[3-tert-Butyl-4-(3-cyano-propoxy)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.40(9H, s), 1.44(3H, t, J=7.2 Hz), 2.17(2H, m), 2.73(2H, t, J=7.2 Hz), 2.85(3H, d, J=4.4 Hz), 4.23(2H, t, J=7.2 Hz), 4.30(2H, q, J=7.2 Hz), 4.87(2H, s), 5.48(2H, s), 7.22(1H, d, J=9.2 Hz), 7.55(1H, s), 7.87(1H, d, J=2.0 Hz), 7.94(1H, dd, J=2.0, 9.2 Hz), 8.22(1H, m), 8.59(1H, s).

Example 784

2-[2-(3-tert-Butyl-5-dimethylamino-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.34(9H, s), 1.43(3H, t, J=6.8 Hz), 2.84(3H, d, J=4.4 Hz), 2.99(6H, s), 4.29(2H, q, J=6.8 Hz), 4.88(2H, s), 5.53(2H, s), 7.06(1H, s), 7.12(1H, s), 7.34(1H, s), 7.56(1H, s), 8.23(1H, q, J=4.4 Hz), 8.58(1H, s), 9.24(1H, s), 9.85(1H, s).

Example 785

(1-{3-tert-Butyl-5-[2-(3-ethoxy-7-imino-2-methyl-carbamoyl-5,7-dihydro-pyrrolo[3,4-b]pyridin-6-yl)-acetyl]-2-hydroxy-phenyl)-pyrrolidin-3-yloxy)-acetic acid hydrochloride 1H-NMR(DMSO-d6) δ: 1.20–1.50(12H, m), 1.93–2.07 (1H, m), 2.10–2.23(1H, m), 2.77(3H, d, J=5.1 Hz), 2.94–3.05(1H, m), 3.06–3.24(2H, m), 3.43–3.54(1H, m), 4.07(3H, s), 4.14–4.55(5H, m), 4.87(2H, s), 5.56(2H, s), 7.61(1H, s), 7.69(1H, s), 7.99(1H, s), 8.52–8.62(1H, s), 9.54(1H, brs), 9.95(1H, brs).

Example 786

3-(Acetyl-(3-tert-butyl-5-[2-(3-ethoxy-7-imino-2-methylcarbamoyl-5,7-dihydro-pyrrolo[3,4-b]pyridin-6-yl)-acetyl]-2-hydroxy-benzyl}-amino)-propanoic acid hydrochloride 1H-NMR(DMSO-d6) δ: 1.23–1.46(12H, m), 2.16(3H, s), 2.60–2.83(5H, m), 3.51–3.69(2H, m), 4.15–4.32(2H, m), 4.48(2H, brs), 4.88(2H, brs), 5.57(2H, brs), 7.81(1H, s), 7.93(2H, brs), 7.99(1H, brs), 8.55–8.64(1H, m), 9.97(1H, brs).

Example 787

4-[2-tert-Butyl-4-[2-(7-imino-2-methyl-5,7-dihydro-pyrrolo[3,4-b]pyridin-6-yl)-acetyl]-6-(2-oxo-piperidin-1-ylmethyl)-phenoxy]-butylamide hydrochloride 1H-NMR(DMSO-d6) δ: 1.38(9H, s), 1.73(4H, br), 2.02 (2H, br), 2.27(2H, t, J=7.6 Hz), 2.58(3H, s), 3.14(2H, br), 3.24–3.40(2H, br), 3.83(2H, t, J=6.8 Hz), 4.53(2H, s), 4.60 (2H, s), 5.15(2H, s), 6.81(1H, s), 7.35(1H, s), 7.46(1H, d, J=8.0 Hz), 7.56(1H, d, J=2.0 Hz), 7.87(1H, d, J=2.0 Hz), 7.95(1H, d, J=8.0 Hz).
MS: m/e (ESI) 534.3 (MH+)

Example 788

2-[2-(7-tert-Butyl-3H-benzimidazol-5-yl)-2-oxo-ethyl]-6-ethoxy-3-imino-2,3-dihydro-1H-isoindole-5-carboxylic acid methylamide trifluoroacetate 1H-NMR(DMSO-d6) δ: 1.43(3H, t, J=7 Hz), 1.54(9H, s), 2.74(3H, d, J=5 Hz), 4.29(2H, q, J=7 Hz), 4.88(2H, s), 5.59(2H, s), 7.57(1H, s), 7.70(1H, s), 8.16(1H, brs), 8.22 (1H, q, J=5 Hz), 8.45(1H, s), 8.57(1H, s), 9.23(1H, s), 9.45(1H, s).
MS: m/e (ESI) 448.0 (MH+)

Example 789

2-[2-(7-tert-Butyl-3-methyl-3H-benzimidazol-5-yl)-2-oxo-ethyl]-6-ethoxy-3-imino-2,3-dihydro-1H-isoindole-5-carboxylic acid methylamide hydrobromide 1H-NMR(DMSO-d6) δ: 1.42(3H, t, J=7 Hz), 1.55(9H, s), 2.74(3H, d, J=4 Hz), 3.94(3H, s), 4.29(2H, q, J=7 Hz), 4.89(2H, s), 5.60(2H, s), 7.55(1H, s), 7.71(1H, s), 8.22(1H, q, J=4 Hz), 8.23(1H, s), 8.42(1H, s), 8.58(1H, s).
MS: m/e (ESI) 462.0 (MH+)

Example 790

2-[2-(7-tert-Butyl-3-carbamoylmethyl-3H-benzimidazol-5-yl)-2-oxo-ethyl]-6-ethoxy-3-imino-2,3-dihydro-1H-isoindole-5-carboxylic acid methylamide hydrobromide 1H-NMR(DMSO-d6) δ: 1.42(3H, t, J=7 Hz), 1.58(9H, s), 2.83(3H, d, J=5 Hz), 4.29(2H, q, J=7 Hz), 4.89(2H, s), 5.13(2H, s), 5.57(2H, s), 7.38(1H, s), 7.55(1H, s), 7.70(1H, d, J=2 Hz), 7.82(1H, s), 8.12(1H, d, J=2 Hz), 8.22(1H, q, J=5 Hz), 8.39(1H, s), 8.58(1H, s), 9.26(1H, d, J=4 Hz), 9.85(1H, d, J=4 Hz).
MS: m/e (ESI) 505.0 (MH+)

Example 791

2-{4-tert-Butyl-6-[2-(5,6-diethoxy-7-fluoro-1-imino-1,3-dihydro-isoindol-2-yl)-acetyl]-benzimidazol-1-yl}-acetamide hydrobromide 1H-NMR(DMSO-d6) δ: 1.28(3H, t, J=7 Hz), 1.40(3H, t, J=7 Hz), 1.56(9H, s), 4.12(2H, q, J=7 Hz), 4.22(2H, q, J=7 Hz), 4.84(2H, s), 5.03(2H, s), 5.55(2H, s), 7.36(1H, s), 7.39(1H, s), 7.67(1H, s), 7.82(1H, s), 8.10(1H, s), 8.39(1H, s), 9.04(1H, brs), 9.39(1H, brs).
MS: m/e (ESI) 510.0 (MH+)

Example 792

2-{4-tert-Butyl-6-[2-(2-cyclopropyl-7-imino-5,7-dihydro-pyrrolo[3,4-b]pyridin-6-yl)-acetyl]-benzimidazol-1-yl}-acetamide hydrobromide 1H-NMR(DMSO-d6) δ: 1.05–1.13(4H, m), 2.33(1H, quint, J=7 Hz), 1.57(9H, s), 4.86(2H, s), 5.03(2H, s), 5.62 (2H, s), 7.38(1H, s), 7.70(1H, s), 7.73(1H, d, J=8 Hz), 7.81(1H, s), 8.10(1H, d, J=8 Hz), 8.11(1,s), 8.39(1H, s), 9.53(1H, brs), 9.66(1H, brs).

MS: m/e (ESI) 445.0 (MH+)

Example 793

2-[2-(3-tert-Butyl-5-dimethylamino-4-hydroxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.41(12H, m), 2.63(6H, s), 2.84 (2H, s), 4.30(2H, q, J=6.8 Hz), 4.86(2H, s), 5.47(2H, s), 7.56(1H, s), 7.66(1H, s), 7.71(1H, s), 8.22(1H, s), 8.57(1H, s), 9.17(1H, s), 9.84(1H, s).

Example 794

4-{2-tert-Butyl-4-[2-(2-cyclopropyl-7-imino-5,7-dihydro-pyrrolo[3,4-b]pyridin-6-yl)-acetyl]-6-(pyrrolidin-1-yl)-phenoxy}-butyric acid trifluoroacetate 1H-NMR(DMSO-d6) δ: 1.01–1.15(4H, m), 1.37(9H, s), 1.82–2.08(6H, m), 2.28–2.43(3H, m), 2.82–3.42(4H and H2O, m), 3.78–3.94(2H, m), 4.81(2H, s), 5.53(2H, s), 7.35 (1H, s), 7.46(1H, s), 7.68–7.75(1H, m), 8.06–8.12(1H, m), 9.44(1H, brs), 9.66(1H, brs).

MS: m/e (ESI) 519.3 (MH+)

Example 795

5-{2-tert-Butyl-4-[2-(2-cyclopropyl-7-imino-5,7-dihydro-pyrrolo[3,4-b]pyridin-6-yl)-acetyl]-6-(pyrrolidin-1-yl)-phenoxy}-pentanoic acid trifluoroacetate 1H-NMR(DMSO-d6) δ: 1.00–1.15(4H, m), 1.38(9H, s), 1.59–1.85(4H, m), 2.23–2.37(3H, m), 3.03–3.20(4H, m), 3.78–3.88(2H, m), 4.81(2H, s), 5.53(2H, s), 7.36(1H, s), 7.46(1H, s), 7.72(1H, d, J=8.0 Hz), 8.09(1H, d, J=8.0 Hz), 9.41–9.49(1H, m), 9.61–9.70(1H, m).

MS: m/e (ESI) 533.3 (MH+)

Example 796

4-{4-[2-(1-Amino-7-fluoro-5,6-dimethoxy-1,3-dihydro-isoindol-2-yl)-acetyl]-2-tert-butyl-6-(pyrrolidin-1-yl)-phenoxy}-buric acid trifluoroacetate 1H-NMR(DMSO-d6) δ: 1.38(9H, s), 1.79–1.96(4H, m), 2.01(2H, t, J=6.8 Hz), 2.41(2H, t, J=7.2 Hz), 3.02–3.20(4H, m), 3.77–3.90(5H, m), 3.95(3H, s), 4.80(2H, s), 5.48(2H, s), 7.35(1H, d, J=2.0 Hz), 7.36(1H, s), 7.45(1H, d, J=2.0 Hz), 9.03–9.11(1H, m), 9.27–9.34(1H, m).

Example 797

5-{2-tert-Butyl-4-[2-(7-fluoro-1-imino-5,6-dimethoxy-1,3-dihydro-isoindol-2-yl)-acetyl]-6-(pyrrolidin-1-yl)-phenoxy}-pentanoic acid trifluoroacetate 1H-NMR(DMSO-d6) δ: 1.38(9H, s), 1.55–1.99(8H, m), 2.17–2.36(2H, m), 2.94–3.20(4H, m), 3.57–4.27(8H and H2O, m), 4.79(2H, s), 5.47(2H, s), 7.36(2H, s), 7.45(1H, s), 9.01–9.11(1H, m), 9.22–9.35(1H, m).

Example 798

2-{2-[3-tert-Butyl-5-(3-cyano-propoxy)-4-(2-hydroxy-ethoxy)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.41(9H, s), 1.44(3H, t, J=7.2 Hz), 2.13(2H, m), 2.75(2H, t, J=7.2 Hz), 2.85(3H, d, J=4.8 Hz), 3.80(2H, t, J=7.2 Hz), 4.11–4.19(4H, m), 4.30(2H, q, J=7.2 Hz), 4.87(2H, s), 5.52(2H, s), 7.76(2H, m), 7.59(1H, s), 8.22(1H, m), 8.59(1H, s), 9.21(1H, m).

Example 799

2,6-Di-tert-butyl-4-[1-hydroxy-2-(3-imino-5,6-dimethoxy-3H-benzo[d]isoxazol-2-yl)-vinyl]-phenol hydrobromide 1H-NMR(DMSO-d6) δ: 1.45(18H, s), 3.90(3H, s), 4.07 (3H, s), 5.96(1H, s), 6.27(1H, brs), 6.52(1H, s), 7.84(1H, s), 7.98(2H, s), 9.55–9.66(2H, m), 9.80(1H, brs).

MS: m/e (ESI) 441.1 (MH+)

Example 800

2-[2-(3-tert-Butyl-4-hydroxy-5-(pyrrolidin-1-yl)-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.41(12H, m), 1.94(4H, s), 2.84 (3H, s), 3.02(4H, s), 4.30(2H, q, 6.4 Hz), 4.86(2H, s), 5.48(2H, s), 7.56(1H, s), 7.62(1H, s), 7.65(1H, s), 8.23(1H, s), 8.57(1H, s), 9.18(1H, s), 9.84(1H, s).

Example 801

({3-tert-Butyl-5-[2-(5-ethoxy-1-imino-6-methylcarbamoyl-1,3-dihydro-isoindol-2-yl)-acetyl]-phenyl}-methyl-amino)-acetic acid hydrochloride 1H-NMR(DMSO-d6) δ: 1.32(9H, s), 1.43(3H, t, J=6.8 Hz), 2.84(3H, d, J=4.4 Hz), 3.06(3H, s), 4.21(2H, s), 4.30 (2H, q, J=6.8 Hz), 4.87(2H, s), 5.54(2H, s), 7.01(1H, s), 7.07(1H, s), 7.35(1H, s), 7.55(1H, s), 8.22(1H, q, J=4.4 Hz), 8.58(1H, s), 9.33(1H, s), 9.89(1H, s).

Example 802

Ethyl ({3-tert-butyl-5-[2-(5-ethoxy-1-imino-6-methylcarbamoyl-1,3-dihydro-isoindol-2-yl]-acetyl]-phenyl)-methyl-amino)-acetate hydrochloride 1H-NMR(DMSO-d6) δ: 1.18(3H, t, J=7.2 Hz), 1.32(9H, s), 1.43(3H, t, J=6.8 Hz), 2.84(3H, d, J=4.4 Hz), 3.08(3H, s), 4.10(2H, q, J=7.2 Hz), 4.30(2H, q, J=6.8 Hz), 4.32(2H, s), 4.87(2H, s), 5.53(2H, s), 7.00(1H, s), 7.08(1H, s), 7.36(1H, s), 7.56(1H, s), 8.23(1H, q, J=4.4 Hz), 8.58(1H, s), 9.30(1H, s), 9.88(1H, s).

Example 803

4-{3-tert-Butyl-2-hydroxy-5-[2-(3-hydroxymethyl-7-imino-2-methyl-5,7-dihydro-pyrrolo[3,4-b]pyridin-6-yl)-acetyl]-phenoxy}-butylamide hydrochloride 1H-NMR(DMSO-d6) δ: 1.38(9H, s), 1.95–2.05(2H, m), 2.28(2H, t, J=7.2 Hz), 2.57(3H, s), 4.04–4.10(2H, m), 4.68 (2H, s), 4.85(2H, s), 5.54(2H, s), 7.03(1H, s), 7.15(1H, s), 7.28(1H, s), 7.44(1H, d, J=1.6 Hz), 7.52(1H, d, J=1.6 Hz), 8.19(1H, s), 9.45–9.51(1H, m), 9.84–9.90(1H, m).

Example 804

4-{2-tert-Butyl-4-[2-(3-hydroxymethyl-7-imino-2-methyl-5,7-dihydro-pyrrolo[3,4-b]pyridin-6-yl)-acetyl]-6-(pyrrolidin-1-yl)-phenoxy}-butyric acid trifluoroacetate 1H-NMR(DMSO-d6) δ: 1.38(9H, s), 1.85–1.92(4H, m), 2.01(2H, m), 2.40(2H, t, J=7.2 Hz), 2.57(3H, s), 3.08–3.15 (4H, m), 3.85(2H, t, J=7.2 Hz), 4.69(2H, s), 4.85(2H, s), 5.54(2H, s), 5.67(1H, s), 7.36(1H, d, J=1.6 Hz), 7.46(1H, d, J=1.6 Hz), 8.20(1H, s).

Example 805

4-({2-tert-Butyl-4-[2-(2-cyclopropyl-7-imino-5,7-dihydro-pyrrolo[3,4-b]pyridin-6-yl)-acetyl]-phenyl}-methyl-amino)-butyric acid trifluoroacetate 1H-NMR(DMSO-d6) δ: 1.04–1.12(4H, m), 1.42(9H, s), 1.70–1.82(2H, m), 2.44(2H, t, J=7.6 Hz), 2.52(3H, s), 2.70–2.80(2H, m), 4.83(2H, s), 5.54(2H, s), 7.58(1H, d, J=8.0 Hz), 7.71(1H, d, J=8.0 Hz), 7.90(1H, dd, J=8.4, 2.0 Hz), 7.94(1H, d, J=2.0 Hz), 8.09(1H, dd, J=8.4 Hz), 9.44–9.50(1H, m), 9.63–9.68(1H, m).

Example 806

4-({2-tert-Butyl-4-[2-(5,6-diethoxy-7-fluoro-1-imino-1,3-dihydro-isoindol-2-yl)-acetyl]-phenyl}-methyl-amino)-butyric acid trifluoroacetate 1H-NMR(DMSO-d6) δ: 1.29(3H, t, J=6.8 Hz), 1.40(3H, t, J=7.2 Hz), 1.43(9H, s), 1.70–1.82(2H, m), 2.24(3H, t, J=6.8 Hz), 2.51(3H, s), 2.70–2.80(2H, m), 4.11(2H, q, J=6.8 Hz), 4.21(2H, q, J=7.2 Hz), 4.80(2H, s), 5.47(2H, s), 7.33 (1H, s), 7.57(1H, d, J=8.4 Hz), 7.88(1H, d, J=8.4 Hz), 7.93(1H, s), 9.04(1H, brs), 9.29(1H, brs).

Example 807

1-(3,5-Di-tert-butyl-4-hydroxy-phenyl)-2-(2-imino-3,3-dimethyl-2,3-dihydro-indol-1-yl)-ethanone hydrobromide 1H-NMR(DMSO-d6) δ: 1.48(18H, s), 1.60(6H, m), 5.77 (2H, s), 7.27(1H, t, J=7.2 Hz), 7.35(1H, t, J=7.2 Hz), 7.40(1H, d, J=7.2 Hz), 7.54(1H, d, J=7.2 Hz), 7.58(2H, s), 8.10(1H, brs), 9.88(1H, brs), 10.04(1H, brs).

Example 808

2-[2-(3-tert-Butyl-5-dimethylamino-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.39(12H, m), 2.77(6H, s), 2.84 (3H, s), 3.85(3H, s), 4.30(2H, q, J=7.2 Hz), 4.86(2H, s), 5.52(2H, s), 7.48(1H, s), 7.56(1H, s), 8.22(1H, s), 8.57(1H, s), 9.18(1H, s), 9.85(1H, s).

Example 809

Ethyl 5-{2-tert-butyl-6-(3-cyano-propoxy)-4-[2-(7-fluoro-1-imino-5,6-dimethoxy-1,3-dihydro-isoindol-2-yl)-acetyl]-phenoxy}-pentanoate hydrobromide 1H-NMR(DMSO-d6) δ: 1.17(3H, t, J=7.2 Hz), 1.37(9H, s), 1.65–1.83(4H, m), 2.05–2.19(2H, m), 2.39(2H, t, J=6.6 Hz), 2.69(2H, t, J=6.8 Hz), 3.87(3H, s), 3.95(3H, s), 4.00–4.19(6H, m), 4.81(2H, s), 5.49(2H, s), 7.37(1H, s), 7.52(1H, s), 7.55(1H, s).
MS: m/e (ESI) 612.3 (MH+)

Example 810

Ethyl 5-{2-tert-butyl-6-(3-cyano-propoxy)-4-[2-(3-ethoxy-7-imino-2-methylcarbamoyl-5,7-dihydro-pyrrolo[3,4-b]pyridin-6-yl)-acetyl]-phenoxy}-pentanoate hydrochloride 1H-NMR(DMSO-d6) δ: 1.17(3H, t, J=7.0 Hz), 1.28–1.44 (12H, m), 1.67–1.84(4H, m), 2.06–2.17(2H, m), 2.39(2H, t, J=6.8 Hz), 2.69(2H, t, J=7.0 Hz), 2.77(3H, d, J=3.6 Hz), 3.99–4.18(6H, m), 4.24(2H, t, J=6.8 Hz), 4.88(2H, s), 5.54 (2H, s), 7.52(1H, s), 7.56(1H, s), 7.99(1H, s), 8.47–8.58(1H, m), 9.44(1H, brs), 9.96(1H, brs).
MS: m/e (ESI) 636.3 (MH+)

Example 811

Ethyl 4-{2-tert-butyl-4-[2-(3-ethoxy-7-imino-2-methylcarbamoyl-5,7-dihydro-pyrrolo[3,4-b]pyridin-6-yl)-acetyl]-6-(pyrrolidin-1-yl)-phenoxy}-butyrate hydrochloride 1H-NMR(DMSO-d6) δ: 1.16(3H, t, J=6.8 Hz), 1.25–1.47 (12H, m), 1.88(4H, brs), 1.98–2.10(2H, m), 2.42–2.55(2H, m), 2.77(3H, brs), 3.11(4H, brs), 3.65–3.88(2H, m), 4.05 (2H, q, J=6.8 Hz), 4.24(2H, q, J=6.8 Hz), 4.87(2H, s), 5.55(2H, s), 7.35(1H, s), 7.45(1H, s), 7.99(1H, s), 8.50–8.58 (1H, m), 9.44(1H, brs), 9.94(1H, brs).
MS: m/e (ESI) 608.3 (MH+)

Example 812

Ethyl 5-{2-tert-butyl-4-[2-(3-ethoxy-7-imino-2-methylcarbamoyl-5,7-dihydro-pyrrolo[3,4-b]pyridin-6-yl)-acetyl]-6-(pyrrolidin-1-yl)-phenoxy}-pentanoate hydrochloride 1H-NMR(DMSO-d6) δ: 1.16(3H, t, J=7.0 Hz), 1.26–1.45 (12H, m), 1.62–1.85(4H, m), 1.88(4H, brs), 2.37(2H, t, J=6.8 Hz), 2.77(3H, brs), 3.12(4H, brs), 3.78–3.91(2H, m), 3.95–4.10(2H, m), 4.12–4.32(2H, m), 4.87(2H, s), 5.54(2H, s), 7.36(1H, s), 7.46(1H, brs), 7.99(1H, s), 8.53(1H, q, J=4.4 Hz), 9.35–9.46(1H, m), 9.92–9.99(1H, m).
MS: m/e (ESI) 622.3 (MH+)

Example 813

2-tert-Butyl-4-[2-(5-ethoxy-1-imino-6-methylcarbamoyl-1,3-dihydro-isoindol-2-yl)-acetyl]-phenyl heptadecanoate hydrobromide 1H-NMR(DMSO-d6) δ: 0.83(3H, t, J=7 Hz), 1.15–1.28 (28H, m), 1.34(9H, s), 1.41(3H, t, J=7 Hz), 1.61–1.70(1H, m), 2.67(2H, t, J=7 Hz), 2.83(3H, d, J=5 Hz), 4.28(2H, q, J=7 Hz), 4.86(2H, s), 5.52(2H, s), 7.28(1H, d, J=8 Hz), 7.54(1H, s), 7.93(1H, d, J=8 Hz), 7.98(1H, s), 8.20(1H, q, J=5 Hz), 8.57(1H, s).

Example 814

2-tert-Butyl-4-[2-(5,6-diethoxy-7-fluoro-1-imino-1,3-dihydro-isoindol-2-yl)-acetyl]-phenyl heptadecanoate hydrobromide 1H-NMR(DMSO-d6) δ: 0.83(3H, t, J=7 Hz), 1.15–1.27 (28H, m), 1.29(3H, t, J=7 Hz), 1.33(9H, s), 1.38(3H, t, J=7 Hz), 1.39(3H, t, J=7 Hz), 1.60–1.70(2H, m), 2.67(2H, t, J=7 Hz), 4.11(2H, q, J=7 Hz), 4.20(2H, q, J=7 Hz), 4.79(2H, s), 5.48(2H, s), 7.28(1H, d, J=8 Hz), 7.32(1H, s), 7.92(1H, d, J=8 Hz), 7.97(1H, s).

Example 815

2-tert-Butyl-4-[2-(3-ethoxy-7-imino-2,4-dimethyl-5,7-dihydro-pyrrolo[3,4-b]pyridin-6-yl)-acetyl]-phenyl acetate hydrobromide 1H-NMR(DMSO-d6) δ: 1.33(3H, t, J=7 Hz), 1.15–1.30 (28H, m), 1.62–1.70(2H, m), 2.32(3H, s), 2.58(3H, s), 2.68(3H, t, J=7 Hz), 3.99(2H, q, J=7 Hz), 4.84(2H, s), 5.57(2H, s), 7.29(1H, d, J=8 Hz), 7.94(1H, d, J=8 Hz), 7.98(1H, s).

Example 816

2-[2-(3,5-Di-tert-butyl-4-hydroxy-phenyl)-2-oxo-ethyl]-5,6-diethoxy-2,3-dihydro-isoindol-1-one 1H-NMR(DMSO-d6) δ: 1.45–1.52(6H, m), 1.46(9H, s), 4.10–4.19(4H, m), 4.42(2H, s), 5.00(2H, s), 5.80(1H, s), 6.91(1H, s), 7.34(1H, s), 7.90(2H, s).

Example 817

(1-{3-tert-Butyl-5-[2-(2-cyclopropyl-7-imino-5,7-dihydro-pyrrolo[3,4-b]pyridin-6-yl)-acetyl]-2-methoxy-phenyl}-pyrrolidin-3-yloxy)-acetic acid trifluoroacetate 1H-NMR(DMSO-d6) δ: 1.08–1.11(4H, m), 2.02–2.08 (2H, m), 2.29–2.34(1H, m), 3.08–3.13(2H, m), 3.15–3.42 (2H, m), 3.65(3H, s), 4.05(2H, s), 4.26(1H, br), 4.82(2H, s), 5.55(2H, d, J=4.8 Hz), 7.34(1H, s), 7.44(1H, s), 7.72(1H, d, J=8.4 Hz), 8.10(1H, d, J=8.4 Hz), 9.45(1H, brs), 9.66(1H, brs).

Example 818

Methyl (1-(3-tert-Butyl-5-[2-(2-cyclopropyl-7-imino-5,7-dihydro-pyrrolo[3,4-b]pyridin-6-yl)-acetyl]-2-methoxy-phenyl)-pyrrolidin-3-yloxy)-acetate hydrochloride 1H-NMR(DMSO-d6) δ: 1.08–1.10(4H, m), 2.01–2.10 (2H, m), 2.30–2.33(1H, m), 3.11–3.14(2H, m), 3.40–3.44 (2H, m), 3.63(3H, s), 3.65(3H, m), 4.17(2H, s), 4.26(1H, br), 4.82(2H, s), 5.56(2H, d, J=4.4 Hz), 7.34(1H, s), 7.44(1H, s), 7.72(1H, d, J=8.0 Hz), 8.09(1H, d, J=8.0 Hz), 9.49(1H, brs), 9.66(1H, brs).

Example 819

Ethyl {2-tert-butyl-6-(3-cyano-propoxy)-4-[2-(5,6-diethoxy-7-fluoro-1-imino-1,3-dihydro-isoindol-2-yl)-acetyl]-phenoxy}-acetate hydrobromide 1H-NMR(DMSO-d6) δ: 1.24(3H, t, J=7.0 Hz), 1.29(3H, t, J=7.0 Hz), 1.32–1.45(12H, m), 1.99–2.12(2H, m), 2.66 (2H, t, J=7.0 Hz), 3.98–4.30(8H, m), 4.77(2H, s), 4.80(2H, s), 5.49(2H, s), 7.34(1H, s), 7.52(1H, s), 7.55(1H, s), 9.06 (1H, brs), 9.32(1H, brs).
MS: m/e (ESI) 598.3 (MH+)

Example 820

5-{2-tert-Butyl-4-[2-(7-fluoro-1-imino-5,6-dimethoxy-1,3-dihydro-isoindol-2-yl)-acetyl]-phenoxy}-pentanoic acid trifluoroacetate 1H-NMR(DMSO-d6) δ: 1.37(9H, s), 1.65–1.75(2H, m), 1.78–1.87(2H, m), 2.23–2.37(3H, m), 3.87(3H, s), 3.95(H, s), 4.13(2H, t, J=7 Hz), 4.81(2H, s), 5.45(2H, s), 7.17(1H, d, J=8 Hz), 7.35(1H, s), 7.83(1H, d, J=2 Hz), 7.88(1H, dd, J=2 Hz, 8 Hz), 9.07(1H, brs), 9.35(1H, brs).

Example 821

5-{2-tert-Butyl-4-[2-(2-cyclopropyl-7-imino-5,7-dihydro-pyrrolo[3,4-b]pyridin-6-yl)-acetyl]-phenoxy}-pentanoic acid trifluoroacetate 1H-NMR(DMSO-d6) δ: 1.05–1.14(4H, m), 1.37(9H, s), 1.65–1.75(2H, m), 1.78–1.88(2H, m), 2.25–2.37(1H, m), 2.30(2H, t, J=7 Hz), 4.13(2H, t, J=7 Hz), 4.82(2H, s), 5.51(2H, s), 7.18(1H, d, J=8 Hz), 7.72(1H, d, J=8 Hz), 7.84(1H, s), 7.91(1H, d, J=8 Hz), 8.09(1H, d, J=8 Hz), 9.51(1H, brs), 9.65(1H, brs).

Example 822

5-[2-tert-Butyl-4-[2-(7-fluoro-1-imino-5,6-dimethoxy-1,3-dihydro-isoindol-2-yl)-acetyl]-6-(3-methoxy-pyrrolidin-1-yl)-phenoxy]-pentanoic acid trifluoroacetate 1H-NMR(DMSO-d6) δ: 1.38(9H, s), 1.63–1.68(2H, m), 1.78–1.82(2H, m), 1.91–1.99(1H, m), 2.03–2.12(1H, m), 2.29(2H, t, J=6.4 Hz), 3.05–3.10(2H, m), 3.23(3H, s), 3.20–3.38(2H, m), 3.73(2H, q, J=4.4 Hz), 3.86(3H, s), 3.94(3H, s), 4.04(1H, brs), 4.79(2H, s), 5.48(2H, s), 7.33 (1H, s), 7.36(1H, s), 7.46(1H, s), 9.07(1H, brs), 9.30(1H, brs).
MS: m/e (ESI) 600.3 (MH+)

Example 823

Methyl 5-[2-tert-butyl-4-[2-(7-fluoro-1-imino-5,6-dimethoxy-1,3-dihydro-isoindol-2-yl)-acetyl]-6-(3-methoxy-pyrrolidin-1-yl)-phenoxy]-pentanoate hydrochloride 1H-NMR(DMSO-d6) δ: 1.37(9H, s), 1.62–1.71(2H, m), 1.76–1.82(2H, m), 1.92–1.98(1H, m), 2.04–2.12(1H, m), 2.39(2H, t, J=6.8 Hz), 3.02–3.12(2H, m), 3.23(3H, s), 3.26–3.34(2H, m), 3.58(3H, s), 3.71–3.76(2H, m), 3.86(3H, s), 3.95(3H, s), 4.01–4.07(1H, m), 4.79(2H, s), 5.49(2H, s), 7.35(1H, s), 7.37(1H, s), 7.46(1H, s), 9.08(1H, s), 9.33(1H, s).

MS: m/e (ESI) 614.3 (MH+)

Example 824

5-{2-tert-Butyl-6-(3-ethoxy-pyrrolidin-1-yl)-4-[2-(7-fluoro-1-imino-5,6-dimethoxy-1,3-dihydro-isoindol-2-yl)-acetyl]-phenoxy}-pentanoic acid trifluoroacetate 1H-NMR(DMSO-d6) δ: 1.09(3H, t, J=6.4 Hz), 1.38(9H, s), 1.68–1.70(2H, m), 1.76–1.84(2H, m), 1.88–1.98(1H, m), 2.04–2.12(1H, m), 2.28(2H, t, J=6.8 Hz), 3.04–3.12(2H, m), 3.26–3.47(3H, m), 3.78(2H, q, J=6.4 Hz), 3.87(3H, s), 3.89–3.90(2H, m), 3.95(3H, s), 4.14(1H, brs), 4.80(2H, s), 5.48(2H, s), 7.34(1H, s), 7.36(1H, s), 7.46(1H, s), 9.07(1H, brs), 9.30(1H, brs).

MS: m/e (ESI) 628.4 (MH+)

Example 825

Methyl 5-(2-tert-butyl-6-(3-ethoxy-pyrrolidin-1-yl)-4-[2-(7-fluoro-1-imino-5,6-dimethoxy-1,3-dihydro-isoindol-2-yl)-acetyl]-phenoxy)-pentanoate hydrochloride 1H-NMR(DMSO-d6) δ: 1.09(3H, t, J=6.7 Hz), 1.37(9H, s), 1.68–1.71(2H, m), 1.74–1.82(2H, m), 1.88–1.98(1H, m), 2.04–2.12(1H, m), 2.39(2H, t, J=6.8 Hz), 3.03–3.11(2H, m), 3.24–3.38(2H, m), 3.77–3.80(2H, m), 3.58(3H, s), 3.86(3H, s), 3.88–3.92(2H, m), 3.95(3H, s), 4.11–4.15(1H, m), 4.79 (2H, s), 5.51(2H, s), 7.35(1H, s), 7.36(1H, s), 7.46(1H, s), 9.09(1H, s), 9.37(1H, s).

MS: m/e (ESI) 628.3 (MH+)

Example 826

Methyl 5-{2-tert-butyl-6-(3-cyano-pyrrolidin-1-yl)-4-[2-(7-fluoro-1-imino-5,6-dimethoxy-1,3-dihydro-isoindol-2-yl)-acetyl]-phenoxy}-pentanoate hydrobromide 1H-NMR(DMSO-d6) δ: 1.38(9H, s), 1.68–1.72(2H, m), 1.77–1.85(2H, m), 2.18–2.21(1H, m), 2.40(2H, t, J=6.8 Hz), 3.08–3.12(1H, m), 3.24–3.38(3H, m), 3.58(3H, s), 3.85(3H, s), 3.86–3.92(3H, m), 3.94(3H, s), 4.75(2H, s), 5.43(2H, s), 7.33(1H, s), 7.40(1H, s), 7.53(1H, s), 7.93(1H, br).

MS: m/e (ESI) 609.3 (MH+)

Example 827

Ethyl 3-{3-tert-butyl-5-[2-(5-ethoxy-1-imino-6-methylcarbamoyl-1,3-dihydro-isoindol-2-yl)-acetyl]-benzyloxy}-4-cyano-butyrate hydrobromide 1H-NMR(DMSO-d6) δ: 1.16(3H, t, J=7.2 Hz), 1.31(9H, s), 1.41(3H, t, J=7.2 Hz), 2.65(2H, t, J=7.2 Hz), 2.75–3.06 (6H, m), 4.08(2H, q, J=7.2 Hz), 4.67(2H, dd, J=11.6 Hz, 11.6 Hz), 4.86(2H, s), 5.51(2H, s), 7.54(1H, s), 7.72(1H, s), 7.77(1H, s), 7.92(1H, s), 8.20(1H, d, J=4.4 Hz), 8.56(1H, s), 9.23(1H, brs), 9.84(1H, brs).

Example 828

Ethyl 4-{2-tert-butyl-6-diethylamino-4-[2-(7-fluoro-1-imino-5,6-dimethoxy-1,3-dihydro-isoindol-2-yl)-acetyl]-phenoxy}-butyrate hydrobromide 1H-NMR(DMSO-d6) δ: 0.91(6H, t, J=6.8 Hz), 1.21(3H, t, J=6.8 Hz), 1.32(9H, s), 2.02–2.13(2H, m), 2.48(2H, t, J=7.6 Hz), 3.04–3.19(4H, m), 3.91(3H, s), 3.93(3H, s), 4.06–4.17(4H, m), 4.72(2H, s), 5.65(2H, s), 6.83(1H, s), 7.49(1H, s), 7.59(1H, s).

MS: m/e (ESI) 586.3 (MH+)

Example 829

Ethyl 4-{2-tert-butyl-6-diethylamino-4-[2-(3-ethoxy-7-imino-2-methylcarbamoyl-5,7-dihydro-pyrrolo[3,4-b]pyridin-6-yl)-acetyl]-phenoxy}-burate trifluoroacetate 1H-NMR(DMSO-d6) δ: 0.93(6H, br), 1.17(3H, br), 1.35 (12H, br), 2.01(2H, br), 2.42–2.56(2H, br), 2.76(3H, br), 3.60–4.48(6H, m), 4.87(2H, s), 5.52(2H, s), 7.48(1H, s), 7.57(1H, s), 7.90(1H, s), 8.53(1H, br), 9.42(1H, s), 9.94(1H, s).

MS: m/e (ESI) 610.4 (MH+)

Example 830

2-{2-[3-tert-Butyl-5-(methanesulfonyl-methyl-amino)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.36(9H, s), 1.43(3H, t, J=6.8 Hz), 2.85(3H, d, J=4.0 Hz), 3.02(3H, s), 3.32(3H, s), 4.30 (2H, q, J=6.8 Hz), 4.89(2H, s), 5.56(2H, s), 7.57(1H, s), 7.79(1H, s), 7.84(1H, s), 7.93(1H, s), 8.23(1H, q, J=4.0 Hz), 8.58(1H, s), 9.25(1H, s), 9.89(1H, s).

Example 831

2-{2-[3-tert-Butyl-5-(dimethanesulfonyl-amino)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.37(9H, s), 1.44(3H, t, J=6.4 Hz), 2.84(3H, s), 3.61(6H, s), 4.30(2H, q, J=6.4 Hz), 4.90 (2H, s), 5.58(2H, s), 7.58(1H, s), 7.87(1H, s), 7.93(1H, s), 8.09(1H, s), 8.22(1H, s), 8.59(1H, s), 9.28(1H, s), 9.88(1H, s).

Example 832

1-(7-tert-Butyl-benzoxazol-5-yl)-2-(5,6-diethoxy-7-fluoro-1-imino-1,3-dihydro-isoindol-2-yl)-ethanone hydrobromide 1H-NMR(DMSO-d6) δ: 1.32(3H, t, J=7.2 Hz), 1.42(3H, t, J=7.2 Hz), 1.50(9H, s), 4.14(2H, d, J=7.2 Hz), 4.24(2H, q, J=7.2 Hz), 4.86(2H, s), 5.62(2H, s), 7.37(1H, s), 7.92(1H, s), 8.44(1H, s), 8.98(1H, s), 9.11(1H, s), 9.40(1H, s).

Example 833

1-{2-tert-Butyl-4-[2-(7-fluoro-1-imino-5,6-dimethoxy-1,3-dihydro-isoindol-2-yl)-acetyl]-phenyl}-pyrrolidine-2,5-dione hydrobromide 1H-NMR(DMSO-d6) δ: 1.27(9H, s), 2.74–2.95(4H, m), 3.86(3H, s), 3.95(3H, s), 4.84(2H, s), 5.53(2H, s), 7.35(1H, d, J=8.0 Hz), 7.37(1H, s), 7.94(1H, dd, J=8.0, 2.0 Hz), 8.10(1H, d, J=2.0 Hz).

Example 834

4-{2-tert-Butyl-4-[2-(2-cyclopropyl-7-imino-5,7-dihydro-pyrrolo[3,4-b]pyridin-6-yl)-acetyl]-phenylamino}-butyric acid trifluoroacetate 1H-NMR(DMSO-d6) δ: 1.10–1.23(4H, m), 1.74–2.10 (2H, m), 2.27–2.35(1H, m), 2.43(1H, t, J=7.2 Hz), 3.42(1H, dd, J=7.2, 6.0 Hz), 3.90(1H, ddd, J=7.2,5.6,1.6 Hz), 4.84 (2H, s), 5.42(2H, s), 5.45(1H, dd, 6.0,1.6 Hz), 6.81(1H, d, J=8.8 Hz), 7.66(1H, d, J=8.8 Hz), 7.83(1H, dd, J=8.4, 2.0 Hz), 7.93(1H, d, J=2.0 Hz), 7.99(1H, d, J=8.4 Hz).

Example 835

4-{2-tert-Butyl-4-[2-(7-fluoro-1-imino-5,6-dimethoxy-1,3-dihydro-isoindol-2-yl)-acetyl]-phenylamino}-butyric acid trifluoroacetate 1H-NMR(DMSO-d6) δ: 1.36(9H, s), 1.75–1.84(2H, m), 2.25–2.31(2H, m), 3.30–3.40(2H, m), 3.86((3H, s), 3.95(3H, s), 4.78(2H, s), 5.35(2H, s), 5.70–5.78(1H, m), 6.75(1H, d, J=8.8 Hz), 7.34(1H, s), 7.70(1H, d, J=8.8 Hz), 7.74(1H, s), 9.00–9.07(1H, m), 9.28–9.32(1H, m).

Example 836

5-[2-tert-Butyl-4-[2-(7-fluoro-1-imino-5,6-dimethoxy-1,3-dihydro-isoindol-2-yl)-acetyl]-6-(3-fluoro-pyrrolidin-1-yl)-phenoxy]-pentanoic acid hydrochloride 1H-NMR(DMSO-d6) δ: 1.38(9H, s), 1.61–1.70(2H, m), 1.76–1.84(2H, m), 2.12–2.22(1H, m), 2.28(2H, t, J=6.8 Hz), 2.36–2.41(1H, m), 3.02–3.10(1H, m), 3.25–3.29(1H, m), 3.42–3.49(1H, m), 3.61–3.70(1H, m), 3.86(3H, s), 3.95(3H, s), 4.01–4.08(2H, m), 4.80(2H, s), 5.40(1H, brd, J=56 Hz), 5.55(2H, d, J=4.4 Hz), 7.36(1H, s), 7.39(1H, s), 7.49(1H, s), 9.10(1H, br), 9.45(1H, br).

MS: m/e (ESI) 588.3 (MH+)

Example 837

Methyl 5-[2-tert-butyl-4-[2-(7-fluoro-1-imino-5,6-dimethoxy-1,3-dihydro-isoindol-2-yl)-acetyl]-6-(3-fluoro-pyrrolidin-1-yl)-phenoxy]-pentanoate hydrochloride 1H-NMR(DMSO-d6) δ: 1.38(9H, s), 1.61–1.72(2H, m), 1.75–1.84(2H, m), 2.08–2.22(2H, m), 2.38(2H, t, J=6.8 Hz), 3.02–3.10(1H, m), 3.25–3.28(1H, m), 3.42–3.50(1H, m), 3.58(3H, s), 3.64–3.68(1H, m), 3.86(3H, s), 3.95(3H, s), 4.40–4.42(2H, m), 4.80(2H, s), 5.40(1H, brd, J=56 Hz), 5.59(2H, d, J=4.0 Hz), 7.36(1H, s), 7.39(1H, s), 7.50(1H, s), 9.12(1H, brs), 9.51(1H, brs).

MS: m/e (ESI) 602.3 (MH+)

Example 838

3-{3-tert-Butyl-5-[2-(5-ethoxy-1-imino-6-methylcarbamoyl-1,3-dihydro-isoindol-2-yl)-acetyl]-benzyloxy}-4-cyano-butyric acid trifluoroacetate 1H-NMR(DMSO-d6) δ: 1.33(9H, s), 1.41(3H, t, J=7.2 Hz), 2.59–3.11(8H, m), 4.29(2H, q, J=7.2 Hz), 4.68(2H, dd, J=12.0 Hz, 12.0 Hz), 4.87(2H, s), 5.50(2H, s), 7.54(1H, s), 7.75(1H, s), 7.79(1H, s), 7.91(1H, s), 8.21(1H, d, J=4.4 Hz), 8.56(1H, s), 9.23(1H, brs), 9.85(1H, brs).

Example 839

Ethyl 5-{2-tert-butyl-4-[2-(7-fluoro-1-imino-5,6-dimethoxy-1,3-dihydro-isoindol-2-yl)-acetyl]-phenoxy}-pentanoate trifluoroacetate 1H-NMR(DMSO-d6) δ: 1.18(3H, t, J=6.8 Hz), 1.38(9H, s), 1.66–1.88(4H, m), 2.25–2.42(2H, m), 3.87(3H, s), 3.95 (3H, s), 4.05(2H, q, J=6.8 Hz), 4.14(2H, t, J=7.0 Hz), 4.78(2H, s), 5.43(2H, s), 7.17(1H, d, J=8.0 Hz), 7.34(1H, s), 7.83(1H, s), 7.90(1H, d, J=8.0 Hz).

Example 840

5-{2-tert-Butyl-4-[2-(7-fluoro-1-imino-5,6-dimethoxy-1,3-dihydro-isoindol-2-yl)-acetyl]-6-(pyrrolidin-1-yl)-phenoxymethyl}-4,5-dihydro-isoxazole-3-carboxylic acid hydrochloride 1H-NMR(DMSO-d6) δ: 1.38(9H, s), 1.85–1.90(4H, m), 3.06–3.14(4H, m), 3.86(3H, s), 3.92–3.99(1H, m), 3.95(3H, s), 4.06–4.10(1H, m), 4.79(2H, s), 5.16–5.22(1H, m), 5.58 (2H, s), 7.36(1H, s), 7.40(1H, s), 7.48(1H, s), 9.11(1H, s), 9.51(1H, s).

Example 841

Methyl 5-{2-tert-butyl-4-[2-(7-fluoro-1-imino-5,6-dimethoxy-1,3-dihydro-isoindol-2-yl)-acetyl]-6-(pyrrolidin-1-yl)-phenoxymethyl}-4,5-dihydro-isoxazole-3-carboxylate hydrochloride 1H-NMR(DMSO-d6) δ: 1.38(9H, s), 1.84–1.91(4H, m), 3.06–3.18(4H, m), 3.78(3H, s), 3.86(3H, s), 3.96–4.00(1H, m), 3.95(3H, s), 4.09(1H, dd, J=7.2, 10.4 Hz), 4.79(2H, s), 5.17–5.26(1H, m), 5.55(2H, s), 7.36(1H, s), 7.40(1H, s), 7.48(1H, d, J=2.0 Hz), 9.10(1H, s), 9.45(1H, s).

Example 842

6-{2-tert-Butyl-4-[2-(5-ethoxy-1-imino-6-methylcarbamoyl-1,3-dihydro-isoindol-2-yl)-acetyl]-phenoxy}-nicotinic acid trifluoroacetate 1H-NMR(DMSO-d6) δ: 1.22–1.58(12H, m), 2.83(3H, brs), 4.20–4.46(2H, m), 4.88(2H, s), 5.52(2H, s), 7.17–7.48 (2H, m), 7.55(1H, s), 7.85–7.99(1H, m), 8.03(1H, s), 8.15–8.26(1H, m), 8.29–8.41(1H, m), 8.57(1H, s), 8.66(1H, brs), 9.18–9.27(1H, m), 9.79–9.97(2H, m).

Example 843

Methyl 6-{2-tert-butyl-4-[2-(5-ethoxy-1-imino-6-methylcarbamoyl-1,3-dihydro-isoindol-2-yl)-acetyl]-phenoxy}-nicotinate trifluoroacetate 1H-NMR(DMSO-d6) δ: 1.34(9H, s), 1.42(3H, t, J=7.2), 2.83(3H, d, J=4.4), 3.85(3H, s), 4.15–4.42(2H, m), 4.88(2H, s), 5.53(2H, s), 7.15–7.35(2H, m), 7.55(1H, s), 7.95(1H, d, J=8.4 Hz), 8.04(1H, s), 8.13–8.28(1H, m), 8.39(1H, dd, J=8.4 and 2.4 Hz), 8.57(1H, s), 8.69(1H, brs), 9.17–9.29(1H, m), 9.80–9.92(2H, m).

Example 844

Methyl 5-{2-tert-butyl-6-(4-cyano-piperidin-1-yl)-4-(2-(2-cyclopropyl-7-imino-5,7-dihydro-pyrrolo[3,4-b]pyridin-6-yl)-acetyl]-phenoxy}-pentanoate hydrobromide 1H-NMR(DMSO-d6) δ: 1.14–1.18(4H, m), 1.21–1.25 (2H, m), 1.38(9H, s), 1.94–2.03(2H, m), 2.09–2.21(3H, m), 2.43(2H, br, t, J=6 Hz), 2.71–2.80(1H, brs), 2.96–3.07(2H, brs), 3.28–3.37(2H, brs), 3.69(3H, s), 3.70(2H, q, J=7 Hz), 4.21–4.26(2H, brs), 4.88(2H, s), 6.40(2H, s), 7.65(1H, d, J=8 Hz), 7.77–7.82(3H, m).

Example 845

Methyl 5-{2-tert-butyl-6-(4-cyano-piperidin-1-yl)-4-[2-(7-fluoro-1-imino-5,6-dimethoxy-1,3-dihydro-isoindol-2-yl)-acetyl]-phenoxy}-pentanoate hydrobromide 1H-NMR(DMSO-d6) δ: 1.20(2H, m), 1.38(9H, s), 1.84–1.92(2H, m), 2.06–2.16(2H, m), 2.44(2H, br, t, J=6 Hz), 2.70–2.79(2H, 1H, brs), 2.95–3.06(2H, brs), 3.26–3.37 (2H, brs), 3.69(3H, s), 3.69(2H, q, J=7 Hz), 3.96(3H, s), 3.98(3H, s), 4.20–4.24(2H, m), 4.85(2H, s), 6.09(2H, s), 6.92(1H, s), 7.76(2H, s).

Example 846

[2-tert-Butyl-4-[2-(5-ethoxy-1-imino-6-methylcarbamoyl-1,3-dihydro-isoindol-2-yl)-acetyl]-6-(2-methyl-pyrrolidin-1-yl)-phenoxy]-acetic acid trifluoroacetate 1H-NMR(DMSO-d6) δ: 0.97(3H, d, J=5.2 Hz), 1.37(9H, s), 1.41(3H, t, J=6.8 Hz), 1.48–2.22(4H, m), 2.70–2.91(1H, m), 2.82(3H, d, J=3.2 Hz), 3.68–3.80(1H, m), 3.85(1H, d, J=15.2 Hz), 4.27(2H, q, J=7.2 Hz), 4.83(2H, s), 5.03(1H, d, J=15.2 Hz), 5.44(1H, d, J=18.8 Hz), 5.52(1H, d, J=18.8 Hz), 7.43(1H, s), 7.50(1H, s), 7.54(1H, s), 8.12–8.30(1H, m), 8.55(1H, s), 9.14(1H, brs), 9.83(1H, brs).

Example 847

Ethyl [2-tert-butyl-4-[2-(5-ethoxy-1-imino-6-methylcarbamoyl-1,3-dihydro-isoindol-2-yl)-acetyl]-6-(2-methyl-pyrrolidin-1-yl)-phenoxy]-acetate trifluoroacetate 1H-NMR(DMSO-d6) δ: 0.97(3H, d, J=5.6 Hz), 1.22(3H, t, J=7.2 Hz), 1.37(9H, s), 1.41(3H, t, J=6.8 Hz), 1.46–1.58 (1H, m), 1.65–1.80(1H, m), 1.81–1.94(1H, m), 2.08–2.22 (1H, m), 2.68–2.80(1H, m), 2.82(3H, d, J=4.0 Hz), 3.40–3.58(1H, m), 3.65–3.79(1H, m), 4.00(1H, d, J=15.6 Hz), 4.10–4.35(4H, m), 4.84(2H, s), 5.07(1H, d, J=15.6 Hz), 5.45(1H, d, J=19.2 Hz), 5.53(1H, d, J=19.2 Hz), 7.45(1H, s), 7.51(1H, s), 7.54(1H, s), 8.20(1H, brs), 8.55(1H, s), 9.15 (1H, brs), 9.84(1H, brs).

Example 848

2-{2-[3-(Acetyl-methyl-amino)-5-tert-butyl-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.34(9H, s), 1.41(3H, t, J=7.2 Hz), 1.81(3H, brs), 2.83(3H, d, J=4.8 Hz), 3.29(3H, s), 4.29(2H, q, J=7.2 Hz), 4.87(2H, s), 5.52(2H, s), 7.55(1H, s), 7.65–7.98(3H, m), 8.12–8.27(1H, m), 8.57(1H, s), 9.22(1H, brs), 9.87(1H, brs).

Example 849

6-[2-(8-tert-Butyl-4-methanesulfonyl-3,4-dihydro-2H-benzo[1,4]oxazin-6-yl)-2-oxo-ethyl]-3-ethoxy-7-imino-6,7-dihydro-5H-pyrrolo[3,4-b]pyridine-2-carboxylic acid methylamide trifluoroacetate 1H-NMR(DMSO-d6) δ: 1.28–1.46(12H, m), 1.81(3H, brs), 2.77(3H, d, J=3.6 Hz), 3.18(3H, s), 3.86(2H, brs), 4.24(2H, q, J=6.8 Hz), 4.45(2H, brs), 4.88(2H, s), 5.49(2H, s), 7.66(1H, s), 7.99(1H, s), 8.14(1H, s), 8.43–8.61(1H, m), 9.34–9.48(1H, m), 9.87–10.01(1H, m).
MS: m/e (ESI) 544.2 (MH+)

Example 850

Ethyl 5-{2-tert-butyl-4-[2-(5-ethoxy-1-imino-6-methylcarbamoyl-1,3-dihydro-isoindol-2-yl)-acetyl]-6-morpholino-phenoxy}-pentanoate hydrochloride 1H-NMR(DMSO-d6) δ: 1.18(3H, t, J=7.0 Hz), 1.37(9H, s), 1.42(3H, t, J=7.0 Hz), 1.68–1.82(4H, m), 2.39(2H, t, J=6.8 Hz), 2.83(3H, d, J=4.0 Hz), 2.94–3.02(4H, m), 3.76–3.83(4H, m), 4.04(2H, q, J=7.0 Hz), 4.24(2H, t, J=6.8 Hz), 4.28(2H, q, J=7.0 Hz), 4.83(2H, s), 5.53(2H, s), 7.51 (1H, s), 7.54(1H, s), 7.63(1H, s), 8.20(1H, q, J=4.0 Hz), 8.57(1H, s), 9.19(1H, brs), 9.86(1H, brs).

Example 851

Ethyl 5-{2-tert-butyl-4-[2-(7-fluoro-1-imino-5,6-dimethoxy-1,3-dihydro-isoindol-2-yl)-acetyl]-6-morpholino-phenoxy}-pentanoate hydrobromide 1H-NMR(DMSO-d6) δ: 1.17(3H, t, J=6.8 Hz), 1.37(9H, s), 1.70–1.84(4H, m), 2.37–2.44(2H, m), 2.96–3.03(4H, m), 3.75–3.92(4H, m), 3.97(3H, s), 3.96(3H, s), 4.04(2H, q, J=6.8 Hz), 4.24(2H, t, J=7.0 Hz), 4.79(2H, s), 5.50(2H, s), 7.37(1H, s), 7.50(1H, s), 7.62(1H, s).

Example 852

(1-{3-tert-Butyl-5-[2-(5-ethoxy-1-imino-6-methyl-carbamoyl-1,3-dihydro-isoindol-2-yl)-acetyl]-2-methoxy-phenyl}-pyrrolidin-3-yloxy)-acetic acid trifluoroacetate 1H-NMR(DMSO-d6) δ: 1.37(9H, s), 1.41(3H, t, J=7.2 Hz), 1.99–2.12(2H, m), 2.82(3H, d, J=3.6 Hz), 3.06–3.16 (2H, m), 3.64(3H, s), 4.05(2H, s), 4.16–4.35(3H, m), 4.83 (2H, s), 5.48(2H, brs), 7.35(1H, s), 7.44(1H, s), 7.53(1H, s), 8.13–8.24(1H, m), 8.55(1H, s), 9.10–9.18(1H, m), 9.79–9.89(1H, m).
MS: m/e (ESI) 581.3 (MH+)

Example 853

(1-{3-tert-Butyl-5-[2-(3-ethoxy-7-imino-2-methyl-carbamoyl-5,7-dihydro-pyrrolo[3,4-b]pyridin-6-yl)-acetyl]-2-methoxy-phenyl}-pyrrolidin-3-yloxy)-acetic acid trifluoroacetate 1H-NMR(DMSO-d6) δ: 1.24–1.54(12H, m), 1.98–2.14 (2H, m), 2.77(3H, d, J=4.4 Hz), 3.06–3.15(2H, m), 3.64(3H, s), 4.05(2H, s), 4.13–4.42(2H, m), 4.87(2H, s), 5.53(2H, brs), 7.34(1H, s), 7.44(1H, s), 7.99(1H, s), 8.42–8.62(1H, m), 9.32–9.45(1H, m), 9.90–10.00(1H, m).
MS: m/e (ESI) 582.3 (MH+)

Example 854

Methyl (1-(3-tert-butyl-5-[2-(5-ethoxy-1-imino-6-methylcarbamoyl-1,3-dihydro-isoindol-2-yl)-acetyl]-2-methoxy-phenyl)-pyrrolidin-3-yloxy)-acetate hydrobromide 1H-NMR(DMSO-d6) δ: 1.38(9H, s), 1.41(3H, t, J=6.8 Hz), 1.98–2.13(2H, m), 2.82(3H, d, J=4.8 Hz), 3.06–3.15 (2H, m), 3.38–3.48(2H, m), 3.63(3H, s), 3.64(3H, s), 4.17 (2H, s), 4.18–4.40(3H, m), 4.84(2H, s), 5.40–5.56(2H, m), 7.34(1H, d, J=2.0 Hz), 7.44(1H, d, J=2.0 Hz), 7.54(1H, s), 8.11–8.28(1H, m), 8.55(1H, s), 9.12–9.18(1H, m), 9.79–9.86(1H, m).
MS: m/e (ESI) 595.3 (MH+)

Example 855

2-tert-Butyl-4-[2-(5-ethoxy-1-imino-6-methylcar-bamoyl-1,3-dihydro-isoindol-2-yl)-acetyl]-phenyl methylcarbamate hydrobromide 1H-NMR(DMSO-d6) δ: 1.35(9H, S), 1.41(3H, t, J=6.8 Hz), 2.70(3H, d, J=4.4 Hz), 2.82(3H, d, J=4.8 Hz), 4.28(2H, q, J=6.8 Hz), 4.86(2H, s), 5.49(2H, s), 7.26(1H, d, J=8.4 Hz), 7.54(1H, s), 7.86–7.93(3H, m), 8.21(1H, q, J=4.8 Hz), 8.56(1H, s), 9.20(1H, brs), 9.85(1H, brs).
MS: m/e (ESI) 481.1 (MH+)

Example 856

2-tert-Butyl-4-[2-(5,6-diethoxy-7-fluoro-1-imino-1,3-dihydro-isoindol-2-yl)-acetyl]-phenyl methylcarbamate hydrobromide 1H-NMR(DMSO-d6) δ: 1.29(3H, t, J=7.0 Hz), 1.35(9H, S), 1.40(3H, t, J=7.0 Hz), 2.70(3H, d, J=4.8 Hz), 4.11(2H, q, J=7.0 Hz), 4.21(2H, q, J=7.0 Hz), 4.80(2H, s), 5.46(2H, s), 7.25(1H, d, J=8.8 Hz), 7.33(1H, s), 7.88–7.92(3H, m).
MS: m/e (ESI) 486.2 (MH+)

Example 857

2-tert-Butyl-4-[2-(3-ethoxy-7-imino-2-methylcar-bamoyl-5,7-dihydro-pyrrolo[3,4-b]pyridin-6-yl)-acetyl]-phenyl methylcarbamate hydrobromide 1H-NMR(DMSO-d6) δ: 1.35(9H, S), 1.36(3H, t, J=7.0 Hz), 2.70(3H, d, J=4.6 Hz), 2.78(3H, d, J=4.6 Hz), 4.24(2H, q, J=7.0 Hz), 4.90(2H, s), 5.53(2H, s), 7.26(1H, d, J=8.4 Hz), 7.87–7.94(3H, m), 8.00(1H, s), 8.53(1H, q, J=4.6 Hz), 9.43(1H, brs), 9.96(1H, brs).
MS: m/e (ESI) 482.1 (MH+)

Example 858

{8-tert-Butyl-6-[2-(5,6-diethoxy-7-fluoro-1-imino-1,3-dihydro-isoindol-2-yl)-acetyl]-4-methyl-3,4-dihydro-2H-benzo[1,4]oxazin-2-yl}-acetic acid hydrochloride 1H-NMR(DMSO-d6) δ: 1.28(3H, t, J=6.8 Hz), 1.32(9H, s), 1.40(3H, t, J=6.8 Hz), 2.56(1H, dd, J=16.8, 8.2 Hz), 2.77(1H, dd, J=16.8, 4.0 Hz), 2.92(3H, s), 3.08(1H, dd, J=16.4, 8.0 Hz), 3.62–3.72(1H, m), 4.12(2H, q, J=6.8 Hz), 7.22(2H, d, J=6.8 Hz), 4.58–4.64(1H, m), 4.78(2H, s), 5.47(2H, s), 7.18(1H, s), 7.24(1H, s).

Example 859

{8-tert-Butyl-6-[2-(7-fluoro-1-imino-5,6-dimethoxy-1,3-dihydro-isoindol-2-yl)-acetyl]-4-methyl-3,4-dihydro-2H-benzo[1,4]oxazin-2-yl}-acetic acid hydrochloride 1H-NMR(DMSO-d6) δ: 1.34(9H, s), 2.54(1H, dd, J=16.8, 8.2 Hz), 2.74(1H, dd, J=16.8, 4.4 Hz), 2.94(3H, s), 3.08(1H, dd, J=16.4, 8.0 Hz), 3.60–3.72(1H, m), 3.86(3H, s), 3.97 (3H, s), 4.57–4.64(1H, m), 4.80(2H, s), 5.49(2H, s), 7.18 (1H, s), 7.27(1H, s), 7.36(1H, s).

Example 860

{8-tert-Butyl-6-[2-(3-ethoxy-7-imino-2-methylcar-bamoyl-5,7-dihydro-pyrrolo[3,4-b]pyridin-6-yl)-acetyl]-4-methyl-3,4-dihydro-2H-benzo[1,4]oxazin-2-yl}-acetic acid hydrochloride 1H-NMR(DMSO-d6) δ: 1.29(9H, s), 1.36(3H, t, J=7.0 Hz), 2.50–2.62(1H, m), 2.75–2.82(1H, m), 2.78(3H, d, J=4.0 Hz), 2.92(3H, s), 3.04–3.12(1H, m), 3.62–3.74(1H, m), 4.24(2H, q, J=7.0 Hz), 4.58–4.64(1H, m), 4.88(2H, s), 5.54(2H, s), 7.19(1H, s), 7.30(1H, s), 7.98(1H, s), 8.56(1H, q, J=4.0 Hz), 9.94(1H, brs).

Example 861

Ethyl {8-tert-butyl-6-[2-(5,6-diethoxy-7-fluoro-1-imino-1,3-dihydro-isoindol-2-yl)-acetyl]-4-methyl-3,4-dihydro-2H-benzo[1,4]oxazin-2-yl}-acetate hydrochloride 1H-NMR(DMSO-d6) δ: 1.20(3H, t, J=6.8 Hz), 1.29(3H, t, J=6.8 Hz), 1.30(9H, s), 1.39(3H, t, J=6.8 Hz), 2.62(1H, dd, J=16.0, 8.8 Hz), 2.88(1H, dd, J=16, 3.6 Hz), 2.90(3H, s), 3.08(1H, dd, J=12, 8.0 Hz), 3.38(1H, dd, J=12, 3.6 Hz), 4.08(2H, q, J=6.8 Hz), 4.10(2H, q, J=6.8 Hz), 4.21(2H, q, J=6.8 Hz), 4.60–4.66(1H, m), 4.78(2H, s), 5.48(2H, s), 7.19(1H, s), 7.28(1H, s), 7.34(1H, s), 9.03(1H, brs), 9.36 (1H, brs).

Example 862

Ethyl {8-tert-butyl-6-[2-(7-fluoro-1-imino-5,6-dimethoxy-1,3-dihydro-isoindol-2-yl)-acetyl]-4-methyl-3,4-dihydro-2H-benzo[1,4]oxazin-2-yl}-acetate hydrochloride 1H-NMR(DMSO-d6) δ: 1.20(3H, t, J=6.8 Hz), 1.30(9H, t), 2.62(1H, dd, J=16, 9.2 Hz), 2.86(1H, dd, J=16, 3.2 Hz), 2.90(3H, s), 3.08(1H, dd, J=12, 8.0 Hz), 3.40(1H, dd, J=12, 2.4 Hz), 3.86(3H, s), 3.95(3H, s), 4.11(2H, q, J=6.8 Hz), 4.60–4.68(1H, m), 4.80(2H, s), 5.45(2H, s), 7.18(1H, d, J=2.0 Hz), 7.28(1H, d, J=2.0 Hz), 7.35(1H, s), 9.04(1H, brs), 9.32(1H, brs).

Example 863

Ethyl {8-tert-butyl-6-[2-(3-ethoxy-7-imino-2-methylcarbamoyl-5,7-dihydro-pyrrolo[3,4-b]pyridin-6-yl)-acetyl]-4-methyl-3,4-dihydro-2H-benzo[1,4]oxazin-2-yl}-acetate hydrochloride 1H-NMR(DMSO-d6) δ: 1.20(3H, t, J=6.8 Hz), 1.29(9H, s), 1.37(3H, t, J=6.8 Hz), 2.62(1H, dd, J=19.2, 8.8 Hz), 2.77(3H, d, J=4.0 Hz), 2.86(1H, dd, J=19.2, 3.2 Hz), 2.91(3H, s), 3.09(1H, dd, J=12, 8.8 Hz), 3.40(1H, dd, J=12, 3.6 Hz), 4.09(2H, q, J=6.8 Hz), 4.23(2H, q, J=6.8 Hz), 4.57–4.70(1H, m), 4.87(2H, s), 5.54(2H, s), 7.20(1H, s), 7.29(1H, s), 7.99(1H, s), 8.55(1H, q, J=4.0 Hz), 9.51(1H, brs), 9.96(1H, brs).

Example 864

2-(1-{3-tert-Butyl-5-[2-(7-fluoro-1-imino-5,6-dimethoxy-1,3-dihydro-isoindol-2-yl)-acetyl]-2-methoxy-phenyl}-pyrrolidin-3-yloxy)-butyric acid trifluoroacetate 1H-NMR(DMSO-d6) δ: 0.92(3H, t, J=7.6 Hz), 1.44(9H, s), 1.61–1.83(2H, m), 2.10–2.24(2H, m), 3.09–3.17(1H, m), 3.19–3.26(1H, m), 3.41–3.56(2H, m), 3.74(3H, s), 3.92(1H, dd, J=7.6 and4.8 Hz), 3.94(3H, s), 4.02(3H, s), 4.25–4.33(1H, m), 4.85(2H, s), 5.45(2H, s), 7.24(1H, s), 7.46(1H, d, J=2.0 Hz), 7.60(1H, d, J=2.0 Hz).

Example 865

2-(1-{3-tert-Butyl-5-[2-(7-fluoro-1-imino-5,6-dimethoxy-1,3-dihydro-isoindol-2-yl)-acetyl]-2-methoxy-phenyl}-pyrrolidin-3-yloxy)-butyric acid trifluoroacetate 1H-NMR(DMSO-d6) δ: 1.00(3H, t, J=7.6 Hz), 1.44(9H, s), 1.63–1.87(2H, m), 2.04–2.19(2H, m), 3.13–3.22(1H, m), 3.22–3.30(1H, m), 3.40–3.57(2H, m), 3.74(3H, s), 3.94(3H, s), 3.98(1H, dd, J=7.6 and 4.4 Hz), 4.02(3H, s), 4.25–4.35(1H, m), 4.86(2H, s), 5.45(2H, s), 7.24(1H, s), 7.46(1H, d, J=2.0 Hz), 7.60(1H, d, J=2.0 Hz).

Example 866

Ethyl 8-tert-butyl-6-[2-(5,6-diethoxy-7-fluoro-1-imino-1,3-dihydro-isoindol-2-yl)-acetyl]-4-methyl-3,4-dihydro-2H-benzo[1,4]oxazine-2-carboxylate hydrochloride 1H-NMR(DMSO-d6) δ: 1.17(3H, t, J=6.8 Hz), 1.28(3H, t, J=6.8 Hz), 1.39(9H, s), 1.27–1.44(3H, m), 2.91(3H, s), 3.42–3.55(2H, m), 4.12(2H, q, J=6.8 Hz), 4.10–4.20(2H, m), 4.22(2H, q, J=6.8 Hz), 4.78(2H, s), 5.28–5.32(1H, m), 5.47(2H, s), 7.17(1H, s), 7.32–7.36(2H, m), 9.03(1H, brs), 9.34(1H, brs).

Example 867

2-(3,5-Di-tert-butyl-4-hydroxy-benzoylamino)-6-ethoxy-3-imino-2,3-dihydro-1H-isoindole-5-carboxylic acid methylamide hydrobromide 1H-NMR(DMSO-d6) δ: 1.41(21H, m), 2.82(3H, d, J=4.8 Hz), 4.27(2H, q, J=6.8 Hz), 4.99(2H, s), 7.47(1H, s), 7.77(2H, s), 8.20(1H, q, 4.8 Hz), 8.52(1H, s).
MS: m/e (ESI) 481.2 (MH+)

Example 868

1-(3-tert-Butyl-5-dimethylamino-4-methoxy-phenyl)-2-(7-fluoro-1-imino-5,6-dimethoxy-1,3-dihydro-isoindol-2-yl)-ethanone hydrobromide 1H-NMR(DMSO-d6) δ: 1.37(9H, s), 2.75(6H, s), 3.82(3H, s), 3.87(3H, s), 3.95(3H, s), 4.80(2H, s), 5.49(2H, s), 7.37(1H, s), 7.45(1H, d, J=2.0 Hz), 7.53(1H, d, J=2.0 Hz), 9.06(1H, brs), 9.28(1H, brs).

Example 869

2-[2-(3-tert-Butyl-5-dimethylamino-4-methoxy-phenyl)-2-oxo-ethyl]-6-dimethylamino-3-imino-2,3-dihydro-1H-isoindole-5-carboxylic acid methylamide hydrobromide 1H-NMR(DMSO-d6) δ: 1.37(9H, s), 2.75(6H, s), 2.77(3H, d, J=4.0 Hz), 2.92(6H, s), 3.82(3H, s), 4.73(2H, s), 5.44(2H, s), 7.15(1H, s), 7.45(1H, s), 7.53(1H, s), 8.06(1H,), 8.36(1H, q, J=4.0 Hz), 8.93(1H, brs), 9.49(1H, brs).

Example 870

6-[2-(3-tert-Butyl-5-dimethylamino-4-methoxy-phenyl)-2-oxo-ethyl]-3-ethoxy-7-imino-6,7-dihydro-5H-pyrrolo[3,4-b]pyridine-2-carboxylic acid methylamide hydrochloride 1H-NMR(DMSO-d6) δ: 1.36(3H, t, J=6.8 Hz), 1.37(9H, s), 2.76(6H, s), 2.77(3H, d, J=4.0 Hz), 3.83(3H, s), 4.24(2H, q, J=6.8 Hz), 4.85(2H, s), 5.60(2H, s), 7.48(1H, s), 7.54(1H, s), 8.00(1H, s), 8.57(1H, q, J=4.0 Hz), 9.56(1H, brs), 9.97(1H, brs).

Example 871

{8-tert-Butyl-6-[2-(5,6-diethoxy-7-fluoro-1-imino-1,3-dihydro-isoindol-2-yl)-acetyl]-3-oxo-3,4-dihydro-2H-benzo[1,4]oxazin-2-yl}-acetic acid hydrochloride 1H-NMR(DMSO-d6) δ: 1.29(3H, t, J=6.8 Hz), 1.35(9H, s), 1.39(3H, t, J=6.8 Hz), 2.81(1H, dd, J=16.8, 8.0 Hz), 3.05(1H, dd, J=16.8, 4.0 Hz), 4.11(2H, q, J=6.8 Hz), 4.21 (2H, q, J=6.8 Hz), 4.79(2H, s), 4.98(1H, d, J=4.0 Hz), 5.45(2H, s), 7.33(1H, s), 7.41(1H, d, J=2.0 Hz), 7.53(1H, d, J=2.0 Hz), 9.03(1H, brs), 10.97(1H, brs).

Example 872

Ethyl {8-tert-butyl-6-[2-(5,6-diethoxy-7-fluoro-1-imino-1,3-dihydro-isoindol-2-yl)-acetyl]-3-oxo-3,4-dihydro-2H-benzo[1,4]oxazin-2-yl}-acetate hydrochloride 1H-NMR(DMSO-d6) δ: 1.17(3H, t, J=7.2 Hz), 1.29(3H, t, J=6.8 Hz), 1.33(9H, s), 1.40(3H, t, J=6.8 Hz), 2.92(1H, dd, J=16 Hz, 8.0 Hz), 3.14(1H, dd, J=16 Hz, 4.0 Hz), 4.04–4.17 (4H, m), 4.20(2H, q, J=6.8 Hz), 4.79(2H, s), 5.04(1H, dd, J=8.0 Hz, 4.0 Hz), 5.44(2H, s), 7.33(1H, s), 7.41(1H, s), 7.52(1H, s), 9.05(1H, brs), 9.32(1H, brs).
MS: m/e (ESI) 570.2 (MH+)

Example 873

Ethyl 2-(1-{3-tert-butyl-5-[2-(7-fluoro-1-imino-5,6-dimethoxy-1,3-dihydro-isoindol-2-yl)-acetyl]-2-methoxy-phenyl}-pyrrolidin-3-yloxy)-butyrate hydrobromide 1H-NMR(DMSO-d6) δ: 0.83 and 0.87[3H(1:1).each t.each J=7.2 Hz], 1.10–1.28(3H, m), 1.38(9H, s), 1.49–1.75 (2H, m), 1.92–2.17(2H, m), 2.99–3.20(2H, m), 3.25–3.52 (2H, m), 3.64(3H, s), 3.87(3H, s), 3.95(3H, s), 4.02–4.29 (3H, m), 4.81(2H, s), 5.51(2H, s), 7.33(1H, s), 7.37(1H, s), 7.44(1H, s), 9.02–9.13(1H, m), 9.26–9.39(1H, m).
MS: m/e (ESI) 614.3 (MH+)

Example 874

1-(3-tert-Butyl-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=6.8 Hz), 1.33(9H, s), 1.40(3H, t, J=6.8 Hz), 4.11(2H, q, J=6.8 Hz), 4.21(2H, q, J=6.8 Hz), 4.82(2H, s), 5.51(2H, s), 7.34(1H, s), 7.55(1H, t, J=8.0 Hz), 7.78(1H, d, J=8.0 Hz), 7.83(1H, d, J=8.0 Hz), 7.97(1H, s), 9.05(1H, brs), 9.35(1H, brs).

Example 875

2-[2-(3-tert-Butyl-5-ethoxy-4-methoxy-phenyl)-2-oxo-ethyl]-6-dimethylamino-3-imino-2,3-dihydro-1H-isoindole-5-carboxylic acid methylamide hydrobromide 1H-NMR(DMSO-d6) δ: 1.36(9H, S), 1.41(3H, t, J=6.8 Hz), 2.77(3H, d, J=4.4 Hz), 2.92(6H, s), 3.89(3H, s), 4.13 (2H, q, J=6.8 Hz), 4.74(2H, s), 5.45(2H, s), 7.15(1H, s), 7.51(2H, d, J=7.6 Hz), 8.07(1H, s), 8.35–8.38(1H, m), 8.94(1H, brs), 9.54(1H, brs).
MS: m/e (ESI) 481.2 (MH+)

Example 876

2-[2-(3-tert-Butyl-5-ethoxy-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.36(9H, S), 1.39–1.43(6H, m), 2.82(3H, d, J=4.8 Hz), 3.89(3H, s), 4.13(2H, q, J=7.0 Hz), 4.28(2H, q, J=7.0 Hz), 4.85(2H, s), 5.50(2H, s), 7.51–7.54 (3H, m), 8.21(1H, q, J=4.8 Hz), 8.56(1H, s), 9.20(1H, brs), 9.85(1H, brs).
MS: m/e (ESI) 482.2 (MH+)

Example 877

1-(3-tert-Butyl-5-ethoxy-4-methoxy-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=7.2 Hz), 1.36(9H, S), 1.38–1.43(6H, m), 3.89(3H, s), 4.08–4.24(6H, m), 4.79 (2H, s), 5.48(2H, s), 7.33(1H, s), 7.51(2H, d, J=5.2 Hz), 9.03(1H, brs), 9.26(1H, brs).
MS: m/e (ESI) 487.2 (MH+)

Example 878

6-[2-(3-tert-Butyl-5-ethoxy-4-methoxy-phenyl)-2-oxo-ethyl]-3-ethoxy-7-imino-6,7-dihydro-5H-pyrrolo[3,4-b]pyridine-2-carboxylic acid methylamide trifluoroacetate 1H-NMR(DMSO-d6) δ: 1.36(9H, S), 1.40–1.43(6H, m), 2.78(3H, d, J=4.8 Hz), 3.90(3H, s), 4.13(2H, q, J=7.0 Hz), 4.24(2H, q, J=7.0 Hz), 4.89(2H, s), 5.54(2H, s), 7.50–7.52 (2H, m), 8.00(1H, s), 8.53(1H, m), 9.42(1H, brs), 9.96(1H, brs).
MS: m/e (ESI) 483.1 (MH+)

Example 879

(1-{3-tert-Butyl-5-[2-(5-ethoxy-1-imino-6-methylcarbamoyl-1,3-dihydro-isoindol-2-yl)-acetyl]-2-methoxy-phenyl}-piperidin-4-yloxy)-acetic acid trifluoroacetate 1H-NMR(DMSO-d6) δ: 1.36(9H, s), 1.41(3H, t, J=7.2 Hz), 1.62–1.77(2H, m), 1.96–2.10(2H, m), 2.68–2.90(5H, m), 3.12–3.59(3H, m), 3.94(3H, s), 4.08(2H, s), 4.28(2H, q, J=7.2 Hz), 4.83(2H, s), 5.48(2H, s), 7.51(1H, s), 7.54(1H, s), 7.58(1H, s), 8.14–8.27(1H, m), 8.55(1H, s), 9.09–9.17(1H, m), 9.78–9.88(1H, m).

Example 880

(1-{3-tert-Butyl-5-[2-(7-fluoro-1-imino-5,6-dimethoxy-1,3-dihydro-isoindol-2-yl)-acetyl]-2-methoxy-phenyl}-piperidin-4-yloxy)-acetic acid trifluoroacetate 1H-NMR(DMSO-d6) δ: 1.36(9H, s), 1.63–1.76(2H, m), 1.97–2.08(2H, m), 2.69–2.82(2H, m), 3.16–3.60(3H, m), 3.87(3H, s), 3.94(3H, s), 3.95(3H, s), 4.07(2H, s), 4.80(2H, s), 5.47(2H, s), 7.36(1H, s), 7.50(1H, s), 7.57(1H, s), 9.06–9.10(1H, m), 9.24–9.32(1H, m).

Example 881

Ethyl (1-{3-tert-butyl-5-[2-(5-ethoxy-1-imino-6-methylcarbamoyl-1,3-dihydro-isoindol-2-yl)-acetyl]-2-methoxy-phenyl}-piperidin-4-yloxy)-acetate hydrobromide 1H-NMR(DMSO-d6) δ: 1.36(9H, S), 1.39–1.43(6H, m), 2.82(3H, d, J=4.8 Hz), 3.89(3H, s), 4.13(2H, q, J=7.0 Hz), methylcarbamoyl-1,3-dihydro-isoindol-2-yl)-acetyl]-2-methoxy-phenyl}-piperidin-4-yloxy)-acetate hydrobromide
1H-NMR(DMSO-d6) δ: 1.19(3H, t, J=7.2 Hz), 1.36(9H, s), 1.41(3H, t, J=6.8 Hz), 1.64–1.78(2H, m), 1.97–2.10(2H, m), 2.69–2.80(2H, m), 2.82(3H, d, J=4.8 Hz), 3.18–3.30(2H, m), 3.49–3.60(1H, m), 3.93(3H, s), 4.11(2H, q, J=7.2 Hz), 4.16(2H, s), 4.28(2H, q, J=7.2 Hz), 4.84(2H, s), 5.49(2H, s), 7.52(1H, s), 7.54(1H, s), 7.58(1H, s), 8.14–8.30(1H, m), 8.55(1H, s), 9.09–9.22(1H, m), 9.77–9.91(1H, m).
MS: m/e (ESI) 623.2 (MH+)

Example 882

Ethyl (1-{3-tert-butyl-5-[2-(7-fluoro-1-imino-5,6-dimethoxy-1,3-dihydro-isoindol-2-yl)-acetyl]-2-methoxy-phenyl}-piperidin-4-yloxy)-acetate hydrobromide 1H-NMR(DMSO-d6) δ: 1.19(3H, t, J=7.2 Hz), 1.36(9H, s), 1.62–1.78(2H, m), 1.97–2.10(2H, m), 2.69–2.84(2H, m), 3.17–3.32(2H, m), 3.50–3.58(1H, m), 3.87(3H, s), 3.94(3H, s), 3.95(3H, s), 4.11(2H, q, J=7.2 Hz), 4.17(2H, s), 4.80(2H, s), 5.49(2H, s), 7.37(1H, s), 7.51(1H, s), 7.57(1H, s), 9.06–9.12(1H, m), 9.24–9.35(1H, m).
MS: m/e (ESI) 600.2 (MH+)

Example 883

2-tert-Butyl-4-[2-(5,6-diethoxy-7-fluoro-1-imino-1,3-dihydro-isoindol-2-yl)-acetyl]-phenyl methanesulfonate hydrobromide 1H-NMR(DMSO-d6) δ: 1.29(3H, t, J=7.0 Hz), 1.38–1.41(12H, m), 3.68(3H, s), 4.12(2H, q, J=7.0 Hz), 4.21(2H, q, J=7.0 Hz), 4.81(2H, s), 5.49(2H, s), 7.34(1H, s), 7.70(1H, d, J=7.6 Hz), 7.95–8.10(2H, m), 9.02(1H, brs), 9.31(1H, brs).
MS: m/e (ESI) 507.1 (MH+)

Example 884

{3-tert-Butyl-5-[2-(7-fluoro-1-imino-5,6-dimethoxy-1,3-dihydro-isoindol-2-yl)-acetyl]-2-methoxy-phenoxy}-acetonitrile hydrobromide 1H-NMR(DMSO-d6) δ: 1.37(9H, s), 3.87(3H, s), 3.89(3H, s), 3.95(3H, s), 4.83(2H, s), 5.34(2H, s), 5.51(2H, s), 7.37(1H, s), 7.64(1H, s), 7.70(1H, s), 9.10(1H, brs), 9.37(1H, brs).

Example 885

4-{3-tert-Butyl-5-[2-(7-fluoro-1-imino-5,6-dimethoxy-1,3-dihydro-isoindol-2-yl)-acetyl]-2-methoxy-phenoxy}-butyronitrile hydrobromide 1H-NMR(DMSO-d6) δ: 1.37(9H, s), 2.07–2.16(2H, m), 2.67–2.75(2H, m), 3.87(3H, s), 3.90(3H, s), 3.95(3H, s), 4.11–4.18(2H, m), 4.82(2H, s), 5.51(2H, s), 7.37(1H, s), 7.49–7.59(2H, m), 9.00–9.17(1H, brs), 9.27–9.40(1H, m).

Example 886

2-[2-(3-tert-Butyl-5-cyanomethoxy-4-methoxy-phenyl)-2-oxo-ethyl]-6-dimethylamino-3-imino-2,3-dihydro-1H-isoindole-5-carboxylic acid methylamide hydrobromide 1H-NMR(DMSO-d6) δ: 1.37(9H, s), 2.73–2.82(3H, m), 2.91(6H, s), 3.89(3H, s), 4.78(2H, s), 5.33(2H, s), 5.46(2H, s), 7.15(1H, s), 7.65(1H, s), 7.69(1H, s), 8.07(1H, s), 8.31–8.46(1H, m), 8.97(1H, brs), 9.55(1H, brs).

Example 887

2-{2-[3-tert-Butyl-5-(3-cyano-propoxy)-4-methoxy-phenyl]-2-oxo-ethyl}-6-dimethylamino-3-imino-2,3-dihydro-1H-isoindole-5-carboxylic acid methylamide hydrobromide 1H-NMR(DMSO-d6) δ: 1.36(9H, s), 2.06–2.17(2H, m), 2.71(2H, t, J=7.6 Hz), 2.77(3H, d, J=4.8 Hz), 2.91(6H, s), 3.89(3H, s), 4.24(2H, t, J=6.0 Hz), 4.74(2H, s), 5.45(2H, s), 7.15(1H, s), 7.53(1H, s), 7.55(1H, s), 8.07(1H, s), 8.33–8.41(1H, m), 8.95(1H, brs), 9.55(1H, brs).

Example 888

2-[2-(8-tert-Butyl-4-cyanomethyl-3,4-dihydro-2H-benzo[1,4]oxazin-6-yl)-2-oxo-ethyl]-6-ethoxy-3-imino-2,3-dihydro-1H-isoindole-5-carboxylic acid methylamide trifluoroacetate 1H-NMR(DMSO-d6) δ: 1.36–1.43(12H, m), 2.82(3H, d, J=5 Hz), 3.30–3.40(2H, m), 4.28(2H, q, J=7 Hz), 4.40(2H, m), 4.66(2H, s), 4.85(2H, s), 5.45(2H, s), 7.42–7.45(2H, m), 7.53(1H, s), 8.21(1H, q, J=5 Hz), 8.56(1H, s), 9.22(1H, brs), 9.82(1H, brs).
MS: m/e (ESI) 504.3 (MH+)

Example 889

6-[2-(8-tert-Butyl-4-cyanomethyl-3,4-dihydro-2H-benzo[1,4]oxazin-6-yl)-2-oxo-ethyl]-3-ethoxy-7-imino-6,7-dihydro-5H-pyrrolo[3,4-b]pyridine-2-carboxylic acid methylamide trifluoroacetate 1H-NMR(DMSO-d6) δ: 1.33–1.38(12H, s), 2.78(3H, d, J=5 Hz), 3.30–3.40(2H, m), 4.25(2H, q, J=7 Hz), 4.40(2H, m), 4.66(2H, s), 4.89(2H, s), 5.49(2H, s), 7.40–7.43(2H, m), 7.99(1H, s), 8.53(1H, q, J=5 Hz), 9.46(1H, brs), 9.93(1H, brs).
MS: m/e (ESI) 505.3 (MH+)

Example 890

{8-tert-Butyl-6-[2-(7-fluoro-1-imino-5,6-dimethoxy-1,3-dihydro-isoindol-2-yl)-acetyl]-2,3-dihydro-benzo[1,4]oxazin-4-yl}-acetonitrile trifluoroacetate 1H-NMR(DMSO-d6) δ: 1.36(9H, s), 3.30–3.40(2H, m), 3.87(3H, s), 3.95(3H, s), 4.40(2H, m), 4.66(2H, s), 4.82(2H, s), 5.45(2H, s), 7.36(1H, s), 7.40–7.42(2H, m), 9.06(1H, brs), 9.35(1H, brs).
MS: m/e (ESI) 481.3 (MH+)

Example 891

{8-tert-Butyl-6-[2-(5,6-diethoxy-7-fluoro-1-imino-1,3-dihydro-isoindol-2-yl)-acetyl]-2,3-dihydro-benzo[1,4]oxazin-4-yl}-acetonitrile trifluoroacetate 1H-NMR(DMSO-d6) δ: 1.29(3H, t, J=7 Hz), 1.33–1.42 (12H, m), 3.30–3.40(2H, m), 4.11(2H, q, J=7 Hz), 4.21(2H, q, J=7 Hz), 4.40(2H, m), 4.66(2H, s), 4.80(2H, s), 5.45(2H, s), 7.33(1H, s), 7.40–7.42(2H, m), 9.03(1H, brs), 9.34(1H, brs).
MS: m/e (ESI) 509.3 (MH+)

Example 892

{8-tert-Butyl-6-[2-(2-cyclopropyl-7-imino-5,7-dihydro-pyrrolo[3,4-b]pyridin-6-yl)-acetyl]-2,3-dihydro-benzo[1,4]oxazin-4-yl}-acetonitrile trifluoroacetate 1H-NMR(DMSO-d6) δ: 1.06–1.11(4H, m), 1.36(9H, s), 2.32(1H, m), 3.30–3.40(2H, m), 4.40(2H, m), 4.66(2H, s), 4.83(2H, s), 5.51(2H, s), 7.41–7.44(2H, m), 7.72(1H, d, J=8 Hz), 8.09(1H, d, J=8 Hz), 9.52(1H, brs), 9.64(1H, brs).
MS: m/e (ESI) 444.3 (MH+)

Example 893

2-[2-(8-tert-Butyl-4-cyanomethyl-3,4-dihydro-2H-benzo[1,4]oxazin-6-yl)-2-oxo-ethyl]-6-dimethylamino-3-imino-2,3-dihydro-1H-isoindole-5-carboxylic acid methylamide trifluoroacetate 1H-NMR(DMSO-d6) δ: 1.36(9H, s), 2.77(3H, d, J=4 Hz), 2.91(6H, s), 3.30–3.40(2H, m), 4.40(2H, m), 4.66(2H, s), 4.75(2H, s), 5.41(2H, s), 7.15(1H, s), 7.41–7.43(2H, m), 8.07(1H, s), 8.37(1H, q, J=4 Hz), 8.98(1H, brs), 9.53(1H, brs).
MS: m/e (ESI) 503.4 (MH+)

Example 894

2-[2-(3-tert-Butyl-5-cyanomethoxy-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.38(9H, s), 1.42(3H, t, J=6.8 Hz), 2.83(3H, d, J=4.8 Hz), 3.89(3H, s), 4.29(2H, q, J=6.8 Hz), 4.86(2H, s), 5.34(2H, s), 5.50(2H, s), 7.54(1H, s), 7.65(1H, s), 7.71(1H, s), 8.15–8.30(1H, m), 8.56(1H, s), 9.14–9.26(1H, m), 9.77–9.93(1H, m).

Example 895

2-{2-[3-tert-Butyl-5-(3-cyano-propoxy)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.36(9H, s), 1.41(3H, t, J=6.8 Hz), 2.06–2.17(2H, m), 2.72(2H, t, J=7.2 Hz), 2.82(3H, d, J=4.8 Hz), 3.90(3H, s), 4.15(2H, t, J=6.0 Hz), 4.28(2H, q, J=6.8 Hz), 4.85(2H, s), 5.50(2H, s), 7.49–7.62(3H, m), 8.15–8.26(1H, m), 8.56(1H, s), 9.18(1H, brs), 9.85(1H, brs).

Example 896

2-(3-tert-Butyl-5-dimethylamino-4-methoxy-benzoylamino)-6-ethoxy-3-imino-2,3-dihydro-1H-isoindole-5-carboxylic acid methylamide hydrobromide 1H-NMR(DMSO-d6) δ: 1.34(9H, s), 1.41(3H, t, 6.8 Hz), 2.74(6H, s), 2.82(3H, d, J=4.8 Hz), 3.80(3H, s), 4.26(2H, q, J=6.8 Hz), 5.00(2H, s), 7.5–7.6(3H, m), 8.21(1H, q, J=4.8 Hz), 8.60(1H, s), 9.75(1H, s), 10.30(1H, s), 11.53(1H, s).
MS: m/e (ESI) 482.1 (MH+)

Example 897

{2-tert-Butyl-4-[2-(7-fluoro-1-imino-5,6-dimethoxy-1,3-dihydro-isoindol-2-yl)-acetyl]-phenoxy}-acetonitrile hydrobromide 1H-NMR(DMSO-d6) δ: 1.37(9H, s), 3.86(3H, s), 3.95(3H, s), 4.79(2H, s), 5.41(2H, s), 5.44(2H, s), 7.31–7.35(2H, m), 7.88(1Hs), 7.97–7.99(1H, m).
MS: m/e (ESI) 440.1 (MH+)

Example 898

{2-tert-Butyl-4-[2-(2-cyclopropyl-7-imino-5,7-dihydro-pyrrolo[3,4-b]pyridin-6-yl)-acetyl]-phenoxy}-acetonitrile hydrobromide 1H-NMR(DMSO-d6) δ: 1.08–1.11(4H, m), 1.37(9H, S), 2.30–2.34(1H, m), 4.83(2H, s), 5.42(2H, s), 5.56(2H, s), 7.33(1H, d, J=8.8 Hz), 7.72(1H, d, J=8.2 Hz), 7.89(1H, s), 8.00(1H, d, J=8.8 Hz), 8.09(1H, d, J=8.2 Hz), 9.60(2H, brs).
MS: m/e (ESI) 403.0 (MH+)

Example 899

2-[2-(3-tert-Butyl-4-cyanomethoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.37(9H, S), 1.42(3H, t, J=7.2 Hz), 2.83(3H, d, J=4.8 Hz), 4.28(2H, q, J=7.2 Hz), 4.86(2H, s), 5.41(2H, s), 5.47(2H, s), 7.33(1H, d, J=8.6 Hz), 7.54(1H, s), 7.89(1H, s), 8.00(1H, d, J=8.6 Hz), 8.21(1H, m), 8.56(1H, s), 9.19(1H, brs), 9.82(1H, brs).
MS: m/e (ESI) 463.1 (MH+)

Example 900

1-(3-tert-Butyl-5-ethoxy-4-methoxy-phenyl)-2-(7-fluoro-1-imino-5,6-dimethoxy-1,3-dihydro-isoindol-2-yl)-ethanone hydrobromide 1H-NMR(DMSO-d6) δ: 1.36(9H, S), 1.41(3H, t, J=7.0 Hz), 3.87(3H, s), 3.89(3H, s), 3.95(3H, s), 4.13(2H, q, J=7.0 Hz), 4.81(2H, s), 5.48(2H, s), 7.36(1H, s), 7.50(1H, s), 7.51(1H, s), 9.03(1H, brs), 9.30(1H, brs).
MS: m/e (ESI) 459.1 (MH+)

Example 901

2-[2-(3-tert-Butyl-4-cyanomethoxy-5-ethoxy-phenyl)-2-oxo-ethyl]-6-dimethylamino-3-imino-2,3-dihydro-1H-isoindole-5-carboxylic acid methylamide hydrobromide 1H-NMR(DMSO-d6) δ: 1.38(9H, S), 1.45(3H, t, J=7.2 Hz), 2.78(3H, d, J=4.6 Hz), 2.92(6H, s), 4.19(2H, q, J=7.2

Hz), 4.74(2H, s), 5.19(2H, s), 5.46(2H, s), 7.15(1H, s), 7.55(2H, s), 8.07(1H, s), 8.36(1H, q, J=4.6 Hz), 8.95(1H, brs), 9.53(1H, brs).

MS: m/e (ESI) 506.2 (MH+)

Example 902

{2-tert-Butyl-6-ethoxy-4-[2-(7-fluoro-1-imino-5,6-dimethoxy-1,3-dihydro-isoindol-2-yl)-acetyl]-phenoxy}-acetonitrile hydrobromide 1H-NMR(DMSO-d6) δ: 1.38(9H, S), 1.45(3H, t, J=6.8 Hz), 3.87(3H, s), 3.95(3H, s), 4.19(2H, q, J=6.8 Hz), 4.81 (2H, s), 5.19(2H, s), 5.50(2H, s), 7.37(1H, s), 7.54(2H, d, J=1.2 Hz), 9.08(1H, brs), 9.33(1H, brs).

MS: m/e (ESI) 484.1 (MH+)

Example 903

2-[2-(3-tert-Butyl-4-cyanomethoxy-phenyl)-2-oxo-ethyl]-6-dimethylamino-3-imino-2,3-dihydro-1H-isoindole-5-carboxylic acid methylamide hydrobromide 1H-NMR(DMSO-d6) δ: 1.37(9H, S), 2.78(3H, d, J=4.8 Hz), 2.92(6H, s), 4.75(2H, s), 5.41(2H, s), 5.43(2H, s), 7.15(1H, s), 7.33(1H, d, J=8.4 Hz), 7.89(1H, s), 7.99(1H, s), 8.07(1H, s), 8.37(1H, q, J=4.8 Hz), 8.95(1H, brs), 9.53(1H, brs).

MS: m/e (ESI) 462.1 (MH+)

Example 904

{2-tert-Butyl-4-[2-(5,6-diethoxy-7-fluoro-1-imino-1,3-dihydro-isoindol-2-yl)-acetyl]-phenoxy}-acetonitrile hydrobromide 1H-NMR(DMSO-d6) δ: 1.29(3H, t, J=7.0 Hz), 1.37(9H, s), 1.40(3H, t, J=7.0 Hz), 4.12(2H, q, J=7.0 Hz), 4.21(2H, q, J=7.0 Hz), 4.81(2H, s), 5.41(2H, s), 5.47(2H, s), 7.33(1H, d, J=8.0 Hz), 7.34(1H, s), 7.88(1H, s), 7.98(1H, d, J=8.4 Hz), 9.02(1H, brs), 9.32(1H, brs).

MS: m/e (ESI) 468.1 (MH+)

Example 905

{2-tert-Butyl-4-[2-(7-imino-2-methyl-5,7-dihydro-pyrrolo[3,4-b]pyridin-6-yl)-acetyl]-phenoxy}-acetonitrile hydrobromide 1H-NMR(DMSO-d6) δ: 1.37(9H, S), 2.67(3H, s), 4.87 (2H, s), 5.41(2H, s), 5.54(2H, s), 7.33(1H, d, J=8.4 Hz), 7.71(1H, d, J=8.4 Hz), 7.89(1H, d, J=2.0 Hz), 8.00(1H, dd, J=2.0, 8.4 Hz), 8.16(1H, d, J=8.4 Hz), 9.50(1H, brs), 9.97 (1H, brs).

MS: m/e (ESI) 377.0 (MH+)

Example 906

{2-tert-Butyl-4-[2-(2-ethyl-7-imino-5,7-dihydro-pyrrolo[3,4-b]pyridin-6-yl)-acetyl]-phenoxy}-acetonitrile hydrobromide 1H-NMR(DMSO-d6) δ: 1.31(3H, t, J=7.6 Hz), 1.37(9H, S), 2.95(2H, q, J=7.6 Hz), 4.87(2H, s), 5.41(2H, s), 5.55(2H, s), 7.33(1H, d, J=8.8 Hz), 7.74(1H, d, J=8.0 Hz), 7.90(1H, s), 8.01(1H, d, J=8.4 Hz), 8.18(1H, d, J=8.0 Hz), 9.52(1H, brs), 9.87(1H, brs).

MS: m/e (ESI) 391.0 (MH+)

Example 907

2-[2-(3-tert-Butyl-4-methoxy-5-morpholino-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.37(9H, s), 1.41(3H, t, J=6.8 Hz), 2.82(3H, d, J=4.0 Hz), 2.94–3.04(4H, m), 3.70–3.86 (4H, m), 3.95(3H, s), 4.28(2H, q, J=6.8 Hz), 4.85(2H, s), 5.51(2H, s), 7.50(1H, s), 7.54(1H, s), 7.61(1H, s), 8.20(1H, q, J=4.0 Hz), 8.56(1H, s), 9.16(1H, brs), 9.84(1H, brs).

MS: m/e (ESI) 524.2 (MH+)

Example 908

1-(3-tert-Butyl-4-methoxy-5-morpholino-phenyl)-2-(7-fluoro-1-imino-5,6-dimethoxy-1,3-dihydro-isoindol-2-yl)-ethanone hydrobromide 1H-NMR(DMSO-d6) δ: 1.37(9H, s), 2.95–3.05(4H, m), 3.74–3.85(4H, m), 3.87(3H, s), 3.95(3H, s), 3.96(3H, s), 4.81(2H, s), 5.51(2H, s), 7.37(1H, s), 7.49(1H, s), 7.60(1H, s).

Example 909

1-(3-tert-Butyl-4-methoxy-5-morpholino-phenyl)-2-(2-cyclopropyl-7-imino-5,7-dihydro-pyrrolo[3,4-b]pyridin-6-yl)-ethanone hydrobromide 1H-NMR(DMSO-d6) δ: 1.08–1.15(4H, m), 1.37(9H, s), 2.28–2.36(1H, m), 2.94–3.06(4H, m), 3.75–3.86(4H, m), 3.95(3H, s), 4.82(2H, s), 5.56(2H, s), 7.50(1H, s), 7.61(1H, s), 7.72(1H, d, J=8.0 Hz), 8.10(1H, d, J=8.0 Hz).

Example 910

{3-tert-Butyl-5-[2-(5,6-diethoxy-7-fluoro-1-imino-1,3-dihydro-isoindol-2-yl)-acetyl]-2-methoxy-phenoxy}-acetonitrile hydrobromide 1H-NMR(DMSO-d6) δ: 1.29(3H, t, J=6.8 Hz), 1.37(9H, s), 1.39(3H, t, J=6.8 Hz), 3.89(3H, s), 4.11(2H, q, J=6.8 Hz), 4.21(2H, q, J=6.8 Hz), 4.81(2H, s), 5.33(2H, s), 5.48(2H, s), 7.34(1H, s), 7.64(1H, s), 7.69(1H, s), 9.00–9.10(1H, m), 9.29–9.37(1H, m).

Example 911

4-{3-tert-Butyl-5-[2-(5,6-diethoxy-7-fluoro-1-imino-1,3-dihydro-isoindol-2-yl)-acetyl]-2-methoxy-phenoxy}-butyronitrile hydrobromide 1H-NMR(DMSO-d6) δ: 1.29(3H, t, J=6.8 Hz), 1.36(9H, s), 1.40(3H, t, J=6.8 Hz), 2.07–2.17(2H, m), 2.72(2H, t, J=7.2 Hz), 3.90(3H, s), 4.07–4.17(4H, m), 4.21(2H, q, J=6.8 Hz), 4.79(2H, s), 5.48(2H, s), 7.33(1H, s), 7.53(1H, s), 7.54(1H, s), 8.96–9.09(1H, m), 9.23–9.36(1H, m).

Example 912

{3-tert-Butyl-5-[2-(2-cyclopropyl-7-imino-5,7-dihydro-pyrrolo[3,4-b]pyridin-6-yl)-acetyl]-2-methoxyphenoxy}-acetonitrile hydrobromide 1H-NMR(DMSO-d6) δ: 1.05–1.16(4H, m), 1.37(9H, s), 2.27–2.37(1H, m), 3.89(3H, s), 4.84(2H, s), 5.33(2H, s), 5.56(2H, s), 7.65(1H, s), 7.70(1H, s), 7.72(1H, d, J=8.0 Hz), 8.10(1H, d, J=8.0 Hz), 9.51(1H, brs), 9.67(1H, brs).

Example 913

4-{3-tert-Butyl-5-[2-(2-cyclopropyl-7-imino-5,7-dihydro-pyrrolo[3,4-b]pyridin-6-yl)-acetyl]-2-methoxy-phenoxy}-butyronitrile hydrobromide 1H-NMR(DMSO-d6) δ: 1.05–1.18(4H, m), 1.36(9H, s), 2.07–2.18(2H, m), 2.28–2.38(1H, m), 2.72(2H, t, J=7.2 Hz), 3.89(3H, s), 4.15(2H, t, J=6.0 Hz), 4.83(2H, s), 5.56(2H, s), 7.55(2H, brs), 7.72(1H, d, J=8.0 Hz), 8.10(1H, d, J=8.0 Hz), 9.04–9.55(2H, m).

Example 914

1-(3-tert-Butyl-5-isopropoxy-4-methoxy-phenyl)-2-(2-cyclopropyl-7-imino-5,7-dihydro-pyrrolo[3,4-b]pyridin-6-yl)-ethanone hydrobromide 1H-NMR(DMSO-d6) δ: 1.03–1.17(4H, m), 1.33(6H, d, J=6.0 Hz), 1.35(9H, s), 2.25–2.37(1H, m), 3.88(3H, s), 4.65–4.79(1H, m), 4.82(2H, s), 5.56(2H, s), 7.51(2H, s), 7.72(1H, d, J=8.0 Hz), 8.10(1H, d, J=8.0 Hz), 9.46–9.73(2H, m).

Example 915

1-(3-tert-Butyl-5-dimethylamino-4-methoxy-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=7.2 Hz), 1.37(9H, s), 1.39(3H, t, J=7.2 Hz), 2.74(6H, s), 3.82(3H, s), 4.14(2H, q, J=7.2 Hz), 4.21(2H, q, J=7.2 Hz), 4.77(2H, s), 5.46(2H, s), 7.32(1H, s), 7.45(1H, d, J=2.0 Hz), 7.53(1H, d, J=2.0 Hz).

MS: m/e (ESI) 486.2 (MH+)

Example 916

1-(3-tert-Butyl-4-methoxy-5-morpholino-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=6.8 Hz), 1.36(9H, s), 1.39(3H, t, J=6.8 Hz), 2.95–3.12(4H, m), 3.75–3.84(4H, m), 3.94(3H, s), 4.12(2H, q, J=6.8 Hz), 4.20(2H, q, J=6.8 Hz), 4.78(2H, s), 5.46(2H, s), 7.33(1H, s), 7.49(1H, s), 7.59(1H, s).

MS: m/e (ESI) 528.2 (MH+)

Example 917

2-tert-Butyl-4-[2-(5-ethoxy-1-imino-6-methylcarbamoyl-1,3-dihydro-isoindol-2-yl)-acetyl]-phenyl methanesulfonate hydrobromide 1H-NMR(DMSO-d6) δ: 1.40–1.43(12H, m), 2.82(3H, d, J=4.8 Hz), 3.68(3H, s), 4.28(2H, q, J=6.8 Hz), 4.86(2H, s), 5.51(2H, s), 7.55(1H, s), 7.70(1H, d, J=8.4 Hz), 7.97–8.00(2H, m), 8.19–8.22(1H, m), 8.56(1H, s), 9.20(1H, brs), 9.86(1H, brs).

MS: m/e (ESI) 502.1 (MH+)

Example 918

2-tert-Butyl-4-[2-(5-dimethylamino-1-imino-6-methylcarbamoyl-1,3-dihydro-isoindol-2-yl)-acetyl]-phenyl methanesulfonate hydrobromide 1H-NMR(DMSO-d6) δ: 1.40(9H, S), 2.77(3H, d, J=4.8 Hz), 2.92(6H, s), 3.68(3H, s), 4.76(2H, s), 5.46(2H, s), 7.15(1H, s), 7.70(1H, d, J=8.4 Hz), 7.95–8.00(2H, m), 8.07(1H, s), 8.34–8.37(1H, m), 8.96(1H, brs), 9.57(1H, brs).

MS: m/e (ESI) 501.1 (MH+)

Example 919

2-tert-Butyl-4-[2-(3-ethoxy-7-imino-2-methylcarbamoyl-5,7-dihydro-pyrrolo[3,4-b]pyridin-6-yl)-acetyl]-phenyl methanesulfonate hydrobromide 1H-NMR(DMSO-d6) δ: 1.36(3H, t, J=6.8 Hz), 1.41(9H, s), 2.77(3H, d, J=4.4 Hz), 3.68(3H, s), 4.24(2H, q, J=6.8 Hz), 4.90(2H, s), 5.54(2H, s), 7.70(1H, d, J=8.4 Hz), 7.95–8.00(3H, m), 8.52(1H, m), 9.44(1H, brs), 9.99(1H, brs).

MS: m/e (ESI) 503.1 (MH+)

Example 920

Ethyl 2-{8-tert-butyl-6-[2-(7-fluoro-1-imino-5,6-dimethoxy-1,3-dihydro-isoindol-2-yl)-acetyl]-2,3-dihydro-benzo[1,4]oxazin-4-yl}-propanoate hydrobromide 1H-NMR(DMSO-d6) δ: 1.15(3H, t, J=7 Hz), 1.33–1.48(12H, m), 3.30–3.40(2H, m), 3.86(3H, s), 3.95(3H, s), 4.10.(2H, m), 4.40(2H, m), 4.71(1H, q, J=6 Hz), 4.79(2H, s), 5.40(1H, d, J=18 Hz), 5.50(1H, d, J=18 Hz), 7.18(1H, brs), 7.27(1H, brs), 7.35(1H, s), 9.06(1H, brs), 9.38(1H, brs).

Example 921

Ethyl 2-{8-tert-butyl-6-[2-(2-cyclopropyl-7-imino-5,7-dihydro-pyrrolo[3,4-b]pyridin-6-yl)-acetyl]-2,3-dihydro-benzo[1,4]oxazin-4-yl}-propanoate hydrobromide 1H-NMR(DMSO-d6) δ: 1.03–1.12(4H, m), 1.15(3H, t, J=7 Hz), 1.35(9H, s), 1.44(3H, d, J=6 Hz), 2.32(1H, m), 3.30–3.40(2H, m), 4.09(2H, m), 4.25–4.30(2H, m), 4.28(2H, m), 4.71(1H, q, J=6 Hz), 4.80(2H, s), 5.43(1H, d, J=18 Hz), 5.52(1H, d, J=18 Hz), 7.20(1H, s), 7.28(1H, s), 7.71(1H, d, J=8 Hz), 8.08(1H, d, J=8 Hz), 9.50(1H, brs), 9.62(1H, brs).

Example 922

2-[2-(3-tert-Butyl-4-cyanomethoxy-5-dimethylamino-phenyl)-2-oxo-ethyl]-6-dimethylamino-3-imino-2,3-dihydro-1H-isoindole-5-carboxylic acid methylamide hydrobromide 1H-NMR(DMSO-d6) δ: 1.39(9H, S), 2.71(6H, s), 2.77(3H, d, J=4.4 Hz), 2.91(6H, s), 4.74(2H, s), 5.25(2H, s),

Example 923

2-[2-(3-tert-Butyl-4-methoxy-5-(pyrrolidin-1-yl)-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.38(9H, S), 1.41(3H, t, J=6.8 Hz), 1.91(4H, brs), 2.82(3H, d, J=4.0 Hz), 3.15(4H, brs), 3.64(3H, s), 4.27(2H, q, J=7.0 Hz), 4.83(2H, s), 5.47(2H, s), 7.35(1H, s), 7.43(1H, s), 7.53(1H, s), 8.18–8.21(1H, m), 8.55(1H, s).

MS: m/e (ESI) 507.2 (MH+)

Example 924

1-(3-tert-Butyl-4-methoxy-5-(pyrrolidin-1-yl)-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=6.8 Hz), 1.37(9H, s), 1.39(3H, t, J=6.8 Hz), 1.91(4H, brs), 3.15(4H, brs), 3.64(3H, s), 4.11(2H, q, J=6.8 Hz), 4.21(2H, q, J=6.8 Hz), 4.78(2H, s), 5.46(2H, s), 7.33(1H, s), 7.34(1H, s), 7.42(1H, s), 9.01(1H, brs), 9.23(1H, brs).

MS: m/e (ESI) 512.2 (MH+)

Example 925

2-[2-(3-tert-Butyl-4-methoxy-5-(pyrrolidin-1-yl)-phenyl)-2-oxo-ethyl]-6-dimethylamino-3-imino-2,3-dihydro-1H-isoindole-5-carboxylic acid methylamide hydrobromide 1H-NMR(DMSO-d6) δ: 1.38(9H, s), 1.91(4H, brs), 2.78(3H, d, J=4.4 Hz), 2.91(6H, s), 3.15(4H, brs), 3.64(3H, s), 4.72(2H, s), 5.42(2H, s), 7.15(1H, s), 7.35(1H, s), 7.43(1H, s), 8.06(1H, s), 8.35–8.38(1H, m).

MS: m/e (ESI) 506.3 (MH+)

Example 926

1-(3-tert-Butyl-4-methoxy-5-(pyrrolidin-1-yl)-phenyl)-2-(2-cyclopropyl-7-imino-5,7-dihydro-pyrrolo[3,4-b]pyridin-6-yl)-ethanone hydrobromide 1H-NMR(DMSO-d6) δ: 1.08–1.11(4H, m), 1.38(9H, s), 1.91(4H, brs), 2.29–2.35(1H, m), 3.15(4H, brs), 3.65(3H, s), 4.81(2H, s), 5.56(2H, s), 7.36(1H, s), 7.44(1H, s), 7.72(1H, d, J=8.6 Hz), 8.09(1H, d, J=8.6 Hz), 9.50(1H, brs), 9.62(1H, brs).

Example 927

1-(3-tert-Butyl-4-methoxy-5-(pyrrolidin-1-yl)-phenyl)-2-(7-fluoro-1-imino-5,6-dimethoxy-1,3-dihydro-isoindol-2-yl)-ethanone hydrobromide 1H-NMR(DMSO-d6) δ: 1.38(9H, s), 1.91(4H, brs), 3.15(4H, brs), 3.65(3H, s), 3.87(3H, s), 3.95(3H, s), 4.80(2H, s), 5.48(2H, s), 7.35(1H, s), 7.36(1H, s), 7.43(1H, s), 9.02(1H, brs), 9.23(1H, brs).

MS: m/e (ESI) 484.2 (MH+)

Example 928

2-[(2-(3-tert-Butyl-5-isopropoxy-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.33(6H, d, J=6.4 Hz), 1.36(9H, s), 1.41(3H, t, J=6.8 Hz), 2.82(3H, d, J=4.4 Hz), 3.88(3H, s), 4.28(2H, q, J=6.8 Hz), 4.64–4.77(1H, m), 4.85(2H, s), 5.49(2H, s), 7.51(2H, s), 7.54(1H, s), 8.14–8.26(1H, m), 8.56(1H, s), 9.12–9.21(1H, m), 9.79–9.89(1H, m).

Example 929

1-(3-tert-Butyl-5-isopropoxy-4-methoxy-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=6.8 Hz), 1.33(6H, d, J=6.0 Hz), 1.35(9H, s), 1.39(3H, t, J=6.8 Hz), 3.88(3H, s), 4.11(2H, q, J=6.8 Hz), 4.21(2H, q, J=6.8 Hz), 4.64–4.77(1H, m), 4.80(2H, s), 5.47(2H, s), 7.33(1H, s), 7.50(2H, s), 9.05(1H, brs), 9.29(1H, brs).

Example 930

1-(3-tert-Butyl-5-isopropoxy-4-methoxy-phenyl)-2-(7-fluoro-1-imino-5,6-dimethoxy-1,3-dihydro-isoindol-2-yl)-ethanone hydrobromide 1H-NMR(DMSO-d6) δ: 1.33(6H, d, J=5.6 Hz), 1.35(9H, s), 3.87(3H, s), 3.88(3H, s), 3.95(3H, s), 4.64–4.76(1H, m), 4.81(2H, s), 5.48(2H, s), 7.36(1H, s), 7.50(2H, s), 8.99–9.16(1H, m), 9.25–9.40(1H, m).

Example 931

Ethyl 2-{8-tert-butyl-6-[2-(5-ethoxy-1-imino-6-methylcarbamoyl-1,3-dihydro-isoindol-2-yl)-acetyl]-2,3-dihydro-benzo[1,4]oxazin-4-yl}-propanoate hydrochloride 1H-NMR(DMSO-d6) δ: 1.15(3H, t, J=7 Hz), 1.30–1.50(15H, m), 2.82(3H, d, J=5 Hz), 3.30–3.40(2H, m), 4.09(2H, m), 4.22–4.36(4H, m), 4.71(1H, q, J=6 Hz), 4.82(2H, s), 5.38(1H, d, J=18 Hz), 5.48(1H, d, J=18 Hz), 7.20(1H, brs), 7.28(1H, brs), 7.53(1H, s), 8.21(1H, q, J=5 Hz), 8.55(1H, s), 9.21(1H, brs), 9.82(1H, brs).

Example 932

Ethyl 2-{8-tert-butyl-6-[2-(3-ethoxy-7-imino-2-methylcarbamoyl-5,7-dihydro-pyrrolo[3,4-b]pyridin-6-yl)-acetyl]-2,3-dihydro-benzo[1,4]oxazin-4-yl}-propanoate hydrochloride 1H-NMR(DMSO-d6) δ: 1.15(3H, t, J=7 Hz), 1.32–1.39(12H, m), 1.44(3H, d, J=7 Hz), 2.33(1H, m), 2.77(3H, d, J=5 Hz), 3.30–3.40(2H, m), 4.09(2H, m), 4.20–4.30(4H, m), 4.71(1H, q, J=7 Hz), 4.86(2H, s), 4.82(2H, s), 5.43(1H, d, J=18 Hz), 5.52(1H, d, J=18 Hz), 7.20(1H, d, J=2 Hz), 7.27(1H, d, J=2 Hz), 7.98(1H, s), 8.55(1H, q, J=5 Hz), 9.47(1H, brs), 9.92(1H, brs).

MS: m/e (ESI) 566.2 (MH+)

Example 933

Ethyl 2-{8-tert-butyl-6-[2-(5-dimethylamino-1-imino-6-methylcarbamoyl-1,3-dihydro-isoindol-2-yl)-acetyl]-2,3-dihydro-benzo[1,4]oxazin-4-yl}-propanoate hydrochloride 1H-NMR(DMSO-d6) δ: 1.15(3H, t, J=7 Hz), 1.32–1.39 (9H, m), 1.44(3H, d, J=7 Hz), 2.77(3H, d, J=5 Hz), 3.30–3.40(2H, m), 4.10(2H, m), 4.27(2H, m), 4.70–4.73(3H, m), 5.35(1H, d, J=18 Hz), 5.46(1H, d, J=18 Hz), 7.14(1H, s), 7.21(1H, d, J=2 Hz), 7.27(1H, d, J=2 Hz), 8.08(1H, s), 8.37(1H, q, J=5 Hz), 9.06(1H, brs), 9.57(1H, brs).

Example 934

2-[2-(3-Dimethylamino-5-isopropyl-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.20(6H, d, J=7.2 Hz), 1.41(3H, t, J=6.8 Hz), 2.78(6H, s), 2.81(3H, d, J=4.4 Hz), 3.77(3H, s), 4.28(2H, q, J=6.8 Hz), 4.84(2H, s), 5.49(2H, s), 7.36(1H, s), 7.51(1H, s), 7.54(1H, s), 8.20(1H, q, J=4.4 Hz), 8.56(1H, s), 9.17(1H, brs), 9.84(1H, brs).

Example 935

2-(5,6-Diethoxy-7-fluoro-1-imino-1,3-dihydro-isoindol-2-yl)-1-(3-dimethylamino-5-isopropyl-4-methoxy-phenyl)-ethanone hydrobromide 1H-NMR(DMSO-d6) δ: 1.20(6H, d, J=6.8 Hz), 1.29(3H, t, J=6.8 Hz), 1.39(3H, t, J=6.8 Hz), 2.78(6H, s), 3.76(3H, s), 4.11(2H, q, J=6.8 Hz), 4.22(2H, q, J=6.8 Hz), 4.79(2H, s), 5.47(2H, s), 7.34–7.36(2H, m), 7.52(1H, s).

Example 936

2-[2-(3-tert-Butyl-4-methoxy-5-methylamino-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.37(9H, s), 1.41(3H, t, J=7.0 Hz), 2.76(3H, d, J=5.0 Hz), 2.82(3H, d, J=4.4 Hz), 3.72(3H, s), 4.28(2H, q, J=7.0 Hz), 4.84(2H, s), 5.47(2H, s), 5.51(1H, q, J=5.0 Hz), 7.05(1H, s), 7.24(1H, s), 7.54(1H, s), 8.21(1H, q, J=4.4 Hz), 8.55(1H, s), 9.17(1H, brs), 9.82(1H, brs).
MS: m/e (ESI) 467.3 (MH+)

Example 937

6-[2-(3-tert-Butyl-5-isopropoxy-4-methoxy-phenyl)-2-oxo-ethyl]-3-ethoxy-7-imino-6,7-dihydro-5H-pyrrolo[3,4-b]pyridine-2-carboxylic acid methylamide trifluoroacetate 1H-NMR(DMSO-d6) δ: 1.26–1.43(18H, m), 2.77(3H, d, J=4.8 Hz), 3.88(3H, s), 4.24(2H, q, J=6.8 Hz), 4.64–4.77(1H, m), 4.88(2H, s), 5.52(2H, s), 7.50(2H, s), 7.99(1H, s), 8.47–8.58(1H, m), 9.34–9.46(1H, m), 9.90–10.03(1H, m).

Example 938

2-[2-(3-tert-Butyl-5-isopropoxy-4-methoxy-phenyl)-2-oxo-ethyl]-6-dimethylamino-3-imino-2,3-dihydro-1H-isoindole-5-carboxylic acid methylamide trifluoroacetate 1H-NMR(DMSO-d6) δ: 1.33(6H, d, J=6.0 Hz), 1.35(9H, s), 2.77(3H, d, J=4.4 Hz), 2.91(6H, s), 3.88(3H, s), 4.63–4.80(3H, m), 5.44(2H, s), 7.15(1H, s), 7.50(2H, s), 8.07(1H, s), 8.31–8.43(1H, m), 8.88–8.99(1H, m), 9.46–9.60(1H, m).

Example 939

2-{2-[3-tert-Butyl-5-(4-cyano-piperidin-1-yl)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.36(9H, s), 1.41(3H, t, J=6.8 Hz), 1.88–2.13(4H, m), 2.82(3H, d, J=4.4 Hz), 2.86–2.98 (2H, m), 3.02–3.18(3H, m), 3.93(3H, s), 4.28(2H, q, J=6.8 Hz), 4.84(2H, s), 5.49(2H, s), 7.52(1H, d, J=1.6 Hz), 7.54 (1H, s), 7.61(1H, d, J=1.6 Hz), 8.14–8.26(1H, m), 8.56(1H, s), 9.10–9.18(1H, m), 9.81–9.88(1H, m).
MS: m/e (ESI) 546.2 (MH+)

Example 940

1-(3-tert-Butyl-4-hydroxy-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=6.8 Hz), 1.37(9H, s), 1.40(3H, t, J=6.8 Hz), 4.11(2H, q, J=6.8 Hz), 4.21(2H, q, J=6.8 Hz), 4.78(2H, s), 5.40(2H, s), 6.95(1H, d, J=8.6 Hz), 7.32(1H, s), 7.75(1H, d, J=8.6 Hz), 7.80(1H, s), 9.00(1H, brs), 9.30(1H, brs).
MS: m/e (ESI) 429.1 (MH+)

Example 941

2-{8-tert-Butyl-6-[2-(5-ethoxy-1-imino-6-methylcarbamoyl-1,3-dihydro-isoindol-2-yl)-acetyl]-2,3-dihydro-benzo[1,4]oxazin-4-yl}-2-methyl-propanoic acid hydrochloride 1H-NMR(DMSO-d6) δ: 1.36(9H, s), 1.38(3H, t, J=7 Hz), 1.48(6H, s), 2.82(3H, d, J=5 Hz), 3.30–3.40(2H, m), 4.22–4.40(4H, m), 4.82(2H, s), 5.40(2H, s), 7.08(1H, brs), 7.30(1H, brs), 7.52(1H, s), 8.21(1H, q, J=5 Hz), 8.55(1H, s), 9.22(1H, brs), 9.83(1H, brs).
MS: m/e (ESI) 551.2 (MH+)

Example 942

2-{8-tert-Butyl-6-[2-(3-ethoxy-7-imino-2-methylcarbamoyl-5,7-dihydro-pyrrolo[3,4-b]pyridin-6-yl)-acetyl]-2,3-dihydro-benzo[1,4]oxazin-4-yl}-2-methyl-propanoic acid hydrochloride 1H-NMR(DMSO-d6) δ: 1.30–1.40(12H, m), 1.48(6H, s), 2.77(3H, d, J=5 Hz), 3.30–3.40(2H, m), 4.22–4.33(4H, m), 4.85(2H, s), 5.43(2H, s), 7.08(1H, brs), 7.29(1H, brs), 7.98 (1H, s), 8.54(1H, q, J=5 Hz), 9.45(1H, brs), 9.91(1H, brs).

Example 943

2-tert-Butyl-6-dimethylamino-4-[2-(5-ethoxy-1-imino-6-methylcarbamoyl-1,3-dihydro-isoindol-2-yl)-acetyl]-phenyl acetate hydrobromide 1H-NMR(DMSO-d6) δ: 1.33(9H, s), 1.41(3H, t, J=7.2 Hz), 2.33(3H, s), 2.65(6H, s), 2.82(3H, d, J=4.8 Hz), 4.27 (2H, q, J=7.2 Hz), 4.85(2H, s), 5.51(2H, s), 7.54(1H, s), 7.58(1H, s), 7.66(1H, s), 8.19–8.21(1H, m), 8.55(1H, s), 9.17(1H, brs), 9.84(1H, brs)
MS: m/e (ESI) 509.2 (MH+)

Example 944

2-{2-[3-tert-Butyl-4-methoxy-5-(2-oxo-oxazolidin-3-yl)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.38(9H, s), 1.41(3H, t, J=6.8 Hz), 2.82(3H, d, J=4.4 Hz), 3.82(3H, s), 3.93(2H, t, J=7.6 Hz), 4.28(2H, q, J=6.8 Hz), 4.54(2H, t, J=7.6 Hz), 4.85(2H, s), 5.46(2H, s), 7.54(1H, s), 7.83(1H, d, J=2.0 Hz), 7.99(1H, d, J=2.0 Hz), 8.20(1H, q, J=4.4 Hz), 8.56(1H, s).

Example 945

2-tert-Butyl-4-[2-(5,6-diethoxy-7-fluoro-1-imino-1,3-dihydro-isoindol-2-yl)-acetyl]-phenyl acetate hydrobromide 1H-NMR(DMSO-d6) δ: 1.29(3H, t, J=7.0 Hz), 1.34(9H, s), 1.40(3H, t, J=7.0 Hz), 2.37(3H, s), 4.12(2H, q, J=7.0 Hz), 4.21(2H, q, J=7.0 Hz), 4.81(2H, s), 5.49(2H, s), 7.31–7.34 (2H, m), 7.93(1H, d, J=8.4 Hz), 7.96(1H, s), 9.02(1H, brs), 9.30(1H, brs).
MS: m/e (ESI) 471.1 (MH+)

Example 946

2-tert-Butyl-4-[2-(5-ethoxy-1-imino-6-methylcarbamoyl-1,3-dihydro-isoindol-2-yl)-acetyl]-phenyl acetate hydrobromide 1H-NMR(DMSO-d6) δ: 1.35(9H, s), 1.42(3H, t, J=7.0 Hz), 2.37(3H, s), 2.83(3H, d, J=4.4 Hz), 4.28(2H, q, J=7.0 Hz), 4.86(2H, s), 5.50(2H, s), 7.33(1H, d, J=8.4 Hz), 7.54 (1H, s), 7.94(1H, d, J=8.4 Hz), 7.97(1H, s), 8.19–8.21(1H, m), 8.56(1H, s), 9.20(1H, brs), 9.82(1H, brs).
MS: m/e (ESI) 466.2 (MH+)

Example 947

{8-tert-Butyl-6-[2-(5,6-diethoxy-7-fluoro-1-imino-1,3-dihydro-isoindol-2-yl)-acetyl]-4-methyl-3,4-dihydro-2H-benzo[1,4]oxazin-2-ylmethoxy}-acetic acid hydrochloride 1H-NMR(DMSO-d6) δ: 1.29(3H, t, J=6.8 Hz), 1.35(9H, s), 1.39(3H, t, J=6.8 Hz), 2.91(3H, s), 3.10–3.48(2H, m), 3.74(2H, d, J=4.8 Hz), 4.02–4.18(2H, m), 4.11(2H, q, J=6.8 Hz), 4.20(2H, q, J=6.8 Hz), 4.37–4.48(1H, m), 4.78(2H, s), 5.46(2H, s), 7.18(1H, s), 7.28(1H, s), 7.32(1H, s), 9.04(1H, brs), 9.33(1H, brs).
MS: m/e (ESI) 572.2 (MH+)

Example 948

Ethyl {8-tert-butyl-6-[2-(5,6-diethoxy-7-fluoro-1-imino-1,3-dihydro-isoindol-2-yl)-acetyl]-4-methoxy-3,4-dihydro-2H-benzo[1,4]oxazin-2-ylmethoxy}-acetate hydrochloride 1H-NMR(DMSO-d6) δ: 1.20(3H, t, J=6.8 Hz), 1.27(3H, t, J=6.8 Hz), 1.35(9H, s), 1.39(3H, t, J=6.8 Hz), 2.91(3H, s), 3.11–3.45(2H, m), 3.75(2H, d, J=4.8 Hz), 4.11(2H, q, J=6.8 Hz), 4.10–4.25(6H, m), 4.38–4.48(1H, m), 4.78(2H, s), 5.47(2H, s), 7.18(1H, s), 7.28(1H, s), 7.32(1H, s), 9.04(1H, brs), 9.36(1H, brs).
MS: m/e (ESI) 600.2 (MH+)

Example 949

2-{2-[3-tert-Butyl-4-methoxy-5-(4-oxo-piperidin-1-yl)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.38(9H, s), 1.41(3H, t, J=6.8 Hz), 2.48–2.62(4H, m), 2.81(3H, d, J=4.0 Hz), 3.22–3.42 (4H, m), 4.03(3H, s), 4.27(2H, q, J=6.8 Hz), 4.84(2H, s), 5.49(2H, s), 7.54(1H, s), 7.57(1H, s), 7.63(1H, s), 8.20(1H, q, J=4.0 Hz), 8.55(1H, s).

Example 950

1-{3-tert-Butyl-5-[2-(5,6-diethoxy-7-fluoro-1-imino-1,3-dihydro-isoindol-2-yl)-acetyl]-2-methoxy-phenyl}-piperidin-4-one hydrobromide 1H-NMR(DMSO-d6) δ: 1.29(3H, t, J=6.8 Hz), 1.38(9H, s), 1.39(3H, t, J=6.8 Hz), 2.48–2.62(4H, m), 3.28–3.45(4H, m), 4.02(3H, s), 4.11(2H, q, J=6.8 Hz), 4.20(2H, q, J=6.8 Hz), 4.79(2H, s), 5.48(2H, s), 7.33(2H, s), 7.56(2H, s), 7.62(2H, s).

Example 951

2-{2-[3-tert-Butyl-4-methoxy-5-(2-oxo-pyrrolidin-1-yl)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.37(9H, s), 1.41(3H, t, J=6.8 Hz), 2.12–2.24(2H, m), 2.82(3H, d, J=4.0 Hz), 3.28–3.40 (2H, m), 3.64–3.72(2H, m), 3.74(3H, s), 4.27(2H, q, J=6.8 Hz), 4.85(2H, s), 5.46(2H, s), 7.54(1H, s), 7.81(1H, d, J=2.0 Hz), 7.83(1H, d, J=2.0 Hz), 8.20(1H, q, J=4.0 Hz), 8.55(1H, s).

Example 952

1-{3-tert-Butyl-5-[2-(5,6-diethoxy-7-fluoro-1-imino-1,3-dihydro-isoindol-2-yl)-acetyl]-2-methoxy-phenyl}-pyrrolidin-2-one hydrobromide 1H-NMR(DMSO-d6) δ: 1.29(3H, t, J=6.8 Hz), 1.37(9H, s), 1.39(3H, t, J=6.8 Hz), 2.12–2.24(2H, m), 3.30–3.40(2H, m), 3.68(2H, t, J=6.8 Hz), 3.74(3H, s), 4.11(2H, q, J=6.8 Hz), 4.20(2H, q, J=6.8 Hz), 4.79(2H, s), 5.44(2H, s), 7.33 (1H, s), 7.80(1H, s), 7.81(1H, s).

Example 953

1-{3-tert-Butyl-5-[2-(5,6-diethoxy-7-fluoro-1-imino-1,3-dihydro-isoindol-2-yl)-acetyl]-2-methoxy-phenyl}-oxazolidin-2-one hydrobromide MS: m/e (ESI) 572.2 (MH+) nyl}-oxazolidin-2-one hydrobromide
1H-NMR(DMSO-d6) δ: 1.29(3H, t, J=6.8 Hz), 1.38(9H, s), 1.39(3H, t, J=6.8 Hz), 3.82(3H, s), 3.91(2H, t, J=5.2 Hz), 4.11(2H, q, J=6.8 Hz), 4.20(2H, q, J=6.8 Hz), 4.54(2H, t, J=5.2 Hz), 4.80(2H, s), 5.45(2H, s), 7.34(1H, s), 7.82(H, d, J=2.0 Hz), 7.97(1H, d, J=2.0).

Example 954

2-{2-[3-tert-Butyl-4-methoxy-5-(4-methoxy-piperidin-1-yl)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.36(9H, s), 1.41(3H, t, J=6.8 Hz), 1.58–1.73(2H, m), 1.93–2.09(2H, m), 2.69–2.81(2H, m), 2.82(3H, d, J=4.4 Hz), 3.13–3.45(6H and H₂O, m), 3.93(3H, s), 4.28(2H, q, J=6.8 Hz), 4.83(2H, s), 5.48(2H, s), 7.52(1H, s), 7.54(1H, s), 7.58(1H, s), 8.09–8.31(1H, m), 8.55(1H, s), 9.14(1H, brs), 9.83(1H, brs)

Example 955

1-[3-tert-Butyl-4-methoxy-5-(4-methoxy-piperidin-1-yl)-phenyl]-2-(5,6-diethoxy-7-fluoro-1-imino-1,3-dihydro-isoindol-2-yl)-ethanone hydrobromide 1H-NMR(DMSO-d6) δ: 1.29(3H, t, J=6.8 Hz), 1.36(9H, s), 1.39(3H, t, J=6.8 Hz), 1.58–1.73(2H, m), 1.95–2.08(2H, m), 2.68–2.81(2H, m), 3.10–3.50(6H and H₂O, m), 3.93(3H, s), 4.11(2H, q, J=6.8 Hz), 4.21(2H, q, J=6.8 Hz), 4.78(2H, s), 5.47(2H, s), 7.33(1H, s), 7.51(1H, s), 7.57(1H, s), 8.96–9.34 (2H, m).

Example 956

2-{2-[3-tert-Butyl-4-methoxy-5-(4-methoxy-piperidin-1-yl)-phenyl]-2-oxo-ethyl}-6-dimethylamino-3-imino-2,3-dihydro-1H-isoindole-5-carboxylic acid methylamide hydrobromide 1H-NMR(DMSO-d6) δ: 1.36(9H, s), 1.59–1.71(2H, m), 1.95–2.06(2H, m), 2.70–2.82(5H, m), 2.91(6H, s), 3.16–3.42(6H and H₂O, m), 3.93(3H, s), 4.73(2H, s), 5.43 (2H, s), 7.15(1H, s), 7.51(1H, s), 7.58(1H, s), 8.06(1H, s), 8.30–8.45(1H, m), 8.85–8.93(1H, m), 9.48–9.57(1H, m).

Example 957

6-{2-[3-tert-Butyl-4-methoxy-5-(4-methoxy-piperidin-1-yl)-phenyl]-2-oxo-ethyl}-3-ethoxy-7-imino-6,7-dihydro-5H-pyrrolo[3,4-b]pyridine-2-carboxylic acid methylamide trifluoroacetate 1H-NMR(DMSO-d6) δ: 1.28–1.47(12H, m), 1.59–1.72 (2H, m), 1.95–2.07(2H, m), 2.70–2.84(5H, m), 3.13–3.52 (6H and H₂O, m), 3.94(3H, s), 4.24(2H, q, J=6.8 Hz), 4.87(2H, s), 5.52(2H, s), 7.51(1H, s), 7.58(1H, s), 7.99(1H, s), 8.47–8.60(1H, m), 9.31–9.44(1H, m), 9.88–10.02(1H, m).

Example 958

1-[3-tert-Butyl-4-methoxy-5-(4-methoxy-piperidin-1-yl)-phenyl]-2-(7-fluoro-1-imino-5,6-dimethoxy-1,3-dihydro-isoindol-2-yl)-ethanone hydrobromide 1H-NMR(DMSO-d6) δ: 1.36(9H, s), 1.59–1.76(2H, m), 1.95–2.12(2H, m), 2.68–2.85(2H, m), 3.15–3.50(6H and H₂O, m), 3.86(3H, s), 3.93(3H, s), 3.95(3H, s), 4.80(2H, s), 5.48(2H, s), 7.36(1H, s), 7.51(1H, s), 7.57(1H, s), 9.00–9.36 (2H, m).

Example 959

2-{2-[3-tert-Butyl-5-(4-cyano-piperidin-1-yl)-4-methoxy-phenyl]-2-oxo-ethyl}-6-dimethylamino-3-imino-2,3-dihydro-1H-isoindole-5-carboxylic acid methylamide hydrobromide 1H-NMR(DMSO-d6) δ: 1.36(9H, s), 1.87–2.13(4H, m), 2.77(3H, d, J=4.4 Hz), 2.85–3.00(5H, m), 3.02–3.17(3H, m), 3.93(3H, s), 4.73(2H, s), 5.44(2H, s), 7.15(1H, s), 7.52(1H, s), 7.60(1H, s), 8.06(1H, s), 8.30–8.45(1H, m), 8.80–9.00 (1H, m), 9.44–9.62(1H, m).

Example 960

6-{2-[3-tert-Butyl-5-(4-cyano-piperidin-1-yl)-4-methoxy-phenyl]-2-oxo-ethyl}-3-ethoxy-7-imino-6,7-dihydro-5H-pyrrolo[3,4-b]pyridine-2-carboxylic acid methylamide trifluoroacetate 1H-NMR(DMSO-d6) δ: 1.28–1.45(12H, m), 1.87–2.14 (4H, m), 2.78(3H, d, J=4.4 Hz), 2.85–2.97(2H, m), 3.02–3.17(3H, m), 3.93(3H, s), 4.24(2H, q, J=6.8 Hz), 4.88(2H, s), 5.53(2H, s), 7.60(1H, s), 7.99(1H, s), 8.46–8.58 (1H, m), 9.32–9.42(1H, m), 9.88–10.02(1H, m).

Example 961

(1-{3-tert-Butyl-5-[2-(5,6-diethoxy-7-fluoro-1-imino-1,3-dihydro-isoindol-2-yl)-acetyl]-2-methoxy-phenyl}-piperidin-4-yl)-acetic acid trifluoroacetate 1H-NMR(DMSO-d6) δ: 1.29(3H, t, J=6.8 Hz), 1.36(9H, s), 1.39(3H, t, J=6.8 Hz), 1.39–1.50(2H, m), 1.72–1.90(3H, m), 2.23(2H, d, J=6.4 Hz), 2.52–2.68(2H, m), 3.93(3H, s), 4.11(2H, q, J=6.8 Hz), 4.21(2H, q, J=6.8 Hz), 4.79(2H, s), 5.47(2H, s), 7.33(1H, s), 7.50(1H, s), 7.57(1H, s), 9.04(1H, brs), 9.27(1H, brs), 12.09(1H, brs).

Example 962

1-(3-tert-Butyl-5-dimethylamino-4-methoxy-phenyl)-2-(5-ethoxy-7-fluoro-1-imino-6-methoxy-1,3-dihydro-isoindol-2-yl)-ethanone hydrobromide 1H-NMR(DMSO-d6) δ: 1.37(9H, s), 1.40(3H, t, J=7.2 Hz), 2.75(6H, s), 3.82(3H, s), 3.87(3H, s), 4.20(2H, q, J=7.2 Hz), 4.78(2H, s), 5.48(2H, s), 7.34(1H, s), 7.45(1H, d, J=2.0 Hz), 7.53(1H, d, J=2.0 Hz).
MS: m/e (ESI) 472.2 (MH+)

Example 963

2-[2-(3-tert-Butyl-4-methoxy-5-thiazol-2-yl-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.39(3H, t, J=6.8 Hz), 1.44(9H, s), 2.78–2.92(3H, m), 3.59(3H, s), 4.28(2H, q, J=6.8 Hz), 4.87(2H, s), 5.57(2H, s), 7.55(1H, s), 7.92–8.08(2H, m), 8.21(1H, s), 8.40(1H, s), 8.56(1H, s), 9.19(1H, brs), 9.87(1H, brs).

Example 964

1-(3-tert-Butyl-4-methoxy-5-thiazol-2-yl-phenyl)-2-(7-fluoro-1-imino-5,6-dimethoxy-1,3-dihydro-isoindol-2-yl)-ethanone hydrobromide 1H-NMR(DMSO-d6) δ: 1.45(9H, s), 3.59(3H, s), 3.87(3H, s), 3.95(3H, s), 4.84(2H, s), 5.57(2H, s), 7.38(1H, s), 7.96–8.05(3H, m), 8.38(1H, s).
MS: m/e (ESI) 498.1 (MH+)

Example 965

1-[3-tert-Butyl-5-(ethyl-methyl-amino)-4-methoxy-phenyl]-2-(5,6-diethoxy-7-fluoro-1-imino-1,3-dihydro-isoindol-2-yl)-ethanone hydrobromide 1H-NMR(DMSO-d6) δ: 1.01(3H, t, J=7.2 Hz), 1.29(3H, t, J=7.2 Hz), 1.37(9H, s), 1.40(3H, t, J=7.2 Hz), 2.74(3H, s), 3.13(2H, q, J=7.2 Hz), 3.83(3H, s), 4.11(2H, q, J=7.2 Hz), 4.21(2H, q, J=7.2 Hz), 4.79(2H, s), 5.47(2H, s), 7.34(1H, s), 7.47(1H, d, J=2.0 Hz), 7.53(1H, d, J=2.0 Hz), 9.02(1H, brs), 9.27(1H, brs).
MS: m/e (ESI) 500.2 (MH+)

Example 966

2-{2-[3-tert-Butyl-5-(ethyl-methyl-amino)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.01(3H, t, J=7.0 Hz), 1.37(9H, s), 1.41(3H, t, J=7.0 Hz), 2.74(3H, s), 2.82(3H, d, J=4.8 Hz), 3.13(2H, q, J=7.0 Hz), 3.83(3H, s), 4.28(2H, q, J=7.0 Hz), 4.84(2H, s), 5.49(2H, s), 7.48(1H, d, J=2.0 Hz), 7.54–7.55(2H, m), 8.21(1H, q, J=4.8 Hz), 8.55(1H, s), 9.14(1H, brs), 9.81(1H, brs).
MS: m/e (ESI) 495.2 (MH+)

Example 967

3-{8-tert-Butyl-6-[2-(5,6-diethoxy-7-fluoro-1-imino-1,3-dihydro-isoindol-2-yl)-acetyl]-2,3-dihydro-benzo[1,4]oxazin-4-yl}-propionitrile hydrobromide 1H-NMR(DMSO-d6) δ: 1.29(3H, t, J=7 Hz), 1.34(9H, s), 1.40(3H, t, J=7 Hz), 2.80(2H, t, J=8 Hz), 3.47(2H, m), 3.70,2H, t, J=8 Hz), 4.11(2H, q, J=7 Hz), 4.20–4.27(4H, m), 4.79(2H, s), 5.45(2H, s), 7.25(2H, m), 7.33(1H, brs), 9.05(1H, brs), 9.32(1H, brs).
MS: m/e (ESI) 523.0 (MH+)

Example 968

1-(3-tert-Butyl-4-methoxy-5-oxazol-5-yl-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=6.8 Hz), 1.38(3H, t, J=6.8 Hz), 1.45(9H, s), 3.59(3H, s), 4.10(2H, q, J=6.8 Hz), 4.21(2H, q, J=6.8 Hz), 4.82(2H, s), 5.56(2H, s), 7.35(1H, s), 7.94–8.05(3H, m), 8.38(1H, m), 9.07(1H, m), 9.30(1H, m).

Example 969

1-[3-tert-Butyl-5-(ethyl-methyl-amino)-4-methoxy-phenyl]-2-(7-fluoro-1-imino-5,6-dimethoxy-1,3-dihydro-isoindol-2-yl)-ethanone hydrobromide 1H-NMR(DMSO-d6) δ: 1.01(3H, t, J=7.0 Hz), 1.37(9H, s), 2.74(3H, s), 3.13(2H, q, J=7.0 Hz), 3.83(3H, s), 3.87(3H, s), 3.95(3H, s), 4.80(2H, s), 5.48(2H, s), 7.37(1H, s), 7.47(1H, d, J=2.0 Hz), 7.54(1H, d, J=2.0 Hz), 9.07(1H, brs), 9.28(1H, brs).
MS: m/e (ESI) 472.2 (MH+)

Example 970

1-[3-tert-Butyl-5-(ethyl-methyl-amino)-4-methoxy-phenyl]-2-(2-cyclopropyl-7-imino-5,7-dihydro-pyrrolo[3,4-b]pyridin-6-yl)-ethanone hydrobromide 1H-NMR(DMSO-d6) δ: 1.01(3H, t, J=7.0 Hz), 1.08–1.10(4H, m), 1.37(9H, s), 2.32(1H, m), 2.74(3H, s), 3.13(2H, q, J=7.0 Hz), 3.83(3H, s), 4.82(2H, s), 5.54(2H, s), 7.48(1H, s), 7.54(1H, s), 7.72(1H, d, J=7.8 Hz), 8.09(1H, d, J=7.8 Hz), 9.43(1H, brs), 9.62(1H, brs).
MS: m/e (ESI) 435.1 (MH+)

Example 971

1-(3-tert-Butyl-4-methoxy-5-thiazol-2-yl-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=6.8 Hz), 1.40(3H, t, J=6.8 Hz), 1.45(9H, s), 3.59(3H, s), 4.11(2H, q, J=6.8 Hz), 4.20(2H, q, J=6.8 Hz), 4.82(2H, s), 5.57(2H, s), 7.34(1H, s), 7.94–8.04(3H, m), 8.38(1H, s), 9.08(1H, brs), 9.32(1H, brs).
MS: m/e (ESI) 526.2 (MH+)

Example 972

6-{2-[3-tert-Butyl-5-(ethyl-methyl-amino)-4-methoxy-phenyl]-2-oxo-ethyl}-3-ethoxy-7-imino-6,7-dihydro-5H-pyrrolo[3,4-b]pyridine-2-carboxylic acid methylamide trifluoroacetate 1H-NMR(DMSO-d6) δ: 1.01(3H, t, J=7.0 Hz), 1.34–1.37(12H, m), 2.74(3H, s), 2.78(3H, d, J=4.8 Hz), 3.13(2H, q, J=7.0 Hz), 3.83(3H, s), 4.24(2H, q, J=7.0 Hz), 4.87(2H, s), 5.52(2H, s), 7.47(1H, d, J=2.0 Hz), 7.54(1H, d, J=2.0 Hz), 7.99(1H, s), 8.53(1H, q, J=4.8 Hz), 9.40(1H, brs), 9.92(1H, brs).
MS: m/e (ESI) 496.2 (MH+)

Example 973

2-tert-Butyl-6-ethoxy-4-[2-(5-ethoxy-1-imino-6-methylcarbamoyl-1,3-dihydro-isoindol-2-yl)-acetyl]-phenyl methanesulfonate hydrobromide 1H-NMR(DMSO-d6) δ: 1.35–1.54(15H, m), 2.82(3H, d, J=4.4 Hz), 3.69(3H, s), 4.15–4.40(4H, m), 4.86(2H, s), 5.52(2H, s), 7.55(1H, s), 7.61(1H, s), 7.64(1H, s), 8.13–8.28(1H, m), 8.56(1H, s), 9.21(1H, brs), 9.87(1H, brs).

Example 974

2-tert-Butyl-4-[2-(5,6-diethoxy-7-fluoro-1-imino-1,3-dihydro-isoindol-2-yl)-acetyl]-6-ethoxy-phenyl methanesulfonate hydrobromide 1H-NMR(DMSO-d6) δ: 1.29(3H, t, J=6.8 Hz), 1.35–1.50(15H, m), 3.68(3H, s), 4.11(3H, t, J=6.8 Hz), 4.15–4.40(4H, m), 4.81(2H, s), 5.51(2H, s), 7.34(1H, s), 7.60(1H, s), 7.62(1H, s), 8.92–9.43(2H, m).

Example 975

2-tert-Butyl-6-ethoxy-4-[2-(7-fluoro-1-imino-5,6-dimethoxy-1,3-dihydro-isoindol-2-yl)-acetyl]-phenyl methanesulfonate hydrobromide 1H-NMR(DMSO-d6) δ: 1.42(3H, t, J=6.8 Hz), 1.44(9H, s), 3.69(3H, s), 3.87(3H, s), 3.95(3H, s), 4.82(2H, s), 5.52(2H, s), 7.37(1H, s), 7.60(1H, s), 7.63(1H, s), 9.00–9.40(2H, m).

Example 976

2-{2-[3-tert-Butyl-5-(ethyl-methyl-amino)-4-methoxy-phenyl]-2-oxo-ethyl}-6-dimethylamino-3-imino-2,3-dihydro-1H-isoindole-5-carboxylic acid methylamide hydrobromide 1H-NMR(DMSO-d6) δ: 1.01(3H, t, J=7.0 Hz), 1.37(9H, s), 2.74(3H, s), 2.77(3H, d, J=5.0 Hz), 2.91(6H, s), 3.12(2H, q, J=7.0 Hz), 3.83(3H, s), 4.73-(2H, s), 5.45(2H, s), 7.15(1H, s), 7.47(1H, s), 7.54(1H, s), 8.06(1H, s), 8.37(1H, q, J=5.0 Hz), 8.92(1H, brs), 9.51(1H, brs).
MS: m/e (ESI) 494.2 (MH+)

Example 977

2-[2-(3-tert-Butyl-5-diethylamino-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 0.98(6H, t, J=7.2 Hz), 1.37(9H, s), 1.42(3H, t, J=7.0 Hz), 2.83(3H, d, J=4.8 Hz), 3.16(4H, q, J=7.2 Hz), 3.86(3H, s), 4.28(2H, q, J=7.0 Hz), 4.84(2H, s), 5.48(2H, s), 7.50(1H, d, J=2.0 Hz), 7.54(1H, s), 7.55(1H, d, J=2.0 Hz), 8.21(1H, q, J=4.8 Hz), 8.56(1H, s), 9.07(1H, brs), 9.80(1H, brs).
MS: m/e (ESI) 509.2 (MH+)

Example 978

1-(3-tert-Butyl-5-diethylamino-4-methoxy-phenyl)-2-(5,6-diethoxy-7-fluoro-1-imino-1,3-dihydro-isoindol-2-yl)-ethanone hydrobromide 1H-NMR(DMSO-d6) δ: 0.98(6H, t, J=7.0 Hz), 1.29(3H, t, J=7.0 Hz), 1.37(9H, s), 1.40(3H, t, J=7.0 Hz), 3.16(4H, q, J=7.0 Hz), 3.86(3H, s), 4.12(2H, q, J=7.0 Hz), 4.21(2H, q, J=7.0 Hz), 4.79(2H, s), 5.47(2H, s), 7.34(1H, s), 7.48(1H, d, J=1.6 Hz), 7.54(1H, d, J=1.6 Hz), 9.02(1H, brs), 9.28(1H, brs).
MS: m/e (ESI) 514.2 (MH+)

Example 979

1-(3-tert-Butyl-5-diethylamino-4-methoxy-phenyl)-2-(7-fluoro-1-imino-5,6-dimethoxy-1,3-dihydro-isoindol-2-yl)-ethanone hydrobromide 1H-NMR(DMSO-d6) δ: 0.98(6H, t, J=7.0 Hz), 1.37(9H, s), 3.16(4H, q, J=7.0 Hz), 3.86(3H, s), 3.87(3H, s), 3.96(3H, s), 4.81(2H, s), 5.49(2H, s), 7.37(1H, s), 7.49(1H, d, J=2.0 Hz), 7.54(1H, d, J=2.0 Hz), 9.06(1H, brs), 9.30(1H, brs).
MS: m/e (ESI) 486.2 (MH+)

Example 980

Ethyl (1-{3-tert-butyl-5-[2-(5,6-diethoxy-7-fluoro-1-imino-1,3-dihydro-isoindol-2-yl)-acetyl]-2-methoxy-phenyl}-piperidin-4-yl)-acetate hydrobromide 1H-NMR(DMSO-d6) δ: 1.18(3H, t, J=6.8 Hz), 1.29(3H, t, J=6.8 Hz), 1.36(9H, s), 1.39(3H, t, J=6.8 Hz), 1.39–1.56(2H, m), 1.73–1.92(3H, m), 2.30(2H, d, J=6.4 Hz), 2.52–2.68(2H, m), 3.92(3H, s), 4.00–4.15(4H, m), 4.20(2H, q, J=6.8 Hz), 4.78(2H, s), 5.47(2H, s), 7.33(1H, s), 7.50(1H, s), 7.57(1H, s), 8.90–9.35(2H, m).
MS: m/e (ESI) 612.3 (MH+)

Example 981

2-tert-Butyl-4-[2-(5,6-diethoxy-7-fluoro-1-imino-1,3-dihydro-isoindol-2-yl)-acetyl]-6-dimethylamino-phenyl methanesulfonate hydrobromide 1H-NMR(DMSO-d6) δ: 1.29(3H, t, J=7.0 Hz), 1.40(3H, t, J=7.0 Hz), 1.44(9H, s), 2.67(6H, s), 3.73(3H, s), 4.12(2H, q, J=7.0 Hz), 4.21(2H, q, J=7.0 Hz), 4.80(2H, s), 5.51(2H, s), 7.34(1H, s), 7.67(1H, s), 7.75(1H, s).
MS: m/e (ESI) 550.1 (MH+)

Example 982

2-tert-Butyl-6-dimethylamino-4-[2-(7-fluoro-1-imino-5,6-dimethoxy-1,3-dihydro-isoindol-2-yl)-acetyl]-phenyl methanesulfonate hydrobromide 1H-NMR(DMSO-d6) δ: 1.44(9H, s), 2.67(6H, s), 3.73(3H, s), 3.87(3H, s), 3.95(3H, s), 4.81(2H, s), 5.51(2H, s), 7.37(1H, s), 7.68(1H, s), 7.75(1H, s).
MS: m/e (ESI) 522.1 (MH+)

Example 983

6-[2-(3-tert-Butyl-5-diethylamino-4-methoxy-phenyl)-2-oxo-ethyl]-3-ethoxy-7-imino-6,7-dihydro-5H-pyrrolo[3,4-b]pyridine-2-carboxylic acid methylamide trifluoroacetate 1H-NMR(DMSO-d6) δ: 0.98(6H, t, J=7.0 Hz), 1.34–1.37 (12H, m), 2.78(3H, d, J=4.4 Hz), 3.16(4H, q, J=7.0 Hz), 3.86(3H, s), 4.24(2H, q, J=7.0 Hz), 4.88(2H, s), 5.52(2H, s), 7.49(1H, s), 7.55(1H, s), 8.00(1H, s), 8.53(1H, q, J=4.4 Hz), 9.39(1H, brs), 9.94(1H, brs).
MS: m/e (ESI) 510.2 (MH+)

Example 984

2-[2-(3-tert-Butyl-5-dimethylamino-4-ethoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.31–1.43(15H, m), 2.75(6H, s), 2.83(3H, d, J=4.6 Hz), 4.13(2H, q, J=7.0 Hz), 4.28(2H, q, J=7.0 Hz), 4.84(2H, s), 5.49(2H, s), 7.45(1H, s), 7.54(1H, s), 7.56(1H, s), 8.21(1H, q, J=4.6 Hz), 8.55(1H, s), 9.13(1H, brs), 9.81(1H, brs).
MS: m/e (ESI) 495.2 (MH+)

Example 985

2-{2-[3-tert-Butyl-5-(4-hydroxy-piperidin-1-yl)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.36(9H, s), 1.41(3H, t, J=6.8 Hz), 1.54–1.67(2H, m), 1.84–1.96(2H, m), 2.66–2.76(2H, m), 2.82(3H, d, J=4.8 Hz), 3.18–3.36(2H, m), 3.52–3.68(1H, m), 3.94(3H, s), 4.27(2H, q, J=6.8 Hz), 4.73(1H, d, J=4.0 Hz), 4.84(2H, s), 5.49(2H, s), 7.52(1H, s), 7.54(1H, s), 7.58(1H, s), 8.12–8.25(1H, m), 8.55(1H, s), 9.14(1H, brs), 9.83(1H, brs).

Example 986

1-[3-tert-Butyl-5-(4-hydroxy-piperidin-1-yl)-4-methoxy-phenyl]-2-(5,6-diethoxy-7-fluoro-1-imino-1,3-dihydro-isoindol-2-yl)-ethanone hydrobromide 1H-NMR(DMSO-d6) δ: 1.29(3H, t, J=6.8 Hz), 1.36(9H, s), 1.40(3H, t, J=6.8 Hz), 1.54–1.68(2H, m), 1.84–1.96(2H, m), 2.65–2.78(2H, m), 3.17–3.42(2H, m), 3.58–3.67(1H, m), 3.94(3H, s), 4.11(2H, q, J=6.8 Hz), 4.21(2H, q, J=6.8 Hz), 4.73(1H, d, J=3.2 Hz), 4.78(2H, s), 5.47(2H, s), 7.34 (1H, s), 7.51(1H, s), 7.56(1H, s), 8.95–9.11(1H, m), 9.18–9.36(1H, brs).

Example 987

6-{2-[3-tert-Butyl-5-(4-hydroxy-piperidin-1-yl)-4-methoxy-phenyl]-2-oxo-ethyl}-3-ethoxy-7-imino-6,7-dihydro-5H-pyrrolo[3,4-b]pyridine-2-carboxylic acid methylamide trifluoroacetate 1H-NMR(DMSO-d6) δ: 1.26–1.50(12H, m), 1.50–1.68 (2H, m), 1.84–2.03(2H, m), 2.64–2.86(5H, m), 3.12–3.68 (3H, m), 3.94(3H, s), 4.23(2H, q, J=6.8 Hz), 4.87(2H, s), 5.52(2H, s), 7.44–7.70(2H, m), 7.99(1H, s), 8.41–8.63(1H, m), 9.37(1H, brs), 9.94(1H, brs).
MS: m/e (ESI) 538.3 (MH+)

Example 988

1-[3-tert-Butyl-5-(4-hydroxy-piperidin-1-yl)-4-methoxy-phenyl]-2-(7-fluoro-1-imino-5,6-dimethoxy-1,3-dihydro-isoindol-2-yl)-ethanone hydrobromide 1H-NMR(DMSO-d6) δ: 1.36(9H, s), 1.54–1.70(2H, m), 1.84–2.00(2H, m), 2.65–2.80(2H, m), 3.19–3.50(2H, m), 3.55–3.70(1H, m), 3.86(3H, s), 3.93(3H, s), 3.95(3H, s), 4.73(1H, d, J=4.0 Hz), 4.80(2H, s), 5.48(2H, s), 7.36(1H, s), 7.51(1H, s), 7.56(1H, s), 8.99–9.40(2H, m).

Example 989

1-[3-tert-Butyl-5-(4-hydroxy-piperidin-1-yl)-4-methoxy-phenyl]-2-(2-cyclopropyl-7-imino-5,7-dihydro-pyrrolo[3,4-b]pyridin-6-yl)-ethanone hydrobromide 1H-NMR(DMSO-d6) δ: 1.00–1.19(4H, m), 1.36(9H, s), 1.54–1.68(2H, m), 1.84–1.96(2H, m), 2.24–2.37(1H, m), 2.64–2.78(2H, m), 3.18–3.46(2H, m), 3.53–3.70(1H, m), 3.94(3H, s), 4.73(1H, d, J=4.0 Hz), 4.82(2H, s), 5.55(2H, s), 7.52(1H, s), 7.57(1H, s), 7.73(1H, d, J=8.0 Hz), 8.10(!H, d, J=8.0 Hz), 9.50–9.76(2H, m).
MS: m/e (ESI) 477.2 (MH+)

Example 990

2-tert-Butyl-4-[2-(2-cyclopropyl-7-imino-5,7-dihydro-pyrrolo[3,4-b]pyridin-6-yl)-acetyl]-6-dimethylamino-phenyl methanesulfonate hydrobromide 1H-NMR(DMSO-d6) δ: 1.08–1.10(4H, m), 1.45(9H, s), 2.30–2.33(1H, m), 2.67(6H, s), 3.73(3H, s), 4.83(2H, s), 5.80(2H, s), 7.68(1H, s), 7.72(1H, d, J=7.8 Hz), 7.53(1H, s), 8.10(1H, d, J=7.8 Hz).
MS: m/e (ESI) 485.1 (MH+)

Example 991

1-(3-tert-Butyl-5-dimethylamino-4-ethoxy-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=7.0 Hz), 1.34–1.41 (15H, m), 2.75(6H, s), 4.08–4.16(4H, m), 4.21(2H, q, J=7.0 Hz), 4.78(2H, s), 5.48(2H, s), 7.33(1H, s), 7.44(1H, s), 7.54(1H, s).
MS: m/e (ESI) 500.2 (MH+)

Example 992

1-(3-tert-Butyl-5-dimethylamino-4-ethoxy-phenyl)-2-(7-fluoro-1-imino-5,6-dimethoxy-1,3-dihydro-isoindol-2-yl)-ethanone hydrobromide 1H-NMR(DMSO-d6) δ: 1.36(3H, t, J=7.0 Hz), 1.38(9H, s), 2.75(6H, s), 3.87(3H, s), 3.95(3H, s), 4.13(2H, q, J=7.0 Hz), 4.79(2H, s), 5.48(2H, s), 7.36(1H, s), 7.44(1H, d, J=1.6 Hz), 7.54(1H, d, J=1.6 Hz).
MS: m/e (ESI) 472.2 (MH+)

Example 993

1-(3-tert-Butyl-5-dimethylamino-4-hydroxy-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=7.0 Hz), 1.38–1.41 (12H, m), 2.61(6H, s), 4.11(2H, q, J=7.0 Hz), 4.21(2H, q, J=7.0 Hz), 4.78(2H, s), 5.44(2H, s), 7.33(1H, s), 7.63(1H, s), 7.68(1H, s), 9.01(1H, brs), 9.26(1H, brs).
MS: m/e (ESI) 472.2 (MH+)

Example 994

2-[2-(3-tert-Butyl-5-dimethylamino-4-ethoxy-phenyl)-2-oxo-ethyl]-6-dimethylamino-3-imino-2,3-dihydro-1H-isoindole-5-carboxylic acid methylamide hydrobromide 1H-NMR(DMSO-d6) δ: 1.37(3H, t, J=7.0 Hz), 1.38(9H, s), 2.75(6H, s), 2.78(3H, d, J=4.6 Hz), 2.91(6H, s), 4.13(2H, q, J=7.0 Hz), 4.73(2H, s), 5.43(2H, s), 7.15(1H, s), 7.45(1H, s), 7.55(1H, s), 8.06(1H, s), 8.37(1H, q, J=4.6 Hz).
MS: m/e (ESI) 494.2 (MH+)

Example 995

6-[2-(3-tert-Butyl-5-dimethylamino-4-ethoxy-phenyl)-2-oxo-ethyl]-3-ethoxy-7-imino-6,7-dihydro-5H-pyrrolo[3,4-b]pyridine-2-carboxylic acid methylamide trifluoroacetate 1H-NMR(DMSO-d6) δ: 1.34–1.39(15H, m), 2.75(6H, s), 2.78(3H, d, J=4.6 Hz), 4.13(2H, q, J=7.0 Hz), 4.24(2H, q, J=7.0 Hz), 4.87(2H, s), 5.52(2H, s), 7.45(1H, s), 7.55(1H, s), 7.99(1H, s), 8.53(1H, q, J=4.6 Hz), 8.55(1H, s), 9.39(1H, brs), 9.92(1H, brs).
MS: m/e (ESI) 496.2 (MH+)

Example 996

2-tert-Butyl-6-dimethylamino-4-[2-(5-dimethylamino-1-imino-6-methylcarbamoyl-1,3-dihydro-isoindol-2-yl)-acetyl]-phenyl methanesulfonate hydrobromide 1H-NMR(DMSO-d6) δ: 1.44(9H, s), 2.67(6H, s), 2.78 (3H, d, J=4.8 Hz), 2.92(6H, s), 3.72(3H, s), 4.75(2H, s), 5.49(2H, s), 7.16(1H, s), 7.68(1H, s), 7.75(1H, s), 8.07(1H, s), 8.37(1H, q, J=4.8 Hz).
MS: m/e (ESI) 544.2 (MH+)

Example 997

1-(3-tert-Butyl-5-dimethylamino-4-ethoxy-phenyl)-2-(2-cyclopropyl-7-imino-5,7-dihydro-pyrrolo[3,4-b]pyridin-6-yl)-ethanone trifluoroacetate 1H-NMR(DMSO-d6) δ: 1.08–1.10(4H, m), 1.37(3H, t, J=7.0 Hz), 1.39(9H, s), 2.75(6H, s), 4.13(2H, q, J=7.0 Hz), 4.81(2H, s), 5.54(2H, s), 7.45(1H, d, J=2.0 Hz), 7.55(1H, d, J=2.0 Hz), 7.72(1H, d, J=8.0 Hz), 8.09(1H, d, J=8.0 Hz).
MS: m/e (ESI) 435.2 (MH+)

Example 998

2-tert-Butyl-6-dimethylamino-4-[2-(3-ethoxy-7-imino-2-methylcarbamoyl-5,7-dihydro-pyrrolo[3,4-b]pyridin-6-yl)-acetyl]-phenyl methanesulfonate trifluoroacetate 1H-NMR(DMSO-d6) δ: 1.36(3H, t, J=7.0 Hz), 1.45(9H, s), 2.67(6H, s), 2.78(3H, d, J=4.8 Hz), 4.24(2H, q, J=7.0 Hz), 4.90(2H, s), 5.57(2H, s), 7.68(1H, s), 7.75(1H, s), 8.01(1H, s), 8.53(1H, q, J=4.8 Hz), 9.43(1H, brs), 9.98(1H, brs).
MS: m/e (ESI) 546.1 (MH+)

Example 999

2-tert-Butyl-4-[2-(2-cyclopropyl-7-imino-5,7-dihydro-pyrrolo[3,4-b]pyridin-6-yl)-acetyl]-6-ethoxy-phenyl methanesulfonate hydrobromide 1H-NMR(DMSO-d6) δ: 1.08–1.10(4H, m), 1.40–1.44 (12H, m), 2.31–2.34(1H, m), 3.69(3H, s), 4.27(2H, q, J=7.2 Hz), 4.84(2H, s), 5.59(2H, s), 7.61(1H, s), 7.64(1H, s), 7.73(1H, d, J=8.2 Hz), 8.11(1H, d, J=8.2 Hz), 9.50(1H, brs), 9.68(1H, brs).
MS: m/e (ESI) 486.1 (MH+)

Example 1000

2-tert-Butyl-4-[2-(5-dimethylamino-1-imino-6-methylcarbamoyl-1,3-dihydro-isoindol-2-yl)-acetyl]-6-ethoxy-phenyl methanesulfonate hydrobromide 1H-NMR(DMSO-d6) δ: 1.40–1.44(12H, m), 2.78(3H, d, J=4.4 Hz), 2.91(6H, s), 3.69(3H, s), 4.26(2H, q, J=7.2 Hz), 4.74(2H, s), 5.47(2H, s), 7.16(1H, s), 7.61(1H, s), 7.64(1H, s), 8.06(1H, s), 8.38(1H, q, J=4.4 Hz).
MS: m/e (ESI) 545.2 (MH+)

Example 1001

1-(3-tert-Butyl-5-diethylamino-4-methoxy-phenyl)-2-(2-cyclopropyl-7-imino-5,7-dihydro-pyrrolo[3,4-b]pyridin-6-yl)-ethanone hydrobromide 1H-NMR(DMSO-d6) δ: 0.98(6H, t, J=7.0 Hz), 1.06–1.10 (4H, m), 1.37(9H, s), 2.29–2.34(1H, m), 3.15–3.19(4H, m), 3.86(3H, s), 3.86(3H, s), 4.82(2H, s), 5.55(2H, s), 7.49(1H, s), 7.55(1H, s), 7.72(1H, d, J=8.0 Hz), 8.11(1H, d, J=8.0 Hz), 9.30(1H, brs), 9.62(1H, brs).
MS: m/e (ESI) 449.2 (MH+)

Example 1002

2-[2-(3-tert-Butyl-5-dimethylamino-4-methoxy-phenyl)-2-oxo-ethyl]-6-dimethylamino-3-imino-2,3-dihydro-1H-isoindole-5-carboxylic acid methylamide hydrobromide 1H-NMR(DMSO-d6) δ: 0.98(6H, t, J=7.0 Hz), 1.37(9H, s), 2.78(3H, d, J=4.8 Hz), 2.92(6H, s), 3.16(4H, q, J=7.0 Hz), 3.85(3H, s), 4.74(2H, s), 5.44(2H, s), 7.15(1H, s), 7.49(1H, d, J=2.0 Hz), 7.55(1H, s), 7.55(1H, d, J=2.0 Hz), 8.07(1H, s), 8.37(1H, q, J=4.8 Hz), 8.92(1H, brs), 9.53(1H, brs).
MS: m/e (ESI) 508.2 (MH+)

Example 1003

2-tert-Butyl-6-ethoxy-4-[2-(3-ethoxy-7-imino-2-methylcarbamoyl-5,7-dihydro-pyrrolo[3,4-b]pyridin-6-yl)-acetyl]-phenyl methanesulfonate trifluoroacetate 1H-NMR(DMSO-d6) δ: 1.36(3H, t, J=7.0 Hz), 1.40–1.44 (12H, m), 2.78(3H, d, J=4.4 Hz), 3.69(3H, s), 4.21–4.29(4H, m), 4.90(2H, s), 5.57(2H, s), 7.60(1H, s), 7.63(1H, s), 8.00(1H, s), 8.53(1H, q, J=4.4 Hz), 9.43(1H, brs), 9.98(1H, brs).

MS: m/e (ESI) 547.1 (MH+)

Example 1004

1-(3-tert-Butyl-4-methoxy-5-methylamino-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=7.0 Hz), 1.37(9H, s), 1.40(3H, t, J=7.0 Hz), 2.76(3H, d, J=5.2 Hz), 3.72(3H, s), 4.11(2H, q, J=7.0 Hz), 4.21(2H, q, J=7.0 Hz), 4.79(2H, s), 5.46(2H, s), 5.50(1H, q, J=5.2 Hz), 7.04(1H, s), 7.23(1H, s), 7.33(1H, s).

MS: m/e (ESI) 472.1 (MH+)

Example 1005

1-[3-tert-Butyl-5-(4-hydroxy-piperidin-1-yl)-4-methoxy-phenyl]-2-(5-ethoxy-7-fluoro-1-imino-6-methoxy-1,3-dihydro-isoindol-2-yl hydrobromide 1H-NMR(DMSO-d6) δ: 1.36(9H, s), 1.40(3H, t, J=6.8 Hz), 1.54–1.68(2H, m), 1.83–1.96(2H, m), 2.64–2.78(2H, m), 3.21–3.48(2H, m), 3.58–3.69(1H, m), 3.87(3H, s), 3.94 (3H, s), 4.22(2H, q, J=6.8 Hz), 4.73(1H, d, J=4.0 Hz), 4.79(2H, s), 5.48(2H, s), 7.34(1H, s), 7.51(1H, s), 7.56(1H, s), 9.00–9.12(1H, m), 9.20–9.34(1H, m).

MS: m/e (ESI) 528.2 (MH+)

Example 1006

2-tert-Butyl-4-[2-(5,6-diethoxy-7-fluoro-1-imino-1,3-dihydro-isoindol-2-yl)-acetyl]-6-methoxy-phenyl methanesulfonate hydrobromide 1H-NMR(DMSO-d6) δ: 1.29(3H, t, J=6.8 Hz), 1.39(3H, t, J=6.8 Hz), 1.43(9H, s), 3.65(3H, s), 3.96(3H, s), 4.11(3H, t, J=6.8 Hz), 4.21(2H, t, J=6.8 Hz), 4.81(2H, s), 5.53(2H, s), 7.35(1H, s), 7.61(1H, s), 7.63(1H, s), 8.99–9.41(2H, m).

Example 1007

2-tert-Butyl-4-[2-(2-cyclopropyl-7-imino-5,7-dihydro-pyrrolo[3,4-b]pyridin-6-yl)-acetyl]-6-methoxy-phenyl methanesulfonate hydrobromide 1H-NMR(DMSO-d6) δ: 1.03–1.20(4H, m), 1.43(9H, s), 2.27–2.37(1H, m), 3.66(3H, s), 3.97(3H, s), 4.84(2H, s), 5.65(2H, s), 7.64(2H, brs), 7.72(1H, d, J=8.4 Hz), 8.11(1H, d, J=8.4 Hz), 9.52–9.82(2H, m).

Example 1008

2-tert-Butyl-4-[2-(5-ethoxy-1-imino-6-methylcarbamoyl-1,3-dihydro-isoindol-2-yl)-acetyl]-6-methoxy-phenyl methanesulfonate hydrobromide 1H-NMR(DMSO-d6) δ: 1.40(9H, s), 1.43(3H, t, J=6.8 Hz), 2.84(3H, d, J=4.8 Hz), 3.55(3H, s), 4.00(3H, s), 4.30 (3H, t, J=6.8 Hz), 4.88(2H, s), 5.52(2H, s), 7.56(1H, s), 7.87(1H, s), 7.91(1H, s), 8.17–8.28(1H, m), 8.58(1H, s), 9.22(1H, brs), 9.88(1H, brs).

Example 1009

3-tert-Butyl-5-[2-(5,6-diethoxy-7-fluoro-1-imino-1,3-dihydro-isoindol-2-yl)-acetyl]-2-methoxy-phenyl methanesulfonate hydrobromide 1H-NMR(DMSO-d6) δ: 1.31(3H, t, J=6.8 Hz), 1.40(9H, s), 1.42(3H, t, J=6.8 Hz), 3.54(3H, s), 4.00(3H, s), 4.13(3H, t, J=6.8 Hz), 4.23(2H, t, J=6.8 Hz), 4.83(2H, s), 5.50(2H, s), 7.36(1H, s), 7.86(1H, s), 7.90(1H, s), 9.01–9.16(1H, m), 9.28–9.43(1H, m).

Example 1010

2-{2-[3-tert-Butyl-5-(4-hydroxy-piperidin-1-yl)-4-methoxy-phenyl]-2-oxo-ethyl}-6-dimethylamino-3-imino-2,3-dihydro-1H-isoindole-5-carboxylic acid methylamide hydrobromide 1H-NMR(DMSO-d6) δ: 1.41(9H, s), 1.54–1.70(2H, m), 1.84–1.98(2H, m), 2.64–2.84(5H, m), 2.91(6H, s), 3.19–3.46(2H, m), 3.54–3.72(1H, m), 3.93(3H, s), 4.52–4.58(3H, m), 5.45(2H, s), 7.15(1H, s), 7.51(1H, s), 7.57(1H, s), 8.06(1H, s), 8.31–8.50(1H, m), 8.80–9.05(1H, m), 9.40–9.65(1H, m).

Example 1011

2-{2-[3-Dimethylamino-5-(1-fluoro-1-methyl-ethyl)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.41(3H, t, J=7 Hz), 1.68(3H, s), 1.74(3H, s), 2.77(6H, s), 2.82(3H, d, J=5 Hz), 3.83(3H, s), 4.28(2H, q, J=7 Hz), 4.84(2H, s), 5.52(2H, s), 7.51(1H, brs), 7.54(1H, brs), 7.66(1H, brs), 8.21(1H, m), 8.56(1H, brs), 9.21(1H, brs), 9.87(1H, brs).

MS: m/e (ESI) 484.4 (MH+)

Example 1012

6-{2-[3-Dimethylamino-5-(1-fluoro-1-methyl-ethyl)-4-methoxy-phenyl]-2-oxo-ethyl}-3-ethoxy-7-imino-6,7-dihydro-5H-pyrrolo[3,4-b]pyridine-2-carboxylic acid methylamide trifluoroacetate 1H-NMR(DMSO-d6) δ: 1.36(3H, t, J=7 Hz), 1.68(3H, s), 1.74(3H, s), 2.78(9H, m), 2.82(3H, d, J=5 Hz), 3.84(3H, s), 4.24(2H, q, J=7 Hz), 4.88(2H, s), 5.53(2H, s), 7.50(1H, brs), 7.66(1H, brs), 8.00(1H, s), 8.54(1H, m).

MS: m/e (ESI) 485.3 (MH+)

Example 1013

2-(5,6-Diethoxy-7-fluoro-1-imino-1,3-dihydro-isoindol-2-yl)-1-[3-dimethylamino-5-(1-fluoro-1-methyl-ethyl)-4-methoxy-phenyl]-ethanone hydrobromide 1H-NMR(DMSO-d6) δ: 1.29(3H, t, J=7 Hz), 1.40(3H, t, J=7 Hz), 1.68(3H, s), 1.74(3H, s), 2.77(6H, s), 3.83(3H, s), 4.11(2H, q, J=7 Hz), 4.21(2H, q, J=7 Hz), 4.80(2H, s), 5.50(2H, s), 7.34(1H, brs), 7.50(1H, brs), 7.65(1H, brs).
MS: m/e (ESI) 490.4 (MH+)

Example 1014

2-(2-Cyclopropyl-7-imino-5,7-dihydro-pyrrolo[3,4-b]pyridin-6-yl)-1-[3-dimethylamino-5-(1-fluoro-1-methyl-ethyl)-4-methoxy-phenyl]-ethanone hydrobromide 1H-NMR(DMSO-d6) δ: 1.02–1.13(4H, m), 1.68(3H, s), 1.74(3H, s), 2.31(1H, m), 2.77(6H, s), 3.83(3H, s), 4.83(2H, s), 5.57(2H, s), 7.51(1H, brs), 7.66(1H, brs), 7.72(1H, d, J=8 Hz), 8.10(1H, d, J=8 Hz), 9.48(1H, brs), 9.67(1H, brs).
MS: m/e (ESI) 425.3 (MH+)

Example 1015

6-Dimethylamino-2-{2-[3-dimethylamino-5-(1-fluoro-1-methyl-ethyl)-4-methoxy-phenyl]-2-oxo-ethyl}-3-imino-2,3-dihydro-1H-isoindole-5-carboxylic acid methylamide hydrobromide 1H-NMR(DMSO-d6) δ: 1.67(3H, s), 1.73(3H, s), 2.77 (9H, m), 2.92(6H, s), 3.83(3H, s), 4.74(2H, s), 5.46(2H, s), 7.15(1H, s), 7.50(1H, d, J=2 Hz), 7.66(1H, d, J=2 Hz), 8.07(1H, s), 8.37(1H, q, J=5 Hz), 8.94(1H, brs), 9.55(1H, brs).
MS: m/e (ESI) 484.4 (MH+)

Example 1016

2-tert-Butyl-6-dimethylamino-4-[2-(5-ethoxy-1-imino-6-methylcarbamoyl-1,3-dihydro-isoindol-2-yl)-acetyl]-phenyl methanesulfonate hydrobromide 1H-NMR(DMSO-d6) δ: 1.42(3H, t, J=6.8 Hz), 1.45(9H, s), 2.67(6H, s), 2.83(3H, d, J=4.8 Hz), 3.73(3H, s), 4.28(2H, q, J=6.8 Hz), 4.85(2H, s), 5.52(2H, s), 7.55(1H, s), 7.68(1H, s), 7.76(1H, s), 8.21(1H, q, J=4.8 Hz), 8.55(1H, s).

Example 1017

1-(3-tert-Butyl-4-methoxy-5-[1,3]oxazinan-3-yl-phenyl)-2-(5,6-diethoxy-7-fluoro-1-imino-1,3-dihydro-isoindol-2-yl)-ethanone hydrobromide 1H-NMR(DMSO-d6) δ: 1.32(3H, t, J=6.8 Hz), 1.36(9H, s), 1.42(3H, t, J=6.8 Hz), 1.56–1.68(2H, m), 3.42–3.48(2H, m), 3.89(3H, s), 3.80–3.92(2H, m), 4.13(2H, q, J=6.8 Hz), 4.23(2H, q, J=6.8 Hz), 4.79(2H, s), 4.82(2H, s), 5.50(2H, s), 7.36(2H, s), 7.60(1H, d, J=2.0 Hz), 7.77(1H, d, J=2.0 Hz).
MS: m/e (ESI) 528.2 (MH+)

Example 1018

2-{2-[3-tert-Butyl-5-(3-hydroxy-pyrrolidin-1-yl)-4-methoxy-phenyl]-2-oxo-ethyl}-6-dimethylamino-3-imino-2,3-dihydro-1H-isoindole-5-carboxylic acid methylamide trifluoroacetate 1H-NMR(DMSO-d6) δ: 1.39(9H, s), 1.80–1.92(1H, m), 1.98–2.11(1H, m), 2.74–2.84(4H, m), 2.94(6H, s), 3.08–3.18(1H, m), 3.26–3.50(2H, m), 3.65(3H, s), 4.32–4.47(1H, m), 4.75(2H, s), 4.64–5.01(1H, m), 5.47(2H, s), 7.17(1H, s), 7.35(1H, s), 7.44(1H, s), 8.09(1H, s), 8.30–8.54(1H, m), 8.94(1H, brs), 9.55(1H, brs).

Example 1019

1-[3-tert-Butyl-5-(3-hydroxy-pyrrolidin-1-yl)-4-methoxy-phenyl]-2-(5,6-diethoxy-7-fluoro-1-imino-1,3-dihydro-isoindol-2-yl)-ethanone trifluoroacetate 1H-NMR(DMSO-d6) δ: 1.40(9H, s), 1.79–1.92(1H, m), 1.98–2.12(1H, m), 2.90–2.99(1H, m), 3.08–3.18(1H, m), 3.20–3.60(2H, m), 3.65(3H, s), 3.89(3H, s), 3.97(3H, s), 4.30–4.43(1H, m), 4.81(2H, s), 5.50(2H, s), 7.34(1H, s), 7.39(1H, s), 7.43(1H, s), 9.08(1H, brs), 9.31(1H, brs).

Example 1020

2-(5,6-Diethoxy-7-fluoro-1-imino-1,3-dihydro-isoindol-2-yl)-1-[3-(4-hydroxy-piperidin-1-yl)-5-isopropyl-4-methoxy-phenyl]-ethanone hydrobromide 1H-NMR(DMSO-d6) δ: 1.21(6H, d, J=7.2 Hz), 1.31(3H, t, J=7.2 Hz), 1.42(3H, t, J=6.8 Hz), 1.54–1.68(2H, m), 1.86–1.96(2H, m), 2.70–2.82(2H, m), 3.20–3.68(3H, m), 3.88(3H, s), 4.13(2H, q, J=7.2 Hz), 4.23(2H, q, J=6.8 Hz), 4.74(1H, d, J=4.0 Hz), 4.81(2H, s), 5.49(2H, s), 7.35(1H, s), 7.43(1H, s), 7.56(1H, s), 8.98–9.12(1H, m), 9.20–9.38(1H, m).
MS: m/e (ESI) 528.4 (MH+)

Example 1021

2-[2-(3-tert-Butyl-5-ethylamino-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.20(3H, t, J=7.0 Hz), 1.37(9H, s), 1.41(3H, t, J=7.0 Hz), 2.82(3H, d, J=4.8 Hz), 3.12–3.17 (2H, m), 3.73(3H, s), 4.28(2H, q, J=7.0 Hz), 4.83(2H, s), 5.29(1H, t, J=6.0 Hz), 5.46(2H, s), 7.11(1H, s), 7.23(1H, s), 7.53(1H, s), 8.21(1H, q, J=4.8 Hz), 8.55(1H, s), 9.18(1H, brs), 9.80(1H, brs).
MS: m/e (ESI) 481.3 (MH+)

Example 1022

1-(3-tert-Butyl-5-ethylamino-4-methoxy-phenyl)-2-(5,6-diethoxy-7-fluoro-1-imino-1,3-dihydro-isoindol-2-yl)-ethanone hydrobromide 1H-NMR(DMSO-d6) δ: 1.20(3H, t, J=7.0 Hz), 1.29(3H, t, J=7.0 Hz), 1.37(9H, s), 1.40(3H, t, J=7.0 Hz), 3.12–3.19 (2H, m), 3.72(3H, s), 4.11(2H, q, J=7.0 Hz), 4.21(2H, q, J=7.0 Hz), 4.79(2H, s), 5.29(1H, t, J=6.0 Hz), 5.45(2H, s), 7.10(1H, s), 7.22(1H, s), 7.33(1H, s), 9.03(1H, brs), 9.28 (1H, brs).
MS: m/e (ESI) 486.3 (MH+)

Example 1023

2-[2-(3-tert-Butyl-5-ethylamino-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.20(3H, t, J=7.0 Hz), 1.37(9H, s), 2.78(3H, d, J=4.6 Hz), 2.92(6H, s), 3.12–3.19(2H, m), 3.72(3H, s), 4.73(2H, s), 5.28(1H, t, J=5.8 Hz), 5.42(2H, s), 7.10(1H, s), 7.15(1H, s), 7.23(1H, s), 8.06(1H, s), 8.37(1H, q, J=4.6 Hz), 8.92(1H, brs), 9.52(1H, brs).
MS: m/e (ESI) 480.3 (MH+)

Example 1024

1-(3-tert-Butyl-5-dimethylamino-4-hydroxy-phenyl)-2-(7-fluoro-1-imino-5,6-dimethoxy-1,3-dihydro-isoindol-2-yl)-ethanone hydrobromide 1H-NMR(DMSO-d6) δ: 1.39(9H, s), 2.61(6H, s), 3.87(3H, s), 3.95(3H, s), 4.80(2H, s), 5.46(2H, s), 7.36(1H, s), 7.63(1H, d, J=2.0 Hz), 7.68(1H, d, J=2.0 Hz).
MS: m/e (ESI) 444.2 (MH+)

Example 1025

6-[2-(3-tert-Butyl-5-ethylamino-4-methoxy-phenyl)-2-oxo-ethyl]-3-ethoxy-7-imino-6,7-dihydro-5H-pyrrolo[3,4-b]pyridine-2-carboxylic acid methylamide trifluoroacetate 1H-NMR(DMSO-d6) δ: 1.20(3H, t, J=7.0 Hz), 1.34–1.37(12H, m), 2.78(3H, d, J=5.0 Hz), 3.12–3.18(2H, m), 3.73(3H, s), 4.24(2H, q, J=7.0 Hz), 4.87(2H, s), 5.29(1H, t, J=6.0 Hz), 5.49(2H, s), 7.10(1H, s), 7.23(1H, s), 7.99(1H, s), 8.52(1H, q, J=5.0 Hz).
MS: m/e (ESI) 482.3 (MH+)

Example 1026

2-[2-(3-tert-Butyl-4-methoxy-5-methylamino-phenyl)-2-oxo-ethyl]-6-dimethylamino-3-imino-2,3-dihydro-1H-isoindole-5-carboxylic acid methylamide hydrobromide 1H-NMR(DMSO-d6) δ: 1.36(9H, s), 2.75–2.78(6H, m), 2.91(6H, s), 3.72(3H, s), 4.71(2H, s), 5.40(2H, s), 5.49(1H, q, J=4.8 Hz), 7.05(1H, s), 7.15(1H, s), 7.24(1H, s), 8.05(1H, s), 8.37(1H, q, J=4.8 Hz).
MS: m/e (ESI) 466.3 (MH+)

Example 1027

2-{2-[3-tert-Butyl-5-(3-hydroxy-pyrrolidin-1-yl)-4-methoxy-phenyl]-2-oxo-ethyl}-6-ethoxy-3-imino-2,3-dihydro-1H-isoindole-5-carboxylic acid methylamide trifluoroacetate 1H-NMR(DMSO-d6) δ: 1.40(9H, s), 1.44(3H, t, J=7.2 Hz), 1.79–1.92(1H, m), 1.98–2.12(1H, m), 2.85(3H, d, J=4.8 Hz), 2.92–2.99(1H, m), 3.08–3.18(1H, m), 3.20–3.65(2H, m), 3.66(3H, m), 4.30(2H, q, J=7.2 Hz), 4.35–4.45(1H, m), 4.86(2H, s), 5.43–5.58(2H, m), 7.36(1H, s), 7.44(1H, s), 7.56(1H, s), 8.16–8.30(1H, m), 8.58(1H, s), 9.17(1H, brs), 9.85(1H, brs).

Example 1028

6-[2-(3-tert-Butyl-4-methoxy-5-methylamino-phenyl)-2-oxo-ethyl]-3-ethoxy-7-imino-6,7-dihydro-5H-pyrrolo[3,4-b]pyridine-2-carboxylic acid methylamide trifluoroacetate 1H-NMR(DMSO-d6) δ: 1.34–1.38(12H, m), 2.75–2.78(6H, m), 3.72(3H, s), 4.24(2H, q, J=7.0 Hz), 4.87(2H, s), 5.51(2H, s), 7.05(1H, s), 7.24(1H, s), 7.99(1H, s), 8.52(1H, q, J=5.2 Hz).
MS: m/e (ESI) 468.3 (MH+)

Example 1029

(1-{5-[2-(5-Ethoxy-1-imino-6-methylcarbamoyl-1,3-dihydro-isoindol-2-yl)-acetyl]-3-isopropyl-2-methoxy-phenyl}-piperidin-4-yl)-acetic acid trifluoroacetate 1H-NMR(DMSO-d6) δ: 1.19(6H, d, J=7.2 Hz), 1.32–1.48(5H, m), 1.70–1.87(3H, m), 2.16–2.26(2H, m), 2.54–2.68(2H, m), 2.82(3H, d, J=3.6 Hz), 3.85(3H, s), 4.27(2H, q, J=6.8 Hz), 4.84(2H, s), 5.47(2H, s), 7.41(1H, s), 7.54(1H, s), 7.55(1H, s), 8.13–8.24(1H, m), 8.55(1H, s), 9.16(1H, brs), 9.83(1H, brs).
MS: m/e (ESI) 565.3 (MH+)

Example 1030

(1-{5-[2-(5,6-Diethoxy-7-fluoro-1-imino-1,3-dihydro-isoindol-2-yl)-acetyl]-3-isopropyl-2-methoxy-phenyl}-piperidin-4-yl)-acetic acid trifluoroacetate 1H-NMR(DMSO-d6) δ: 1.19(6H, d, J=6.8 Hz), 1.29(3H, t, J=6.8 Hz), 1.33–1.48(5H, m), 1.72–1.86(3H, m), 2.18–2.25(2H, m), 2.54–2.66(2H, m), 3.85(3H, s), 4.11(2H, q, J=6.8 Hz), 4.21(2H, q, J=6.8 Hz), 4.79(2H, s), 5.46(2H, s), 7.33(1H, s), 7.39(1H, s), 7.54(1H, s), 8.99–9.08(1H, m), 9.24–9.36(1H, m).
MS: m/e (ESI) 570.4 (MH+)

Example 1031

1-(3-tert-Butyl-5-ethylamino-4-methoxy-phenyl)-2-(7-fluoro-1-imino-5,6-dimethoxy-1,3-dihydro-isoindol-2-yl)-ethanone hydrobromide 1H-NMR(DMSO-d6) δ: 1.20(3H, t, J=7.0 Hz), 1.37(9H, s), 3.12–3.19(2H, m), 3.73(3H, s), 3.87(3H, s), 4.79(2H, s), 5.29(1H, t, J=6.0 Hz), 5.45(2H, s), 7.10(1H, s), 7.23(1H, s), 7.36(1H, s), 9.00(1H, brs), 9.28(1H, brs).
MS: m/e (ESI) 458.2 (MH+)

Example 1032

1-(3-tert-Butyl-5-ethylamino-4-methoxy-phenyl)-2-(2-cyclopropyl-7-imino-5,7-dihydro-pyrrolo[3,4-b]pyridin-6-yl)-ethanone hydrobromide 1H-NMR(DMSO-d6) δ: 1.08–1.10(4H, m), 1.20(3H, t, J=7.0 Hz), 1.37(9H, s), 2.26–2.35(1H, m), 3.12–3.18(2H, m), 3.73(3H, s), 4.81(2H, s), 5.29(1H, t, J=6.0 Hz), 5.54(2H, s), 7.11(1H, s), 7.23(1H, s), 7.71(1H, d, J=8.0 Hz), 8.09(1H, d, J=8.0 Hz).
MS: m/e (ESI) 421.2 (MH+)

Example 1033

1-(3-tert-Butyl-5-ethoxy-4-hydroxy-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=7.0 Hz), 1.36–1.41 (15H, m), 4.08–4.15(4H, m), 4.21(2H, q, J=7.0 Hz), 4.78 (2H, s), 5.44(2H, s), 7.33(1H, s), 7.42(1H, s), 7.50(1H, s), 9.00(1H, brs), 9.30(1H, brs), 9.44(1H, brs).
MS: m/e (ESI) 473.2 (MH+)

Example 1034

2-[2-(3-tert-Butyl-5-ethoxy-4-hydroxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.36–1.43(15H, m), 2.82(3H, d, J=4.6 Hz), 4.12(2H, q, J=7.0 Hz), 4.28(2H, q, J=7.0 Hz), 4.83(2H, s), 5.45(2H, s), 7.43(1H, s), 7.51(1H, s), 7.53(1H, s), 8.20(1H, q, J=4.6 Hz), 8.55(1H, s).
MS: m/e (ESI) 468.2 (MH+)

Example 1035

2-tert-Butyl-4-[2-(5,6-diethoxy-7-fluoro-1-imino-1,3-dihydro-isoindol-2-yl)-acetyl]-6-ethoxy-phenyl ethyl-carbamate hydrobromide 1H-NMR(DMSO-d6) δ: 1.08(3H, t, J=7.0 Hz), 1.27–1.33 (15H, m), 1.40(3H, t, J=6.8 Hz), 3.06–3.14(2H, m), 4.03–4.14(4H, m), 4.21(2H, q, J=7.0 Hz), 4.80(2H, s), 5.50(2H, s), 7.34(1H, s), 7.51(1H, s), 7.55(1H, s), 7.86(1H, t, J=4.8 Hz), 9.02(1H, brs), 9.33(1H, brs).
MS: m/e (ESI) 544.3 (MH+)

Example 1036

2-tert-Butyl-6-ethoxy-4-[2-(5-ethoxy-1-imino-6-methylcarbamoyl-1,3-dihydro-isoindol-2-yl)-acetyl]-phenyl ethyl-carbamate hydrobromide 1H-NMR(DMSO-d6) δ: 1.09(3H, t, J=7.0 Hz), 1.31(3H, t, J=7.0 Hz), 1.34(9H, s), 1.42(3H, t, J=7.0 Hz), 2.82(3H, d, J=4.8 Hz), 3.05–3.11(2H, m), 4.07(2H, q, J=7.0 Hz), 4.28 (2H, q, J=7.0 Hz), 4.85(2H, s), 5.51(2H, s), 7.52(1H, s), 7.54(1H, s), 7.57(1H, s), 7.86(1H, t, J=6.0 Hz), 8.21(1H, q, J=4.8 Hz), 8.55(1H, s).
MS: m/e (ESI) 539.4 (MH+)

Example 1037

2-tert-Butyl-6-(3-cyano-propoxy)-4-[2-(5,6-diethoxy-7-fluoro-1-imino-1,3-dihydro-isoindol-2-yl)-acetyl]-phenyl methanesulfonate hydrobromide 1H-NMR(DMSO-d6) δ: 1.29(3H, t, J=7.0 Hz), 1.40(3H, t, J=7.0 Hz), 1.44(9H, s), 2.10–2.17(2H, m), 2.69(2H, t, J=7.2 Hz), 3.67(3H, s), 4.12(2H, q, J=7.0 Hz), 4.21(2H, q, J=7.0 Hz), 4.82(2H, s), 5.53(2H, s), 7.35(1H, s), 7.63(1H, s), 7.66(1H, s), 9.08(1H, brs), 9.32(1H, brs).
MS: m/e (ESI) 590.2 (MH+)

Example 1038

1-(3-Dimethylamino-5-isopropenyl-4-methoxy-phenyl)-2-(7-fluoro-1-imino-5,6-dimethoxy-1,3-dihydro-isoindol-2-yl)-ethanone hydrobromide 1H-NMR(DMSO-d6) δ: 2.09(3H, s), 2.80(6H, s), 3.72 (3H, s), 3.87(3H, s), 3.95(3H, s), 4.81(2H, s), 5.04(1H, m), 5.23(1H, m), 5.49(2H, s), 7.37(1H, brs), 7.40–7.42(2H, m).
MS: m/e (ESI) 442.3 (MH+)

Example 1039

2-tert-Butyl-6-(3-cyanopropoxy)-4-[2-(5-ethoxy-1-imino-6-methylcarbamoyl-1,3-dihydro-isoindol-2-yl)-acetyl]-phenyl methanesulfonate hydrobromide 1H-NMR(DMSO-d6) δ: 1.42(3H, t, J=7.0 Hz), 1.44(9H, s), 2.11–2.17(2H, m), 2.69(2H, t, J=7.2 Hz), 2.83(3H, d, J=4.8 Hz), 3.67(3H, s), 4.25–4.30(4H, m), 4.86(2H, s), 5.53(2H, s), 7.55(1H, s), 7.64(1H, s), 7.67(1H, s), 8.21(1H, q, J=4.8 Hz), 8.56(1H, s), 9.20(1H, brs), 9.82(1H, brs).
MS: m/e (ESI) 585.3 (MH+)

Example 1040

1-[3-tert-Butyl-5-(4-hydroxy-4-methyl-piperidin-1-yl)-4-methoxy-phenyl]-2-(5,6-diethoxy-7-fluoro-1-imino-1,3-dihydro-isoindol-2-yl)-ethanone hydrobromide 1H-NMR(DMSO-d6) δ: 1.18(3H, s), 1.28(3H, t, J=6.8 Hz), 1.35(9H, s), 1.39(3H, t, J=6.8 Hz), 1.59–1.80(4H, m), 2.88–3.09(4H, m), 3.93(3H, s), 4.11(3H, q, J=6.8 Hz), 4.21(3H, q, J=6.8 Hz), 4.78(2H, s), 5.48(2H, s), 7.33(1H, s), 7.53(1H, s), 7.55(1H, s), 8.98–9.10(1H, m), 9.20–9.33(1H, m).
MS: m/e (ESI) 556.4 (MH+)

Example 1041

1-(3-tert-Butyl-4-methoxy-5-piperazin-1-yl-phenyl)-2-(5,6-diethoxy-7-fluoro-1-imino-1,3-dihydro-isoindol-2-yl)-ethanone dihydrochloride 1H-NMR(DMSO-d6) δ: 1.29(3H, t, J=7.0 Hz), 1.37(9H, s), 1.40(3H, t, J=7.0 Hz), 3.21(4H, brs), 3.32(4H, brs), 3.94(3H, s), 4.11(2H, q, J=7.0 Hz), 4.21(2H, q, J=7.0 Hz), 4.79(2H, s), 5.55(2H, s), 7.34(1H, s), 7.50(1H, s), 7.64(1H, s), 9.04–9.16(3H, m), 9.40(1H, brs).
MS: m/e (ESI) 527.3 (MH+)

Example 1042

2-(2-{3-tert-Butyl-4-methoxy-5-[(2-methoxyethyl)-methylamino]-phenyl}-2-oxo-ethyl)-6-ethoxy-3-imino-2,3-dihydro-1H-isoindole-5-carboxylic acid methylamide hydrobromide 1H-NMR(DMSO-d6) δ: 1.16(3H, t, J=6.8), 1.36(9H, s), 1.39(3H, t, J=6.8 Hz), 2.68–2.95(6H, m), 3.18(3H, s), 3.20–3.48(4H, m), 3.81(3H, s), 4.27(2H, q, J=6.8 Hz), 4.84(2H, s), 5.49(2H, s), 7.46–7.60(3H, m), 8.20(1H, q, J=4.0 Hz), 8.55(1H, s), 9.16(1H, brs), 9.83(1H, s).
MS: m/e (ESI) 525.4 (MH+)

Example 1043

2-(2-{3-tert-Butyl-4-methoxy-5-[(2-methoxyethyl)-methylamino]-phenyl}-2-oxo-ethyl)-6-dimethylamino-3-imino-2,3-dihydro-1H-isoindole-5-carboxylic acid methylamide hydrobromide 1H-NMR(DMSO-d6) δ: 1.36(9H, s), 2.77(3H, d, J=4.0 Hz), 2.80(3H, s), 2.91(6H, s), 3.18(3H, s), 3.20–3.48(4H, m), 3.81(3H, s), 4.73(2H, s), 5.43(2H, s), 7.15(1H, s), 7.50(1H, s), 7.53(1H, s), 8.06(1H, s), 8.36(1H, q, J=4.0 Hz).
MS: m/e (ESI) 524.3 (MH+)

Example 1044

1-{3-tert-Butyl-4-methoxy-5-[(2-methoxyethyl)-methylamino]-phenyl}-2-(5,6-diethoxy-7-fluoro-1-imino-1,3-dihydro-isoindol-2-yl)-ethanone hydrobromide 1H-NMR(DMSO-d6) δ: 1.29(3H, t, J=6.8 Hz), 1.36(9H, s), 1.39(3H, t, J=6.8 Hz), 2.81(3H, s), 3.18(3H, s), 3.22–3.44 (4H, m), 3.81(3H, s), 4.11(2H, q, J=6.8 Hz), 4.20(2H, q, J=6.8 Hz), 4.79(2H, s), 5.49(2H, s), 7.34(1H, s), 7.50(1H, d, J=2.0 Hz), 7.52(1H, d, J=2.0 Hz).

Example 1045

1-(3-tert-Butyl-4-ethoxy-5-morpholino-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=7.0 Hz), 1.34–1.42 (15H, m), 3.00(4H, brs), 3.79(4H, brs), 4.01(2H, q, J=7.0 Hz), 4.21(2H, q, J=7.0 Hz), 4.29(2H, q, J=7.0 Hz), 4.79(2H, s), 5.47(2H, s), 7.34(1H, s), 7.47(1H, d, J=2.0 Hz), 7.61(1H, d, J=2.0 Hz), 9.02(13H, brs), 9.27(1H, brs).
MS: m/e (ESI) 542.3 (MH+)

Example 1046

2-[2-(3-tert-Butyl-4-ethoxy-5-morpholino-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.34–1.43(15H, m), 2.83(3H, d, J=4.6 Hz), 3.00(4H, brs), 3.79(4H, brs), 4.25–4.32(4H, m), 4.83(2H, s), 5.48(2H, s), 7.49(1H, s), 7.53(1H, s), 7.62(1H, s), 8.20(1H, q, J=4.6 Hz), 8.55(1H, s).
MS: m/e (ESI) 537.4 (MH+)

Example 1047

1-[3-tert-Butyl-5-(2-hydroxyethylamino)-4-methoxy-phenyl]-2-(5,6-diethoxy-7-fluoro-1-imino-1,3-dihydro-isoindol-2-yl)-ethanone hydrochloride 1H-NMR(DMSO-d6) δ: 1.38(3H, t, J=6.8 Hz), 1.45(9H, s), 1.50(3H, t, J=6.8 Hz), 3.44(2H, t, J=5.4 Hz), 3.83(2H, t, J=5.4 Hz), 3.89(3H, s), 4.18(2H, q, J=6.8 Hz), 4.24(2H, q, J=6.8 Hz), 4.91(2H, s), 5.49(2H, s), 7.21(1H, s), 7.55(1H, d, J=2.0 Hz), 7.66(1H, d, J=2.0 Hz).
MS: m/e (ESI) 502.3 (MH+)

Example 1048

1-[3-tert-Butyl-5-(2-hydroxyethylamino)-4-methoxy-phenyl]-2-(7-fluoro-1-imino-5,6-dimethoxy-1,3-dihydro-isoindol-2-yl)-ethanone dihydrochloride 1H-NMR(DMSO-d6) δ: 1.44(9H, s), 3.38(2H, t, J=5.6 Hz), 3.83(2H, t, J=5.6 Hz), 3.86(3H, s), 3.94(3H, s), 4.02 (3H, s), 4.91(2H, s), 5.46(2H, s), 7.25(1H, s), 7.40(1H, d, J=2.0 Hz), 7.54(1H, d, J=2.0 Hz).

Example 1049

1-{3-tert-Butyl-5-[(2-hydroxyethyl)-methylamino]-4-methoxy-phenyl}-2-(5,6-diethoxy-7-fluoro-1-imino-1,3-dihydro-isoindol-2-yl)-ethanone dihydrochloride 1H-NMR(DMSO-d6) δ: 1.36(3H, t, J=6.8 Hz), 1.44(9H, s), 1.49(3H, t, J=6.8 Hz), 3.04(3H, brs), 3.38–3.75(4H, m), 3.95(3H, s), 5.49(2H, s), 7.21(1H, s), 7.77–7.95(2H, m).
MS: m/e (ESI) 516.4 (MH+)

Example 1050

2-({3-tert-Butyl-5-[2-(5,6-diethoxy-7-fluoro-1-imino-1,3-dihydro-isoindol-2-yl)-acetyl]-2-methoxy-phenyl}-methylamino)-ethyl acetate hydrochloride 1H-NMR(DMSO-d6) δ: 1.27(3H, t, J=6.8 Hz), 1.36(9H, s), 1.39(3H, t, J=6.8 Hz), 1.87(3H, s), 2.81(3H, s), 2.72–2.85 (2H, m), 3.38(2H, t, J=6.0 Hz), 3.81(3H, s), 4.12(2H, q, J=6.8 Hz), 4.20(2H, q, J=6.8 Hz), 4.79(2H, s), 5.55(2H, s), 7.33(1H, s), 7.52(1H, s), 7.54(1H, s), 9.07(1H, brs), 9.44 (1H, brs).
MS: m/e (ESI) 558.4 (MH+)

Example 1051

2-{2-[3-tert-Butyl-5-(3,4-dihydroxy-pyrrolidin-1-yl)-4-methoxy-phenyl]-2-oxo-ethyl}-6-ethoxy-3-imino-2,3-dihydro-1H-isoindole-5-carboxylic acid methylamide trifluoroacetate 1H-NMR(DMSO-d6) δ: 1.37(9H, s), 1.41(3H, t, J=6.8 Hz), 2.82(3H, d, J=4.8 Hz), 2.88–2.95(2H, m), 3.50–3.59 (2H, m), 3.61(3H, s), 4.02(2H, brs), 4.28(2H, q, J=6.8 Hz), 4.83(2H, s), 5.37–5.60(2H, m), 7.29(1H, s), 7.38(1H, s), 7.54(1H, s), 8.12–8.28(1H, m), 8.55(1H, s), 9.14(1H, brs), 9.82(1H, brs).

Example 1052

1-[3-tert-Butyl-5-(3,4-dihydroxy-pyrrolidin-1-yl)-4-methoxy-phenyl]-2-(5,6-diethoxy-7-fluoro-1-imino-1,3-dihydro-isoindol-2-yl)-ethanone trifluoroacetate 1H-NMR(DMSO-d6) δ: 1.29(3H, t, J=6.8 Hz), 1.37(9H, s), 1.40(3H, t, J=6.8 Hz), 2.87–2.97(2H, m), 3.48–3.58(2H, m), 3.61(3H, s), 4.02(2H, brs), 4.11(2H, q, J=6.8 Hz), 4.21(2H, q, J=6.8 Hz), 4.78(2H, s), 5.36–5.58(2H, m), 7.28(1H, s), 7.34(1H, s), 7.37(1H, s), 9.04(1H, brs), 9.26 (1H, brs).

Example 1053

2-{2-[3-tert-Butyl-5-((3R,4R)-3-hydroxy-4-methoxy-pyrrolidin-1-yl)-4-methoxy-phenyl]-2-oxo-ethyl}-6-ethoxy-3-imino-2,3-dihydro-1H-isoindole-5-carboxylic acid methylamide trifluoroacetate 1H-NMR(DMSO-d6) δ: 1.37(9H, s), 1.41(3H, t, J=6.8 Hz), 2.82(3H, d, J=4.4 Hz), 2.82–3.11(2H, m), 3.30(3H, s), 3.40–3.58(2H, m), 3.63(3H, s), 3.72–3.79(1H, m), 4.10–4.25(1H, m), 4.27(2H, q, J=6.8 Hz), 4.83(2H, s), 5.38–5.62(2H, m), 7.32(1H, s), 7.42(1H, s), 7.54(1H, s), 8.14–8.28(1H, m), 8.55(1H, s), 9.13(1H, brs), 9.83(1H, brs).

Example 1054

1-[3-tert-Butyl-5-((3R,4R)-3-hydroxy-4-methoxy-pyrrolidin-1-yl)-4-methoxy-phenyl]-2-(5,6-diethoxy-7-fluoro-1-imino-1,3-dihydro-isoindol-2-yl)-ethanone trifluoroacetate 1H-NMR(DMSO-d6) δ: 1.29(3H, t, J=7.2 Hz), 1.37(9H, s), 1.39(3H, t, J=7.2 Hz), 2.91–2.99(1H, m), 3.03–3.12(1H, m), 3.30(3H, s), 3.40–3.58(2H, m), 3.63(3H, s), 3.71–3.79 (1H, m), 4.10(2H, q, J=7.2 Hz), 4.10–4.30(3H, m), 4.78(2H, s), 5.38–5.60(2H, m), 7.30(1H, s), 7.33(1H, s), 7.41(1H, s), 8.99–9.12(1H, m), 9.20–9.40(1H, m).

Example 1055

6-(2-{3-tert-Butyl-5-[(2-hydroxyethyl)methylamino]-4-methoxy-phenyl}-2-oxo-ethyl)-3-ethoxy-7-imino-6,7-dihydro-5H-pyrrolo[3,4-b]pyridine-2-carboxylic acid methylamide hydrochloride 1H-NMR(DMSO-d6) δ: 1.26–1.44(3H, m), 1.36(9H, s), 2.77(3H, d, J=4.0 Hz), 2.81(3H, s), 3.17(2H, t, J=6.4 Hz), 3.52(2H, t, J=6.4 Hz), 3.82(3H, s), 4.23(2H, q, J=6.8 Hz), 4.87(2H, s), 5.60(2H, s), 7.51–7.53(2H, m), 8.00(1H, s), 8.57(1H, q, J=4.0 Hz), 9.57(1H, brs), 9.97(1H, brs).

Example 1056

2-(2-{3-tert-Butyl-5-[(2-hydroxyethyl)-methylamino]-4-methoxy-phenyl}-2-oxo-ethyl)-6-ethoxy-3-imino-2,3-dihydro-1H-isoindole-5-carboxylic acid methylamide hydrochloride 1H-NMR(DMSO-d6) δ: 1.36(9H, s), 1.41(3H, t, J=6.8 Hz), 2.75–2.90(3H, m), 3.06–3.26(2H, m), 3.14(3H, s), 3.54(2H, t, J=4.0 Hz), 3.82(3H, s), 4.26(2H, q, J=6.8 Hz), 4.83(2H, s), 5.54(2H, s), 7.45–7.60(3H, m), 8.20(1H, q, J=4.0 Hz), 8.55(1H, s), 9.33(1H, brs), 9.91(1H, brs).

Example 1057

({3-tert-Butyl-5-[2-(5,6-diethoxy-7-fluoro-1-imino-1,3-dihydro-isoindol-2-yl)-acetyl]-2-methoxy-phenyl}-methylamino)-acetonitrile hydrobromide 1H-NMR(DMSO-d6) δ: 1.29(3H, t, J=7 Hz), 1.35–1.42 (12H, m), 2.87(3H, s), 3.80(3H, s), 4.11(2H, q, J=7 Hz), 4.21(2H, q, J=7 Hz), 4.36(2H, s), 4.81(2H, s), 5.53(2H, s), 7.35(1H, brs), 7.58(1H, brs), 7.66(1H, brs), 9.06(1H, brs), 9.32(1H, brs).

Example 1058

2-{2-[3-tert-Butyl-5-(cyanomethyl-amino)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.35–1.42(12H, m), 2.81(3H, d, J=5 Hz), 3.71(3H, s), 4.24–4.38(4H, m), 4.84(2H, s), 5.46 (2H, s), 6.05(1H, m), 7.30(1H, brs), 7.39(1H, brs), 7.50(1H, brs), 8.23(1H, m), 8.52(1H, s).

MS: m/e (ESI) 492.2 (MH+)

Example 1059

{3-tert-Butyl-5-[2-(5,6-diethoxy-7-fluoro-1-imino-1,3-dihydro-isoindol-2-yl)-acetyl]-2-methoxy-phenylamino}-acetonitrile hydrobromide 1H-NMR(DMSO-d6) δ: 1.29(3H, t, J=7 Hz), 1.35–1.42 (12H, m), 3.72(3H, s), 4.11(2H, q, J=7 Hz), 4.21(2H, q, J=7 Hz), 4.36(2H, m), 4.81(2H, s), 5.49(2H, s), 6.15(1H, m), 7.32(1H, brs), 7.34(1H, brs), 7.39(1H, brs).

MS: m/e (ESI) 497.2 (MH+)

Example 1060

2-{2-[3-tert-Butyl-5-(cyanomethyl-methylamino)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.35–1.42(12H, m), 2.82(3H, d, J=5 Hz), 2.87(3H, s), 3.81(3H, s), 4.25–4.37(4H, m), 4.85 (2H, s), 5.53(2H, s), 7.54(1H, brs), 7.58(1H, brs), 7.67(1H, brs), 8.20(1H, m), 8.55(1H, brs).

MS: m/e (ESI) 506.2 (MH+)

Example 1061

1-(3-tert-Butyl-4-methoxymethoxy-5-morpholin-4-yl-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=7.0 Hz), 1.37–1.43 (15H, m), 2.94(4H, brs), 3.54(3H, s), 3.79(4H, brs), 4.11 (2H, q, J=7.0 Hz), 4.21(2H, q, J=7.0 Hz), 4.77(2H, s), 5.34(2H, s), 5.45(2H, s), 7.32(1H, s), 7.52(1H, s), 7.64(1H, s), 9.02(1H, brs), 9.27(1H, brs).

MS: m/e (ESI) 558.3 (MH+)

Example 1062

2-{2-[3-tert-Butyl-5-((3R,4R)-3-hydroxy-4-methoxy-pyrrolidin-1-yl)-4-methoxy-phenyl]-2-oxo-ethyl}-6-dimethylamino-3-imino-2,3-dihydro-1H-isoindole-5-carboxylic acid methylamide trifluoroacetate 1H-NMR(DMSO-d6) δ: 1.36(9H, s), 2.77(3H, d, J=4.0 Hz), 2.85–3.14(8H, m), 3.29(3H, s), 3.62(3H, s), 3.70–3.80 (1H, m), 4.13–4.27(1H, m), 4.72(2H, s), 5.35–5.60(2H, m), 7.15(1H, s), 7.31(1H, s), 7.41(1H, s), 8.05(1H, s), 8.30–8.44 (1H, m), 8.90(1H, brs), 9.52(1H, brs).

Example 1063

6-{2-[3-tert-Butyl-5-((3R,4R)-3-hydroxy-4-methoxy-pyrrolidin-1-yl)-4-methoxy-phenyl]-2-oxo-ethyl}-3-ethoxy-7-imino-6,7-dihydro-5H-pyrrolo[3,4-b]pyridine-2-carboxylic acid methylamide trifluoroacetate 1H-NMR(DMSO-d6) δ: 1.26–1.54(12H, m), 2.77(3H, d, J=4.8 Hz), 2.70–3.01(1H, m), 3.02–3.13(1H, m), 3.30(3H, s), 3.40–3.58(2H, m), 3.63(3H, s), 3.71–3.82(1H, m), 4.10–4.45(3H, m), 4.87(2H, s), 5.23(1H, d, J=3.6 Hz), 5.40–5.70(2H, m), 7.31(1H, s), 7.42(1H, s), 7.99(1H, s), 8.40–8.63(1H, m), 9.28–9.48(2H, m).

Example 1064

2-[2-(3-tert-Butyl-4-methoxymethoxy-5-morpholino-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.40–1.43(12H, m), 2.82(3H, d, J=4.8 Hz), 2.95(4H, brs), 3.55(3H, s), 3.79(4H, brs), 4.28 (2H, q, J=7.0 Hz), 4.85(2H, s), 5.34(2H, s), 5.49(2H, s), 7.52–7.54(2H, m), 7.65(1H, s), 8.21(1H, d, J=4.8 Hz), 9.16(1H, brs), 9.85(1H, brs).
MS: m/e (ESI) 553.3 (MH+)

Example 1065

1-(3-tert-Butyl-4-hydroxy-5-morpholino-phenyl)-2-(5,6-diethoxy-7-fluoro-1-imino-1,3-dihydro-isoindol-2-yl)-ethanone hydrochloride 1H-NMR(DMSO-d6) δ: 1.29(3H, t, J=7.0 Hz), 1.38–1.41 (12H, m), 2.78–2.79(4H, m), 3.81–3.83(4H, m), 4.11(2H, q, J=7.0 Hz), 4.21(2H, q, J=7.0 Hz), 4.79(2H, s), 5.44(2H, s), 7.33(1H, s), 7.67(1H, s), 7.73(1H, s), 9.03(1H, brs), 9.20 (1H, brs), 9.28(1H, brs).
MS: m/e (ESI) 514.3 (MH+)

Example 1066

2-[2-(3-tert-Butyl-4-hydroxy-5-morpholino-phenyl)-2-oxo-ethyl]-6-ethoxy-3-imino-2,3-dihydro-1H-isoindole-5-carboxylic acid methylamide trifluoroacetate 1H-NMR(DMSO-d6) δ: 1.40–1.43(12H, m), 2.77–2.80 (4H, m), 2.82(3H, d, J=4.4 Hz), 3.81–3.83(4H, m), 4.28(2H, q, J=7.0 Hz), 4.84(2H, s), 5.45(2H, s), 7.54(1H, s), 7.68(1H, s), 7.74(1H, s), 8.21(1H, q, J=4.4 Hz), 8.56(1H, s), 9.14(1H, brs), 9.20(1H, brs), 9.82(1H, brs).
MS: m/e (ESI) 509.3 (MH+)

Example 1067

2-(5,6-Diethoxy-7-fluoro-1-imino-1,3-dihydro-isoindol-2-yl)-1-(3-isopropyl-4-methoxy-5-morpholino-phenyl)-ethanone hydrobromide 1H-NMR(DMSO-d6) δ: 1.20(6H, d, J=6.8 Hz), 1.29(3H, t, J=6.8 Hz), 1.40(3H, t, J=6.8 Hz), 2.90–3.10(5H, m), 3.66–3.88(4H, m), 3.87(3H, s), 4.04–4.26(4H, m), 4.80(2H, s), 5.50(2H, s), 7.34(1H, s), 7.39(1H, s), 7.58(1H, s), 9.06 (1H, brs), 9.34(1H, brs).

Example 1068

2-(2-{3-tert-Butyl-5-[ethyl-(2-hydroxyethyl)-amino]-4-methoxy-phenyl}-2-oxo-ethyl)-6-ethoxy-3-imino-2,3-dihydro-1H-isoindole-5-carboxylic acid methylamide hydrochloride 1H-NMR(DMSO-d6) δ: 0.96(3H, t, J=6.8 Hz), 1.36(9H, s), 1.42(3H, t, J=6.8 Hz), 2.82(3H, d, J=4.0 Hz), 3.12–3.28 (4H, m), 3.20–3.65(2H, m), 3.84(3H, s), 4.27(2H, q, J=6.8 Hz), 4.84(2H, s), 5.49(2H, s), 7.48–7.60(3H, m), 8.21(1H, brs), 8.56(1H, s), 9.21(1H, brs), 9.86(1H, brs).
MS: m/e (ESI) 525.3 (MH+)

Example 1069

2-(2-{3-tert-Butyl-5-[ethyl-(2-hydroxyethyl)-amino]-4-methoxy-phenyl}-2-oxo-ethyl)-6-dimethylamino-3-imino-2,3-dihydro-1H-isoindole-5-carboxylic acid methylamide hydrochloride 1H-NMR(DMSO-d6) δ: 0.95(3H, t, J=6.8 Hz), 1.36(9H, s), 2.77(3H, d, J=4.0 Hz), 2.91(6H, s), 3.08–3.18(4H, m), 3.47(2H, t, J=5.6 Hz), 3.84(3H, s), 4.73(2H, s), 5.49(2H, s), 7.14(1H, s), 7.53(1H, s), 7.55(1H, s), 8.08(1H, s), 3.37(1H, q, J=4.0 Hz), 9.08(1H, brs), 9.60(1H, brs).

Example 1070

1-{3-tert-Butyl-5-[ethyl-(2-hydroxyethyl)-amino]-4-methoxy-phenyl}-2-(5,6-diethoxy-7-fluoro-1-imino-1,3-dihydro-isoindol-2-yl)-acetyl hydrochloride 1H-NMR(DMSO-d6) δ: 0.96(3H, t, J=6.4 Hz), 1.28(3H, t, J=6.8 Hz), 1.37(9H, s), 1.39(3H, t, J=6.8 Hz), 3.14–3.26 (4H, m), 3.47(2H, t, J=6.0 Hz), 3.84(3H, s), 4.11(2H, q, J=6.8 Hz), 4.20(2H, q, J=6.8 Hz), 4.79(2H, s), 5.61(2H, s), 7.33(1H, s), 7.55(1H, s), 7.60(1H, s), 9.10(1H, brs), 9.57 (1H, brs).

Example 1071

6-(2-{3-tert-Butyl-5-[ethyl-(2-hydroxyethyl)-amino]-4-methoxy-phenyl}-2-oxo-ethyl)-3-ethoxy-7-imino-6,7-dihydro-5H-pyrrolo[3,4-b]pyridine-2-carboxylic acid methylamide hydrochloride 1H-NMR(DMSO-d6) δ: 0.96(3H, t, J=6.8 Hz), 1.36(3H, t, J=6.8 Hz), 1.36(9H, s), 2.78(3H, d, J=4.0 Hz), 3.14–3.28 (4H, m), 3.30–3.64(2H, m), 3.84(3H, s), 4.24(2H, q, J=6.8 Hz), 4.88(2H, s), 5.56(2H, s), 7.53(1H, s), 7.55(1H, s), 8.00(1H, s), 8.55(1H, q, J=4.0 Hz), 9.49(1H, brs), 9.96(1H, brs).

Example 1072

2-{2-[3-tert-Butyl-5-(4-hydroxy-4-methyl-piperidin-1-yl)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.18(3H, s), 1.36(9H, s), 1.41 (3H, t, J=6.8 Hz), 1.57–1.76(4H, m), 2.82(3H, d, J=4.8 Hz), 2.90–3.07(4H, m), 3.93(3H, s), 4.16–4.37(3H, m), 4.83(2H, s), 5.48(2H, s), 7.53(1H, s), 7.55(1H, s), 7.56(1H, s), 8.10–8.26(1H, m), 8.55(1H, s).

Example 1073

2-{2-[3-tert-Butyl-5-(4-hydroxy-4-methyl-piperidin-1-yl)-4-methoxy-phenyl]-2-oxo-ethyl}-6-dimethylamino-3-imino-2,3-dihydro-1H-isoindole-5-carboxylic acid methylamide hydrobromide 1H-NMR(DMSO-d6) δ: 1.18(3H, s), 1.35(9H, s), 1.57–1.76(4H, m), 2.77(3H, d, J=4.4 Hz), 2.91(6H, s), 2.94–3.07(4H, m), 3.93(3H, s), 4.30(1H, s), 4.73(2H, s), 5.44(2H, s), 7.15(1H, s), 7.54(1H, s), 7.56(1H, s), 8.06(1H, s), 8.28–8.42(1H, m), 8.80–8.98(1H, m), 9.38–9.60(1H, m).

Example 1074

6-{2-[3-tert-Butyl-5-(4-hydroxy-4-methyl-piperidin-1-yl)-4-methoxy-phenyl]-2-oxo-ethyl}-3-ethoxy-7-imino-6,7-dihydro-5H-pyrrolo[3,4-b]pyridine-2-carboxylic acid methylamide trifluoroacetate 1H-NMR(DMSO-d6) δ: 1.18(3H, s), 1.30–1.44(12H, m), 1.58–1.76(4H, m), 2.77(3H, d, J=4.8 Hz), 2.91–3.08(4H, m), 3.93(3H, s), 4.13–4.40(3H, m), 4.87(2H, s), 5.52(2H, s), 7.54(1H, s), 7.56(1H, s), 7.99(1H, s), 8.42–8.60(1H, m), 9.31–9.44(1H, m), 9.88–10.02(1H, m).

Example 1075

2-tert-Butyl-4-[2-(5,6-diethoxy-7-fluoro-1-imino-1,3-dihydro-isoindol-2-yl)-acetyl]-6-morpholino-phenyl methanesulfonate hydrobromide 1H-NMR(DMSO-d6) δ: 1.29(3H, t, J=7.0 Hz), 1.40(3H, t, J=7.0 Hz), 1.45(9H, s), 2.95(4H, brs), 3.79(4H, brs), 3.84(3H, s), 4.121(2H, q, J=7.0 Hz), 4.21(2H, q, J=7.0 Hz), 4.80(2H, s), 5.51(2H, s), 7.34(1H, s), 7.72(1H, d, J=2.0 Hz), 7.83(1H, d, J=2.0 Hz).
MS: m/e (ESI) 592.3 (MH+)

Example 1076

2-tert-Butyl-4-[2-(5-ethoxy-1-imino-6-methylcarbamoyl-1,3-dihydro-isoindol-2-yl)-acetyl]-6-morpholino-phenyl methanesulfonate hydrobromide 1H-NMR(DMSO-d6) δ: 1.42(3H, t, J=7.0 Hz), 1.45(9H, s), 2.82(3H, d, J=4.6 Hz), 2.95(4H, brs), 3.78(4H, brs), 3.85(3H, s), 4.28(2H, q, J=7.0 Hz), 4.86(2H, s), 5.53(2H, s), 7.55(1H, s), 7.73(1H, d, J=2.0 Hz), 7.84(1H, d, J=2.0 Hz), 8.21(1H, q, J=4.6 Hz), 8.56(1H, s).
MS: m/e (ESI) 587.3 (MH+)

Example 1077

1-[3-tert-Butyl-5-(4-methanesulfonyl-piperazin-1-yl)-4-methoxy-phenyl]-2-(5,6-diethoxy-7-fluoro-1-imino-1,3-dihydro-isoindol-2-yl)-ethanone hydrobromide 1H-NMR(DMSO-d6) δ: 1.29(3H, t, J=7.0 Hz), 1.37(9H, s), 1.39(3H, t, J=7.0 Hz), 2.95(3H, s), 3.09(4H, brs), 3.28(4H, brs), 3.95(3H, s), 4.11(2H, q, J=7.0 Hz), 4.21(2H, q, J=7.0 Hz), 4.78(2H, brs), 5.45(2H, brs), 7.32(1H, s), 7.53(1H, s), 7.62(1H, s).
MS: m/e (ESI) 605.3 (MH+)

Example 1078

2-[2-(3-tert-Butyl-4-methoxy-5-morpholino-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.37(9H, s), 1.41(3H, t, J=7.0 Hz), 2.82(3H, d, J=4.0 Hz), 2.95(3H, s), 3.09(4H, brs), 3.18(4H, brs), 3.95(3H, s), 4.27(2H, q, J=7.0 Hz), 4.83(2H, s), 5.48(2H, s), 7.53(1H, s), 7.63(1H, s), 8.20(1H, q, J=4.0 Hz), 8.54(1H, s).
MS: m/e (ESI) 600.3 (MH+)

Example 1079

6-Ethoxy-3-imino-2-[2-(3-isopropyl-4-methoxy-5-morpholino-phenyl)-2-oxo-ethyl]-2,3-dihydro-1H-isoindole-5-carboxylic acid methylamide hydrobromide 1H-NMR(DMSO-d6) δ: 1.20(6H, d, J=7.2 Hz), 1.41(3H, t, J=6.8 Hz), 2.81(3, d, J=4.0 Hz), 2.94–3.08(4H, m), 3.68–3.88(4H, m), 3.87(3H, s), 4.28(2H, q, J=6.8 Hz), 4.85(2H, s), 5.49(2H, s), 7.39(1H, s), 7.54(1H, s), 7.59(1H, s), 8.20(1H, q, J=4.0 Hz), 8.56(1H, s).

Example 1080

6-Dimethylamino-3-imino-2-[2-(3-isopropyl-4-methoxy-5-morpholino-phenyl)-2-oxo-ethyl]-2,3-dihydro-1H-isoindole-5-carboxylic acid methylamide hydrobromide 1H-NMR(DMSO-d6) δ: 1.20(6H, d, J=6.4 Hz), 2.77(3H, d, J=4.4 Hz), 2.91(6H, s), 2.90–3.10(5H, m), 3.68–3.92(4H, m), 3.87(3H, s), 4.74(2H, s), 5.45(2H, s), 7.15(2H, s), 7.39(1H, s), 7.58(1H, s), 8.07(1H, s), 8.37(1H, q, J=4.4 Hz), 8.95(1H, brs), 9.54(1H, brs).

Example 1081

6-{2-[3-tert-Butyl-5-((3R,4R)-3,4-dihydro-pyrrolidin-1-yl)-4-methoxy-phenyl]-2-oxo-ethyl}-3-ethoxy-7-imino-6,7-dihydro-5H-pyrrolo[3,4-b]pyridine-2-carboxylic acid methylamide trifluoroacetate 1H-NMR(DMSO-d6) δ: 1.36(3H, t, J=6.8 Hz), 1.37(9H, s), 2.77(3H, d, J=4.8 Hz), 2.87–2.98(2H, m), 3.50–3.59(2H, m), 3.61(3H, s), 4.33–4.43(2H, m), 4.24(2H, q, J=6.8 Hz), 4.87(2H, s), 5.40–5.62(2H, m), 7.29(1H, s), 7.38(1H, s), 7.99(1H, s), 8.45–8.62(1H, m), 9.37(1H, brs), 9.94(1H, brs).

Example 1082

2-tert-Butyl-4-[2-(5,6-diethoxy-7-fluoro-1-imino-1,3-dihydro-isoindol-2-yl)-acetyl]-6-ethoxy-phenoxymethyl 2,2-dimethylpropionate hydrobromide 1H-NMR(DMSO-d6) δ: 1.14(9H, S), 1.29(3H, t, J=7.0 Hz), 1.36(9H, S), 1.38–1.42(6H, m), 4.08–4.24(6H, m), 4.79(2H, s), 5.47(2H, s), 5.88(2H, s), 7.33(1H, s), 7.52(1H, s), 7.54(1H, s).
MS: m/e (ESI) 587.4 (MH+)

Example 1083

2-tert-Butyl-6-ethoxy-4-[2-(5-ethoxy-1-imino-6-methylcarbamoyl-1,3-dihydro-isoindol-2-yl)-acetyl]-phenoxymethyl 2,2-dimethylpropionate hydrobromide 1H-NMR(DMSO-d6) δ: 1.15(9H, S), 1.36(9H, S), 1.39–1.43(6H, m), 2.82(3H, d, J=4.4 Hz), 4.14(2H, q, J=7.0 Hz), 4.28(2H, q, J=7.0 Hz), 4.83(2H, s), 5.47(2H, s), 5.88 (2H, s), 7.53(1H, s), 7.54(1H, s), 7.55(1H, s), 8.20(1H, q, J=4.4 Hz), 8.54(1H, s).
MS: m/e (ESI) 582.4 (MH+)

Example 1084

(4-{3-tert-Butyl-5-[2-(5,6-diethoxy-7-fluoro-1-imino-1,3-dihydro-isoindol-2-yl)-acetyl]-2-methoxy-phenyl}-piperazin-1-yl)-acetonitrile hydrobromide 1H-NMR(DMSO-d6) δ: 1.29(3H, t, J=7.0 Hz), 1.37(9H, s), 1.40(3H, t, J=7.0 Hz), 2.71(4H, brs), 3.06(4H, brs), 3.83(2H, s), 3.94(3H, s), 4.11(2H, q, J=7.0 Hz), 4.21(2H, q, J=7.0 Hz), 4.79(2H, s), 5.48(2H, s), 7.34(1H, s), 7.50(1H, d, J=2.0 Hz), 7.59(1H, d, J=2.0 Hz), 9.05(1Hbrs), 9.27(1H, brs).
MS: m/e (ESI) 566.3 (MH+)

Example 1085

2-{2-[3-tert-Butyl-5-(4-cyanomethylpiperazin-1-yl)-4-methoxy-phenyl]-2-oxo-ethyl}-6-ethoxy-3-imino-2,3-dihydro-1H-isoindole-5-carboxylic acid methylamide dihydrochloride 1H-NMR(DMSO-d6) δ: 1.37(9H, s), 1.41(3H, t, J=7.0 Hz), 2.71(4H, brs), 2.82(3H, d, J=4.8 Hz), 3.05(4H, brs), 3.82(2H, s), 3.94(3H, s), 4.27(2H, q, J=7.0 Hz), 4.82(2H, s), 5.46(2H, s), 7.51(1H, s), 7.53(1H, s), 7.60(1H, s), 8.20(1H, q, J=4.8 Hz), 8.54(1H, s).
MS: m/e (ESI) 561.4 (MH+)

Example 1086

{3-tert-Butyl-5-[2-(5,6-diethoxy-7-fluoro-1-imino-1,3-dihydro-isoindol-2-yl)-acetyl]-2-methoxy-phenylamino}-acetic acid hydrochloride 1H-NMR(DMSO-d6) δ: 1.29(3H, t, J=7.0 Hz), 1.38(9H, s), 1.40(3H, t, J=7.0 Hz), 3.76(3H, s), 3.92(2H, s), 4.11(2H, q, J=7.0 Hz), 4.21(2H, q, J=7.0 Hz), 4.78(2H, s), 5.43(2H, s), 6.99(1H, s), 7.25(1H, s), 7.33(1H, s), 9.01(1Hbrs), 9.30 (1H, brs).
MS: m/e (ESI) 516.3 (MH+)

Example 1087

2-(2-{3-tert-Butyl-5-[(2-hydroxyethyl)-methylamino]-4-methoxy-phenyl}-2-oxo-ethyl)-6-dimethylamino-3-imino-2,3-dihydro-1H-isoindole-5-carboxylic acid methylamide dihydrochloride 1H-NMR(DMSO-d6) δ: 1.36(9H, s), 2.75(3H, d, J=4.0 Hz), 2.81(3H, s), 2.91(6H, s), 3.17(2H, t, J=5.6 Hz), 3.52 (2H, t, J=5.4 Hz), 4.73(2H, s), 5.52(2H, s), 7.15(1H, s), 7.53(1H, s), 8.10(1H, s), 8.38(1H, q, J=4.0 Hz), 9.17(1H, brs), 9.65(1H, brs).

Example 1088

2-(2-{3-tert-Butyl-5-[(3-hydroxypropyl)-methylamino]-4-methoxy-phenyl}-2-oxo-ethyl)-6-ethoxy-3-imino-2,3-dihydro-1H-isoindole-5-carboxylic acid methylamide dihydrochloride 1H-NMR(DMSO-d6) δ: 1.35(9H, s), 1.39(3H, t, J=6.8 Hz), 1.60(2H, t, J=6.4 Hz), 2.73(3H, s), 2.81(3H, d, J=4.8 Hz), 3.13(2H, t, J=6.4 Hz), 3.37(2H, t, J=6.4 Hz), 3.81(3H, s), 4.26(2H, q, J=6.8 Hz), 4.83(2H, s), 5.49(2H, s), 7.50(2H, s), 7.53(1H, s), 8.22(1H, q, J=4.8 Hz), 8.52(1H, s), 9.25(1H, brs), 9.89(1H, brs).

Example 1089

1-{3-tert-Butyl-5-[(3-hydroxypropyl)-methylamino]-4-methoxy-phenyl}-2-(5,6-diethoxy-7-fluoro-1-imino-1,3-dihydro-isoindol-2-yl)-ethanone dihydrochloride 1H-NMR(DMSO-d6) δ: 1.28(3H, t, J=6.8 Hz), 1.36(9H, s), 1.39(3H, t, J=6.8 Hz), 1.61(2H, t, J=6.4 Hz), 2.75(3H, s), 3.14(2H, t, J=6.4 Hz), 3.38(2H, t, J=6.4 Hz), 3.82(3H, s), 4.11(2H, q, J=6.8 Hz), 4.20(2H, q, J=6.8 Hz), 4.79(2H, s), 5.55(2H, s), 7.33(1H, s), 7.51(1H, s), 7.54(1H, s), 9.08(1H, brs), 9.45(1H, brs).

Example 1090

2-{2-[3-tert-Butyl-5-(3-hydroxypropylamino)-4-methoxy-phenyl]-2-oxo-ethyl}-6-ethoxy-3-imino-2,3-dihydro-1H-isoindole-5-carboxylic acid methylamide dihydrochloride 1H-NMR(DMSO-d6) δ: 1.36(9H, s), 1.41(3H, t, J=6.8 Hz), 1.77(2H, t, J=6.0 Hz), 2.81(3H, d, J=4.4 Hz), 3.19(2H, t, J=6.4 Hz), 3.40–3.66(2H, m), 3.73(3H, s), 4.26(2H, q, J=6.8 Hz), 4.83(2H, s), 5.53(2H, s), 7.13(1H, s), 7.23(1H, s), 7.52(1H, s), 8.20(1H, q, J=4.4 Hz), 8.56(1H, s), 9.36(1H, brs), 9.91(1H, brs).

Example 1091

1-[3-tert-Butyl-5-(3-hydroxypropylamino)-4-methoxy-phenyl]-2-(5,6-diethoxy-7-fluoro-1-imino-1,3-dihydro-isoindol-2-yl)-ethanone dihydrochloride 1H-NMR(DMSO-d6) δ: 1.29(3H, t, J=6.8 Hz), 1.36(9H, s), 1.39(3H, t, J=6.8 Hz), 1.77(2H, t, J=6.4 Hz), 3.07–3.24 (2H, m), 3.45–3.60(2H, m), 3.73(3H, s), 4.11(2H, q, J=6.8 Hz), 4.22(2H, q, J=6.8 Hz), 4.60(1H, t, J=4.0 Hz), 4.78(2H, s), 5.37(1H, t, J=4.0 Hz), 5.47(2H, s), 7.10(1H, s), 7.22(1H, s), 7.33(1H, s), 9.03(1H, brs), 9.32(1H, brs).

Example 1092

2-{2-[3-tert-Butyl-5-(2-methanesulfonylamino-ethylamino)-4-methoxy-phenyl]-2-oxo-ethyl}-6-ethoxy-3-imino-2,3-dihydro-1H-isoindole-5-carboxylic acid methylamide hydrochloride 1H-NMR(DMSO-d6) δ: 1.35–1.42(12H, m), 2.81(3H, d, J=5 Hz), 2.91(3H, s), 3.15–3.30(4H, m), 3.73(3H, s), 4.27 (2H, q, J=7 Hz), 4.84(2H, s), 5.53(2H, s), 7.18(1H, brs), 7.26(1H, brs), 7.53(1H, s), 8.20(1H, q, J=5 Hz), 8.56(1H, s), 9.36(1H, brs), 9.91(1H, brs).

Example 1093

N-(2-{3-tert-Butyl-5-[2-(5,6-diethoxy-7-fluoro-1-imino-1,3-dihydro-isoindol-2-yl)-acetyl]-2-methoxy-phenylamino}-ethyl)-methanesulfonamide hydrochloride 1H-NMR(DMSO-d6) δ: 1.29(3H, t, J=7 Hz), 1.35–1.42 (12H, m), 2.91(3H, s), 3.15–3.30(4H, m), 3.73(3H, s), 4.11(2H, q, J=7 Hz), 4.21(2H, q, J=7 Hz), 4.79(2H, s), 5.50(2H, s), 7.17(1H, brs), 7.25(1H, brs), 7.27–7.35(2H, m), 9.07(1H, brs), 9.41(1H, brs).

Example 1094

{3-tert-Butyl-5-[2-(5-ethoxy-1-imino-6-methylcarbamoyl-1,3-dihydro-isoindol-2-yl)-acetyl]-2-methoxy-phenylamino}-acetic acid dihydrochloride 1H-NMR(DMSO-d6) δ: 1.38(9H, s), 1.41(3H, t, J=7.0 Hz), 2.83(3H, d, J=4.6 Hz), 3.76(3H, s), 3.93(2H, s), 4.28 (2H, q, J=7.0 Hz), 4.83(2H, s), 5.45(2H, s), 7.00(1H, d, J=2.0 Hz), 7.27(1H, d, J=2.0 Hz), 7.53(1H, s), 8.21(1H, q, J=4.6 Hz), 8.55(1H, s), 9.21(1H, brd, J=5.2 Hz), 9.83(1H, brd, J=6.4 Hz).

MS: m/e (ESI) 511.3 (MH+)

Example 1095

2-{2-[3-tert-Butyl-4-methoxy-5-(2-methoxy-ethylamino)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.36(9H, s), 1.41(3H, t, J=7.2 Hz), 2.82(3H, d, J=4.0 Hz), 3.20–3.50(2H, m), 3.28(3H, s), 3.55(2H, t, J=6.0 Hz), 3.72(3H, s), 4.27(2H, q, J=7.2 Hz), 4.84(2H, s), 5.22(1H, t, J=6.0 Hz), 5.47(2H, s), 7.17(1H, s), 7.25(1H, s), 7.54(1H, s), 8.20(1H, q, J=4.0 Hz), 8.55(1H, s), 9.18(1H, brs), 9.82(1H, brs).

MS: m/e (ESI) 511.3 (MH+)

Example 1096

1-[3-tert-Butyl-4-methoxy-5-(2-methoxy-ethylamino)-phenyl]-2-(5,6-diethoxy-7-fluoro-1-imino-1,3-dihydro-isoindol-2-yl)-ethanone hydrobromide 1H-NMR(DMSO-d6) δ: 1.29(3H, t, J=7.2 Hz), 1.36(9H, s), 1.40(3H, t, J=7.2 Hz), 3.25–3.41(2H, m), 3.54(2H, d, J=5.6 Hz), 3.72(3H, s), 4.10(2H, q, J=7.2 Hz), 4.20(2H, q, J=7.2 Hz), 4.79(2H, s), 5.22(1H, t, J=4.0 Hz), 5.46(s,2H), 7.15(1H, s), 7.24(1H, s), 7.33(s,1H).

MS: m/e (ESI) 516.3 (MH+)

Example 1097

2-(2-{3-tert-Butyl-5-[(2-hydroxyethyl)-(2-methoxy-ethyl)-amino]-4-methoxy-phenyl}-2-oxo-ethyl)-6-ethoxy-3-imino-2,3-dihydro-1H-isoindole-5-carboxylic acid methylamide dihydrochloride 1H-NMR(DMSO-d6) δ: 1.36(9H, s), 1.41(3H, t, J=7.2 Hz), 2.81(3H, d, J=4.4 Hz), 3.15(3H, s), 3.28(2H, t, J=6.0 Hz), 3.26–3.64(6H, m), 3.82(3H, s), 4.27(2H, q, J=7.2 Hz), 4.84(2H, s), 5.54(2H, s), 7.51(1H, s), 7.52(1H, s), 7.60(1H, s), 8.21(1H, q, J=4.4 Hz), 8.56(1H, s), 9.36(1H, s), 9.92(1H, s).

Example 1098

1-{3-tert-Butyl-5-[(2-hydroxyethyl)-(2-methoxy-ethyl)-amino]-4-methoxy-phenyl}-2-(5,6-diethoxy-7-fluoro-1-imino-1,3-dihydro-isoindol-2-yl)-ethanone dihydrochloride 1H-NMR(DMSO-d6) δ: 1.29(3H, t, J=7.2 Hz), 1.36(9H, s), 1.39(3H, t, J=7.2 Hz), 3.15(3H, s), 3.28(2H, t, J=6.0 Hz), 3.20–3.78(4H, m), 3.46(2H, t, J=6.0 Hz), 3.82(3H, s), 4.12 (2H, q, J=7.2 Hz), 4.21(2H, q, J=7.2 Hz), 4.79(2H, s), 5.51(2H, s), 7.33(1H, s), 7.51(1H, s), 7.58(1H, s), 9.06(1H, brs), 9.39(1H, brs).

Example 1099

1-[3-tert-Butyl-4-methoxy-5-(2-morpholino-2-oxo-ethoxy)-phenyl]-2-(5,6-diethoxy-7-fluoro-1-imino-1,3-dihydro-isoindol-2-yl)-ethanone hydrobromide 1H-NMR(DMSO-d6) δ: 1.29(3H, t, J=7.0 Hz), 1.38(9H, s), 1.40(3H, t, J=7.0 Hz), 3.44–3.62(8H, m), 3.97(3H, s), 4.11(2H, q, J=7.0 Hz), 4.21(2H, q, J=7.0 Hz), 4.78(2H, s), 5.02(2H, s), 5.45(2H, s), 7.33(1H, s), 7.44(1H, d, J=2.0 Hz), 7.53(1H, d, J=2.0 Hz).

MS: m/e (ESI) 586.3 (MH+)

Example 1100

2-{2-[3-tert-Butyl-4-methoxy-5-(2-morpholino-2-oxo-ethoxy)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.38(9H, s), 1.42(3H, t, J=7.0 Hz), 2.82(3H, d, J=4.6 Hz), 3.44–3.62(8H, m), 3.97(3H, s), 4.28(2H, q, J=7.0 Hz), 4.84(2H, s), 5.02(2H, s), 5.47(2H, s), 7.45(1H, s), 7.54(2H, s), 8.20(1H, q, J=4.6 Hz), 8.55(1H, s).

MS: m/e (ESI) 581.3 (MH+)

Example 1101

1-[3-tert-Butyl-5-((3R,4R)-3-hydroxy-4-methoxy-pyrrolidin-1-yl)-4-methoxy-phenyl]-2-(5,6-diethoxy-7-fluoro-1-imino-1,3-dihydro-isoindol-2-yl)-ethanone trifluoroacetate 1H-NMR(DMSO-d6) δ: 1.29(3H, t, J=7.2 Hz), 1.37(9H, s), 1.39(3H, t, J=7.2 Hz), 2.91–2.99(1H, m), 3.03–3.12(1H, m), 3.30(3H, s), 3.40–3.58(2H, m), 3.63(3H, s), 3.71–3.79 (1H, m), 4.10(2H, q, J=7.2 Hz), 4.10–4.30(3H, m), 4.78(2H, s), 5.25(1H, brs), 5.38–5.60(2H, m), 7.30(1H, s), 7.33(1H, s), 7.41(1H, s), 8.99–9.12(1H, m), 9.20–9.40(1H, m).

MS: m/e (ESI) 558.3 (MH+)

Example 1102

2-[2-(3-tert-Butyl-5-cyclopropylamino-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 0.48–0.58(2H, m), 0.72(2H, m), 1.37(9H, s), 1.41(3H, t, J=7.2 Hz), 2.34–2.38(1H, m), 2.82

(3H, d, J=4.4 Hz), 3.66(3H, s), 4.28(2H, q, J=7.2 Hz), 4.85(2H, s), 5.48(2H, s), 5.83(1H, s), 7.28(1H, d, J=2.0 Hz), 7.47(1H, d, J=2.0 Hz), 7.54(1H, s), 8.20(1H, d, J=4.4 Hz), 8.55(1H, s), 9.18(1H, brs), 9.83(1H, brs).

MS: m/e (ESI) 493.3 (MH+)

Example 1103

1-(3-tert-Butyl-5-cyclopropylamino-4-methoxy-phenyl)-2-(5,6-diethoxy-7-fluoro-1-imino-1,3-dihydro-isoindol-2-yl)-ethanone hydrobromide 1H-NMR(DMSO-d6) δ: 0.47–0.54(2H, m), 0.72–0.80 (2H, m), 1.29(3H, t, J=7.2 Hz), 1.36(9H, s), 1.40(3H, t, J=7.2 Hz), 2.32–2.38(1H, m), 3.66(3H, s), 4.11(2H, q, J=7.2 Hz), 4.21(2H, q, J=7.2 Hz), 4.79(2H, s), 5.46(2H, s), 5.82 (1H, s), 7.27(1H, s), 7.33(1H, s), 7.46(1H, s).

MS: m/e (ESI) 498.3 (MH+)

Example 1104

2-[2-(3-tert-Butyl-5-cyclopentylamino-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.36(9H, s), 1.42(3H, t, J=7.2 Hz), 1.40–1.65(6H, m), 1.86–2.02(2H, m), 2.82(3H, d, J=4.8 Hz), 3.71(3H, s), 3.62–3.82(1H, s), 4.27(2H, q, J=7.2 Hz), 4.84(2H, s), 5.05(1H, d, J=6.4 Hz), 5.47(2H, s), 7.14(1H, d, J=2.0 Hz), 7.23(1H, d, J=2.0 Hz), 7.54(1H, s), 8.21(1H, d, J=4.8 Hz), 8.55(1H, s), 9.17(1H, brs), 9.82(1H, brs).

MS: m/e (ESI) 521.3 (MH+)

Example 1105

1-(3-tert-Butyl-5-cyclopentylamino-4-methoxy-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=7.2 Hz), 1.36(9H, s), 1.40(3H, t, J=7.2 Hz), 1.48–1.76(6H, m), 1.90–2.02(2H, m), 3.71(3H, s), 3.72–3.84(1H, m), 4.11(2H, q, J=7.2 Hz), 4.21(2H, q, J=7.2 Hz), 4.78(2H, s), 5.04(1H, d, J=6.4 Hz), 5.45(2H, s), 7.13(1H, d, J=2.0 Hz), 7.22(1H, d, J=2.0 Hz), 7.32(1H, s).

Example 1106

1-(3-Amino-5-tert-butyl-4-methoxy-phenyl)-2-(5,6-diethoxy-7-fluoro-1-imino-1,3-dihydro-isoindol-2-yl)-ethanone hydrobromide 1H-NMR(DMSO-d6) δ: 1.38(3H, t, J=7.2 Hz), 1.43(9H, s), 1.50(3H, t, J=7.2 Hz), 3.85(3H, s), 4.17(2H, q, J=7.2 Hz), 4.24(2H, q, J=7.2 Hz), 4.82(2H, s), 5.39(2H, s), 7.19(1H, s), 7.44(1H, d, J=2.0 Hz), 7.48(1H, d, J=2.0 Hz).

MS: m/e (ESI) 458.2 (MH+)

Example 1107

1-(3-tert-Butyl-4-methoxy-5-nitro-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=7.6 Hz), 1.40(12H, s and t, J=7.6 Hz), 3.84(3H, s), 4.11(2H, q, J=7.6 Hz), 4.21(2H, q, J=7.6 Hz), 4.81(2H, s), 5.49(2H, s), 7.32(1H, s), 8.07(1H, d, J=2.0 Hz), 8.39(1H, d, J=2.0 Hz).

MS: m/e (ESI) 488.2 (MH+)

Example 1108

2-[2-(3-tert-Butyl-5-isopropylamino-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.19(6H, d, J=6.0 Hz), 1.36(9H, s), 1.41(3H, t, J=7.2 Hz), 2.82(3H, d, J=4.4 Hz), 3.60–3.78 (1H, m), 3.71(3H, s), 4.28(2H, q, J=7.2 Hz), 4.83(2H, s), 4.90(1H, d, J=6.0 Hz), 5.46(2H, s), 7.14(1H, s), 7.22(1H, s), 7.53(1H, s), 8.20(1H, d, J=4.4 Hz), 8.55(1H, s).

Example 1109

1-(3-tert-Butyl-5-isopropylamino-4-methoxy-phenyl)-2-(5,6-diethoxy-7-fluoro-1-imino-1,3-dihydro-isoindol-2-yl)-ethanone hydrobromide 1H-NMR(DMSO-d6) δ: 1.19(6H, d, J=6.4 Hz), 1.29(3H, t, J=7.2 Hz), 1.36(9H, s), 1.40(3H, t, J=7.2 Hz), 3.60–3.76 (1H, m), 3.71(3H, s), 4.11(2H, q, J=7.2 Hz), 4.21(2H, q, J=7.2 Hz), 4.78(2H, s), 4.89(1H, d, J=8.4 Hz), 5.45(2H, s), 7.13(1H, s), 7.20(1H, s), 7.33(1H, s).

Example 1110

2-[2-(3-tert-Butyl-5-cyclobutylamino-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 1.36(9H, s), 1.40(3H, t, J=7.2 Hz), 1.64–1.80(2H, m), 1.87–2.02(2H, m), 2.28–2.40(2H, m), 2.82(3H, d, J=6.4 Hz), 3.73(3H, s), 3.84–3.98(1H, m), 4.28(2H, q, J=7.2 Hz), 4.84(2H, s), 5.46(2H, s), 5.50(1H, d, J=6.0 Hz), 7.03(1H, s), 7.24(1H, s), 7.54(1H, s), 8.20(1H, d, J=6.4 Hz), 8.55(1H, s), 9.16(1H, brs), 9.81(1H, brs).

Example 1111

1-(3-tert-Butyl-5-cyclobutylamino-4-methoxy-phenyl)-2-(5,6-diethoxy-7-fluoro-1-imino-1,3-dihydro-isoindol-2-yl)-ethanone hydrobromide 1H-NMR(DMSO-d6) δ: 1.29(3H, t, J=7.2 Hz), 1.36(9H, s), 1.40(3H, t, J=7.2 Hz), 1.60–1.78(2H, m), 1.86–2.02(2H, m), 2.37–2.40(2H, m), 3.73(3H, s), 3.86–3.97(1H, m), 4.11 (2H, q, J=7.2 Hz), 4.21(2H, q, J=7.2 Hz), 4.78(2H, s), 5.45(2H, s), 5.49(1H, s, J=6.0 Hz), 7.02(1H, s), 7.23(1H, s), 7.33(1H, s).

Example 1112

1-[3-(4-Acetyl-piperazin-1-yl)-5-tert-butyl-4-methoxy-phenyl]-2-(5,6-diethoxy-7-fluoro-1-imino-1,3-dihydro-isoindol-2-yl)-ethanone hydrobromide 1H-NMR(DMSO-d6) δ: 1.29(3H, t, J=7.0 Hz), 1.37(9H, s), 1.40(3H, t, J=7.0 Hz), 2.04(3H, s), 2.93(2H, brs), 2.99 (2H, brs), 3.65(4H, brs), 3.96(3H, s), 4.11(2H, q, J=7.0 Hz), 4.21(2H, q, J=7.0 Hz), 4.79(2H, s), 5.47(2H, s), 7.34(1H, s), 7.49(1H, sz), 7.61(1H, s), 9.05(1Hbrs), 9.27(1H, brs).
MS: m/e (ESI) 569.4 (MH+)

Example 1113

2-tert-Butyl-4-[2-(5,6-diethoxy-7-fluoro-1-imino-1,3-dihydro-isoindol-2-yl)-acetyl]-6-ethoxy-phenyl isopropylcarbamate hydrobromide 1H-NMR(DMSO-d6) δ: 1.13(6H, d, J=6.4 Hz), 1.27–1.34 (15H, m), 1.40(3H, t, J=7.0 Hz), 3.61–3.70(1H, m), 4.07 (2H, q, J=7.0 Hz), 4.12(2H, q, J=7.0 Hz), 4.21(2H, q, J=7.0 Hz), 4.81(2H, s), 5.50(2H, s), 7.34(1H, s), 7.50(1H, d, J=2.0 Hz), 7.55(1H, d, J=2.0 Hz), 7.78(1H, d, J=8.0 Hz), 9.07(1H, brd, J=6.8 Hz), 9.33(1H, brs).
MS: m/e (ESI) 558.3 (MH+)

Example 1114

2-{2-[3-(4-Acetyl-piperazin-1-yl)-5-tert-butyl-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.38(9H, s), 1.42(3H, t, J=7.0 Hz), 2.04(3H, s), 2.83(3H, d, J=4.8 Hz), 2.93(2H, brs), 3.00(2H, brs), 3.65(4H, brs), 3.97(3H, s), 4.28(2H, q, J=7.0 Hz), 4.84(2H, s), 5.48(2H, s), 7.51(1H, d, J=2.0 Hz), 7.54 (1H, s), 7.62(1H, d, J=2.0 Hz), 8.21(1H, q, J=4.8 Hz), 8.56(1H, s).
MS: m/e (ESI) 564.3 (MH+)

Example 1115

2-tert-Butyl-6-ethoxy-4-[2-(5-ethoxy-1-imino-6-methylcarbamoyl-1,3-dihydro-isoindol-2-yl)-acetyl]-phenyl isopropyl-carbamate hydrobromide 1H-NMR(DMSO-d6) δ: 1.13(6H, d, J=6.4 Hz), 1.31(3H, t, J=7.0 Hz), 1.34(9H, s), 1.42(3H, t, J=7.0 Hz), 2.83(3H, d, J=4.6 Hz), 3.61–3.68(1H, m), 4.07(2H, q, J=7.0 Hz), 4.28 (2H, q, J=7.0 Hz), 4.86(2H, s), 5.51(2H, s), 7.51(1H, d, J=2.0 Hz), 7.55(1H, s), 7.57(1H, d, J=2.0 Hz), 7.78(1H, d, J=8.0 Hz), 8.21(1H, q, J=4.6 Hz), 8.56(1H, s), 9.21(1H, brs), 9.86(1H, brs).
MS: m/e (ESI) 553.3 (MH+)

Example 1116

1-[3-tert-Butyl-5-((3S,4S)-3-hydroxy-4-methoxy-pyrrolidin-1-yl)-4-methoxy-phenyl]-2-(5,6-diethoxy-7-fluoro-1-imino-1,3-dihydro-isoindol-2-yl)-ethanone trifluoroacetate 1H-NMR(DMSO-d6) δ: 1.29(3H, t, J=7.2 Hz), 1.37(9H, s), 1.39(3H, t, J=7.2 Hz), 2.91–2.99(1H, m), 3.03–3.12(1H, m), 3.30(3H, s), 3.40–3.58(2H, m), 3.63(3H, s), 3.71–3.79 (1H, m), 4.10(2H, q, J=7.2 Hz), 4.10–4.30(3H, m), 4.78(2H, s), 5.38–5.60(2H, m), 7.30(1H, s), 7.33(1H, s), 7.41(1H, s), 8.99–9.12(1H, m), 9.20–9.40(1H, m).
MS: m/e (ESI) 558.3 (MH+)

Example 1117

2-tert-Butyl-4-[2-(5,6-diethoxy-7-fluoro-1-imino-1,3-dihydro-isoindol-2-yl)-acetyl]-6-ethoxy-phenyl dimethylcarbamate hydrobromide 1H-NMR(DMSO-d6) δ: 1.29(6H, t, J=7.0 Hz), 1.34(9H, s), 1.40(3H, t, J=7.0 Hz), 2.92(3H, s), 3.09(3H, s), 4.08–4.24 (6H, m), 4.80(2H, s), 5.50(2H, s), 7.34(1H, s), 7.51(1H, d, J=2.0 Hz), 7.56(1H, d, J=2.0 Hz), 9.02(1H, brs), 9.33(1H, brs).
MS: m/e (ESI) 544.3 (MH+)

Example 1118

1-[3-tert-Butyl-4-methoxy-5-(2-morpholino-2-oxo-ethylamino)-phenyl]-2-(5,6-diethoxy-7-fluoro-1-imino-1,3-dihydro-isoindol-2-yl)-ethanone hydrobromide 1H-NMR(DMSO-d6) δ: 1.29(3H, t, J=7.0 Hz), 1.38(9H, s), 1.40(3H, t, J=7.0 Hz), 3.47–3.63(8H, m), 3.77(3H, s), 4.02(2H, s), 4.11(2H, q, J=7.0 Hz), 4.21(2H, q, J=7.0 Hz), 4.79(2H, s), 5.44(2H, s), 7.13(1H, d, J=2.0 Hz), 7.27(1H, d, J=2.0 Hz), 7.34(1H, s), 9.13(1H, brs), 9.31(1H, brs).
MS: m/e (ESI) 585.3 (MH+)

Example 1119

2-tert-Butyl-6-ethoxy-4-[2-(5-ethoxy-1-imino-6-methylcarbamoyl-1,3-dihydro-isoindol-2-yl)-acetyl]-phenyl dimethylcarbamate hydrobromide 1H-NMR(DMSO-d6) δ: 1.29(3H, t, J=7.0 Hz), 1.34(9H, s), 1.42(3H, t, J=7.0 Hz), 2.83(3H, d, J=5.0 Hz), 2.93(3H, s), 3.10(3H, s), 3.94–4.02(1H, m), 4.12–4.20(1H, m), 4.28(2H, q, J=7.0 Hz), 4.86(2H, s), 5.53(2H, s), 7.52(1H, d, J=2.0 Hz), 7.55(1H, s), 7.58(1H, d, J=2.0 Hz), 8.21(1H, q, J=5.0 Hz), 8.56(1H, s), 9.22(1H, brs), 9.86(1H, brs).
MS: m/e (ESI) 539.3 (MH+)

Example 1120

2-{2-[3-tert-Butyl-4-methoxy-5-(2-methoxy-1-methyl-ethylamino)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.17(3H, d, J=6.4 Hz), 1.41(3H, t, J=7.2 Hz), 2.82(3H, d, J=4.2 Hz), 3.27(3H, s), 3.37–3.48 (2H, m), 3.71(3H, s), 3.71–3.85(1H, m), 4.27(2H, q, J=7.2 Hz), 4.84(2H, s), 4.90(1H, d, J=6.0 Hz), 5.46(2H, s), 7.18 (1H, s), 7.23(1H, s), 7.53(1H, s), 8.20(1H, s, J=4.2 Hz), 8.55(1H, s), 9.16(1H, brs), 9.81(1H, s).
MS: m/e (ESI) 525.3 (MH+)

Example 1121

1-[3-tert-Butyl-4-methoxy-5-(2-methoxy-1-methyl-ethylamino)-phenyl]-2-(5,6-diethoxy-7-fluoro-1-imino-1,3-dihydro-isoindol-2-yl)-ethanone hydrobromide 1H-NMR(DMSO-d6) δ: 1.17(3H, d, J=6.4 Hz), 1.29(3H, t, J=7.2 Hz), 1.36(9H, s), 1.40(3H, t, J=7.2 Hz), 3.28(3H, s), 3.37–3.48(2H, m), 3.71(3H, s), 3.62–3.79(1H, m), 4.11(2H, q, J=7.2 Hz), 4.21(2H, q, J=7.2 Hz), 4.79(2H, s), 4.90(1H, d, J=6.0 Hz), 5.46(2H, s), 7.17(1H, d, J=2.0 Hz), 7.22(1H, d, J=2.0 Hz), 7.33(1H, s), 9.03(1H, brs), 9.28(1H, brs).

Example 1122

2-{2-[3-tert-Butyl-4-methoxy-5-(tetrahydropyran-4-ylamino)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.37(9H, s), 1.41(3H, t, J=7.2 Hz), 1.57–1.72(2H, m), 2.08–2.21(2H, m), 2.55–2.90(5H, m), 3.72(3H, s), 4.29(2H, q, J=7.2 Hz), 4.84(2H, s), 5.11(1H, d, J=6.0 Hz), 5.46(2H, s), 7.14(1H, d, J=2.0 Hz), 7.22(1H, d, J=2.0 Hz), 7.53(1H, s), 8.20(1H, q, J=4.2 Hz), 8.55(1H, s), 9.16(1H, s), 9.82(1H, s).
MS: m/e (ESI) 553.3 (MH+)

Example 1123

1-[3-tert-Butyl-4-methoxy-5-(tetrahydropyran-4-ylamino)-phenyl]-2-(5,6-diethoxy-7-fluoro-1-imino-1,3-dihydro-isoindol-2-yl)-ethanone hydrobromide 1H-NMR(DMSO-d6) δ: 1.29(3H, t, J=7.2 Hz), 1.36(9h, s), 1.40(3H, t, J=7.2 Hz), 1.58–1.77(2H, m), 2.08–2.20(2H, m), 2.50–2.81(5H, m), 3.72(s,3H), 4.11(2H, q, J=7.2 Hz), 4.21(2H, q, J=7.2 Hz), 4.78(2H, s), 5.10(1H, d, J=6.0 Hz), 5.43(2H, s), 7.13(1H, s), 7.21(1H, s), 7.33(1H, s).
MS: m/e (ESI) 558.3 (MH+)

Example 1124

1-(3-tert-Butyl-5-isobutylamino-4-methoxy-phenyl)-2-(5,6-diethoxy-7-fluoro-1-imino-1,3-dihydro-isoindol-2-yl)-ethanone hydrobromide 1H-NMR(DMSO-d6) δ: 0.94(6H, d, J=6.8 Hz), 1.29(3H, t, J=7.0 Hz), 1.37(9H, s), 1.40(3H, t, J=7.0 Hz), 1.93–2.00 (1H, m), 2.90–2.93(2H, m), 3.75(3H, s), 4.11(2H, q, J=7.0 Hz), 4.21(2H, q, J=7.0 Hz), 4.79(2H, s), 5.38(1H, brs), 5.48(2H, s), 7.06(1H, s), 7.20(1H, s), 7.33(1H, s), 9.05(1H, brs), 9.29(1H, brs).
MS: m/e (ESI) 514.3 (MH+)

Example 1125

2-[2-(3-tert-Butyl-5-isobutylamino-4-methoxy-phenyl)-2-oxo-ethyl]-6-ethoxy-3-imino-2,3-dihydro-1H-isoindole-5-carboxylic acid methylamide hydrobromide 1H-NMR(DMSO-d6) δ: 0.94(6H, d, J=6.8 Hz), 1.37(9H, s), 1.42(3H, t, J=7.0 Hz), 1.93–2.00(1H, m), 2.82(3H, d, J=4.8 Hz), 2.91–2.93(2H, m), 3.75(3H, s), 4.28(2H, q, J=7.0 Hz), 4.84(2H, s), 5.38(1H, t, J=6.0 Hz), 5.46(2H, s), 7.07 (1H, d, J=2.0 Hz), 7.22(1H, d, J=2.0 Hz), 7.54(1H, s), 8.21(1H, q, J=4.8 Hz), 8.56(1H, s), 9.15(1H, d, J=5.8 Hz), 9.82(1H, d, J=5.8 Hz).
MS: m/e (ESI) 509.3 (MH+)

Example 1126

2-[2-(3-tert-Butyl-5-isobutylamino-4-methoxy-phenyl)-2-oxo-ethyl]-6-dimethylamino-3-imino-2,3-dihydro-1H-isoindole-5-carboxylic acid methylamide hydrobromide 1H-NMR(DMSO-d6) δ: 0.94(6H, d, J=6.8 Hz), 1.37(9H, s), 1.93–2.00(1H, m), 2.78–2.87(3H, m), 2.92(8H, brs), 3.75(3H, s), 4.73(2H, s), 5.37(1H, t, J=5.6 Hz), 5.42(2H, s), 7.07(1H, s), 7.15(1H, s), 7.21(1H, s), 8.07(1H, s), 8.37(1H, q, J=4.6 Hz), 8.91(1H, brs), 9.51(1H, brs).
MS: m/e (ESI) 508.3 (MH+)

Example 1127

1-[3-tert-Butyl-5-((3S,4S)-3,4-dimethoxy-pyrrolidin-1-yl)-4-methoxy-phenyl]-2-(5,6-diethoxy-7-fluoro-1-imino-1,3-dihydro-isoindol-2-yl)-ethanone hydrobromide 1H-NMR(DMSO-d6) δ: 1.28(3H, t, J=7.2 Hz), 1.37(9H, s), 1.39(3H, t, J=7.2 Hz), 3.03–3.16(2H, m), 3.29(6H, s), 3.36–3.52(2H, m), 3.64(3H, s), 3.91(2H, brs), 4.11(2H, q, J=7.2 Hz), 4.21(2H, q, J=7.2 Hz), 4.78(2H, s), 5.36–5.62 (2H, m), 7.33(2H, s), 7.44(1H, s), 8.95–9.35(2H, m).
MS: m/e (ESI) 572.4 (MH+)

Example 1128

2-{2-[3-tert-Butyl-5-((3S,4S)-3,4-dimethoxy-pyrrolidin-1-yl)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.37(9H, s), 1.41(3H, t, J=6.8 Hz), 2.79–2.87(3H, m), 3.05–3.15(2H, m), 3.29(6H, s), 3.38–3.52(2H, m), 3.64(3H, s), 3.91(2H, brs), 4.27(2H, q, J=6.8 Hz), 4.84(2H, s), 5.40–5.62(2H, m), 7.34(1H, s), 7.46(1H, s), 7.54(1H, s), 8.13–8.30(1H, m), 8.55(1H, s), 9.05–9.22(1H, m), 9.77–9.92(1H, m).
MS: m/e (ESI) 567.3 (MH+)

Example 1129

2-{2-[3-tert-Butyl-5-(2-cyano-ethylamino)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.33–1.42(12H, m), 2.78–2.88 (5H, m), 3.45(2H, m), 3.75(3H, s), 4.27(2H, q, J=7 Hz), 4.84(2H, s), 5.47(2H, s), 5.74(1H, m), 7.16(1H, s), 7.28(1H, s), 7.53(1H, s), 8.20(1H, q, J=5 Hz), 8.55(1H, s), 9.15(1H, brs), 9.83(1H, brs).

Example 1130

3-{3-tert-Butyl-5-[2-(5,6-diethoxy-7-fluoro-1-imino-1,3-dihydro-isoindol-2-yl)-acetyl]-2-methoxy-phenylamino}-propionitrile hydrobromide 1H-NMR(DMSO-d6) δ: 1.29(3H, t, J=7 Hz), 1.33–1.42 (12H, m), 2.83(2H, t, J=6 Hz), 3.45(2H, m), 3.75(3H, s), 4.11(2H, q, J=7 Hz), 4.21(2H, q, J=7 Hz), 4.79(2H, s), 5.47(2H, s), 5.74(1H, m), 7.15(1H, brs), 7.27(1H, brs), 7.33(1H, brs), 9.04(1H, brs), 9.29(1H, brs).

Example 1131

2-[2-(3-tert-Butyl-4-methoxy-5-piperazin-1-yl-phenyl)-2-oxo-ethyl]-6-ethoxy-3-imino-2,3-dihydro-1H-isoindole-5-carboxylic acid methylamide dihydrochloride 1H-NMR(DMSO-d6) δ: 1.38(9H, s), 1.42(3H, t, J=7.0 Hz), 2.82(3H, d, J=4.8 Hz), 3.21(4H, brs), 3.34(2H, m), 3.41–3.48(1H, m), 3.63–3.70(1H, m), 3.94(3H, s), 4.28(2H, q, J=7.0 Hz), 4.84(2H, s), 5.57(2H, s), 7.51(1H, s), 7.54(1H, s), 7.65(1H, s), 8.21(1H, q, J=4.8 Hz), 8.56(1H, s), 9.12(1H, brs), 9.18(1H, brs), 9.32(1H, brs), 9.90(1H, brs).
MS: m/e (ESI) 522.3 (MH+)

Example 1132

1-[3-tert-Butyl-5-(4-isopropyl-piperazin-1-yl)-4-methoxy-phenyl]-2-(5,6-diethoxy-7-fluoro-1-imino-1,3-dihydro-isoindol-2-yl)-ethanone dihydrochloride 1H-NMR(DMSO-d6) δ: 1.22–1.38(21H, m), 3.02–3.58 (8H, m), 3.94(3H, s), 4.11(2H, q, J=7.0 Hz), 4.21(2H, q, J=7.0 Hz), 4.80(2H, s), 5.56(2H, s), 7.34(1H, s), 7.50(1H, s), 7.64(1H, s), 9.08(1Hbrs), 9.43(1H, brs).
MS: m/e (ESI) 569.4 (MH+)

Example 1133

4-{3-tert-Butyl-5-[2-(5,6-diethoxy-7-fluoro-1-imino-1,3-dihydro-isoindol-2-yl)-acetyl]-2-methoxy-phenyl}-piperazine-1-carboxylic acid dimethylamide hydrobromide 1H-NMR(DMSO-d6) δ: 1.29(3H, t, J=7.0 Hz), 1.37(9H, s), 1.40(3H, t, J=7.0 Hz), 2.77(6H, s), 2.99(4H, brs), 3.37 (4H, brs), 3.95(3H, s), 4.11(2H, q, J=7.0 Hz), 4.21(2H, q, J=7.0 Hz), 4.79(2H, s), 5.48(2H, s), 7.34(1H, s), 7.52(1H, s), 7.60(1H, s), 9.05(1Hbrs), 9.27(1H, brs).
MS: m/e (ESI) 598.3 (MH+)

Example 1134

2-{2-[3-tert-Butyl-5-(4-dimethylcarbamoyl-piperazin-1-yl)-4-methoxy-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.37(9H, s), 1.42(3H, t, J=7.0 Hz), 2.77(6H, s), 2.83(3H, d, J=5.2 Hz), 3.00(4H, brs), 3.31(4H, brs), 3.95(3H, s), 4.28(2H, q, J=7.0 Hz), 4.84(2H, s), 5.49(2H, s), 7.53(1H, s), 7.54(1H, s), 7.61(1H, s), 8.21 (1H, q, J=5.2 Hz), 8.56(1H, s).
MS: m/e (ESI) 593.4 (MH+)

Example 1135

(4-{3-tert-Butyl-5-[2-(5,6-diethoxy-7-fluoro-1-imino-1,3-dihydro-isoindol-2-yl)-acetyl]-2-methoxy-phenyl}-piperazin-1-yl)-acetic acid dihydrochloride 1H-NMR(DMSO-d6) δ: 1.29(3H, t, J=7.0 Hz), 1.38(9H, s), 1.40(3H, t, J=7.0 Hz), 3.10–3.69(10H, m), 3.93(3H, s), 4.12(2H, q, J=7.0 Hz), 4.21(2H, q, J=7.0 Hz), 4.22(2H, brs), 4.80(2H, s), 5.54(2H, s), 7.34(1H, s), 7.49(1H, s), 7.64(1H, s), 9.10(1H, brs), 9.40(1H, brs).
MS: m/e (ESI) 585.3 (MH+)

Example 1136

2-{2-[3-tert-Butyl-4-methoxy-5-(2-morpholino-ethylamino)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.33–1.42(12H, m), 2.40–2.60 (4H, m), 2.80–2.86(5H, m), 3.20–3.36(2H, m), 3.58(4H, m), 3.75(3H, s), 4.28(2H, q, J=7 Hz), 4.84(2H, s), 5.49(2H, s), 7.15(1H, brs), 7.25(1H, brs), 7.54(1H, s), 8.21(1H, m), 8.56(1H, s).

Example 1137

1-[3-tert-Butyl-4-methoxy-5-(2-morpholino-ethylamino)-phenyl]-2-(5,6-diethoxy-7-fluoro-1-imino-1,3-dihydro-isoindol-2-yl)-ethanone hydrobromide 1H-NMR(DMSO-d6) δ: 1.29(3H, t, J=7 Hz), 1.33–1.42 (12H, m), 2.40–2.60(4H, m), 3.20–3.40(4H, m), 3.58(4H, m), 3.74(3H, s), 4.11(2H, q, J=7 Hz), 4.21(2H, q, J=7 Hz), 4.79(2H, s), 5.48(2H, s), 7.14(1H, brs), 7.24(1H, brs), 7.34 (1H, brs).

Example 1138

1-{3-tert-Butyl-5-[4-(2-hydroxy-acetyl)-piperazin-1-yl]-4-methoxy-phenyl}-2-(5,6-diethoxy-7-fluoro-1-imino-1,3-dihydro-isoindol-2-yl)-ethanone hydrobromide 1H-NMR(DMSO-d6) δ: 1.29(3H, t, J=7.0 Hz), 1.37(9H, s), 1.40(3H, t, J=7.0 Hz), 2.98(4H, brs), 3.57(2H, brs), 3.70(2H, brs), 3.96(3H, s), 4.11(2H, q, J=7.0 Hz), 4.12(2H, s), 4.21(2H, q, J=7.0 Hz), 4.79(2H, s), 5.47(2H, s), 7.34(1H, s), 7.49(1H, d, J=2.0 Hz), 7.61(1H, d, J=2.0 Hz), 9.05(1H, brs), 9.27(1H, brs).
MS: m/e (ESI) 585.3 (MH+)

Example 1139

2-(2-{3-tert-Butyl-5-[4-(2-hydroxy-acetyl)-piperazin-1-yl]-4-methoxy-phenyl}-2-oxo-ethyl)-6-ethoxy-3-imino-2,3-dihydro-1H-isoindole-5-carboxylic acid methylamide hydrobromide 1H-NMR(DMSO-d6) δ: 1.37(9H, s), 1.41(3H, t, J=7.0 Hz), 2.82(3H, d, J=4.8 Hz), 2.98(4H, brs), 3.57(2H, brs), 3.69(2H, brs), 3.97(3H, s), 4.13(2H, d, J=5.6 Hz), 4.28(2H, q, J=7.0 Hz), 4.66(1H, t, J=5.6 Hz), 4.84(2H, s), 5.49(2H, s), 7.50(1H, d, J=2.0 Hz), 7.54(1H, s), 7.62(1H, d, J=2.0 Hz), 8.21(1H, q, J=4.8 Hz), 8.55(1H, s).
MS: m/e (ESI) 580.3 (MH+)

Example 1140

4-{3-tert-Butyl-5-[2-(5,6-diethoxy-7-fluoro-1-imino-1,3-dihydro-isoindol-2-yl)-acetyl]-2-methoxy-phenyl}-piperazine-1-carboxylic acid ethylamide hydrobromide 1H-NMR(DMSO-d6) δ: 1.01(3H, t, J=7.0 Hz), 1.30(3H, t, J=7.0 Hz), 1.37(9H, s), 1.40(3H, t, J=7.0 Hz), 2.93(4H, brs), 3.02–3.08(2H, m), 3.49(4H, brs), 3.95(3H, s), 4.12(2H, q, J=7.0 Hz), 4.22(2H, q, J=7.0 Hz), 4.79(2H, s), 5.48(2H, s), 7.34(1H, s), 7.50(1H, s), 7.60(1H, s).
MS: m/e (ESI) 598.3 (MH+)

Example 1141

2-(2-{3-tert-Butyl-5-(4-ethylcarbamoyl-piperazin-1-yl]-4-methoxy-phenyl}-2-oxo-ethyl)-6-ethoxy-3-imino-2,3-dihydro-1H-isoindole-5-carboxylic acid methylamide hydrobromide 1H-NMR(DMSO-d6) δ: 1.01(3H, t, J=7.0 Hz), 1.37(9H, s), 1.41(3H, t, J=7.0 Hz), 2.83(3H, d, J=4.6 Hz), 2.93(4H, brs), 3.05(2H, q, J=7.0 Hz), 3.49(4H, brs), 3.95(3H, s), 4.28(2H, q, J=7.0 Hz), 4.84(2H, s), 5.49(2H, s), 6.58(1H, m), 7.51(1H, s), 7.54(1H, s), 7.61(1H, s), 8.21(1H, q, J=4.6 Hz), 8.56(1H, s), 9.16(1H, brs), 9.85(1H, brs).
MS: m/e (ESI) 593.4 (MH+)

Example 1142

Ethyl (4-{3-tert-butyl-5-[2-(5,6-diethoxy-7-fluoro-1-imino-1,3-dihydro-isoindol-2-yl)-acetyl]-2-methoxy-phenyl}-piperazin-1-yl)-acetate dihydrochloride 1H-NMR(DMSO-d6) δ: 1.25(3H, t, J=7.0 Hz), 1.29(3H, t, J=7.0 Hz), 1.37(9H, s), 1.40(3H, t, J=7.0 Hz), 3.02–3.70 (10H, m), 3.93(3H, s), 4.11(2H, q, J=7.0 Hz), 4.18–4.25(4H, m), 4.28(1H, brs), 4.80(2H, s), 5.54(2H, s), 7.34(1H, s), 7.50(1H, s), 7.64(1H, s), 9.08(1H, brs), 9.37(1H, brs).
MS: m/e (ESI) 613.4 (MH+)

Example 1143

1-{3-tert-Butyl-4-methoxy-5-[4-(2-methoxy-acetyl)-piperazin-1-yl]-phenyl}-2-(5,6-diethoxy-7-fluoro-1-imino-1,3-dihydro-isoindol-2-yl)-ethanone hydrobromide 1H-NMR(DMSO-d6) δ: 1.29(3H, t, J=7.0 Hz), 1.37(9H, s), 1.40(3H, t, J=7.0 Hz), 2.98(4H, brs), 3.29(3H, s), 3.61 (2H, brs), 3.67(2H, brs), 3.96(3H, s), 4.11(2H, q, J=7.0 Hz), 4.12(2H, s), 4.21(2H, q, J=7.0 Hz), 4.79(2H, s), 5.47(2H, s), 7.34(1H, s), 7.50(1H, d, J=2.0 Hz), 7.61(1H, d, J=2.0 Hz), 9.03(1H, brs), 9.28(1H, brs).
MS: m/e (ESI) 599.4 (MH+)

Example 1144

2-{2-[3-tert-Butyl-5-(2-methanesulfonyl-ethylamino)-4-methoxy-phenyl]-2-oxo-ethyl}-6-ethoxy-3-imino-2,3-dihydro-1H-isoindole-5-carboxylic acid methylamide trifluoroacetate 1H-NMR(DMSO-d6) δ: 1.30–1.44(12H, m), 2.82(3H, d, J=5 Hz), 3.07(3H, s), 3.47(2H, m), 3.59(2H, m), 3.74(3H, s), 4.28(2H, q, J=7 Hz), 4.85(2H, s), 5.49(2H, s), 7.17(1H, d, J=2 Hz), 7.30(1H, d, J=2 Hz), 7.53(1H, s), 8.21(1H, q, J=5 Hz), 8.55(1H, s), 9.22(1H, brs), 9.86(1H, brs).

Example 1145

1-[3-tert-Butyl-5-(2-methanesulfonyl-ethylamino)-4-methoxy-phenyl]-2-(5,6-diethoxy-7-fluoro-1-imino-1,3-dihydro-isoindol-2-yl)-ethanone trifluoroacetate 1H-NMR(DMSO-d6) δ: 1.29(3H, t, J=7 Hz), 1.35–1.42 (12H, m), 3.07(3H, s), 3.45(2H, m), 3.58(2H, m), 3.73(3H, s), 4.11(2H, q, J=7 Hz), 4.21(2H, q, J=7 Hz), 4.79(2H, s), 5.47(2H, s), 7.16(1H, d, J=2 Hz), 7.29(1H, d, J=2 Hz), 7.33(1H, brs), 9.06(1H, brs), 9.31(1H, brs).

Example 1146

2-(2-{3-tert-Butyl-4-methoxy-5-[4-(2-methoxy-acetyl)-piperazin-1-yl]-phenyl}-2-oxo-ethyl)-6-ethoxy-3-imino-2,3-dihydro-1H-isoindole-5-carboxylic acid methylamide hydrobromide 1H-NMR(DMSO-d6) δ: 1.37(9H, s), 1.42(3H, t, J=7.0 Hz), 2.82(3H, d, J=4.4 Hz), 2.99(4H, brs), 3.29(3H, s), 3.61(2H, brs), 3.67(2H, brs), 3.97(3H, s), 4.12(2H, s), 4.27 (2H, q, J=7.0 Hz), 4.84(2H, s), 5.49(2H, s), 7.51(1H, d, J=2.0 Hz), 7.54(1H, s), 7.62(1H, d, J=2.0 Hz), 8.21(1H, q, J=4.4 Hz), 8.56(1H, s), 9.16(1H, brs), 9.85(1H, brs).
MS: m/e (ESI) 594.4 (MH+)

Example 1147

1-(4-{3-tert-Butyl-5-[2-(5,6-diethoxy-7-fluoro-1-imino-1,3-dihydro-isoindol-2-yl)-acetyl]-2-methoxy-phenyl}-piperazin-1-yl)-propan-1-one hydrobromide 1H-NMR(DMSO-d6) δ: 1.00(3H, t, J=7.0 Hz), 1.29(3H, t, J=7.0 Hz), 1.37(9H, s), 1.40(3H, t, J=7.0 Hz), 2.36(2H, q, J=7.0 Hz), 2.94(2H, brs), 2.98(2H, brs), 3.66(4H, brs), 3.96(3H, s), 4.11(2H, q, J=7.0 Hz), 4.21(2H, q, J=7.0 Hz), 4.79(2H, s), 5.47(2H, s), 7.34(1H, s), 7.50(1H, d, J=2.0 Hz), 7.61(1H, d, J=2.0 Hz), 9.06(1H, brs), 9.28(1H, brs).
MS: m/e (ESI) 583.4 (MH+)

Example 1148

2-{2-[3-tert-Butyl-4-methoxy-5-(4-propionyl-piperazin-1-yl)-phenyl]-2-oxo-ethyl}-6-ethoxy-3-imino-2,3-dihydro-1H-isoindole-5-carboxylic acid methylamide hydrobromide 1H-NMR(DMSO-d6) δ: 1.00(3H, t, J=7.0 Hz), 1.38(9H, s), 1.42(3H, t, J=7.0 Hz), 2.36(2H, q, J=7.0 Hz), 2.83(3H, d, J=4.8 Hz), 2.94(2H, brs), 2.99(2H, brs), 3.66(4H, brs), 3.97(3H, s), 4.28(2H, q, J=7.0 Hz), 4.84(2H, s), 5.48(2H, s), 7.51(1H, d, J=2.0 Hz), 7.54(1H, s), 7.62(1H, d, J=2.0 Hz), 8.21(1H, q, J=4.8 Hz), 8.56(1H, s), 9.15(1H, d, J=5.6 Hz), 9.84(1H, d, J=5.6 Hz).
MS: m/e (ESI) 578.4 (MH+)

Example 1149

1-[3-tert-Butyl-5-((3S,4S)-3-ethoxy-4-hydroxy-pyrrolidin-1-yl)-4-methoxy-phenyl]-2-(5,6-diethoxy-7-fluoro-1-imino-1,3-dihydro-isoindol-2-yl)-ethanone trifluoroacetate 1H-NMR(DMSO-d6) δ: 1.10(3H, t, J=6.8 Hz), 1.29(3H, t, J=6.8 Hz), 1.37(9H, s), 1.39(3H, t, J=6.8 Hz), 2.90–3.12 (2H, m), 3.28–3.58(4H, m), 3.63(3H, s), 3.80–3.89(1H, m), 4.11(2H, q, J=6.8 Hz), 4.12–4.31(3H, m), 4.79(2H, s), 5.38–5.57(2H, m), 7.30(1H, s), 7.34(1H, s), 7.41(1H, s), 8.98–9.10(1H, m), 9.20-9.35(1H, m).
MS: m/e (ESI) 572.4 (MH+)

Example 1150

2-{2-[3-tert-Butyl-5-((3S,4S)-3-ethoxy-4-hydroxy-pyrrolidin-1-yl)-4-methoxy-phenyl]-2-oxo-ethyl}-6-ethoxy-3-imino-2,3-dihydro-1H-isoindole-5-carboxylic acid methylamide trifluoroacetate 1H-NMR(DMSO-d6) δ: 1.10(3H, t, J=6.8 Hz), 1.37(9H, s), 1.41(3H, t, J=6.8 Hz), 2.83(3H, d, J=4.4 Hz), 2.82–3.12

(2H, m), 3.34–3.60(4H, m), 3.64(3H, s), 3.79–3.92(1H, m), 4.10–4.22(1H, m), 4.28(2H, q, J=6.8 Hz), 4.84(2H, s), 5.35–5.60(2H, m), 7.32(1H, s), 7.42(1H, s), 7.54(1H, s), 8.14–8.26(1H, m), 8.55(1H, s), 9.16(1H, brs), 9.84(1H, brs).

MS: m/e (ESI) 567.4 (MH+)

Example 1151

1-{3-tert-Butyl-5-[(3-ethoxy-isoxazol-5-ylmethyl)-amino]-4-methoxy-phenyl}-2-(5,6-diethoxy-7-fluoro-1-imino-1,3-dihydro-isoindol-2-yl)-ethanone hydrobromide 1H-NMR(DMSO-d6) δ: 1.24–1.50(6H, m), 1.37(9H, s), 3.75(3H, s), 4.05–4.16(4H, m), 4.20(2H, q, J=7.2 Hz), 4.43(1H, d, J=6.0 Hz), 4.77(2H, s), 5.41(2H, s), 6.04(1H, s), 6.13(1H, t, J=6.0 Hz), 7.11(1H, s), 7.26(1H, s), 7.32(1H, s), 9.01(1H, brs), 9.28(1H, brs).

MS: m/e (ESI) 583.3 (MH+)

Example 1152

1-{3-tert-Butyl-4-methoxy-5-[(3-methoxy-isoxazol-5-ylmethyl)-amino]-phenyl}-2-(5,6-diethoxy-7-fluoro-1-imino-1,3-dihydro-isoindol-2-yl)-ethanone hydrobromide 1H-NMR(DMSO-d6) δ: 1.29(3H, t, J=7.2 Hz), 1.37(s, 9H), 1.39(3H, t, J=7.2 Hz), 3.75(3H, s), 3.82(3H, s), 4.11(2H, q, J=7.2 Hz), 4.20(2H, q, J=7.2 Hz), 4.43(2H, d, J=6.0 Hz), 4.78(2H, s), 5.41(2H, s), 6.05(1H, s), 6.14(1H, s, J=7.2 Hz), 7.11(1H, d, J=2.0 Hz), 7.27(1H, d, J=2.0 Hz), 7.32(1H, s), 9.02(1H, brs), 9.29(1H, brs).

MS: m/e (ESI) 569.3 (MH+)

Example 1153

2-(2-{3-tert-Butyl-4-methoxy-5-[(2-methoxy-pyridin-3-ylmethyl)-amino]-phenyl}-2-oxo-ethyl)-6-ethoxy-3-imino-2,3-dihydro-1H-isoindole-5-carboxylic acid methylamide hydrobromide 1H-NMR(DMSO-d6) δ: 1.37–1.42(12H, m), 2.81(3H, d, J=5 Hz), 3.82(3H, s), 3.92(3H, s), 4.26(2H, q, J=7 Hz), 4.30(2H, m), 4.79(2H, s), 5.37(2H, s), 6.09(1H, m), 6.89–6.95(2H, m), 7.24(1H, d, J=2 Hz), 7.50–7.55(2H, m), 8.03(1H, m), 8.19(1H, m), 8.53(1H, s), 9.11(1H, brs), 9.78(1H, brs).

Example 1154

1-{3-tert-Butyl-4-methoxy-5-[(2-methoxy-pyridin-3-ylmethyl)-amino]-phenyl}-2-(5,6-diethoxy-7-fluoro-1-imino-1,3-dihydro-isoindol-2-yl)-ethanone hydrobromide 1H-NMR(DMSO-d6) δ: 1.28(3H, t, J=7 Hz), 1.35–1.43 (12H, m), 3.82(3H, s), 3.93(3H, s), 4.11(2H, q, J=7 Hz), 4.20(2H, q, J=7 Hz), 4.30(2H, m), 4.73(2H, s), 5.35(2H, s), 6.09(1H, m), 6.89–6.95(2H, m), 7.22(1H, d, J=2 Hz), 7.30(1H, brs), 7.52(1H, m), 8.03(1H, m)

Example 1155

1-[3-tert-Butyl-5-((3R,4S)-3,4-dihydroxy-pyrrolidin-1-yl)-4-methoxy-phenyl]-2-(5,6-diethoxy-7-fluoro-1-imino-1,3-dihydro-isoindol-2-yl)-ethanone trifluoroacetate 1H-NMR(DMSO-d6) δ: 1.29(3H, t, J=6.8 Hz), 1.37(9H, s), 1.40(3H, t, J=6.8 Hz), 3.02–3.11(2H, m), 3.30–3.54(2H, m), 3.60(3H, s), 4.00–4.16(4H, m), 4.21(2H, q, J=6.8 Hz), 4.79(2H, s), 5.47(2H, s), 7.26(1H, s), 7.33(1H, s), 7.38(1H, s), 9.00–9.08(1H, m), 9.23–9.31(1H, m).

MS: m/e (ESI) 544.3 (MH+)

Example 1156

Ethyl (4-{3-tert-butyl-5-[2-(5-ethoxy-1-imino-6-methylcarbamoyl-11,3-dihydro-isoindol-2-yl)-acetyl]-2-methoxy-phenyl}-piperazin-1-yl)-acetate hydrobromide 1H-NMR(DMSO-d6) δ: 1.19(3H, t, J=7.0 Hz), 1.36(9H, s), 1.41(3H, t, J=7.0 Hz), 2.74(4H, brs), 2.83(3H, d, J=4.8 Hz), 3.01(4H, brs), 3.30(2H, s), 3.93(3H, s), 4.09(2H, q, J=7.0 Hz), 4.28(2H, q, J=7.0 Hz), 4.84(2H, s), 5.49(2H, s), 7.51(1H, d, J=2.0 Hz), 7.54(1H, s), 7.59(1H, d, J=2.0 Hz), 8.21(1H, q, J=4.8 Hz), 8.55(1H, s).

MS: m/e (ESI) 608.4 (MH+)

Example 1157

2-(2-{3-tert-Butyl-4-methoxy-5-[(2-oxo-1,2-dihydropyridin-3-ylmethyl)-amino]-phenyl}-2-oxo-ethyl)-6-ethoxy-3-imino-2,3-dihydro-1H-isoindole-5-carboxylic acid methylamide trifluoroacetate 1H-NMR(DMSO-d6) δ: 1.35–1.45(12H, m), 2.82(3H, d, J=5 Hz), 3.80(3H, s), 4.14(2H, s), 4.27(2H, q, J=7 Hz), 4.81(2H, s), 5.39(2H, s), 6.15(1H, m), 6.97(1H, brs), 7.23–7.29(4H, m), 7.51(1H, brs), 8.20(1H, q, J=5 Hz), 8.53(1H, brs), 9.15(1H, brs), 9.80(1H, brs).

MS: m/e (ESI) 559.2 (MH+)

Example 1158

3-({3-tert-Butyl-5-[2-(5,6-diethoxy-7-fluoro-1-imino-1,3-dihydro-isoindol-2-yl)-acetyl]-2-methoxy-phenylamino}-methyl)-1H-pyridin-2-one trifluoroacetate 1H-NMR(DMSO-d6) δ: 1.28(3H, t, J=7 Hz), 1.35–1.42 (12H, m), 3.80(3H, s), 4.10–4.23(6H, m), 4.75(2H, s), 5.38(2H, s), 6.14(1H, m), 6.96(1H, brs), 7.23(1H, brs), 7.26–7.32(4H, m), 9.00(1H, brs), 9.28(1H, brs).

MS: m/e (ESI) 565.3 (MH+)

Example 1159

1-[3-tert-Butyl-5-(3,4-dihydroxy-pyrrolidin-1-yl)-4-methoxy-phenyl]-2-(5,6-diethoxy-7-fluoro-1-imino-1,3-dihydro-isoindol-2-yl)-ethanone hydrochloride 1H-NMR(DMSO-d6) δ: 1.29(3H, t, J=6.8 Hz), 1.37(9H, s), 1.40(3H, t, J=6.8 Hz), 2.92(2H, d, J=10 Hz), 3.61(3H, s), 4.11(2H, q, J=6.8 Hz), 4.21(2H, q, J=6.8 Hz), 3.98–4.28(4H, m), 4.78(2H, s), 5.48(2H, s), 7.29(1H, s), 7.34(1H, s), 7.38(1H, s), 9.04(1H, brs), 9.29(1H, brs).

Example 1160

1-(3-tert-Butyl-4-methoxy-5-morpholino-phenyl)-2-(5,6-diethoxy-7-fluoro-1-imino-1,3-dihydro-isoindol-2-yl)-ethanone hydrochloride 1H-NMR(DMSO-d6) δ: 1.29(3H, t, J=6.8 Hz), 1.36(9H, s), 1.39(3H, t, J=6.8 Hz), 2.94–3.08(4H, m), 3.76–3.85(4H, m), 3.94(3H, s), 4.11(2H, q), 4.20(2H, q, J=6.8 Hz), 4.77 (2H, s), 5.49(2H, s), 7.32(1H, s), 7.49(1H, s), 7.60(1H, s).

The following Example compounds were synthesized as numerous small specimens in 12 mmΦ test tubes. Specifically, various 2-bromo-1-ethanone derivatives (10 mg) were added to dimethylformamide (2 ml) solutions of various amidines (5 mg), 2-imino-dihydropyrrolo[3,4-b~e]pyridine, 1-iminoisoindoline, 2-iminopyrrolidine, 2-imino-2,3-dihydro-1H-imidazole or 2-imino-2,3-dihydro-1H-benz[d]imidazole, and the reaction mixture was stirred overnight at room temperature. After completion of the reaction, nitrogen was sprayed for removing of the solvent and the residue was purified by LC-MS [developing solvent: 0.1% trifluoroacetic acid-containing acetonitrile solution:0.1% trifluoroacetic acid-containing aqueous solution=1:99~100:0/20 minute cycle, flow rate: 20 ml/min, column: YMC Combiprep ODS-AM, 20 mmΦ×50 mm (Long)], to yield the title compound.

Example 1161

7-tert-Butyl-5-[2-(2-ethyl-7-imino-5,7-dihydro-pyrrolo[3,4-b]pyridin-6-yl)-acetyl]-2-methyl-benzofuran-3-carboxylic acid hydrobromide MS: m/e (ESI) 434.0 (MH+)

Example 1162

3-tert-Butyl-5-[2-(2-ethyl-7-imino-5,7-dihydro-pyrrolo[3,4-b]pyridin-6-yl)-acetyl]-2-hydroxy-benzoic acid hydrobromide MS: m/e (ESI) 396.2 (MH+)

Example 1163

3-tert-Butyl-5-[2-(2-ethyl-7-imino-5,7-dihydro-pyrrolo[3,4-b]pyridin-6-yl)-acetyl]-2-methoxy-benzoic acid hydrobromide MS: m/e (ESI) 410.3 (MH+)

Example 1164

Methyl 3-tert-butyl-2-carboxymethoxy-5-[2-(2-ethyl-7-imino-5,7-dihydro-pyrrolo[3,4-b]pyridin-6-yl)-acetyl]-benzoate hydrobromide MS: m/e (ESI) 468.3 (MH+)

Example 1165

{3-tert-Butyl-5-[2-(2-ethyl-7-imino-5,7-dihydro-pyrrolo[3,4-b]pyridin-6-yl)-acetyl]-2-methoxy-benzoylamino}-acetic acid hydrobromide MS: m/e (ESI) 467.4 (MH+)

Example 1166

({3-tert-Butyl-5-[2-(2-ethyl-7-imino-5,7-dihydro-pyrrolo[3,4-b]pyridin-6-yl)-acetyl]-2-methoxy-benzoyl}-methyl-amino)-acetic acid hydrobromide MS: m/e (ESI) 481.4 (MH+)

Example 1167

1-(2-tert-Butyl-pyridin-4-yl)-2-(2-ethyl-7-imino-5,7-dihydro-pyrrolo[3,4-b]pyridin-6-yl)-ethanone hydrobromide MS: m/e (ESI) 337.4 (MH+)

Example 1168

Methyl {2-tert-butyl-4-[2-(2-ethyl-7-imino-5,7-dihydro-pyrrolo[3,4-b]pyridin-6-yl)-acetyl]-6-methoxy-phenoxy}-acetate hydrobromide MS: m/e (ESI) 454.4 (MH+)

Example 1169

{2-tert-Butyl-6-[2-(2-ethyl-7-imino-5,7-dihydro-pyrrolo[3,4-b]pyridin-6-yl)-acetyl]-phenoxy}-acetic acid hydrobromide MS: m/e (ESI) 410.4 (MH+)

Example 1170

{4-tert-Butyl-2-[2-(2-ethyl-7-imino-5,7-dihydro-pyrrolo[3,4-b]pyridin-6-yl)-acetyl]-phenoxy}-acetic acid hydrobromide MS: m/e (ESI) 410.4 (MH+)

Example 1171

Ethyl 3-{3-tert-butyl-5-[2-(2-ethyl-7-imino-5,7-dihydro-pyrrolo[3,4-b]pyridin-6-yl)-acetyl]-2-hydroxy-phenyl}-propionate hydrobromide MS: m/e (ESI) 452.4 (MH+)

Example 1172

N-{2-tert-Butyl-4-[2-(2-ethyl-7-imino-5,7-dihydro-pyrrolo[3,4-b]pyridin-6-yl)-acetyl]-phenyl}-methanesulfonamide hydrobromide MS: m/e (ESI) 429.4 (MH+)

Example 1173

3-{2-tert-Butyl-4-[2-(2-ethyl-7-imino-5,7-dihydro-pyrrolo[3,4-b]pyridin-6-yl)-acetyl]-phenyl}-propionic acid hydrobromide MS: m/e (ESI) 408.4 (MH+)

Example 1174

3-{2-tert-Butyl-4-[2-(2-ethyl-7-imino-5,7-dihydro-pyrrolo[3,4-b]pyridin-6-yl)-acetyl]-phenoxy}-propionic acid hydrobromide MS: m/e (ESI) 424.4 (MH+) -

Example 1175

{3-tert-Butyl-5-[2-(2-ethyl-7-imino-5,7-dihydro-pyrrolo[3,4-b]pyridin-6-yl)-acetyl]-2-methoxy-phenoxy}-acetic acid hydrobromide MS: m/e (ESI) 440.4 (MH+)

Example 1176

5-tert-Butyl-7-[2-(2-ethyl-7-imino-5,7-dihydro-pyrrolo[3,4-b]pyridin-6-yl)-acetyl]-2,3-dihydro-benzo[1,4]dioxane-2-carboxylic acid hydrobromide MS: m/e (ESI) 438.4 (MH+)

Example 1177

1-(3,5-Di-tert-butyl-4-hydroxy-phenyl)-2-(2-ethyl-7-imino-5,7-dihydro-pyrrolo[3,4-b]pyridin-6-yl)-ethanone hydrobromide MS: m/e (ESI) 408.5 (MH+)

Example 1178

1-(7-Ethyl-3,3-dimethyl-2,3-dihydro-benzofuran-5-yl)-2-(2-ethyl-7-imino-5,7-dihydro-pyrrolo[3,4-b]pyridin-6-yl)-ethanone hydrobromide MS: m/e (ESI) 378.4 (MH+)

Example 1179

N-{5-[2-(2-Ethyl-7-imino-5,7-dihydro-pyrrolo[3,4-b]pyridin-6-yl)-acetyl]-3,3-dimethyl-2,3-dihydro-benzofuran-7-yl}-N-methyl-acetamide hydrobromide MS: m/e (ESI) 421.4 (MH+)

Example 1180

N-{3-Ethyl-5-[2-(2-ethyl-7-imino-5,7-dihydro-pyrrolo[3,4-b]pyridin-6-yl)-acetyl]-2-hydroxy-phenyl}-N-methyl-methanesulfonamide hydrobromide MS: m/e (ESI) 431.4 (MH+)

Example 1181

1-(7-tert-Butyl-2,3-dihydro-benzofuran-5-yl)-2-(2-ethyl-7-imino-5,7-dihydro-pyrrolo[3,4-b]pyridin-6-yl)-ethanone hydrobromide MS: m/e (ESI) 378.4 (MH+)

Example 1182

7-tert-Butyl-5-[2-(5,6-diethoxy-7-fluoro-1-imino-1,3-dihydro-isoindol-2-yl)-acetyl]-2-methyl-benzofuran-3-carboxylic acid hydrobromide MS: m/e (ESI) 511.4 (MH+)

Example 1183

3-tert-Butyl-5-[2-(5,6-diethoxy-7-fluoro-1-imino-1,3-dihydro-isoindol-2-yl)-acetyl]-2-hydroxy-benzoic acid hydrobromide MS: m/e (ESI) 473.4 (MH+)

Example 1184

3-tert-Butyl-5-[2-(5,6-diethoxy-7-fluoro-1-imino-1,3-dihydro-isoindol-2-yl)-acetyl]-2-methoxy-benzoic acid hydrobromide MS: m/e (ESI) 487.4 (MH+)

Example 1185

{3-tert-Butyl-5-[2-(5,6-diethoxy-7-fluoro-1-imino-1,3-dihydro-isoindol-2-yl)-acetyl]-2-methoxy-benzoylamino}-acetic acid hydrobromide MS: m/e (ESI) 544.5 (MH+)

Example 1186

({3-tert-Butyl-5-[2-(5,6-diethoxy-7-fluoro-1-imino-1,3-dihydro-isoindol-2-yl)-acetyl]-2-methoxy-benzoyl}-methyl-amino)-acetic acid hydrobromide MS: m/e (ESI) 558.5 (MH+)

Example 1187

1-(2-tert-Butyl-pyridin-4-yl)-2-(5,6-diethoxy-7-fluoro-1-imino-1,3-dihydro-isoindol-2-yl)-ethanone hydrobromide MS: m/e (ESI) 413.5 (MH+)

Example 1188

Methyl {2-tert-butyl-4-[2-(5,6-diethoxy-7-fluoro-1-imino-1,3-dihydro-isoindol-2-yl)-acetyl]-6-methoxy-phenoxy}-acetate hydrobromide MS: m/e (ESI) 531.5 (MH+)

Example 1189

Ethyl 3-{3-tert-butyl-5-[2-(5,6-diethoxy-7-fluoro-1-imino-1,3-dihydro-isoindol-2-yl)-acetyl]-2-hydroxy-phenyl}-propionate hydrobromide MS: m/e (ESI) 529.4 (MH+)

Example 1190

N-{2-tert-Butyl-4-[2-(5,6-diethoxy-7-fluoro-1-imino-1,3-dihydro-isoindol-2-yl)-acetyl]-phenyl}-methanesulfonamide hydrobromide MS: m/e (ESI) 506.4 (MH+)

Example 1191

3-{2-tert-Butyl-4-[2-(5,6-diethoxy-7-fluoro-1-imino-1,3-dihydro-isoindol-2-yl)-acetyl]-phenyl}-propionic acid hydrobromide MS: m/e (ESI) 485.5 (MH+)

Example 1192

3-{2-tert-Butyl-4-[2-(5,6-diethoxy-7-fluoro-1-imino-1,3-dihydro-isoindol-2-yl)-acetyl]-phenoxy}-propionic acid hydrobromide MS: m/e (ESI) 501.5 (MH+)

Example 1193

2-{2-tert-Butyl-4-[2-(5,6-diethoxy-7-fluoro-1-imino-1,3-dihydro-isoindol-2-yl)-acetyl]-phenoxy}-acetamide hydrobromide MS: m/e (ESI) 486.5 (MH+)

Example 1194

{3-tert-Butyl-5-[2-(5,6-diethoxy-7-fluoro-1-imino-1,3-dihydro-isoindol-2-yl)-acetyl]-2-methoxy-phenoxy}-acetic acid hydrobromide MS: m/e (ESI) 517.4 (MH+)

Example 1195

1-(3,5-Di-tert-butyl-4-hydroxy-phenyl)-2-(5,6-diethoxy-7-fluoro-1-imino-1,3-dihydro-isoindol-2-yl)-ethanone hydrobromide MS: m/e (ESI) 485.5 (MH+)

Example 1196

2-(5,6-Diethoxy-7-fluoro-1-imino-1,3-dihydro-isoindol-2-yl)-1-(7-ethyl-3,3-dimethyl-2,3-dihydro-benzofuran-5-yl)-ethanone hydrobromide MS: m/e (ESI) 455.4 (MH+)

Example 1197

N-{5-[2-(5,6-Diethoxy-7-fluoro-1-imino-1,3-dihydro-isoindol-2-yl)-acetyl]-3,3-dimethyl-2,3-dihydro-benzofuran-7-yl}-N-methyl-acetamide hydrobromide MS: m/e (ESI) 498.4 (MH+)

Example 1198

N-{5-[2-(5,6-Diethoxy-7-fluoro-1-imino-1,3-dihydro-isoindol-2-yl)-acetyl]-3-ethyl-2-hydroxy-phenyl}-N-methyl-methanesulfonamide hydrobromide MS: m/e (ESI) 508.4 (MH+)

Example 1199

1-(7-tert-Butyl-2,3-dihydro-benzofuran-5-yl)-2-(5,6-diethoxy-7-fluoro-1-imino-1,3-dihydro-isoindol-2-yl)-ethanone hydrobromide MS: m/e (ESI) 455.4 (MH+)

Example 1200

{8-tert-Butyl-6-[2-(5,6-diethoxy-7-fluoro-1-imino-1,3-dihydro-isoindol-2-yl)-acetyl]-2,3-dihydro-benzo[1,4]oxazin-4-yl}-acetic acid hydrobromide MS: m/e (ESI) 528.5 (MH+)

Example 1201

2-[2-(3,5-Di-tert-butyl-4-hydroxy-phenyl)-2-oxo-ethyl]-6-ethoxy-3-imino-2,3-dihydro-1H-isoindole-5-acetic acid methylamide hydrobromide MS: m/e (ESI) 480.5 (MH+)

Example 1202

6-Ethoxy-2-[2-(7-ethyl-3,3-dimethyl-2,3-dihydro-benzofuran-5-yl)-2-oxo-ethyl]-3-imino-2,3-dihydro-1H-isoindole-5-carboxylic acid methylamide hydrobromide MS: m/e (ESI) 450.4 (MH+)

Example 1203

2-{2-[7-(Acetyl-methyl-amino)-3,3-dimethyl-2,3-dihydro-benzofuran-5-yl]-2-oxo-ethyl}-6-ethoxy-3-imino-2,3-dihydro-1H-isoindole-5-acetic acid methylamide hydrobromide MS: m/e (ESI) 493.4 (MH+)

Example 1204

6-Ethoxy-2-{2-[3-ethyl-4-hydroxy-5-(methanesulfonyl-methyl-amino)-phenyl]-2-oxo-ethyl}-3-imino-2,3-dihydro-1H-isoindole-5-carboxylic acid methylamide hydrobromide MS: m/e (ESI) 503.4 (MH+)

Example 1205

2-[2-(7-tert-Butyl-2,3-dihydro-benzofuran-5-yl)-2-oxo-ethyl]-6-ethoxy-3-imino-2,3-dihydro-1H-isoindole-5-acetic acid methylamide hydrobromide MS: m/e (ESI) 450.4 (MH+)

Example 1206

3-tert-Butyl-2-ethoxy-5-[2-(2-ethyl-7-imino-5,7-dihydro-pyrrolo[3,4-b]pyridin-6-yl)-acetyl]-benzoic acid hydrobromide MS: m/e (ESI) 423.9 (MH+)

Example 1207

3-tert-Butyl-5-[2-(2-ethyl-7-imino-5,7-dihydro-pyrrolo[3,4-b]pyridin-6-yl)-acetyl]-2-propoxy-benzoic acid hydrobromide MS: m/e (ESI) 438.2 (MH+)

Example 1208

3-tert-Butyl-5-[2-(2-ethyl-7-imino-5,7-dihydro-pyrrolo[3,4-b]pyridin-6-yl)-acetyl]-2-isopropoxy-benzoic acid hydrobromide MS: m/e (ESI) 438.3 (MH+)

Example 1209

1-(3-tert-Butyl-5-ethoxy-4-hydroxy-phenyl)-2-(2-ethyl-7-imino-5,7-dihydro-pyrrolo[3,4-b]pyridin-6-yl)-ethanone hydrobromide MS: m/e (ESI) 396.4 (MH+)

Example 1210

{2-tert-Butyl-6-ethoxy-4-[2-(2-ethyl-7-imino-5,7-dihydro-pyrrolo[3,4-b]pyridin-6-yl)-acetyl]-phenoxy}-acetic acid hydrobromide MS: m/e (ESI) 454.4 (MH+)

Example 1211

1-(3-tert-Butyl-5-hydroxy-4-methoxy-phenyl)-2-(2-ethyl-7-imino-5,7-dihydro-pyrrolo[3,4-b]pyridin-6-yl)-ethanone hydrobromide MS: m/e (ESI) 382.4 (MH+)

Example 1212

Ethyl 4-{3-[2-(2-ethyl-7-imino-5,7-dihydro-pyrrolo[3,4-b]pyridin-6-yl)-acetyl]-phenyl}-4-methyl-pent-2-enoate hydrobromide MS: m/e (ESI) 420.5 (MH+)

Example 1213

Methyl 2-{3-[2-(2-ethyl-7-imino-5,7-dihydro-pyrrolo[3,4-b]pyridin-6-yl)-acetyl]-phenyl}-2-methyl-propionate hydrobromide MS: m/e (ESI) 380.4 (MH+)

Example 1214

Ethyl 3-{3-tert-butyl-5-[2-(2-ethyl-7-imino-5,7-dihydro-pyrrolo[3,4-b]pyridin-6-yl)-acetyl]-2-methoxy-phenyl}-propionate hydrobromide MS: m/e (ESI) 466.5 (MH+)

Example 1215

3-{3-tert-Butyl-5-[2-(2-ethyl-7-imino-5,7-dihydro-pyrrolo[3,4-b]pyridin-6-yl)-acetyl]-2-methoxy-phenyl}-propionic acid hydrobromide MS: m/e (ESI) 438.5 (MH+)

Example 1216

5-[2-(2-Ethyl-7-imino-5,7-dihydro-pyrrolo[3,4-b]pyridin-6-yl)-acetyl]-3,3-dimethyl-1,3-dihydro-indol-2-one hydrobromide MS: m/e (ESI) 363.4 (MH+)

Example 1217

5-[2-(2-Ethyl-7-imino-5,7-dihydro-pyrrolo[3,4-b]pyridin-6-yl)-acetyl]-1,3,3-trimethyl-1,3-dihydro-indol-2-one hydrobromide MS: m/e (ESI) 377.5 (MH+)

Example 1218

{5-[2-(2-Ethyl-7-imino-5,7-dihydro-pyrrolo[3,4-b]pyridin-6-yl)-acetyl]-3,3-dimethyl-2-oxo-2,3-dihydro-indol-1-yl}-acetic acid hydrobromide MS: m/e (ESI) 421.5 (MH+)

Example 1219

1-(3-tert-Butyl-4-hydroxy-phenyl)-2-(2-ethyl-7-imino-5,7-dihydro-pyrrolo[3,4-b]pyridin-6-yl)-ethanone hydrobromide MS: m/e (ESI) 352.5 (MH+)

Example 1220

3-tert-Butyl-5-[2-(5,6-diethoxy-7-fluoro-1-imino-1,3-dihydro-isoindol-2-yl)-acetyl]-2-ethoxy-benzoic acid hydrobromide MS: m/e (ESI) 501.5 (MH+)

Example 1221

3-tert-Butyl-5-[2-(5,6-diethoxy-7-fluoro-1-imino-1,3-dihydro-isoindol-2-yl)-acetyl]-2-propoxy-benzoic acid hydrobromide MS: m/e (ESI) 515.6 (MH+)

Example 1222

3-tert-Butyl-5-[2-(5,6-diethoxy-7-fluoro-1-imino-1,3-dihydro-isoindol-2-yl)-acetyl]-2-isopropoxy-benzoic acid hydrobromide MS: m/e (ESI) 515.6 (MH+)

Example 1223

1-(3-tert-Butyl-5-ethoxy-4-hydroxy-phenyl)-2-(5,6-diethoxy-7-fluoro-1-imino-1,3-dihydro-isoindol-2-yl)-ethanone hydrobromide MS: m/e (ESI) 473.5 (MH+)

Example 1224

{2-tert-Butyl-4-[2-(5,6-diethoxy-7-fluoro-1-imino-1,3-dihydro-isoindol-2-yl)-acetyl]-6-ethoxy-phenoxy}-acetic acid hydrobromide MS: m/e (ESI) 531.6 (MH+)

Example 1225

1-(3-tert-Butyl-5-hydroxy-4-methoxy-phenyl)-2-(5,6-diethoxy-7-fluoro-1-imino-1,3-dihydro-isoindol-2-yl)-ethanone hydrobromide MS: m/e (ESI) 459.5 (MH+)

Example 1226

Ethyl 3-{3-tert-butyl-5-[2-(5,6-diethoxy-7-fluoro-1-imino-1,3-dihydro-isoindol-2-yl)-acetyl]-2-methoxy-phenyl}-propionate hydrobromide MS: m/e (ESI) 543.6 (MH+)

Example 1227

3-{3-tert-Butyl-5-[2-(5,6-diethoxy-7-fluoro-1-imino-1,3-dihydro-isoindol-2-yl)-acetyl]-2-methoxy-phenyl}-propionic acid hydrobromide MS: m/e (ESI) 515.6 (MH+)

Example 1228

5-[2-(5,6-Diethoxy-7-fluoro-1-imino-1,3-dihydro-isoindol-2-yl)-acetyl]-3,3-dimethyl-1,3-dihydro-indol-2-one hydrobromide MS: m/e (ESI) 440.5 (MH+)

Example 1229

5-[2-(5,6-Diethoxy-7-fluoro-1-imino-1,3-dihydro-isoindol-2-yl)-acetyl]-1,3,3-trimethyl-1,3-dihydro-indol-2-one hydrobromide MS: m/e (ESI) 454.5 (MH+)

Example 1230

{5-[2-(5,6-Diethoxy-7-fluoro-1-imino-1,3-dihydro-isoindol-2-yl)-acetyl]-3,3-dimethyl-2-oxo-2,3-dihydro-indol-1-yl}-acetic acid hydrobromide MS: m/e (ESI) 498.5 (MH+)

Example 1231

1-(3-tert-Butyl-4-hydroxy-phenyl)-2-(5,6-diethoxy-7-fluoro-1-imino-1,3-dihydro-isoindol-2-yl)-ethanone hydrobromide MS: m/e (ESI) 429.5 (MH+)

Example 1232

3-tert-Butyl-2-ethoxy-5-[2-(5-ethoxy-1-imino-6-methylcarbamoyl-1,3-dihydro-isoindol-2-yl)-acetyl]-benzoic acid hydrobromide MS: m/e (ESI) 496.5 (MH+)

Example 1233

3-tert-Butyl-5-[2-(5-ethoxy-1-imino-6-methylcarbamoyl-1,3-dihydro-isoindol-2-yl)-acetyl]-2-propoxy-benzoic acid hydrobromide MS: m/e (ESI) 510.5 (MH+)

Example 1234

3-tert-Butyl-5-[2-(5-ethoxy-1-imino-6-methylcarbamoyl-1,3-dihydro-isoindol-2-yl)-acetyl]-2-isopropoxy-benzoic acid hydrobromide MS: m/e (ESI) 510.5 (MH+)

Example 1235

2-[2-(3-tert-Butyl-5-ethoxy-4-hydroxy-phenyl)-2-oxo-ethyl]-6-ethoxy-3-imino-2,3-dihydro-1H-isoindole-5-acetic acid methylamide hydrobromide MS: m/e (ESI) 468.5 (MH+)

Example 1236

{2-tert-Butyl-6-ethoxy-4-[2-(5-ethoxy-1-imino-6-methylcarbamoyl-1,3-dihydro-isoindol-2-yl)-acetyl]-phenoxy}-acetic acid hydrobromide MS: m/e (ESI) 526.5 (MH+)

Example 1237

{3-tert-Butyl-2-ethoxy-5-[2-(2-ethyl-7-imino-5,7-dihydro-pyrrolo[3,4-b]pyridin-6-yl)-acetyl]-benzoylamino}-acetic acid hydrobromide MS: m/e (ESI) 481.5 (MH+)

Example 1238

2-{3-tert-Butyl-5-[2-(2-ethyl-7-imino-5,7-dihydro-pyrrolo[3,4-b]pyridin-6-yl)-acetyl]-2-methoxy-benzoylamino}-propionic acid hydrobromide MS: m/e (ESI) 481.5 (MH+)

Example 1239

1-(3-tert-Butyl-4-pyrrolidin-1-yl-phenyl)-2-(2-ethyl-7-imino-5,7-dihydro-pyrrolo[3,4-b]pyridin-6-yl)-ethanone hydrobromide MS: m/e (ESI) 405.5 (MH+)

Example 1240

{2-tert-Butyl-4-[2-(2-ethyl-7-imino-5,7-dihydro-pyrrolo[3,4-b]pyridin-6-yl)-acetyl]-phenylamino}-acetic acid hydrobromide MS: m/e (ESI) 409.4 (MH+)

Example 1241

{4-tert-Butyl-6-[2-(2-ethyl-7-imino-5,7-dihydro-pyrrolo[3,4-b]pyridin-6-yl)-acetyl]-2-methyl-benzimidazol-1-yl}-acetic acid hydrobromide MS: m/e (ESI) 448.5 (MH+)

Example 1242

{2-[(Acetyl-methyl-amino)-methyl]-6-tert-butyl-4-[2-(5,6-diethoxy-7-fluoro-1-imino-1,3-dihydro-isoindol-2-yl)-acetyl]-phenoxy}-acetic acid hydrobromide MS: m/e (ESI) 572.5 (MH+)

Example 1243

{3-tert-Butyl-5-[2-(5,6-diethoxy-7-fluoro-1-imino-1,3-dihydro-isoindol-2-yl)-acetyl]-2-ethoxy-benzoylamino}-acetic acid hydrobromide MS: m/e (ESI) 558.5 (MH+)

Example 1244

2-{3-tert-Butyl-5-[2-(5,6-diethoxy-7-fluoro-1-imino-1,3-dihydro-isoindol-2-yl)-acetyl]-2-methoxy-benzoylamino}-propionic acid hydrobromide MS: m/e (ESI) 558.5 (MH+)

Example 1245

{4-tert-Butyl-6-[2-(5,6-diethoxy-7-fluoro-1-imino-1,3-dihydro-isoindol-2-yl)-acetyl]-2-methyl-benzimidazol-1-yl}-acetic acid hydrobromide MS: m/e (ESI) 525.5 (MH+)

Example 1246

1-(8-tert-Butyl-4-ethyl-3,4-dihydro-2H-benzo[1,4]oxazin-6-yl)-2-(5,6-diethoxy-7-fluoro-1-imino-1,3-dihydro-isoindol-2-yl)-ethanone hydrobromide MS: m/e (ESI) 498.5 (MH+)

Example 1247

1-(8-tert-Butyl-4-propyl-3,4-dihydro-2H-benzo[1,4]oxazin-6-yl)-2-(5,6-diethoxy-7-fluoro-1-imino-1,3-dihydro-isoindol-2-yl)-ethanone hydrobromide MS: m/e (ESI) 512.5 (MH+)

Example 1248

{3-tert-Butyl-2-ethoxy-5-[2-(3-ethoxy-7-imino-2,4-dimethyl-5,7-dihydro-pyrrolo[3,4-b]pyridin-6-yl)-acetyl]-benzoylamino}-acetic acid hydrobromide MS: m/e (ESI) 525.5 (MH+)

Example 1249

2-{3-tert-Butyl-5-[2-(3-ethoxy-7-imino-2,4-dimethyl-5,7-dihydro-pyrrolo[3,4-b]pyridin-6-yl)-acetyl]-2-methoxy-benzoylamino}-propionic acid hydrobromide MS: m/e (ESI) 525.5 (MH+)

Example 1250

1-(3-tert-Butyl-4-pyrrolidin-1-yl-phenyl)-2-(3-ethoxy-7-imino-2,4-dimethyl-5,7-dihydro-pyrrolo[3,4-b]pyridin-6-yl)-ethanone hydrobromide MS: m/e (ESI) 449.5 (MH+)

Example 1251

{2-tert-Butyl-4-[2-(3-ethoxy-7-imino-2,4-dimethyl-5,7-dihydro-pyrrolo[3,4-b]pyridin-6-yl)-acetyl]-phenylamino}-acetic acid hydrobromide MS: m/e (ESI) 453.5 (MH+)

Example 1252

{2-[(Acetyl-methyl-amino)-methyl]-6-tert-butyl-4-[2-(5-ethoxy-1-imino-6-methylcarbamoyl-1,3-dihydro-isoindol-2-yl)-acetyl]-phenoxy}-acetic acid hydrobromide MS: m/e (ESI) 567.5 (MH+)

Example 1253

{3-tert-Butyl-2-ethoxy-5-[2-(5-ethoxy-1-imino-6-methylcarbamoyl-1,3-dihydro-isoindol-2-yl)-acetyl]-benzoylamino}-acetic acid hydrobromide MS: m/e (ESI) 553.5 (MH+)

Example 1254

2-{3-tert-Butyl-5-[2-(5-ethoxy-1-imino-6-methylcarbamoyl-1,3-dihydro-isoindol-2-yl)-acetyl]-2-methoxy-benzoylamino}-propionic acid hydrobromide MS: m/e (ESI) 553.5 (MH+)

Example 1255

2-[2-(3-tert-Butyl-4-pyrrolidin-1-yl-phenyl)-2-oxo-ethyl]-6-ethoxy-3-imino-2,3-dihydro-1H-isoindole-5-acetic acid methylamide hydrobromide MS: m/e (ESI) 477.5 (MH+)

Example 1256

{2-tert-Butyl-4-[2-(5-ethoxy-1-imino-6-methylcarbamoyl-1,3-dihydro-isoindol-2-yl)-acetyl]-phenylamino}-acetic acid hydrobromide MS: m/e (ESI) 481.5 (MH+)

Example 1257

{4-tert-Butyl-6-[2-(5-ethoxy-1-imino-6-methylcarbamoyl-1,3-dihydro-isoindol-2-yl)-acetyl]-2-methyl-benzimidazol-1-yl}-acetic acid hydrobromide MS: m/e (ESI) 520.5 (MH+)

Example 1258

2-[2-(8-tert-Butyl-4-ethyl-3,4-dihydro-2H-benzo[1,4]oxazin-6-yl)-2-oxo-ethyl]-6-ethoxy-3-imino-2,3-dihydro-1H-isoindole-5-acetic acid methylamide hydrobromide MS: m/e (ESI) 493.5 (MH+)

Example 1259

2-[2-(8-tert-Butyl-4-propyl-3,4-dihydro-2H-benzo[1,4]oxazin-6-yl)-2-oxo-ethyl]-6-ethoxy-3-imino-2,3-dihydro-1H-isoindole-5-acetic acid methylamide hydrobromide MS: m/e (ESI) 507.5 (MH+)

Example 1260

Methyl 2-acetylamino-3-{2-tert-butyl-4-[2-(2-ethyl-7-imino-5,7-dihydro-pyrrolo[3,4-b]pyridin-6-yl)-acetyl]-phenyl}-acrylate hydrobromide MS: m/e (ESI) 477.2 (MH+)

Example 1261

3-{3-tert-Butyl-5-[2-(2-ethyl-7-imino-5,7-dihydro-pyrrolo[3,4-b]pyridin-6-yl)-acetyl]-2-methoxy-benzoylamino}-propionic acid hydrobromide MS: m/e (ESI) 481.2 (MH+)

Example 1262

N-{2-tert-Butyl-4-[2-(2-ethyl-7-imino-5,7-dihydro-pyrrolo[3,4-b]pyridin-6-yl)-acetyl]-phenyl}-N-methyl-succinamic acid hydrobromide MS: m/e (ESI) 465.3 (MH+)

Example 1263

8-tert-Butyl-6-[2-(2-ethyl-7-imino-5,7-dihydro-pyrrolo[3,4-b]pyridin-6-yl)-acetyl]-4-methyl-4H-benzo[1,4]oxazin-3-one hydrobromide MS: m/e (ESI) 421.4 (MH+)

Example 1264

8-tert-Butyl-6-[2-(2-ethyl-7-imino-5,7-dihydro-pyrrolo[3,4-b]pyridin-6-yl)-acetyl]-4H-benzo[1,4]oxazin-3-one hydrobromide MS: m/e (ESI) 407.4 (MH+)

Example 1265

1-(3-tert-Butyl-4,5-dimethoxy-phenyl)-2-(2-ethyl-7-imino-5,7-dihydro-pyrrolo[3,4-b]pyridin-6-yl)-ethanone hydrobromide MS: m/e (ESI) 396.4 (MH+)

Example 1266

1-(5-tert-Butyl-furan-3-yl)-2-(2-ethyl-7-imino-5,7-dihydro-pyrrolo[3,4-b]pyridin-6-yl)-ethanone hydrobromide MS: m/e (ESI) 326.4 (MH+)

Example 1267

Methyl 2-acetylamino-3-{2-tert-butyl-4-[2-(2-ethyl-7-imino-5,7-dihydro-pyrrolo[3,4-b]pyridin-6-yl)-acetyl]-phenyl}-propionate hydrobromide MS: m/e (ESI) 479.2 (MH+)

Example 1268

Methyl 2-acetylamino-3-{2-tert-butyl-4-[2-(5,6-diethoxy-7-fluoro-1-imino-1,3-dihydro-isoindol-2-yl)-acetyl]-phenyl}-acrylate hydrobromide MS: m/e (ESI) 554.5 (MH+)

Example 1269

3-{3-tert-Butyl-5-[2-(5,6-diethoxy-7-fluoro-1-imino-1,3-dihydro-isoindol-2-yl)-acetyl]-2-methoxy-benzoylamino}-propionic acid hydrobromide MS: m/e (ESI) 558.5 (MH+)

Example 1270

N-{2-tert-Butyl-4-[2-(5,6-diethoxy-7-fluoro-1-imino-1,3-dihydro-isoindol-2-yl)-acetyl]-phenyl}-N-methyl-succinamic acid hydrobromide MS: m/e (ESI) 542.5 (MH+)

Example 1271

8-tert-Butyl-6-[2-(5,6-diethoxy-7-fluoro-1-imino-1,3-dihydro-isoindol-2-yl)-acetyl]-4-methyl-4H-benzo[1,4]oxazin-3-one hydrobromide MS: m/e (ESI) 498.4 (MH+)

Example 1272

5-tert-Butyl-7-[2-(5,6-diethoxy-7-fluoro-1-imino-1,3-dihydro-isoindol-2-yl)-acetyl]-2,3-dihydro-benzo[1,4]dioxane-2-carboxylic acid hydrobromide MS: m/e (ESI) 515.4 (MH+)

Example 1273

1-(3-tert-Butyl-4,5-dimethoxy-phenyl)-2-(5,6-diethoxy-7-fluoro-1-imino-1,3-dihydro-isoindol-2-yl)-ethanone hydrobromide MS: m/e (ESI) 473.4 (MH+)

Example 1274

1-(5-tert-Butyl-furan-3-yl)-2-(5,6-diethoxy-7-fluoro-1-imino-1,3-dihydro-isoindol-2-yl)-ethanone hydrobromide MS: m/e (ESI) 403.4 (MH+)

Example 1275

Methyl 2-acetylamino-3-{2-tert-butyl-4-[2-(5,6-diethoxy-7-fluoro-1-imino-1,3-dihydro-isoindol-2-yl)-acetyl]-phenyl}-propionate hydrobromide MS: m/e (ESI) 556.3 (MH+)

Example 1276

Methyl 2-acetylamino-3-{2-tert-butyl-4-[2-(5-ethoxy-1-imino-6-methylcarbamoyl-1,3-dihydro-isoindol-2-yl)-acetyl]-phenyl}-acrylate hydrobromide MS: m/e (ESI) 549.2 (MH+)

Example 1277

3-{3-tert-Butyl-5-[2-(5-ethoxy-1-imino-6-methylcarbamoyl-1,3-dihydro-isoindol-2-yl)-acetyl]-2-methoxy-benzoylamino}-propionic acid hydrobromide MS: m/e (ESI) 553.3 (MH+)

Example 1278

N-{2-tert-Butyl-4-[2-(5-ethoxy-1-imino-6-methylcarbamoyl-1,3-dihydro-isoindol-2-yl)-acetyl]-phenyl}-N-methyl-succinamic acid hydrobromide MS: m/e (ESI) 537.4 (MH+)

Example 1279

2-[2-(8-tert-Butyl-4-methyl-3-oxo-3,4-dihydro-2H-benzo[1,4]oxazin-6-yl)-2-oxo-ethyl]-6-ethoxy-3-imino-2,3-dihydro-1H-isoindole-5-acetic acid methylamide hydrobromide MS: m/e (ESI) 493.4 (MH+)

Example 1280

2-[2-(8-tert-Butyl-3-oxo-3,4-dihydro-2H-benzo[1,4]oxazin-6-yl)-2-oxo-ethyl]-6-ethoxy-3-imino-2,3-dihydro-1H-isoindole-5-acetic acid methylamide hydrobromide MS: m/e (ESI) 479.4 (MH+)

Example 1281

2-[2-(4-Acetyl-8-tert-butyl-3,4-dihydro-2H-benzo[1,4]oxazin-6-yl)-2-oxo-ethyl]-6-ethoxy-3-imino-2,3-dihydro-1H-isoindole-5-acetic acid methylamide hydrobromide MS: m/e (ESI) 507.4 (MH+)

Example 1282

2-[2-(3-tert-Butyl-4-hydroxy-5-nitro-phenyl)-2-oxo-ethyl]-6-ethoxy-3-imino-2,3-dihydro-1H-isoindole-5-acetic acid methylamide hydrobromide MS: m/e (ESI) 469.2 (MH+)

Example 1283

5-tert-Butyl-7-[2-(6-carbamoyl-5-ethoxy-1-imino-1,3-dihydro-isoindol-2-yl)-acetyl]-2,3-dihydro-benzo[1,4]dioxane-2-carboxylic acid hydrobromide MS: m/e (ESI) 496.4 (MH+)

Example 1284

2-[2-(3-tert-Butyl-4,5-dimethoxy-phenyl)-2-oxo-ethyl]-6-ethoxy-3-imino-2,3-dihydro-1H-isoindole-5-carboxamide hydrobromide MS: m/e (ESI) 454.4 (MH+)

Example 1285

2-(2-Ethyl-7-imino-5,7-dihydro-pyrrolo[3,4-b]pyridin-6-yl)-1-(1,3,3-trimethyl-2,3-dihydro-1H-indol-5-yl)-ethanone hydrobromide MS: m/e (ESI) 363.4 (MH+)

Example 1286

6-[2-(2-Ethyl-7-imino-5,7-dihydro-pyrrolo[3,4-b]pyridin-6-yl)-acetyl]-1,4,4-trimethyl-3,4-dihydro-1H-quinolin-2-one hydrobromide MS: m/e (ESI) 391.4 (MH+)

Example 1287

1-[3-tert-Butyl-4-(1H-tetrazol-5-ylmethoxy)-phenyl]-2-(2-ethyl-7-imino-5,7-dihydro-pyrrolo[3,4-b]pyridin-6-yl)-ethanone hydrobromide MS: m/e (ESI) 434.4 (MH+)

Example 1288

2-(2-Ethyl-7-imino-5,7-dihydro-pyrrolo[3,4-b]pyridin-6-yl)-1-(1,2,3,3-tetramethyl-2,3-dihydro-1H-indol-5-yl)-ethanone hydrobromide MS: m/e (ESI) 377.4 (MH+)

Example 1289

1-(7-tert-Butyl-3,3-dimethyl-2,3-dihydro-benzo[b]thiophen-5-yl)-2-(2-ethyl-7-imino-5,7-dihydro-pyrrolo[3,4-b]pyridin-6-yl)-ethanone hydrobromide MS: m/e (ESI) 422.4 (MH+)

Example 1290

1-(8-tert-Butyl-4,4-dimethyl-thiochroman-6-yl)-2-(2-ethyl-7-imino-5,7-dihydro-pyrrolo[3,4-b]pyridin-6-yl)-ethanone hydrobromide MS: m/e (ESI) 436.4 (MH+)

Example 1291

2-(5,6-Diethoxy-7-fluoro-1-imino-1,3-dihydro-isoindol-2-yl)-1-(1,3,3-trimethyl-2,3-dihydro-1H-indol-5-yl)-ethanone hydrobromide MS: m/e (ESI) 440.5 (MH+)

Example 1292

6-[2-(5,6-Diethoxy-7-fluoro-1-imino-1,3-dihydro-isoindol-2-yl)-acetyl]-1,4,4-trimethyl-3,4-dihydro-1H-quinolin-2-one hydrobromide MS: m/e (ESI) 468.5 (MH+)

Example 1293

2-(5,6-Diethoxy-7-fluoro-1-imino-1,3-dihydro-isoindol-2-yl)-1-(1,2,3,3-tetramethyl-2,3-dihydro-1H-indol-5-yl)-ethanone hydrobromide MS: m/e (ESI) 454.5 (MH+)

Example 1294

1-(7-tert-Butyl-3,3-dimethyl-2,3-dihydro-benzo[b]thiophen-5-yl)-2-(5,6-diethoxy-7-fluoro-1-imino-1,3-dihydro-isoindol-2-yl)-ethanone hydrobromide MS: m/e (ESI) 499.5 (MH+)

Example 1295

1-(8-tert-Butyl-4,4-dimethyl-thiochroman-6-yl)-2-(5,6-diethoxy-7-fluoro-1-imino-1,3-dihydro-isoindol-2-yl)-ethanone hydrobromide MS: m/e (ESI) 513.5 (MH+)

Example 1296

Ethyl 4-{8-tert-butyl-6-[2-(5-ethoxy-1-imino-6-methylcarbamoyl-1,3-dihydro-isoindol-2-yl)-acetyl]-2,3-dihydro-benzo(1,4]oxazin-4-yl}-4-oxo-butanoate hydrobromide MS: m/e (ESI) 593.6 (MH+)

Example 1297

2-[2-(7-tert-Butyl-3,3-dimethyl-2,3-dihydro-benzo[b]thiophen-5-yl)-2-oxo-ethyl]-6-ethoxy-3-imino-2,3-dihydro-1H-isoindole-5-acetic acid methylamide hydrobromide MS: m/e (ESI) 494.5 (MH+)

Example 1298

{2-[(Acetyl-methyl-amino)-methyl]-6-tert-butyl-4-[2-(7-fluoro-1-imino-5,6-dimethoxy-1,3-dihydro-isoindol-2-yl)-acetyl]-phenoxy}-acetic acid hydrobromide MS: m/e (ESI) 544.5 (MH+)

Example 1299

2-(7-Fluoro-1-imino-5,6-dimethoxy-1,3-dihydro-isoindol-2-yl)-1-(1,3,3-trimethyl-2,3-dihydro-1H-indol-5-yl)-ethanone hydrobromide MS: m/e (ESI) 412.4 (MH+)

Example 1300

1-[3-tert-Butyl-4-(1H-tetrazol-5-ylmethoxy)-phenyl]-2-(7-fluoro-1-imino-5,6-dimethoxy-1,3-dihydro-isoindol-2-yl)-ethanone hydrobromide MS: m/e (ESI) 483.4 (MH+)

Example 1301

{2-[(Acetyl-methyl-amino)-methyl]-6-tert-butyl-4-[2-(5-ethoxy-7-fluoro-1-imino-6-methoxy-1,3-dihydro-isoindol-2-yl)-acetyl]-phenoxy}-acetic acid hydrobromide MS: m/e (ESI) 558.5 (MH+)

Example 1302

(Acetyl-{3-tert-butyl-5-[2-(2-ethyl-7-imino-5,7-dihydro-pyrrolo[3,4-b]pyridin-6-yl)-acetyl]-2-hydroxy-benzyl}-amino)-acetic acid hydrobromide MS: m/e (ESI) 481.1 (MH+)

Example 1303

{3-tert-Butyl-5-[2-(2-ethyl-7-imino-5,7-dihydro-pyrrolo[3,4-b]pyridin-6-yl)-acetyl]-2-hydroxy-benzylamino}-acetic acid hydrobromide MS: m/e (ESI) 439.1 (MH+)

Example 1304

4-{3-tert-Butyl-5-[2-(2-ethyl-7-imino-5,7-dihydro-pyrrolo[3,4-b]pyridin-6-yl)-acetyl]-2-hydroxy-phenoxy}-butanoic acid hydrobromide MS: m/e (ESI) 454.2 (MH+)

Example 1305

4-{3-tert-Butyl-5-[2-(2-ethyl-7-imino-5,7-dihydro-pyrrolo[3,4-b]pyridin-6-yl)-acetyl]-2-hydroxy-phenoxy}-butylamide hydrobromide MS: m/e (ESI) 453.2 (MH+)

Example 1306

4-{2-tert-Butyl-4-[2-(2-ethyl-7-imino-5,7-dihydro-pyrrolo[3,4-b]pyridin-6-yl)-acetyl]-6-methoxy-phenoxy}-butanoic acid hydrobromide MS: m/e (ESI) 468.3 (MH+)

Example 1307

4-{2-tert-Butyl-4-[2-(2-ethyl-7-imino-5,7-dihydro-pyrrolo[3,4-b]pyridin-6-yl)-acetyl]-6-methoxy-phenoxy}-butylamide hydrobromide MS: m/e (ESI) 467.4 (MH+)

Example 1308

1-(8-tert-Butyl-4,4-dimethyl-1,1-dioxo-1lambda*6*-thiochroman-6-yl)-2-(2-ethyl-7-imino-5,7-dihydro-pyrrolo[3,4-b]pyridin-6-yl)-ethanone hydrobromide MS: m/e (ESI) 468.4 (MH+)

Example 1309

1-(8-tert-Butyl-4,4-dimethyl-chroman-6-yl)-2-(2-ethyl-7-imino-5,7-dihydro-pyrrolo[3,4-b]pyridin-6-yl)-ethanone hydrobromide MS: m/e (ESI) 420.4 (MH+)

Example 1310

{2-tert-Butyl-4-[2-(2-ethyl-7-imino-5,7-dihydro-pyrrolo[3,4-b]pyridin-6-yl)-acetyl]-phenyl}-acetic acid hydrobromide MS: m/e (ESI) 394.4 (MH+)

Example 1311

{2-tert-Butyl-4-[2-(2-ethyl-7-imino-5,7-dihydro-pyrrolo[3,4-b]pyridin-6-yl)-acetyl]-6-thiophen-2-yl-phenoxy}-acetic acid hydrobromide MS: m/e (ESI) 492.4 (MH+)

Example 1312

2-{2-tert-Butyl-4-[2-(2-ethyl-7-imino-5,7-dihydro-pyrrolo[3,4-b]pyridin-6-yl)-acetyl]-phenoxy}-propionic acid hydrobromide MS: m/e (ESI) 424.4 (MH+)

Example 1313

[2-tert-Butyl-4-[2-(2-ethyl-7-imino-5,7-dihydro-pyrrolo[3,4-b]pyridin-6-yl)-acetyl]-6-(methanesulfonyl-methyl-amino)-phenoxy]-acetic acid hydrobromide MS: m/e (ESI) 517.4 (MH+)

Example 1314

(Acetyl-{3-tert-butyl-5-[2-(5-ethoxy-1-imino-6-methylcarbamoyl-1,3-dihydro-isoindol-2-yl)-acetyl]-2-hydroxy-benzyl}-amino)-acetic acid hydrobromide MS: m/e (ESI) 553.5 (MH+)

Example 1315

{3-tert-Butyl-5-[2-(5-ethoxy-1-imino-6-methylcarbamoyl-1,3-dihydro-isoindol-2-yl)-acetyl]-2-hydroxy-benzylamino}-acetic acid hydrobromide MS: m/e (ESI) 511.5 (MH+)

Example 1316

4-{3-tert-Butyl-5-[2-(5-ethoxy-1-imino-6-methylcarbamoyl-1,3-dihydro-isoindol-2-yl)-acetyl]-2-hydroxy-phenoxy}-butanoic acid hydrobromide MS: m/e (ESI) 526.5 (MH+)

Example 1317

2-{2-[3-tert-Butyl-5-(3-carbamoyl-propoxy)-4-hydroxy-phenyl]-2-oxo-ethyl}-6-ethoxy-3-imino-2,3-dihydro-1H-isoindole-5-acetic acid methylamide hydrobromide MS: m/e (ESI) 525.5 (MH+)

Example 1318

4-{2-tert-Butyl-4-[2-(5-ethoxy-1-imino-6-methylcarbamoyl-1,3-dihydro-isoindol-2-yl)-acetyl]-6-methoxy-phenoxy}-butanoic acid hydrobromide MS: m/e (ESI) 540.5 (MH+)

Example 1319

2-{2-[3-tert-Butyl-4-(3-carbamoyl-propoxy)-5-methoxy-phenyl]-2-oxo-ethyl}-6-ethoxy-3-imino-2,3-dihydro-1H-isoindole-5-acetic acid methylamide hydrobromide MS: m/e (ESI) 539.5 (MH+)

Example 1320

2-[2-(8-tert-Butyl-4,4-dimethyl-1,1-dioxo-1lambda*6*-thiochroman-6-yl)-2-oxo-ethyl]-6-ethoxy-3-imino-2,3-dihydro-1H-isoindole-5-acetic acid methylamide hydrobromide MS: m/e (ESI) 540.5 (MH+)

Example 1321

2-[2-(8-tert-Butyl-4,4-dimethyl-chroman-6-yl)-2-oxo-ethyl]-6-ethoxy-3-imino-2,3-dihydro-1H-isoindole-5-acetic acid methylamide hydrobromide MS: m/e (ESI) 492.5 (MH+)

Example 1322

{2-tert-Butyl-4-[2-(5-ethoxy-1-imino-6-methylcarbamoyl-1,3-dihydro-isoindol-2-yl)-acetyl]-phenyl}-acetic acid hydrobromide MS: m/e (ESI) 466.4 (MH+)

Example 1323

{2-tert-Butyl-4-[2-(5-ethoxy-1-imino-6-methylcarbamoyl-1,3-dihydro-isoindol-2-yl)-acetyl]-6-thiophen-2-yl-phenoxy}-acetic acid hydrobromide MS: m/e (ESI) 564.5 (MH+)

Example 1324

[2-tert-Butyl-4-[2-(5-ethoxy-1-imino-6-methylcarbamoyl-1,3-dihydro-isoindol-2-yl)-acetyl]-6-(methanesulfonyl-methyl-amino)-phenoxy]-acetic acid hydrobromide MS: m/e (ESI) 589.5 (MH+)

Example 1325

4-{3-tert-Butyl-5-[2-(6-carbamoyl-5-ethoxy-1-imino-1,3-dihydro-isoindol-2-yl)-acetyl]-2-hydroxy-phenoxy}-butanoic acid hydrobromide MS: m/e (ESI) 512.5 (MH+)

Example 1326

2-{2-[3-tert-Butyl-5-(3-carbamoyl-propoxy)-4-hydroxy-phenyl]-2-oxo-ethyl}-6-ethoxy-3-imino-2,3-dihydro-1H-isoindole-5-carboxamide hydrobromide MS: m/e (ESI) 511.5 (MH+)

Example 1327

4-{2-tert-Butyl-4-[2-(6-carbamoyl-5-ethoxy-1-imino-1,3-dihydro-isoindol-2-yl)-acetyl]-6-methoxy-phenoxy}-butanoic acid hydrobromide MS: m/e (ESI) 526.4 (MH+)

Example 1328

2-{2-[3-tert-Butyl-4-(3-carbamoyl-propoxy)-5-methoxy-phenyl]-2-oxo-ethyl}-6-ethoxy-3-imino-2,3-dihydro-1H-isoindole-5-carboxamide hydrobromide MS: m/e (ESI) 525.4 (MH+)

Example 1329

2-[2-(8-tert-Butyl-4,4-dimethyl-1,1-dioxo-1lambda*6*-thiochroman-6-yl)-2-oxo-ethyl]-6-ethoxy-3-imino-2,3-dihydro-1H-isoindole-5-carboxamide hydrobromide MS: m/e (ESI) 526.2 (MH+)

Example 1330

2-[2-(8-tert-Butyl-4,4-dimethyl-chroman-6-yl)-2-oxo-ethyl]-6-ethoxy-3-imino-2,3-dihydro-1H-isoindole-5-carboxamide hydrobromide MS: m/e (ESI) 478.4 (MH+)

Example 1331

4-{3-tert-Butyl-5-[2-(5,6-diethoxy-7-fluoro-1-imino-1,3-dihydro-isoindol-2-yl)-acetyl]-2-hydroxy-phenoxy}-butanoic acid hydrobromide MS: m/e (ESI) 531.4 (MH+)

Example 1332

4-{3-tert-Butyl-5-[2-(5,6-diethoxy-7-fluoro-1-imino-1,3-dihydro-isoindol-2-yl)-acetyl]-2-hydroxy-phenoxy}-butylamide hydrobromide MS: m/e (ESI) 530.4 (MH+)

Example 1333

4-{2-tert-Butyl-4-[2-(5,6-diethoxy-7-fluoro-1-imino-1,3-dihydro-isoindol-2-yl)-acetyl]-6-methoxy-phenoxy}-butanoic acid hydrobromide MS: m/e (ESI) 545.4 (MH+)

Example 1334

4-{2-tert-Butyl-4-[2-(5,6-diethoxy-7-fluoro-1-imino-1,3-dihydro-isoindol-2-yl)-acetyl]-6-methoxy-phenoxy}-butylamide hydrobromide MS: m/e (ESI) 544.4 (MH+)

Example 1335

1-(8-tert-Butyl-4,4-dimethyl-1,1-dioxo-1lambda*6*-thiochroman-6-yl)-2-(5,6-diethoxy-7-fluoro-1-imino-1,3-dihydro-isoindol-2-yl)-ethanone hydrobromide MS: m/e (ESI) 545.4 (MH+)

Example 1336

1-(8-tert-Butyl-4,4-dimethyl-chroman-6-yl)-2-(5,6-diethoxy-7-fluoro-1-imino-1,3-dihydro-isoindol-2-yl)-ethanone hydrobromide MS: m/e (ESI) 497.4 (MH+)

Example 1337

{2-tert-Butyl-4-[2-(5,6-diethoxy-7-fluoro-1-imino-1,3-dihydro-isoindol-2-yl)-acetyl]-phenyl}-acetic acid hydrobromide MS: m/e (ESI) 471.4 (MH+)

Example 1338

{2-tert-Butyl-4-[2-(5,6-diethoxy-7-fluoro-1-imino-1,3-dihydro-isoindol-2-yl)-acetyl]-6-thiophen-2-yl-phenoxy}-acetic acid hydrobromide MS: m/e (ESI) 569.3 (MH+)

Example 1339

2-{2-tert-Butyl-4-[2-(5,6-diethoxy-7-fluoro-1-imino-1,3-dihydro-isoindol-2-yl)-acetyl]-phenoxy}-propionic acid hydrobromide MS: m/e (ESI) 501.4 (MH+)

Example 1340

[2-tert-Butyl-4-[2-(5,6-diethoxy-7-fluoro-1-imino-1,3-dihydro-isoindol-2-yl)-acetyl]-6-(methanesulfonyl-methyl-amino)-phenoxy]-acetic acid hydrobromide MS: m/e (ESI) 594.4 (MH+)

Example 1341

{6-[2-(5,6-Diethoxy-7-fluoro-1-imino-1,3-dihydro-isoindol-2-yl)-acetyl]-4,4-dimethyl-2-oxo-3,4-dihydro-2H-quinolin-1-yl}-acetic acid hydrobromide MS: m/e (ESI) 512.3 (MH+)

Example 1342

(Acetyl-{3-tert-butyl-5-[2-(7-fluoro-1-imino-5,6-dimethoxy-1,3-dihydro-isoindol-2-yl)-acetyl]-2-hydroxy-benzyl}-amino)-acetic acid hydrobromide MS: m/e (ESI) 530.4 (MH+)

Example 1343

{3-tert-Butyl-5-[2-(7-fluoro-1-imino-5,6-dimethoxy-1,3-dihydro-isoindol-2-yl)-acetyl]-2-hydroxy-benzylamino}-acetic acid hydrobromide MS: m/e (ESI) 488.3 (MH+)

Example 1344

{2-tert-Butyl-4-[2-(7-fluoro-1-imino-5,6-dimethoxy-1,3-dihydro-isoindol-2-yl)-acetyl]-phenyl}-acetic acid hydrobromide MS: m/e (ESI) 443.3 (MH+)

Example 1345

{2-tert-Butyl-4-[2-(7-fluoro-1-imino-5,6-dimethoxy-1,3-dihydro-isoindol-2-yl)-acetyl]-6-thiophen-2-yl-phenoxy}-acetic acid hydrobromide MS: m/e (ESI) 541.4 (MH+)

Example 1346

2-{2-tert-Butyl-4-[2-(7-fluoro-1-imino-5,6-dimethoxy-1,3-dihydro-isoindol-2-yl)-acetyl]-phenoxy}-propionic acid hydrobromide MS: m/e (ESI) 473.3 (MH+)

Example 1347

{6-[2-(7-Fluoro-1-imino-5,6-dimethoxy-1,3-dihydro-isoindol-2-yl)-acetyl]-4,4-dimethyl-2-oxo-3,4-dihydro-2H-quinolin-1-yl}-acetic acid hydrobromide MS: m/e (ESI) 484.3 (MH+)

Example 1348

{2-tert-Butyl-4-[2-(5,6-diethoxy-7-fluoro-1-imino-1,3-dihydro-isoindol-2-yl)-acetyl]-6-dimethylamino-phenoxy}-acetic acid hydrobromide MS: m/e (ESI) 530.1 (MH+)

Example 1349

{2-tert-Butyl-4-[2-(6-carbamoyl-5-ethoxy-1-imino-1,3-dihydro-isoindol-2-yl)-acetyl]-6-dimethylamino-phenoxy}-acetic acid hydrobromide MS: m/e (ESI) 511.2 (MH+)

Example 1350

{2-tert-Butyl-6-dimethylamino-4-[2-(1-imino-5-isopropoxy-6-methylcarbamoyl-1,3-dihydro-isoindol-2-yl)-acetyl]-phenoxy}-acetic acid hydrobromide MS: m/e (ESI) 539.3 (MH+)

Example 1351

{2-tert-Butyl-6-dimethylamino-4-[2-(1-imino-6-methylcarbamoyl-5-propoxy-1,3-dihydro-isoindol-2-yl)-acetyl]-phenoxy}-acetic acid hydrobromide MS: m/e (ESI) 539.3 (MH+)

Example 1352

{2-tert-Butyl-6-dimethylamino-4-[2-(1-imino-5-methoxy-6-methylcarbamoyl-1,3-dihydro-isoindol-2-yl)-acetyl]-phenoxy}-acetic acid hydrobromide MS: m/e (ESI) 511.4 (MH+)

Example 1353

{2-tert-Butyl-6-dimethylamino-4-[2-(5-ethoxy-1-imino-6-methylcarbamoyl-1,3-dihydro-isoindol-2-yl)-acetyl]-phenoxy}-acetic acid hydrobromide MS: m/e (ESI) 525.4 (MH+)

Example 1354

({2-tert-Butyl-4-[2-(5,6-diethoxy-7-fluoro-1-imino-1,3-dihydro-isoindol-2-yl)-acetyl]-6-diethylamino-phenoxy}-acetic acid hydrobromide MS: m/e (ESI) 558.4 (MH+)

Example 1355

{2-tert-Butyl-4-[2-(6-carbamoyl-5-ethoxy-1-imino-1,3-dihydro-isoindol-2-yl)-acetyl]-6-diethylamino-phenoxy}-acetic acid hydrobromide MS: m/e (ESI) 539.4 (MH+)

Example 1356

{2-tert-Butyl-6-diethylamino-4-[2-(1-imino-5-isopropoxy-6-methylcarbamoyl-1,3-dihydro-isoindol-2-yl)-acetyl]-phenoxy}-acetic acid hydrobromide MS: m/e (ESI) 567.5 (MH+)

Example 1357

{2-tert-Butyl-6-diethylamino-4-[2-(1-imino-6-methylcarbamoyl-5-propoxy-1,3-dihydro-isoindol-2-yl)-acetyl]-phenoxy}-acetic acid hydrobromide MS: m/e (ESI) 567.5 (MH+)

Example 1358

{2-tert-Butyl-6-diethylamino-4-[2-(1-imino-5-methoxy-6-methylcarbamoyl-1,3-dihydro-isoindol-2-yl}-acetyl]-phenoxy)-acetic acid hydrobromide MS: m/e (ESI) 539.5 (MH+)

Example 1359

(Acetyl-{2-tert-butyl-4-[2-(5,6-diethoxy-7-fluoro-1-imino-1,3-dihydro-isoindol-2-yl)-acetyl]-phenyl}-amino)-acetic acid hydrobromide MS: m/e (ESI) 528.5 (MH+)

Example 1360

(Acetyl-{2-tert-butyl-4-[2-(3-ethoxy-7-imino-2,4-dimethyl-5,7-dihydro-pyrrolo[3,4-b]pyridin-6-yl)-acetyl]-phenyl}-amino)-acetic acid hydrobromide MS: m/e (ESI) 495.5 (MH+)

Example 1361

(Acetyl-{2-tert-butyl-4-[2-(6-carbamoyl-5-ethoxy-1-imino-1,3-dihydro-isoindol-2-yl)-acetyl]-phenyl}-amino)-acetic acid hydrobromide MS: m/e (ESI) 509.5 (MH+)

Example 1362

(Acetyl-{2-tert-butyl-4-[2-(1-imino-5-isopropoxy-6-methylcarbamoyl-1,3-dihydro-isoindol-2-yl)-acetyl]-phenyl}-amino)-acetic acid hydrobromide MS: m/e (ESI) 537.5 (MH+)

Example 1363

(Acetyl-{2-tert-butyl-4-[2-(1-imino-6-methylcarbamoyl-5-propoxy-1,3-dihydro-isoindol-2-yl)-acetyl]-phenyl}-amino)-acetic acid hydrobromide MS: m/e (ESI) 537.5 (MH+)

Example 1364

(Acetyl-{2-tert-butyl-4-[2-(1-imino-5-methoxy-6-methylcarbamoyl-1,3-dihydro-isoindol-2-yl)-acetyl]-phenyl}-amino)-acetic acid hydrobromide MS: m/e (ESI) 509.5 (MH+)

Example 1365

({2-tert-Butyl-4-[2-(5,6-diethoxy-7-fluoro-1-imino-1,3-dihydro-isoindol-2-yl)-acetyl]-phenyl}-methyl-amino)-acetic acid hydrobromide MS: m/e (ESI) 500.5 (MH+)

Example 1366

({2-tert-Butyl-4-[2-(3-ethoxy-7-imino-2,4-dimethyl-5,7-dihydro-pyrrolo[3,4-b]pyridin-6-yl)-acetyl]-phenyl}-methyl-amino)-acetic acid hydrobromide MS: m/e (ESI) 467.5 (MH+)

Example 1367

({2-tert-Butyl-4-[2-(6-carbamoyl-5-ethoxy-1-imino-1,3-dihydro-isoindol-2-yl)-acetyl]-phenyl}-methyl-amino)-acetic acid hydrobromide MS: m/e (ESI) 481.5 (MH+)

Example 1368

({2-tert-Butyl-4-[2-(1-imino-5-isopropoxy-6-methylcarbamoyl-1,3-dihydro-isoindol-2-yl)-acetyl]-phenyl}-methyl-amino)-acetic acid hydrobromide MS: m/e (ESI) 509.5 (MH+)

Example 1369

({2-tert-Butyl-4-[2-(1-imino-6-methylcarbamoyl-5-propoxy-1,3-dihydro-isoindol-2-yl)-acetyl]-phenyl}-methyl-amino)-acetic acid hydrobromide MS: m/e (ESI) 509.5 (MH+)

Example 1370

({2-tert-Butyl-4-[2-(1-imino-5-methoxy-6-methylcarbamoyl-1,3-dihydro-isoindol-2-yl)-acetyl]-phenyl}-methyl-amino)-acetic acid hydrobromide MS: m/e (ESI) 481.5 (MH+)

Example 1371

1-(3-tert-Butyl-4-hydroxy-5-isopropoxy-phenyl)-2-(5,6-diethoxy-7-fluoro-1-imino-1,3-dihydro-isoindol-2-yl)-ethanone hydrobromide MS: m/e (ESI) 487.5 (MH+)

Example 1372

2-[2-(3-tert-Butyl-4-hydroxy-5-isopropoxy-phenyl)-2-oxo-ethyl]-6-ethoxy-3-imino-2,3-dihydro-1H-isoindole-5-carboxamide hydrobromide MS: m/e (ESI) 468.5 (MH+)

Example 1373

7-tert-Butyl-9-[2-(2-ethyl-7-imino-5,7-dihydro-pyrrolo[3,4-b]pyridin-6-yl)-acetyl]-6-oxa-10b-aza-benzo[e]azulen-4-one hydrobromide MS: m/e (ESI) 457.4 (MH+)

Example 1374

{8-tert-Butyl-6-[2-(2-ethyl-7-imino-5,7-dihydro-pyrrolo[3,4-b]pyridin-6-yl)-acetyl]-3-oxo-2,3-dihydro-benzo[1,4]oxazin-4-yl}-acetic acid hydrobromide MS: m/e (ESI) 465.4 (MH+)

Example 1375

3-{8-tert-Butyl-6-[2-(2-ethyl-7-imino-5,7-dihydro-pyrrolo[3,4-b]pyridin-6-yl)-acetyl]-2,3-dihydro-benzo[1,4]oxazin-4-yl}-propionic acid hydrobromide MS: m/e (ESI) 465.4 (MH+)

Example 1376

2-{8-tert-Butyl-6-[2-(2-ethyl-7-imino-5,7-dihydro-pyrrolo[3,4-b]pyridin-6-yl)-acetyl]-2,3-dihydro-benzo[1,4]oxazin-4-yl}-propionic acid hydrobromide MS: m/e (ESI) 465.4 (MH+)

Example 1377

2-{8-tert-Butyl-6-[2-(2-ethyl-7-imino-5,7-dihydro-pyrrolo[3,4-b]pyridin-6-yl)-acetyl]-2,3-dihydro-benzo[1,4]oxazin-4-yl}-2-methyl-propionic acid hydrobromide MS: m/e (ESI) 479.5 (MH+)

Example 1378

2-[2-(7-tert-Butyl-4-oxo-4,5-dihydro-6-oxa-10b-aza-benzo[e]azulen-9-yl)-2-oxo-ethyl]-6-ethoxy-3-imino-2,3-dihydro-1H-isoindole-5-acetic acid methylamide hydrobromide MS: m/e (ESI) 529.5 (MH+)

Example 1379

{8-tert-Butyl-6-[2-(5-ethoxy-1-imino-6-methylcarbamoyl-1,3-dihydro-isoindol-2-yl)-acetyl]-3-oxo-2,3-dihydro-benzo[1,4]oxazin-4-yl}-acetic acid hydrobromide MS: m/e (ESI) 537.5 (MH+)

Example 1380

3-{8-tert-Butyl-6-[2-(5-ethoxy-1-imino-6-methylcarbamoyl-1,3-dihydro-isoindol-2-yl)-acetyl]-2,3-dihydro-benzo[1,4]oxazin-4-yl}-propionic acid hydrobromide MS: m/e (ESI) 537.5 (MH+)

Example 1381

7-tert-Butyl-9-[2-(5,6-diethoxy-7-fluoro-1-imino-1,3-dihydro-isoindol-2-yl)-acetyl]-6-oxa-10b-aza-benzo[e]azulen-4-one hydrobromide MS: m/e (ESI) 534.5 (MH+)

Example 1382

7-tert-Butyl-9-[2-(5,6-diethoxy-7-fluoro-1-imino-1,3-dihydro-isoindol-2-yl)-acetyl]-6-oxa-10b-aza-benzo[e]azulen-4-one hydrobromide MS: m/e (ESI) 542.5 (MH+)

Example 1383

3-{8-tert-Butyl-6-[2-(5,6-diethoxy-7-fluoro-1-imino-1,3-dihydro-isoindol-2-yl)-acetyl]-2,3-dihydro-benzo[1,4]oxazin-4-yl}-propionic acid hydrobromide MS: m/e (ESI) 542.5 (MH+)

Example 1384

7-tert-Butyl-9-[2-(7-fluoro-1-imino-5,6-dimethoxy-1,3-dihydro-isoindol-2-yl)-acetyl]-6-oxa-10b-aza-benzo[e]azulen-4-one hydrobromide MS: m/e (ESI) 506.4 (MH+)

Example 1385

{8-tert-Butyl-6-[2-(7-fluoro-1-imino-5,6-dimethoxy-1,3-dihydro-isoindol-2-yl)-acetyl]-3-oxo-2,3-dihydro-benzo[1,4]oxazin-4-yl}-acetic acid hydrobromide MS: m/e (ESI) 514.4 (MH+)

Example 1386

3-{8-tert-Butyl-6-[2-(7-fluoro-1-imino-5,6-dimethoxy-1,3-dihydro-isoindol-2-yl)-acetyl]-2,3-dihydro-benzo[1,4]oxazin-4-yl}-propionic acid hydrobromide MS: m/e (ESI) 514.4 (MH+)

Example 1387

3-{3-tert-Butyl-5-[2-(2-ethyl-7-imino-5,7-dihydro-pyrrolo[3,4-b]pyridin-6-yl)-acetyl]-2-hydroxy-benzylamino}-propionic acid hydrobromide MS: m/e (ESI) 453.4 (MH+)

Example 1388

3-(Acetyl-{3-tert-butyl-5-[2-(2-ethyl-7-imino-5,7-dihydro-pyrrolo[3,4-b]pyridin-6-yl)-acetyl]-2-hydroxy-benzyl}-amino)-propionic acid hydrobromide MS: m/e (ESI) 495.4 (MH+)

Example 1389

{2-tert-Butyl-4-[2-(2-ethyl-7-imino-5,7-dihydro-pyrrolo[3,4-b]pyridin-6-yl)-acetyl]-6-methylaminomethyl-phenoxy}-acetic acid hydrobromide MS: m/e (ESI) 453.4 (MH+)

Example 1390

4-{8-tert-Butyl-6-[2-(2-ethyl-7-imino-5,7-dihydro-pyrrolo[3,4-b]pyridin-6-yl)-acetyl]-2,3-dihydro-benzo[1,4]oxazin-4-yl}-butanoic acid hydrobromide MS: m/e (ESI) 479.4 (MH+)

Example 1391

4-{2-tert-Butyl-4-[2-(2-ethyl-7-imino-5,7-dihydro-pyrrolo[3,4-b]pyridin-6-yl)-acetyl]-6-pyrrolidin-1-yl-phenoxy}-butanoic acid hydrobromide MS: m/e (ESI) 507.5 (MH+)

Example 1392

5-{2-tert-Butyl-4-[2-(2-ethyl-7-imino-5,7-dihydro-pyrrolo[3,4-b]pyridin-6-yl)-acetyl]-6-pyrrolidin-1-yl-phenoxy}-pentanoic acid hydrobromide MS: m/e (ESI) 521.5 (MH+)

Example 1393

[2-tert-Butyl-4-[2-(2-ethyl-7-imino-5,7-dihydro-pyrrolo[3,4-b]pyridin-6-yl)-acetyl]-6-(2-oxo-pyrrolidin-1-yl)-phenoxy]-acetic acid hydrobromide MS: m/e (ESI) 493.4 (MH+)

Example 1394

4-{2-tert-Butyl-4-[2-(2-cyclopropyl-7-imino-5,7-dihydro-pyrrolo[3,4-b]pyridin-6-yl)-acetyl]-6-pyrrolidin-1-yl-phenoxy}-butanoic acid hydrobromide MS: m/e (ESI) 519.5 (MH+)

Example 1395

5-{2-tert-Butyl-4-[2-(2-cyclopropyl-7-imino-5,7-dihydro-pyrrolo[3,4-b]pyridin-6-yl)-acetyl]-6-pyrrolidin-1-yl-phenoxy}-pentanoic acid hydrobromide MS: m/e (ESI) 533.5 (MH+)

Example 1396

3-{3-tert-Butyl-5-[2-(5-dimethylamino-1-imino-6-methylcarbamoyl-1,3-dihydro-isoindol-2-yl)-acetyl]-2-hydroxy-benzylamino}-propionic acid hydrobromide MS: m/e (ESI) 524.2 (MH+)

Example 1397

3-(Acetyl-{3-tert-butyl-5-[2-(5-dimethylamino-1-imino-6-methylcarbamoyl-1,3-dihydro-isoindol-2-yl)-acetyl]-2-hydroxy-benzyl}-amino)-propionic acid hydrobromide MS: m/e (ESI) 566.5 (MH+)

Example 1398

{2-tert-Butyl-4-[2-(5-dimethylamino-1-imino-6-methylcarbamoyl-1,3-dihydro-isoindol-2-yl)-acetyl]-6-methylaminomethyl-phenoxy}-acetic acid hydrobromide MS: m/e (ESI) 524.4 (MH+)

Example 1399

4-{8-tert-Butyl-6-[2-(5-dimethylamino-1-imino-6-methylcarbamoyl-1,3-dihydro-isoindol-2-yl)-acetyl]-2,3-dihydro-benzo[1,4]oxazin-4-yl}-butanoic acid hydrobromide MS: m/e (ESI) 550.5 (MH+)

Example 1400

4-{2-tert-Butyl-4-[2-(5-dimethylamino-1-imino-6-methylcarbamoyl-1,3-dihydro-isoindol-2-yl)-acetyl]-6-pyrrolidin-1-yl-phenoxy}-butanoic acid hydrobromide MS: m/e (ESI) 578.5 (MH+)

Example 1401

5-{2-tert-Butyl-4-[2-(5-dimethylamino-1-imino-6-methylcarbamoyl-1,3-dihydro-isoindol-2-yl)-acetyl]-6-pyrrolidin-1-yl-phenoxy}-pentanoic acid hydrobromide MS: m/e (ESI) 592.6 (MH+)

Example 1402

[2-tert-Butyl-4-[2-(5-dimethylamino-1-imino-6-methylcarbamoyl-1,3-dihydro-isoindol-2-yl)-acetyl]-6-(2-oxo-pyrrolidin-1-yl)-phenoxy]-acetic acid hydrobromide MS: m/e (ESI) 564.5 (MH+)

Example 1403

{2-tert-Butyl-6-dimethylamino-4-[2-(5-dimethylamino-1-imino-6-methylcarbamoyl-1,3-dihydro-isoindol-2-yl)-acetyl]-phenoxy}-acetic acid hydrobromide MS: m/e (ESI) 524.5 (MH+)

Example 1404

3-{3-tert-Butyl-5-[2-(5-ethoxy-1-imino-6-methylcarbamoyl-1,3-dihydro-isoindol-2-yl)-acetyl]-2-hydroxy-benzylamino}-propionic acid hydrobromide MS: m/e (ESI) 525.5 (MH+)

Example 1405

3-(Acetyl-{3-tert-butyl-5-[2-(5-ethoxy-1-imino-6-methylcarbamoyl-1,3-dihydro-isoindol-2-yl)-acetyl]-2-hydroxy-benzyl}-amino)-propionic acid hydrobromide MS: m/e (ESI) 567.5 (MH+)

Example 1406

{2-tert-Butyl-4-[2-(5-ethoxy-1-imino-6-methylcarbamoyl-1,3-dihydro-isoindol-2-yl)-acetyl]-6-methylaminomethyl-phenoxy}-acetic acid hydrobromide MS: m/e (ESI) 525.5 (MH+)

Example 1407

4-{8-tert-Butyl-6-[2-(5-ethoxy-1-imino-6-methylcarbamoyl-1,3-dihydro-isoindol-2-yl)-acetyl]-2,3-dihydro-benzo[1,4]oxazin-4-yl}-butanoic acid hydrobromide MS: m/e (ESI) 551.5 (MH+)

Example 1408

4-{2-tert-Butyl-4-[2-(6-carbamoyl-5-ethoxy-1-imino-1,3-dihydro-isoindol-2-yl)-acetyl]-6-pyrrolidin-1-yl-phenoxy}-butanoic acid hydrobromide MS: m/e (ESI) 565.5 (MH+)

Example 1409

5-{2-tert-Butyl-4-[2-(6-carbamoyl-5-ethoxy-1-imino-1,3-dihydro-isoindol-2-yl)-acetyl]-6-pyrrolidin-1-yl-phenoxy}-pentanoic acid hydrobromide MS: m/e (ESI) 579.5 (MH+)

Example 1410

[2-tert-Butyl-4-[2-(6-carbamoyl-5-ethoxy-1-imino-1,3-dihydro-isoindol-2-yl)-acetyl]-6-(2-oxo-pyrrolidin-1-yl)-phenoxy]-acetic acid hydrobromide MS: m/e (ESI) 551.4 (MH+)

Example 1411

3-{3-tert-Butyl-5-[2-(5,6-diethoxy-7-fluoro-1-imino-1,3-dihydro-isoindol-2-yl)-acetyl]-2-hydroxy-benzylamino}-propionic acid hydrobromide MS: m/e (ESI) 530.5 (MH+)

Example 1412

3-(Acetyl-{3-tert-butyl-5-[2-(5,6-diethoxy-7-fluoro-1-imino-1,3-dihydro-isoindol-2-yl)-acetyl]-2-hydroxy-benzyl}-amino)-propionic acid hydrobromide MS: m/e (ESI) 572.5 (MH+)

Example 1413

{2-tert-Butyl-4-[2-(5,6-diethoxy-7-fluoro-1-imino-1,3-dihydro-isoindol-2-yl)-acetyl]-6-methylaminomethyl-phenoxy}-acetic acid hydrobromide MS: m/e (ESI) 530.5 (MH+)

Example 1414

4-{8-tert-Butyl-6-[2-(5,6-diethoxy-7-fluoro-1-imino-1,3-dihydro-isoindol-2-yl)-acetyl]-2,3-dihydro-benzo[1,4]oxazin-4-yl}-butanoic acid hydrobromide MS: m/e (ESI) 556.5 (MH+)

Example 1415

3-{3-tert-Butyl-5-[2-(7-fluoro-1-imino-5,6-dimethoxy-1,3-dihydro-isoindol-2-yl}-acetyl]-2-hydroxy-benzylamino)-propionic acid hydrobromide MS: m/e (ESI) 502.4 (MH+)

Example 1416

3-(Acetyl-{3-tert-butyl-5-[2-(7-fluoro-1-imino-5,6-dimethoxy-1,3-dihydro-isoindol-2-yl)-acetyl]-2-hydroxy-benzyl}-amino)-propionic acid hydrobromide MS: m/e (ESI) 544.4 (MH+)

Example 1417

{2-tert-Butyl-4-[2-(7-fluoro-1-imino-5,6-dimethoxy-1,3-dihydro-isoindol-2-yl)-acetyl]-6-methylaminomethyl-phenoxy}-acetic acid hydrobromide MS: m/e (ESI) 502.4 (MH+)

Example 1418

4-{8-tert-Butyl-6-[2-(7-fluoro-1-imino-5,6-dimethoxy-1,3-dihydro-isoindol-2-yl)-acetyl]-2,3-dihydro-benzo[1,4]oxazin-4-yl}-butanoic acid hydrobromide MS: m/e (ESI) 528.4 (MH+)

Example 1419

4-{2-tert-Butyl-4-[2-(7-fluoro-1-imino-5,6-dimethoxy-1,3-dihydro-isoindol-2-yl)-acetyl]-6-pyrrolidin-1-yl-phenoxy}-butanoic acid hydrobromide MS: m/e (ESI) 556.4 (MH+)

Example 1420

5-{2-tert-Butyl-4-[2-(7-fluoro-1-imino-5,6-dimethoxy-1,3-dihydro-isoindol-2-yl)-acetyl]-6-pyrrolidin-1-yl-phenoxy}-pentanoic acid hydrobromide MS: m/e (ESI) 570.5 (MH+)

Example 1421

[2-tert-Butyl-4-[2-(7-fluoro-1-imino-5,6-dimethoxy-1,3-dihydro-isoindol-2-yl)-acetyl]-6-(2-oxo-pyrrolidin-1-yl)-phenoxy]-acetic acid hydrobromide MS: m/e (ESI) 542.4 (MH+)

Example 1422

[2-tert-Butyl-4-[2-(2-cyclopropyl-7-imino-5,7-dihydro-pyrrolo[3,4-b]pyridin-6-yl)-acetyl]-6-(3-hydroxy-pyrrolidin-1-yl)-phenoxy]-acetic acid hydrobromide MS: m/e (ESI) 507.4 (MH+)

Example 1423

[2-tert-Butyl-4-[2-(5-ethoxy-1-imino-6-methylcarbamoyl-1,3-dihydro-isoindol-2-yl)-acetyl]-6-(3-hydroxy-pyrrolidin-1-yl)-phenoxy]-acetic acid hydrobromide MS: m/e (ESI) 567.4 (MH+)

Example 1424

[2-tert-Butyl-4-[2-(5-dimethylamino-1-imino-6-methylcarbamoyl-1,3-dihydro-isoindol-2-yl)-acetyl]-6-(3-hydroxy-pyrrolidin-1-yl)-phenoxy]-acetic acid hydrobromide MS: m/e (ESI) 566.5 (MH+)

Example 1425

[2-tert-Butyl-4-[2-(5,6-diethoxy-7-fluoro-1-imino-1,3-dihydro-isoindol-2-yl)-acetyl]-6-(3-hydroxy-pyrrolidin-1-yl)-phenoxy]-acetic acid hydrobromide MS: m/e (ESI) 572.4 (MH+)

Example 1426

[2-tert-Butyl-4-[2-(7-fluoro-1-imino-5,6-dimethoxy-1,3-dihydro-isoindol-2-yl)-acetyl]-6-(3-hydroxy-pyrrolidin-1-yl)-phenoxy]-acetic acid hydrobromide MS: m/e (ESI) 544.4 (MH+)

Example 1427

(1-{3-tert-Butyl-5-[2-(2-cyclopropyl-7-imino-5,7-dihydro-pyrrolo[3,4-b]pyridin-6-yl)-acetyl]-2-hydroxy-phenyl}-pyrrolidin-3-yloxy)-acetic acid hydrobromide MS: m/e (ESI) 507.1 (MH+)

Example 1428

(1-{3-tert-Butyl-5-[2-(5-ethoxy-1-imino-6-methylcarbamoyl-1,3-dihydro-isoindol-2-yl)-acetyl]-2-hydroxy-phenyl}-pyrrolidin-3-yloxy)-acetic acid hydrobromide MS: m/e (ESI) 567.2 (MH+)

Example 1429

(1-{3-tert-Butyl-5-[2-(5-dimethylamino-1-imino-6-methylcarbamoyl-1,3-dihydro-isoindol-2-yl)-acetyl]-2-hydroxy-phenyl}-pyrrolidin-3-yloxy)-acetic acid hydrobromide MS: m/e (ESI) 566.3 (MH+)

Example 1430

(1-{3-tert-Butyl-5-[2-(5,6-diethoxy-7-fluoro-1-imino-1,3-dihydro-isoindol-2-yl)-acetyl]-2-hydroxy-phenyl}-pyrrolidin-3-yloxy)-acetic acid hydrobromide MS: m/e (ESI) 572.3 (MH+)

Example 1431

(1-{3-tert-Butyl-5-[2-(7-fluoro-1-imino-5,6-dimethoxy-1,3-dihydro-isoindol-2-yl)-acetyl]-2-hydroxy-phenyl}-pyrrolidin-3-yloxy)-acetic acid hydrobromide MS: m/e (ESI) 544.3 (MH+)

Example 1432

1-{3-tert-Butyl-5-[2-(2-cyclopropyl-7-imino-5,7-dihydro-pyrrolo[3,4-b]pyridin-6-yl)-acetyl]-2-hydroxy-benzyl}-5-oxo-pyrrolidine-2-carboxylic acid hydrobromide MS: m/e (ESI) 505.4 (MH+)

Example 1433

1-{3-tert-Butyl-5-[2-(5-ethoxy-1-imino-6-methylcarbamoyl-1,3-dihydro-isoindol-2-yl)-acetyl]-2-hydroxy-benzyl}-5-oxo-pyrrolidine-2-carboxylic acid hydrobromide MS: m/e (ESI) 565.4 (MH+)

Example 1434

1-{3-tert-Butyl-5-[2-(5-dimethylamino-1-imino-6-methylcarbamoyl-1,3-dihydro-isoindol-2-yl)-acetyl]-2-hydroxy-benzyl}-5-oxo-pyrrolidine-2-carboxylic acid hydrobromide MS: m/e (ESI) 564.4 (MH+)

Example 1435

1-{3-tert-Butyl-5-[2-(5,6-diethoxy-7-fluoro-1-imino-1,3-dihydro-isoindol-2-yl)-acetyl]-2-hydroxy-benzyl}-5-oxo-pyrrolidine-2-carboxylic acid hydrobromide MS: m/e (ESI) 570.4 (MH+)

Example 1436

1-{3-tert-Butyl-5-[2-(7-fluoro-1-imino-5,6-dimethoxy-1,3-dihydro-isoindol-2-yl)-acetyl]-2-hydroxy-benzyl}-5-oxo-pyrrolidine-2-carboxylic acid hydrobromide MS: m/e (ESI) 542.4 (MH+)

Example 1437

{2-Cyclopentyl-4-[2-(5,6-diethoxy-7-fluoro-1-imino-1,3-dihydro-isoindol-2-yl)-acetyl]-phenoxy}-acetic acid hydrobromide MS: m/e (ESI) 499.3 (MH+)

Example 1438

{2-Cyclopentyl-4-[2-(2-cyclopropyl-7-imino-5,7-dihydro-pyrrolo[3,4-b]pyridin-6-yl)-acetyl]-phenoxy}-acetic acid hydrobromide MS: m/e (ESI) 434.3 (MH+)

Example 1439

1-(7-tert-Butyl-2-methyl-benzoxazol-5-yl)-2-(5,6-diethoxy-7-fluoro-1-imino-1,3-dihydro-isoindol-2-yl)-ethanone hydrobromide MS: m/e (ESI) 468.4 (MH+)

Example 1440

1-(7-tert-Butyl-2-methyl-benzoxazol-5-yl)-2-(2-cyclopropyl-7-imino-5,7-dihydro-pyrrolo[3,4-b]pyridin-6-yl)-ethanone hydrobromide MS: m/e (ESI) 403.4 (MH+)

Example 1441

4-{2-tert-Butyl-4-[2-(5-dimethylamino-1-imino-6-methylcarbamoyl-1,3-dihydro-isoindol-2-yl)-acetyl)]-6-methoxy-phenoxy}-butanoic acid hydrobromide MS: m/e (ESI) 539.5 (MH+)

Example 1442

4-{2-tert-Butyl-4-[2-(2-cyclopropyl-7-imino-5,7-dihydro-pyrrolo[3,4-b]pyridin-6-yl)-acetyl]-6-methoxy-phenoxy}-butanoic acid hydrobromide MS: m/e (ESI) 480.4 (MH+)

Example 1443

2-{2-[3-tert-Butyl-4-(3-carbamoyl-propoxy)-5-methoxy-phenyl]-2-oxo-ethyl}-6-dimethylamino-3-imino-2,3-dihydro-1H-isoindole-5-carboxylic acid methylamide hydrobromide MS: m/e (ESI) 538.5 (MH+)

Example 1444

4-{2-tert-Butyl-4-[2-(2-cyclopropyl-7-imino-5,7-dihydro-pyrrolo[3,4-b]pyridin-6-yl)-acetyl]-6-methoxy-phenoxy}-butylamide hydrobromide MS: m/e (ESI) 479.5 (MH+)

Example 1445

{2-tert-Butyl-4-[2-(6-carbamoyl-5-ethoxy-1-imino-1,3-dihydro-isoindol-2-yl)-acetyl]-6-morpholin-4-yl-phenoxy}-acetic acid hydrobromide MS: m/e (ESI) 553.5 (MH+)

Example 1446

{2-tert-Butyl-4-[2-(2-cyclopropyl-7-imino-5,7-dihydro-pyrrolo[3,4-b]pyridin-6-yl)-acetyl]-6-morpholin-4-yl-phenoxy}-acetic acid hydrobromide MS: m/e (ESI) 507.5 (MH+)

Example 1447

2-{2-[3-(Acetyl-methyl-amino)-5-tert-butyl-4-(3-carbamoyl-propoxy)-phenyl]-2-oxo-ethyl}-6-ethoxy-3-imino-2,3-dihydro-1H-isoindole-5-acetic acid methylamide hydrobromide MS: m/e (ESI) 580.6 (MH+)

Example 1448

4-{3-tert-Butyl-2-hydroxy-5-[2-(1-imino-1,3-dihydro-isoindol-2-yl)-acetyl]-phenoxy}-butylamide hydrobromide MS: m/e (ESI) 424.1 (MH+)

Example 1449

4-{3-tert-Butyl-5-[2-(6-ethoxy-1-imino-1,3-dihydro-isoindol-2-yl)-acetyl]-2-hydroxy-phenoxy}-butylamide hydrobromide MS: m/e (ESI) 468.2 (MH+)

Example 1450

4-{3-tert-Butyl-5-[2-(5-ethoxy-1-imino-1,3-dihydro-isoindol-2-yl)-acetyl]-2-hydroxy-phenoxy}-butylamide hydrobromide MS: m/e (ESI) 468.3 (MH+)

Example 1451

4-{3-tert-Butyl-2-hydroxy-5-[2-(1-imino-5-methoxy-1,3-dihydro-isoindol-2-yl)-acetyl]-phenoxy}-butylamide hydrobromide MS: m/e (ESI) 454.3 (MH+)

Example 1452

4-{3-tert-Butyl-5-[2-(6-fluoro-1-imino-1,3-dihydro-isoindol-2-yl)-acetyl]-2-hydroxy-phenoxy}-butylamide hydrobromide MS: m/e (ESI) 442.3 (MH+)

Example 1453

4-{3-tert-Butyl-5-[2-(5-ethoxy-7-fluoro-1-imino-1,3-dihydro-isoindol-2-yl)-acetyl]-2-hydroxy-phenoxy}-butylamide hydrobromide MS: m/e (ESI) 486.4 (MH+)

Example 1454

4-{3-tert-Butyl-5-[2-(1-imino-1,3-dihydro-isoindol-2-yl)-acetyl]-2-methoxy-phenoxy}-butylamide hydrobromide MS: m/e (ESI) 438.4 (MH+)

Example 1455

4-{3-tert-Butyl-5-[2-(6-ethoxy-1-imino-1,3-dihydro-isoindol-2-yl)-acetyl]-2-methoxy-phenoxy}-butylamide hydrobromide MS: m/e (ESI) 482.5 (MH+)

Example 1456

4-{3-tert-Butyl-5-[2-(5-ethoxy-1-imino-1,3-dihydro-isoindol-2-yl)-acetyl]-2-methoxy-phenoxy}-butylamide hydrobromide MS: m/e (ESI) 482.5 (MH+)

Example 1457

4-{3-tert-Butyl-5-[2-(1-imino-5-methoxy-1,3-dihydro-isoindol-2-yl)-acetyl]-2-methoxy-phenoxy}-butylamide hydrobromide MS: m/e (ESI) 468.4 (MH+)

Example 1458

4-{3-tert-Butyl-5-[2-(6-fluoro-1-imino-1,3-dihydro-isoindol-2-yl)-acetyl]-2-methoxy-phenoxy}-butylamide hydrobromide MS: m/e (ESI) 456.4 (MH+)

Example 1459

4-{3-tert-Butyl-5-[2-(5-ethoxy-7-fluoro-1-imino-1,3-dihydro-isoindol-2-yl)-acetyl]-2-methoxy-phenoxy}-butylamide hydrobromide MS: m/e (ESI) 500.5 (MH+)

Example 1460

[2-tert-Butyl-4-[2-(6-ethoxy-1-imino-1,3-dihydro-isoindol-2-yl)-acetyl]-6-(3-hydroxy-pyrrolidin-1-yl)-phenoxy]-acetic acid hydrobromide MS: m/e (ESI) 510.4 (MH+)

Example 1461

[2-tert-Butyl-4-[2-(5-ethoxy-1-imino-1,3-dihydro-isoindol-2-yl)-acetyl]-6-(3-hydroxy-pyrrolidin-1-yl)-phenoxy]-acetic acid hydrobromide MS: m/e (ESI) 510.4 (MH+)

Example 1462

{2-tert-Butyl-6-(3-hydroxy-pyrrolidin-1-yl)-4-[2-(1-imino-5-methoxy-1,3-dihydro-isoindol-2-yl)-acetyl]-phenoxy}-acetic acid hydrobromide MS: m/e (ESI) 496.4 (MH+)

Example 1463

[2-tert-Butyl-4-[2-(6-fluoro-1-imino-1,3-dihydro-isoindol-2-yl)-acetyl]-6-(3-hydroxy-pyrrolidin-1-yl)-phenoxy]-acetic acid hydrobromide MS: m/e (ESI) 484.3 (MH+)

Example 1464

[2-tert-Butyl-4-[2-(5-ethoxy-7-fluoro-1-imino-1,3-dihydro-isoindol-2-yl)-acetyl]-6-(3-hydroxy-pyrrolidin-1-yl)-phenoxy]-acetic acid hydrobromide MS: m/e (ESI) 528.3 (MH+)

Example 1465

(1-{3-tert-Butyl-2-hydroxy-5-[2-(1-imino-1,3-dihydro-isoindol-2-yl)-acetyl]-phenyl}-pyrrolidin-3-yloxy)-acetic acid hydrobromide MS: m/e (ESI) 466.4 (MH+)

Example 1466

(1-{3-tert-Butyl-5-[2-(6-ethoxy-1-imino-1,3-dihydro-isoindol-2-yl)-acetyl]-2-hydroxy-phenyl}-pyrrolidin-3-yloxy)-acetic acid hydrobromide MS: m/e (ESI) 510.4 (MH+)

Example 1467

(1-{3-tert-Butyl-5-[2-(5-ethoxy-1-imino-1,3-dihydro-isoindol-2-yl)-acetyl]-2-hydroxy-phenyl}-pyrrolidin-3-yloxy)-acetic acid hydrobromide MS: m/e (ESI) 510.4 (MH+)

Example 1468

(1-{3-tert-Butyl-2-hydroxy-5-[2-(1-imino-5-methoxy-1,3-dihydro-isoindol-2-yl)-acetyl]-phenyl}-pyrrolidin-3-yloxy)-acetic acid hydrobromide MS: m/e (ESI) 496.4 (MH+)

Example 1469

(1-{3-tert-Butyl-5-[2-(6-fluoro-1-imino-1,3-dihydro-isoindol-2-yl)-acetyl]-2-hydroxy-phenyl}-pyrrolidin-3-yloxy)-acetic acid hydrobromide MS: m/e (ESI) 484.4 (MH+)

Example 1470

(1-{3-tert-Butyl-5-[2-(5-ethoxy-7-fluoro-1-imino-1,3-dihydro-isoindol-2-yl)-acetyl]-2-hydroxy-phenyl}-pyrrolidin-3-yloxy)-acetic acid hydrobromide MS: m/e (ESI) 528.3 (MH+)

Example 1471

({3-tert-Butyl-5-[2-(5-ethoxy-1-imino-6-methylcarbamoyl-1,3-dihydro-isoindol-2-yl)-acetyl]-2-hydroxy-benzyl}-methoxycarbonyl-amino)-acetic acid hydrobromide MS: m/e (ESI) 569.5 (MH+)

Example 1472

({3-tert-Butyl-5-[2-(5-dimethylamino-1-imino-6-methylcarbamoyl-1,3-dihydro-isoindol-2-yl)-acetyl]-2-hydroxy-benzyl}-methoxycarbonyl-amino)-acetic acid hydrobromide MS: m/e (ESI) 568.5 (MH+)

Example 1473

({3-tert-Butyl-5-[2-(5,6-diethoxy-7-fluoro-1-imino-1,3-dihydro-isoindol-2-yl)-acetyl]-2-hydroxy-benzyl}-methoxycarbonyl-amino)-acetic acid hydrobromide MS: m/e (ESI) 574.4 (MH+)

Example 1474

({3-tert-Butyl-5-[2-(7-fluoro-1-imino-5,6-dimethoxy-1,3-dihydro-isoindol-2-yl)-acetyl]-2-hydroxy-benzyl}-methoxycarbonyl-amino)-acetic acid hydrobromide MS: m/e (ESI) 546.3 (MH+)

Example 1475

({3-tert-Butyl-5-[2-(2-ethyl-7-imino-5,7-dihydro-pyrrolo[3,4-b]pyridin-6-yl)-acetyl]-2-hydroxy-benzyl}-methanesulfonyl-amino)-acetic acid hydrobromide MS: m/e (ESI) 517.3 (MH+)

Example 1476

({3-tert-Butyl-5-[2-(5-ethoxy-1-imino-6-methylcarbamoyl-1,3-dihydro-isoindol-2-yl)-acetyl]-2-hydroxy-benzyl}-methanesulfonylamino)-acetic acid hydrobromide MS: m/e (ESI) 589.4 (MH+)

Example 1477

({3-tert-Butyl-5-[2-(5-dimethylamino-1-imino-6-methylcarbamoyl-1,3-dihydro-isoindol-2-yl)-acetyl]-2-hydroxy-benzyl}-methanesulfonyl-amino)-acetic acid hydrobromide MS: m/e (ESI) 588.4 (MH+)

Example 1478

({3-tert-Butyl-5-[2-(5,6-diethoxy-7-fluoro-1-imino-1,3-dihydro-isoindol-2-yl)-acetyl]-2-hydroxy-benzyl}-methanesulfonyl-amino)-acetic acid hydrobromide MS: m/e (ESI) 594.5 (MH+)

Example 1479

({3-tert-Butyl-5-[2-(7-fluoro-1-imino-5,6-dimethoxy-1,3-dihydro-isoindol-2-yl)-acetyl]-2-hydroxy-benzyl}-methanesulfonyl-amino)-acetic acid hydrobromide MS: m/e (ESI) 566.4 (MH+)

Example 1480

{2-tert-Butyl-6-(3-carbamoyl-propoxy)-4-[2-(2-ethyl-7-imino-5,7-dihydro-pyrrolo[3,4-b]pyridin-6-yl)-acetyl]-phenoxy}-acetic acid hydrobromide MS: m/e (ESI) 511.4 (MH+)

Example 1481

{2-tert-Butyl-6-(3-carbamoyl-propoxy)-4-[2-(5-ethoxy-1-imino-6-methylcarbamoyl-1,3-dihydro-isoindol-2-yl)-acetyl]-phenoxy}-acetic acid hydrobromide MS: m/e (ESI) 583.5 (MH+)

Example 1482

{2-tert-Butyl-6-(3-carbamoyl-propoxy)-4-[2-(5,6-diethoxy-7-fluoro-1-imino-1,3-dihydro-isoindol-2-yl)-acetyl]-phenoxy}-acetic acid hydrobromide MS: m/e (ESI) 588.5 (MH+)

Example 1483

(1-{3-tert-Butyl-2-hydroxy-5-[2-(7-imino-2-methyl-5,7-dihydro-pyrrolo[3,4-b]pyridin-6-yl)-acetyl]-phenyl}-pyrrolidin-3-yloxy)-acetic acid hydrobromide MS: m/e (ESI) 481.4 (MH+)

Example 1484

{2-tert-Butyl-6-(3-hydroxy-pyrrolidin-1-yl)-4-[2-(7-imino-2-methyl-5,7-dihydro-pyrrolo[3,4-b]pyridin-6-yl)-acetyl]-phenoxy}-acetic acid hydrobromide MS: m/e (ESI) 481.4 (MH+)

Example 1485

{2-tert-Butyl-6-dimethylamino-4-[2-(7-imino-2-methyl-5,7-dihydro-pyrrolo[3,4-b]pyridin-6-yl)-acetyl]-phenoxy}-acetic acid hydrobromide MS: m/e (ESI) 439.4 (MH+)

Example 1486

(1-{3-tert-Butyl-5-[2-(2-ethyl-7-imino-5,7-dihydro-pyrrolo[3,4-b]pyridin-6-yl)-acetyl]-2-hydroxy-phenyl}-pyrrolidin-3-yloxy)-acetic acid hydrobromide MS: m/e (ESI) 495.3 (MH+)

Example 1487

[2-tert-Butyl-4-[2-(2-ethyl-7-imino-5,7-dihydro-pyrrolo[3,4-b]pyridin-6-yl)-acetyl]-6-(3-hydroxy-pyrrolidin-1-yl)-phenoxy]-acetic acid hydrobromide MS: m/e (ESI) 495.4 (MH+)

Example 1488

{2-tert-Butyl-6-dimethylamino-4-[2-(2-ethyl-7-imino-4,4a,5,7-tetrahydro-pyrrolo[3,4-b]pyridin-6-yl)-acetyl]-phenoxy}-acetic acid hydrobromide MS: m/e (ESI) 453.4 (MH+)

Example 1489

4-{2-tert-Butyl-6-dimethylamino-4-[2-(5-ethoxy-1-imino-6-methylcarbamoyl-1,3-dihydro-isoindol-2-yl)-acetyl]-phenoxy}-butanoic acid hydrobromide MS: m/e (ESI) 553.2 (MH+)

Example 1490

6-{2-tert-Butyl-6-dimethylamino-4-[2-(5-ethoxy-1-imino-6-methylcarbamoyl-1,3-dihydro-isoindol-2-yl)-acetyl]-phenoxy}-hexanoic acid hydrobromide MS: m/e (ESI) 581.5 (MH+)

Example 1491

{2-(4-Acetylamino-butoxy)-6-tert-butyl-4-[2-(5-ethoxy-1-imino-6-methylcarbamoyl-1,3-dihydro-isoindol-2-yl)-acetyl]-phenoxy}-acetic acid hydrobromide MS: m/e (ESI) 611.5 (MH+)

Example 1492

4-{2-Acetylamino-6-tert-butyl-4-[2-(5-ethoxy-1-imino-6-methylcarbamoyl-1,3-dihydro-isoindol-2-yl)-acetyl]-phenoxy}-butanoic acid hydrobromide MS: m/e (ESI) 567.5 (MH+)

Example 1493

6-Ethoxy-3-imino-2-[2-(8-isopropyl-4-methyl-3,4-dihydro-2H-benzo[1,4]oxazin-6-yl)-2-oxo-ethyl]-2,3-dihydro-1H-isoindole-5-carboxylic acid methylamide hydrobromide MS: m/e (ESI) 465.4 (MH+)

Example 1494

{6-[2-(5-Ethoxy-1-imino-6-methylcarbamoyl-1,3-dihydro-isoindol-2-yl)-acetyl]-8-isopropyl-2,3-dihydro-benzo[1,4]oxazin-4-yl}-acetic acid hydrobromide MS: m/e (ESI) 509.3 (MH+)

Example 1495

4-{6-[2-(5-Ethoxy-1-imino-6-methylcarbamoyl-1,3-dihydro-isoindol-2-yl)-acetyl]-4,4-dimethyl-2-oxo-3,4-dihydro-2H-quinolin-1-yl}-butanoic acid hydrobromide MS: m/e (ESI) 535.4 (MH+)

Example 1496

4-{2-tert-Butyl-4-[2-(6-carbamoyl-5-ethoxy-1-imino-1,3-dihydro-isoindol-2-yl)-acetyl]-6-dimethylamino-phenoxy}-butanoic acid hydrobromide MS: m/e (ESI) 539.3 (MH+)

Example 1497

6-{2-tert-Butyl-4-[2-(6-carbamoyl-5-ethoxy-1-imino-1,3-dihydro-isoindol-2-yl)-acetyl]-6-dimethylamino-phenoxy}-hexanoic acid hydrobromide MS: m/e (ESI) 567.5 (MH+)

Example 1498

4-{2-tert-Butyl-6-dimethylamino-4-[2-(5-ethoxy-4-fluoro-1-imino-6-methylcarbamoyl-1,3-dihydro-isoindol-2-yl)-acetyl]-phenoxy}-butanoic acid hydrobromide MS: m/e (ESI) 571.3 (MH+)

Example 1499

6-{2-tert-Butyl-6-dimethylamino-4-[2-(5-ethoxy-4-fluoro-1-imino-6-methylcarbamoyl-1,3-dihydro-isoindol-2-yl)-acetyl]-phenoxy}-hexanoic acid hydrobromide MS: m/e (ESI) 599.5 (MH+)

Example 1500

(1-{3-tert-Butyl-5-[2-(5-ethoxy-4-fluoro-1-imino-6-methylcarbamoyl-1,3-dihydro-isoindol-2-yl)-acetyl]-2-hydroxy-phenyl}-pyrrolidin-3-yloxy)-acetic acid hydrobromide MS: m/e (ESI) 585.5 (MH+)

Example 1501

4-{6-[2-(5-Dimethylamino-1-imino-6-methylcarbamoyl-1,3-dihydro-isoindol-2-yl)-acetyl]-4,4-dimethyl-2-oxo-3,4-dihydro-2H-quinolin-1-yl}-butanoic acid hydrobromide MS: m/e (ESI) 534.4 (MH+)

Example 1502

4-{2-tert-Butyl-4-[2-(5,6-diethoxy-7-fluoro-1-imino-1,3-dihydro-isoindol-2-yl)-acetyl]-6-dimethylamino-phenoxy}-butanoic acid hydrobromide MS: m/e (ESI) 558.4 (MH+)

Example 1503

6-{2-tert-Butyl-4-[2-(5,6-diethoxy-7-fluoro-1-imino-1,3-dihydro-isoindol-2-yl)-acetyl]-6-dimethylamino-phenoxy}-hexanoic acid hydrobromide MS: m/e (ESI) 586.5 (MH+)

Example 1504

{2-(4-Acetylamino-butoxy)-6-tert-butyl-4-[2-(5,6-diethoxy-7-fluoro-1-imino-1,3-dihydro-isoindol-2-yl)-acetyl]-phenoxy}-acetic acid hydrobromide MS: m/e (ESI) 616.5 (MH+)

Example 1505

4-{2-Acetylamino-6-tert-butyl-4-[2-(5,6-diethoxy-7-fluoro-1-imino-1,3-dihydro-isoindol-2-yl)-acetyl]-phenoxy}-butanoic acid hydrobromide MS: m/e (ESI) 572.5 (MH+)

Example 1506

2-(5,6-Diethoxy-7-fluoro-1-imino-1,3-dihydro-isoindol-2-yl)-1-(8-isopropyl-4-methyl-3,4-dihydro-2H-benzo[1,4]oxazin-6-yl)-ethanone hydrobromide MS: m/e (ESI) 470.4 (MH+)

Example 1507

{6-[2-(5,6-Diethoxy-7-fluoro-1-imino-1,3-dihydro-isoindol-2-yl)-acetyl]-8-isopropyl-2,3-dihydro-benzo[1,4]oxazin-4-yl}-acetic acid hydrobromide MS: m/e (ESI) 514.3 (MH+)

Example 1508

Ethyl (4-{3-tert-butyl-5-[2-(5,6-diethoxy-7-fluoro-1-imino-1,3-dihydro-isoindol-2-yl)-acetyl]-benzyl}-piperazin-1-yl)-acetate hydrobromide MS: m/e (ESI) 597.5 (MH+)

Example 1509

4-{6-[2-(5,6-Diethoxy-7-fluoro-1-imino-1,3-dihydro-isoindol-2-yl)-acetyl]-4,4-dimethyl-2-oxo-3,4-dihydro-2H-quinolin-1-yl}-butanoic acid hydrobromide MS: m/e (ESI) 540.4 (MH+)

Example 1510

4-{2-tert-Butyl-6-dimethylamino-4-[2-(7-fluoro-1-imino-5,6-dimethoxy-1,3-dihydro-isoindol-2-yl)-acetyl]-phenoxy}-butanoic acid hydrobromide MS: m/e (ESI) 530.4 (MH+)

Example 1511

6-{2-tert-Butyl-6-dimethylamino-4-[2-(7-fluoro-1-imino-5,6-dimethoxy-1,3-dihydro-isoindol-2-yl)-acetyl]-phenoxy}-hexanoic acid hydrobromide MS: m/e (ESI) 558.5 (MH+)

Example 1512

{2-(4-Acetylamino-butoxy)-6-tert-butyl-4-[2-(7-fluoro-1-imino-5,6-dimethoxy-1,3-dihydro-isoindol-2-yl)-acetyl]-phenoxy}-acetic acid hydrobromide MS: m/e (ESI) 588.5 (MH+)

Example 1513

4-{2-Acetylamino-6-tert-butyl-4-[2-(7-fluoro-1-imino-5,6-dimethoxy-1,3-dihydro-isoindol-2-yl)-acetyl]-phenoxy}-butanoic acid hydrobromide MS: m/e (ESI) 544.4 (MH+)

Example 1514

2-(7-Fluoro-1-imino-5,6-dimethoxy-1,3-dihydro-isoindol-2-yl)-1-(8-isopropyl-4-methyl-3,4-dihydro-2H-benzo[1,4]oxazin-6-yl)-ethanone hydrobromide MS: m/e (ESI) 442.4 (MH+)

Example 1515

{6-[2-(7-Fluoro-1-imino-5,6-dimethoxy-1,3-dihydro-isoindol-2-yl)-acetyl]-8-isopropyl-2,3-dihydro-benzo[1,4]oxazin-4-yl}-acetic acid hydrobromide MS: m/e (ESI) 486.3 (MH+)

Example 1516

Ethyl (4-{3-tert-butyl-5-[2-(7-fluoro-1-imino-5,6-dimethoxy-1,3-dihydro-isoindol-2-yl)-acetyl]-benzyl}-piperazin-1-yl)-acetate hydrobromide MS: m/e (ESI) 569.5 (MH+)

Example 1517

4-{6-[2-(7-Fluoro-1-imino-5,6-dimethoxy-1,3-dihydro-isoindol-2-yl)-acetyl]-4,4-dimethyl-2-oxo-3,4-dihydro-2H-quinolin-1-yl}-butanoic acid hydrobromide MS: m/e (ESI) 512.4 (MH+)

Example 1518

{2-(4-Acetylamino-butoxy)-6-tert-butyl-4-[2-(2-ethyl-7-imino-5,7-dihydro-pyrrolo[3,4-b]pyridin-6-yl)-acetyl]-phenoxy}-acetic acid hydrobromide MS: m/e (ESI) 539.5 (MH+)

Example 1519

4-{2-Acetylamino-6-tert-butyl-4-[2-(2-ethyl-7-imino-5,7-dihydro-pyrrolo[3,4-b]pyridin-6-yl)-acetyl]-phenoxy}-butanoic acid hydrobromide MS: m/e (ESI) 495.4 (MH+)

Example 1520

2-(2-Ethyl-7-imino-5,7-dihydro-pyrrolo[3,4-b]pyridin-6-yl)-1-(8-isopropyl-4-methyl-3,4-dihydro-2H-benzo[1,4]oxazin-6-yl)-ethanone hydrobromide MS: m/e (ESI) 393.4 (MH+)

Example 1521

{6-[2-(2-Ethyl-7-imino-5,7-dihydro-pyrrolo[3,4-b]pyridin-6-yl)-acetyl]-8-isopropyl-2,3-dihydro-benzo[1,4]oxazin-4-yl}-acetic acid hydrobromide MS: m/e (ESI) 437.3 (MH+)

Example 1522

Ethyl (4-{3-tert-butyl-5-[2-(2-ethyl-7-imino-5,7-dihydro-pyrrolo[3,4-b]pyridin-6-yl)-acetyl]-benzyl}-piperazin-1-yl)-acetate hydrobromide MS: m/e (ESI) 520.5 (MH+)

Example 1523

4-{6-[2-(2-Ethyl-7-imino-5,7-dihydro-pyrrolo[3,4-b]pyridin-6-yl)-acetyl]-4,4-dimethyl-2-oxo-3,4-dihydro-2H-quinolin-1-yl}-butanoic acid hydrobromide MS: m/e (ESI) 463.4 (MH+)

Example 1524

{2-(4-Acetylamino-butoxy)-6-tert-butyl-4-[2-(2-cyclopropyl-7-imino-5,7-dihydro-pyrrolo[3,4-b]pyridin-6-yl)-acetyl]-phenoxy}-acetic acid hydrobromide MS: m/e (ESI) 551.5 (MH+)

Example 1525

4-{2-Acetylamino-6-tert-butyl-4-[2-(2-cyclopropyl-7-imino-5,7-dihydro-pyrrolo[3,4-b]pyridin-6-yl)-acetyl]-phenoxy}-butanoic acid hydrobromide MS: m/e (ESI) 507.4 (MH+)

Example 1526

2-(2-Cyclopropyl-7-imino-5,7-dihydro-pyrrolo[3,4-b]pyridin-6-yl)-1-(8-isopropyl-4-methyl-3,4-dihydro-2H-benzo[1,4]oxazin-6-yl)-ethanone hydrobromide MS: m/e (ESI) 405.4 (MH+)

Example 1527

{6-[2-(2-Cyclopropyl-7-imino-5,7-dihydro-pyrrolo[3,4-b]pyridin-6-yl)-acetyl]-8-isopropyl-2,3-dihydro-benzo[1,4]oxazin-4-yl}-acetic acid hydrobromide MS: m/e (ESI) 449.3 (MH+)

Example 1528

Ethyl (4-{3-tert-butyl-5-[2-(2-cyclopropyl-7-imino-5,7-dihydro-pyrrolo[3,4-b]pyridin-6-yl)-acetyl]-benzyl}-piperazin-1-yl)-acetate hydrobromide MS: m/e (ESI) 532.5 (MH+)

Example 1529

4-{6-[2-(2-Cyclopropyl-7-imino-5,7-dihydro-pyrrolo[3,4-b]pyridin-6-yl)-acetyl]-4,4-dimethyl-2-oxo-3,4-dihydro-2H-quinolin-1-yl}-butanoic acid hydrobromide MS: m/e (ESI) 475.4 (MH+)

Example 1530

Ethyl [4-(3-tert-butyl-5-{2-[5-ethoxy-1-imino-6-(1-methoxy-propyl)-1,3-dihydro-isoindol-2-yl]-acetyl}-benzyl)-piperazin-1-yl]-acetate hydrobromide MS: m/e (ESI) 607.6 (MH+)

Example 1531

(2-tert-Butyl-6-dimethylamino-4-{2-[5-ethoxy-1-imino-6-(1-methoxy-propyl)-1,3-dihydro-isoindol-2-yl]-acetyl}-phenoxy)-acetic acid hydrobromide MS: m/e (ESI) 540.4 (MH+)

Example 1532

Ethyl (4-{3-tert-butyl-5-[2-(6-tert-butyl-1-imino-1,3-dihydro-isoindol-2-yl)-acetyl]-benzyl}-piperazin-1-yl)-acetate hydrobromide MS: m/e (ESI) 547.2 (MH+)

Example 1533

{2-tert-Butyl-4-[2-(6-tert-butyl-1-imino-1,3-dihydro-isoindol-2-yl)-acetyl]-6-dimethylamino-phenoxy}-acetic acid hydrobromide MS: m/e (ESI) 480.4 (MH+)

Example 1534

{2-(4-Acetylamino-butoxy)-6-tert-butyl-4-[2-(6-tert-butyl-1-imino-1,3-dihydro-isoindol-2-yl)-acetyl]-phenoxy}-acetic acid hydrobromide MS: m/e (ESI) 566.5 (MH+)

Example 1535

{2-tert-Butyl-4-[2-(6-tert-butyl-1-imino-1,3-dihydro-isoindol-2-yl)-acetyl]-6-pyrrolidin-1-yl-phenoxy}-acetic acid hydrobromide MS: m/e (ESI) 506.5 (MH+)

Example 1536

4-{3-tert-Butyl-5-[2-(6-tert-butyl-1-imino-1,3-dihydro-isoindol-2-yl)-acetyl]-2-methoxy-phenoxy}-butylamide hydrobromide MS: m/e (ESI) 494.5 (MH+)

Example 1537

4-{3-tert-Butyl-5-[2-(6-tert-butyl-1-imino-1,3-dihydro-isoindol-2-yl)-acetyl]-2-hydroxy-phenoxy}-butylamide hydrobromide MS: m/e (ESI) 480.5 (MH+)

Example 1538

4-{2-tert-Butyl-4-[2-(6-tert-butyl-1-imino-1,3-dihydro-isoindol-2-yl)-acetyl]-6-methoxy-phenoxy}-butylamide hydrobromide MS: m/e (ESI) 494.3 (MH+)

Example 1539

{2-tert-Butyl-4-[2-(6-tert-butyl-1-imino-1,3-dihydro-isoindol-2-yl)-acetyl]-6-morpholin-4-yl-phenoxy}-acetic acid hydrobromide MS: m/e (ESI) 522.3 (MH+)

Example 1540

4-{3-tert-Butyl-2-hydroxy-5-[2-(7-imino-2-methyl-5,7-dihydro-pyrrolo[3,4-b]pyridin-6-yl)-acetyl]-phenoxy}-butylamide hydrobromide MS: m/e (ESI) 439.4 (MH+)

Example 1541

{2-tert-Butyl-4-[2-(2-cyclopropyl-7-imino-5,7-dihydro-pyrrolo[3,4-b]pyridin-6-yl)-acetyl]-6-pyrrolidin-1-ylmethyl-phenoxy}-acetic acid hydrobromide MS: m/e (ESI) 505.1 (MH+)

Example 1542

1-{3-tert-Butyl-5-[2-(2-cyclopropyl-7-imino-5,7-dihydro-pyrrolo[3,4-b]pyridin-6-yl)-acetyl]-2-methoxy-phenyl}-pyrrolidine-3-carboxylic acid hydrobromide MS: m/e (ESI) 491.2 (MH+)

Example 1543

4-{2-Acetylamino-6-tert-butyl-4-[2-(2-cyclopropyl-7-imino-5,7-dihydro-pyrrolo[3,4-b]pyridin-6-yl)-acetyl]-phenoxy}-butylamide hydrobromide MS: m/e (ESI) 506.2 (MH+)

Example 1544

5-{2-Acetylamino-6-tert-butyl-4-[2-(2-cyclopropyl-7-imino-5,7-dihydro-pyrrolo[3,4-b]pyridin-6-yl)-acetyl]-phenoxy}-pentanoic acid hydrobromide MS: m/e (ESI) 521.3 (MH+)

Example 1545

1-{3-tert-Butyl-4-hydroxy-5-[3-(2-methoxy-ethoxy)-propoxy]-phenyl}-2-(2-cyclopropyl-7-imino-5,7-dihydro-pyrrolo[3,4-b]pyridin-6-yl)-ethanone hydrobromide MS: m/e (ESI) 496.3 (MH+)

Example 1546

4-{3-tert-Butyl-5-[2-(2-cyclopropyl-7-imino-5,7-dihydro-pyrrolo[3,4-b]pyridin-6-yl)-acetyl]-2-hydroxy-phenoxy}-butyronitrile hydrobromide MS: m/e (ESI) 447.3 (MH+)

Example 1547

3-{7-tert-Butyl-5-[2-(2-cyclopropyl-7-imino-5,7-dihydro-pyrrolo[3,4-b]pyridin-6-yl)-acetyl]-benzoxazol-2-yl}-propionic acid hydrobromide MS: m/e (ESI) 461.3 (MH+)

Example 1548

{2-tert-Butyl-4-[2-(5-ethoxy-1-imino-6-methylcarbamoyl-1,3-dihydro-isoindol-2-yl)-acetyl]-6-pyrrolidin-1-ylmethyl-phenoxy}-acetic acid hydrobromide MS: m/e (ESI) 565.4 (MH+)

Example 1549

1-{3-tert-Butyl-5-[2-(5-ethoxy-1-imino-6-methylcarbamoyl-1,3-dihydro-isoindol-2-yl)-acetyl]-2-methoxy-phenyl}-pyrrolidine-3-carboxylic acid hydrobromide MS: m/e (ESI) 551.3 (MH+)

Example 1550

2-{2-[3-Acetylamino-5-tert-butyl-4-(3-carbamoyl-propoxy)-phenyl]-2-oxo-ethyl}-6-ethoxy-3-imino-2,3-dihydro-1H-isoindole-5-acetic acid methylamide hydrobromide MS: m/e (ESI) 566.4 (MH+)

Example 1551

5-{2-Acetylamino-6-tert-butyl-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 581.4 (MH+)

Example 1552

{2-tert-Butyl-4-[2-(5,6-diethoxy-7-fluoro-1-imino-1,3-dihydro-isoindol-2-yl)-acetyl]-6-pyrrolidin-1-ylmethyl-phenoxy}-acetic acid hydrobromide MS: m/e (ESI) 570.4 (MH+)

Example 1553

1-{3-tert-Butyl-5-[2-(5,6-diethoxy-7-fluoro-1-imino-1,3-dihydro-isoindol-2-yl)-acetyl]-2-methoxy-phenyl}-pyrrolidine-3-carboxylic acid hydrobromide MS: m/e (ESI) 556.3 (MH+)

Example 1554

1-{3-tert-Butyl-4-hydroxy-5-[3-(2-methoxy-ethoxy)-propoxy]-phenyl}-2-(5,6-diethoxy-7-fluoro-1-imino-1,3-dihydro-isoindol-2-yl)-ethanone hydrobromide MS: m/e (ESI) 561.4 (MH+)

Example 1555

4-{3-tert-Butyl-5-[2-(5,6-diethoxy-7-fluoro-1-imino-1,3-dihydro-isoindol-2-yl)-acetyl]-2-hydroxy-phenoxy}-butyronitrile hydrobromide MS: m/e (ESI) 512.3 (MH+)

Example 1556

3-{7-tert-Butyl-5-[2-(5,6-diethoxy-7-fluoro-1-imino-1,3-dihydro-isoindol-2-yl)-acetyl]-benzoxazol-2-yl}-propionic acid hydrobromide MS: m/e (ESI) 526.3 (MH+)

Example 1557

4-{2-Acetylamino-6-tert-butyl-4-[2-(7-fluoro-1-imino-5,6-dimethoxy-1,3-dihydro-isoindol-2-yl)-acetyl]-phenoxy}-butylamide hydrobromide MS: m/e (ESI) 543.3 (MH+)

Example 1558

5-{2-Acetylamino-6-tert-butyl-4-[2-(7-fluoro-1-imino-5,6-dimethoxy-1,3-dihydro-isoindol-2-yl)-acetyl]-phenoxy}-pentanoic acid hydrobromide MS: m/e (ESI) 558.4 (MH+)

Example 1559

(1-{5-[2-(2-Cyclopropyl-7-imino-5,7-dihydro-pyrrolo[3,4-b]pyridin-6-yl)-acetyl]-2-hydroxy-phenyl}-pyrrolidin-3-yloxy)-acetic acid hydrobromide MS: m/e (ESI) 451.3 (MH+)

Example 1560

(1-{5-[2-(5-Ethoxy-1-imino-6-methylcarbamoyl-1,3-dihydro-isoindol-2-yl)-acetyl]-2-hydroxy-phenyl}-pyrrolidin-3-yloxy)-acetic acid hydrobromide MS: m/e (ESI) 511.4 (MH+)

Example 1561

(1-{5-[2-(7-Fluoro-1-imino-5,6-dimethoxy-1,3-dihydro-isoindol-2-yl)-acetyl]-2-hydroxy-phenyl}-pyrrolidin-3-yloxy)-acetic acid hydrobromide MS: m/e (ESI) 488.3 (MH+)

Example 1562

(1-{3-[2-(5-Ethoxy-1-imino-6-methylcarbamoyl-1,3-dihydro-isoindol-2-yl)-acetyl]-phenyl}-pyrrolidin-3-yloxy)-acetic acid hydrobromide MS: m/e (ESI) 495.4 (MH+)

Example 1563

{4-tert-Butyl-6-[2-(5-ethoxy-1-imino-6-methylcarbamoyl-1,3-dihydro-isoindol-2-yl)-acetyl]-benzimidazol-1-yl}-acetic acid hydrobromide MS: m/e (ESI) 506.4 (MH+)

Example 1564

{4-tert-Butyl-6-[2-(5,6-diethoxy-7-fluoro-1-imino-1,3-dihydro-isoindol-2-yl)-acetyl]-benzimidazol-1-yl}-acetic acid hydrobromide MS: m/e (ESI) 511.3 (MH+)

Example 1565

[4-[2-(2-Cyclopropyl-7-imino-5,7-dihydro-pyrrolo[3,4-b]pyridin-6-yl)-acetyl]-2-(3-hydroxy-pyrrolidin-1-yl)-phenoxy]-acetic acid hydrobromide MS: m/e (ESI) 451.2 (MH+)

Example 1566

[4-[2-(5-Ethoxy-1-imino-6-methylcarbamoyl-1,3-dihydro-isoindol-2-yl)-acetyl]-2-(3-hydroxy-pyrrolidin-1-yl)-phenoxy]-acetic acid hydrobromide MS: m/e (ESI) 511.3 (MH+)

Example 1567

[4-[2-(7-Fluoro-1-imino-5,6-dimethoxy-1,3-dihydro-isoindol-2-yl)-acetyl]-2-(3-hydroxy-pyrrolidin-1-yl)-phenoxy]-acetic acid hydrobromide MS: m/e (ESI) 488.3 (MH+)

Example 1568

(1-{3-tert-Butyl-5-[2-(2-cyclopropyl-7-imino-5,7-dihydro-pyrrolo[3,4-b]pyridin-6-yl)-acetyl]-2-methoxy-phenyl}-pyrrolidin-2-yl)-acetic acid hydrobromide MS: m/e (ESI) 505.4 (MH+)

Example 1569

1-(7-tert-Butyl-3-methyl-3H-benzimidazol-5-yl)-2-(2-cyclopropyl-7-imino-5,7-dihydro-pyrrolo[3,4-b]pyridin-6-yl)-ethanone hydrobromide MS: m/e (ESI) 402.3 (MH+)

Example 1570

1-(7-tert-Butyl-3H-benzimidazol-5-yl)-2-(2-cyclopropyl-7-imino-5,7-dihydro-pyrrolo[3,4-b]pyridin-6-yl)-ethanone hydrobromide MS: m/e (ESI) 388.3 (MH+)

Example 1571

1-[3-tert-Butyl-4-hydroxy-5-(4-hydroxy-butoxy)-phenyl]-2-(2-cyclopropyl-7-imino-5,7-dihydro-pyrrolo[3,4-b]pyridin-6-yl)-ethanone hydrobromide MS: m/e (ESI) 452.4 (MH+)

Example 1572

[2-tert-Butyl-4-[2-(2-cyclopropyl-7-imino-5,7-dihydro-pyrrolo[3,4-b]pyridin-6-yl)-acetyl]-6-(4-hydroxy-butoxy)-phenoxy]-acetic acid hydrobromide MS: m/e (ESI) 510.4 (MH+)

Example 1573

1-(3-tert-Butyl-phenyl)-2-(2-cyclopropyl-7-imino-5,7-dihydro-pyrrolo[3,4-b]pyridin-6-yl)-ethanone hydrobromide MS: m/e (ESI) 348.4 (MH+)

Example 1574

(1-{3-tert-Butyl-5-[2-(5-ethoxy-1-imino-6-methylcarbamoyl-1,3-dihydro-isoindol-2-yl)-acetyl]-2-methoxy-phenyl}-pyrrolidin-2-yl)-acetic acid hydrobromide MS: m/e (ESI) 565.4 (MH+)

Example 1575

2-[2-(7-tert-Butyl-3-methyl-3H-benzimidazol-5-yl)-2-oxo-ethyl]-6-ethoxy-3-imino-2,3-dihydro-1H-isoindole-5-acetic acid methylamide hydrobromide MS: m/e (ESI) 462.4 (MH+)

Example 1576

2-[2-(7-tert-Butyl-3H-benzimidazol-5-yl)-2-oxo-ethyl]-6-ethoxy-3-imino-2,3-dihydro-1H-isoindole-5-acetic acid methylamide hydrobromide MS: m/e (ESI) 448.0 (MH+)

Example 1577

2-{2-[3-tert-Butyl-4-hydroxy-5-(4-hydroxy-butoxy)-phenyl]-2-oxo-ethyl}-6-ethoxy-3-imino-2,3-dihydro-1H-isoindole-5-acetic acid methylamide hydrobromide MS: m/e (ESI) 512.2 (MH+)

Example 1578

[2-tert-Butyl-4-[2-(5-ethoxy-1-imino-6-methylcarbamoyl-1,3-dihydro-isoindol-2-yl)-acetyl]-6-(4-hydroxy-butoxy)-phenoxy]-acetic acid hydrobromide MS: m/e (ESI) 570.3 (MH+)

Example 1579

2-{2-[3-tert-Butyl-4-hydroxy-5-(4-hydroxy-butoxy)-phenyl]-2-oxo-ethyl}-6-dimethylamino-3-imino-2,3-dihydro-1H-isoindole-5-carboxylic acid methylamide hydrobromide MS: m/e (ESI) 511.3 (MH+)

Example 1580

[2-tert-Butyl-4-[2-(5-dimethylamino-1-imino-6-methylcarbamoyl-1,3-dihydro-isoindol-2-yl)-acetyl]-6-(4-hydroxy-butoxy)-phenoxy]-acetic acid hydrobromide MS: m/e (ESI) 569.3 (MH+)

Example 1581

(1-{3-tert-Butyl-5-[2-(5,6-diethoxy-7-fluoro-1-imino-1,3-dihydro-isoindol-2-yl)-acetyl]-2-methoxy-phenyl}-pyrrolidin-2-yl)-acetic acid hydrobromide MS: m/e (ESI) 570.3 (MH+)

Example 1582

1-(7-tert-Butyl-3-methyl-3H-benzimidazol-5-yl)-2-(5,6-diethoxy-7-fluoro-1-imino-1,3-dihydro-isoindol-2-yl)-ethanone hydrobromide MS: m/e (ESI) 467.3 (MH+)

Example 1583

1-(7-tert-Butyl-3H-benzimidazol-5-yl)-2-(5,6-diethoxy-7-fluoro-1-imino-1,3-dihydro-isoindol-2-yl)-ethanone hydrobromide MS: m/e (ESI) 453.3 (MH+)

Example 1584

1-[3-tert-Butyl-4-hydroxy-5-(4-hydroxy-butoxy)-phenyl]-2-(5,6-diethoxy-7-fluoro-1-imino-1,3-dihydro-isoindol-2-yl)-ethanone hydrobromide MS: m/e (ESI) 517.4 (MH+)

Example 1585

[2-tert-Butyl-4-[2-(5,6-diethoxy-7-fluoro-1-imino-1,3-dihydro-isoindol-2-yl)-acetyl]-6-(4-hydroxy-butoxy)-phenoxy]-acetic acid hydrobromide MS: m/e (ESI) 575.4 (MH+)

Example 1586

1-(3-tert-Butyl-phenyl)-2-(5,6-diethoxy-7-fluoro-1-imino-1,3-dihydro-isoindol-2-yl)-ethanone hydrobromide MS: m/e (ESI) 413.4 (MH+)

Example 1587

1-[3-tert-Butyl-4-hydroxy-5-(4-hydroxy-butoxy)-phenyl]-2-(7-fluoro-1-imino-5,6-dimethoxy-1,3-dihydro-isoindol-2-yl)-ethanone hydrobromide MS: m/e (ESI) 489.4 (MH+)

Example 1588

[2-tert-Butyl-4-[2-(7-fluoro-1-imino-5,6-dimethoxy-1,3-dihydro-isoindol-2-yl)-acetyl]-6-(4-hydroxy-butoxy)-phenoxy]-acetic acid hydrobromide MS: m/e (ESI) 547.4 (MH+)

Example 1589

5-{2-tert-Butyl-4-[2-(7-imino-2-methyl-5,7-dihydro-pyrrolo[3,4-b]pyridin-6-yl)-acetyl]-6-pyrrolidin-1-yl-phenoxy}-pentanoic acid hydrobromide MS: m/e (ESI) 507.5 (MH+)

Example 1590

1-(7-tert-Butyl-benzoxazol-5-yl)-2-(2-cyclopropyl-7-imino-5,7-dihydro-pyrrolo[3,4-b]pyridin-6-yl)-ethanone hydrobromide MS: m/e (ESI) 389.3 (MH+)

Example 1591

4-{2-tert-Butyl-4-[2-(2-cyclopropyl-7-imino-5,7-dihydro-pyrrolo[3,4-b]pyridin-6-yl)-acetyl]-phenoxy}-butyronitrile hydrobromide MS: m/e (ESI) 431.3 (MH+)

Example 1592

(1-{5-[2-(2-Cyclopropyl-7-imino-5,7-dihydro-pyrrolo[3,4-b]pyridin-6-yl)-acetyl]-3-ethyl-2-hydroxy-phenyl}-pyrrolidin-3-yloxy)-acetic acid hydrobromide MS: m/e (ESI) 479.3 (MH+)

Example 1593

(1-{5-[2-(2-Cyclopropyl-7-imino-5,7-dihydro-pyrrolo[3,4-b]pyridin-6-yl)-acetyl]-2-hydroxy-3-isopropyl-phenyl}-pyrrolidin-3-yloxy)-acetic acid hydrobromide MS: m/e (ESI) 493.3 (MH+)

Example 1594

[2-tert-Butyl-4-[2-(2-cyclopropyl-7-imino-5,7-dihydro-pyrrolo[3,4-b]pyridin-6-yl)-acetyl]-6-(3-methoxy-pyrrolidin-1-yl)-phenoxy]-acetic acid hydrobromide MS: m/e (ESI) 521.4 (MH+)

Example 1595

[2-tert-Butyl-4-[2-(2-cyclopropyl-7-imino-5,7-dihydro-pyrrolo[3,4-b]pyridin-6-yl)-acetyl]-6-(3-ethoxy-pyrrolidin-1-yl)-phenoxy]-acetic acid hydrobromide MS: m/e (ESI) 535.4 (MH+)

Example 1596

1-(7-tert-Butyl-benzoxazol-5-yl)-2-(5,6-diethoxy-7-fluoro-1-imino-1,3-dihydro-isoindol-2-yl)-ethanone hydrobromide MS: m/e (ESI) 454.3 (MH+)

Example 1597

4-{2-tert-Butyl-4-[2-(5,6-diethoxy-7-fluoro-1-imino-1,3-dihydro-isoindol-2-yl}-acetyl]-phenoxy)-butyronitrile hydrobromide MS: m/e (ESI) 496.4 (MH+)

Example 1598

(1-{5-[2-(5,6-Diethoxy-7-fluoro-1-imino-1,3-dihydro-isoindol-2-yl)-acetyl]-3-ethyl-2-hydroxy-phenyl}-pyrrolidin-3-yloxy)-acetic acid hydrobromide MS: m/e (ESI) 544.4 (MH+)

Example 1599

(1-{5-[2-(5,6-Diethoxy-7-fluoro-1-imino-1,3-dihydro-isoindol-2-yl)-acetyl]-2-hydroxy-3-isopropyl-phenyl}-pyrrolidin-3-yloxy)-acetic acid hydrobromide MS: m/e (ESI) 558.4 (MH+)

Example 1600

[2-tert-Butyl-4-[2-(5,6-diethoxy-7-fluoro-1-imino-1,3-dihydro-isoindol-2-yl)-acetyl]-6-(3-methoxy-pyrrolidin-1-yl)-phenoxy]-acetic acid hydrobromide MS: m/e (ESI) 586.4 (MH+)

Example 1601

[2-tert-Butyl-4-[2-(5,6-diethoxy-7-fluoro-1-imino-1,3-dihydro-isoindol-2-yl)-acetyl]-6-(3-ethoxy-pyrrolidin-1-yl)-phenoxy]-acetic acid hydrobromide MS: m/e (ESI) 600.5 (MH+)

Example 1602

(1-{5-[2-(5-Ethoxy-1-imino-6-methylcarbamoyl-1,3-dihydro-isoindol-2-yl)-acetyl]-3-ethyl-2-hydroxy-phenyl}-pyrrolidin-3-yloxy)-acetic acid hydrobromide MS: m/e (ESI) 539.4 (MH+)

Example 1603

(1-{5-[2-(5-Ethoxy-1-imino-6-methylcarbamoyl-1,3-dihydro-isoindol-2-yl)-acetyl]-2-hydroxy-3-isopropyl-phenyl}-pyrrolidin-3-yloxy)-acetic acid hydrobromide MS: m/e (ESI) 553.4 (MH+)

Example 1604

[2-tert-Butyl-4-[2-(5-ethoxy-1-imino-6-methylcarbamoyl-1,3-dihydro-isoindol-2-yl)-acetyl]-6-(3-ethoxy-pyrrolidin-1-yl)-phenoxy]-acetic acid hydrobromide MS: m/e (ESI) 595.5 (MH+)

Example 1605

[2-tert-Butyl-4-[2-(7-fluoro-1-imino-5,6-dimethoxy-1,3-dihydro-isoindol-2-yl)-acetyl]-6-(3-methoxy-pyrrolidin-1-yl)-phenoxy]-acetic acid hydrobromide MS: m/e (ESI) 558.4 (MH+)

Example 1606

{2-tert-Butyl-6-(3-ethoxy-pyrrolidin-1-yl)-4-[2-(7-fluoro-1-imino-5,6-dimethoxy-1,3-dihydro-isoindol-2-yl)-acetyl]-phenoxy}-acetic acid hydrobromide MS: m/e (ESI) 572.4 (MH+)

Example 1607

4-(3-tert-Butyl-5-{2-[5-(4-hydroxy-3,5-dimethoxy-phenyl)-2-imino-thiazol-3-yl]-acetyl}-2-methoxy-phenoxy)-butylamide hydrobromide MS: m/e (ESI) 558.3 (MH+)

Example 1608

6-{2-[3-tert-Butyl-5-(3-carbamoyl-propoxy)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 540.2 (MH+)

Example 1609

{2-tert-Butyl-6-(3-cyano-propoxy)-4-[2-(5-ethoxy-1-imino-6-methylcarbamoyl-1,3-dihydro-isoindol-2-yl)-acetyl]-phenoxy}-acetic acid hydrobromide MS: m/e (ESI) 565.1 (MH+)

Example 1610

5-{2-tert-Butyl-6-(3-cyano-propoxy)-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 607.4 (MH+)

Example 1611

(3-{3-tert-Butyl-5-[2-(5-ethoxy-1-imino-6-methylcarbamoyl-1,3-dihydro-isoindol-2-yl)-acetyl]-2-hydroxy-phenoxy}-pyrrolidin-1-yl)-acetic acid hydrobromide MS: m/e (ESI) 567.4 (MH+)

Example 1612

{1-Acetyl-5-[2-(5-ethoxy-1-imino-6-methylcarbamoyl-1,3-dihydro-isoindol-2-yl)-acetyl]-3,3-dimethyl-2,3-dihydro-1H-indol-2-yl}-acetic acid hydrobromide MS: m/e (ESI) 521.3 (MH+)

Example 1613

2-{2-[3-tert-Butyl-4-(3-cyano-propoxy)-5-(2-oxo-piperidin-1-ylmethyl)-phenyl]-2-oxo-ethyl}-6-ethoxy-3-imino-2,3-dihydro-1H-isoindole-5-acetic acid methylamide hydrobromide MS: m/e (ESI) 602.3 (MH+)

Example 1614

{2-tert-Butyl-6-(3-cyano-propoxy)-4-[2-(5,6-diethoxy-7-fluoro-1-imino-1,3-dihydro-isoindol-2-yl)-acetyl]-phenoxy}-acetic acid hydrobromide MS: m/e (ESI) 570.2 (MH+)

Example 1615

(3-{3-tert-Butyl-5-[2-(5,6-diethoxy-7-fluoro-1-imino-1,3-dihydro-isoindol-2-yl)-acetyl]-2-hydroxy-phenoxy}-pyrrolidin-1-yl)-acetic acid hydrobromide MS: m/e (ESI) 572.4 (MH+)

Example 1616

{1-Acetyl-5-[2-(5,6-diethoxy-7-fluoro-1-imino-1,3-dihydro-isoindol-2-yl)-acetyl]-3,3-dimethyl-2,3-dihydro-1H-indol-2-yl}-acetic acid hydrobromide MS: m/e (ESI) 526.3 (MH+)

Example 1617

4-[2-tert-Butyl-4-[2-(5,6-diethoxy-7-fluoro-1-imino-1,3-dihydro-isoindol-2-yl)-acetyl]-6-(2-oxo-piperidin-1-ylmethyl)-phenoxy]-butyronitrile hydrobromide MS: m/e (ESI) 607.5 (MH+)

Example 1618

{2-tert-Butyl-6-(3-cyano-propoxy)-4-[2-(2-cyclopropyl-7-imino-5,7-dihydro-pyrrolo[3,4-b]pyridin-6-yl)-acetyl]-phenoxy}-acetic acid hydrobromide MS: m/e (ESI) 505.4 (MH+)

Example 1619

(3-{3-tert-Butyl-5-[2-(2-cyclopropyl-7-imino-5,7-dihydro-pyrrolo[3,4-b]pyridin-6-yl)-acetyl]-2-hydroxy-phenoxy}-pyrrolidin-1-yl)-acetic acid hydrobromide MS: m/e (ESI) 507.4 (MH+)

Example 1620

{1-Acetyl-5-[2-(2-cyclopropyl-7-imino-5,7-dihydro-pyrrolo[3,4-b]pyridin-6-yl)-acetyl]-3,3-dimethyl-2,3-dihydro-1H-indol-2-yl}-acetic acid hydrobromide MS: m/e (ESI) 461.3 (MH+)

Example 1621

4-[2-tert-Butyl-4-[2-(2-cyclopropyl-7-imino-5,7-dihydro-pyrrolo[3,4-b]pyridin-6-yl)-acetyl]-6-(2-oxo-piperidin-1-ylmethyl)-phenoxy]-butyronitrile hydrobromide MS: m/e (ESI) 542.4 (MH+)

Example 1622

{2-tert-Butyl-6-(3-cyano-propoxy)-4-[2-(7-fluoro-1-imino-5,6-dimethoxy-1,3-dihydro-isoindol-2-yl)-acetyl]-phenoxy}-acetic acid hydrobromide MS: m/e (ESI) 542.2 (MH+)

Example 1623

5-{2-tert-Butyl-6-(3-cyano-propoxy)-4-[2-(7-fluoro-1-imino-5,6-dimethoxy-1,3-dihydro-isoindol-2-yl)-acetyl]-phenoxy}-pentanoic acid hydrobromide MS: m/e (ESI) 584.4 (MH+)

Example 1624

(3-{3-tert-Butyl-5-[2-(7-fluoro-1-imino-5,6-dimethoxy-1,3-dihydro-isoindol-2-yl)-acetyl]-2-hydroxy-phenoxy}-pyrrolidin-1-yl)-acetic acid hydrobromide MS: m/e (ESI) 544.4 (MH+)

Example 1625

4-[2-tert-Butyl-4-[2-(7-fluoro-1-imino-5,6-dimethoxy-1,3-dihydro-isoindol-2-yl)-acetyl]-6-(2-oxo-piperidin-1-ylmethyl)-phenoxy]-butyronitrile hydrobromide MS: m/e (ESI) 579.4 (MH+)

Example 1626

4-[2-tert-Butyl-4-[2-(7-imino-2-methyl-5,7-dihydro-pyrrolo[3,4-b]pyridin-6-yl)-acetyl]-6-(2-oxo-piperidin-1-ylmethyl)-phenoxy]-butyronitrile hydrobromide MS: m/e (ESI) 516.4 (MH+)

Example 1627

{2-tert-Butyl-6-(3-cyano-propoxy)-4-[2-(3-ethoxy-7-imino-2-methylcarbamoyl-5,7-dihydro-pyrrolo[3,4-b]pyridin-6-yl)-acetyl]-phenoxy}-acetic acid hydrobromide MS: m/e (ESI) 566.3 (MH+)

Example 1628

5-{2-tert-Butyl-6-(3-cyano-propoxy)-4-[2-(3-ethoxy-7-imino-2-methylcarbamoyl-5,7-dihydro-pyrrolo[3,4-b]pyridin-6-yl)-acetyl]-phenoxy}-pentanoic acid hydrobromide MS: m/e (ESI) 608.4 (MH+)

Example 1629

4-{2-tert-Butyl-4-[2-(3-ethoxy-7-imino-2-methylcarbamoyl-5,7-dihydro-pyrrolo[3,4-b]pyridin-6-yl)-acetyl]-6-pyrrolidin-1-yl-phenoxy}-butanoic acid hydrobromide MS: m/e (ESI) 580.4 (MH+)

Example 1630

5-{2-tert-Butyl-4-[2-(3-ethoxy-7-imino-2-methylcarbamoyl-5,7-dihydro-pyrrolo[3,4-b]pyridin-6-yl)-acetyl]-6-pyrrolidin-1-yl-phenoxy}-pentanoic acid hydrobromide MS: m/e (ESI) 594.5 (MH+)

Example 1631

4-{2-tert-Butyl-4-[2-(2-cyclopropyl-7-imino-5,7-dihydro-pyrrolo[3,4-b]pyridin-6-yl)-acetyl]-6-methanesulfonylamino-phenoxy}-butylamide hydrobromide MS: m/e (ESI) 542.3 (MH+)

Example 1632

(1-{3-tert-Butyl-5-[2-(2-cyclopropyl-7-imino-5,7-dihydro-pyrrolo[3,4-b]pyridin-6-yl)-acetyl]-benzyl}-piperidin-4-yloxy)-acetic acid hydrobromide MS: m/e (ESI) 519.3 (MH+)

Example 1633

1-(3-tert-Butyl-5-dimethylamino-phenyl)-2-(2-cyclopropyl-7-imino-5,7-dihydro-pyrrolo[3,4-b]pyridin-6-yl)-ethanone hydrobromide MS: m/e (ESI) 391.3 (MH+)

Example 1634

5-{2-tert-Butyl-6-(3-cyanopropoxy)-4-[2-(2-cyclopropyl-7-imino-5,7-dihydro-pyrrolo[3,4-b]pyridin-6-yl)-acetyl]-phenoxy}-pentanoic acid hydrobromide MS: m/e (ESI) 547.3 (MH+)

Example 1635

2-{2-[3-tert-Butyl-4-(3-carbamoyl-propoxy)-5-methanesulfonylamino-phenyl]-2-oxo-ethyl}-6-ethoxy-3-imino-2,3-dihydro-1H-isoindole-5-acetic acid methylamide hydrobromide MS: m/e (ESI) 602.4 (MH+)

Example 1636

(1-{3-tert-Butyl-5-[2-(5-ethoxy-1-imino-6-methylcarbamoyl-1,3-dihydro-isoindol-2-yl)-acetyl]-benzyl}-piperidin-4-yloxy)-acetic acid hydrobromide MS: m/e (ESI) 579.4 (MH+)

Example 1637

4-({2-tert-Butyl-4-[2-(5-ethoxy-1-imino-6-methylcarbamoyl-1,3-dihydro-isoindol-2-yl)-acetyl]-phenyl}-methyl-amino)-butanoic acid hydrobromide MS: m/e (ESI) 523.4 (MH+)

Example 1638

4-({2-tert-Butyl-4-[2-(5-dimethylamino-1-imino-6-methylcarbamoyl-1,3-dihydro-isoindol-2-yl)-acetyl]-phenyl}-methyl-amino)-butanoic acid hydrobromide MS: m/e (ESI) 522.4 (MH+)

Example 1639

4-{2-tert-Butyl-4-[2-(7-fluoro-1-imino-5,6-dimethoxy-1,3-dihydro-isoindol-2-yl)-acetyl]-6-methanesulfonylamino-phenoxy}-butylamide hydrobromide MS: m/e (ESI) 579.4 (MH+)

Example 1640

(1-{3-tert-Butyl-5-[2-(7-fluoro-1-imino-5,6-dimethoxy-1,3-dihydro-isoindol-2-yl)-acetyl]-benzyl}-piperidin-4-yloxy)-acetic acid hydrobromide MS: m/e (ESI) 556.4 (MH+)

Example 1641

1-(3-tert-Butyl-5-dimethylamino-phenyl)-2-(7-fluoro-1-imino-5,6-dimethoxy-1,3-dihydro-isoindol-2-yl)-ethanone hydrobromide MS: m/e (ESI) 428.4 (MH+)

Example 1642

4-[2-tert-Butyl-4-[2-(2-cyclopropyl-7-imino-5,7-dihydro-pyrrolo[3,4-b]pyridin-6-yl)-acetyl]-6-(3-methoxy-pyrrolidin-1-yl)-phenoxy]-butanoic acid hydrobromide MS: m/e (ESI) 549.4 (MH+)

Example 1643

5-[2-tert-Butyl-4-[2-(2-cyclopropyl-7-imino-5,7-dihydro-pyrrolo[3,4-b]pyridin-6-yl)-acetyl]-6-(3-methoxy-pyrrolidin-1-yl)-phenoxy]-pentanoic acid hydrobromide MS: m/e (ESI) 563.4 (MH+)

Example 1644

4-[2-tert-Butyl-4-[2-(2-cyclopropyl-7-imino-5,7-dihydro-pyrrolo[3,4-b]pyridin-6-yl)-acetyl]-6-(3-ethoxy-pyrrolidin-1-yl)-phenoxy]-butanoic acid hydrobromide MS: m/e (ESI) 563.4 (MH+)

Example 1645

4-[2-tert-Butyl-4-[2-(5-ethoxy-1-imino-6-methylcarbamoyl-1,3-dihydro-isoindol-2-yl)-acetyl]-6-(3-methoxy-pyrrolidin-1-yl)-phenoxy]-butanoic acid hydrobromide MS: m/e (ESI) 609.5 (MH+)

Example 1646

5-[2-tert-Butyl-4-[2-(5-ethoxy-1-imino-6-methylcarbamoyl-1,3-dihydro-isoindol-2-yl)-acetyl]-6-(3-methoxy-pyrrolidin-1-yl)-phenoxy]-pentanoic acid hydrobromide MS: m/e (ESI) 623.5 (MH+)

Example 1647

4-[2-tert-Butyl-4-[2-(5-ethoxy-1-imino-6-methylcarbamoyl-1,3-dihydro-isoindol-2-yl)-acetyl]-6-(3-ethoxy-pyrrolidin-1-yl)-phenoxy]-butanoic acid hydrobromide MS: m/e (ESI) 623.5 (MH+)

Example 1648

5-[2-tert-Butyl-4-[2-(5-ethoxy-1-imino-6-methylcarbamoyl-1,3-dihydro-isoindol-2-yl)-acetyl]-6-(3-ethoxy-pyrrolidin-1-yl)-phenoxy]-pentanoic acid hydrobromide MS: m/e (ESI) 637.6 (MH+)

Example 1649

4-[2-tert-Butyl-4-[2-(7-fluoro-1-imino-5,6-dimethoxy-1,3-dihydro-isoindol-2-yl)-acetyl]-6-(3-methoxy-pyrrolidin-1-yl)-phenoxy]-butanoic acid hydrobromide MS: m/e (ESI) 586.5 (MH+)

Example 1650

5-[2-tert-Butyl-4-[2-(7-fluoro-1-imino-5,6-dimethoxy-1,3-dihydro-isoindol-2-yl)-acetyl]-6-(3-methoxy-pyrrolidin-1-yl)-phenoxy]-pentanoic acid hydrobromide MS: m/e (ESI) 600.5 (MH+)

Example 1651

4-{2-tert-Butyl-6-(3-ethoxy-pyrrolidin-1-yl)-4-[2-(7-fluoro-1-imino-5,6-dimethoxy-1,3-dihydro-isoindol-2-yl)-acetyl]-phenoxy}-butanoic acid hydrobromide MS: m/e (ESI) 600.5 (MH+)

Example 1652

5-{2-tert-Butyl-6-(3-ethoxy-pyrrolidin-1-yl)-4-[2-(7-fluoro-1-imino-5,6-dimethoxy-1,3-dihydro-isoindol-2-yl)-acetyl]-phenoxy}-pentanoic acid hydrobromide MS: m/e (ESI) 614.5 (MH+)

Example 1653

2-{2-[3-tert-Butyl-4-(2,5-dioxo-pyrrolidin-1-yl)-phenyl]-2-oxo-ethyl}-6-ethoxy-3-imino-2,3-dihydro-1H-isoindole-5-acetic acid methylamide hydrobromide MS: m/e (ESI) 505.3 (MH+)

Example 1654

1-{2-tert-Butyl-4-[2-(7-fluoro-1-imino-5,6-dimethoxy-1,3-dihydro-isoindol-2-yl)-acetyl]-phenyl}-pyrrolidine-2,5-dione hydrobromide MS: m/e (ESI) 482.3 (MH+)

Example 1655

6-{2-[3-tert-Butyl-4-(2,5-dioxo-pyrrolidin-1-yl)-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 506.3 (MH+)

Example 1656

1-{2-tert-Butyl-4-[2-(2-cyclopropyl-7-imino-5,7-dihydro-pyrrolo[3,4-b]pyridin-6-yl)-acetyl]-phenyl}-pyrrolidine-2,5-dione hydrobromide MS: m/e (ESI) 445.3 (MH+)

Example 1657

4-{2-tert-Butyl-6-diethylamino-4-[2-(5-ethoxy-1-imino-6-methylcarbamoyl-1,3-dihydro-isoindol-2-yl)-acetyl]-phenoxy}-butanoic acid hydrobromide MS: m/e (ESI) 581.5 (MH+)

Example 1658

4-{2-tert-Butyl-6-diethylamino-4-[2-(7-fluoro-1-imino-5,6-dimethoxy-1,3-dihydro-isoindol-2-yl)-acetyl]-phenoxy}-butanoic acid hydrobromide MS: m/e (ESI) 558.4 (MH+)

Example 1659

4-{2-tert-Butyl-6-diethylamino-4-[2-(3-ethoxy-7-imino-2-methylcarbamoyl-5,7-dihydro-pyrrolo[3,4-b]pyridin-6-yl)-acetyl]-phenoxy}-butanoic acid hydrobromide MS: m/e (ESI) 582.5 (MH+)

Example 1660

4-{2-tert-Butyl-4-[2-(2-cyclopropyl-7-imino-5,7-dihydro-pyrrolo[3,4-b]pyridin-6-yl)-acetyl]-6-diethylamino-phenoxy}-butanoic acid hydrobromide MS: m/e (ESI) 521.5 (MH+)

Example 1661

4-{2-tert-Butyl-6-diethylamino-4-[2-(7-imino-2-methyl-5,7-dihydro-pyrrolo[3,4-b]pyridin-6-yl)-acetyl]-phenoxy}-butanoic acid hydrobromide MS: m/e (ESI) 495.4 (MH+)

Example 1662

5-{2-tert-Butyl-6-diethylamino-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 595.5 (MH+)

Example 1663

5-{2-tert-Butyl-6-diethylamino-4-[2-(7-fluoro-1-imino-5,6-dimethoxy-1,3-dihydro-isoindol-2-yl)-acetyl]-phenoxy}-pentanoic acid hydrobromide MS: m/e (ESI) 572.5 (MH+)

Example 1664

5-{2-tert-Butyl-6-diethylamino-4-[2-(3-ethoxy-7-imino-2-methylcarbamoyl-5,7-dihydro-pyrrolo[3,4-b]pyridin-6-yl)-acetyl]-phenoxy}-pentanoic acid hydrobromide MS: m/e (ESI) 596.5 (MH+)

Example 1665

5-{2-tert-Butyl-4-[2-(2-cyclopropyl-7-imino-5,7-dihydro-pyrrolo[3,4-b]pyridin-6-yl)-acetyl]-6-diethylamino-phenoxy}-pentanoic acid hydrobromide MS: m/e (ESI) 535.5 (MH+)

Example 1666

5-{2-tert-Butyl-6-diethylamino-4-[2-(7-imino-2-methyl-5,7-dihydro-pyrrolo[3,4-b]pyridin-6-yl)-acetyl]-phenoxy}-pentanoic acid hydrobromide MS: m/e (ESI) 509.4 (MH+)

Example 1667

2-{2-[3-tert-Butyl-5-(methanesulfonyl-methyl-amino)-phenyl]-2-oxo-ethyl}-6-ethoxy-3-imino-2,3-dihydro-1H-isoindole-5-acetic acid methylamide hydrobromide MS: m/e (ESI) 515.4 (MH+)

Example 1668

N-{3-tert-Butyl-5-[2-(7-fluoro-1-imino-5,6-dimethoxy-1,3-dihydro-isoindol-2-yl)-acetyl]-phenyl}-N-methyl-methanesulfonamide hydrobromide MS: m/e (ESI) 492.3 (MH+)

Example 1669

N-{3-tert-Butyl-5-[2-(2-cyclopropyl-7-imino-5,7-dihydro-pyrrolo[3,4-b]pyridin-6-yl)-acetyl]-phenyl}-N-methyl-methanesulfonamide hydrobromide MS: m/e (ESI) 455.3 (MH+)

Example 1670

(1-{3-tert-Butyl-5-[2-(1-imino-5-methoxy-6-methyl-carbamoyl-1,3-dihydro-isoindol-2-yl)-acetyl]-2-methoxy-phenyl}-pyrrolidin-3-yloxy)-acetic acid hydrobromide MS: m/e (ESI) 567.4 (MH+)

Example 1671

(1-{3-tert-Butyl-5-[2-(7-fluoro-1-imino-5,6-dimethoxy-1,3-dihydro-isoindol-2-yl)-acetyl]-2-methoxy-phenyl}-pyrrolidin-3-yloxy)-acetic acid hydrobromide MS: m/e (ESI) 558.4 (MH+)

Example 1672

4-{2-tert-Butyl-6-(3-cyano-pyrrolidin-1-yl)-4-[2-(2-cyclopropyl-7-imino-5,7-dihydro-pyrrolo[3,4-b]pyridin-6-yl)-acetyl]-phenoxy}-butanoic acid hydrobromide MS: m/e (ESI) 544.2 (MH+)

Example 1673

5-{2-tert-Butyl-6-(3-cyano-pyrrolidin-1-yl)-4-[2-(2-cyclopropyl-7-imino-5,7-dihydro-pyrrolo[3,4-b]pyridin-6-yl)-acetyl]-phenoxy}-pentanoic acid hydrobromide MS: m/e (ESI) 558.2 (MH+)

Example 1674

4-{2-tert-Butyl-6-(3-cyano-pyrrolidin-1-yl)-4-[2-(5-ethoxy-1-imino-6-methylcarbamoyl-1,3-dihydro-isoindol-2-yl)-acetyl]-phenoxy}-butanoic acid hydrobromide MS: m/e (ESI) 604.3 (MH+)

Example 1675

5-{2-tert-Butyl-6-(3-cyano-pyrrolidin-1-yl)-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 618.3 (MH+)

Example 1676

4-{2-tert-Butyl-6-(3-cyano-pyrrolidin-1-yl)-4-[2-(7-fluoro-1-imino-5,6-dimethoxy-1,3-dihydro-isoindol-2-yl)-acetyl]-phenoxy}-butanoic acid hydrobromide MS: m/e (ESI) 581.2 (MH+)

Example 1677

5-{2-tert-Butyl-6-(3-cyano-pyrrolidin-1-yl)-4-[2-(7-fluoro-1-imino-5,6-dimethoxy-1,3-dihydro-isoindol-2-yl)-acetyl]-phenoxy}-pentanoic acid hydrobromide MS: m/e (ESI) 595.2 (MH+)

Example 1678

5-{2-tert-Butyl-6-(3-carbamoyl-pyrrolidin-1-yl)-4-[2-(2-cyclopropyl-7-imino-5,7-dihydro-pyrrolo[3,4-b]pyridin-6-yl)-acetyl]-phenoxy}-pentanoic acid hydrobromide MS: m/e (ESI) 576.3 (MH+)

Example 1679

4-{2-tert-Butyl-6-(3-carbamoyl-pyrrolidin-1-yl)-4-[2-(5-ethoxy-1-imino-6-methylcarbamoyl-1,3-dihydro-isoindol-2-yl)-acetyl]-phenoxy}-butanoic acid hydrobromide MS: m/e (ESI) 622.3 (MH+)

Example 1680

5-{2-tert-Butyl-6-(3-carbamoyl-pyrrolidin-1-yl)-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 636.3 (MH+)

Example 1681

4-{2-tert-Butyl-6-(3-carbamoyl-pyrrolidin-1-yl)-4-[2-(7-fluoro-1-imino-5,6-dimethoxy-1,3-dihydro-isoindol-2-yl)-acetyl]-phenoxy}-butanoic acid hydrobromide MS: m/e (ESI) 599.2 (MH+)

Example 1682

5-{2-tert-Butyl-6-(3-carbamoyl-pyrrolidin-1-yl)-4-[2-(7-fluoro-1-imino-5,6-dimethoxy-1,3-dihydro-isoindol-2-yl)-acetyl]-phenoxy}-pentanoic acid hydrobromide MS: m/e (ESI) 613.3 (MH+)

Example 1683

4-{2-tert-Butyl-6-(3-cyano-propoxy)-4-[2-(2-cyclopropyl-7-imino-5,7-dihydro-pyrrolo[3,4-b]pyridin-6-yl)-acetyl]-phenoxy}-butyronitrile hydrobromide MS: m/e (ESI) 514.2 (MH+)

Example 1684

5-{4-[2-(2-Cyclopropyl-7-imino-5,7-dihydro-pyrrolo[3,4-b]pyridin-6-yl)-acetyl]-2-pyrrolidin-1-yl-phenoxy}-pentanoic acid hydrobromide MS: m/e (ESI) 477.2 (MH+)

Example 1685

6-{2-tert-Butyl-4-[2-(2-cyclopropyl-7-imino-5,7-dihydro-pyrrolo[3,4-b]pyridin-6-yl)-acetyl]-6-pyrrolidin-1-yl-phenoxy}-hexanoic acid hydrobromide MS: m/e (ESI) 547.3 (MH+)

Example 1686

4-{2-tert-Butyl-4-[2-(2-cyclopropyl-7-imino-5,7-dihydro-pyrrolo[3,4-b]pyridin-6-yl)-acetyl]-6-dimethylamino-phenoxy}-butanoic acid hydrobromide MS: m/e (ESI) 493.3 (MH+)

Example 1687

5-{2-tert-Butyl-4-[2-(2-cyclopropyl-7-imino-5,7-dihydro-pyrrolo[3,4-b]pyridin-6-yl)-acetyl]-6-dimethylamino-phenoxy}-pentanoic acid hydrobromide MS: m/e (ESI) 507.3 (MH+)

Example 1688

4-[2-tert-Butyl-4-[2-(2-cyclopropyl-7-imino-5,7-dihydro-pyrrolo[3,4-b]pyridin-6-yl)-acetyl]-6-(methyl-propyl-amino)-phenoxy]-butanoic acid hydrobromide MS: m/e (ESI) 521.3 (MH+)

Example 1689

5-[2-tert-Butyl-4-[2-(2-cyclopropyl-7-imino-5,7-dihydro-pyrrolo[3,4-b]pyridin-6-yl)-acetyl]-6-(methyl-propyl-amino)-phenoxy]-pentanoic acid hydrobromide MS: m/e (ESI) 535.4 (MH+)

Example 1690

6-{2-[3-tert-Butyl-4,5-bis-(3-cyano-propoxy)-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 575.3 (MH+)

Example 1691

5-{4-[2-(3-Ethoxy-7-imino-2-methylcarbamoyl-5,7-dihydro-pyrrolo[3,4-b]pyridin-6-yl)-acetyl]-2-pyrrolidin-1-yl-phenoxy}-pentanoic acid hydrobromide MS: m/e (ESI) 538.3 (MH+)

Example 1692

6-{2-tert-Butyl-4-[2-(3-ethoxy-7-imino-2-methylcarbamoyl-5,7-dihydro-pyrrolo[3,4-b]pyridin-6-yl)-acetyl]-6-pyrrolidin-1-yl-phenoxy}-hexanoic acid hydrobromide MS: m/e (ESI) 608.4 (MH+)

Example 1693

4-{2-tert-Butyl-6-dimethylamino-4-[2-(3-ethoxy-7-imino-2-methylcarbamoyl-5,7-dihydro-pyrrolo[3,4-b]pyridin-6-yl)-acetyl]-phenoxy}-butanoic acid hydrobromide MS: m/e (ESI) 554.3 (MH+)

Example 1694

5-{2-tert-Butyl-6-dimethylamino-4-[2-(3-ethoxy-7-imino-2-methylcarbamoyl-5,7-dihydro-pyrrolo[3,4-b]pyridin-6-yl)-acetyl]-phenoxy}-pentanoic acid hydrobromide MS: m/e (ESI) 568.4 (MH+)

Example 1695

4-[2-tert-Butyl-4-[2-(3-ethoxy-7-imino-2-methylcarbamoyl-5,7-dihydro-pyrrolo[3,4-b]pyridin-6-yl)-acetyl]-6-(methyl-propyl-amino)-phenoxy]-butanoic acid hydrobromide MS: m/e (ESI) 582.4 (MH+)

Example 1696

5-[2-tert-Butyl-4-[2-(3-ethoxy-7-imino-2-methylcarbamoyl-5,7-dihydro-pyrrolo[3,4-b]pyridin-6-yl)-acetyl]-6-(methyl-propyl-amino)-phenoxy]-pentanoic acid hydrobromide MS: m/e (ESI) 596.4 (MH+)

Example 1697

4-{2-tert-Butyl-6-dimethylamino-4-[2-(7-imino-2-methyl-5,7-dihydro-pyrrolo[3,4-b]pyridin-6-yl)-acetyl]-phenoxy}-butanoic acid hydrobromide MS: m/e (ESI) 467.3 (MH+)

Example 1698

5-{2-tert-Butyl-6-dimethylamino-4-[2-(7-imino-2-methyl-5,7-dihydro-pyrrolo[3,4-b]pyridin-6-yl)-acetyl]-phenoxy}-pentanoic acid hydrobromide MS: m/e (ESI) 481.3 (MH+)

Example 1699

4-[2-tert-Butyl-4-[2-(7-imino-2-methyl-5,7-dihydro-pyrrolo[3,4-b]pyridin-6-yl)-acetyl]-6-(methyl-propyl-amino)-phenoxy]-butanoic acid hydrobromide MS: m/e (ESI) 495.3 (MH+)

Example 1700

5-[2-tert-Butyl-4-[2-(7-imino-2-methyl-5,7-dihydro-pyrrolo[3,4-b]pyridin-6-yl)-acetyl]-6-(methyl-propyl-amino)-phenoxy]-pentanoic acid hydrobromide MS: m/e (ESI) 509.4 (MH+)

Example 1701

4-{2-tert-Butyl-6-(3-cyano-propoxy)-4-[2-(7-fluoro-1-imino-5,6-dimethoxy-1,3-dihydro-isoindol-2-yl)-acetyl]-phenoxy}-butyronitrile hydrobromide MS: m/e (ESI) 551.3 (MH+)

Example 1702

5-{4-[2-(7-Fluoro-1-imino-5,6-dimethoxy-1,3-dihydro-isoindol-2-yl)-acetyl]-2-pyrrolidin-1-yl-phenoxy}-pentanoic acid hydrobromide MS: m/e (ESI) 514.3 (MH+)

Example 1703

6-{2-tert-Butyl-4-[2-(7-fluoro-1-imino-5,6-dimethoxy-1,3-dihydro-isoindol-2-yl)-acetyl]-6-pyrrolidin-1-yl-phenoxy}-hexanoic acid hydrobromide MS: m/e (ESI) 584.3 (MH+)

Example 1704

4-{2-tert-Butyl-6-dimethylamino-4-[2-(7-fluoro-1-imino-5,6-dimethoxy-1,3-dihydro-isoindol-2-yl)-acetyl]-phenoxy}-butanoic acid hydrobromide MS: m/e (ESI) 530.3 (MH+)

Example 1705

5-{2-tert-Butyl-6-dimethylamino-4-[2-(7-fluoro-1-imino-5,6-dimethoxy-1,3-dihydro-isoindol-2-yl)-acetyl]-phenoxy}-pentanoic acid hydrobromide MS: m/e (ESI) 544.3 (MH+)

Example 1706

4-[2-tert-Butyl-4-[2-(7-fluoro-1-imino-5,6-dimethoxy-1,3-dihydro-isoindol-2-yl)-acetyl]-6-(methyl-propyl-amino)-phenoxy]-butanoic acid hydrobromide MS: m/e (ESI) 558.3 (MH+)

Example 1707

5-[2-tert-Butyl-4-[2-(7-fluoro-1-imino-5,6-dimethoxy-1,3-dihydro-isoindol-2-yl)-acetyl]-6-(methyl-propyl-amino)-phenoxy]-pentanoic acid hydrobromide MS: m/e (ESI) 572.3 (MH+)

Example 1708

4-{2-tert-Butyl-6-(3-cyano-propoxy)-4-[2-(5,6-diethoxy-7-fluoro-1-imino-1,3-dihydro-isoindol-2-yl)-acetyl]-phenoxy}-butyronitrile hydrobromide MS: m/e (ESI) 579.3 (MH+)

Example 1709

5-{4-[2-(5,6-Diethoxy-7-fluoro-1-imino-1,3-dihydro-isoindol-2-yl)-acetyl]-2-pyrrolidin-1-yl-phenoxy}-pentanoic acid hydrobromide MS: m/e (ESI) 542.3 (MH+)

Example 1710

2-{2-[3-tert-Butyl-4,5-bis-(3-cyano-propoxy)-phenyl]-2-oxo-ethyl}-6-ethoxy-3-imino-2,3-dihydro-1H-isoindole-5-acetic acid methylamide hydrobromide MS: m/e (ESI) 574.4 (MH+)

Example 1711

5-{4-[2-(5-Ethoxy-1-imino-6-methylcarbamoyl-1,3-dihydro-isoindol-2-yl)-acetyl]-2-pyrrolidin-1-yl-phenoxy}-pentanoic acid hydrobromide MS: m/e (ESI) 537.3 (MH+)

Example 1712

6-{2-tert-Butyl-4-[2-(5-ethoxy-1-imino-6-methylcarbamoyl-1,3-dihydro-isoindol-2-yl)-acetyl]-6-pyrrolidin-1-yl-phenoxy}-hexanoic acid hydrobromide MS: m/e (ESI) 607.4 (MH+)

Example 1713

4-{2-tert-Butyl-6-dimethylamino-4-[2-(5-ethoxy-1-imino-6-methylcarbamoyl-1,3-dihydro-isoindol-2-yl)-acetyl]-phenoxy}-butanoic acid hydrobromide MS: m/e (ESI) 553.4 (MH+)

Example 1714

5-{2-tert-Butyl-6-dimethylamino-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 567.4 (MH+)

Example 1715

4-[2-tert-Butyl-4-[2-(5-ethoxy-1-imino-6-methylcarbamoyl-1,3-dihydro-isoindol-2-yl)-acetyl]-6-(methyl-propyl-amino)-phenoxy]-butanoic acid hydrobromide MS: m/e (ESI) 581.4 (MH+)

Example 1716

5-[2-tert-Butyl-4-[2-(5-ethoxy-1-imino-6-methylcarbamoyl-1,3-dihydro-isoindol-2-yl)-acetyl]-6-(methyl-propyl-amino)-phenoxy]-pentanoic acid hydrobromide MS: m/e (ESI) 595.4 (MH+)

Example 1717

1-(3,5-Di-tert-butyl-4-hydroxy-phenyl)-2-(2-hydroxymethyl-7-imino-5,7-dihydro-pyrrolo[3,4-b]pyridin-6-yl)-ethanone hydrobromide MS: m/e (ESI) 410.3 (MH+)

Example 1718

{2-tert-Butyl-4-[2-(2-hydroxymethyl-7-imino-5,7-dihydro-pyrrolo[3,4-b]pyridin-6-yl)-acetyl]-6-pyrrolidin-1-yl-phenoxy}-acetic acid hydrobromide MS: m/e (ESI) 481.3 (MH+)

Example 1719

5-{2-tert-Butyl-4-[2-(2-hydroxymethyl-7-imino-5,7-dihydro-pyrrolo[3,4-b]pyridin-6-yl)-acetyl]-6-pyrrolidin-1-yl-phenoxy}-pentanoic acid hydrobromide MS: m/e (ESI) 523.4 (MH+)

Example 1720

{2-tert-Butyl-6-(3-cyano-propoxy)-4-[2-(2-hydroxymethyl-7-imino-5,7-dihydro-pyrrolo[3,4-b]pyridin-6-yl)-acetyl]-phenoxy}-acetic acid hydrobromide MS: m/e (ESI) 495.3 (MH+)

Example 1721

5-{2-tert-Butyl-6-(3-cyano-propoxy)-4-[2-(2-hydroxymethyl-7-imino-5,7-dihydro-pyrrolo[3,4-b]pyridin-6-yl)-acetyl]-phenoxy}-pentanoic acid hydrobromide MS: m/e (ESI) 537.3 (MH+)

Example 1722

1-(3,5-Di-tert-butyl-4-hydroxy-phenyl)-2-(2-fluoromethyl-7-imino-5,7-dihydro-pyrrolo[3,4-b]pyridin-6-yl)-ethanone hydrobromide MS: m/e (ESI) 412.3 (MH+)

Example 1723

{2-tert-Butyl-4-[2-(2-fluoromethyl-7-imino-5,7-dihydro-pyrrolo[3,4-b]pyridin-6-yl)-acetyl]-6-pyrrolidin-1-yl-phenoxy}-acetic acid hydrobromide MS: m/e (ESI) 483.3 (MH+)

Example 1724

5-{2-tert-Butyl-4-[2-(2-fluoromethyl-7-imino-5,7-dihydro-pyrrolo[3,4-b]pyridin-6-yl)-acetyl]-6-pyrrolidin-1-yl-phenoxy}-pentanoic acid hydrobromide MS: m/e (ESI) 525.4 (MH+)

Example 1725

{2-tert-Butyl-6-(3-cyano-propoxy)-4-[2-(2-fluoromethyl-7-imino-5,7-dihydro-pyrrolo[3,4-b]pyridin-6-yl)-acetyl]-phenoxy}-acetic acid hydrobromide MS: m/e (ESI) 497.3 (MH+)

Example 1726

5-{2-tert-Butyl-6-(3-cyano-propoxy)-4-[2-(2-fluoromethyl-7-imino-5,7-dihydro-pyrrolo[3,4-b]pyridin-6-yl)-acetyl]-phenoxy}-pentanoic acid hydrobromide MS: m/e (ESI) 539.3 (MH+)

Example 1727

5-{2-tert-Butyl-4-[2-(5-ethoxy-1-imino-6-methylcarbamoyl-1,3-dihydro-isoindol-2-yl)-acetyl]-6-pent-4-enyloxy-phenoxy}-pentanoic acid hydrobromide MS: m/e (ESI) 608.4 (MH+)

Example 1728

5-{2-tert-Butyl-4-[2-(7-fluoro-1-imino-5,6-dimethoxy-1,3-dihydro-isoindol-2-yl)-acetyl]-6-pent-4-enyloxy-phenoxy}-pentanoic acid hydrobromide MS: m/e (ESI) 585.4 (MH+)

Example 1729

5-{2-tert-Butyl-4-[2-(2-cyclopropyl-7-imino-5,7-dihydro-pyrrolo[3,4-b]pyridin-6-yl)-acetyl]-6-pent-4-enyloxy-phenoxy}-pentanoic acid hydrobromide MS: m/e (ESI) 548.4 (MH+)

Example 1730

5-{2-tert-Butyl-4-[2-(3-ethoxy-7-imino-2-methylcarbamoyl-5,7-dihydro-pyrrolo[3,4-b]pyridin-6-yl)-acetyl]-6-pent-4-enyloxy-phenoxy}-pentanoic acid hydrobromide MS: m/e (ESI) 609.4 (MH+)

Example 1731

4-[2-tert-Butyl-4-[2-(2-cyclopropyl-7-imino-5,7-dihydro-pyrrolo[3,4-b]pyridin-6-yl)-acetyl]-6-(3-fluoro-pyrrolidin-1-yl)-phenoxy]-butanoic acid hydrobromide MS: m/e (ESI) 537.2 (MH+)

Example 1732

5-[2-tert-Butyl-4-[2-(2-cyclopropyl-7-imino-5,7-dihydro-pyrrolo[3,4-b]pyridin-6-yl)-acetyl]-6-(3-fluoro-pyrrolidin-1-yl)-phenoxy]-pentanoic acid hydrobromide MS: m/e (ESI) 551.3 (MH+)

Example 1733

4-[2-tert-Butyl-4-[2-(5-ethoxy-1-imino-6-methylcarbamoyl-1,3-dihydro-isoindol-2-yl)-acetyl]-6-(3-fluoro-pyrrolidin-1-yl)-phenoxy]-butanoic acid hydrobromide MS: m/e (ESI) 597.3 (MH+)

Example 1734

5-[2-tert-Butyl-4-[2-(5-ethoxy-1-imino-6-methylcarbamoyl-1,3-dihydro-isoindol-2-yl)-acetyl]-6-(3-fluoro-pyrrolidin-1-yl)-phenoxy]-pentanoic acid hydrobromide MS: m/e (ESI) 611.3 (MH+)

Example 1735

4-[2-tert-Butyl-4-[2-(7-fluoro-1-imino-5,6-dimethoxy-1,3-dihydro-isoindol-2-yl)-acetyl]-6-(3-fluoro-pyrrolidin-1-yl)-phenoxy]-butanoic acid hydrobromide MS: m/e (ESI) 574.3 (MH+)

Example 1736

5-[2-tert-Butyl-4-[2-(7-fluoro-1-imino-5,6-dimethoxy-1,3-dihydro-isoindol-2-yl)-acetyl]-6-(3-fluoro-pyrrolidin-1-yl)-phenoxy]-pentanoic acid hydrobromide MS: m/e (ESI) 588.3 (MH+)

Example 1737

Ethyl 4-[2-tert-butyl-4-[2-(5-ethoxy-1-imino-6-methylcarbamoyl-1,3-dihydro-isoindol-2-yl)-acetyl]-6-(4-oxo-piperidin-1-yl)-phenoxy]-butanoate hydrobromide MS: m/e (ESI) 635.2 (MH+)

Example 1738

Ethyl 4-[2-tert-butyl-4-[2-(7-fluoro-1-imino-5,6-dimethoxy-1,3-dihydro-isoindol-2-yl)-acetyl]-6-(4-oxo-piperidin-1-yl)-phenoxy]-butanoate hydrobromide MS: m/e (ESI) 612.4 (MH+)

Example 1739

Ethyl 4-[2-tert-butyl-4-[2-(5,6-diethoxy-7-fluoro-1-imino-1,3-dihydro-isoindol-2-yl)-acetyl]-6-(4-oxo-piperidin-1-yl)-phenoxy]-butanoate hydrobromide MS: m/e (ESI) 640.2 (MH+)

Example 1740

Ethyl 4-[2-tert-butyl-4-[2-(2-cyclopropyl-7-imino-5,7-dihydro-pyrrolo[3,4-b]pyridin-6-yl)-acetyl]-6-(4-oxo-piperidin-1-yl)-phenoxy]-butanoate hydrobromide MS: m/e (ESI) 575.2 (MH+)

Example 1741

Ethyl 4-[2-tert-butyl-4-[2-(3-ethoxy-7-imino-2-methylcarbamoyl-5,7-dihydro-pyrrolo[3,4-b]pyridin-6-yl)-acetyl]-6-(4-oxo-piperidin-1-yl)-phenoxy]-butanoate hydrobromide MS: m/e (ESI) 736.3 (MH+) (Boc-protected)

Example 1742

Ethyl 4-[2-tert-butyl-4-[2-(5-ethoxy-4-fluoro-1-imino-6-methylcarbamoyl-1,3-dihydro-isoindol-2-yl)-acetyl]-6-(4-oxo-piperidin-1-yl)-phenoxy]-butanoate hydrobromide MS: m/e (ESI) 653.2 (MH+)

Example 1743

Ethyl 4-[2-tert-butyl-4-[2-(5-ethoxy-1-imino-6-methylcarbamoyl-1,3-dihydro-isoindol-2-yl)-acetyl]-6-(4-hydroxy-piperidin-1-yl)-phenoxy]-butanoate hydrobromide MS: m/e (ESI) 637.3 (MH+)

Example 1744

Ethyl 4-[2-tert-butyl-4-[2-(7-fluoro-1-imino-5,6-dimethoxy-1,3-dihydro-isoindol-2-yl)-acetyl]-6-(4-hydroxy-piperidin-1-yl)-phenoxy]-butanoate hydrobromide MS: m/e (ESI) 614.2 (MH+)

Example 1745

Ethyl 4-[2-tert-butyl-4-[2-(5,6-diethoxy-7-fluoro-1-imino-1,3-dihydro-isoindol-2-yl)-acetyl]-6-(4-hydroxy-piperidin-1-yl)-phenoxy]-butanoate hydrobromide MS: m/e (ESI) 642.3 (MH+)

Example 1746

Ethyl 4-[2-tert-butyl-4-[2-(2-cyclopropyl-7-imino-5,7-dihydro-pyrrolo[3,4-b]pyridin-6-yl)-acetyl]-6-(4-hydroxy-piperidin-1-yl)-phenoxy]-butanoate hydrobromide MS: m/e (ESI) 577.2 (MH+)

Example 1747

Ethyl 4-[2-tert-butyl-4-[2-(3-ethoxy-7-imino-2-methylcarbamoyl-5,7-dihydro-pyrrolo[3,4-b]pyridin-6-yl)-acetyl]-6-(4-hydroxy-piperidin-1-yl)-phenoxy]-butanoate hydrobromide MS: m/e (ESI) 738.2 (MH+) (Boc-protected)

Example 1748

Ethyl 4-[2-tert-butyl-4-[2-(5-ethoxy-4-fluoro-1-imino-6-methylcarbamoyl-1,3-dihydro-isoindol-2-yl)-acetyl]-6-(4-hydroxy-piperidin-1-yl)-phenoxy]-butanoate hydrobromide MS: m/e (ESI) 655.1 (MH+)

Example 1749

4-{2-tert-Butyl-6-(3-carboxy-propoxy)-4-[2-(5-ethoxy-1-imino-6-methylcarbamoyl-1,3-dihydro-isoindol-2-yl)-acetyl]-phenoxy}-butanoic acid hydrobromide MS: m/e (ESI) 612.1 (MH+)

Example 1750

4-{2-tert-Butyl-6-(3-carboxy-propoxy)-4-[2-(7-fluoro-1-imino-5,6-dimethoxy-1,3-dihydro-isoindol-2-yl)-acetyl]-phenoxy}-butanoic acid hydrobromide MS: m/e (ESI) 589.0 (MH+)

Example 1751

4-{2-tert-Butyl-6-(3-carboxy-propoxy)-4-[2-(5,6-diethoxy-7-fluoro-1-imino-1,3-dihydro-isoindol-2-yl)-acetyl]-phenoxy}-butanoic acid hydrobromide MS: m/e (ESI) 617.0 (MH+)

Example 1752

4-{2-tert-Butyl-6-(3-carboxy-propoxy)-4-[2-(2-cyclopropyl-7-imino-5,7-dihydro-pyrrolo[3,4-b]pyridin-6-yl)-acetyl]-phenoxy}-butanoic acid hydrobromide MS: m/e (ESI) 552.0 (MH+)

Example 1753

4-{2-tert-Butyl-6-(3-carboxy-propoxy)-4-[2-(3-ethoxy-7-imino-2-methylcarbamoyl-5,7-dihydro-pyrrolo[3,4-b]pyridin-6-yl)-acetyl]-phenoxy}-butanoic acid hydrobromide MS: m/e (ESI) 613.0 (MH+)

Example 1754

5-{2-tert-Butyl-6-(4-carboxy-butoxy)-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 640.0 (MH+)

Example 1755

5-{2-tert-Butyl-6-(4-carboxy-butoxy)-4-[2-(7-fluoro-1-imino-5,6-dimethoxy-1,3-dihydro-isoindol-2-yl)-acetyl]-phenoxy}-pentanoic acid hydrobromide MS: m/e (ESI) 617.0 (MH+)

Example 1756

5-{2-tert-Butyl-6-(4-carboxy-butoxy)-4-[2-(5,6-diethoxy-7-fluoro-1-imino-1,3-dihydro-isoindol-2-yl)-acetyl]-phenoxy}-pentanoic acid hydrobromide MS: m/e (ESI) 645.0 (MH+)

Example 1757

5-{2-tert-Butyl-6-(4-carboxy-butoxy)-4-[2-(2-cyclopropyl-7-imino-5,7-dihydro-pyrrolo[3,4-b]pyridin-6-yl)-acetyl]-phenoxy}-pentanoic acid hydrobromide MS: m/e (ESI) 580.0 (MH+)

Example 1758

5-{2-tert-Butyl-6-(4-carboxy-butoxy)-4-[2-(3-ethoxy-7-imino-2-methylcarbamoyl-5,7-dihydro-pyrrolo[3,4-b]pyridin-6-yl)-acetyl]-phenoxy}-pentanoic acid hydrobromide MS: m/e (ESI) 641.0 (MH+)

Example 1759

4-{2-tert-Butyl-6-(ethyl-methyl-amino)-4-[2-(7-fluoro-1-imino-5,6-dimethoxy-1,3-dihydro-isoindol-2-yl)-acetyl]-phenoxy}-butanoic acid hydrobromide MS: m/e (ESI) 544.2 (MH+)

Example 1760

4-[2-tert-Butyl-4-[2-(5-ethoxy-1-imino-6-methylcarbamoyl-1,3-dihydro-isoindol-2-yl)-acetyl]-6-(ethyl-methyl-amino)-phenoxy]-butanoic acid hydrobromide MS: m/e (ESI) 567.3 (MH+)

Example 1761

4-[2-tert-Butyl-4-[2-(2-cyclopropyl-7-imino-5,7-dihydro-pyrrolo[3,4-b]pyridin-6-yl)-acetyl]-6-(ethyl-methyl-amino)-phenoxy]-butanoic acid hydrobromide MS: m/e (ESI) 507.3 (MH+)

Example 1762

4-[2-tert-Butyl-4-[2-(3-ethoxy-7-imino-2-methylcarbamoyl-5,7-dihydro-pyrrolo[3,4-b]pyridin-6-yl)-acetyl]-6-(ethyl-methyl-amino)-phenoxy]-butanoic acid hydrobromide MS: m/e (ESI) 568.3 (MH+)

Example 1763

4-{2-tert-Butyl-6-(ethyl-methyl-amino)-4-[2-(7-imino-2-methyl-5,7-dihydro-pyrrolo[3,4-b]pyridin-6-yl)-acetyl]-phenoxy}-butanoic acid hydrobromide MS: m/e (ESI) 481.3 (MH+)

Example 1764

5-{2-tert-Butyl-6-(ethyl-methyl-amino)-4-[2-(7-fluoro-1-imino-5,6-dimethoxy-1,3-dihydro-isoindol-2-yl)-acetyl]-phenoxy}-pentanoic acid hydrobromide MS: m/e (ESI) 558.3 (MH+)

Example 1765

5-[2-tert-Butyl-4-[2-(5-ethoxy-1-imino-6-methylcarbamoyl-1,3-dihydro-isoindol-2-yl)-acetyl]-6-(ethyl-methyl-amino)-phenoxy]-pentanoic acid hydrobromide MS: m/e (ESI) 581.3 (MH+)

Example 1766

5-[2-tert-Butyl-4-[2-(2-cyclopropyl-7-imino-5,7-dihydro-pyrrolo[3,4-b]pyridin-6-yl)-acetyl]-6-(ethyl-methyl-amino)-phenoxy]-pentanoic acid hydrobromide MS: m/e (ESI) 521.3 (MH+)

Example 1767

5-[2-tert-Butyl-4-[2-(3-ethoxy-7-imino-2-methylcarbamoyl-5,7-dihydro-pyrrolo[3,4-b]pyridin-6-yl)-acetyl]-6-(ethyl-methyl-amino)-phenoxy]-pentanoic acid hydrobromide MS: m/e (ESI) 582.3 (MH+)

Example 1768

5-{2-tert-Butyl-6-(ethyl-methyl-amino)-4-[2-(7-imino-2-methyl-5,7-dihydro-pyrrolo[3,4-b]pyridin-6-yl)-acetyl]-phenoxy}-pentanoic acid hydrobromide MS: m/e (ESI) 495.3 (MH+)

Example 1769

{2-tert-Butyl-4-[2-(2-cyclopropyl-7-imino-5,7-dihydro-pyrrolo[3,4-b]pyridin-6-yl)-acetyl]-6-diethylamino-phenoxy}-acetic acid hydrobromide MS: m/e (ESI) 493.3 (MH+)

Example 1770

{2-tert-Butyl-6-diethylamino-4-[2-(3-ethoxy-7-imino-2-methylcarbamoyl-5,7-dihydro-pyrrolo[3,4-b]pyridin-6-yl)-acetyl]-phenoxy}-acetic acid hydrobromide MS: m/e (ESI) 554.3 (MH+)

Example 1771

{2-tert-Butyl-6-diethylamino-4-[2-(7-fluoro-1-imino-5,6-dimethoxy-1,3-dihydro-isoindol-2-yl)-acetyl]-phenoxy}-acetic acid hydrobromide MS: m/e (ESI) 530.3 (MH+)

Example 1772

{2-tert-Butyl-6-diethylamino-4-[2-(5-ethoxy-1-imino-6-methylcarbamoyl-1,3-dihydro-isoindol-2-yl)-acetyl]-phenoxy}-acetic acid hydrobromide MS: m/e (ESI) 553.4 (MH+)

Example 1773

Ethyl 4-{2-tert-butyl-6-(4-cyano-piperidin-1-yl)-4-[2-(2-cyclopropyl-7-imino-5,7-dihydro-pyrrolo[3,4-b]pyridin-6-yl)-acetyl]-phenoxy}-butanoate hydrobromide MS: m/e (ESI) 586.5 (MH+)

Example 1774

Ethyl 4-{2-tert-butyl-6-(4-cyano-piperidin-1-yl)-4-[2-(3-ethoxy-7-imino-2-methylcarbamoyl-5,7-dihydro-pyrrolo[3,4-b]pyridin-6-yl)-acetyl]-phenoxy}-butanoate hydrobromide MS: m/e (ESI) 647.5 (MH+)

Example 1775

Ethyl 4-{2-tert-butyl-6-(4-cyano-piperidin-1-yl)-4-[2-(7-fluoro-1-imino-5,6-dimethoxy-1,3-dihydro-isoindol-2-yl)-acetyl]-phenoxy}-butanoate hydrobromide MS: m/e (ESI) 623.5 (MH+)

Example 1776

Ethyl 4-{2-tert-butyl-6-(4-cyano-piperidin-1-yl)-4-[2-(5,6-diethoxy-7-fluoro-1-imino-1,3-dihydro-isoindol-2-yl)-acetyl]-phenoxy}-butanoate hydrobromide MS: m/e (ESI) 651.5 (MH+)

Example 1777

Ethyl 4-{2-tert-butyl-6-(4-cyano-piperidin-1-yl)-4-[2-(5-ethoxy-1-imino-6-methylcarbamoyl-1,3-dihydro-isoindol-2-yl)-acetyl]-phenoxy}-butanoate hydrobromide MS: m/e (ESI) 646.5 (MH+)

Example 1778

4-{3-tert-Butyl-2-(3-cyano-propoxy)-5-[2-(2-cyclopropyl-7-imino-5,7-dihydro-pyrrolo[3,4-b]pyridin-6-yl)-acetyl]-phenoxy}-butanoic acid hydrobromide MS: m/e (ESI) 533.4 (MH+)

Example 1779

4-{3-tert-Butyl-2-(3-cyano-propoxy)-5-[2-(3-ethoxy-7-imino-2-methylcarbamoyl-5,7-dihydro-pyrrolo[3,4-b]pyridin-6-yl)-acetyl]-phenoxy}-butanoic acid hydrobromide MS: m/e (ESI) 594.5 (MH+)

Example 1780

4-{3-tert-Butyl-2-(3-cyano-propoxy)-5-[2-(7-fluoro-1-imino-5,6-dimethoxy-1,3-dihydro-isoindol-2-yl)-acetyl]-phenoxy}-butanoic acid hydrobromide MS: m/e (ESI) 570.4 (MH+)

Example 1781

4-{3-tert-Butyl-2-(3-cyano-propoxy)-5-[2-(5,6-diethoxy-7-fluoro-1-imino-1,3-dihydro-isoindol-2-yl)-acetyl]-phenoxy}-butanoic acid hydrobromide MS: m/e (ESI) 598.5 (MH+)

Example 1782

4-{3-tert-Butyl-2-(3-cyano-propoxy)-5-[2-(5-ethoxy-1-imino-6-methylcarbamoyl-1,3-dihydro-isoindol-2-yl)-acetyl]-phenoxy}-butanoic acid hydrobromide MS: m/e (ESI) 593.5 (MH+)

Example 1783

5-{3-tert-Butyl-2-(3-cyano-propoxy)-5-[2-(2-cyclopropyl-7-imino-5,7-dihydro-pyrrolo[3,4-b]pyridin-6-yl)-acetyl]-phenoxy}-pentanoic acid hydrobromide MS: m/e (ESI) 547.4 (MH+)

Example 1784

5-{3-tert-Butyl-2-(3-cyano-propoxy)-5-[2-(3-ethoxy-7-imino-2-methylcarbamoyl-5,7-dihydro-pyrrolo[3,4-b]pyridin-6-yl)-acetyl]-phenoxy}-pentanoic acid hydrobromide MS: m/e (ESI) 608.5 (MH+)

Example 1785

5-{3-tert-Butyl-2-(3-cyano-propoxy)-5-[2-(7-fluoro-1-imino-5,6-dimethoxy-1,3-dihydro-isoindol-2-yl)-acetyl]-phenoxy}-pentanoic acid hydrobromide MS: m/e (ESI) 584.5 (MH+)

Example 1786

5-{3-tert-Butyl-2-(3-cyano-propoxy)-5-[2-(5,6-diethoxy-7-fluoro-1-imino-1,3-dihydro-isoindol-2-yl)-acetyl]-phenoxy}-pentanoic acid hydrobromide MS: m/e (ESI) 612.5 (MH+)

Example 1787

5-{3-tert-Butyl-2-(3-cyano-propoxy)-5-[2-(5-ethoxy-1-imino-6-methylcarbamoyl-1,3-dihydro-isoindol-2-yl)-acetyl]-phenoxy}-pentanoic acid hydrobromide MS: m/e (ESI) 607.2 (MH+)

Example 1788

4-{2-tert-Butyl-4-[2-(3-ethoxy-7-imino-2-methylcarbamoyl-5,7-dihydro-pyrrolo[3,4-b]pyridin-6-yl)-acetyl]-phenylamino}-butanoic acid hydrobromide MS: m/e (ESI) 510.2 (MH+)

Example 1789

4-{2-tert-Butyl-4-[2-(5-ethoxy-1-imino-6-methylcarbamoyl-1,3-dihydro-isoindol-2-yl)-acetyl]-phenylamino}-butanoic acid hydrobromide MS: m/e (ESI) 509.2 (MH+)

Example 1790

5-{2-tert-Butyl-6-(2-cyano-ethyl)-4-[2-(2-cyclopropyl-7-imino-5,7-dihydro-pyrrolo[3,4-b]pyridin-6-yl)-acetyl]-phenoxy}-pentanoic acid hydrobromide MS: m/e (ESI) 517.2 (MH+)

Example 1791

5-{2-tert-Butyl-6-(2-cyano-ethyl)-4-[2-(7-fluoro-1-imino-5,6-dimethoxy-1,3-dihydro-isoindol-2-yl)-acetyl]-phenoxy}-pentanoic acid hydrobromide MS: m/e (ESI) 554.2 (MH+)

Example 1792

5-{2-tert-Butyl-6-(2-cyano-ethyl)-4-[2-(5,6-diethoxy-7-fluoro-1-imino-1,3-dihydro-isoindol-2-yl)-acetyl]-phenoxy}-pentanoic acid hydrobromide MS: m/e (ESI) 582.3 (MH+)

Example 1793

5-{2-tert-Butyl-6-(2-cyano-ethyl)-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 577.3 (MH+)

Example 1794

4-[2-tert-Butyl-4-[2-(7-fluoro-1-imino-5,6-dimethoxy-1,3-dihydro-isoindol-2-yl)-acetyl]-6-(3-thiazol-2-yl-propoxy)-phenoxy]-butanoic acid hydrobromide MS: m/e (ESI) 628.2 (MH+)

Example 1795

1-(3,5-Di-tert-butyl-4-hydroxy-phenyl)-2-(2,3-diethoxy-5-imino-5,7-dihydro-pyrrolo[3,4-b]pyrazin-6-yl)-ethanone hydrobromide MS: m/e (ESI) 469.3 (MH+)

Example 1796

5-{2-tert-Butyl-4-[2-(2,3-diethoxy-5-imino-5,7-dihydro-pyrrolo[3,4-b]pyrazin-6-yl)-acetyl]-6-pyrrolidin-1-yl-phenoxy}-pentanoic acid hydrobromide MS: m/e (ESI) 582.4 (MH+)

Example 1797

{2-tert-Butyl-4-[2-(2,3-diethoxy-5-imino-5,7-dihydro-pyrrolo[3,4-b]pyrazin-6-yl)-acetyl]-6-pyrrolidin-1-yl-phenoxy}-acetic acid hydrobromide MS: m/e (ESI) 540.3 (MH+)

Example 1798

4-{3-tert-Butyl-5-[2-(2,3-diethoxy-5-imino-5,7-dihydro-pyrrolo[3,4-b]pyrazin-6-yl)-acetyl]-2-hydroxy-phenoxy}-butyronitrile hydrobromide MS: m/e (ESI) 496.2 (MH+)

Example 1799

4-{2-tert-Butyl-4-[2-(2,3-diethoxy-5-imino-5,7-dihydro-pyrrolo[3,4-b]pyrazin-6-yl)-acetyl]-6-methoxy-phenoxy}-butylamide hydrobromide MS: m/e (ESI) 528.3 (MH+)

Example 1800

{2-tert-Butyl-6-(3-cyano-propoxy)-4-[2-(2,3-diethoxy-5-imino-5,7-dihydro-pyrrolo[3,4-b]pyrazin-6-yl)-acetyl]-phenoxy}-acetic acid hydrobromide MS: m/e (ESI) 554.3 (MH+)

Example 1801

5-{2-tert-Butyl-6-(3-cyano-propoxy)-4-[2-(2,3-diethoxy-5-imino-5,7-dihydro-pyrrolo[3,4-b]pyrazin-6-yl)-acetyl]-phenoxy}-pentanoic acid hydrobromide MS: m/e (ESI) 596.3 (MH+)

Example 1802

5-{2-tert-Butyl-4-[2-(2-cyclopropyl-7-imino-5,7-dihydro-pyrrolo[3,4-b]pyridin-6-yl)-acetyl]-6-pyrrolidin-1-yl-phenoxymethyl}-isoxazole-3-carboxylic acid hydrobromide MS: m/e (ESI) 558.3 (MH+)

Example 1803

5-{2-tert-Butyl-4-[2-(2-cyclopropyl-7-imino-5,7-dihydro-pyrrolo[3,4-b]pyridin-6-yl)-acetyl]-6-pyrrolidin-1-yl-phenoxymethyl}-4,5-dihydro-isoxazole-3-carboxylic acid hydrobromide MS: m/e (ESI) 560.3 (MH+)

Example 1804

5-{2-tert-Butyl-4-[2-(7-fluoro-1-imino-5,6-dimethoxy-1,3-dihydro-isoindol-2-yl)-acetyl]-6-pyrrolidin-1-yl-phenoxymethyl}-isoxazole-3-carboxylic acid hydrobromide MS: m/e (ESI) 595.3 (MH+)

Example 1805

5-{2-tert-Butyl-4-[2-(7-fluoro-1-imino-5,6-dimethoxy-1,3-dihydro-isoindol-2-yl)-acetyl]-6-pyrrolidin-1-yl-phenoxymethyl}-4,5-dihydro-isoxazole-3-carboxylic acid hydrobromide MS: m/e (ESI) 597.3 (MH+)

Example 1806

5-{2-tert-Butyl-4-[2-(5-ethoxy-1-imino-6-methylcarbamoyl-1,3-dihydro-isoindol-2-yl)-acetyl]-6-pyrrolidin-1-yl-phenoxymethyl}-isoxazole-3-carboxylic acid hydrobromide MS: m/e (ESI) 618.3 (MH+)

Example 1807

5-{2-tert-Butyl-4-[2-(5-ethoxy-1-imino-6-methylcarbamoyl-1,3-dihydro-isoindol-2-yl)-acetyl]-6-pyrrolidin-1-yl-phenoxymethyl}-4,5-dihydro-isoxazole-3-carboxylic acid hydrobromide MS: m/e (ESI) 620.3 (MH+)

Example 1808

5-{2-(2-Cyano-1,1-dimethyl-ethyl)-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 549.4 (MH+)

Example 1809

5-{2-tert-Butyl-6-(3-cyano-propyl)-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 591.4 (MH+)

Example 1810

5-{2-tert-Butyl-6-(3-cyano-propoxy)-4-[4-(5-ethoxy-1-imino-6-methylcarbamoyl-1,3-dihydro-isoindol-2-yl)-3-oxo-butyl]-phenoxy}-pentanoic acid hydrobromide MS: m/e (ESI) 635.5 (MH+)

Example 1811

{2-tert-Butyl-6-(3-cyano-propoxy)-4-[4-(5-ethoxy-1-imino-6-methylcarbamoyl-1,3-dihydro-isoindol-2-yl)-3-oxo-butyl]-phenoxy}-acetic acid hydrobromide MS: m/e (ESI) 593.4 (MH+)

Example 1812

6-{2-tert-Butyl-4-[2-(5-ethoxy-1-imino-6-methylcarbamoyl-1,3-dihydro-isoindol-2-yl)-acetyl]-phenoxy}-nicotinic acid hydrobromide MS: m/e (ESI) 545.3 (MH+)

Example 1813

2-{2-tert-Butyl-4-[2-(5-ethoxy-1-imino-6-methylcarbamoyl-1,3-dihydro-isoindol-2-yl)-acetyl]-6-pyrrolidin-1-yl-phenoxymethyl}-cyclopropanecarboxylic acid hydrobromide MS: m/e (ESI) 591.4 (MH+)

Example 1814

5-{2-tert-Butyl-4-[2-(5-ethoxy-1-imino-6-methylcarbamoyl-1,3-dihydro-isoindol-2-yl)-acetyl]-6-morpholin-4-yl-phenoxy}-pentanoic acid hydrobromide MS: m/e (ESI) 609.5 (MH+)

Example 1815

5-{2-tert-Butyl-6-(3-cyano-propyl)-4-[2-(7-fluoro-1-imino-5,6-dimethoxy-1,3-dihydro-isoindol-2-yl)-acetyl]-phenoxy}-pentanoic acid hydrobromide MS: m/e (ESI) 568.4 (MH+)

Example 1816

5-{2-tert-Butyl-6-(3-cyano-propoxy)-4-[4-(7-fluoro-1-imino-5,6-dimethoxy-1,3-dihydro-isoindol-2-yl)-3-oxo-butyl]-phenoxy}-pentanoic acid hydrobromide MS: m/e (ESI) 612.4 (MH+)

Example 1817

{2-tert-Butyl-6-(3-cyano-propoxy)-4-[4-(7-fluoro-1-imino-5,6-dimethoxy-1,3-dihydro-isoindol-2-yl)-3-oxo-butyl]-phenoxy}-acetic acid hydrobromide MS: m/e (ESI) 570.3 (MH+)

Example 1818

6-{2-tert-Butyl-4-[2-(7-fluoro-1-imino-5,6-dimethoxy-1,3-dihydro-isoindol-2-yl)-acetyl]-phenoxy}-nicotinic acid hydrobromide MS: m/e (ESI) 522.3 MH+)

Example 1819

2-{2-tert-Butyl-4-[2-(7-fluoro-1-imino-5,6-dimethoxy-1,3-dihydro-isoindol-2-yl)-acetyl]-6-pyrrolidin-1-yl-phenoxymethyl}-cyclopropanecarboxylic acid hydrobromide MS: m/e (ESI) 568.4 (MH+)

Example 1820

5-{2-tert-Butyl-6-(4-cyano-piperidin-1-yl)-4-[2-(7-fluoro-1-imino-5,6-dimethoxy-1,3-dihydro-isoindol-2-yl)-acetyl]-phenoxy}-pentanoic acid hydrobromide MS: m/e (ESI) 609.4 (MH+)

Example 1821

(2-{2-tert-Butyl-4-[2-(7-fluoro-1-imino-5,6-dimethoxy-1,3-dihydro-isoindol-2-yl)-acetyl]-6-pyrrolidin-1-yl-phenoxy}-ethoxy)-acetic acid hydrobromide MS: m/e (ESI) 572.3 (MH+)

Example 1822

5-{2-(2-Cyano-1 μl-dimethyl-ethyl)-4-[2-(2-cyclopropyl-7-imino-5,7-dihydro-pyrrolo[3,4-b]pyridin-6-yl)-acetyl]-phenoxy}-pentanoic acid hydrobromide MS: m/e (ESI) 489.3 (MH+)

Example 1823

5-{2-tert-Butyl-6-(3-cyano-propyl)-4-[2-(2-cyclopropyl-7-imino-5,7-dihydro-pyrrolo[3,4-b]pyridin-6-yl)-acetyl]-phenoxy}-pentanoic acid hydrobromide MS: m/e (ESI) 531.4 (MH+)

Example 1824

5-{2-tert-Butyl-6-(3-cyano-propoxy)-4-[4-(2-cyclopropyl-7-imino-5,7-dihydro-pyrrolo[3,4-b]pyridin-6-yl)-3-oxo-butyl]-phenoxy}-pentanoic acid hydrobromide MS: m/e (ESI) 575.4 (MH+)

Example 1825

{2-tert-Butyl-6-(3-cyano-propoxy)-4-[4-(2-cyclopropyl-7-imino-5,7-dihydro-pyrrolo[3,4-b]pyridin-6-yl)-3-oxo-butyl]-phenoxy}-acetic acid hydrobromide MS: m/e (ESI) 533.3 (MH+)

Example 1826

6-{2-tert-Butyl-4-[2-(2-cyclopropyl-7-imino-5,7-dihydro-pyrrolo[3,4-b]pyridin-6-yl)-acetyl]-phenoxy}-nicotinic acid hydrobromide MS: m/e (ESI) 485.2 (MH+)

Example 1827

2-{2-tert-Butyl-4-[2-(2-cyclopropyl-7-imino-5,7-dihydro-pyrrolo[3,4-b]pyridin-6-yl)-acetyl]-6-pyrrolidin-1-yl-phenoxymethyl}-cyclopropanecarboxylic acid hydrobromide MS: m/e (ESI) 531.1 (MH+)

Example 1828

5-{2-tert-Butyl-4-[2-(2-cyclopropyl-7-imino-5,7-dihydro-pyrrolo[3,4-b]pyridin-6-yl)-acetyl]-6-morpholin-4-yl-phenoxy}-pentanoic acid hydrobromide MS: m/e (ESI) 549.5 (MH+)

Example 1829

4-{2-tert-Butyl-4-[2-(2-cyclopropyl-7-imino-5,7-dihydro-pyrrolo[3,4-b]pyridin-6-yl)-acetyl]-6-piperidin-1-yl-phenoxy}-butanoic acid hydrobromide MS: m/e (ESI) 532.9 (MH+)

Example 1830

4-[2-tert-Butyl-4-[2-(2-cyclopropyl-7-imino-5,7-dihydro-pyrrolo[3,4-b]pyridin-6-yl)-acetyl]-6-(4-oxo-piperidin-1-yl)-phenoxy]-butanoic acid hydrobromide MS: m/e (ESI) 546.9 (MH+)

Example 1831

4-[2-tert-Butyl-4-[2-(2-cyclopropyl-7-imino-5,7-dihydro-pyrrolo[3,4-b]pyridin-6-yl)-acetyl]-6-(4-hydroxy-piperidin-1-yl)-phenoxy]-butanoic acid hydrobromide MS: m/e (ESI) 548.9 (MH+)

Example 1832

4-{2-tert-Butyl-6-(4-cyano-piperidin-1-yl)-4-[2-(2-cyclopropyl-7-imino-5,7-dihydro-pyrrolo[3,4-b]pyridin-6-yl)-acetyl]-phenoxy}-butanoic acid hydrobromide MS: m/e (ESI) 557.9 (MH+)

Example 1833

5-[2-tert-Butyl-4-[2-(2-cyclopropyl-7-imino-5,7-dihydro-pyrrolo[3,4-b]pyridin-6-yl)-acetyl]-6-(4-oxo-piperidin-1-yl)-phenoxy]-pentanoic acid hydrobromide MS: m/e (ESI) 560.9 (MH+)

Example 1834

5-[2-tert-Butyl-4-[2-(2-cyclopropyl-7-imino-5,7-dihydro-pyrrolo[3,4-b]pyridin-6-yl)-acetyl]-6-(4-hydroxy-piperidin-1-yl)-phenoxy]-pentanoic acid hydrobromide MS: m/e (ESI) 562.9 (MH+)

Example 1835

5-{2-tert-Butyl-6-(4-cyano-piperidin-1-yl)-4-[2-(2-cyclopropyl-7-imino-5,7-dihydro-pyrrolo[3,4-b]pyridin-6-yl)-acetyl]-phenoxy}-pentanoic acid hydrobromide MS: m/e (ESI) 571.9 (MH+)

Example 1836

(2-{2-tert-Butyl-4-[2-(2-cyclopropyl-7-imino-5,7-dihydro-pyrrolo[3,4-b]pyridin-6-yl)-acetyl]-6-pyrrolidin-1-yl-phenoxy}-ethoxy)-acetic acid hydrobromide MS: m/e (ESI) 534.8 (MH+)

Example 1837

5-{2-(2-Cyano-1,1-dimethyl-ethyl)-4-[2-(3-ethoxy-7-imino-2-methylcarbamoyl-5,7-dihydro-pyrrolo[3,4-b]pyridin-6-yl)-acetyl]-phenoxy}-pentanoic acid hydrobromide MS: m/e (ESI) 549.8 (MH+)

Example 1838

5-{2-tert-Butyl-6-(3-cyano-propyl)-4-[2-(3-ethoxy-7-imino-2-methylcarbamoyl-5,7-dihydro-pyrrolo[3,4-b]pyridin-6-yl)-acetyl]-phenoxy}-pentanoic acid hydrobromide MS: m/e (ESI) 591.9 (MH+)

Example 1839

5-{2-tert-Butyl-6-(3-cyano-propoxy)-4-[4-(3-ethoxy-7-imino-2-methylcarbamoyl-5,7-dihydro-pyrrolo[3,4-b]pyridin-6-yl)-3-oxo-butyl]-phenoxy}-pentanoic acid hydrobromide MS: m/e (ESI) 635.9 (MH+)

Example 1840

{2-tert-Butyl-6-(3-cyano-propoxy)-4-[4-(3-ethoxy-7-imino-2-methylcarbamoyl-5,7-dihydro-pyrrolo[3,4-b]pyridin-6-yl)-3-oxo-butyl]-phenoxy}-acetic acid hydrobromide MS: m/e (ESI) 593.8 (MH+)

Example 1841

6-{2-tert-Butyl-4-[2-(3-ethoxy-7-imino-2-methylcarbamoyl-5,7-dihydro-pyrrolo[3,4-b]pyridin-6-yl)-acetyl]-phenoxy}-nicotinic acid hydrobromide MS: m/e (ESI) 545.8 (MH+)

Example 1842

(2-{2-tert-Butyl-4-[2-(3-ethoxy-7-imino-2-methylcarbamoyl-5,7-dihydro-pyrrolo[3,4-b]pyridin-6-yl)-acetyl]-6-pyrrolidin-1-yl-phenoxy}-ethoxy)-acetic acid hydrobromide MS: m/e (ESI) 595.9 (MH+)

Example 1843

5-{2-(2-Cyano-1,1-dimethyl-ethyl)-4-[2-(5,6-diethoxy-7-fluoro-1-imino-1,3-dihydro-isoindol-2-yl)-acetyl]-phenoxy}-pentanoic acid hydrobromide MS: m/e (ESI) 553.8 (MH+)

Example 1844

5-{2-tert-Butyl-6-(3-cyano-propyl)-4-[2-(5,6-diethoxy-7-fluoro-1-imino-1,3-dihydro-isoindol-2-yl)-acetyl]-phenoxy}-pentanoic acid hydrobromide MS: m/e (ESI) 595.9 (MH+)

Example 1845

5-{2-tert-Butyl-6-(3-cyano-propoxy)-4-[4-(5,6-diethoxy-7-fluoro-1-imino-1,3-dihydro-isoindol-2-yl)-3-oxo-butyl]-phenoxy}-pentanoic acid hydrobromide MS: m/e (ESI) 640.9 (MH+)

Example 1846

(6-{2-tert-Butyl-4-[2-(5-ethoxy-1-imino-6-methylcarbamoyl-1,3-dihydro-isoindol-2-yl)-acetyl]-phenoxy}-pyridin-3-yl)-acetic acid hydrobromide MS: m/e (ESI) 559.1 (MH+)

Example 1847

5-{2-(Cyano-dimethyl-methyl)-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 535.2 (MH+)

Example 1848

3-[2-tert-Butyl-4-[2-(5-ethoxy-1-imino-6-methylcarbamoyl-1,3-dihydro-isoindol-2-yl)-acetyl]-6-(3-thiazol-2-yl-propoxy)-phenoxy]-propionic acid hydrobromide MS: m/e (ESI) 637.3 (MH+)

Example 1849

5-[2-tert-Butyl-4-[2-(5-ethoxy-1-imino-6-methylcarbamoyl-1,3-dihydro-isoindol-2-yl)-acetyl]-6-(3-thiazol-2-yl-propoxy)-phenoxy]-pentanoic acid hydrobromide MS: m/e (ESI) 665.3 (MH+)

Example 1850

(6-{2-tert-Butyl-4-[2-(7-fluoro-1-imino-5,6-dimethoxy-1,3-dihydro-isoindol-2-yl)-acetyl]-phenoxy}-pyridin-3-yl)-acetic acid hydrobromide MS: m/e (ESI) 536.2 (MH+)

Example 1851

5-{2-(Cyano-dimethyl-methyl)-4-[2-(7-fluoro-1-imino-5,6-dimethoxy-1,3-dihydro-isoindol-2-yl)-acetyl]-phenoxy}-pentanoic acid hydrobromide MS: m/e (ESI) 512.2 (MH+)

Example 1852

5-[2-tert-Butyl-4-[2-(7-fluoro-1-imino-5,6-dimethoxy-1,3-dihydro-isoindol-2-yl)-acetyl]-6-(3-thiazol-2-yl-propoxy)-phenoxy]-pentanoic acid hydrobromide MS: m/e (ESI) 642.3 (MH+)

Example 1853

(6-{2-tert-Butyl-4-[2-(5,6-diethoxy-7-fluoro-1-imino-1,3-dihydro-isoindol-2-yl)-acetyl]-phenoxy}-pyridin-3-yl)-acetic acid hydrobromide MS: m/e (ESI) 564.2 (MH+)

Example 1854

5-{2-(Cyano-dimethyl-methyl)-4-[2-(5,6-diethoxy-7-fluoro-1-imino-1,3-dihydro-isoindol-2-yl)-acetyl]-phenoxy}-pentanoic acid hydrobromide MS: m/e (ESI) 540.2 (MH+)

Example 1855

5-{2-tert-Butyl-4-[2-(5,6-diethoxy-7-fluoro-1-imino-1,3-dihydro-isoindol-2-yl)-acetyl]-6-(3-thiazol-2-yl-propoxy}-phenoxy]-pentanoic acid hydrobromide MS: m/e (ESI) 670.2 (MH+)

Example 1856

(6-{2-tert-Butyl-4-[2-(2-cyclopropyl-7-imino-5,7-dihydro-pyrrolo[3,4-b]pyridin-6-yl)-acetyl]-phenoxy}-pyridin-3-yl)-acetic acid hydrobromide MS: m/e (ESI) 499.1 (MH+)

Example 1857

5-{2-(Cyano-dimethyl-methyl)-4-[2-(2-cyclopropyl-7-imino-5,7-dihydro-pyrrolo[3,4-b]pyridin-6-yl)-acetyl]-phenoxy}-pentanoic acid hydrobromide MS: m/e (ESI) 475.2 (MH+)

Example 1858

4-[2-tert-Butyl-4-[2-(2-cyclopropyl-7-imino-5,7-dihydro-pyrrolo[3,4-b]pyridin-6-yl)-acetyl]-6-(3-thiazol-2-yl-propoxy)-phenoxy]-butanoic acid hydrobromide MS: m/e (ESI) 591.2 (MH+)

Example 1859

5-[2-tert-Butyl-4-[2-(2-cyclopropyl-7-imino-5,7-dihydro-pyrrolo[3,4-b]pyridin-6-yl)-acetyl]-6-(3-thiazol-2-yl-propoxy)-phenoxy]-pentanoic acid hydrobromide MS: m/e (ESI) 605.2 (MH+)

Example 1860

(6-{2-tert-Butyl-4-[2-(3-ethoxy-7-imino-2-methylcarbamoyl-5,7-dihydro-pyrrolo[3,4-b]pyridin-6-yl)-acetyl]-phenoxy}-pyridin-3-yl)-acetic acid hydrobromide MS: m/e (ESI) 560.1 (MH+)

Example 1861

5-{2-(Cyano-dimethyl-methyl)-4-[2-(3-ethoxy-7-imino-2-methylcarbamoyl-5,7-dihydro-pyrrolo[3,4-b]pyridin-6-yl)-acetyl]-phenoxy}-pentanoic acid hydrobromide MS: m/e (ESI) 536.2 (MH+)

Example 1862

4-[2-tert-Butyl-4-[2-(3-ethoxy-7-imino-2-methylcarbamoyl-5,7-dihydro-pyrrolo[3,4-b]pyridin-6-yl)-acetyl]-6-(3-thiazol-2-yl-propoxy)-phenoxy]-butanoic acid hydrobromide MS: m/e (ESI) 652.2 (MH+)

Example 1863

5-[2-tert-Butyl-4-[2-(3-ethoxy-7-imino-2-methylcarbamoyl-5,7-dihydro-pyrrolo[3,4-b]pyridin-6-yl)-acetyl]-6-(3-thiazol-2-yl-propoxy)-phenoxy]-pentanoic acid hydrobromide MS: m/e (ESI) 666.2 (MH+)

Example 1864

4-{5-[2-(5-Ethoxy-1-imino-6-methylcarbamoyl-1,3-dihydro-isoindol-2-yl)-acetyl]-3,3-dimethyl-2,3-dihydro-indol-1-yl}-butanoic acid hydrobromide MS: m/e (ESI) 506.3 (MH+)

Example 1865

4-{5-[2-(7-Fluoro-1-imino-5,6-dimethoxy-1,3-dihydro-isoindol-2-yl)-acetyl]-3,3-dimethyl-2,3-dihydro-indol-1-yl}-butanoic acid hydrobromide MS: m/e (ESI) 483.3 (MH+)

Example 1866

4-{5-[2-(5,6-Diethoxy-7-fluoro-1-imino-1,3-dihydro-isoindol-2-yl)-acetyl]-3,3-dimethyl-2,3-dihydro-indol-1-yl}-butanoic acid hydrobromide MS: m/e (ESI) 511.3 (MH+)

Example 1867

4-{5-[2-(2-Cyclopropyl-7-imino-5,7-dihydro-pyrrolo[3,4-b]pyridin-6-yl)-acetyl]-3,3-dimethyl-2,3-dihydro-indol-1-yl}-butanoic acid hydrobromide MS: m/e (ESI) 447.3 (MH+)

Example 1868

4-{5-[2-(3-Ethoxy-7-imino-2-methylcarbamoyl-5,7-dihydro-pyrrolo[3,4-b]pyridin-6-yl)-acetyl]-3,3-dimethyl-2,3-dihydro-indol-1-yl}-butanoic acid hydrobromide MS: m/e (ESI) 508.3 (MH+)

Example 1869

{3-[2-(5-Ethoxy-1-imino-6-methylcarbamoyl-1,3-dihydro-isoindol-2-yl)-acetyl]-5-pyrrolidin-1-yl-phenoxy}-acetic acid hydrobromide MS: m/e (ESI) 495.3 (MH+)

Example 1870

4-{3-[2-(5-Ethoxy-1-imino-6-methylcarbamoyl-1,3-dihydro-isoindol-2-yl)-acetyl]-5-pyrrolidin-1-yl-phenoxy}-butanoic acid hydrobromide MS: m/e (ESI) 523.3 (MH+)

Example 1871

5-{3-[2-(5-Ethoxy-1-imino-6-methylcarbamoyl-1,3-dihydro-isoindol-2-yl)-acetyl]-5-pyrrolidin-1-yl-phenoxy}-pentanoic acid hydrobromide MS: m/e (ESI) 537.3 (MH+)

Example 1872

{3-[2-(7-Fluoro-1-imino-5,6-dimethoxy-1,3-dihydro-iso-isoindol-2-yl)-acetyl]-5-pyrrolidin-1-yl-phenoxy}-acetic acid hydrobromide MS: m/e (ESI) 472.2 (MH+)

Example 1873

4-{3-[2-(7-Fluoro-1-imino-5,6-dimethoxy-1,3-dihydro-isoindol-2-yl)-acetyl]-5-pyrrolidin-1-yl-phenoxy}-butanoic acid hydrobromide MS: m/e (ESI) 500.2 (MH+)

Example 1874

5-{3-[2-(7-Fluoro-1-imino-5,6-dimethoxy-1,3-dihydro-isoindol-2-yl)-acetyl]-5-pyrrolidin-1-yl-phenoxy}-pentanoic acid hydrobromide MS: m/e (ESI) 514.3 (MH+)

Example 1875

{3-[2-(2-Cyclopropyl-7-imino-5,7-dihydro-pyrrolo[3,4-b]pyridin-6-yl)-acetyl]-5-pyrrolidin-1-yl-phenoxy}-acetic acid hydrobromide MS: m/e (ESI) 435.2 (MH+)

Example 1876

4-{3-[2-(2-Cyclopropyl-7-imino-5,7-dihydro-pyrrolo[3,4-b]pyridin-6-yl)-acetyl]-5-pyrrolidin-1-yl-phenoxy}-butanoic acid hydrobromide MS: m/e (ESI) 463.3 (MH+)

Example 1877

5-{3-[2-(2-Cyclopropyl-7-imino-5,7-dihydro-pyrrolo[3,4-b]pyridin-6-yl)-acetyl]-5-pyrrolidin-1-yl-phenoxy}-pentanoic acid hydrobromide MS: m/e (ESI) 477.3 (MH+)

Example 1878

{3-[2-(3-Ethoxy-7-imino-2-methylcarbamoyl-5,7-dihydro-pyrrolo[3,4-b]pyridin-6-yl)-acetyl]-5-pyrrolidin-1-yl-phenoxy}-acetic acid hydrobromide MS: m/e (ESI) 496.2 (MH+)

Example 1879

4-{3-[2-(3-Ethoxy-7-imino-2-methylcarbamoyl-5,7-dihydro-pyrrolo[3,4-b]pyridin-6-yl)-acetyl]-5-pyrrolidin-1-yl-phenoxy}-butanoic acid hydrobromide MS: m/e (ESI) 524.3 (MH+)

Example 1880

5-{3-[2-(3-Ethoxy-7-imino-2-methylcarbamoyl-5,7-dihydro-pyrrolo[3,4-b]pyridin-6-yl)-acetyl]-5-pyrrolidin-1-yl-phenoxy}-pentanoic acid hydrobromide MS: m/e (ESI) 538.3 (MH+)

Example 1881

{3-[2-(5,6-Diethoxy-7-fluoro-1-imino-1,3-dihydro-isoindol-2-yl)-acetyl]-5-pyrrolidin-1-yl-phenoxy}-acetic acid hydrobromide MS: m/e (ESI) 500.2 (MH+)

Example 1882

4-{3-[2-(5,6-Diethoxy-7-fluoro-1-imino-1,3-dihydro-isoindol-2-yl)-acetyl]-5-pyrrolidin-1-yl-phenoxy}-butanoic acid hydrobromide MS: m/e (ESI) 528.2 (MH+)

Example 1883

5-{3-[2-(5,6-Diethoxy-7-fluoro-1-imino-1,3-dihydro-isoindol-2-yl)-acetyl]-5-pyrrolidin-1-yl-phenoxy}-pentanoic acid hydrobromide MS: m/e (ESI) 542.3 (MH+)

Example 1884

2-{2-[3-tert-Butyl-4-(methanesulfonyl-methyl-amino)-phenyl]-2-oxo-ethyl}-6-ethoxy-3-imino-2,3-dihydro-1H-isoindole-5-acetic acid methylamide hydrobromide MS: m/e (ESI) 515.5 (MH+)

Example 1885

5-[2-tert-Butyl-4-[2-(5-ethoxy-1-imino-6-methylcarbamoyl-1,3-dihydro-isoindol-2-yl)-acetyl]-6-(3-thiophen-2-yl-propoxy)-phenoxy]-pentanoic acid hydrobromide MS: m/e (ESI) 664.3 (MH+)

Example 1886

[2-tert-Butyl-4-[2-(5-ethoxy-1-imino-6-methylcarbamoyl-1,3-dihydro-isoindol-2-yl)-acetyl]-6-(2-methyl-pyrrolidin-1-yl)-phenoxy]-acetic acid hydrobromide MS: m/e (ESI) 565.2 (MH+)

Example 1887

5-[2-tert-Butyl-4-[2-(5-ethoxy-1-imino-6-methylcarbamoyl-1,3-dihydro-isoindol-2-yl)-acetyl]-6-(2-methyl-pyrrolidin-1-yl)-phenoxy]-pentanoic acid hydrobromide MS: m/e (ESI) 607.3 (MH+)

Example 1888

{2-tert-Butyl-4-[4-(5-ethoxy-1-imino-6-methylcarbamoyl-1,3-dihydro-isoindol-2-yl)-3-oxo-butyl]-6-pyrrolidin-1-yl-phenoxy}-acetic acid hydrobromide MS: m/e (ESI) 579.3 (MH+)

Example 1889

4-{2-tert-Butyl-4-[2-(5-ethoxy-1-imino-6-methylcarbamoyl-1,3-dihydro-isoindol-2-yl)-acetyl]-6-piperidin-1-yl-phenoxy}-butanoic acid hydrobromide MS: m/e (ESI) 593.3 (MH+)

Example 1890

5-{2-tert-Butyl-6-(4-cyano-piperidin-1-yl)-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 632.3 (MH+)

Example 1891

N-{2-tert-Butyl-4-[2-(7-fluoro-1-imino-5,6-dimethoxy-1,3-dihydro-isoindol-2-yl)-acetyl]-phenyl}-N-methyl-methanesulfonamide hydrobromide MS: m/e (ESI) 492.2 (MH+)

Example 1892

5-[2-tert-Butyl-4-[2-(7-fluoro-1-imino-5,6-dimethoxy-1,3-dihydro-isoindol-2-yl)-acetyl]-6-(3-thiophen-2-yl-propoxy)-phenoxy]-pentanoic acid hydrobromide MS: m/e (ESI) 641.2 (MH+)

Example 1893

[2-tert-Butyl-4-[2-(7-fluoro-1-imino-5,6-dimethoxy-1,3-dihydro-isoindol-2-yl)-acetyl]-6-(2-methyl-pyrrolidin-1-yl)-phenoxy]-acetic acid hydrobromide MS: m/e (ESI) 542.2 (MH+)

Example 1894

5-[2-tert-Butyl-4-[2-(7-fluoro-1-imino-5,6-dimethoxy-1,3-dihydro-isoindol-2-yl)-acetyl]-6-(2-methyl-pyrrolidin-1-yl)-phenoxy]-pentanoic acid hydrobromide MS: m/e (ESI) 584.3 (MH+)

Example 1895

5-{2-tert-Butyl-4-[2-(7-fluoro-1-imino-5,6-dimethoxy-1,3-dihydro-isoindol-2-yl)-acetyl]-6-morpholin-4-yl-phenoxy}-pentanoic acid hydrobromide MS: m/e (ESI) 586.3 (MH+)

Example 1896

N-{2-tert-Butyl-4-[2-(5,6-diethoxy-7-fluoro-1-imino-1,3-dihydro-isoindol-2-yl)-acetyl]-phenyl}-N-methyl-methanesulfonamide hydrobromide MS: m/e (ESI) 520.2 (MH+)

Example 1897

5-[2-tert-Butyl-4-[2-(5,6-diethoxy-7-fluoro-1-imino-1,3-dihydro-isoindol-2-yl)-acetyl]-6-(3-thiophen-2-yl-propoxy)-phenoxy]-pentanoic acid hydrobromide MS: m/e (ESI) 669.3 (MH+)

Example 1898

[2-tert-Butyl-4-[2-(5,6-diethoxy-7-fluoro-1-imino-1,3-dihydro-isoindol-2-yl)-acetyl]-6-(2-methyl-pyrrolidin-1-yl)-phenoxy]-acetic acid hydrobromide MS: m/e (ESI) 570.3 (MH+)

Example 1899

5-[2-tert-Butyl-4-[2-(5,6-diethoxy-7-fluoro-1-imino-1,3-dihydro-isoindol-2-yl)-acetyl]-6-(2-methyl-pyrrolidin-1-yl)-phenoxy]-pentanoic acid hydrobromide MS: m/e (ESI) 612.3 (MH+)

Example 1900

{2-tert-Butyl-4-[4-(5,6-diethoxy-7-fluoro-1-imino-1,3-dihydro-isoindol-2-yl)-3-oxo-butyl]-6-pyrrolidin-1-yl-phenoxy}-acetic acid hydrobromide MS: m/e (ESI) 584.3 (MH+)

Example 1901

5-{2-tert-Butyl-6-(4-cyano-piperidin-1-yl)-4-[2-(5,6-diethoxy-7-fluoro-1-imino-1,3-dihydro-isoindol-2-yl)-acetyl]-phenoxy}-pentanoic acid hydrobromide MS: m/e (ESI) 637.2 (MH+)

Example 1902

5-[2-tert-Butyl-4-[2-(2-cyclopropyl-7-imino-5,7-dihydro-pyrrolo[3,4-b]pyridin-6-yl)-acetyl]-6-(3-thiophen-2-yl-propoxy)-phenoxy]-pentanoic acid hydrobromide MS: m/e (ESI) 604.2 (MH+)

Example 1903

[2-tert-Butyl-4-[2-(2-cyclopropyl-7-imino-5,7-dihydro-pyrrolo[3,4-b]pyridin-6-yl)-acetyl]-6-(2-methyl-pyrrolidin-1-yl)-phenoxy]-acetic acid hydrobromide MS: m/e (ESI) 505.2 (MH+)

Example 1904

{2-tert-Butyl-4-[4-(2-cyclopropyl-7-imino-5,7-dihydro-pyrrolo[3,4-b]pyridin-6-yl)-3-oxo-butyl]-6-pyrrolidin-1-yl-phenoxy}-acetic acid hydrobromide MS: m/e (ESI) 519.2 (MH+)

Example 1905

6-{2-[3-tert-Butyl-4-(methanesulfonyl-methyl-amino)-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 516.1 (MH+)

Example 1906

5-[2-tert-Butyl-4-[2-(3-ethoxy-7-imino-2-methylcarbamoyl-5,7-dihydro-pyrrolo[3,4-b]pyridin-6-yl)-acetyl]-6-(3-thiophen-2-yl-propoxy)-phenoxy]-pentanoic acid hydrobromide MS: m/e (ESI) 665.2 (MH+)

Example 1907

{2-tert-Butyl-4-[4-(7-fluoro-1-imino-5,6-dimethoxy-1,3-dihydro-isoindol-2-yl)-3-oxo-butyl]-6-pyrrolidin-1-yl-phenoxy}-acetic acid hydrobromide MS: m/e (ESI) 556.2 (MH+)

Example 1908

4-{2-tert-Butyl-4-[2-(7-fluoro-1-imino-5,6-dimethoxy-1,3-dihydro-isoindol-2-yl)-acetyl]-6-piperidin-1-yl-phenoxy}-butanoic acid hydrobromide MS: m/e (ESI) 570.3 (MH+)

Example 1909

N-{2-tert-Butyl-4-[2-(2-cyclopropyl-7-imino-5,7-dihydro-pyrrolo[3,4-b]pyridin-6-yl)-acetyl]-phenyl}-N-methyl-methanesulfonamide hydrobromide MS: m/e (ESI) 455.2 (MH+)

Example 1910

5-[2-tert-Butyl-4-[2-(2-cyclopropyl-7-imino-5,7-dihydro-pyrrolo[3,4-b]pyridin-6-yl)-acetyl]-6-(2-methyl-pyrrolidin-1-yl)-phenoxy]-pentanoic acid hydrobromide MS: m/e (ESI) 547.3 (MH+)

Example 1911

[2-tert-Butyl-4-[2-(3-ethoxy-7-imino-2-methylcarbamoyl-5,7-dihydro-pyrrolo[3,4-b]pyridin-6-yl)-acetyl]-6-(2-methyl-pyrrolidin-1-yl)-phenoxy]-acetic acid hydrobromide MS: m/e (ESI) 566.2 (MH+)

Example 1912

5-[2-tert-Butyl-4-[2-(3-ethoxy-7-imino-2-methylcarbamoyl-5,7-dihydro-pyrrolo[3,4-b]pyridin-6-yl)-acetyl]-6-(2-methyl-pyrrolidin-1-yl)-phenoxy]-pentanoic acid hydrobromide MS: m/e (ESI) 608.2 (MH+)

Example 1913

{2-tert-Butyl-4-[4-(3-ethoxy-7-imino-2-methylcarbamoyl-5,7-dihydro-pyrrolo[3,4-b]pyridin-6-yl)-3-oxo-butyl]-6-pyrrolidin-1-yl-phenoxy}-acetic acid hydrobromide MS: m/e (ESI) 580.2 (MH+)

Example 1914

5-{2-tert-Butyl-6-(4-cyano-piperidin-1-yl)-4-[2-(3-ethoxy-7-imino-2-methylcarbamoyl-5,7-dihydro-pyrrolo[3,4-b]pyridin-6-yl)-acetyl]-phenoxy}-pentanoic acid hydrobromide MS: m/e (ESI) 633.2 (MH+)

Example 1915

2-{2-[3-(Acetyl-methyl-amino)-5-tert-butyl-phenyl]-2-oxo-ethyl}-6-ethoxy-3-imino-2,3-dihydro-1H-isoindole-5-acetic acid methylamide hydrobromide MS: m/e (ESI) 479.4 (MH+)

Example 1916

{2-tert-Butyl-4-[3-(5-ethoxy-1-imino-6-methylcarbamoyl-1,3-dihydro-isoindol-2-yl)-2-oxo-propyl]-6-pyrrolidin-1-yl-phenoxy}-acetic acid hydrobromide MS: m/e (ESI) 565.4 (MH+)

Example 1917

{2-tert-Butyl-4-[3-(5,6-diethoxy-7-fluoro-1-imino-1,3-dihydro-isoindol-2-yl)-2-oxo-propyl]-6-pyrrolidin-1-yl-phenoxy}-acetic acid hydrobromide MS: m/e (ESI) 570.4 (MH+)

Example 1918

N-{3-tert-Butyl-5-[2-(7-fluoro-1-imino-5,6-dimethoxy-1,3-dihydro-isoindol-2-yl)-acetyl]-phenyl}-N-methyl-acetamide hydrobromide MS: m/e (ESI) 456.3 (MH+)

Example 1919

{2-tert-Butyl-4-[3-(7-fluoro-1-imino-5,6-dimethoxy-1,3-dihydro-isoindol-2-yl)-2-oxo-propyl]-6-pyrrolidin-1-yl-phenoxy}-acetic acid hydrobromide MS: m/e (ESI) 542.1 (MH+)

Example 1920

5-{2-tert-Butyl-4-[2-(7-fluoro-1-imino-5,6-dimethoxy-1,3-dihydro-isoindol-2-yl)-acetyl]-6-pyrrolidin-1-yl-phenoxy}-2-fluoro-pentanoic acid hydrobromide MS: m/e (ESI) 588.2 (MH+)

Example 1921

{2-tert-Butyl-4-[3-(2-cyclopropyl-7-imino-5,7-dihydro-pyrrolo[3,4-b]pyridin-6-yl)-2-oxo-propyl]-6-pyrrolidin-1-yl-phenoxy}-acetic acid hydrobromide MS: m/e (ESI) 505.2 (MH+)

Example 1922

5-{2-tert-Butyl-4-[2-(2-cyclopropyl-7-imino-5,7-dihydro-pyrrolo[3,4-b]pyridin-6-yl)-acetyl]-6-pyrrolidin-1-yl-phenoxy}-2-fluoro-pentanoic acid hydrobromide MS: m/e (ESI) 551.3 (MH+)

Example 1923

6-{2-[3-(Acetyl-methyl-amino)-5-tert-butyl-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 480.3 (MH+)

Example 1924

{2-tert-Butyl-4-[3-(3-ethoxy-7-imino-2-methylcarbamoyl-5,7-dihydro-pyrrolo[3,4-b]pyridin-6-yl)-2-oxo-propyl]-6-pyrrolidin-1-yl-phenoxy}-acetic acid hydrobromide MS: m/e (ESI) 566.3 (MH+)

Example 1925

4-[2-tert-Butyl-4-[2-(5-ethoxy-1-imino-6-methylcarbamoyl-1,3-dihydro-isoindol-2-yl)-acetyl]-6-(3-thiophen-2-yl-propoxy)-phenoxy]-butanoic acid hydrobromide MS: m/e (ESI) 650.2 (MH+)

Example 1926

4-{2-tert-Butyl-4-[2-(5-ethoxy-1-imino-6-methylcarbamoyl-1,3-dihydro-isoindol-2-yl)-acetyl]-6-[(3-fluoro-propyl)-methyl-amino]-phenoxy}-butanoic acid hydrobromide MS: m/e (ESI) 599.2 (MH+)

Example 1927

5-{2-tert-Butyl-4-[2-(5-ethoxy-1-imino-6-methylcarbamoyl-1,3-dihydro-isoindol-2-yl)-acetyl]-6-[(2-methoxy-ethyl)-methyl-amino]-phenoxy}-pentanoic acid hydrobromide MS: m/e (ESI) 611.3 (MH+)

Example 1928

{8-tert-Butyl-4-cyclopropyl-6-[2-(5-ethoxy-1-imino-6-methylcarbamoyl-1,3-dihydro-isoindol-2-yl)-acetyl]-3,4-dihydro-2H-benzo[1,4]oxazin-3-yl}-acetic acid hydrobromide MS: m/e (ESI) 563.2 (MH+)

Example 1929

5-{4-[2-(5-Ethoxy-1-imino-6-methylcarbamoyl-1,3-dihydro-isoindol-2-yl)-acetyl]-2-isopropoxy-phenoxy}-pentanoic acid hydrobromide MS: m/e (ESI) 526.2 (MH+)

Example 1930

2-[2-(8-tert-Butyl-4-methanesulfonyl-3,4-dihydro-2H-benzo[1,4]oxazin-6-yl)-2-oxo-ethyl]-6-ethoxy-3-imino-2,3-dihydro-1H-isoindole-5-acetic acid methylamide hydrobromide MS: m/e (ESI) 543.2 (MH+)

Example 1931

4-[2-tert-Butyl-4-[2-(7-fluoro-1-imino-5,6-dimethoxy-1,3-dihydro-isoindol-2-yl)-acetyl]-6-(3-thiophen-2-yl-propoxy)-phenoxy]-butanoic acid hydrobromide MS: m/e (ESI) 627.2 (MH+)

Example 1932

4-{2-tert-Butyl-4-[2-(7-fluoro-1-imino-5,6-dimethoxy-1,3-dihydro-isoindol-2-yl)-acetyl]-6-[(3-fluoro-propyl)-methyl-amino]-phenoxy}-butanoic acid hydrobromide MS: m/e (ESI) 576.3 (MH+)

Example 1933

5-{2-tert-Butyl-4-[2-(7-fluoro-1-imino-5,6-dimethoxy-1,3-dihydro-isoindol-2-yl)-acetyl]-6-[(2-methoxy-ethyl)-methyl-amino]-phenoxy}-pentanoic acid hydrobromide MS: m/e (ESI) 588.3 (MH+)

Example 1934

{8-tert-Butyl-4-cyclopropyl-6-[2-(7-fluoro-1-imino-5,6-dimethoxy-1,3-dihydro-isoindol-2-yl)-acetyl]-3,4-dihydro-2H-benzo[1,4]oxazin-3-yl}-acetic acid hydrobromide MS: m/e (ESI) 540.2 (MH+)

Example 1935

5-{4-[2-(7-Fluoro-1-imino-5,6-dimethoxy-1,3-dihydro-isoindol-2-yl)-acetyl]-2-isopropoxy-phenoxy}-pentanoic acid hydrobromide MS: m/e (ESI) 503.2 (MH+)

Example 1936

1-(8-tert-Butyl-4-methanesulfonyl-3,4-dihydro-2H-benzo[1,4]oxazin-6-yl)-2-(7-fluoro-1-imino-5,6-dimethoxy-1,3-dihydro-isoindol-2-yl)-ethanone hydrobromide MS: m/e (ESI) 520.2 (MH+)

Example 1937

4-[2-tert-Butyl-4-[2-(2-cyclopropyl-7-imino-5,7-dihydro-pyrrolo[3,4-b]pyridin-6-yl)-acetyl]-6-(3-thiophen-2-yl-propoxy)-phenoxy]-butanoic acid hydrobromide MS: m/e (ESI) 590.3 (MH+)

Example 1938

4-{2-tert-Butyl-4-[2-(2-cyclopropyl-7-imino-5,7-dihydro-pyrrolo[3,4-b]pyridin-6-yl)-acetyl]-6-[(3-fluoro-propyl)-methyl-amino]-phenoxy}-butanoic acid hydrobromide MS: m/e (ESI) 539.3 (MH+)

Example 1939

5-{2-tert-Butyl-4-[2-(2-cyclopropyl-7-imino-5,7-dihydro-pyrrolo[3,4-b]pyridin-6-yl)-acetyl]-6-[(2-methoxy-ethyl)-methyl-amino]-phenoxy}-pentanoic acid hydrobromide MS: m/e (ESI) 551.3 (MH+)

Example 1940

{8-tert-Butyl-4-cyclopropyl-6-[2-(2-cyclopropyl-7-imino-5,7-dihydro-pyrrolo[3,4-b]pyridin-6-yl)-acetyl]-3,4-dihydro-2H-benzo[1,4]oxazin-3-yl}-acetic acid hydrobromide MS: m/e (ESI) 503.3 (MH+)

Example 1941

5-{4-[2-(2-Cyclopropyl-7-imino-5,7-dihydro-pyrrolo[3,4-b]pyridin-6-yl)-acetyl]-2-isopropoxy-phenoxy}-pentanoic acid hydrobromide MS: m/e (ESI) 466.2 (MH+)

Example 1942

1-(8-tert-Butyl-4-methanesulfonyl-3,4-dihydro-2H-benzo[1,4]oxazin-6-yl)-2-(2-cyclopropyl-7-imino-5,7-dihydro-pyrrolo[3,4-b]pyridin-6-yl)-ethanone hydrobromide MS: m/e (ESI) 483.2 (MH+)

Example 1943

4-[2-tert-Butyl-4-[2-(3-ethoxy-7-imino-2-methylcarbamoyl-5,7-dihydro-pyrrolo[3,4-b]pyridin-6-yl)-acetyl]-6-(3-thiophen-2-yl-propoxy)-phenoxy]-butanoic acid hydrobromide MS: m/e (ESI) 651.3 (MH+)

Example 1944

4-{2-tert-Butyl-4-[2-(3-ethoxy-7-imino-2-methylcarbamoyl-5,7-dihydro-pyrrolo[3,4-b]pyridin-6-yl)-acetyl]-6-[(3-fluoro-propyl)-methyl-amino]-phenoxy}-butanoic acid hydrobromide MS: m/e (ESI) 600.3 (MH+)

Example 1945

5-{2-tert-Butyl-4-[2-(3-ethoxy-7-imino-2-methylcarbamoyl-5,7-dihydro-pyrrolo[3,4-b]pyridin-6-yl)-acetyl]-6-[(2-methoxy-ethyl)-methyl-amino]-phenoxy}-pentanoic acid hydrobromide MS: m/e (ESI) 612.3 (MH+)

Example 1946

{8-tert-Butyl-4-cyclopropyl-6-[2-(3-ethoxy-7-imino-2-methylcarbamoyl-5,7-dihydro-pyrrolo[3,4-b]pyridin-6-yl)-acetyl]-3,4-dihydro-2H-benzo[1,4]oxazin-3-yl}-acetic acid hydrobromide MS: m/e (ESI) 564.2 (MH+)

Example 1947

5-{4-[2-(3-Ethoxy-7-imino-2-methylcarbamoyl-5,7-dihydro-pyrrolo[3,4-b]pyridin-6-yl)-acetyl]-2-isopropoxy-phenoxy}-pentanoic acid hydrobromide MS: m/e (ESI) 527.2 (MH+)

Example 1948

6-[2-(8-tert-Butyl-4-methanesulfonyl-3,4-dihydro-2H-benzo[1,4]oxazin-6-yl)-2-oxo-ethyl]-3-ethoxy-7-imino-6,7-dihydro-5H-pyrrolo[3,4-b]pyridine-2-carboxylic acid methylamide hydrobromide MS: m/e (ESI) 544.1 (MH+)

Example 1949

Ethyl {8-tert-butyl-6-[2-(5-ethoxy-1-imino-6-methylcarbamoyl-1,3-dihydro-isoindol-2-yl)-acetyl]-4-methyl-3,4-dihydro-2H-benzo[1,4]oxazin-2-yl}-acetate hydrobromide MS: m/e (ESI) 565.4 (MH+)

Example 1950

Ethyl {8-tert-butyl-6-[2-(7-fluoro-1-imino-5,6-dimethoxy-1,3-dihydro-isoindol-2-yl)-acetyl]-4-methyl-3,4-dihydro-2H-benzo[1,4]oxazin-2-yl}-acetate hydrobromide MS: m/e (ESI) 542.3 (MH+)

Example 1951

Ethyl {8-tert-butyl-6-[2-(2-cyclopropyl-7-imino-5,7-dihydro-pyrrolo[3,4-b]pyridin-6-yl)-acetyl]-4-methyl-3,4-dihydro-2H-benzo[1,4]oxazin-2-yl}-acetate hydrobromide MS: m/e (ESI) 505.4 (MH+)

Example 1952

5-{2-tert-Butyl-6-(3-cyanomethyl-pyrrolidin-1-yl)-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 632.3 (MH+)

Example 1953

5-{2-tert-Butyl-6-(3-cyanomethyl-pyrrolidin-1-yl)-4-[2-(7-fluoro-1-imino-5,6-dimethoxy-1,3-dihydro-isoindol-2-yl)-acetyl]-phenoxy}-pentanoic acid hydrobromide MS: m/e (ESI) 609.3 (MH+)

Example 1954

5-{2-tert-Butyl-6-(3-cyanomethyl-pyrrolidin-1-yl)-4-[2-(2-cyclopropyl-7-imino-5,7-dihydro-pyrrolo[3,4-b]pyridin-6-yl)-acetyl]-phenoxy}-pentanoic acid hydrobromide MS: m/e (ESI) 572.4 (MH+)

Example 1955

5-{2-tert-Butyl-6-(3-cyanomethyl-pyrrolidin-1-yl)-4-[2-(3-ethoxy-7-imino-2-methylcarbamoyl-5,7-dihydro-pyrrolo[3,4-b]pyridin-6-yl)-acetyl]-phenoxy}-pentanoic acid hydrobromide MS: m/e (ESI) 633.5 (MH+)

Example 1956

5-{4-[2-(5-Ethoxy-1-imino-6-methylcarbamoyl-1,3-dihydro-isoindol-2-yl)-acetyl]-2-isopropoxy-6-pyrrolidin-1-yl-phenoxy}-pentanoic acid hydrobromide MS: m/e (ESI) 595.0 (MH+)

Example 1957

5-{4-[2-(7-Fluoro-1-imino-5,6-dimethoxy-1,3-dihydro-isoindol-2-yl)-acetyl]-2-isopropoxy-6-pyrrolidin-1-yl-phenoxy}-pentanoic acid hydrobromide MS: m/e (ESI) 572.0 (MH+)

Example 1958

5-{4-[2-(2-Cyclopropyl-7-imino-5,7-dihydro-pyrrolo[3,4-b]pyridin-6-yl)-acetyl]-2-isopropoxy-6-pyrrolidin-1-yl-phenoxy}-pentanoic acid hydrobromide MS: m/e (ESI) 535.1 (MH+)

Example 1959

5-{4-[2-(3-Ethoxy-7-imino-2-methylcarbamoyl-5,7-dihydro-pyrrolo[3,4-b]pyridin-6-yl)-acetyl]-2-isopropoxy-6-pyrrolidin-1-yl-phenoxy}-pentanoic acid hydrobromide MS: m/e (ESI) 596.2 (MH+)

Example 1960

Ethyl {8-tert-butyl-6-[2-(3-ethoxy-7-imino-2-methylcarbamoyl-5,7-dihydro-pyrrolo[3,4-b]pyridin-6-yl)-acetyl]-4-methyl-3,4-dihydro-2H-benzo[1,4]oxazin-2-yl}-acetate hydrobromide MS: m/e (ESI) 566.3 (MH+)

Example 1961

2-tert-Butyl-4-[2-(5,6-diethoxy-7-fluoro-1-imino-1,3-dihydro-isoindol-2-yl)-acetyl]-phenyl methylcarbamate hydrobromide MS: m/e (ESI) 486.2 (MH+)

Example 1962

2-tert-Butyl-4-[2-(7-fluoro-1-imino-5,6-dimethoxy-1,3-dihydro-isoindol-2-yl)-acetyl]-phenyl methylcarbamate hydrobromide MS: m/e (ESI) 458.2 (MH+)

Example 1963

2-tert-Butyl-4-[2-(2-cyclopropyl-7-imino-5,7-dihydro-pyrrolo[3,4-b]pyridin-6-yl)-acetyl]-phenyl methylcarbamate hydrobromide MS: m/e (ESI) 421.3 (MH+)

Example 1964

2-tert-Butyl-4-[2-(5-ethoxy-1-imino-6-methylcarbamoyl-1,3-dihydro-isoindol-2-yl)-acetyl]-phenyl methylcarbamate hydrobromide MS: m/e (ESI) 481.3 (MH+)

Example 1965

2-tert-Butyl-4-[2-(3-ethoxy-7-imino-2-methylcarbamoyl-5,7-dihydro-pyrrolo[3,4-b]pyridin-6-yl)-acetyl]-phenyl methylcarbamate hydrobromide MS: m/e (ESI) 482.3 (MH+)

Example 1966

2-tert-Butyl-4-[2-(5,6-diethoxy-7-fluoro-1-imino-1,3-dihydro-isoindol-2-yl)-acetyl]-phenyl pyrrolidine-1-carboxylate hydrobromide MS: m/e (ESI) 526.4 (MH+)

Example 1967

2-tert-Butyl-4-[2-(7-fluoro-1-imino-5,6-dimethoxy-1,3-dihydro-isoindol-2-yl)-acetyl]-phenyl pyrrolidine-1-carboxylate hydrobromide MS: m/e (ESI) 498.4 (MH+)

Example 1968

2-tert-Butyl-4-[2-(2-cyclopropyl-7-imino-5,7-dihydro-pyrrolo[3,4-b]pyridin-6-yl)-acetyl]-phenyl pyrrolidine-1-carboxylate hydrobromide MS: m/e (ESI) 461.4 (MH+)

Example 1969

2-tert-Butyl-4-[2-(5-ethoxy-1-imino-6-methylcarbamoyl-1,3-dihydro-isoindol-2-yl)-acetyl]-phenyl pyrrolidine-1-carboxylate hydrobromide MS: m/e (ESI) 521.4 (MH+)

Example 1970

2-tert-Butyl-4-[2-(3-ethoxy-7-imino-2-methylcarbamoyl-5,7-dihydro-pyrrolo[3,4-b]pyridin-6-yl)-acetyl]-phenyl pyrrolidine-1-carboxylate hydrobromide MS: m/e (ESI) 522.4 (MH+)

Example 1971

(1-{2-Butoxy-3-tert-butyl-5-[2-(5-ethoxy-1-imino-6-methylcarbamoyl-1,3-dihydro-isoindol-2-yl)-acetyl]-phenyl}-pyrrolidin-3-yloxy)-acetic acid hydrobromide MS: m/e (ESI) 623.5 (MH+)

Example 1972

(1-{2-Butoxy-3-tert-butyl-5-[2-(7-fluoro-1-imino-5,6-dimethoxy-1,3-dihydro-isoindol-2-yl)-acetyl]-phenyl}-pyrrolidin-3-yloxy)-acetic acid hydrobromide MS: m/e (ESI) 600.4 (MH+)

Example 1973

(1-{2-Butoxy-3-tert-butyl-5-[2-(2-cyclopropyl-7-imino-5,7-dihydro-pyrrolo[3,4-b]pyridin-6-yl)-acetyl]-phenyl}-pyrrolidin-3-yloxy)-acetic acid hydrobromide MS: m/e (ESI) 563.4 (MH+)

Example 1974

(1-{2-Butoxy-3-tert-butyl-5-[2-(3-ethoxy-7-imino-2-methylcarbamoyl-5,7-dihydro-pyrrolo[3,4-b]pyridin-6-yl)-acetyl]-phenyl}-pyrrolidin-3-yloxy)-acetic acid hydrobromide MS: m/e (ESI) 624.5 (MH+)

Example 1975

5-[2-tert-Butyl-4-[2-(5-ethoxy-1-imino-6-methylcarbamoyl-1,3-dihydro-isoindol-2-yl)-acetyl]-6-(3-methoxymethyl-pyrrolidin-1-yl)-phenoxy]-pentanoic acid hydrobromide MS: m/e (ESI) 637.5 (MH+)

Example 1976

5-[2-tert-Butyl-4-[2-(7-fluoro-1-imino-5,6-dimethoxy-1,3-dihydro-isoindol-2-yl)-acetyl]-6-(3-methoxymethyl-pyrrolidin-1-yl)-phenoxy]-pentanoic acid hydrobromide MS: m/e (ESI) 614.4 (MH+)

Example 1977

5-[2-tert-Butyl-4-[2-(2-cyclopropyl-7-imino-5,7-dihydro-pyrrolo[3,4-b]pyridin-6-yl)-acetyl]-6-(3-methoxymethyl-pyrrolidin-1-yl)-phenoxy]-pentanoic acid hydrobromide MS: m/e (ESI) 577.4 (MH+)

Example 1978

5-[2-tert-Butyl-4-[2-(3-ethoxy-7-imino-2-methylcarbamoyl-5,7-dihydro-pyrrolo[3,4-b]pyridin-6-yl)-acetyl]-6-(3-methoxymethyl-pyrrolidin-1-yl)-phenoxy]-pentanoic acid hydrobromide MS: m/e (ESI) 638.5 (MH+)

Example 1979

[2-tert-Butyl-4-[2-(5-ethoxy-1-imino-6-methylcarbamoyl-1,3-dihydro-isoindol-2-yl)-acetyl]-6-(3-methoxymethyl-pyrrolidin-1-yl)-phenoxy]-acetic acid hydrobromide MS: m/e (ESI) 595.4 (MH+)

Example 1980

[2-tert-Butyl-4-[2-(7-fluoro-1-imino-5,6-dimethoxy-1,3-dihydro-isoindol-2-yl)-acetyl]-6-(3-methoxymethyl-pyrrolidin-1-yl)-phenoxy]-acetic acid hydrobromide MS: m/e (ESI) 572.3 (MH+)

Example 1981

[2-tert-Butyl-4-[2-(2-cyclopropyl-7-imino-5,7-dihydro-pyrrolo[3,4-b]pyridin-6-yl)-acetyl]-6-(3-methoxymethyl-pyrrolidin-1-yl)-phenoxy]-acetic acid hydrobromide MS: m/e (ESI) 535.3 (MH+)

Example 1982

[2-tert-Butyl-4-[2-(3-ethoxy-7-imino-2-methylcarbamoyl-5,7-dihydro-pyrrolo[3,4-b]pyridin-6-yl)-acetyl]-6-(3-methoxymethyl-pyrrolidin-1-yl)-phenoxy]-acetic acid hydrobromide MS: m/e (ESI) 596.4 (MH+)

Example 1983

{8-tert-Butyl-6-[2-(5-ethoxy-1-imino-6-methylcarbamoyl-1,3-dihydro-isoindol-2-yl)-acetyl]-4-methyl-3,4-dihydro-2H-benzo[1,4]oxazin-2-yl}-acetic acid hydrobromide MS: m/e (ESI) 537.3 (MH+)

Example 1984

{8-tert-Butyl-6-[2-(7-fluoro-1-imino-5,6-dimethoxy-1,3-dihydro-isoindol-2-yl)-acetyl]-4-methyl-3,4-dihydro-2H-benzo[1,4]oxazin-2-yl}-acetic acid hydrobromide MS: m/e (ESI) 514.3 (MH+)

Example 1985

{8-tert-Butyl-6-[2-(2-cyclopropyl-7-imino-5,7-dihydro-pyrrolo[3,4-b]pyridin-6-yl)-acetyl]-4-methyl-3,4-dihydro-2H-benzo[1,4]oxazin-2-yl}-acetic acid hydrobromide MS: m/e (ESI) 477.3 (MH+)

Example 1986

{8-tert-Butyl-6-[2-(3-ethoxy-7-imino-2-methylcarbamoyl-5,7-dihydro-pyrrolo[3,4-b]pyridin-6-yl)-acetyl]-4-methyl-3,4-dihydro-2H-benzo[1,4]oxazin-2-yl}-acetic acid hydrobromide MS: m/e (ESI) 538.3 (MH+)

Example 1987

2-(1-{3-tert-Butyl-5-[2-(5-ethoxy-1-imino-6-methylcarbamoyl-1,3-dihydro-isoindol-2-yl)-acetyl]-2-methoxy-phenyl}-pyrrolidin-3-yloxy)-butanoic acid hydrobromide MS: m/e (ESI) 609.2 (MH+)

Example 1988

2-(1-{3-tert-Butyl-5-[2-(7-fluoro-1-imino-5,6-dimethoxy-1,3-dihydro-isoindol-2-yl)-acetyl]-2-methoxy-phenyl}-pyrrolidin-3-yloxy)-butanoic acid hydrobromide MS: m/e (ESI) 586.2 (MH+)

Example 1989

2-(1-{3-tert-Butyl-5-[2-(2-cyclopropyl-7-imino-5,7-dihydro-pyrrolo[3,4-b]pyridin-6-yl)-acetyl]-2-methoxy-phenyl}-pyrrolidin-3-yloxy)-butanoic acid hydrobromide MS: m/e (ESI) 549.3 (MH+)

Example 1990

2-(1-{3-tert-Butyl-5-[2-(3-ethoxy-7-imino-2-methylcarbamoyl-5,7-dihydro-pyrrolo[3,4-b]pyridin-6-yl)-acetyl]-2-methoxy-phenyl}-pyrrolidin-3-yloxy)-butanoic acid hydrobromide MS: m/e (ESI) 610.5 (MH+)

Example 1991

2-{2-tert-Butyl-6-(3-cyano-propoxy)-4-[2-(5,6-diethoxy-7-fluoro-1-imino-1,3-dihydro-isoindol-2-yl)-acetyl]-phenoxy}-pentanoic acid hydrobromide MS: m/e (ESI) 612.6 (MH+)

Example 1992

2-{2-tert-Butyl-6-(3-cyano-propoxy)-4-[2-(7-fluoro-1-imino-5,6-dimethoxy-1,3-dihydro-isoindol-2-yl)-acetyl]-phenoxy}-pentanoic acid hydrobromide MS: m/e (ESI) 584.5 (MH+)

Example 1993

2-{2-tert-Butyl-6-(3-cyano-propoxy)-4-[2-(2-cyclopropyl-7-imino-5,7-dihydro-pyrrolo[3,4-b]pyridin-6-yl)-acetyl]-phenoxy}-pentanoic acid hydrobromide MS: m/e (ESI) 547.5 (MH+)

Example 1994

2-{2-tert-Butyl-6-(3-cyano-propoxy)-4-[2-(5-ethoxy-1-imino-6-methylcarbamoyl-1,3-dihydro-isoindol-2-yl)-acetyl]-phenoxy}-pentanoic acid hydrobromide MS: m/e (ESI) 607.5 (MH+)

Example 1995

2-{2-tert-Butyl-6-(3-cyano-propoxy)-4-[2-(3-ethoxy-7-imino-2-methylcarbamoyl-5,7-dihydro-pyrrolo[3,4-b]pyridin-6-yl)-acetyl]-phenoxy}-pentanoic acid hydrobromide MS: m/e (ESI) 608.5 (MH+)

Example 1996

1-{2-tert-Butyl-4-[2-(5,6-diethoxy-7-fluoro-1-imino-1,3-dihydro-isoindol-2-yl)-acetyl]-phenyl}pyrrolidine-1,2-dicarboxylate hydrobromide MS: m/e (ESI) 570.4 (MH+)

Example 1997

1-{2-tert-Butyl-4-[2-(7-fluoro-1-imino-5,6-dimethoxy-1,3-dihydro-isoindol-2-yl)-acetyl]-phenyl}pyrrolidine-1,2-dicarboxylate hydrobromide MS: m/e (ESI) 542.4 (MH+)

Example 1998

1-{2-tert-Butyl-4-[2-(2-cyclopropyl-7-imino-5,7-dihydro-pyrrolo[3,4-b]pyridin-6-yl)-acetyl]-phenyl}pyrrolidine-1,2-dicarboxylate hydrobromide MS: m/e (ESI) 505.4 (MH+)

Example 1999

1-{2-tert-Butyl-4-[2-(5-ethoxy-1-imino-6-methylcarbamoyl-1,3-dihydro-isoindol-2-yl)-acetyl]-phenyl}pyrrolidine-1,2-dicarboxylate hydrobromide MS: m/e (ESI) 565.5 (MH+)

Example 2000

1-{2-tert-Butyl-4-[2-(3-ethoxy-7-imino-2-methylcarbamoyl-5,7-dihydro-pyrrolo[3,4-b]pyridin-6-yl)-acetyl]-phenyl}pyrrolidine-1,2-dicarboxylate hydrobromide MS: m/e (ESI) 566.5 (MH+)

Example 2001

Ethyl 8-tert-butyl-6-[2-(7-fluoro-1-imino-5,6-dimethoxy-1,3-dihydro-isoindol-2-yl)-acetyl]-4-methyl-3,4-dihydro-2H-benzo[1,4]oxazine-2-carboxylate hydrobromide MS: m/e (ESI) 528.4 (MH+)

Example 2002

Ethyl 8-tert-butyl-6-[2-(5,6-diethoxy-7-fluoro-1-imino-1,3-dihydro-isoindol-2-yl)-acetyl]-4-methyl-3,4-dihydro-2H-benzo[1,4]oxazine-2-carboxylate hydrobromide MS: m/e (ESI) 556.4 (MH+)

Example 2003

Ethyl 8-tert-butyl-6-[2-(2-cyclopropyl-7-imino-5,7-dihydro-pyrrolo[3,4-b]pyridin-6-yl)-acetyl]-4-methyl-3,4-dihydro-2H-benzo[1,4]oxazine-2-carboxylate hydrobromide MS: m/e (ESI) 491.5 (MH+)

Example 2004

(1-{3-tert-Butyl-5-[2-(5-ethoxy-1-imino-6-methylcarbamoyl-1,3-dihydro-isoindol-2-yl)-acetyl]-2-methoxy-phenyl}-piperidin-4-yloxy)-acetic acid hydrobromide MS: m/e (ESI) 594.7 (MH+)

Example 2005

(1-{3-tert-Butyl-5-[2-(7-fluoro-1-imino-5,6-dimethoxy-1,3-dihydro-isoindol-2-yl)-acetyl]-2-methoxy-phenyl}-piperidin-4-yloxy)-acetic acid hydrobromide MS: m/e (ESI) 571.7 (MH+)

Example 2006

(1-{3-tert-Butyl-5-[2-(3-ethoxy-7-imino-2-methylcarbamoyl-5,7-dihydro-pyrrolo[3,4-b]pyridin-6-yl)-acetyl]-2-methoxy-phenyl}-piperidin-4-yloxy)-acetic acid hydrobromide MS: m/e (ESI) 595.8 (MH+)

Example 2007

1-(3-tert-Butyl-5-dimethylamino-4-methoxy-phenyl)-2-(7-fluoro-1-imino-5,6-dimethoxy-1,3-dihydro-isoindol-2-yl)-ethanone hydrobromide MS: m/e (ESI) 458.3 (MH+)

Example 2008

1-(3-tert-Butyl-5-dimethylamino-4-methoxy-phenyl)-2-(2-cyclopropyl-7-imino-5,7-dihydro-pyrrolo[3,4-b]pyridin-6-yl)-ethanone hydrobromide MS: m/e (ESI) 421.3 (MH+)

Example 2009

6-[2-(3-tert-Butyl-5-dimethylamino-4-methoxy-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 482.4 (MH+)

Example 2010

2-[2-(3-tert-Butyl-5-dimethylamino-4-methoxy-phenyl)-2-oxo-ethyl]-6-dimethylamino-3-imino-2,3-dihydro-1H-isoindole-5-carboxylic acid methylamide hydrobromide MS: m/e (ESI) 480.4 (MH+)

Example 2011

Ethyl 8-tert-butyl-6-[2-(5-ethoxy-1-imino-6-methylcarbamoyl-1,3-dihydro-isoindol-2-yl)-acetyl]-4-methyl-3,4-dihydro-2H-benzo[1,4]oxazine-2-carboxylate hydrobromide MS: m/e (ESI) 551.5 (MH+)

Example 2012

{8-tert-Butyl-6-[2-(5-ethoxy-1-imino-6-methylcarbamoyl-1,3-dihydro-isoindol-2-yl)-acetyl]-3-oxo-3,4-dihydro-2H-benzo[1,4]oxazin-2-yl}-acetic acid hydrobromide MS: m/e (ESI) 537.3 (MH+)

Example 2013

{8-tert-Butyl-6-[2-(5,6-diethoxy-7-fluoro-1-imino-1,3-dihydro-isoindol-2-yl)-acetyl]-3-oxo-3,4-dihydro-2H-benzo[1,4]oxazin-2-yl}-acetic acid hydrobromide MS: m/e (ESI) 542.3 (MH+)

Example 2014

{8-tert-Butyl-6-[2-(7-fluoro-1-imino-5,6-dimethoxy-1,3-dihydro-isoindol-2-yl)-acetyl]-3-oxo-3,4-dihydro-2H-benzo[1,4]oxazin-2-yl}-acetic acid hydrobromide MS: m/e (ESI) 514.3 (MH+)

Example 2015

{8-tert-Butyl-6-[2-(2-cyclopropyl-7-imino-5,7-dihydro-pyrrolo[3,4-b]pyridin-6-yl)-acetyl]-3-oxo-3,4-dihydro-2H-benzo[1,4]oxazin-2-yl}-acetic acid hydrobromide MS: m/e (ESI) 477.3 (MH+)

Example 2016

{8-tert-Butyl-6-[2-(3-ethoxy-7-imino-2-methylcarbamoyl-5,7-dihydro-pyrrolo[3,4-b]pyridin-6-yl)-acetyl]-3-oxo-3,4-dihydro-2H-benzo[1,4]oxazin-2-yl}-acetic acid hydrobromide MS: m/e (ESI) 538.3 (MH+)

Example 2017

2-tert-Butyl-4-[2-(5-dimethylamino-1-imino-6-methylcarbamoyl-1,3-dihydro-isoindol-2-yl)-acetyl]-phenyl methanesulfonate hydrobromide MS: m/e (ESI) 500.8 (MH+)

Example 2018

2-tert-Butyl-4-[2-(5,6-diethoxy-7-fluoro-1-imino-1,3-dihydro-isoindol-2-yl)-acetyl]-phenyl methanesulfonate hydrobromide MS: m/e (ESI) 506.8 (MH+)

Example 2019

2-tert-Butyl-4-[2-(7-fluoro-1-imino-5,6-dimethoxy-1,3-dihydro-isoindol-2-yl)-acetyl]-phenyl methanesulfonate hydrobromide MS: m/e (ESI) 478.8 (MH+)

Example 2020

2-tert-Butyl-4-[2-(2-cyclopropyl-7-imino-5,7-dihydro-pyrrolo[3,4-b]pyridin-6-yl)-acetyl]-phenyl methanesulfonate hydrobromide MS: m/e (ESI) 441.9 (MH+)

Example 2021

2-tert-Butyl-4-[2-(5-ethoxy-1-imino-6-methylcarbamoyl-1,3-dihydro-isoindol-2-yl)-acetyl]-phenyl methanesulfonate hydrobromide MS: m/e (ESI) 501.9 (MH+)

Example 2022

2-tert-Butyl-4-[2-(3-ethoxy-7-imino-2-methylcarbamoyl-5,7-dihydro-pyrrolo[3,4-b]pyridin-6-yl)-acetyl]-phenyl methanesulfonate hydrobromide MS: m/e (ESI) 502.9 (MH+)

Example 2023

2-tert-Butyl-4-[2-(5-dimethylamino-1-imino-6-methylcarbamoyl-1,3-dihydro-isoindol-2-yl)-acetyl]-phenyl methylcarbamate hydrobromide MS: m/e (ESI) 480.0 (MH+)

Example 2024

(1-{3-tert-Butyl-5-[2-(5-ethoxy-1-imino-6-methylcarbamoyl-1,3-dihydro-isoindol-2-yl)-acetyl]-phenyl}-piperidin-4-yloxy)-acetic acid hydrobromide MS: m/e (ESI) 565.0 (MH+)

Example 2025

(1-{3-tert-Butyl-5-[2-(7-fluoro-1-imino-5,6-dimethoxy-1,3-dihydro-isoindol-2-yl)-acetyl]-phenyl}-piperidin-4-yloxy)-acetic acid hydrobromide MS: m/e (ESI) 542.0 (MH+)

Example 2026

(1-{3-tert-Butyl-5-[2-(2-cyclopropyl-7-imino-5,7-dihydro-pyrrolo[3,4-b]pyridin-6-yl)-acetyl]-phenyl}-piperidin-4-yloxy)-acetic acid hydrobromide MS: m/e (ESI) 505.0 (MH+)

Example 2027

(1-{3-tert-Butyl-5-[2-(3-ethoxy-7-imino-2-methylcarbamoyl-5,7-dihydro-pyrrolo[3,4-b]pyridin-6-yl)-acetyl]-phenyl}-piperidin-4-yloxy)-acetic acid hydrobromide MS: m/e (ESI) 566.0 (MH+)

Example 2028

2-tert-Butyl-4-[2-(5-dimethylamino-1-imino-6-methylcarbamoyl-1,3-dihydro-isoindol-2-yl)-acetyl]-phenyl dimethylcarbamate hydrobromide MS: m/e (ESI) 493.9 (MH+)

Example 2029

2-tert-Butyl-4-[2-(5,6-diethoxy-7-fluoro-1-imino-1,3-dihydro-isoindol-2-yl)-acetyl]-phenyl dimethylcarbamate hydrobromide MS: m/e (ESI) 499.9 (MH+)

Example 2030

2-tert-Butyl-4-[2-(7-fluoro-1-imino-5,6-dimethoxy-1,3-dihydro-isoindol-2-yl)-acetyl]-phenyl dimethylcarbamate hydrobromide MS: m/e (ESI) 471.8 (MH+)

Example 2031

2-tert-Butyl-4-[2-(2-cyclopropyl-7-imino-5,7-dihydro-pyrrolo[3,4-b]pyridin-6-yl)-acetyl]-phenyl dimethylcarbamate hydrobromide MS: m/e (ESI) 434.9 (MH+)

Example 2032

2-tert-Butyl-4-[2-(5-ethoxy-1-imino-6-methylcarbamoyl-1,3-dihydro-isoindol-2-yl)-acetyl]-phenyl dimethylcarbamate hydrobromide MS: m/e (ESI) 494.9 (MH+)

Example 2033

2-tert-Butyl-4-[2-(3-ethoxy-7-imino-2-methylcarbamoyl-5,7-dihydro-pyrrolo[3,4-b]pyridin-6-yl)-acetyl]-phenyl dimethylcarbamate hydrobromide MS: m/e (ESI) 495.9 (MH+)

Example 2034

2-[2-(3-tert-Butyl-5-ethoxy-4-methoxy-phenyl)-2-oxo-ethyl]-6-dimethylamino-3-imino-2,3-dihydro-1H-isoindole-5-carboxylic acid methylamide hydrobromide MS: m/e (ESI) 480.9 (MH+)

Example 2035

1-(3-tert-Butyl-5-ethoxy-4-methoxy-phenyl)-2-(5,6-diethoxy-7-fluoro-1-imino-1,3-dihydro-isoindol-2-yl)-ethanone hydrobromide MS: m/e (ESI) 486.9 (MH+)

Example 2036

1-(3-tert-Butyl-5-ethoxy-4-methoxy-phenyl)-2-(7-fluoro-1-imino-5,6-dimethoxy-1,3-dihydro-isoindol-2-yl)-ethanone hydrobromide MS: m/e (ESI) 458.9 (MH+)

Example 2037

1-(3-tert-Butyl-5-ethoxy-4-methoxy-phenyl)-2-(2-cyclopropyl-7-imino-5,7-dihydro-pyrrolo[3,4-b]pyridin-6-yl)-ethanone hydrobromide MS: m/e (ESI) 421.9 (MH+)

Example 2038

2-[2-(3-tert-Butyl-5-ethoxy-4-methoxy-phenyl)-2-oxo-ethyl]-6-ethoxy-3-imino-2,3-dihydro-1H-isoindole-5-acetic acid methylamide hydrobromide MS: m/e (ESI) 481.9 (MH+)

Example 2039

6-[2-(3-tert-Butyl-5-ethoxy-4-methoxy-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 482.9 (MH+)

Example 2040

2-{2-tert-Butyl-4-[2-(5-dimethylamino-1-imino-6-methylcarbamoyl-1,3-dihydro-isoindol-2-yl)-acetyl]-phenoxy}-3-phenyl-propionic acid hydrobromide MS: m/e (ESI) 571.0 (MH+)

Example 2041

2-{2-tert-Butyl-4-[2-(5,6-diethoxy-7-fluoro-1-imino-1,3-dihydro-isoindol-2-yl)-acetyl]-phenoxy}-3-phenyl-propionic acid hydrobromide MS: m/e (ESI) 577.0 (MH+)

Example 2042

2-{2-tert-Butyl-4-[2-(7-fluoro-1-imino-5,6-dimethoxy-1,3-dihydro-isoindol-2-yl)-acetyl]-phenoxy}-3-phenyl-propionic acid hydrobromide MS: m/e (ESI) 548.9 (MH+)

Example 2043

2-{2-tert-Butyl-4-[2-(2-cyclopropyl-7-imino-5,7-dihydro-pyrrolo[3,4-b]pyridin-6-yl)-acetyl]-phenoxy}-3-phenyl-propionic acid hydrobromide MS: m/e (ESI) 511.9 (MH+)

Example 2044

2-{2-tert-Butyl-4-[2-(5-ethoxy-1-imino-6-methylcarbamoyl-1,3-dihydro-isoindol-2-yl)-acetyl]-phenoxy}-3-phenyl-propionic acid hydrobromide MS: m/e (ESI) 572.0 (MH+)

Example 2045

2-{2-tert-Butyl-4-[2-(3-ethoxy-7-imino-2-methylcarbamoyl-5,7-dihydro-pyrrolo[3,4-b]pyridin-6-yl)-acetyl]-phenoxy}-3-phenyl-propionic acid hydrobromide MS: m/e (ESI) 573.0 (MH+)

Example 2046

2-[2-(8-tert-Butyl-4-cyanomethyl-3,4-dihydro-2H-benzo[1,4]oxazin-6-yl)-2-oxo-ethyl]-6-ethoxy-3-imino-2,3-dihydro-1H-isoindole-5-acetic acid methylamide hydrobromide MS: m/e (ESI) 504.3 (MH+)

Example 2047

6-[2-(8-tert-Butyl-4-cyanomethyl-3,4-dihydro-2H-benzo[1,4]oxazin-6-yl)-2-oxo-ethyl]-3-ethoxy-7-imino-6,7-dihydro-5H-pyrrolo[3,4-b]pyridine-2-carboxylic acid methylamide hydrobromide MS: m/e (ESI) 505.3 (MH+)

Example 2048

{8-tert-Butyl-6-[2-(5,6-diethoxy-7-fluoro-1-imino-1,3-dihydro-isoindol-2-yl)-acetyl]-2,3-dihydro-benzo[1,4]oxazin-4-yl}-acetonitrile hydrobromide MS: m/e (ESI) 509.4 (MH+)

Example 2049

{8-tert-Butyl-6-[2-(2-cyclopropyl-7-imino-5,7-dihydro-pyrrolo[3,4-b]pyridin-6-yl)-acetyl]-2,3-dihydro-benzo[1,4]oxazin-4-yl}-acetonitrile hydrobromide MS: m/e (ESI) 444.3 (MH+)

Example 2050

2-[2-(8-tert-Butyl-4-cyanomethyl-3,4-dihydro-2H-benzo[1,4]oxazin-6-yl)-2-oxo-ethyl]-6-dimethylamino-3-imino-2,3-dihydro-1H-isoindole-5-carboxylic acid methylamide hydrobromide MS: m/e (ESI) 503.4 (MH+)

Example 2051

2-{2-[8-tert-Butyl-4-(3H-[1,2,3]triazol-4-ylmethyl)-3,4-dihydro-2H-benzo[1,4]oxazin-6-yl]-2-oxo-ethyl}-6-ethoxy-3-imino-2,3-dihydro-1H-isoindole-5-acetic acid methylamide hydrobromide MS: m/e (ESI) 546.0 (MH+)

Example 2052

6-{2-[8-tert-Butyl-4-(3H-[1,2,3]triazol-4-ylmethyl)-3,4-dihydro-2H-benzo[1,4]oxazin-6-yl]-2-oxo-ethyl}-3-ethoxy-7-imino-6,7-dihydro-5H-pyrrolo[3,4-b]pyridine-2-carboxylic acid methylamide hydrobromide MS: m/e (ESI) 547.0 (MH+)

Example 2053

1-[8-tert-Butyl-4-(3H-[1,2,3]triazol-4-ylmethyl)-3,4-dihydro-2H-benzo[1,4]oxazin-6-yl]-2-(5,6-diethoxy-7-fluoro-1-imino-1,3-dihydro-isoindol-2-yl)-ethanone hydrobromide MS: m/e (ESI) 551.0 (MH+)

Example 2054

1-[8-tert-Butyl-4-(3H-[1,2,3]triazol-4-ylmethyl)-3,4-dihydro-2H-benzo[1,4]oxazin-6-yl]-2-(2-cyclopropyl-7-imino-5,7-dihydro-pyrrolo[3,4-b]pyridin-6-yl)-ethanone hydrobromide MS: m/e (ESI) 486.0 (MH+)

Example 2055

2-{2-[8-tert-Butyl-4-(3H-[1,2,3]triazol-4-ylmethyl)-3,4-dihydro-2H-benzo[1,4]oxazin-6-yl]-2-oxo-ethyl}-6-dimethylamino-3-imino-2,3-dihydro-1H-isoindole-5-carboxylic acid methylamide hydrobromide MS: m/e (ESI) 545.0 (MH+)

Example 2056

{8-tert-Butyl-6-[2-(5-ethoxy-7-fluoro-1-imino-6-methoxy-1,3-dihydro-isoindol-2-yl)-acetyl]-3-oxo-3,4-dihydro-2H-benzo[1,4]oxazin-2-yl}-acetic acid hydrobromide MS: m/e (ESI) 528.3 (MH+)

Example 2057

2-{8-tert-Butyl-6-[2-(5-ethoxy-1-imino-6-methylcarbamoyl-1,3-dihydro-isoindol-2-yl)-acetyl]-2,3-dihydro-benzo[1,4]oxazin-4-yl}-propionic acid hydrobromide MS: m/e (ESI) 536.8 (MH+)

Example 2058

2-{8-tert-Butyl-6-[2-(3-ethoxy-7-imino-2-methylcarbamoyl-5,7-dihydro-pyrrolo[3,4-b]pyridin-6-yl)-acetyl]-2,3-dihydro-benzo[1,4]oxazin-4-yl}-propionic acid hydrobromide MS: m/e (ESI) 537.8 (MH+)

Example 2059

2-{8-tert-Butyl-6-[2-(7-fluoro-1-imino-5,6-dimethoxy-1,3-dihydro-isoindol-2-yl)-acetyl]-2,3-dihydro-benzo[1,4]oxazin-4-yl}-propionic acid hydrobromide MS: m/e (ESI) 513.8 (MH+)

Example 2060

2-{8-tert-Butyl-6-[2-(5,6-diethoxy-7-fluoro-1-imino-1,3-dihydro-isoindol-2-yl)-acetyl]-2,3-dihydro-benzo[1,4]oxazin-4-yl}-propionic acid hydrobromide MS: m/e (ESI) 541.9 (MH+)

Example 2061

2-{8-tert-Butyl-6-[2-(2-cyclopropyl-7-imino-5,7-dihydro-pyrrolo[3,4-b]pyridin-6-yl)-acetyl]-2,3-dihydro-benzo[1,4]oxazin-4-yl}-propionic acid hydrobromide MS: m/e (ESI) 476.9 (MH+)

Example 2062

2-{8-tert-Butyl-6-[2-(5-dimethylamino-1-imino-6-methylcarbamoyl-1,3-dihydro-isoindol-2-yl)-acetyl]-2,3-dihydro-benzo[1,4]oxazin-4-yl}-propionic acid hydrobromide MS: m/e (ESI) 536.0 (MH+)

Example 2063

2-{2-[8-tert-Butyl-4-(1H-tetrazol-5-ylmethyl)-3,4-dihydro-2H-benzo[1,4]oxazin-6-yl]-2-oxo-ethyl}-6-ethoxy-3-imino-2,3-dihydro-1H-isoindole-5-acetic acid methylamide hydrobromide MS: m/e (ESI) 546.8 (MH+)

Example 2064

6-{2-[8-tert-Butyl-4-(1H-tetrazol-5-ylmethyl)-3,4-dihydro-2H-benzo[1,4]oxazin-6-yl]-2-oxo-ethyl}-3-ethoxy-7-imino-6,7-dihydro-5H-pyrrolo[3,4-b]pyridine-2-carboxylic acid methylamide hydrobromide MS: m/e (ESI) 548.3 (MH+)

Example 2065

1-[8-tert-Butyl-4-(1H-tetrazol-5-ylmethyl)-3,4-dihydro-2H-benzo[1,4]oxazin-6-yl]-2-(7-fluoro-1-imino-5,6-dimethoxy-1,3-dihydro-isoindol-2-yl)-ethanone hydrobromide MS: m/e (ESI) 523.8 (MH+)

Example 2066

1-[8-tert-Butyl-4-(1H-tetrazol-5-ylmethyl)-3,4-dihydro-2H-benzo[1,4]oxazin-6-yl]-2-(5,6-diethoxy-7-fluoro-1-imino-1,3-dihydro-isoindol-2-yl)-ethanone hydrobromide MS: m/e (ESI) 552.3 (MH+)

Example 2067

1-[8-tert-Butyl-4-(1H-tetrazol-5-ylmethyl)-3,4-dihydro-2H-benzo[1,4]oxazin-6-yl]-2-(2-cyclopropyl-7-imino-5,7-dihydro-pyrrolo[3,4-b]pyridin-6-yl)-ethanone hydrobromide MS: m/e (ESI) 487.3 (MH+)

Example 2068

2-{2-[8-tert-Butyl-4-(1H-tetrazol-5-ylmethyl)-3,4-dihydro-2H-benzo[1,4]oxazin-6-yl]-2-oxo-ethyl}-6-dimethylamino-3-imino-2,3-dihydro-1H-isoindole-5-carboxylic acid methylamide hydrobromide MS: m/e (ESI) 546.3 (MH+)

Example 2069

{8-tert-Butyl-4-cyanomethyl-6-[2-(5-ethoxy-1-imino-6-methylcarbamoyl-1,3-dihydro-isoindol-2-yl)-acetyl]-3-oxo-3,4-dihydro-2H-benzo[1,4]oxazin-2-yl}-acetic acid hydrobromide MS: m/e (ESI) 576.3 (MH+)

Example 2070

{8-tert-Butyl-4-cyanomethyl-6-[2-(5,6-diethoxy-7-fluoro-1-imino-1,3-dihydro-isoindol-2-yl)-acetyl]-3-oxo-3,4-dihydro-2H-benzo[1,4]oxazin-2-yl}-acetic acid hydrobromide MS: m/e (ESI) 581.3 (MH+)

Example 2071

{8-tert-Butyl-4-cyanomethyl-6-[2-(7-fluoro-1-imino-5,6-dimethoxy-1,3-dihydro-isoindol-2-yl)-acetyl]-3-oxo-3,4-dihydro-2H-benzo[1,4]oxazin-2-yl}-acetic acid hydrobromide MS: m/e (ESI) 553.3 (MH+)

Example 2072

{8-tert-Butyl-4-cyanomethyl-6-[2-(2-cyclopropyl-7-imino-5,7-dihydro-pyrrolo[3,4-b]pyridin-6-yl)-acetyl]-3-oxo-3,4-dihydro-2H-benzo[1,4]oxazin-2-yl}-acetic acid hydrobromide MS: m/e (ESI) 516.3 (MH+)

Example 2073

{8-tert-Butyl-4-cyanomethyl-6-[2-(3-ethoxy-7-imino-2-methylcarbamoyl-5,7-dihydro-pyrrolo[3,4-b]pyridin-6-yl)-acetyl]-3-oxo-3,4-dihydro-2H-benzo[1,4]oxazin-2-yl}-acetic acid hydrobromide MS: m/e (ESI) 577.3 (MH+)

Example 2074

{8-tert-Butyl-4-carbamoylmethyl-6-[2-(5-ethoxy-1-imino-6-methylcarbamoyl-1,3-dihydro-isoindol-2-yl)-acetyl]-3-oxo-3,4-dihydro-2H-benzo[1,4]oxazin-2-yl}-acetic acid hydrobromide MS: m/e (ESI) 594.3 (MH+)

Example 2075

{8-tert-Butyl-4-carbamoylmethyl-6-[2-(5,6-diethoxy-7-fluoro-1-imino-1,3-dihydro-isoindol-2-yl)-acetyl]-3-oxo-3,4-dihydro-2H-benzo[1,4]oxazin-2-yl}-acetic acid hydrobromide MS: m/e (ESI) 599.3 (MH+)

Example 2076

{8-tert-Butyl-4-carbamoylmethyl-6-[2-(7-fluoro-1-imino-5,6-dimethoxy-1,3-dihydro-isoindol-2-yl)-acetyl]-3-oxo-3,4-dihydro-2H-benzo[1,4]oxazin-2-yl}-acetic acid hydrobromide MS: m/e (ESI) 571.2 (MH+)

Example 2077

{8-tert-Butyl-4-carbamoylmethyl-6-[2-(2-cyclopropyl-7-imino-5,7-dihydro-pyrrolo[3,4-b]pyridin-6-yl)-acetyl]-3-oxo-3,4-dihydro-2H-benzo[1,4]oxazin-2-yl}-acetic acid hydrobromide MS: m/e (ESI) 534.2 (MH+)

Example 2078

{8-tert-Butyl-4-carbamoylmethyl-6-[2-(3-ethoxy-7-imino-2-methylcarbamoyl-5,7-dihydro-pyrrolo[3,4-b]pyridin-6-yl)-acetyl]-3-oxo-3,4-dihydro-2H-benzo[1,4]oxazin-2-yl}-acetic acid hydrobromide MS: m/e (ESI) 595.3 (MH+)

Example 2079

2-[2-(3-tert-Butyl-4-cyanomethoxy-5-ethoxy-phenyl)-2-oxo-ethyl]-6-dimethylamino-3-imino-2,3-dihydro-1H-isoindole-5-carboxylic acid methylamide hydrobromide MS: m/e (ESI) 505.9 (MH+)

Example 2080

{2-tert-Butyl-4-[2-(5,6-diethoxy-7-fluoro-1-imino-1,3-dihydro-isoindol-2-yl)-acetyl]-6-ethoxy-phenoxy}-acetonitrile hydrobromide MS: m/e (ESI) 511.8 (MH+)

Example 2081

{2-tert-Butyl-6-ethoxy-4-[2-(7-fluoro-1-imino-5,6-dimethoxy-1,3-dihydro-isoindol-2-yl)-acetyl]-phenoxy}-acetonitrile hydrobromide MS: m/e (ESI) 483.8 (MH+)

Example 2082

{2-tert-Butyl-4-[2-(2-cyclopropyl-7-imino-5,7-dihydro-pyrrolo[3,4-b]pyridin-6-yl)-acetyl]-6-ethoxy-phenoxy}-acetonitrile hydrobromide MS: m/e (ESI) 446.9 (MH+)

Example 2083

2-[2-(3-tert-Butyl-4-cyanomethoxy-5-ethoxy-phenyl)-2-oxo-ethyl]-6-ethoxy-3-imino-2,3-dihydro-1H-isoindole-5-acetic acid methylamide hydrobromide MS: m/e (ESI) 506.9 (MH+)

Example 2084

6-[2-(3-tert-Butyl-4-cyanomethoxy-5-ethoxy-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 507.9 (MH+)

Example 2085

2-[2-(3-tert-Butyl-4-cyanomethoxy-phenyl)-2-oxo-ethyl]-6-dimethylamino-3-imino-2,3-dihydro-1H-isoindole-5-carboxylic acid methylamide hydrobromide MS: m/e (ESI) 461.9 (MH+)

Example 2086

{2-tert-Butyl-4-[2-(5,6-diethoxy-7-fluoro-1-imino-1,3-dihydro-isoindol-2-yl)-acetyl]-phenoxy}-acetonitrile hydrobromide MS: m/e (ESI) 467.9 (MH+)

Example 2087

{2-tert-Butyl-4-[2-(7-fluoro-1-imino-5,6-dimethoxy-1,3-dihydro-isoindol-2-yl)-acetyl]-phenoxy}-acetonitrile hydrobromide MS: m/e (ESI) 439.9 (MH+)

Example 2088

{2-tert-Butyl-4-[2-(2-cyclopropyl-7-imino-5,7-dihydro-pyrrolo[3,4-b]pyridin-6-yl)-acetyl]-phenoxy}-acetonitrile hydrobromide MS: m/e (ESI) 402.9 (MH+)

Example 2089

2-[2-(3-tert-Butyl-4-cyanomethoxy-phenyl)-2-oxo-ethyl]-6-ethoxy-3-imino-2,3-dihydro-1H-isoindole-5-acetic acid methylamide hydrobromide MS: m/e (ESI) 462.9 (MH+)

Example 2090

6-[2-(3-tert-Butyl-4-cyanomethoxy-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 463.9 (MH+)

Example 2091

2-[2-(3-tert-Butyl-5-cyanomethoxy-4-methoxy-phenyl)-2-oxo-ethyl]-6-ethoxy-3-imino-2,3-dihydro-1H-isoindole-5-acetic acid methylamide hydrobromide MS: m/e (ESI) 493.2 (MH+)

Example 2092

2-[2-(3-tert-Butyl-5-cyanomethoxy-4-methoxy-phenyl)-2-oxo-ethyl]-6-dimethylamino-3-imino-2,3-dihydro-1H-isoindole-5-carboxylic acid methylamide hydrobromide MS: m/e (ESI) 492.3 (MH+)

Example 2093

{3-tert-Butyl-5-[2-(5,6-diethoxy-7-fluoro-1-imino-1,3-dihydro-isoindol-2-yl)-acetyl]-2-methoxy-phenoxy}-acetonitrile hydrobromide MS: m/e (ESI) 498.3 (MH+)

Example 2094

{3-tert-Butyl-5-[2-(7-fluoro-1-imino-5,6-dimethoxy-1,3-dihydro-isoindol-2-yl)-acetyl]-2-methoxy-phenoxy}-acetonitrile hydrobromide MS: m/e (ESI) 470.3 (MH+)

Example 2095

6-[2-(3-tert-Butyl-5-cyanomethoxy-4-methoxy-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 494.3 (MH+)

Example 2096

{3-tert-Butyl-5-[2-(2-cyclopropyl-7-imino-5,7-dihydro-pyrrolo[3,4-b]pyridin-6-yl)-acetyl]-2-methoxy-phenoxy}-acetonitrile hydrobromide MS: m/e (ESI) 433.3 (MH+)

Example 2097

2-{2-[3-tert-Butyl-5-(3-cyano-propoxy)-4-methoxy-phenyl]-2-oxo-ethyl}-6-ethoxy-3-imino-2,3-dihydro-1H-isoindole-5-acetic acid methylamide hydrobromide MS: m/e (ESI) 521.3 (MH+)

Example 2098

2-{2-[3-tert-Butyl-5-(3-cyano-propoxy)-4-methoxy-phenyl]-2-oxo-ethyl}-6-dimethylamino-3-imino-2,3-dihydro-1H-isoindole-5-carboxylic acid methylamide hydrobromide MS: m/e (ESI) 520.4 (MH+)

Example 2099

4-{3-tert-Butyl-5-[2-(5,6-diethoxy-7-fluoro-1-imino-1,3-dihydro-isoindol-2-yl)-acetyl]-2-methoxy-phenoxy}-butyronitrile hydrobromide MS: m/e (ESI) 526.4 (MH+)

Example 2100

4-{3-tert-Butyl-5-[2-(7-fluoro-1-imino-5,6-dimethoxy-1,3-dihydro-isoindol-2-yl)-acetyl]-2-methoxy-phenoxy}-butyronitrile hydrobromide MS: m/e (ESI) 498.3 (MH+)

Example 2101

6-{2-[3-tert-Butyl-5-(3-cyano-propoxy)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 522.4 (MH+)

Example 2102

4-{3-tert-Butyl-5-[2-(2-cyclopropyl-7-imino-5,7-dihydro-pyrrolo[3,4-b]pyridin-6-yl)-acetyl]-2-methoxy-phenoxy}-butyronitrile hydrobromide MS: m/e (ESI) 461.3 (MH+)

Example 2103

2-[2-(3-tert-Butyl-4-cyanomethoxy-5-dimethylamino-phenyl)-2-oxo-ethyl]-6-dimethylamino-3-imino-2,3-dihydro-1H-isoindole-5-carboxylic acid methylamide hydrobromide MS: m/e (ESI) 504.8 (MH+)

Example 2104

{2-tert-Butyl-4-[2-(5,6-diethoxy-7-fluoro-1-imino-1,3-dihydro-isoindol-2-yl)-acetyl]-6-dimethylamino-phenoxy}-acetonitrile hydrobromide MS: m/e (ESI) 510.8 (MH+)

Example 2105

{2-tert-Butyl-6-dimethylamino-4-[2-(7-fluoro-1-imino-5,6-dimethoxy-1,3-dihydro-isoindol-2-yl)-acetyl]-phenoxy}-acetonitrile hydrobromide MS: m/e (ESI) 482.8 (MH+)

Example 2106

{2-tert-Butyl-4-[2-(2-cyclopropyl-7-imino-5,7-dihydro-pyrrolo[3,4-b]pyridin-6-yl)-acetyl]-6-dimethylamino-phenoxy}-acetonitrile hydrobromide MS: m/e (ESI) 445.9 (MH+)

Example 2107

2-[2-(3-tert-Butyl-4-cyanomethoxy-5-dimethylamino-phenyl)-2-oxo-ethyl]-6-ethoxy-3-imino-2,3-dihydro-1H-isoindole-5-acetic acid methylamide hydrobromide MS: m/e (ESI) 505.9 (MH+)

Example 2108

6-[2-(3-tert-Butyl-4-carbamoylmethoxy-5-dimethylamino-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 524.9 (MH+)

Example 2109

2-{8-tert-Butyl-6-[2-(5-ethoxy-1-imino-6-methylcarbamoyl-1,3-dihydro-isoindol-2-yl)-acetyl]-2,3-dihydro-benzo[1,4]oxazin-4-yl}-2-methyl-propionic acid hydrobromide MS: m/e (ESI) 551.4 (MH+)

Example 2110

2-{8-tert-Butyl-6-[2-(3-ethoxy-7-imino-2-methylcarbamoyl-5,7-dihydro-pyrrolo[3,4-b]pyridin-6-yl)-acetyl]-2,3-dihydro-benzo[1,4]oxazin-4-yl}-2-methyl-propionic acid hydrobromide MS: m/e (ESI) 552.4 (MH+)

Example 2111

2-{8-tert-Butyl-6-[2-(7-fluoro-1-imino-5,6-dimethoxy-1,3-dihydro-isoindol-2-yl)-acetyl]-2,3-dihydro-benzo[1,4]oxazin-4-yl}-2-methyl-propionic acid hydrobromide MS: m/e (ESI) 528.3 (MH+)

Example 2112

2-{8-tert-Butyl-6-[2-(5,6-diethoxy-7-fluoro-1-imino-1,3-dihydro-isoindol-2-yl)-acetyl]-2,3-dihydro-benzo[1,4]oxazin-4-yl}-2-methyl-propionic acid hydrobromide MS: m/e (ESI) 556.4 (MH+)

Example 2113

2-{8-tert-Butyl-6-[2-(2-cyclopropyl-7-imino-5,7-dihydro-pyrrolo[3,4-b]pyridin-6-yl)-acetyl]-2,3-dihydro-benzo[1,4]oxazin-4-yl}-2-methyl-propionic acid hydrobromide MS: m/e (ESI) 491.4 (MH+)

Example 2114

2-{8-tert-Butyl-6-[2-(5-dimethylamino-1-imino-6-methylcarbamoyl-1,3-dihydro-isoindol-2-yl)-acetyl]-2,3-dihydro-benzo[1,4]oxazin-4-yl}-2-methyl-propionic acid hydrobromide MS: m/e (ESI) 550.4 (MH+)

Example 2115

2-[2-(3-tert-Butyl-4-methoxy-5-morpholin-4-yl-phenyl)-2-oxo-ethyl]-6-ethoxy-3-imino-2,3-dihydro-1H-isoindole-5-acetic acid methylamide hydrobromide MS: m/e (ESI) 523.4 (MH+)

Example 2116

1-(3-tert-Butyl-4-methoxy-5-morpholin-4-yl-phenyl)-2-(5,6-diethoxy-7-fluoro-1-imino-1,3-dihydro-isoindol-2-yl)-ethanone hydrobromide MS: m/e (ESI) 528.4 (MH+)

Example 2117

1-(3-tert-Butyl-4-methoxy-5-morpholin-4-yl-phenyl)-2-(7-fluoro-1-imino-5,6-dimethoxy-1,3-dihydro-isoindol-2-yl)-ethanone hydrobromide MS: m/e (ESI) 500.3 (MH+)

Example 2118

1-(3-tert-Butyl-4-methoxy-5-morpholin-4-yl-phenyl)-2-(2-cyclopropyl-7-imino-5,7-dihydro-pyrrolo[3,4-b]pyridin-6-yl)-ethanone hydrobromide MS: m/e (ESI) 463.4 (MH+)

Example 2119

2-[2-(3-tert-Butyl-4-methoxy-5-pyrrolidin-1-yl-phenyl)-2-oxo-ethyl]-6-dimethylamino-3-imino-2,3-dihydro-1H-isoindole-5-carboxylic acid methylamide hydrobromide MS: m/e (ESI) 506.0 (MH+)

Example 2120

1-(3-tert-Butyl-4-methoxy-5-pyrrolidin-1-yl-phenyl)-2-(5,6-diethoxy-7-fluoro-1-imino-1,3-dihydro-isoindol-2-yl)-ethanone hydrobromide MS: m/e (ESI) 512.0 (MH+)

Example 2121

1-(3-tert-Butyl-4-methoxy-5-pyrrolidin-1-yl-phenyl)-2-(7-fluoro-1-imino-5,6-dimethoxy-1,3-dihydro-isoindol-2-yl)-ethanone hydrobromide MS: m/e (ESI) 483.9 (MH+)

Example 2122

1-(3-tert-Butyl-4-methoxy-5-pyrrolidin-1-yl-phenyl)-2-(2-cyclopropyl-7-imino-5,7-dihydro-pyrrolo[3,4-b]pyridin-6-yl)-ethanone hydrobromide MS: m/e (ESI) 447.0 (MH+)

Example 2123

2-[2-(3-tert-Butyl-4-methoxy-5-pyrrolidin-1-yl-phenyl)-2-oxo-ethyl]-6-ethoxy-3-imino-2,3-dihydro-1H-isoindole-5-acetic acid methylamide hydrobromide MS: m/e (ESI) 507.0 (MH+)

Example 2124

6-[2-(3-tert-Butyl-4-methoxy-5-pyrrolidin-1-yl-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 508.0 (MH+)

Example 2125

2-[2-(4-Cyanomethoxy-3-isopropyl-phenyl)-2-oxo-ethyl]-6-ethoxy-3-imino-2,3-dihydro-1H-isoindole-5-acetic acid methylamide hydrobromide MS: m/e (ESI) 449.3 (MH+)

Example 2126

2-[2-(4-Cyanomethoxy-3-isopropyl-phenyl)-2-oxo-ethyl]-6-dimethylamino-3-imino-2,3-dihydro-1H-isoindole-5-carboxylic acid methylamide hydrobromide MS: m/e (ESI) 448.3 (MH+)

Example 2127

{4-[2-(5,6-Diethoxy-7-fluoro-1-imino-1,3-dihydro-isoindol-2-yl)-acetyl]-2-isopropyl-phenoxy}-acetonitrile hydrobromide MS: m/e (ESI) 454.3 (MH+)

Example 2128

{4-[2-(7-Fluoro-1-imino-5,6-dimethoxy-1,3-dihydro-isoindol-2-yl)-acetyl]-2-isopropyl-phenoxy}-acetonitrile hydrobromide MS: m/e (ESI) 426.3 (MH+)

Example 2129

{4-[2-(2-Cyclopropyl-7-imino-5,7-dihydro-pyrrolo[3,4-b]pyridin-6-yl)-acetyl]-2-isopropyl-phenoxy}-acetonitrile hydrobromide MS: m/e (ESI) 389.3 (MH+)

Example 2130

6-[2-(4-Carbamoylmethoxy-3-isopropyl-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 468.4 (MH+)

Example 2131

2-[2-(3-Dimethylamino-5-isopropyl-4-methoxy-phenyl)-2-oxo-ethyl]-6-ethoxy-3-imino-2,3-dihydro-1H-isoindole-5-acetic acid methylamide hydrobromide MS: m/e (ESI) 467.3 (MH+)

Example 2132

2-(5,6-Diethoxy-7-fluoro-1-imino-1,3-dihydro-isoindol-2-yl)-1-(3-dimethylamino-5-isopropyl-4-methoxy-phenyl)-ethanone hydrobromide MS: m/e (ESI) 472.4 (MH+)

Example 2133

1-(3-Dimethylamino-5-isopropyl-4-methoxy-phenyl)-2-(7-fluoro-1-imino-5,6-dimethoxy-1,3-dihydro-isoindol-2-yl)-ethanone hydrobromide MS: m/e (ESI) 444.3 (MH+)

Example 2134

2-(2-Cyclopropyl-7-imino-5,7-dihydro-pyrrolo[3,4-b]pyridin-6-yl)-1-(3-dimethylamino-5-isopropyl-4-methoxy-phenyl)-ethanone hydrobromide MS: m/e (ESI) 407.3 (MH+)

Example 2135

6-[2-(3-Dimethylamino-5-isopropyl-4-methoxy-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 468.4 (MH+)

Example 2136

(1-{3-tert-Butyl-5-[2-(5,6-diethoxy-7-fluoro-1-imino-1,3-dihydro-isoindol-2-yl)-acetyl]-2-methoxy-phenyl}-piperidin-4-yloxy)-acetic acid hydrobromide MS: m/e (ESI) 599.7 (MH+)

Example 2137

(1-{3-tert-Butyl-5-[2-(2-cyclopropyl-7-imino-5,7-dihydro-pyrrolo[3,4-b]pyridin-6-yl)-acetyl]-2-methoxy-phenyl}-piperidin-4-yloxy)-acetic acid hydrobromide MS: m/e (ESI) 534.8 (MH+)

Example 2138

(1-{3-tert-Butyl-5-[2-(5-dimethylamino-1-imino-6-methylcarbamoyl-1,3-dihydro-isoindol-2-yl)-acetyl]-2-methoxy-phenyl}-piperidin-4-yloxy)-acetic acid hydrobromide MS: m/e (ESI) 593.9 (MH+)

Example 2139

2-[2-(3-tert-Butyl-5-isopropoxy-4-methoxy-phenyl)-2-oxo-ethyl]-6-ethoxy-3-imino-2,3-dihydro-1H-isoindole-5-acetic acid methylamide hydrobromide MS: m/e (ESI) 495.9 (MH+)

Example 2140

1-(3-tert-Butyl-5-isopropoxy-4-methoxy-phenyl)-2-(5,6-diethoxy-7-fluoro-1-imino-1,3-dihydro-isoindol-2-yl)-ethanone hydrobromide MS: m/e (ESI) 500.9 (MH+)

Example 2141

1-(3-tert-Butyl-5-isopropoxy-4-methoxy-phenyl)-2-(7-fluoro-1-imino-5,6-dimethoxy-1,3-dihydro-isoindol-2-yl)-ethanone hydrobromide MS: m/e (ESI) 472.9 (MH+)

Example 2142

1-(3-tert-Butyl-5-isopropoxy-4-methoxy-phenyl)-2-(2-cyclopropyl-7-imino-5,7-dihydro-pyrrolo[3,4-b]pyridin-6-yl)-ethanone hydrobromide MS: m/e (ESI) 436.0 (MH+)

Example 2143

6-[2-(3-tert-Butyl-5-isopropoxy-4-methoxy-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 497.0 (MH+)

Example 2144

2-[2-(3-tert-Butyl-5-isopropoxy-4-methoxy-phenyl)-2-oxo-ethyl]-6-dimethylamino-3-imino-2,3-dihydro-1H-isoindole-5-carboxylic acid methylamide hydrobromide MS: m/e (ESI) 495.0 (MH+)

Example 2145

2-[2-(3-tert-Butyl-phenyl)-2-oxo-ethyl]-6-dimethylamino-3-imino-2,3-dihydro-1H-isoindole-5-carboxylic acid methylamide hydrobromide MS: m/e (ESI) 408.3 (MH+)

Example 2146

1-(3-tert-Butyl-phenyl)-2-(7-fluoro-1-imino-5,6-dimethoxy-1,3-dihydro-isoindol-2-yl)-ethanone hydrobromide MS: m/e (ESI) 385.3 (MH+)

Example 2147

6-[2-(3-tert-Butyl-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 409.3 (MH+)

Example 2148

1-(3-tert-Butyl-4-methoxy-5-morpholin-4-yl-phenyl)-2-(7-imino-2-methyl-5,7-dihydro-pyrrolo[3,4-b]pyridin-6-yl)-ethanone hydrobromide MS: m/e (ESI) 437.4 (MH+)

Example 2149

1-(3-tert-Butyl-4-methoxy-5-morpholin-4-yl-phenyl)-2-(2-ethyl-7-imino-5,7-dihydro-pyrrolo[3,4-b)pyridin-6-yl)-ethanone hydrobromide MS: m/e (ESI) 451.4 (MH+)

Example 2150

2-{2-[3-tert-Butyl-4-methoxy-5-(4-oxo-piperidin-1-yl)-phenyl]-2-oxo-ethyl}-6-ethoxy-3-imino-2,3-dihydro-1H-isoindole-5-acetic acid methylamide hydrobromide MS: m/e (ESI) 535.3 (MH+)

Example 2151

1-{3-tert-Butyl-5-[2-(5,6-diethoxy-7-fluoro-1-imino-1,3-dihydro-isoindol-2-yl)-acetyl]-2-methoxy-phenyl}-piperidin-4-one hydrobromide MS: m/e (ESI) 540.3 (MH+)

Example 2152

1-{3-tert-Butyl-5-[2-(7-fluoro-1-imino-5,6-dimethoxy-1,3-dihydro-isoindol-2-yl)-acetyl]-2-methoxy-phenyl}-piperidin-4-one hydrobromide MS: m/e (ESI) 512.3 (MH+)

Example 2153

1-{3-tert-Butyl-5-[2-(2-cyclopropyl-7-imino-5,7-dihydro-pyrrolo[3,4-b]pyridin-6-yl)-acetyl]-2-methoxy-phenyl}-piperidin-4-one hydrobromide MS: m/e (ESI) 475.4 (MH+)

Example 2154

6-{2-[3-tert-Butyl-4-methoxy-5-(4-oxo-piperidin-1-yl)-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 536.4 (MH+)

Example 2155

2-{2-[3-tert-Butyl-4-methoxy-5-(2-oxo-piperidin-1-yl)-phenyl]-2-oxo-ethyl}-6-ethoxy-3-imino-2,3-dihydro-1H-isoindole-5-acetic acid methylamide hydrobromide MS: m/e (ESI) 535.3 (MH+)

Example 2156

1-{3-tert-Butyl-5-[2-(5,6-diethoxy-7-fluoro-1-imino-1,3-dihydro-isoindol-2-yl)-acetyl]-2-methoxy-phenyl}-piperidin-2-one hydrobromide MS: m/e (ESI) 540.3 (MH+)

Example 2157

1-{3-tert-Butyl-5-[2-(7-fluoro-1-imino-5,6-dimethoxy-1,3-dihydro-isoindol-2-yl)-acetyl]-2-methoxy-phenyl}-piperidin-2-one hydrobromide MS: m/e (ESI) 512.4 (MH+)

Example 2158

1-{3-tert-Butyl-5-[2-(2-cyclopropyl-7-imino-5,7-dihydro-pyrrolo[3,4-b]pyridin-6-yl)-acetyl]-2-methoxy-phenyl}-piperidin-2-one hydrobromide MS: m/e (ESI) 475.4 (MH+)

Example 2159

6-{2-[3-tert-Butyl-4-methoxy-5-(2-oxo-piperidin-1-yl)-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 536.4 (MH+)

Example 2160

2-(1-{3-tert-Butyl-5-[2-(5-ethoxy-1-imino-6-methyl-carbamoyl-1,3-dihydro-isoindol-2-yl)-acetyl]-2-methoxy-phenyl}-piperidin-4-yloxy)-propionic acid hydrobromide MS: m/e (ESI) 609.1 (MH+)

Example 2161

2-(1-{3-tert-Butyl-5-[2-(5,6-diethoxy-7-fluoro-1-imino-1,3-dihydro-isoindol-2-yl)-acetyl]-2-methoxy-phenyl}-piperidin-4-yloxy)-propionic acid hydrobromide MS: m/e (ESI) 614.1 (MH+)

Example 2162

2-(1-{3-tert-Butyl-5-[2-(5-dimethylamino-1-imino-6-methylcarbamoyl-1,3-dihydro-isoindol-2-yl)-acetyl]-2-methoxy-phenyl}-piperidin-4-yloxy)-propionic acid hydrobromide MS: m/e (ESI) 608.1 (MH+)

Example 2163

2-(1-{3-tert-Butyl-5-[2-(3-ethoxy-7-imino-2-methyl-carbamoyl-5,7-dihydro-pyrrolo[3,4-b]pyridin-6-yl)-acetyl]-2-methoxy-phenyl}-piperidin-4-yloxy)-propionic acid hydrobromide MS: m/e (ESI) 610.1 (MH+)

Example 2164

2-(1-{3-tert-Butyl-5-[2-(7-fluoro-1-imino-5,6-dimethoxy-1,3-dihydro-isoindol-2-yl)-acetyl]-2-methoxy-phenyl}-piperidin-4-yloxy)-propionic acid hydrobromide MS: m/e (ESI) 586.1 (MH+)

Example 2165

2-(1-{3-tert-Butyl-5-[2-(2-cyclopropyl-7-imino-5,7-dihydro-pyrrolo[3,4-b]pyridin-6-yl)-acetyl]-2-methoxy-phenyl}-piperidin-4-yloxy)-propionic acid hydrobromide MS: m/e (ESI) 549.1 (MH+)

Example 2166

2-{2-[3-tert-Butyl-4-methoxy-5-(4-methoxy-piperidin-1-yl)-phenyl]-2-oxo-ethyl}-6-ethoxy-3-imino-2,3-dihydro-1H-isoindole-5-acetic acid methylamide hydrobromide MS: m/e (ESI) 551.0 (MH+)

Example 2167

1-[3-tert-Butyl-4-methoxy-5-(4-methoxy-piperidin-1-yl)-phenyl]-2-(5,6-diethoxy-7-fluoro-1-imino-1,3-dihydro-isoindol-2-yl)-ethanone hydrobromide MS: m/e (ESI) 556.0 (MH+)

Example 2168

2-{2-[3-tert-Butyl-4-methoxy-5-(4-methoxy-piperidin-1-yl)-phenyl]-2-oxo-ethyl}-6-dimethylamino-3-imino-2,3-dihydro-1H-isoindole-5-carboxylic acid methylamide hydrobromide MS: m/e (ESI) 550.1 (MH+)

Example 2169

6-{2-[3-tert-Butyl-4-methoxy-5-(4-methoxy-piperidin-1-yl)-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 552.1 (MH+)

Example 2170

1-[3-tert-Butyl-4-methoxy-5-(4-methoxy-piperidin-1-yl)-phenyl]-2-(7-fluoro-1-imino-5,6-dimethoxy-1,3-dihydro-isoindol-2-yl)-ethanone hydrobromide MS: m/e (ESI) 528.0 (MH+)

Example 2171

1-[3-tert-Butyl-4-methoxy-5-(4-methoxy-piperidin-1-yl)-phenyl]-2-(2-cyclopropyl-7-imino-5,7-dihydro-pyrrolo[3,4-b]pyridin-6-yl)-ethanone hydrobromide MS: m/e (ESI) 491.0 (MH+)

Example 2172

2-{2-[3-tert-Butyl-4-methoxy-5-(2-oxo-pyrrolidin-1-yl)-phenyl]-2-oxo-ethyl}-6-ethoxy-3-imino-2,3-dihydro-1H-isoindole-5-acetic acid methylamide hydrobromide MS: m/e (ESI) 521.3 (MH+)

Example 2173

1-{3-tert-Butyl-5-[2-(5,6-diethoxy-7-fluoro-1-imino-1,3-dihydro-isoindol-2-yl)-acetyl]-2-methoxy-phenyl}-pyrrolidin-2-one hydrobromide MS: m/e (ESI) 526.3 (MH+)

Example 2174

1-{3-tert-Butyl-5-[2-(7-fluoro-1-imino-5,6-dimethoxy-1,3-dihydro-isoindol-2-yl)-acetyl]-2-methoxy-phenyl}-pyrrolidin-2-one hydrobromide MS: m/e (ESI) 498.3 (MH+)

Example 2175

1-{3-tert-Butyl-5-[2-(2-cyclopropyl-7-imino-5,7-dihydro-pyrrolo[3,4-b]pyridin-6-yl)-acetyl]-2-methoxy-phenyl}-pyrrolidin-2-one hydrobromide MS: m/e (ESI) 461.3 (MH+)

Example 2176

6-{2-[3-tert-Butyl-4-methoxy-5-(2-oxo-pyrrolidin-1-yl)-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 522.4 (MH+)

Example 2177

{8-tert-Butyl-6-[2-(5-ethoxy-1-imino-6-methylcarbamoyl-1,3-dihydro-isoindol-2-yl)-acetyl]-4-methyl-3,4-dihydro-2H-benzo[1,4]oxazin-2-ylmethoxy}-acetic acid hydrobromide MS: m/e (ESI) 567.3 (MH+)

Example 2178

{8-tert-Butyl-6-[2-(5,6-diethoxy-7-fluoro-1-imino-1,3-dihydro-isoindol-2-yl)-acetyl]-4-methyl-3,4-dihydro-2H-benzo[1,4]oxazin-2-ylmethoxy}-acetic acid hydrobromide MS: m/e (ESI) 572.3 (MH+)

Example 2179

{8-tert-Butyl-6-[2-(7-fluoro-1-imino-5,6-dimethoxy-1,3-dihydro-isoindol-2-yl)-acetyl]-4-methyl-3,4-dihydro-2H-benzo[1,4]oxazin-2-ylmethoxy}-acetic acid hydrobromide MS: m/e (ESI) 544.3 (MH+)

Example 2180

{8-tert-Butyl-6-[2-(2-cyclopropyl-7-imino-5,7-dihydro-pyrrolo[3,4-b]pyridin-6-yl)-acetyl]-4-methyl-3,4-dihydro-2H-benzo[1,4]oxazin-2-ylmethoxy}-acetic acid hydrobromide MS: m/e (ESI) 507.3 (MH+)

Example 2181

{8-tert-Butyl-6-[2-(3-ethoxy-7-1-mino-2-methylcarbamoyl-5,7-dihydro-pyrrolo[3,4-b]pyridin-6-yl)-acetyl]-4-methyl-3,4-dihydro-2H-benzo[1,4]oxazin-2-ylmethoxy}-acetic acid hydrobromide MS: m/e (ESI) 568.4 (MH+)

Example 2182

2-{2-[3-tert-Butyl-4-methoxy-5-(2-oxo-oxazolidin-3-yl)-phenyl]-2-oxo-ethyl}-6-ethoxy-3-imino-2,3-dihydro-1H-isoindole-5-acetic acid methylamide hydrobromide MS: m/e (ESI) 523.3 (MH+)

Example 2183

3-{3-tert-Butyl-5-(2-(5,6-diethoxy-7-fluoro-1-imino-1,3-dihydro-isoindol-2-yl)-acetyl]-2-methoxy-phenyl}-oxazolidin-2-one hydrobromide MS: m/e (ESI) 528.3 (MH+)

Example 2184

3-{3-tert-Butyl-5-[2-(7-fluoro-1-imino-5,6-dimethoxy-1,3-dihydro-isoindol-2-yl)-acetyl]-2-methoxy-phenyl}-oxazolidin-2-one hydrobromide MS: m/e (ESI) 500.3 (MH+)

Example 2185

3-{3-tert-Butyl-5-[2-(2-cyclopropyl-7-imino-5,7-dihydro-pyrrolo[3,4-b]pyridin-6-yl)-acetyl]-2-methoxy-phenyl}-oxazolidin-2-one hydrobromide MS: m/e (ESI) 463.3 (MH+)

Example 2186

6-{2-[3-tert-Butyl-4-methoxy-5-(2-oxo-oxazolidin-3-yl)-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 524.3 (MH+)

Example 2187

1-{3-tert-Butyl-5-[2-(5,6-diethoxy-7-fluoro-1-imino-1,3-dihydro-isoindol-2-yl)-acetyl]-2-methoxy-phenyl}-piperidine-4-carbonitrile hydrobromide MS: m/e (ESI) 551.0 (MH+)

Example 2188

2-{2-[3-tert-Butyl-5-(4-cyano-piperidin-1-yl)-4-methoxy-phenyl]-2-oxo-ethyl}-6-dimethylamino-3-imino-2,3-dihydro-1H-isoindole-5-carboxylic acid methylamide hydrobromide MS: m/e (ESI) 545.1 (MH+)

Example 2189

6-{2-[3-tert-Butyl-5-(4-cyano-piperidin-1-yl)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 547.0 (MH+)

Example 2190

1-{3-tert-Butyl-5-[2-(7-fluoro-1-imino-5,6-dimethoxy-1,3-dihydro-isoindol-2-yl)-acetyl]-2-methoxy-phenyl}-piperidine-4-carbonitrile hydrobromide MS: m/e (ESI) 523.0 (MH+)

Example 2191

1-{3-tert-Butyl-5-[2-(2-cyclopropyl-7-imino-5,7-dihydro-pyrrolo[3,4-b]pyridin-6-yl)-acetyl]-2-methoxy-phenyl}-piperidine-4-carbonitrile hydrobromide MS: m/e (ESI) 486.0 (MH+)

Example 2192

(1-{3-tert-Butyl-5-[2-(5-ethoxy-1-imino-6-methylcarbamoyl-1,3-dihydro-isoindol-2-yl)-acetyl]-2-methoxy-phenyl}-piperidin-4-yl)-acetic acid hydrobromide MS: m/e (ESI) 578.7 (MH+)

Example 2193

(1-{3-tert-Butyl-5-[2-(5,6-diethoxy-7-fluoro-1-imino-1,3-dihydro-isoindol-2-yl)-acetyl]-2-methoxy-phenyl}-piperidin-4-yl)-acetic acid hydrobromide MS: m/e (ESI) 583.8 (MH+)

Example 2194

(1-{3-tert-Butyl-5-[2-(5-dimethylamino-1-imino-6-methylcarbamoyl-1,3-dihydro-isoindol-2-yl)-acetyl]-2-methoxy-phenyl}-piperidin-4-yl)-acetic acid hydrobromide MS: m/e (ESI) 577.9 (MH+)

Example 2195

(1-{3-tert-Butyl-5-[2-(3-ethoxy-7-imino-2-methylcarbamoyl-5,7-dihydro-pyrrolo[3,4-b]pyridin-6-yl)-acetyl]-2-methoxy-phenyl}-piperidin-4-yl)-acetic acid hydrobromide MS: m/e (ESI) 580.0 (MH+)

Example 2196

(1-{3-tert-Butyl-5-[2-(7-fluoro-1-imino-5,6-dimethoxy-1,3-dihydro-isoindol-2-yl)-acetyl]-2-methoxy-phenyl}-piperidin-4-yl)-acetic acid hydrobromide MS: m/e (ESI) 556.0 (MH+)

Example 2197

(1-{3-tert-Butyl-5-[2-(2-cyclopropyl-7-imino-5,7-dihydro-pyrrolo[3,4-b]pyridin-6-yl)-acetyl]-2-methoxy-phenyl}-piperidin-4-yl)-acetic acid hydrobromide MS: m/e (ESI) 519.0 (MH+)

Example 2198

2-[2-(3-Chloro-5-dimethylamino-4-methoxy-phenyl)-2-oxo-ethyl]-6-ethoxy-3-imino-2,3-dihydro-1H-isoindole-5-acetic acid methylamide hydrobromide MS: m/e (ESI) 459.2 (MH+)

Example 2199

1-(3-Chloro-5-dimethylamino-4-methoxy-phenyl)-2-(5,6-diethoxy-7-fluoro-1-imino-1,3-dihydro-isoindol-2-yl)-ethanone hydrobromide MS: m/e (ESI) 464.3 (MH+)

Example 2200

1-(3-Chloro-5-dimethylamino-4-methoxy-phenyl)-2-(2-cyclopropyl-7-imino-5,7-dihydro-pyrrolo[3,4-b]pyridin-6-yl)-ethanone hydrobromide MS: m/e (ESI) 399.2 (MH+)

Example 2201

2-[2-(3-Chloro-5-dimethylamino-4-methoxy-phenyl)-2-oxo-ethyl]-6-dimethylamino-3-imino-2,3-dihydro-1H-isoindole-5-carboxylic acid methylamide hydrobromide MS: m/e (ESI) 458.3 (MH+)

Example 2202

6-[2-(3-Chloro-5-dimethylamino-4-methoxy-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 460.3 (MH+)

Example 2203

2-[2-(3-Bromo-5-dimethylamino-4-methoxy-phenyl)-2-oxo-ethyl]-6-ethoxy-3-imino-2,3-dihydro-1H-isoindole-5-acetic acid methylamide hydrobromide MS: m/e (ESI) 505.3 (MH+)

Example 2204

1-(3-Bromo-5-dimethylamino-4-methoxy-phenyl)-2-(5,6-diethoxy-7-fluoro-1-imino-1,3-dihydro-isoindol-2-yl)-ethanone hydrobromide MS: m/e (ESI) 508.3 (MH+)

Example 2205

1-(3-Bromo-5-dimethylamino-4-methoxy-phenyl)-2-(2-cyclopropyl-7-imino-5,7-dihydro-pyrrolo[3,4-b]pyridin-6-yl)-ethanone hydrobromide MS: m/e (ESI) 443.2 (MH+)

Example 2206

2-[2-(3-Bromo-5-dimethylamino-4-methoxy-phenyl)-2-oxo-ethyl]-6-dimethylamino-3-imino-2,3-dihydro-1H-isoindole-5-carboxylic acid methylamide hydrobromide MS: m/e (ESI) 502.3 (MH+)

Example 2207

6-[2-(3-Bromo-5-dimethylamino-4-methoxy-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 504.3 (MH+)

Example 2208

2-[2-(3-Dimethylamino-4-methoxy-5-thiazol-2-yl-phenyl)-2-oxo-ethyl]-6-ethoxy-3-imino-2,3-dihydro-1H-isoindole-5-acetic acid methylamide hydrobromide MS: m/e (ESI) 508.3 (MH+)

Example 2209

2-(5,6-Diethoxy-7-fluoro-1-imino-1,3-dihydro-isoindol-2-yl)-1-(3-dimethylamino-4-methoxy-5-thiazol-2-yl-phenyl)-ethanone hydrobromide MS: m/e (ESI) 513.3 (MH+)

Example 2210

1-(3-Dimethylamino-4-methoxy-5-thiazol-2-yl-phenyl)-2-(7-fluoro-1-imino-5,6-dimethoxy-1,3-dihydro-isoindol-2-yl)-ethanone hydrobromide MS: m/e (ESI) 485.3 (MH+)

Example 2211

2-(2-Cyclopropyl-7-imino-5,7-dihydro-pyrrolo[3,4-b]pyridin-6-yl)-1-(3-dimethylamino-4-methoxy-5-thiazol-2-yl-phenyl)-ethanone hydrobromide MS: m/e (ESI) 448.3 (MH+)

Example 2212

6-Dimethylamino-2-[2-(3-dimethylamino-4-methoxy-5-thiazol-2-yl-phenyl)-2-oxo-ethyl]-3-imino-2,3-dihydro-1H-isoindole-5-carboxylic acid methylamide hydrobromide MS: m/e (ESI) 507.4 (MH+)

Example 2213

6-[2-(3-Dimethylamino-4-methoxy-5-thiazol-2-yl-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 508.3 (MH+)

Example 2214

2-{2-[3-tert-Butyl-5-(4-ethoxy-piperidin-1-yl)-4-methoxy-phenyl]-2-oxo-ethyl}-6-ethoxy-3-imino-2,3-dihydro-1H-isoindole-5-acetic acid methylamide hydrobromide MS: m/e (ESI) 565.0 (MH+)

Example 2215

1-[3-tert-Butyl-5-(4-ethoxy-piperidin-1-yl)-4-methoxy-phenyl]-2-(5,6-diethoxy-7-fluoro-1-imino-1,3-dihydro-isoindol-2-yl)-ethanone hydrobromide MS: m/e (ESI) 570.0 (MH+)

Example 2216

1-[3-tert-Butyl-5-(4-ethoxy-piperidin-1-yl)-4-methoxy-phenyl]-2-(7-fluoro-1-imino-5,6-dimethoxy-1,3-dihydro-isoindol-2-yl)-ethanone hydrobromide MS: m/e (ESI) 542.0 (MH+)

Example 2217

2-{2-[3-tert-Butyl-5-(4-hydroxy-piperidin-1-yl)-4-methoxy-phenyl]-2-oxo-ethyl}-6-ethoxy-3-imino-2,3-dihydro-1H-isoindole-5-acetic acid methylamide hydrobromide MS: m/e (ESI) 537.0 (MH+)

Example 2218

1-[3-tert-Butyl-5-(4-hydroxy-piperidin-1-yl)-4-methoxy-phenyl]-2-(5,6-diethoxy-7-fluoro-1-imino-1,3-dihydro-isoindol-2-yl)-ethanone hydrobromide MS: m/e (ESI) 542.0 (MH+)

Example 2219

2-{2-[3-tert-Butyl-5-(4-hydroxy-piperidin-1-yl)-4-methoxy-phenyl]-2-oxo-ethyl}-6-dimethylamino-3-imino-2,3-dihydro-1H-isoindole-5-carboxylic acid methylamide hydrobromide MS: m/e (ESI) 536.1 (MH+)

Example 2220

6-{2-[3-tert-Butyl-5-(4-hydroxy-piperidin-1-yl)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 538.1 (MH+)

Example 2221

1-[3-tert-Butyl-5-(4-hydroxy-piperidin-1-yl)-4-methoxy-phenyl]-2-(7-fluoro-1-imino-5,6-dimethoxy-1,3-dihydro-isoindol-2-yl)-ethanone hydrobromide MS: m/e (ESI) 514.0 (MH+)

Example 2222

1-[3-tert-Butyl-5-(4-hydroxy-piperidin-1-yl)-4-methoxy-phenyl]-2-(2-cyclopropyl-7-imino-5,7-dihydro-pyrrolo[3,4-b]pyridin-6-yl)-ethanone hydrobromide MS: m/e (ESI) 476.3 (MH+)

Example 2223

1-(3-tert-Butyl-4-methoxy-5-methylamino-phenyl)-2-(5,6-diethoxy-7-fluoro-1-imino-1,3-dihydro-isoindol-2-yl)-ethanone hydrobromide MS: m/e (ESI) 471.8 (MH+)

Example 2224

1-(3-tert-Butyl-4-methoxy-5-methylamino-phenyl)-2-(7-fluoro-1-imino-5,6-dimethoxy-1,3-dihydro-isoindol-2-yl)-ethanone hydrobromide MS: m/e (ESI) 443.9 (MH+)

Example 2225

1-(3-tert-Butyl-4-methoxy-5-methylamino-phenyl)-2-(2-cyclopropyl-7-imino-5,7-dihydro-pyrrolo[3,4-b]pyridin-6-yl)-ethanone hydrobromide MS: m/e (ESI) 407.0 (MH+)

Example 2226

2-tert-Butyl-4-[2-(5-dimethylamino-1-imino-6-methylcarbamoyl-1,3-dihydro-isoindol-2-yl)-acetyl]-6-ethoxy-phenyl methanesulfonate hydrobromide MS: m/e (ESI) 545.0 (MH+)

Example 2227

2-tert-Butyl-4-[2-(5,6-diethoxy-7-fluoro-1-imino-1,3-dihydro-isoindol-2-yl)-acetyl]-6-ethoxy-phenyl methanesulfonate hydrobromide MS: m/e (ESI) 551.0 (MH+)

Example 2228

2-tert-Butyl-6-ethoxy-4-[2-(7-fluoro-1-imino-5,6-dimethoxy-1,3-dihydro-isoindol-2-yl)-acetyl]-phenyl methanesulfonate hydrobromide MS: m/e (ESI) 522.9 (MH+)

Example 2229

2-tert-Butyl-4-[2-(2-cyclopropyl-7-imino-5,7-dihydro-pyrrolo[3,4-b]pyridin-6-yl)-acetyl]-6-ethoxy-phenyl methanesulfonate hydrobromide MS: m/e (ESI) 486.0 (MH+)

Example 2230

2-tert-Butyl-6-ethoxy-4-[2-(5-ethoxy-1-imino-6-methylcarbamoyl-1,3-dihydro-isoindol-2-yl)-acetyl]-phenyl methanesulfonate hydrobromide MS: m/e (ESI) 546.0 (MH+)

Example 2231

2-tert-Butyl-6-ethoxy-4-[2-(3-ethoxy-7-imino-2-methylcarbamoyl-5,7-dihydro-pyrrolo[3,4-b]pyridin-6-yl)-acetyl]-phenyl methanesulfonate hydrobromide MS: m/e (ESI) 547.0 (MH+)

Example 2232

2-[2-(3-tert-Butyl-4-methoxy-5-thiazol-2-yl-phenyl)-2-oxo-ethyl]-6-ethoxy-3-imino-2,3-dihydro-1H-isoindole-5-acetic acid methylamide hydrobromide MS: m/e (ESI) 521.3 (MH+)

Example 2233

1-(3-tert-Butyl-4-methoxy-5-thiazol-2-yl-phenyl)-2-(5,6-diethoxy-7-fluoro-1-imino-1,3-dihydro-isoindol-2-yl)-ethanone hydrobromide MS: m/e (ESI) 526.3 (MH+)

Example 2234

1-(3-tert-Butyl-4-methoxy-5-thiazol-2-yl-phenyl)-2-(7-fluoro-1-imino-5,6-dimethoxy-1,3-dihydro-isoindol-2-yl)-ethanone hydrobromide MS: m/e (ESI) 498.3 (MH+)

Example 2235

1-(3-tert-Butyl-4-methoxy-5-thiazol-2-yl-phenyl)-2-(2-cyclopropyl-7-imino-5,7-dihydro-pyrrolo[3,4-b]pyridin-6-yl)-ethanone hydrobromide MS: m/e (ESI) 461.3 (MH+)

Example 2236

6-[2-(3-tert-Butyl-4-methoxy-5-thiazol-2-yl-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 522.4 (MH+)

Example 2237

2-{2-[3-(Acetyl-methyl-amino)-5-tert-butyl-4-methoxy-phenyl]-2-oxo-ethyl}-6-ethoxy-3-imino-2,3-dihydro-1H-isoindole-5-acetic acid methylamide hydrobromide MS: m/e (ESI) 509.4 (MH+)

Example 2238

N-{3-tert-Butyl-5-[2-(5,6-diethoxy-7-fluoro-1-imino-1,3-dihydro-isoindol-2-yl)-acetyl]-2-methoxy-phenyl}-N-methyl-acetamide hydrobromide MS: m/e (ESI) 514.4 (MH+)

Example 2239

N-{3-tert-Butyl-5-[2-(7-fluoro-1-imino-5,6-dimethoxy-1,3-dihydro-isoindol-2-yl)-acetyl]-2-methoxy-phenyl}-N-methyl-acetamide hydrobromide MS: m/e (ESI) 486.4 (MH+)

Example 2240

N-{3-tert-Butyl-5-[2-(2-cyclopropyl-7-imino-5,7-dihydro-pyrrolo[3,4-b]pyridin-6-yl)-acetyl]-2-methoxy-phenyl}-N-methyl-acetamide hydrobromide MS: m/e (ESI) 449.4 (MH+)

Example 2241

6-{2-[3-(Acetyl-methyl-amino)-5-tert-butyl-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 510.5 (MH+)

Example 2242

2-[2-(3-tert-Butyl-5-diethylamino-4-methoxy-phenyl)-2-oxo-ethyl]-6-dimethylamino-3-imino-2,3-dihydro-1H-isoindole-5-carboxylic acid methylamide hydrobromide MS: m/e (ESI) 508.0 (MH+)

Example 2243

1-(3-tert-Butyl-5-diethylamino-4-methoxy-phenyl)-2-(5,6-diethoxy-7-fluoro-1-imino-1,3-dihydro-isoindol-2-yl)-ethanone hydrobromide MS: m/e (ESI) 514.0 (MH+)

Example 2244

1-(3-tert-Butyl-5-diethylamino-4-methoxy-phenyl)-2-(7-fluoro-1-imino-5,6-dimethoxy-1,3-dihydro-isoindol-2-yl)-ethanone hydrobromide MS: m/e (ESI) 486.0 (MH+)

Example 2245

1-(3-tert-Butyl-5-diethylamino-4-methoxy-phenyl)-2-(2-cyclopropyl-7-imino-5,7-dihydro-pyrrolo[3,4-b]pyridin-6-yl)-ethanone hydrobromide MS: m/e (ESI) 449.0 (MH+)

Example 2246

2-[2-(3-tert-Butyl-5-diethylamino-4-methoxy-phenyl)-2-oxo-ethyl]-6-ethoxy-3-imino-2,3-dihydro-1H-isoindole-5-acetic acid methylamide hydrobromide MS: m/e (ESI) 509.1 (MH+)

Example 2247

6-[2-(3-tert-Butyl-5-diethylamino-4-methoxy-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 510.1 (MH+)

Example 2248

2-{2-[3-tert-Butyl-5-(ethyl-methyl-amino)-4-methoxy-phenyl]-2-oxo-ethyl}-6-dimethylamino-3-imino-2,3-dihydro-1H-isoindole-5-carboxylic acid methylamide hydrobromide MS: m/e (ESI) 493.8 (MH+)

Example 2249

1-[3-tert-Butyl-5-(ethyl-methyl-amino)-4-methoxy-phenyl]-2-(5,6-diethoxy-7-fluoro-1-imino-1,3-dihydro-isoindol-2-yl)-ethanone hydrobromide MS: m/e (ESI) 499.9 (MH+)

Example 2250

1-[3-tert-Butyl-5-(ethyl-methyl-amino)-4-methoxy-phenyl]-2-(7-fluoro-1-imino-5,6-dimethoxy-1,3-dihydro-isoindol-2-yl)-ethanone hydrobromide MS: m/e (ESI) 471.9 (MH+)

Example 2251

1-[3-tert-Butyl-5-(ethyl-methyl-amino)-4-methoxy-phenyl]-2-(2-cyclopropyl-7-imino-5,7-dihydro-pyrrolo[3,4-b]pyridin-6-yl)-ethanone hydrobromide MS: m/e (ESI) 435.0 (MH+)

Example 2252

2-{2-[3-tert-Butyl-5-(ethyl-methyl-amino)-4-methoxy-phenyl]-2-oxo-ethyl}-6-ethoxy-3-imino-2,3-dihydro-1H-isoindole-5-acetic acid methylamide hydrobromide MS: m/e (ESI) 495.0 (MH+)

Example 2253

6-{2-[3-tert-Butyl-5-(ethyl-methyl-amino)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 496.0 (MH+)

Example 2254

2-[2-(3-tert-Butyl-4-methoxy-5-oxazol-5-yl-phenyl)-2-oxo-ethyl]-6-ethoxy-3-imino-2,3-dihydro-1H-isoindole-5-acetic acid methylamide hydrobromide MS: m/e (ESI) 505.3 (MH+)

Example 2255

1-(3-tert-Butyl-4-methoxy-5-oxazol-5-yl-phenyl)-2-(5,6-diethoxy-7-fluoro-1-imino-1,3-dihydro-isoindol-2-yl)-ethanone hydrobromide MS: m/e (ESI) 510.4 (MH+)

Example 2256

1-(3-tert-Butyl-4-methoxy-5-oxazol-5-yl-phenyl)-2-(7-fluoro-1-imino-5,6-dimethoxy-1,3-dihydro-isoindol-2-yl)-ethanone hydrobromide MS: m/e (ESI) 482.3 (MH+)

Example 2257

1-(3-tert-Butyl-4-methoxy-5-oxazol-5-yl-phenyl)-2-(2-cyclopropyl-7-imino-5,7-dihydro-pyrrolo[3,4-b]pyridin-6-yl)-ethanone hydrobromide MS: m/e (ESI) 445.4 (MH+)

Example 2258

6-[2-(3-tert-Butyl-4-methoxy-5-oxazol-5-yl-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 506.4 (MH+)

Example 2259

2-{2-[8-tert-Butyl-4-(2-cyano-ethyl)-3,4-dihydro-2H-benzo[1,4]oxazin-6-yl]-2-oxo-ethyl}-6-ethoxy-3-imino-2,3-dihydro-1H-isoindole-5-acetic acid methylamide hydrobromide MS: m/e (ESI) 517.8 (MH+)

Example 2260

6-{2-[8-tert-Butyl-4-(2-cyano-ethyl)-3,4-dihydro-2H-benzo[1,4]oxazin-6-yl]-2-oxo-ethyl}-3-ethoxy-7-imino-6,7-dihydro-5H-pyrrolo[3,4-b]pyridine-2-carboxylic acid methylamide hydrobromide MS: m/e (ESI) 519.0 (MH+)

Example 2261

3-{8-tert-Butyl-6-[2-(7-fluoro-1-imino-5,6-dimethoxy-1,3-dihydro-isoindol-2-yl)-acetyl]-2,3-dihydro-benzo[1,4]oxazin-4-yl}-propionitrile hydrobromide MS: m/e (ESI) 495.0 (MH+)

Example 2262

3-{8-tert-Butyl-6-[2-(5,6-diethoxy-7-fluoro-1-imino-1,3-dihydro-isoindol-2-yl)-acetyl]-2,3-dihydro-benzo[1,4]oxazin-4-yl}-propionitrile hydrobromide MS: m/e (ESI) 523.0 (MH+)

Example 2263

3-{8-tert-Butyl-6-[2-(2-cyclopropyl-7-imino-5,7-dihydro-pyrrolo[3,4-b]pyridin-6-yl)-acetyl]-2,3-dihydro-benzo[1,4]oxazin-4-yl}-propionitrile hydrobromide MS: m/e (ESI) 485.0 (MH+)

Example 2264

2-{2-[8-tert-Butyl-4-(2-cyano-ethyl)-3,4-dihydro-2H-benzo[1,4]oxazin-6-yl]-2-oxo-ethyl}-6-dimethylamino-3-imino-2,3-dihydro-1H-isoindole-5-carboxylic acid methylamide hydrobromide MS: m/e (ESI) 517.1 (MH+)

Example 2265

2-tert-Butyl-6-dimethylamino-4-[2-(5-dimethylamino-1-imino-6-methylcarbamoyl-1,3-dihydro-isoindol-2-yl)-acetyl]-phenyl methanesulfonate hydrobromide MS: m/e (ESI) 544.2 (MH+)

Example 2266

2-tert-Butyl-4-[2-(5,6-diethoxy-7-fluoro-1-imino-1,3-dihydro-isoindol-2-yl)-acetyl]-6-dimethylamino-phenyl methanesulfonate hydrobromide MS: m/e (ESI) 550.2 (MH+)

Example 2267

2-tert-Butyl-6-dimethylamino-4-[2-(7-fluoro-1-imino-5,6-dimethoxy-1,3-dihydro-isoindol-2-yl)-acetyl]-phenyl methanesulfonate hydrobromide MS: m/e (ESI) 521.3 (MH+)

Example 2268

2-tert-Butyl-4-[2-(2-cyclopropyl-7-imino-5,7-dihydro-pyrrolo[3,4-b]pyridin-6-yl)-acetyl]-6-dimethylamino-phenyl methanesulfonate hydrobromide MS: m/e (ESI) 484.9 (MH+)

Example 2269

2-tert-Butyl-6-dimethylamino-4-[2-(5-ethoxy-1-imino-6-methylcarbamoyl-1,3-dihydro-isoindol-2-yl)-acetyl]-phenyl methanesulfonate hydrobromide MS: m/e (ESI) 545.2 (MH+)

Example 2270

2-tert-Butyl-6-dimethylamino-4-[2-(3-ethoxy-7-imino-2-methylcarbamoyl-5,7-dihydro-pyrrolo[3,4-b]pyridin-6-yl)-acetyl]-phenyl methanesulfonate hydrobromide MS: m/e (ESI) 546.0 (MH+)

Example 2271

1-(3-tert-Butyl-4-methoxy-5-pyridin-4-yl-phenyl)-2-(5,6-diethoxy-7-fluoro-1-imino-1,3-dihydro-isoindol-2-yl)-ethanone hydrobromide MS: m/e (ESI) 520.3 (MH+)

Example 2272

1-(3-tert-Butyl-4-methoxy-5-pyridin-4-yl-phenyl)-2-(7-fluoro-1-imino-5,6-dimethoxy-1,3-dihydro-isoindol-2-yl)-ethanone hydrobromide MS: m/e (ESI) 492.2 (MH+)

Example 2273

1-(3-tert-Butyl-4-methoxy-5-pyridin-4-yl-phenyl)-2-(2-cyclopropyl-7-imino-5,7-dihydro-pyrrolo[3,4-b]pyridin-6-yl)-ethanone hydrobromide MS: m/e (ESI) 455.2 (MH+)

Example 2274

6-[2-(3-tert-Butyl-4-methoxy-5-pyridin-4-yl-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 516.3 (MH+)

Example 2275

2-[2-(3-tert-Butyl-5-dimethylamino-4-methoxy-phenyl)-2-oxo-ethyl]-6-ethoxy-7-fluoro-3-imino-2,3-dihydro-1H-isoindole-5-carboxylic acid methylamide hydrobromide MS: m/e (ESI) 499.2 (MH+)

Example 2276

1-(3-tert-Butyl-5-dimethylamino-4-hydroxy-phenyl)-2-(5,6-diethoxy-7-fluoro-1-imino-1,3-dihydro-isoindol-2-yl)-ethanone hydrobromide MS: m/e (ESI) 472.0 (MH+)

Example 2277

6-[2-(3-tert-Butyl-5-dimethylamino-4-hydroxy-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 468.0 (MH+)

Example 2278

2-[2-(3-tert-Butyl-5-dimethylamino-4-ethoxy-phenyl)-2-oxo-ethyl]-6-dimethylamino-3-imino-2,3-dihydro-1H-isoindole-5-carboxylic acid methylamide hydrobromide MS: m/e (ESI) 493.8 (MH+)

Example 2279

1-(3-tert-Butyl-5-dimethylamino-4-ethoxy-phenyl)-2-(5,6-diethoxy-7-fluoro-1-imino-1,3-dihydro-isoindol-2-yl)-ethanone hydrobromide MS: m/e (ESI) 499.9 (MH+)

Example 2280

1-(3-tert-Butyl-5-dimethylamino-4-ethoxy-phenyl)-2-(7-fluoro-1-imino-5,6-dimethoxy-1,3-dihydro-isoindol-2-yl)-ethanone hydrobromide MS: m/e (ESI) 471.9 (MH+)

Example 2281

1-(3-tert-Butyl-5-dimethylamino-4-ethoxy-phenyl)-2-(2-cyclopropyl-7-imino-5,7-dihydro-pyrrolo[3,4-b]pyridin-6-yl)-ethanone hydrobromide MS: m/e (ESI) 434.9 (MH+)

Example 2282

2-[2-(3-tert-Butyl-5-dimethylamino-4-ethoxy-phenyl)-2-oxo-ethyl]-6-ethoxy-3-imino-2,3-dihydro-1H-isoindole-5-acetic acid methylamide hydrobromide MS: m/e (ESI) 495.0 (MH+)

Example 2283

6-[2-(3-tert-Butyl-5-dimethylamino-4-ethoxy-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 496.0 (MH+)

Example 2284

4-[2-(5,6-Diethoxy-7-fluoro-1-imino-1,3-dihydro-isoindol-2-yl)-acetyl]-2-dimethylamino-6-methoxy-phenyl methanesulfonate hydrobromide MS: m/e (ESI) 524.3 (MH+)

Example 2285

2-Dimethylamino-4-[2-(7-fluoro-1-imino-5,6-dimethoxy-1,3-dihydro-isoindol-2-yl)-acetyl]-6-methoxy-phenyl methanesulfonate hydrobromide MS: m/e (ESI) 496.3 (MH+)

Example 2286

4-[2-(2-Cyclopropyl-7-imino-5,7-dihydro-pyrrolo[3,4-b]pyridin-6-yl)-acetyl]-2-dimethylamino-6-methoxy-phenyl methanesulfonate hydrobromide MS: m/e (ESI) 459.3 (MH+)

Example 2287

2-Dimethylamino-4-[2-(3-ethoxy-7-imino-2-methylcarbamoyl-5,7-dihydro-pyrrolo[3,4-b]pyridin-6-yl)-acetyl]-6-methoxy-phenyl methanesulfonate hydrobromide MS: m/e (ESI) 520.3 (MH+)

Example 2288

2-tert-Butyl-4-[2-(5-ethoxy-1-imino-6-methylcarbamoyl-1,3-dihydro-isoindol-2-yl)-acetyl]-6-methoxy-phenyl methanesulfonate hydrobromide MS: m/e (ESI) 532.0 (MH+)

Example 2289

2-tert-Butyl-4-[2-(5,6-diethoxy-7-fluoro-1-imino-1,3-dihydro-isoindol-2-yl)-acetyl]-6-methoxy-phenyl methanesulfonate hydrobromide MS: m/e (ESI) 537.0 (MH+)

Example 2290

2-tert-Butyl-4-[2-(5-dimethylamino-1-imino-6-methylcarbamoyl-1,3-dihydro-isoindol-2-yl)-acetyl]-6-methoxy-phenyl methanesulfonate hydrobromide MS: m/e (ESI) 531.0 (MH+)

Example 2291

2-tert-Butyl-4-[2-(3-ethoxy-7-imino-2-methylcarbamoyl-5,7-dihydro-pyrrolo[3,4-b]pyridin-6-yl)-acetyl]-6-methoxy-phenyl methanesulfonate hydrobromide MS: m/e (ESI) 533.0 (MH+)

Example 2292

2-tert-Butyl-4-[2-(7-fluoro-1-imino-5,6-dimethoxy-1,3-dihydro-isoindol-2-yl)-acetyl]-6-methoxy-phenyl methanesulfonate hydrobromide MS: m/e (ESI) 509.0 (MH+)

Example 2293

2-tert-Butyl-4-[2-(2-cyclopropyl-7-imino-5,7-dihydro-pyrrolo[3,4-b]pyridin-6-yl)-acetyl]-6-methoxy-phenyl methanesulfonate hydrobromide MS: m/e (ESI) 472.0 (MH+)

Example 2294

3-tert-Butyl-5-[2-(5-ethoxy-1-imino-6-methylcarbamoyl-1,3-dihydro-isoindol-2-yl)-acetyl]-2-methoxy-phenyl methanesulfonate hydrobromide MS: m/e (ESI) 532.1 (MH+)

Example 2295

3-tert-Butyl-5-[2-(5,6-diethoxy-7-fluoro-1-imino-1,3-dihydro-isoindol-2-yl)-acetyl]-2-methoxy-phenyl methanesulfonate hydrobromide MS: m/e (ESI) 537.1 (MH+)

Example 2296

3-tert-Butyl-5-[2-(5-dimethylamino-1-imino-6-methylcarbamoyl-1,3-dihydro-isoindol-2-yl)-acetyl]-2-methoxy-phenyl methanesulfonate hydrobromide MS: m/e (ESI) 531.1 (MH+)

Example 2297

3-tert-Butyl-5-[2-(3-ethoxy-7-imino-2-methylcarbamoyl-5,7-dihydro-pyrrolo[3,4-b]pyridin-6-yl)-acetyl]-2-methoxy-phenyl methanesulfonate hydrobromide MS: m/e (ESI) 533.1 (MH+)

Example 2298

3-tert-Butyl-5-[2-(7-fluoro-1-imino-5,6-dimethoxy-1,3-dihydro-isoindol-2-yl)-acetyl]-2-methoxy-phenyl methanesulfonate hydrobromide MS: m/e (ESI) 509.0 (MH+)

Example 2299

3-tert-Butyl-5-[2-(2-cyclopropyl-7-imino-5,7-dihydro-pyrrolo[3,4-b]pyridin-6-yl)-acetyl]-2-methoxy-phenyl methanesulfonate hydrobromide MS: m/e (ESI) 472.0 (MH+)

Example 2300

2-{2-[3-tert-Butyl-5-(3-hydroxy-pyrrolidin-1-yl)-4-methoxy-phenyl]-2-oxo-ethyl}-6-ethoxy-3-imino-2,3-dihydro-1H-isoindole-5-acetic acid methylamide hydrobromide MS: m/e (ESI) 523.4 (MH+)

Example 2301

1-[3-tert-Butyl-5-(3-hydroxy-pyrrolidin-1-yl)-4-methoxy-phenyl]-2-(5,6-diethoxy-7-fluoro-1-imino-1,3-dihydro-isoindol-2-yl)-ethanone hydrobromide MS: m/e (ESI) 528.5 (MH+)

Example 2302

2-{2-[3-tert-Butyl-5-(3-hydroxy-pyrrolidin-1-yl)-4-methoxy-phenyl]-2-oxo-ethyl}-6-dimethylamino-3-imino-2,3-dihydro-1H-isoindole-5-carboxylic acid methylamide hydrobromide MS: m/e (ESI) 522.5 (MH+)

Example 2303

6-{2-[3-tert-Butyl-5-(3-hydroxy-pyrrolidin-1-yl)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 524.5 (MH+)

Example 2304

1-[3-tert-Butyl-5-(3-hydroxy-pyrrolidin-1-yl)-4-methoxy-phenyl]-2-(7-fluoro-1-imino-5,6-dimethoxy-1,3-dihydro-isoindol-2-yl)-ethanone hydrobromide MS: m/e (ESI) 500.4 (MH+)

Example 2305

1-[3-tert-Butyl-5-(3-hydroxy-pyrrolidin-1-yl)-4-methoxy-phenyl]-2-(2-cyclopropyl-7-imino-5,7-dihydro-pyrrolo[3,4-b]pyridin-6-yl)-ethanone hydrobromide MS: m/e (ESI) 463.4 (MH+)

Example 2306

2-{2-[3-Dimethylamino-5-(1-fluoro-1-methyl-ethyl)-4-methoxy-phenyl]-2-oxo-ethyl}-6-ethoxy-3-imino-2,3-dihydro-1H-isoindole-5-acetic acid methylamide hydrobromide MS: m/e (ESI) 485.3 (MH+)

Example 2307

6-{2-[3-Dimethylamino-5-(1-fluoro-1-methyl-ethyl)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 486.4 (MH+)

Example 2308

1-[3-Dimethylamino-5-(1-fluoro-1-methyl-ethyl)-4-methoxy-phenyl]-2-(7-fluoro-1-imino-5,6-dimethoxy-1,3-dihydro-isoindol-2-yl)-ethanone hydrobromide MS: m/e (ESI) 462.3 (MH+)

Example 2309

2-(5,6-Diethoxy-7-fluoro-1-imino-1,3-dihydro-isoindol-2-yl)-1-[3-dimethylamino-5-(1-fluoro-1-methyl-ethyl)-4-methoxy-phenyl]-ethanone hydrobromide MS: m/e (ESI) 490.4 (MH+)

Example 2310

2-(2-Cyclopropyl-7-imino-5,7-dihydro-pyrrolo[3,4-b]pyridin-6-yl)-1-[3-dimethylamino-5-(1-fluoro-1-methyl-ethyl)-4-methoxy-phenyl]-ethanone hydrobromide MS: m/e (ESI) 425.4 (MH+)

Example 2311

6-Dimethylamino-2-{2-[3-dimethylamino-5-(1-fluoro-1-methyl-ethyl)-4-methoxy-phenyl]-2-oxo-ethyl}-3-imino-2,3-dihydro-1H-isoindole-5-carboxylic acid methylamide hydrobromide MS: m/e (ESI) 484.4 (MH+)

Example 2312

2-{2-[3-tert-Butyl-5-(2-hydroxy-ethylamino)-4-methoxy-phenyl]-2-oxo-ethyl}-6-ethoxy-3-imino-2,3-dihydro-1H-isoindole-5-acetic acid methylamide hydrobromide MS: m/e (ESI) 497.4 (MH+)

Example 2313

2-{2-[3-tert-Butyl-5-(2-hydroxy-ethylamino)-4-methoxy-phenyl]-2-oxo-ethyl}-6-dimethylamino-3-imino-2,3-dihydro-1H-isoindole-5-carboxylic acid methylamide hydrobromide MS: m/e (ESI) 496.4 (MH+)

Example 2314

1-[3-tert-Butyl-5-(2-hydroxy-ethylamino)-4-methoxy-phenyl]-2-(5,6-diethoxy-7-fluoro-1-imino-1,3-dihydro-isoindol-2-yl)-ethanone hydrobromide MS: m/e (ESI) 502.4 (MH+)

Example 2315

1-[3-tert-Butyl-5-(2-hydroxy-ethylamino)-4-methoxy-phenyl]-2-(7-fluoro-1-imino-5,6-dimethoxy-1,3-dihydro-isoindol-2-yl)-ethanone hydrobromide MS: m/e (ESI) 474.4 (MH+)

Example 2316

1-[3-tert-Butyl-5-(2-hydroxy-ethylamino)-4-methoxy-phenyl]-2-(2-cyclopropyl-7-imino-5,7-dihydro-pyrrolo[3,4-b]pyridin-6-yl)-ethanone hydrobromide MS: m/e (ESI) 437.4 (MH+)

Example 2317

6-{2-[3-tert-Butyl-5-(2-hydroxy-ethylamino)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 498.4 (MH+)

Example 2318

2-{2-[3-tert-Butyl-5-(3-hydroxy-propylamino)-4-methoxy-phenyl]-2-oxo-ethyl}-6-ethoxy-3-imino-2,3-dihydro-1H-isoindole-5-acetic acid methylamide hydrobromide MS: m/e (ESI) 511.5 (MH+)

Example 2319

2-{2-[3-tert-Butyl-5-(3-hydroxy-propylamino)-4-methoxy-phenyl]-2-oxo-ethyl}-6-dimethylamino-3-imino-2,3-dihydro-1H-isoindole-5-carboxylic acid methylamide hydrobromide MS: m/e (ESI) 510.5 (MH+)

Example 2320

1-[3-tert-Butyl-5-(3-hydroxy-propylamino)-4-methoxy-phenyl]-2-(5,6-diethoxy-7-fluoro-1-imino-1,3-dihydro-isoindol-2-yl)-ethanone hydrobromide MS: m/e (ESI) 516.5 (MH+)

Example 2321

1-[3-tert-Butyl-5-(3-hydroxy-propylamino)-4-methoxy-phenyl]-2-(7-fluoro-1-imino-5,6-dimethoxy-1,3-dihydro-isoindol-2-yl)-ethanone hydrobromide MS: m/e (ESI) 488.4 (MH+)

Example 2322

1-[3-tert-Butyl-5-(3-hydroxy-propylamino)-4-methoxy-phenyl]-2-(2-cyclopropyl-7-imino-5,7-dihydro-pyrrolo[3,4-b]pyridin-6-yl)-ethanone hydrobromide MS: m/e (ESI) 451.4 (MH+)

Example 2323

6-{2-[3-tert-Butyl-5-(3-hydroxy-propylamino)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 512.5 (MH+)

Example 2324

2-[2-(3-tert-Butyl-4-methoxy-5-morpholin-4-yl-phenyl)-2-oxo-ethyl]-6-dimethylamino-3-imino-2,3-dihydro-1H-isoindole-5-carboxylic acid methylamide hydrobromide MS: m/e (ESI) 522.5 (MH+)

Example 2325

2-[2-(3-Dimethylamino-5-isopropenyl-4-methoxy-phenyl)-2-oxo-ethyl]-6-ethoxy-3-imino-2,3-dihydro-1H-isoindole-5-acetic acid methylamide hydrobromide MS: m/e (ESI) 465.3 (MH+)

Example 2326

6-[2-(3-Dimethylamino-5-isopropenyl-4-methoxy-phenyl)-2-oxo-ethyl]-3-ethoxy-7-imino-6,7-dihydro-5H-pyrrolo[3,4-b]pyridine-2-carboxylic acid methylamide hydrobromide MS: m/e (ESI) 466.3 (MH+)

Example 2327

1-(3-Dimethylamino-5-isopropenyl-4-methoxy-phenyl)-2-(7-fluoro-1-imino-5,6-dimethoxy-1,3-dihydro-isoindol-2-yl)-ethanone hydrobromide MS: m/e (ESI) 442.3 (MH+)

Example 2328

2-(5,6-Diethoxy-7-fluoro-1-imino-1,3-dihydro-isoindol-2-yl)-1-(3-dimethylamino-5-isopropenyl-4-methoxy-phenyl)-ethanone hydrobromide MS: m/e (ESI) 470.4 (MH+)

Example 2329

2-(2-Cyclopropyl-7-imino-5,7-dihydro-pyrrolo[3,4-b]pyridin-6-yl)-1-(3-dimethylamino-5-isopropenyl-4-methoxy-phenyl)-ethanone hydrobromide MS: m/e (ESI) 405.4 (MH+)

Example 2330

6-Dimethylamino-2-[2-(3-dimethylamino-5-isopropenyl-4-methoxy-phenyl)-2-oxo-ethyl]-3-imino-2,3-dihydro-1H-isoindole-5-carboxylic acid methylamide hydrobromide MS: m/e (ESI) 464.4 (MH+)

Example 2331

2-tert-Butyl-4-[2-(5-dimethylamino-1-imino-6-methylcarbamoyl-1,3-dihydro-isoindol-2-yl)-acetyl]-6-ethoxy-phenyl ethylcarbamate hydrobromide MS: m/e (ESI) 538.4 (MH+)

Example 2332

2-tert-Butyl-4-[2-(5,6-diethoxy-7-fluoro-1-imino-1,3-dihydro-isoindol-2-yl)-acetyl]-6-ethoxy-phenyl ethylcarbamate hydrobromide MS: m/e (ESI) 544.4 (MH+)

Example 2333

2-tert-Butyl-6-ethoxy-4-[2-(7-fluoro-1-imino-5,6-dimethoxy-1,3-dihydro-isoindol-2-yl)-acetyl]-phenyl ethylcarbamate hydrobromide MS: m/e (ESI) 516.4 (MH+)

Example 2334

2-tert-Butyl-4-[2-(2-cyclopropyl-7-imino-5,7-dihydro-pyrrolo[3,4-b]pyridin-6-yl)-acetyl]-6-ethoxy-phenyl ethylcarbamate hydrobromide MS: m/e (ESI) 479.4 (MH+)

Example 2335

2-tert-Butyl-6-ethoxy-4-[2-(5-ethoxy-1-imino-6-methylcarbamoyl-1,3-dihydro-isoindol-2-yl)-acetyl]-phenyl ethylcarbamate hydrobromide MS: m/e (ESI) 539.5 (MH+)

Example 2336

2-tert-Butyl-6-ethoxy-4-[2-(3-ethoxy-7-imino-2-methylcarbamoyl-5,7-dihydro-pyrrolo[3,4-b]pyridin-6-yl)-acetyl]-phenyl ethylcarbamate hydrobromide MS: m/e (ESI) 540.5 (MH+)

Example 2337

1-(3-tert-Butyl-5-dimethylamino-4-hydroxy-phenyl)-2-(7-fluoro-1-imino-5,6-dimethoxy-1,3-dihydro-isoindol-2-yl)-ethanone hydrobromide MS: m/e (ESI) 444.4 (MH+)

Example 2338

2-[2-(7-Dimethylamino-3,3-dimethyl-2,3-dihydro-benzofuran-5-yl)-2-oxo-ethyl]-6-ethoxy-3-imino-2,3-dihydro-1H-isoindole-5-acetic acid methylamide hydrobromide MS: m/e (ESI) 465.4 (MH+)

Example 2339

2-(5,6-Diethoxy-7-fluoro-1-imino-1,3-dihydro-isoindol-2-yl)-1-(7-dimethylamino-3,3-dimethyl-2,3-dihydro-benzofuran-5-yl)-ethanone hydrobromide MS: m/e (ESI) 470.4 (MH+)

Example 2340

6-Dimethylamino-2-[2-(7-dimethylamino-3,3-dimethyl-2,3-dihydro-benzofuran-5-yl)-2-oxo-ethyl]-3-imino-2,3-dihydro-1H-isoindole-5-carboxylic acid methylamide hydrobromide MS: m/e (ESI) 464.4 (MH+)

Example 2341

6-[2-(7-Dimethylamino-3,3-dimethyl-2,3-dihydro-benzofuran-5-yl)-2-oxo-ethyl]-3-ethoxy-7-imino-6,7-dihydro-5H-pyrrolo[3,4-b]pyridine-2-carboxylic acid methylamide hydrobromide MS: m/e (ESI) 466.4 (MH+)

Example 2342

1-(7-Dimethylamino-3,3-dimethyl-2,3-dihydro-benzofuran-5-yl)-2-(7-fluoro-1-imino-5,6-dimethoxy-1,3-dihydro-isoindol-2-yl)-ethanone hydrobromide MS: m/e (ESI) 442.4 (MH+)

Example 2343

2-(2-Cyclopropyl-7-imino-5,7-dihydro-pyrrolo[3,4-b]pyridin-6-yl)-1-(7-dimethylamino-3,3-dimethyl-2,3-dihydro-benzofuran-5-yl)-ethanone hydrobromide MS: m/e (ESI) 405.4 (MH+)

Example 2344

2-[2-(3,3-Dimethyl-7-methylamino-2,3-dihydro-benzofuran-5-yl)-2-oxo-ethyl]-6-ethoxy-3-imino-2,3-dihydro-1H-isoindole-5-acetic acid methylamide hydrobromide MS: m/e (ESI) 451.4 (MH+)

Example 2345

2-(5,6-Diethoxy-7-fluoro-1-imino-1,3-dihydro-isoindol-2-yl)-1-(3,3-dimethyl-7-methylamino-2,3-dihydro-benzofuran-5-yl)-ethanone hydrobromide MS: m/e (ESI) 456.4 (MH+)

Example 2346

6-Dimethylamino-2-[2-(3,3-dimethyl-7-methylamino-2,3-dihydro-benzofuran-5-yl)-2-oxo-ethyl]-3-imino-2,3-dihydro-1H-isoindole-5-carboxylic acid methylamide hydrobromide MS: m/e (ESI) 450.4 (MH+)

Example 2347

6-[2-(3,3-Dimethyl-7-methylamino-2,3-dihydro-benzofuran-5-yl)-2-oxo-ethyl]-3-ethoxy-7-imino-6,7-dihydro-5H-pyrrolo[3,4-b]pyridine-2-carboxylic acid methylamide hydrobromide MS: m/e (ESI) 452.4 (MH+)

Example 2348

1-(3,3-Dimethyl-7-methylamino-2,3-dihydro-benzofuran-5-yl)-2-(7-fluoro-1-imino-5,6-dimethoxy-1,3-dihydro-isoindol-2-yl)-ethanone hydrobromide MS: m/e (ESI) 428.4 (MH+)

Example 2349

2-(2-Cyclopropyl-7-imino-5,7-dihydro-pyrrolo[3,4-b]pyridin-6-yl)-1-(3,3-dimethyl-7-methylamino-2,3-dihydro-benzofuran-5-yl)-ethanone hydrobromide MS: m/e (ESI) 391.4 (MH+)

Example 2350

2-{2-[3-Dimethylamino-5-(1-hydroxy-1-methylethyl)-4-methoxy-phenyl]-2-oxo-ethyl}-6-ethoxy-3-imino-2,3-dihydro-1H-isoindole-5-acetic acid methylamide hydrobromide MS: m/e (ESI) 483.2 (MH+)

Example 2351

6-{2-[3-Dimethylamino-5-(1-hydroxy-1-methylethyl)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 484.2 (MH+)

Example 2352

1-[3-Dimethylamino-5-(1-hydroxy-1-methyl-ethyl)-4-methoxy-phenyl]-2-(7-fluoro-1-imino-5,6-dimethoxy-1,3-dihydro-isoindol-2-yl)-ethanone hydrobromide MS: m/e (ESI) 460.2 (MH+)

Example 2353

2-(5,6-Diethoxy-7-fluoro-1-imino-1,3-dihydro-isoindol-2-yl)-1-[3-dimethylamino-5-(1-hydroxy-1-methyl-ethyl)-4-methoxy-phenyl]-ethanone hydrobromide MS: m/e (ESI) 488.3 (MH+)

Example 2354

2-(2-Cyclopropyl-7-imino-5,7-dihydro-pyrrolo[3,4-b]pyridin-6-yl)-1-[3-dimethylamino-5-(1-hydroxy-1-methyl-ethyl)-4-methoxy-phenyl]-ethanone hydrobromide MS: m/e (ESI) 423.3 (MH+)

Example 2355

6-Dimethylamino-2-{2-[3-dimethylamino-5-(1-hydroxy-1-methyl-ethyl)-4-methoxy-phenyl]-2-oxo-ethyl}-3-imino-2,3-dihydro-1H-isoindole-5-carboxylic acid methylamide hydrobromide MS: m/e (ESI) 482.3 (MH+)

Example 2356

6-Ethoxy-2-{2-[3-(4-hydroxy-piperidin-1-yl)-5-isopropyl-4-methoxy-phenyl]-2-oxo-ethyl}-3-imino-2,3-dihydro-1H-isoindole-5-carboxylic acid methylamide hydrobromide MS: m/e (ESI) 523.2 (MH+)

Example 2357

6-Dimethylamino-2-{2-[3-(4-hydroxy-piperidin-1-yl)-5-isopropyl-4-methoxy-phenyl]-2-oxo-ethyl}-3-imino-2,3-dihydro-1H-isoindole-5-carboxylic acid methylamide hydrobromide MS: m/e (ESI) 522.2 (MH+)

Example 2358

3-Ethoxy-6-{2-[3-(4-hydroxy-piperidin-1-yl)-5-isopropyl-4-methoxy-phenyl]-2-oxo-ethyl}-7-imino-6,7-dihydro-5H-pyrrolo[3,4-b]pyridine-2-carboxylic acid methylamide hydrobromide MS: m/e (ESI) 524.3 (MH+)

Example 2359

2-(7-Fluoro-1-imino-5,6-dimethoxy-1,3-dihydro-isoindol-2-yl)-1-[3-(4-hydroxy-piperidin-1-yl)-5-isopropyl-4-methoxy-phenyl]-ethanone hydrobromide MS: m/e (ESI) 500.2 (MH+)

Example 2360

2-(2-Cyclopropyl-7-imino-5,7-dihydro-pyrrolo[3,4-b]pyridin-6-yl)-1-[3-(4-hydroxy-piperidin-1-yl)-5-isopropyl-4-methoxy-phenyl]-ethanone hydrobromide MS: m/e (ESI) 463.3 (MH+)

Example 2361

(1-{5-[2-(5-Dimethylamino-1-imino-6-methylcarbamoyl-1,3-dihydro-isoindol-2-yl)-acetyl]-3-isopropyl-2-methoxy-phenyl}-piperidin-4-yl)-acetic acid hydrobromide MS: m/e (ESI) 564.2 (MH+)

Example 2362

(1-{5-[2-(3-Ethoxy-7-imino-2-methylcarbamoyl-5,7-dihydro-pyrrolo[3,4-b]pyridin-6-yl)-acetyl]-3-isopropyl-2-methoxy-phenyl}-piperidin-4-yl)-acetic acid hydrobromide MS: m/e (ESI) 566.2 (MH+)

Example 2363

(1-{5-[2-(7-Fluoro-1-imino-5,6-dimethoxy-1,3-dihydro-isoindol-2-yl)-acetyl]-3-isopropyl-2-methoxy-phenyl}-piperidin-4-yl)-acetic acid hydrobromide MS: m/e (ESI) 542.2 (MH+)

Example 2364

(1-{5-[2-(2-Cyclopropyl-7-imino-5,7-dihydro-pyrrolo[3,4-b]pyridin-6-yl)-acetyl]-3-isopropyl-2-methoxy-phenyl}-piperidin-4-yl)-acetic acid hydrobromide MS: m/e (ESI) 505.2 (MH+)

Example 2365

2-(2-{3-tert-Butyl-4-methoxy-5-[(2-methoxy-ethyl)-methyl-amino]-phenyl}-2-oxo-ethyl)-6-ethoxy-3-imino-2,3-dihydro-1H-isoindole-5-acetic acid methylamide hydrobromide MS: m/e (ESI) 525.2 (MH+)

Example 2366

2-(2-{3-tert-Butyl-4-methoxy-5-[(2-methoxy-ethyl)-methyl-amino]-phenyl}-2-oxo-ethyl)-6-dimethylamino-3-imino-2,3-dihydro-1H-isoindole-5-carboxylic acid methylamide hydrobromide MS: m/e (ESI) 524.3 (MH+)

Example 2367

1-{3-tert-Butyl-4-methoxy-5-[(2-methoxy-ethyl)-methyl-amino]-phenyl}-2-(5,6-diethoxy-7-fluoro-1-imino-1,3-dihydro-isoindol-2-yl)-ethanone hydrobromide MS: m/e (ESI) 530.3 (MH+)

Example 2368

1-{3-tert-Butyl-4-methoxy-5-[(2-methoxy-ethyl)-methyl-amino]-phenyl}-2-(7-fluoro-1-imino-5,6-dimethoxy-1,3-dihydro-isoindol-2-yl)-ethanone hydrobromide MS: m/e (ESI) 502.2 (MH+)

Example 2369

1-{3-tert-Butyl-4-methoxy-5-[(2-methoxy-ethyl)-methyl-amino]-phenyl}-2-(2-cyclopropyl-7-imino-5,7-dihydro-pyrrolo[3,4-b]pyridin-6-yl)-ethanone hydrobromide MS: m/e (ESI) 465.3 (MH+)

Example 2370

6-(2-{3-tert-Butyl-4-methoxy-5-[(2-methoxy-ethyl)-methyl-amino]-phenyl}-2-oxo-ethyl)-3-ethoxy-7-imino-6,7-dihydro-5H-pyrrolo[3,4-b]pyridine-2-carboxylic acid methylamide hydrobromide MS: m/e (ESI) 526.3 (MH+)

Example 2371

2-{2-[3-Dimethylamino-4-methoxy-5-(1-methoxy-1-methyl-ethyl)-phenyl]-2-oxo-ethyl}-6-ethoxy-3-imino-2,3-dihydro-1H-isoindole-5-acetic acid methylamide hydrobromide MS: m/e (ESI) 497.2 (MH+)

Example 2372

6-{2-[3-Dimethylamino-4-methoxy-5-(1-methoxy-1-methyl-ethyl)-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 498.2 (MH+)

Example 2373

1-[3-Dimethylamino-4-methoxy-5-(1-methoxy-1-methyl-ethyl)-phenyl]-2-(7-fluoro-1-imino-5,6-dimethoxy-1,3-dihydro-isoindol-2-yl)-ethanone hydrobromide MS: m/e (ESI) 474.1 (MH+)

Example 2374

2-(5,6-Diethoxy-7-fluoro-1-imino-1,3-dihydro-isoindol-2-yl)-1-[3-dimethylamino-4-methoxy-5-(1-methoxy-1-methyl-ethyl)-phenyl]-ethanone hydrobromide MS: m/e (ESI) 502.2 (MH+)

Example 2375

2-(2-Cyclopropyl-7-imino-5,7-dihydro-pyrrolo[3,4-b]pyridin-6-yl)-1-[3-dimethylamino-4-methoxy-5-(1-methoxy-1-methyl-ethyl)-phenyl]-ethanone hydrobromide MS: m/e (ESI) 437.2 (MH+)

Example 2376

6-Dimethylamino-2-{(2-[3-dimethylamino-4-methoxy-5-(1-methoxy-1-methyl-ethyl)-phenyl]-2-oxo-ethyl}-3-imino-2,3-dihydro-1H-isoindole-5-carboxylic acid methylamide hydrobromide MS: m/e (ESI) 496.2 (MH+)

Example 2377

2-{2-[3-tert-Butyl-5-(3,4-dihydroxy-pyrrolidin-1-yl)-4-methoxy-phenyl]-2-oxo-ethyl}-6-ethoxy-3-imino-2,3-dihydro-1H-isoindole-5-acetic acid methylamide hydrobromide MS: m/e (ESI) 539.2 (MH+)

Example 2378

1-[3-tert-Butyl-5-(3,4-dihydroxy-pyrrolidin-1-yl)-4-methoxy-phenyl]-2-(5,6-diethoxy-7-fluoro-1-imino-1,3-dihydro-isoindol-2-yl)-ethanone hydrobromide MS: m/e (ESI) 544.2 (MH+)

Example 2379

2-{2-[3-tert-Butyl-5-(3,4-dihydroxy-pyrrolidin-1-yl)-4-methoxy-phenyl]-2-oxo-ethyl}-6-dimethylamino-3-imino-2,3-dihydro-1H-isoindole-5-carboxylic acid methylamide hydrobromide MS: m/e (ESI) 538.2 (MH+)

Example 2380

6-{2-[3-tert-Butyl-5-(3,4-dihydroxy-pyrrolidin-1-yl)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 540.2 (MH+)

Example 2381

1-[3-tert-Butyl-5-(3,4-dihydroxy-pyrrolidin-1-yl)-4-methoxy-phenyl]-2-(7-fluoro-1-imino-5,6-dimethoxy-1,3-dihydro-isoindol-2-yl)-ethanone hydrobromide MS: m/e (ESI) 516.2 (MH+)

Example 2382

1-[3-tert-Butyl-5-(3,4-dihydroxy-pyrrolidin-1-yl)-4-methoxy-phenyl]-2-(2-cyclopropyl-7-imino-5,7-dihydro-pyrrolo[3,4-b]pyridin-6-yl)-ethanone hydrobromide MS: m/e (ESI) 479.2 (MH+)

Example 2383

2-{2-[3-tert-Butyl-5-(3-hydroxy-4-methoxy-pyrrolidin-1-yl)-4-methoxy-phenyl]-2-oxo-ethyl}-6-ethoxy-3-imino-2,3-dihydro-1H-isoindole-5-acetic acid methylamide hydrobromide MS: m/e (ESI) 553.1 (MH+)

Example 2384

1-[3-tert-Butyl-5-(3-hydroxy-4-methoxy-pyrrolidin-1-yl)-4-methoxy-phenyl]-2-(5,6-diethoxy-7-fluoro-1-imino-1,3-dihydro-isoindol-2-yl)-ethanone hydrobromide MS: m/e (ESI) 558.1 (MH+)

Example 2385

2-{2-[3-tert-Butyl-5-(3-hydroxy-4-methoxy-pyrrolidin-1-yl)-4-methoxy-phenyl]-2-oxo-ethyl}-6-dimethylamino-3-imino-2,3-dihydro-1H-isoindole-5-carboxylic acid methylamide hydrobromide MS: m/e (ESI) 552.2 (MH+)

Example 2386

6-{2-[3-tert-Butyl-5-(3-hydroxy-4-methoxy-pyrrolidin-1-yl)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 554.2 (MH+)

Example 2387

1-[3-tert-Butyl-5-(3-hydroxy-4-methoxy-pyrrolidin-1-yl)-4-methoxy-phenyl]-2-(7-fluoro-1-imino-5,6-dimethoxy-1,3-dihydro-isoindol-2-yl)-ethanone hydrobromide MS: m/e (ESI) 530.2 (MH+)

Example 2388

1-[3-tert-Butyl-5-(3-hydroxy-4-methoxy-pyrrolidin-1-yl)-4-methoxy-phenyl]-2-(2-cyclopropyl-7-imino-5,7-dihydro-pyrrolo[3,4-b]pyridin-6-yl)-ethanone hydrobromide MS: m/e (ESI) 493.2 (MH+)

Example 2389

2-{2-[3-tert-Butyl-5-(cyanomethyl-methyl-amino)-4-methoxy-phenyl]-2-oxo-ethyl}-6-ethoxy-3-imino-2,3-dihydro-1H-isoindole-5-acetic acid methylamide hydrobromide MS: m/e (ESI) 506.2 (MH+)

Example 2390

6-{2-[3-tert-Butyl-5-(cyanomethyl-methyl-amino)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 507.2 (MH+)

Example 2391

({3-tert-Butyl-5-[2-(7-fluoro-1-imino-5,6-dimethoxy-1,3-dihydro-isoindol-2-yl)-acetyl]-2-methoxy-phenyl}-methyl-amino)-acetonitrile hydrobromide MS: m/e (ESI) 483.2 (MH+)

Example 2392

({3-tert-Butyl-5-[2-(5,6-diethoxy-7-fluoro-1-imino-1,3-dihydro-isoindol-2-yl)-acetyl]-2-methoxy-phenyl}-methyl-amino)-acetonitrile hydrobromide MS: m/e (ESI) 511.3 (MH+)

Example 2393

({3-tert-Butyl-5-[2-(2-cyclopropyl-7-imino-5,7-dihydro-pyrrolo[3,4-b]pyridin-6-yl)-acetyl]-2-methoxy-phenyl}-methyl-amino)-acetonitrile hydrobromide MS: m/e (ESI) 446.2 (MH+)

Example 2394

2-{2-[3-tert-Butyl-5-(cyanomethyl-methyl-amino)-4-methoxy-phenyl]-2-oxo-ethyl}-6-dimethylamino-3-imino-2,3-dihydro-1H-isoindole-5-carboxylic acid methylamide hydrobromide MS: m/e (ESI) 505.2 (MH+)

Example 2395

2-{2-[3-tert-Butyl-5-(cyanomethyl-amino)-4-methoxy-phenyl]-2-oxo-ethyl}-6-ethoxy-3-imino-2,3-dihydro-1H-isoindole-5-acetic acid methylamide hydrobromide MS: m/e (ESI) 492.2 (MH+)

Example 2396

6-{2-[3-tert-Butyl-5-(cyanomethyl-amino)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 493.2 (MH+)

Example 2397

{3-tert-Butyl-5-[2-(7-fluoro-1-imino-5,6-dimethoxy-1,3-dihydro-isoindol-2-yl)-acetyl]-2-methoxy-phenylamino}-acetonitrile hydrobromide MS: m/e (ESI) 469.2 (MH+)

Example 2398

{3-tert-Butyl-5-[2-(5,6-diethoxy-7-fluoro-1-imino-1,3-dihydro-isoindol-2-yl)-acetyl]-2-methoxy-phenylamino}-acetonitrile hydrobromide MS: m/e (ESI) 497.2 (MH+)

Example 2399

{3-tert-Butyl-5-[2-(2-cyclopropyl-7-imino-5,7-dihydro-pyrrolo[3,4-b]pyridin-6-yl)-acetyl]-2-methoxy-phenylamino}-acetonitrile hydrobromide MS: m/e (ESI) 432.2 (MH+)

Example 2400

2-{2-[3-tert-Butyl-5-(cyanomethyl-amino)-4-methoxy-phenyl]-2-oxo-ethyl}-6-dimethylamino-3-imino-2,3-dihydro-1H-isoindole-5-carboxylic acid methylamide hydrobromide MS: m/e (ESI) 491.2 (MH+)

Example 2401

2-{2-[3-tert-Butyl-5-(4-hydroxy-4-methyl-piperidin-1-yl)-4-methoxy-phenyl]-2-oxo-ethyl}-6-ethoxy-3-imino-2,3-dihydro-1H-isoindole-5-acetic acid methylamide hydrobromide MS: m/e (ESI) 551.3 (MH+)

Example 2402

2-{2-[3-tert-Butyl-5-(4-hydroxy-4-methyl-piperidin-1-yl)-4-methoxy-phenyl]-2-oxo-ethyl}-6-dimethylamino-3-imino-2,3-dihydro-1H-isoindole-5-carboxylic acid methylamide hydrobromide MS: m/e (ESI) 550.3 (MH+)

Example 2403

6-{2-[3-tert-Butyl-5-(4-hydroxy-4-methyl-piperidin-1-yl)-4-methoxy-phenyl]-2-oxo-ethyl}-3-ethoxy-7-imino-6,7-dihydro-5H-pyrrolo[3,4-b]pyridine-2-carboxylic acid methylamide hydrobromide MS: m/e (ESI) 552.3 (MH+)

Example 2404

1-[3-tert-Butyl-5-(4-hydroxy-4-methyl-piperidin-1-yl)-4-methoxy-phenyl]-2-(7-fluoro-1-imino-5,6-dimethoxy-1,3-dihydro-isoindol-2-yl)-ethanone hydrobromide MS: m/e (ESI) 528.2 (MH+)

Example 2405

6-Ethoxy-3-imino-2-[2-(3-isopropyl-4-methoxy-5-morpholin-4-yl-phenyl)-2-oxo-ethyl]-2,3-dihydro-1H-isoindole-5-carboxylic acid methylamide hydrobromide MS: m/e (ESI) 509.2 (MH+)

Example 2406

6-Dimethylamino-3-imino-2-[2-(3-isopropyl-4-methoxy-5-morpholin-4-yl-phenyl)-2-oxo-ethyl]-2,3-dihydro-1H-isoindole-5-carboxylic acid methylamide hydrobromide MS: m/e (ESI) 508.2 (MH+)

Example 2407

2-(5,6-Diethoxy-7-fluoro-1-imino-1,3-dihydro-isoindol-2-yl)-1-(3-isopropyl-4-methoxy-5-morpholin-4-yl-phenyl)-ethanone hydrobromide MS: m/e (ESI) 514.2 (MH+)

Example 2408

2-(7-Fluoro-1-imino-5,6-dimethoxy-1,3-dihydro-isoindol-2-yl)-1-(3-isopropyl-4-methoxy-5-morpholin-4-yl-phenyl)-ethanone hydrobromide MS: m/e (ESI) 486.2 (MH+)

Example 2409

2-(2-Cyclopropyl-7-imino-5,7-dihydro-pyrrolo[3,4-b]pyridin-6-yl)-1-(3-isopropyl-4-methoxy-5-morpholin-4-yl-phenyl)-ethanone hydrobromide MS: m/e (ESI) 449.2 (MH+)

Example 2410

3-Ethoxy-7-imino-6-[2-(3-isopropyl-4-methoxy-5-morpholin-4-yl-phenyl)-2-oxo-ethyl]-6,7-dihydro-5H-pyrrolo[3,4-b]pyridine-2-carboxylic acid methylamide hydrobromide MS: m/e (ESI) 510.2 (MH+)

Example 2411

2-(2-{3-tert-Butyl-5-[ethyl-(2-hydroxy-ethyl)-amino]-4-methoxy-phenyl}-2-oxo-ethyl)-6-ethoxy-3-imino-2,3-dihydro-1H-isoindole-5-acetic acid methylamide hydrobromide MS: m/e (ESI) 525.2 (MH+)

Example 2412

2-(2-{3-tert-Butyl-5-[ethyl-(2-hydroxy-ethyl)-amino]-4-methoxy-phenyl}-2-oxo-ethyl)-6-dimethylamino-3-imino-2,3-dihydro-1H-isoindole-5-carboxylic acid methylamide hydrobromide MS: m/e (ESI) 524.2 (MH+)

Example 2413

1-{3-tert-Butyl-5-[ethyl-(2-hydroxy-ethyl)-amino]-4-methoxy-phenyl}-2-(5,6-diethoxy-7-fluoro-1-imino-1,3-dihydro-isoindol-2-yl)-ethanone hydrobromide MS: m/e (ESI) 530.2 (MH+)

Example 2414

1-{3-tert-Butyl-5-[ethyl-(2-hydroxy-ethyl)-amino]-4-methoxy-phenyl}-2-(7-fluoro-1-imino-5,6-dimethoxy-1,3-dihydro-isoindol-2-yl)-ethanone hydrobromide MS: m/e (ESI) 502.2 (MH+)

Example 2415

1-{3-tert-Butyl-5-[ethyl-(2-hydroxy-ethyl)-amino]-4-methoxy-phenyl}-2-(2-cyclopropyl-7-imino-5,7-dihydro-pyrrolo[3,4-b]pyridin-6-yl)-ethanone hydrobromide MS: m/e (ESI) 465.2 (MH+)

Example 2416

6-(2-{3-tert-Butyl-5-[ethyl-(2-hydroxy-ethyl)-amino]-4-methoxy-phenyl}-2-oxo-ethyl)-3-ethoxy-7-imino-6,7-dihydro-5H-pyrrolo[3,4-b]pyridine-2-carboxylic acid methylamide hydrobromide MS: m/e (ESI) 526.2 (MH+)

The compounds of the following examples were synthesized as ring-opened prodrugs of the aforementioned 1-iminoisoindoline derivatives.

Example 2417

N1-Methyl-5-cyano-4-[(1-{2-[3,5-di(tert-butyl)-4-hydroxyphenyl]-2-oxoethyl}amino)methyl]-2-ethoxybenzamide hydrochloride

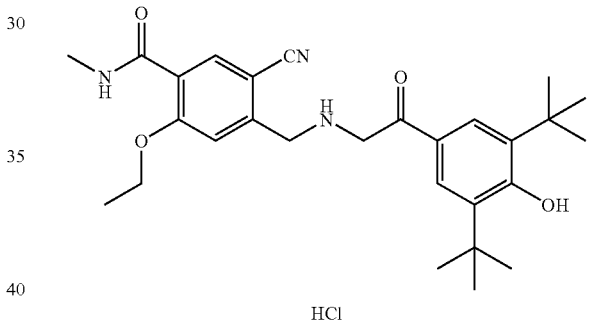

(Step 1) Ethyl 5-bromo-4-(bromomethyl)-2-ethoxybenzoate

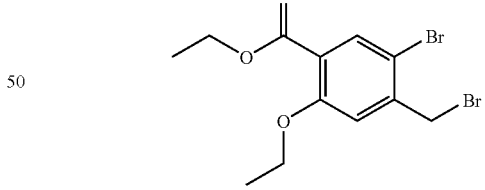

After dissolving ethyl 5-bromo-2-ethoxy-4-methylbenzoate (19.72 g) in carbon tetrachloride, azobisisobutyronitrile (1.13 g) was added and the mixture was heated to reflux for 30 minutes. N-bromosuccinimide was added and the mixture was further heated to reflux for 1 hour. The reaction mixture was filtered and the filtrate was concentrated. The residue was purified by silica gel column chromatography (solvent: n-hexane-ethyl acetate) to yield the title compound (10.54 g) as a colorless oil.

1H-NMR(CDCl3) δ (ppm) 1.37(3H, t, J=7.2 Hz), 1.46 (3H, t, J=7.2H), 4.11(2H, q, J=7.2 Hz), 4.35(2H, q, J=7.2 Hz), 4.54(2H, s), 7.04(1H, s), 7.94(1H, s).

(Step 2) 4-(Azidomethyl)-5-bromo-2-ethoxybenzoic acid

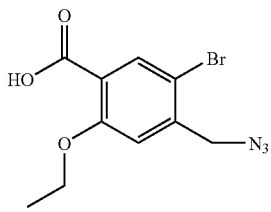

After dissolving the ethyl 5-bromo-4-(bromomethyl)-2-ethoxybenzoate (7.807 g) in dimethylformamide (50 ml), sodium azide (2.0 g) was added and the mixture was stirred at room temperature overnight. The reaction mixture was diluted with ethyl acetate and washed with water, 1 N hydrochloric acid and brine, and then the organic layer was dried over anhydrous magnesium sulfate, filtered and concentrated to yield a light yellow oil (6.96 g). After dissolving this in ethanol (100 ml), 5 N sodium hydroxide was added and the mixture was stirred at 50° C. for 1 hour. It was then neutralized with 5 N hydrochloric acid (5 ml) and extraction was performed with ethyl acetate. The organic layer was dried over anhydrous magnesium sulfate, filtered and concentrated to yield a light yellow oil (7.60 g).

1H-NMR(CDCl3) δ (ppm) 1.59(3H, t, J=6.8 Hz), 4.37 (2H, q, J=6.8 Hz), 4.57(2H, s), 7.14(1H, s), 8.37(1H, s).

(Step 3) N1-Methyl-4-(azidomethyl)-5-bromo-2-ethoxybenzamide

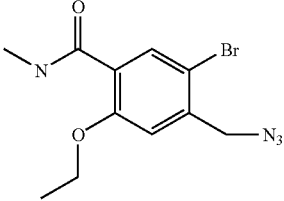

After dissolving the 4-(azidomethyl)-5-bromo-2-ethoxybenzoic acid (7.67 g) in tetrahydrofuran (100 ml), triethylamine (3.2 ml) and ethyl chloroformate (2.11 ml) were added in that order and the mixture was stirred at room temperature for 30 minutes. Aqueous methylamine (3.2 ml) was added and the mixture was stirred at room temperature for 30 minutes. The mixture was diluted with ethyl acetate and washed with water and 1 N hydrochloric acid, and then the organic layer was dried over anhydrous magnesium sulfate, filtered and concentrated to yield the title compound (5.328 g) as a white solid.

1H-NMR(CDCl3) δ (ppm) 1.53(3H, t, J=6.8 Hz), 3.00 (3H, d, J=4.8 Hz), 4.23(2H, q, J=7.2 Hz), 4.51(2H, s), 7.01(1H, s), 7.88(1H, br), 8.40(1H, s).

(Step 4) N1-Methyl-4-(aminomethyl)-5-bromo-2-ethoxybenzamide

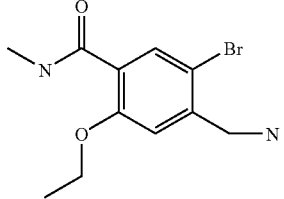

After dissolving the N1-methyl-4-(azidomethyl)-5-bromo-2-ethoxybenzamide (5.32 g) in tetrahydrofuran (50 ml) and water (3 ml), triphenylphosphine (5.4 g) was added and the mixture was stirred at room temperature for 4 days. The reaction mixture was concentrated and the residue was purified by silica gel column chromatography (solvent: n-hexane-ethyl acetate) to yield the title compound (5.11 g) as a light yellow solid.

1H-NMR(CDCl3) δ (ppm) 1.38(3H, t, J=7.2 Hz), 2.79 (3H, d, J=4.8 Hz), 3.71(2H, s), 4.20(2H, q, J=7.2 Hz), 7.34(1H, s), 7.84(1H, s), 8.03(1H, br).

(Step 5) N1-Methyl-5-bromo-2-ethoxy-4-({[(4-nitrophenyl)sulfonyl]amino}methyl)benzamide

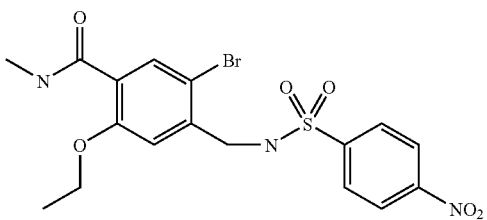

After dissolving the N1-methyl-4-(aminomethyl)-5-bromo-2-ethoxybenzamide (6.77 g) in pyridine (50 ml), 4-nitrobenzenesulfonyl chloride (5.3 g) was added and the mixture was stirred at room temperature overnight. Water and ethyl acetate were then added for separation. The organic layer was washed with 1 N hydrochloric acid and brine and the precipitated crystals were filtered out (5.57 g). The organic layer of the filtrate was dried over anhydrous magnesium sulfate, filtered and concentrated and the residue was washed with ethyl acetate and filtered. A total of 8.31 g of the title compound was obtained as a white solid.

1H-NMR(CDCl3) δ (ppm) 1.34(3H, t, J=9.2 Hz), 2.76 (3H, d, J=4.4 Hz), 4.03(2H, q, J=7.2 Hz), 4.16(2H, d, J=6.4 Hz), 7.03(1H, s), 7.75(1H, s), 7.96–8.02(1H, m), 7.98(2H, d, J=11.6 Hz), 8.34(2H, d, J=11.6 Hz), 8.66–8.72(1H, m).

(Step 6) N1-Methyl-5-bromo-4-({{2-[3,5-di(tert-butyl)-4-hydroxyphenyl]-2-oxoethyl}[4-nitrophenyl)sulfonyl]amino}methyl)-2-ethoxybenzamide

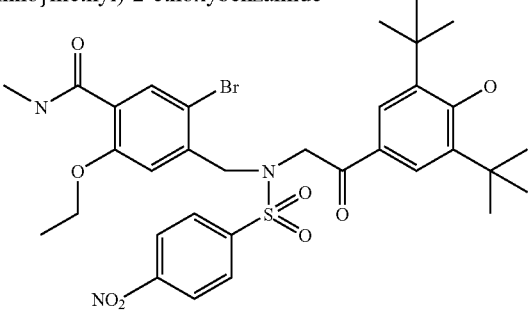

After suspending the N1-methyl-5-bromo-2-ethoxy-4-({[(4-nitrophenyl)sulfonyl]amino}methyl)benzamide (2.10 g) in acetonitrile (20 ml), 2-bromo-1-[3,5-di(tert-butyl)-4-hydroxyphenyl]-1-ethanone (1.74 g) and cesium carbonate (1.74 g) were added in that order. The mixture was stirred at room temperature for 3 days, diluted with ethyl acetate and washed with water and 1 N hydrochloric acid. The organic layer was dried over anhydrous magnesium sulfate, filtered and concentrated, and the residue was washed with ethyl acetate-diisopropyl ether and filtered to yield the title compound (3.04 g) as a white solid.

1H-NMR(CDCl3) δ (ppm) 1.43(18H, s), 1.51(3H, t, J=6.8 Hz), 3.00(3H, d, J=4.8 Hz), 4.18(2H, q, J=6.8 Hz), 4.65(2H, s), 4.72(2H, s), 5.82(1H, s), 7.28(1H, s), 7.61(2H, s), 7.83–7.89(1H, m), 8.05(2H, d, J=11.6 Hz), 8.32(1H, s), 8.37(2H, d, J=9.2 Hz)

619

(Step 7) N1-Methyl-5-bromo-4-[({2-[3,5-di(tert-butyl)-4-hydroxyphenyl]-2-oxoethyl}amino)methyl]-2-ethoxybenzamide

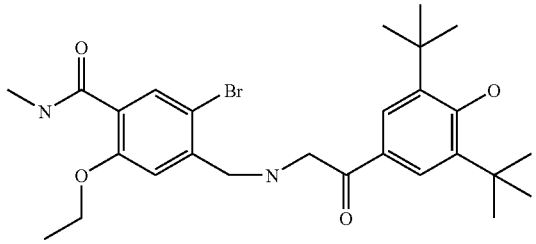

After dissolving thiophenol (1.27 ml) in dimethylformamide (20 ml), sodium hydride (480 mg) was added. The mixture was stirred at room temperature for 30 minutes and then the N1-methyl-5-bromo-4-({{2-[3,5-di(tert-butyl)-4-hydroxyphenyl]-2-oxoethyl}[(4-nitrophenyl)sulfonyl]amino}methyl)-2-ethoxybenzamide (2.95 g) was added. After stirring at room temperature for 1 hour, the mixture was diluted with ethyl acetate and washed with water and brine, and then the organic layer was dried over anhydrous magnesium sulfate, filtered and concentrated and the residue was purified by silica gel column chromatography (solvent: n-hexane-ethyl acetate) to yield the title compound (1.75 g) as a light orange oil. (78% yield)

1H-NMR(CDCl3) δ (ppm) 1.42(18H, s), 1.48(3H, t, J=6.8 Hz), 2.99(3H, d, J=4.8 Hz), 4.31(2H, q, J=6.8 Hz), 4.36(2H, s), 4.42(2H, s), 5.86(1H, s), 7.73(2H, s), 7.75(1H, s), 7.93 (1H, brs), 8.39(1H, d, J=3.6 Hz).

(Step 8) tert-Butyl N-{2-bromo-5-ethoxy-4-[(methylamino)carbonyl]benzyl}-N-{2-[3,5-di(tert-butyl)-4-hydroxyphenyl]-2-oxoethyl}carbamate

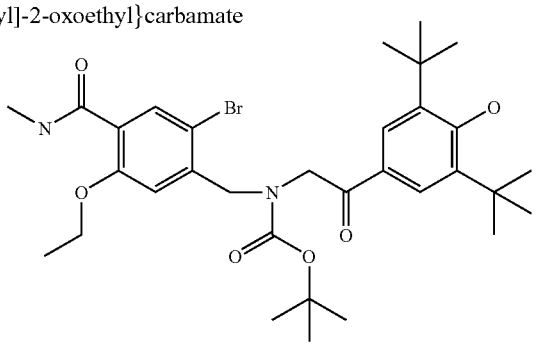

After dissolving the N1-methyl-5-bromo-4-[({2-[3,5-di(tert-butyl)-4-hydroxyphenyl]-2-oxoethyl}amino)methyl]-2-ethoxybenzamide (1.75 g) in tetrahydrofuran (20 ml), tert-butyl dicarbonate (770 mg) was added. The mixture was heated to reflux for 2 hours, the reaction mixture was concentrated and the residue was purified by silica gel column chromatography (solvent: n-hexane-ethyl acetate) to yield the title compound (1.97 g) as a white solid.

1H-NMR(CDCl3) δ (ppm) 1.42, 1.44, 1.46(27H, each s), 1.50(3H, t, J=7.2 Hz), 3.00, 3.02(3H, each d, J=4.8 Hz and J=5.2 Hz), 4.15, 4.23(2H, each q, J=7.2 Hz and 6.8 Hz), 4.56, 4.57(2H, each s), 4.63, 4.67(2H, each s), 5.75(1H, s), 7.12, 7.29(1H, s), 7.72, 7.80(2H, each s), 7.87–7.94(1H, m), 8.32, 8.35(1H, each s).

620

(Step 9) tert-Butyl N-{2-cyano-5-ethoxy-4-[(methylamino)carbonyl]benzyl}-N-{2-[3,5-di(tert-butyl)-4-hydroxyphenyl]-2-oxoethyl}carbamate

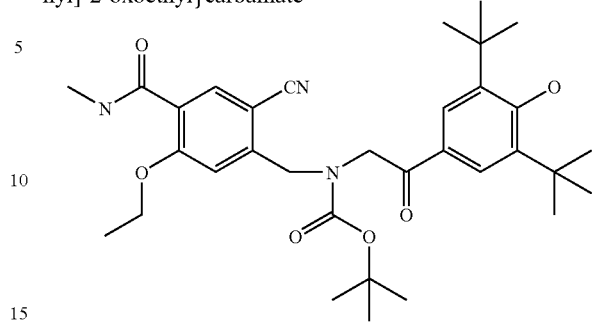

After dissolving the tert-butyl N-{2-bromo-5-ethoxy-4-[(methylamino)carbonyl]benzyl}-N-{2-[3,5-di(tert-butyl)-4-hydroxyphenyl]-2-oxoethyl}carbamate (2.71 g) in propionitrile (11 ml), sodium cyanide (420 mg), copper iodide (163 mg) and tetrakis(triphenylphosphine)palladium (495 mg) were added under a nitrogen atmosphere and the mixture was heated to reflux for one hour. Additional copper iodide (170 mg) and tetrakis(triphenylphosphine)palladium (500 mg) were added and heating to reflux was continued for 4 hours. Ethyl acetate and water were added to the reaction mixture and the resultant mixture was filtered with celite. The filtrate was washed with water and brine. The organic layer was dried over anhydrous magnesium sulfate and, after filtering off the insoluble portion, was concentrated. The residue was purified by silica gel column chromatography (solvent: n-hexane-ethyl acetate) to yield the title compound (788 mg) as a white solid.

1H-NMR(CDCl3) δ (ppm) 1.38, 1.41, 1.45(18H, each s), 1.54(3H, t, J=6.8 Hz), 1.57(9H, s), 3.00, 3.01(3H, each d, J=4.4 Hz and J=4.8 Hz), 4.29, 4.36(2H, each q, J=6.8 Hz), 4.66, 4.69(2H, each s), 4.71, 4.75(2H, each s), 5.76(1H, s), 7.47, 7.51(1H, each s), 7.72, 7.82(2H, each s), 7.76–7.82 (1H, m), 8.46, 8.50(1H, each s).

Example 2417

Final Step

After dissolving the tert-butyl N-{2-cyano-5-ethoxy-4-[(methylamino)carbonyl]benzyl}-N-{2-[3,5-di(tert-butyl)-4-hydroxyphenyl]-2-oxoethyl}carbamate (454 mg) in a 4 N hydrogen chloride-dioxane solution, the mixture was stirred at room temperature for one hour. The reaction mixture was concentrated to yield the target compound (410 mg) as a white solid.

1H-NMR(DMSO-d6) δ (ppm) 1.39(3H, t, J=6.8 Hz), 1.40(18H, s), 2.79(3H, d, J=3.6 Hz), 4.28(2H, q, J=6.8 Hz), 4.38(2H, brs), 4.89(2H, brs), 7.74(2H, s), 7.81(1H, s), 8.04 (1H, s), 8.14(1H, s), 8.17(1H, d, J=4.8 Hz).

Example 2418

5-Bromo-4-{[2-(3,5-di-tert-butyl-4-hydroxy-phenyl)-2-oxo-ethylamino]-methyl}-2-ethoxy-3-fluoro-N-methyl-benzamide 1H-NMR(DMSO-d6) δ: 1.40(3H, t, J=7.2 Hz), 1.45(18H, s), 3.00(3H, d, J=4.8 Hz), 4.12(4H, s), 4.20(2H, q, J=7.2 Hz), 5.76(1H, s), 7.76(2H, s), 7.82(1H, br), 8.12(1H, s).

Example 2419

5-Cyano-4-{[2-(3,5-di-tert-butyl-4-hydroxy-phenyl)-2-oxo-ethylamino]-methyl}-2-ethoxy-3-fluoro-N-methyl-benzamide 1H-NMR(DMSO-d6) δ: 1.31(3H, t, J=7.2 Hz), 1.41(18H, s), 2.78(3H, t, J=4.4 Hz), 4.27(2H, q, J=7.2 Hz), 4.36(2H, brs), 4.89(2H, brs), 7.75(2H, s), 8.13(1H, s), 8.38–8.42(1H, m).

Example 2420

5-Cyano-4-{[2-(3,5-di-tert-butyl-4-hydroxy-phenyl)-2-oxo-ethylamino]-methyl}-2-ethoxy-N-methyl-benzamide hydrochloride 1H-NMR(DMSO-d6) δ: 1.39(3H, t, J=6.8 Hz), 1.40(18H, s), 2.79(3H, d, J=3.6 Hz), 4.28(2H, q, J=6.8 Hz), 4.38(2H, brs), 4.89(2H, brs), 7.74(2H, s), 7.81(1H, s), 8.04(1H, s), 8.14(1H, s), 8.17(1H, d, J=4.8 Hz).

Example 2421

4-({(2-Amino-acetyl)-[2-(3,5-di-tert-butyl-4-hydroxy-phenyl)-2-oxo-ethyl]-amino}-methyl)-5-cyano-2-ethoxy-N-methyl-benzamide hydrochloride 1H-NMR(DMSO-d6) δ: 1.36(3H, t, J=7.2 Hz), 1.40(9H, s), 2.77(3H, d, J=4.8 Hz), 4.22(2H, q, J=7.2 Hz), 4.46(2H, brs), 4.87(2H, brs), 5.20(2H, brs), 7.12(1H, s), 7.76(2H, s), 8.03(1H, s), 8.05–8.12(1H, m), 8.25(1H, br).

Example 2422

5-Cyano-4-({[2-(3,5-di-tert-butyl-4-hydroxy-phenyl)-2-oxo-ethyl]-methyl-amino}-methyl)-2-ethoxy-N-methyl-benzamide 1H-NMR(DMSO-d6) δ: 1.33(3H, t, J=7.2 Hz), 1.37(18H, s), 2.36(3H, s), 2.77(3H, d, J=4.4 Hz), 3.86(2H, s), 3.98(2H, s), 4.10(2H, q, J=7, 2 Hz), 7.25(1H, s), 7.70(2H, s), 7.78(1H, brs), 7.93(1H, s), 8.03–8.07(1H, m).

Example 2423

Methyl {2-tert-butyl-4-[(2-(2-cyano-5-ethoxy-4-methylcarbamoyl-benzylamino)-acetyl]-phenoxy}-acetate hydrochloride 1H-NMR(DMSO-d6) δ: 1.31(9H, s), 1.38(3H, t, J=6.8 Hz), 2.76(3H, d, J=4.8 Hz), 3.25(2H, d, J=7.2 Hz), 3.70(3H, s), 4.19–4.30(2H, m), 4.93(2H, d, J=6.4 Hz), 5.41(1H, br), 6.91(1H, d, J=8.8 Hz), 7.37(1H, s), 7.67(1H, d, J=2.4 Hz), 7.80(1H, dd, J=2.0, 8.8 Hz), 7.82(1H, s), 7.98–8.01(1H, m), 8.56(2H, br).

Example 2424

5-Cyano-4-({[2-(3,5-di-tert-butyl-4-hydroxy-phenyl)-2-oxo-ethyl]-methyl-amino}-methyl)-2-ethoxy-benzamide 1H-NMR(DMSO-d6) δ: 1.34(3H, t, J=6.4 Hz), 1.37(9H, s), 2.36(3H, s), 3.86(2H, s), 3.97(2H, s), 4.09(2H, q, J=6.4 Hz), 7.25(1H, s), 7.54(1H, br), 7.69(2H, s), 7.71(1H, br), 7.78(1H, br), 7.99(1H, s).

Example 2425

4-[({2-[3-tert-Butyl-5-(3-carbamoyl-propoxy)-4-hydroxy-phenyl]-2-oxo-ethyl}-methyl-amino)-methyl]-5-cyano-2-ethoxy-N-methyl-benzamide 1H-NMR(DMSO-d6) δ: 1.34(3H, t, J=7.2 Hz), 1.36(9H, s), 1.97(2H, quint, J=6.8 Hz), 2.29(2H, t, J=6.8 Hz), 2.35(3H, s), 2.79(3H, d, J=4.4 Hz), 3.88(2H, s), 4.00(4H, m), 4.12(2H, q, J=7.2 Hz), 6.83(1H, s), 7.28(1H, s), 7.33(1H, s), 7.37(1H, s), 7.48(1H, s), 7.96(1H, s), 8.08(1H, q, J=4.4 Hz), 9.16(1H, s).

Example 2426

4-[({2-[3-tert-Butyl-5-(3-carbamoyl-propoxy)-4-hydroxy-phenyl]-2-oxo-ethyl}-methyl-amino)-methyl]-5-cyano-2-ethoxy-benzamide 1H-NMR(DMSO-d6) δ: 1.36(12H, m), 1.98(2H, quint, J=7.2 Hz), 2.29(2H, t, J=7.2 Hz), 2.36(3H, s), 3.88(2H, s), 4.00(4H, m), 4.12(2H, q, J=6.8 Hz), 6.83(1H, s), 7.29(1H, s), 7.33(1H, s), 7.37(1H, s), 7.47(1H, s), 7.57(1H, s), 7.73(1H, s), 8.01(1H, s), 9.16(1H, s).

Example 2427

4-(3-tert-Butyl-5-{2-[(2-cyano-5-ethoxy-benzyl)-methyl-amino]-acetyl}-2-hydroxy-phenoxy)-butylamide ¹H-NMR(DMSO-d6) δ: 1.29(3H, t, J=7 Hz), 1.34(9H, s), 1.92–2.01(2H, m), 2.45–2.55(2H, m), 2.55(3H, s), 3.92–4.06(4H, m), 4.15(2H, q, J=7 Hz), 5.38(2H, s), 7.18–7.42(2H, m), 7.45–7.66(2H, m), 7.68–7.82(2H, m).

Example 2428

4-({2-[3-tert-Butyl-5-(3-carbamoyl-propoxy)-4-hydroxy-phenyl]-2-oxo-ethylamino}-methyl)-5-cyano-2-ethoxy-N-methyl-benzamide hydrochloride 1H-NMR(DMSO-d6) δ: 1.38(9H, s), 1.40(3H, t, J=6.8 Hz), 1.99(2H, t, J=6.8 Hz), 2.29(2H, t, J=6.8 Hz), 2.79(3H, d, J=4.8 Hz), 4.05(2H, t, J=6.4 Hz), 4.29(2H, q, J=6.8 Hz), 4.38(2H, brs), 4.88(2H, brs), 6.81(1H, brs), 7.36(1H, brs), 7.42(1H, s), 7.48(1H, s), 7.86(1H, s), 8.03(1H, s), 8.18(1H, q, J=3.6 Hz), 9.51(1H, brs).

TEST EXAMPLES

The biochemical activities of compounds of the invention and salts thereof and their actions and effects as medicines (thrombin receptor binding capacity, platelet aggregation inhibitory action and smooth muscle cell proliferation inhibitory action) were evaluated by the following methods.

Test Example 1

[Receptor Binding Assay]
Blood was sampled from a healthy adult who had taken no drugs for one week, and 3.8% citric acid (a ratio of 1:9 with respect to the blood) was added as an anticoagulant. The mixture was then centrifuged at 100 g for 10 minutes at room temperature to yield platelet rich plasma (PRP). The platelet precipitate obtained by centrifuging the PRP was homogenized with a Dounce homogenizer, and then centrifuged at 40,000 g for 60 minutes to yield platelet membrane.

The platelet membrane was suspended in a solution prepared by adding DMSO (dimethyl sulfoxide) at 1% concentration to Buffer 1: a 50 mM Tris-HCl buffer containing 10 mM $MgCl_2$ and 1 mM EGTA (ethylene glycol tetraacetic acid), and the suspension was stored at −80° C. Bovine albumin and DMSO were added to Buffer 1 at 0.1% and 20%, respectively, to make preparation solutions for the test compound. The test compounds (20 μl) diluted at various concentrations with the preparation solutions were added to a 96-well multiscreen plate. Next, 80 μl of 25 nM [3H]Ala-(4-fluoro)Phe-Arg-(cyclohexyl)Ala-(homo)Arg-Tyr-$NH_2$ (high affinity TRAP) diluted with Buffer 1 was added and thoroughly mixed therewith. After then adding 100 μl of the previously prepared platelet membrane suspension (0.4 mg/ml) and mixing, incubation was performed at 37° C. for 1 hour. The reaction mixture was suction filtered and then rinsed 3 times with 200 μl of Buffer 1. Next, 30 μl of liquid scintillator was added for measurement of the radioactivity of the plate using a Top Counter (Packard), the value of the radioactivity in the presence of the test compound minus non-specific binding portion was divided by the specific binding value (the value of the binding in the absence of the compound minus the non-specific binding portion) to determine the binding ratio, from which the $IC_{50}$ value was calculated. The non-specific binding was the value obtained with addition of 10 μM of high affinity TRAP. The results are shown in Tables 1 to 4.

Test Example 2

[Inhibitory Effects on Platelet Aggregation Using Platelet Rich Plasma]

Blood was sampled from a healthy adult who had taken no drugs for one week, and 3.8% citric acid (a ratio of 1:9 with respect to the blood) was added as an anticoagulant. The mixture was then centrifuged at 100 g for 10 minutes at room temperature to yield platelet rich plasma (PRP). The PRP-removed blood was further centrifuged at 1000 g for 10 minutes to yield platelet poor plasma (PPP). The number of platelet was counted using a multi-parameter automatic hemocyte counter (K4500, Sysmex), and the PRP was diluted to approximately 300,000/μl with the PPP. The platelet aggregation activity was determined in the following manner using an Aggregometer (MC Medical). GPRP-$NH_2$ (final concentration 1 mM, 25 μl) was added as a fibrin polymerization inhibitor to the PRP (175 μl), after which Ca-free Tyrode solution (control) or the test compound suspension (25 μl) at different concentrations was added, incubation was performed at 37° C. for 3 minutes and then 25 μl of thrombin at the minimum concentration required to produce maximum aggregation (final concentration: optimum concentration among 0.5–1.5 units/ml) was added, for initiation of platelet aggregation. PRP and Ca-free Tyrode solution (control) or the preparation solutions at various concentrations were pre-incubated at 37° C. for 60 minutes, prior to the platelet aggregation reaction in some experiments. After addition of thrombin, the aggregation reaction was examined for 6 minutes and the areas under the aggregation curves were compared to determine the inhibition ratio, from which the $IC_{50}$ value was calculated. The results are shown in Tables 1 to 4.

Test Example 3

[Rat Smooth Muscle Cell Proliferation Assay]

Vascular smooth muscle cells (rSMC) were isolated from male SD rat aorta by the explant method. DMEM medium (Sigma) containing 10% fetal bovine serum (GibcoBRL), streptomycin and penicillin was used as the proliferation medium, and subculture was carried out at 37° C. in the presence of 5% $CO_2$. Culture was initiated after adding 100 μl of rSMC suspension in proliferation medium at a concentration of $1 \times 10^4$ cells/ml, to a 96-well plate. After 3 days, cells were rinsed twice with 100 μl of DMEM medium, the medium was exchanged with 100 μl of DMEM medium containing 0.1% albumin (starvation medium), and serum starvation was initiated. The medium was exchanged two days after the serum starvation, 80 μl of starvation medium and 10 μl of the test compound diluted to different concentrations with the starvation medium were added, and then 10 μl of thrombin dissolved in the starvation medium (final concentration: 0.1 unit/ml) was added prior to further incubation for 2 days.

Upon adding 20 μl of MTT (3-[4,5-dimethylthiazol-2-yl]-2,5-diphenyltetrazolium bromide) dissolved in DPBS to 7.5 mg/ml, incubation was continued for 4 hours. The medium was removed by suction, 50 μl of a 10% SDS/0.029% ammonia solution was added, and the mixture was allowed to stand for 2 hours in a $CO_2$ incubator for complete lysis of the cells. As an index of cell proliferation, the OD 590 nm was measured using a plate reader (EL340, BIO-TEK Instruments Inc.), and the control OD value (OD value in the absence of the test compound) minus the OD value in the presence of the test compound was divided by the control OD value minus the blank OD value (OD value without thrombin stimulation) to determine the inhibition ratio, from which the $IC_{50}$ value was calculated. The results are shown in Tables 1 to 4.

TABLE 1

| Example No. | Compound | Compound name | RBA $IC_{50}$ (μM) | Thr $IC_{50}$ (μM) | Rat SMC $IC_{50}$ (μM) |
|---|---|---|---|---|---|
| Example 5 | [structure] | {8-tert-Butyl-6-[2-(5,6-diethoxy-7-fluoro-1-imino-1,3-dihydro-isoindol-2-yl)-acetyl]-2,3-dihydrobenzo[1,4]oxazin-4-yl)-acetonitrile hydrobromide | 0.017 | 0.29 | 0.0061 |

TABLE 1-continued

| Example No. | Compound | Compound name | RBA IC$_{50}$ (µM) | Thr IC$_{50}$ (µM) | Rat SMC IC$_{50}$ (µM) |
| --- | --- | --- | --- | --- | --- |
| Example 6 | | 1-(3-tert-Butyl-5-dimethylamino-4-methoxy-phenyl)-2-(5,6-diethoxy-7-fluoro-1-imino-1,3-dihydro-isoindol-2-yl)-ethanone hydrobromide | 0.024 | 0.072 | 0.019 |
| Example 7 | | 1-(3-tert-Butyl-4-methoxy-5-morpholino-phenyl)-2-(5,6-diethoxy-7-fluoro-1-imino-1,3-dihydro-isoindol-2-yl)-ethanone hydrobromide | 0.026 | 0.041 | 0.032 |
| Example 8 | | 1-[3-tert-Butyl-5-(4-hydroxy-piperidin-1-yl)-4-methoxy-phenyl]-2-(5,6-diethoxy-7-fluoro-1-imino-1,3-dihydro-isoindol-2-yl)ethanone hydrobromide | 0.029 | 0.084 | 0.023 |
| Example 10 | | {3-tert-Butyl-5-[2-(5,6-diethoxy-7-fluoro-1-imino-1,3-dihydroisoindol-2-yl)acetyl]-2-methoxy-phenylamino}-acetonitrile hydrobromide | 0.026 | 0.024 | 0.034 |

TABLE 2

| Example No. | Compound | Compound name | RBA IC$_{50}$ (µM) | THr IC$_{50}$ (µM) | Rat SMC IC$_{50}$ (µM) |
|---|---|---|---|---|---|
| Example 11 | | (4-{3-tert-Butyl-5-[2-(5,6-diethoxy-7-fluoro-1-imino-1,3-dihydro-isoindol-2-yl)-acetyl]-2-methoxy-phenyl}-piperazin-1-yl)-acetonitrile hydrobromide | 0.045 | 0.057 | 0.075 |
| Example 12 | | 1-[3-tert-Butyl-5-((3R,4R)-3-hydroxy-4-methoxy-pyrrolidin-1-yl)-4-methoxy-phenyl]-2-(5,6-diethoxy-7-fluoro-1-imino-1,3-dihydroisoindol-2-yl)-ethanone trifluoroacetate | 0.045 | 0.041 | 0.021 |
| Example 13 | | 1-[3-(4-Acetyl-piperazin-1-yl)-5-tert-butyl-4-methoxy-phenyl]-2-(5,6-diethoxy-7-fluoro-1-imino-1,3-dihydro-isoindol-2-yl)-ethanone hydrobromide | 0.046 | 0.045 | 0.12 |
| Example 16 | | 1-{3-tert-Butyl-4-methoxy-5-[4-(2-ethoxy-acetyl)-piperazin-1-yl]-phenyl}-2-(5,6-diethoxy-7-fluoro-1-imino-1,3-dihydroisoindol-2-yl)-ethanone hydrobromide | 0.053 | 0.057 | 0.059 |

TABLE 3

| Example No. | Compound | Compound name | RBA IC$_{50}$ (µM) | Thr IC$_{50}$ (µM) | Rat SMC IC$_{50}$ (µM) |
|---|---|---|---|---|---|
| Example 17 | | 1-[3-tert-Butyl-5-((3S,4S)-3-ethoxy-4-hydroxy-pyrrolidin-1-yl)-4-methoxy-phenyl]-2-(5,6-diethoxy-7-fluoro-1-imino-1,3-dihydroisoindol-2-yl)-ethanone trifluoroacetate | 0.032 | 0.08 | — |
| Example 26 | | 1-(3-tert-Butyl-5-isopropylamino-4-methoxy-phenyl)-2-(5,6-diethoxy-7-fluoro-1-imino-1,3-dihydro-isoindol-2-yl)-ethanone hydrobromide | 0.017 | 0.079 | 0.062 |
| Example 28 | | 1-(3-tert-Butyl-5-ethoxy-4-methoxy-phenyl)-2-(5,6-diethoxy-7-fluoro-1-imino-1,3-dihydro-isoindol-2-yl)-ethanone hydrobromide | 0.026 | 0.044 | 0.05 |
| Example 29 | | 2-tert-Butyl-4-[2-(5,6-diethoxy-7-fluoro-1-imino-1,3-dihydro-isoindol-2-yl)-acetyl]-6-ethoxy-phenyl ethyl-carbamate hydrobromide | 0.076 | 0.052 | 0.07 |

TABLE 4

| Example No. | Compound name | RBA IC$_{50}$ (µM) | Thr IC$_{50}$ (µM) | Rat SMC IC$_{50}$ (µM) |
|---|---|---|---|---|
| Example 94 | 1-{3-tert-Butl-5-[2-(5,6-diethoxy-7-fluoro-1-imino-1,3-dihydro-isoindol-2-yl)-acetyl]-2-methoxy-phenyl]-piperidin-4-one hydrobromide | 0.013 | 0.029 | 0.044 |
| Example 109 | 2-[2-(3-tert-Butyl-5-ethoxy-4-hydroxy-phenyl)-2-oxo-ethyl)-6-ethoxy-3-imino-2,3-dihydro-1H-isoindole-5-carboxylic acid ethylamide hydrobromide | 0.03 | 0.012 | 0.042 |
| Example 112 | 1-(3-tert-Butyl-4-methoxy-5-piperazin-1-yl-phenyl)-2-(5,6-diethoxy-7-fluoro-1-imino-1,3-dihydro-isoindol-2-yl)-ethanone dihydrochloride | 0.03 | 0.028 | 0.052 |
| Example 127 | (4-{3-tert-Butyl-5-[2-(5,6-diethoxy-7-fluoro-1-imino-1,3-dihydro-isoindol-2-yl)-acetyl]-2-methoxy-phenyl}-piperazin-1-yl)-acetic acid dihydrochloride | 0.017 | 0.021 | 0.15 |

The compounds of the present invention and salts thereof exhibited excellent thrombin receptor binding capacity in Test Example 1, and especially selective binding capacity with PAR1 thrombin receptor. In addition, the compounds of the invention and salts thereof exhibited excellent platelet aggregation inhibitory action in Test Example 2. The compounds of the invention and salts thereof also exhibited excellent smooth muscle cell proliferation inhibitory action in Test Example 3.

INDUSTRIAL APPLICABILITY

The present invention provides novel 2-iminopyrrolidine derivatives represented by the formula (I) and salts thereof. The compounds of the invention represented by the formula (I) and salts thereof exhibit excellent thrombin receptor antagonism and especially selective antagonism for PAR1 thrombin receptors. The compounds of the invention and salts thereof can therefore inhibit cellular response to thrombin which includes platelet aggregation, without inhibiting the catalytic activity of thrombin which converts fibrinogen to fibrin, and can also inhibit vascular smooth muscle proliferation occurring as a result of damage to vascular walls by coronary angioplasty and the like, based on selective inhibition of PAR1.

Thus the compounds of the invention and salts thereof are useful as thrombin receptor antagonists (especially PAR1 thrombin receptor antagonists), platelet aggregation inhibitors (antithrombotic agents) and smooth muscle cell proliferation inhibitors, while also being useful as therapeutic or preventive agents for restenosis during or following angioplasty, unstable angina, stable angina, myocardial infarction, cerebral infarction, peripheral arterial occlusion and the like, as therapeutic or preventive agents for venous thromboses such as deep venous thrombosis, pulmonary embolism and cerebral embolism accompanying atrial fibrillation, glomerulonephritis and the like, as anti-inflammatory agents or as anti-restenosis agents.

The invention claimed is:

1. 1-(3-tert-Butyl-4-methoxy-5-morpholino-phenyl)-2-(5,6-diethoxy-7-fluoro-1-imino-1,3-dihydro-isoindol-2-yl)-ethanone hydrobromide.

2. 1-{3-tert-Butyl-5-[4-(2-hydroxy-acetyl)piperazin-1-yl]-4-methoxy-phenyl}-2-(5,6-diethoxy-7-fluoro-1-imino-1,3-dihydro-isoindol-2-yl)-ethanone hydrobromide.

3. Ethyl (4-{3-tert-butyl-5-[2-(5,6-diethoxy-7-fluoro-1-imino-1,3-dihydro-isoindol-2-yl)-acetyl]-2-methoxy-phenyl}piperazin-1-yl)-acetate dihydrochloride.

4. 1-(3-tert-Butyl-4-methoxy-5-piperazin-1-yl-phenyl)-2-(5,6-diethoxy-7-fluoro-1-imino-1,3-dihydro-isoindol-2-yl)-ethanone dihydrochloride.

5. (4-{3-tert-Butyl-5-[2-(5,6-diethoxy-7-fluoro-1-imino-1,3-dihydro-isoindol-2-yl)-acetyl]-2-methoxy-phenyl}-piperazin-1-yl)-acetic acid dihydrochloride.

6. A compound represented by the formula:

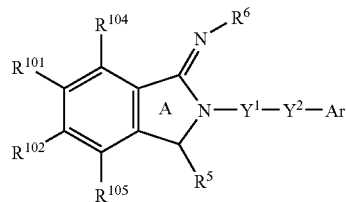

[wherein $R^{101}$ represents $C_{1-6}$ alkoxy or $C_{1-6}$ alkylaminocarbonyl;

$R^{102}$ represents $C_{1-6}$ alkoxy;

$R^{104}$ represents hydrogen or halogen;

$R^{105}$ represents hydrogen;

$R^5$ hydrogen;

$R^6$ represents hydrogen;

$Y^1$ represents —CH$_2$—;

$Y^2$ represents —CO—; and

Ar represents a group represented by the formula:

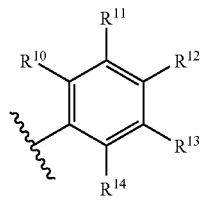

(wherein $R^{10}$ represents hydrogen;

$R^{11}$ represents $C_{1-6}$ alkyl;

$R^{12}$ represents hydroxyl, $C_{1-6}$ alkoxy or $C_{1-6}$ alkylaminocarbonyloxy;

$R^{13}$ represents $C_{1-6}$ alkylamino, di($C_{1-6}$ alkyl)amino, $C_{1-6}$ alkoxy or 5- to 14-membered non-aromatic heterocyclic group, each of the foregoing members being optionally substituted with at least one group selected from hydroxyl, cyano, $C_{1-6}$ alkoxy, $C_{2-7}$ acyl, $C_{1-6}$ alkoxyalkylcarbonyl, $C_{1-6}$ alkylamino, oxo, $C_{1-6}$ carboxyalkyl and hydroxymethylcarbonyl;

$R^{14}$ represents hydrogen; and $R^{12}$ and $R^{13}$ may bond together to form a 5- to 8-membered heterocycle optionally having 1 to 4 hetero atoms selected from N, S and O and also optionally substituted by cyano-$C_{1-6}$ alkyl)]

or a salt thereof.

7. A compound selected from any one of the group consisting of:
1-(3-tert-Butyl-4-methoxy-5-morpholino-phenyl)-2-(5,6-diethoxy-7-fluoro-1-imino-1,3-dihydro-isoindol-2-yl)-ethanone;
1-{3-tert-Butyl-5-[4-(2-hydroxy-acetyl)piperazin-1-yl]-4-methoxy-phenyl}-2-(5,6-diethoxy-7-fluoro-1-imino-1,3-dihydro-isoindol-2-yl)-ethanone;
Ethyl (4-{3-tert-butyl-5-[2-(5,6-diethoxy-7-fluoro-1-imino-1,3-dihydro-isoindol-2-yl)-acetyl]-2-methoxy-phenyl}piperazin-1-yl)-acetate;
1-(3-tert-Butyl-4-methoxy-5-piperazin-1-yl-phenyl)-2-(5,6-diethoxy-7-fluoro-1-imino-1,3-dihydro-isoindol-2-yl)-ethanone; and
(4-{3-tert-Butyl-5-[2-(5,6-diethoxy-7-fluoro-1-imino-1,3-dihydro-isoindol-2-yl)-acetyl]-2-methoxy-phenyl}-piperazin-1-yl)-acetic acid;
or a salt thereof.

8. 1-(3-tert-Butyl-4-methoxy-5-morpholino-phenyl)-2-(5,6-diethoxy-7-fluoro-1-imino-1,3-dihydro-isoindol-2-yl)-ethanone, or a salt thereof.

9. 1-{3-tert-Butyl-5-[4-(2-hydroxy-acetyl)piperazin-1-yl]-4-methoxy-phenyl}-2-(5,6-diethoxy-7-fluoro-1-imino-1,3-dihydro-isoindol-2-yl)-ethanone, or a salt thereof.

10. Ethyl (4-{3-tert-butyl-5-[2-(5,6-diethoxy-7-fluoro-1-imino-1,3-dihydro-isoindol-2-yl)-acetyl]-2-methoxy-phenyl}piperazin-1-yl)-acetate, or a salt thereof.

11. 1-(3-tert-Butyl-4-methoxy-5-piperazin-1-yl-phenyl)-2-(5,6-diethoxy-7-fluoro-1-imino-1,3-dihydro-isoindol-2-yl)-ethanone, or a salt thereof.

12. (4-{3-tert-Butyl-5-[2-(5,6-diethoxy-7-fluoro-1-imino-1,3-dihydro-isoindol-2-yl)-acetyl]-2-methoxy-phenyl}-piperazin-1-yl)-acetic acid, or a salt thereof.

13. A pharmaceutical composition comprising a compound according to any one of claims 1 to 5 or 7 to 12.

14. A pharmaceutical composition comprising a compound according to claim 6.

15. A method for treating thrombosis, vascular restenosis, deep venous thrombosis, and inflammatory disease, comprising administering to a patient a compound according to claim 6, or a pharmaceutical composition comprising a compound according to claim 6, in an amount effective to antagonize a thrombin receptor.

16. The method according to claim 15, wherein the thrombin receptor is a PAR-1 thrombin receptor.

* * * * *

UNITED STATES PATENT AND TRADEMARK OFFICE
CERTIFICATE OF CORRECTION

| | |
|---|---|
| PATENT NO. | : 7,244,730 B2 |
| APPLICATION NO. | : 10/475188 |
| DATED | : July 17, 2007 |
| INVENTOR(S) | : Suzuki et al. |

Page 1 of 1

It is certified that error appears in the above-identified patent and that said Letters Patent is hereby corrected as shown below:

column 149, line 34: "fter" should be --After--.

Claim 6, column 633, line 62: "$R^5$ hydrogen" should be --$R^5$ represents hydrogen--.

Claim 6, column 634, line 28: "cyano-$C_{1-6}$ alkyl" should be --cyano-$C_{1-4}$ alkyl--.

Signed and Sealed this

Twenty-ninth Day of April, 2008

JON W. DUDAS
*Director of the United States Patent and Trademark Office*